United States Patent
Chen et al.

(10) Patent No.: US 9,868,721 B2
(45) Date of Patent: *Jan. 16, 2018

(54) TRIAZOLE AGONISTS OF THE APJ RECEPTOR

(71) Applicant: AMGEN INC., Thousand Oaks, CA (US)

(72) Inventors: Ning Chen, Thousand Oaks, CA (US); Xiaoqi Chen, Palo Alto, CA (US); Yinhong Chen, Hayward, CA (US); Alan C. Cheng, San Francisco, CA (US); Richard V. Connors, Mesa, AZ (US); Jeffrey Deignan, San Francisco, CA (US); Paul John Dransfield, Arlington, MA (US); Xiaohui Du, Belmont, CA (US); Zice Fu, Foster City, CA (US); Julie Anne Heath, Chico, CA (US); Daniel B. Horne, Natick, MA (US); Jonathan Houze, Cambridge, MA (US); Matthew R. Kaller, Ventura, CA (US); Aarif Yusuf Khakoo, Woodside, CA (US); David John Kopecky, Studio City, CA (US); Su-Jen Lai, Boston, MA (US); Zhihua Ma, Lexington, MA (US); Lawrence R. McGee, Pacifica, CA (US); Julio C. Medina, San Carlos, CA (US); Jeffrey T. Mihalic, San Francisco, CA (US); Nobuko Nishimura, West Hills, CA (US); Steven H. Olson, Millbrae, CA (US); Vatee Pattaropong, Bedford, MA (US); Gayathri Swaminath, Brisbane, CA (US); Xiaodong Wang, Johns Creek, GA (US); Kevin Yang, San Gabriel, CA (US); Wen-Chen Yeh, Belmont, CA (US); Mikkel V. Debenedetto, Waltham, MA (US); Robert P. Farrell, Thousand Oaks, CA (US); Simon J. Hedley, Thousand Oaks, CA (US); Ted C. Judd, Granada Hills, CA (US); Frank Kayser, San Francisco, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,272

(22) Filed: Oct. 19, 2016

(65) Prior Publication Data
US 2017/0037026 A1  Feb. 9, 2017

Related U.S. Application Data

(63) Continuation of application No. 15/158,174, filed on May 18, 2016, now Pat. No. 9,573,936.
(Continued)

(51) Int. Cl.
*C07D 401/14* (2006.01)
*C07D 401/04* (2006.01)
(Continued)

(52) U.S. Cl.
CPC .......... *C07D 401/14* (2013.01); *A61K 31/437* (2013.01); *A61K 31/444* (2013.01);
(Continued)

(58) Field of Classification Search
CPC .. C07D 401/04; C07D 401/14; C07D 471/04; C07D 471/14; C07F 7/08; C07B 59/002; C07B 2200/05
See application file for complete search history.

(56) References Cited

U.S. PATENT DOCUMENTS

| 4,941,912 A | 7/1990 | Kirsten et al. |
| 5,302,718 A | 4/1994 | Agback et al. |

(Continued)

FOREIGN PATENT DOCUMENTS

| AU | 199886243 B2 | 4/1999 |
| AU | 2012200157 A1 | 9/2012 |

(Continued)

OTHER PUBLICATIONS

SciFinder Stucture Search with Substances Performed May 20, 2016.
(Continued)

*Primary Examiner* — Yong L Chu
(74) *Attorney, Agent, or Firm* — Bernard P. Friedrichsen

(57) ABSTRACT

Compounds of Formula I and Formula II, pharmaceutically acceptable salt thereof, stereoisomers of any of the foregoing, or mixtures thereof are agonists of the APJ Receptor and have use in treating cardiovascular and other conditions. Compounds of Formula I and Formula II have the following structures:

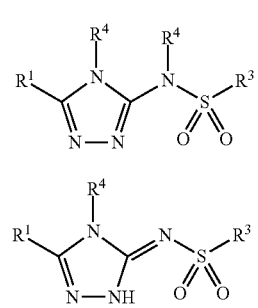

where the definitions of the variables are provided herein.

60 Claims, 15 Drawing Sheets

Related U.S. Application Data

(60) Provisional application No. 62/164,106, filed on May 20, 2015.

(51) Int. Cl.

| | | |
|---|---|---|
| C07D 413/04 | (2006.01) | |
| A61K 31/4439 | (2006.01) | |
| A61K 31/444 | (2006.01) | |
| A61K 31/497 | (2006.01) | |
| A61K 31/501 | (2006.01) | |
| A61K 31/506 | (2006.01) | |
| A61K 31/513 | (2006.01) | |
| A61K 45/06 | (2006.01) | |
| C07B 57/00 | (2006.01) | |
| C07B 59/00 | (2006.01) | |
| C07D 211/54 | (2006.01) | |
| C07D 213/71 | (2006.01) | |
| C07D 213/82 | (2006.01) | |
| C07D 239/26 | (2006.01) | |
| C07D 239/30 | (2006.01) | |
| C07D 241/12 | (2006.01) | |
| C07D 241/24 | (2006.01) | |
| C07D 249/08 | (2006.01) | |
| C07D 405/14 | (2006.01) | |
| C07D 413/14 | (2006.01) | |
| C07D 417/14 | (2006.01) | |
| C07D 471/04 | (2006.01) | |
| C07D 401/12 | (2006.01) | |
| A61K 31/695 | (2006.01) | |
| C07F 7/08 | (2006.01) | |
| A61K 31/437 | (2006.01) | |
| C07C 311/13 | (2006.01) | |
| C07D 213/61 | (2006.01) | |
| C07D 239/34 | (2006.01) | |
| C07D 241/18 | (2006.01) | |
| C07D 295/16 | (2006.01) | |

(52) U.S. Cl.
CPC ........ *A61K 31/4439* (2013.01); *A61K 31/497* (2013.01); *A61K 31/501* (2013.01); *A61K 31/506* (2013.01); *A61K 31/513* (2013.01); *A61K 31/695* (2013.01); *A61K 45/06* (2013.01); *C07B 57/00* (2013.01); *C07B 59/002* (2013.01); *C07C 311/13* (2013.01); *C07D 211/54* (2013.01); *C07D 213/61* (2013.01); *C07D 213/71* (2013.01); *C07D 213/82* (2013.01); *C07D 239/26* (2013.01); *C07D 239/30* (2013.01); *C07D 239/34* (2013.01); *C07D 241/12* (2013.01); *C07D 241/18* (2013.01); *C07D 241/24* (2013.01); *C07D 249/08* (2013.01); *C07D 295/16* (2013.01); *C07D 401/04* (2013.01); *C07D 401/12* (2013.01); *C07D 405/14* (2013.01); *C07D 413/04* (2013.01); *C07D 413/14* (2013.01); *C07D 417/14* (2013.01); *C07D 471/04* (2013.01); *C07F 7/08* (2013.01); *C07B 2200/05* (2013.01); *C07B 2200/07* (2013.01)

(56) References Cited

U.S. PATENT DOCUMENTS

| | | | |
|---|---|---|---|
| 5,328,803 A | 7/1994 | Fukijura et al. | |
| 5,411,839 A | 5/1995 | Harder et al. | |
| 5,451,588 A | 9/1995 | Baker et al. | |
| 5,510,362 A | 4/1996 | Matassa et al. | |
| 5,563,026 A | 10/1996 | Singer | |
| 5,910,504 A | 6/1999 | Hutchinson | |
| 6,069,141 A | 5/2000 | Barbachyn et al. | |
| 6,194,090 B1 | 2/2001 | Okada | |
| 6,555,693 B2 | 4/2003 | Ge et al. | |
| 6,586,423 B2 | 7/2003 | Bilodeau et al. | |
| 6,727,364 B2 | 4/2004 | Tullis et al. | |
| 6,787,555 B2 | 9/2004 | Tullis et al. | |
| 6,790,846 B2 | 9/2004 | Clark et al. | |
| 7,084,145 B2 | 8/2006 | Armour et al. | |
| 7,084,164 B2 | 8/2006 | Tobe et al. | |
| 7,169,797 B2 | 1/2007 | Xin et al. | |
| 7,297,168 B2 | 11/2007 | Murphy et al. | |
| 7,361,669 B2 | 4/2008 | Scarborough et al. | |
| 7,371,757 B2 | 5/2008 | Morningstar et al. | |
| 7,615,569 B2 | 11/2009 | Fulp et al. | |
| 7,635,751 B2 | 12/2009 | Kitada et al. | |
| 7,638,541 B2 | 12/2009 | Chen et al. | |
| 7,718,683 B2 | 5/2010 | Charvat et al. | |
| 7,776,897 B2 | 8/2010 | Murakami et al. | |
| 7,820,665 B2 | 10/2010 | Booker et al. | |
| 8,034,834 B2 | 10/2011 | Du et al. | |
| 8,053,456 B2 | 11/2011 | Sun et al. | |
| 8,063,083 B2 | 11/2011 | Foley | |
| 8,076,486 B2 | 12/2011 | Goutopoulos et al. | |
| 8,101,618 B2 | 1/2012 | Kawamoto et al. | |
| 8,252,822 B2 | 8/2012 | An et al. | |
| 8,299,107 B2 | 10/2012 | Chimmanamada et al. | |
| 8,318,790 B2 | 11/2012 | Ying et al. | |
| 8,399,464 B2 | 3/2013 | Kuramochi et al. | |
| 8,415,377 B2 | 4/2013 | Sun et al. | |
| 8,426,602 B2 | 4/2013 | Meibom et al. | |
| 8,431,604 B2 | 4/2013 | Netz et al. | |
| 8,445,518 B2 | 5/2013 | Charvat et al. | |
| 8,466,170 B2 | 6/2013 | Klein | |
| 8,492,427 B2 | 7/2013 | Gancia et al. | |
| 8,563,741 B2 | 10/2013 | Qian et al. | |
| 8,648,104 B2 | 2/2014 | Du et al. | |
| 8,673,848 B2 | 3/2014 | Zecri et al. | |
| 8,742,133 B2 | 6/2014 | Ying et al. | |
| 8,778,977 B2 | 7/2014 | Lind et al. | |
| 8,835,464 B2 | 9/2014 | Sun et al. | |
| 8,883,827 B2 | 11/2014 | Holsworth et al. | |
| 9,156,796 B2 | 10/2015 | Hachtel et al. | |
| 9,573,936 B2 * | 2/2017 | Chen .................... | C07C 311/13 |
| 2002/0107245 A1 | 8/2002 | Wagle et al. | |
| 2004/0167188 A1 | 8/2004 | Xin et al. | |
| 2005/0075275 A1 | 4/2005 | Albrecht et al. | |
| 2005/0165015 A1 | 7/2005 | Ncube | |
| 2005/0170431 A1 | 8/2005 | Ibrahim et al. | |
| 2005/0288347 A1 | 12/2005 | Hodge et al. | |
| 2006/0156480 A1 | 7/2006 | Lim | |
| 2006/0281749 A1 | 12/2006 | Wagle et al. | |
| 2008/0153869 A1 | 6/2008 | Bressi et al. | |
| 2008/0249131 A1 | 10/2008 | Girardet et al. | |
| 2009/0318438 A1 | 12/2009 | Chen et al. | |
| 2010/0130472 A1 | 5/2010 | Young et al. | |
| 2010/0249185 A1 | 9/2010 | Du et al. | |
| 2010/0280032 A1 | 11/2010 | Zhou et al. | |
| 2011/0046125 A1 | 2/2011 | Ying | |
| 2011/0158940 A1 | 6/2011 | Byrd et al. | |
| 2011/0190257 A1 | 8/2011 | Heald et al. | |
| 2011/0207788 A1 | 8/2011 | Amberg et al. | |
| 2011/0265691 A1 | 11/2011 | Orth et al. | |
| 2012/0094837 A1 | 4/2012 | Muhlthau et al. | |
| 2012/0208828 A1 | 8/2012 | Holsworth et al. | |
| 2012/0238576 A1 | 9/2012 | Tao et al. | |
| 2013/0034536 A1 | 2/2013 | Gedulin | |
| 2013/0040950 A1 | 2/2013 | Short et al. | |
| 2013/0059807 A1 | 3/2013 | Gedulin et al. | |
| 2013/0059845 A1 | 3/2013 | Song et al. | |
| 2013/0108573 A1 | 5/2013 | Gedulin et al. | |
| 2013/0109671 A1 | 5/2013 | Gedulin et al. | |
| 2013/0150385 A1 | 6/2013 | Blackman et al. | |
| 2013/0156755 A1 | 6/2013 | Blackman et al. | |
| 2013/0266636 A1 | 10/2013 | Cheresh et al. | |
| 2013/0303505 A1 | 11/2013 | Bollu et al. | |
| 2014/0005181 A1 | 1/2014 | Smith et al. | |

(56) References Cited

U.S. PATENT DOCUMENTS

| | | | |
|---|---|---|---|
| 2016/0058705 | A1 | 3/2016 | Rajadas et al. |
| 2016/0060349 | A1 | 3/2016 | Van Schravendijk et al. |

FOREIGN PATENT DOCUMENTS

| | | | | |
|---|---|---|---|---|
| DE | 3928605 | A1 | 3/1991 | |
| DE | 4035141 | A1 | 5/1992 | |
| EP | 0330959 | A2 | 2/1989 | |
| EP | 0409332 | A2 | 1/1991 | |
| EP | 0484750 | A1 | 10/1991 | |
| JP | 2003-5356 | A | 8/2003 | |
| JP | 2003-321456 | A | 11/2003 | |
| JP | 2005-170939 | A | 6/2005 | |
| WO | 91/11909 | A1 | 8/1991 | |
| WO | 99/43671 | A1 | 9/1999 | |
| WO | 01/87855 | A1 | 11/2001 | |
| WO | 2005/039569 | A1 | 5/2005 | |
| WO | 2006/026488 | A1 | 3/2006 | |
| WO | 2006/055760 | A1 | 5/2006 | |
| WO | 2006/080533 | A1 | 8/2006 | |
| WO | 2006/095783 | A1 | 9/2006 | |
| WO | 2006/100588 | A1 | 9/2006 | |
| WO | 2006/109817 | A1 | 10/2006 | |
| WO | 2007/007688 | A1 | 1/2007 | |
| WO | 2007/139952 | A2 | 12/2007 | |
| WO | 2007/139967 | A2 | 12/2007 | |
| WO | 2008/008375 | A2 | 1/2008 | |
| WO | 2008/021364 | A2 | 2/2008 | |
| WO | 2008/103352 | A1 | 8/2008 | |
| WO | 2009/075890 | A2 | 6/2009 | |
| WO | 2009/115503 | A1 | 9/2009 | |
| WO | 2010/017545 | A2 | 2/2010 | |
| WO | 2011/146801 | A1 | 11/2011 | |
| WO | 2012/076898 | A1 | 6/2012 | |
| WO | WO 2012076898 | A1 * | 6/2012 | .......... C07D 401/12 |
| WO | 2012/116247 | A1 | 8/2012 | |
| WO | 2013/067162 | A1 | 5/2013 | |
| WO | 2013/067165 | A1 | 5/2013 | |
| WO | 2013/074594 | A1 | 5/2013 | |
| WO | 2013/106437 | A1 | 7/2013 | |
| WO | 2013/106614 | A1 | 7/2013 | |
| WO | 2013/111110 | A2 | 8/2013 | |
| WO | 2013/148857 | A1 | 10/2013 | |
| WO | 2013/184755 | A2 | 12/2013 | |
| WO | 2014/044738 | A1 | 3/2014 | |
| WO | 2014/099984 | A1 | 6/2014 | |
| WO | 2014/150326 | A1 | 9/2014 | |
| WO | 2014/194270 | A1 | 12/2014 | |
| WO | 2015/140296 | A2 | 9/2015 | |
| WO | 2015/163818 | A1 | 10/2015 | |
| WO | 2015/184011 | A2 | 12/2015 | |
| WO | 2015/188073 | A1 | 12/2015 | |
| WO | 2017/066402 | A1 | 4/2017 | |
| WO | 2017/10058 | A1 | 6/2017 | |
| WO | 2017/091513 | A1 | 6/2017 | |
| WO | 2017/096130 | A1 | 6/2017 | |

OTHER PUBLICATIONS

SciFinder Stucture Search with References Performed May 20, 2016.
SciFinder Structure Search Sulfonamide Tail with Substance Performed May 12, 2016.
Berry, M. F. et al., "Apelin Has In Vivo Inotropic Effects on Normal and Failing Hearts," Circulation 110, pp. II187-II193, (2004).
Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett.6b00038; lccn:2009200243; oclcnum:455500725; serissn:1948-5875; itc:84452717; itcp:10547084 (2016).
Chun, H. et al., "Apelin Signaling ANG II Effects in Mouse Models of Atherosclerosis," J. Clin. Invest. 118(10), pp. 3343-3354.
Japp, A. G. et al., "Acute Cardiovascular Effects of Apelin in Humans," Circulation 121, pp. 1818-1827 (2010).
Modzelewska-Banachiewicz et al., "Synthesis and Biological Action of 3-4-Disubstituted 5-Arylsulphonylamino-1,2,4-triazoles," Pharmazie 54, pp. 588-589 (1999).
Pauli, A. et al., "Toddler: An Embryonic Signal That Promotes Cell Movement via Apelin Receptors," Science 343, pp. 1248636-0-1248636-8 (2014).
Siddiquee, K. et al., "The Apelin receptor Inhibits the Angiotensin II Type 1 Receptor Via Allosteric Trans-Inhibition," Br. J. Pharmacol. 168, pp. 1104-1117 (2013).
Siddiquee, K. et al., "Apelin Protects Against Angiotensin II-Induced Cardiovascular Fibrosis and Decreases Plasminogen Activator Inhibitor Type-1 Production," J. Hypertension 29, pp. 724-731 (2011).
Tatemoto, K. et al., "Isolation and Characterization of a Novel Endogenous Peptide Ligand for the Human APJ Receptor," Bioch. Biophys. Res. Comm., 251, pp. 471-476 (1998).
Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).
Maguire, J. J. et al., "[Pyr$^1$]Apelin-13 Identified as the Predominant Apelin Isoform in the Human Heart: Vasoactive Mechanism and Inotropic Action in Disease," Hypertension 54(3), pp. 598-604, (2009).
Barnes, G. et al., "Translational Promise of the Apelin-APJ System," Heart 96(13), pp. 1011-1016 (2010).
Kawamata, Y. et al., "Molecular Properties of Apelin: Tissue Distribution and Receptor Binding," Biochemica et Biophysica Acta 1538(2-3), pp. 162-171 (2001).
Nishizawa, N. et al., "High Potency Analog of Apelin, a Ligand of Orphan GPCT APJ," T Shiori (ed.) Petptide Science 2000: Proceedings of the 37$^{th}$ Japanese Peptide Symposium, pp. 151-154 (2000).
Medhurst, A. D. et al., "Pharmacological and Immunohistochemical Characteization of the APJ Receptor and its Endogenous Ligand Apelin," J. Neurochem. 84(5), pp. 1162-1172 (2003).
Hamada, J. et al., "Evaluation of Novel Cyclic Analogoues of Apelin," Int. J. Mol. Med. 22, pp. 547-552 (2008).
Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).
Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).
Thomas, J.B. et al., "Identification of N-[5-{[(4-Methylphenyl)sulfonyl]amino}-3-(trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).
Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett. 25, pp. 2060-2064 (2015).
Thompson, M. E. "α,N-Alkanesulfonamide Dianions: Formation and Chemoselective C-Alkylation," J. Org. Chem. 49, pp. 1700-1703 (1984).
Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).
Singh, O. M. et al., "A Facile One-Pot Synthetic Method for 1,2,4-Triazoles and 1,3-Disubstituted Thioureas," J. Chem. Res. pp. 483-485 (2006).
Carlsen, P.J.J. et al., "Synthesis of Unsymmetrically Substituted 4H-1,2,4-Triazoles," J. Heterocyclic Chem. 31, pp. 805-807 (1994).
Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).
Hassan, A. A. et al., "Thiosemicarbazides in Heterocyclization," J. Heterocyclic Chem. 48, pp. 495-516 (2011).

(56) References Cited

OTHER PUBLICATIONS

Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).

Ivanova, N. V. et al., "A Convenient Synthesis of 4,5-Disubstituted 1,2,4-Triazoles Functionalized in Position 3," Synthesis 1, pp. 156-160 (2005).

Modzelewska-Banaschiewicz, B et al., "Antiviral Activity of the Products of Cyclization of Dimethyl 2-[1-arylamino-1-alylmethylideine)hydrazono]succinate," Eur. J. Med. Chem. 36, pp. 93-99 (2001).

SciFinder Structure Search with Substances Performed Sep. 1, 2016.

SciFinder Structure Search with References Performed Sep. 1, 2016.

Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).

International Search Report and Written Opinion for analogous PCT Application No. PCT/US2016/033088, mailed on Aug. 24, 2016.

Johnson, M. G. et al., "Convenient Route to Secondary Sulfinates: Application to the Stereospecific Synthesis of α-C-Chiral Sulfonamides," Organic Letters 16(23), pp. 6248-6251 (2014).

Enders, D. et al., "Asymmetric Synthesis of α-Substituted N-Methylsulfonamides," Helvetica Chimica Acta, 85, pp. 3657-3677 (2002).

Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).

Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).

Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).

\* cited by examiner

TRIAZOLE AGONISTS OF THE APJ RECEPTOR

CROSS REFERENCES TO RELATED APPLICATIONS

This application is a continuation of, and claims priority to, U.S. patent application Ser. No. 15/158,174, filed on May 18, 2016, now U.S. Pat. No. 9,573,936, which claims priority to U.S. Provisional Application No. 62/164,106, filed on May 20, 2015, both of which are hereby incorporated by reference in their entireties and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to treat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77—also referred to as Apelin-36) and a smaller 13 residue polypeptide (Apelin 65-77—also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65]Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at subnanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275: 21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than aplein-13. Nishizawa et al., in: T. Shioiri (ed.), Peptide Science 2000: Proceedings of the 37$^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. ChemMed-Chem 7:318-325, 2012. Additionally, PCT/US2013/075773 describes a group of modifications, including substitution of non-canonical amino acids and changes at the N- and C-terminal of the apelin molecule that can affect, inter al/a, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

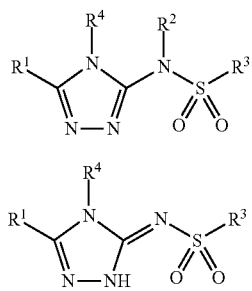

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted pyridyl, pyridonyl, or pyridine N-oxide, or is a pyridyl, pyridonyl, or pyridine N-oxide substituted with 1, 2, 3, or 4 $R^{1a}$ substituents;

$R^{1a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —C(=O)-(heterocyclyl), or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 lea substituents, a group of formula —($CR^{3b}R^{3c}$)-Q, a group of formula NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), $C_2$-$C_6$ alkenyl, $C_2$-$C_6$ alkynyl, —$NH_2$, —NH($C_1$-$C_6$ alkyl), or $C_6$ alkyl)$_2$;

$R^{3b}$ and $R^{3c}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

$R^{3d}$ and $R^{3e}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

$R^{3f}$ and $R^{3g}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, or a monocyclic or bicyclic heterocyclyl group with 5 to 10 ring members containing 1, 2, 3, or 4 heteroatoms independently selected from N, O, or S, wherein the $C_6$-$C_{10}$ aryl group, the heteroaryl group, or the heterocyclyl group are unsubstituted or are substituted with 1, 2, or 3 $R^{4a}$ substituents; and $R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$, and the heterocyclyl $R^4$ group may be further substituted with 1 oxo substituent.

In some embodiments of the compound of Formula I or Formula II or the pharmaceutically acceptable salt thereof, the tautomer thereof, the pharmaceutically acceptable salt of the tautomer, the stereoisomer of any of the foregoing, or the mixture thereof, at least one of the following is true if $R^4$ is an unsubstituted or substituted phenyl ring and $R^3$ is a group of formula —($CR^{3b}$=$CR^{3c}$)-Q:

a) $R^4$ is substituted with at least one —O—($C_1$-$C_6$ alkyl) group;

b) Q is not an oxadiazole;

c) $R^{3b}$ is not H;

d) $R^{3c}$ is not H;

e) $R^1$ is not a 2-pyridyl group; or f) $R^4$ is substituted with two or more —O—($C_1$-$C_6$ alkyl) groups.

Numerous other embodiments of the compound of Formula I or Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy or chronic kidney disease.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy.

Other objects, features and advantages of the invention will become apparent to those skilled in the art from the following description and claims.

DETAILED DESCRIPTION OF THE INVENTION

Figure 1A:
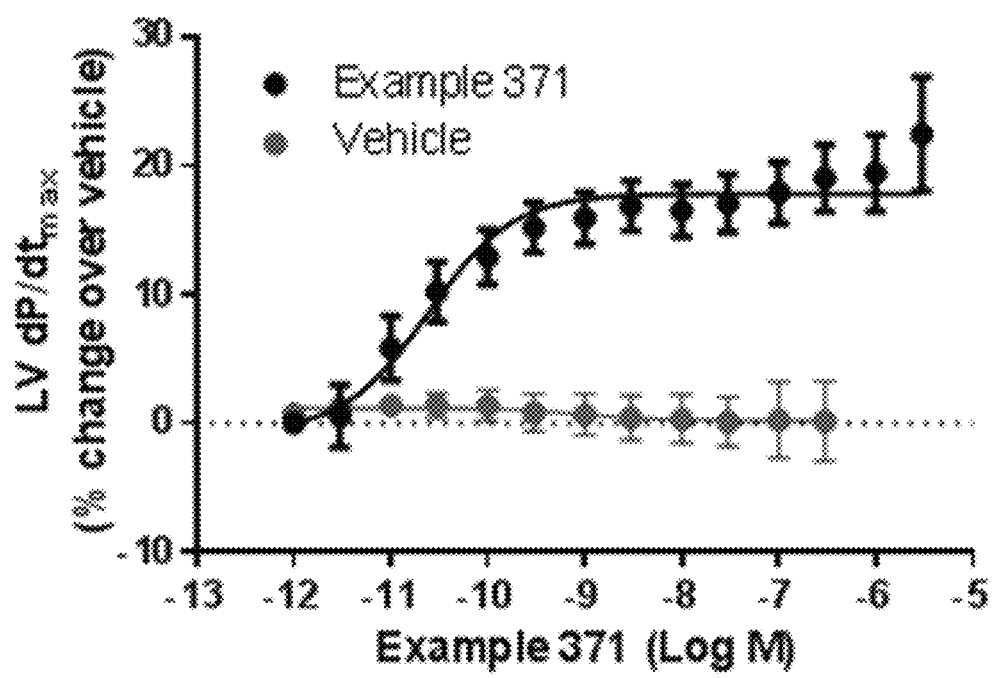
FIG. 1A is a graph of left ventricular dP/dt$_{max}$ as a function of concentration of Example 371 compared with vehicle in ex vivo naive Sprague Dawley rat hearts obtained using the Langendorff apparatus. This shows Example 371 increases load independent cardiac contractility in isolated perfused rat hearts.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when $R^4$ is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

As noted above, compounds of the invention may exist in multiple tautomeric forms. This is particularly true in compounds of Formula I where $R^2$ is H. These forms are illustrated below as Tautomer A and Tautomer B:

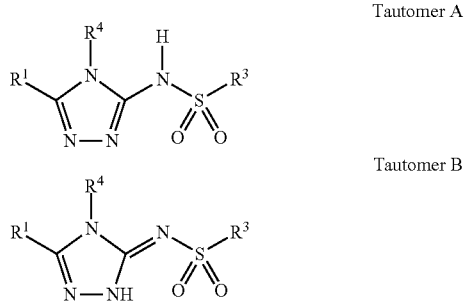

Tautomer A

Tautomer B

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at RT whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

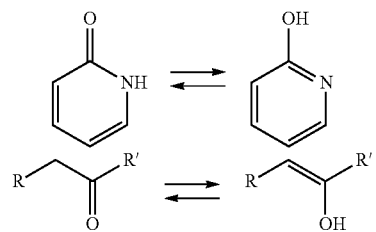

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as $(C_1-C_4)$ alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$)alkyl group and an alkyl group having 1 to 4 carbon atoms may be referred to as a ($C_1$-$C_4$)alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—($C_1$-$C_6$ alkyl)-OH will be recognized as a group where an —O atom is bonded to a $C_1$-$C_6$ alkyl group and one of the H atoms bonded to a C atom of the $C_1$-$C_6$ alkyl group is replaced with a bond to the 0 atom of an OH group. As another example, a group —O—($C_1$-$C_6$ alkyl)-O—($C_1$-$C_6$ alkyl) will be recognized as a group where an —O atom is bonded to a first $C_1$-$C_6$ alkyl group and one of the H atoms bonded to a C atom of the first $C_1$-$C_6$ alkyl group is replaced with a bond to a second O atom that is bonded to a second $C_1$-$C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as alkyl) groups. In some embodiments, an alkoxy group may include 1 to 4 carbon atoms and may be designated as —O—($C_1$-$C_4$) alkyl or as —O—($C_1$-$C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical C(O) or C(=O) group.
"Carboxy" refers to the radical C(O)OH.
"Cyano" refers to the radical CN.
"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example a cycloalkyl group having 3 to 7 ring members may be referred to as a ($C_3$-$C_7$)cycloalkyl and a cycloalkyl group having 4 to 7 ring members may be referred to as a ($C_4$-$C_7$)cycloalkyl. In certain embodiments, the cycloalkyl group can be a ($C_3$-$C_{10}$)cycloalkyl, a ($C_3$-$C_8$)cycloalkyl, a ($C_3$-$C_7$)cycloalkyl, a ($C_3$-$C_6$)cycloalkyl, or a ($C_4$-$C_7$)cycloalkyl group and these may be referred to as $C_3$-$C_{10}$ cycloalkyl, $C_3$-$C_8$ cycloalkyl, $C_3$-$C_7$ cycloalkyl, $C_3$-$C_6$ cycloalkyl, or $C_4$-$C_7$ cycloalkyl groups using alternative language.

"Heterocyclyl" refers to a cyclic group that includes at least one saturated or unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

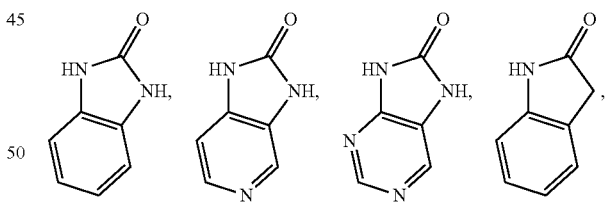

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

EMBODIMENTS

The embodiments listed below are presented in numbered form for convenience and in ease and clarity of reference in referring back to multiple embodiments.

1. In a first embodiment, the invention provides a compound of Formula I or Formula II:

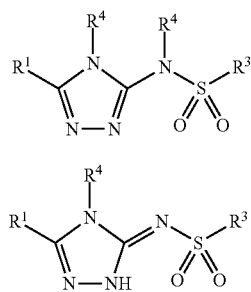

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted pyridyl, pyridonyl, or pyridine N-oxide, or is a pyridyl, pyridonyl, or pyridine N-oxide substituted with 1, 2, 3, or 4 $R^{1a}$ substituents;

$R^{1a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —C(=O)-(heterocyclyl), or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

$R^2$ is selected from —H, or $C_1$-$C_4$ alkyl or is absent in the compounds of Formula II;

$R^3$ is selected from an unsubstituted $C_1$-$C_4$ alkyl, a $C_1$-$C_4$ alkyl substituted with 1, 2, or 3 $R^{3a}$ substituents, a group of formula —($CR^{3b}R^{3c}$)-Q, a group of formula NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), $C_2$-$C_6$ alkenyl, $C_2$-$C_6$ alkynyl, —$NH_2$, —NH($C_1$-$C_6$ alkyl), or $C_6$ alkyl)$_2$;

$R^{3b}$ and $R^{3c}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

$R^{3d}$ and $R^{3e}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

$R^{3f}$ and $R^{3g}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O) OH, —C(=O)—O—($C_1$-$C_6$ alkyl), —C(O)$NH_2$, —C(=O) NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

R[4] is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, or a monocyclic or bicyclic heterocyclyl group with 5 to 10 ring members containing 1, 2, 3, or 4 heteroatoms independently selected from N, O, or S, wherein the $C_6$-$C_{10}$ aryl group, the heteroaryl group, or the heterocyclyl group are unsubstituted or are substituted with 1, 2, or 3 R[4a] substituents;

R[4a] in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$, and the heterocyclyl R[4] group may be further substituted with 1 oxo substituent; and further wherein:

if R[4] is an unsubstituted or substituted phenyl ring and R[3] is a group of formula —(CR[3b]=CR[3c])-Q, then at least one of the following is true:

a) R[4] is substituted with at least one —O—($C_1$-$C_6$ alkyl) group;
b) Q is not an oxadiazole;
c) R[3b] is not —H;
d) R[3c] is not —H;
e) R[1] is not a 2-pyridyl group; or
f) R[4] is substituted with two or more —O—($C_1$-$C_6$ alkyl) groups.

1. In an alternative first embodiment, the invention provides a compound of Formula I or Formula II:

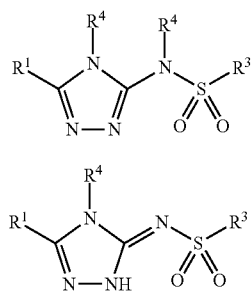

or a pharmaceutically acceptable salt thereof, a tautomer thereof, a pharmaceutically acceptable salt of the tautomer, a stereoisomer of any of the foregoing, or a mixture thereof, wherein:

R[1] is an unsubstituted pyridyl, pyridonyl, or pyridine N-oxide, or is a pyridyl, pyridonyl, or pyridine N-oxide substituted with 1, 2, 3, or 4 R[1a] substituents;

R[1a] in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_1$-$C_6$ alkyl-OH, —$C_1$-$C_6$ haloalkyl-OH, —$C_1$-$C_6$ perhaloalkyl-OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —C(=O)-(heterocyclyl), a $C_3$-$C_6$ cycloalkyl group or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

R[2] is selected from —H, or $C_1$-$C_4$ alkyl or is absent in the compounds of Formula II;

R[3] is selected from an unsubstituted $C_1$-$C_4$ alkyl, a $C_1$-$C_4$ alkyl substituted with 1, 2, or 3 R[3a] substituents, a group of formula —(CR[3b]R[3c])-Q, a group of formula NH—(CR[3b]R[3c])-Q, a group of formula —(CR[3b]R[3c])—C(=O)-Q, a group of formula —(CR[3d]R[3e])—(CR[3f]R[3g])-Q, a group of formula —(CR[3b]=CR[3c])-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 R[3h] substituents;

R[3a] in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), $C_2$-$C_6$ alkenyl, $C_2$-$C_6$ alkynyl, —$NH_2$, —NH($C_1$-$C_6$ alkyl), or $C_6$ alkyl)$_2$;

R[3b] and R[3c] are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

R[3d] and R[3e] are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or N($C_1$-$C_6$ alkyl)$_2$;

R[3f] and R[3g] are independently selected from H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, a $C_3$-$C_6$ cycloalkyl group, or a 3 to 7 membered heterocyclyl group containing 1, 2, or 3 heteroatoms selected from N, O, or S, wherein the $C_3$-$C_6$ cycloalkyl group, or the 3 to 7 membered heterocyclyl R[3f] or R[3g] group may be unsubstituted or substituted with 1 or 2 substituents independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

R[3h] in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 R[Q] substituent;

R[Q] in each instance is independently selected from —F, —Cl, —Br, —I, —CN, —$C_1$-$C_6$ alkyl, —$C_1$-$C_6$ haloalkyl, —C₁-C₆ perhaloalkyl, —C₂-C₆ alkenyl, —C₂-C₆ alkynyl, —OH, —O—(C₁-C₆ alkyl), —O—(C₁-C₆ haloalkyl), —O—(C₁-C₆ perhaloalkyl), —NH₂, —NH(C₁-C₆ alkyl), —N(C₁-C₆ alkyl)₂, —C(=O)—(C₁-C₆ alkyl), —C(=O)OH, —C(=O)—O—(C₁-C₆ alkyl), —C(O)NH₂, —C(=O)NH(C₁-C₆ alkyl), —C(=O)N(C₁-C₆ alkyl)₂, —S(=O)₂—(C₁-C₆ alkyl), phenyl, or a heteroaryl group with 5 to 10 ring members containing 1, 2, or 3 heteroatoms selected from N, O, or S, a C₃-C₈ cycloalkyl group, or a 3 to 7 membered heterocyclyl group containing 1, 2, or 3 heteroatoms selected from N, O, or S, and the Q heterocyclyl group and the Q cycloalkyl group may be substituted with 1 oxo $R^Q$ substituent, and the $R^Q$ cycloalkyl group and the $R^Q$ heterocyclycl group may be unsubstituted or substituted with 1 or 2 substituents independently selected from F, —Cl, —Br, —I, —CN, —C₁-C₆ alkyl, —C₁-C₆ haloalkyl, —C₁-C₆ perhaloalkyl, —C₂-C₆ alkenyl, —C₂-C₆ alkynyl, —OH, —O—(C₁-C₆ alkyl), —O—(C₁-C₆ haloalkyl), —O—(C₁-C₆ perhaloalkyl), —NH₂, —NH(C₁-C₆ alkyl), —N(C₁-C₆ alkyl)₂, —C(=O)—(C₁-C₆ alkyl), —C(=O)OH, —C(=O)—O—(C₁-C₆ alkyl), —C(=O)NH₂, —C(=O)NH(C₁-C₆ alkyl), or —C(=O)N(C₁-C₆ alkyl)₂;

$R^4$ is selected from a monocyclic or bicyclic C₆-C₁₀ aryl group, a monocyclic or bicyclic heteroaryl group with 5 to 10 ring members containing 1, 2, or 3 heteroatoms independently selected from N, O, or S, or a monocyclic or bicyclic heterocyclyl group with 5 to 10 ring members containing 1, 2, 3, or 4 heteroatoms independently selected from N, O, or S, wherein the C₆-C₁₀ aryl group, the heteroaryl group, or the heterocyclyl group are unsubstituted or are substituted with 1, 2, or 3 $R^{4a}$ substituents;

$R^{4a}$ in each instance is independently selected from —F, —Cl, —Br, —I, —CN, —C₁-C₆ alkyl, —C₁-C₆ haloalkyl, —C₁-C₆ perhaloalkyl, —OH, —O—(C₁-C₆ alkyl), —O—(C₁-C₆ haloalkyl), —O—(C₁-C₆ perhaloalkyl), —NH₂, —NH(C₁-C₆ alkyl), —N(C₁-C₆ alkyl)₂, —C(=O)—(C₁-C₆ alkyl), —C(=O)OH, —C(=O)—O—(C₁-C₆ alkyl), —C(=O)NH₂, —C(=O)NH(C₁-C₆ alkyl), or —C(=O)N(C₁-C₆ alkyl)₂, and the heterocyclyl $R^3$ group may be further substituted with 1 oxo substituent; and further wherein:

if $R^4$ is an unsubstituted or substituted phenyl ring and $R^3$ is a group of formula —(CR³ᵇ=CR³ᶜ)-Q, then at least one of the following is true:

a) $R^4$ is substituted with at least one —O—(C₁-C₆ alkyl) group;
b) Q is not an oxadiazole;
c) $R^{3b}$ is not H;
d) $R^{3c}$ is not H;
e) $R^1$ is not a 2-pyridyl group; or
f) $R^4$ is substituted with two or more —O—(C₁-C₆ alkyl) groups.

2. The compound of embodiment 1 or the pharmaceutically acceptable salt thereof, the stereoisomer of any of the foregoing, or the mixture thereof, wherein $R^1$ is an unsubstituted pyridyl or is a pyridyl substituted with 1 or 2 $R^{1a}$ substituents.

3. The compound of embodiment 1 or the pharmaceutically acceptable salt thereof, the stereoisomer of any of the foregoing, or the mixture thereof, wherein $R^1$ is a pyridyl having the formula

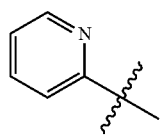 [SMILES: *c1ccccn1]

wherein the pyridyl is unsubstituted or is substituted with 1 or 2 $R^{1a}$ substituents, and the symbol ⌇, when drawn across a bond, indicates the point of attachment to the rest of the molecule.

4. The compound of embodiment 1 or the pharmaceutically acceptable salt thereof, the stereoisomer of any of the foregoing, or the mixture thereof, wherein $R^1$ is a pyridyl having the formula

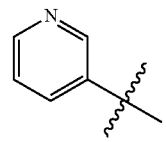 [SMILES: *c1cccnc1]

wherein the pyridyl is unsubstituted or is substituted with 1 or 2 $R^{1a}$ substituents, and the symbol ⌇, when drawn across a bond, indicates the point of attachment to the rest of the molecule.

5. The compound of embodiment 1 or the pharmaceutically acceptable salt thereof, the stereoisomer of any of the foregoing, or the mixture thereof, wherein $R^1$ is a pyridyl having the formula

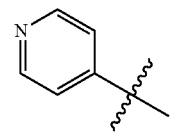 [SMILES: *c1ccncc1]

wherein the pyridyl is unsubstituted or is substituted with 1 or 2 $R^{1a}$ substituents, and the symbol ⌇, when drawn across a bond, indicates the point of attachment to the rest of the molecule.

6. The compound of any one of embodiments 1-5 or the pharmaceutically acceptable salt thereof, the stereoisomer of any of the foregoing, or the mixture thereof, wherein $R^1$ is an unsubstituted pyridyl.

7. The compound of any one of embodiments 1-5 or the pharmaceutically acceptable salt thereof, the stereoisomer of any of the foregoing, or the mixture thereof, wherein $R^{1a}$ in each instance is independently selected from CH₃, —CH₂CH₃, —F, —Cl, —Br, —CN, —CF₃, —CH=CH₂, —C(=O)NH₂, —C(=O)NH(CH₃), —C(=O)N(CH₃)₂, —C(=O)NH(CH₂CH₃), —OH, —OCH₃, —OCHF₂, —OCH₂CH₃, —OCH₂CF₃, —OCH₂CH₂OH, —OCH₂C(CH₃)₂OH, —OCH₂C(CF₃)₂OH, —OCH₂CH₂OCH₃, —NH₂, —NHCH₃, —N(CH₃)₂, phenyl, or a group of formula

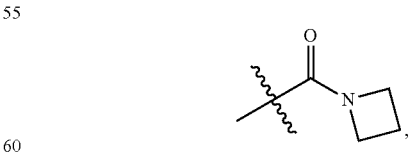

wherein the symbol ⌇, when drawn across a bond, indicates the point of attachment to the rest of the molecule.

8. The compound of embodiment 1 or the pharmaceutically acceptable salt thereof, the stereoisomer of any of the foregoing, or the mixture thereof, wherein $R^1$ is selected from

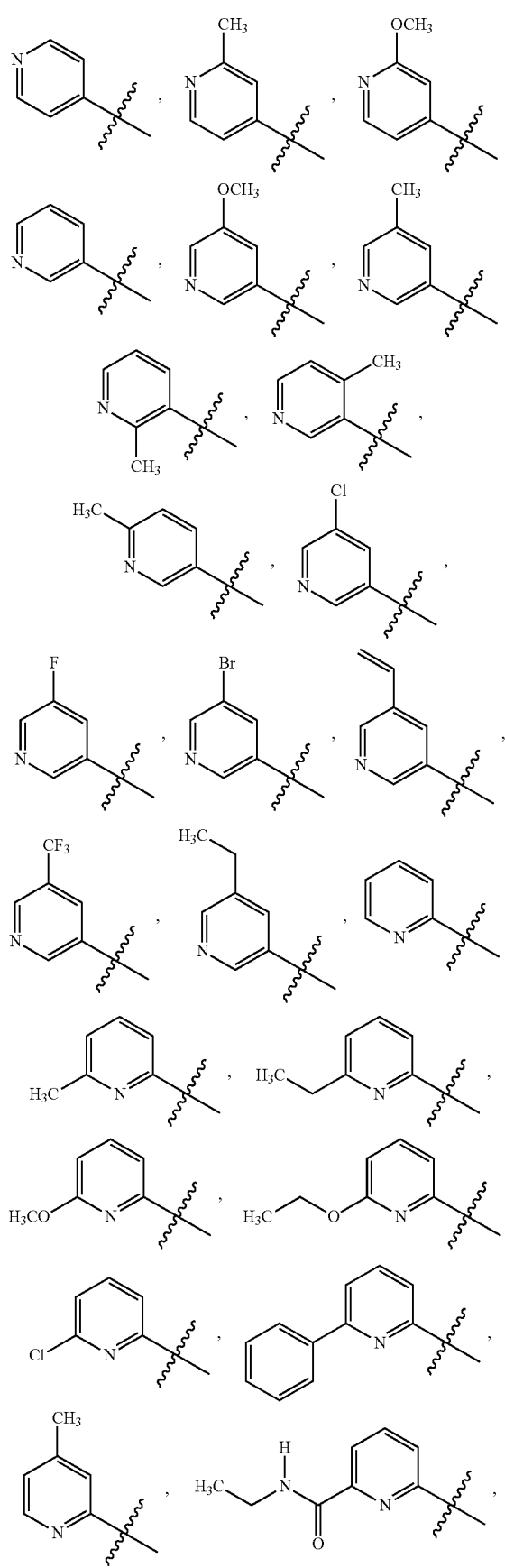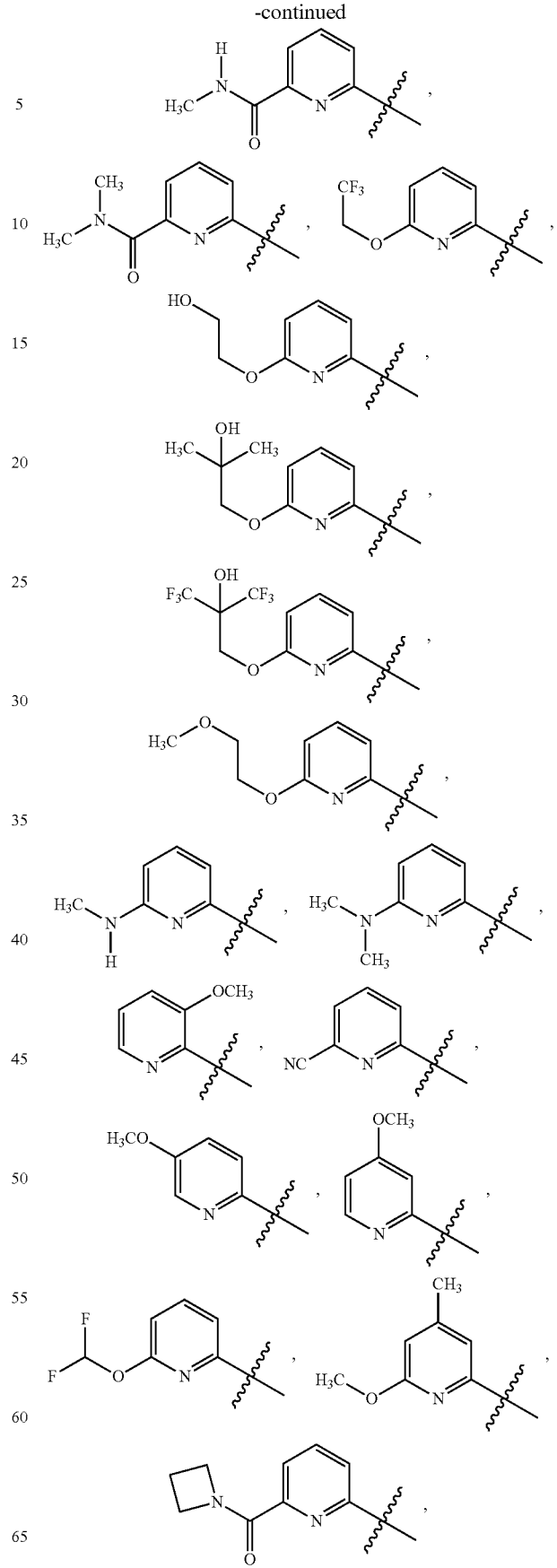

-continued

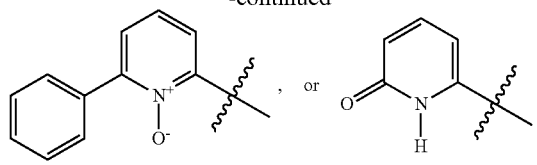, or wherein the symbol ~, when drawn across a bond, indicates the point of attachment to the rest of the molecule.

9. The compound of embodiment 1 or the pharmaceutically acceptable salt thereof, the stereoisomer of any of the foregoing, or the mixture thereof, wherein $R^1$ is selected from

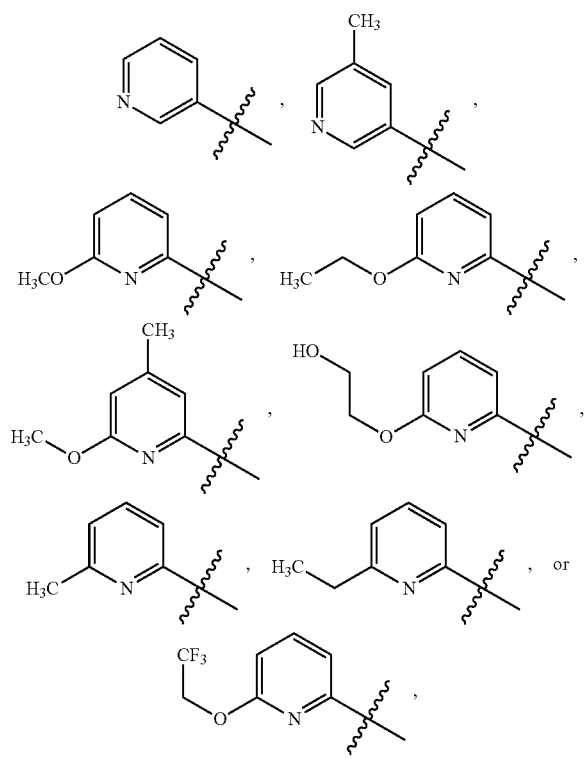

wherein the symbol ~, when drawn across a bond, indicates the point of attachment to the rest of the molecule.

10. The compound of embodiment 9 or the pharmaceutically acceptable salt thereof, the stereoisomer of any of the foregoing, or the mixture thereof, wherein $R^1$ is selected from

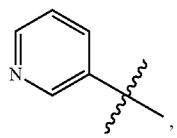

wherein the symbol ~, when drawn across a bond, indicates the point of attachment to the rest of the molecule.

11. The compound of embodiment 9 or the pharmaceutically acceptable salt thereof, the stereoisomer of any of the foregoing, or the mixture thereof, wherein $R^1$ is selected from

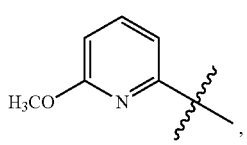 [SMILES: *c1cccc(OC)n1]

wherein the symbol ~, when drawn across a bond, indicates the point of attachment to the rest of the molecule.

12. The compound of embodiment 9 or the pharmaceutically acceptable salt thereof, the stereoisomer of any of the foregoing, or the mixture thereof, wherein $R^1$ is selected from

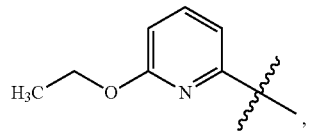

wherein the symbol ~, when drawn across a bond, indicates the point of attachment to the rest of the molecule.

13. The compound of embodiment 9 or the pharmaceutically acceptable salt thereof, the stereoisomer of any of the foregoing, or the mixture thereof, wherein $R^1$ is selected from

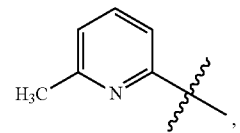

wherein the symbol ~, when drawn across a bond, indicates the point of attachment to the rest of the molecule.

14. The compound of embodiment 9 or the pharmaceutically acceptable salt thereof, the stereoisomer of any of the foregoing, or the mixture thereof, wherein $R^1$ is selected from

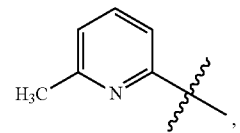

wherein the symbol ~, when drawn across a bond, indicates the point of attachment to the rest of the molecule.

15. The compound of any one of embodiments 1-14 or the pharmaceutically acceptable salt thereof, the stereoisomer of any of the foregoing, or the mixture thereof, wherein $R^2$ is selected from —H or —CH$_3$.

16. The compound of any one of embodiments 1-15 or the pharmaceutically acceptable salt thereof, the stereoisomer of any of the foregoing, or the mixture thereof, wherein $R^2$ is —H.

17. The compound of any one of embodiments 1-16 or the pharmaceutically acceptable salt thereof, the stereoisomer of any of the foregoing, or the mixture thereof, wherein $R^4$ is a phenyl, pyridyl, pyrimidinyl, isoxazolyl, indolyl, naphthyl, or pyridinyl any of which may be unsubstituted or substituted with 1, 2, or 3 $R^{4a}$ substituents.

18. The compound of any one of embodiments 1-17 or the pharmaceutically acceptable salt thereof, the stereoisomer of any of the foregoing, or the mixture thereof, wherein $R^{4a}$ is in each instance independently selected from $CH_3$, —F, —Cl, —Br, —CN, —$CF_3$, —$OCH_3$, —$OCHF_2$, —$OCH_2CH_3$, —C(=O)$OCH_3$, —C(=O)$CH_3$, or N($CH_3$)$_2$.

19. The compound of any one of embodiments 1-16 or the pharmaceutically acceptable salt thereof, the stereoisomer of any of the foregoing, or the mixture thereof, wherein $R^4$ is selected from

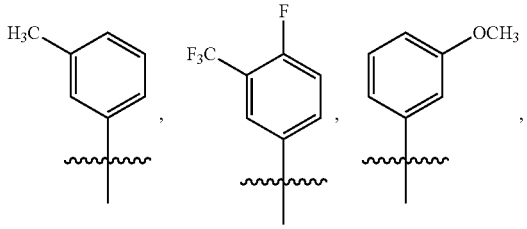
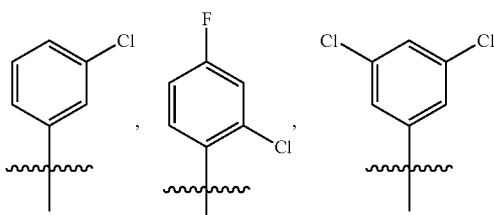
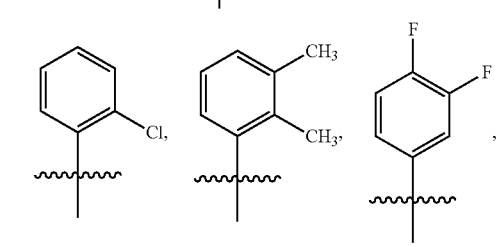
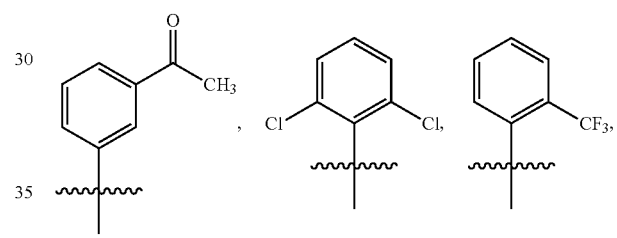
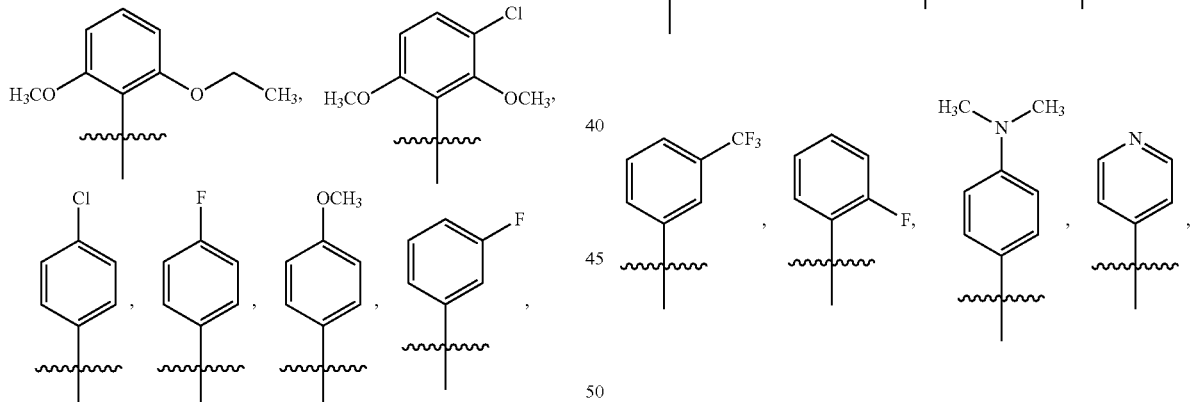
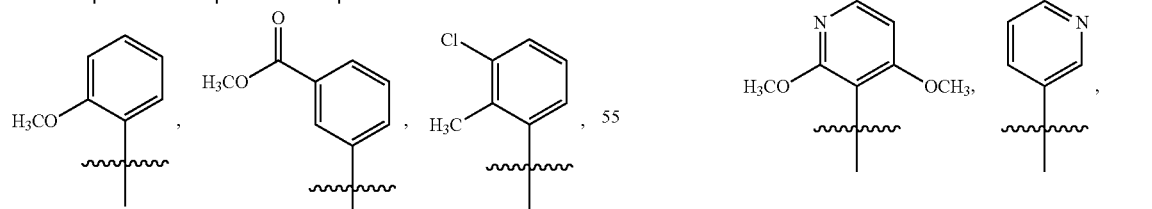
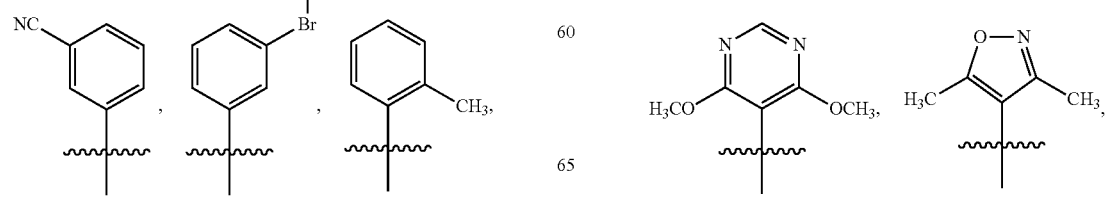

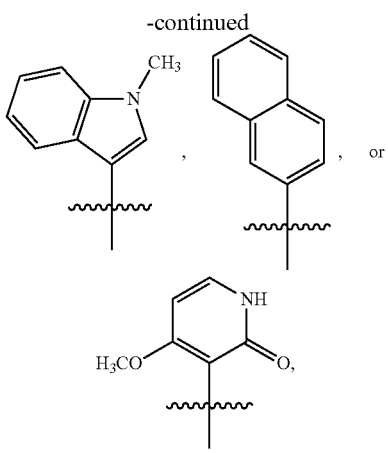

wherein the symbol ⌇, when drawn across a bond, indicates the point of attachment to the rest of the molecule.

20. The compound of any one of embodiments 1-16 or the pharmaceutically acceptable salt thereof, the stereoisomer of any of the foregoing, or the mixture thereof, wherein $R^4$ is a phenyl substituted with 1 or 2 $R^{4a}$ substituents.

21. The compound of embodiment 20 or the pharmaceutically acceptable salt thereof, the stereoisomer of any of the foregoing, or the mixture thereof, wherein the $R^{4a}$ substituents are —O—($C_1$-$C_2$ alkyl) groups.

22. The compound of embodiment 21 or the pharmaceutically acceptable salt thereof, the stereoisomer of any of the foregoing, or the mixture thereof, wherein $R^4$ is

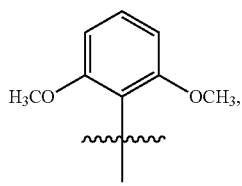

wherein the symbol ⌇, when drawn across a bond, indicates the point of attachment to the rest of the molecule.

23. The compound of any one of embodiments 1-22 or the pharmaceutically acceptable salt thereof, the stereoisomer of any of the foregoing, or the mixture thereof, $R^3$ is an unsubstituted $C_1$-$C_8$ alkyl or a $C_1$-$C_8$ alkyl substituted with 1 or 2 $R^{3a}$ substituents.

24. The compound of embodiment 23 or the pharmaceutically acceptable salt thereof, the stereoisomer of any of the foregoing, or the mixture thereof, wherein $R^3$ is selected from, —$CH_3$, —$CH_2CH_3$, —$CH(CH_3)_2$, or a group selected from

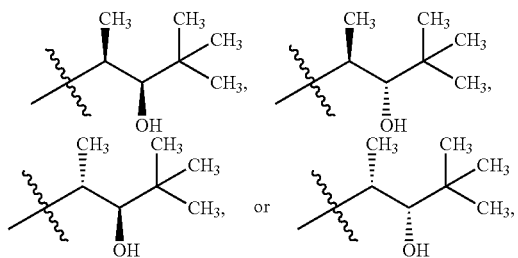

wherein the symbol ⌇, when drawn across a bond, indicates the point of attachment to the rest of the molecule.

25. The compound of any one of embodiments 1-23 or the pharmaceutically acceptable salt thereof, the stereoisomer of any of the foregoing, or the mixture thereof, wherein $R^{3a}$ is OH.

26. The compound of any one of embodiments 1-22 or the pharmaceutically acceptable salt thereof, the stereoisomer of any of the foregoing, or the mixture thereof, wherein $R^3$ is selected from a group of formula —($CR^{3b}R^{3c}$)-Q, a group of formula NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents.

27. The compound of embodiment 26 or the pharmaceutically acceptable salt thereof, the stereoisomer of any of the foregoing, or the mixture thereof, wherein Q is selected from pyrimidinyl, pyridyl, isoxazolyl, thiazolyl, imidazolyl, phenyl, tetrahydropyrimidinonyl, cyclopropyl, cyclobutyl, cyclohexyl, morpholinyl, pyrrolidinyl, pyrazinyl, imidazo[1,2-a]pyridinyl, pyrazolyl, or oxetanyl any which may be unsubstituted or substituted with 1, 2, or 3, $R^Q$ substituents.

28. The compound of embodiment 26 or the pharmaceutically acceptable salt thereof, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

29. The compound of embodiment 28 or the pharmaceutically acceptable salt thereof, the stereoisomer of any of the foregoing, or the mixture thereof, wherein Q is a pyrimidinyl or pyridyl group and Q is unsubstituted or is substituted with 1 or 2 $R^Q$ substituents.

30. The compound of any one of embodiments 1-22 or the pharmaceutically acceptable salt thereof, the stereoisomer of any of the foregoing, or the mixture thereof, wherein Q is selected from

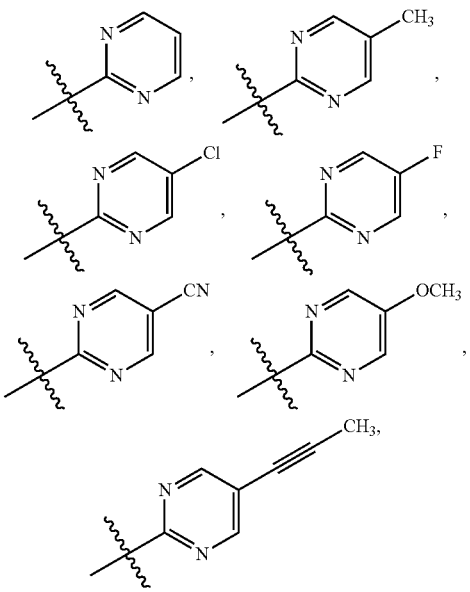

-continued

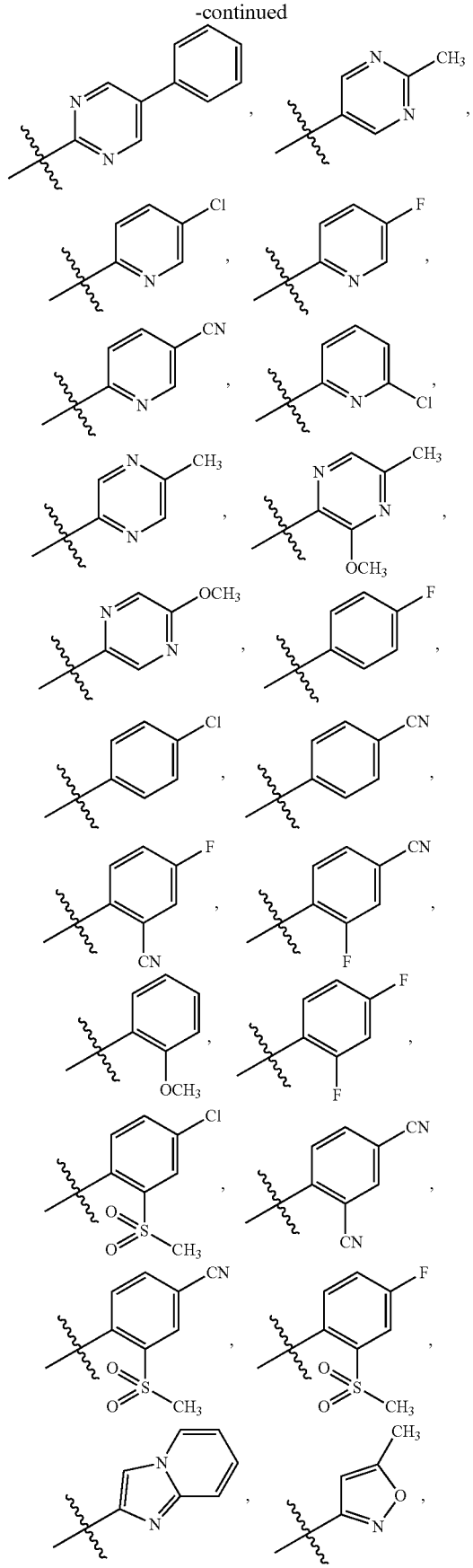

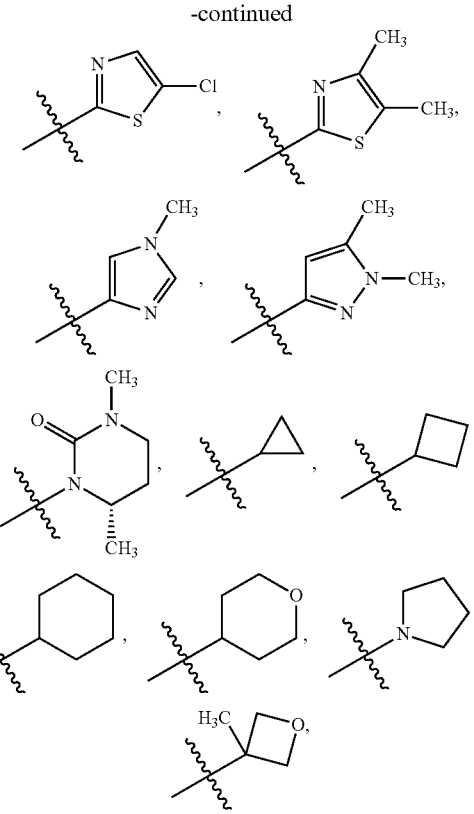

wherein the symbol ~~~, when drawn across a bond, indicates the point of attachment to the rest of the molecule.

31. The compound of embodiment 30 or the pharmaceutically acceptable salt thereof, the stereoisomer of any of the foregoing, or the mixture thereof, wherein Q is

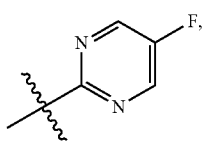 [SMILES: *c1ncc(F)cn1]

wherein the symbol ~~~, when drawn across a bond, indicates the point of attachment to the rest of the molecule.

32. The compound of embodiment 30 or the pharmaceutically acceptable salt thereof, the stereoisomer of any of the foregoing, or the mixture thereof, wherein Q is

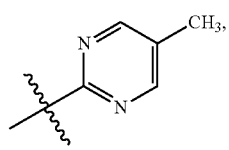 [SMILES: *c1ncc(C)cn1]

wherein the symbol ~~~, when drawn across a bond, indicates the point of attachment to the rest of the molecule.

33. The compound of embodiment 30 or the pharmaceutically acceptable salt thereof, the stereoisomer of any of the foregoing, or the mixture thereof, wherein Q is

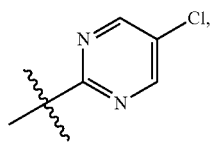 [SMILES: *c1ncc(Cl)cn1]

wherein the symbol ⌇, when drawn across a bond, indicates the point of attachment to the rest of the molecule.

34. The compound of embodiment 30 or the pharmaceutically acceptable salt thereof, the stereoisomer of any of the foregoing, or the mixture thereof, wherein Q is

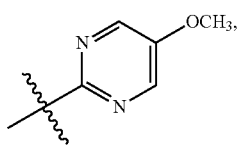 [SMILES: *c1ncc(OC)cn1]

wherein the symbol ⌇, when drawn across a bond, indicates the point of attachment to the rest of the molecule.

35. The compound of embodiment 30 or the pharmaceutically acceptable salt thereof, the stereoisomer of any of the foregoing, or the mixture thereof, wherein Q is

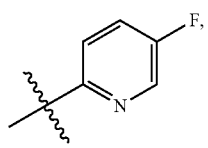 [SMILES: *c1ccc(F)cn1]

wherein the symbol ⌇, when drawn across a bond, indicates the point of attachment to the rest of the molecule.

36. The compound of embodiment 30 or the pharmaceutically acceptable salt thereof, the stereoisomer of any of the foregoing, or the mixture thereof, wherein Q is

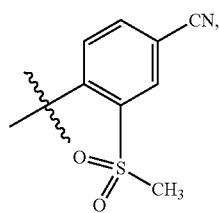 [SMILES: *c1ccc(C#N)cc1S(C)(=O)=O]

wherein the symbol ⌇, when drawn across a bond, indicates the point of attachment to the rest of the molecule.

37. The compound of embodiment 30 or the pharmaceutically acceptable salt thereof, the stereoisomer of any of the foregoing, or the mixture thereof, wherein Q is

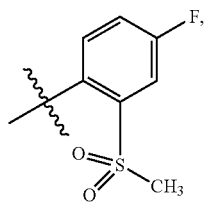 [SMILES: *c1ccc(F)cc1S(C)(=O)=O]

wherein the symbol ⌇, when drawn across a bond, indicates the point of attachment to the rest of the molecule.

38. The compound of embodiment 30 or the pharmaceutically acceptable salt thereof, the stereoisomer of any of the foregoing, or the mixture thereof, wherein Q is

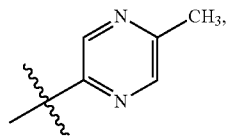 [SMILES: *c1cnc(C)cn1]

wherein the symbol ⌇, when drawn across a bond, indicates the point of attachment to the rest of the molecule.

39. The compound of embodiment 30 or the pharmaceutically acceptable salt thereof, the stereoisomer of any of the foregoing, or the mixture thereof, wherein Q is

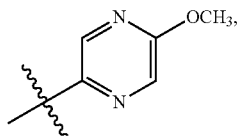 [SMILES: *c1cnc(OC)cn1]

wherein the symbol ⌇, when drawn across a bond, indicates the point of attachment to the rest of the molecule.

40. The compound of any one of embodiments 1-22 or 26-39 or the pharmaceutically acceptable salt thereof, the stereoisomer of any of the foregoing, or the mixture thereof, wherein $R^3$ is a group of formula —$(CR^{3b}R^{3c})$-Q.

41. The compound of embodiment 40 or the pharmaceutically acceptable salt thereof, the stereoisomer of any of the foregoing, or the mixture thereof, wherein one of $R^{3b}$ and $R^{3c}$ is H and the other is H or $CH_3$.

42. The compound of any one of embodiments 1-22 or 26-39 or the pharmaceutically acceptable salt thereof, the stereoisomer of any of the foregoing, or the mixture thereof, wherein $R^3$ is a group of formula NH—$(CR^{3b}R^{3c})$-Q.

43. The compound of embodiment 42 or the pharmaceutically acceptable salt thereof, the stereoisomer of any of the foregoing, or the mixture thereof, wherein one of $R^{3b}$ and $R^{3c}$ is H and the other is H or $CH_3$.

44. The compound of any one of embodiments 1-22 or 26-39 or the pharmaceutically acceptable salt thereof, the stereoisomer of any of the foregoing, or the mixture thereof, wherein $R^3$ is a group of formula —$(CR^{3b}R^{3c})$—C(=O)-Q.

45. The compound of embodiment 44 or the pharmaceutically acceptable salt thereof, the stereoisomer of any of the foregoing, or the mixture thereof, wherein one of $R^{3b}$ and $R^{3c}$ is H and the other is H or $CH_3$.

46. The compound of any one of embodiments 1-22 or 26-39 or the pharmaceutically acceptable salt thereof, the stereoisomer of any of the foregoing, or the mixture thereof, wherein $R^3$ is a group of formula —$(CR^{3b}=CR^{3c})$-Q.

47. The compound of embodiment 46 or the pharmaceutically acceptable salt thereof, the stereoisomer of any of the foregoing, or the mixture thereof, wherein $R^{3b}$ and $R^{3c}$ are independently selected from H or $CH_3$.

48. The compound of any one of embodiments 1-22 or 26-39 or the pharmaceutically acceptable salt thereof, the stereoisomer of any of the foregoing, or the mixture thereof, wherein $R^3$ is a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3b}$ substituents.

49. The compound of embodiment 48 or the pharmaceutically acceptable salt thereof, the stereoisomer of any of the foregoing, or the mixture thereof, wherein $R^3$ is a group of formula

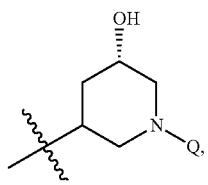

wherein the symbol ⌇, when drawn across a bond, indicates the point of attachment to the rest of the molecule.

50. The compound of any one of embodiments 1-22 or 26-39 or the pharmaceutically acceptable salt thereof, the stereoisomer of any of the foregoing, or the mixture thereof, wherein $R^3$ is a group of formula —$(CR^{3d}R^{3e})$—$(CR^{3f}R^{3g})$-Q.

51. The compound of embodiment 50 or the pharmaceutically acceptable salt thereof, the stereoisomer of any of the foregoing, or the mixture thereof, wherein $R^3$ has the formula

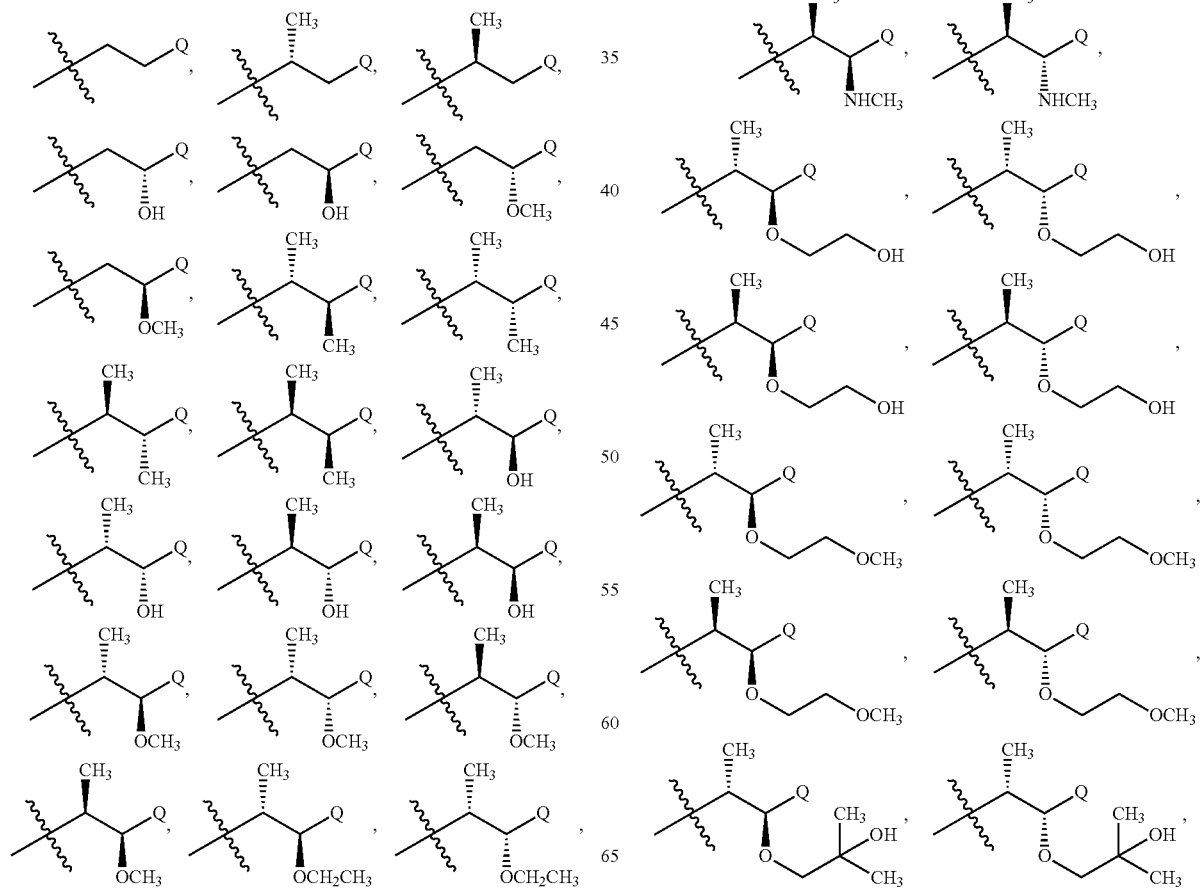
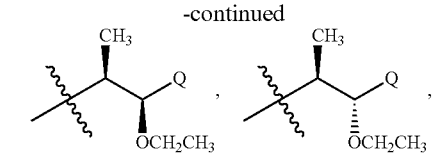
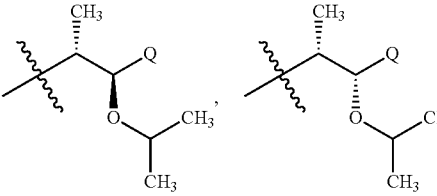
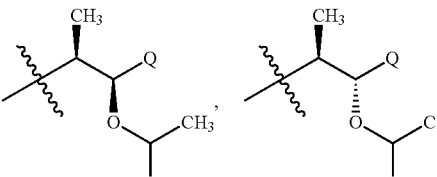
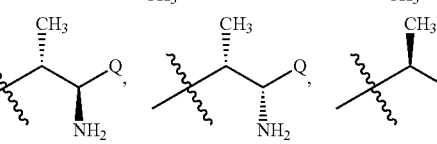
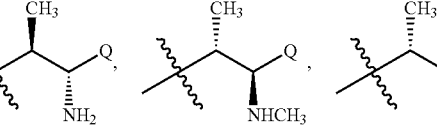
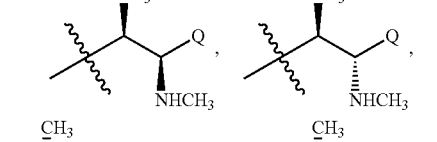
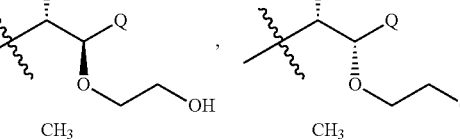

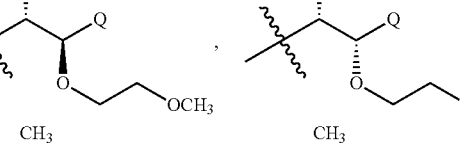
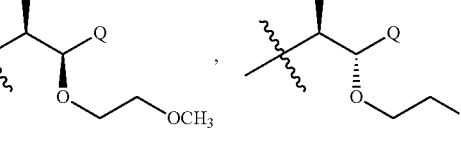
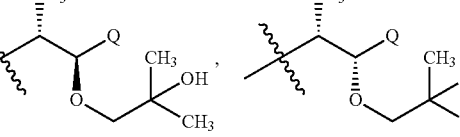

-continued

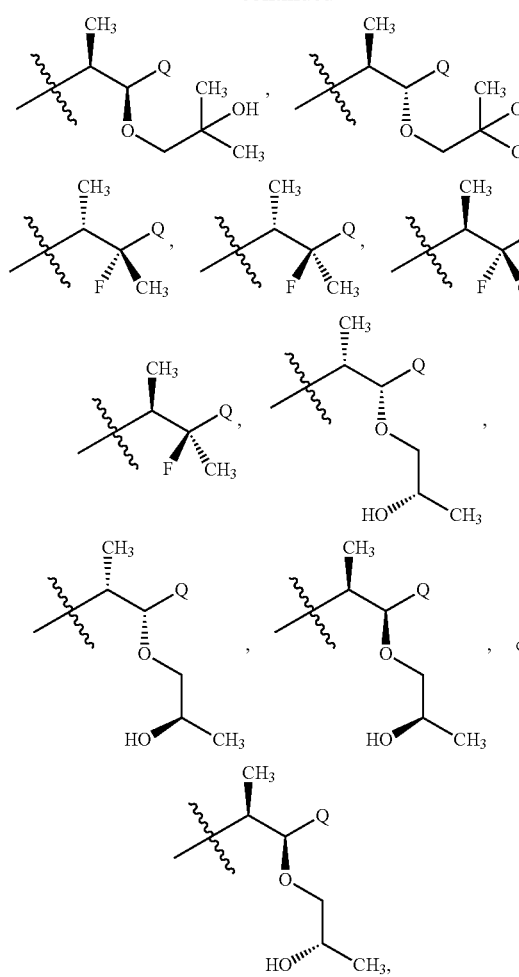

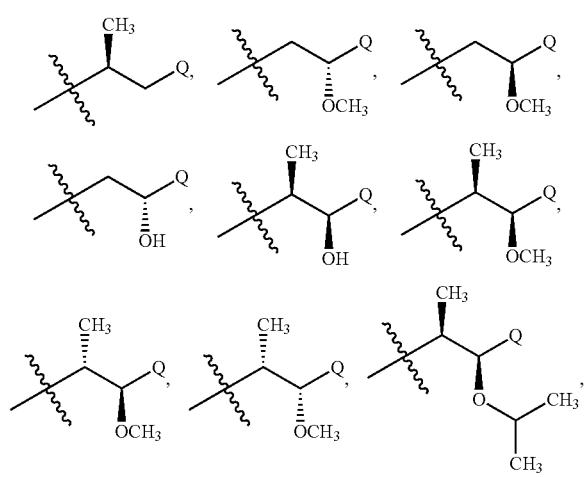

wherein the symbol ⌇, when drawn across a bond, indicates the point of attachment to the rest of the molecule.

52. The compound of embodiment 51 or the pharmaceutically acceptable salt thereof, the stereoisomer of any of the foregoing, or the mixture thereof, wherein R³ has the formula -continued

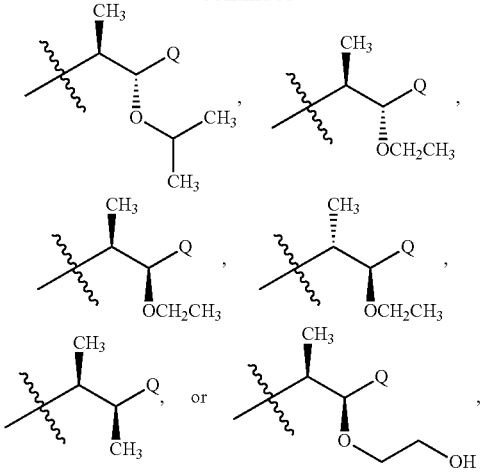

wherein the symbol ⌇, when drawn across a bond, indicates the point of attachment to the rest of the molecule.

53. The compound of embodiment 52 or the pharmaceutically acceptable salt thereof, the stereoisomer of any of the foregoing, or the mixture thereof, wherein R³ has the formula

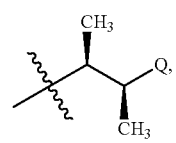

wherein the symbol ⌇, when drawn across a bond, indicates the point of attachment to the rest of the molecule.

54. The compound of embodiment 52 or the pharmaceutically acceptable salt thereof, the stereoisomer of any of the foregoing, or the mixture thereof, wherein R³ has the formula

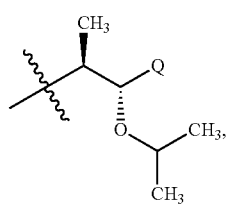

wherein the symbol ⌇, when drawn across a bond, indicates the point of attachment to the rest of the molecule.

55. The compound of embodiment 52 or the pharmaceutically acceptable salt thereof, the stereoisomer of any of the foregoing, or the mixture thereof, wherein R³ has the formula

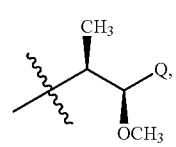

wherein the symbol ⌇, when drawn across a bond, indicates the point of attachment to the rest of the molecule.

56. The compound of embodiment 52 or the pharmaceutically acceptable salt thereof, the stereoisomer of any of the foregoing, or the mixture thereof, wherein $R^3$ has the formula

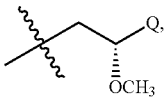

wherein the symbol ⌇, when drawn across a bond, indicates the point of attachment to the rest of the molecule.

57. The compound of embodiment 52 or the pharmaceutically acceptable salt thereof, the stereoisomer of any of the foregoing, or the mixture thereof, wherein $R^3$ has the formula

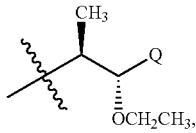

wherein the symbol ⌇, when drawn across a bond, indicates the point of attachment to the rest of the molecule.

58. The compound of embodiment 52 or the pharmaceutically acceptable salt thereof, the stereoisomer of any of the foregoing, or the mixture thereof, wherein $R^3$ has the formula

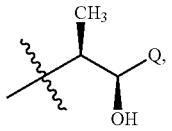

wherein the symbol ⌇, when drawn across a bond, indicates the point of attachment to the rest of the molecule.

59. The compound of embodiment 52 or the pharmaceutically acceptable salt thereof, the stereoisomer of any of the foregoing, or the mixture thereof, wherein $R^3$ has the formula

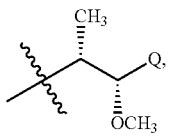

wherein the symbol ⌇, when drawn across a bond, indicates the point of attachment to the rest of the molecule.

60. The compound of embodiment 52 or the pharmaceutically acceptable salt thereof, the stereoisomer of any of the foregoing, or the mixture thereof, wherein $R^3$ has the formula

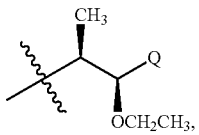

wherein the symbol ⌇, when drawn across a bond, indicates the point of attachment to the rest of the molecule.

61. The compound of embodiment 52 or the pharmaceutically acceptable salt thereof, the stereoisomer of any of the foregoing, or the mixture thereof, wherein $R^3$ has the formula

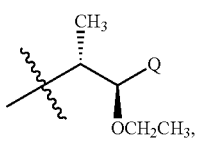

wherein the symbol ⌇, when drawn across a bond, indicates the point of attachment to the rest of the molecule.

62. The compound of embodiment 52 or the pharmaceutically acceptable salt thereof, the stereoisomer of any of the foregoing, or the mixture thereof, wherein $R^3$ has the formula

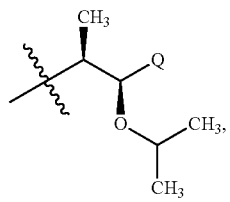

wherein the symbol ⌇, when drawn across a bond, indicates the point of attachment to the rest of the molecule.

63. The compound of embodiment 1 or the pharmaceutically acceptable salt thereof, the stereoisomer of any of the foregoing, or the mixture thereof, wherein the compound is
(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide;
(2S,3R)—N-(4-(2,6-dimethoxyphenyl)-5-(5-methyl-3-pyridinyl)-4H-1,2,4-triazol-3-yl)-3-(5-methyl-2-pyrimidinyl)-2-butane sulfonamide;
(1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide;
(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;
(1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide;
(1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide;
(1R,2S)—N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide;

(2S,3R)—N-(4-(2,6-dimethoxyphenyl)-5-(3-pyridinyl)-4H-1,2,4-triazol-3-yl)-3-(5-methyl-2-pyrimidinyl)-2-butanesulfonamide;

(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide;

(1R,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide;

(1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide;

(1R,2S)—N-(4-(2,6-dimethoxyphenyl)-5-(6-methyl-2-pyridinyl)-4H-1,2,4-triazol-3-yl)-1-hydroxy-1-(5-methyl-2-pyrimidinyl)-2-propanesulfonamide;

(1R,2S)—N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide;

(2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide;

(1R,2S)—N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide;

(1S,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide;

(1R,2S)—N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide;

(2S,3R)—N-(4-(2,6-dimethoxyphenyl)-5-(3-pyridinyl)-4H-1,2,4-triazol-3-yl)-3-(5-methyl-2-pyrazinyl)-2-butanesulfonamide;

(1R,2S)—N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide;

(1R,2S)—N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide;

(1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide; or (1S,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide.

64. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide.

65. The compound of embodiment 1 or the pharmaceutically acceptable salt thereof, the stereoisomer of any of the foregoing, or the mixture thereof, wherein the compound is (2S,3R)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide.

66. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide.

67. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide.

68. The compound of embodiment 1 or the pharmaceutically acceptable salt thereof, the stereoisomer of any of the foregoing, or the mixture thereof, wherein the compound is (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide.

69. The compound of embodiment 1 or the pharmaceutically acceptable salt thereof, the stereoisomer of any of the foregoing, or the mixture thereof, wherein the compound is (1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide.

70. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide.

71. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide.

72. The compound of embodiment 1 or the pharmaceutically acceptable salt thereof, the stereoisomer of any of the foregoing, or the mixture thereof, wherein the compound is (2S,3R)—N-(4-(2, 6-dimethoxyphenyl)-5-(3-pyridinyl)-4H-1,2,4-triazol-3-yl)-3-(5-methyl-2-pyrimidinyl)-2-butane sulfonamide.

73. The compound of embodiment 1 or the pharmaceutically acceptable salt thereof, the stereoisomer of any of the foregoing, or the mixture thereof, wherein the compound is (1R,2S)-1-(5-chloro-2-pyrimidinyl)-N-(4-(2, 6-dimethoxyphenyl)-5-(3-pyridinyl)-4H-1,2,4-triazol-3-yl)-1-ethoxy-2-propanesulfonamide.

74. The compound of embodiment 1 or the pharmaceutically acceptable salt thereof, the stereoisomer of any of the foregoing, or the mixture thereof, wherein the compound is (1R,2S)—N-(4-(2, 6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide.

75. The compound of embodiment 1 or the pharmaceutically acceptable salt thereof, the stereoisomer of any of the foregoing, or the mixture thereof, wherein the compound is (1S,2R)—N-(4-(2, 6-dimethoxyphenyl)-5-(3-pyridinyl)-4H-1,2,4-triazol-3-yl)-1-methoxy-1-(5-methyl-2-pyrazinyl)-2-propanesulfonamide.

76. The compound of embodiment 1 or the pharmaceutically acceptable salt thereof, the stereoisomer of any of the foregoing, or the mixture thereof, wherein the compound is (1R,2S)—N-(4-(2, 6-dimethoxyphenyl)-5-(6-methyl-2-pyridinyl)-4H-1,2,4-triazol-3-yl)-1-hydroxy-1-(5-methyl-2-pyrimidinyl)-2-propanesulfonamide.

77. The compound of embodiment 1 or the pharmaceutically acceptable salt thereof, the stereoisomer of any of the foregoing, or the mixture thereof, wherein the compound is (1R,2S)—N-(4-(2, 6-dimethoxyphenyl)-5-(3-pyridinyl)-4H-1,2,4-triazol-3-yl)-1-ethoxy-1-(5-methyl-2-pyrimidinyl)-2-propanesulfonamide.

78. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide.

79. The compound of embodiment 1 or the pharmaceutically acceptable salt thereof, the stereoisomer of any of the foregoing, or the mixture thereof, wherein the compound is (2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide.

80. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide.

81. The compound of embodiment 1 or the pharmaceutically acceptable salt thereof, the stereoisomer of any of the foregoing, or the mixture thereof, wherein the compound is (1S,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide.

82. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide.

83. The compound of embodiment 1 or the pharmaceutically acceptable salt thereof, the stereoisomer of any of the foregoing, or the mixture thereof, wherein the compound is (1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide.

84. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide 85. The compound of embodiment 1 or the pharmaceutically acceptable salt thereof, the stereoisomer of any of the foregoing, or the mixture thereof, wherein the compound is (2S,3R)—N-(4-(2,6-dimethoxyphenyl)-5-(3-pyridinyl)-4H-1,2,4-triazol-3-yl)-3-(5-methyl-2-pyrazinyl)-2-butanesulfonamide.

86. The compound of embodiment 1 or the pharmaceutically acceptable salt thereof, the stereoisomer of any of the foregoing, or the mixture thereof, wherein the compound is (1R,2S)—N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide.

87. The compound of embodiment 1 or the pharmaceutically acceptable salt thereof, the stereoisomer of any of the foregoing, or the mixture thereof, wherein the compound is (1R,2S)—N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide.

88. The compound of embodiment 1 or the pharmaceutically acceptable salt thereof, the stereoisomer of any of the foregoing, or the mixture thereof, wherein the compound is (1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide.

89. The compound of embodiment 1 or the pharmaceutically acceptable salt thereof, the stereoisomer of any of the foregoing, or the mixture thereof, wherein the compound is (1S,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide.

90. The compound of embodiment 1 or the pharmaceutically acceptable salt thereof, the stereoisomer of any of the foregoing, or the mixture thereof, wherein the compound is (2S,3R)—N-(4-(2,6-dimethoxyphenyl)-5-(2-methoxy-4-pyridinyl)-4H-1,2,4-triazol-3-yl)-3-(5-methyl-2-pyrimidinyl)-2-butanesulfonamide;

(2S,3R)—N-(4-(2,6-dimethoxyphenyl)-5-(2-methyl-4-pyridinyl)-4H-1,2,4-triazol-3-yl)-3-(5-methyl-2-pyrimidinyl)-2-butanesulfonamide;

(2S,3R)—N-(4-(2,6-dimethoxyphenyl)-5-(5-methoxy-3-pyridinyl)-4H-1,2,4-triazol-3-yl)-3-(5-methyl-2-pyrimidinyl)-2-butane sulfonamide;

(2S,3R)—N-(4-(2,6-dimethoxyphenyl)-5-(6-methyl-2-pyridinyl)-4H-1,2,4-triazol-3-yl)-3-(5-methyl-2-pyrimidinyl)-2-butane sulfonamide;

(1R,2S)-1-(5-chloro-2-pyrimidinyl)-N-(4-(2,6-dimethoxyphenyl)-5-(6-methyl-2-pyridinyl)-4H-1,2,4-triazol-3-yl)-1-methoxy-2-propanesulfonamide;

(1S,2R)-1-(5-chloro-2-pyrimidinyl)-N-(4-(2,6-dimethoxyphenyl)-5-(6-methyl-2-pyridinyl)-4H-1,2,4-triazol-3-yl)-1-methoxy-2-propanesulfonamide;

(1R,2S)—N-(4-(4,6-dimethoxy-5-pyrimidinyl)-5-(6-methyl-2-pyridinyl)-4H-1,2,4-triazol-3-yl)-1-methoxy-1-(5-methyl-2-pyrimidinyl)-2-propanesulfonamide;

(1S,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1R,2R)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1R,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide;

(1S,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide;

(1S,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide;

(1R,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide;

(1S,2S)—N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide;

(1R,2S)—N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide;

(1S,2R)—N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide;

(1R,2R)—N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide;

(1R,2S)—N-(4-(2,6-dimethoxyphenyl)-5-(6-methyl-2-pyridinyl)-4H-1,2,4-triazol-3-yl)-1-hydroxy-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1S,2R)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(2R,3S)—N-(4-(2,6-dimethoxyphenyl)-5-(6-methoxy-2-pyridinyl)-4H-1,2,4-triazol-3-yl)-3-(5-methyl-2-pyrimidinyl)-2-butane sulfonamide;

(2S,3R)—N-(4-(2,6-dimethoxyphenyl)-5-(6-methoxy-2-pyridinyl)-4H-1,2,4-triazol-3-yl)-3-(5-methyl-2-pyrimidinyl)-2-butane sulfonamide;

N-(4-(2,6-dimethoxyphenyl)-5-(5-methyl-3-pyridinyl)-4H-1,2,4-triazol-3-yl)-2-((6S)-3,6-dimethyl-2-oxotetrahydro-1(2H)-pyrimidinyl)ethanesulfonamide;

(2R)—N-(4-(2,6-dimethoxyphenyl)-5-(2-pyridinyl)-4H-1,2,4-triazol-3-yl)-1-(5-fluoro-2-pyrimidinyl)-2-propanesulfonamide;

(2S)—N-(4-(2,6-dimethoxyphenyl)-5-(2-pyridinyl)-4H-1,2,4-triazol-3-yl)-1-(5-fluoro-2-pyrimidinyl)-2-propanesulfonamide;

2-(2-cyano-4-fluorophenyl)-N-(4-(4,6-dimethoxy-5-pyrimidinyl)-5-(6-methoxy-2-pyridinyl)-4H-1,2,4-triazol-3-yl)ethanesulfonamide;

(1R,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide;

(1S,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide;

(1R,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide;

(1S,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide;

(2R,3S)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butane sulfonamide;

(2R,3S)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butane sulfonamide;

(2S,3R)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butane sulfonamide;

(1R,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide;

(1S,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide;

(2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentane sulfonamide;

(2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentane sulfonamide;

(2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentane sulfonamide;

(2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentane sulfonamide;

(1R,2S)-1-cyclopropyl-N-(4-(2,6-dimethoxy phenyl)-5-(6-methoxy-2-pyridinyl)-4H-1,2,4-triazol-3-yl)-1-hydroxy-2-propanesulfonamide;

(1S,2R)-1-cyclopropyl-N-(4-(2,6-dimethoxy phenyl)-5-(6-methoxy-2-pyridinyl)-4H-1,2,4-triazol-3-yl)-1-hydroxy-2-propanesulfonamide;

(2S,3R)—N-(4-(2,6-dimethoxyphenyl)-5-(6-methyl-2-pyridinyl)-4H-1,2,4-triazol-3-yl)-3-(5-fluoro-2-pyrimidinyl)-2-butane sulfonamide;

(2R,3S)—N-(4-(2,6-dimethoxyphenyl)-5-(6-methyl-2-pyridinyl)-4H-1,2,4-triazol-3-yl)-3-(5-fluoro-2-pyrimidinyl)-2-butane sulfonamide;

(2S,3R)—N-(5-(6-chloro-2-pyridinyl)-4-(2,6-dimethoxyphenyl)-4H-1,2,4-triazol-3-yl)-3-(5-fluoro-2-pyrimidinyl)-2-butane sulfonamide;

(2S,3R)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide;

(1S,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide;

(1R,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide;

(1S,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide;

(1R,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide;

(2S,3R)—N-(4-(2,6-dimethoxyphenyl)-5-(1-oxido-6-phenyl-2-pyridinyl)-4H-1,2,4-triazol-3-yl)-3-(5-fluoro-2-pyrimidinyl)-2-butanesulfonamide;

(2S,3R)—N-(4-(2,6-dimethoxyphenyl)-5-(6-phenyl-2-pyridinyl)-4H-1,2,4-triazol-3-yl)-3-(5-fluoro-2-pyrimidinyl)-2-butanesulfonamide;

(1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide;

(2S)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide;

(2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide;

(2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide;

(1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide;

(1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide;

(2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide;

(2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide;

(2R)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide;

(2S)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide;

(2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide;
(2S)—N-(4-(2, 6-dimethoxyphenyl)-5-(6-methoxy-2-pyridinyl)-4H-1,2,4-triazol-3-yl)-2-hydroxy-2-(3-methyl-5-isoxazolyl)ethanesulfonamide;
(2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide;
(2S)—N-(4-(2, 6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide;
(2R)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide;
(1S,2S)-1-(4-cyano-2-fluorophenyl)-N-(4-(2, 6-dimethoxyphenyl)-5-(5-methyl-3-pyridinyl)-4H-1,2,4-triazol-3-yl)-1-hydroxy-2-propanesulfonamide;
(1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide;
(1S,2S)—N-(4-(2, 6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide;
(1R,2R)-1-(4-cyano-2-fluorophenyl)-N-(4-(2, 6-dimethoxyphenyl)-5-(5-methyl-3-pyridinyl)-4H-1,2,4-triazol-3-yl)-1-hydroxy-2-propanesulfonamide;
(1R,2S)—N-(4-(2, 6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide;
(1S,2R)—N-(4-(2, 6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide;
(1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide;
(1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide;
(1S,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide;
(1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide;
(1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide;
(1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide;
(2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide;
(2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide;
(2S)—N-(4-(2,6-dimethoxyphenyl)-5-(3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide;
2-(2-cyano-4-fluorophenyl)-N-(4-(2,6-dimethoxyphenyl)-5-(5-methyl-3-pyridinyl)-4H-1,2,4-triazol-3-yl)ethanesulfonamide;
(2S)—N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide;
N-(5-(5-chloro-3-pyridinyl)-4-(2,6-dimethoxyphenyl)-4H-1,2,4-triazol-3-yl)-2-(2-cyano-4-fluorophenyl)ethanesulfonamide;
(2S)—N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide;
(2R)—N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide;
(2S)—N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide;
(2S,3R)—N-(4-(2, 6-dimethoxyphenyl)-5-(5-methyl-3-pyridinyl)-4H-1,2,4-triazol-3-yl)-3-(5-fluoro-2-pyrimidinyl)-2-butane sulfonamide;
(2R,3S)—N-(4-(2, 6-dimethoxyphenyl)-5-(5-methyl-3-pyridinyl)-4H-1,2,4-triazol-3-yl)-3-(5-fluoro-2-pyrimidinyl)-2-butane sulfonamide;
(2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butane sulfonamide;
(2S,3S)—N-(4-(2, 6-dimethoxyphenyl)-5-(5-methyl-3-pyridinyl)-4H-1,2,4-triazol-3-yl)-3-(5-fluoro-2-pyrimidinyl)-2-butane sulfonamide;
(1R,2S)-1-(4-cyanophenyl)-N-(4-(2, 6-dimethoxyphenyl)-5-(5-methyl-3-pyridinyl)-4H-1,2,4-triazol-3-yl)-1-hydroxy-2-propanesulfonamide;

(1S,2R)-1-(4-cyanophenyl)-N-(4-(2, 6-dimethoxyphenyl)-5-(5-methyl-3-pyridinyl)-4H-1,2,4-triazol-3-yl)-1-hydroxy-2-propanesulfonamide;

(1R,2S)-1-(4-cyanophenyl)-N-(4-(2, 6-dimethoxyphenyl)-5-(6-methoxy-2-pyridinyl)-4H-1,2,4-triazol-3-yl)-1-hydroxy-2-propanesulfonamide;

(1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide;

(1S,2R)-1-(4-cyanophenyl)-N-(4-(2, 6-dimethoxyphenyl)-5-(6-methoxy-2-pyridinyl)-4H-1,2,4-triazol-3-yl)-1-hydroxy-2-propanesulfonamide;

(1R,2R)-1-(4-cyanophenyl)-N-(4-(2, 6-dimethoxy phenyl)-5-(6-methoxy-2-pyridinyl)-4H-1,2,4-triazol-3-yl)-1-hydroxy-2-propanesulfonamide;

(2R,3S)—N-(4-(2, 6-dimethoxyphenyl)-5-(3-pyridinyl)-4H-1,2,4-triazol-3-yl)-3-(5-fluoro-2-pyrimidinyl)-2-butane sulfonamide;

(2S,3R)—N-(4-(2, 6-dimethoxyphenyl)-5-(3-pyridinyl)-4H-1,2,4-triazol-3-yl)-3-(5-fluoro-2-pyrimidinyl)-2-butane sulfonamide;

6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-ethyl-2-pyridinecarboxamide;

6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-ethyl-2-pyridinecarboxamide;

6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N,N-dimethyl-2-pyridinecarboxamide;

6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N,N-dimethyl-2-pyridinecarboxamide;

(2S,3R)—N-(4-(2,6-dimethoxyphenyl)-5-(6-(2,2,2-trifluoroethoxy)-2-pyridinyl)-4H-1,2,4-triazol-3-yl)-3-(5-fluoro-2-pyrimidinyl)-2-butane sulfonamide;

(2S,3R)—N-(4-(2,6-dimethoxyphenyl)-5-(6-(2-hydroxyethoxy)-2-pyridinyl)-4H-1,2,4-triazol-3-yl)-3-(5-fluoro-2-pyrimidinyl)-2-butane sulfonamide;

(1R,2S)—N-(4-(2,6-dimethoxyphenyl)-5-(6-(2,2,2-trifluoroethoxy)-2-pyridinyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(6-(2-hydroxyethoxy)-2-pyridinyl)-4H-1,2,4-triazol-3-yl)-1-methoxy-1-(5-methyl-2-pyrimidinyl)-2-propanesulfonamide;

(1R,2S)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide;

(1S,2R)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide;

(2S,3R)—N-(4-(2,6-dimethoxyphenyl)-5-(6-(2-hydroxy-2-methylpropoxy)-2-pyridinyl)-4H-1,2,4-triazol-3-yl)-3-(5-fluoro-2-pyrimidinyl)-2-butane sulfonamide;

(1R,2S)—N-(4-(2,6-dimethoxyphenyl)-5-(6-(2-hydroxy-2-methylpropoxy)-2-pyridinyl)-4H-1,2,4-triazol-3-yl)-1-methoxy-1-(5-methyl-2-pyrimidinyl)-2-propanesulfonamide;

(2S,3R)—N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(5-fluoro-2-pyrimidinyl)-2-butane sulfonamide;

(1R,2S)—N-(4-(2,6-dimethoxyphenyl)-5-(6-(methylamino)-2-pyridinyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(6-(2-methoxyethoxy)-2-pyridinyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(6-(dimethylamino)-2-pyridinyl)-4H-1,2,4-triazol-3-yl)-1-methoxy-1-(5-methyl-2-pyrimidinyl)-2-propanesulfonamide;

(1R,2R)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide;

(1S,2S)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide;

(1S,2R)—N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide;

(1R,2S)—N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide;

2-(4-chlorophenyl)-N-(4-(2,6-dimethoxyphenyl)-5-(2-pyridinyl)-4H-1,2,4-triazol-3-yl)ethanesulfonamide;

2-(4-chlorophenyl)-N-(4-(2,6-dimethoxyphenyl)-5-(3-pyridinyl)-4H-1,2,4-triazol-3-yl)ethanesulfonamide;

2-(4-chlorophenyl)-N-(4-(2,6-dimethoxyphenyl)-5-(6-methyl-3-pyridinyl)-4H-1,2,4-triazol-3-yl)ethanesulfonamide;

(1R,2S)-1-methoxy-N-(5-(6-methoxy-2-pyridinyl)-4-phenyl-4H-1,2,4-triazol-3-yl)-1-(5-methyl-2-pyrimidinyl)-2-propanesulfonamide;

(1R,2S)—N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2,6-bis([$^2$H$_3$])methyloxy)phenyl)-5-(6-methoxypyridin-2-yl)-4H-1,2,4-triazol-3-yl)-1-methoxy-1-(5-methylpyrimidin-2-yl)propane-2-sulfonamide;

(1R,2S)—N-(4-(2,6-bis([$^2$H$_3$])methyloxy)phenyl)-5-(6-([$^2$H$_3$])methoxy)-2-pyridinyl)-4H-1,2,4-triazol-3-yl)-1-methoxy-1-(5-methylpyrimidin-2-yl)propane-2-sulfonamide;

(1R,2S)—N-(4-(2,6-dimethoxyphenyl)-5-(6-([$^2$H$_3$])methoxy)-2-pyridinyl)-4H-1,2,4-triazol-3-yl)-1-methoxy-1-(5-methylpyrimidin-2-yl)propane-2-sulfonamide;

(1R,2S)—N-(4-(3,5-bis(trifluoromethyl)phenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)-1-methoxy-N-(4-(2-methoxy-5-methylphenyl)-5-(6-methoxy-2-pyridinyl)-4H-1,2,4-triazol-3-yl)-1-(5-methyl-2-pyrimidinyl)-2-propanesulfonamide;

(1R,2S)—N-(4-(2,6-bis(difluoromethoxy)phenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)-1-methoxy-N-(5-(6-methoxy-2-pyridinyl)-4-(4-pyridinyl)-4H-1,2,4-triazol-3-yl)-1-(5-methyl-2-pyrimidinyl)-2-propanesulfonamide;

(1R,2S)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide;

(1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide;

(1R,2S)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide;

(1R,2S)—N-(4-(2,6-dimethoxyphenyl)-5-(3-pyridinyl)-4H-1,2,4-triazol-3-yl)-1-(5-fluoro-2-pyrimidinyl)-1-methoxy-2-propanesulfonamide;

(1R)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide;

(1S)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide;

(2R)—N-(4-(2,6-dimethoxyphenyl)-5-(6-methoxy-2-pyridinyl)-4H-1,2,4-triazol-3-yl)-1-oxo-1-(1-pyrrolidinyl)-2-propanesulfonamide;

(2S)—N-(4-(2,6-dimethoxyphenyl)-5-(6-methoxy-2-pyridinyl)-4H-1,2,4-triazol-3-yl)-1-oxo-1-(1-pyrrolidinyl)-2-propanesulfonamide;

(1R,2S)—N-(4-(4-chlorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)-1-methoxy-N-(4-(4-methoxyphenyl)-5-(6-methoxy-2-pyridinyl)-4H-1,2,4-triazol-3-yl)-1-(5-methyl-2-pyrimidinyl)-2-propanesulfonamide;

(1R,2S)—N-(4-(3-fluorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(6-methoxy-2-pyridinyl)-4H-1,2,4-triazol-3-yl)-1-ethoxy-1-(5-fluoro-2-pyrimidinyl)-2-propanesulfonamide;

(1R,2S)—N-(4-(2,6-dimethoxyphenyl)-5-(6-methoxy-2-pyridinyl)-4H-1,2,4-triazol-3-yl)-1-methoxy-1-(5-methoxy-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide;

(1R,2S)-1-ethoxy-1-(5-fluoro-2-pyrimidinyl)-N-(5-(6-methoxy-2-pyridinyl)-4-phenyl-4H-1,2,4-triazol-3-yl)-2-propanesulfonamide;

(1R,2S)—N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide;

(1R,2S)—N-(4-(2,6-dimethoxyphenyl)-5-(3-pyridinyl)-4H-1,2,4-triazol-3-yl)-1-(5-fluoro-2-pyrimidinyl)-1-hydroxy-2-propanesulfonamide;

(1R,2S)-1-methoxy-N-(4-(2-methoxyphenyl)-5-(6-methoxy-2-pyridinyl)-4H-1,2,4-triazol-3-yl)-1-(5-methyl-2-pyrimidinyl)-2-propanesulfonamide;

(1R,2S)-1-methoxy-N-(5-(6-methoxy-2-pyridinyl)-4-(2-naphthalenyl)-4H-1,2,4-triazol-3-yl)-1-(5-methyl-2-pyrimidinyl)-2-propanesulfonamide;

methyl 3-(3-(((((1S,2R)-2-methoxy-1-methyl-2-(5-methyl-2-pyrimidinyl)methyl)sulfonyl)amino)-5-(6-methoxy-2-pyridinyl)-4H-1,2,4-triazol-4-yl)benzoate;

(1R,2S)—N-(4-(3-chloro-2-methylphenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(3-cyanophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-methoxy-1-(5-methoxy-2-pyrimidinyl)-2-propanesulfonamide;

(1R,2S)—N-(4-(2,6-dimethoxyphenyl)-5-(3-pyridinyl)-4H-1,2,4-triazol-3-yl)-1-methoxy-1-(5-methoxy-2-pyrimidinyl)-2-propanesulfonamide;

(1R,2S)-1-methoxy-1-(5-methoxy-2-pyrimidinyl)-N-(5-(5-methyl-3-pyridinyl)-4-phenyl-4H-1,2,4-triazol-3-yl)-2-propanesulfonamide;

(1R,2S)—N-(4-(3-bromophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)-1-methoxy-N-(5-(6-methoxy-2-pyridinyl)-4-(2-methylphenyl)-4H-1,2,4-triazol-3-yl)-1-(5-methyl-2-pyrimidinyl)-2-propanesulfonamide;

(1R,2S)-1-methoxy-N-(5-(6-methoxy-2-pyridinyl)-4-(3-methylphenyl)-4H-1,2,4-triazol-3-yl)-1-(5-methyl-2-pyrimidinyl)-2-propanesulfonamide;

(1R,2S)—N-(4-(4-fluoro-3-(trifluoromethyl)phenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)-1-methoxy-N-(4-(3-methoxyphenyl)-5-(6-methoxy-2-pyridinyl)-4H-1,2,4-triazol-3-yl)-1-(5-methyl-2-pyrimidinyl)-2-propanesulfonamide;

(1R,2S)—N-(4-(4-fluorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(3-chlorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2-chloro-4-fluorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(3,5-dichlorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2-chlorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2,3-dimethylphenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(3,4-difluorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(3-acetylphenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2,6-dichlorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)-1-methoxy-N-(5-(6-methoxy-2-pyridinyl)-4-(2-(trifluoromethyl)phenyl)-4H-1,2,4-triazol-3-yl)-1-(5-methyl-2-pyrimidinyl)-2-propanesulfonamide;

(1R,2S)-1-methoxy-N-(5-(6-methoxy-2-pyridinyl)-4-(3-(trifluoromethyl)phenyl)-4H-1,2,4-triazol-3-yl)-1-(5-methyl-2-pyrimidinyl)-2-propanesulfonamide;

(1R,2S)—N-(4-(2-fluorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(4-(dimethylamino)phenyl)-5-(6-methoxy-2-pyridinyl)-4H-1,2,4-triazol-3-yl)-1-methoxy-1-(5-methyl-2-pyrimidinyl)-2-propanesulfonamide;

(2S,3R)-3-(5-fluoro-2-pyrimidinyl)-N-(5-(6-methoxy-2-pyridinyl)-4-phenyl-4H-1,2,4-triazol-3-yl)-2-butane sulfonamide;

(1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide;

N-(4-(2,6-dimethoxyphenyl)-5-(5-methyl-3-pyridinyl)-4H-1,2,4-triazol-3-yl)-N'-((1S)-1-(5-fluoro-2-pyrimidinyl)ethyl) sulfamide;

(1S,2R)—N-(4-(2,6-dimethoxyphenyl)-5-(5-methyl-3-pyridinyl)-4H-1,2,4-triazol-3-yl)-1-(2-hydroxy ethoxy)-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-(2-hydroxy ethoxy)-1-(5-methyl-2-pyrimidinyl)-2-propanesulfonamide;
(1S,2R)—N-(4-(2,6-dimethoxyphenyl)-5-(5-methyl-3-pyridinyl)-4H-1,2,4-triazol-3-yl)-1-(2-methoxy ethoxy)-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-(2-methoxy ethoxy)-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-(2-methoxy ethoxy)-N-methyl-1-(5-methyl-2-pyrimidinyl)-2-propanesulfonamide;
(1S,2R)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide;
(1S,2R)—N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide;
(1R,2S)—N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide;
(1S,2S)—N-(4-(2,6-dimethoxyphenyl)-5-(5-methyl-3-pyridinyl)-4H-1,2,4-triazol-3-yl)-1-(2-hydroxy ethoxy)-1-(5-methyl-2-pyrimidinyl)-2-propanesulfonamide;
(1R,2R)—N-(4-(2,6-dimethoxyphenyl)-5-(5-methyl-3-pyridinyl)-4H-1,2,4-triazol-3-yl)-1-(2-hydroxy ethoxy)-1-(5-methyl-2-pyrimidinyl)-2-propanesulfonamide;
(1S,2R)—N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide;
(1R,2S)—N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide;
(1S,2S)—N-(4-(2,6-dimethoxyphenyl)-5-(5-methyl-3-pyridinyl)-4H-1,2,4-triazol-3-yl)-1-(2-hydroxy-2-methyl-propoxy)-1-(5-methyl-2-pyrimidinyl)-2-propanesulfonamide;
(1R,2R)—N-(4-(2,6-dimethoxyphenyl)-5-(5-methyl-3-pyridinyl)-4H-1,2,4-triazol-3-yl)-1-(2-hydroxy-2-methyl-propoxy)-1-(5-methyl-2-pyrimidinyl)-2-propanesulfonamide;
(1S,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide;
(1R,2R)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide;
(1S,2S)—N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide;
(1R,2R)—N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide;
(1S,2S)—N-(4-(2,6-dimethoxyphenyl)-5-(5-methyl-3-pyridinyl)-4H-1,2,4-triazol-3-yl)-1-(2-methoxy ethoxy)-1-(5-methyl-2-pyrimidinyl)-2-propanesulfonamide;
(1S,2R)—N-(4-(2,6-dimethoxyphenyl)-5-(6-methoxy-2-pyridinyl)-4H-1,2,4-triazol-3-yl)-1-(2-hydroxy ethoxy)-1-(5-methyl-2-pyrimidinyl)-2-propanesulfonamide;
(1R,2S)—N-(4-(2,6-dimethoxyphenyl)-5-(6-methoxy-2-pyridinyl)-4H-1,2,4-triazol-3-yl)-1-(2-hydroxy ethoxy)-1-(5-methyl-2-pyrimidinyl)-2-propanesulfonamide;
(1S,2R)—N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide;
(1S,2R)—N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide;
(1S,2R)—N-(4-(2,6-dimethoxyphenyl)-5-(5-methyl-3-pyridinyl)-4H-1,2,4-triazol-3-yl)-1-(2-hydroxy-2-methyl-propoxy)-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-(2-hydroxy-2-methyl-propoxy)-1-(5-methyl-2-pyrimidinyl)-2-propanesulfonamide;
(1R,2S)—N-(4-(2,6-dimethoxyphenyl)-5-(6-ethoxy-2-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide;
(2S)—N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide;
(2R)—N-(5-(5-bromo-3-pyridinyl)-4-(2,6-dimethoxyphenyl)-4H-1,2,4-triazol-3-yl)-1-(5-fluoro-2-pyrimidinyl)-2-propanesulfonamide;
(2S)—N-(5-(5-bromo-3-pyridinyl)-4-(2,6-dimethoxy phenyl)-4H-1,2,4-triazol-3-yl)-1-(5-fluoro-2-pyrimidinyl)-2-propanesulfonamide;
(1S,2R)—N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide;
(1R,2S)—N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide;
(1S,2R)—N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide;
(1R,2S)—N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide;
(2R,3S)—N-(4-(2,6-dimethoxyphenyl)-5-(6-methoxy-2-pyridinyl)-4H-1,2,4-triazol-3-yl)-3-(S-fluoro-2-pyrimidinyl)-2-butane sulfonamide;

(2S,3R)—N-(4-(2,6-dimethoxyphenyl)-5-(6-methoxy-2-pyridinyl)-4H-1,2,4-triazol-3-yl)-3-(S-fluoro-2-pyrimidinyl)-2-butane sulfonamide;
(2R)—N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide;
(1S,2R)—N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide;
(1R,2S)—N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide;
(2S)—N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide;
6-(4-(2,6-dimethoxyphenyl)-5-(((((1S)-2-(5-fluoro-2-pyrimidinyl)-1-methylethyl)sulfonyl)amino)-4H-1,2,4-triazol-3-yl)-N-methyl-2-pyridinecarboxamide;
6-(4-(2,6-dimethoxyphenyl)-5-(((((1R)-2-(5-fluoro-2-pyrimidinyl)-1-methylethyl)sulfonyl)amino)-4H-1,2,4-triazol-3-yl)-N-methyl-2-pyridinecarboxamide;
(2S)—N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide;
(2R)—N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide;
(2S)—N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide;
(2S)—N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide;
(2R)—N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide;
(2S)—N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide;
(2R)—N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide;
(2S,3R)—N-(4-(2,6-dimethoxyphenyl)-5-(6-ethoxy-2-pyridinyl)-4H-1,2,4-triazol-3-yl)-3-(5-fluoro-2-pyrimidinyl)-2-butanesulfonamide;
(2R,3S)—N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide;
(2S,3R)—N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide;
6-(4-(2,6-dimethoxyphenyl)-5-(((((1R,2S)-2-(5-fluoro-2-pyrimidinyl)-1-methylpropyl)sulfonyl)amino)-4H-1,2,4-triazol-3-yl)-N-methyl-2-pyridinecarboxamide;
6-(4-(2,6-dimethoxyphenyl)-5-(((((1S,2R)-2-(5-fluoro-2-pyrimidinyl)-1-methylpropyl)sulfonyl)amino)-4H-1,2,4-triazol-3-yl)-N-methyl-2-pyridinecarboxamide;
(2S,3R)—N-(4-(2,6-dimethoxyphenyl)-5-(6-oxo-1,6-dihydro-2-pyridinyl)-4H-1,2,4-triazol-3-yl)-3-(5-fluoro-2-pyrimidinyl)-2-butanesulfonamide;
(2S)—N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide;
(2R)—N-(5-(6-(difluoromethoxy)-2-pyridinyl)-4-(2,6-dimethoxy phenyl)-4H-1,2,4-triazol-3-yl)-1-(5-fluoro-2-pyrimidinyl)-2-propanesulfonamide;
(1R,2S)—N-(4-(2,6-dimethoxyphenyl)-5-(6-ethyl-2-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(6-ethyl-2-pyridinyl)-4H-1,2,4-triazol-3-yl)-1-hydroxy-1-(5-methyl-2-pyrimidinyl)-2-propanesulfonamide;
(2S,3R)—N-(4-(2,6-dimethoxyphenyl)-5-(6-ethyl-2-pyridinyl)-4H-1,2,4-triazol-3-yl)-3-(5-methyl-2-pyrimidinyl)-2-butane sulfonamide;
(2S,3R)—N-(4-(2,6-dimethoxyphenyl)-5-(6-methoxy-4-methyl-2-pyridinyl)-4H-1,2,4-triazol-3-yl)-3-(5-fluoro-2-pyrimidinyl)-2-butane sulfonamide;
(2S,3R)—N-(4-(2,6-dimethoxyphenyl)-5-(6-ethoxy-2-pyridinyl)-4H-1,2,4-triazol-3-yl)-3-(5-methyl-2-pyrimidinyl)-2-butane sulfonamide;
(2S,3R)—N-(4-(2,6-dimethoxyphenyl)-5-(6-methoxy-4-methyl-2-pyridinyl)-4H-1,2,4-triazol-3-yl)-3-(5-methyl-2-pyrimidinyl)-2-butane sulfonamide;
(1R,2S)—N-(4-(2,6-dimethoxyphenyl)-5-(6-methoxy-4-methyl-2-pyridinyl)-4H-1,2,4-triazol-3-yl)-1-methoxy-1-(5-methyl-2-pyrimidinyl)-2-propanesulfonamide;
(2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide;
(2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide;

N-(4-(2,6-dimethoxyphenyl)-5-(5-methyl-3-pyridinyl)-4H-1,2,4-triazol-3-yl)-2-((6R)-3,6-dimethyl-2-oxotetrahydro-1(2H)-pyrimidinyl)ethanesulfonamide;

2-(2-cyano-4-fluorophenyl)-N-(4-(2,6-dimethoxyphenyl)-5-(6-methoxy-2-pyridinyl)-4H-1,2,4-triazol-3-yl)ethanesulfonamide;

2-(2-cyano-4-fluorophenyl)-N-(4-(2,6-dimethoxyphenyl)-5-(6-oxo-1,6-dihydro-2-pyridinyl)-4H-1,2,4-triazol-3-yl)ethanesulfonamide;

(3R,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidine sulfonamide;

(3S,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidine sulfonamide;

(3R,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidine sulfonamide;

(3S,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidine sulfonamide;

(3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidine sulfonamide;

(3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidine sulfonamide;

(3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidine sulfonamide;

(3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidine sulfonamide;

(3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidine sulfonamide;

(3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidine sulfonamide;

(1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide;

(1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide;

(1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide;

(1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide;

(1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide;

(1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide;

(2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide;

(2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide;

(2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide;

(2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide;

(2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxy ethane sulfonamide;

(2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxy ethane sulfonamide;

(2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide;

(2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide;

N-(4-(2,6-dimethoxyphenyl)-5-(6-methoxy-2-pyridinyl)-4H-1,2,4-triazol-3-yl)methanesulfonamide;

(1R,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide;

(1S,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide;

(2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide;

(2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide;

(1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide;

(1R,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide;

(2E)-N-(4-(2,6-dimethoxyphenyl)-5-(5-methyl-3-pyridinyl)-4H-1,2,4-triazol-3-yl)-3-(5-fluoro-2-pyrimidinyl)-2-butene-2-sulfonamide;

(1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide;

(1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide;

(2E)-N-(4-(2,6-dimethoxyphenyl)-5-(6-methoxy-2-pyridinyl)-4H-1,2,4-triazol-3-yl)-3-(5-fluoro-2-pyrimidinyl)-2-butene-2-sulfonamide;

(1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide;

(1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide;

(2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butane sulfonamide;

(2S,3R)—N-(4-(2,6-dimethoxyphenyl)-5-(6-methoxy-2-pyridinyl)-4H-1,2,4-triazol-3-yl)-3-(5-methyl-2-pyrazinyl)-2-butane sulfonamide;

(1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide;

(1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide;

(1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide;
(1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide;
(1S,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide;
(1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide;
(1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide;
(1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide;
(2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide;
(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide;
(2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxy ethane sulfonamide;
(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxy ethane sulfonamide;
(2S,3R)—N-(4-(2,4-dimethoxy-3-pyridinyl)-5-(6-methoxy-2-pyridinyl)-4H-1,2,4-triazol-3-yl)-3-(5-fluoro-2-pyrimidinyl)-2-butane sulfonamide;
(2S,3R)-3-(5-fluoro-2-pyrimidinyl)-N-(4-(4-methoxy-2-oxo-1,2-dihydro-3-pyridinyl)-5-(6-methoxy-2-pyridinyl)-4H-1,2,4-triazol-3-yl)-2-butane sulfonamide;
(1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide;
(1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide;
(1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide;
(1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide;
(2R,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butane sulfonamide;
(2S,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butane sulfonamide;
(1S,2R)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide;
(1R,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide;
(1S,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide;
(1S,2R)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide;
2-(5-cyano-2-pyridinyl)-N-(4-(2,6-dimethoxyphenyl)-5-(6-methoxy-2-pyridinyl)-4H-1,2,4-triazol-3-yl)ethanesulfonamide;
(1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide;
(1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide;
(1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide;
(1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide;
(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;
(1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;
(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;
(1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;
(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide;
(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide;
(1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide;
(1R,2S)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide;
(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide;
(1S,2R)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide;
(1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide;
(1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide;
(1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide;
(1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide;
(1S,2R)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide;
(1R,2S)—N-(4-(2,6-dimethoxyphenyl)-5-(5-methyl-3-pyridinyl)-4H-1,2,4-triazol-3-yl)-1-hydroxy-1-methyl-2-pyrazinyl)-2-propanesulfonamide;
(1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide;

(1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide;
(2R,3S)—N-(4-(2,6-dimethoxyphenyl)-5-(3-pyridinyl)-4H-1,2,4-triazol-3-yl)-3-(5-methyl-2-pyrimidinyl)-2-butanesulfonamide;
(2S,3R)—N-(4-(2,6-dimethoxyphenyl)-5-(3-pyridinyl)-4H-1,2,4-triazol-3-yl)-3-(5-methyl-2-pyrimidinyl)-2-butanesulfonamide;
(1S,2R)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide;
(1R,2S)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide;
(1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide;
(1R,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide;
(1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide;
(1S,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide;
(1R,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide;
(1S,2R)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide;
(1R,2S)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide;
(1S,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide;
(1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide;
(1S,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide;
(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide;
(1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide;
(1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide;
(1R,2S)—N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide;
(1S,2R)—N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide;
(1R,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide;
(1R,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide;
(1S,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide;
(1R,2S)—N-(4-(2,6-dimethoxyphenyl)-5-(3-pyridinyl)-4H-1,2,4-triazol-3-yl)-1-hydroxy-1-(5-methyl-2-pyrimidinyl)-2-propanesulfonamide;
N-(4-(2,6-dimethoxyphenyl)-5-(6-methoxy-2-pyridinyl)-4H-1,2,4-triazol-3-yl)-2-propanesulfonamide;
(1R,2S)—N-(4-(2,6-dimethoxyphenyl)-5-(6-methyl-2-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(2-methoxy-4-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(2-methyl-4-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(5-methoxy-3-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(4-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-methoxy-1-(2-pyrimidinyl)-2-propanesulfonamide;
(2R)—N-(4-(2,6-dimethoxyphenyl)-5-(5-methyl-3-pyridinyl)-4H-1,2,4-triazol-3-yl)-2-hydroxy-2-(3-methyl-3-oxetanyl)ethanesulfonamide;
(2S)—N-(4-(2,6-dimethoxyphenyl)-5-(5-methyl-3-pyridinyl)-4H-1,2,4-triazol-3-yl)-2-hydroxy-2-(3-methyl-3-oxetanyl)ethanesulfonamide;
(2R)-2-cyclobutyl-N-(4-(2,6-dimethoxyphenyl)-5-(5-methyl-3-pyridinyl)-4H-1,2,4-triazol-3-yl)-2-hydroxyethanesulfonamide;
(2S)-2-cyclobutyl-N-(4-(2,6-dimethoxyphenyl)-5-(5-methyl-3-pyridinyl)-4H-1,2,4-triazol-3-yl)-2-hydroxyethanesulfonamide;
(1S,2S)-1-cyclobutyl-N-(4-(2,6-dimethoxy phenyl)-5-(6-methoxy-2-pyridinyl)-4H-1,2,4-triazol-3-yl)-1-methoxy-2-propanesulfonamide;
(1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide;
(1R,2S)-1-cyclobutyl-N-(4-(2,6-dimethoxy phenyl)-5-(6-methoxy-2-pyridinyl)-4H-1,2,4-triazol-3-yl)-1-methoxy-2-propanesulfonamide;
(1S,2R)-1-cyclobutyl-N-(4-(2,6-dimethoxy phenyl)-5-(6-methoxy-2-pyridinyl)-4H-1,2,4-triazol-3-yl)-1-methoxy-2-propanesulfonamide;
(2R)—N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide;
(2S)—N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide;
(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide;
(2S,3R)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide;
(2R,3S)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide;

(1S,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide;

N-(4-(2,6-dimethoxyphenyl)-5-(6-methoxy-2-pyridinyl)-4H-1,2,4-triazol-3-yl)ethanesulfonamide;

(1R,2S)—N-(4-(2,6-dimethoxyphenyl)-5-(6-methoxy-2-pyridinyl)-4H-1,2,4-triazol-3-yl)-1-hydroxy-1-imidazo[1,2-a]pyridin-2-yl-2-propanesulfonamide;

(1S,2R)—N-(4-(2,6-dimethoxyphenyl)-5-(6-methoxy-2-pyridinyl)-4H-1,2,4-triazol-3-yl)-1-hydroxy-1-imidazo[1,2-a]pyridin-2-yl-2-propanesulfonamide;

N-(4-(2,6-dimethoxyphenyl)-5-(6-methyl-2-pyridinyl)-4H-1,2,4-triazol-3-yl)ethanesulfonamide;

(2R)—N-(4-(2,6-dimethoxyphenyl)-5-(6-methoxy-2-pyridinyl)-4H-1,2,4-triazol-3-yl)-2-hydroxy-2-imidazo[1,2-a]pyridin-2-ylethanesulfonamide;

(2S)—N-(4-(2,6-dimethoxyphenyl)-5-(6-methoxy-2-pyridinyl)-4H-1,2,4-triazol-3-yl)-2-hydroxy-2-imidazo[1,2-a]pyridin-2-ylethanesulfonamide;

(1R,2S)—N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide;

(1S,2R)—N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide;

(1R,2R)—N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide;

(1S,2S)—N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide;

(1R,2S)—N-(4-(2,6-dimethoxyphenyl)-5-(6-methoxy-2-pyridinyl)-4H-1,2,4-triazol-3-yl)-1-(1,5-dimethyl-1H-pyrazol-3-yl)-1-hydroxy-2-propanesulfonamide;

(1S,2R)—N-(4-(2,6-dimethoxyphenyl)-5-(6-methoxy-2-pyridinyl)-4H-1,2,4-triazol-3-yl)-1-(1,5-dimethyl-1H-pyrazol-3-yl)-1-hydroxy-2-propanesulfonamide;

(2R)-1-(5-fluoro-2-pyrimidinyl)-N-(4-(2-methoxyphenyl)-5-(6-methoxy-2-pyridinyl)-4H-1,2,4-triazol-3-yl)-2-propanesulfonamide;

(2S)-1-(5-fluoro-2-pyrimidinyl)-N-(4-(2-methoxyphenyl)-5-(6-methoxy-2-pyridinyl)-4H-1,2,4-triazol-3-yl)-2-propanesulfonamide;

(2R)—N-(4-(3,5-dimethyl-4-isoxazolyl)-5-(6-methoxy-2-pyridinyl)-4H-1,2,4-triazol-3-yl)-1-(5-fluoro-2-pyrimidinyl)-2-propanesulfonamide;

(2S)—N-(4-(3,5-dimethyl-4-isoxazolyl)-5-(6-methoxy-2-pyridinyl)-4H-1,2,4-triazol-3-yl)-1-(5-fluoro-2-pyrimidinyl)-2-propanesulfonamide;

(1R,2S)-1-methoxy-N-(5-(6-methoxy-2-pyridinyl)-4-(3-pyridinyl)-4H-1,2,4-triazol-3-yl)-1-(5-methyl-2-pyrimidinyl)-2-propanesulfonamide;

(1S,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide;

(1R,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide;

(1S,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide;

(1R,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide;

(1R,2R)—N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide;

(1S,2S)—N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide;

(2R)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide;

(2S)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide;

(1S,2S)—N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide;

(1R,2R)—N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide;

(1R,2S)—N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide;

(1S,2R)—N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide;

(2R)—N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide;

(2S)—N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide;

(2R)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide;

(2S)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide;

(2R)—N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide;

(2S)—N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide;

(2R)—N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide;

(2S)—N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide;

(1S,2R)—N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide;

(1R,2S)—N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide;

(1R,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide;

(1S,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide;

(2S,3R)—N-(4-(2,6-dimethoxyphenyl)-5-(3-pyridinyl)-4H-1,2,4-triazol-3-yl)-3-(5-methyl-2-pyrazinyl)-2-butane sulfonamide;

(2R,3S)—N-(4-(2,6-dimethoxyphenyl)-5-(5-methyl-3-pyridinyl)-4H-1,2,4-triazol-3-yl)-3-(5-methyl-2-pyrazinyl)-2-butane sulfonamide;

(1S,2S)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide;

(1R,2R)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide;
(1S,2R)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide;
(1R,2S)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide;
(1S,2S)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide;
(1R,2R)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide;
(1S,2R)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide;
(1R,2S)—N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide;
(1R,2S)—N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide;
(1S,2R)—N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide;
(1R,2R)—N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide;
(1S,2S)—N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide;
(1R,2S)—N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide;
(1S,2R)—N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide;
(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide;
(1R,2S)—N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide;
(1S,2R)—N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide;
(1S,2S)—N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide;
(1R,2R)—N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-methoxy-1-(5-phenyl-2-pyrimidinyl)-2-propanesulfonamide;
(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide;
4-(3-chloro-2,6-dimethoxyphenyl)-N-(2-(4-chlorophenyl)ethyl)-5-(5-methyl-3-pyridinyl)-4H-1,2,4-triazole-3-sulfonamide;
(2R)—N-(4-(2,6-dimethoxyphenyl)-5-(5-methyl-3-pyridinyl)-4H-1,2,4-triazol-3-yl)-2-methyl-3-phenylpropanamide; or
(2S)—N-(4-(2,6-dimethoxyphenyl)-5-(5-methyl-3-pyridinyl)-4H-1,2,4-triazol-3-yl)-2-methyl-3-phenylpropanamide.

91. In another embodiment, the invention provides one of the compounds listed below or the pharmaceutically acceptable salt thereof, the stereoisomer of any of the foregoing, or the mixture thereof, wherein the compound is
(1S,2R)—N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide;
(1R,2R)—N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide;
(1R,2S)—N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide;
(1S,2S)—N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide;
(1R,2S)—N-(4-(4,6-dimethoxy-5-pyrimidinyl)-5-(2-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(2-pyridinyl)-4H-1,2,4-triazol-3-yl)-1-methoxy-1-(5-methyl-2-pyrimidinyl)-2-propanesulfonamide;
(1R,2R)—N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide;
(1S,2S)—N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide;
(2S,3R)—N-(4-(2,6-dimethoxyphenyl)-5-(5-methylpyridin-3-yl)-4H-1,2,4-triazol-3-yl)-N-methyl-3-(5-methylpyrimidin-2-yl)butane-2-sulfonamide;
(1S,2R)—N-(4-(2,6-dimethoxyphenyl)-5-(5-methyl-3-pyridinyl)-4H-1,2,4-triazol-3-yl)-1-methoxy-1-(5-methyl-1,3-oxazol-2-yl)-2-propanesulfonamide;
(1R,2S)—N-(4-(2,6-dimethoxyphenyl)-5-(5-methyl-3-pyridinyl)-4H-1,2,4-triazol-3-yl)-1-methoxy-1-(5-methyl-1,3-oxazol-2-yl)-2-propanesulfonamide;
(1R,2S)—N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide;
(1R,2S)—N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide;
(1S,2R)—N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide;
(2S,3R)—N-(4-(2,6-dimethoxyphenyl)-5-(6-(2-methoxyethoxy)-2-pyridinyl)-4H-1,2,4-triazol-3-yl)-3-(5-fluoro-2-pyrimidinyl)-2-butanesulfonamide;
(2S,3R)—N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(4-((2R)-1,4-dioxan-2-yl)-5-fluoro-2-pyrimidinyl)-2-butanesulfonamide;
(2S,3R)—N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(4-((2S)-1,4-dioxan-2-yl)-5-fluoro-2-pyrimidinyl)-2-butanesulfonamide;
(2S,3R)—N-(4-(2,6-dimethoxyphenyl)-5-(6-(methylamino)-2-pyridinyl)-4H-1,2,4-triazol-3-yl)-3-(5-fluoro-2-pyrimidinyl)-2-butanesulfonamide;
(1R,2S)-1-(5-bromo-6-methyl-2-pyridinyl)-N-(4-(2,6-dimethoxyphenyl)-5-(3-pyridinyl)-4H-1,2,4-triazol-3-yl)-1-hydroxy-2-propanesulfonamide;

(1S,2R)-1-(5-bromo-6-methyl-2-pyridinyl)-N-(4-(2,6-dimethoxyphenyl)-5-(3-pyridinyl)-4H-1,2,4-triazol-3-yl)-1-hydroxy-2-propanesulfonamide;

(2R,3R)—N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide;

(2S,3S)—N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide;

(2S,3R)—N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide;

(2R,3S)—N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide;

(2R,3R)—N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide;

(2R,3S)—N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide;

(2S,3R)—N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide;

(2S,3S)—N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide;

(2R,3R)—N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide;

(2R,3S)—N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide;

(2S,3R)—N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide;

(2S,3S)—N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide;

(2R,3R)—N-(4-(2,6-dimethoxyphenyl)-5-(6-methoxy-2-pyridinyl)-4H-1,2,4-triazol-3-yl)-3-(4-methyl-1H-pyrazol-1-yl)-2-butane sulfonamide;

(2R,3S)—N-(4-(2,6-dimethoxyphenyl)-5-(6-methoxy-2-pyridinyl)-4H-1,2,4-triazol-3-yl)-3-(4-methyl-1H-pyrazol-1-yl)-2-butane sulfonamide;

(2S,3R)—N-(4-(2,6-dimethoxyphenyl)-5-(6-methoxy-2-pyridinyl)-4H-1,2,4-triazol-3-yl)-3-(4-methyl-1H-pyrazol-1-yl)-2-butane sulfonamide;

(2S,3S)—N-(4-(2,6-dimethoxyphenyl)-5-(6-methoxy-2-pyridinyl)-4H-1,2,4-triazol-3-yl)-3-(4-methyl-1H-pyrazol-1-yl)-2-butane sulfonamide;

(2S)—N-(4-(2,6-dimethoxyphenyl)-5-(6-(methylamino)-2-pyridinyl)-4H-1,2,4-triazol-3-yl)-1-(5-fluoro-2-pyrimidinyl)-2-propanesulfonamide;

(2R)—N-(4-(2,6-dimethoxyphenyl)-5-(6-(methylamino)-2-pyridinyl)-4H-1,2,4-triazol-3-yl)-1-(5-fluoro-2-pyrimidinyl)-2-propanesulfonamide;

(1R,2S)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2-(difluoromethoxy)-6-methoxyphenyl)-5-(3-pyridinyl)-4H-1,2,4-triazol-3-yl)-1-methoxy-1-(5-methyl-2-pyrimidinyl)-2-propanesulfonamide;

(1R,2S)—N-(4-(2-(difluoromethoxy)-6-methoxy phenyl)-5-(5-methyl-3-pyridinyl)-4H-1,2,4-triazol-3-yl)-1-methoxy-1-(5-methyl-2-pyrimidinyl)-2-propanesulfonamide;

(1R,2S)—N-(4-(2,6-bis(difluoromethoxy)phenyl)-5-(3-pyridinyl)-4H-1,2,4-triazol-3-yl)-1-methoxy-1-(5-methyl-2-pyrimidinyl)-2-propanesulfonamide;

(1R,2S)—N-(4-(2,6-bis(difluoromethoxy)phenyl)-5-(5-methyl-3-pyridinyl)-4H-1,2,4-triazol-3-yl)-1-methoxy-1-(5-methyl-2-pyrimidinyl)-2-propanesulfonamide;

(2R,3R)—N-(4-(2,6-dimethoxyphenyl)-5-(5-methyl-3-pyridinyl)-4H-1,2,4-triazol-3-yl)-3-(5-methyl-2-pyrimidinyl)-2-butane sulfonamide;

(2S,3S)—N-(4-(2,6-dimethoxyphenyl)-5-(5-methyl-3-pyridinyl)-4H-1,2,4-triazol-3-yl)-3-(5-methyl-2-pyrimidinyl)-2-butane sulfonamide;

(2S,3R)—N-(4-(2,6-dimethoxyphenyl)-5-(3-pyridinyl)-4H-1,2,4-triazol-3-yl)-3-(5-methoxy-2-pyrimidinyl)-2-butane sulfonamide;

(1R,2S)—N-(4-(2,6-dimethylphenyl)-5-(5-methyl-3-pyridinyl)-4H-1,2,4-triazol-3-yl)-1-methoxy-1-(5-methyl-2-pyrimidinyl)-2-propanesulfonamide;

(1R,2S)—N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(2,6-dichlorophenyl)-5-(5-methyl-3-pyridinyl)-4H-1,2,4-triazol-3-yl)-1-methoxy-1-(5-methyl-2-pyrimidinyl)-2-propanesulfonamide;

N-(4-(2,6-dimethoxyphenyl)-5-(6-methoxy-2-pyridinyl)-4H-1,2,4-triazol-3-yl)-2-(5-fluoro-2-pyrimidinyl)ethanesulfonamide;

(1R,2S)—N-(4-(2,6-difluorophenyl)-5-(5-methyl-3-pyridinyl)-4H-1,2,4-triazol-3-yl)-1-methoxy-1-(5-methyl-2-pyrimidinyl)-2-propanesulfonamide;

(2R,3S)-3-(5-chloro-2-pyrimidinyl)-N-(4-(2,6-dimethoxyphenyl)-5-(5-methyl-3-pyridinyl)-4H-1,2,4-triazol-3-yl)-2-butane sulfonamide;

(2S,3R)-3-(5-chloro-2-pyrimidinyl)-N-(4-(2,6-dimethoxyphenyl)-5-(5-methyl-3-pyridinyl)-4H-1,2,4-triazol-3-yl)-2-butane sulfonamide;

(2R,3S)-3-(5-chloro-2-pyrimidinyl)-N-(4-(2,6-dimethoxyphenyl)-5-(3-pyridinyl)-4H-1,2,4-triazol-3-yl)-2-butane sulfonamide;

(2S,3R)-3-(5-chloro-2-pyrimidinyl)-N-(4-(2,6-dimethoxyphenyl)-5-(3-pyridinyl)-4H-1,2,4-triazol-3-yl)-2-butane sulfonamide;

(2S,3R)—N-(4-(2,6-dimethoxyphenyl)-5-(5-methyl-3-pyridinyl)-4H-1,2,4-triazol-3-yl)-3-(5-methoxy-2-pyrimidinyl)-2-butane sulfonamide;

(1R,2S)—N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide;

(1R,2R)—N-(4-(2,6-dimethoxyphenyl)-5-(5-methyl-3-pyridinyl)-4H-1,2,4-triazol-3-yl)-1-methoxy-1-(5-methoxy-2-pyrimidinyl)-2-propanesulfonamide;

(2S,3R)—N-(4-(2-fluoro-6-methoxyphenyl)-5-(5-methyl-3-pyridinyl)-4H-1,2,4-triazol-3-yl)-3-(S-methyl-2-pyrimidinyl)-2-butane sulfonamide;

(1R,2S)—N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide;

(1R,2S)—N-(4-(2,6-dimethoxyphenyl)-5-(6-methoxy-2-pyridinyl)-4H-1,2,4-triazol-3-yl)-1-(2-methoxy ethoxy)-1-(5-methyl-2-pyrimidinyl)-2-propanesulfonamide;

(2S,3R)-3-(5-chloro-2-pyrimidinyl)-N-(4-(2,6-dimethoxyphenyl)-5-(6-methoxy-2-pyridinyl)-4H-1,2,4-triazol-3-yl)-2-butane sulfonamide;

(2S,3R)-3-(5-cyano-2-pyrimidinyl)-N-(4-(2,6-dimethoxyphenyl)-5-(5-methyl-3-pyridinyl)-4H-1,2,4-triazol-3-yl)-2-butane sulfonamide;

(1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide;

(1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide;

(2R,3S)—N-(4-(2,6-dimethoxyphenyl)-5-(3-pyridinyl)-4H-1,2,4-triazol-3-yl)-3-(5-methyl-2-pyrazinyl)-2-butane sulfonamide;

(2S,3R)—N-(4-(2,6-dimethoxyphenyl)-5-(3-pyridinyl)-4H-1,2,4-triazol-3-yl)-3-(5-methyl-2-pyrazinyl)-2-butane sulfonamide;

(1R,2S)—N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide;

(1S,2R)—N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide;

(2R,3R)—N-(4-(2,6-dimethoxyphenyl)-5-(3-pyridinyl)-4H-1,2,4-triazol-3-yl)-3-(5-methoxy-2-pyrazinyl)-2-butane sulfonamide;

(2R,3S)—N-(4-(2,6-dimethoxyphenyl)-5-(3-pyridinyl)-4H-1,2,4-triazol-3-yl)-3-(5-methoxy-2-pyrazinyl)-2-butane sulfonamide;

(2S,3R)—N-(4-(2,6-dimethoxyphenyl)-5-(3-pyridinyl)-4H-1,2,4-triazol-3-yl)-3-(5-methoxy-2-pyrazinyl)-2-butane sulfonamide;

(2S,3S)—N-(4-(2,6-dimethoxyphenyl)-5-(3-pyridinyl)-4H-1,2,4-triazol-3-yl)-3-(5-methoxy-2-pyrazinyl)-2-butane sulfonamide;

(2R,3S)—N-(4-(2,6-dimethoxyphenyl)-5-(6-methoxy-2-pyridinyl)-4H-1,2,4-triazol-3-yl)-3-(5-methoxy-2-pyrazinyl)-2-butane sulfonamide;

(2S,3R)—N-(4-(2,6-dimethoxyphenyl)-5-(6-methoxy-2-pyridinyl)-4H-1,2,4-triazol-3-yl)-3-(5-methoxy-2-pyrazinyl)-2-butane sulfonamide;

(2S,3R)-3-(5-chloro-2-pyrimidinyl)-N-(4-(4,6-dimethoxy-5-pyrimidinyl)-5-(3-pyridinyl)-4H-1,2,4-triazol-3-yl)-2-butane sulfonamide;

(2S,3R)-3-(5-chloro-2-pyrimidinyl)-N-(4-(4,6-dimethoxy-5-pyrimidinyl)-5-(6-methoxy-2-pyridinyl)-4H-1,2,4-triazol-3-yl)-2-butane sulfonamide;

(1R,2S)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide;

(1R,2S)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide;

(2R,3S)-3-(5-chloro-2-pyrimidinyl)-N-(4-(2,4-dimethoxy-3-pyridinyl)-5-(3-pyridinyl)-4H-1,2,4-triazol-3-yl)-2-butane sulfonamide;

(2S,3R)-3-(5-chloro-2-pyrimidinyl)-N-(4-(2,4-dimethoxy-3-pyridinyl)-5-(3-pyridinyl)-4H-1,2,4-triazol-3-yl)-2-butane sulfonamide;

(1R,2S)-1-cyclobutyl-N-(4-(2,6-dimethoxyphenyl)-5-(5-methyl-3-pyridinyl)-4H-1,2,4-triazol-3-yl)-1-methoxy-2-propanesulfonamide;

(1S,2R)-1-cyclobutyl-N-(4-(2,6-dimethoxyphenyl)-5-(5-methyl-3-pyridinyl)-4H-1,2,4-triazol-3-yl)-1-methoxy-2-propanesulfonamide;

(1R,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide;

(1R,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide;

(1S,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide;

(1S,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide;

(1S,2S)—N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide;

(1R,2R)—N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide;

(1R,2S)—N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide;

(1S,2R)—N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide;

(2R)—N-(4-(2,6-dimethoxyphenyl)-5-(5-methyl-3-pyridinyl)-4H-1,2,4-triazol-3-yl)-2-hydroxy-2-(5-methyl-2-pyrimidinyl)ethanesulfonamide;

(2S)—N-(4-(2,6-dimethoxyphenyl)-5-(5-methyl-3-pyridinyl)-4H-1,2,4-triazol-3-yl)-2-hydroxy-2-(5-methyl-2-pyrimidinyl)ethanesulfonamide;

(1R,2S)—N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide;

(1S,2R)—N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide;

(2S,3R)—N-(4-(3,5-dibromo-2,6-dimethoxy phenyl)-5-(5-methyl-3-pyridinyl)-4H-1,2,4-triazol-3-yl)-3-(5-methyl-2-pyrimidinyl)-2-butane sulfonamide;

(2S,3R)—N-(5-(5-bromo-3-pyridinyl)-4-(2,6-dimethoxyphenyl)-4H-1,2,4-triazol-3-yl)-3-(5-methyl-2-pyrimidinyl)-2-butane sulfonamide;

(2S,3R)—N-(5-(5-cyclopropyl-3-pyridinyl)-4-(2,6-dimethoxyphenyl)-4H-1,2,4-triazol-3-yl)-3-(5-methyl-2-pyrimidinyl)-2-butane sulfonamide;

(1S,2R)—N-(4-(2,6-dimethoxyphenyl)-5-(3-pyridinyl)-4H-1,2,4-triazol-3-yl)-1-hydroxy-1-imidazo[1,2-a]pyridin-2-yl-2-propanesulfonamide;

(1R,2S)—N-(4-(2,6-dimethoxyphenyl)-5-(3-pyridinyl)-4H-1,2,4-triazol-3-yl)-1-hydroxy-1-imidazo[1,2-a]pyridin-2-yl-2-propanesulfonamide;

(1R,2S)—N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide;

(1S,2S)—N-(4-(2,6-dimethoxyphenyl)-5-(6-methyl-2-pyridinyl)-4H-1,2,4-triazol-3-yl)-1-(1-methylethoxy)-1-(5-methyl-2-pyrimidinyl)-2-propanesulfonamide;

(1R,2S)-1-methoxy-N-(4-(4-methoxy-6-oxo-1,6-dihydropyrimidin-5-yl)-5-(6-methoxypyridin-2-yl)-4H-1,2,4-triazol-3-yl)-1-(5-methylpyrimidin-2-yl)propane-2-sulfonamide;

(1R,2S)-1-methoxy-N-(4-(2-methoxy-3-pyridinyl)-5-(6-methoxy-2-pyridinyl)-4H-1,2,4-triazol-3-yl)-1-(5-methyl-2-pyrimidinyl)-2-propanesulfonamide;

(1R,2R)—N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide;

(1S,2S)—N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide;

(1R,2R)-1-(5-chloro-2-pyridinyl)-N-(4-(2,6-dimethoxyphenyl)-5-(5-methyl-3-pyridinyl)-4H-1,2,4-triazol-3-yl)-1-(1-methylethoxy)-2-propanesulfonamide;

(1S,2S)-1-(5-chloro-2-pyridinyl)-N-(4-(2,6-dimethoxyphenyl)-5-(5-methyl-3-pyridinyl)-4H-1,2,4-triazol-3-yl)-1-(1-methylethoxy)-2-propanesulfonamide;

(1R,2R)—N-(4-(2,6-dimethoxyphenyl)-5-(5-methyl-3-pyridinyl)-4H-1,2,4-triazol-3-yl)-1-(1-methylethoxy)-1-(5-methyl-2-pyrazinyl)-2-propanesulfonamide;

(1S,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrazinyl)-2-propanesulfonamide;

(1S,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide;

(1R,2S)-1-(5-(3,6-dihydro-2H-pyran-4-yl)-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;

(1R,2S)—N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide;

(1S,2R)—N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide;

(1R,2R)—N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide;

(1S,2S)—N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-methoxy-1-(5-(3-pyridinyl)-2-pyrimidinyl)-2-propanesulfonamide;

(1R,2S)—N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide;

(1S,2R)—N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide;

(1R,2R)—N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide;

(1S,2S)—N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide;

(2S,3R)—N-(4-(2,6-bis(difluoromethoxy)phenyl)-5-(5-methyl-3-pyridinyl)-4H-1,2,4-triazol-3-yl)-3-(5-methyl-2-pyrimidinyl)-2-butane sulfonamide;

(2R,3S)—N-(4-(2,6-dimethoxyphenyl)-5-(5-methyl-3-pyridinyl)-4H-1,2,4-triazol-3-yl)-3-hydroxy-4-hexyne-2-sulfonamide;

(2S,3R)—N-(4-(2,6-dimethoxyphenyl)-5-(5-methyl-3-pyridinyl)-4H-1,2,4-triazol-3-yl)-3-hydroxy-4-hexyne-2-sulfonamide;

(1R,2S)—N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide;

(1S,2R)—N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide;

(1R,2S)—N-(4-(2,6-dimethoxyphenyl)-5-(3-pyridinyl)-4H-1,2,4-triazol-3-yl)-1-hydroxy-1-(6-methyl-3-pyridazinyl)-2-propanesulfonamide;

(1S,2R)—N-(4-(2,6-dimethoxyphenyl)-5-(3-pyridinyl)-4H-1,2,4-triazol-3-yl)-1-hydroxy-1-(6-methyl-3-pyridazinyl)-2-propanesulfonamide;

(1S,2S)—N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide;

(1R,2R)—N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide;

(2S,3R)—N-(4-(4,6-dimethoxy-5-pyrimidinyl)-5-(2-pyridinyl)-4H-1,2,4-triazol-3-yl)-3-(5-methyl-2-pyrazinyl)-2-butane sulfonamide;

(2S,3R)—N-(4-(2,6-dimethoxyphenyl)-5-(2-pyridinyl)-4H-1,2,4-triazol-3-yl)-3-(5-methyl-2-pyrazinyl)-2-butane sulfonamide;

(2S,3R)—N-(4-(2,6-dimethoxyphenyl)-5-(2-pyridinyl)-4H-1,2,4-triazol-3-yl)-3-(5-methyl-2-pyrimidinyl)-2-butane sulfonamide;

(2S,3R)—N-(4-(4,6-dimethoxy-5-pyrimidinyl)-5-(2-pyridinyl)-4H-1,2,4-triazol-3-yl)-3-(5-methyl-2-pyrimidinyl)-2-butane sulfonamide;

(1S,2S)—N-(4-(4,6-dimethoxy-5-pyrimidinyl)-5-(2-pyridinyl)-4H-1,2,4-triazol-3-yl)-1-(1-methylethoxy)-1-(5-methyl-2-pyrimidinyl)-2-propanesulfonamide;

(1S,2S)—N-(4-(2,6-dimethoxyphenyl)-5-(2-pyridinyl)-4H-1,2,4-triazol-3-yl)-1-(1-methylethoxy)-1-(5-methyl-2-pyrimidinyl)-2-propanesulfonamide;

(1R,2S)—N-(4-(4,6-dimethoxy-5-pyrimidinyl)-5-(2-pyridinyl)-4H-1,2,4-triazol-3-yl)-1-methoxy-1-(5-methyl-2-pyrazinyl)-2-propanesulfonamide;

(1R,2S)—N-(4-(2,6-dimethoxyphenyl)-5-(2-pyridinyl)-4H-1,2,4-triazol-3-yl)-1-methoxy-1-(5-methyl-2-pyrazinyl)-2-propanesulfonamide;

(2S,3R)—N-(4-(2,6-difluorophenyl)-5-(6-methyl-2-pyridinyl)-4H-1,2,4-triazol-3-yl)-3-(5-methyl-2-pyrimidinyl)-2-butane sulfonamide;

(2S,3R)—N-(4-(2,6-difluorophenyl)-5-(6-methoxy-2-pyridinyl)-4H-1,2,4-triazol-3-yl)-3-(5-methyl-2-pyrimidinyl)-2-butane sulfonamide;

(2S,3R)—N-(4-(2,6-difluorophenyl)-5-(2-pyridinyl)-4H-1,2,4-triazol-3-yl)-3-(5-methyl-2-pyrimidinyl)-2-butane sulfonamide;

(2S,3R)-3-(5-chloro-2-pyrimidinyl)-N-(4-(2,6-difluorophenyl)-5-(6-methoxy-2-pyridinyl)-4H-1,2,4-triazol-3-yl)-2-butane sulfonamide;

(2S,3R)—N-(4-(2,6-difluorophenyl)-5-(6-methoxy-2-pyridinyl)-4H-1,2,4-triazol-3-yl)-3-(5-methoxy-2-pyrazinyl)-2-butane sulfonamide;

(2S,3R)-3-(5-chloro-2-pyrimidinyl)-N-(4-(2,6-difluorophenyl)-5-(6-methyl-2-pyridinyl)-4H-1,2,4-triazol-3-yl)-2-butane sulfonamide;

(2S,3R)—N-(4-(2,6-difluorophenyl)-5-(6-methoxy-2-pyridinyl)-4H-1,2,4-triazol-3-yl)-3-(5-methyl-2-pyrazinyl)-2-butane sulfonamide;

(2S,3R)—N-(4-(2,6-difluorophenyl)-5-(6-methoxy-2-pyridinyl)-4H-1,2,4-triazol-3-yl)-3-(5-methyl-2-pyrazinyl)-2-butane sulfonamide;

(2S,3R)—N-(4-(2,6-difluorophenyl)-5-(6-(methylamino)-2-pyridinyl)-4H-1,2,4-triazol-3-yl)-3-(5-methyl-2-pyrimidinyl)-2-butane sulfonamide;

(1S,2R)—N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide;

(2S,3R)—N-(4-(2,6-difluorophenyl)-5-(3-pyridinyl)-4H-1,2,4-triazol-3-yl)-3-(5-methyl-2-pyrimidinyl)-2-butane sulfonamide;

(2S,3R)—N-(4-(2,6-difluorophenyl)-5-(5-methyl-3-pyridinyl)-4H-1,2,4-triazol-3-yl)-3-(5-methoxy-2-pyrazinyl)-2-butane sulfonamide;
(2S,3R)—N-(4-(2,6-difluorophenyl)-5-(5-methyl-3-pyridinyl)-4H-1,2,4-triazol-3-yl)-3-(5-methyl-2-pyrazinyl)-2-butane sulfonamide;
(2S,3R)-3-(5-chloro-2-pyrimidinyl)-N-(4-(2,6-difluorophenyl)-5-(5-methyl-3-pyridinyl)-4H-1,2,4-triazol-3-yl)-2-butane sulfonamide;
(2S,3R)—N-(4-(2-methoxy phenyl)-5-(5-methyl-3-pyridinyl)-4H-1,2,4-triazol-3-yl)-3-(5-methyl-2-pyrimidinyl)-2-butane sulfonamide;
(2S,3R)—N-(4-(6-bromo-3-methoxy-2-pyridinyl)-5-(6-methoxy-2-pyridinyl)-4H-1,2,4-triazol-3-yl)-3-(5-fluoro-2-pyrimidinyl)-2-butane sulfonamide;
(2S,3R)—N-(4-(4,6-dimethoxy-5-pyrimidinyl)-5-(6-methoxy-2-pyridinyl)-4H-1,2,4-triazol-3-yl)-3-(5-methyl-2-pyrazinyl)-2-butane sulfonamide;
(3R,5S)—N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidine sulfonamide;
(3S,5R)—N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidine sulfonamide;
(2S,3R)-3-(5-chloro-2-pyridinyl)-N-(4-(4,6-dimethoxy-5-pyrimidinyl)-5-(3-pyridinyl)-4H-1,2,4-triazol-3-yl)-2-butane sulfonamide;
(2S,3R)—N-(4-(4,6-dimethoxy-5-pyrimidinyl)-5-(3-pyridinyl)-4H-1,2,4-triazol-3-yl)-3-(5-methoxy-2-pyrazinyl)-2-butane sulfonamide;
(1R,2S)—N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide;
(1S,2R)—N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide;
(3R,5S)—N-(4-(2,6-dimethoxyphenyl)-5-(3-pyridinyl)-4H-1,2,4-triazol-3-yl)-1-(5-fluoro-2-pyrimidinyl)-5-hydroxy-3-piperidine sulfonamide;
(3S,5R)—N-(4-(2,6-dimethoxyphenyl)-5-(3-pyridinyl)-4H-1,2,4-triazol-3-yl)-1-(5-fluoro-2-pyrimidinyl)-5-hydroxy-3-piperidine sulfonamide;
(2S,3R)—N-(4-(4,6-dimethoxy-5-pyrimidinyl)-5-(3-pyridinyl)-4H-1,2,4-triazol-3-yl)-3-(5-methyl-2-pyrazinyl)-2-butane sulfonamide;
(2S,3R)-3-(5-chloro-2-pyridinyl)-N-(4-(4-methoxy-6-oxo-1,6-dihydro-5-pyrimidinyl)-5-(3-pyridinyl)-4H-1,2,4-triazol-3-yl)-2-butane sulfonamide;
(2S,3R)-3-(5-chloro-2-pyridinyl)-N-(4-(4-hydroxy-6-oxo-1,6-dihydro-5-pyrimidinyl)-5-(3-pyridinyl)-4H-1,2,4-triazol-3-yl)-2-butane sulfonamide;
(3S,5S)—N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidine sulfonamide;
(3S,5R)—N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidine sulfonamide;
(3R,5S)—N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidine sulfonamide;
(3R,5R)—N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidine sulfonamide;
(3R,5R)—N-(4-(2,6-dimethoxyphenyl)-5-(3-pyridinyl)-4H-1,2,4-triazol-3-yl)-1-(5-fluoro-2-pyrimidinyl)-5-methoxy-3-piperidine sulfonamide;
(3S,5R)—N-(4-(2,6-dimethoxyphenyl)-5-(3-pyridinyl)-4H-1,2,4-triazol-3-yl)-1-(5-fluoro-2-pyrimidinyl)-5-methoxy-3-piperidine sulfonamide;
(3R,5S)—N-(4-(2,6-dimethoxyphenyl)-5-(3-pyridinyl)-4H-1,2,4-triazol-3-yl)-1-(5-fluoro-2-pyrimidinyl)-5-methoxy-3-piperidine sulfonamide;
(3S,5S)—N-(4-(2,6-dimethoxyphenyl)-5-(3-pyridinyl)-4H-1,2,4-triazol-3-yl)-1-(5-fluoro-2-pyrimidinyl)-5-methoxy-3-piperidine sulfonamide;
(3R,5S)—N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidine sulfonamide;
(3S,5R)—N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidine sulfonamide;
(3R,5R)—N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidine sulfonamide;
(3S,5S)—N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidine sulfonamide;
(1S,2S)—N-(4-(2,6-dimethoxyphenyl)-5-(6-methyl-2-pyridinyl)-4H-1,2,4-triazol-3-yl)-1-(1-methylethoxy)-1-(5-methyl-2-pyrazinyl)-2-propanesulfonamide;
(1S,2S)—N-(4-(2,6-dimethoxyphenyl)-5-(6-methoxy-2-pyridinyl)-4H-1,2,4-triazol-3-yl)-1-(1-methylethoxy)-1-(5-methyl-2-pyrazinyl)-2-propanesulfonamide;
(2S,3R)—N-(4-(2,6-difluorophenyl)-5-(5-methyl-3-pyridinyl)-4H-1,2,4-triazol-3-yl)-3-(5-methyl-2-pyrimidinyl)-2-butane sulfonamide;
(1R,2R)—N-(4-(2,6-dimethoxyphenyl)-5-(3-pyridinyl)-4H-1,2,4-triazol-3-yl)-1-imidazo[1,2-a]pyridin-2-yl-1-(1-methylethoxy)-2-propanesulfonamide;
(1S,2S)—N-(4-(2,6-dimethoxyphenyl)-5-(3-pyridinyl)-4H-1,2,4-triazol-3-yl)-1-imidazo[1,2-a]pyridin-2-yl-1-(1-methylethoxy)-2-propanesulfonamide;
(1S,2S)—N-(4-(4,6-dimethoxy-5-pyrimidinyl)-5-(5-methyl-3-pyridinyl)-4H-1,2,4-triazol-3-yl)-1-(1-methylethoxy)-1-(5-methyl-2-pyrimidinyl)-2-propanesulfonamide;
(3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidine sulfonamide;
(3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidine sulfonamide;
1-cyclopropyl-N-(4-(2,6-dimethoxyphenyl)-5-(6-methoxy-2-pyridinyl)-4H-1,2,4-triazol-3-yl)methanesulfonamide;
(2S,3R)—N-(5-(5-cyano-3-pyridinyl)-4-(2,6-dimethoxyphenyl)-4H-1,2,4-triazol-3-yl)-3-(5-methyl-2-pyrimidinyl)-2-butane sulfonamide;
5-(4-(2,6-dimethoxyphenyl)-5-(((((1S,2R)-1-methyl-2-(5-methyl-2-pyrimidinyl)propyl)sulfonyl)amino)-4H-1,2,4-triazol-3-yl)-3-pyridinecarboxylic acid;
(2S,3R)-3-(5-chloro-2-pyrimidinyl)-N-(5-(6-methoxy-2-pyridinyl)-4-(tetrahydro-2H-pyran-4-yl)-4H-1,2,4-triazol-3-yl)-2-butane sulfonamide;
(1R,2S)-1-(5-chloro-2-pyrimidinyl)-1-methoxy-N-(5-(6-methoxy-2-pyridinyl)-4-(tetrahydro-2H-pyran-4-yl)-4H-1,2,4-triazol-3-yl)-2-propanesulfonamide;
(1S,2S)—N-(5-(6-methoxy-2-pyridinyl)-4-(tetrahydro-2H-pyran-4-yl)-4H-1,2,4-triazol-3-yl)-1-(1-methylethoxy)-1-(5-methyl-2-pyrimidinyl)-2-propanesulfonamide;
(2S,3R)-3-(5-chloro-2-pyrimidinyl)-N-(4-(4-methoxy-2-oxo-1,2-dihydro-3-pyridinyl)-5-(3-pyridinyl)-4H-1,2,4-triazol-3-yl)-2-butane sulfonamide;

(2S,3R)-3-(5-chloro-2-pyridinyl)-N-(5-(6-methoxy-2-pyridinyl)-4-(tetrahydro-2H-pyran-4-yl)-4H-1,2,4-triazol-3-yl)-2-butane sulfonamide;

(1R,2S)-1-(5-chloro-2-pyridinyl)-1-methoxy-N-(5-(6-methoxy-2-pyridinyl)-4-(tetrahydro-2H-pyran-4-yl)-4H-1,2,4-triazol-3-yl)-2-propanesulfonamide;

(2S,3R)—N-(5-(6-methoxy-2-pyridinyl)-4-(tetrahydro-2H-pyran-4-yl)-4H-1,2,4-triazol-3-yl)-3-(5-methoxy-2-pyrimidinyl)-2-butanesulfonamide;

(2S,3R)—N-(5-(6-methoxy-2-pyridinyl)-4-(tetrahydro-2H-pyran-4-yl)-4H-1,2,4-triazol-3-yl)-3-(5-methyl-2-pyrazinyl)-2-butanesulfonamide;

(2S,3R)-3-(5-methoxy-2-pyrazinyl)-N-(5-(6-methoxy-2-pyridinyl)-4-(tetrahydro-2H-pyran-4-yl)-4H-1,2,4-triazol-3-yl)-2-butanesulfonamide;

(2S,3R)-3-(5-methoxy-2-pyridinyl)-N-(5-(6-methoxy-2-pyridinyl)-4-(tetrahydro-2H-pyran-4-yl)-4H-1,2,4-triazol-3-yl)-2-butanesulfonamide; or (2S,3R)—N-(4-(2,6-dimethoxyphenyl)-5-(5-(hydroxymethyl)-3-pyridinyl)-4H-1,2,4-triazol-3-yl)-3-(5-methyl-2-pyrimidinyl)-2-butanesulfonamide.

92. In some embodiments, the invention provides the compound of embodiment 91 or the pharmaceutically acceptable salt thereof, the stereoisomer of any of the foregoing, or the mixture thereof, wherein the compound is (1R,2S)—N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide.

93. In some embodiments, the invention provides the compound of embodiment 91 or the pharmaceutically acceptable salt thereof, the stereoisomer of any of the foregoing, or the mixture thereof, wherein the compound is (1R,2S)—N-(4-(4,6-dimethoxy-5-pyrimidinyl)-5-(2-pyridinyl)-4H-1,2,4-triazol-3-yl)-1-methoxy-1-(5-methyl-2-pyrimidinyl)-2-propanesulfonamide.

94. A pharmaceutical composition, comprising the compound of any one of embodiments 1-93 or the pharmaceutically acceptable salt thereof, the stereoisomer of any of the foregoing, or the mixture thereof, and at least one pharmaceutically acceptable excipient, carrier, or diluent.

95. The pharmaceutical composition of embodiment 94, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

96. The pharmaceutical composition of embodiment 94, further comprising a therapeutic agent selected from an angiotensin converting enzyme (ACE) inhibitor or an angiotensin-receptor blocker (ARB).

97. A method of treating a cardiovascular condition, the method comprising: administering to a subject an effective amount of the compound of any one of embodiments 1-93 or the pharmaceutically acceptable salt thereof, the stereoisomer of any of the foregoing, or the mixture thereof, or the pharmaceutical composition of embodiment 94.

98. The method of embodiment 97, wherein the cardiovascular condition is heart failure.

99. The method of embodiment 97, wherein the cardiovascular condition is heart failure with reduced ejection fraction.

100. The method of embodiment 97, wherein the cardiovascular condition is heart failure with preserved ejection fraction.

101. The method of embodiment 97, wherein the cardiovascular condition is chronic systolic heart failure or chronic diastolic heart failure.

102. The method of embodiment 97, wherein the cardiovascular condition is acute heart failure.

103. The method of embodiment 97, wherein the cardiovascular condition is hypertension.

104. A method of improving cardiac contractility in a subject suffering from a cardiovascular condition, the method comprising: administering to the subject an effective amount of the compound of any one of embodiments 1-93 or the pharmaceutically acceptable salt thereof, the stereoisomer of any of the foregoing, or the mixture thereof, or the pharmaceutical composition of embodiment 94, wherein cardiac contractility is improved after administration.

105. A method of increasing ejection fraction in a subject suffering from a cardiovascular condition, the method comprising: administering to the subject an effective amount of the compound of any one of embodiments 1-93 or the pharmaceutically acceptable salt thereof, the stereoisomer of any of the foregoing, or the mixture thereof, or the pharmaceutical composition of embodiment 94, wherein the ejection fraction is increased in the subject after administration.

106. A method of treating a condition in a subject where it is desired to activate the APJ Receptor, comprising administering to the subject an effective amount of the compound of any one of embodiments 1-93 or the pharmaceutically acceptable salt thereof, the stereoisomer of any of the foregoing, or the mixture thereof or the pharmaceutical composition of embodiment 94.

107. The method of embodiment 106, wherein the condition is obesity or diabetes.

108. The method of embodiment 106, wherein the condition is diabetic nephropathy or chronic kidney disease.

109. The method of any one of embodiments 97-108, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

110. The method of any one of embodiments 97-108, wherein the method includes administering at least one additional therapeutic agent to the subject, wherein the additional therapeutic agent is selected from an angiotensin converting enzyme (ACE) inhibitor or an angiotensin-receptor blocker (ARB).

111. A compound of any one of embodiments 1-93 or the pharmaceutically acceptable salt thereof, the stereoisomer of any of the foregoing, or the mixture thereof, or the pharmaceutical composition of embodiment 94 for use in treating a cardiovascular condition.

112. The compound of embodiment 111, wherein the cardiovascular condition is heart failure.

113. The compound of embodiment 111, wherein the cardiovascular condition is heart failure with reduced ejection fraction.

114. The compound of embodiment 111, wherein the cardiovascular condition is heart failure with preserved ejection fraction.

115. The compound of embodiment 111, wherein the cardiovascular condition is chronic systolic heart failure or chronic diastolic heart failure.

116. The compound of embodiment 111, wherein the cardiovascular condition is acute heart failure.

117. The compound of embodiment 111, wherein the cardiovascular condition is hypertension.

118. A compound of any one of embodiments 1-93 or the pharmaceutically acceptable salt thereof, the stereoisomer of any of the foregoing, or the mixture thereof, or the pharmaceutical composition of embodiment 94 for use in activating the APJ Receptor or for treating a condition where it is desirable to activate the APJ Receptor.

119. The compound of embodiment 118, wherein the condition is obesity or diabetes.

120. The compound of embodiment 118, wherein the condition is diabetic nephropathy or chronic kidney disease.

121. A use of the compound of any one of embodiments 1-93 or the pharmaceutically acceptable salt thereof, the stereoisomer of any of the foregoing, or the mixture thereof in the preparation of a medicament for treating a cardiovascular condition.

122. The use of embodiment 121, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

123. The use of embodiment 121, further comprising a therapeutic agent selected from an angiotensin converting enzyme (ACE) inhibitor or an angiotensin-receptor blocker (ARB).

124. The use of embodiment 121, wherein the cardiovascular condition is heart failure.

125. The use of embodiment 121, wherein the cardiovascular condition is heart failure with reduced ejection fraction.

126. The use of embodiment 121, wherein the cardiovascular condition is heart failure with preserved ejection fraction.

127. The use of embodiment 121, wherein the cardiovascular condition is chronic systolic heart failure or chronic diastolic heart failure.

128. The use of embodiment 121, wherein the cardiovascular condition is acute heart failure.

129. The use of embodiment 121, wherein the cardiovascular condition is acute heart failure.

130. A use of the compound of any one of embodiments 1-93 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

131. The use of embodiment 130, wherein the condition is obesity or diabetes.

132. The use of embodiment 130, wherein the condition is diabetic nephropathy or chronic kidney disease.

133. A treatment regimen for a cardiovascular disease, the regimen comprising: the compound of any one of embodiments 1-93 or the pharmaceutically acceptable salt thereof, the stereoisomer of any of the foregoing, or the mixture thereof.

134. The treatment regimen of embodiment 133, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

135. The treatment regiment of embodiment 133, wherein the regimen further comprises a therapeutic agent selected from an angiotensin converting enzyme (ACE) inhibitor or an angiotensin-receptor blocker (ARB).

136. A kit, the kit comprising: the compound of any one of embodiments 1-93 or the pharmaceutically acceptable salt thereof, the stereoisomer of any of the foregoing, or the mixture thereof.

137. The kit of embodiment 136, wherein the kit further comprises a therapeutic agent selected from an α-blocker, a 0-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

138. The kit of embodiment 136, wherein the kit further comprises a therapeutic agent selected from an angiotensin converting enzyme (ACE) inhibitor or an angiotensin-receptor blocker (ARB).

139 In another embodiment, the invention provides a compound of Formula V, a salt thereof, a tautomer thereof, or a salt of the tautomer:

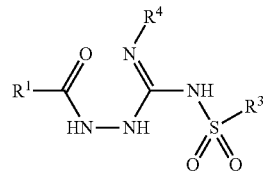

V wherein:

$R^1$ is an unsubstituted pyridyl, pyridonyl, or pyridine N-oxide, or is a pyridyl, pyridonyl, or pyridine N-oxide substituted with 1, 2, 3, or 4 $R^{1a}$ substituents;

$R^{1a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, haloalkyl)-O—($C_1$-$C_6$ alkyl), —O—($C_1$-$C_6$ perhaloalkyl)-OH, perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O) OH, —C(=O)—O—($C_1$-$C_6$ alkyl), —C(O)$NH_2$, —C(=O)NH($C_1$-$C_6$ alkyl), —C(=O)N($C_1$-$C_6$ alkyl)$_2$, phenyl, —C(=O)-(heterocyclyl), or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3b}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, alkyl)-O—($C_1$-$C_6$ alkyl), $C_2$-$C_6$ alkenyl, $C_2$-$C_6$ alkynyl, —$NH_2$, —NH($C_1$-$C_6$ alkyl), or $C_6$ alkyl)$_2$;

$R^{3b}$ and $R^{3c}$ are independently selected from H, —F, —Cl, —CN, —$C_1$-$C_6$ alkyl, —$C_1$-$C_6$ haloalkyl, —$C_1$-$C_6$ perhaloalkyl, —OH, —O—(C$_1$-C$_6$ alkyl), —O—(C$_1$-C$_6$ haloalkyl), perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3d}$ and R$^{3e}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3f}$ and R$^{3g}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3h}$ in each instance is independently selected from —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), —N(C$_1$-C$_6$ alkyl)$_2$, or oxo;

Q is a monocyclic or bicyclic C$_6$-C$_{10}$ aryl group, a monocyclic or bicyclic heteroaryl group with 5 to 10 ring members containing 1, 2, or 3 heteroatoms selected from N, O, or S, a C$_3$-C$_8$ cycloalkyl group, or a 3 to 7 membered heterocyclyl group containing 1, 2, or 3 heteroatoms selected from N, O, or S, wherein the C$_6$-C$_{10}$ aryl group, the heteroaryl group, the cycloalkyl group, and the heterocyclyl group are unsubstituted or are substituted with 1, 2, 3, or 4 R$^Q$ substituent;

R$^Q$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —C$_2$-C$_6$ alkenyl, —C$_2$-C$_6$ alkynyl, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(O)NH$_2$, —C(=O)NH(C$_1$-C$_6$ alkyl), —C(=O)N(C$_1$-C$_6$ alkyl)$_2$, —S(=O)$_2$—(C$_1$-C$_6$ alkyl), phenyl, or a heteroaryl group, and the Q heterocyclyl group may be substituted with 1 oxo R$^Q$ substituent;

R$^4$ is selected from a monocyclic or bicyclic C$_6$-C$_{10}$ aryl group, a monocyclic or bicyclic heteroaryl group with 5 to 10 ring members containing 1, 2, or 3 heteroatoms independently selected from N, O, or S, or a monocyclic or bicyclic heterocyclyl group with 5 to 10 ring members containing 1, 2, 3, or 4 heteroatoms independently selected from N, O, or S, wherein the C$_6$-C$_{10}$ aryl group, the heteroaryl group, or the heterocyclyl group are unsubstituted or are substituted with 1, 2, or 3 R$^{4a}$ substituents; and R$^{4a}$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), or —C(=O)N(C$_1$-C$_6$ alkyl)$_2$, and the heterocyclyl R$^1$ group may be further substituted with 1 oxo substituent.

140. The compound of embodiment 139, the salt thereof, the tautomer thereof, or the salt of the tautomer, wherein the compound has any of the R$^1$, R$^{1a}$, R$^3$, R$^{3a}$, R$^{3b}$, R$^{3c}$, R$^{3d}$, R$^{3e}$, R$^{3f}$, R$^{3g}$, R$^{3h}$, R$^4$, R$^{4a}$, Q, or R$^Q$, values or combinations of values of any one of embodiments 2-62.

141. In another embodiment, the invention provides a method for preparing a compound of Formula VI, a salt thereof, a tautomer thereof, or a salt of the tautomer:

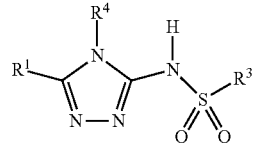

VI the method comprising:
a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

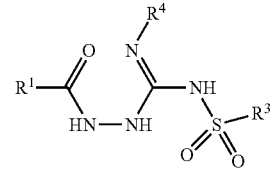

V wherein:
R$^1$ is an unsubstituted pyridyl, pyridonyl, or pyridine N-oxide, or is a pyridyl, pyridonyl, or pyridine N-oxide substituted with 1, 2, 3, or 4 R$^{1a}$ substituents;

R$^{1a}$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —C$_2$-C$_6$ alkenyl, —O—(C$_1$-C$_6$ alkyl)-OH, —O—(C$_1$-C$_6$ alkyl)-O—(C$_1$-C$_6$ alkyl), —O—(C$_1$-C$_6$ haloalkyl)-OH, haloalkyl)-O—(C$_1$-C$_6$ alkyl), —O—(C$_1$-C$_6$ perhaloalkyl)-OH, perhaloalkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(O)NH$_2$, —C(=O)NH(C$_1$-C$_6$ alkyl), —C(=O)N(C$_1$-C$_6$ alkyl)$_2$, phenyl, —C(=O)-(heterocyclyl), or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;

R$^3$ is selected from an unsubstituted C$_1$-C$_{10}$ alkyl, a C$_1$-C$_{10}$ alkyl substituted with 1, 2, or 3 R$^{3a}$ substituents, a group of formula —(CR$^{3b}$R$^{3c}$)-Q, a group of formula —NH—(CR$^{3b}$R$^{3c}$)-Q, a group of formula —(CR$^{3b}$R$^{3c}$)—C(=O)-Q, a group of formula —(CR$^{3d}$R$^{3e}$)—(CR$^{3f}$R$^{3g}$)-Q, a group of formula —(CR$^{3b}$=CR$^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 R$^{3b}$ substituents;

R$^{3a}$ in each instance is independently selected from —F, —Cl, —CN, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, alkyl)-O—(C$_1$-C$_6$ alkyl), C$_2$-C$_6$ alkenyl, C$_2$-C$_6$ alkynyl, —NH$_2$, —NH(C$_1$-C$_6$ alkyl), or C$_6$ alkyl)$_2$;

R$^{3b}$ and R$^{3c}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), perhaloalkyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), perhaloalkyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), perhaloalkyl), alkyl)-OH, alkyl)-O—($C_1$-$C_6$ alkyl), —$NH_2$, —NH($C_1$-$C_6$ alkyl), or —N($C_1$-$C_6$ alkyl)$_2$;

$R^{3b}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, or a monocyclic or bicyclic heterocyclyl group with 5 to 10 ring members containing 1, 2, 3, or 4 heteroatoms independently selected from N, O, or S, wherein the $C_6$-$C_{10}$ aryl group, the heteroaryl group, or the heterocyclyl group are unsubstituted or are substituted with 1, 2, or 3 $R^{4a}$ substituents; and $R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$, and the heterocyclyl $R^4$ group may be further substituted with 1 oxo substituent.

142. The method of embodiment 141, wherein $R^1$, $R^{1a}$, $R^3$, $R^{3a}$, $R^{3b}$, $R^{3c}$, $R^{3d}$, $R^{3e}$, $R^{3f}$, $R^{3g}$, $R^{3h}$, $R^4$, $R^{4a}$, Q, or $R^Q$, have any of the values or combination of values of any one of embodiments 2-62.

143. The method of embodiment 141 or embodiment 142, wherein cyclizing further comprises heating the compound of Formula V, the salt thereof, the tautomer thereof, or the salt of the tautomer in the presence of the acid or the base.

144. The method of embodiment 143, wherein heating the compound of Formula V, the salt thereof, the tautomer thereof, or the salt of the tautomer comprises heating the compound to a temperature of from 50° C. to 100° C.

145. The method of embodiment 143, wherein heating the compound of Formula V, the salt thereof, the tautomer thereof, or the salt of the tautomer comprises heating the compound to a temperature of from 60° C. to 85° C.

146. The method of any one of embodiments 141-145, wherein the cyclizing of the compound of Formula V, the salt thereof, the tautomer thereof, or the salt of the tautomer is performed in the presence of the base.

147 The method of any one of embodiments 141-146, wherein the base is a metal hydroxide.

148. The method of embodiment 147, wherein the metal hydroxide is selected from NaOH or LiOH.

149. The method of any one of embodiments 146-148, wherein the cyclizing is carried out in an alcohol solvent.

150. The method of embodiment 149, wherein the alcohol is isopropanol.

151. The method of any one of embodiments 141-145, wherein cyclizing further comprises heating the compound of Formula V, the salt thereof, the tautomer thereof, or the salt of the tautomer in the presence of the acid.

152. The method of embodiment 151, wherein the acid is selected from a sulfonic acid, a carboxylic acid, polyphosphoric acid, phosphoric acid, sulfuric acid, or hydrochloric acid.

153. The method of embodiment 152, wherein the sulfonic acid is methanesulfonic acid.

154. The method of embodiment 152, wherein the acid is trifluoroacetic acid, acetic acid, or trichloroacetic acid.

155. The method of any one of embodiments 151-154, wherein the cyclizing is carried out in a cyclic ether, an acyclic ether, N,N-dimethylformamide, or acetonitrile.

156. The method of embodiment 155, wherein the cyclizing is carried out in a cyclic ether.

157. The method of embodiment 156, wherein the cyclic ether is selected from tetrahydrofuran, tetrahydropyran, or 1,4-dioxane.

158. The method of embodiment 156, wherein the cyclic ether is 1,4-dioxane.

159. In another embodiment, the invention provides a compound of Formula VII, a salt thereof, a tautomer thereof, or a salt of the tautomer:

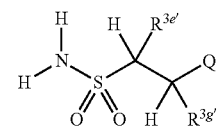

VII wherein:

$R^{3e'}$ is a —$C_1$-$C_6$ alkyl;

$R^{3g'}$ is selected from —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, or —O—($C_1$-$C_6$ alkyl)-O—($C_1$-$C_6$ alkyl);

Q' is a monocyclic 6-membered heteroaryl group with 1, 2, or 3 N heteroatoms, wherein the heteroaryl group is unsubstituted or is substituted with 1, 2, or 3 4 $R^{Q'}$ substituent;

$R^{Q'}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl).

160. The compound of embodiment 159, the salt thereof, the tautomer thereof, or the salt of the tautomer, wherein Q' is selected from a pyridinyl, pyrimidinyl, or pyrazinyl group that is unsubstituted or is substituted with 1, or 2 $R^{Q'}$ substituent.

161. The compound of embodiment 159, the salt thereof, the tautomer thereof, or the salt of the tautomer, wherein Q is selected from

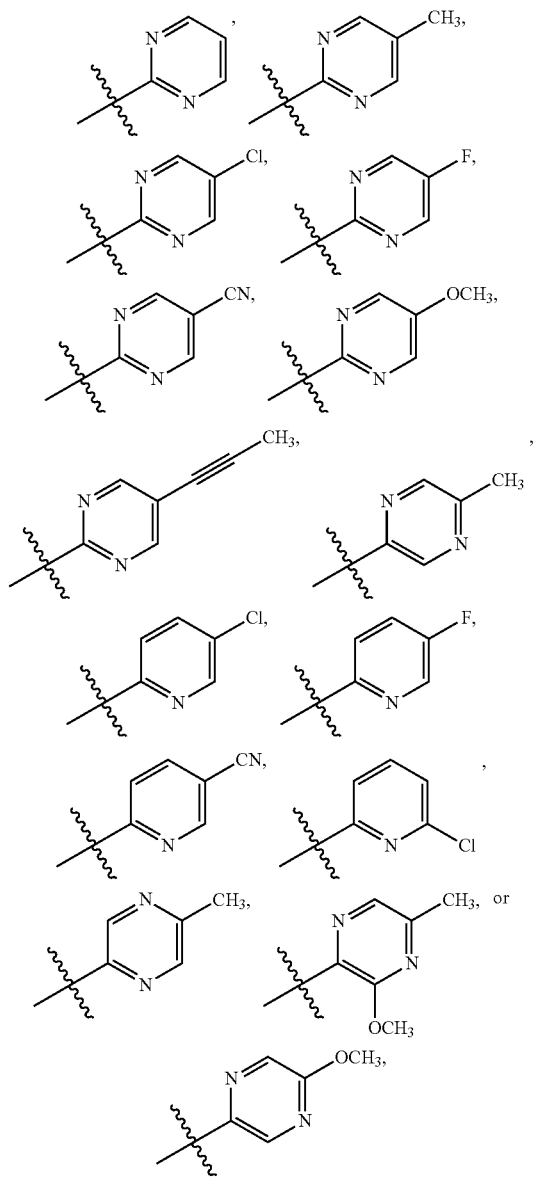

wherein the symbol ∿, when drawn across a bond, indicates the point of attachment to the rest of the molecule.

162. The compound of embodiment 159, the salt thereof, the tautomer thereof, or the salt of the tautomer, wherein Q' is selected from

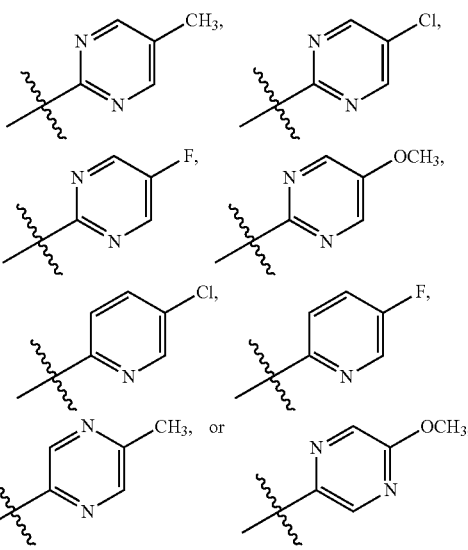

wherein the symbol ∿, when drawn across a bond, indicates the point of attachment to the rest of the molecule.

163. The compound of any one of embodiments 159-162, the salt thereof, the tautomer thereof, or the salt of the tautomer, wherein $R^{3e'}$ is a —CH$_3$.

164. The compound of any one of embodiments 159-163, the salt thereof, the tautomer thereof, or the salt of the tautomer, wherein $R^{3g'}$ is a —$C_1$-$C_6$ alkyl.

165. The compound of embodiment 164, the salt thereof, the tautomer thereof, or the salt of the tautomer, wherein $R^{3g'}$ is a CH$_3$.

166. The compound of any one of embodiments 159-163, the salt thereof, the tautomer thereof, or the salt of the tautomer, wherein $R^{3g'}$ is a alkyl).

167. The compound of embodiment 166, the salt thereof, the tautomer thereof, or the salt of the tautomer, wherein $R^{3g'}$ is selected from —O—CH$_3$, —O—CH$_2$CH$_3$, or —O—CH(CH$_3$)$_2$.

168. The compound of any one of embodiments 159-162, the salt thereof, the tautomer thereof, or the salt of the tautomer, wherein the compound is selected from

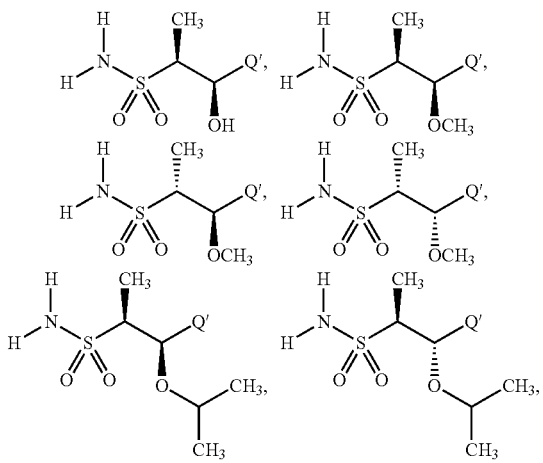

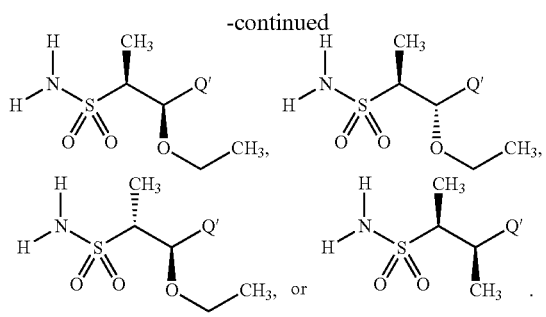

169. In still other embodiments, the invention provides any one of the compounds of embodiment 168.

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet where the effective amount of the active ingredient ranges from 5 mg to 60 mg, from 6 mg to 58 mg, from 10 mg to 40 mg, from 15 mg to 30 mg, from 16 mg to 25 mg, or from 17 mg to 20 mg. In some such compositions, the amount of active ingredient is 17 mg.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to treat a number of diseases and disorders. Thus, in some embodiments, the invention provides a method of treating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrythymia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, edema, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for treating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for treating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes. In other embodiments, the condition is cardiac wasting.

The compounds of the invention may find utility in treating a number of other conditions. For example, the compounds of the invention may find utility in treating patients with conditions related to renal perfusion, hyperclycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activitating stem cells and progeneitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current (If) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisturesensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 min at 1.5 mL/minute; System B: Zorbax SB-C8, 4.6×75 mm, 10 to 90% ACN in $H_2O$ with 0.1% formic acid for 12 min at 1.0 mL/minute). Silica gel chromatography was generally performed with prepacked silica gel cartridges (Biotage or Teledyne-Isco). $^1H$ NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 μL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

The following Abbreviations are used to refer to various reagents and solvents:
ACN Acetonitrile
AcOH Acetic Acid
CV Column volumn
day or days
DAST Diethylaminosulfur trifluoride
DCM Dichloromethane
DIEA N,N-Diisopropylethylamine
DMF N,N-Dimethylformamide
DMA Dimethylacetamide
DMAP 4-Dimethylaminopyridine
DMSO Dimethylsulfoxide
EDCI 1-Ethyl-3-(3-dimethylaminopropyl)carbodiimide
EtOAc Ethyl Acetate
EtOH Ethanol
h hour or hours
HATU 1-[Bis(dimethylamino)methylene]-1H-1,2,3-triazolo[4,5-b]pyridinium 3-oxid hexafluorophosphate
IPA Isopropanol
min minute or minutes
LAH Lithium aluminum hydride
MeOH Methanol
MTBE Methyl t-butyl ether
NBS N-Bromosuccinimide
NMP N-Methylpyrrolidone
RT Room temperature
TBAF Tetrabutylammonium fluoride
TBME t-Butyl methyl ether
TBS t-Butyldimethylsilane
TEA Triethylamine
TFA Trifluoroacetic acid
THF Tetrahydrofuran
TLC Thin Layer Chromatography Example 1: Preparation of 2-isothiocyanato-1,3-dimethoxybenzene

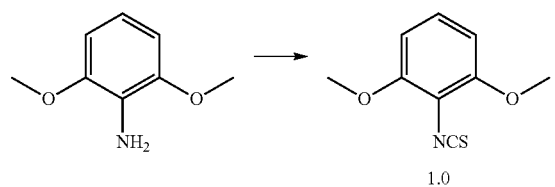

2-isothiocyanato-1,3-dimethoxybenzene, Example 1.0

To a solution of 2,6-dimethoxyaniline (500 g, 3.25 mol, 1 eq) in DCM (5.0 L) was added 2,6-lutidine (1.5 L, 13.0 mol, 4 eq). The reaction mixture was cooled to 0° C. (internal temperature) and $CSCl_2$ (374 mL, 4.88 mol, 1.5 eq) was added drop-wise. The reaction mixture was allowed to stir for 2 h. The solvent was evaporated under reduced pressure and the residue was purified on silica gel to provide the title compound 1.0, 2-isothiocyanato-1,3-dimethoxybenzene as white solid (1.06 g, 2.80 mol, 86%). LCMS (ESI pos. ion) m/z: 196 (M+H)$^+$. $^1H$ NMR (400 MHz, CDCl$_3$) δ 7.16 (t, J=8.48 Hz, 1H), 6.55 (d, J=8.48 Hz, 2H), 3.90 (s, 6H).

The compounds set forth in the following Table were synthesized following the procedure in Example 1.0 using the known starting material as described.

TABLE 1

| Example | Reagents | Structure, Name and Data |
|---|---|---|
| 1.1 | 4,6-dimethoxypyrimidin-5-amine (D-L Chiral chemicals) | 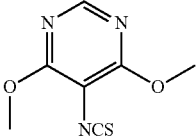  5-isothiocyanato-4,6-dimethoxypyrimidine. LCMS-ESI (POS.) m/z: 198.1 (M + H)+. |
| 1.2 | o-Anisidine (Acros) | 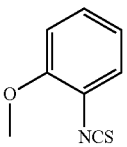  1-isothiocyanato-2-methoxybenzene. $^1$H NMR (400 MHz, DMSO-d6) δ 3.89 (s, 3H), 6.96 (td, J = 7.68, 1.27 Hz, 1H), 7.16 (dd, J = 8.31, 1.27 Hz, 1H), 7.30 (dd, J = 7.92, 1.66 Hz, 1H), 7.31-7.37 (m, 1H). |

Example 1.3: Preparation of 3-isothiocyanato-1-methyl-1H-indole

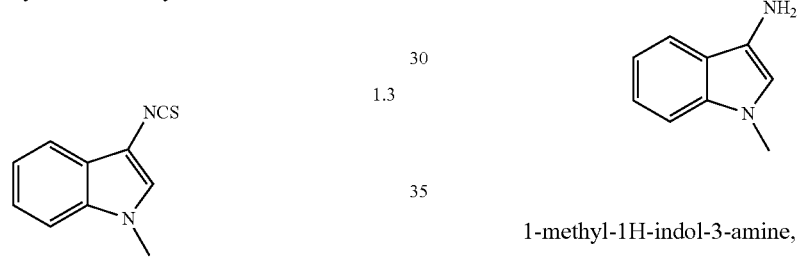

tert-butyl (1-methyl-1H-indol-3-yl)carbamate, Example 1.31

To a stirred solution of 1-methylindole-3-carboxylic acid (commercially available from Sigma-Aldrich Corp, St. Louis, Mo., USA) (10 g, 57.1 mmol) in THF (190 mL) was added TEA (7.9 mL, 57.1 mmol) followed by diphenyl phosphoryl azide (12.3 mL, 57.1 mmol). The reaction was stirred for 36 h, after which the reaction was concentrated in vacuo and placed in tert-butanol (54.6 mL). The reaction was further stirred at 90° C. over the weekend. Thereafter, water was added to the reaction and the mixture was extracted with EtOAc and concentrated in vacuo. The residue was purified on silica gel eluting with 0-30% EtOAc in hexanes to give 1.31 (7.1 g, 28.8 mmol, 51%). LCMS-ESI (POS.) m/z: 247.3 (M+H)+.

1-methyl-1H-indol-3-amine, Example 1.32

To a stirred solution of 1.31 (7.1 g, 28.8 mmol) in EtOAc (96 mL) was added concentrated HCl (28.8 mL). The reaction was then stirred for 7 d. Thereafter, the mixture was partially concentrated in vacuo to form a precipitate which was filtered off. The solid 1.32 (1.0 g, 6.84 mmol) was taken on without further purification to the next step. LCMS-ESI (POS.) m/z: 147.2 (M+H)+.

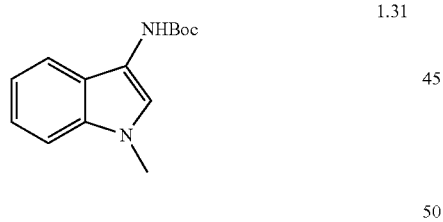

3-isothiocyanato-1-methyl-1H-indole, Example 1.3

To a stirred solution of 1,1"-thiocarbonyldi-2(1H)-pyridone (1.6 g, 6.84 mmol) in dry DCM (17.1 mL) was added a solution of 1-methyl-1H-indol-3-amine 1.32 (1 g, 6.84 mmol) in DCM (17.1 mL) via an addition funnel at RT over 40 min. The reaction was further stirred for 16 h. Thereafter, the reaction was concentrated in vacuo and purified on a silica gel column, employing a gradient of 0-30% EtOAc in heptanes, to give 1.3 as a white solid (1.0 g, 5.31 mmol, 78%). LCMS-ESI (POS.) m/z: 189.1 (M+H)+.

Example 1.4: Preparation of 2-isothiocyanato-1,3-di ([²H₃]methoxy)benzene

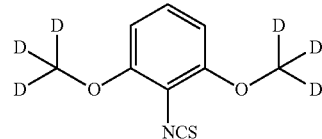

1.4

Step 1: 2-bromo-1,3-di([²H₃]methoxy)benzene, Example 1.41

To a round-bottomed flask containing 2-bromoresorcinol (1.00 g, 5.29 mmol, Chem Impex International) was added DMF (10 mL), potassium carbonate (1.828 g, 13.23 mmol), and methyl iodide-1)₃ (0.988 mL, 15.87 mmol, IsoTec). The reaction was stirred at RT under N₂ for 20 h. The reaction was diluted with water (50 mL) and extracted with EtOAc (3×40 mL), the organic layers were combined, dried (MgSO₄), and concentrated. Purification by flash chromatography (40 g SiO₂ 0-20% EtOAc/hexanes) gave 2-bromo-1,3-di([²H₃]methoxy)benzene (1.41, 1.06 g, 4.75 mmol, 90% yield) as a white solid.

Step 2: 2-amino-1,3-di([²H₃]methoxy)benzene, Example 1.42

To a 25 mL round bottom flask containing 2-bromo-1,3-di([²H₃]methoxy)benzene (Example 1.41, 960 mg, 4.30 mmol), 2,2,2-trifluoroacetamide (973 mg, 8.61 mmol), potassium carbonate (2379 mg, 17.21 mmol), and copper(I) iodide (164 mg, 0.861 mmol) was added ACN (10 mL) and trans-N1,N2-dimethylcyclohexanes-1,2-diamine (0.166 mL, 1.72 mmol). The bright blue suspension was sparged with Argon for 5 min, then the flask was fitted with an air cooled condenser and heated in a 80° C. oil bath and stirred for 16 h under N₂. The reaction was cooled to RT, MeOH (5 mL) and H₂O (5 mL) were added, and the reaction was heated in a 65° C. oil bath for 7 h. The mixture was cooled to RT and EtOAc (25 mL) and water (25 mL) were added. The mixture was transferred to a separatory funnel and the layers were separated. The aqueous layer was extracted EtOAc (50 mL). The combined organic extracts were washed with water (50 mL), brine (100 mL), dried (MgSO₄), filtered and concentrated to give the amine as a tan foam. Purification by flash chromatography (12 g SiO₂, 0-100% 3:1 EtOAc:EtOH/heptane) gave 2-amino-1,3-di([²H₃]methoxy)benzene (1.42, 400 mg, 2.51 mmol, 58% yield) as a tan foam. LCMS-ESI (POS.) m/z: 160.2 (M+H)⁺.

2-isothiocyanato-1,3-di([²H₃]methoxy)benzene, Example 1.4

To a 100 mL round bottom flask containing 2-amino-1,3-di([²H₃]methoxy)benzene (1.42, 400 mg, 2.51 mmol) in DCM (20 mL) at RT was added 1,1''-thiocarbonyldi-2(1H)-pyridone (613 mg, 2.64 mmol). The reaction was stirred at RT under N₂ for 16 h. The reaction mixture was then concentrated to 10 mL and directly purified by flash chromatography (40 g SiO₂, 20-100% EtOAc/hexanes) to provide 1.4 (480 mg, 2.39 mmol, 95% yield) as a white solid.

¹H NMR (300 MHz, CDCl₃) δ=7.15 (t, J=8.4 Hz, 1H), 6.54 (d, J=8.5 Hz, 2H). LCMS-ESI (POS.) m/z: 202.2 (M+H)⁺.

Example 1.5: Preparation of 1,3-bis(difluoromethoxy)-2-isothiocyanatobenzene

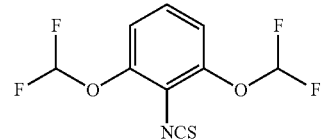

1.5

Step 1: 2-bromo-1,3-bis(difluoromethoxy)benzene, 1.51

To a round bottom flask containing 2-bromoresorcinol (1.07 g, 5.66 mmol, Chem Impex International) was added DMF (10 mL), cesium carbonate (5.53 g, 16.98 mmol) and sodium 2-chloro-2,2-difluoroacetate (2.59 g, 16.98 mmol, Aldrich). The reaction was heated in a 100° C. oil bath under N₂ for 3 h. The reaction was cooled to RT, diluted with water (25 mL) and extracted with EtOAc (3×20 mL). The combined organic layers were dried (MgSO₄) and concentrated. Purification by flash chromatography (40 g SiO₂, 0-20% EtOAc/hexanes) gave 2-bromo-1,3-bis(difluoromethoxy)benzene (1.51, 680 mg, 2.35 mmol, 41.6% yield) as a clear, colorless oil.

Step 2: 2,6-bis(difluoromethoxy)aniline, 1.52

To a round bottom flask containing 2-bromo-1,3-bis(difluoromethoxy)benzene (1.51, 410 mg, 1.42 mmol) was added copper(i) iodide (54.0 mg, 0.28 mmol), sodium azide (277 mg, 4.26 mmol), and (+)-sodium 1-ascorbate (56.2 mg, 0.28 mmol). EtOH (5 mL) and water (2 mL) were added, and the reaction mixture was stirred under N₂ and degassed with Ar for 10 min. Trans-N,N'-dimethyl-1,2,cyclohexanesdiamine (44.7 µL, 0.28 mmol) was added via syringe, and the blue suspension was heated in an 80° C. oil bath for 18 h. The reaction was cooled to RT, diluted into 9:1 saturated aqueous ammonium chloride ammonium hydroxide (50 mL), and extracted with EtOAc (2×25 mL). The organic layers were combined, washed with 9:1 saturated aqueous ammonium chloride ammonium hydroxide (20 mL), dried (MgSO₄), and concentrated to give a brown oil (1.52), which was used without purification in the next step. The oil from above was dissolved in THF (5 mL) and water (2 mL) and trimethylphosphine (1.0M solution in THF, 1.4 mL, 1.4 mmol) was added. The reaction was stirred under N₂ for 4 h at RT. The reaction was poured into saturated aqueous sodium bicarbonate (25 mL) and extracted with EtOAc (2×25 mL). The combined organic layers were dried (MgSO₄) and concentrated to give a yellow oil. Purification by flash chromatography (12 g SiO₂, 0-50% EtOAc/hexanes) gave 2,6-bis(difluoromethoxy)aniline (1.52, 106 mg, 0.47 mmol, 33% yield over 2 steps) as a light yellow oil. LCMS-ESI (POS.) m/z: 226.1 (M+H)⁺.

Step 3: 1,3-bis(difluoromethoxy)-2-isothiocyanatobenzene, 1.5

To a round bottom flask with 2,6-bis(difluoromethoxy)aniline (251 mg, 1.12 mmol) in DCM (5 mL) at was added 1,1"-thiocarbonyldi-2(1H)-pyridone (272 mg, 1.17 mmol, Aldrich). The reaction was stirred at RT under N₂ for 5.5 h. The reaction mixture obtained was concentrated to give an orange solid which was used without further purification.

Example 1.6: Preparation of 4-isothiocyanatopyridine

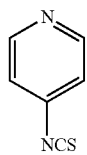

4-isothiocyanatopyridine, Example 1.6

To a 20 mL vial containing pyridin-4-amine (30.0 mg, 0.32 mmol, Aldrich) in DCM (2 mL) at RT was added 1,1"-thiocarbonyldi-2(1H)-pyridone (78 mg, 0.34 mmol, Aldrich). The reaction was stirred at RT under N₂ for 5 h. The reaction was concentrated to give an orange solid which was used without further purification. LCMS-ESI (POS.) m/z: 137.1 (M+H)⁺.

Example 1.7: Preparation of 1-ethoxy-2-isothiocyanato-3-methoxybenzene

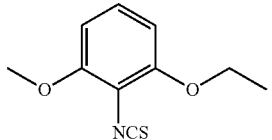

Step 1: 1-ethoxy-3-methoxy-2-nitrobenzene, Example 1.71

To a flask containing 1-fluoro-3-methoxy-2-nitrobenzene (219 mg, 1.28 mmol, Apollo Scientific) under N₂ was added EtOH (1 mL) and potassium 2-methylpropan-2-olate (1.0 M in THF), 2.56 mL, 2.56 mmol). The reaction was stirred under N₂ at RT for 73 h. The reaction was diluted with water (10 mL) and extracted with EtOAc (3×10 mL). The organic layers were combined, dried (MgSO₄) and concentrated in vacuo. Purification by flash chromatography (12 g SiO₂, 0-50% EtOAc/hexanes) gave 1-ethoxy-3-methoxy-2-nitrobenzene as a light tan oil which was isolated as a 2:1 mixture of desired product and an undesired by-product (that was not characterized), the mixture was used in the next step without further purification.

Step 2: 2-ethoxy-6-methoxyaniline, Example 1.72

To 1-ethoxy-3-methoxy-2-nitrobenzene (1.71) was added iron powder (142 mg, 2.54 mmol) and ammonium chloride (27.1 mg, 0.507 mmol). EtOH (8 mL) and H₂O (0.8 mL) were added, and the vial was sealed and heated in an oil bath at 80° C. for 2 h. The suspension was filtered and the filtrate concentrated. Purification by flash chromatography (12 g SiO₂, 0-50% EtOAc/hexanes) gave 2-ethoxy-6-methoxyaniline (1.72) as a light yellow oil. LCMS-ESI (POS.) m/z: 168.2 (M+H)⁺.

Step 3: 1-ethoxy-2-isothiocyanato-3-methoxybenzene, Example 1.7

To a 50 mL round bottom flask containing 2-ethoxy-6-methoxyaniline (85 mg, 0.508 mmol) in DCM (5 mL) at RT was added 1,1'-thiocarbonylbis(pyridin-2(1H)-one) (118 mg, 0.51 mmol). The reaction was stirred at RT under N₂ for 20 h. The reaction mixture obtained was concentrated to give the title compound as an orange solid which was used without further purification. LCMS-ESI (POS.) m/z: 210.2 (M+H)⁺.

Example 1.8: Preparation of 5-isothiocyanato-4,6-dimethoxypyrimidine

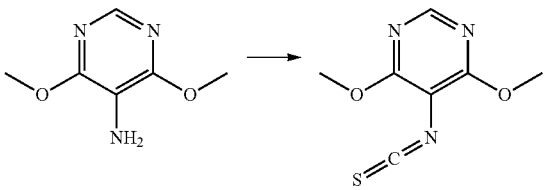

5-isothiocyanato-4,6-dimethoxypyrimidine, Example 1.8

To a stirred solution of 1,1"-thiocarbonyldi-2(1H)-pyridone (14.97 g, 64.5 mmol) in dry DCM (75 mL), was added a solution of 4,6-dimethoxypyrimidin-5-amine (D-L Chiral chemicals, 10 g, 64.5 mmol) in DCM (75 mL) dropwise via an addition funnel at RT over 40 min. The reaction was further stirred for 16 h. The reaction was concentrated in vacuo and purified on silica gel (0-30% EtOAc in heptanes) to give the desired compound 1.8 as a white solid (12.75 g, 64.7 mmol, 100% yield). LCMS-ESI (POS.) m/z: 198.1 (M+H)⁺.

Example 2.0: Preparation of 3-(5-bromo-4-(2,6-dimethoxyphenyl)-4H-1,2,4-triazol-3-yl)-5-methylpyridine

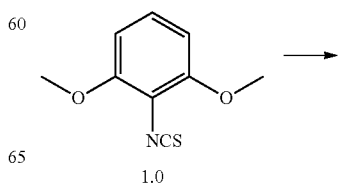

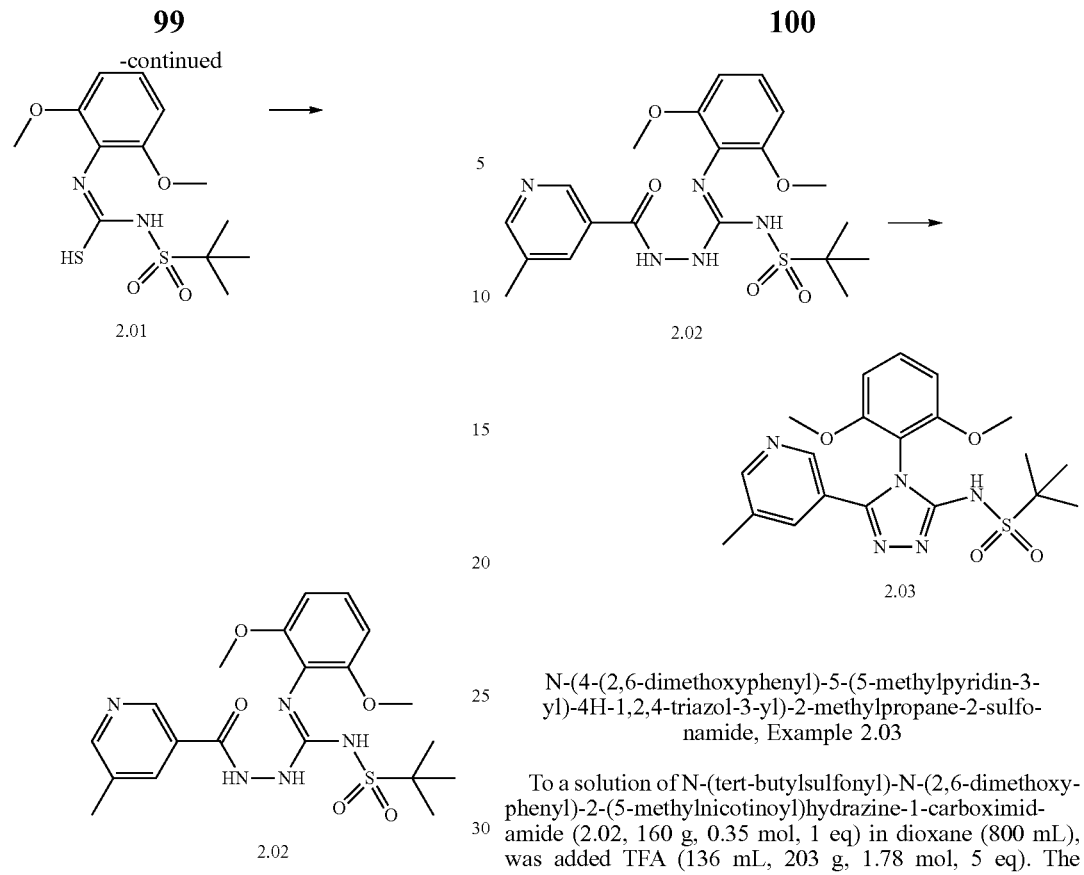

2.01

2.02

2.03

N-(4-(2,6-dimethoxyphenyl)-5-(5-methylpyridin-3-yl)-4H-1,2,4-triazol-3-yl)-2-methylpropane-2-sulfonamide, Example 2.03

To a solution of N-(tert-butylsulfonyl)-N-(2,6-dimethoxyphenyl)-2-(5-methylnicotinoyl)hydrazine-1-carboximidamide (2.02, 160 g, 0.35 mol, 1 eq) in dioxane (800 mL), was added TFA (136 mL, 203 g, 1.78 mol, 5 eq). The reaction mixture was heated to reflux at 100° C. for 18 h. The reaction mixture was evaporated to dryness and carried forward to the next step without further purification. MS (ESI pos. ion) m/z: 431.8 (M)+. $^1$H-NMR (300 MHz, DMSO-$d_6$) δ 13.19 (br. s, 1H), 8.47 (d, J=1.35 Hz, 1H), 8.19 (d, J=1.71 Hz, 1H), 7.63 (d, J=0.69 Hz, 1H), 7.49 (t, J=8.49 Hz, 1H), 6.82 (d, J=8.58 Hz, 2H), 3.87 (s, 6H), 2.24 (s, 3H), 1.18 (s, 9H).

N-(tert-butylsulfonyl)-N'-(2,6-dimethoxyphenyl)-2-(5-methylnicotinoyl)hydrazine-1-carboximidamide, Example 2.02

To a solution of tert-butylsulfonamide (63 g, 0.46 mol, 1.05 eq) and 2-isothiocyanato-1,3-dimethoxybenzene (1.0, 86 g, 0.44 mol, 1 eq) in ACN (1.8 L), was added cesium carbonate (186 g, 0.57 mol, 1.3 eq) in 8-10 portions. The mixture was stirred overnight at RT. The formation of the isothiourea was confirmed by LCMS and NMR. MS (ESI pos. ion) m/z: 333.4 (M+H)+. $^1$H-NMR (400 MHz, DMSO-$d_6$) δ 7.07 (t, J=8.40 Hz, 1H), 6.56 (d, J=8.36 Hz, 2H), 3.68 (s, 6H), 1.06 (br. s, 9H). To the isothiourea, were added successively 5-methylnicotinohydrazide (70 g, 0.46 mol, 1.05 eq) and silver nitrate (149 g, 0.88 mol, 2 eq) in 10 portions (Note: the addition was mildly exothermic). The resulting mixture was then stirred for 2 h. Celite® brand filter agent (2 w/w) was added to the reaction and the mixture was stirred for 10-15 min. The reaction mixture was again passed through Celite® brand filter agent. After rinsing the Celite® brand filter agent plug with DCM and 5% MeOH in DCM, the mixture was concentrated under reduced pressure to afford a black residue, which was purified by column chromatography [SiO$_2$ (60-120 mesh); using DCM and MeOH as eluent (product was eluted with 2-5% MeOH in DCM)] to provide 160 g of the title compound 2.02 as a white solid (0.35 mol, 80%). MS (ESI pos. ion) m/z: (M+H)+=450.7. MS (ESI neg. ion) m/z: (M−H)+=448.4. $^1$H NMR (400 MHz, DMSO-$d_6$) δ 10.68 (br. s, 1H), 9.09 (br. s, 1H), 8.91-8.53 (m, 3H), 8.14-7.97 (m, 1H), 7.25 (d, J=7.64 Hz, 1H), 6.76-6.67 (m, 2H), 3.75-3.72 (m, 6H), 2.35 (s, 3H), 1.26-1.21 (m, 9H).

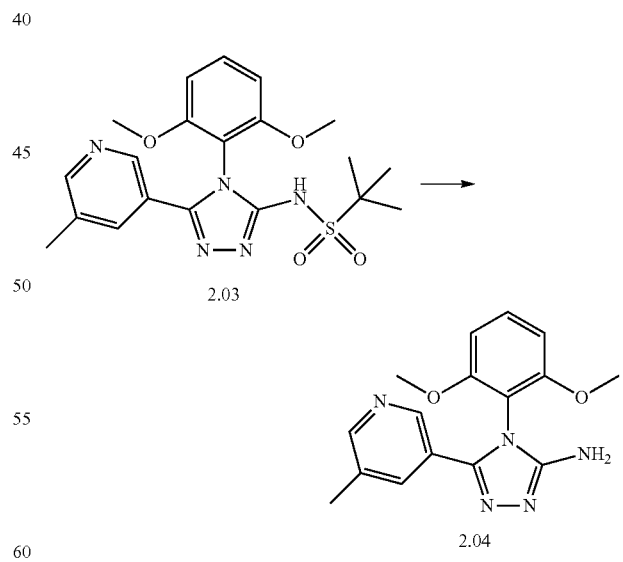

2.03

2.04

4-(2,6-dimethoxyphenyl)-5-(5-methylpyridin-3-yl)-4H-1,2,4-triazol-3-amine, Example 2.04

To N-(4-(2,6-dimethoxyphenyl)-5-(5-methylpyridin-3-yl)-4H-1,2,4-triazol-3-yl)-2-methylpropane-2-sulfonamide (Example 2.03, 153.0 g, 0.36 mol) in TFA (neat, 760 mL, 5 v/w) was added anisole (115 g, 1.06 mol, 3 eq), the resulting mixture was heated overnight at 100° C. (TFA boils vigorously). After completion of the reaction, TFA was removed using a high vacuum pump. The residue was taken in a minimum amount of ice and basified to pH 8-9 using 10% NaHCO$_3$ solution. The solids that formed were filtered using a Buchner funnel, washed with water, petroleum ether and diethyl ether. The solid was dried to obtain the title compound Example 2.04 as a white solid (88 g, 0.29 mol, 82% for two steps). MS (ESI pos. ion) m/z: 312.4 (M+H)$^+$. $^1$H-NMR (400 MHz, DMSO-d$_6$) δ 8.36 (d, J=1.44 Hz, 1H), 8.14 (d, J=1.88 Hz, 1H), 7.53-7.48 (m, 2H), 6.84 (d, J=8.56 Hz, 2H), 6.31 (br. s, 2H), 3.70 (s, 6H), 2.22 (s, 3H).

3-(5-bromo-4-(2,6-dimethoxyphenyl)-4H-1,2,4-triazol-3-yl)-5-methylpyridine, Example 2.0

To a stirred solution of 4-(2,6-dimethoxyphenyl)-5-(5-methylpyridin-3-yl)-4H-1,2,4-triazol-3-amine (Example 2.04, 88 g, 0.28 mol, 1 eq) in dibromomethane (3.5 L) was added benzyltriethylammonium bromide (231 g, 0.85 mol, 3 eq) and sodium nitrite (390 g, 5.65 mol, 20 eq) at RT. Dichloroacetic acid (46 mL, 73 g, 0.66 mol, 2 eq) was added dropwise at 0° C. (internal temperature) and the resulting solution was stirred at RT for 18 h. The reaction mixture was concentrated and loaded on silica gel and purified by silica gel column chromatography (elution with 80% EtOAc in petroleum ether) to yield 36 g (0.09 mol, 34%) of the title compound as pale yellow solid. MS (ESI pos. ion) m/z: (M+H)$^+$=375.2. $^1$H NMR (400 MHz, CDCl$_3$) δ 8.42 (t, J=0.56 Hz, 1H), 8.32 (d, J=1.96 Hz, 1H), 7.86 (t, J=0.68 Hz, 1H), 7.46 (t, J=8.48 Hz, 1H), 6.67 (d, J=8.52 Hz, 2H), 3.74 (s, 6H), 2.33 (s, 3H). $^1$H-NMR (400 MHz, DMSO-d$_6$) δ 8.46 (d, J=1.44 Hz, 1H), 8.22 (d, J=1.88 Hz, 1H), 7.66-7.65 (m, 1H), 7.56 (t, J=8.52 Hz, 1H), 6.89 (d, J=8.56 Hz, 2H), 3.71 (s, 6H), 2.25 (s, 3H).

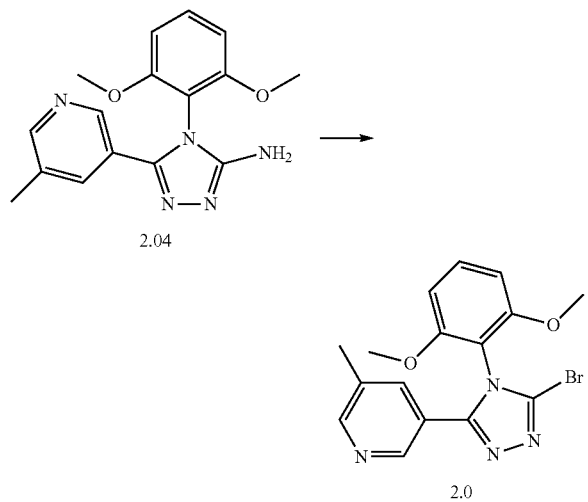

The compounds in the following Table were synthesized using the procedure in Example 2.0 using the known starting material as described.

TABLE 2

| Example | Reagents | Structure, Name and Data |
|---|---|---|
| 2.1 | Example 1.0, nicotinohydrazide | 3-(5-bromo-4-(2,6-dimethoxyphenyl)-4H-1,2,4-triaazol-3-yl)pyridine. MS (ESI) m/z = 361.2. |
| 2.2 | Example 1.0, 6-methoxypicolinohydrazide | 2-(5-bromo-4-(2,6-dimethoxyphenyl)-4H-1,2,4-triazol-3-yl)-6-methoxypyridine. MS (ESI) m/z = 391.0. |

TABLE 2-continued

| Example | Reagents | Structure, Name and Data |
|---|---|---|
| 2.3 | Example 1.0, 6-methylpicolino-hydrazide | 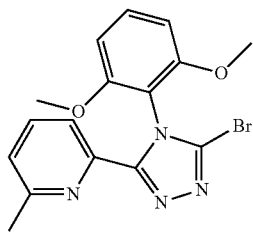 [SMILES: COc1cccc(OC)c1-n1c(Br)nnc1-c1cccc(C)n1] 2-(5-bromo-4-(2,6-dimethoxyphenyl)-4H-1,2,4-triazol-3-yl)-6-methylpyridine. MS (ESI) m/z = 375.2 |

Example 3.0: Preparation of 6-(difluoromethoxy)picolinohydrazide

Methyl 6-(difluoromethoxy)picolinate 3.01

To a 10-mL round bottom flask was added sodium chlorodifluoroacetate (0.603 g, 3.96 mmol), sodium hydroxide (0.046 mL, 2.43 mmol) and methyl 6-oxo-1,6-dihyrdopyridine-2-carboxylate (0.303 g, 1.98 mmol) in DMF (3 mL). The reaction mixture was heated at 60° C. for 18 h and then at 80° C. for 24 h. The reaction mixture was cooled to RT, diluted with saturated aqueous NaHCO₃ solution and extracted with EtOAc. The organic extracts were dried over MgSO₄. The solution was filtered and concentrated in vacuo to give the product as a white oil. The material obtained was absorbed onto a plug of silica gel and purified by silica gel chromatography eluting with a gradient of 0-50% EtOAc in hexanes, to provide Example 3.01 (0.281 g, 1.38 mmol, 70% yield) as white oil. $^1$H NMR (400 MHz, CDCl$_3$) δ 7.84-7.96 (m, 2H), 7.42-7.83 (m, 1H), 7.11 (dd, J=8.02, 0.98 Hz, 1H), 3.98 (s, 3H). LCMS-ESI (POS.) m/z: 203.9 (M+H)$^+$.

6-(difluoromethoxy)picolinohydrazide, Example 3.0

To a solution of Example 3.01 (0.280 g, 1.38 mmol) in MeOH (9 mL) was added hydrazine (0.047 mL, 2.07 mmol). The reaction mixture was stirred at RT for 18 h, afterwhich it was concentrated in vacuo. Water (10 mL) was added to the residue. The white suspension was frozen by a dry ice/acetone bath and lyophilized to give Example 3.0 (0.280 g, 1.38 mmol, 100% yield). $^1$H NMR (400 MHz, CDCl$_3$) δ 7.10 (dd, J=8.12, 0.88 Hz, 1H), 7.36 (t, J=73.55 Hz, 1H), 7.94 (d, J=8.02 Hz, 1H), 8.00 (d, J=0.98 Hz, 1H). LCMS-ESI (POS.) m/z: 203.9 (M+H)$^+$.

The compounds in Table 3 were synthesized following the procedure in Example 3.0 using the known starting material as described.

TABLE 3

| Example | Reagents | Structure, Name and and Data |
|---|---|---|
| 3.1 | 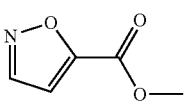 | isoxazole-5-carbohydrazide. $^1$H NMR (400 MHz, CD$_3$OD) δ 8.50 (d, J = 1.96 Hz, 1H), 6.94 (d, J = 1.96 Hz, 1H). MS (ESI) m/z 128.1. |

TABLE 3-continued

| Example | Reagents | Structure, Name and and Data |
|---|---|---|
| 3.2 | | 2-methylisonicotinohydrazide. $^1$H NMR (400 MHz, CDCl$_3$) δ 8.64 (1H, br. s), 7.57 (1H, br. s), 7.44 (1H, br. s), 2.53-2.75 (3H, s). |
| 3.3 | Matrix Scientific, Columbia, SC, USA | 5-methoxynicotinohydrazide. LCMS-ESI (POS.) m/z: 168.2 (M + H)$^+$. |
| 3.4 | Ark Pharm Inc, Libertyville, IL, USA | 6-methylpicolinohydrazide. LCMS-ESI (POS.) m/z: 152.1 (M + H)$^+$. |
| 3.5 | Ark Pharm Inc, Libertyville IL, USA | 3-methoxypicolinohydrazide. LCMS-ESI (POS.) m/z: 168.1 (M + H)$^+$. |
| 3.6 | Oakwood Products, Inc. West Columbia, SC, USA | 5-bromonicotinohydrazide. LCMS-ESI (POS.) m/z: 215.8, 217.9 (M + H)$^+$. |
| 3.7 | Example 3.53 | 6-(hydrazinecarbonyl)-N-methylpicolinamide. LCMS-ESI (POS.) m/z: 195.1 (M + H)$^+$. |
| 3.8 or 3.48 | comercially available from Ark Pharm Inc, Libertyville, IL, USA | 6-cyanopicolinohydrazide. LCMS-ESI (POS.) m/z: 162.9 (M + H)$^+$. |

TABLE 3-continued

| Example | Reagents | Structure, Name and and Data |
|---|---|---|
| 3.9 | Example 3.54 | 6-(azetidine-1-carbonyl)picolinohydrazide. LCMS-ESI (POS.) m/z: 221.0 (M + H)+. |
| 3.10 | Ark Pharm Inc, Libertyville, IL, USA | 6-oxo-1,6-dihydropyridine-2-carbohydrazide. LCMS-ESI (POS.) m/z: 153.9 (M + H)+. |
| 3.11 | VWR Interntional, LLC | 5-methylnicotinohydrazide. LCMS-ESI (POS.) m/z: 152.1 (M + H)+. |
| 3.12 | (Sigma-Aldrich Chemical Company, Inc.) | 2-methylnicotinohydrazide. LCMS-ESI (POS.) m/z: 152.1 (M + H)+. |
| 3.13 | (Sigma-Aldrich Chemical Company, Inc.) | 6-methylnicotinohydrazide. LCMS-ESI (POS.) m/z: 152.1 (M + H)+. |
| 3.14 | (Astatech, Inc..) | 4-methylnicotinohydrazide. LCMS-ESI (POS.) m/z: 152.1 (M + H)+. |
| 3.15 | (Example 3.38) | 5-chloronicotinohydrazide. LCMS-ESI (POS.) m/z: 172.1 (M + H)+. |

TABLE 3-continued

| Example | Reagents | Structure, Name and and Data |
|---|---|---|
| 3.16 | (Sigma Aldrich) | 4-methylpicolinohydrazide. LCMS-ESI (POS.) m.z: 152.1 (M + H)⁺. |
| 3.17 | (Combi-Blocks Inc.) | 5-fluoronicotinohydrazide. LCMS-ESI (POS.) m/z: 156.1 (M + H)⁺. |
| 3.18 | (Sigma-Aldrich) | 6-methoxypicolinohydrazide. LCMS-ESI (POS.) m/z: 168.1 (M + H)⁺. |
| 3.19 | (Example 3.28) | N-ethyl-6-(hydrazinecarbonyl)picolinaide. LCMS-ESI (POS.) m/z: 209.1 (M + H)⁺. |
| 3.20 | (Example 3.29) | 6-(hydrazinecarbonyl)-N,N-dimethylpicolinamide. LCMS-ESI (POS.) m/z: 209.1 (M + H)⁺. |
| 3.21 | (Example 3.31) | 6-(2,2,2-trifluoromethoxy)picolinohydrazide. LCMS-ESI (POS.) m/z: 236.1 (M + H)⁺. |
| 3.22 | | |

TABLE 3-continued

| Example | Reagents | Structure, Name and Data |
|---|---|---|
| | (Example 3.31) | 6-(2-((tert-butyldimethylsilyl)oxy)ethoxy)-icolinohydrazide. LCMS-ESI (POS.) m/z: 312.2 (M + H)+. |
| 3.23 | 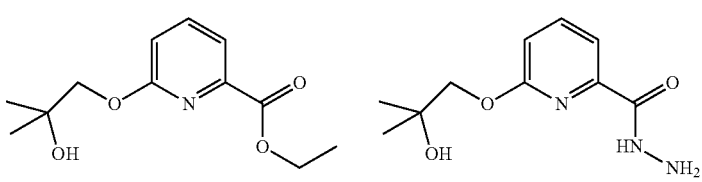 (Example 3.34) | 6-(2-hydroxy-2-methylpropoxy)-picolinohydrazide. LCMS-ESI (POS.) m/z: 226.1 (M + H)+. |
| 3.24 | 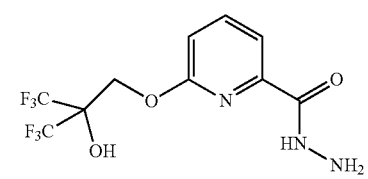 (Example 3.35) | 6-(3,3,3-trifluoro-2-hydroxy-2-(trifluoromethyl)propoxy)picolinohydrazide. LCMS-ESI (POS.) m/z: 334.0 (M + H)+. |
| 3.25 | 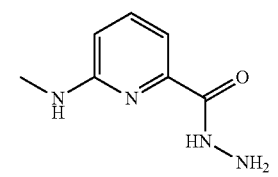 (Example 3.36) | 6-(methylamino)picolinohydrazide. LCMS-ESP (POS.) m/z: 167.1 (M + H)+. |
| 3.26 | 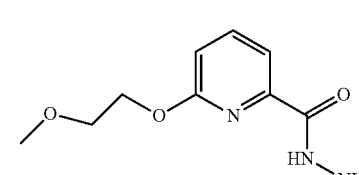 (Example 3.33) | 6-(2-methoxyethoxy)picolinohydrazide. LCMS-ESI (POS.) m/z: 212.1 (M + H)+. |
| 3.27 | 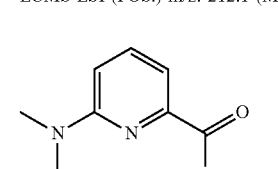 (Example 3.37) | 6-(dimethylamino)picolinohydrazide. LCMS-ESI (POS.) m/z: 181.1 (M + H)+. |

Example 3.28: Preparation of methyl 6-(ethylcarbamoyl)picolinate

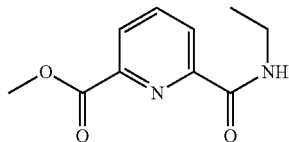

Methyl 6-(ethylcarbamoyl)picolinate, Example 3.28

To a mixture of 6-(methoxycarbonyl)pyridine-2-carboxylic acid (0.74 mL, 5.52 mmol) (available from Matrix Scientific) and ethanamine hydrochloride (0.675 g, 8.28 mmol, Fluka Chemie GmbH) in DMF (10 mL) was added N-[(Dimethylamino)-1H-1,2,3-triazolo-[4,5-b]pyridin-1-yl-methylene]-N-methylmethanaminium hexafluorophosphate N-oxide (2.31 g, 6.07 mmol, Oakwood Products, Inc.) in portions at RT, followed by addition of N,N-diisopropylethylamine (1.921 mL, 11.04 mmol, Sigma-Aldrich Chemical Company, Inc.). The resulting mixture was stirred at RT and monitored by LCMS. Upon completion, the mixture was directly absorbed onto a plug of silica gel and purified by chromatography through a Redi-Sep pre-packed silica gel column (125 g), eluting with a gradient of 0 to 100% EtOAc in hexanes, to give the title compound (1.11 g, 5.33 mmol, 97% yield). LCMS-ESI (POS.) m/z: 209.1 (M+H)$^+$.

Example 3.29: Preparation of Methyl 6-(dimethylcarbamoyl)picolinate

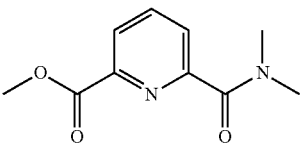

Methyl 6-(dimethylcarbamoyl)picolinate, Example 3.29

This compound was prepared using the procedure described in Example 3.28. LCMS-ESI (POS.) m/z: 209.1 (M+H)$^+$.

Example 3.30: Preparation of Methyl 6-(2,2,2-trifluoroethoxy)picolinate

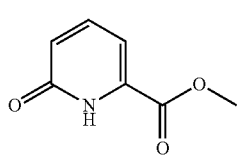

Methyl 6-oxo-1,6-dihydropyridine-2-carboxylate, Example 3.31

To a cooled suspension of 6-oxo-1,6-dihydropyridine-2-carboxylic acid (5.0 g, 35.9 mmol, Sigma Aldrich) in MeOH (100 mL, 35.9 mmol) in an ice/water bath was added dropwise thionyl chloride (7.82 mL, 108 mmol, Sigma Aldrich). The resulting mixture was stirred at RT for 24 h. The mixture was then concentrated in vacuo and dried to give the title compound (5.6 g, 100%). LCMS-ESI (POS.) m/z: 154.1 (M+H)$^+$.

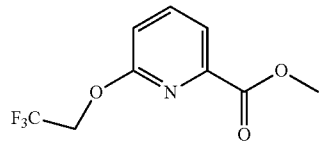

Methyl 6-(2,2,2-trifluoroethoxy)picolinate, Example 3.30

To a mixture of methyl 6-oxo-1,6-dihydropyridine-2-carboxylate (1.0 g, 6.53 mmol) (Example 3.31) and cesium carbonate (3.19 g, 9.80 mmol) in DMF (10 mL) was added 1,1,1-trifluoro-2-iodoethane (2.74 g, 13.06 mmol, Sigma Aldrich). The resulting mixture was stirred at 50° C. for 2 d. The mixture was cooled to RT, 30 mL of water was added, and a 1N HCl solution was used to neutralize the mixture to pH=5. The resulting mixture was then extracted with EtOAc (50 mL×4). The combined extracts were washed with water and brine, dried (Na$_2$SO$_4$) and concentrated in vacuo. The residue was purified by silica gel column chromatography using 0-100% EtOAc gradient in heptanes as the eluent to give of methyl 6-(2,2,2-trifluoroethoxy)picolinate (134 mg, 9%). LCMS-ESI (POS.) m/z: 236.1 (M+H)$^+$.

Example 3.32: Preparation of Methyl 6-(2-((tert-butyldimethylsilyl)oxy)ethoxy)picolinate

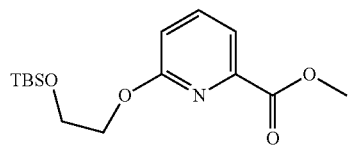

Methyl 6-(2-((tert-butyldimethylsilyl)oxy)ethoxy) picolinate, Example 3.32

To a solution of methyl 6-oxo-1,6-dihydropyridine-2-carboxylate (3.31, 1.0 g, 6.53 mmol) in DMF (16.33 mL) was added tert-butyl(2-iodoethoxy)dimethylsilane (2.80 g, 9.80 mmol, Sigma Aldrich). The resulting mixture was stirred at 80° C. and monitored by LCMS. Upon completion, 100 mL of saturated aqueous ammonium chloride solution was added, and the resulting mixture was extracted with EtOAc (4×100 mL). The combined extracts were washed with water (×2) and brine (×2), dried (Na$_2$SO$_4$) and concentrated in vacuo. The residue was purified by CombiFlash on a 120 g silica gel column using 0-80% EtOAc gradient in

Example 3.33: Preparation of Methyl 6-(2-methoxyethoxy)picolinate

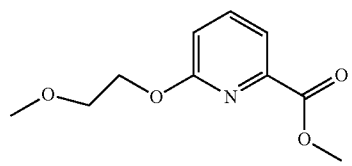

Methyl 6-(2-methoxyethoxy)picolinate, Example 3.33

The title compound was prepared using the procedure described in Example 3.32. LCMS-ESI (POS.) m/z: 212.0 (M+H)⁺.

Example 3.34: Preparation of Ethyl 6-(2-hydroxy-2-methylpropoxy)picolinate

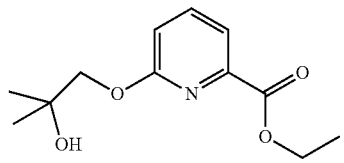 [SMILES: CCOC(=O)c1cccc(OCC(C)(C)O)n1]

Ethyl 6-(2-hydroxy-2-methylpropoxy)picolinate, Example 3.34

To a mixture of ethyl 6-hydroxypyridine-2-carboxylate (0.41 mL, 2.99 mmol, Matrix Scientific) and cesium carbonate (0.29 mL, 3.59 mmol) in DMF (5.98 mL) was added isobutylene oxide (0.32 mL, 3.59 mmol, TCI America) at RT. The resulting mixture was stirred at 40° C. and monitored by LCMS. Upon completion, the mixture was filtered and washed with EtOAc (100 mL). The filtate was transferred to a separatory funnel and washed with water (×2), brine, dried with anhydrous sodium sulfate and concentrated in vacuo. The residue was purified by silca gel column chromatography using 0-100% EtOAc in heptane as the eluent to give the title compound (3.34, 564 mg, 79%). LCMS-ESI (POS.) m/z: 240.1 (M+H)⁺.

Example 3.35: Preparation of Methyl 6-(3,3,3-trifluoro-2-hydroxy-2-(trifluoromethyl)propoxy)picolinate

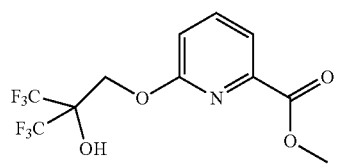 [SMILES: COC(=O)c1cccc(OCC(O)(C(F)(F)F)C(F)(F)F)n1]

Methyl 6-(3,3,3-trifluoro-2-hydroxy-2-(trifluoromethyl)propoxy)picolinate, Example 3.35

To a stirred mixture of methyl 6-hydroxypicolinate (3.31, 1.50 g, 9.80 mmol) and cesium carbonate (4.79 g, 14.69 mmol) in DMF (19.59 mL) was added 2,2-bis(trifluoromethyl)oxirane (2.65 mL, 14.69 mmol, Apollo Scientific Ltd.) at RT, and the mixture was stirred at RT and monitored by LCMS. Upon completion of the reaction, the mixture was filtered and the filter cake was washed with EtOAc. The organic solution was washed with water (×2) and brine, dried with anhydrous sodium sulfate and concentrated in vacuo. The residue was purified by silica gel column chromatography using 0-100% EtOAc in heptanes as the eluent to give the title compound (3.35, 1.13 g, 34.6%). LCMS-ESI (POS.) m/z: 334.0 (M+H)⁺.

Example 3.36: Preparation of Methyl 6-(methylamino)picolinate

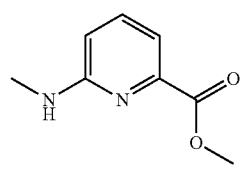

Methyl 6-(methylamino)picolinate, Example 3.36

To a mixture of 6-amino-2-picolinic acid (0.96 mL, 9.77 mmol, Chem Impex International) and cesium carbonate (7.82 mL, 97.7 mmol) in DMF (10 mL) was added iodomethane (1.52 mL, 24.43 mmol, Sigma Aldrich). The mixture was stirred at RT and monitored by LCMS. The mixture was filtered through a pad of Celite® brand filter agent and washed with EtOAc. The filtrate was concentrated, and the residue was purified on by silica gel column chromatography using 0-100% EtOAc in heptane as the eluent to give the title compound (3.36, 283 mg, 27%). LCMS-ESI (POS.) m/z: 167.1 (M+H)⁺.

Example 3.37: Preparation of Methyl 6-(dimethylamino)picolinate

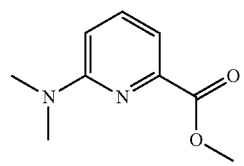

Methyl 6-(dimethylamino)picolinate, Example 3.37

The title compound was prepared using the procedure described in Example 3.36. LCMS-ESI (POS.) m/z: 181.1 (M+H)⁺.

Example 3.38: Preparation of Methyl 5-chloronicotinate

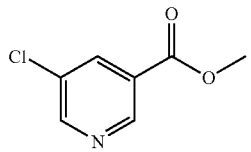

Methyl 5-chloronicotinate, Example 3.38

To a suspension of 5-chloronicotinic acid (0.68 mL, 6.35 mmol) in MeOH (8 mL) was added thionyl chloride (1.5 mL, 20.55 mmol) at 0° C. dropwise. The resulting mixture was heated at reflux for 24 h. The mixture was concentrated and 50 mL of saturated aqueous sodium bicarbonate solution was added to the residue. The resulting mixture was extracted with EtOAc (4×50 mL). The combined extracts were washed with sodium bicarbonate solution, water, and brine, and then dried with anhydrous sodium sulfate. The drying agent was removed by filtration and washed with EtOAc. The filtrate was concentrated in vacuo and dried to give the title compound (3.38, 698 mg). $^1$H NMR (400 MHz, CDCl$_3$) δ 9.80 (d, J=1.7 Hz, 1H), 8.73 (d, J=2.4 Hz, 1H), 8.27 (dd, J=2.4, 2.4 Hz, 1H), 3.96 (s, 3H).

Example 3.40: Preparation of 6-([$^2$H$_3$]methoxy)picolinohydrazide

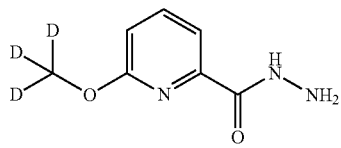

Step 1: ([$^2$H$_3$]methyl)-6-([$^2$H$_3$]methoxy)picolinate, 3.39

To a 25 mL round-bottomed flask was added methyl 6-chloropicolinate (2.00 g, 11.66 mmol, Matrix Scientific), 1,4-dioxane, CD$_3$OD (5.31 mL, 117 mmol, Aldrich) and potassium 2-methylpropan-2-olate (1.31 g, 11.66 mmol, Aldrich). The reaction was stirred at RT for 19 h, and then at 50° C. for an additional 24 h. The reaction was cooled to RT, diluted with water (20 mL) and saturated aqueous sodium bicarbonate (20 mL) and extracted with EtOAc (2×25 mL). The combined organic layers were dried (MgSO$_4$), and concentrated in vacuo. Purification by flash chromatography (120 g SiO$_2$, 0-100% EtOAc/hexanes) gave ([$^2$H$_3$]methyl)-6-([$^2$H$_3$]methoxy)picolinate (3.39, 840 mg, 4.85 mmol, 41.6% yield) as a white solid.

Step 2: 6-([$^2$H$_3$]methoxy)picolinohydrazide, 3.40

To a solution of ([$^2$H$_3$])methyl)-6-([$^2$H$_3$])methoxy)picolinate (3.39, 840 mg, 4.85 mmol) in MeOH (26 mL) in an ambient temperature water bath was added hydrazine (0.244 mL, 7.76 mmol) (anhydrous) over 1 min. The reaction was then stirred at RT under N$_2$ for 22 h. The reaction was concentrated, the resulting solid was suspended in EtOAc (5 mL), and the suspension was filtered to collect the solid. The solid was washed with EtOAc (2×5 mL) and dried to obtain the title compound (3.40, 545 mg, 3.20 mmol, 66.0% yield) as a white solid. $^1$H NMR (300 MHz, CDCl$_3$) δ 9.74 (br. s., 1H), 7.84 (dd, J=8.3, 7.3 Hz, 1H), 7.56 (dd, J=7.2, 0.8 Hz, 1H), 6.97 (dd, J=8.3, 0.7 Hz, 1H), 4.56 (d, J=3.9 Hz, 2H). LCMS-ESI (POS.) m/z: 171.2 (M+H)$^+$.

Example 3.42: Preparation of 6-Methylpicolinohydrazide

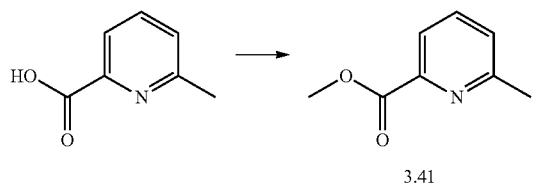

Methyl 6-methylpicolinate 3.41

To a 250-mL round-bottomed flask was added 6-methyl-picolinic acid (TCI, 5.35 g, 39.0 mmol) and MeOH (100 mL). Concentrated sulfuric acid (3.12 mL, 58.5 mmol) was added dropwise. The reaction was heated at reflux for 48 h. After cooling to RT, most of the solvent was evaporated. The resulting residue was diluted with saturated aqueous NaHCO$_3$ and extracted with DCM (2×100 mL). The organic extracts were dried over MgSO$_4$, filtered and concentrated in vacuo to give 6-methylpicolinate (5.33 g, 35.3 mmol, 90% yield) as a light-yellow oil. MS (M+H)$^+$ 152.0.

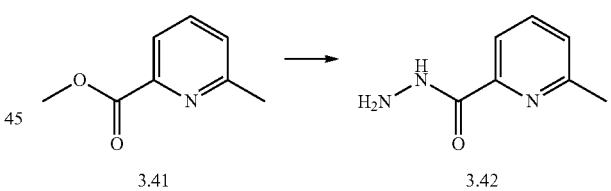

6-Methylpicolinohydrazide 3.42

To a stirred solution of methyl 6-methylpicolinate (1.50 g, 9.96 mmol) in MeOH (50 mL) in a 250-mL round-bottomed flask, was added hydrazine (0.407 mL, 12.95 mmol) dropwise at RT. The mixture was stirred at RT for 18 h after-which, the mixture was concentrated in vacuo. The resulting solid was triturated with EtOAc and hexanes and dried under vacuum to afford the title compound (1.40 g, 9.26 mmol, 93% yield) as an off-white solid. $^1$H NMR (CDCl$_3$) δ: 9.02 (br. s., 1H), 7.97 (d, J=7.7 Hz, 1H), 7.73 (t, J=7.7 Hz, 1H), 7.30 (d, J=7.7 Hz, 1H), 4.07 (br. s., 2H), 2.57 (s, 3H). LCMS-ESI (POS.) m/z: 152.1 (M+H)$^+$.

The compounds in Table 4 were synthesized following the procedure in Example 3.42 using the known starting material as described.

TABLE 4

| Example | Reagents | Structure, Name and Data |
|---|---|---|
| 3.43 | 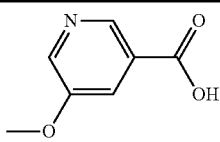<br>5-methoxynicotinic acid<br>(Matrix Scientific) | 5-methoxynicotinohydrazide. $^1$H NMR (DMSO-d$_6$) δ: 9.93 (br. s., 1H), 8.57 (br s, 1H), 8.40 (br s, 1H), 7.71 (br. s., 1H), 4.56 (br. s., 2H), 3.87 (br. s., 3H). LCMS-ESI (POS.) m/z: 168.1 (M + H)$^+$. |
| 3.44 | 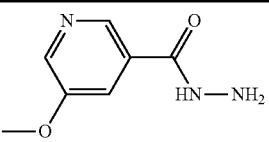<br>(comercially available from Richmond Chemical Corp, Oak Brook, IL, USA) | 2-methylisonicotinohydrazide. LCMS-ESI (POS.) m/z: 152.0 (M + H)$^+$. |
| 3.45 | 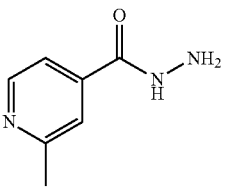<br>(comercially available from Apollo Scientific Ltd, Stockport, Chesire, UK) | 5-(trifluoromethyl)nicotinohydrazide. LCMS-ESI (POS.) m/z: 205.9 (M + H)$^+$. |
| 3.46 | 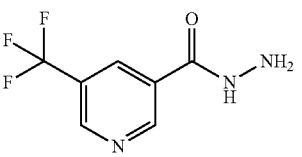 [SMILES: NNC(=O)c1cncc(C(F)(F)F)c1]<br>(comercially available from Matrix Scientific, Columbia, SC, USA) | 6-ethoxypicolinohydrazide. LCMS-ESI (POS.) m/z: 182.0 (M + H)$^+$. |
| 3.47 | 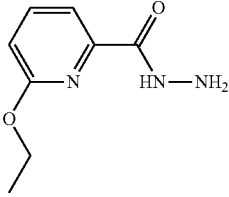<br>(Example 3.53) | 6-(hydrazinecarbonyl)-N-methylpicolinamide. LCMS-ESI (POS.) m/z: 195.1 (M + H)$^+$. |
| 3.48 or 3.8 | 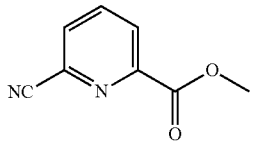<br>(comercially available from Ark Pharm Inc, Libertyville, IL, USA) | 6-cyanopicolinohydrazide. LCMS-ESI (POS.) m/z: 162.9 (M + H)$^+$. |

TABLE 4-continued

| Example | Reagents | Structure, Name and Data |
|---|---|---|
| 3.49 | (comercially available from Ark Pharm Inc, Libertyville, IL, USA) | 5-methoxypicolinohydrazide. LCMS-ESI (POS.) m/z: 167.9 (M + H)+. |
| 3.50 | (comercially available from Oakwood Products, Inc, West Columbia, SC, USA) | 6-ethylpicolinohydrazide. LCMS-ESI (POS.) m/z: 166.0 (M + H)+. |
| 3.51 | (comercially available from ACES Pharma, Inc, Princeton, NJ, USA) | 6-methoxy-4-methylpicolinohydrazide. LCMS-ESI (POS.) m/z: 182.0 (M + H)+. |

Example 3.52: Preparation of methyl 6-(ethylcarbamoyl)picolinate

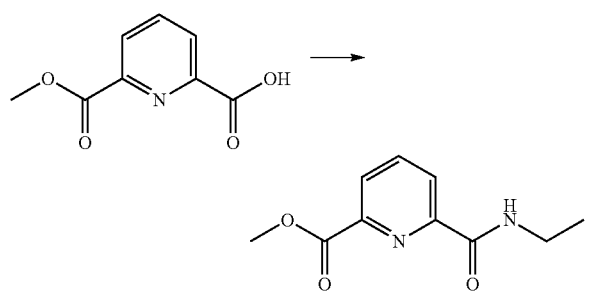

Methyl 6-(ethylcarbamoyl)picolinate, Example 3.52

To a mixture of 6-(methoxycarbonyl)pyridine-2-carboxylic acid (0.735 mL, 5.52 mmol, commercially available from Matrix Scientific, Columbia, S.C., USA) and ethanamine hydrochloride (0.675 g, 8.28 mmol, commercially available from Fluka, Buchs, St. Gallen, Switzerland) in DMF (10 mL) was added (1-[Bis(dimethylamino)methylene]-1H-1,2,3-triazolo[4,5-b]pyridinium 3-oxid hexafluorophosphate) (2.31 g, 6.07 mmol, commercially available from Oakwood Products, Inc. West Columbia, S.C., USA) in portions at RT, followed by addition of N,N-diisopropylethylamine (1.92 mL, 11.04 mmol, commercially available from Sigma-Aldrich Corp, St. Louis, Mo., USA). The resulting mixture was stirred at RT and monitored by LCMS. Upon completion, the mixture was directly absorbed onto a plug of silica gel and purified by column chromatography through a Redi-Sep pre-packed silica gel column (125 g), eluting with a gradient of 0-100% EtOAc in hexanes, to give the title compound, methyl 6-(ethylcarbamoyl)picolinate (1.11 g, 5.33 mmol, 97% yield). LCMS-ESI (POS.) m/z: 209.1 (M+H)+.

The compounds in the following Table 5 were synthesized following the procedure in Example 3.52 using the known starting material as described.

TABLE 5

| Example | Reagents | Structure, Name and Data |
|---|---|---|
| 3.53 | Methylamine hydrochloride (comercially available from Sigma-Aldrich Corp, St. Louis, MO, USA) | 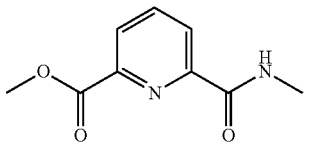<br>Methyl 6-(methylcarbamoyl)picolinate. LCMS-ESI (POS.) m/z: 195.1 (M + H)+. |
| 3.54 | Azetidine (comercially available from Acros Organic, NJ, USA) | 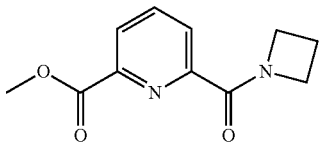 [SMILES: COC(=O)c1cccc(C(=O)N2CCC2)n1]<br>Methyl 6-(azitidine-1-carbonyl)picolinate. LCMS-ESI (POS.) m/z: 221.1 (M + H)+. |

Example 3.55: Preparation of Methyl 6-(ethylcarbamoyl)picolinate

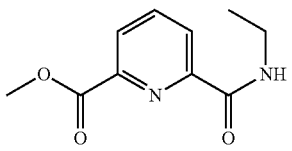

3.55

Methyl 6-(ethylcarbamoyl)picolinate, Example 3.55

The title compound was prepared using the procedure described in Example 3.52. LCMS-ESI (POS.) m/z: 209.1 (M+H)+.

Example 3.56: Preparation of Methyl 6-(dimethylcarbamoyl)picolinate

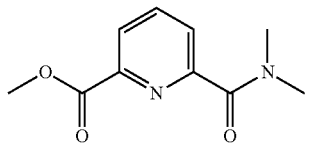

3.56

Methyl 6-(dimethylcarbamoyl)picolinate, Example 3.56

The title compound was prepared using the procedure described in Example 3.52. LCMS-ESI (POS.): 209.1 (M+H)+.

Example 4.0: Preparation of N-(4-(2,6-dimethoxyphenyl)-5-(6-methoxypyridin-2-yl)-4H-1,2,4-triazol-3-yl)-N-(2-(trimethylsilyl)ethyl)methanesulfonamide 1.0

4.01

(Z)—N'-(2,6-dimethoxyphenyl)-2-(6-methoxypicolinoyl)-N-(methylsulfonyl)hydrazinecarboximidamide, Example 4.01

To a solution of 2-isothiocyanato-1,3-dimethoxybenzene (Example 1.0, 3.83 g, 19.62 mmol) and methanesulfonamide (1.96 g, 20.60 mmol) in ACN (98 mL) at RT was added cesium carbonate. The reaction was stirred overnight under $N_2$. 6-Methoxy-pyridine-2-carboxylic acid hydrazide (Example 3.18, 3.44 g, 20.60 mmol) was added to the mixture in one portion followed by silver(I) nitrate (6.66 g, 39.2 mmol). The mixture was then stirred for 2 h. The material obtained was absorbed onto a plug of silica gel and purified by silica gel column chromatography, eluting with a gradient of 0-15% MeOH in DCM, to provide the title compound 4.01 (3.83 g, 9.04 mmol, 46% yield) as a yellow solid. LCMS-ESI (neg.) m/z: 448.4 (M–H)+.

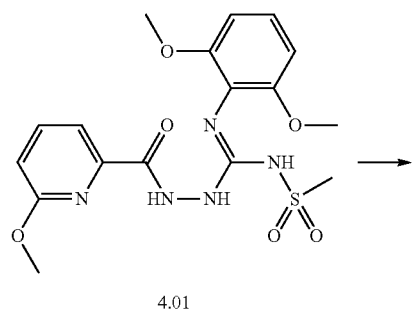

4.01

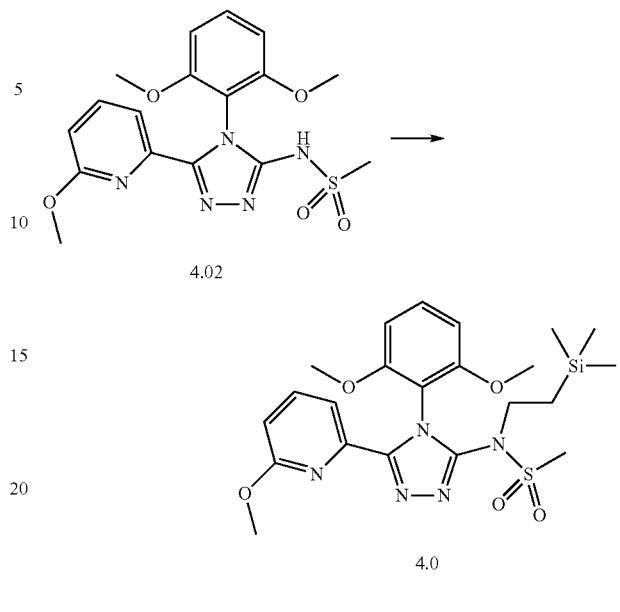

4.02

N-(4-(2,6-dimethoxyphenyl)-5-(6-methoxypyridin-2-yl)-4H-1,2,4-triazol-3-yl)methanesulfonamide, Example 4.02

To a suspension of (Z)—N'-(2,6-dimethoxyphenyl)-2-(6-methoxypicolinoyl)-N-(methylsulfonyl)hydrazinecarboximidamide (3.82 g, 9.02 mmol, Example 4.01) in 1,4-dioxane (45 mL), was added TFA (3.35 mL, 45.1 mmol). The reaction was heated at 100° C. for 18 h. The reaction mixture was partitioned between DCM (100 mL) and saturated NaHCO3(aqueous) (100 mL). The layers were separated. The aqueous layer was extracted with DCM (2×50 mL). The organic extracts were combined and dried over Na2SO4. The solution was filtered and concentrated in vacuo to give the product, which was absorbed onto a plug of silica gel and purified by silica gel column chromatography, eluting with a gradient of 0-50% B/A (B=26% EtOH in EtOAc, A=DCM), to provide the title compound 4.02 (2.98 g, 7.35 mmol, 81% yield) as an off-white solid. $^1$H NMR (400 MHz, DMSO-d$_6$) δ 13.34 (s, 1H), 7.80 (dd, J=8.31, 7.53 Hz, 1H), 7.57 (dd, J=7.43, 0.59 Hz, 1H), 7.40 (t, J=8.51 Hz, 1H), 6.83 (dd, J=8.22, 0.59 Hz, 1H), 6.79 (d, J=8.41 Hz, 2H), 3.67 (s, 6H), 3.10 (s, 3H), 2.82 (s, 3H). LCMS-ESI (POS.) m/z: 406.2 (M+H)+.

N-(4-(2,6-dimethoxyphenyl)-5-(6-methoxypyridin-2-yl)-4H-1,2,4-triazol-3-yl)-N-(2-(trimethylsilyl)ethyl)methanesulfonamide, Example 4.0

N-(4-(2,6-dimethoxyphenyl)-5-(6-methoxypyridin-2-yl)-4H-1,2,4-triazol-3-yl)methanesulfonamide 4.02 (2.86 g, 7.05 mmol) was azeotroped with toluene and then suspended in toluene (35 mL). To this mixture was added 2-(trimethylsilyl)ethanol (2.022 mL, 14.11 mmol) and N$_2$ was bubbled through the solution for 3 min. Cyanomethylenetributyl-phosphorane (3.06 mL, 12.70 mmol) was added and N$_2$ was bubbled through the solution again for 2 min. The reaction mixture was then heated at 90° C. for 15 min. The reaction mixture was then cooled to RT, absorbed onto a plug of silica gel and purified by chromatography through a Redi-Sep pre-packed silica gel column (330 g), eluting with a gradient of 0-50% EtOAc in hexanes, to provide the title compound 4.0 (3.07 g, 6.07 mmol, 86% yield) as an off-white solid. $^1$H NMR (400 MHz, CD$_2$Cl$_2$) δ 7.60-7.65 (m, 1H), 7.55-7.58 (m, 1H), 7.35 (t, J=8.51 Hz, 1H), 6.70 (dd, J=8.12, 0.88 Hz, 1H), 6.64 (d, J=8.61 Hz, 2H), 4.34-4.40 (m, 2H), 3.71 (s, 6H), 3.16 (s, 3H), 2.66 (s, 3H), 1.27-1.38 (m, 2H), 0.09-0.12 (m, 9H). LCMS-ESI (POS.) m/z: 506.1 (M+H)+.

Example 5.0: Preparation of N-(4-(2,6-dimethoxyphenyl)-5-(6-methoxypyridin-2-yl)-4H-1,2,4-triazol-3-yl)-N-(2-(trimethylsilyl)ethyl)ethanesulfonamide

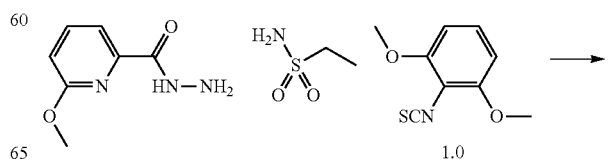

1.0

-continued

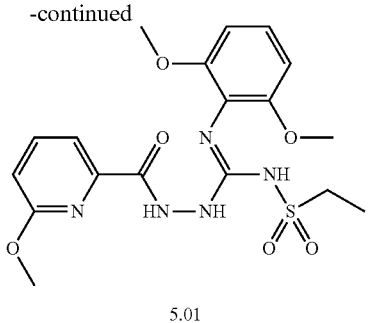

5.01

(Z)—N'-(2,6-dimethoxyphenyl)-2-(6-methoxypicolinoyl)-N-(methylsulfonyl)hydrazinecarboximidamide, Example 5.01

To a solution of 2-isothiocyanato-1,3-dimethoxybenzene (Example 1.0, 3.90 g, 20.0 mmol) and ethyl sulfonamide (1.81 mL, 21.0 mmol) in ACN (100 mL) at ambient temperature, was added cesium carbonate (8.46 g, 26.0 mmol) in one portion. The reaction was stirred over the weekend. To the mixture was added 6-methoxypicolinohydrazide (3.51 g, 21.0 mmol) in one portion followed by silver(I) nitrate (6.79 g, 40.0 mmol). The mixture was stirred for 15 min. The material obtained was absorbed onto a plug of silica gel and purified by chromatography through a Redi-Sep pre-packed silica gel column (40 g), eluting with a gradient of 0-100% B/A (B=15% MeOH/DCM, A=DCM), to provide the title compound 5.01 (8.22 g, 18.8 mmol, 94% yield) as an off-white powder. LCMS-ESI (POS.) m/z: 438.2 (M+H)$^+$.

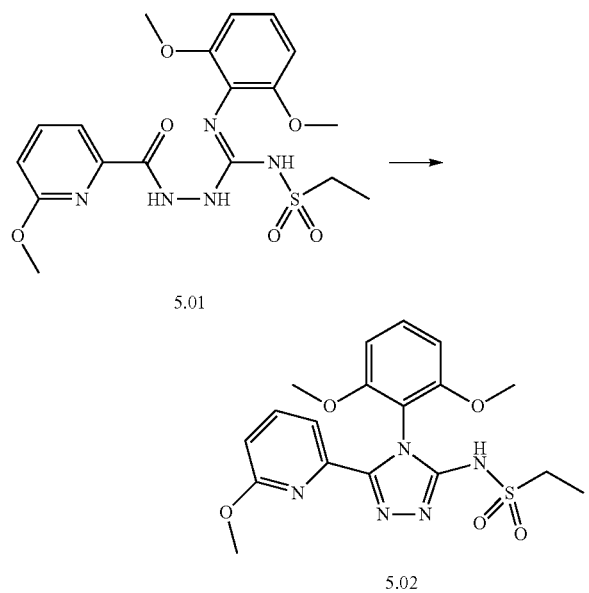

N-(4-(2,6-dimethoxyphenyl)-5-(6-methoxypyridin-2-yl)-4H-1,2,4-triazol-3-yl)ethanesulfonamide, Example 5.02

To a solution of (Z)—N'-(2,6-dimethoxyphenyl)-N-(ethylsulfonyl)-2-(6-methoxypicolinoyl)hydrazinecarboximidamide 5.01 (7.18 g, 16.4 mmol) in 1,4-dioxane (80 mL) was added TFA (6.1 mL, 82 mmol). The reaction mixture was heated at 100° C. for 20 h. The solvent and TFA were removed as much as possible on a rotary evaporator at 50° C. The residue was partitioned between DCM (200 mL) and water (200 mL), and the pH was adjusted to 7~8 by adding saturated NaHCO$_3$(aqueous). The layers were separated. The aqueous layer was extracted with DCM (2×100 mL). The combined organic extracts were dried over Na$_2$SO$_4$. The solution was filtered and concentrated in vacuo. The material thus obtained was absorbed onto a plug of silica gel and purified by chromatography through a Redi-Sep pre-packed silica gel column (330 g), eluting with a gradient of 0-50% B/A (B=23% EtOH in EtOAc, A=DCM), to provide the title compound 5.02 (6.47 g, 15.4 mmol, 94% yield) as an off-white powder. $^1$H NMR (400 MHz, DMSO-d$_6$) δ 13.26 (s, 1H), 7.80 (dd, J=8.31, 7.53 Hz, 1H), 7.56 (dd, J=7.43, 0.59 Hz, 1H), 7.40 (t, J=8.51 Hz, 1H), 6.82 (dd, J=8.31, 0.68 Hz, 1H), 6.79 (d, J=8.61 Hz, 2H), 3.67 (s, 6H), 3.10 (s, 3H), 2.88 (q, J=7.30 Hz, 2H), 1.13 (t, J=7.34 Hz, 3H). LCMS-ESI (POS.) m/z: 420.2 (M+H)$^+$.

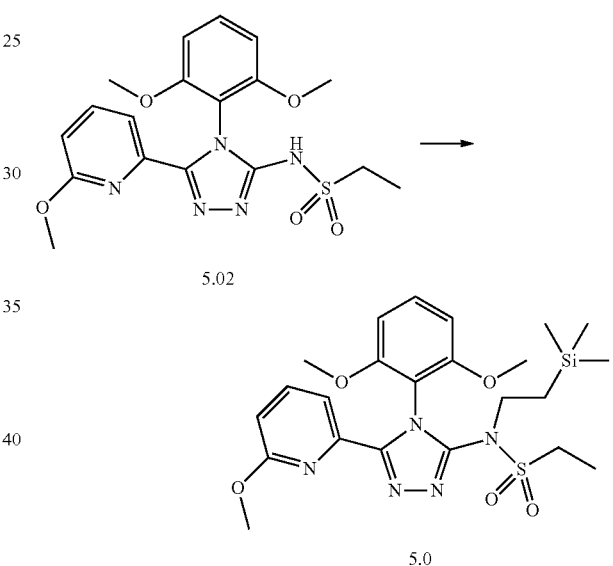

N-(4-(2,6-dimethoxyphenyl)-5-(6-methoxypyridin-2-yl)-4H-1,2,4-triazol-3-yl)-N-(2-(trimethylsilyl)ethyl)ethanesulfonamide, Example 5.0

N-(4-(2,6-dimethoxyphenyl)-5-(6-methoxypyridin-2-yl)-4H-1,2,4-triazol-3-yl)ethanesulfonamide 5.02 (7.36 g, 17.6 mmol) was azeotroped with toluene and suspended in toluene (88 mL). To the mixture was added 2-(trimethylsilyl)ethanol (5.03 mL, 35.1 mmol). The mixture was bubbled with nitrogen gas for 3 min. Cyanomethylenetributyl-phosphorane (7.62 mL, 31.6 mmol) was then added and the reaction was further purged with nitrogen for 2 min. The reaction was heated at 90° C. for 15 min. The reaction was cooled to RT. The solution was absorbed onto a plug of silica gel and purified by chromatography through a Redi-Sep pre-packed silica gel column (330 g), eluting with a gradient of 0-50% EtOAc in hexanes, to provide the title compound 5.0 (7.90 g, 15.2 mmol, 87% yield) as an off-white solid. $^1$H NMR (400 MHz, CD$_2$Cl$_2$) δ 7.60-7.65 (m, 1H), 7.55-7.59 (m, 1H), 7.35 (t, J=8.41 Hz, 1H), 6.69 (dd, J=8.12, 0.88 Hz, 1H), 6.63 (d, J=8.61 Hz, 2H), 4.38-4.45 (m, 2H), 3.70 (s, 6H), 3.16 (s, 3H), 2.72 (q, J=7.24 Hz, 2H), 1.32-1.38 (m, 2H), 1.01 (t, J=7.34 Hz, 3H), 0.09-0.12 (m, 9H). LCMS-ESI (POS.) m/z: 520.3 (M+H)⁺.

Example 6.0: Preparation of N-(4-(2,6-dimethoxyphenyl)-5-(5-methylpyridin-3-yl)-4H-1,2,4-triazol-3-yl)-N-(2-(trimethylsilyl)ethyl)methanesulfonamide

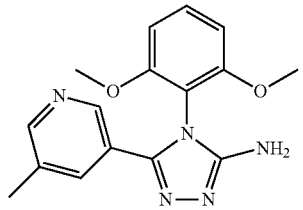

6.01

4-(2,6-dimethoxyphenyl)-5-(5-methylpyridin-3-yl)-4H-1,2,4-triazol-3-amine, Example 6.01

Example 6.01 was prepared in an analogous fashion to that of Example 2.04, using 5-methylnicotinohydrazide (Commercially available from Apollo scientific),

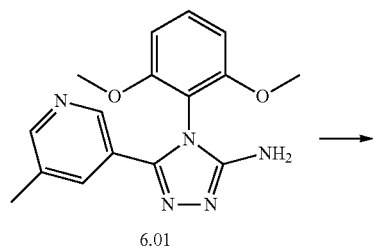

N-(4-(2,6-dimethoxyphenyl)-5-(5-methylpyridin-3-yl)-4H-1,2,4-triazol-3-yl)methanesulfonamide, Example 6.02

To a 250-mL round-bottomed flask was added 6.01 (2.09 g, 6.71 mmol) in THF (48 mL). Potassium tert-butoxide (1.0M solution in THF, 14.77 mL, 14.77 mmol) was added dropwise with stirring under N₂. The reaction mixture changed to a brown solution. The reaction mixture was then stirred at 23° C. for 15 min and methanesulfonyl chloride (0.571 mL, 7.38 mmol) was added dropwise. The resulting mixture was stirred for 3.5 h and LCMS analysis indicated the reaction was almost complete. The reaction was quenched with saturated aqueous NH₄Cl and extracted with EtOAc. The insoluble white solid was isolated by filtration and found to be the desired product. The organic extract was washed with brine and dried over Na₂SO₄. The solution was filtered and concentrated in vacuo to give the material as a light-yellow solid. The two portions of the product were combined to afford 6.02 (1.5 g, 3.85 mmol, 57.4% yield) as a light-yellow solid, which was directly used in the next step. LCMS-ESI (POS), m/z: 390.2 (M+H)⁺.

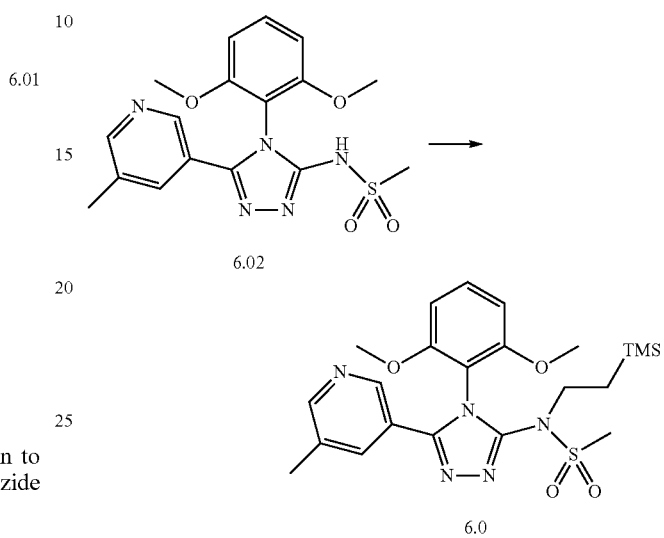

N-(4-(2,6-dimethoxyphenyl)-5-(5-methylpyridin-3-yl)-4H-1,2,4-triazol-3-yl)-N-(2-(trimethylsilyl)ethyl) methanesulfonamide, Example 6.0

6.02 (1.5 g, 3.85 mmol) was azeotroped with toluene and then suspended in toluene (30 mL). 2-(Trimethylsilyl)ethanol (1.10 mL, 7.70 mmol) and cyanomethylenetributylphosphorane (1.67 mL, 6.93 mmol) were added under N₂. The reaction mixture was stirred at 90° C. for 25 min. The reaction mixture was cooled to RT and purified by silica gel chromatography (a gradient of 0-100% EtOAc in DCM) to provide the title compound 6.0 (1.4 g, 2.86 mmol, 74% yield) as a yellow solid. ¹H NMR (500 MHz, CDCl₃) δ 8.31 (d, J=1.47 Hz, 1H), 8.23 (d, J=1.96 Hz, 1H), 7.48 (s, 1H), 7.28 (t, J=8.39 Hz, 1H), 6.49 (d, J=8.31 Hz, 2H), 4.17-4.23 (m, 2H), 3.65 (s, 6H), 2.69 (s, 3H), 2.16-2.19 (m, 3H), 1.14-1.26 (m, 2H), 0.00 (s, 9H). LCMS-ESI (POS), m/z: 490.3 (M+H)⁺.

Example 7.0: Preparation of 2-(5-fluoropyrimidin-2-yl)ethanesulfonamide

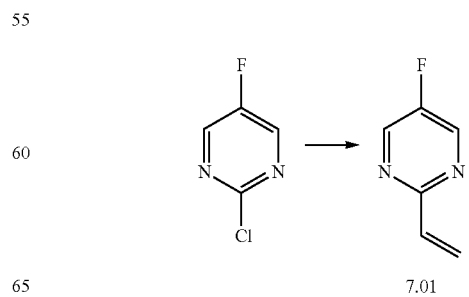

7.01

5-fluoro-2-vinylpyrimidine, Example 7.01

To a solution of 2-chloro-5-fluoropyrimidine (10.0 g, 75.46 mmol, Sigma Aldrich) in DMF (100 mL) was added tributyl(vinyl)tin (31.1 g, 98.09 mmol) at ambient temperature. The reaction mixture was purged with $N_2$ for 5 min and $Pd(PPh_3)_4$ (2.62 g, 2.26 mmol) was added. The reaction mixture was further degassed with $N_2$ for 5 min and stirred at 100° C. for 24 h. After completion of the reaction (monitored by TLC), the reaction mixture was cooled to ambient temperature and quenched with water (100 mL). The aqueous layer was extracted with diethyl ether (2×100 mL) and the combined organic layers were washed with brine (100 mL), dried over anhydrous $Na_2SO_4$ and concentrated under reduced pressure to get initial product which was purified by silica gel column chromatography (Redisep column 120 g; elution: 6% EtOAc in hexanes) to provide 7.01 (8.0 g, 85.1%) as an oil. MS (ESI, positive ion) m/z: 125.1. $^1H$ NMR (400 MHz, $CDCl_3$) δ 8.58-8.49 (m, 2H), 6.86 (dd, J=17.4, 10.6 Hz, 1H), 6.53 (d, J=17.3 Hz, 1H), 5.70 (d, J=10.6 Hz, 1H).

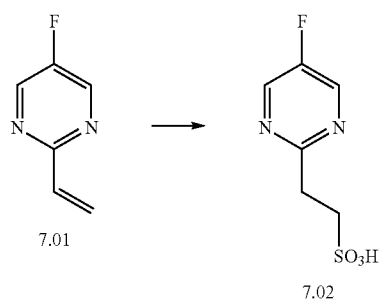

2-(5-fluoropyrimidin-2-yl) ethanesulfonic acid, Example 7.02

A solution of 7.01 (20.0 g, 16.12 mmol) in saturated aqueous $NaHSO_3$ (80 mL) was stirred at ambient temperature for 12 h. After completion of the reaction (monitored by TLC), the reaction mixture was concentrated under reduced pressure, and the residue was purified by flash column chromatography (120 g Redisep elution: 4-10% $H_2O$ in ACN) to provide the title compound 7.02 (16.0 g, 47.9%) as white solid. $^1H$ NMR (400 MHz, DMSO-$d_6$) δ 8.89-8.73 (m, 2H), 3.17 (t, J=8.2 Hz, 2H), 2.85 (t, J=8.2 Hz, 2H).

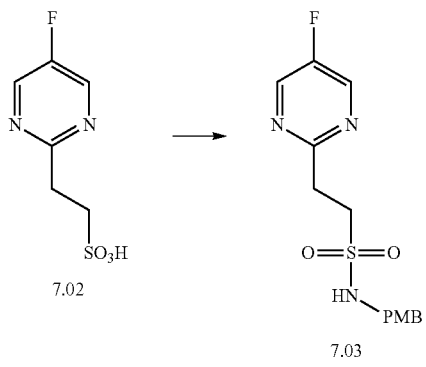

2-(5-fluoropyrimidin-2-yl)-N-(4-methoxybenzyl) ethanesulfonamide, Example 7.03

To a suspension of 7.02 (16.0 g, 77.30 mmol) in DCM (385 mL) was added oxalyl chloride (29.4 g, 231.8 mmol) followed by DMF (1 mL) at 0° C. The reaction mixture was stirred at ambient temperature for 1 h and concentrated under reduced pressure. The reaction mixture was azeotroped with cyclopentylmethylether to remove the traces of oxalyl chloride. The reaction mixture was diluted with DCM (385 mL), cooled to 0° C. and 4-methoxybenzylamine (31.8 g, 231.88 mmol) followed by TEA (39.1 g, 386.4 mmol) were added. The reaction mixture was stirred at ambient temperature for 12 h. After completion of the reaction (monitored by TLC), the reaction mixture was quenched with water (500 mL). The aqueous layer was extracted with DCM (2×400 mL). The organic layers were combined and washed with brine (1000 mL), dried over anhydrous $Na_2SO_4$ and concentrated under reduced pressure to obtain the initial material which was purified by column chromatography (silica gel, 100-200 mesh; elution 55% EtOAc in hexanes) to provide the title compound 7.03 (13.5 g, 53.5%) as an off yellow solid. MS (ESI, positive ion) m/z: 326.1.

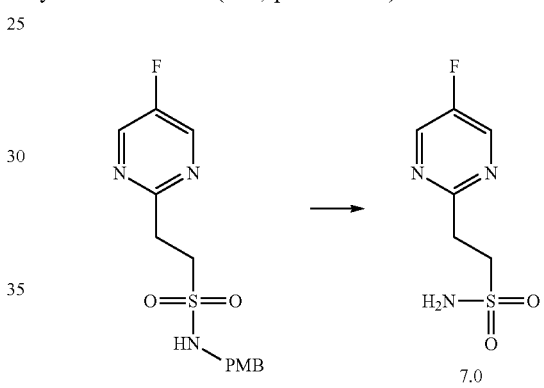

2-(5-fluoropyrimidin-2-yl)ethanesulfonamide, Example 7.0

To a suspension of 7.03 (13.5 g, 41.41 mmol) in DCM (46 mL) was added TFA (207 mL) at 0° C. The reaction mixture was stirred at RT for 12 h. After completion of the reaction, the reaction mixture was concentrated under reduced pressure providing a residue which was purified by flash chromatography (elution: 65% EtOAc in hexanes) to provide the title compound 7.0 (5.3 g, 62.5%) as an off yellow solid. MS (ESI, positive ion) m/z: 206.0. $^1H$ NMR (400 MHz, DMSO-$d_6$) δ 8.77 (s, 2H), 6.92 (s, 2H), 3.54-3.48 (m, 2H), 3.24-3.20 (s, 2H).

Example 8.0: Preparation of 2-(2-cyano-4-fluorophenyl)ethanesulfonamide

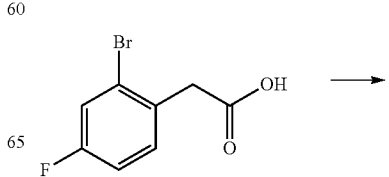

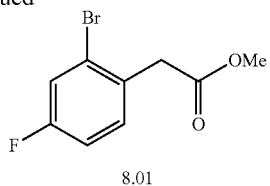

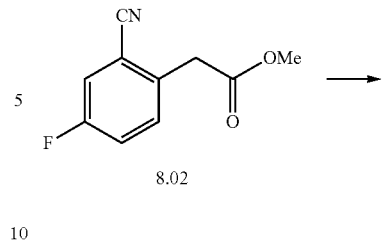

Methyl 2-(2-bromo-4-fluorophenyl) acetate, Example 8.01

To a solution of 2-bromo-4-fluorophenyl acetic acid (commercially available from Combi-Blocks Inc., San Diego, Calif., USA) (25.0 g, 0.11 mol) in MeOH (100 mL) was added thionyl chloride (23.5 mL, 0.32 mol) dropwise at 0° C. The resulting mixture was then heated at 80° C. for 16 h. The mixture was cooled to RT and the volatiles were removed under vacuum. The material thus obtained was diluted with DCM and washed with an aqueous solution of sodium bicarbonate and water. The organic layers were dried over sodium sulfate, filtered and evaporated to afford the title compound 8.01 (26 g, 100%), which was used as such in the next step. $^1$H NMR (400 MHz, DMSO-$d_6$) δ 7.59 (dd, J=8.6, 2.6 Hz, 1H), 7.47 (dd, J=8.5, 6.2 Hz, 1H), 7.25 (td, J=8.5, 2.7 Hz, 1H), 3.82 (s, 2H), 3.63 (s, 3H).

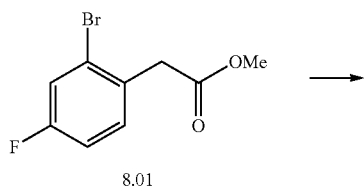

Methyl 2-(2-cyano-4-fluorophenyl) acetate, Example 8.02

To a solution of 8.01 (8.0 g, 0.032 mol) in dimethyl acetamide (60 mL) was added zinc cyanide (5.7 g, 0.049 mol). The flask was then degassed with argon and bis-(tri-tert-butylphosphine)palladium (1.7 g, 0.003 mol) was added. The resulting mixture was then heated at 110° C. for 18 h in a sealed tube. Thereafter, the reaction mixture was cooled to RT, diluted with water and extracted with EtOAc. The combined organic layers were dried over sodium sulphate and evaporated in vacuo. The product thus obtained was purified by column chromatography using silica gel and 20-25% EtOAc and hexanes as eluent to obtain the title compound 8.02 (5.4 g, 86%) as a light brown liquid. $^1$H NMR (400 MHz, DMSO-$d_6$) δ 7.91-7.81 (m, 1H), 7.68-7.51 (m, 2H), 3.95 (s, 2H), 3.65 (s, 3H). MS-ESI (NEG.) m/z: 192.2 (M−H)$^−$.

5-fluoro-2-(2-hydroxyethyl)benzonitrile, Example 8.03

To a solution of 8.02 (5.3 g, 0.027 mol) in THF (60 mL) at 0° C. was added LiBH$_4$ (1.20 g, 0.055 mol) portion-wise. The resulting mixture was stirred at 25° C. for 5 h. After completion of the reaction (monitored by TLC), the reaction mixture was cooled to 0° C. and quenched with water. The solvent was evaporated to obtain the initial material which was further diluted with water and extracted with EtOAc. The combined organic layers were dried over Na$_2$SO$_4$, filtered and evaporated in vacuo to obtain the product, which was further purified by column chromatography using silica gel and 15-20% EtOAc in hexanes as eluent to obtain the title compound 8.03 (3.1 g, 67%) as a light brown liquid. $^1$H NMR (400 MHz, DMSO-$d_6$) δ 7.81-7.73 (m, 1H), 7.52 (dd, J=10.6, 8.0 Hz, 2H), 4.82 (t, J=5.2 Hz, 1H), 3.64 (dd, J=11.9, 6.5 Hz, 2H), 2.91 (t, J=6.6 Hz, 2H).

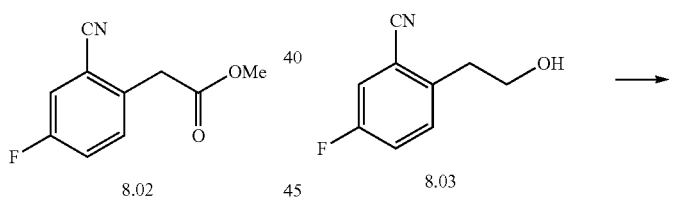

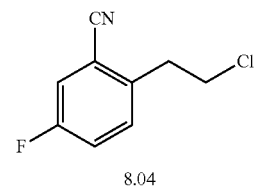

2-(2-chloroethyl)-5-fluorobenzonitrile, Example 8.04

To a solution of 8.03 (3.0 g, 0.018 mol) in DCM (50 mL) was added thionyl chloride (6.6 mL, 0.091 mol) dropwise followed by DMF (4 drops) at 0° C. The resulting mixture was heated at 55° C. for 7 h. After completion of the reaction (monitored by TLC), the reaction mixture was concentrated in vacuo to obtain the initial product, which was diluted with water and extracted with EtOAc. The combined organic layers were dried over Na$_2$SO$_4$, filtered and evaporated in vacuo to obtain the title compound 8.04 (3.0 g, 90%) as a brown liquid which was used in the next step without further purification. $^1$H NMR (400 MHz, DMSO-d$_6$) δ 7.81-7.84 (dd, J=2.4 Hz, 8.8 Hz, 1H), 7.56-7.66 (m, 2H), 3.90-3.94 (t, J=6.8 Hz, 13.6 Hz, 2H), 3.22-3.25 (t, J=6.8 Hz, 13.2 Hz, 2H). MS-ESI (neg.) m/z: 182.0 (M–H)$^-$.

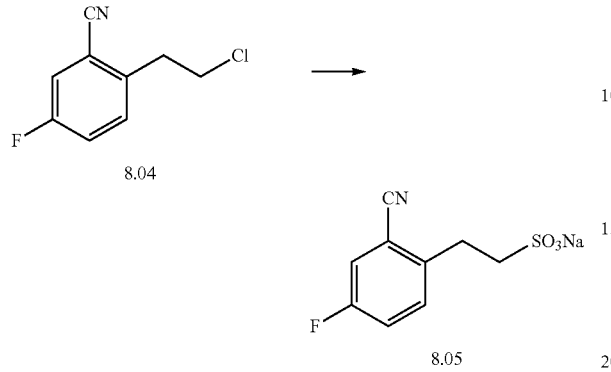

Sodium 2-(2-cyano-4-fluorophenyl)ethanesulfonate, Example 8.05

To a solution of 8.04 (3.0 g, 0.016 mol) in H$_2$O (50 mL) at RT was added sodium sulfite (3.1 g, 0.024 mol). The reaction mixture was heated at reflux for 18 h. After completion of the reaction (monitored by TLC), the reaction mixture was concentrated in vacuo to obtain the initial material, which was further stirred with EtOAc and filtered to obtain 8.05 (5.8 g) as an off-white solid, which was used for the next reaction without further purification. $^1$H NMR (400 MHz, DMSO-d$_6$) δ 7.74-7.76 (dd, J=2 Hz, 8.4 Hz, 1H), 7.47-7.55 (m, 2H), 3.05-3.09 (t, J=8 Hz, 16.4 Hz, 2H), 2.69-2.74 (t, J=8.4 Hz, 16.4 Hz, 2H). MS-ESI (neg.) m/z: 228.0 (M–H)$^-$.

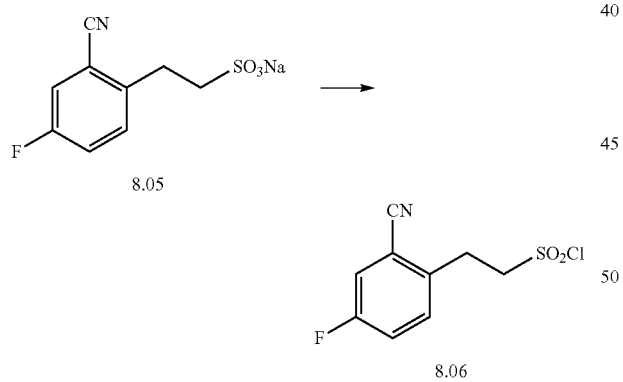

2-(2-cyano-4-fluorophenyl)ethanesulfonyl chloride, Example 8.06

To a solution of 8.05 (5.8 g) in benzene (50 mL) was added thionyl chloride (2.5 mL, 0.035 mol) dropwise followed by DMF (3 drops) at 0° C. The resulting mixture was heated to reflux for 16 h. After completion of the reaction (monitored by TLC), the mixture was cooled to 25° C., poured into ice water and extracted with EtOAc. The EtOAc layer was dried over Na$_2$SO$_4$, filtered and evaporated in vacuo to obtain the title compound 8.06 (3.4 g, 84% over two steps) as a brown solid. $^1$H NMR (400 MHz, CDCl$_3$) δ 7.47-7.38 (m, 2H), 7.33 (td, J=8.2, 2.7 Hz, 1H), 3.98 (dd, J=8.7, 6.7 Hz, 2H), 3.56-3.53 (m, 2H). MS-ESI (neg.) m/z: 245.9 (M–H)$^-$.

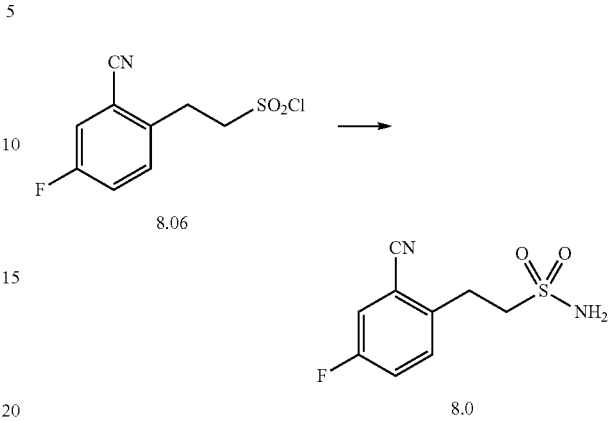

2-(2-cyano-4-fluorophenyl)ethanesulfonamide, Example 8.0

To a mixture of aqueous ammonia (10 mL, 77 mmol) and DCM (30 mL, 468 mmol) was added 8.06 (1.42 g, 5.73 mmol) in portions at RT. The reaction mixture was stirred at 23° C. for 2 h. LCMS analysis indicated the reaction was complete. The mixture was neutralized by adding concentrated HCl solution, and then extracted with DCM. The extract was washed with water and saturated sodium bicarbonate solution twice, dried over Na$_2$SO$_4$ and concentrated in vacuo. The residue was dried to give the title compound 8.0 (1.1 g, 4.82 mmol, 84% yield) as a white solid. LCMS-ESI (POS), m/z: 229.1 (M+H)$^+$.

Example 9.0: Preparation of (S)-1-(5-fluoropyrimidin-2-yl)propane-2-sulfonamide and (R)-1-(5-fluoropyrimidin-2-yl)propane-2-sulfonamide

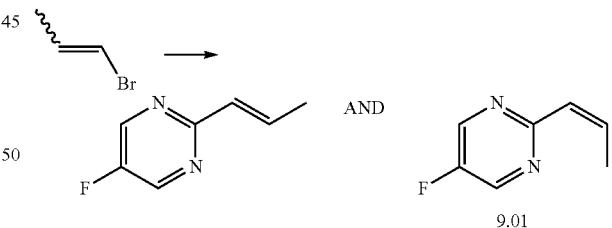

(E)-5-fluoro-2-(prop-1-en-1-yl)pyrimidine and (Z)-5-fluoro-2-(prop-1-en-1-yl)pyrimidine, Example 9.01

To magnesium turnings (9.0 g, 371.9 mmol) was added 1-2 crystals of iodine under anhydrous conditions. The mixture was heated at 60° C. for 5 min under reduced pressure to activate the magnesium. The flask was then cooled to RT and THF (370 mL) was added. The resulting mixture was heated to 65° C., (Z/E)-1-bromo-1-propene (45 g, 371.9 mmol) was added dropwise, and the mixture was stirred at 65° C. for 2 h under a nitrogen atmosphere.

Thereafter, the mixture was cooled to RT and transferred to an ice bath. Zinc chloride (1M in diethyl ether, 283 mL, 283 mmol) was then added dropwise over 10 min. The internal temperature of the reaction was kept at ~10° C.-15° C. during the addition, and the resulting organozinc reagent was stirred at RT for 45 min. In a separate round bottomed flask, a solution of 2-chloro-5-fluoropyrimidine (commercially available from Novochemy, Jupiter, Fla., USA) (25 g, 189 mmol), 5-phos (7.7 g, 18.8 mmol) and palladium (II) acetate (2.1 g, 9.4 mmol) in THF (38 mL) were degassed with nitrogen gas for 5 min. The organozinc reagent was then added dropwise. The resulting mixture was heated at 60° C. for 12 h. After completion of reaction (monitored by TLC), the reaction mixture was quenched with water (50 mL) and acidified with 1N hydrochloric acid (700 mL, pH 2). The mixture was then extracted with diethyl ether (2×500 mL). The combined organic layers were washed with brine (200 mL), dried over sodium sulphate and concentrated under reduced pressure at 20° C. to a volume of approximately 50 mL, which was used as such in the next step.

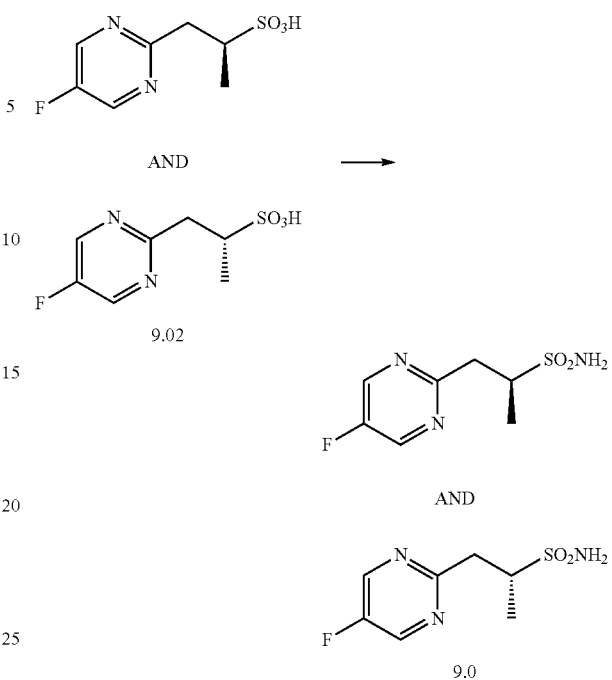

(S)-1-(5-fluoropyrimidin-2-yl)propane-2-sulfonamide and (R)-1-(5-fluoropyrimidin-2-yl)propane-2-sulfonamide, Example 9.0

A solution of 9.02 (80 g, 360 mmol) in thionyl chloride (268 mL, 3600 mmol) was heated at 60° C. for 3 h. The reaction was concentrated under reduced pressure to afford the sulfonyl chloride compound, which was azeotroped with toluene (3×300 mL). The residue was diluted with DCM (1.0 L) and ammonia gas was bubbled through the solution for 15 min at −78° C. The mixture was then stirred at RT for 1 h. Thereafter, the reaction mixture was filtered through a Celite® brand filter agent pad and the pad was washed with DCM (100 mL) and EtOAc (100 mL). The combined filtrate was concentrated under reduced pressure to obtain a residue which was purified by column chromatography (silica gel, elution 0-60% EtOAc in hexanes) to furnish the title compound 9.0 (43 g, 54%) as a white solid. $^1$H NMR (400 MHz, DMSO-$d_6$) δ 8.86 (d, J=1.1 Hz, 2H), 6.90 (s, 2H), 3.57-3.51 (m, 2H), 2.93 (dd, J=15.4, 11.1 Hz, 1H), 1.19 (d, J=6.5 Hz, 3H). MS-ESI (POS.) m/z: 220.0 (M+H)$^+$.

Example 10.0: Preparation of Example (2S,3R)-3-(5-methylpyrimidin-2-yl)butane-2-sulfonamide

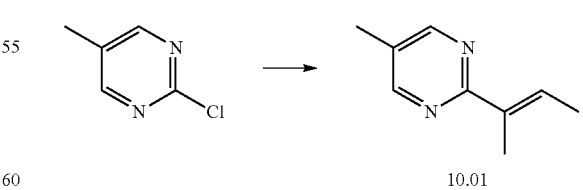

(E)-2-(but-2-en-2-yl)-5-methylpyrimidine, Example 10.01

2-Chloro-5-methyl-pyrimidine (18 mL, 151 mmol), potassium (Z)-but-2-en-2-yltrifluoroborate (Sigma Aldrich, (S)-1-(5-fluoropyrimidin-2-yl)propane-2-sulfonic acid and (R)-1-(5-fluoropyrimidin-2-yl)propane-2-sulfonic acid, Example 9.02

To a solution of 9.01 (188.6 mmol) in THF (50 mL) was added an aqueous solution of sodium bisulfite (19.6 g, 188.6 mmol in 100 mL of H$_2$O). The reaction mixture was stirred at ambient temperature for 20 h. Once the reaction was complete, (monitored by TLC), the mixture was acidified to approximately pH 1 with concentrated HCl (10 mL). The aqueous layer was concentrated under reduced pressure to furnish the initial product which was suspended in EtOH (250 mL). The product thus obtained was heated to reflux, filtered hot, and rinsed with hot EtOH (100 mL). The filtrate was concentrated under reduced pressure to give a brown solid, which was recrystallized from IPA (50 mL) to afford the title compound 9.02 (20 g, 48%) as a brown solid. $^1$H NMR (400 MHz, D$_2$O) δ 8.69 (s, 2H), 3.47 (td, J=9.8, 8.2, 4.0 Hz, 2H), 3.06 (dd, J=16.1, 10.2 Hz, 1H), 1.24 (d, J=6.5 Hz, 3H). MS-ESI (neg.) m/z: 118.9 (M−H)$^−$.

31 g, 191 mmol), tricyclohexylphosphine (8.5 g, 30.2 mmol), and Pd$_2$(dba)$_3$ (13.82 g, 15.09 mmol) were added to a flask, which was then degassed and backfilled with nitrogen. To the flask was added 1,4-dioxane (252 mL) and aqueous potassium phosphate tribasic (37.5 mL, 453 mmol). The resulting reaction was heated at 100° C. for 16 h. The reaction was then cooled to RT. The residue was filtered through a plug of silica gel, then loaded onto silica gel (0-20% EtOAc in heptanes) to afford (E)-2-(but-2-en-2-yl)-5-methylpyrimidine 10.01 (19 g, 125 mmol, 83% yield).

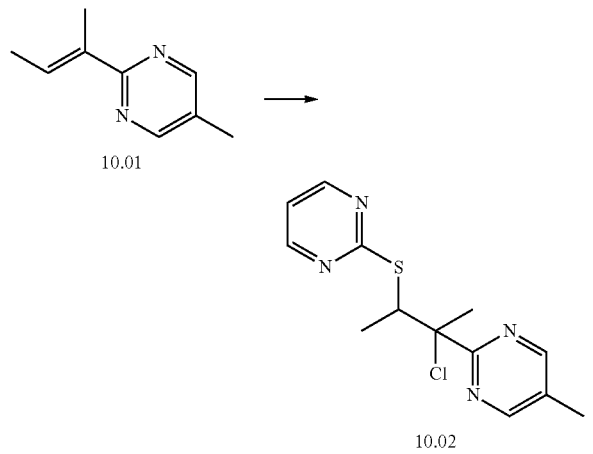

2-(2-chloro-3-(pyrimidin-2-ylthio)butan-2-yl)-5-fluoropyrimidine, Example 10.02

To a solution of pyrimidine-2-thiol (14.8 g, 132 mmol) in DCM (440 mL) was added sulfuryl chloride (10.73 mL, 132 mmol). The reaction was stirred at 0° C. for 1 h and a further 1 h at 23° C. To the cloudy reaction mixture was added (E)-2-(but-2-en-2-yl)-5-methylpyrimidine 10.01 (20 g, 132 mmol) dropwise, and the mixture was further stirred for 2 h. The reaction mixture was then concentrated in vacuo. Aqueous sodium bicarbonate was added to the mixture to neutralize the reaction mixture. The reaction was extracted with EtOAc and concentrated in vacuo. The residue was purified on silica gel with 0-25% EtOAc in hexanes to give the desired product 2-(2-chloro-3-(pyrimidin-2-ylthio)butan-2-yl)-5-fluoropyrimidine 10.02 (30 g, 76% yield).

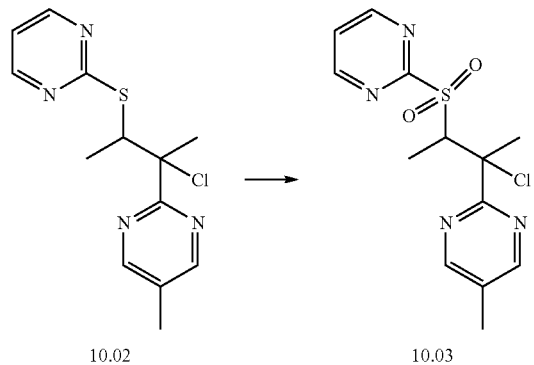 [SMILES: Cc1cnc(C(C)(Cl)C(C)Sc2ncccn2)nc1 ; Cc1cnc(C(C)(Cl)C(C)S(=O)(=O)c2ncccn2)nc1]

2-(2-chloro-3-(pyrimidin-2-ylsulfonyl)butan-2-yl)-5-methylpyrimidine, Example 10.03

To a solution of 2-(2-chloro-3-(pyrimidin-2-ylthio)butan-2-yl)-5-methylpyrimidine 10.02 (30 g, 100 mmol) in DCM (201 mL) was added meta-chloroperoxybenzoic acid (45.0 g, 201 mmol). The reaction was stirred at 23° C. for 1 d. The reaction was concentrated in vacuo and aqueous sodium bicarbonate and sodium thiosulfate were added. The mixture was extracted with EtOAc and concentrated in vacuo to give the desired product 2-(2-chloro-3-(pyrimidin-2-ylsulfonyl)butan-2-yl)-5-methylpyrimidine 10.03 (33.2 g, 100 mmol, 100% yield).

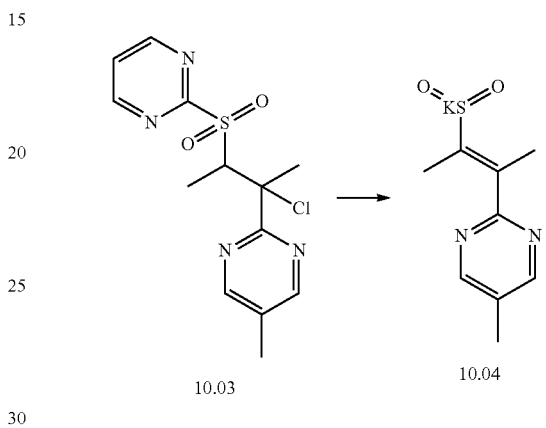

Potassium (E)-3-(5-methylpyrimidin-2-yl)but-2-ene-2-sulfinate, Example 10.04

To a solution of 2-(2-chloro-3-(pyrimidin-2-ylsulfonyl)butan-2-yl)-5-fluoropyrimidine 10.03 (33 g, 100 mmol) in MeOH (249 mL) was added potassium carbonate (27.6 g, 200 mmol). The reaction was stirred at 23° C. for 16 h. The reaction was concentrated in vacuo to give the desired product potassium (E)-3-(5-methylpyrimidin-2-yl)but-2-ene-2-sulfinate 10.04 (21.57 g, 100% yield), that was used without further purification.

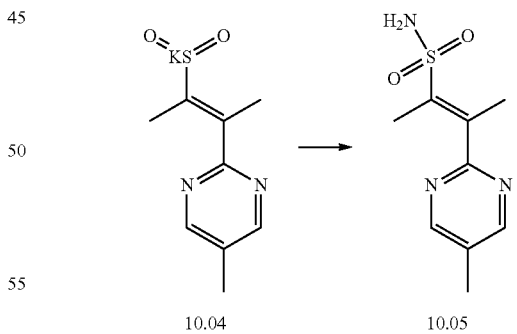

(E)-3-(5-methylpyrimidin-2-yl)but-2-ene-2-sulfonamide, Example 10.05

To a solution of potassium (E)-3-(5-methylpyrimidin-2-yl)but-2-ene-2-sulfinate (Example 10.04, 21.57 g, 85 mmol) in water (424 mL, 85 mmol) was added potassium acetate (5.30 mL, 85 mmol), followed by amidoperoxymonosulfuric acid (19.18 g, 170 mmol). The reaction was stirred at 23° C.

for 24 h. The reaction was extracted with EtOAc and concentrated in vacuo. The product thus obtained was purified on silica gel eluting with 0-50% EtOAc in hexanes to give the desired product (E)-3-(5-methylpyrimidin-2-yl)but-2-ene-2-sulfonamide 10.05 (12 g, 61% yield).

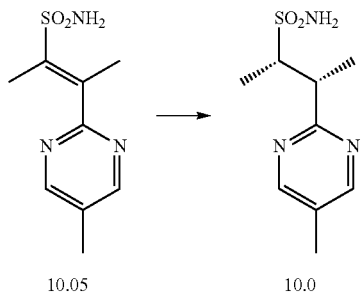

10.05    10.0

(2S,3R)-3-(5-methylpyrimidin-2-yl)butane-2-sulfonamide, Example 10.0

To a solution of (E)-3-(5-methylpyrimidin-2-yl)but-2-ene-2-sulfonamide 10.05 (1.0 g, 4.32 mmol) in EtOH (10.81 mL) was added zinc trifluoromethanesulfonate (0.314 g, 0.865 mmol), (E)-(−)-4, 12-bis(diphenylphosphino)[2.2]paracyclophane(1,5-cyclooctadiene)rhodium tetrafluroborate (strem chemicals, 0.151 g, 0.173 mmol) followed by hydrogen (8.72 mg, 4.32 mmol). The reaction was stirred for 3 h. The reaction was filtered to give (2S,3R)-3-(5-methylpyrimidin-2-yl)butane-2-sulfonamide 10.0 (0.65 g, 64% yield). The mother liquor was concentrated in vacuo and the material was purified on silica gel eluting with EtOAc/EtOH (3/1) in hexanes to give the desired product as a colorless solid. The ee of the material was increased, through recrystalisation from EtOH to >99% ee. 1H NMR (400 MHz, DMSO-$d_6$) δ 1.20 (d, J=6.85 Hz, 3H), 1.32 (d, J=6.85 Hz, 3H), 2.25 (s, H 3H), 3.60-3.79 (m, 2H), 6.82 (s, 2H), 8.61 (s, 2H). MS ESI (pos.) m/z: 230.2 (M+H)$^+$.

The compounds in the following Table were synthesized following the procedure in Example 10.0 using the known starting material as described.

TABLE 6

| Example | Reagents | Structure, Name and Data |
|---|---|---|
| 10.1 | 2-chloro-5-fluoro-pyrimidine | (2S,3R)-3-(5-fluoropyrimidin-2-yl)butane-2-sulfonamide. MS ESI (pos.) m/z: 234.2 (M + H)$^+$. |
| 10.2 | 2-bromo-5-methylpyrazine | (2S,3R)-3-(5-methylpyrazin-2-yl)butane-2-sulfonamide. The title compound was the first isomer to elute under the following SFC conditions: Run on Thar 200 SFC with 250 × 30 m AD-H column with 20 mL/min MeOH (+20 mM NH3) + 80 g/min $CO_2$, 20% co-solvent at 100 g/min. Temperature. = 29° C., Outlet pressure = 100 bar, Wavelength = 271 nm. Injected 1.0 mL of 550 mg of the enantiomerically enriched product disolved in 20 mL MeOH:DCM, 15:5, c = 27.5 mg/mL and 27.5 mg per injecvtion. Cycle time 5.0 min, run time 13 min. LCMS-ESI (POS.) m/z: 230.0 (M + H)$^+$. |

TABLE 6-continued

| Example | Reagents | Structure, Name and Data |
|---|---|---|
| 10.3 | 2-bromo-5-methylpyrazine | 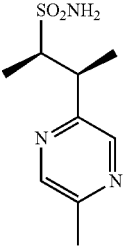<br>(2R,3S)-3-(5-methylpyrazin-2-yl)butane-2-sulfonamide is the enantiomer of Example 10.2. Example 10.2 was the second isomer to elute from AD-H column on subjecting the enantiomerically enriched product to the SFC conditions described in Example 10.2. LCMS-ESI (POS.) m/z: 230.0 (M + H)+. |

Example 11.0: Preparation of (1R,2S)-1-hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide

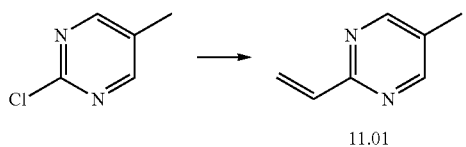

5-methyl-2-vinylpyrimidine, Example 11.01

A 3 L 3-necked round bottomed flask was fitted with a reflux condenser, a temperature controller and a septum and was charged with 2-chloro-5-methylpyrimidine (81 mL, 778 mmol), potassium vinyltrifluoroborate (156 g, 1167 mmol), triphenylphosphine (18.02 mL, 78 mmol), cesium carbonate (156 mL, 1945 mmol) and a large stir bar. Water (1565 mL) was added and the mixture was stirred for several minutes and then THF (244 mL) was added. Argon was bubbled through the mixture for 5 min and then added palladium (II) chloride (1.72 g, 38.9 mmol) was added. The reaction was further sparged with argon for 5 mins. The temperature was raised to 62° C. and stirring continued to completion. The reaction was then cooled to RT and filtered through two Whatman GF/F filter cups, rinsing with ether. The mixture was transferred to a separatory funnel, and the layers were separated. The aqueous layer was further extracted with diethyl ether (4×200 mL). The organic layers were combined and dried over anydrous MgSO4 and then filtered. The mixture was partially concentrated on the roto evaporator at 20° C. and 115 torr for an extended period of time to give an orange liquid. The material was further purified by Kugelrohr distillation to isolate the title compound (65.4 g, 70%) as a light yellow oil. $^1$H NMR (400 MHz, CDCl$_3$) δ 2.31 (s, 3H), 5.68 (d, J=10.56 Hz, 1H), 6.55 (d, J=17.22 Hz, 1H), 6.86 (dd, J=17.41, 10.56 Hz, 1H), 8.54 (s, 2H). LCMS-ESI (pos.) m/z: 121.1 (M+H)+.

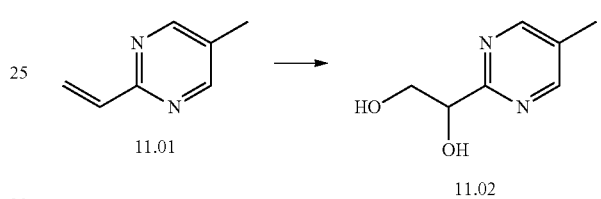

1-(5-methylpyrimidin-2-yl)ethane-1,2-diol, Example 11.02

To a 2000 mL round-bottomed flask was added 5-methyl-2-vinylpyrimidine (64.5 g, 537 mmol), osmium tetroxide (0.204 mL, 3.93 mmol) and 1,4-dioxane (537 mL, 537 mmol), 4-methylmorpholine-n-oxide, 50% wt. in water (40 mL, 341 mmol) and 4-methylmorpholine-4-oxide (94 g, 805 mmol). The reaction mixture was stirred over 2 d. LCMS showed that the reaction was complete and the solvent was removed in vacuo. The compound was purified by silica gel. The gradient was 100% heptane for 3CV's, then 0-100% EtOAc-EtOH (3:1) in heptane for 6 CV's, then 100% EtOAc:EtOH (3:1) for 5 CV's. The desired compound was collected and concentrated in vacuo. The material was triturated with 40% EtOAc in hexanes to give a solid, which was filtered. The solid was washed with 20% EtOAc in hexanes several times and then dried to give the title compound (67.3 g). $^1$H NMR (400 MHz, CDCl$_3$) δ 8.59 (s, 2H), 4.81-4.98 (m, 1H), 3.88-4.19 (m, 2H), 2.36 (s, 3H).

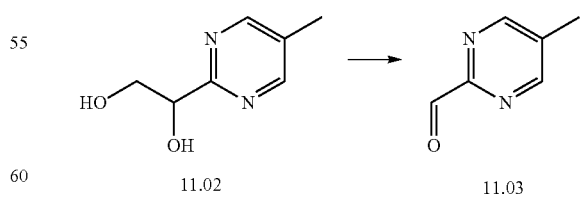

5-methylpyrimidine-2-carbaldehyde, Example 11.03

A 5 L flask equipped with a mechanical stirrer was charged with 1-(5-methylpyrimidin-2-yl)ethane-1,2-diol (64.3 g, 417 mmol), 1,4-dioxane (1043 mL) and water (261 mL). The reaction was cooled in an ice-water bath. Sodium periodate (223 g, 1043 mmol) was added and the internal temperature was monitored until it returned to RT. The reaction was further stirred at RT for 2 hr and 20 min. DCM (2 L) was then added. The resulting solution was filtered through a plug of dried MgSO$_4$ (700 g). The plug was washed with DCM (7 L). The solvent was concentrated in vacuo and the aldehyde was azeotroped with toluene to deliver the title compound (44 g) as a white solid. LCMS-ESI (pos.) m/z: 122.8 (M+H)$^+$.

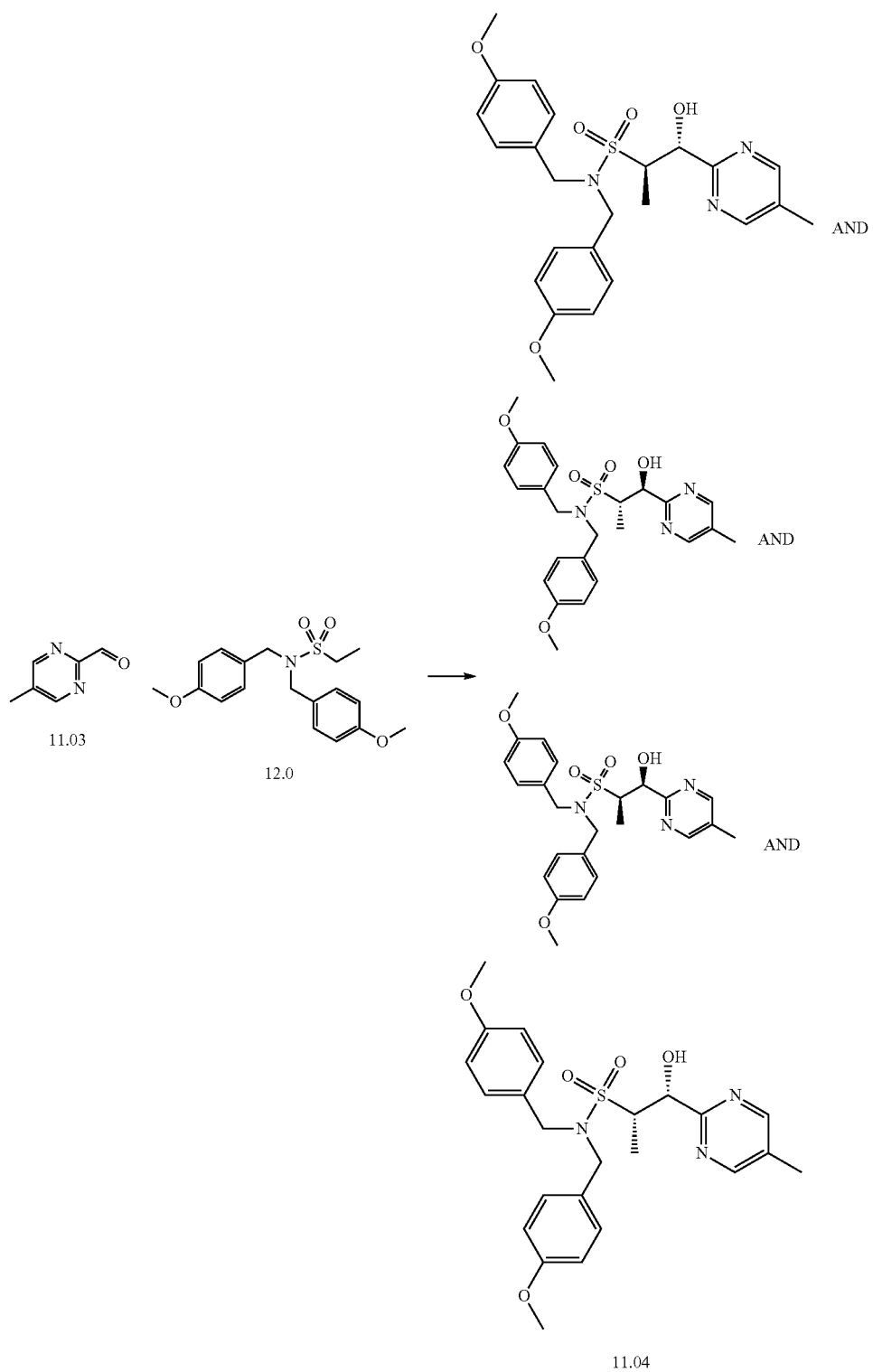

(1R,2S)-1-hydroxy-N,N-bis(4-methoxybenzyl)-1-(5-methylpyrimidin-2-yl)propane-2-sulfonamide and
(1S,2S)-1-hydroxy-N,N-bis(4-methoxybenzyl)-1-(5-methylpyrimidin-2-yl)propane-2-sulfonamide and
(1R,2R)-1-hydroxy-N,N-bis(4-methoxybenzyl)-1-(5-methylpyrimidin-2-yl)propane-2-sulfonamide and
(1S,2R)-1-hydroxy-N,N-bis(4-methoxybenzyl)-1-(5-methylpyrimidin-2-yl)propane-2-sulfonamide,
Example 11.04

The sulfonamide 12.0 was azeotroped with toluene. A 3 L flask was charged with N,N-bis(4-methoxybenzyl)ethanesulfonamide (151 g, 432 mmol) and anhydrous THF (1200 mL) under nitrogen and then equipped with a pre-dried addition funnel under nitrogen. The flask was cooled in an dry ice-acetone bath. n-Butyllithium (1.6M, 270 mL, 432 mmol) was first cannulated into the additional funnel. It was added slowly into the reaction flask and stirred for 10 min. 5-Methylpyrimidine-2-carbaldehyde (11.03, 44 g, 360 mmol) in THF (300 mL) was cannulated into the reaction. The reaction continued at −78° C. for 45 min and then was warmed to RT and stirring continued for 2 h and 10 min. A saturated solution of ammonium chloride was added to quench the reaction and the mixture was extracted with EtOAc and concentrated in vacuo to give the product.

(1R,2S)-1-hydroxy-N,N-bis(4-methoxybenzyl)-1-(5-methylpyrimidin-2-yl)propane-2-sulfonamide and
(1S,2R)-1-hydroxy-N,N-bis(4-methoxybenzyl)-1-(5-methylpyrimidin-2-yl)propane-2-sulfonamide,
Example 11.0

The mixture of diastereomers was separated and purified on silica gel eluting with 0-50% EtOAc gradient in DCM to give the title compound (56.4 g). LCMS-ESI (pos.) m/z: 472.1 (M+H)$^+$.

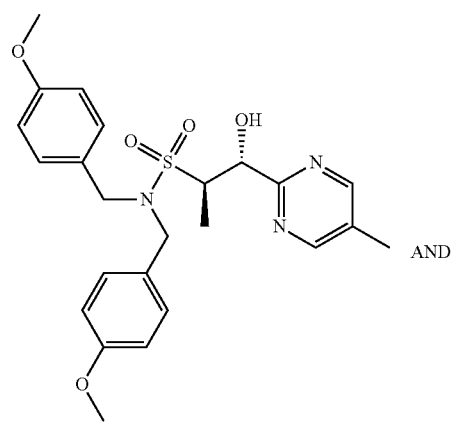

11.0

AND

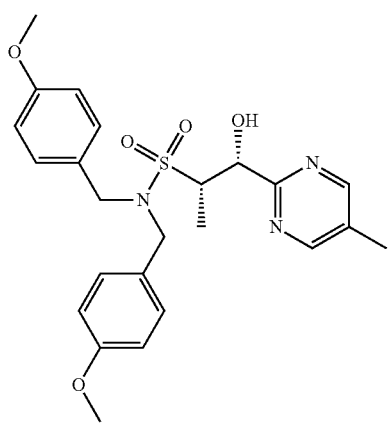

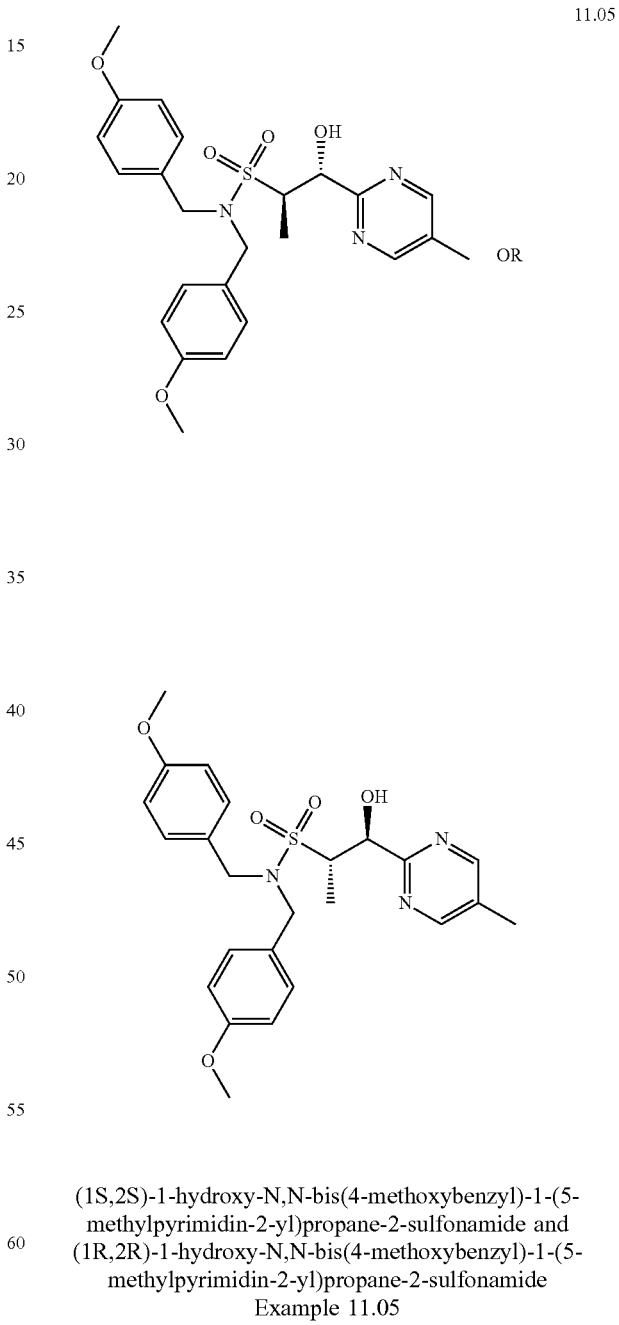

(1S,2S)-1-hydroxy-N,N-bis(4-methoxybenzyl)-1-(5-methylpyrimidin-2-yl)propane-2-sulfonamide and
(1R,2R)-1-hydroxy-N,N-bis(4-methoxybenzyl)-1-(5-methylpyrimidin-2-yl)propane-2-sulfonamide
Example 11.05

Further elution under the conditions described in Example 11.0 delivered the title compound. LCMS-ESI (pos.) m/z: 472.1 (M+H)$^+$.

Example 12.0: Preparation of N,N-bis(4-methoxybenzyl)ethanesulfonamide

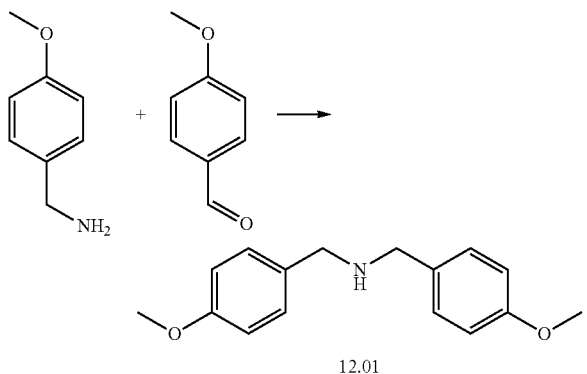

Bis(4-methoxybenzyl)amine, Example 12.01

4-methoxybenzylamine (neat, 600 g, 4.37 mol, 1 eq) and 4-methoxybenzaldehyde (532 mL, 4.37 mol, 1 eq) were added to a 10 L round bottomed flask at ambient temperature with stirring. The reaction spontaneously warmed and a white precipitate was observed. The mixture was stirred for 1 h. To the above mixture was added anhydrous EtOH (4.8 L) and stirring was continued at RT for 15-30 min. This was followed by the addition of sodium borohydride granules (99 g, 2.62 mol, 0.6 eq) portionwise over ~2 h (Note: During the addition of NaBH$_4$, the internal temperature of the reaction rose up to 42° C.) and further stirred at ambient temperature overnight. The reaction was quenched slowly with water (600 mL). The mixture was concentrated on a rotary evaporator at 50° C. The residue was partitioned between water (4 L) and DCM (4 L). The aqueous layer was extracted with more DCM (2×2 L). The combined organic layers were dried over Na$_2$SO$_4$, filtered and concentrated in vacuo to give bis(4-methoxybenzyl)amine 12.01 (1112 g, 99% yield) as a semi-solid. The material was used directly in the next step without further purification. $^1$H NMR (400 MHz, CDCl$_3$) δ 7.28 (t, J=7.12 Hz, 4H), 6.89 (d, J=8.60 Hz, 4H), 3.83 (s, 6H), 3.76 (s, 4H) (—NH proton not observed). MS (ESI pos. ion) m/z: =258.4 (M+H)$^+$.

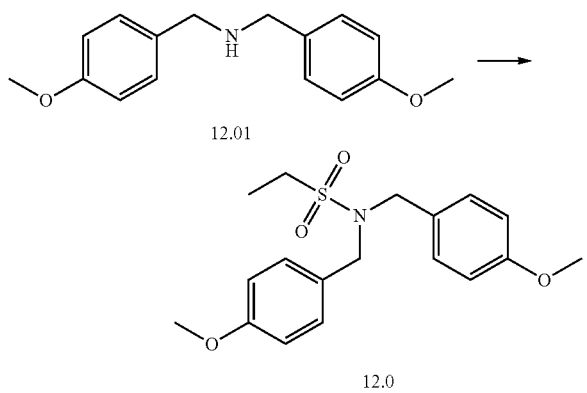

N,N-bis(4-methoxybenzyl)ethanesulfonamide, Example 12.0

To a solution of bis(4-methoxybenzyl)amine 12.01 (900 g, 3.49 mol, 1 eq) in DCM (9 L) was added TEA (634 mL, 4.55 mol, 1.3 eq), followed by dropwise addition of ethanesulfonyl chloride (399 mL, 4.19 mol, 1.2 eq). (The internal temperature was kept between 5-10° C. during the addition of the ethane sulfonyl chloride). Once the addition was complete, the cooling bath was removed. After 1.5 h, TLC showed complete loss of starting material. The reaction was quenched by the addition of water (4 L) to the reaction mixture. The layers were separated and the aqueous layer extracted with DCM (2×2 L). The combined organic layers were washed with brine (2×1 L), dried over Na$_2$SO$_4$, and concentrated in vacuo. The material thus obtained was adsorbed onto a plug of silica gel and purified by chromatography (silica gel (60-120 mesh) eluting with a gradient of 10-80% EtOAc in hexanes) to provide the title compound 12.0 (1125 g, 3.22 mol, 92%) as white solid. $^1$H NMR (400 MHz, CDCl$_3$) δ 7.23 (dd, J=2.08, 6.62 Hz, 4H), 6.90 (dd, J=2.12, 6.60 Hz, 4H), 4.29 (s, 4H), 3.83 (s, 6H), 2.92 (q, J=7.40 Hz, 2H), 1.33 (t, J=7.40 Hz, 3H). GC-MS (ESI pos. ion) m/z: 372.2 (M+Na)$^+$.

Example 13.0: Preparation of N,N-bis(4-methoxybenzyl)methanesulfonamide

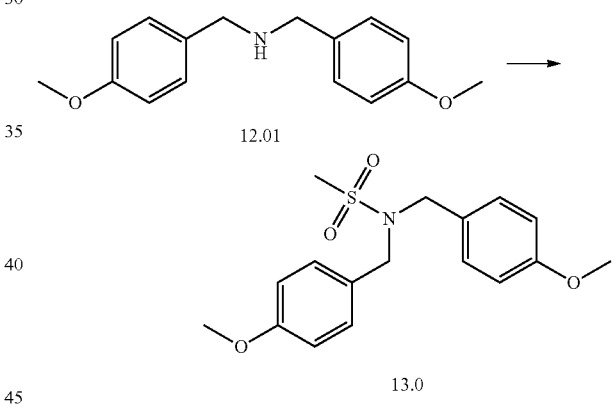

N,N-bis(4-methoxybenzyl)methanesulfonamide, Example 13.0

To a solution of bis(4-methoxybenzyl)amine 12.01 (100 g, 0.389 mol, 1 eq) in DCM (1 L) was added TEA (71 mL, 0.506 mol, 1.3 eq) followed by dropwise addition of methanesulfonyl chloride (36 mL, 0.46 mol, 1.2 eq). (The internal temperature was kept between 5-10° C. during the addition of the methane sulfonyl chloride). Once the addition was complete, the cooling bath was removed. After 1.5 h, TLC showed complete loss of starting material. Water (1 L) was added to the reaction. The layers were separated and the aqueous layer was extracted with DCM (2×500 mL). The combined organic layers were washed with brine (2×1 L), dried over Na$_2$SO$_4$, and concentrated in vacuo. The material thus obtained was absorbed onto a plug of silica gel and purified by chromatography (silica gel (60-120 mesh) eluting with a gradient of 10-80% EtOAc in hexanes) to provide 120 g (0.36 mol, 92%) of the title compound Example 13.0 as white solid. $^1$H NMR (400 MHz, CDCl$_3$) δ 7.26 (dd, J=2.12, 6.60 Hz, 4H), 6.91 (dd, J=2.12, 6.62 Hz, 4H), 4.28 (s, 4H), 3.83 (s, 6H), 2.75 (s, 3H). GC-MS (ESI pos. ion) m/z: =335 (M+H)⁺.

Example 14.0: Preparation of (1R,2S)-1-methoxy-1-(5-methylpyrimidin-2-yl)propane-2-sulfonamide, 14.0

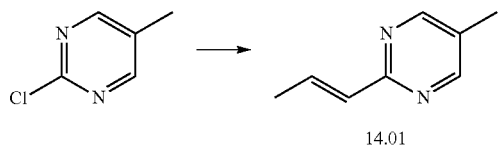

(E)-5-methyl-2-(prop-1-en-1-yl)pyrimidine, Example 14.01

To a 500 mL round bottomed flask was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was purged with $N_2$ (5×) and then 1,4-dioxane (200 mL) and water (20 mL) were added. The resulting yellow suspension was bubbled with Ar for 15 min and then 1,1-bis[(di-t-butyl-p-methylaminophenyl]palladium(II) chloride (Amphos, commercially available from Strem, 2.64 g, 3.73 mmol) was added, a reflux condenser was attached and the reaction warmed to 90° C. in an oil bath and stirred under $N_2$ for 16.5 h. The reaction was then cooled to RT. The reaction was diluted with water (250 mL), and extracted with EtOAc (2×250 mL). The organic layers were combined, dried (MgSO₄), and concentrated. The residue was purified by flash chromatography on silica gel eluting with 0-20% EtOAc/hexanes) to afford (E)-5-methyl-2-(prop-1-en-1-yl)pyrimidine 14.01 (12.96 g, 97 mmol, 100% yield) as a yellow/orange oily solid. ¹H NMR (300 MHz, CDCl₃) δ=8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 3H). MS (ESI pos. ion) m/z: 135.2 (M+H)⁺.

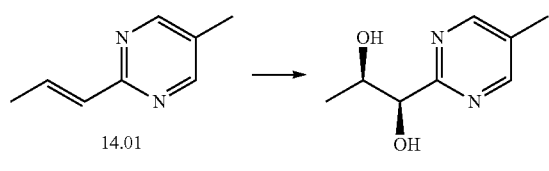

(1R,2R)-1-(5-methylpyrimidin-2-yl)propane-1,2-diol, Example 14.02

Racemic conditions. To a solution of (E)-5-methyl-2-(prop-1-en-1-yl)pyrimidine, 14.01 (5.75 g, 42.9 mmol) and 4-methylmorpholine-4-oxide (7.53 g, 64.3 mmol) in acetone (60 mL) and water (6 mL) was added osmium tetroxide, 4 wt. %, in water (0.681 mL, 0.11 mmol). The resulting reaction mixture was stirred at RT under $N_2$ for 21.5 h. The reaction was passed through a Varian Chem-Elut cartridge and concentrated in vacuo. The residue was dissolved in DCM, dried (MgSO₄), and concentrated. The residue was purified by flash chromatography (120 g SiO₂, 0-10% MeOH/DCM) to give the racemic syn-diol (1S,2S)-1-(5-methylpyrimidin-2-yl)propane-1,2-diol and (2R,2R)-1-(5-methylpyrimidin-2-yl)propane-1,2-diol (5.85 g, 34.8 mmol, 81% yield) as a light yellow solid. ¹H NMR (300 MHz, CDCl₃) δ 8.59 (s, 2H), 4.67 (br. s., 1H), 4.33 (br. s., 1H), 4.09-4.25 (m, 1H), 2.86 (d, J=7.2 Hz, 1H), 2.36 (s, 3H), 1.30 (d, J=6.6 Hz, 3H). MS (ESI pos. ion) m/z: 169.2 (M+H). Chiral conditions. A batch of AD-mix-beta was prepared from: (26 mg, 0.07 mmol) K₂OsO₂(OH)₄; (16.4 g, 49.9 mmol) K₃Fe(CN)₆; (6.89 g, 49.9 mmol) K₂CO₃; (125 mg, 0.16 mmol) (DHQD)₂PHAL. In a 50 mL round bottom flask was added t-BuOH (5 mL), water (5.00 mL), and 1.4 g of AD-mix-beta (prepared above) and methanesulfonamide (95 mg, 1.00 mmol). The mixture was stirred at RT until clear, and then cooled to 0° C. (E)-5-methyl-2-(prop-1-en-1-yl) pyrimidine (intermediate 14.01 168 mg, 1 mmol) in t-BuOH (1 mL) was added and the slurry was stirred at 0° C. 2 h. LCMS (1.5 h) shows ~10% conversion. The reaction was allowed to warm slowly to RT as the ice bath melted and stirred an additional 22 h. LCMS showed ~90% conversion. The reaction was quenched with saturated aqueous sodium sulfite (10 mL), and extracted with EtOAc (2×20 mL). The combined organic layers were washed with 2 N NaOH (10 mL), dried (MgSO₄), and concentrated. The aqueous layer was extracted with DCM (2×50 mL), EtOAc (2×50 mL), and 10% iPrOH in CHCl₃ (2×50 mL). The combined organic layers were concentrated and the residue purified by flash column chromatography (12 g SiO₂, 5-100% 3:1 EtOAc: EtOH/heptane) to give (1R,2R)-1-(5-methylpyrimidin-2-yl) propane-1,2-diol (Example 14.02, 88.6 mg, 0.527 mmol, 52.7% yield) as a clear, colorless oil. Chiral Analysis: SFC Chiral Analysis shows the % ee to be 94.8% using an AS-H (100×2.1 mm, 3 um), 10% organic modifier (iPrOH with 20 mM ammonia), 90% carbon dioxide. F=1.0 mL/min, column temperature=RT, BRP=105 bar.

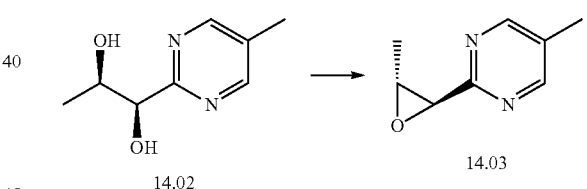

5-Methyl-2-((2R,3R)-3-methyloxiran-2-yl)pyrimidine, Example 14.03

To a solution of syn-diol (1R,2R)-1-(5-methylpyrimidin-2-yl)propane-1,2-diol 14.02 (1.46 g, 8.68 mmol) in DCM (25 mL) (cooled with a RT water bath) was added 1,1,1-trimethoxyethane (2.50 mL, 2.29 mmol). Chlorotrimethylsilane (2.50 mL, 19.7 mmol) was then added in 2 portions 5 min apart. The reaction had a small exotherm on the first portion of addition of TMSCl (23-28° C.). The reaction was stirred at RT under $N_2$ for 23 h. LCMS indicated incomplete conversion. Thus, an additional 1.25 equiv. of 1,1,1-trimethoxy ethane (1.25 mL, 9.95 mmol) and chlorotrimethylsilane (1.25 mL, 9.85 mmol) were added and the reaction was stirred for an additional 24 h. LCMS; ((M+H)⁺=229). The reaction was concentrated in vacuo. The residue was dissolved in MeOH (20 mL) and potassium carbonate (1.50 g, 10.85 mmol) was added and the reaction stirred at RT for 4 h. LCMS (4 h) shows complete conversion to product corresponding to desired epoxide LCMS;

((M+H)⁺=151). The reaction was filtered, the filter cake washed with DCM (5 mL), and the combined filtrates concentrated in vacuo. The residue was purified by flash column chromatography on silica gel eluting with 0-100% EtOAc/hexanes) to afford 5-methyl-2-((2R,3R)-3-methyl-oxiran-2-yl)pyrimidine 14.03 (1.00 g, 6.6 mmol, 77%) as a clear, light yellow oil. ¹H NMR (300 MHz, CDCl₃) δ 8.54 (s, 2H), 3.81 (d, J=1.9 Hz, 1H), 3.32-3.53 (m, 1H), 2.31 (s, 3H), 1.50 (d, J=5.1 Hz, 3H). MS (ESI pos. ion) m/z: 151.2 (M+H)⁺.

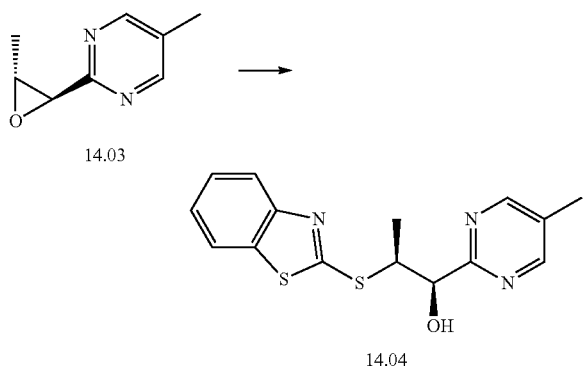

(1R,2S)-2-(benzo[d]thiazol-2-ylthio)-1-(5-methylpyrimidin-2-yl)propan-1-ol, Example 14.04

To a solution of 5-methyl-2-((2R,3R)-3-methyloxiran-2-yl)pyrimidine 14.03 (250 mg, 1.33 mmol) in DCM (5 mL) was added benzo[d]thiazole-2-thiol (245 mg, 1.465 mmol), followed by tris(((trifluoromethyl)sulfonyl)oxy)ytterbium (83 mg, 0.133 mmol). The suspension was heated in a 35° C. heating block for 17 h and showed 100% conversion to the desired product. The reaction was cooled to RT, loaded on a plug of silica, and purified by flash chromatography (12 g SiO₂, 5-100% 3:1 EtOAc:EtOH/heptane) to afford (1R,2S)-2-(benzo[d]thiazol-2-ylthio)-1-(5-methylpyrimidin-2-yl)propan-1-ol 14.04 (428 mg, 1.35 mmol, 100% yield) as a clear colorless oil. ¹H NMR (300 MHz, CDCl₃) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). MS (ESI pos. ion) m/z: 318.2 (M+H)⁺.

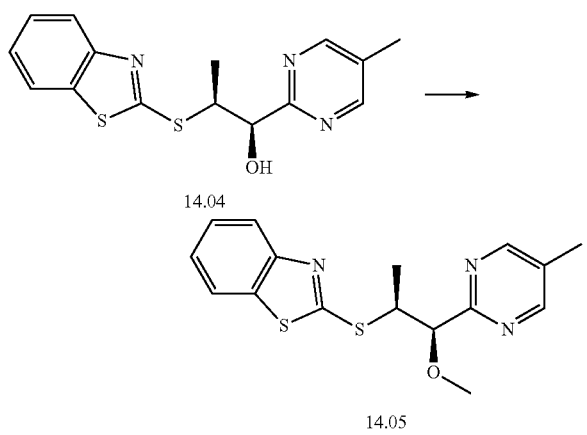

2-(((1R,2S)-1-methoxy-1-(5-methylpyrimidin-2-yl)propan-2-yl)thio)benzo[d]thiazole, Example 14.05

To a 50 mL flask equipped with a magnetic stirrer was charged a (1R,2S)-2-(benzo[d]thiazol-2-ylthio)-1-(5-methylpyrimidin-2-yl)propan-1-ol 14.04 (350 mg, 1.103 mmol) in 2-methyltetrahydrofuran (1.1 mL). The reaction mixture was cooled to −78° C. and potassium bis(trimethylsilyl)amide (1M solution in THF, 1.32 μL, 1.32 mmol)) was added dropwise (total addition time: 2 min., turned to yellow solution). The resulting mixture was stirred for 1 h and then methyl trifluoromethanesulfonate (374 μL, 3.31 mmol) was added dropwise (turned lighter yellow solution). The reaction mixture was stirred at −78° C. for 15 min. LCMS showed complete conversion to the product. The reaction mixture was quenched by saturated aqueous NH₄Cl solution (30 mL) at −78° C. The reaction was allowed to warm to RT and the aqueous layer was back extracted with EtOAc (3×75 mL). The combined organic layers were washed with brine, dried (Na₂SO₄), and concentrated. The material thus obtained was purified by chromatography through a Biotage 50 g ultra silica gel column, eluting with a gradient of 0-25% EtOAc in hexanes, to provide 2-(((1R,2S))-1-methoxy-1-(5-methylpyrimidin-2-yl)propan-2-yl)thio)benzo[d]thiazole 14.05 (0.32 g, 75% for two runs) as a light-yellow oil.

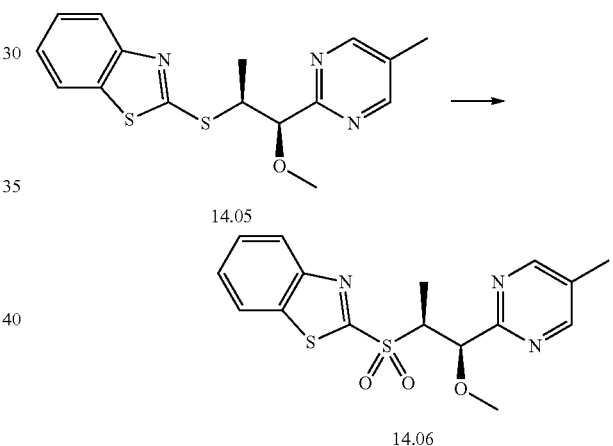

2-(((1R,2S)-1-methoxy-1-(5-methylpyrimidin-2-yl)propan-2-yl)sulfonyl)benzo[d]thiazole, Example, Example 14.06

A solution of 2-(((1R,2S)-1-methoxy-1-(5-methylpyrimidin-2-yl)propan-2-yl)thio)benzo[d]thiazole 14.05 (313 mg, 0.94 mmol) in DCM (2.8 mL) at 0° C. was treated with 3-chloroperoxybenzoic acid, 77% max. (476 mg, 2.13 mmol). The reaction was stirred at 0° C. for 1 h before the ice bath was removed. The mixture was allowed to warm to ambient temperature and stirred for an additional 40 h. The reaction was quenched with saturated aqueous sodium bisulfite (6 mL), saturated aqueous sodium bicarbonate (5 mL), and was then stirred for 10 min. The reaction was extracted with EtOAc (2×20 mL) and the organic layers were combined, washed with saturated aqueous NaHCO₃ (10 mL), brine (10 mL), dried (MgSO₄) and filtered. Iodide/starch strip indicator showed no peroxide present. The filtrates were concentrated to give a clear, colorless oil (360 mg). Purification of the residue by flash chromatography (40 g SiO$_2$, 0-100% 3:1 EtOAc:EtOH/heptane) gave 2-(((1R,2S)-1-methoxy-1-(5-methylpyrimidin-2-yl)propan-2-yl)sulfonyl)benzo[d]thiazole 14.06 (285 mg, 0.78 mmol, 83% yield, 77% purity) as a white foam. $^1$H NMR (300 MHz, CDCl$_3$) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=7.2 Hz, 3H). MS (ESI pos. ion) m/z: 364.0 (M+H).

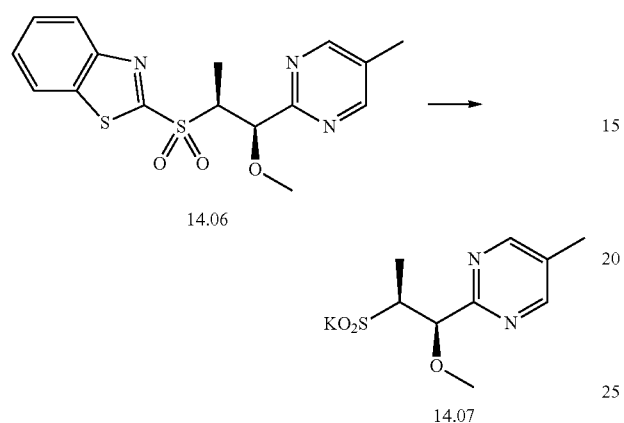

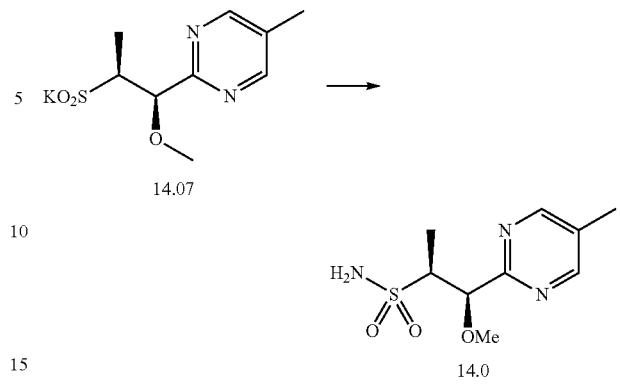

Potassium (1R,2S)-1-methoxy-1-(5-methylpyrimidin-2-yl)propane-2-sulfinate, Example 14.07

To a solution of 2-(((1R,2S)-1-methoxy-1-(5-methylpyrimidin-2-yl)propan-2-yl)sulfonyl)benzo[d]thiazole 14.06 (268 mg, 0.74 mmol) in MeOH (1843 μL) was added potassium carbonate (204 mg, 1.48 mmol). The reaction was stirred at RT for 17 h. LCMS showed desired product formation as the sulfinic acid 14.07. LCMS ((M+H)$^+$ =231.1). The reaction was concentrated in vacuo (yellow solid) and used directly in the following step. Note: Epimerization occurred in this reaction (~15%).

(1R,2S)-1-methoxy-1-(5-methylpyrimidin-2-yl)propane-2-sulfonamide, Example 14.0

To a suspension of potassium (1R,2S)-1-methoxy-1-(5-methylpyrimidin-2-yl)propane-2-sulfinate (Example 14.07, 198 mg, 0.74 mmol) in water (3.7 mL) was added potassium acetate (72.4 mg, 0.74 mmol), followed by hydroxylamine-o-sulfonic acid, 97% (167 mg, 1.476 mmol). The reaction mixture was stirred at RT for 4.5 h. LCMS showed desired product formation plus a small peak that corresponded to the stereoisomer. The reaction mixture was extracted with EtOAc (2×) and the organic layers were combined, dried (Na$_2$SO$_4$), and concentrated in vacuo. The residue was loaded onto a silica gel column eluting with 0-30% (3:1 EtOAc:EtOH)/DCM to afford (1R,2S)-1-methoxy-1-(5-methylpyrimidin-2-yl)propane-2-sulfonamide 14.0 (114 mg, 0.465 mmol, 63.0% yield) as a white solid. (contained 15% other diastereomer). $^1$H NMR (300 MHz, CDCl$_3$) δ 8.63 (s, 2H), 5.10 (d, J=3.3 Hz, 1H), 4.78 (br. s., 2H), 3.74 (qd, J=7.1, 3.3 Hz, 1H), 3.51 (s, 3H), 2.36 (s, 3H), 1.33 (d, J=7.1 Hz, 3H). MS (ESI pos. ion) m/z: 246.1 (M+H)$^+$.

The compounds set forth in the following Table 7 were synthesized following the procedure in Example 14.0 using the known starting material as described.

TABLE 7

| Example | Reagents | Structure, Name and Data |
|---|---|---|
| 14.1 | 2-bomo-5-methyl pyrazine (NOWA pharmaceuticals) | (1R,2S)-1-methoxy-1-(5-methylpyrazin-2-yl)propane-2-sulfonamide. LCMS-ESI (POS.) m/z: 246.2 (M + H)$^+$. |
| 14.2 | 2-chloro-5-fluoropyrimidine (Oakwood) | (1R,2S)-1-(5-fluoropyrimidin-2-yl)-1-methoxypropane-2-sulfonamide. LCMS-ESI (POS.) m/z: 250.1 (M + H)$^+$. |

TABLE 7-continued

| Example | Reagents | Structure, Name and Data |
|---|---|---|
| 14.3 | 2,5-dichloropyrimidine (Oakwood) | (1R,2S)-1-(5-chloropyrimiin-2-yl)-1-methoxypropane-2-sulfonamide. LCMS-ESI (POS.) m/z: 265.9 (M + H)+. |
| 14.4 | 2-chloopyimiine (acros organics) | (1R,2S)-1-methoxy-1-(pyrimidin-2-yl)propane-2-sulfonamide. LCMS-ESI (POS.) m/z: 232.0 (M + H)+. |
| 14.5 | 2-chloro-5-fluoropyrimidine (Oakwood) EtOTf used in place of MeOTf in Example 14.05 | (1R,2S)-1-ethoxy-1-(5-fluoropyrimidin-2-yl)propane-2-sulfonamide. LCMS-ESI (POS.) m/z: 264.0 (M + H)+. |
| 14.6 | 2-chloro-5-fluoropyrimidine (Oakwood) TBSOTf used in place of MeOTf in Example 14.05 | (1R,2S)-1-((tert-butyldimethylsilyl)oxy)-1-(5-fluoropyrimidin-2-yl)propane-2-sulfonamide. LCMS-ESI (POS.) m/z: 350.1 (M + H)+. |
| 14.7 | 2,5-dichloropyrimidine (Oakwood), EtOTf used in place of MeOTf in Example 14.05 | (1R,2S)-1-(5-chloropyrimidin-2-yl)-1-ethoxypropane-2-sulfonamide. LCMS-ESI (POS.) m/z: 279.9. |

Example 14.8: Preparation of (1R,2S)-1-methoxy-1-(5-methoxypyrimidin-2-yl)propane-2-sulfonamide

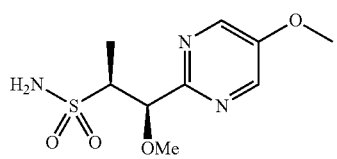

14.8

(1R,2S)-1-methoxy-1-(5-methoxypyrimidin-2-yl)propane-2-sulfonamide, Example 14.8

This compound was obtained as a by-product of the synthesis of (1R,2S)-1-methoxy-1-(5-fluoropyrimidin-2-yl)propane-2-sulfonamide (Example 14.2) during step 14.07 and isolated in the final step of the synthesis of Example 14.2 to give the title compound 14.8 (240 mg, 10% yield) as a white solid. $^1$H NMR (CDCl$_3$) δ: 8.46 (s, 2H), 5.11 (d, J=3.4 Hz, 1H), 4.77 (br. s, 2H), 3.97 (s, 3H), 3.67-3.77 (m, 1H), 3.50 (s, 3H), 1.35 (d, J=7.0 Hz, 3H). LCMS-ESI (POS.) m/z: 284.1 (M+Na)+.

Example 15.0: Preparation of Examples (1R,2S)-1-ethoxy-1-(5-methylpyrimidin-2-yl)propane-2-sulfonamide and (1S,2R)-1-ethoxy-1-(5-methylpyrimidin-2-yl)propane-2-sulfonamide

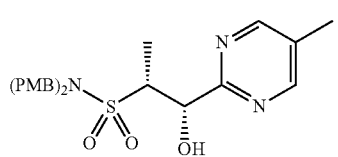

AND

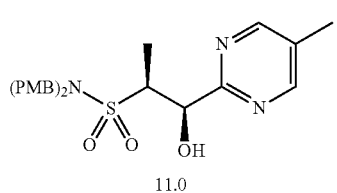

11.0

↓

15.01

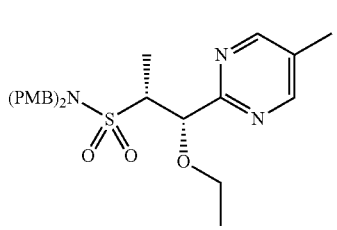

AND

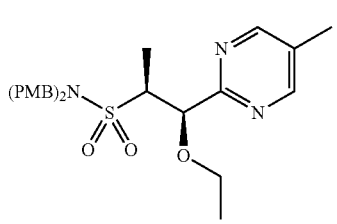

15.01

(1R,2S)-1-ethoxy-N,N-bis(4-methoxybenzyl)-1-(5-methylpyrimidin-2-yl)propane-2-sulfonamide and (1S,2R)-1-ethoxy-N,N-bis(4-methoxybenzyl)-1-(5-methylpyrimidin-2-yl)propane-2-sulfonamide, Example 15.01

To a −78° C. solution of 11.0 (1.62 g, 3.4 mmol) in THF (70 mL) was added potassium bis(trimethylsilyl)amide (1 M solution in THF, 10.6 mL, 10.6 mmol) slowly via syringe. After 1.25 h, ethyl trifluoromethanesulfonate (1.4 mL, 10.6 mmol) was added slowly via syringe. The resulting orange solution was stirred at −78° C. for 45 min and then was quenched with an 2:1 mixture of saturated aqueous ammonium chloride and water (75 mL). The resulting mixture was extracted with EtOAc (4×). The combined organic layers were dried over anhydrous sodium sulfate and concentrated in vacuo. The residue was purified by silica gel chromatography (eluent: 10-65% EtOAc in hexanes over a 40 min period) to provide 15.01 (1.02 g, 60% yield) as a light yellow oil. LCMS-ESI (POS.) m/z: 500.1 (M+H)+.

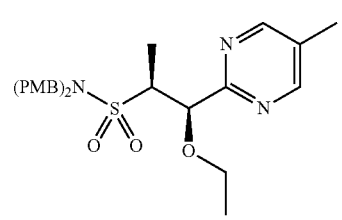

AND

↓

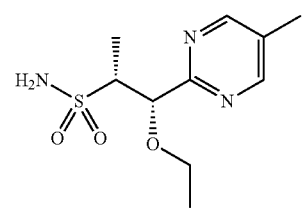

AND

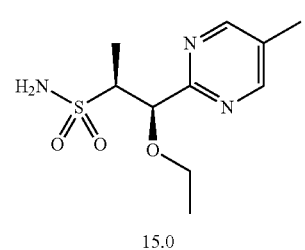

15.0

(1R,2S)-1-ethoxy-1-(5-methylpyrimidin-2-yl)propane-2-sulfonamide and (1S,2R)-1-ethoxy-1-(5-methylpyrimidin-2-yl)propane-2-sulfonamide, Example 15.0

Example 15.01 (1.02 g, 2.0 mmol) was dissolved in TFA (14 mL). Anisole (466 μL, 4.3 mmol) was then added via syringe. The resulting orange solution was stirred at RT for 16.5 h and then concentrated in vacuo. The residue was purified by silica gel chromatography (eluent: pure DCM grading to 4.5% MeOH in DCM over a 45 min period) to provide the title compound 15.0 (495 mg, 93% yield) as a white solid. LCMS-ESI (POS.) m/z: 260.0 (M+H)+.

The compounds set forth in the following Table were synthesized following the procedure in Example 15.0 using the known starting material as described.

TABLE 8

| Example Reagents | Structure, Name and Data |
|---|---|
| 15.1 | 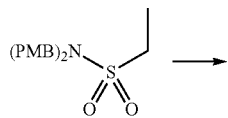<br><br>Material prepared in an analogous maner to that of Example 11.0 employing the cis olefin | (1R,2R)-1-ethoxy-1-(5-methylpyrimidin-2-yl)propane-2-sulfonamide and (1S,2S)-1-ethoxy-1-(5-methylpyrimidin-2-yl)propane-2-sulfonamide, LCMS-ESI (POS.) mz: 260.0 (M + H)+. |

Example 16.0: Preparation of Example (R)-1-oxo-1-(pyrrolidin-1-yl)propane-2-sulfonamide and (S)-1-oxo-1-(pyrrolidin-1-yl)propane-2-sulfonamide

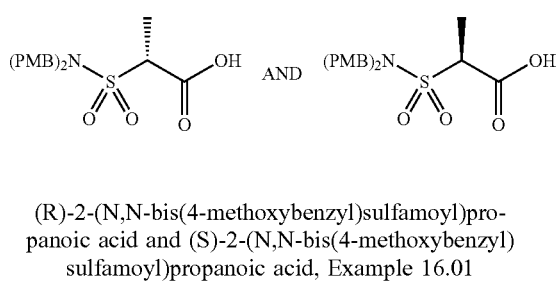

(R)-2-(N,N-bis(4-methoxybenzyl)sulfamoyl)propanoic acid and (S)-2-(N,N-bis(4-methoxybenzyl)sulfamoyl)propanoic acid, Example 16.01

To an oven-dried 2-necked round bottomed flask was added N,N-bis(4-methoxybenzyl)ethanesulfonamide (978 mg, 2.80 mmol, Example 12.0) and 2-methyltetrahydrofuran (12 mL). The solution was cooled in a dry ice/acetone bath to −78° C. and treated with butyllithium solution (1.9 mL, 3.04 mmol, 1.6M in hexanes) at a rate that kept the temperature below −60° C. After stirring for 10 min, the reaction was warmed to −20° C. and stirred for 1 minute and was then cooled to −75° C. and treated with ethyl chloroformate (0.37 mL, 3.87 mmol). After 30 min, the reaction was quenched with saturated NH$_4$C$_1$. The reaction was diluted with water. The aqueous solution was then extracted with EtOAc (2×15 mL). The combined EtOAc layers were concentrated in vacuo and taken up in THF (10 mL):MeOH (3 mL) and treated with lithium hydroxide (8 mL, 8.00 mmol, 1M aqueous solution). The solution was then stirred at RT. After 3 d, the reaction was diluted with water and washed with EtOAc (2×20 mL). The aqueous solution was acidified with aqueous 1N HCl and extracted with EtOAc (3×20 mL). The combined organic layers were dried over MgSO$_4$ and concentrated in vacuo to give the title compound (0.64 g, 58% yield) as a light yellow oil. $^1$H NMR (CDCl$_3$) δ: 7.18 (d, J=8.6 Hz, 4H), 6.82-6.89 (m, 4H), 4.25-4.41 (m, 4H), 4.14 (q, J=7.2 Hz, 1H), 3.77-3.84 (m, 6H), 1.61 (d, J=7.2 Hz, 3H). LCMS-ESI (POS.) m/z: 416.1 (M+Na)+.

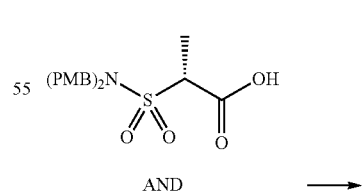

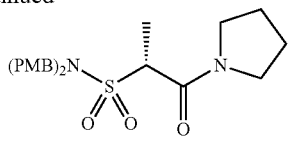

AND

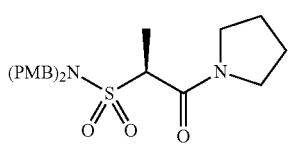

16.02

(R)—N,N-bis(4-methoxybenzyl)-1-oxo-1-(pyrrolidin-1-yl)propane-2-sulfonamide and (S)—N,N-bis(4-methoxybenzyl)-1-oxo-1-(pyrrolidin-1-yl)propane-2-sulfonamide, Example 16.02

To a solution of (R)-2-(N,N-bis(4-methoxybenzyl)sulfamoyl)propanoic acid and (S)-2-(N,N-bis(4-methoxybenzyl)sulfamoyl)propanoic acid (396 mg, 1.01 mmol) and DMF (3 mL) was added propylphosphonic anhydride solution (1.5 mL, 2.52 mmol, 50 wt. % in EtOAc), followed by pyrrolidine (95 μL, 1.135 mmol, Alfa Aesar). After stirring at RT for 16 h, the reaction was poured into water (50 mL). The aqueous solution was extracted with EtOAc (3×5 mL). The combined organic layers were then washed with brine (40 mL), dried over MgSO₄, and concentrated in vacuo to give the title compound (462 mg, 103% yield), as a golden oil. The material was carried forward without any further purification. LCMS-ESI (POS.) m/z: 447.2 (M+H)⁺.

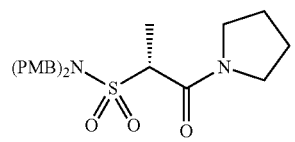

AND

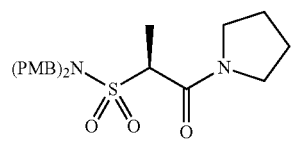

16.02

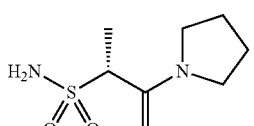

AND

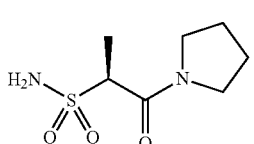

16.0

(R)-1-oxo-1-(pyrrolidin-1-yl)propane-2-sulfonamide and (S)-1-oxo-1-(pyrrolidin-1-yl)propane-2-sulfonamide, Example 16.0

To a solution of (R)—N,N-bis(4-methoxybenzyl)-1-oxo-1-(pyrrolidin-1-yl)propane-2-sulfonamide and (S)—N,N-bis(4-methoxybenzyl)-1-oxo-1-(pyrrolidin-1-yl)propane-2-sulfonamide (449 mg, 1.005 mmol) and anisole (0.5 mL, 4.55 mmol) was added TFA (5 mL) dropwise. After stirring over the weekend, the reaction was concentrated in vacuo and adsorbed onto a plug of silica gel and purified through a GraceResolv Silica gel column (12 g), eluting with 0-100% EtOAc:EtOH (3:1) in heptane, to provide the title compound (200 mg, 96% yield) as a white solid. ¹H NMR (DMSO-d₆) δ: 6.86 (s, 2H), 4.21 (q, J=6.7 Hz, 1H), 3.59-3.70 (m, 1H), 3.53 (dt, J=10.2, 6.6 Hz, 1H), 3.28-3.36 (m, 2H), 1.73-1.91 (m, 4H), 1.40 (d, J=6.9 Hz, 3H). LCMS-ESI (POS.) m/z: 207.2 (M+H)⁺.

Example 17.0: Preparation of (S)-2-(5-fluoropyrimidin-2-yl)ethane-1-sulfamide

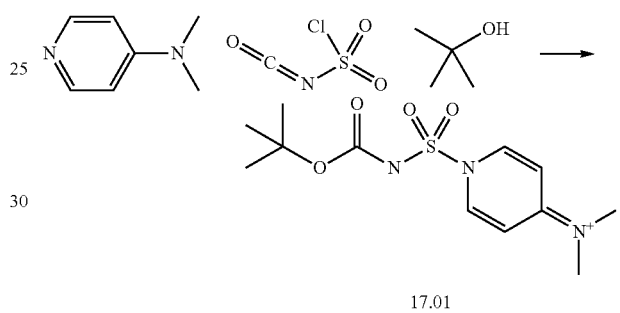

17.01

(tert-Butoxycarbonyl)((4-(dimethyliminio)pyridin-1(4H)-yl)sulfonyl)amide, Example 17.01

To an ice-cooled solution of tert-butanol (3.3 mL, 34.5 mmol) in DCM (80 mL) was added chlorosulfonyl isocyanate (3.0 mL, 34.5 mmol, Sigma-Aldrich) slowly via syringe. After 10 min, 4-(dimethylamino)pyridine (8.42 g, 68.9 mmol) was added. The resulting thick white slurry was warmed to RT and stirred for 24 h. The reaction mixture was diluted with DCM (100 mL) and washed with water (3×). The organic layer was dried over anhydrous sodium sulfate and concentrated to provide 17.01 (6.61 g, 64% yield) as a white solid which was used without further purification. LCMS-ESI (POS.) m/z: 302.0 (M+H)⁺.

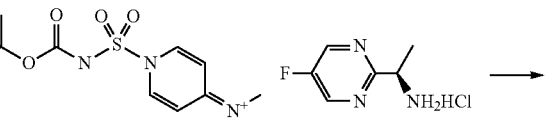

17.02

(S)-tert-Butyl N-(1-(5-fluoropyrimidin-2-yl)ethyl)sulfamoylcarbamate, Example 17.02

To a slurry of 17.01 (1.60 g, 5.3 mmol) in DCM (30 mL) was added (S)-1-(5-fluoro-pyrimidin-2-yl)-ethylamine hydrochloride (943 mg, 5.3 mmol, J&W PharmLab) directly followed by TEA (775 µL, 5.6 mmol) via syringe. The resulting white slurry was stirred at RT for 17 h, afterwhich it was concentrated in vacuo. The residue was purified by silica gel chromatography (eluent: 10-100% EtOAc in hexanes over a 40 min period) to provide the title compound 17.02 (1.56 g, 92% yield) as a white solid. LCMS-ESI (POS.) m/z: 343.0 (M+Na)⁺.

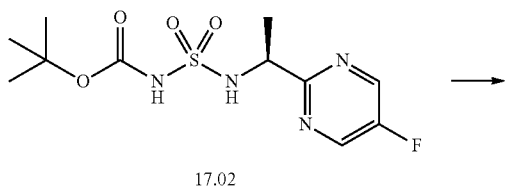

17.02

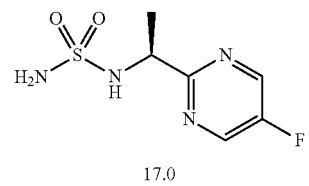

17.0

(S)-2-(5-fluoropyrimidin-2-yl)ethane-1-sulfamide, Example 17.0

To an ice-cooled solution of 17.02 (1.56 g, 49 mmol) in DCM (14 mL) was added TFA (6.5 mL, 88 mmol) via syringe. The ice bath was removed and the resulting colorless solution was stirred at RT for 3 h. The reaction mixture was recooled to 0° C., and the reaction was then quenched by slow addition of saturated aqueous sodium bicarbonate (140 mL) over a 10 minute period. The resulting mixture was partially concentrated to remove some of the water and then was extracted with DCM (×6). The combined organic layers were dried over anhydrous sodium sulfate and concentrated to provide 17.0 (967 mg, 90% yield) as a white solid. LCMS-ESI (POS.) m/z: 221.0 (M+H)⁺.

Example 18.0: Preparation of (1R,2S)-1-((tert-butyldimethylsilyl)oxy)-N,N-bis(4-methoxybenzyl)-1-(5-methylpyrimidin-2-yl)propane-2-sulfonamide

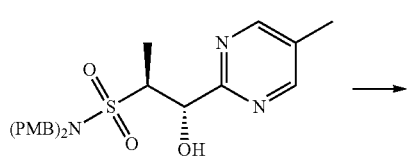

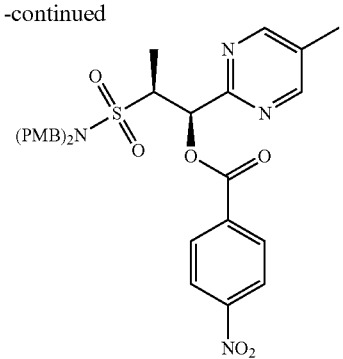

18.01

(1R,2S)-2-(N,N-bis(4-methoxybenzyl)sulfamoyl)-1-(5-methylpyrimidin-2-yl)propyl 4-nitrobenzoate, Example 18.01

To a stirred solution of (1S,2S)-1-hydroxy-N,N-bis(4-methoxybenzyl)-1-(5-methylpyrimidin-2-yl)propane-2-sulfonamide (22.7 g, 48.1 mmol) in toluene (241 mL) was added 4-nitrobenzoic acid (12.07 g, 72.2 mmol), triphenylphosphine (18.94 g, 72.2 mmol) followed by dropwise addition of (E)-diisopropyldiazene-1,2-dicarboxylate (14.22 mL, 72.2 mmol). The mixture was stirred at RT overnight, to show desired product by LCMS. The reaction was concentrated in vacuo and purified on silica gel eluting with 0-50% EtOAc/hexanes to give the desired compound (1R,2S)-2-(N,N-bis(4-methoxybenzyl)sulfamoyl)-1-(5-methylpyrimidin-2-yl)propyl 4-nitrobenzoate (29.9 g, 48.1 mmol, 100% yield). LCMS-ESI (POS.) m/z: 621.3 (M+H)⁺.

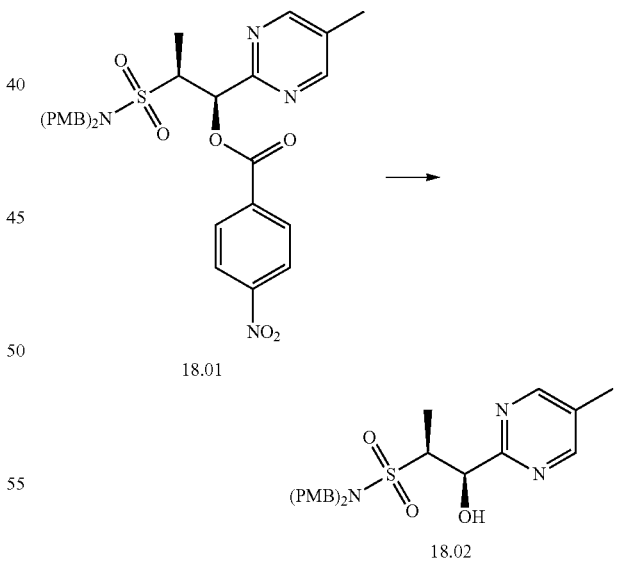

(1R,2S)-2-(N,N-bis(4-methoxybenzyl)sulfamoyl)-1-(5-methylpyrimidin-2-yl)propyl 4-nitrobenzoate, Example 18.02

To a stirred solution of 18.01 (76 g, 122 mmol) in MeOH (612 mL) at 0° C. was added potassium carbonate (16.92 g, 122 mmol). The mixture was allowed to warm to RT over 1 h to show the desired product by LCMS: The reaction was concentrated in vacuo and purified on silica gel eluting with 0-40% EtOAc in hexanes to give (1R,2S)-1-hydroxy-N,N-bis(4-methoxybenzyl)-1-(5-methylpyrimidin-2-yl)propane-2-sulfonamide. LCMS-ESI (POS.) m/z: 472.0 (M+H)+.

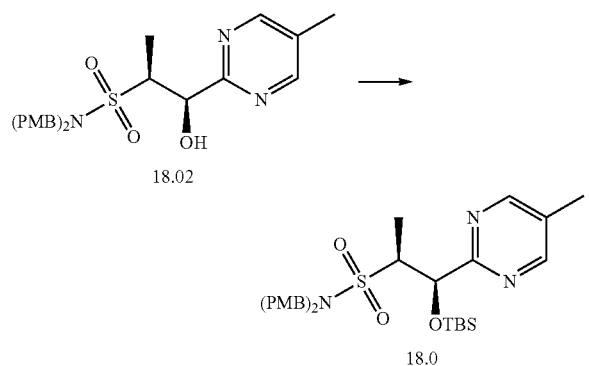

(1R,2S)-1-(((tert-butyldimethylsilyl)oxy)-N,N-bis(4-methoxybenzyl)-1-(5-methylpyrimidin-2-yl)propane-2-sulfonamide, Example 18.0

To a stirred solution of (1R,2S)-1-hydroxy-N,N-bis(4-methoxybenzyl)-1-(5-methylpyrimidin-2-yl)propane-2-sulfonamide (18.02, 28 g, 59.4 mmol) in DCM (297 mL, 59.4 mmol) at 0° C. was added tert-butyldimethylsilyl trifluoromethanesulfonate (15.00 mL, 65.3 mmol), followed by TEA (9.12 mL, 65.3 mmol). The mixture was allowed to warm to RT over 1 h, to show the desired product by LCMS. The reaction was concentrated in vacuo, and purified on silica gel eluting with 0-30% EtOAc in hexane to give the desired compound (1R,2S)-1-((tert-butyldimethylsilyl)oxy)-N,N-bis(4-methoxybenzyl)-1-(5-methylpyrimidin-2-yl)propane-2-sulfonamide (15 g, 25.6 mmol, 43% yield). LCMS-ESI (POS.) m/z: 586.0 (M+H)+.

Example 19.0: Preparation of (S)-1-(5-methylpyrimidin-2-yl)-1-oxopropane-2-sulfonamide and (R)-1-(5-methylpyrimidin-2-yl)-1-oxopropane-2-sulfonamide

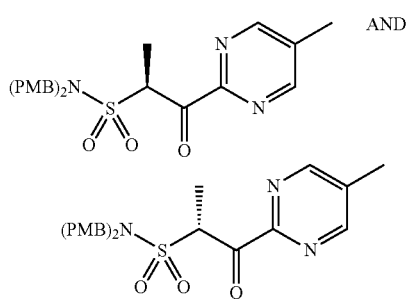

(S)—N,N-bis(4-methoxybenzyl)-1-(5-methylpyrimidin-2-yl)-1-oxopropane-2-sulfonamide and (R)—N,N-bis(4-methoxybenzyl)-1-(5-methylpyrimidin-2-yl)-1-oxopropane-2-sulfonamide, Example 19.1

To a solution of 11.0 (5.0 g, 10.6 mmol) in DCM (80 mL) was added Dess-Martin periodinane (4.95 g, 11.7 mmol, Aldrich, St. Louis, Mo.). The resulting mixture was stirred at RT under $N_2$ for 7 h. Water (20 mL) and DCM (40 mL) were added. The layers were separated and the aqueous layer was extracted with DCM (40 mL), 10% iPrOH in $CHCl_3$ (4×40 mL). The combined organic layers were dried over $MgSO_4$, filtered, and concentrated. The product thus obtained was purified by column chromatography (220 g of silica, 10-40% acetone in hexanes) providing (S)—N,N-bis(4-methoxybenzyl)-1-(5-methylpyrimidin-2-yl)-1-oxopropane-2-sulfonamide and (R)—N,N-bis(4-methoxybenzyl)-1-(5-methylpyrimidin-2-yl)-1-oxopropane-2-sulfonamide as a light yellow foam 19.1, (4.9 g). $^1$H NMR ($CDCl_3$) δ: 8.74 (s, 2H), 7.13-7.19 (m, 4H), 6.74-6.82 (m, 4H), 5.98 (q, J=7.0 Hz, 1H), 4.26-4.36 (m, 4H), 3.74-3.86 (m, 7H), 2.44 (s, 3H), 1.70 (d, J=7.0 Hz, 3H). MS-ESI (POS.) m/z: 470.0 (M+H)+.

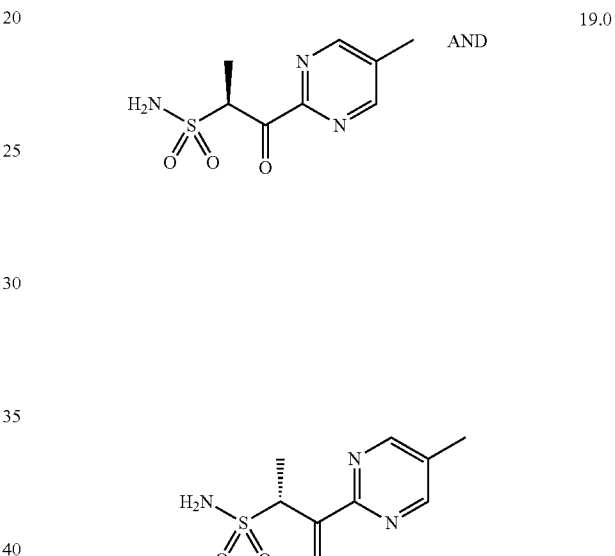

(S)-1-(5-methylpyrimidin-2-yl)-1-oxopropane-2-sulfonamide and (R)-1-(5-methylpyrimidin-2-yl)-1-oxopropane-2-sulfonamide, Example 19.0

To a solution of (S)—N,N-bis(4-methoxybenzyl)-1-(5-methylpyrimidin-2-yl)-1-oxopropane-2-sulfonamide and (R)—N,N-bis(4-methoxybenzyl)-1-(5-methylpyrimidin-2-yl)-1-oxopropane-2-sulfonamide 19.1 (4.9 g, 10.44 mmol) in DCM (30 mL) was added anisole (5.3 mL, 48.8 mmol, Aldrich, St. Louis, Mo.). The reaction mixture was cooled in an ice bath and treated with TFA (30.0 mL) dropwise via an addition funnel. After the addition, the resulting mixture was stirred for 1 h and then warmed to RT and further stirred for 2 d. After this period, the reaction mixture was concentrated. The initially obtained product was purified by column chromatography (330 g of silica, 5-50% acetone in hexanes) providing (S)-1-(5-methylpyrimidin-2-yl)-1-oxopropane-2-sulfonamide and (R)-1-(5-methylpyrimidin-2-yl)-1-oxopropane-2-sulfonamide as white foam 19.0 (1.9 g). $^1$H NMR ($CDCl_3$) δ: 8.80 (s, 2H), 5.97 (q, J=7.1 Hz, 1H), 4.86 (br. s., 2H), 2.48 (s, 3H), 1.76 (d, J=7.0 Hz, 3H). MS-ESI (POS.) m/z: 230.0 (M+H)+.

Example 20.0: Preparation of (1S,2S)-1-((tert-butyldimethylsilyl)oxy)-1-(5-fluoropyrimidin-2-yl)propane-2-sulfonamide and (1R,2R)-1-((tert-butyldimethylsilyl)oxy)-1-(5-fluoropyrimidin-2-yl)propane-2-sulfonamide

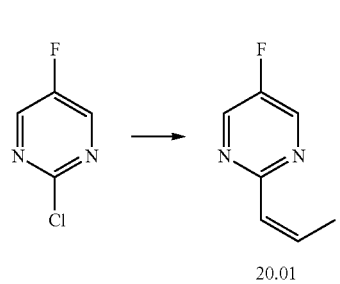

20.01

(Z)-5-fluoro-2-(prop-1-en-1-yl)pyrimidine, Example 20.01

Tetrakis(triphenylphosphine)palladium (4.62 g, 4.00 mmol) was added to a degassed solution of 2-chloro-5-fluoropyrimidine (21.2 g, 160 mmol, Matrix Scientific), cis-1-propen-1-ylboronic acid (16.5 g, 192 mmol, Sigma-Aldrich) and sodium carbonate (33.9 g, 320 mmol) in a mixture of THF (213 mL) and water (107 mL). The reaction vessel was sealed, and the reaction was heated at 100° C. for 2.5 d. After this time period, the white precipitate was filtered off and rinsed with ether. The filtrate was extracted with DCM (2×). The combined organic layers were then dried over anhydrous magnesium sulfate and partially concentrated (note that the product is volatile). The residue was purified by silica gel chromatography (eluent: 0-50% DCM in hexanes) to provide 20.01 (19.4 g, 88% yield). $^1$H NMR (500 MHz, CDCl$_3$) δ: 8.58 (s, 2H), 6.51-6.60 (m, 1H), 6.25 (dq, J=11.8, 7.3 Hz, 1H), 2.24 (dd, J=7.2, 1.8 Hz, 3H). LCMS-ESI (POS.) m/z: 139.4 (M+H)$^+$.

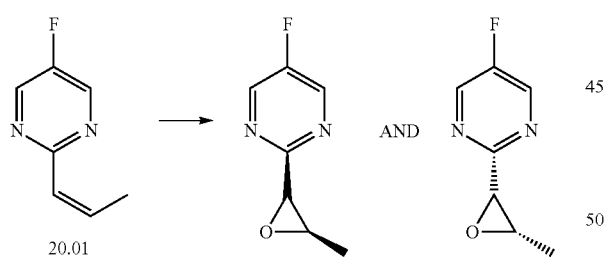

(5-fluoro-2-((2S,3R)-3-methyloxiran-2-yl)pyrimidine and 5-fluoro-2-((2R,3S)-3-methyloxiran-2-yl)pyrimidine, Example 20.02

To an ice-cooled solution of 20.01 (12.65 g, 92 mmol) in a mixture of tert-butanol and water (1/1, v/v, 183 mL) was added N-bromosuccinimide (32.6 g, 183 mmol). The reaction was allowed to warm to RT overnight and then a 10 M solution of NaOH (27.5 mL, 275 mmol) was slowly added being careful to not allow the internal temperature to exceed 32° C. The mixture was extracted with EtOAc (3×) and the combined organic layers were dried over anhydrous magnesium sulfate and concentrated. The residue was purified by silica gel chromatography (eluent: pure hexanes grading to pure DCM) to provide the title compound 20.02 (10.2 g, 72% yield). LCMS-ESI (POS.) m/z: 155.2 (M+H)$^+$.

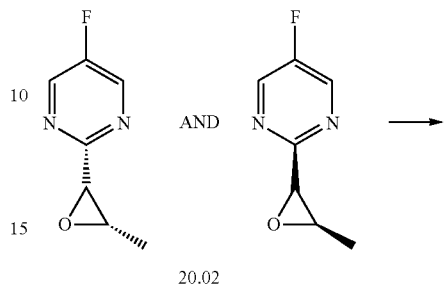

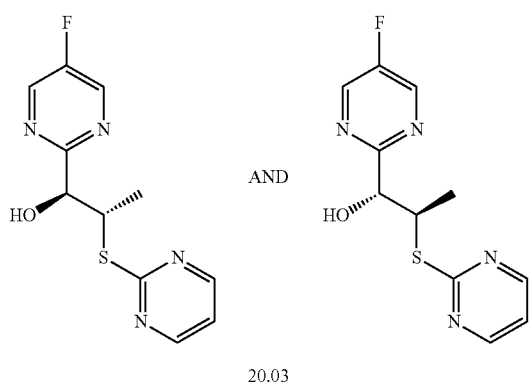

(1S,2S)-1-(5-fluoropyrimidin-2-yl)-2-(pyrimidin-2-ylthio)propan-1-ol and (1R,2R)-1-(5-fluoropyrimidin-2-yl)-2-(pyrimidin-2-ylthio)propan-1-ol, Example 20.03

To a solution of 20.02 (2.14 g, 13.9 mmol) in DCM (46 mL) was added pyrimidine-2-thiol (3.11 g, 27.8 mmol, Sigma-Aldrich) followed by ytterbium(III)trifluoromethanesulfonate (431 mg, 0.69 mmol, Sigma-Aldrich). The resulting yellow slurry was stirred overnight and then additional ytterbium(III)trifluoromethanesulfonate (431 mg, 0.69 mmol) was added. After another 3 h, the reaction was filtered through Celite® brand filter agent and the filtrate was neutralized with saturated aqueous sodium bicarbonate solution. The mixture was extracted with DCM (3×), and the combined organic layers were dried over anhydrous magnesium sulfate and concentrated. The residue was purified by silica gel chromatography (eluent: 30-60% EtOAc in hexanes) to provide the title compound 20.03 (2.53 g, 68% yield). LCMS-ESI (POS.) m/z: 267.0 (M+H)$^+$.

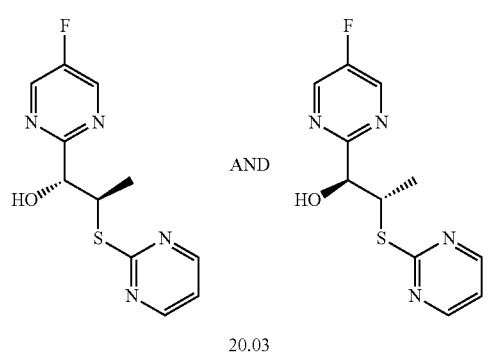

20.03

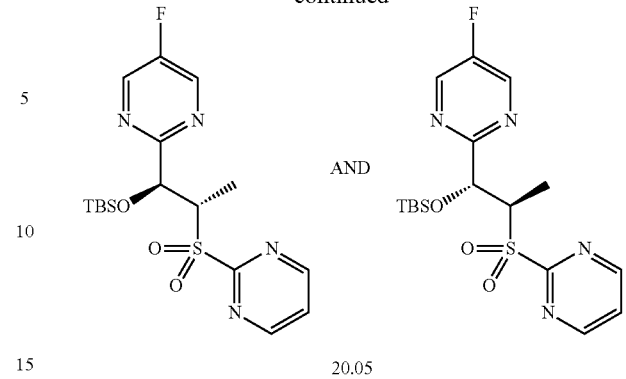

20.05

2-((1S,2S)-1-((tert-butyldimethylsilyl)oxy)-2-(pyrimidin-2-ylsulfonyl)propyl)-5-fluoropyrimidine and 2-((1R,2R)-1-((tert-butyldimethylsilyl)oxy)-2-(pyrimidin-2-ylsulfonyl)propyl)-5-fluoropyrimidine, Example 20.05

To a solution of 20.04 (3.27 g, 8.59 mmol) in DCM (43 mL) was added 3-chloroperoxybenzoic acid, 77% max. (3.85 g, 17.2 mmol). After 4 h at RT, the reaction was heated at 40° C. for an additional 2 h. After this time period, the heating bath was removed and stirring was continued at RT overnight. The reaction was concentrated and the residue was purified by silica gel chromatography (eluent: 10-100% EtOAc in hexanes) to provide 20.05 (3.54 g, 100%). LCMS-ESI (POS.) m/z: 413.0 (M+H)$^+$.

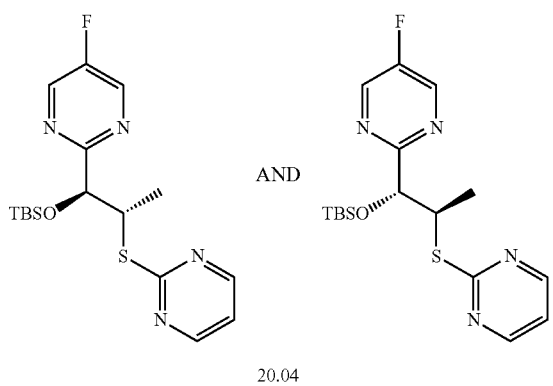

20.04

2-((1S,2S)-1-((tert-butyldimethylsilyl)oxy)-2-(pyrimidin-2-ylthio)propyl)-5-fluoropyrimidine and 2-((1R,2R)-1-((tert-butyldimethylsilyl)oxy)-2-(pyrimidin-2-ylthio)propyl)-5-fluoropyrimidine, Example 20.04

To a solution of 20.03 (2.44 g, 9.16 mmol) in DCM (92 mL) was added tert-butyldimethylsilyl triflate (2.32 mL, 10.08 mmol, Sigma-Aldrich) followed by 2,6-lutidine (1.17 mL, 10.08 mmol). After 20 min, the reaction was concentrated. The residue was purified by silica gel chromatography (eluent: 10-50% EtOAc in hexanes) to provide 20.04 (3.28 g, 94% yield) as a colorless oil. LCMS-ESI (POS.) m/z: 381.0 (M+H)$^+$.

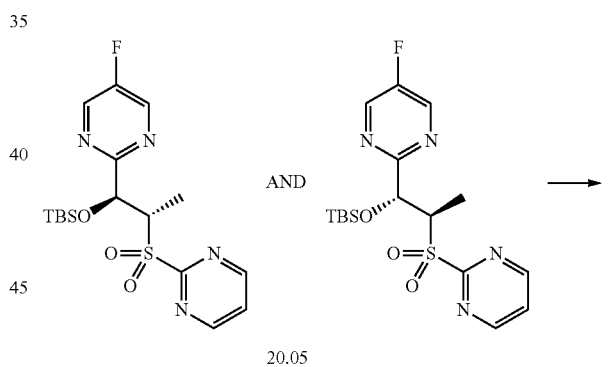

20.05

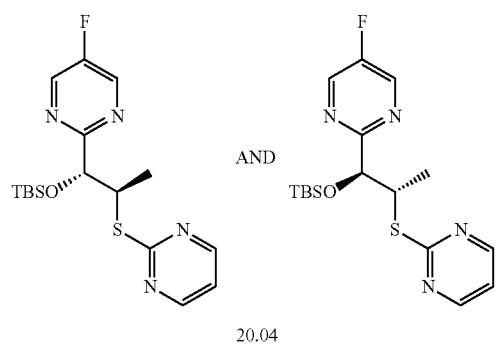

20.04

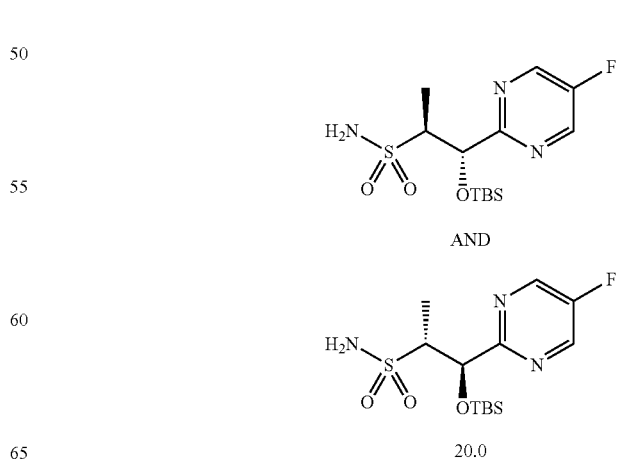

20.0

(1S,2S)-1-((tert-butyldimethylsilyl)oxy)-1-(5-fluoro-pyrimidin-2-yl)propane-2-sulfonamide and (1R,2R)-1-((tert-butyldimethylsilyl)oxy)-1-(5-fluoropyrimi-din-2-yl)propane-2-sulfonamide, Example 20.0

To a solution of 20.05 (3.40 g, 8.2 mmol) in MeOH (41 mL) was added potassium carbonate (1.14 g, 8.2 mmol). After stirring at RT overnight, additional potassium carbonate (342 mg, 2.8 mmol) was added. After another 6 h at RT, the reaction was concentrated in vacuo. The residue was dissolved in water (80 mL) and then potassium acetate (1.29 g, 13.2 mmol) and hydroxylamine-O-sulfonic acid (1.21 g, 10.7 mmol) were added sequentially. The reaction mixture was stirred at RT for 2 h and then was extracted with EtOAc (3×). The combined organic layers were dried over anhydrous magnesium sulfate and concentrated. The residue was purified by silica gel chromatography (eluent: 10-40% EtOAc in hexanes) to provide the title compound 20.0 (1.51 g, 54% yield) as a white solid. LCMS-ESI (POS.) m/z: 350.1 (M+H)$^+$.

The compounds set forth in the following Table were synthesized following the procedure in Example 20.0 using the known starting material as described.

TABLE 9

| Example | Reagents | Structure, Name and Data |
|---|---|---|
| 20.1 | trans-1-propen-1-ylboronic acid (Sigma-Aldrich) | 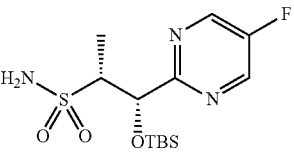 [SMILES: C[C@H]([C@@H](O[Si](C)(C)C(C)(C)C)c1ncc(F)cn1)S(N)(=O)=O]<br>AND<br>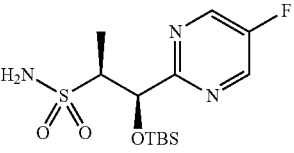 [SMILES: C[C@@H]([C@H](O[Si](C)(C)C(C)(C)C)c1ncc(F)cn1)S(N)(=O)=O]<br>(1S,2R)-1-((tert-butylsimethylsilyl)oxy)-1-(5-fluoropyrimidin-2-yl)propane-2-sulfonamide and (1R,2S)-1-((tert-butyldimethylsilyl)oxy)-1-(5-fluoropyrimidin-2-yl)propane-2-sulfonamide. LCMS-ESI (POS.) m/z: 350.1 (M + H)$^+$. |

Example 21.0: Preparation of (1R,2R)-1-((tert-butyldimethylsilyl)oxy)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide and (1S,2S)-1-((tert-butyldimethylsilyl)oxy)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide

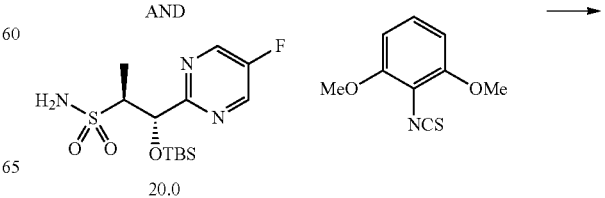<br>20.0

-continued

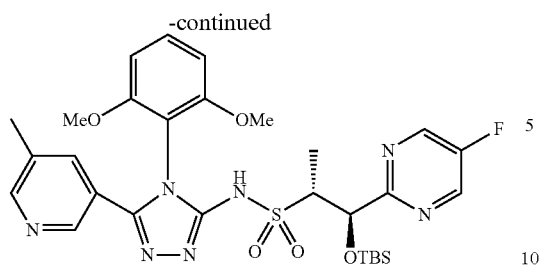

AND

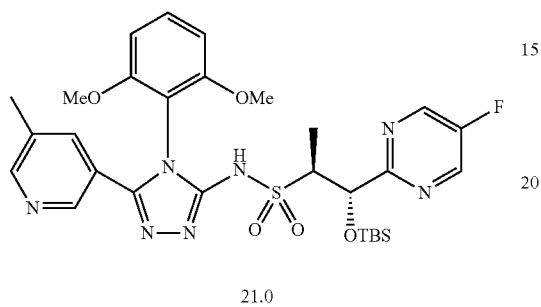

21.0

(1R,2R)-1-((tert-butyldimethylsilyl)oxy)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide and (1S,2S)-1-((tert-butyldimethylsilyl)oxy)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide, Example 21.0

This compound was prepared following the procedure in Example A; Example 20.0 (700 mg, 2.00 mmol), 5-methylnicotinichydrazide (363 mg, 2.40 mmol) and Intermediate 1.0. (411 mg, 2.10 mmol) were coupled to provide the title compound 21.0 (857 mg, 65% yield). LCMS-ESI (POS.) m/z: 644.2 (M+H)⁺.

Example 22.0: Preparation of (1S,2R)-1-(5-fluoropyrimidin-2-yl)-1-methoxypropane-2-sulfonamide and (1R,2S)-1-(5-fluoropyrimidin-2-yl)-1-methoxypropane-2-sulfonamide

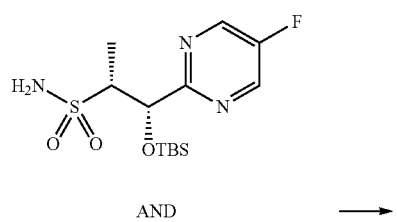

AND →

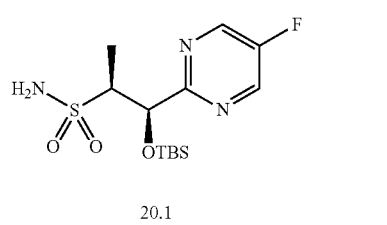

20.1

-continued

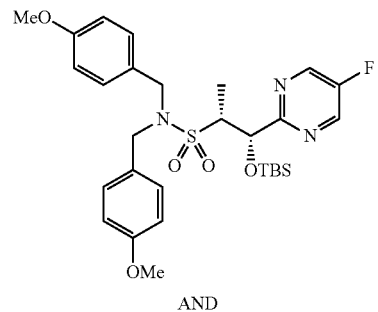

AND

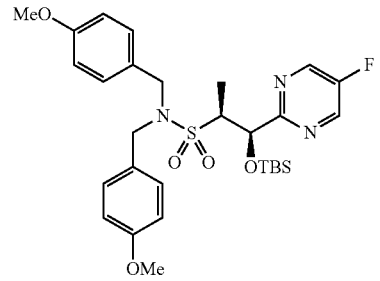

22.01

(1S,2R)-1-((tert-butyldimethylsilyl)oxy)-1-(5-fluoropyrimidin-2-yl)-N,N-bis(4-methoxybenzyl)propane-2-sulfonamide and (1R,2S)-1-((tert-butyldimethylsilyl)oxy)-1-(5-fluoropyrimidin-2-yl)-N,N-bis(4-methoxybenzyl)propane-2-sulfonamide, Example 22.01

To a solution of 20.1 (5.50 g, 15.7 mmol) in 2-butanone (52.5 mL) was added potassium carbonate (7.84 g, 47.2 mmol), 4-methoxybenzyl chloride (4.70 mL, 34.6 mmol) and potassium iodide (261 mg, 1.57 mmol). The resulting mixture was heated at 50° C. overnight and then additional potassium carbonate (2.61 g, 15.7 mmol) and 4-methoxybenzyl chloride (2.14 mL, 15.7 mmol) were added. The reaction was heated at 70° C. overnight, and then was partitioned between water and EtOAc. The organic layer was washed with additional water (1×), dried over anhydrous magnesium sulfate and concentrated. The residue was purified by silica gel chromatography (eluent: 10-20% EtOAc in hexanes) to provide 22.01 (5.51 g, 59% yield) as a colorless oil. LCMS-ESI (POS.) m/z: 590.2 (M+H)⁺.

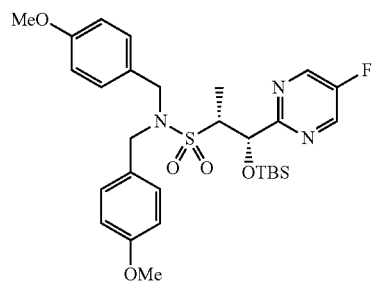

AND

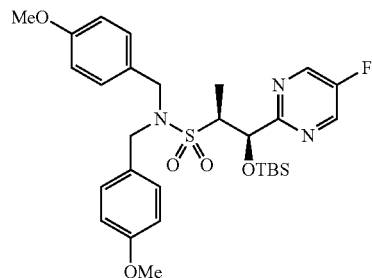

22.01

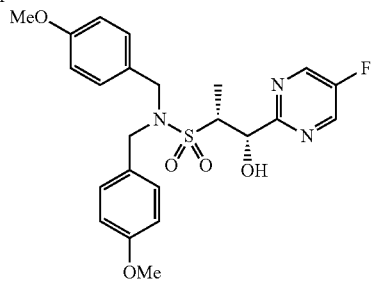

AND

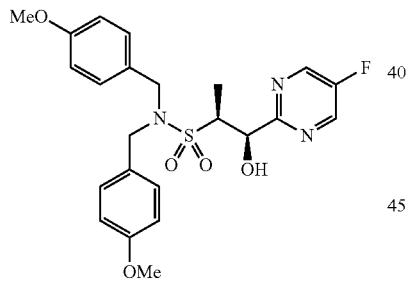

22.02

(1S,2R)-1-(5-fluoropyrimidin-2-yl)-1-hydroxy-N,N-bis(4-methoxybenzyl)propane-2-sulfonamide and (1R,2S)-1-(5-fluoropyrimidin-2-yl)-1-hydroxy-N,N-bis(4-methoxybenzyl)propane-2-sulfonamide, Example 22.02

To a solution of 22.01 (5.51 g, 9.3 mmol) in THF (31 mL) was added a solution of tetrabutylammonium fluoride in THF (1.0M, 19.6 mL, 19.6 mmol). The resulting orange solution was stirred at RT for 10 min and then was concentrated. The residue was dissolved in EtOAc and washed with water (3×). The organic layer was dried over anhydrous magnesium sulfate and concentrated. The residue was purified by silica gel chromatography (eluent: 0-10% EtOAc in DCM) to provide 22.02 (3.36 g, 76% yield). LCMS-ESI (POS.) m/z: 498.0 (M+Na)+.

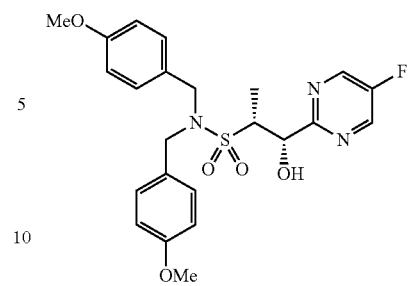

AND

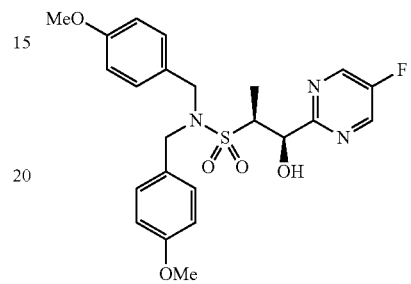

22.02

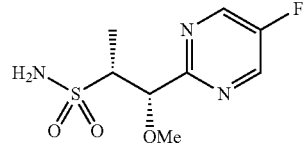

AND

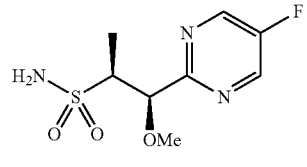

22.0

(1S,2R)-1-(5-fluoropyrimidin-2-yl)-1-methoxypropane-2-sulfonamide and (1R,2S)-1-(5-fluoropyrimidin-2-yl)-1-methoxypropane-2-sulfonamide, Example 22.0

To a −78° C. solution of 22.02 (3.20 g, 6.7 mmol) in THF (67 mL) was added potassium bis(trimethylsilyl)amide (1.0 M solution in THF, 16.8 mL, 16.8 mmol) slowly via syringe. The resulting brown solution was warmed to −50° C. for 10 min and then recooled to −78° C. Methyl trifluoromethanesulfonate (2.95 mL, 26.9 mmol) was added slowly via syringe. The reaction was stirred at −78° C. for 10 min and then was quenched with saturated aqueous ammonium chloride. The mixture was extracted with EtOAc (2×), and the combined organic layers were dried over anhydrous magnesium sulfate and concentrated. The residue was dissolved in DCM (20 mL) and then was treated with anisole (2.19 mL, 20.2 mmol) and TFA (500 µL, 6.7 mmol) sequentially. The reaction was stirred overnight and then was concentrated. The residue was purified by silica gel chromatography (eluent: 0-10% MeOH in DCM) to provide the initial product. The product thus obtained was repurified by silica gel chromatography (eluent: 0-50% of a 3:1 EtOAc/EtOH mixture in DCM) to provide 22.0 (867 mg, 52% yield) as a white solid. LCMS-ESI (POS.) m/z: 249.9 (M+H)+.

Example 23.0: Preparation of (R)-2-(2,4-difluorophenyl)-2-hydroxyethanesulfonamide and (S)-2-(2,4-difluorophenyl)-2-hydroxyethanesulfonamide

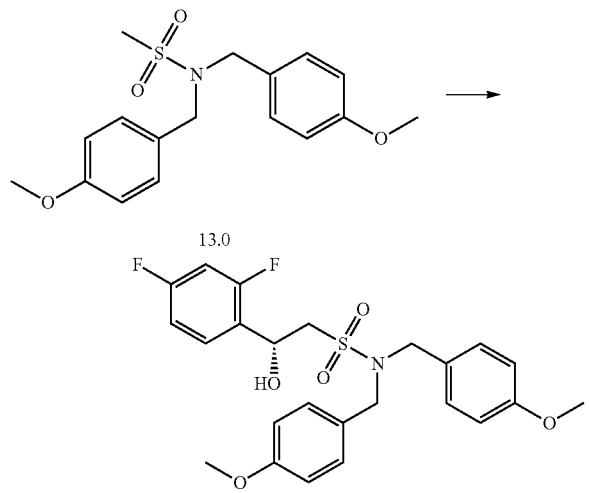

13.0

AND 23.01

(R)-2-(2,4-difluorophenyl)-2-hydroxy-N,N-bis(4-methoxybenzyl)ethanesulfonamide and (S)-2-(2,4-difluorophenyl)-2-hydroxy-N,N-bis(4-methoxybenzyl)ethanesulfonamide, Example 23.01

To a −78° C. solution of 13.0 (2.62 g, 7.8 mmol) in THF (15.5 mL) was added a solution of n-butyllithium in hexanes (1.6M, 7.3 mL, 11.7 mmol) slowly via syringe. After 30 min, a solution of 2,4-difluorobenzaldehyde (1.67 g, 11.7 mmol) in THF (5 mL) was added via cannula. The reaction was allowed to warm to RT overnight and then was quenched with saturated aqueous ammonium chloride solution. The resulting mixture was extracted with EtOAc (3×) and the combined organic layers were dried over anhydrous magnesium sulfate and concentrated. The residue was purified by silica gel chromatography (eluent: 0-100% EtOAc in hexanes) to provide the title compound 23.01 (2.86 g, 77% yield) as a white solid. LCMS-ESI (POS.) m/z: 500.0 (M+Na)+.

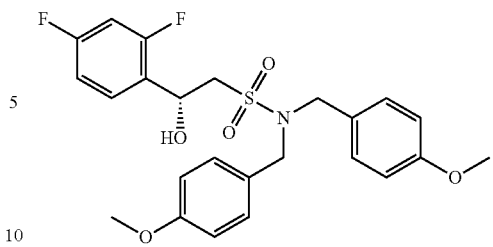

AND

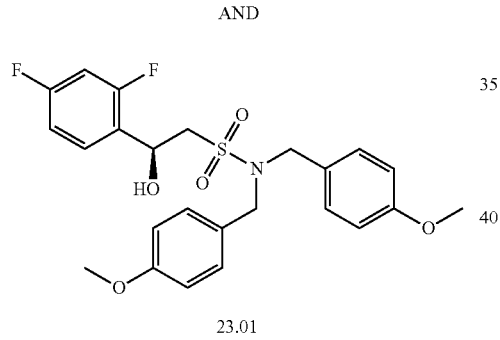

23.01

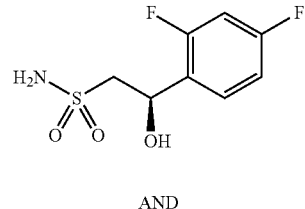

AND

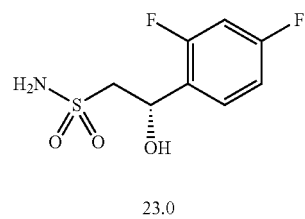

23.0

(R)-2-(2,4-difluorophenyl)-2-hydroxyethanesulfonamide and (S)-2-(2,4-difluorophenyl)-2-hydroxyethanesulfonamide, Example 23.0

Example 23.01 (2.65 g, 5.6 mmol) was dissolved in TFA (18.5 mL). Anisole (2.43 mL, 22.2 mmol) was added via syringe. The reaction was stirred at RT overnight and then was concentrated. The residue was purified by silica gel chromatography (eluent: 0-100% EtOAc in hexanes) to provide the title compound 23.0 (807 mg, 61% yield) as a white solid. LCMS-ESI (POS.) m/z: 260.0 (M+Na)+.

Example 24.0: Preparation of (1R,2S)-1-cyclobutyl-1-methoxypropane-2-sulfonamide and (1S,2R)-1-cyclobutyl-1-methoxypropane-2-sulfonamide or (1S,2S)-1-cyclobutyl-1-methoxypropane-2-sulfonamide and (1R,2R)-1-cyclobutyl-1-methoxypropane-2-sulfonamide

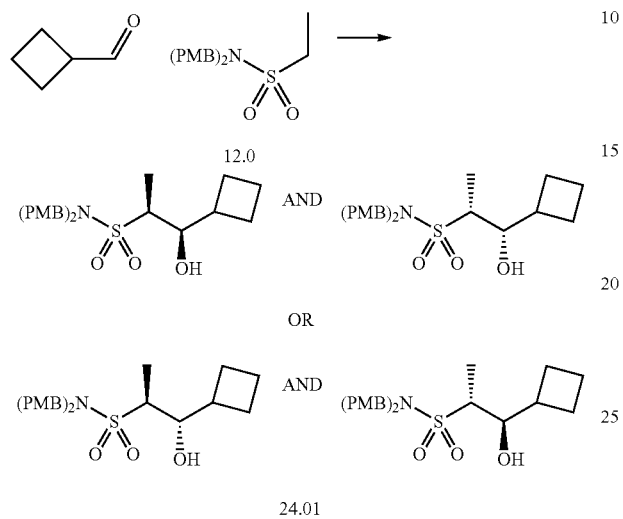

24.01

(1R,2S)-1-cyclobutyl-1-hydroxy-N,N-bis(4-methoxybenzyl)propane-2-sulfonamide and (1S,2R)-1-cyclobutyl-1-hydroxy-N,N-bis(4-methoxybenzyl)propane-2-sulfonamide or (1S,2S)-1-cyclobutyl-1-hydroxy-N,N-bis(4-methoxybenzyl)propane-2-sulfonamide and (1R,2R)-1-cyclobutyl-1-hydroxy-N,N-bis(4-methoxybenzyl)propane-2-sulfonamide, Example 24.01

Example 12.0 (3.01 g, 8.62 mmol) was dissolved in THF (25 mL) in a 250 mL round bottom flask and cooled in a dry ice/acetone bath. When the internal temperature reached −75° C., nBuLi (Aldrich, 2.5 M in hexanes, 3.79 mL, 9.48 mmol) was added dropwise over 22 min keeping the internal temperature below −71° C., giving an orange colored mixture. The mixture was stirred for 15 min. Cyclobutanecarbaldehyde (AstaTech, 0.739 mL, 9.48 mmol) was then added dropwise over 10 min keeping the internal temperature below −70° C. The mixture was stirred as the cold bath expired and the temperature slowly rose to RT (overnight). The reaction was quenched with 2 mL of a saturated aqueous NH$_4$Cl solution. The reaction mixture was then partitioned between half-saturated aqueous ammonium chloride (50 mL) and EtOAc (20 mL). The aqueous phase was extracted with EtOAc (20 mL). The combined organic phases were washed with water (50 mL) and saturated aqueous sodium chloride (50 mL). The organic phase was dried by passing through a Chem Elute extraction cartridge (10 mL 1219-8007) eluting with EtOAc (2×20 mL). The organic layer was then concentrated and the residue was purified by silica gel column chromatography (a gradient of 0-40% EtOAc in hexanes). To give the first eluting peak (24.01) as a clear oil (1.31 g, 3.02 mmol, 35% yield). LCMS-ESI (POS.) m/z: 456.0 (M+Na)$^+$.

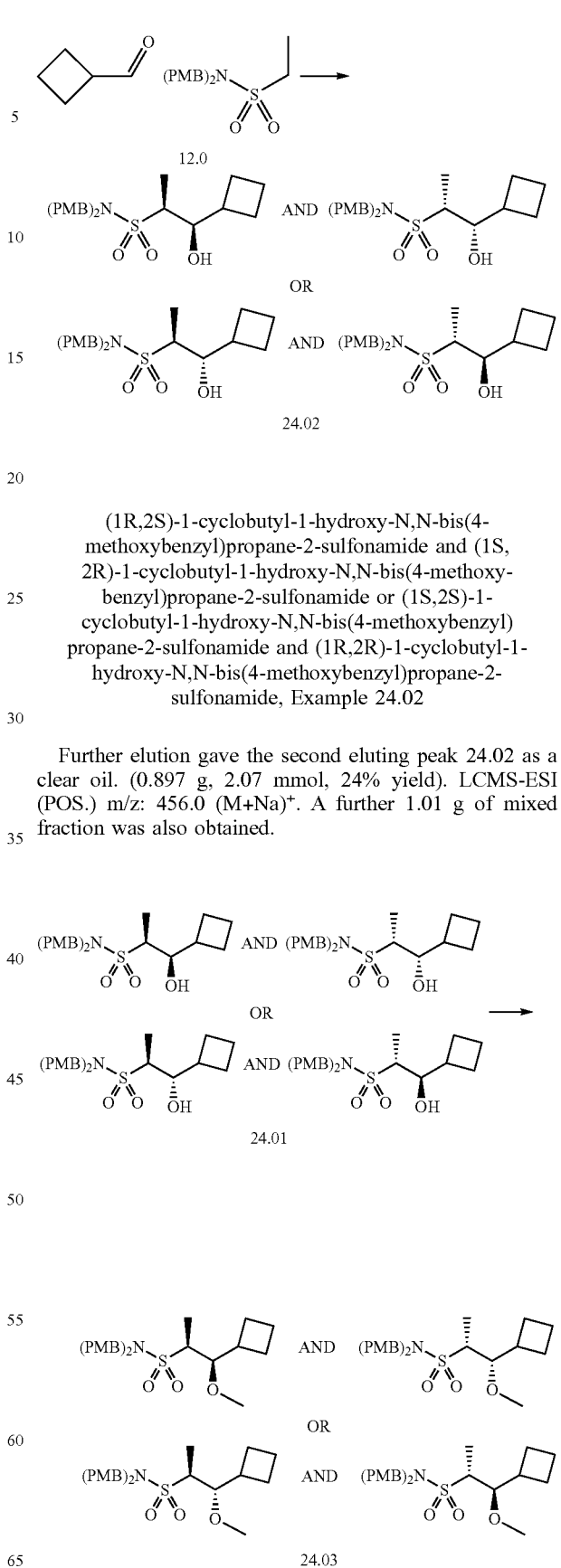

(1R,2S)-1-cyclobutyl-1-hydroxy-N,N-bis(4-methoxybenzyl)propane-2-sulfonamide and (1S,2R)-1-cyclobutyl-1-hydroxy-N,N-bis(4-methoxybenzyl)propane-2-sulfonamide or (1S,2S)-1-cyclobutyl-1-hydroxy-N,N-bis(4-methoxybenzyl)propane-2-sulfonamide and (1R,2R)-1-cyclobutyl-1-hydroxy-N,N-bis(4-methoxybenzyl)propane-2-sulfonamide, Example 24.02

Further elution gave the second eluting peak 24.02 as a clear oil. (0.897 g, 2.07 mmol, 24% yield). LCMS-ESI (POS.) m/z: 456.0 (M+Na)$^+$. A further 1.01 g of mixed fraction was also obtained.

(1R,2S)-1-cyclobutyl-1-methoxy-N,N-bis(4-methoxybenzyl)propane-2-sulfonamide and (1S,2R)-1-cyclobutyl-1-methoxy-N,N-bis(4-methoxybenzyl)propane-2-sulfonamide or (1S,2S)-1-cyclobutyl-1-methoxy-N,N-bis(4-methoxybenzyl)propane-2-sulfonamide and (1R,2R)-1-cyclobutyl-1-methoxy-N,N-bis(4-methoxybenzyl)propane-2-sulfonamide, Example 24.03

The title compound was prepared in an analogous fashion to that of Example 14.05 using Example 24.01.

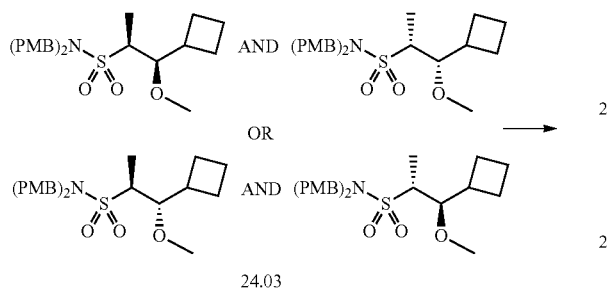

24.03

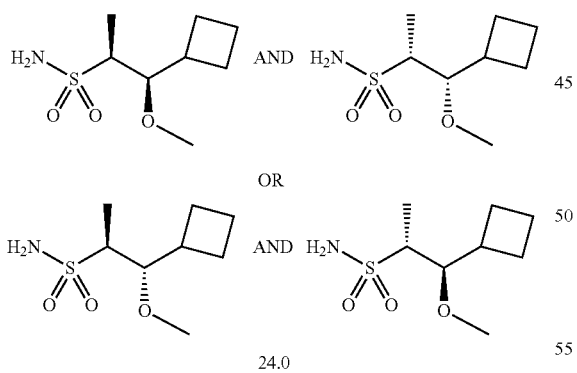

24.0

(1R,2S)-1-cyclobutyl-1-methoxypropane-2-sulfonamide and (1S,2R)-1-cyclobutyl-1-methoxypropane-2-sulfonamide or (1S,2S)-1-cyclobutyl-1-methoxypropane-2-sulfonamide and (1R,2R)-1-cyclobutyl-1-methoxypropane-2-sulfonamide, Example 24.0

The title compound was prepared in an analogous fashion to that of Example 15.0 using 24.03.

Example 25.0: Preparation of (1S,2R)-1-(allyloxy)-1-(5-methylpyrimidin-2-yl)propane-2-sulfonamide and (1R,2S)-1-(allyloxy)-1-(5-methylpyrimidin-2-yl)propane-2-sulfonamide

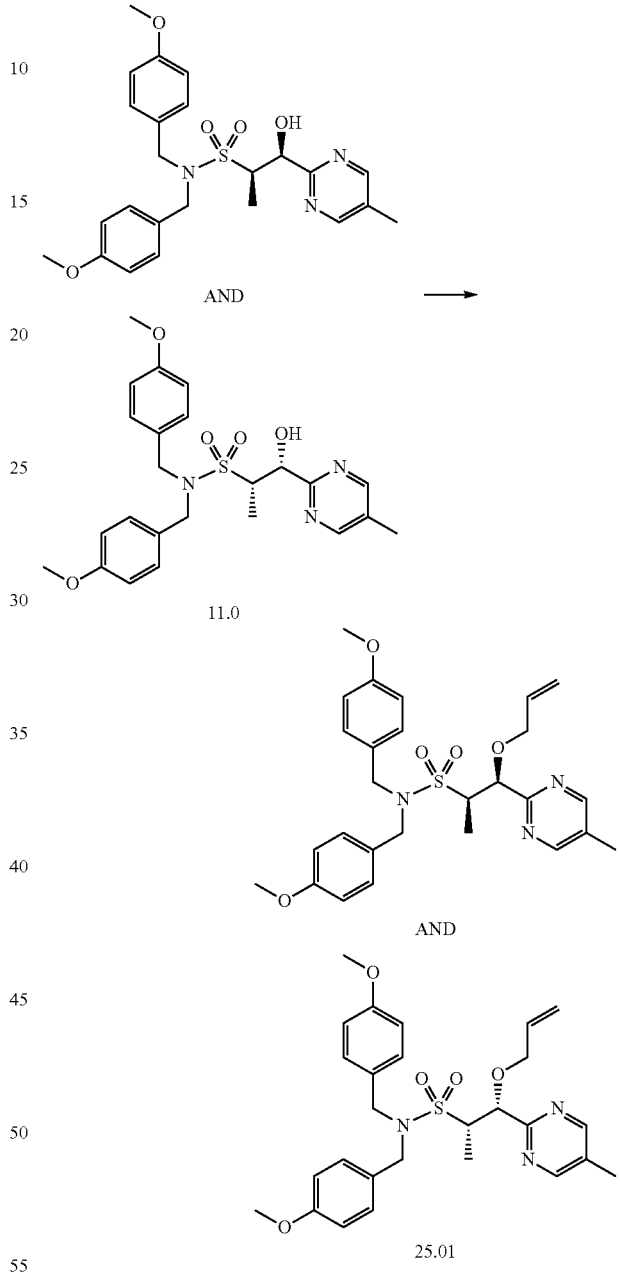

(1S,2R)-1-(allyloxy)-N,N-bis(4-methoxybenzyl)-1-(5-methylpyrimidin-2-yl)propane-2-sulfonamide and (1R,2S)-1-(allyloxy)-N,N-bis(4-methoxybenzyl)-1-(5-methylpyrimidin-2-yl)propane-2-sulfonamide, Example 25.01

To a −78° C. solution of 11.0 (2.01 g, 43 mmol) in THF (45 mL) was added potassium bis(trimethylsilyl)amide (1 M solution in THF, 5.8 mL, 5.8 mmol) slowly via syringe. After 5 min, allyl bromide (1.5 mL, 17.1 mmol) was added slowly via syringe. The resulting bright yellow solution was stirred at −78° C. for 5 min and then was warmed to 0° C. and stirred for an additional 60 min. The reaction mixture was quenched with a 6:1 mixture of saturated aqueous ammonium chloride and water (70 mL) and then was extracted with EtOAc (4×). The combined organic layers were dried over anhydrous sodium sulfate and concentrated. The residue was purified by silica gel chromatography (eluent: 5-75% EtOAc in hexanes over a 40 min period) to provide 25.01 (1.39 g, 64% yield) as a light yellow solid. LCMS-ESI (POS.) m/z: 512.0 (M+H)+.

syringe. The resulting orange solution was stirred at RT for 29 h and then concentrated in vacuo. The residue was purified by silica gel chromatography (eluent: 4.5-100% MeOH in DCM over a 40 min period) to provide 25.0 (682 mg, 93% yield) as a white solid. LCMS-ESI (POS.) m/z: 272.0 (M+H)+.

Example 26.0: Preparation of (1R,2R)-1-(allyloxy)-1-(5-methylpyrimidin-2-yl)propane-2-sulfonamide and (1S,2S)-1-(allyloxy)-1-(5-methylpyrimidin-2-yl)propane-2-sulfonamide

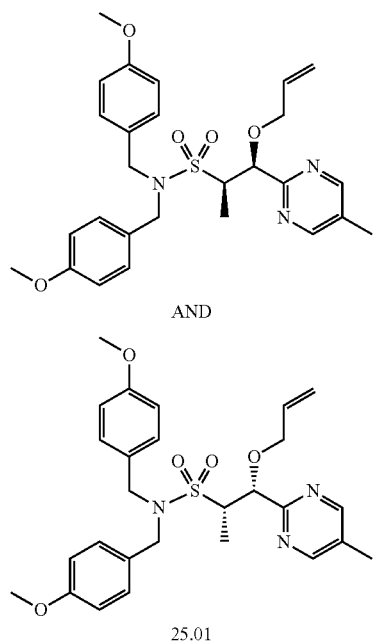

25.01

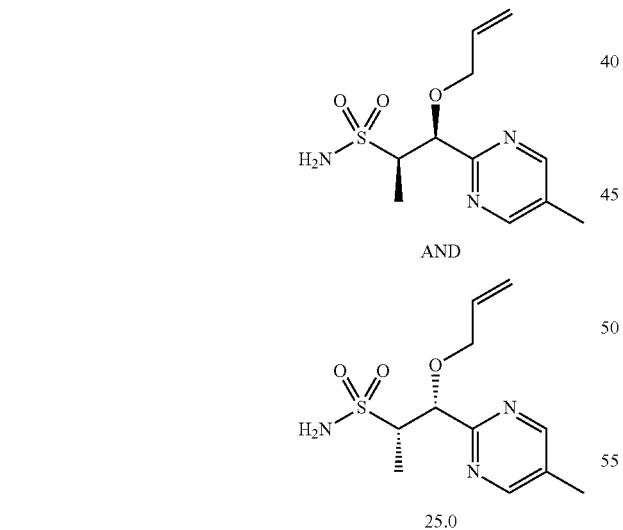

(1S,2R)-1-(allyloxy)-1-(5-methylpyrimidin-2-yl)propane-2-sulfonamide and (1R,2S)-1-(allyloxy)-1-(5-methylpyrimidin-2-yl)propane-2-sulfonamide, Example 25.0

Example 25.01 (1.39 g, 2.7 mmol) was dissolved in TFA (15 mL). Anisole (620 µL, 5.7 mmol) was then added via

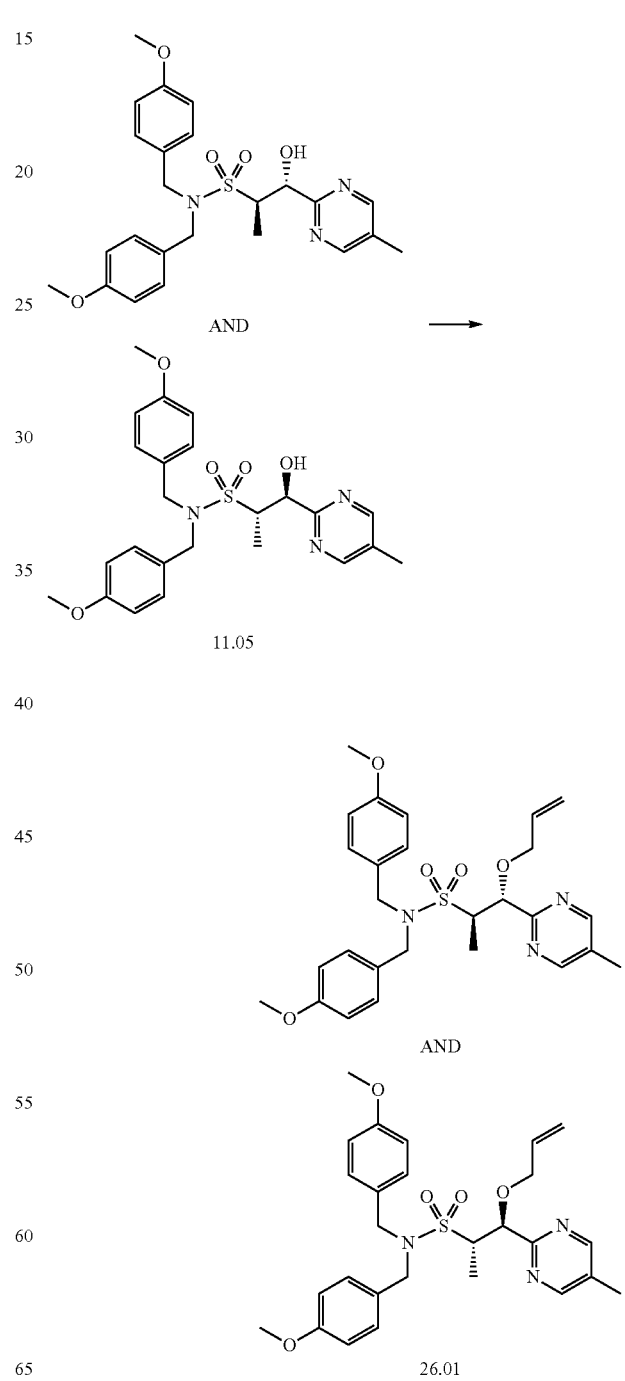

11.05

26.01

(1R,2R)-1-(allyloxy)-N,N-bis(4-methoxybenzyl)-1-(5-methylpyrimidin-2-yl)propane-2-sulfonamide and (1S,2S)-1-(allyloxy)-N,N-bis(4-methoxybenzyl)-1-(5-methylpyrimidin-2-yl)propane-2-sulfonamide, Example 26.01

To a −78° C. solution of Example 11.05 (3.18 g, 6.7 mmol) in THF (70 mL) was added potassium bis(trimethylsilyl)amide (1 M solution in THF, 9.1 mL, 9.1 mmol) slowly via syringe. After 5 min, allyl bromide (2.3 mL, 27.0 mmol) was added slowly via syringe. The resulting bright yellow solution was stirred at −78° C. for 5 min and then was warmed to 0° C. and stirred for an additional 1.75 h. The reaction mixture was quenched with an 11:1 mixture of saturated aqueous ammonium chloride and water (110 mL) and then was extracted with EtOAc (4×). The combined organic layers were dried over anhydrous sodium sulfate and concentrated. The residue was purified by silica gel chromatography (eluent: 5-75% EtOAc in hexanes over a 40 min period) to provide 26.01 (1.62 g, 47% yield) as a white solid. LCMS-ESI (POS.) m/z: 512.0 (M+H)$^+$.

(1R,2R)-1-(allyloxy)-1-(5-methylpyrimidin-2-yl)propane-2-sulfonamide and (1S,2S)-1-(allyloxy)-1-(5-methylpyrimidin-2-yl)propane-2-sulfonamide, Example 26.0

Example 26.01 (1.62 g, 3.2 mmol) was dissolved in TFA (13 mL). Anisole (755 μL, 6.9 mmol) was then added via syringe. The resulting yellow solution was stirred at RT for 21.5 h and then was concentrated. The residue was purified by silica gel chromatography (eluent: 4.5-100% MeOH in DCM over a 45 min period) to provide 26.0 (807 mg, 94% yield) as a light yellow solid. LCMS-ESI (POS.) m/z: 272.0 (M+H)$^+$.

Example A

Example 27.0: Preparation of (1R,2S)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide

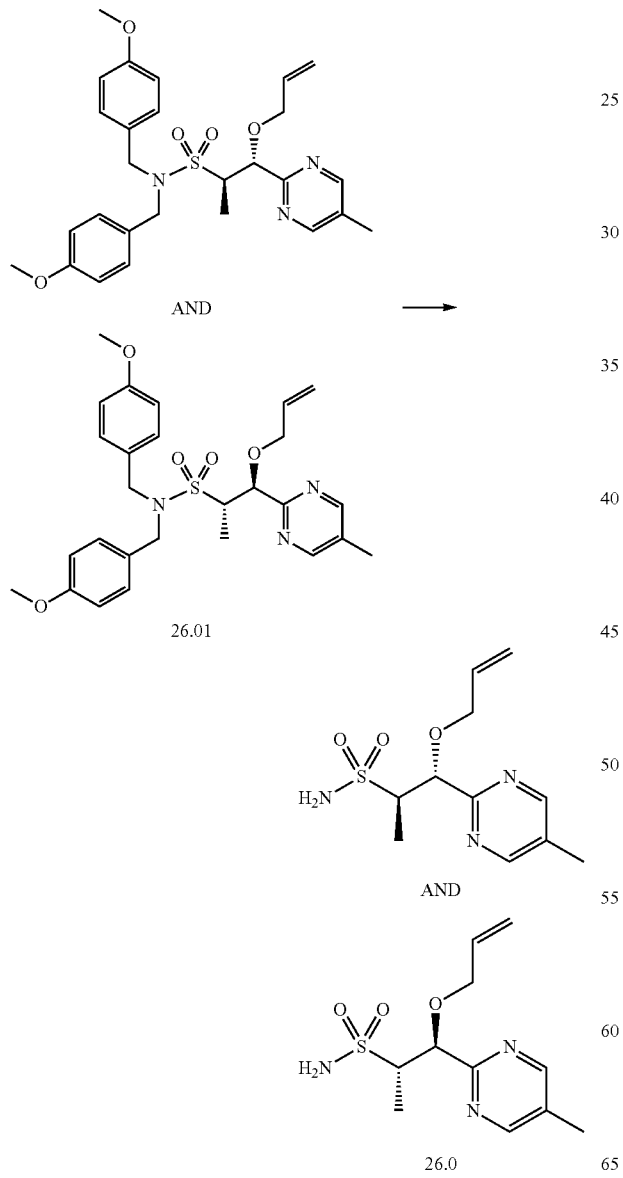

(Z)—N'-(2,6-dimethoxyphenyl)-N-(((1S,2R)-1-methoxy-1-(5-methylpyrimidin-2-yl)propan-2-yl)sulfonyl)-2-(6-methoxypicolinoyl)hydrazinecarboximidamide, Example 27.01

To a flask containing 14.0 (617 mg, 2.51 mmol) and 1.0 (522 mg, 2.67 mmol) in ACN (7.5 mL) was added cesium carbonate (1.07 g, 3.27 mmol) in one portion. The mixture was stirred at 23° C. and monitored with LC-MS. After 19 h, the mixture was cooled in an ice-water bath. After 15 min, 6-methoxy-pyridine-2-carboxylic acid hydrazide (454 mg, 2.71 mmol) and then silver nitrate (859 mg, 5.06 mmol) were carefully added in portions. The mixture was allowed to warm to 23° C. and monitored with TLC and LC-MS. After an additional 5 min, the mixture was concentrated under reduced pressure. The black residue was diluted with DCM then loaded onto a silica gel column (0-70% 3:1 EtOAc: EtOH in heptanes). Fractions containing desired product were combined then concentrated under reduced pressure to afford a light orange film that solidified into an off white sticky foam as (Z)—N'-(2,6-dimethoxyphenyl)-N-(((1S,2R)-1-methoxy-1-(5-methylpyrimidin-2-yl)propan-2-yl)sulfonyl)-2-(6-methoxypicolinoyl)hydrazinecarboximidamide 27.01 (1.35 g, 2.36 mmol, 94% yield) that was used without further purification. MS (pos.) m/e: 574.2 (M+H)⁺.

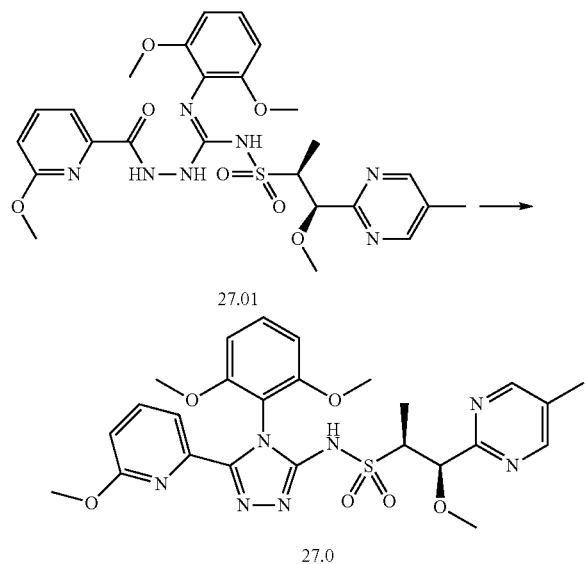

(1S,2R)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide, Example 27.0

To a flask containing (Z)—N'-(2,6-dimethoxyphenyl)-N-(((1S,2R)-1-methoxy-1-(5-methylpyrimidin-2-yl)propan-2-yl)sulfonyl)-2-(6-methoxypicolinoyl)hydrazinecarboximidamide 27.01 (1.35 g, 2.36 mmol) in 1,4-dioxane (6.6 mL) was added methanesulfonic acid (0.55 mL, 8.48 mmol) carefully dropwise to the reaction mixture. Upon complete addition of methanesulfonic acid, the mixture was heated on a preheated stir plate at 90° C. After 5 h, the reaction was cooled to RT and then diluted with water. The pH was carefully adjusted with dropwise addition of saturated aqueous sodium bicarbonate solution to pH-7. The solid was filtered, rinsed once with water, and then suspended in IPA. After 5 min, the suspension was filtered to afford a white solid as (1S,2R)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide 27.0, (800 mg, 1.44 mmol, 61.0% yield). $^1$H NMR (500 MHz, DMSO-$d_6$) δ 13.25 (s, 1H), 8.65 (s, 2H), 7.80 (dd, J=8.3, 7.6 Hz, 1H), 7.58 (d, J=7.4 Hz, 1H), 7.40 (t, J=8.4 Hz, 1H), 6.82 (d, J=8.3 Hz, 1H), 6.78 (d, J=8.7 Hz, 2H), 4.82 (d, J=3.7 Hz, 1H), 3.65 (s, 3H) 3.63 (s, 3H), 3.42 (dd, J=7.1, 3.7 Hz, 1H), 3.15 (s, 3H), 3.10 (s, 3H), 2.26 (s, 3H), 1.13 (d, J=7.1 Hz, 3H). MS (pos.) m/z: 556.2 (M+H)⁺.

The compounds set forth in the following Table were synthesized following the procedure in Example A using the known starting material as described.

TABLE 10

| Example | Reagents | Structure, Name and and Data |
|---|---|---|
| 28.0 | (1S,2R)-1-methoxy-1-(5-methylpyrimidin-2-yl)propane-2-sulfonamide, (made from the minor enantiomer from Example 14.0), Example 1.0, 5-methylnicotinohydrazide (comercially available from Bellen Chemistry Co.) | (1S,2R)-N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide<br>$^1$H NMR (400 MHz, DMSO-$d_6$) δ 13.31 (s, 1H), 8.65 (d, J = 0.6 Hz, 2H), 8.47 (d, J = 1.4 Hz, 1H), 8.20 (d, J = 1.8 Hz, 1H), 7.57-7.64 (m, 1H), 7.50 (t, J = 8.5 Hz, 1H), 6.83 (d, J = 8.6 Hz, 2H), 4.83 (d, J = 3.5 Hz, 1H), 3.71 (s, 3H), 3.69 (s, 3H), 3.42 (qd, J = 6.9, 3.6 Hz, 1H), 3.14-3.18 (m, 3H), 2.27 (s, 3H, ), 2.23-2.26 (m, 3H), 1.14 (d, J = 7.0 Hz, 3H). MS (pos.) m/z: 540.2 (M + H)⁺. |

TABLE 10-continued

| Example | Reagents | Structure, Name and and Data |
|---|---|---|
| 29.0 | 6-methoxy-pyridine-2-carboxylic acid hydrazide, Example 1.0, ethanesulfonamide | N-(4-(2,6-dimethoxyphenyl)-5-(6-methoxypyridin-2-yl)-4H-1,2,4-triazol-3-yl)ethanesulfonamide.<br>$^1$H NMR (500 MHz, DMSO-d$_6$) δ 13.27 9s, 1H), 7.80 (dd, J = 8.2, 7.5 Hz, 1H), 7.54-7.59 (m, 1H), 7.40 (t, J = 8.4 Hz, 1H), 6.76-6.84 (m, 3H), 3.67 (s, 6H), 3.10 (s, 3H), 2.88 (q, J = 7.3 Hz, 2H), 1.13 (t, J = 7.3 Hz, 3H). MS (pos.) m/z: 420.1 (M + H)$^+$. |
| 30.0 | 6-methylpicolino hydrazide (Example 3.10) and Example 1.0 and ethanesulfonamide | N-(4-(2,6-dimethoxyphenyl)-5-(6-methylpyridin-2-yl)-4H-1,2,4-triazol-3-yl)ethanesulfonamide<br>$^1$H NMR (500 MHz, DMSO-d$_6$) δ 13.23 (s, 1H), 7.75 (t, J = 7.8 Hz, 1H), 7.64 (d, J = 7.8 Hz, 1H), 7.43 (t, J = 8.4 Hz, 1H), 7.25 (d, J = 7.8 Hz, 1H), 6.74-6.80 (m, 2H), 3.65 (s, 6H), 2.89 (q, J = 7.3 Hz, 2H), 2.09 (s, 3H), 1.14 (t, J = 7.3 Hz, 3H). LCMS-ESI (POS.) m/z: 404.1 (M + H)$^+$. |
| 31.0 | Example 1.2 and Example 9.0 and 6-methoxy-pyridine-2-carboxylic acid hydrazide | AND<br><br>(2R)-1-(5-fluoropyrimidin-2-yl)-N-(4-(2-methoxyphenyl)-5-(6-methoxypyridin-2-yl)-4H-1,2,4-triazol-3-yl)propane-2-sulfonamide and (2S)-1-(5-fluoropyrimidin-2-yl)-N-(4-(2-methoxyphenyl)-5-(6-methoxypyridin-2-yl)-4H-1,2,4-triazol-3-yl)propane-2-sulfonamide<br>$^1$H NMR (500 MHz, DMSO-d$_6$) δ 13.38 (d, J = 7.6 Hz, 1H), 8.76-8.88 (m, 2H), 7.81 |

TABLE 10-continued

| Example | Reagents | Structure, Name and and Data |
|---|---|---|
| | | (dd, J = 8.3, 7.6 Hz, 1H), 7.52-7.62 (m, 1H), 7.33-7.49 (m, 2H), 7.12-7.21 (m, 1H), 7.05 (td, J = 7.7, 1.2 Hz, 1H), 6.82 (d, J = 8.1 Hz, 1H), 3.60 (s, 3H), 3.43-3.58 (m, 2H), 3.06 (s, 3H), 2.80-2.91 (m, 1H), 1.11 (dd, J = 8.7, 6.7 Hz, 3H). LCMS-ESI (POS.) m/z: 500.1 (M + H)+. |
| 32.0 | 3,5-dimethyl-4-isoxazoyl isothiocyanate and Example 9.0 and 6-methoxy-pyridin-2-carboxylic acid hydrazide | 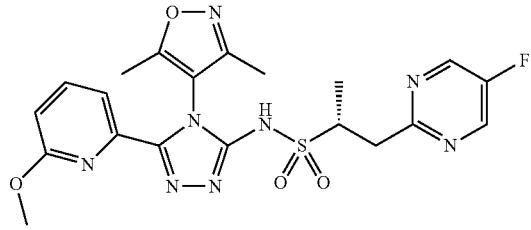 [SMILES: COc1cccc(-c2nnc(NS(=O)(=O)[C@H](C)Cc3ncc(F)cn3)n2-c2c(C)noc2C)n1]<br><br>AND<br><br>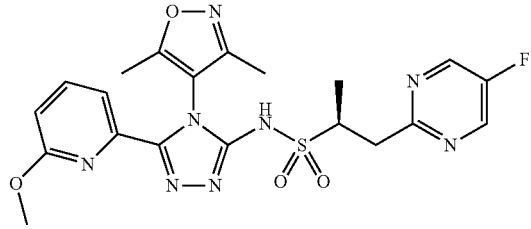<br><br>(2R)-N-(4-(3,5-dimethyisoxazol-4-yl)-5-(6-methoxypyridin-2-yl)-4H-1,2,4-triazol-3-yl)-1-(5-fluoropyrimidin-2-yl)propane-2-sulfonamide and (2S)-N-(4-(3,5-dimethylisoxazol-4-yl)-5-(6-methoxypyridin-2-yl)-4H-1,2,4-triazol-3-yl)-1-(5-fluoropyrimidin-2-yl)propane-2-sulfonamide<br>1H NMR (500 MHz, DMSO-d6) δ 13.61 (br. s, 1H), 7.87-8.87 (m, 2H), 7.88 (dd, J = 8.3, 7.3 Hz, 1H), 7.67 (d, J 7.3 Hz, 1H), 6.94 (d, J = 8.3 Hz, 1H), 3.60 (dd, J = 9.7, 4.5 Hz, 1H), 3.51 (dd, J = 14.5, 4.0 Hz, 1H), 3.38 (s, 3H), 2.85-2.96 (m, 1H), 2.23 (d, J = 2.7 Hz, 3H), 2.04 (d, J = 2.4 Hz, 3H), 1.17 (d, J = 6.8 Hz, 3H). LCMS-ESI (POS.) m/z: 489.1 (M + H)+. |
| 33.0 | 3-pyridyl isothiocyanate and Example 14.0 and 6-methoxy-pyridine-2-carboxylic acid hydrazide | 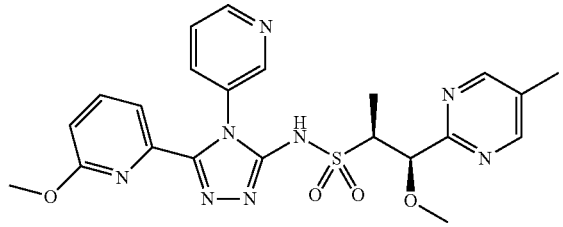<br><br>(1R,2S)-1-methoxy-N-(5-(6-methoxypyridin-2-yl)-4-(pyridin-3-yl)-4H-1,2,4-triazol-2-sulfonamide<br>1H NMR (500 MHz, DMSO-d6) δ = 13.49 (s, 1H), 8.70-8.59 (m, 4H), 7.89 (d, J = 7.8 Hz, 1H), 7.84 (t, J = 7.8 Hz, 1H), 7.67-7.63 (m, 1H), 7.59 (dd, J = 4.8, 7.9 Hz, 1H), 6.85 (d, J = 8.1 Hz, 1H), 4.88 (d, J = 3.4 Hz, 1H), 3.53-3.38 (m, 1H), 3.09 (s, 3H), 3.03 (s, 3H), 2.25 (s, 3H), 1.13 (d, J = 7.1 Hz, 3H). LCMS-ESI (POS.) m/z: 497.3 (M + H)+. |

TABLE 10-continued

| Example | Reagents | Structure, Name and Data |
|---|---|---|
| 34.0 | (1R,2S)-1-methoxy-1-(5-methylpyrimidin-2-yl)propane-2-sulfonamide (Example 14.0), 6-methoxypicolinohydrazide (Example 3.18), isothiocyanatobenzene (Aldrich) | 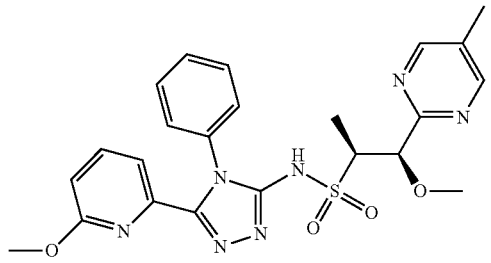<br>(1R,2S)-1-methoxy-N-(5-(6-methoxypyridin-2-yl)-4-phenyl-4H-1,2,4-triszol-3-yl)-1-(5-methylpyrimidin-2-yl)propane-2-sulfonamide<br>$^1$H NMR (300 MHz, DMSO-d$_6$) δ = 13.34 (br. s., 1H), 8.65 (s, 2H), 7.82 (dd, J = 8.3, 7.5 Hz, 1H), 7.59 (d, J = 6.9 Hz, 1H), 7.41-7.54 (m, 3H), 7.34-7.40 (m, 2H), 6.83 (d, J = 7.7 Hz, 1H), 4.89 (d, J = 3.4 Hz, 1H), 3.36-3.49 (m, 1H), 3.09 (s, 3H), 3.07 (s, 3H), 2.26 (s, 3H), 1.15 (d, J = 7.0 Hz, 3H). LCMS-ESI (POS.) m/z: 496.1 (M + H)$^+$. |
| 35.0 | (1R,2S)-1-methoxy-1-(5-methylpyrimidin-2-yl)propane-2-sulfonamide (Example 14.0), 6-methoxypicolinohydrazide (Example 3.18), 5-isothiocyanato-4,6-dimethoxypyrimidine (Example 1.1) | 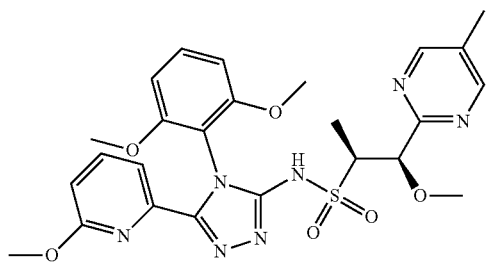<br>(1R,2S)-N-(4-(4,6-dimethoxypyrimidin-5-yl)-5-(6-methoxypyridin-2-yl)-4H-1,2,4-triazol-3-yl)-1-methoxy-1-(5-methylpyrimidin-2-yl)propane-2-sulfonamide<br>$^1$H NMR (300 MHz, CD$_3$OD) δ = 8.69 (s, 2H), 8.52 (s, 1H), 7.66-7.84 (m, 2H), 6.83 (dd, J = 8.1, 0.9 Hz, 1H), 5.02 (d, J = 3.5 Hz, 1H), 3.96 (s, 3H), 3.94 (s, 3H), 3.52-3.63 (m, 1H), 3.27 (s, 3H), 3.24 (s, 3H), 2.37 (s, 3H), 1.26 (d, J = 7.0 Hz, 3H). LCMS-ESI (POS.) m/z: 558.2 (M + H)$^+$. |
| 36.0 | (1R,2S)-1-methoxy-1-(5-methylpyrimidin-2-yl)propane-2-sulfonamide (Example 14.0), 6-methoxypicolinohydrazide (Example 3.18), 2-isothiocyanato-1,3-di([$^2$H$_3$]methoxy)benzene (Example 1.4) | 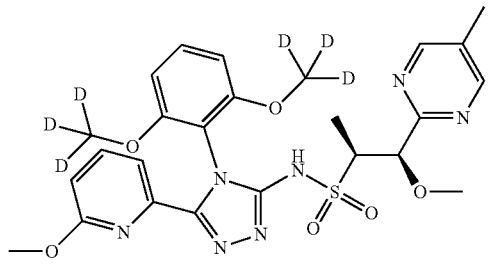<br>(1R,2S)-N-(4-(2,6-bis([$^2$H$_3$]methyloxy)phenyl)-5-(6-methoxypyridin-2-yl)-4H-1,2,4-triazol-3-yl)-1-methoxy-1-(5-methylpyrimidin-2-yl)propane-2-sulfonamide<br>$^1$H NMR (300 MHz, CDCl$_3$) δ = 8.62 (s, 2H), 7.51-7.71 (m, 2H), 7.28-7.38 (m, 1H), 6.70 (dd, J = 6.9, 2.2 Hz, 1H), 6.59 (dd, J = 8.4, 1.1 Hz, 2H), 4.98 (d, J = 4.7 Hz, 1H), 3.76 (dd, J = 6.9, 4.8 Hz, 1H), 3.34 (s, 3H), 3.17 (s, 3H), 2.33 (s, 3H), 1.39 (d, J = 6.9 Hz, 3H). LCMS-ESI (POS.) m/z: 562.3 (M + H)$^+$. |

TABLE 10-continued

| Example | Reagents | Structure, Name and and Data |
|---|---|---|
| 37.0 | (1R,2S)-1-methoxy-1-(5-methylpyrimidin-2-yl)propane-2-sulfonamide (Example 14.0), 6-([$^2$H$_3$]methoxy)picolinohydrazide (Example 3.40), 2-isothiocyanato-1,3-di([$^2$H$_3$]methoxy)benzene (Example 1.4) | 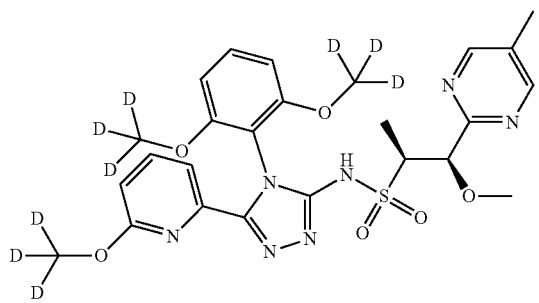 [SMILES: [2H]C([2H])([2H])Oc1cccc(-c2nnc(NS(=O)(=O)[C@@H](C)[C@H](OC)c3ncc(C)cn3)n2-c2c(OC([2H])([2H])[2H])cccc2OC([2H])([2H])[2H])n1]<br>(1R,2S)-N-(4-(2,6-bis([$^2$H$_3$]methyloxy)phenyl)-5-(6-($^2$H$_3$)methyloxy)-2-pyridinyl)-4H-1,2,4-triazol-3-yl)-1-methoxy-1-(5-methylpyrimidin-2-yl)propane-2-sulfonamide<br>$^1$H NMR (400 MHz, CDCl$_3$) δ 11.18 (br. s., 1H), 8.59 (s, 2H), 7.54-7.69 (m, 2H), 7.27-7.33 (m, 1H), 6.68 (d, J = 7.4 Hz, 1H), 6.58 (d, J = 8.6 Hz, 2H), 4.96 (d, J = 4.3 Hz, 1H), 3.64-3.83 (m, 1H), 3.33 (s, 3H), 2.32 (s, 3H), 1.38 (d, J = 6.8 Hz, 3H). LCMS-ESI (POS.) m/z: 565.3 (M + H)$^+$. |
| 38.0 | (1R,2S)-1-methoxy-1-(5-methylpyrimidin-2-yl)propane-2-sulfonamide (Example 14.0), 6-([$^2$H$_3$]methoxy)picolinohydrazide (Example 3.40), 2-isothiocyanato-1,3-dimethoxybenzoate (Example 1.0) | 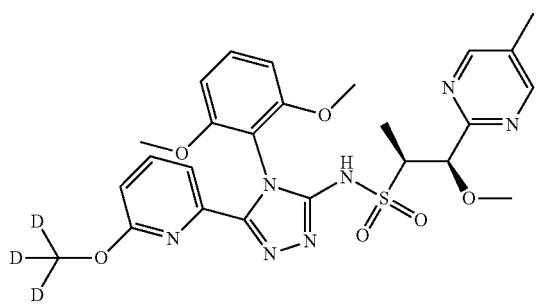 [SMILES: [2H]C([2H])([2H])Oc1cccc(-c2nnc(NS(=O)(=O)[C@@H](C)[C@H](OC)c3ncc(C)cn3)n2-c2c(OC)cccc2OC)n1]<br>(1R,2S)-N-(4-(2,6-dimethoxyphenyl)-5-(6-([$^2$H$_3$]methoxy)-2-pyridinyl)-4H-1,2,4-triazol-3-yl)-1-methoxy-1-(5-methylpyrimidin-2-yl)propane-2-sulfonamide<br>$^1$H NMR (400 MHz, CDCl$_3$) δ = 11.19 (br. s., 1H), 8.59 (s, 2H), 7.52-7.67 (m, 2H), 7.30 (t, J = 8.5 Hz, 1H), 6.69 (dd, J = 7.0, 1.8 Hz, 1H), 6.59 (d, J = 8.4 Hz, 2H), 4.97 (d, J = 4.7 Hz, 1H), 3.73-3.80 (m, 1H), 3.71 (s, 3H), 3.69 (s, 3H), 3.34 (s, 3H), 2.32 (s, 3H), 1.38 (d, J = 7.0 Hz, 3H). LCMS-ESI (POS.) m/z: 559.2 (M + H)$^+$. |
| 39.0 | (1R,2S)-1-methoxy-1-(5-methylpyrimidin-2-yl)propane-2-sulfonamide (Example 14.0 Example 14.0), 6-methoxypicolinohydrazide (Example 3.18), 1-isothiocyanato-3,5-bis(trifluoromethyl)benzene (Aldrich) | 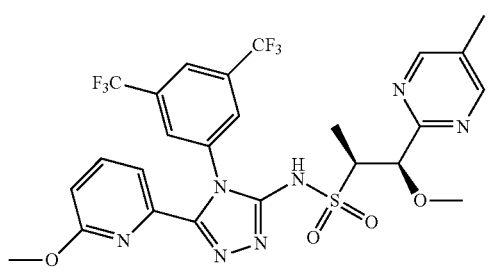<br>(1R,2S)-N-(4-(3,5-bis(trifluoromethyl)phenyl)-5-(6-methoxypyidin-2-yl)-4H-1,2,4-triazol-3-yl)-1-methoxy-1-(5-methylpyrimidin-2-yl)propane-2-sulfonamide<br>$^1$H NMR (300 MHz, CDCl$_3$) δ 8.73 (s, 2H), 7.97 (s, 1H), 7.92 (s, 2H), 7.66-7.75 (m, 2H), 6.75-6.83 (m, 1H), 5.04 (d, J = 4.4 Hz, 1H), 3.68-3.79 (m, 1H), 3.30 (s, 3H), 3.06 (s, 3H), 2.41 (s, 3H), 1.35 (d, J = 7.0 Hz, 3H). LCMS-ESI (POS.) m/z: 632.0 (M + H)$^+$. |

TABLE 10-continued

| Example | Reagents | Structure, Name and and Data |
|---|---|---|
| 40.0 | (1R,2S)-1-methoxy-1-(5-methylpyrimidin-2-yl)propane-2-sulfonamide (Example 14.0), 6-methoxypicolinohydrazide (Example 3.18), 2-isothiocyanato-1-methoxy-4-methylbenzene (Aldrich) | 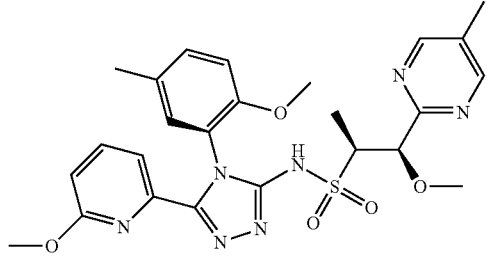<br>AND<br>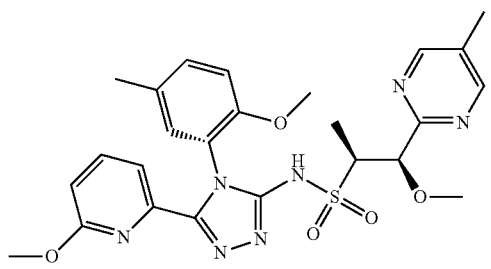<br>(1R,2S,P)-1-methoxy-N-(4-(2-methoxy-5-methylphenyl)-5-(6-methoxypyridin-2-yl)-4H-1,2,4-triazol-3-yl)-1-(5-methylpyrimidin-2-yl)propane-2-sulfonamide and (1R,2S,M)-1-methoxy-N-(4-(2-methoxy-5-methylphenyl)-5-(6-methoxypyridin-2-yl)-4H-1,2,4-triazol-3-yl)-1-(5-methylpyrimidin-2-yl)propane-2-sulfonamide<br>$^1$H NMR (300 MHz, CDCl$_3$) (3:2 ratio of P and M atropisomers) δ = 8.72 (s, 1.2H), 8.70 (s, 0.8H), 7.53-7.67 (m, 2H), 7.31 (d, J = 1.9 Hz, 0.6H), 7.12-7.20 (m, 1.3H), 6.81 (d, J = 8.3 Hz, 1H), 6.68-6.74 (m, 1H), 5.10 (d, J = 3.7 Hz, 0.6H), 5.00 (d, J = 4.7 Hz, 0.4H), 3.65-3.81 (m, 1H), 3.59 (s, 1.2H), 3.56 (s, 1.8H), 3.36 (s, 1.2H), 3.25 (s, 1.8H), 3.18 (s, 1.8H), 3.17 (s, 1.2H), 2.39 (s, 1.8H), 2.37 (s, 1.2H), 2.31 (s, 3H), 1.30-1.40 (m, 3H). LCMS-ESI (POS.) m/z: 540.2 (M + H)$^+$. |
| 41.0 | (1R,2S)-1-methoxy-1-(5-methylpyrimidin-2-yl)propane-2-sulfonamide (Example 14.0), ), 6-methoxypicolinohydrazide (Example 3.18), 1,3-bis(difluoromethoxy)-2-isothiocyanatobenzene (Example 1.5) | 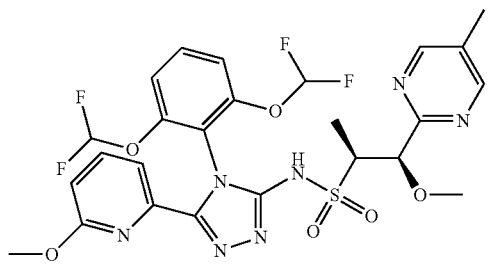<br>(1R,2S)-N-(4-(2,6-bis(difluoromethoxy)phenyl)-5-(6-methoxypyridin-2-yl)-4H-1,2,4-triazol-3-yl)-1-methoxy-1-(5-methylpyrimidin-2-yl)propane-2-sulfonamide<br>$^1$H NMR (400 MHz, CDCl$_3$) δ = 8.69 (s, 2H), 7.62-7.74 (m, 2H), 7.43-7.52 (m, 1H), 7.20 (t, J = 8.5 Hz, 2H), 6.31-6.80 (m, 3H), 4.95 (d, J = 4.5 Hz, 1H), 3.64-3.78 (m, 1H), 3.28 (s, 3H), 3.13 (s, 3H), 2.37 (s, 3H), 1.32 (d, J = 6.8 Hz, 3H).<br>LCMS-ESI (POS.) m/z: 628.1 (M + H)$^+$. |

TABLE 10-continued

| Example | Reagents | Structure, Name and Data |
|---|---|---|
| 42.0 | (1R,2S)-1-methoxy-1-(5-methylpyrimidin-2-yl)propane-2-sulfonamide (Example 14.0), ), 6-methoxypicolinohydrazide (Example 3.18), 4-isothiocyanatopyridine (Example 1.6) | 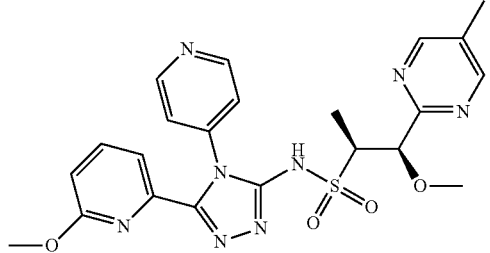<br>(1R,2S)-1-methoxy-N-(5-(6-methoxypyridin-2-yl)-4-(pyridin-4-yl)-4H-1,2,4-triszol-3-yl)-1-(5-methylpyrimidin-2-yl)propane-2-sulfonamide<br>$^1$H NMR (300 MHz, CDCl$_3$) δ = 8.69 (dd, J = 4.9, 1.4 Hz, 1H), 8.60-8.70 (m, 3H), 7.90 (dt, J = 8.2, 1.9 Hz, 1H), 7.64-7.75 (m, 2H), 7.51 (dd, J = 8.2, 5.0 Hz, 1H), 6.78 (dd, J = 7.5, 1.6 Hz, 1H), 5.08 (d, J = 3.4 Hz, 1H), 3.70 (dd, J = 7.0, 3.5 Hz, 1H), 3.32 (s, 3H), 3.14 (s, 3H), 2.36 (s, 3H), 1.36 (d, J = 7.2 Hz, 3H). LCMS-ESI (POS.) m/z: 497.0 (M + H)$^+$. |
| 43.0 | (1R,2S)-1-methoxy-1-(5-methylpyrimidin-2-yl)propane-2-sulfonamide (Example 14.0), 6-methoxypicolinohydrazide (Example 3.18), 1-erthoxy-2-isothiocyanato-3-methoxybenzene (Example 1.7) | 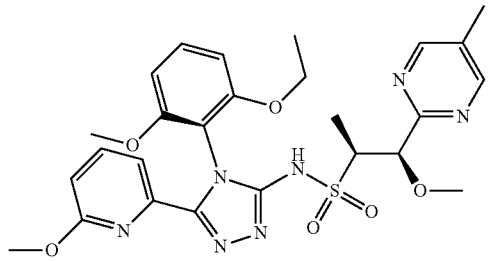<br>AND<br>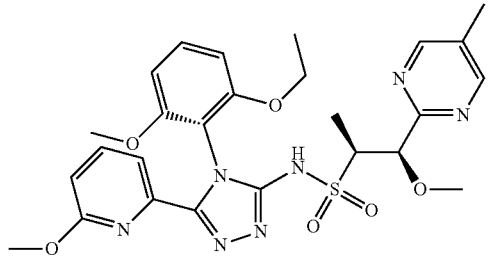<br>(1R,2S,P)-N-(4-(2-ethoxy-6-methoxyphenyl)-5-(6-methoxypyridin-2-yl)-4H-1,2,4-triazol-3-yl)-1-methoxy-1-(5-methylpyrimidin-2-yl)propane-2-sulfonamide and (1R,2S,M)-N-(4-(2-ethoxy-6-methoxyphenyl)-5-(6-methoxypyridin-2-yl)-4H-1,2,4-triazol-3-yl)-1-methoxy-1-(5-methylpyrimidin-2-yl)propane-2-sulfonamide<br>$^1$H NMR (300 MHz, CDCl$_3$) ) (1:1 ratio of P and M atropisomers) δ = 8.76 (s, 2H), 8.75 (s, 2H), 7.54-7.70 (m, 4H), 6.70 (dd, J = 7.7, 1.4 Hz, 2H), 6.50-6.55 (m, 4H), 5.03 (dd, J = 8.0, 4.7 Hz, 2H), 3.93-4.07 (m, 4H), 3.80-3.91 (m, 4H), 3.76 (s, 3H), 3.76 (s, 3H), 3.32 (s, 3H), 3.31 (s, 3H), 3.18 (s, 6H), 2.40 (s, 6H), 1.37 (dd, J = 6.9, 3.6 Hz, 6H), 1.12 (dt, J = 8.5, 7.0 Hz, 6H). LCMS-ESI (POS.) m/z: 570.2 (M + H)$^+$. |

TABLE 10-continued

| Example | Reagents | Structure, Name and and Data |
|---|---|---|
| 44.0 | (1R,2S)-1-methoxy-1-(5-methylpyrazin-2-yl)propane-2-sulfonamide (Example 14.1), nicotinohydrazide (Aldrich), 2-isothiocyanato-1,3-dimethoxybenzene (Example 1.0) | 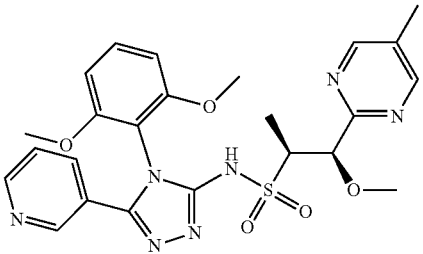 [SMILES: COc1cccc(OC)c1-n1c(NS(=O)(=O)[C@@H](C)[C@H](OC)c2ncc(C)cn2)nnc1-c1cccnc1]<br>(1R,2S)-N-(4-(2,6-dimethoxyphenyl)-5-(pyridin-3-yl)-4H-1,2,4-triazol-3-yl)-1-methoxy-1-(5-methylpyrazin-2-yl)propane-2-sulfonamide<br>$^1$H NMR (300 MHz, CDCl$_3$) δ = 11.21 (br. s., 1H), 8.64 (br. s., 2H), 8.53 (s, 1H), 8.43 (s, 1H), 7.76 (d, J = 8.0 Hz, 1H), 7.40 (t, J = 8.5 Hz, 1H), 7.24-7.31 (m, 1H), 6.62 (dd, J = 8.4, 4.3 Hz, 2H), 5.05 (d, J = 2.6 Hz, 1H), 3.74 (s, 6H), 3.48-3.61 (m, 1H), 3.33 (s, 3H), 2.58 (s, 3H), 1.27 (d, J = 7.0 Hz, 3H). LCMS-ESI (POS.) m/z: 526.12 (M + H)$^+$. |
| 45.0 | (1R,2S)-1-methoxy-1-(5-methylpyrimidin-2-yl)propane-2-sulfonamide (Example 14.0) 4-chlorophenyl isocyanate (Fluka), 6-methoxypicolino-hydrazide (Adesis, Inc) | 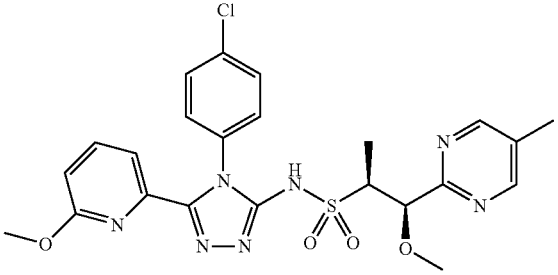<br>(1R,2S)-N-(4-(4-chlorophenyl)-5-(6-methoxy-2-pyridinyl)-4H-1,2,4-triazol-3-yl)-1-methoxy-1-(5-methyl-2-pyrimidiunyl)-2-propanesulfonamide<br>$^1$H NMR (CDCl$_3$) δ: 8.61 (s, 2H), 7.62-7.70 (m, 1H), 7.57-7.62 (m, 1H), 7.36-7.45 (m, 2H), 7.29-7.36 (m, 2H), 6.75 (dd, J = 8.1, 0.8 Hz, 1H), 5.10 (d, J = 3.4 Hz, 1H), 3.68 (dd, J = 7.1, 3.3 Hz, 1H), 3.31 (s, 3H), 3.21 (s, 3H), 2.34 (s, 3H), 1.36 (d, J = 7.0 Hz, 3H). LCMS-ESI (POS.) m/z: 530.2 (M + H)$^+$. |
| 46.0 | (1R,2S)-1-methoxy-1-(5-methylpyrimidin-2-yl)propane-2-sulfonamide (Example 14.0), 4-methoxyphenyl isothiocyanate (Sigma-Aldrich), 6-methoxypicolino-hydrazide (Adesis, Inc) | 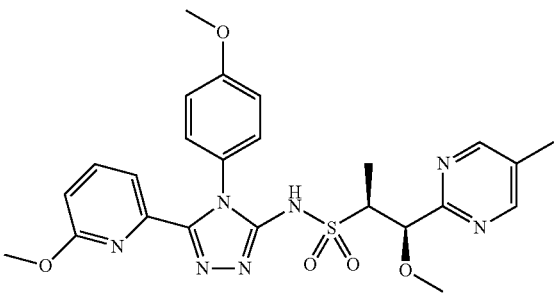<br>(1R,2S)-1-methoxy-N-(4-(4-methoxyphenyl)-5-(6-methoxy-2-pyridinyl)-4H-1,2,4-triazol-3-yl)-1-(5-methyl-2-pyrimidinyl)-2-propanesulfonamide<br>$^1$H NMR (CDCl$_3$) δ: 8.65 (s, 2H), 7.65 (t, J = 7.7 Hz, 1H), 7.53 (d, J = 7.4 Hz, 1H), 7.24-7.32 (m, 2H), 6.88-6.98 (m, 2H), 6.74 (dd, J = 8.2, 0.7 Hz, 1H), 5.10 (d, J = 3.8 Hz, 1H), 3.84 (s, 3H), 3.72 (dd, J = 7.0, 3.8 Hz, 1H), 3.33 (s, 3H), 3.27 (s, 3H), 2.36 (s, 3H), 1.38 (d, J = 7.0 Hz, 3H). LCMS-ESI (POS.) m/z: 526.1 (M + H)$^+$. |

TABLE 10-continued

| Example | Reagents | Structure, Name and and Data |
|---|---|---|
| 47.0 | (1R,2S)-1-methoxy-1-(5-methylpyrimidin-2-yl)propane-2-sulfonamide (Example 14.0), 1-fluoro-3-isothiocyanato-benzene (Sigma-Aldrich), 6-methoxypicolino-hydrazide (Adeis, Inc) | 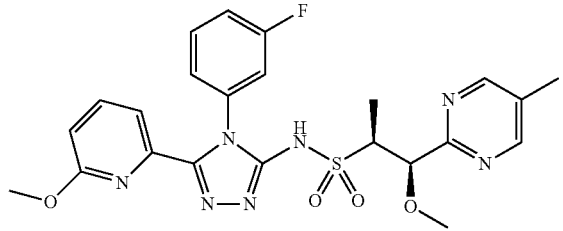(1R,2S)-N-(4-(3-fluorophenyl)-5-(6-methoxy-2-pyrimdinyl)-4H-1,2,4-triazol-3-yl)-1-methoxy-1-(5-methyl-2-pyrimidinyl)-2-propanesulfonamide<br>$^1$H NMR (CDCl$_3$) δ: 8.71 (s, 2H), 7.64-7.71 (m, 1H), 7.59-7.64 (m, 1H), 7.38-7.47 (m, 1H), 7.12-7.21 (m, 3H), 6.77 (dd, J = 8.2, 1.0 Hz, 1H), 5.10 (d, J = 3.7 Hz, 1H), 3.69 (dd, J = 7.1, 3.7 Hz, 1H), 3.29 (s, 3H), 3.22 (s, 3H), 2.39 (s, 3H), 1.34 (d, J = 7.0 Hz, 3H). LCMS-ESI (POS.) m/z: 514.1 (M + H)$^+$. |
| 48.0 | (1R,2S)-1-ethoxy-1-(5-fluoropyrimidin-2-yl)propane-2-sulfonamide, (Example 14.5), 2-isothiocyanato-1,3-dimethoxybenzene (Example 1.0), 6-methoxypicolino-hydrazide (Adesis, Inc) | 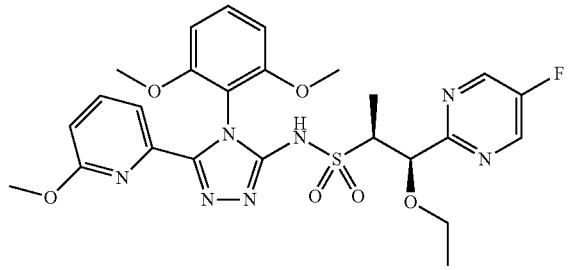 [SMILES: CCO[C@H](c1ncc(F)cn1)[C@H](C)S(=O)(=O)Nc1nnc(-c2cccc(OC)n2)n1-c1c(OC)cccc1OC](1R,2S)-N-(4-(2,6-dimethoxyphenyl)-5-(6-methoxy-2-pyridinyl)-4H-1,2,4-triazol-3-yl)-1-ethoxy-1-(5-fluoro-2-pyrimidinyl)-2-propanesulfonamide<br>$^1$H NMR (CDCl$_3$) δ: 11.03 (s, 1H), 8.61 (s, 2H), 7.57-7.66 (m, 2H), 7.29-7.36 (m, 1H), 6.71 (dd, J = 7.6, 1.6 Hz, 1H), 6.60 (dd, J = 8.5, 3.2 Hz, 2H), 5.02 (d, J = 6.1 Hz, 1H), 3.75-3.85 (m, 1H), 3.73 (s, 3H), 3.69 (s, 3H), 3.46-3.56 (m, 2H), 3.18 (s, 3H), 1.46 (d, J = 7.0 Hz, 3H), 1.16 (t, J = 7.0 Hz, 3H). LCMS-ESI (POS.) m/z: 574.2 (M + H)$^+$. |
| 49.0 | (1R,2S)-1-methoxy-1-(5-methoxypyrimidin-2-yl)propane-2-sulfonamide (Example 14.8), 2-isothiocyanato-1,3-dimethoxybenzene (Example 1.0), 6-methoxypicolino-hyrazdize (Adesis, Inc) | 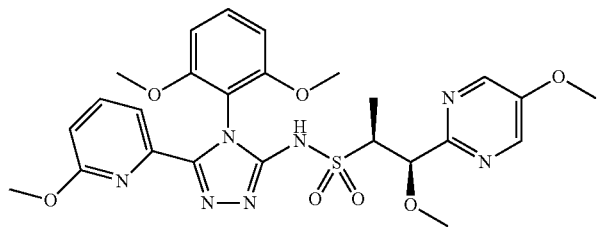(1R,2S)-N-(4-(2,6-dimethoxyphenyl)-5-(6-methoxy-2-pyridinyl)-4H-1,2,4-triazol-3-yl)-1-methoxy-1-(5-methoxy-2-pyrimidinyl)-2-propanesulfonamide<br>$^1$H NMR (CDCl$_3$) δ: 11.13 (br. s, 1H), 8.44 (s, 2H), 7.57-7.66 (m, 2H), 7.29-7.35 (m, 1H), 6.71 (dd, J = 7.2, 2.0 Hz, 1H), 6.60 (d, J = 8.6 Hz, 2H), 4.96 (d, J = 4.8 Hz, 1H), 3.94 (s, 3H), 3.68-3.80 (m, 7H), 3.33 (s, 3H), 3.18 (s, 3H), 1.41 (d, J = 7.0 Hz, 3H). LCMS-ESI (POS.) m/z: 572.2 (M + H)$^+$. |

TABLE 10-continued

| Example | Reagents | Structure, Name and and Data |
|---|---|---|
| 50.0 | (1R,2S)-1-ethoxy-1-(5-fluoropyrimidin-2-yl)propane-2-sulfonamide (Example 14.5), phenyl isothiocyanate (Sigma-Aldrich), 6-methoxypicolinohydrazide (Adesis, Inc) | 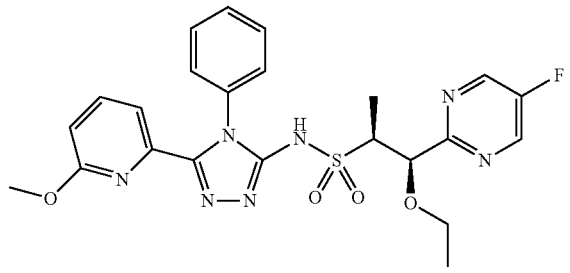 [SMILES: CCO[C@H](c1ncc(F)cn1)[C@H](C)S(=O)(=O)Nc1nnc(-c2cccc(OC)n2)n1-c1ccccc1]<br>(1R,2S)-1-ethoxy-1-(5-fluoro-2-pyrimidinyl)-N-(5-(6-methoxy-2-pyridinyl)-4-phenyl-4H-1,2,4-triazol-3-yl)-2-propanesulfonamide<br>$^1$H NMR (CDCl$_3$) δ: 8.68 (s, 2H), 7.66 (t, J = 7.8 Hz, 1H), 7.57 (d, J = 7.2 Hz, 1H), 7.40-7.49 (m, 3H), 7.30-7.36 (m, 2H), 6.74 (d, J = 8.4 Hz, 1H), 5.14 (d, J = 4.7 Hz, 1H), 3.71 (dd, J = 7.0, 4.7 Hz, 1H), 3.39-356 (m, 2H), 3.13 (s, 3H), 1.40 (d, J = 7.0 Hz, 3H), 1.08 (t, J = 7.0 Hz, 3H). LCMS-ESI (POS.) m/z: 514.1 (M + H)$^+$. |
| 51.0 | (1R,2S)-1-ethoxy-1-(5-fluoropyrimidin-2-yl)propane-2-ulfonamide (Example 14.5), 2-isothiocyanato-1,3-dimethoxybenzoate (Example 1.0), nicotinohydrazide (Alfa Aesar) | 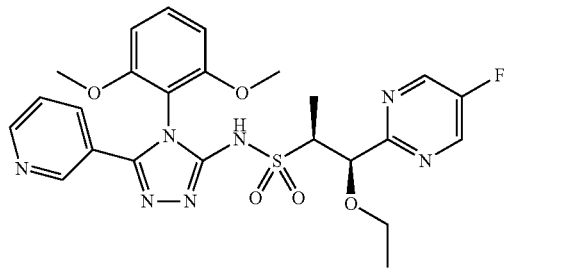 [SMILES: CCO[C@H](c1ncc(F)cn1)[C@H](C)S(=O)(=O)Nc1nnc(-c2cccnc2)n1-c1c(OC)cccc1OC]<br>(1R,2S)-N-(4-(2,6-dimethoxyphenyl)-5-(3-pyidinyl)-4H-1,2,4-triazol-3-yl)-1-ethoxy-1-(5-fluoro-2-pyrimidinyl)-2-propanesulfonamide<br>$^1$H NMR (CDCl$_3$) δ: 8.66-8.72 (m, 2H), 8.63 (s, 2H), 8.01 (dt, J = 8.1, 1.8 Hz, 1H), 7.48-7.53 (m, 1H), 7.44 (t, J = 8.6 Hz, 1H), 6.65 (dd, J = 8.6, 4.0 Hz, 2H), 5.04 (d, J = 5.8 Hz, 1H), 3.73-3.82 (m, 7H), 3.52 (qd, J = 7.0, 5.4 Hz, 2H), 1.45 (d, J = 6.9 Hz, 3H), 1.15 (t, J = 7.0 Hz, 3H). LCMS-ESI (POS.) m/z: 544.1 (M + H)$^+$. |
| 52.0 | (1R,2S)-1-methoxy-1-(5-methylpyrimidin-2-yl)propane-2-sulfonamide (Example 14.0), 1-isothiocyanto-2-methoxybenzene (FSSI), 6-methoxypicolinohydrazide (Adesis, Inc) | 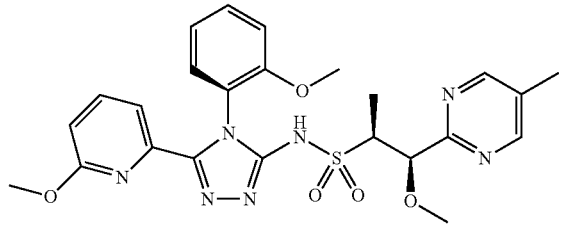<br>AND<br>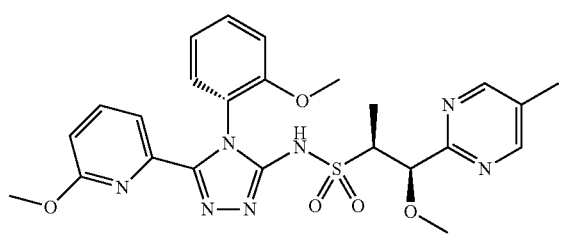<br>(1R,2S,P)-1-methoxy-N-(4-(2-methoxyphenyl)-5-(6-methoxy-2-pyridinyl)-4H-1,2,4-triazol-3-yl)-1-(5-methyl-2- |

| Example | Reagents | Structure, Name and and Data |
|---|---|---|
| | | pyrimidinyl)-2-propanesulfonamide and (1R,2S,M)-1-methoxy-N-(4-(2-methoxyphenyl)-5-(6-methoxy-2-pyridinyl)-4H-1,2,4-triazol-3-yl)-1-(5-methyl-2-pyrimidinyl)-2-propanesulfonamide<br>$^1$H NMR (CDCl$_3$) δ: 11.20 (br. s, 1H), 8.52 (s, 1.2H), 8.60 (s, 0.8H), 7.61-7.68 (m, 1H), 7.54-7.61 (m, 1.5H), 7.33-7.44 (m, 1.5H), 7.02-7.09 (m, 1H), 6.91 (d, J = 4.3 Hz, 1H), 6.71 (d, J = 8.0 Hz, 1H), 5.11 (d, J = 3.4 Hz, 0.6H), 4.99 (d, J = 4.2 Hz, 0.4H), 3.63-3.78 (m, 1H), 3.60 (s, 1.2H), 3.56 (s, 1.8H), 3.37 (s, 1.2H), 3.29 (s, 1.8H), 3.14 (s, 3H), 2.34 (s, 1.8H), 2.32 (s, 1.2H), 1.38 (dd, J = 7.0, 1.3 Hz, 3H). LCMS-ESI (POS.) m/z: 526.1 (M + H)$^+$. |
| 53.0 | (1R,2S)-1-methoxy-1-(5-methylpyrimidin-2-yl)propane-2-sulfonamide (Example 14.0), 2-isothiocyanato-naphthalene (FSSI), 6-methoxypicolino-hydrazide (Adesis, Inc) | 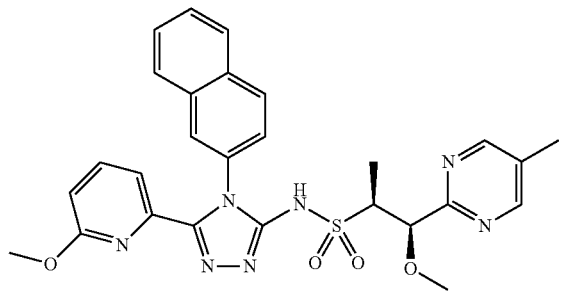<br>(1R,2S)-1-methoxy-N-(5-(6-methoxy-2-pyridinyl)-4-(2-naphthalenyl)-4H-1,2,4-triazol-3-yl)-1-(5-methyl-2-pyrimidinyl)-2-propanesulfonamide<br>$^1$H NMR (CDCl$_3$) δ: 8.72 (s, 2H), 7.76-7.99 (m, 4H), 7.48-7.70 (m, 4H), 7.44 (d, J = 8.6 Hz, 1H), 6.68 (d, J = 7.3 Hz, 1H), 5.10 (d, J = 3.3 Hz, 1H), 3.67 (dd, J = 6.8, 3.6 Hz, 1H), 3.24 (s, 3H), 2.81 (s, 3H), 2.37 (s, 3H), 1.31 (d, J = 6.9 Hz, 3H). LCMS-ESI (POS.) m/z: 546.2 (M + H)$^+$. |
| 54.0 | (1R,2S)-1-methoxy-1-(5-methylpyrimidin-2-yl)propane-2-sulfonamide (Example 14.0), methyl 3-isothiocyanato-benzoate (FSSI), 6-methoxypicolino-hydrazide (Adesis, Inc) | 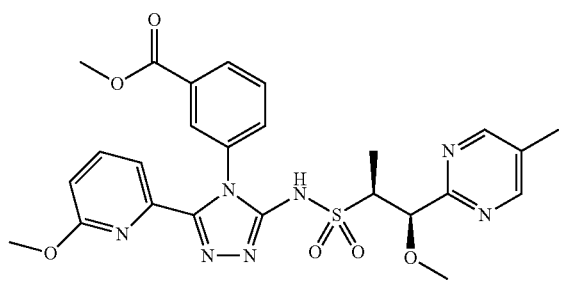<br>methyl 3-(3-(((((1S,2R)-2-methoxy-1-methyl-2-(5-methyl-2-pyrimidinyl)ethyl)sulfonyl)amino)-5-(6-methoxy-2-pyridinyl)-4H-1,2,4-triazol-4-yl)benzoate<br>$^1$H NMR (CDCl$_3$) δ: 8.70 (s, 2H), 8.11 (dt, J = 3.7 Hz, 1H), 8.00 (t, J = 1.6 Hz, 1H), 7.54-7.70 (m, 4H), 6.75 (dd, J = 7.9, 1.2 Hz, 1H), 5.08 (d, J = 3.8 Hz, 1H), 3.91 (s, 3H), 3.69 (dd, J = 7.1, 3.9 Hz, 1H), 3.29 (s, 3H), 3.10 (s, 3H), 2.39 (s, 3H), 1.34 (d, J = 7.2 Hz, 3H). LCMS-ESI (POS.) m/z: 554.2 (M + H)$^+$. |

TABLE 10-continued

| Example | Reagents | Structure, Name and Data |
|---|---|---|
| 55.0 | (1R,2S)-1-methoxy-1-(3-methylpyrimidin-2-yl)propane-2-sulfonamide (Example 14.0), 1-chloro-3-isothiocyanato-2-methylbenzene (FSSI), 6-methoxypicolino-hydrazide (Adesis, Inc) | 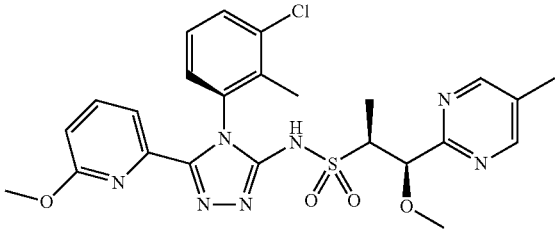<br>AND<br>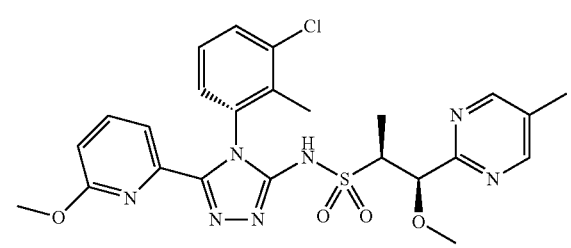<br>(1R,2S,P)-N-(4-(3-chloro-2-methylphenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(3-chloro-2-methylphenyl)-5-(6-methoxy-2-pyridinyl)-4H-1,2,4-triaol-3-yl)-1-methoxy-1-(5-methyl-2-pyrimidinyl)-2-propanesulfonamide<br>$^{1}$H NMR (CDCl$_{3}$) δ: 8.79 (s, 1H), 8.77 (s, 1H), 7.61-7.70 (m, 2H), 7.49 (d, J = 8.0 Hz, 0.5 H), 7.28-7.34 (m, 1.5H), 7.14-7.25 (m, 1H), 6.70-6.80 (m, 1H), 5.13 (d, J = 3.5 Hz, 0.5H), 5.06 (d, J = 4.4 Hz, 0.5H), 3.61-3.78 (m, 1H), 3.35 (s, 1.5H), 3.24 (s, 1.5H), 3.17 (s, 3H), 2.42 (s, 1.5H), 2.41 (s, 1.5H), 2.39 (s, 3H), 1.35 (d, J = 6.9 Hz, 1.5H), 1.30 (d, J = 7.0 Hz, 1.5H). LCMS-ESI (POS.) m/z: 544.1 (M + H)$^{+}$. |
| 56.0 | (1R,2S)-1-methoxy-1-(5-methylpyrimidin-2-yl)propane-2-sulfonamide (Example 14.0), 3-isothiocyanato-benzonitrile (FSSI), 6-methoxypicolino-hydrazide (Adesis, Inc) | 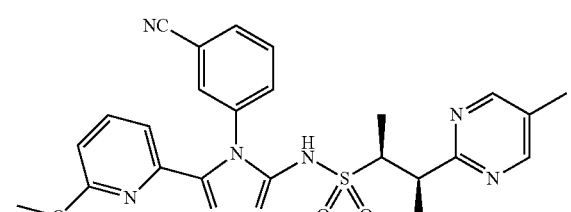<br>(1R,2S)-N-(4-(3-cyanophenyl)-5-(6-methoxy-2-pyridinyl)-4H-1,2,4-triazol-3-yl)-1-methoxy-1-(5-methyl-2-pyrimidinyl)-2-propanesulfonamide<br>$^{1}$H NMR (CDCl$_{3}$) δ: 8.77 (s, 2H), 7.59-7.79 (m, 6H), 6.79 (dd, J = 7.8, 1.2 Hz, 1H), 5.12 (d, J = 3.5 Hz, 1H), 3.68 (dd, J = 7.1, 3.6 Hz, 1H), 3.28 (s, 3H), 3.14 (s, 3H), 2.42 (s, 3H), 1.31 (d, J = 7.0 Hz, 3H). LCMS-ESI (POS.) m/z: 521.1 (M + H)$^{+}$. |
| 57.0 | (1R,2S)-1-methoxy-1-(5-methylpyrimidin-2-yl)propane-2-sulfonamide (Example 14.8), 2-isothiocyanato-1,3-dimethoxybenzene (Example 1.0), 5-methylnicotino-hydrazide (JPM$^{2}$ Pharmaceuticals) | 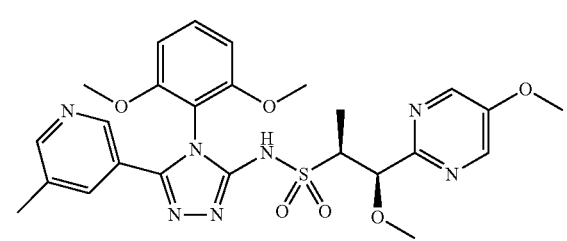 |

TABLE 10-continued

| Example | Reagents | Structure, Name and and Data |
|---|---|---|
| | | (1R,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.51 (d, J = 1.5 Hz, 1H), 8.45 (s, 2H), 8.39 (d, J = 1.6 Hz, 1H), 7.84 (s, J = 3.0 Hz, 1H), 7.42 (t, J = 8.5 Hz, 1H), 6.64 (d, J = 8.5 Hz, 2H), 4.96 (d, J = 4.8 Hz, 1H), 3.95 (s, 3H), 3.71-3.81 (m, 7H), 3.33 (s, 3H), 2.38 (s, 3H), 1.41 (d, J = 7.0 Hz, 3H). LCMS-ESI (POS.) m/z: 556.3 (M + H)$^+$. |
| 58.0 | (1R,2S)-1-methoxy-1-(5-methylpyrimidin-2-yl)propane-2-sulfonamide (Example 14.8), 2-isothiocyanato1,3-dimethoxybenzene (Example 1.0), nicotinohydrazide (Alfa Aesar) | 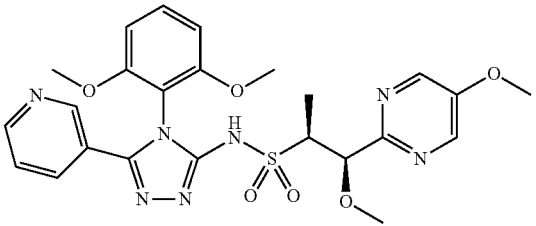 [SMILES: COc1cnc([C@@H](OC)[C@H](C)S(=O)(=O)Nc2nnc(-c3cccnc3)n2-c2c(OC)cccc2OC)nc1]<br>(1R,2S)-N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.67-8.73 (m, 2H), 8.50 (s, 2H), 8.05 (dt, J = 8.0, 1.8 Hz, 1H), 7.50-7.55 (m, 1H), 7.44 (t, J = 8.5 Hz, 1H), 6.65 (d, J = 8.5 Hz, 2H), 4.97 (d, J = 4.7 Hz, 1H), 3.96 (s, 3H), 3.79 (s, 3H), 3.77 (s, 3H), 3.73 (dd, J = 7.0, 4.8 Hz, 1H), 3.31 (s, 3H), 1.39 (d, J = 7.0 Hz, 3H). LCMS-ESI (POS.) m/z: 542.2 (M + H)$^+$. |
| 59.0 | (1R,2S)-1-methoxy-1-(5-methoxypyrimidin-2-yl)propane-2-sulfonamide (Example 14.8), phenyl isothiocyanate (Sigma-Aldrich), 5-methylnicotinohydrazide (JPM$^2$ Pharmaceuticals) | 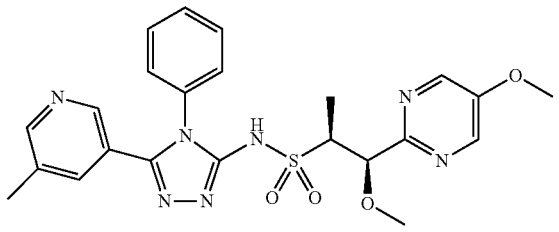<br>(1R,2S)-1-methoxy-1-(5-methoxy-2-pyrimidinyl)-N-(5-(5-methyl-3-(pyridinyl)-4-phenyl-4H-1,2,4-triazol-3-yl)-2-propanesulfonamide<br>$^1$H NMR (CDCl$_3$) δ: 8.59 (s, 1H), 8.50 (s, 2H), 8.41 (s, 1H), 7.77 (s, 1H), 7.48-7.57 (m, 3H), 7.30-7.40 (m, 2H), 5.06 (d, J = 3.8 Hz, 1H), 3.96 (s, 3H), 3.69 (dd, J = 6.9, 3.9 Hz, 1H), 3.28 (s, 3H), 2.39 (s, 3H), 1.37 (d, J = 7.0 Hz, 3H). LCMS-ESI (POS.) m/z: 496.1 (M + H)$^+$. |
| 60.0 | (1R,2S)-1-methoxy-1-(5-methoxypyrimidin-2-yl)propane-2-sulfonamide (Example 14.0), 1-bromo-3-isothiocyanato-benzene (FSSI), 6-methylnicotinohydrazide (Adesis, Inc) | 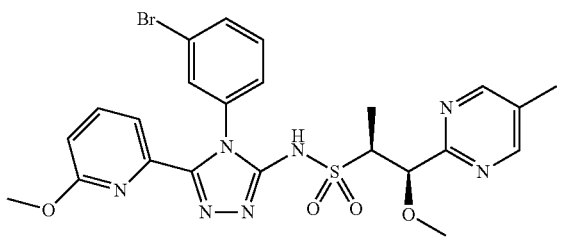<br>(1R,2S)-N-(4-(3-bromophenyl)-5-(methoxy-2-pyrimidinyl)-4H-1,2,4-triazol-3-yl)-1-methoxy-1-(5-methyl-2-pyrimidinyl)-2-propanesulfonamide<br>$^1$H NMR (CDCl$_3$) δ: 8.67 (s, 2H), 7.55-7.71 (m, 4H), 7.31-7.36 (m, 2H), 6.76 (d, J = 8.0 Hz, 1H), 5.08 (d, J = 3.7 Hz, 1H), 3.70 (dd, J = 7.1, 3.6 Hz, 1H), 3.31 (s, 3H), 3.23 (s, 3H), 2.37 (s, 3H), |

//

| Example | Reagents | Structure, Name and and Data |
|---|---|---|
| | | 1.36 (d, J = 7.0 Hz, 3H). LCMS-ESI (POS.) m/z: 574.1 (M + H)+. |
| 61.0 | (1R,2S)-1-methoxy-1-(5-methylpyrimidin-2-yl)propane-2-sulfonamide (Example 14.0), 1-isothiocyanato-2-methylbenzene (FSSI), 6-methoxypicolino-hydrazide (Adesis, Inc) | 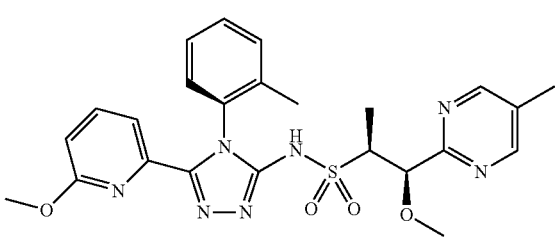 AND 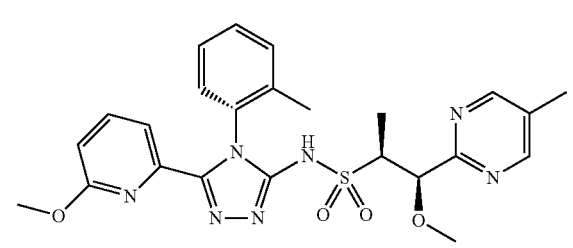 (1R,2S,P)-1-methoxy-N-(5-(6-methoxy-2-pyridinyl)-4-(2-methylphenyl)-4H-1,2,4-triazol-3-yl)-1-(5-methyl-2-pyrimidinyl)-2-propanesulfonamide and (1R,2S,M)-1-methoxy-N-(5-(6-methoxy-2-pyridinyl)-4-(2-methylphenyl)-4H-1,2,4-triazol-3-yl)-1-(5-methyl-2-pyrimidinyl)-2-propanesulfonamide<br>$^1$H NMR (CDCl$_3$) δ: 8.72 (s, 1H), 8.70 (s, 1H), 7.60-7.68 (m, 2H), 7.23-7.37 (m, 3.5H), 7.15 (d, J = 7.6 Hz, 0.5H), 6.74 (t, J = 2.1 Hz, 0.5H), 6.72 (t, J = 2.0 Hz, 0.5H), 5.09 (d, J = 3.5 Hz, 0.5H), 5.05 (d, J = 3.9 Hz, 0.5H), 3.67 (ddd, J = 16.2, 7.0, 3.9 Hz, 1H), 3.29 (s, 1.5H), 3.25 (s, 1.5H), 3.12 (s, 3H), 2.39 (s, 1.5H), 2.38 (s, 1.5H), 2.24 (s, 1.5H), 2.15 (s, 1.5H), 1.32 (d, J = 7.2 Hz, 1.5H), 1.28 (d, J = 7.0 Hz, 1.5H). LCMS-ESI (POS.) m/z: 510.2 (M + H)+. |
| 62.0 | (1R,2S)-1-methoxy-1-(5-methylpyrimidin-2-yl)propane-2-sulfonamide (Example 14.0), 1-isothiocyanato-3-methylbenzene (FSSI), 6-methoxypicolino-hydrazide (Adesis, Inc) | 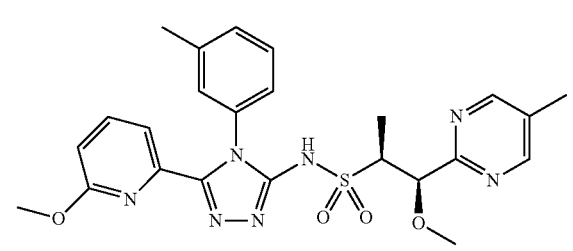 (1R,2S)-1-methoxy-N-(5-(6-methoxy-2-pyridinyl)-4-(3-methylphenyl)-4H-1,2,4-triazol-3-yl)-1-(5-methyl-2-pyrimidinyl)-2-propanesulfonamide<br>$^1$H NMR (CDCl$_3$) δ: 8.67 (s, 2H), 7.61-7.69 (m, 1H), 7.55-7.59 m, 1H), 7.28-7.36 (m, 1H), 7.18-7.25 (m, 1H), 7.12-7.18 (m, 2H), 6.74 (dd, J = 8.3, 0.8 Hz, 1H), 5.09 (d, J = 3.7 Hz, 1H), 3.69 (dd, J = 7.1, 3.7 Hz, ,1H), 3.29 (s, 3H), 3.18 (s, 3H), 2.37 (s, 3H), 2.36 (s, 3H), 1.;35 (d, J = 7.0 Hz, 3H). LCMS-ESI (POS.) m/z: 510.2 (M + H)+. |

TABLE 10-continued

| Example | Reagents | Structure, Name and Data |
|---|---|---|
| 63.0 | (1R,2S)-1-methoxy-1-(5-methylpyrimidin-2-yl)propane-2-sulfonamide (Example 14.0), 1-fluoro-4-isothiocyanato-2-(trifluoromethyl)-benzene (FSSI) 6-methoxypicolino-hydrazide (Adesis, Inc) | 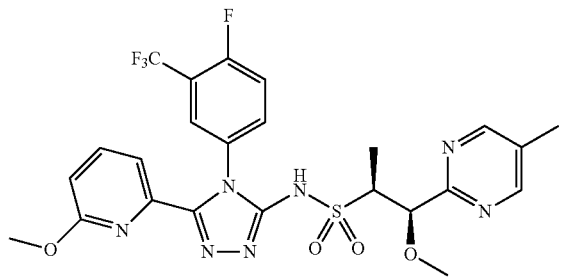<br>(1R,2S)-N-(4-(4-fluoro-3-(trifluoromethyl)phenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.68 (s, 2H), 7.58-7.74 (m, 4H), 7.29-7.35 (m, 1H), 6.79 (dd, J = 7.9, 1.3 Hz, 1H), 5.08 (d, J = 3.5 Hz, 1H), 3.65-3.74 (m, 1H), 3.30 (s, 3H), 3.21 (s, 3H), 2.38 (s, 3H), 1.34 (d, J = 7.2 Hz, 3H). LCMS-ESI (POS.) m/z: 582.2 (M + H)$^+$. |
| 64.0 | (1R,2S)-1-methoxy-1-(5-methylpyrimidin-2-yl)propane-2-sulfonamide (Example 14.0), 1-isothiocyanato-3-methoxybenzene (FSSI), 6-methoxypicolino-hydrazide (Adesis, Inc) | 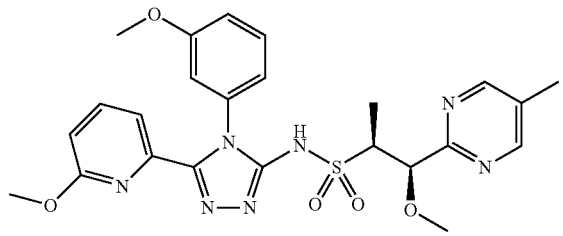<br>(1R,2S)-1-methoxy-N-(4-(3-methoxyphenyl)-5-(6-methoxy-2-pyridinyl)-4H-1,2,4-triazol-3-yl)-1-(5-methyl-2-pyrimidinyl)-2-propanesulfonamide<br>$^1$H NMR (CDCl$_3$) δ: 8.68 (s, 2H), 7.60-7.70 (m, 1H), 7.54-7.60 (m, 1H), 7.32 (d, J = 7.9 Hz, 1H), 6.95 (dd, J = 8.0, 2.0 Hz, 2H), 6.87-6.92 (m, 1H), 6.74 (d, J = 8.1 Hz, 1H), 5.09 (d, J = 3.8 Hz, 1H), 3.79 (s, 3H), 3.70 (dd, J = 7.09, 3.8 Hz, 1H), 3.30 (s, 3H), 3.23 (s, 3H), 2.37 (s, 3H), 1.36 (d, J = 7.2 Hz, 3H). LCMS-ESI (POS.) m/z: 526.1 (M + H)$^+$. |
| 65.0 | (1R,2S)-1-methoxy-1-(5-methylpyrimidin-2-yl)propane-2-sulfonamide (Example 14.0), 1-fluoro-4-isothiocyanato-benzene (FSSI), 6-methoxypicolino-hydrazide (Adesis, Inc) | 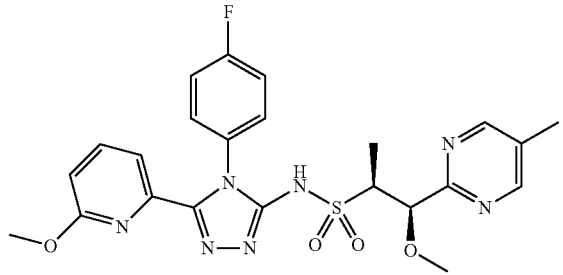<br>(1R,2S)-N-(4-(4-fluorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.67 (s, 2H), 7.62-7.70 (m, 1H), 7.56-7.62 (m, 1H), 7.35 (d, J = 4.7 Hz, 2H), 7.10-7.19 (m, 2H), 6.76 (dd, J = 8.2, 0.9 Hz, 1H), 5.11 (d, J = 3.4 Hz, 1H), 3.63-3.74 (m, 1H), 3.29 (s, 3H), 3.24 (s, 3H), 2.37 (s, 3H), 1.33 (d, J = 7.0 Hz, 3H). LCMS-ESI (POS.) m/z: 514.1 (M + H)$^+$. |

TABLE 10-continued

| Example | Reagents | Structure, Name and Data |
|---|---|---|
| 66.0 | (1R,2S)-1-methoxy-1-(5-methylpyrimidin-2-yl)propane-2-sulfonamide (Example 14.0), 1-chloro-3-isothiocyanato-benzene (FSSI), 6-methoxypicolino-hydrazide (Adesis, Inc) | 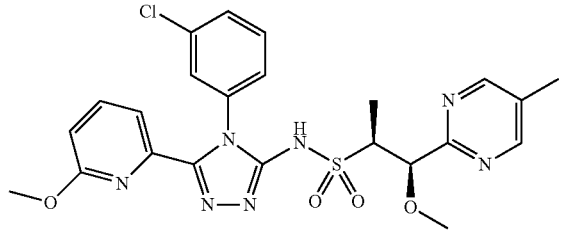<br>(1R,2S)-N-(4-(3-chlorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.67 (s, 2H), 7.64-7.71 (m, 1H), 7.59-7.64 (m, 1H), 7.36-7.45 (m, 3H), 7.29-7.32 (m, 1H), 6.77 (dd, J = 8.0, 0.9 Hz, 1H), 5.08 (d, J = 3.7 Hz, 1H), 3.70 (dd, J = 6.8, 3.7 Hz, 1H), 3.31 (s, 3H), 3.22 (s, 3H), 2.37 s, 3H), 1.36 (d, J = 7.0 Hz, 3H). LCMS-ESI (POS.) m/z: 530.2 (M + H)$^+$. |
| 67.0 | (1R,2S)-1-methoxy-1-(5-methylpyrimidin-2-yl)propane-2-sulfonamide (Example 14.0), 2-chloro-4-fluoro-1-isothiocyanato-benzene (FSSI), 6-methoxypicolino-hydrazide (Adesis, Inc) | 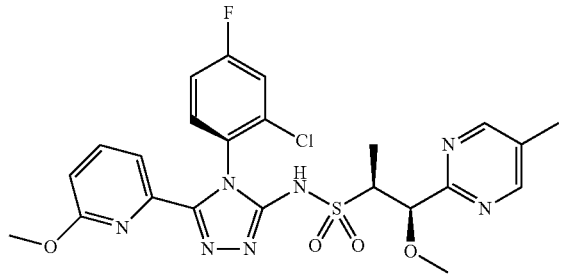<br>AND<br>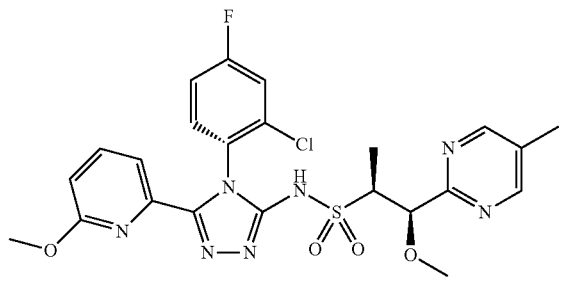<br>(1R,2S,P)-N-(4-(2-chloro-4-fluorophenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2-chloro-4-fluorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.76 (s, 1H), 8.72 (s, 1H), 7.62-7.71 (m, 2.5H), 7.45 (dd, J = 8.8, 5.4 Hz, 0.5H), 7.23-7.30 (m, 1H), 7.09-7.20 (m, 1H), 6.74-6.81 (m, 1H), 5.13 (d, J = 3.5 Hz, 0.5H), 5.04 (d, J 4.2 Hz, 0.5H), 3.60-3.79 (m, 1H), 3.36 (s, 1.5H), 3.25 (s, 1.5H), 3.23 (d, J = 0.7 Hz, 3H), 2.41 (s, 1.5H), 2.39 (s, 1.5H), 1.35 (d, J = 6.9 Hz, 1.5H), 1.30 (d, J = 7.0 Hz, 1.5H). LCMS-ESI (POS.) m/z: 548.2 (M + H)$^+$. |

TABLE 10-continued

| Example | Reagents | Structure, Name and and Data |
|---|---|---|
| 68.0 | (1R,2S)-1-methoxy-1-(5-methylpyrimidin-2-yl)propane-2-sulfonamide (Example 14.0), 1,3-dichloro-5-isothiocyanato-benzene (FSSI), 6-methoxypicolino-hydrazide (Adesis, Inc) | 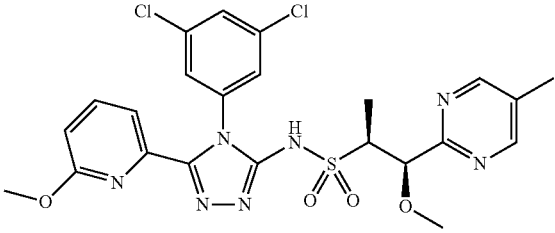<br>(1R,2S)-N-(4-(3,5-dichlorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.70 (s, 2H), 7.62-7.73 (m, 2H), 7.346 (t, J = 1.8 Hz, 1H), 7.36 (d, J = 1.9 Hz, 2H), 6.80 (dd, J = 8.0, 1.1 Hz, 1H), 5.07 (d, J = 3.9 Hz, 1H), 3.68-3.77 (m, 1H), 3.32 (s, 3H), 3.30 (s, 3H), 2.39 (s, 3H), 1.37 (d, J = 7.0 Hz, 3H). LCMS-ESI (POS.) m/z: 564.0 (M + H)$^+$. |
| 69.0 | (1R,2S)-1-methoxy-1-(5-methylpyrimidin-2-yl)propane-2-sulfonamide (Example 14.0), 1-chloro-2-isothiocyanato-benzene (FSSI), 6-methoxypicolino-hydrazide (Adesis, Inc) | 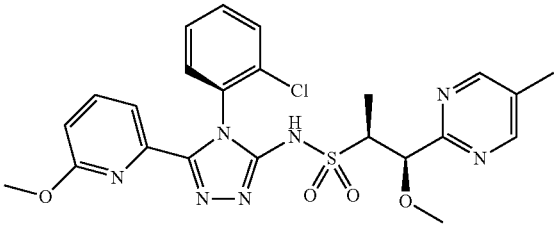<br>AND<br>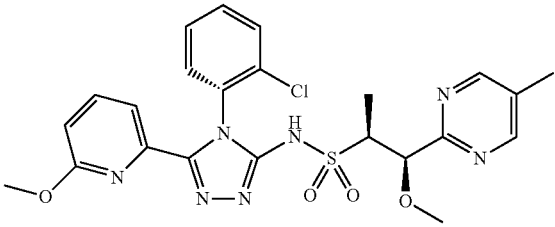<br>(1R,2S,P)-N-(4-(2-chlorophenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2-chlorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.71 (s, 1H), 8.68 (s, 1H), 7.60-7.70 (m, 2.5H), 7.48-7.53 (m, 1H), 7.38-7.48 (m, 2.5H), 6.71-6.78 (m, 1H), 5.10 (d, J = 3.5 Hz, 0.5H), 5.02 (d, J = 4.4 Hz, 0.5H), 3.60-3.76 (m, 1H), 3.35 (s, 1.5H), 3.25 (s, 1.5H), 3.11 (s, 3H), 2.39 (s, 1.5H), 2.37 (s, 1.5H), 1.35 (d, J = 7.0 Hz, 1.5H), 1.32 (d, J = 7.2 Hz, 1.5H). LCMS-ESI (POS.) m/z: 530.2 (M + H)$^+$. |
| 70.0 | (1R,2S)-1-methoxy-1-(5-methylpyrimidin-2-yl)propane-2-sulfonamide (Example 14.0), 1-isothiocyanato-2,3-dimethylbenzene (FSSI), 6-methoxypicolino-hydrazide (Adesis, Inc) | 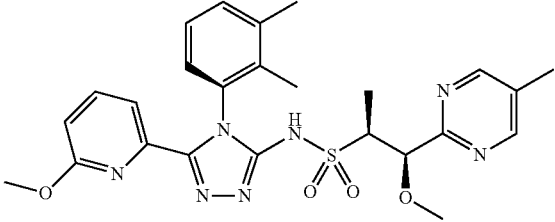<br>AND |

| Example | Reagents | Structure, Name and and Data |
|---|---|---|
| | | (1R,2S,P)-N-(4-(2,3-dimethylphenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2,3-dimethylphenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.80 (s, 1H), 8.79 (s, 1H), 7.58-7.59 (m, 2H), 7.11-7.25 (m, 2.5H), 6.98 (d, J 7.7 Hz, 0.5H), 6.74 (t, J = 2.0 Hz, 0.5H), 6.71 (t, J = 2.0 Hz, 0.5H), 5.12 (d, J = 3.5 Hz, 0.5H), 5.08 (d, J = 4.1 Hz, 0.5H), 3.68 (ddd, J = 18.9, 7.0, 3.9 Hz, 1H), 3.29 (s, 1.5H), 3.22 (s, 1.5H), 3.13 (d, J = 0.7 Hz, 3H), 2.453 (s, 3H), 2.32 (s, 3H), 2.11 (s, 1.5H), 2.02 (s, 1.5H), 1.31 (d, J = 7.0 Hz, 1.5H), 1.26 (d, J = 7.0 Hz, 1.5H). LCMS-ESI (POS.) m/z: 524.2 (M + H)$^+$. |
| 71.0 | (1R,2S)-1-methoxy-1-(5-methylpyrimidin-2-yl)propane-2-sulfonamide (Example 14.0), 1,2-difluoro-4-isothiocyanato-benzene (FSSI), 6-methoxypicolino-hydrazide (Adesis, Inc) | (1R,2S)-N-(4-(3,4-difluorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.70 (s, 2H), 7.59-7.73 (m, 2H), 7.29-7.37 (m, 1H), 7.19-7.27 (m, 1H), 7.11-7.19 (m, 1H), 6.79 (dd, J = 8.3, 0.8 Hz, 1H), 5.11 (d, J = 3.5 Hz, 1H), 3.68 (dq, J = 7.1, 3.4 Hz, 1H), 3.29 (s, 6H), 2.38 (s, 3H), 1.33 (d, J = 7.0 Hz, 3H). LCMS-ESI (POS.) m/z: 532.1 (M + H)$^+$. |
| 72.0 | (1R,2S)-1-methoxy-1-(5-methylpyrimidin-2-yl)propane-2-sulfonamide (Example 14.0), 1-(3-isothiocyanatophenyl)ethanone (FSSI), 6-methoxypicolino-hydrazide (Adesis, Inc) | (1R,2S)-N-(4-(3-acetylphenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.73 (s, 2H), 8.02 (d, J = 7.4 Hz, 1H), 7.91 (t, J = 1.6 Hz, 1H), 7.57- |

TABLE 10-continued

| Example | Reagents | Structure, Name and Data |
|---|---|---|
|  |  | 7.71 (m, 4H), 6.75 (dd, J = 7.9, 1.2 Hz, 1H), 5.09 (d, J = 3.8 Hz, 1H), 3.69 (dd, J = 7.0, 3.8 Hz, 1H), 3.28 (s, 3H), 3.08 (s, 3H), 2.60 (s, 3H), 2.40 (s, 3H), 1.33 (d, J = 7.0 Hz, 3H). LCMS-ESI (POS.) m/z: 538.1 (M + H)+. |
| 73.0 | (1R,2S)-1-methoxy-1-(5-methylpyrimidin-2-yl)propane-2-sulfonamide (Example 14.0), 1,3-dichloro-2-isothiocyanato-benzene (FSSI), 6-methoxypicolino-hydrazide (Adesis, Inc) | (1R,2S)-N-(4-(2,6-dichlorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.69 (s, 2H), 7.64-7.74 (m, 2H), 7.44-7.49 (m, 2H), 7.31-7.39 (m, 1H), 6.77 (dd, J = 7.7, 1.5 Hz, 1H), 5.01 (d, J = 4.5 Hz, 1H), 3.75 (dd, J = 7.0, 4.5 Hz, 1H), 3.34 (s, 3H), 3.16 (s, 3H), 2.38 (s, 3H), 1.40 (d, J = 7.0 Hz, 3H). LCMS-ESI (POS.) m/z: 564.0 (M + H)+. |
| 74.0 | (1R,2S)-1-methoxy-1-(5-methylpyrimidin-2-yl)propane-2-sulfonamide (Example 14.0), 1-isothiocyanato-2-(trifluoromethyl)-benzene (FSSI), 6-methoxypicolino-hydrazide (Adesis, Inc) | AND<br><br>(1R,2S,P)-1-methoxy-N-(5(6-methoxy-2-pyridinyl)-4-(2-trifluoromethyl)phenyl)-4H-1,2,4-triazol-3-yl)-1-(5-methyl-2-pyrimidinyl)-2-propanesulfonamide and (1R,2S,M)-1-methoxy-N-(5(6-methoxy-2-pyridinyl))-4-(2-trifluoromethyl)phenyl)-4H-1,2,4-triazol-3-yl)-1-(5-methyl-2-pyrimidinyl)-2-propanesulfonamide<br>$^1$H NMR (CDCl$_3$) δ: 8.70 (s, 1H), 8.68 (s, 1H), 7.52-7.80 (m, 6H), 6.69-6.74 (m, 1H), 5.09 (d, J = 3.5 Hz, 0.5H), 4.94 (d, J = 4.7 Hz, 0.5H), 3.56-3.79 (m, 1H), 3.35 (s, 1.5H), 3.27 (s, 1.5H), 3.03 (s, 1.5H), 3.01 (s, 1.5H), 2.39 (s, 1.5H), 2.37 (s, 1.5H), 1.25-1.38 (m, 3H). LCMS-ESI (POS.) m/z: 564.2 (M + H)+. |

TABLE 10-continued

| Example | Reagents | Structure, Name and Data |
|---|---|---|
| 75.0 | (1R,2S)-1-methoxy-1-(5-methylpyrimidin-2-yl)propane-2-sulfonamide (Example 14.0), 1-isothiocyanato-3-(trifluoromethyl)-benzene (FSSI) 6-methoxypicolino-hydrazide (Adesis, Inc) | 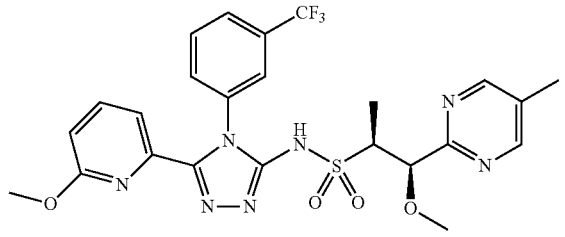<br>(1R,2S)-1-methoxy-N-(5-(6-methoxy-2-pyridinyl)-4-(3-(trifluoromethyl)phenyl)-4H-1,2,4-triazol-3-yl)-1-(5-methyl-2-pyrimidinyl)-2-propanesulfonamide<br>$^1$H NMR (CDCl$_3$) δ: 8.68 (s, 2H), 7.56-7.76 (m, 6H), 6.76 (dd, J = 7.7, 1.3 Hz, 1H), 5.07 (d, J = 3.7 Hz, 1H), 3.65-3.74 (m, 1H), 3.30 (s, 3H), 3.09 (s, 3H), 2.37 (s, 4H), 1.35 (d, J = 7.0 Hz, 3H). LCMS-ESI (POS.) m/z: 564.2 (M + H)$^+$. |
| 76.0 | (1R,2S)-1-methoxy-1-(5-methylpyrimidin-2-yl)propane-2-sulfonamide (Example 14.0), 1-fluoro-2-isothiocyanato-benzene (FSSI), 6-methoxypicolino-hydrazide (Adesis, Inc) | 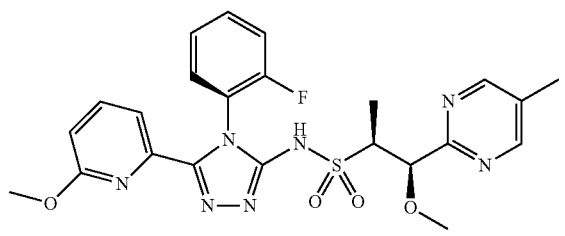<br>AND<br>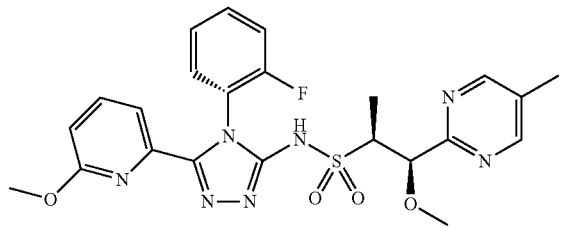<br>(1R,2S,P)-N-(4-(2-fluorophenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2-fluorophenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.68 (s, 1H), 8.65 (s, 1H), 7.59-7.71 (m, 2.5H), 7.38-7.50 (m, 1.5H), 7.31 (m, 0.5H), 7.13-7.27 (m, 1.5H), 6.72-6.79 (m, 1H), 5.11 (d, J = 3.4 Hz, 0.5H), 5.02 (d, J = 3.9 Hz, 0.5H), 3.70 (td, J = 7.1, 3.7 Hz, 1H), 3.34 (s, 1.5H), 3.27 (s, 1.5H), 3.13 (s, 3H), 2.37 (s, 1.5H), 2.35 (s, 1.5H), 1.35 (d, J = 7.0 Hz, 3H). LCMS-ESI (POS.) m/z: 514.1 (M + H)$^+$. |
| 77.0 | (1R,2S)-1-methoxy-1-(5-methylpyrimidin-2-yl)propane-2-sulfonamide (Example 14.0), 4-isothiocyanato-N,N-dimethylaniline (FSSI), 6-methoxypicolino-hydrazide (Adesis, Inc) | 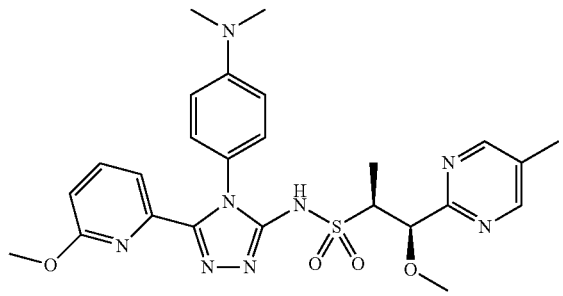 |

| Example | Reagents | Structure, Name and and Data |
|---|---|---|
| | | (1R,2S)-N-(4-(4-(dimethylamino)phenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (CDCl$_3$) δ: 8.72 (s, 2H), 7.66 (dd, J = 7.9 Hz, 1H), 7.52 (d, J = 7.3 Hz, 1H), 7.32 (d, J = 9.1 Hz, 2H), 7.06 (d, J = 8.9 Hz, 2H), 6.76 (d, J = 8.3 Hz, 1H), 5.13 (d, J = 3.7 Hz, 1H), 3.62-3.73 (m, 1H), 3.28 (s, 3H), 3.28 (s, 3H), 3.06 (s, 6H), 2.39 (s, 3H), 1.34 (d, J = 7.2 Hz, 3H). LCMS-ESI (POS.) m/z: 539.2 (M + H)$^+$. |
| 78.0 | (2S,3R)-3-(5-fluoropyrimidin-2-yl)butane-2-sulfonamide (Example 10.1), phenyl isothiocyanate, (Sigma-Aldrich), 6-methoxypicolino-hydrazide (Adesis, Inc) | 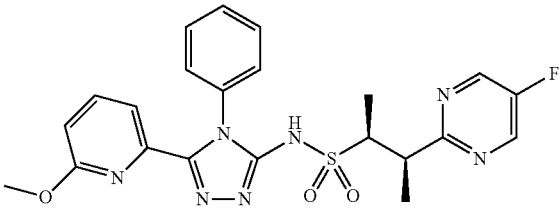 [SMILES: COc1cccc(-c2nnc(NS(=O)(=O)[C@@H](C)[C@H](C)c3ncc(F)cn3)n2-c2ccccc2)n1]<br>(2S,3R)-3-(5-fluoro-2-pyrimidinyl)-N-(5-(6-methoxy-2-pyridinyl)-4-phenyl-4H-1,2,4-triazol-3-yl)-2-butanesulfonamide<br>$^1$H NMR (CDCl$_3$) δ: 8.53 (s, 2H), 7.63-7.69 (m, 1H), 7.56-7.60 (m, 1H), 7.39-7.47 (m, 3H), 7.30 (m, 1H), 7.26 (m, 1H), 6.73 (d, J = 8.3 Hz, 1H), 3.91 (dt, J = 16.3, 6.2 Hz, 2H), 3.13 (s, 3H), 1.37 (dd, J = 6.8, 1.4 Hz, 6H). LCMS-ESI (POS.) m/z: 484.1 (M + H)$^+$. |
| 79.0 | (1R,2S)-1-ethoxy-1-(5-fluoropyrimidin-2-yl)propane-2-sulfonamide, (Example 14.5), 2-isothiocyanato-1,3-dimethoxybenzene (Example 1.0), 5-methylnicotino-hydrazide (JPM$^2$ Pharmaceuticals) | 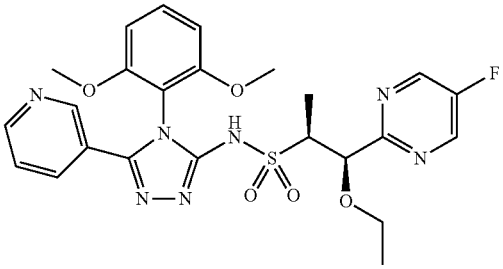<br>(1R,2S)-N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide<br>$^1$H NMR (CDCl$_3$) δ: 8.62 (s, 2H), 8.45 (d, J = 1.5 Hz, 1H), 8.34 (d, J = 1.9 Hz, 1H), 7.61-7.65 (m, 1H), 7.40 (t, J = 8.7 Hz, 1H), 6.61 (dd, J = 8.6, 4.2 Hz, 2H), 5.03 (d, J = 6.0 Hz, 1H), 3.71-3.83 (m, 7H), 3.52 (td, J = 7.0, 2.3 Hz, 2H), 2.31 (s, 3H), 1.46 (d, J = 7.0 Hz, 3H), 1.16 (t, J = 7.0 Hz, ,3H). LCMS-ESI (POS.) m/z: 558.2 (M + H)$^+$. |
| 80.0 | (1R,2S)-1-methoxy-1-(5-fluoro-pyrimidin-2-yl)propane-2-sulfonamide, (Example 14.2), 2-isothiocyanato-1,3-dimethoxybenzene (Example 1.0), 5-methylnicotino-hydrazide (JPM$^2$ Pharmaceuticals) | 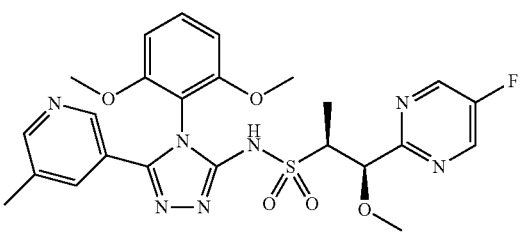 [SMILES: COc1cccc(OC)c1-n1c(NS(=O)(=O)[C@@H](C)[C@H](OC)c2ncc(F)cn2)nnc1-c1cncc(C)c1]<br>(1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide<br>$^1$H NMR (CDCl$_3$) δ: 11.10 br.s, 1H), 8.63 (s, 2H), 8.46 (d, J = 1.5 Hz, 1H), 8.35 (d, J = 1.9 Hz, 1H), 7.70 (s, 1H), 7.41 (t, J = 8.5 Hz, 1H), 6.62 |

TABLE 10-continued

| Example | Reagents | Structure, Name and and Data |
|---|---|---|
| | | (d, J = 8.5 Hz, 2H), 5.00 (d, J = 5.0 Hz, 1H), 3.71-3.80 (m, 7H), 3.35 (s, 3H), 2.33 (s, 3H), 1.41 (d, J = 7.0 Hz, 3H). LCMS-ESI (POS.) m/z: 544.1 (M + H)+. |
| 81.0 | (1R,2S)-1-methoxy-1-(5-fluoropyrimidin-2-yl)propane-2-sulfonamide (Example 14.2), 2-isothiocyanato-1,3-dimethoxybenzene (Example 1.0), nicotinohydrazide (Alfa Aesar) | (1R,2S)-N-(4-(2,6-dimethoxyphenyl)-5-(3-pyridinyl)-4H-1,2,4-triazol-3-yl)-1-(5-fluoro-2-pyrimidinyl)-1-methoxy-2-propanesulfonamide <br> 1H NMR (CDCl3) δ: 11.11 (br. s, 1H), 8.61-8.66 (m, 4H), 7.80 (dt, J = 5.2 Hz, 1H), 7.37-7.45 (m, 1H), 7.31 (dd, J = 7.7, 5.3 Hz, 1H), 6.63 (d, J = 8.6 Hz, 2H), 5.00 (d, J = 4.8 Hz, 1H), 3.71-3.79 (m, 7H), 3.35 (s, 3H), 1.41 (d, J = 7.0 Hz, 3H). LCMS-ESI (POS.) m/z: 530.2 (M + H)+. |
| 82.0 | (1R,2S)-1-((tert-butyldimethylsilyl)oxy)-1-(5-fluoropyrimidin-2-yl)propane-2-sulfonamide (Example 14.6), 2-isothiocyanato-1,3-dimethoxybenzene (Example 1.0), nicotinohydrazide (Alfa Aesar) | (1R,2S)-N-(4-(2,6-dimethoxyphenyl)-5-(3-pyridinyl)-4H-1,2,4-triazol-3-yl)-1-(5-fluoro-2-pyrimidinyl)-1-hydroxy-2-propanesulfonamide <br> 3149269. 1H NMR (CDCl3) δ: 1.11 (br. s, 1H), 8.57-8.70 (m, 4H), 7.76 (dt, J = 7.9, 2.0 Hz, 1H), 7.42 (t, J = 8.6 Hz, 1H), 7.25-7.31 (m, 4H), 6.66 (d, J = 8.7 Hz, 1H), 6.62 (d, J = 6.9 Hz, 1H), 5.63 (s, 1H), 3.97 (d, J = 3.1 Hz, 1H), 3.84 (dd, J = 7.0, 1.6 Hz, 1H), 3.74 (s, 3H), 1.25 (d, J = 7.0 Hz, 3H). LCMS-ESI (POS.) m/z: 516.2 (M + H)+. |
| 83.0 | (R)-1-oxo-1-(pyrrolidin-1-yl)propane-2-sulfonamide and (S)-1-oxo-1-(pyrrolidin-1-yl)propane-2-sulfonamide (Example 15.0), 2-isothiocyanato-1,3-dimethoxybenzene (Example 1.0), 6-methoxypicolino-hydrazide (Adesis, Inc) | AND |

TABLE 10-continued

| Example | Reagents | Structure, Name and and Data |
|---|---|---|
| | | (2R)-N-(4-(2,6-dimethoxyphenyl)-5-(6-methoxy-2-pyridinyl)-4H-1,2,4-triazol-3-yl)-1-oxo-1-(1-pyrrolidinyl)-2-propanesulfonamide and (2S)-N-(4-(2,6-dimethoxyphenyl)-5-(6-methoxy-2-pyridinyl)-4H-1,2,4-triazol-3-yl)-1-oxo-1-(1-pyrrolidinyl)-2-propanesulfonamide <br> $^1$H NMR (CDCl$_3$) δ: 7.58-7.60 (m, 1H), 7.58-7.66 (m, 2H), 7.33 (t, J = 8.5 Hz, 1H), 6.71 (dd, J = 6.7, 2.3 Hz, 1H), 6.58-6.65 (m, 2H), 4.24 (q, J = 6.9 Hz, 1H), 3.90 (dt, J = 10.2, 6.4 Hz, 1H), 3.75 (s, 3H), 3.69 (s, 3H), 3.41-3.57 (m, 3H), 3.18 (s, 3H), 1.83-2.01 (m, 4H), 1.59 (d, J = 6.9 Hz, 3H). LCMS-ESI (POS.) m/z: 517.2 (M + H)$^+$. |
| 84.0 | (2R,3S)-3-(5-methylpyrimidin-2-yl)butane-2-sulfonamide (Example 10.0), 2-methoxyisonicotinohydrazide (Combi-Blocks Inc.), 2-isothiocyanato-1,3-dimethoxybenzene (Example 1.0) | 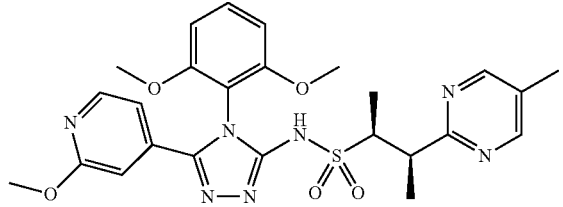 <br> (2S,3R)-N-(4-(2,6-dimethoxyphenyl)-5-(2-methoxypyridin-4-yl)-4H-1,2,4-triazol-3-yl)-3-(5-methylpyrimidin-2-yl)butane-2-sulfonamide <br> $^1$H NMR (CDCl$_3$) δ: 11.35 (br. s., 1H), 8.53 (s, 2H), 8.09 (d, J = 5.5 Hz, 1H), 7.40 (t, J = 8.5 Hz, 1H), 6.90 (dd, J = 5.4, 1.3 Hz, 1H), 6.70 (s, 1H), 6.61 (t, J = 7.6 Hz, 2H), 3.83-3.95 (m, 4H), 3.66-3.80 (m, 7H), 2.29 (s, 1H), 1.36 (dd, J = 11.1, 7.1 Hz, 6H). LCMS-ESI (POS.) m/z: 540.0 (M + H)$^+$. |
| 85.0 | (2R,3S)-3-(5-methylpyrimidin-2-yl)butane-2-sulfonamide (Example 10.0), 2-methoxyisonicotinohydrazide (Example 3.2), 2-isothiocyanato-1,3-dimethoxybenzene (Example 1.0) | 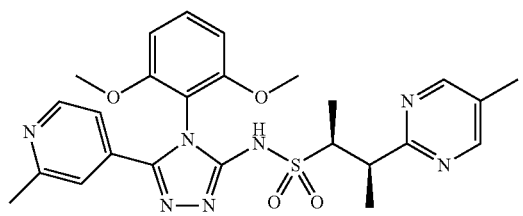 <br> (2S,3R)-N-(4-(2,6-dimethoxyphenyl)-5-(2-methoxypyridin-4-yl)-4H-1,2,4-triazol-3-yl)-3-(5-methylpyrimidin-2-yl)butane-2-sulfonamide <br> $^1$H NMR (CDCl$_3$) δ: 11.41 (br. s., 1H), 8.53 (s, 2H), 8.42 (d, J = 5.3 Hz, 1H), 7.42 (t, J = 8.5 Hz, 1H), 6.98 (d, J = 5.3 Hz, 1H), 6.62 (t, J = 7.9 Hz, 2H), 3.84-3.95 (m, 1H), 3.73-3.82 (m, 1H), 3.74 (s, 3H), 3.71 (s, 3H), 2.51 (s, 3H), 2.29 (s, 3H), 1.37 (dd, J = 10.1, 7.1 Hz, 6H). LCMS-ESI (POS.) m/z: 524.2 (M + H)$^+$. |
| 86.0 | (2R,3S)-3-(5-methylpyrimidin-2-yl)butane-2-sulfonamide (Example 10.0), 5-methoxyisonicotinohydrazide (Example 3.43), 2-isothiocyanato-1,3-dimethoxybenzene (Example 1.0) | 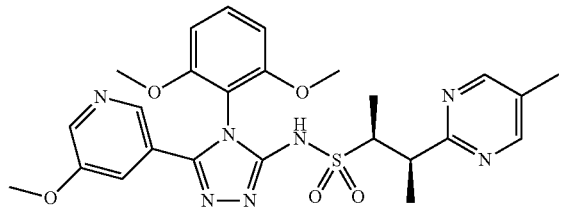 <br> (2S,3R)-N-(4-(2,6-dimethoxyphenyl)-5-(5-methoxypyridin-3-yl)-4H-1,2,4-triazol-3-yl)-3-(5-methylpyrimidin-2-yl)butane-2-sulfonamide <br> $^1$H NMR (CDCl$_3$) δ: 11.35 (br. s., 1H), 8.54 (s, 2H), 8.32 (d, J = 2.8 Hz, 1H), 8.21 (d, J = 1.6 Hz, 1H), 7.40 (t, J = 8.5 Hz, 1H), 7.29 (br. s., 1H), 6.62 (dd, J = 8.5, 4.5 Hz, 2H), 3.83-3.98 (m, |

TABLE 10-continued

| Example | Reagents | Structure, Name and and Data |
|---|---|---|
| | | 1H), 3.67-3.83 (m, 10H), 2.30 (s, 3H), 1.38 (t, J = 7.2 Hz, 6H). LCMS-ESI (POS.) m/z: 540.0 (M + H)+. |
| 87.0 | (2R,3S)-3-(5-methylpyrimidin-2-yl)butane-2-sulfonamide (Example 10.0), 6-methoxyisonicotinohydrazide (Example 3.10), 2-isothiocyanato-1,3-dimethoxybenzene (Example 1.0) | 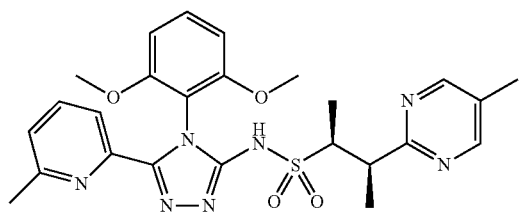<br>(2S,3R)-N-(4-(2,6-dimethoxyphenyl)-5-(6-methoxypyridin-3-yl)-4H-1,2,4-triazol-3-yl)-3-(5-methylpyrimidin-2-yl)butane-2-sulfonamide<br>1H NMR (CDCl3) δ: 11.28 (br. s., 1H), 8.53 (s, 2H), 7.51-7.62 (m, 2H), 7.35 (t, J = 8.5 Hz, 1H), 7.10 (dd, J = 6.7, 2.0 Hz, 1H), 6.51-6.65 (m, 2H), 3.86-3.99 (m, 1H), 3.76-3.86 (m, 1H), 3.63-3.75 (m, 6H), 2.27 (d, J = 14.8 Hz, 6H), 1.38 (t, J = 7.4 Hz, 6H). LCMS-ESI (POS.) m/z: 524.0 (M + H)+. |
| 88.0 | (1R,2S)-1-(5-chloropyrimidin-2-yl)-1-methoxypropane-2-sulfonamide and (1S,2R)-1-(5-chloropyrimidin-2-yl)-1-methoxypropane-2-sulfonamide, ((Example 14.3), (6-methylpicolinohydrazide (Example 3.4), 2-isothiocyanato-1,3-dimethoxybenzene (Example 1.0) | 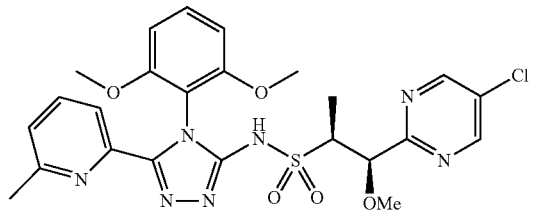 [SMILES: COc1cccc(OC)c1-n1c(NS(=O)(=O)[C@@H](C)[C@H](OC)c2ncc(Cl)cn2)nnc1-c1cccc(C)n1]<br>(1R,2S)-1-(5-chloropyrimidin-2-yl)-N-(4-(2,6-dimethoxyphenyl)-5-(6-methylpyridin-2-yl)-4H-1,2,4-triazol-3-yl)-1-methoxypropane-2-sulfonamide<br>1H NMR (CDCl3) δ: 11.06 (br. s., 1H), 8,72 (s, 2H), 7.53-7.61 (m, 2H), 7.37 (t, J = 8.5 Hz, 1H), 7.10 (dd, J = 6.3, 2.5 Hz, 1H), 6.6o0 (d, J = 8.5 Hz, 2H), 4.99 (d, J = 5.0 Hz, 1H), 3.75-3.81 (m, 1H), 3.67-3.75 (m, 6H), 3.36 (s, 3H), 2.24 (s, 3H), 1.41 (d, J = 7.0 Hz, 3H). LCMS-ESI (POS.) m/z: 560.0 (M + H)+. |
| 89.0 | (1R,2S)-1-(5-chloropyrimidin-2-yl)-1-methoxypropane-2-sulfonamide and (1S,2R)-1-(5-chloropyrimidin-2-yl)-1-methoxypropane-2-sulfonamide (Example 14.3), 6-methylpicolinohydrazide (Example 3.4), 2-isothiocyanato-1,3-dimethoxybenzene (Example 1.0) | 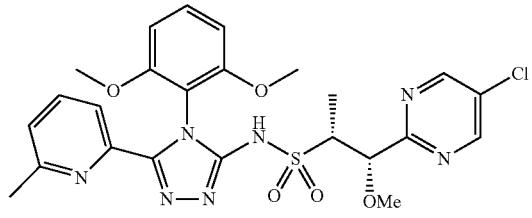 [SMILES: COc1cccc(OC)c1-n1c(NS(=O)(=O)[C@H](C)[C@@H](OC)c2ncc(Cl)cn2)nnc1-c1cccc(C)n1]<br>(1S,2R)-1-(5-chloropyrimidin-2-yl)-N-(4-(2,6-dimethoxyphenyl)-5-(6-methylpyridin-2-yl)-4H-1,2,4-triazol-3-yl)-1-methoxypropane-2-sulfonamide<br>1H NMR (CDCl3) δ: 11.06 (br. s., 1H), 8.72 (s, 2H), 7.53-7.61 (m, 2H), 7.37 (t, J = 8.5 Hz, 1H), 7.10 (dd, J = 6.3, 2.5 Hz, 1H), 6.60 (d, J = 8.5 Hz, 2H), 4.99 (d, J = 5.0 Hz, 1H), 3.75-3.81 (m, 1H), 3.67-3.75 (m, 6H), 3.36 (s, 3H), 2.24 (s, 3H), 1.41 (d, J = 7.0 Hz, 3H). LCMS-ESI (POS.) m/z: 560.0 (M + H)+. |

TABLE 10-continued

| Example | Reagents | Structure, Name and Data |
|---|---|---|
| 90.0 | (1R,2S)-1-methoxy-1-(5-methylpyrimidin-2-yl)propane-2-sulfonamide (Example 14.0), 6-methylpicolinohydrazide (Example 3.10), 5-isothiocyanato-4,6-dimethoxypyrimidine (Example 1.1) | 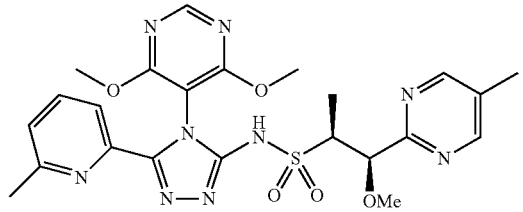<br>(1R,2S)-N-(4-(4,6-dimethoxypyrimidin-5-yl)-5-(6-methylpyridin-2-yl)-4H-1,2,4-triazol-3-yl)-1-methoxy-1-(5-methylpyrimidin-2-yl)propane-2-sulfonamide<br><sup>1</sup>H NMR (CDCl$_3$) δ: 11.23 (br. s., 1H), 8.61 (s, 2H), 8.50 (s, 1H), 7.81 (d, J = 7.9 Hz, 1H), 7.58-7.71 (m, 1H), 7.13 (d, J = 7.6 Hz, 1H), 4.97 (d, J = 4.7 Hz, 1H), 3.86-3.97 (m, 6H), 3.72-3.84 (m, 1H), 3.36 (s, 3H), 2.33 (s, 3H), 2.19 (s, 3H), 1.42 (d, J = 7.0 Hz, 3H). LCMS-ESI (POS.) m/z: 542.1 (M + H)<sup>+</sup>. |
| 91.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine, (Example 2.0). The racemic mixture was purified by preparative SFC method #1 (Purification #1): Column: ChiralPak AD-H (Reversed) (250 × 21 m, 5 μm) Mobile Phase: 80:20 (A:B) A: Liquid CO$_2$, B: EtOH (20 mM, NH$_3$), Flow Rate: 70 mL/min, Column/Oven temp.: 40 C., 220 nm, 179-186 bar inlet pressure. Then by Preparative SFC method #2 (Purification #2): Column: ChiralPak AD-H (Reversed) (250 × 21 m, 5 μm) Mobile Phase: 82:18 (A:B) A: Liquid CO$_2$, B: EtOH (20 mM NH$_3$), Flow Rate: 70 mL/min, Column/Oven temp.: 40 C., 220 nm, 179 bar inlet pressure to deliver peak 1. | 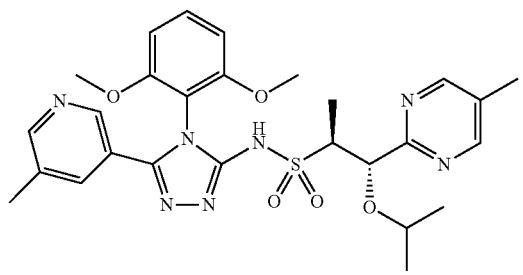<br>(1S,2S)-N-(4-(2,6-dimethoxyphenyl)-5-(5-methylpyridin-3-yl)-4H-1,2,4-triazol-3-yl)-1-isopropoxy-1-(5-methylpyrimidin-2-yl)propane-2-sulfonamide<br><sup>1</sup>H NMR (CDCl$_3$) δ: 12.86 (br. s., 1H), 8.66 (s, 2H), 8.44 (d, J = 1.6 Hz, 1H), 8.36 (d, J = 1.8 Hz, 1H), 7.61 (s, 1H), 7.37 (t, J = 8.5 Hz, 1H), 6.61 (dd, J = 18.8, 8.6 Hz, 2H), 4.92 (d, J = 4.1 Hz, 1H), 3.83 (s, 3H), 3.75 (dd, J = 7.2, 4.2 Hz, 1H), 3.69 (s, 3H), 3.61 (quin, J = 6.0 Hz, 1H), 2.36 (s, 3H), 2.31 (s, 3H), 1.48 (d, J = 7.2 Hz, 3H), 1.15 (d, J = 6.0 Hz, 3H), 1.03 (d, J = 6.1 Hz, 3H). LCMS-ESI (POS.) m/z: 568.1 (M + H)<sup>+</sup>. |
| 92.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine, (Example 2). The racemic mixture was purified by preparative SFC method #1 (Purification #1): Column: ChiralPak AD-H (Reversed) (250 × 21 m, 5 μm) Mobile Phase: 80:20 (A:B) A: Liquid CO$_2$, B: EtOH (20 mM NH$_3$), Flow Rate: 70 mL/min, Column/Oven temp.: 40 C., 220 nm, 179-186 bar inlet pressure. Then by Preparative SFC method #2 (Purification #2): Column: ChiralPak AD-H (Reversed) (250 × 21 m, 5 μm) Mobile Phase: 82:18 (A:B) A: Liquid CO$_2$, B: EtOH (20 mM NH$_3$), Flow Rate: 70 mL/min, Column/Oven temp.: 40 C., 220 nm, 179 bar inlet pressure to deliver peak 2. | 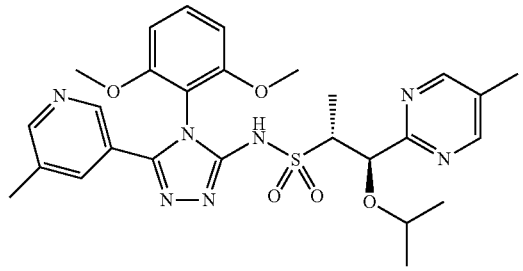<br>(1R,2R)-N-(4-(2,6-dimethoxyphenyl)-5-(5-methylpyridin-3-yl)-4H-1,2,4-triazol-3-yl)-1-isopropoxy-1-(5-methylpyrimidin-2-yl)propane-2-sulfonamide<br><sup>1</sup>H NMR (CDCl$_3$) δ: 12.86 (br. s., 1H), 8.66 (s, 2H), 8.44 (d, J = 1.6 Hz, 1H), 8.36 (d, J = 1.8 Hz, 1H), 7.61 (s, 1H), 7.37 (t, J = 8.5 Hz, 1H), 6.61 (dd, J = 18.8, 8.6 Hz, 2H), 4.92 (d, J = 4.1 Hz, 1H), 3.83 (s, 3H), 3.75 (dd, J = 7.2, 4.2 Hz, 1H), 3.69 (s, 3H), 3.61 (quin, J = 6.0 Hz, 1H), 2.36 (s, 3H), 2.31 (s, 3H), 1.48 (d, J = 7.2 Hz, 3H), 1.15 (d, J = 6.0 Hz, 3H), 1./03 (d, J = 6.1 Hz, 3H). LCMS-ESI (POS.) m/z: 568.1 (M + H)<sup>+</sup>. |

TABLE 10-continued

| Example | Reagents | Structure, Name and and Data |
|---|---|---|
| 93.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine, (Example 2). The racemic mixture was purified by preparative SFC method #1 (Purification #1): Column: ChiralPak AD-H (Reversed) (250 × 21 m, 5 μm) Mobile Phase: 80:20 (A:B) A: Liquid $CO_2$, B: EtOH (20 mM $NH_3$), Flow Rate: 70 mL/min, Column/Oven temp.: 40 C., 220 nm, 179-186 bar inlet pressure. Then by Preparative SFC method #2 (Purification #2): Column: ChiralPak AD-H (Reversed) (250 × 21 m, 5 μm) Mobile Phase: 82:18 (A:B) A: Liquid $CO_2$, B: EtOH (20 mM $NH_3$), Flow Rate: 70 mL/min, Column/Oven temp.: 40 C., 220 nm, 179 bar inlet pressure to deliver peak 4. | 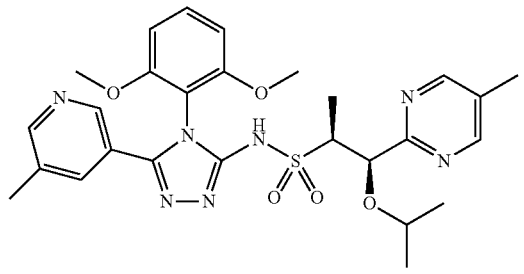<br>(1R,2S)-N-(4-(2,6-dimethoxyphenyl)-5-(5-methylpyridin-3-yl)-4H-1,2,4-triazol-3-yl)-1-isopropoxy-1-(5-methylpyrimidin-2-yl)propane-2-sulfonamide<br>$^1$H NMR (CDCl$_3$) δ: 8.60 (s, 2H), 8.45 (s, 1H), 8.34 (s, 1H), 7.63 (d, J = 2.2 Hz, 1H), 7.39 (t, J = 8.6 Hz, 1H), 6.56-6.66 (m, 2H), 5.02 (d, J = 6.4 Hz, 1H), 3.66-3.84 (m, 8H), 2.32 (d, J = 5.1 Hz, 6H), 1.48 (d, J = 7.0 Hz, 3H), 1.18 (d, J = 6.0 Hz, 3H), 1.01 (d, J = 6.1 Hz, 3H). LCMS-ESI (POS.) m/z: 568.1 (M + H)$^+$. |
| 94.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine, (Example 2). The racemic mixture was purified by preparative SFC method #1 (Purification #1): Column: ChiralPak AD-H (Reversed) (250 × 21 m, 5 μm) Mobile Phase: 80:20 (A:B) A: Liquid $CO_2$, B: EtOH (20 mM $NH_3$), Flow Rate: 70 mL/min, Column/Oven temp.: 40 C., 220 nm, 179-186 bar inlet pressure. Then by Preparative SFC method #2 (Purification #2): Column: ChiralPak AD-H (Reversed) (250 × 21 m, 5 μm) Mobile Phase: 82:18 (A:B) A: Liquid $CO_2$, B: EtOH (20 mM $NH_3$), Flow Rate: 70 mL/min, Column/Oven temp.: 40 C., 220 nm, 179 bar inlet pressure to deliver peak 3. | 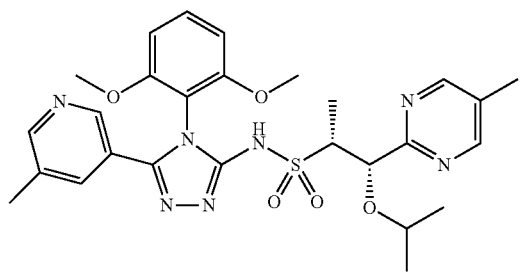<br>(1S,2R)-N-(4-(2,6-dimethoxyphenyl)-5-(5-methylpyridin-3-yl)-4H-1,2,4-triazol-3-yl)-1-isopropoxy-1-(5-methylpyrimidin-2-yl)propane-2-sulfonamide<br>$^1$H NMR (CDCl$_3$) δ: 8.60 (s, 2H), 8.45 (s, 1H), 8.34 (s, 1H), 7.63 (d, J = 2.2 Hz, 1H), 7.39 (t, J = 8.6 Hz, 1H), 6.56-6.66 (m, 2H), 5.02 (d, J = 6.4 Hz, 1H), 3.66-3.84 (m, 8H), 2.32 (d, J = 5.1 Hz, 6H), 1.48 (d, J = 7.0 Hz, 3H), 1.18 (d, J = 6.0 Hz, 3H), 1.01 (d, J = 6.1 Hz, 3H). LCMS-ESI (POS.) m/z: 568.1 (M + H)$^+$. |
| 95.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine (Example 2.2). The racemic mixture was purified by preparative SFC ChiralPak AD-H (250 × 20) 15% EtOH, 70 mL/min, 296-nm, 156 Bar.<br>100 mg disolved in 4 mL MeOH/ 2 mL DCM, to deliver peak 1. | 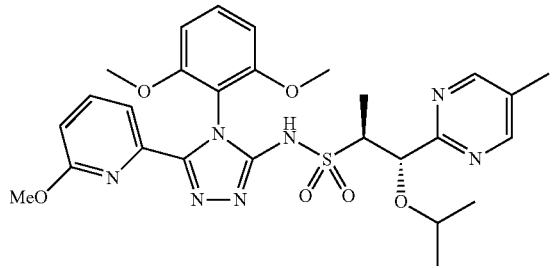 [SMILES: COc1cccc(-c2nnc(NS(=O)(=O)[C@@H](C)[C@@H](OC(C)C)c3ncc(C)cn3)n2-c2c(OC)cccc2OC)n1]<br>(1S,2S)-N-(4-(2,6-dimethoxyphenyl)-5-(6-methoxypyridin-3-yl)-4H-1,2,4-triazol-3-yl)-1-isopropoxy-1-(5-methylpyrimidin-2-yl)propane-2-sulfonamide<br>$^1$H NMR (CDCl$_3$) δ: 8.63 (s, 2H), 7.55-7.63 (m, 2H), 7.28 (s, 1H), 6.65-6.71 (m, 1H), 6.58 (dd, J = 15.8, 8.4 Hz, 2H), 4.91 (d, J = 4.5 Hz, 1H), 3.76 (s, 3H), 3.72 (dd, J = 7.0, 4.7 Hz, 1H), 3.66 (s, 3H), 3.59 (dt, J = 12.2, 6.1 Hz, 1H), 3.17 (s, 3H), 2.33 (s, 3H), 1.40 (d, J = 7.0 Hz, 3H), 1.12 |

TABLE 10-continued

| Example | Reagents | Structure, Name and and Data |
|---|---|---|
| | | (d, J = 5.9 Hz, 3H), 1.00 (d, J = 6.1 Hz, 3H). LCMS-ESI (POS.) m/z: 584.2 (M + H)⁺. |
| 96.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine (Example 2.2). The racemic mixture was purified by preparative SFC Chiralpak AD-H (250 × 20) 15% EtOH, 70 mL/min, 296-nm, 156 Bar. 100 mg disolved in 4 mL MeOH/ 2 mL DCM, to deliver peak 4. | (1R,2S)-N-(4-(2,6-dimethoxyphenyl)-5-(6-methoxypyridin-2-yl)-4H-1,2,4-triazol-3-yl)-1-isopropoxy-1-(5-methylpyrimidin-2-yl)propane-2-sulfonamide<br>¹H NMR (CDCl₃) δ: 8.57 (s, 2H), 7.53-7.64 (m, 2H), 7.27-7.34 (m, 1H), 6.63-6.764 (m, 1H), 6.58 (t, J = 8.3 Hz, 2H), 5.00 (d, J = 6.5 Hz, 1H), 3.60-3.82 (m, 8H), 3.16 (s, 3H), 2.30 (s, 3H), 1.45 (d, J = 7.0 Hz, 3H), 1.15-1.18 (m, 3H), 0.98 (d, J = 6.3 Hz, 3H). LCMS-ESI (POS.) m/z: 584.2 (M + H)⁺. |
| 97.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine (Example 2.2). The racemic mixture was purified by preparative SFC Chiralpak AD-H (250 × 20) 15% EtOH, 70 mL/min, 296-nm, 156 Bar. 100 mg disolved in 4 mL MeOH/ 2 mL DCM, to deliver peak 2. | (1S,2R)-N-(4-(2,6-dimethoxyphenyl)-5-(6-methoxypyridin-2-yl)-4H-1,2,4-triazol-3-yl)-1-isopropoxy-1-(5-methylpyrimidin-2-yl)propane-2-sulfonamide<br>¹H NMR (CDCl₃) δ: 8.57 (s, 2H), 7.53-7.64 (m, 2H), 7.27-7.34 (m, 1H), 6.63-6.74 (m, 1H), 6.58 (t, J = 8.3 Hz, 2H), 5.00 (d, J = 6.5 Hz, 1H), 3.60-3.82 (m, 8H), 3.16 (s, 3H), 2.30 (s, 3H), 1.45 (d, J = 7.0 Hz, 3H), 1.15-1.18 (m, 3H), 0.98 (d, J = 6.3 Hz, 3H). LCMS-ESI (POS.) m/z: 584.2 (M + H)⁺. |
| 98.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-5-methylpyridine (Example 2.2). The racemic mixture was purified by preparative SFC Chiralpak AD-H (250 × 20) 15% EtOH, 70 mL/min, 296-nm, 156 Bar. 100 mg disolved in 4 mL MeOH/ 2 mL DCM, to deliver peak 3. | (1R,2R)-N-(4-(2,6-dimethoxyphenyl)-5-(6-methoxypyridin-2-yl)-4H-1,2,4-triazol-3-yl)-1-isopropoxy-1-(5-methylpyrimidin-2-yl)propane-2-sulfonamide<br>¹H NMR (CDCl₃) δ: 8.63 (s, 2H), 7.55-7.63 (m, 2H), 7.28 (s, 1H), 6.65-6.71 (m, 1H), 6.58 (dd, J = 15.8, 8.4 Hz, 2H), 4.91 (d, J = 4,5 Hz, 1H), 3.76 (s, 3H), 3.72 (dd, J = 7.0, 4.7 Hz, 1H), 3.66 (s, 3H), 3.59 (dt, J = 12.2, 6.1 Hz, 1H), 3.17 (s, |

TABLE 10-continued

| Example | Reagents | Structure, Name and and Data |
|---|---|---|
| | | 3H), 2.33 (s, 3H), 1.40 (d, J = 7.0 Hz, 3H), 1.12 (d, J = 5.9 Hz, 3H), 1.00 (d, J = 6.1 Hz, 3H). LCMS-ESI (POS.) m/z: 584.2 (M + H)+. |
| 99.0 | (1R,2S)-1-((tert-butyldimethylsilyl)oxy)-1-(5-methylpyrimidin-2-yl)propane-2-sulfonamide (Example 18.0), 6-methylpicolinohydrazide (Example 3.4), 2-isothiocyanato-1,3-dimethoxybenzene (Example 1.0) | (1R,2S)-N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide<br>$^1$H NMR (CDCl$_3$) δ: 11.09 (br. s., 1H), 8.58 (s, 2H), 7.58 (d, J = 4.5 Hz, 2H), 7.36 (t, J = 8.5 Hz, 1H), 7.10 (t, J 4.4 Hz, 1H), 6.60 (dd, J = 10.6, 8.6 Hz, 2H), 5.61 (br. s., 1H), 4.07 (d, J = 3.2 Hz, 1H), 3.81-3.95 (m, 1H), 3.71 (d, J = 10.2 Hz, 6H), 2.33 (s, 3H), 2.23 (s, 3H), 1.22 (d, J = 7.0 Hz, 3H). LCMS-ESI (POS.) m/z: 526.0 (M + H)+. |
| 100.0 | propane-2-sulfonamide (Ark Pharm), 6-methoxypicolinohydrazide (Adeis, Inc.), 2-isothiocyanato-1,3-dimethoxybenzene (Example 1.0) | N-(4-(2,6-dimethoxyphenyl)-5-(6-methoxypyridin-2-yl)-4H-1,2,4-triazol-3-yl)propane-2-sulfonamid<br>$^1$H NMR (CDCl$_3$) δ: 10.99 (br. s., 1H), 7.56-7.65 (m, 2H), 7.31 (t, J = 8.5 Hz, 1H), 6.70 (dd, J = 7.5, 1.6 Hz, 1H), 6.59 (d, J = 8.5 Hz, 2H), 3.71 (s, 6H), 3.09-3.21 (m, 4H), 1.33 (d, J = 6.9 Hz, 6H). LCMS-ESI (POS.) m/z: 433.9 (M + H)+. |
| 101.0 | (1R,2S)-1-methoxy-1-(5-methylpyrimidin-2-yl)propane-2-sulfonamide (Example 14.0), 2-methoxyisonicotinohydrazide, (Combi-Blocks, Inc.), 2-isothiocyanato-1,3-dimethoxybenzene (Example 1.0) | (1R,2S)-N-(4-(2,6-dimethoxyphenyl)-5-(2-methoxypyridin-4-yl)-4H-1,2,4-triazol-3-yl)-1-isopropoxy-1-(5-methylpyrimidin-2-yl)propane-2-sulfonamide<br>$^1$H NMR (CDCl$_3$) δ: 11.26 (br. s., 1H), 8.60 (s, 2H), 8.11 (d, J = 5.4 Hz, 1H), 7.41 (t, J = 8.5 Hz, 1H), 6.91 (dd, J = 5.3, 1.4 Hz, 1H), 6.71 (s, 1H), 6.63 (d, J = 8.5 Hz, 2H), 4.96 (d, J = 4.8 Hz, 1H), 3.88 (s, 3H), 3.74 (d, J = 7.7 Hz, 7H), 3.34 (s, 3H), 2.33 (s, 3H), 1.38 (d, J = 7.2 Hz, 3H). LCMS-ESI (POS.) m/z: 555.9 (M + H)+. |

TABLE 10-continued

| Example | Reagents | Structure, Name and and Data |
|---|---|---|
| 102.0 | (1R,2S)-1-methoxy-1-(5-methylpyrimidin-2-yl)propane-2-sulfonamide (Example 14.0), Isonicotinohydrazide (Frotier Scientific), 2-isothiocyanato-1,3-dimethoxybenzene (Example 1.0) | 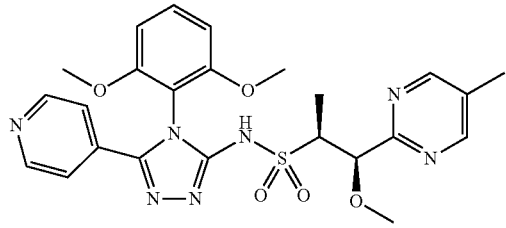 [SMILES: COc1cccc(OC)c1-n1c(NS(=O)(=O)[C@@H](C)[C@H](OC)c2ncc(C)cn2)nnc1-c1ccncc1]<br>(1R,2S)-N-(4-(2,6-dimethoxyphenyl)-5-(pyridin-4-yl)-4H-1,2,4-triazol-3-yl)-1-methoxy-1-(5-methylpyrimidin-2-yl)propane-2-sulfonamide<br>$^1$H NMR (DMSO-d$_6$) δ: 13.49 (br. s., 1H), 8.59-8.69 (m, 4H), 7.52 (t, J = 8.5 Hz, 1H), 7.36 (d, J = 5.9 Hz, 2H), 6.85 (d, J = 8.6 Hz, 2H), 4.82 (d, J = 3.5 Hz, 1H), 3.70 (d, J = 9.5 Hz, 6H), 3.43 (dd, J = 7.0, 3.6 Hz, 1H), 3.15 (s, 3H), 2.26 (s, 3H), 1.14 (d, J = 7.0 Hz, 3H). LCMS-ESI (POS.) m/z: 526.1 (M + H)$^+$. |
| 103.0 | (1R,2S)-1-methoxy-1-(5-methylpyrimidin-2-yl)propane-2-sulfonamide (Example 14.0), 6-methylpicolinohydrazide (Intermediate 3.10), 2-isothiocyanato-1,3-dimethoxybenzene (Example 1.0) | 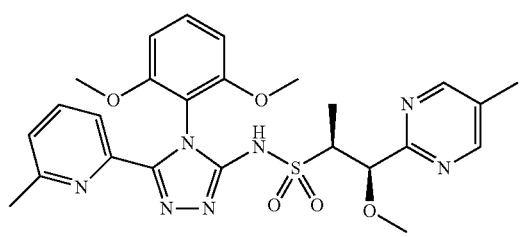<br>(1R,2S)-N-(4-(2,6-dimethoxyphenyl)-5-(6-methylpyridin-2-yl)-4H-1,2,4-triazol-3-yl)-1-methoxy-1-(5-methylpyrimidin-2-yl)propane-2-sulfonamide<br>$^1$H NMR (CDCl$_3$) δ: 11.20 (s, 1H), 8.60 (s, 2)H, 7.52-7.60 (m, 2H), 7.34 (t, J = 8.5 Hz, 1H), 7.09 (dd, J = 6.4, 2.2 Hz, 1H), 6.58 (d, J = 8.5 Hz, 2H), 4.98 (d, J = 4.7 Hz, 1H), 3.73-3.81 (m, 1H), 3.70 (d, J = 7.3 Hz, 6H), 3.35 (s, 3H), 2.32 (s, 3H), 2.23 (s, 3H), 1.40 (d, J = 7.0 Hz, 3H). LCMS-ESI (POS.) m/z: 540.1 (M + H)$^+$. |
| 104.0 | (1R,2S)-1-methoxy-1-(5-methylpyrimidin-2-yl)propane-2-sulfonamide (Example 14.0), 2-methylisonicotinohydrazide (Intermediate 3.2), 2-isothiocyanato-1,3-dimethoxybenzene (Example 1.0) | 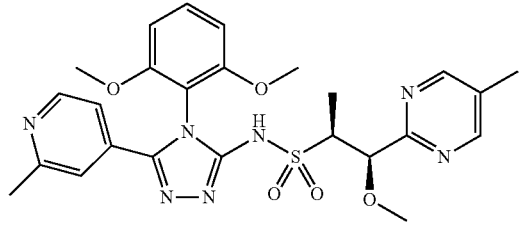<br>(1R,2S)-N-(4-(2,6-dimethoxyphenyl)-5-(2-methylpyridin-4-yl)-4H-1,2,4-triazol-3-yl)-1-methoxy-1-(5-methylpyrimidin-2-yl)propane-2-sulfonamide<br>$^1$H NMR (CDCl$_3$) δ: 8.60-8.67 (m, 3H), 7.60 (s, 1H), 7.48 (t, J = 8.5 Hz, 1H), 7.29 (br. s., 1H), 6.68 (d, J = 8.6 Hz, 2H), 4.96 (d, J = 4.4 Hz, 1H), 3.77 (d, J = 7.5 Hz, 7H), 3.33 (s, 3H), 2.69 (s, 3H), 2.34 (s, 3H), 1.37 (d, J = 7.0 Hz, 3H). NH not observed. LCMS-ESI (POS.) m/z: 539.9. |

TABLE 10-continued

| Example | Reagents | Structure, Name and and Data |
|---|---|---|
| 105.0 | (1R,2S)-1-methoxy-1-(5-methylpyrimidin-2-yl)propane-2-sulfonamide (Example 14.0), 5-methoxynicotinohydrazide (Intermediate 3.43), 2-isothiocyanato-1,3-dimethoxybenzene (Example 1.0) | 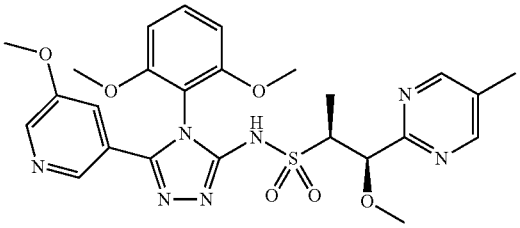<br>(1R,2S)-N-(4-(2,6-dimethoxyphenyl)-5-(2-methylpyridin-4-yl)-4H-1,2,4-triazol-3-yl)-1-methoxy-1-(5-methylpyrimidin-2-yl)propane-2-sulfonamide<br>$^1$H NMR (CDCl$_3$) δ: 11.26 (br. s., 1H), 8.61 (s, 2H), 8.32 (d, J = 2.8 Hz, 1H), 8.21 (d, J = 1.8 Hz, 1H), 7.31-7.45 (m, 2H), 6.63 (d, J = 8.6 Hz, 2H), 4.97 (d, J = 4.7 Hz, 1H), 3.70-3.83 (m, 10H), 3.34 (s, 3H), 2.33 (s, 3H), 1.39 (d, J = 7.0 Hz, 3H). LCMS-ESI (POS.) m/z: 555.9 (M + H)$^+$. |
| 106.0 | (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamide (Example 15.0), 6-methoxypicolino hydrazide, 2-isothiocyanato-1,3-dimethoxybenzene (Example 1.0). The racemic mixture was purified by preparative SFC with a Chiralpak AS-H column (250 × 21 m, 5 µm), 20% MeOH, 70 mL/min, 220 nm, 186 bar inlet pressure. | First eluting peak:<br>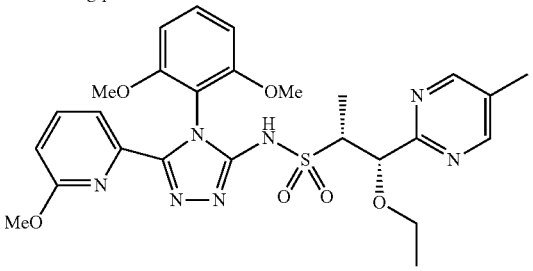<br>OR<br>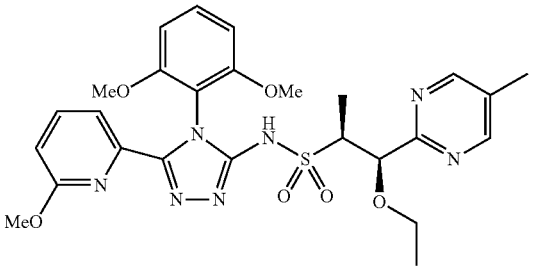 [SMILES: CCO[C@H](c1ncc(C)cn1)[C@H](C)S(=O)(=O)Nc1nnc(-c2cccc(OC)n2)n1-c1c(OC)cccc1OC]<br>(1S,2R)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.64 (s, 2H), 7.56-7.64 (m, 2H), 7.27-7.34 (m, 1H), 6.70 (dd, J = 7.4, 1.6 Hz, 1H), 6.59 (dd, J = 8.4, 2.0 Hz, 2H), 5.01 (d, J = 5.9 Hz, 1H), 3.79-3.89 (m, 1H), 3.72 (s, 3H), 3.69 (s, 3H), 3.52 (dd, J = 12.1, 6.8 Hz, 2H), 3.17 (s, 3H), 2.34 (s, 3H), 1.45 (d, J = 6.8 Hz, 3H), 1.15 (t, J = 7.0 Hz, 3H). LCMS-ESI (POS.) m/z: 569.9 (M + H)$^+$. |

TABLE 10-continued

| Example | Reagents | Structure, Name and Data |
|---|---|---|
| 107.0 | | Second eluting peak:<br>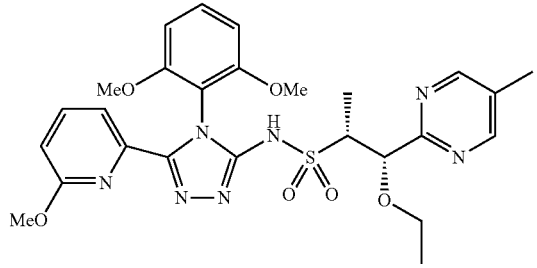 [SMILES: CCO[C@@H](c1ncc(C)cn1)[C@@H](C)S(=O)(=O)Nc1nnc(-c2cccc(OC)n2)n1-c1c(OC)cccc1OC]<br>OR<br>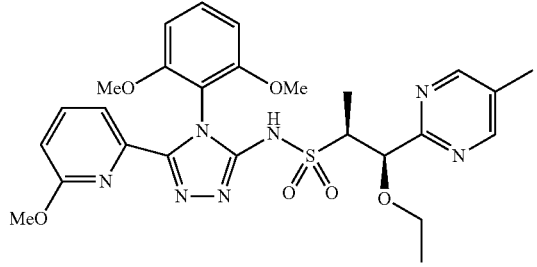 [SMILES: CCO[C@H](c1ncc(C)cn1)[C@H](C)S(=O)(=O)Nc1nnc(-c2cccc(OC)n2)n1-c1c(OC)cccc1OC]<br>(1S,2R)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.62 (s, 2H), 7.54-7.65 (m, 2H), 7.27-7.34 (m, 1H), 6.68 (d, J = 7.6 Hz, 1H), 6.58 (dd, J = 8.4, 2.5 Hz, 2H), 5.00 (d, J = 5.9 Hz, 1H), 3.78-3.87 (m, 1H), 3.71 (s, 3H), 3.68 (s, 3H), 3.51 (dd, J = 12.7, 6.8 Hz, 2H), 3.16 (s, 3H), 2.33 (s, 3H), 1.44 (d, J = 7.0 Hz, 3H), 1.14 (t, J = 6.9 Hz, 3H). LCMS-ESI (POS.) m/z: 570.0 (M + H)$^+$. |
| 108.0 | (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamide (Example 15.0), nicotinic hydrazide (Sigma-Aldrich), 2-isothiocyanato-1,3-dimethoxybenzene (Example 1.0). The racemic mixture was purified by preparative SFC with a Chiralpak AS-H column (250 × 21 m, 5 μm), 15% MeOH, 60 mL/min, 220 nm, 206-213 bar inlet pressure. | First eluting peak:<br>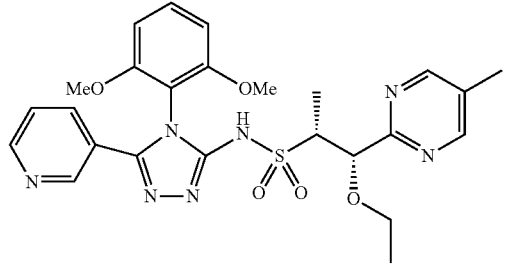 [SMILES: CCO[C@@H](c1ncc(C)cn1)[C@@H](C)S(=O)(=O)Nc1nnc(-c2cccnc2)n1-c1c(OC)cccc1OC]<br>(1S,2R)-N-(4-(2,6-dimethoxyphenyl)-5-(pyridin-3-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.57-8.67 (m, 4H), 7.83 (d, J = 8.2 Hz, 1H), 7.40 (t, J = 8.5 Hz, 1H), 7.34 (dd, J = 7.9, 5.0 Hz, 1H), 6.61 (dd, J = 7.7, 6.4 Hz, 2H), 5.00 (d, J = 5.7 Hz, 1H), 3.78-3.83 (m, 1H), 3.76 (s, 3H), 3.72 (s, 3H), 3.45-3.59 (m, 2H), 2.33 (s, 3H), 1.45 (d, J = 7.0 Hz, 3H), 1.15 (t, J = 6.9 Hz, 3H). LCMS-ESI (POS.) m/z: 540.0 (M + H)$^+$. |

TABLE 10-continued

| Example | Reagents | Structure, Name and and Data |
|---|---|---|
| 109.0 | | Second eluting peak: 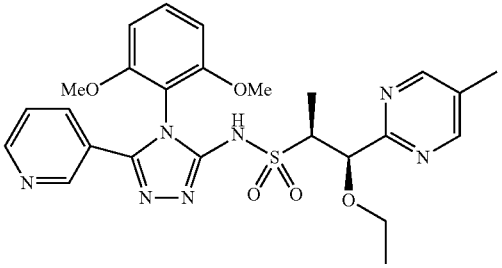 [SMILES: CCO[C@H](c1ncc(C)cn1)[C@H](C)S(=O)(=O)Nc1nnc(-c2cccnc2)n1-c1c(OC)cccc1OC]<br><br>(1R,2S)-N-(4-(2,6-dimethoxyphenyl)-5-(pyridin-3-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.58-8.68 (m, 4H), 7.88 (d, J = 7.4 Hz, 1H), 7.35-7.42 (m, 2H), 6.62 (dd, J = 8.4, 1.6 Hz, 2H), 5.00 (d, J = 5.7 Hz, 1H), 3.78-3.83 (m, 1H), 3.77 (s, 3H), 3.72 (s, 3H), 3.45-3.59 (m, 2H), 2.33 (s, 3H), 1.45 (d, J = 6.8 Hz, 3H), 1.15 (t, J = 7.0 Hz, 3H). LCMS-ESI (POS.) m/z: 540.0 (M + H)$^+$. |
| 110.0 | (1S,2S)-1-ethoxy-1-(5-methylpyrimidin-2-yl)propane-2-sulfonamide and (1R,2R)-1-ethoxy-1-(5-methylpyrimidin-2-yl)propane-2-sulfonamide (Example 15.1), 6-methoxypicolino hydrazide, 2-isothiocyanato-1,3-dimethoxybenzene (Example 1.0). The racemic mixture was purified by preparative SFC with a Chiralpak OZ-H column (250 × 21 m, 5 μm), 40% MeOH, 70 mL/min, 220 nm, 220-227 bar inlet pressure. | First eluting peak: 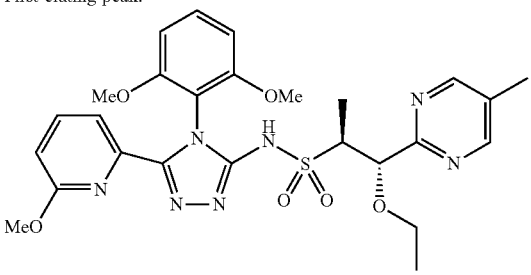<br><br>OR<br><br>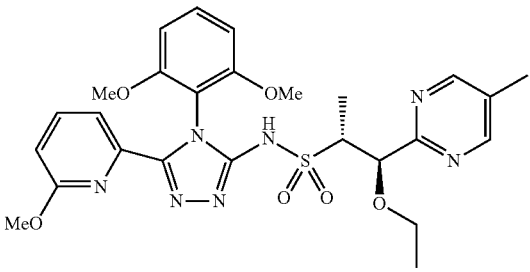 [SMILES: CCO[C@H](c1ncc(C)cn1)[C@@H](C)S(=O)(=O)Nc1nnc(-c2cccc(OC)n2)n1-c1c(OC)cccc1OC]<br><br>(1S,2S)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide or (1R,2R)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.69 (s, 2H), 7.61 (d, J = 4.3 Hz, 2H), 7.27-7.32 (m, 1H), 6.65-6.72 (m, 1H), 6.59 (dd, J = 14.2, 8.5 Hz, 2H), 4.83 (d, J = 5.1 Hz, 1H), 3.78 (s, 3H), 3.77-3.84 (m, 1H), 3.67 (s, 3H), 3.52-3.62 (m, 1H), 3.36-3.45 (m, 1H), 3.18 (s, 3H), 2.37 (s, 3H), 1.39 (d, J = 7.0 Hz, 3H), 1.11 (t, J = 7.1 Hz, 3H). LCMS-ESI (POS.) m/z: 570.0 (M + H)$^+$. |

US 9,868,721 B2

TABLE 10-continued

| Example | Reagents | Structure, Name and and Data |
|---|---|---|

111.0

Second eluting peak:

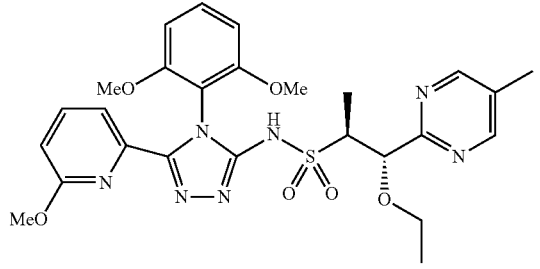 [SMILES: CCO[C@@H](c1ncc(C)cn1)[C@H](C)S(=O)(=O)Nc1nnc(-c2cccc(OC)n2)n1-c1c(OC)cccc1OC]

OR

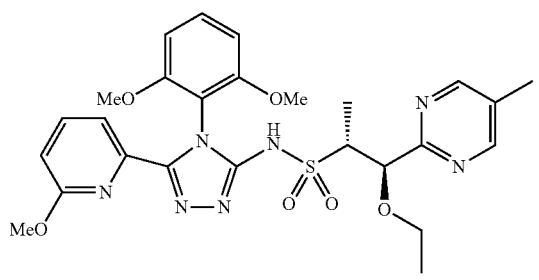 [SMILES: CCO[C@H](c1ncc(C)cn1)[C@@H](C)S(=O)(=O)Nc1nnc(-c2cccc(OC)n2)n1-c1c(OC)cccc1OC]

(1S,2S)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide or (1R,2R)-N-(4-(2,6-dimethoxyphenyl)-5-(6-methoxypyridin-2-yl)-4H-1,2,4-triazol-3-yl)-1-ethoxy-1-(5-methylpyrimidin-2-yl)propane-2-sulfonamide
$^1$H NMR (500 MHz, CDCl$_3$) δ: 8.66 (s, 2H), 7.61 (d, J = 2.7 Hz, 1H), 7.60 (s, 1H), 7.27-7.32 (m, 1H), 6.66-6.71 (m, 1H), 6.61 (d, J = 8.4 Hz, 1H), 6.58 (d, J = 8.4 Hz, 1H), 4.83 (d, J = 5.1 Hz, 1H), 3.73-3.83 (m, 4H), 3.68 (s, 3H), 3.50-3.59 (m, 1H), 3.34-3.45 (m, 1H), 3.18 (s, 3H), 2.36 (s, 3H), 1.37 (d, J = 7.0 Hz, 3H), 1.10 (t, J = 6.9 Hz, 3H). LCMS-ESI (POS.) m/z: 570.0 (M + H)$^+$.

112.0    (S)-1-(5-fluoropyrimidin-2-yl)propane-2-sulfonamide and (R) 1-(5-fluoropyrmidin-2-yl)propane-2-sulfonamide (Example 9.0) and 5-methoxynicotinohydrazide (Example 3.3), 2-isothiocyanato-1,3-dimethoxybenzene (Example 1.0), and mercury (II) acetate (comercially available from VWR International, Radnor, PA, USA) was used instead of silver nitrate, TFA was used instead of methanesulfonic acid.

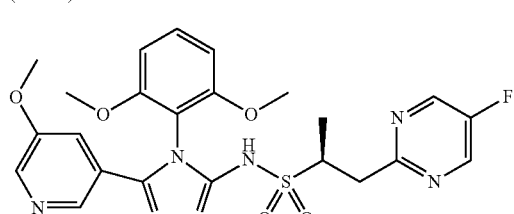

AND (2S)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide
$^1$H NMR (CDCl$_3$) δ: 11.19 (br s, 1H), 8.54 (s, TABLE 10-continued

| Example | Reagents | Structure, Name and and Data |
|---|---|---|
| | | 2H), 8.34 (d, J = 2.7 Hz, 1H), 8.21 (s, 1H), 7.36-7.46 (m, 2H), 6.64 (dd, J = 8.5, 1.1 Hz, 2H), 3.81 (s, 3H), 3.77 (s, 3H), 3.74 (s, 3H), 3.66-3.73 (m, 1H), 3.09 (dd, J = 14.8, 9.9 Hz, 2H), 2.05 (s, 1H), 1.32 (d, J = 6.8 Hz, 3H). LCMS-ESI (POS.) m/z: 529.7 (M + H)+. |
| 113.0 | The racemic compound 112.0 was separated by supercritical fluid chromatography (2 × 15 cm AD-H column with 60 mL/min 20% MeOH (0.1% NH4OH)/CO2. Outlet pressure = 100 bar; wavelength = 220 nm; injection volume = 0.5-1 mL, 7 mg/mL MeOH). The was the first isomer to elute under these conditions. | 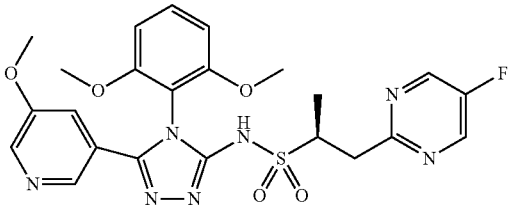 [SMILES: COc1cncc(-c2nnc(NS(=O)(=O)[C@@H](C)Cc3ncc(F)cn3)n2-c2c(OC)cccc2OC)c1]<br>OR<br>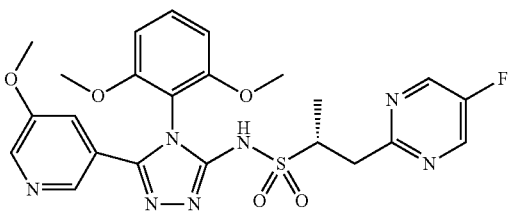 [SMILES: COc1cncc(-c2nnc(NS(=O)(=O)[C@H](C)Cc3ncc(F)cn3)n2-c2c(OC)cccc2OC)c1]<br>(2S)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide<br>$^1$H NMR (400 MHz, DMSO-d$_6$) δ: 13.48 (br. s, 1H), 8.85 (d, J = 0.8 Hz, 2H), 8.37 (d, J = 2.9 Hz, 1H), 8.13 (d, J = 1.6 Hz, 1H), 7.53 (t, J = 8.5 Hz, 1H), 7.20 (dd, J = 2.7, 1.8 Hz, 1H), 6.79-6.95 (m, 2H), 3.73 (s, 3H), 3.73 (s, 6H), 3.44-3.57 (m, 2H), 2.76-2.97 (m, 1H), 1.12 (d, J = 6.8 Hz, 3H). LCMS-ESI (POS.) m/z: 529.7 (M + H)+. |
| 114.0 | The racemic compound 112.0 was separated by supercritical fluid chromatography (2 × 15 cm AD-H column with 60 mL/min 20% MeOH (0.1% NH4OH)/CO2. Outlet pressure = 100 bar; wavelength = 220 nm; injection volume = 0.5-1 mL, 7 mg/mL MeOH). The was the first isomer to elute under these conditions. | 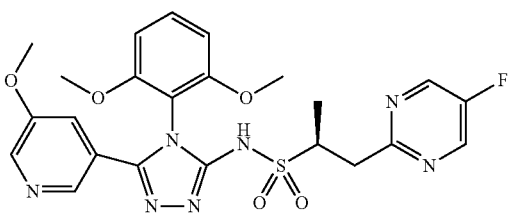 [SMILES: COc1cncc(-c2nnc(NS(=O)(=O)[C@@H](C)Cc3ncc(F)cn3)n2-c2c(OC)cccc2OC)c1]<br>OR<br>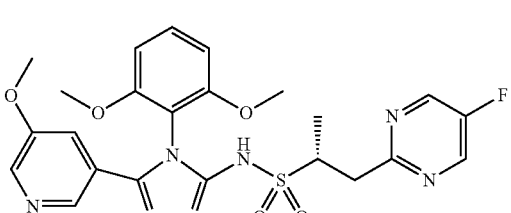<br>(2S)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide<br>$^1$H NMR (400 MHz, DMSO-d$_6$) δ: 13.49 (br. s, 1H), 8.72-8.92 (m, 2H), 8.36 (s, 1H), 8.13 (d, |

| Example | Reagents | Structure, Name and and Data |
|---|---|---|
| | | J = 1.8 Hz, 1H), 7.52 (t, J = 8.5 Hz, 1H), 7.19 (d, J = 1.8 Hz, 1H), 6.86 (d, J = 8.6 Hz, 2H), 3.73 (s, 3H), 3.72 (s, 6H), 3.44-3.62 (m, 2H), 2.86 (dd, J = 14.2, 10.7 Hz, 1H), 1.11 (d, J = 6.8 Hz, 3H). LCMS-ESI (POS.) m/z: 529.7 (M + H)+. |
| 115.0 | (S)-1-(5-fluoropyrimidin-2-yl)propane-2-sulfonamide and (R)-1-(5-fluoropyrimidin-2-yl)propane-2-sulfonamide (Example 9.0) and 6-methoxypicolinohydrazide (comercially available from Sigma-Aldrich Corp, St. Louis, MO, USA), 2-isothiocyanato-1,3-dimethoxybenzene (Example 1.0), TFA was used instead of methanesulfonic acid. | 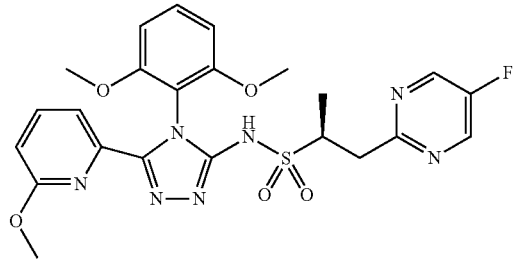 [SMILES: COc1cccc(-c2nnc(NS(=O)(=O)[C@@H](C)Cc3ncc(F)cn3)n2-c2c(OC)cccc2OC)n1]<br>AND<br>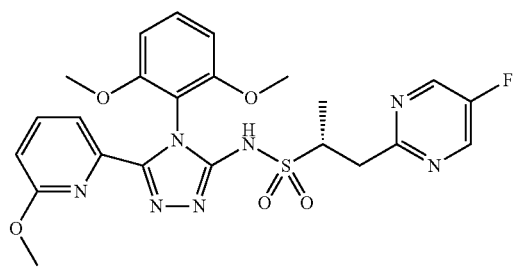 [SMILES: COc1cccc(-c2nnc(NS(=O)(=O)[C@H](C)Cc3ncc(F)cn3)n2-c2c(OC)cccc2OC)n1]<br>(2S)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(6-methoxy-3-pyridinyl)-4H-1,2,4-triazol-3-yl)-1-(5-fluoro-2-pyrimidinyl)-2-propanesulfonamide<br>1H NMR (400 MHz, CDCl3) δ: 1.11 (br s, 1H), 8.53 (s, 2H), 7.53-7.66 (m, 2H), 7.32 (s, 1H), 6.70 (dd, J = 7.6, 1.4 Hz, 1H), 6.60 (dd, J = 8.6, 2.0 Hz, 2H), 3.92-4.11 (m, 1H), 3.85-3.90 (m, 1H), 3.80 (ddd, J = 9.9, 6.7, 4.3 Hz, 1H), 3.64-3.75 (m, 6H), 3.17 (s, 3H), 3.10 (dd, J = 14.8, 9.9 Hz, 1H), 1.31 (d, J = 6.7 Hz, 3H). LCMS-ESI (POS.) m/z: 529.7 (M + H)+. |
| 116.0 | The racemic compound 115.0 was separated by superficial fluid chromatography (2 × 15 cm IA column with 60 mL/min 20% MeOH/CO2. Outlet pressure = 100 bar; wavelength = 220 nm; injection volume = 1 mL, 8 mg/mL 1:2 DCM:MeOH). This was the first isomer to elute under these conditions. | 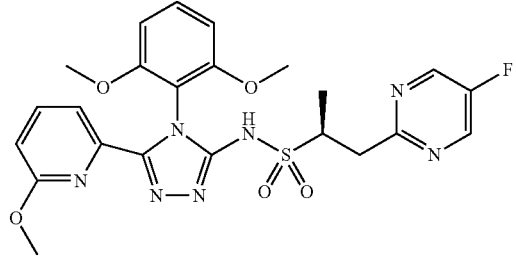 [SMILES: COc1cccc(-c2nnc(NS(=O)(=O)[C@@H](C)Cc3ncc(F)cn3)n2-c2c(OC)cccc2OC)n1]<br>OR<br>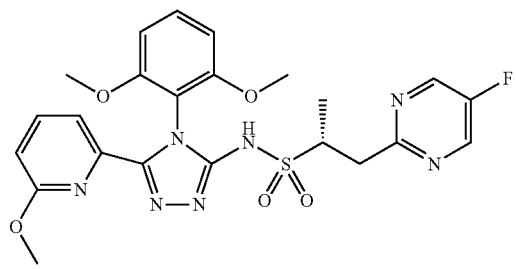 [SMILES: COc1cccc(-c2nnc(NS(=O)(=O)[C@H](C)Cc3ncc(F)cn3)n2-c2c(OC)cccc2OC)n1] |

TABLE 10-continued

| Example | Reagents | Structure, Name and and Data |
|---|---|---|
| | | (2S)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide<br>$^1$H NMR (400 MHz, DMSO-d$_6$) δ: 13.36 (br. s, 1H), 8.85 (d, J = 0.8 Hz, 2H), 7.81 (t, J = 7.9 Hz, 1H), 7.60 (d, J = 6.8 Hz, 1H), 7.42 (t, J = 8.5 Hz, 1H), 6.72-6.90 (m, 3H), 3.65 (s, 3H), 3.66 (s, 3H), 3.42-3.58 (m, 2H), 3.11 (s, 3H), 2.85 (dd, J = 14.4, 10.7 Hz, 1H), 1.11 (d, J = 6.8 Hz, 3H). LCMS-ESI (POS.) m/z: 529.7 (M + H)$^+$. |
| 117.0 | The racemic compound 115.0 was separated by superficial fluid chromatography (2 × 15 cm IA column with 60 mL/min 20% MeOH/CO$_2$. Outlet pressure = 100 bar; wavelength = 220 nm; injection volume = 1 mL, 8 mg/mL 1:2 DCM:MeOH). This was the second isomer to elute under these conditions. | 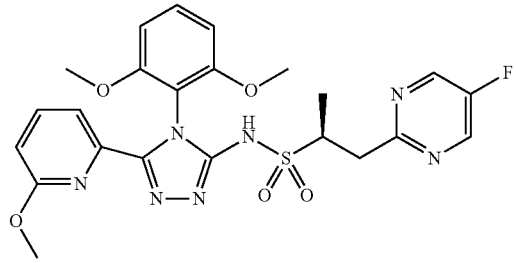 [SMILES: COc1cccc(-c2nnc(NS(=O)(=O)[C@@H](C)Cc3ncc(F)cn3)n2-c2c(OC)cccc2OC)n1]<br>OR<br>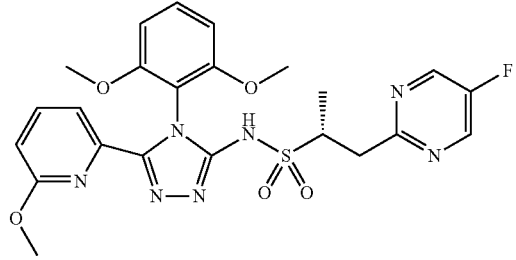 [SMILES: COc1cccc(-c2nnc(NS(=O)(=O)[C@H](C)Cc3ncc(F)cn3)n2-c2c(OC)cccc2OC)n1]<br>(2S)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide<br>$^1$H NMR (400 MHz, DMSO-d$_6$) δ: 13.36 (br. s, 1H), 8.77-8.93 (m, 2H), 7.81 (t, J = 7.8 Hz, 1H), 7.59 (d, J = 7.2 Hz, 1H), 7.41 (t, J = 8.5 Hz, 1H), 6.70-6.90 (m, 3H), 3.65 (s, 3H), 3.66 (s, 3H), 3.43-3.62 (m, 2H), 3.11 (s, 3H), 2.85 (dd, J = 14.3, 10.8 Hz, 1H), 1.11 (d, J 6.8 Hz, 3H). LCMS-ESI (POS.) m/z: 529.7 (M + H)$^+$. |
| 118.0 | (S)-1-(5-fluoropyrimidin-2-tl)propane-2-sulfonamide and (R)-1-(5-fluoropyrimidin-2-yl)propane-2-sulfonamide (Example 9.0) and 2-methylisonicotinohydrazide (Example 3.44), 2-isothiocyanato-1,3-dimethoxybenzene (Example 1.0), TFA was used instead of methanesulfonic acid. | 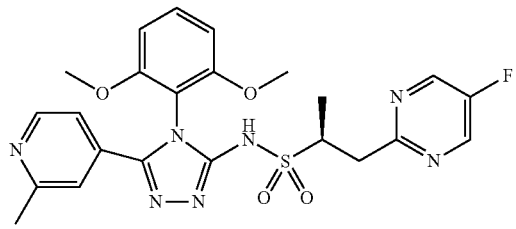 [SMILES: COc1cccc(OC)c1-n1c(NS(=O)(=O)[C@@H](C)Cc2ncc(F)cn2)nnc1-c1ccnc(C)c1]<br>AND |

TABLE 10-continued

| Example | Reagents | Structure, Name and and Data |
|---|---|---|
| | | 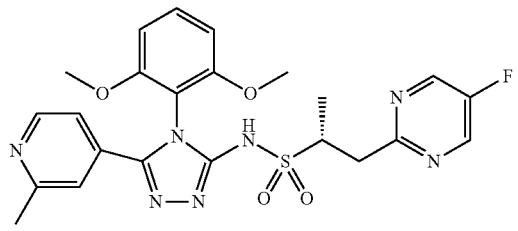 [SMILES: COc1cccc(OC)c1-n1c(NS(=O)(=O)[C@H](C)Cc2ncc(F)cn2)nnc1-c1ccnc(C)c1] (2S)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide<br>$^1$H NMR (400 MHz, DMSO-$d_6$) δ: 8.56 (s, 2H), 8.46 (d, J = 5.3 Hz, 1H), 7.45 (t, J = 8.5 Hz, 1H), 7.32 (s, 1H), 7.02 (d, J = 5.3 Hz, 1H), 6.66 (dd, J = 8.5, 1.1 Hz, 2H), 3.79-3.93 (m, 1H), 3.75 (s, 3H), 3.77 (s, 3H), 3.66-3.73 (m, 1H), 3.11 (dd, J = 14.8, 9.9 Hz, 1H), 2.55 (s, 3H), 1.34 (d, J = 6.7 Hz, 3H). LCMS-ESI (POS.) m/z: 513.8 (M + H)$^+$. |
| 119.0 | The racemic compound 118.0 was separated by superficial fluid chromatography (2 × 15 cm AD-H column with 60 mL/min 15% MeOH/CO$_2$. Outlet pressure = 100 bar; wavelength = 220 nm; injection volume = 0.5-1 mL, 6 mg/mL 1:1 DCM:MeOH). This was the first isomer to elute under these conditions. | 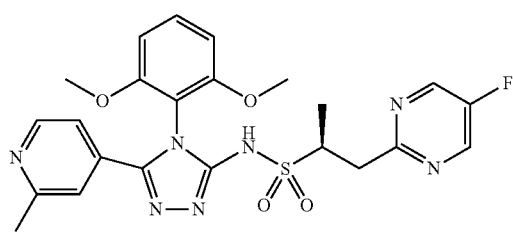 [SMILES: COc1cccc(OC)c1-n1c(NS(=O)(=O)[C@@H](C)Cc2ncc(F)cn2)nnc1-c1ccnc(C)c1]<br>OR<br>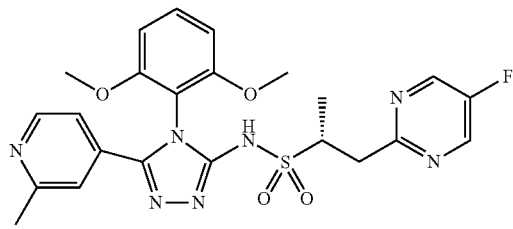 [SMILES: COc1cccc(OC)c1-n1c(NS(=O)(=O)[C@H](C)Cc2ncc(F)cn2)nnc1-c1ccnc(C)c1]<br>(2S)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide<br>$^1$H NMR (400 MHz, DMSO-$d_6$) δ: 13.54 (br. s, 1H), 8.85 (d, J = 0.8 Hz, 2H), 8.44 (d, J = 5.3 Hz, 1H), 7.54 (t, J = 8.5 Hz, 1H), 7.26 (s, 1H), 6.98 (dd, J = 5.2, 1.1 Hz, 1H), 6.86 (dd, J = 8.6, 1.2 Hz, 2H), 3.72 (s, 3H), 3.71 (s, 3H), 3.42-3.62 (m, 2H), 2.85 (dd, J = 14.4, 10.5 Hz, 1H), 2.43 (s, 3H), 1.11 (d, J = 6.8 Hz, 3H). LCMS-ESI (POS.) m/z: 513.8 (M + H)$^+$. |
| 120.0 | The racemic compound 118.0 was separated by superficial fluid chromatography (2 × 15 cm AD-H column with 60 mL/min 15% MeOH/CO$_2$. Outlet pressure = 100 bar; wavelength = 220 nm; injection volume = 0.5-1 mL, 6 mg/mL 1:1 DCM:MeOH). This was the second isomer to elute under these conditions | 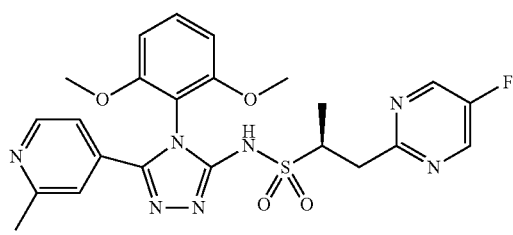 [SMILES: COc1cccc(OC)c1-n1c(NS(=O)(=O)[C@@H](C)Cc2ncc(F)cn2)nnc1-c1ccnc(C)c1] |

TABLE 10-continued

| Example | Reagents | Structure, Name and and Data |
|---|---|---|
| | | OR<br>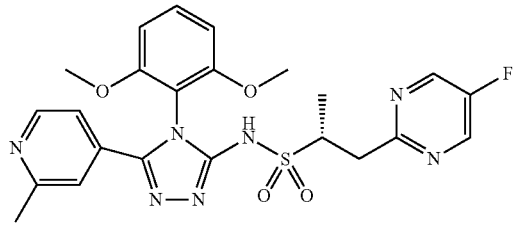 [SMILES: COc1cccc(OC)c1-n1c(NS(=O)(=O)[C@H](C)Cc2ncc(F)cn2)nnc1-c1ccnc(C)c1]<br>(2S)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide<br>$^1$H NMR (400 MHz, DMSO-d$_6$) δ: 13.54 (br. s, 1H), 8.85 (d, J = 0.8 Hz, 2H), 8.45 (d, J = 5.1 Hz, 1H), 7.54 (t, J = 8.5 Hz, 1H), 7.26 (s, 1H), 6.98 (dd, J = 5.2, 1.1 Hz, 1H), 6.87 (dd, J = 8.6, 1.4 Hz, 2H), 3.72 (s, 3H), 3.71 (s, 3H), 3.41-3.61 (m, 2H), 2.85 (dd, J = 14.2, 10.5 Hz, 1H), 2.43 (s, 3H), 1.12 (d, J = 6.7 Hz, 3H). LCMS-ESI (POS.) m/z: 513.8 (M + H)$^+$. |
| 121.0 | (1R,2S)-1-((tert-butyldimethylsilyl)oxy)-1-(5-fluoropyrimidin-2-yl)propane-2-sulfonamide and (1R,2S)-1-((tert-butyldimethylsilyl)oxy)-1-(5-fluoropyrimidin-2-yl)propane-2-sulfonamide (Example 11.0), 6-methylpicolinohydrazide (Example 3.4), 2-isothiocyanato-1,3-dimethoxybenzene (Example 1.0), TFA was used instead of methanesulfonic acid | 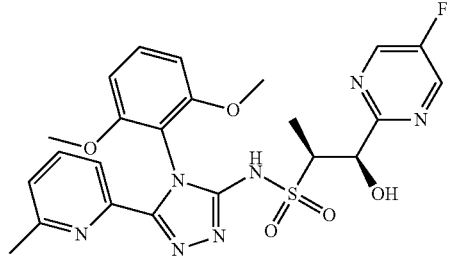 [SMILES: COc1cccc(OC)c1-n1c(NS(=O)(=O)[C@@H](C)[C@H](O)c2ncc(F)cn2)nnc1-c1cccc(C)n1]<br>AND<br>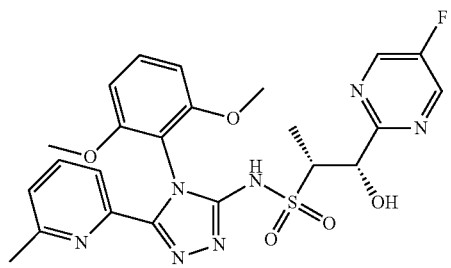 [SMILES: COc1cccc(OC)c1-n1c(NS(=O)(=O)[C@H](C)[C@@H](O)c2ncc(F)cn2)nnc1-c1cccc(C)n1]<br>(1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide and (1R,2S)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide<br>$^1$H NMR (400 MHz, CDCl$_3$) δ: 8.64 (s, 2H), 7.55-7.65 (m, 2H), 7.39 (t, J = 8.4 Hz, 1H), 7.06-7.17 (m, 1H), 6.65 (d, J = 8.6 Hz, 1H), 6.60 (d, J = 7.8 Hz, 1H), 5.66 (s, 1H), 3.83-3.92 (m, 1H), 3.77 (s, 3H), 3.71 (s, 3H), 2.24 (s, 3H), 1.27 (d, J = 7.0 Hz, 3H). LCMS-ESI (POS.) m/z: 529.7 (M + H)$^+$. |

TABLE 10-continued

| Example | Reagents | Structure, Name and and Data |
|---|---|---|
| 122.0 | The racemic compound 121.0 was separated by superficial fluid chromatography (2 × 15 cm IC column with 60 mL/min 40% MeOH/CO$_2$. Outlet pressure = 100 bar; wavelength = 220 nm; injection volume = 1 mL, 6 mg/mL MeOH). This was the first isomer to elute under these conditions | 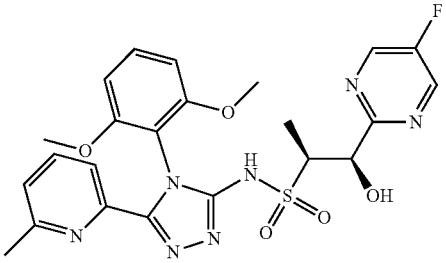 [SMILES: COc1cccc(OC)c1-n1c(NS(=O)(=O)[C@@H](C)[C@H](O)c2ncc(F)cn2)nnc1-c1cccc(C)n1]<br>OR<br>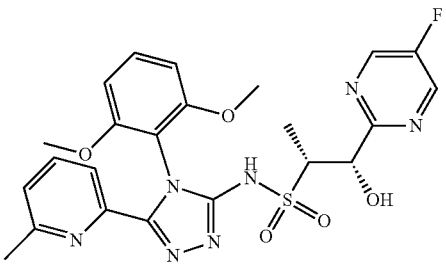 [SMILES: COc1cccc(OC)c1-n1c(NS(=O)(=O)[C@H](C)[C@@H](O)c2ncc(F)cn2)nnc1-c1cccc(C)n1]<br>(1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide<br>$^1$H NMR (400 MHz, DMSO-d$_6$) δ: 11.00 (br s, 1H), 8.61 (s, 2H), 7.58 (d, J = 4.7 Hz, 2H), 7.36 (t, J = 8.5 Hz, 1H), 7.10 (t, J = 4.3 Hz, 1H), 6.58 (d, J = 8.4 Hz, 1H), 6.63 (d, J = 8.4 Hz, 1H), 5.64 (s, 1H), 3.78-3.88 (m, 1H), 3.74 (s, 3H), 3.69 (s, 3H), 2.22 (s, 3H), 1.24 (d, J = 7.0 Hz, 3H). LCMS-ESI (POS.) m/z: 529.7 (M + H)$^+$. |
| 123.0 | The racemic compound 121.0 was separated by superficial fluid chromatography (2 × 15 cm IC column with 60 mL/min 40% MeOH/CO$_2$. Outlet pressure = 100 bar; wavelength = 220 nm; injection volume = 1 mL, 6 mg/mL MeOH). This was the second isomer to elute under these conditions | 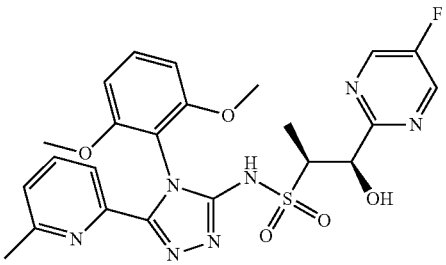 [SMILES: COc1cccc(OC)c1-n1c(NS(=O)(=O)[C@@H](C)[C@H](O)c2ncc(F)cn2)nnc1-c1cccc(C)n1]<br>OR<br>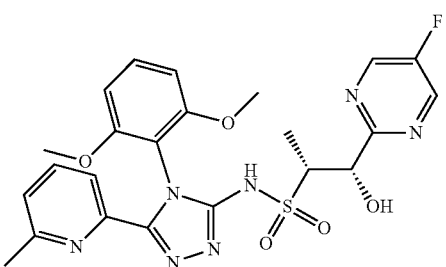 [SMILES: COc1cccc(OC)c1-n1c(NS(=O)(=O)[C@H](C)[C@@H](O)c2ncc(F)cn2)nnc1-c1cccc(C)n1]<br>(1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(6-methyl-2-pyridinyl)-4H-1,2,4-triazol-3-yl)-1-(5-fluoro-2- |

| Example | Reagents | Structure, Name and and Data |
|---|---|---|
| | | pyrimidinyl)-1-hydroxy-2-propanesulfonamide $^1$H NMR (400 MHz, DMSO-d$_6$) δ: 8.52 (s, 2H), 7.48 (s, 2H), 7.28 (t, J = 8.4 Hz, 1H), 7.01 (d, J = 6.5 Hz, 1H), 6.54 (d, J = 8.6 Hz, 1H), 6.50 (d, J = 8.2 Hz, 1H), 5.56 (s, 1H), 3.74 (d, J = 6.8 Hz, 1H), 3.65 (s, 3H), 3.60 (s, 3H), 2.15 (s, 3H), 1.16 (d, J = 6.8 Hz, 3H). LCMS-ESI (POS.) m/z: 529.7 (M + H)$^+$. |
| 124.0 | (1R,2S)-1-((tert-butyldimethylsilyl)oxy)-1-(5-fluoropyrimidin-2-yl)propane-2-sulfonamide and (1R,2S)-1-((tert-butyldimethylsilyl)oxy)-1-(5-fluoropyrimidin-2-yl)propane-2-sulfonamide (Example 11.0), 5-methylnicotinohydrazide (comercially available from Bellen Chemistry Co. Shun Yi District, Beijing, China) 2-isothiocyanato-1,3-dimethoxybenzene (Example 1.0), TFA (comercially available from Sigma-Aldrich Corp, St. Louis MO, USA) was used instead of methanesulfonic acid | 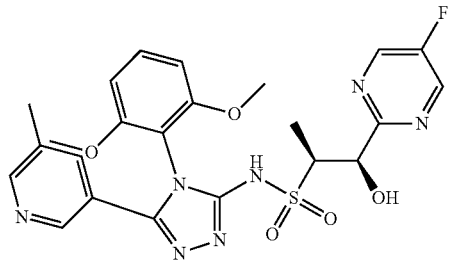 [SMILES: COc1cccc(OC)c1-n1c(NS(=O)(=O)[C@@H](C)[C@H](O)c2ncc(F)cn2)nnc1-c1cncc(C)c1] AND 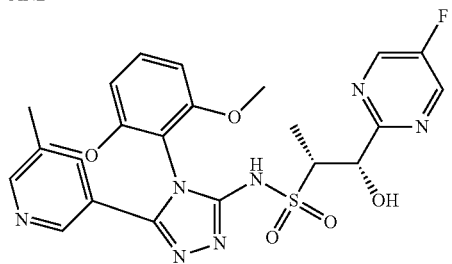 (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide and (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide $^1$H NMR (400 MHz, DMSO-d$_6$) δ: 8.64 (s, 2H), 8.58 (s, 1H), 8.41 (s, 1H), 8.13 (s, 1H), 7.47 (s, 1H), 6.67 (d, J = 8.2 Hz, 1H), 6.62 (d, J = 8.8 Hz, 1H), 5.60 (s, 1H), 3.87 (d, J = 3.5 Hz, 1H), 3.81 (s, 3H), 3.78 (s, 3H), 2.48 (s, 3H), 1.07-1.27 (m, 3H). LCMS-ESI (POS.) m/z: 529.7 (M + H)$^+$. |
| 125.0 | The racemic compound 124.0 was separated by superficial fluid chromatography (2 × 15 cm AD-H column with 50 mL/min 50% IPA (0.1% N-propyl amine)/CO$_2$. Outlet pressure = 100 bar; wavelength = 220 nm; injection volume = 0.7 mL, 5 mg/mL 1:2 DCM:MeOH). This was the first isomer to elute under these conditions | 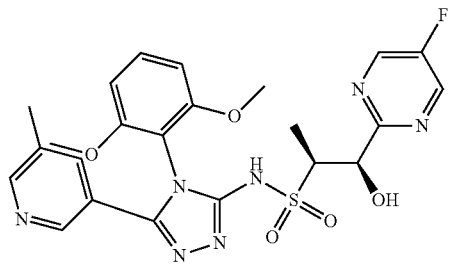 [SMILES: COc1cccc(OC)c1-n1c(NS(=O)(=O)[C@@H](C)[C@H](O)c2ncc(F)cn2)nnc1-c1cncc(C)c1] OR 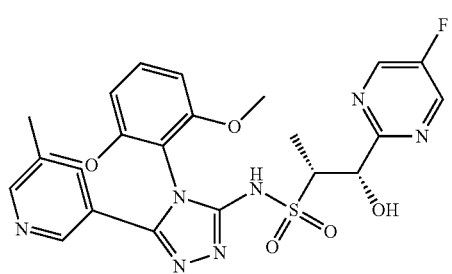 [SMILES: COc1cccc(OC)c1-n1c(NS(=O)(=O)[C@H](C)[C@@H](O)c2ncc(F)cn2)nnc1-c1cncc(C)c1] |

TABLE 10-continued

| Example | Reagents | Structure, Name and and Data |
|---|---|---|
| | | (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide <br> $^1$H NMR (400 MHz, DMSO-d$_6$) δ: 8.62 (s, 2H), 8.46 (s, 1H), 8.34 (s, 1H), 7.69 (s, 1H), 7.41 (t, J = 8.6 Hz, 1H), 6.65 (d, J = 8.4 Hz, 1H), 6.61 (d, J = 8.2 Hz, 1H), 5.62 (s, 1H), 3./81-3.84 (m, 1H), 3.78 (s, 3H), 3.73 (s, 3H), 2.32 (s, 3H), 1.23 (d, J = 6.8 Hz, 3H). LCMS-ESI (POS.) m/z: 529.7 (M + H)$^+$. |
| 126.0 | The racemic compound 124.0 was separated by superficial fluid chromatography (2 × 15 cm AD-H column with 50 mL/min 50% IPA (0.1% N-propyl amine)/CO$_2$. Outlet pressure = 100 bar; wavelength = 220 nm; injection volume = 0.7 mL, 5 mg/mL 1:2 DCM:MeOH). This was the second isomer to elute under these conditions | 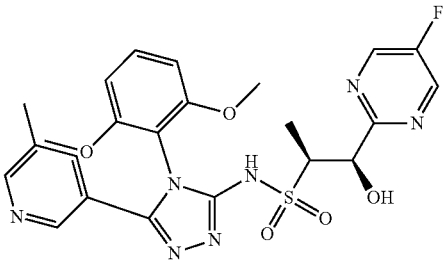 [SMILES: COc1cccc(OC)c1-n1c(NS(=O)(=O)[C@@H](C)[C@H](O)c2ncc(F)cn2)nnc1-c1cncc(C)c1] <br> OR <br> 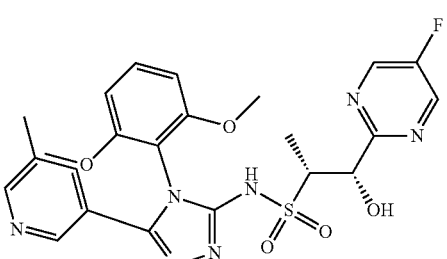 <br> (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide <br> $^1$H NMR (400 MHz, DMSO-d$_6$) δ: 8.62 (s, 2H), 8.46 (s, 1H), 8.34 (s, 1H), 7.68 (s, 1H), 7.41 (t, J = 8.5 Hz, 1H), 6.65 (d, J = 8.4 Hz, 1H), 6.61 (d, J = 8.2 Hz, 1H), 5.62 (s, 1H), 3.80-3.86 (m, 1H), 3.78 (s, 3H), 3.73 (s, 3H), 2.32 (s, 3H), 1.21-1.25 (m, 3H). LCMS-ESI (POS.) m/z: 529.7 (M + H)$^+$. |
| 127.0 | (2R,3S)-3-(5-fluoropyrimidin-2-yl)butane-2-sulfonamide and (2S,3R)-3-(5-fluoropyrimidin-2-yl)butane-2-sulfonamide (Example 10.0), 6-methoxypicolinohydrazide (comercially available from Sigma-Aldrich Corp, St. Louis, MO, USA), 2-isothiocyanato-1,3-dimethoxybenzene (Example 1.0), TFA (comercially available from Sigma-Aldrich Corp, St. Louis, MO, USA) was used instead of methanesulfonic acid | 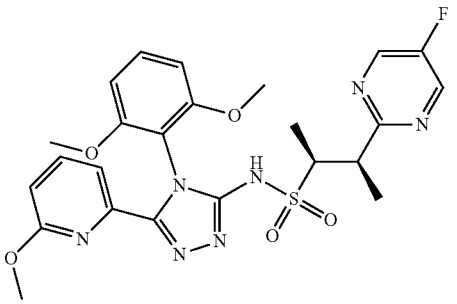 [SMILES: COc1cccc(-c2nnc(NS(=O)(=O)[C@@H](C)[C@H](C)c3ncc(F)cn3)n2-c2c(OC)cccc2OC)n1] <br> AND |

| Example | Reagents | Structure, Name and and Data |
|---------|----------|------------------------------|
| | | 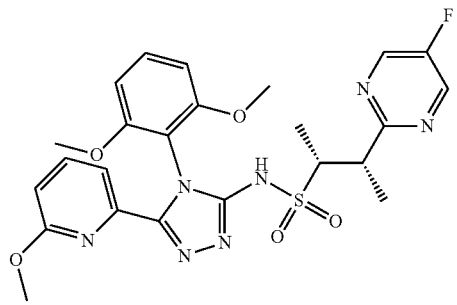 [SMILES: COc1cccc(-c2nnc(NS(=O)(=O)[C@H](C)[C@@H](C)c3ncc(F)cn3)n2-c2c(OC)cccc2OC)n1]

(2R,3S)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide and (2S,3R)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide
¹H NMR (400 MHz, DMSO-d₆) δ: 8.54 (s, 2H), 7.53-7.74 (m, 2H), 7.31 (t, J = 8.4 Hz, 1H), 6.70 (dd, J = 7.6, 1.4 Hz, 1H), 6.53-6.63 (m, 2H), 3.77-3.93 (m, 2H), 3.71 (s, 3H), 3.68 (s, 3H), 3.17 (s, 3H), 1.38 (d, J = 6.8 Hz, 3H), 1.36 (d, J = 6.8 Hz, 3H). LCMS-ESI (POS.) m/z: 543.8 (M + H)⁺. |
| 128.0 | The racemic compound 127.0 was separated by superficial fluid chromatography (2 × 25 cm AS-H column with 60 mL/min 15% MeOH/CO₂. Outlet pressure = 100 bar; wavelength = 220 nm; injection volume = 0.8 mL, 6 mg/mL 1:1 DCM:MeOH). This was the first isomer to elute under these conditions | 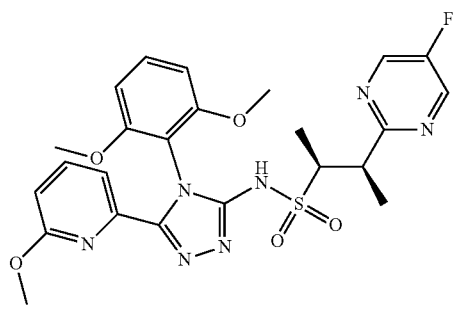 [SMILES: COc1cccc(-c2nnc(NS(=O)(=O)[C@@H](C)[C@H](C)c3ncc(F)cn3)n2-c2c(OC)cccc2OC)n1]

OR

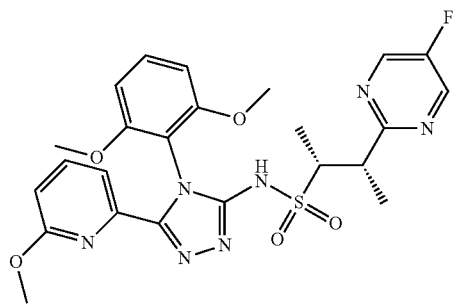 [SMILES: COc1cccc(-c2nnc(NS(=O)(=O)[C@H](C)[C@@H](C)c3ncc(F)cn3)n2-c2c(OC)cccc2OC)n1]

(2R,3S)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide or (2S,3R)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide
¹H NMR (400 MHz, CDCl₃) δ: 8.54 (s, 2H), 7.54-7.67 (m, 2H), 7.31 (t, J = 8.4 Hz, 1H), 6.70 (dd, J = 7.6, 1.4 Hz, 1H), 6.52-6.65 (m, 2H), 3.76-3.91 (m, 2H), 3.71 (s, 3H), 3.68 (s, 3H), 3.17 (s, 3H), 1.31-1.43 (m, 6H). LCMS-ESI (POS.) m/z: 543.8 (M + H)⁺. |

TABLE 10-continued

| Example | Reagents | Structure, Name and and Data |
|---|---|---|
| 129.0 | The racemic compound 127.0 was separated by superficial fluid chromatography (2 × 25 cm AS-H column with 60 mL/min 15% MeOH/CO$_2$. Outlet pressure = 100 bar; wavelength = 220 nm; injection volume = 0.8 mL, 6 mg/mL 1:1 DCM:MeOH). This was the second isomer to elute under these conditions | 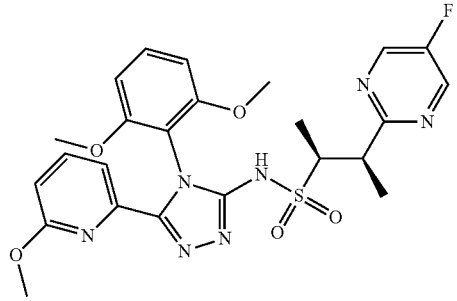 [SMILES: COc1cccc(-c2nnc(NS(=O)(=O)[C@@H](C)[C@H](C)c3ncc(F)cn3)n2-c2c(OC)cccc2OC)n1]<br>OR<br>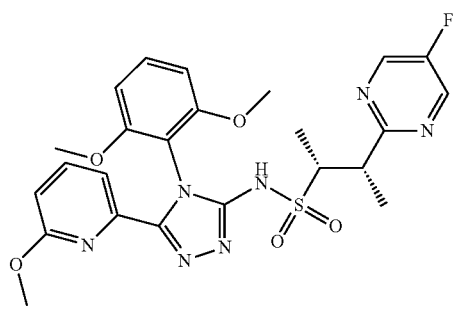 [SMILES: COc1cccc(-c2nnc(NS(=O)(=O)[C@H](C)[C@@H](C)c3ncc(F)cn3)n2-c2c(OC)cccc2OC)n1]<br>(2R,3S)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide or (2S,3R)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide <sup></sup>$^1$H NMR (400 MHz, CDCl$_3$) δ: 8.54 (s, 2H), 7.52-7.72 (m, 2H), 7.31 (t, J = 8.4 Hz, 1H), 6.70 (d, J = 7.4 Hz, 1H), 6.59 (t, J = 6.6 Hz, 2H), 3.85 (m, 2H), 3.71 (s, 3H), 3.68 (s, 3H), 3.17 (s, 3H), 1.36 (t, J = 6.4 Hz, 6H). LCMS-ESI (POS.) m/z: 543.8 (M + H)$^+$. |
| 130.0 | (1S,2R)-1-((tert-butyldimethylsilyl)oxy)-1-(5-fluoropyrimidin-2-yl)propane-2-sulfonamide and (1R,2S)-1-((tert-butyldimethylsilyl)oxy)-1-(5-fluoropyrimidin-2-yl)propane-2-sulfonamide (Example 11.0), 6-methoxypicolinohydrazide (comercially available from Sigma-Aldrich Corp, St. Louis, MO, USA), 2-isothiocyanato-1,3-dimethoxybenzene (Example 1.0), TFA (comercially available from Sigma-Aldrich Corp, St. Louis, MO, USA) was used instead of methanesulfonic acid | 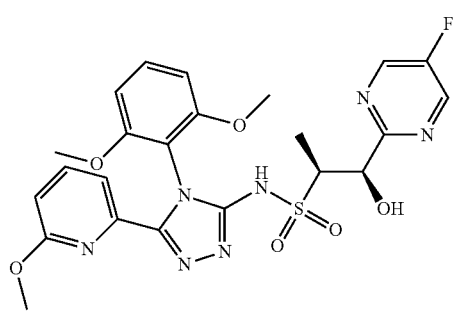 [SMILES: COc1cccc(-c2nnc(NS(=O)(=O)[C@@H](C)[C@H](O)c3ncc(F)cn3)n2-c2c(OC)cccc2OC)n1]<br>AND<br>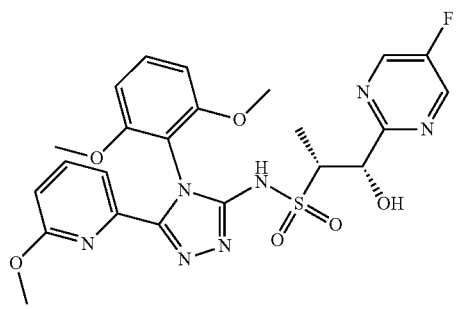 [SMILES: COc1cccc(-c2nnc(NS(=O)(=O)[C@H](C)[C@@H](O)c3ncc(F)cn3)n2-c2c(OC)cccc2OC)n1] |

TABLE 10-continued

| Example | Reagents | Structure, Name and Data |
|---|---|---|
| | | (1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-proanesulfonamide<br>$^1$H NMR (400 MHz, CDCl$_3$) δ: 11.12 (br s, 1H), 8.67 (s, 2H), 7.58-7.71 (m, 2H), 7.35 (t, J = 8.5 Hz, 1H), 6.56-6.81 (m, 3H), 5.64 (s, 1H), 3.84-3.88 (m, 1H), 3.78 (s, 3H), 3.71 (s, 3H), 3.18 (s, 3H), 1.25 (d, J = 7.0 Hz, 3H). LCMS-ESI (POS.) m/z: 545.8 (M + H)$^+$. |
| 131.0 | The racemic compound 130.0 was separated by superficial fluid chromatography (250 × 21 m AD-H column on Thar 80 with 25 g/min EtOH(neat) + 30 g/min CO$_2$, 45% co-solvent at 55 g/min. Outlet pressure = 100 bar; wavelength = 297 nm; injection volume = 0.8 mL of 130 mg sample disolved in 19 mL of (1:1) MeOH:DCM). This was the first isomer to elute under these conditions | 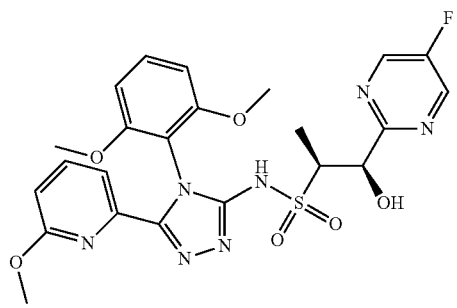 [SMILES: COc1cccc(-c2nnc(NS(=O)(=O)[C@@H](C)[C@H](O)c3ncc(F)cn3)n2-c2c(OC)cccc2OC)n1]<br>OR<br>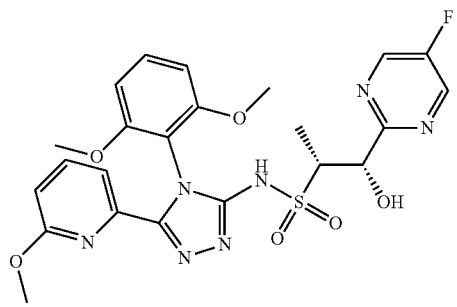 [SMILES: COc1cccc(-c2nnc(NS(=O)(=O)[C@H](C)[C@@H](O)c3ncc(F)cn3)n2-c2c(OC)cccc2OC)n1]<br>(1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-proanesulfonamide<br>$^1$H NMR (400 MHz, CDCl$_3$) δ: 11.01 (br s, 1H), 8.62 (s, 2H), 7.57-7.70 (m, 2H), 7.33 (s, 1H), 6.71 (dd, J = 7.3, 1.7 Hz, 1H), 6.55-6.69 (m, 2H), 5.63 (s, 1H), 3.82 (d, J = 6.5 Hz, 1H), 3.76 (s, 3H), 3.69 (s, 3H), 3.17 (s, 3H), 1.24 (d, J = 6.8 Hz, 3H). LCMS-ESI (POS.) m/z: 545.8 (M + H)$^+$. |
| 132.0 | The racemic compound 130.0 was separated by superficial fluid chromatography (250 × 21 m AD-H column on Thar 80 with 25 g/min EtOH(neat) + 30 g/min CO$_2$, 45% co-solvent at 55 g/min. Outlet pressure = 100 bar; wavelength = 297 nm; injection volume = 0.8 mL of 130 mg sample disolved in 19 mL of (1:1) MeOH:DCM). This was the second isomer to elute under these conditions | 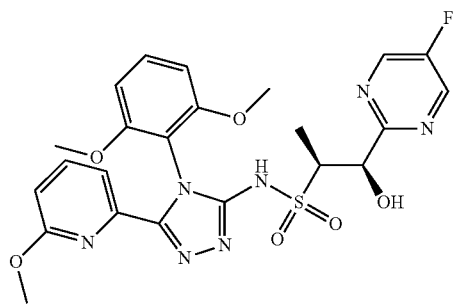 [SMILES: COc1cccc(-c2nnc(NS(=O)(=O)[C@@H](C)[C@H](O)c3ncc(F)cn3)n2-c2c(OC)cccc2OC)n1]<br>OR |

| Example | Reagents | Structure, Name and and Data |
|---|---|---|
| | | 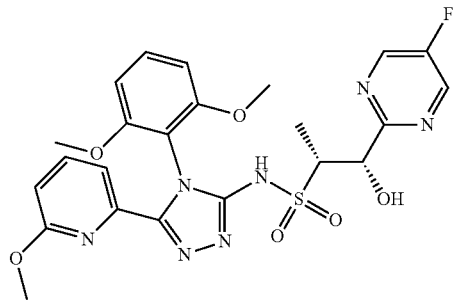 [SMILES: COc1cccc(-c2nnc(NS(=O)(=O)[C@H](C)[C@@H](O)c3ncc(F)cn3)n2-c2c(OC)cccc2OC)n1]<br>(1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide or (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-proanesulfonamide<br>$^1$H NMR (400 MHz, CDCl$_3$) δ: 8.62 (s, 2H), 7.61 (s, 2H), 7.30-7.38 (m, 1H), 6.72 (d, J = 7.2 Hz, 1H), 6.55-6.69 (m, 2H), 5.63 (s, 1H), 3.79-3.87 (m, 1H), 3.76 (s, 3H), 3.70 (s, 3H), 3.17 (s, 3H), 1.24 (d, J = 6.8 Hz, 3H). LCMS-ESI (POS.) m/z: 545.8 (M + H)$^+$. |
| 133.0 | (S)-1-(5-fluoropyrimidin-2-yl)propane-2-sulfonamide and (R)-1-(5-fluoropyrimidin-2-yl)propane-2-sulfonamide (Example 9.0), 2-methoxyisonicotinohydrazide (comercially available from Combi-Blocks Inc, San Diego, CA, USA), 2-isothiocyanato-1,3-dimethoxybenzene (Example 1.0), TFA (comercially available from Sigma-Aldrich Corp, St.<br><br>Louis, MO, USA) was used instead of methanesulfonic acid. | 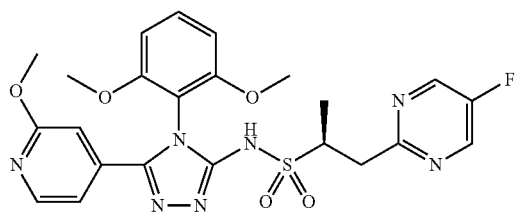 [SMILES: COc1cc(-c2nnc(NS(=O)(=O)[C@@H](C)Cc3ncc(F)cn3)n2-c2c(OC)cccc2OC)ccn1]<br>AND<br>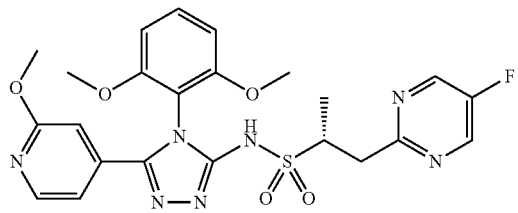<br>(2S)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.56 (s, 2H), 8.14 (d, J = 5.5 Hz, 1H), 7.45 (t, J = 8.5 Hz, 1H), 6.94 (dd, J = 5.5, 1.4 Hz, 1H), 6.75 (d, J = 0.6 Hz, 1H), 6.66 (dd, J = 8.6, 1.4 Hz, 2H), 3.93 (s, 3H), 3.79-3.88 (m, 1H), 3.78 (s, 3H), 3.76 (s, 3H), 3.71 (dd, J = 14.7, 4.3 Hz, 1H), 3.11 (dd, J = 14.7, 9.8 Hz, 1H), 1.33 (d, J = 6.8 Hz, 3H). LCMS-ESI (POS.) m/z: 529.7 (M + H)$^+$. |
| 134.0 | The racemic compound 133.0 was separated by superficial fluid chromatography (2 × 15 cm IA column on with 70 mL/min 18% MeOH/CO$_2$. Outlet pressure = 100 bar; wavelength = 220 nm; injection volume = 1.5 mL, 5 | |

| Example | Reagents | Structure, Name and and Data |
|---|---|---|
| | mg/mL MeOH). This was the first isomer to elute under these conditions. | 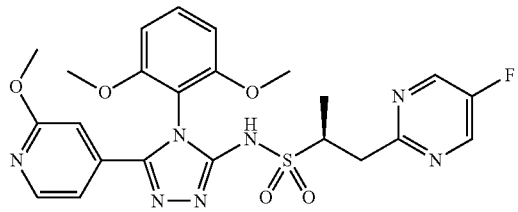 [SMILES: COc1cc(-c2nnc(NS(=O)(=O)[C@@H](C)Cc3ncc(F)cn3)n2-c2c(OC)cccc2OC)ccn1]

OR

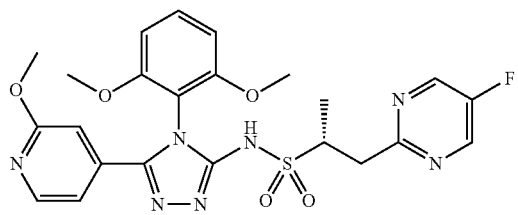 [SMILES: COc1cc(-c2nnc(NS(=O)(=O)[C@H](C)Cc3ncc(F)cn3)n2-c2c(OC)cccc2OC)ccn1]

(2S)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide
$^1$H NMR (400 MHz, CDCl$_3$) δ: 8.53 (s, 2H), 8.10 (s, 1H), 7.42 (t, J = 8.5 Hz, 1H), 6.90 (d, J = 4.9 Hz, 1H), 6.71 (s, 1H), 6.63 (dd, J = 8.5, 1.3 Hz, 2H), 3.88 (s, 3H), 3.78-3.84 (m, 1H), 3.75 (s, 3H), 3.73 (s, 3H), 3.67 (d, J = 3.7 Hz, 1H), 3.09 (dd, J = 14.7, 10.0 Hz, 1H), 1.31 (d, J = 6.7 Hz, 3H). LCMS-ESI (POS.) m/z: 529.7 (M + H)$^+$. |
| 135.0 | The racemic compound 133.0 was separated by superficial fluid chromatography (2 × 15 cm IA column on with 70 mL/min 18% MeOH/CO$_2$. Outlet pressure = 100 bar; wavelength = 220 nm; injection volume = 1.5 mL, 5 mg/mL MeOH). This was the second isomer to elute under these conditions | 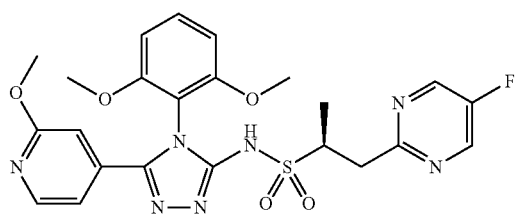

OR

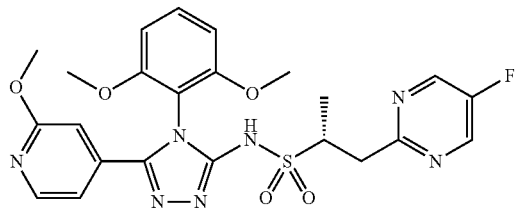 [SMILES: COc1cc(-c2nnc(NS(=O)(=O)[C@H](C)Cc3ncc(F)cn3)n2-c2c(OC)cccc2OC)ccn1]

(2S)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide
$^1$H NMR (400 MHz, CDCl$_3$) δ: 8.53 (s, 2H), 8.11 (d, J = 5.28 Hz, 1H), 7.42 (t, J = 8.51 Hz, 1H), 6.90 (d, J = 4.30 Hz, 1H), 6.70 (s, 1H), 6.56-6.66 (m, 2H), 3.88 (s, 3H), 3.78-3.84 (m, 1H), 3.75 (s, 3H), 3.73 (s, 3H), 3.68 (d, J = 3.52 Hz, 1H), 3.08 (dd, J = 14.67, 9.78 Hz, 1H), 1.31 (d, J = 6.85 Hz, 3H). LCMS-ESI (POS.) m/z: 529.7 (M + H)$^+$. |

TABLE 10-continued

| Example | Reagents | Structure, Name and and Data |
|---|---|---|
| 136.0 | (S)-1-(5-fluoropyrimidin-2-yl)propane-2-sulfonamide and (R)-1-(5-fluoropyrimidin-2-yl)propane-2-sulfonamide (Example 9.0), 5-(trifluoromethyl)nicotinohydrazide (Example 3.45), 2-isothiocyanato-1,3-dimethoxybenzene (Example 1.0), TFA (comercially available from Sigma-Aldrich Corp, St. Louis, MO, USA) was used instead of methanesulfonic acid. | 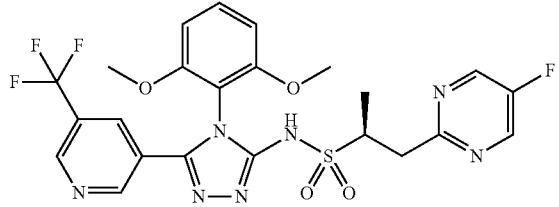 [SMILES: COc1cccc(OC)c1-n1c(NS(=O)(=O)[C@@H](C)Cc2ncc(F)cn2)nnc1-c1cncc(C(F)(F)F)c1]<br>AND<br>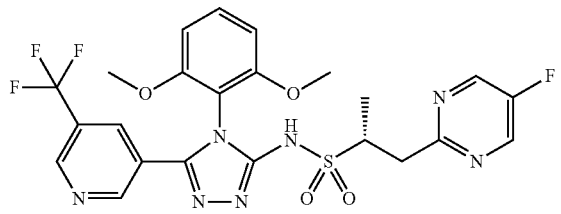 [SMILES: COc1cccc(OC)c1-n1c(NS(=O)(=O)[C@H](C)Cc2ncc(F)cn2)nnc1-c1cncc(C(F)(F)F)c1]<br>(2S)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.89 (d, J = 1.2 Hz, 1H), 8.81 (d, J = 2.0 Hz, 1H), 8.54 (s, 2H), 7.96-8.08 (m, 1H), 7.43 (t, J = 8.5 Hz, 1H), 6.64 (d, J = 8.4 Hz, 2H), 3.79-3.89 (m, 1H), 3.77 (s, 3H), 3.74 (s, 3H), 3.70 (dd, J = 14.8, 4.4 Hz, 1H), 3.10 (dd, J = 14.7, 9.8 Hz, 1H), 1.32 (d, J = 6.7 Hz, 3H). LCMS-ESI (POS.) m/z: 567.8 (M + H)$^+$. |
| 137.0 | The racemic compound 136.0 was separated by superficial fluid chromatography (2 × 15 cm IA column on with 60 mL/min 15% MeOH(0.1% NH$_4$OH/CO$_2$). Outlet pressure = 100 bar; wavelength = 220 nm; injection volume = 1 mL, 7 mg/mL 1:2 DCM:MeOH). This was the first isomer to elute under these conditions. | <br>OR<br>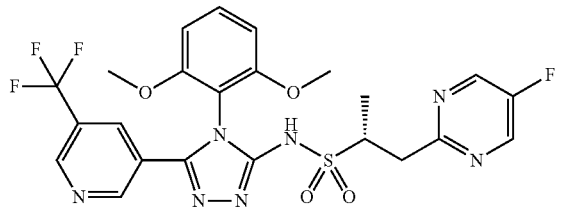 [SMILES: COc1cccc(OC)c1-n1c(NS(=O)(=O)[C@H](C)Cc2ncc(F)cn2)nnc1-c1cncc(C(F)(F)F)c1]<br>(2S)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 11.27 (br s, 1H), 8.75-8.93 (m, 2H), 8.50-8.59 (m, 2H), 8.01 (s, 1H), 7.43 (t, J = 8.51 Hz, 1H), 6.60-6.66 (m, 2H), 3.78-3.86 (m, 1H), 3.77 (s, 3H), 3.74 (s, 3H), 3.70 (dd, J = 14.97, 3.62 Hz, 1H), 3.02-3.18 (m, 1H), 1.32 (d, J = 6.85 Hz, 3H). LCMS-ESI (POS.) m/z: 567.8 (M + H)$^+$. |

TABLE 10-continued

| Example | Reagents | Structure, Name and and Data |
|---|---|---|
| 138.0 | The racemic compound 136.0 was separated by superficial fluid chromatography (2 × 15 cm IA column on with 60 mL/min 15% MeOH(0.1% NH$_4$OH/CO$_2$). Outlet pressure = 100 bar; wavelength = 220 nm; injection volume = 1 mL, 7 mg/mL 1:2 DCM:MeOH). This was the second isomer to elute under these conditions | 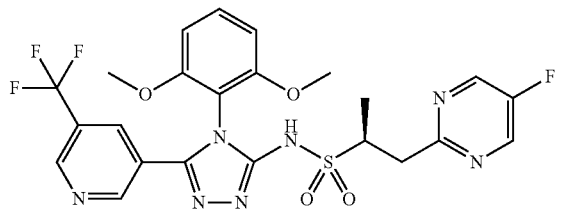 [SMILES: COc1cccc(OC)c1-n1c(NS(=O)(=O)[C@@H](C)Cc2ncc(F)cn2)nnc1-c1cncc(C(F)(F)F)c1]<br>OR<br>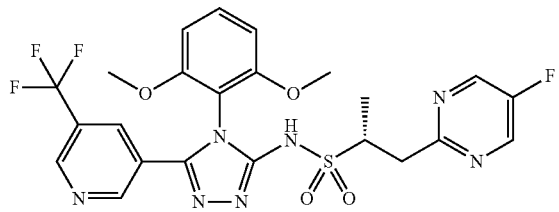 [SMILES: COc1cccc(OC)c1-n1c(NS(=O)(=O)[C@H](C)Cc2ncc(F)cn2)nnc1-c1cncc(C(F)(F)F)c1]<br>(2S)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 11.35 (br. s, 1H), 8.75-8.94 (m, 2H), 8.49-8.61 (m, 2H), 8.01 (s, 1H), 7.43 (t, J = 8.61 Hz, 1H), 6.57-6.72 (m, 2H), 3.79-3.85 (m, 1H), 3.77 (s, 3H), 3.74 (s, 3H), 3.69 (dd, J = 15.06, 4.30 Hz, 1H), 3.00-3.20 (m, 1H), 1.32 (d, J = 6.65 Hz, 3H).<br>LCMS-ESI (POS.) m/z: 567.7 (M + H)$^+$. |
| 139.0 | (S)-1-(5-fluoropyrimidin-2-yl)propane-2-sulfonamide and (R)-1-(5-fluoropyrimidin-2-yl)propane-2-sulfonamide (Example 9.0), 3-methoxypicolinohydrazide (Example 3.5), 2-isothiocyanato-1,3-dimethoxybenzene (Example 1.0), TFA (comercially available from Sigma-Aldrich Corp, St. Louis, MO, USA) was used instead of methanesulfonic acid. | 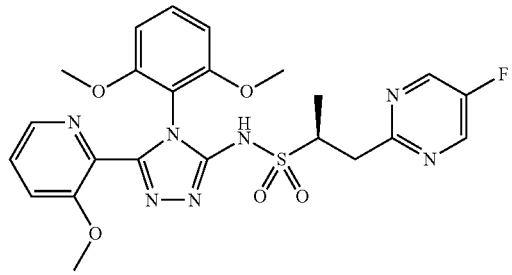 [SMILES: COc1cccnc1-c1nnc(NS(=O)(=O)[C@@H](C)Cc2ncc(F)cn2)n1-c1c(OC)cccc1OC]<br>AND<br>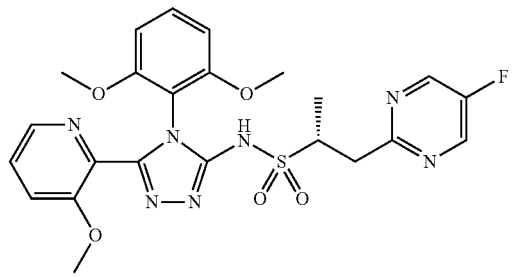 [SMILES: COc1cccnc1-c1nnc(NS(=O)(=O)[C@H](C)Cc2ncc(F)cn2)n1-c1c(OC)cccc1OC]<br>(2S)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.54 (s, 2H), 8.13 (d, J = 3.52 Hz, 1H), 7.19-7.26 (m, 2H), 6.50 (dd, J = 8.51, 2.84 Hz, 2H), 3.79-3.91 (m, |

TABLE 10-continued

| Example | Reagents | Structure, Name and and Data |
|---|---|---|
| | | 1H), 3.72-3.79 (m, 1H), 3.70 (s, 3H), 3.68 (s, 3H), 3.67 s, 3H), 3.66-3.68 (m, 1H), 3.05-3.22 (m, 1H), 1.36 (dd, J = 6.65 Hz, 3H). LCMS-ESI (POS.) m/z: 529.7 (M + H)$^+$. |
| 140.0 | The racemic compound 139.0 was separated by superficial fluid chromatography (2 × 25 cm OD-H column on with 50 mL/min 35% MeOH/CO$_2$. Outlet pressure = 100 bar; wavelength = 220 nm; injection volume = 1 mL, 4 mg/mL MeOH). This was the first isomer to elute under these conditions. | 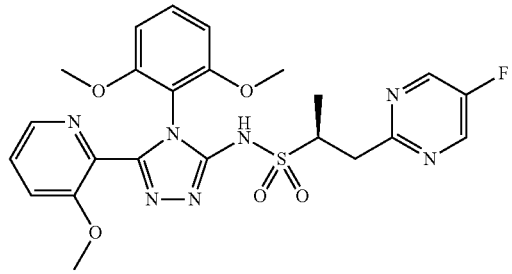 [SMILES: COc1cccnc1-c1nnc(NS(=O)(=O)[C@@H](C)Cc2ncc(F)cn2)n1-c1c(OC)cccc1OC] OR 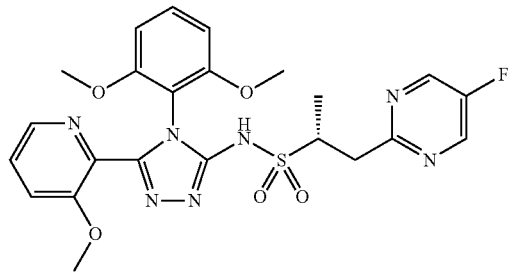 [SMILES: COc1cccnc1-c1nnc(NS(=O)(=O)[C@H](C)Cc2ncc(F)cn2)n1-c1c(OC)cccc1OC] (2S)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide $^1$H NMR (400 MHz, CDCl$_3$) δ: 11.19 (s, 1H), 8.53 (s, 2H), 8.10 (dd, J = 4.50, 1.37 Hz, 1H), 7.22-7.27 (m, 2H), 7.17-7.21 (m, 1H), 6.49 (dd, J = 8.51, 2.64 Hz, 2H), 3.80-3.87 (m, 1H), 3.72-3.78 (m, 1H), 3.70 (s, 3H), 3.67 (s, 3H), 3.67 (s, 3H), 3.14 (dd, J = 14.67, 9.78 Hz, 1H), 1.35 (d, J = 6.65 Hz, 3H). LCMS-ESI (POS.) m/z: 529.7 (M + H)$^+$. |
| 141.0 | The racemic compound 139.0 was separated by superficial fluid chromatography (2 × 25 cm OD-H column on with 50 mL/min 35% MeOH/CO$_2$. Outlet pressure = 100 bar; wavelength = 220 nm; injection volume = 1 mL, 4 mg/mL MeOH). This was the second isomer to elute under these conditions | 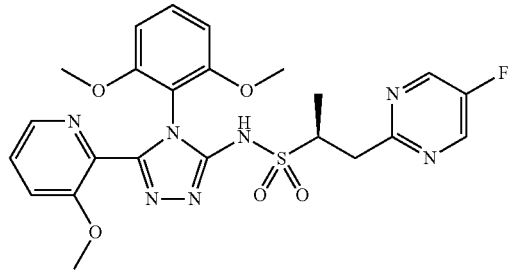 [SMILES: COc1cccnc1-c1nnc(NS(=O)(=O)[C@@H](C)Cc2ncc(F)cn2)n1-c1c(OC)cccc1OC] OR |

TABLE 10-continued

| Example | Reagents | Structure, Name and and Data |
|---|---|---|
| | | 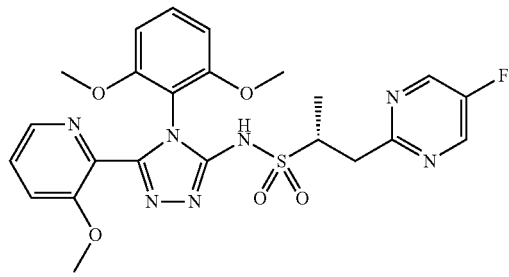 [SMILES: COc1cccnc1-c1nnc(NS(=O)(=O)[C@H](C)Cc2ncc(F)cn2)n1-c1c(OC)cccc1OC]<br>(2S)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.55 (s, 2H), 8.12 (dd, J = 4.50, 1.17 Hz, 1H), 7.24-7.29 (m, 2H), 7.19-7.23 (m, 1H), 6.51 (dd, J = 8.61, 2.74 Hz, 2H), 3.85 (ddd, J = 9.83, 6.80, 4.50 Hz, 1H), 3.77 (dd, J = 14.97, 3.81 Hz, 1H), 3.72 (s, 3H), 3.69 (s, 3H), 3.68 (s, 3H), 3.16 (dd, J = 14.67, 9.78 Hz, 1H), 1.37 (d, J = 6.65 Hz, 3H). LCMS-ESI (POS.) m/z: 529.7 (M + H)$^+$. |
| 142.0 | (S)-1-(5-fluoropyrimidin-2-yl)propane-2-sulfonamide and (R)-1-(5-fluoropyrimidin-2-yl)propane-2-sulfonamide (Example 9.0), 6-ethoxypicolinohydrazide (Example 3.46), 2-isothiocyanato-1,3-dimethoxybenzene (Example 1.0), TFA (comercially available from Sigma-Aldrich Corp, St. Louis, MO, USA) was used instead of methanesulfonic acid. The racemic compound was seperated by supercritical fluid chromatography (2 × 15 × 3 cm IA column on Thar 80 with 36.0 g/min MeOH (20 mM NH$_3$) + 44 g/min CO$_2$, 45% co-solvent at 80 g/min. Temperature = 24° C.; outlet pressure = 100 bar; wavelength = 215 nm; injection volume = 0.35 mL of 115 mg sample disolved in 13 mL MeOH (25% DCM). This was the first isomer to elute under these conditions. | 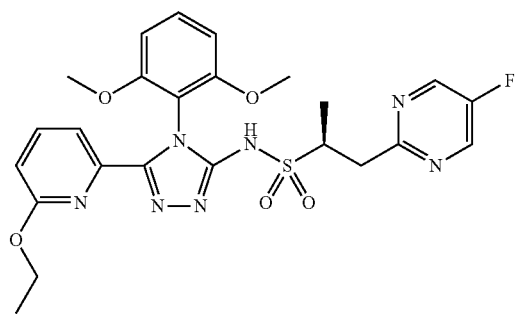 [SMILES: CCOc1cccc(-c2nnc(NS(=O)(=O)[C@@H](C)Cc3ncc(F)cn3)n2-c2c(OC)cccc2OC)n1]<br>OR<br>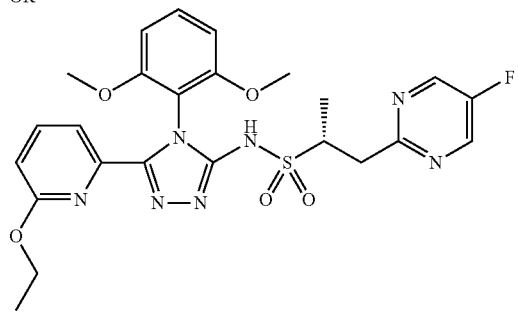<br>(2S)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.53 (s, 2H), 7.55-7.66 (m, 2H), 7.32 (t, J = 8.51 Hz, 1H), 6.68 (dd, J = 7.82, 1.37 Hz, 1H), 6.60 (dd, J = 8.61, 1.96 Hz, 2H), 3.75-3.83 (m, 1H), 3.71 (s, 3H), 3.69 (s, 3H), 3.68 (m, J = 0.39 Hz, 1H), 3.44 (d, J = 7.04 Hz, 2H), 3.09 (dd, J = 14.87, 9.98 Hz, 1H), 1.31 (d, J = 6.65 Hz, 3H), 1.08 (t, J = 7.04 Hz, 3H). LCMS-ESI (POS.) m/z: 543.8 (M + H)$^+$. |

TABLE 10-continued

| Example | Reagents | Structure, Name and and Data |
|---|---|---|
| 143.0 | The racemic compound was separated by supercritical fluid chromatography (2 × 15 × 3 cm IA column on That 80 with 36.0 g/min MeOH (20 mM NH$_3$) + 44 g/min CO$_2$, 45% co-solvent at 80 g/min. Temperature = 24° C.; outlet pressure = 100 bar, wavelength = 215 nm; injection volume = 0.35 mL of 115 mg sample disolved in 13 mL MeOH (25% DCM). This was the second isomer to elute under these conditions. | 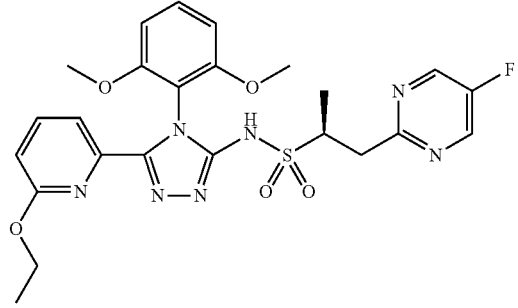 [SMILES: CCOc1cccc(-c2nnc(NS(=O)(=O)[C@@H](C)Cc3ncc(F)cn3)n2-c2c(OC)cccc2OC)n1]<br>OR<br>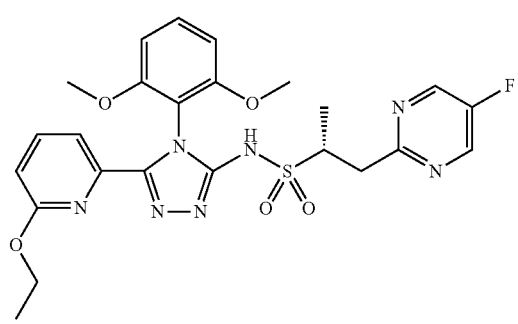 [SMILES: CCOc1cccc(-c2nnc(NS(=O)(=O)[C@H](C)Cc3ncc(F)cn3)n2-c2c(OC)cccc2OC)n1]<br>(2S)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.53 (s, 2H), 7.53-7.65 (m, 2H), 7.32 (t, J = 8.51 Hz, 1H), 6.68 (dd, J = 7.73, 1.08 Hz, 1H), 6.60 (dd, J = 8.51, 1.86 Hz, 2H), 3.76-3.83 (m, 1H), 3.72-3.74 (m, 1H), 3.71 (s, 3H), 3.69 (s, 3H), 3.44 (q, J = 7.17 Hz, 2H), 3.09 (dd, J = 14.77, 9.88 Hz, 1H), 1.31 (d, J = 6.65 Hz, 3H), 1.08 (t, J = 7.04 Hz, 3H). LCMS-ESI (POS.) m/z: 543.7 (M + H)$^+$. |
| 144.0 | (S)-1-(5-fluoropyrimidin-2-yl)propane-2-sulfonamide and (R)-1-(5-fluoropyrimidin-2-yl)propane-2-sulfonamide (Example 9.0), 4-methoxypicolinohydrazide (comercially available from Matrix Scientific, Columbia, SC, USA), 2-isothiocyanato-1,3-dimethoxybenzene (Example 1.0), TFA (comercially available from Sigma-Aldrich Corp, St. Louis, MO, USA) was used instead of methanesulfonic acid. The racemic compound was seperated by supercritical fluid chromatography (250 × 21 m IA column on Thar 200 with 20 g/min MeOH (neat) + 60 g/min CO$_2$, 25% co-solvent at 80 g/min. Temperature = 22° C.; wavelength = 220 nm; injection volume = 0.5 mL of 30 mg sample disolved in 11 mL MeOH:DCM). This was the first isomer to elute under these conditions. | 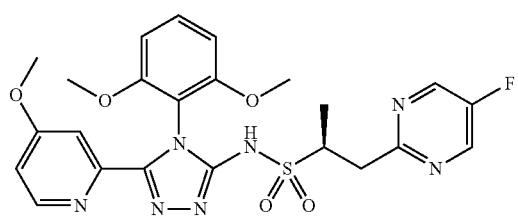 [SMILES: COc1ccnc(-c2nnc(NS(=O)(=O)[C@@H](C)Cc3ncc(F)cn3)n2-c2c(OC)cccc2OC)c1]<br>OR<br>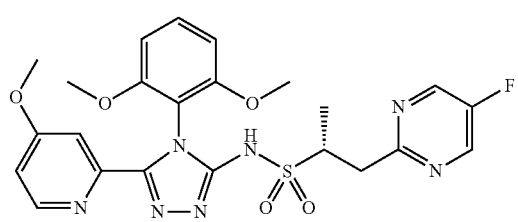<br>(2S)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide |

TABLE 10-continued

| Example | Reagents | Structure, Name and and Data |
|---|---|---|
| | | ¹H NMR (400 MHz, CDCl₃) δ: 11.14 (br. s., 1H), 8.53 (s, 2H), 8.19 (d, J = 5.67 Hz, 1H), 7.36 (t, J = 8.51 Hz, 1H), 7.21 (d, J = 2.54 Hz, 1H), 6.77 (dd, J = 5.67, 2.54 Hz, 1H), 6.60 (dd, J = 8.51, 2.05 Hz, 2H), 3.86 (d, J = 2.15 Hz, 1H), 3.81 (s, 3H), 3.72 (s, 3H), 3.70 (s, 3H), 3.50 (d, J = 4.70 Hz, 1H), 3.10 (dd, J = 14.57, 9.88 Hz, 1H), 1.32 (d, J = 6.65 Hz, 3H). LCMS-ESI (POS.) m/z: 529.7 (M + H)⁺. |
| 145.0 | The racemic compound was separated by supercritical fluid chromatography (250 × 21 m IA column on That 200 with 20 g/min MeOH (neat) + 60 g/min CO₂, 25% co-solvent at 80 g/min. Temperature = 22° C.; wavelength = 225 nm; injection volume = 0.5 mL of 30 mg sample disolved in 11 mL MeOH:DCM). This was the second isomer to elute under these conditions. | 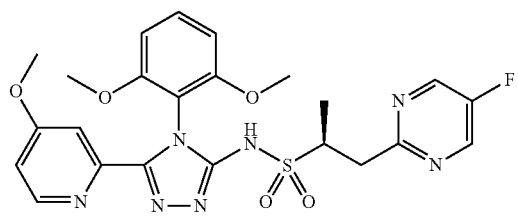 [SMILES: COc1ccnc(-c2nnc(NS(=O)(=O)[C@@H](C)Cc3ncc(F)cn3)n2-c2c(OC)cccc2OC)c1]

OR

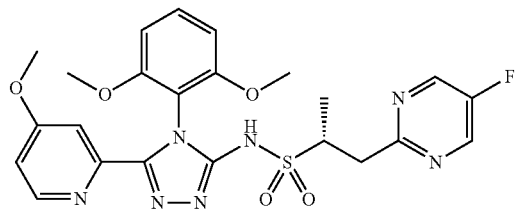 [SMILES: COc1ccnc(-c2nnc(NS(=O)(=O)[C@H](C)Cc3ncc(F)cn3)n2-c2c(OC)cccc2OC)c1]

(2S)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide
¹H NMR (400 MHz, CDCl₃) δ: 8.53 (s, 2H), 8.19 (d, J = 5.67 Hz, 1H), 7.36 (t, J = 8.51 Hz, 1H), 7.21 (d, J = 2.35 Hz, 1H), 6.77 (dd, J = 5.67, 2.54 Hz, 1H), 6.60 (dd, J = 8.41, 2.15 Hz, 2H), 3.83 (m, J = 2.35 Hz, 1H), 3.81 (s, 3H), 3.72 (s, 3H), 3.70 (s, 3H), 3.36 (s, 1H), 3.10 (dd, J = 14.77, 9.88 Hz, 1H), 1.32 (d, J = 6.65 Hz, 3H). LCMS-ESI (POS.) m/z: 529.7 (M + H)⁺. |
| 146.0 | (S)-1-(5-fluoropyrimidin-2-yl)propane-2-sulfonamide and (R)-1-(5-fluoropyrimidin-2-yl)propane-2-sulfonamide (Example 9.0), 5-bromonicotinohydrazide (Example 3.6), 2-isothicyanato-1,3-dimethoxybenzene (Example 1.0), TFA (comercially availabe from Sigma-Aldrich Corp, St. Louis, MO, USA) was used instead of methanesulfonic acid. | 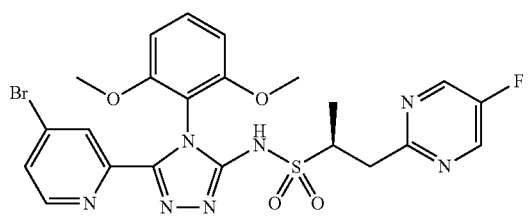 [SMILES: COc1cccc(OC)c1-n1c(NS(=O)(=O)[C@@H](C)Cc2ncc(F)cn2)nnc1-c1cc(Br)ccn1]

AND

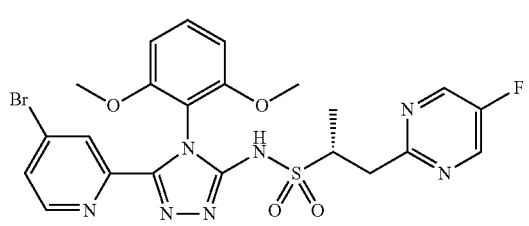 [SMILES: COc1cccc(OC)c1-n1c(NS(=O)(=O)[C@H](C)Cc2ncc(F)cn2)nnc1-c1cc(Br)ccn1]

(2R)-N-(5-(3-bromo-3-pyridinyl)-4-(2,6-dimethoxyphenyl)-4H-1,2,4-triazol-3-yl)-1-(5-fluoro-2-pyrimidinyl)-2-propanesulfonamide
and (2S)-N-(5-(5-bromo-3-pyridinyl)-4-(2,6-dimethoxyphenyl)-4H-1,2,4-triazol-3-yl)-1-(5- |

TABLE 10-continued

| Example | Reagents | Structure, Name and and Data |
|---|---|---|
| | | fluoro-2-pyrimidinyl)-2-propanesulfonamide<br>¹H NMR (400 MHz, CDCl₃) δ: 8.68 (d, J = 2.15 Hz, 1H), 8.54 (s, 2H), 8.47 (d, J = 1.76 Hz, 1H), 7.99 (t, J = 2.05 Hz, 1H), 7.37-7.49 (m, 1H), 6.64 (dd, J = 8.61, 0.98 Hz, 2H), 3.78-3.87 (m, 1H), 3.77 (s, 3H), 3.75 (s, 3H), 3.69 (dd, J = 15.06, 4.50 Hz, 1H), 3.09 (dd, J = 14.77, 9.88 Hz, 1H), 1.32 (d, J = 6.85 Hz, 3H). LCMS-ESI (POS.) m/z: 577.5, 579.5 (M + H)⁺. |
| 147.0 | (S)-1-(5-fluoropyrimidin-2-yl)propane-2-sulfonamide and (R)-1-(5-fluoropyrimidin-2-yl)propane-2-sulfonamide (Example 9.0), 6-(hydrazinecarbonyl)-N-methylpicolinamzide (Example 3.7), 2-isothicyanato-1,3-dimethoxybenzene (Example 1.0), TFA (comercially availabe from Sigma-Aldrich Corp, St. Louis, MO, USA) was used instead of methanesulfonic acid. | 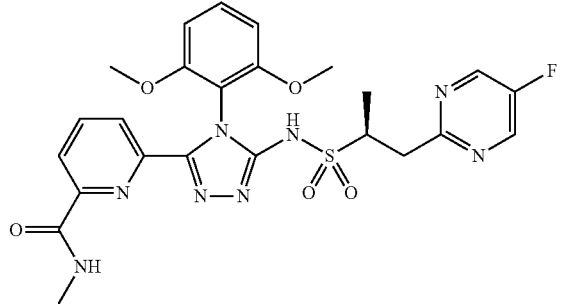 [SMILES: CNC(=O)c1cccc(-c2nnc(NS(=O)(=O)[C@@H](C)Cc3ncc(F)cn3)n2-c2c(OC)cccc2OC)n1]AND<br><br>6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-methyl-2-pyridinecarboxamide and 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-methyl-2-pyridinecarboxamide<br>¹H NMR (400 MHz, CDCl₃) δ: 8.51-8.61 (m, 2H), 8.23 (dd, J = 7.8, 1.6 Hz, 1H), 8.15 (dd, J = 7.8, 1.0 Hz, 1H), 7.94 (t, J = 7.8 Hz, 1H), 7.49 (t, J = 8.5 Hz, 1H), 6.71 (dd, J = 8.5, 1.3 Hz, 2H), 3.81-3.90 (m, 1H), 3.74 (s, 3H), 3.71 (s, 3H), 3.05-3.19 (m, 2H), 2.74 (d, J = 5.1 Hz, 3H)., 1.33 (d, J = 6.8 Hz, 3H). LCMS-ESI (POS.) m/z: 556.7 (M + H)⁺. |
| 148.0 | The racemic compound 147.0 was separated by superficial fluid chromatography (2 × 15 cm IA column on with 60 mL/min 25% MeOH/CO₂. Outlet pressure = 100 bar; wavelength = 220 nm; injection volume = 1 mL, 2 mg/mL 1:3 DCM:MeOH). This was the first isomer to elute under these conditions. | 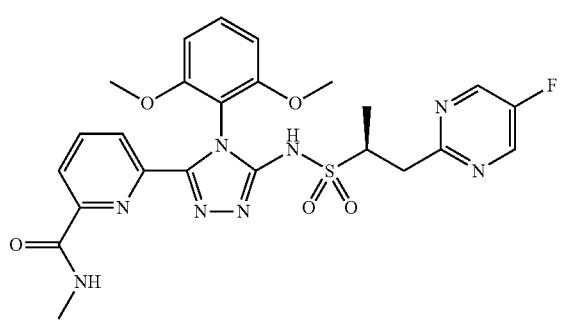 [SMILES: CNC(=O)c1cccc(-c2nnc(NS(=O)(=O)[C@@H](C)Cc3ncc(F)cn3)n2-c2c(OC)cccc2OC)n1]OR |

| Example | Reagents | Structure, Name and and Data |
|---|---|---|
| | | 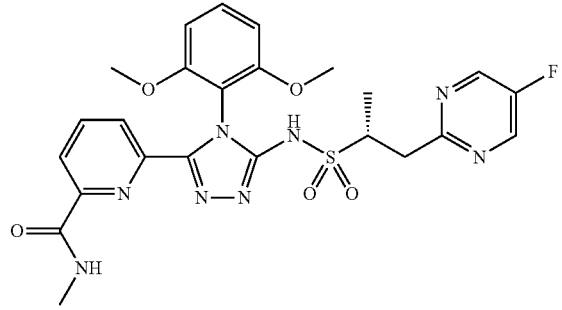
6-(4-(2,6-dimethoxyphenyl)-5-(((((1S)-2-(5-fluoro-2-pyrimidinyl)-1-methylethyl)sulfonyl)amino)-4H-1,2,4-triazol-3-yl)-N-methyl-2-pyridinecarboxamide and 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-methyl-2-pyridinecarboxamide
$^1$H NMR (400 MHz, CDCl$_3$) δ: 11.24 (br s, 1H), 8.54 (s, 2H), 8.23 (dd, J = 7.92, 1.08 Hz, 1H), 8.15 (dd, J = 7.73, 1.08 Hz, 1H), 7.91-7.97 (m, 1H), 7.48 (t, J = 8.51 Hz, 1H), 6.71 (dd, J = 8.51, 1.27 Hz, 2H), 6.29 (d, J = 4.89 Hz, 1H), 3.82 (ddd, J = 9.88, 6.75, 4.50 Hz, 1H), 3.73 (s, 3H), 3.71 (s, 3H), 3.69 (t, J = 2.91 Hz, 1H), 3.10 (dd, J = 14.87, 9.98 Hz, 1H), 2.73 (d, J = 5.09 Hz, 3H), 1.32 (d, J = 6.85 Hz, 3H). LCMS-ESI (POS.) m/z: 556.7 (M + H)$^+$. |
| 149.0 | The racemic compound 147.0 was separated by superficial fluid chromatography (2 × 15 cm IA column on with 60 mL/min 25% MeOH/CO$_2$. Outlet pressure = 100 bar; wavelength = 220 nm; injection volume = 1 mL, 2 mg/mL 1:3 DCM:MeOH). This was the second isomer to elute under these conditions. | 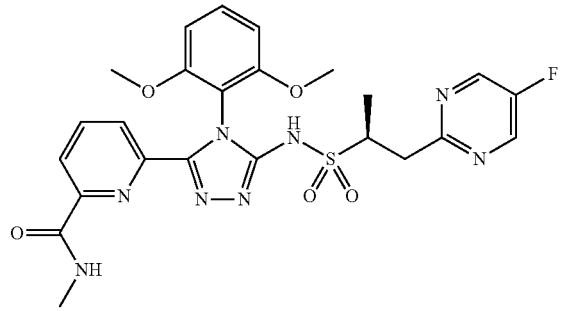
OR
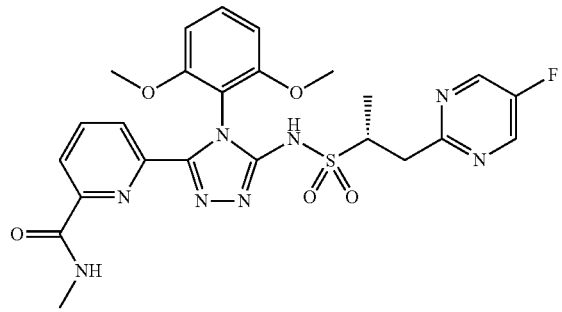 [SMILES: CNC(=O)c1cccc(-c2nnc(NS(=O)(=O)[C@H](C)Cc3ncc(F)cn3)n2-c2c(OC)cccc2OC)n1]
6-(4-(2,6-dimethoxyphenyl)-5-(((((1S)-2-(5-fluoro-2-pyrimidinyl)-1-methylethyl)sulfonyl)amino)-4H-1,2,4-triazol-3-yl)-N-methyl-2-pyridinecarboxamide or 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-methyl-2-pyridinecarboxamide
$^1$H NMR (400 MHz, CDCl$_3$) δ: 11.25 (br s, 1H), 8.54 (s, 2H), 8.23 (dd, J = 7.92, 1.08 Hz, |

| Example | Reagents | Structure, Name and and Data |
|---|---|---|
| | | 1H), 8.15 (dd, J = 7.82, 0.98 Hz, 1H), 7.94 (t, J = 7.70 Hz, 1H), 7.48 (t, J = 8.51 Hz, 1H), 6.70 (dd, J = 8.51, 1.74 Hz, 2H), 6.29 (d, J = 4.70 Hz, 1H), 3.82 (ddd, J = 9.88, 6.75, 4.50 Hz, 1H), 3.73 (s, 2H), 3.71 (s, 3H), 3.69 (d, J = 3.52 Hz, 1H), 3.10 (dd, J = 14.67, 9.78 Hz, 1H), 2.73 (d, J = 5.09 Hz, 3H), 1.32 (d, J = 6.65 Hz, 3H). LCMS-ESI (POS.) m/z: 556.7 (M + H)+. |
| 150.0 | (S)-1-(5-fluoropyrimidin-2-yl)propane-2-sulfonamide and (R)-1-(5-fluoropyrimidin-2-yl)propane-2-sulfonamide (Example 9.0), 6-cyanopicolinohydrazid (Example 3.8), 2-isothiocyanato-1,3-dimethoxybenzene (Example 1.0), TFA (comercially availabe from Sigma-Aldrich Corp, St. Louis, MO, USA) was used instead of methanesulfonic acid. | 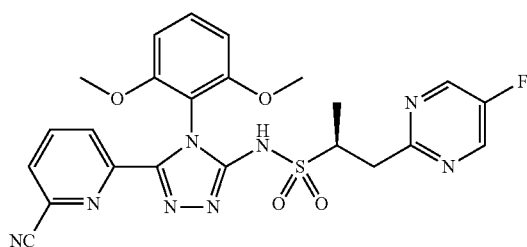 [SMILES: COc1cccc(OC)c1-n1c(NS(=O)(=O)[C@@H](C)Cc2ncc(F)cn2)nnc1-c1cccc(C#N)n1]<br><br>AND<br><br>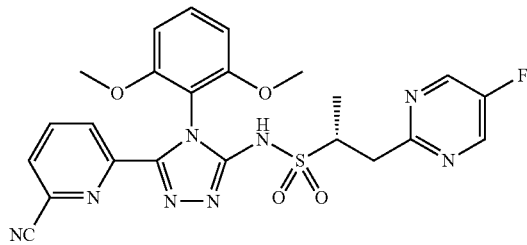 [SMILES: COc1cccc(OC)c1-n1c(NS(=O)(=O)[C@H](C)Cc2ncc(F)cn2)nnc1-c1cccc(C#N)n1]<br><br>(2S)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide and (2R)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide<br>1H NMR (400 MHz, CDCl3) δ: 8.54 (s, 2H), 8.18 (dd, J = 8.2, 1.0 Hz, 1H), 8.03 (s, 1H), 7.91 (t, J = 8.0 Hz, 1H), 7.63 (dd, J = 7.8, 1.0 Hz, 1H), 7.41 (t, J = 8.5 Hz, 1H), 6.58-6.67 (m, 2H), 3.79-3.89 (m, 1H), 3.74 (s, 3H), 3.71 (s, 3H), 3.69 (d, J = 4.3 Hz, 1H), 3.11 (dd, J = 14.8, 9.9 Hz, 1H), 1.33 (d, J = 6.8 Hz, 3H). LCMS-ESI (POS.) m/z: 525.2 (M + H)+. |
| 151.0 | The racemic compound 150.0 was separated by supercritical fluid chromatography (250 × 30 m AD column on Thar 80 with 28 g/min MeOH (+20 mM NH3) + 52 g/min CO2, 35% co-solvent at 80 g/min. Temperature = 23° C.; outlet pressure = 100 bar; wavelength = 218 nm; injection volume = 0.5 mL of 40 mg sample disolved in 10 mL MeOH:DCM (7:3). This was the first isomer to elute under these conditions. | 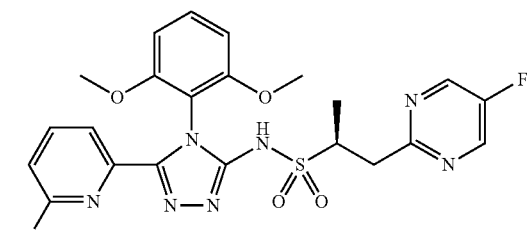<br><br>OR<br><br>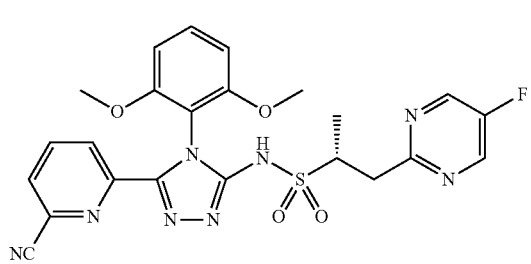 [SMILES: COc1cccc(OC)c1-n1c(NS(=O)(=O)[C@H](C)Cc2ncc(F)cn2)nnc1-c1cccc(C#N)n1] |

| Example | Reagents | Structure, Name and and Data |
|---|---|---|
| | | (2S)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide <br> $^1$H NMR (400 MHz, CDCl$_3$) δ: 8.53 (s, 2H), 8.18 (dd, J = 8.22, 0.98 Hz, 1H), 7.91 (s, 1H), 7.63 (dd, J = 7.73, 0.88 Hz, 1H), 7.42 (t, J = 8.41 Hz, 1H), 6.63 (dd, J = 8.51, 1.08 Hz, 2H), 3.83 (ddd, J = 9.73, 6.99, 4.40 Hz, 1H), 3.74 (s, 3H), 3.71 (s, 3H), 3.69 (d, J = 5.28 Hz, 1H), 3.11 (dd, J = 14.97, 9.88 Hz, 1H), 1.33 (d, J = 6.65 Hz, 3H). LCMS-ESI (POS.) m/z: 525.2 (M + H)$^+$. |
| 152.0 | The racemic compound 150.0 was separated by supercritical fluid chromatography (250 × 30 m AD column on Thar 80 with 28 g/min MeOH (+20 mM NH$_3$) + 52 g/min CO$_2$, 35% co-solvent at 80 g/min. Temperature = 23° C.; outlet pressure = 100 bar; wavelength = 218 nm; injection volume = 0.5 mL of 40 mg sample disolved in 10 mL MeOH:DCM (7:3). This was the second isomer to elute under these conditions. | 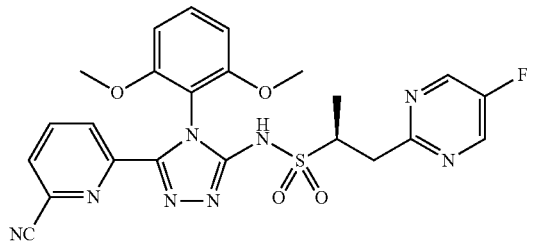 [SMILES: COc1cccc(OC)c1-n1c(NS(=O)(=O)[C@@H](C)Cc2ncc(F)cn2)nnc1-c1cccc(C#N)n1] <br> OR <br> 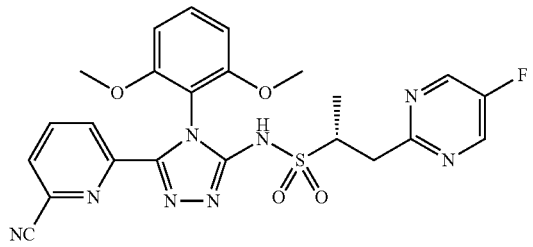 [SMILES: COc1cccc(OC)c1-n1c(NS(=O)(=O)[C@H](C)Cc2ncc(F)cn2)nnc1-c1cccc(C#N)n1] <br> (2S)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide <br> $^1$H NMR (400 MHz, CDCl$_3$) δ: 8.56 (s, 2H), 8.21 (dd, J = 8.22, 0.98 Hz, 1H), 7.93 (t, J = 7.92 Hz, 1H), 7.66 (dd, J = 7.63, 0.98 Hz, 1H), 7.44 (t, J = 8.51 Hz, 1H), 6.66 (dd, J = 8.51, 1.08 Hz, 2H), 3.85 (ddd, J = 9.73, 6.90, 4.50 Hz, 1H), 3.76 (s, 3H), 3.73 (s, 3H), 3.71 (d, J = 4.50 Hz, 1H), 3.13 (dd, J = 14.67, 9.78 Hz, 1H), 1.35 (d, J = 6.85 Hz, 3H). LCMS-ESI (POS.) m/z: 525.2 (M + H)$^+$. |
| 153.0 | (S)-1-(5-fluoropyrimidin-2-yl)propane-2-sulfonamide and (R)-1-(5-fluoropyrimidin-2-yl)propane-2-sulfonamide (Example 9.0), 5-methoxypicolinohydrazide (Example 3.49), 2-isothiocyanato-1,3-dimethoxybenzene (Example 1.0), TFA (comercially available from Sigma-Aldrich Corp, St. Louis, MO, USA) was used instead of methanesulfonic acid. | 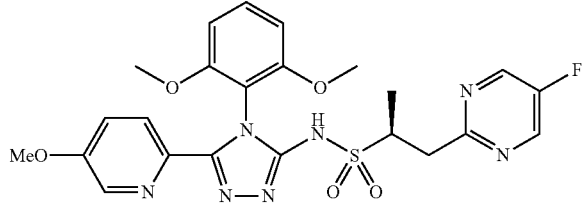 [SMILES: COc1ccc(-c2nnc(NS(=O)(=O)[C@@H](C)Cc3ncc(F)cn3)n2-c2c(OC)cccc2OC)nc1] <br> AND |

TABLE 10-continued

| Example | Reagents | Structure, Name and and Data |
|---|---|---|
| | | 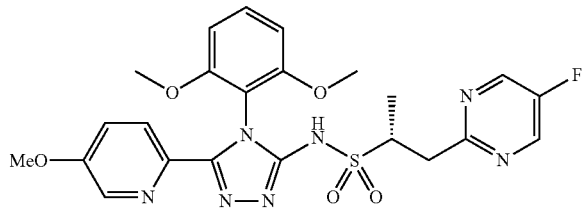 [SMILES: COc1ccc(-c2nnc(NS(=O)(=O)[C@H](C)Cc3ncc(F)cn3)n2-c2c(OC)cccc2OC)nc1]<br>(2S)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.54 (s, 3H), 7.63 (d, J = 8.8 Hz, 1H), 7.36 (t, J = 8.5 Hz, 1H), 7.18 (dd, J = 8.8, 2.9 Hz, 1H), 6.58 (s, 1H), 6.61 (s, 1H), 3.91-3.96 (m, 1H), 3.85 (s, 3H), 3.80-3.82 (m, 1H), 3.72 (s, 3H), 3.70 (s, 3H), 3.04-3.21 (m, 1H), 1.32 (d, J = 6.8 Hz, 3H). LCMS-ESI (POS.) m/z: 529.7 (M + H)$^+$. |
| 154.0 | The racemic compound 153.0 was separated by supercritical fluid chromatography (2 × 15 cm IA column with 70 mL/min 25% MeOH/CO$_2$. Outlet pressure = 100 bar; wavelength = 220 nm; injection volume = 1 mL, 3 mg/mL MeOH). This was the first isomer to elute under these conditions. | 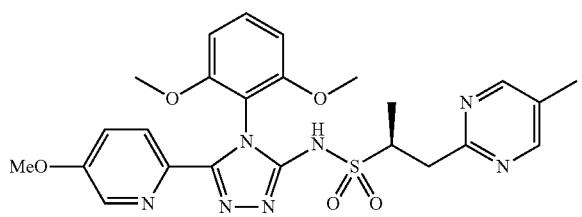<br>OR<br>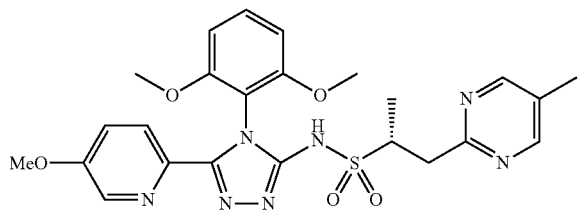<br>(2S)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.53 (s, 2H), 8.06 (d, J = 2.74 Hz, 1H), 7.65 (d, J = 8.80 Hz, 1H), 7.36 (t, J = 8.41 Hz, 1H), 7.16 (dd, J = 8.71, 2.84 Hz, 1H), 6.59 (dd, J = 8.51, 2.05 Hz, 2H), 3.84 (s, 3H), 3.77-3.82 (m, 1H), 3.72-3.75 (m, 1H), 3.71 (s, 3H), 3.69 (s, 3H), 3.10 (dd, J = 14.77, 9.88 Hz, 1H), 1.32 (d, J = 6.85 Hz, 3H). LCMS-ESI (POS.) m/z: 529.7 (M + H)$^+$. |
| 155.0 | The racemic compound 153.0 was separated by supercritical fluid chromatography (2 × 15 cm IA column with 70 mL/min 25% MeOH/CO$_2$. Outlet pressure = 100 bar; wavelength = 220 nm; injection volume = 1 mL, 3 mg/mL MeOH). This was the second isomer to elute under these conditions. | 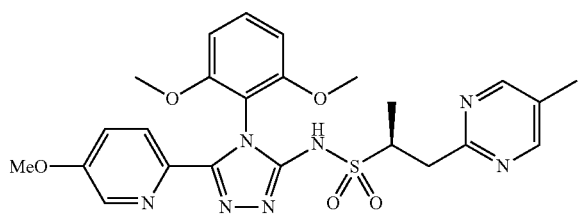 [SMILES: COc1ccc(-c2nnc(NS(=O)(=O)[C@@H](C)Cc3ncc(C)cn3)n2-c2c(OC)cccc2OC)nc1]<br>OR |

| Example | Reagents | Structure, Name and and Data |
|---|---|---|
| | | 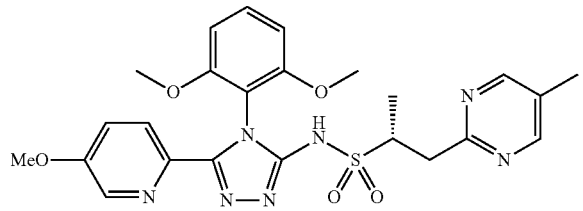<br>(2S)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.53 (s, 2H), 8.06 (d, J = 2.74 Hz, 1H), 7.65 (d, J = 8.80 Hz, 1H), 7.36 (t, J = 8.51 Hz, 1H), 7.16 (dd, J = 8.71, 2.84 Hz, 1H), 6.59 (dd, J = 8.61, 2.15 Hz, 2H), 3.84 (s, 3H), 3.80 (t, J = 6.16 Hz, 1H), 3.73-3.74 (m, 1H), 3.71 (s, 3H), 3.70 (s, 3H), 3.10 (dd, J = 14.67, 9.98 Hz, 1H), 1.32 (d, J = 6.65 Hz, 3H). LCMS-ESI (POS.) m/z: 529.7 (M + H)$^+$. |
| 156.0 | (S)-1-(5-fluoropyrimidin-2-yl)propane-2-sulfonamide and (R)-1-(5-fluoropyrimidin-2-yl)propane-2-sulfonamide (Example 9.0), 6-ethylpicolinohydrazide (Example 3.50), 2-isothiocyanato-1,3-dimethoxybenzene (Example 1.0), TFA (comercially available from Sigma-Aldrich Corp, St. Louis, MO, USA) was used instead of methanesulfonic acid. | 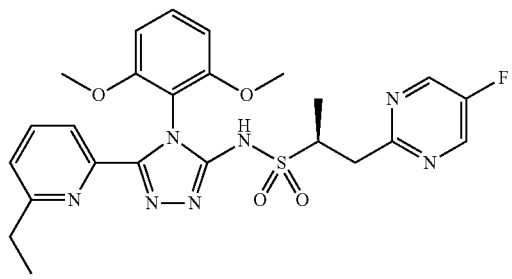 [SMILES: CCc1cccc(-c2nnc(NS(=O)(=O)[C@@H](C)Cc3ncc(F)cn3)n2-c2c(OC)cccc2OC)n1]<br>AND<br>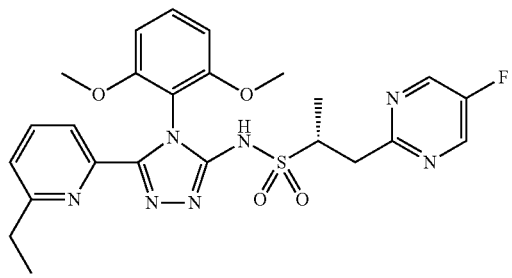 [SMILES: CCc1cccc(-c2nnc(NS(=O)(=O)[C@H](C)Cc3ncc(F)cn3)n2-c2c(OC)cccc2OC)n1]<br>(2S)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.54 (s, 2H), 7.62-7.68 (m, 2H), 7.34 (t, J = 8.51 Hz, 1H), 7.12 (dd, J = 6.85, 1.76 Hz, 1H), 6.58 (dd, J = 8.51, 1.66 Hz, 2H), 3.78-3.86 (m, 2H), 3.73 (m, J = 5.28 Hz, 1H), 3.70 (s, 3H), 3.68 (s, 3H), 3.12 (dd, J = 14.87, 9.78 Hz, 1H), 2.53 (q, J = 7.63 Hz, 2H), 1.33 (d, J = 6.65 Hz, 3H), 0.87-0.94 (m, 3H). LCMS-ESI (POS.) m/z: 527.8 (M + H)$^+$. |

TABLE 10-continued

| Example | Reagents | Structure, Name and and Data |
|---|---|---|
| 157.0 | The racemic compound 156.0 was separated by supercritical fluid chromatography (2 × 15 cm IA column with 65 mL/min 20% MeOH (0.1% NH$_4$OH)/CO$_2$. Outlet pressure = 100 bar; wavelength = 220 nm; injection volume = 1 mL, 6 mg/mL 1:3 DCM:MeOH). This was the first isomer to elute under these conditions. | OR<br><br>(2S)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.53 (s, 2H), 7.65-7.70 (m, 1H), 7.58-7.64 (m, 1H), 7.33 (t, J = 8.51 Hz, 1H), 7.09 (d, J = 7.63 Hz, 1H), 6.58 (dd, J = 8.51, 1.47 Hz, 2H), 3.81 (ddd, J = 9.88, 6.75, 4.50 Hz, 1H), 3.74 (d, J = 4.69 Hz, 1H), 3.69 (s, 3H), 3.68 (s, 3H), 3.11 (dd, J = 14.77, 9.88 Hz, 1H), 2.47 (q, J = 7.56 Hz, 2H), 1.32 (d, J = 6.65 Hz, 3H), 0.87 (t, J = 7.53 Hz, 3H). LCMS-ESI (POS.) m/z: 527.8 (M + H)$^+$. |
| 158.0 | The racemic compound 156.0 was separated by supercritical fluid chromatography (2 × 15 cm IA column with 65 mL/min 20% MeOH (0.1% NH$_4$OH)/CO$_2$. Outlet pressure = 100 bar; wavelength = 220 nm; injection volume = 1 mL, 6 mg/mL 1:3 DCM:MeOH). This was the second isomer to elute under these conditions. | OR |

TABLE 10-continued

| Example | Reagents | Structure, Name and and Data |
|---|---|---|
| | | (2S)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide<br>$^1$H NMR (400 MHz, CDCl$_3$) δ: 8.55 (s, 2H), 7.68-7.73 (m, 1H), 7.60-7.66 (m, 1H), 7.35 (t, J = 8.51 Hz, 1H), 7.10 (d, J = 7.63 Hz, 1H), 6.60 (dd, J = 8.61, 1.57 Hz, 2H), 3.79-3.87 (m, 1H), 3.72-3.77 (m, 1H), 3.71 (s, 3H), 3.69 (s, 3H), 3.13 (dd, J = 14.77, 9.88 Hz, ,1H), 2.49 (q, J = 7.50 Hz, 2H), 1.34 (d, J = 6.85 Hz, 3H), 0.89 (t, J = 7.63 Hz, 3H). LCMS-ESI (POS.) m/z: 527.8 (M + H)$^+$. |
| 159.0 | (S)-1-(5-fluoropyrimidin-2-yl)propane-2-sulfonamide and (R)-1-(5-fluoropyrimidin-2-yl)propane-2-sulfonamide (Example 9.0), 6-(azetidine-1-carbonyl)picolinohydrazide (Example 3.9), 2-isothiocyanato-1,3-dimethoxybenzene (Example 1.0), TFA was used instead of methanesulfonic acid. The racemic compound was separated by supercritical fluid chromatography (2 × 15 cm IA column with 65 mL/min 25% MeOH/CO$_2$. Outlet pressure = 100 bar; wavelength = 220 nm; injection volume = 0.5 mL, 4 mg/mL 1:1 DCM:MeOH).<br><br>This weas the first isomer to elute under these conditions. | 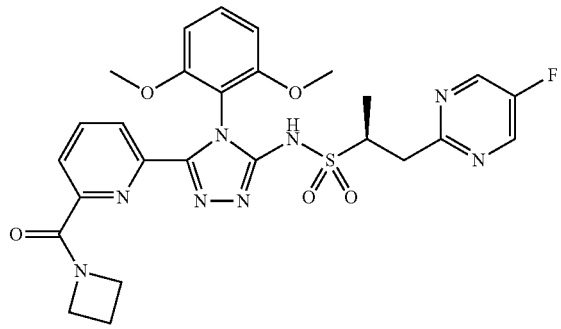 [SMILES: COc1cccc(OC)c1-n1c(NS(=O)(=O)[C@@H](C)Cc2ncc(F)cn2)nnc1-c1cccc(C(=O)N2CCC2)n1]<br>OR<br>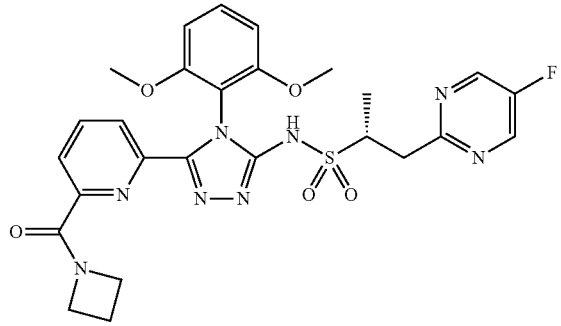 [SMILES: COc1cccc(OC)c1-n1c(NS(=O)(=O)[C@H](C)Cc2ncc(F)cn2)nnc1-c1cccc(C(=O)N2CCC2)n1]<br>(2S)-N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(6-(1-azetidnylcarbonyl)-2-pyridinyl)-4-(2,6-dimethoxyphenyl)-4H-1,2,4-triazol-3-yl)-1-(5-fluoro-2-pyrimidinyl)-2-propanesulfonamide<br>$^1$H NMR (400 MHz, CDCl$_3$) δ: 11.21 (br. s, 1H), 8.53 (s, 2H), 8.10 (dd, J = 7.04, 1.76 Hz, 1H), 7.83-7.90 (m, 2H), 7.37 (t, J = 8.51 Hz, 1H), 6.58 (dd, J = 8.51, 1.27 Hz, 2H), 4.11 (t, J = 7.73 Hz, 2H), 3.97 (t, J = 7.63 Hz, 2H), 3.82 (ddd, J = 9.93, 6.70, 4.50 Hz, 1H), 3.72 (dd, J = 14.38, 4.79 Hz, 1H), 3.65 (s, 3H), 3.63 (s, 3H), 3.14 (d, J = 9.78 Hz, 1H), 2.17 (quin, J = 7.73 Hz, 2H), 1.34 (d, J = 6.85 Hz, 3H). LCMS-ESI (POS.) m/z: 582.8 (M + H)$^+$. |

TABLE 10-continued

| Example | Reagents | Structure, Name and and Data |
|---|---|---|
| 160.0 | The racemic compound was separated by supercritical fluid chromatography (2 × 15 cm IA column with 65 mL/min 25% MeOH/CO$_2$. Outlet pressure = 100 bar; wavelength = 220 nm; injection volume = 0.5 mL, 4 mg/mL 1:1 DCM:MeOH). This was the second isomer to elute under these conditions. | 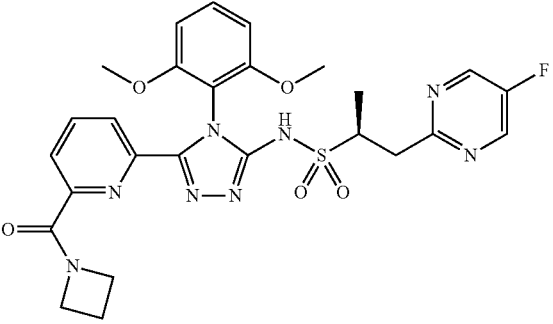 [SMILES: COc1cccc(OC)c1-n1c(NS(=O)(=O)[C@@H](C)Cc2ncc(F)cn2)nnc1-c1cccc(C(=O)N2CCC2)n1]  OR  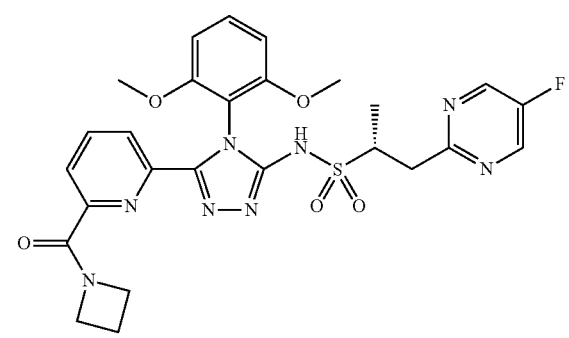 [SMILES: COc1cccc(OC)c1-n1c(NS(=O)(=O)[C@H](C)Cc2ncc(F)cn2)nnc1-c1cccc(C(=O)N2CCC2)n1]  (2S)-N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(6-(1-azetidnylcarbonyl)-2-pyridinyl)-4-(2,6-dimethoxyphenyl)-4H-1,2,4-triazol-3-yl)-1-(5-fluoro-2-pyrimidinyl)-2-propanesulfonamide  $^1$H NMR (400 MHz, CDCl$_3$) δ: 11.20 (br. s, 1H), 8.53 (s, 2H), 8.10 (dd, J = 7.14, 1.66 Hz, 1H), 7.83-7.90 (m, 2H), 7.37 (t, J = 8.51 Hz, 1H), 6.58 (dd, J = 8.51, 1.27 Hz, 2H), 4.11 (t, J = 7.82 Hz, 2H), 3.97 (t, J = 7.92 Hz, 2H), 3.82 (ddd, J = 9.83, 6.80, 4.50 Hz, 1H), 3.72 (dd, J = 14.48, 4.70 Hz, 1H), 3.65 (s, 3H), 3.63 (s, 3H), 3.12 (dd, J = 14.67, 9.78 Hz, 1H), 2.17 (quin, J = 7.73 Hz, 2H), 1.34 (d, J = 6.65 Hz, 3H). LCMS-ESI (POS.) m/z: 582.7 (M + H)$^+$. |
| 161.0 | (2S,3R)-3-(5-fluoropyrimidin-2-yl)butane-2-sulfonamide (Example 10.1), 6-ethoxypicolinohydrazide (Example 3.46), 2-isothiocyanato-1,3-dimethoxybenzene (Example 1.0), TFA was used instead of methanesulfonic acid. | 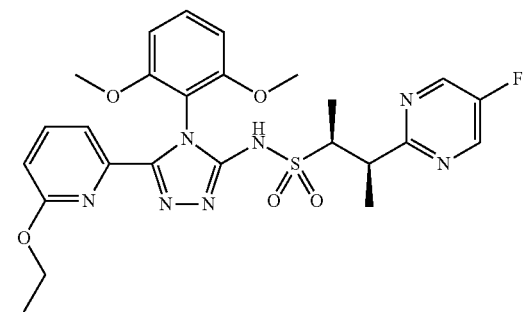 [SMILES: CCOc1cccc(-c2nnc(NS(=O)(=O)[C@@H](C)[C@H](C)c3ncc(F)cn3)n2-c2c(OC)cccc2OC)n1]  (2S,3R)-N-(4-(2,6-dimethoxyphenyl)-5-(6-ethoxy-2-pyridinyl)-4H-1,2,4-triazol-3-yl)-3-(5-fluoro-2-pyrimidinyl)-2-butanesulfonamide  $^1$H NMR (400 MHz, CDCl$_3$) δ: 11.00 (br. s, 1H), 8.53 (s, 2H), 7.54-7.64 (m, 2H), 7.32 (t, J = 8.51 Hz, 1H), 6.68 (dd, J = 7.82, 1.37 Hz, 1H), 6.53-6.62 (m, 2H), 3.79-3.89 (m, 2H), 3.70 (s, 3H), 3.68 (s, 3H), 3.44 (qd, J = 7.08, |

TABLE 10-continued

| Example | Reagents | Structure, Name and and Data |
|---|---|---|
| | | 1.08 Hz, 2H), 1.36 (dd, J = 8.61, 6.85 Hz, 6H), 1.08 (t, J = 7.14 Hz, 3H). LCMS-ESI (POS.) m/z: 557.8 (M + H)+. |
| 162.0 | (2S,3R)-3-(5-fluoropyrimidin-2-yl)butane-2-sulfonamide and (2S,3R)-3-(5-fluoropyrimidin-2-yl)butane-2-sulfonamide (Example 10.0), 6-ethoxypicolinohydrazide (Example 3.50), 2-isothiocyanato-1,3-dimethoxybenzene (Example 1.0), TFA was used instead of methanesulfonic acid. | 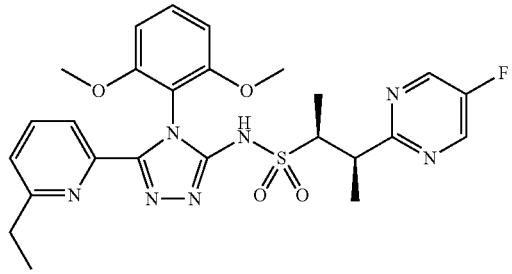 [SMILES: CCc1cccc(-c2nnc(NS(=O)(=O)[C@@H](C)[C@H](C)c3ncc(F)cn3)n2-c2c(OC)cccc2OC)n1]<br><br>AND<br><br>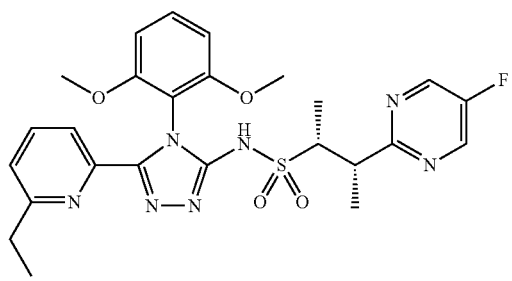 [SMILES: CCc1cccc(-c2nnc(NS(=O)(=O)[C@H](C)[C@@H](C)c3ncc(F)cn3)n2-c2c(OC)cccc2OC)n1]<br><br>(2R,3S)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide and (2S,3R)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide<br>$^1$H NMR (400 MHz, CDCl$_3$) δ: 8.55 (s, 2H), 7.61-7.68 (m, 2H), 7.33 (t, J = 8.41 Hz, 1H), 7.11 (dd, J = 7.14, 1.66 Hz, 1H), 6.54-6.61 (m, 2H), 3.83-3.90 (m, 2H), 3.70 (s, 3H), 3.67 (s, 3H), 2.52 (q, J = 7.56 Hz, 2H), 1.38 (t, J = 7.14 Hz, 6H), 0.90 (t, J = 7.53 Hz, 3H). LCMS-ESI (POS.) m/z: 541.7 (M + H)+. |
| 163.0 | The racemic compound 162.0 was separated by supercritical fluid chromatography (2 × 15 cm AS-H column with 65 mL/min 25% MeOH/CO$_2$. Outlet pressure = 100 bar; wavelength = 220 nm; injection volume = 0.75 mL, 5 mg/mL 1:1 DCM:MeOH). This was the first isomer to elute under these conditions | 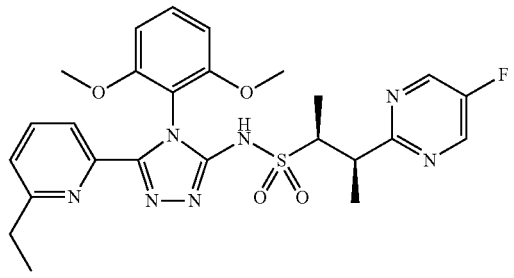 [SMILES: CCc1cccc(-c2nnc(NS(=O)(=O)[C@@H](C)[C@H](C)c3ncc(F)cn3)n2-c2c(OC)cccc2OC)n1]<br><br>OR<br><br>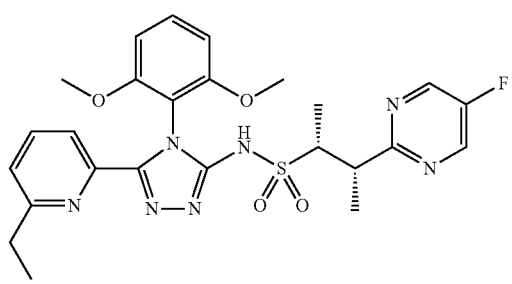 [SMILES: CCc1cccc(-c2nnc(NS(=O)(=O)[C@H](C)[C@@H](C)c3ncc(F)cn3)n2-c2c(OC)cccc2OC)n1] |

TABLE 10-continued

| Example | Reagents | Structure, Name and and Data |
|---|---|---|
| | | (2R,3S)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide or (2S,3R)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide<br>$^1$H NMR (400 MHz, CDCl$_3$) δ: 11.02 (br. s, 1H), 8.53 (s, 2H), 7.65-7.73 (m, 1H), 7.54-7.65 (m, 1H), 7.33 (t, J = 8.51 Hz, 1H), 7.08 (d, J = 7.63 Hz, 1H), 6.57 (td, J = 8.31, 0.98 Hz, 2H), 3.79-3.93 (m, 2H), 3.69 (s, 3H), 3.66 (s, 3H), 2.47 (q, J = 7.63 Hz, 2H), 1.37 (t, J = 6.94 Hz, 6H), 0.87 (t, J = 7.53 Hz, 3H). LCMS-ESI (POS.) m/z: 541.7 (M + H)$^+$. |
| 164.0 | The racemic compound 162.0 was separated by supercritical fluid chromatography (2 × 15 cm AS-H column with 65 mL/min 25% MeOH/CO$_2$. Outlet pressure = 100 bar; wavelength = 220 nm; injection volume = 0.75 mL, 5 mg/mL 1:1 DCM:MeOH). This was the second isomer to elute under these conditions | 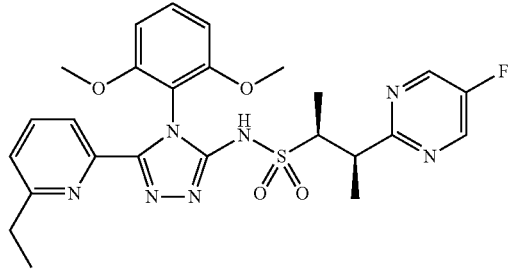 [SMILES: CCc1cccc(-c2nnc(NS(=O)(=O)[C@@H](C)[C@H](C)c3ncc(F)cn3)n2-c2c(OC)cccc2OC)n1]<br>OR<br>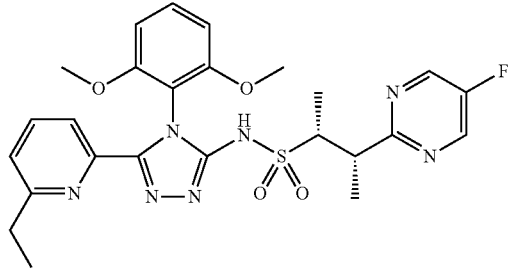 [SMILES: CCc1cccc(-c2nnc(NS(=O)(=O)[C@H](C)[C@@H](C)c3ncc(F)cn3)n2-c2c(OC)cccc2OC)n1]<br>(2R,3S)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide or (2S,3R)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide<br>$^1$H NMR (400 MHz, CDCl$_3$) δ: 11.02 (br. s, 1H), 8.53 (s, 2H), 7.64-7.71 (m, 1H), 7.53-7.64 (m, 1H), 7.33 (t, J = 8.41 Hz, 1H), 7.08 (dd, J = 7.53, 1.08 Hz, 1H), 6.57 (td, J = 8.31, 0.78 Hz, 2H), 3.80-3.93 (m, 2H), 3.69 (s, 3H), 3.66 (s, 3H), 2.47 (q, J = 7.63 Hz, 2H), 1.37 (t, J = 6.94 Hz, 6H), 0.87 (t, J = 7.53 Hz, 3H). LCMS-ESI (POS.) m/z: 541.7 (M + H)$^+$. |
| 165.0 | (2S,3R)-3-(5-fluoropyrimidin-2-yl)butane-2-sulfonamide and (2S,3R)-3-(5-fluoropyrimidin-2-yl)butane-2-sulfonamide (Example 10.0), 6-(hydrazinecarbonyl)-N-methylpicolinamide (Example 3.7), 2-isothiocyanato-1,3-dimethoxybenzene (Example 1.0), TFA was used instead of methanesulfonic acid | 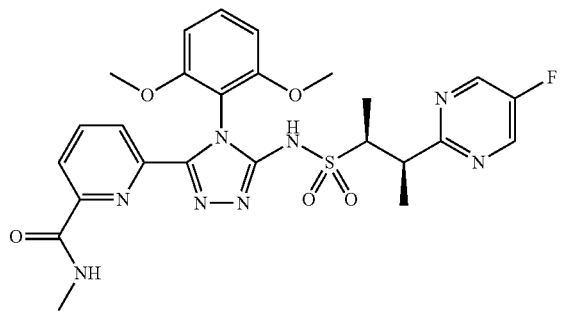 [SMILES: CNC(=O)c1cccc(-c2nnc(NS(=O)(=O)[C@@H](C)[C@H](C)c3ncc(F)cn3)n2-c2c(OC)cccc2OC)n1]<br>AND |

315
316

TABLE 10-continued

| Example | Reagents | Structure, Name and and Data |
|---|---|---|
| | | 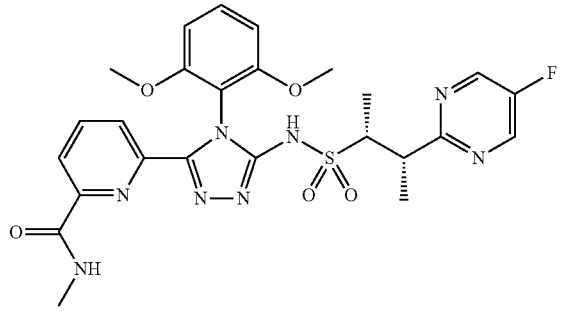 [SMILES: CNC(=O)c1cccc(-c2nnc(NS(=O)(=O)[C@H](C)[C@@H](C)c3ncc(F)cn3)n2-c2c(OC)cccc2OC)n1]<br>6-(4-(2,6-dimethoxyphenyl)-5-(((((1R,2S)-2-(5-fluoro-2-pyrrimidinyl)-1-methylpropyl)sulfonyl)amino)-4H-1,2,4-triazol-3-yl)-N-methyl-2-pyridinecarboxamide and 6-(4-(2,6-dimethoxyphenyl)-5-(((((1S,2R)-2-(5-fluoro-2-pyrimidinyl)-1-methylpropyl)sulfonyl)amino)-4H-1,2,4-triazol-3-yl)-N-methyl-2-pyridinecarboxamide<br>$^1$H NMR (400 MHz, CDCl$_3$) δ: 8.54 (s, 2H), 8.23 (dd, J = 8.02, 0.98 Hz, 1H), 8.15 (dd, J = 7.83, 0.98 Hz, 1H), 7.94 (t, J = 7.92 Hz, 1H), 7.47 (t, J = 8.26 Hz, 1H), 6.65-6.75 (m, 2H), 6.30 (d, J = 4.70 Hz, 1H), 3.78-3.90 (m, 2H), 3.72 (s, 3H), 3.70 (s, 3H), 2.73 (d, J = 5.09 Hz, 3H), 1.37 (t, J = 6.55 Hz, 6H), LCMS-ESI (POS.) m/z: 570.8 (M + H)$^+$. |
| 166.0 | The racemic compound 165.0 was separated by supercritical fluid chromatography (250 × 21 cm AS-H column with 15 g/min MeOH + 45 g/min CO$_2$. Outlet pressure = 100 bar; wavelength = 220 nm; injection volume = 0.5 mL, 21 mg/mL 1:1 DCM:MeOH). This was the first isomer to elute under these conditions. | 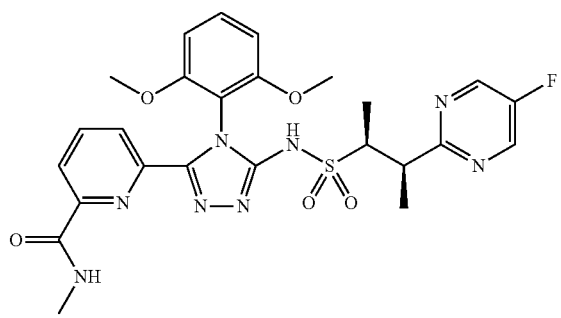 [SMILES: CNC(=O)c1cccc(-c2nnc(NS(=O)(=O)[C@@H](C)[C@H](C)c3ncc(F)cn3)n2-c2c(OC)cccc2OC)n1]<br>OR<br>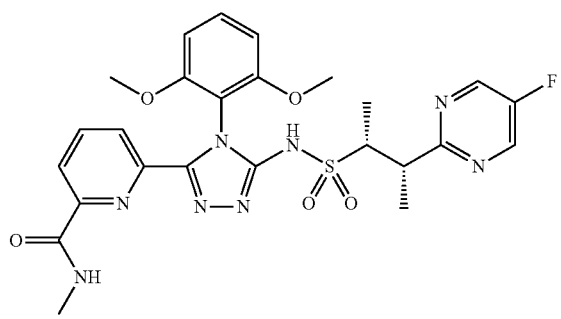 [SMILES: CNC(=O)c1cccc(-c2nnc(NS(=O)(=O)[C@H](C)[C@@H](C)c3ncc(F)cn3)n2-c2c(OC)cccc2OC)n1]<br>6-(4-(2,6-dimethoxyphenyl)-5-(((((1R,2S)-2-(5-fluoro-2-pyrrimidinyl)-1-methylpropyl)sulfonyl)amino)-4H-1,2,4-triazol-3-yl)-N-methyl-2-pyridinecarboxamide or 6-(4-(2,6-dimethoxyphenyl)-5-(((((1S,2R)-2-(5-fluoro-2-pyrimidinyl)-1-methylpropyl)sulfonyl)amino)-4H-1,2,4-triazol-3-yl)-N-methyl-2-pyridinecarboxamide<br>$^1$H NMR (400 MHz, CDCl$_3$) δ: 8.54 (s, 2H), 8.22 (d, J = 6.46 Hz, 1H), 8.08-8.18 (m, 1H), 7.84-7.99 (m, 1H), 7.41-7.51 (m, 1H), 6.69 (t, J = 7.73 Hz, 2H), 6.23-6.36 (m, 1H), 3.78- |

TABLE 10-continued

| Example | Reagents | Structure, Name and Data |
|---|---|---|
| | | 3.91 (m, 2H), 3.70 (d, J = 11.54 Hz, 6H), 2.73 (3d, J = 4.89 Hz, 3H), 1.36 (dd, J = 1.00 Hz, 6H). LCMS-ESI (POS.) m/z: 570.8 (M + H)+. |
| 167.0 | The racemic compound 165.0 was separated by supercritical fluid chromatography (250 × 21 cm AS-H column with 15 g/min MeOH + 45 g/min CO₂. Outlet pressure = 100 bar; wavelength = 220 nm; injection volume = 0.5 mL, 21 mg/mL 1:1 DCM;MeOH). This was the second isomer to elute under these conditions. | OR<br><br>6-(4-(2,6-dimethoxyphenyl)-5-((((1R,2S)-2-(5-fluoro-2-pyrimidinyl)-1-methylpropyl)sulfonyl)amino)-4H-1,2,4-triazol-3-yl)-N-methyl-2-pyridinecarboxamide or 6-(4-(2,6-dimethoxyphenyl)-5-((((1S,2R)-2-(5-fluoro-2-pyrimidinyl)-1-methylpropyl)sulfonyl)amino)-4H-1,2,4-triazol-3-yl)-N-methyl-2-pyridinecarboxamide<br>¹H NMR (400 MHz, CDCl₃) δ: 8.53 (s, 2H), 8.08-8.26 (m, 2H), 7.87-7.97 (m, 1H), 7.46 (t, J = 9.10 Hz, 1H), 6.69 (t, J = 7.63 Hz, 2H), 6.24-6.34 (m, 1H), 3.80-3.90 (m, 2H), 3.71 (br. s, 3H), 3.69 (s, 3H), 2.73 (d, J = 4.89 Hz, 3H), 1.36 (m, J = 6.65 Hz, 6H). LCMS-ESI (POS.) m/z: 570.8 (M + H)+. |
| 168.0 | (2S,3R)-3-(5-fluoropyrimidin-2-yl)butane-2-sulfonamide (Example 10.1), 6-oxo-1,6-dihydropyridine-2-carbohydrazide (Example 3.10), 2-isothiocyanato-1,3-dimethoxybenzene (Example 1.0), TFA was used instead of methanesulfonic acid. | (2S,3R)-N-(4-(2,6-dimethoxyphenyl)-5-(6-oxo-1,6-dihydro-2-pyridinyl)-4H-1,2,4-triazol-3-yl)-3-(5-fluoro-2-pyrimidinyl)-2-butanesulfonamide<br>¹H NMR (400 MHz, CDCl₃) δ: 12.27 (br s, 1H), 9.94 (br s, 1H), 8.57 (s, 2H), 7.51 (t, J = 8.51 Hz, 1H), 7.19 (dd, J = 9.29, 6.94 Hz, 1H), 6.68-6.75 (m, 2H), 6.66 (dd, J = 9.29, 0.88 Hz, 1H), 5.87 (dd, J = 6.94, 0.88 Hz, 1H), 3.86-3.94 (m, 2H), 3.82 (s, 3H), 3.80 (s, 3H), 1.38 (d, J = 3.13 Hz, 3H), 1.37 (d, J = 3.13 Hz, 3H). LCMS-ESI (POS.) m/z: 529.7 (M + H)+. |

TABLE 10-continued

| Example | Reagents | Structure, Name and and Data |
|---|---|---|
| 169.0 | S)-1-(5-fluoropyrimidin-2-yl)propane-2-sulfonamide and (R) 1-(5-fluoropyrimidin-2-yl)propane-2-sulfonamide (Example 9.0), 6-(difluoromethoxy)picolinohydrazide (Example 3.0), 2-isothiocyanato-1,3-dimethoxybenzene (Example 1.0), TFA was used instead of methanesulfonic acid. | 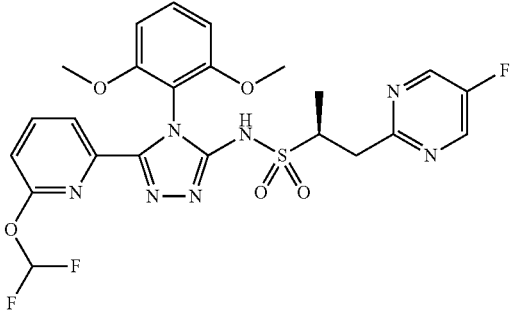 [SMILES: COc1cccc(OC)c1-n1c(NS(=O)(=O)[C@@H](C)Cc2ncc(F)cn2)nnc1-c1cccc(OC(F)F)n1]<br>AND<br>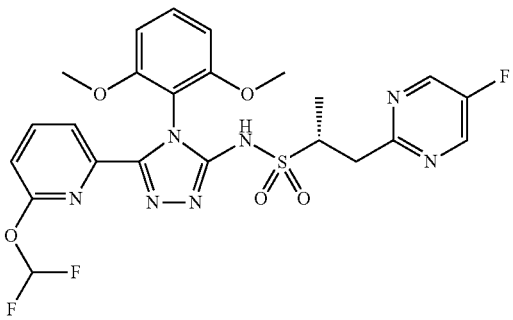 [SMILES: COc1cccc(OC)c1-n1c(NS(=O)(=O)[C@H](C)Cc2ncc(F)cn2)nnc1-c1cccc(OC(F)F)n1]<br>(2S)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide and (2R)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide<br>$^1$H NMR (400 MHz, CDCl$_3$) δ: 8.56 (s, 2H), 7.88-7.93 (m, 1H), 7.80-7.87 (m, 1H), 7.44 (t, J = 8.51 Hz, 1H), 6.89 (dd, J = 8.02, 0.78 Hz, 1H), 6.70 (dd, J = 8.51, 1.27 Hz, 2H), 5.79-6.18 (m, 1H), 3.81-3.87 (m, 1H), 3.76 (s, 3H), 3.74 (s, 3H), 3.70 (d, J = 5.48 Hz, 1H), 3.12 (dd, J = 14.87, 9.78 Hz, 1H), 1.34 (d, J = 6.85 Hz, 3H). LCMS-ESI (POS.) m/z: 565.7 (M + H)$^+$. |
| 170.0 | The racemic compound 169.0 was separated by supercritical fluid chromatography (250 × 21 m AS-H column on Thar 80 with 9 g/min MeOH + 41 g/min CO$_2$, 18% co-solvent at 50 g/min. Temperature = 22° C.; outlet pressure = 100 bar; wavelength = 295 nm; injection volume = 0.22 mL or 35 mg sample disolved in 4 mL of MeOH:DCM 1:1). This was the first isomer to elute under these conditions | 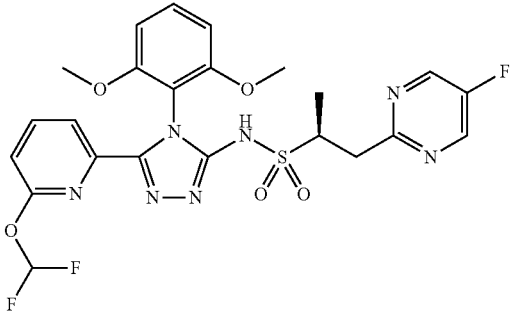 [SMILES: COc1cccc(OC)c1-n1c(NS(=O)(=O)[C@@H](C)Cc2ncc(F)cn2)nnc1-c1cccc(OC(F)F)n1]<br>OR |

| Example | Reagents | Structure, Name and and Data |
|---|---|---|
| | | 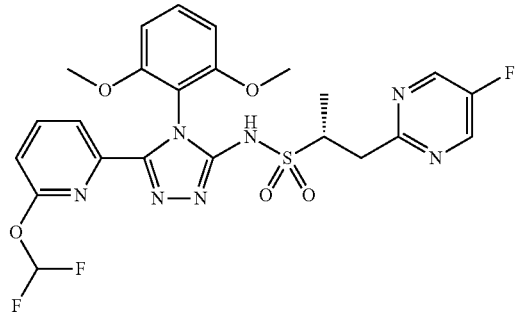 [SMILES: COc1cccc(OC)c1-n1c(NS(=O)(=O)[C@H](C)Cc2ncc(F)cn2)nnc1-c1cccc(OC(F)F)n1]<br>(2S)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide<br>$^1$H NMR (400 MHz, CDCl$_3$) δ: 8.55 (s, 2H), 7.87-7.97 (m, 1H), 7.77-7.87 (m, 1H), 7.44 (t, J = 8.51 Hz, 1H), 6.88 (d, J = 8.02 Hz, 1H), 6.69 (d, J = 8.41 Hz, 2H), 5.74-6.20 (m, 1H), 3.78-3.88 (m, 1H), 3.75 (s, 3H), 3.73 (s, 3H), 3.70 (d, J = 3.91 Hz, 1H), 2.97-3.18 (m, 1H), 1.33 (d, J = 6.46 Hz, 3H). LCMS-ESI (POS.) m/z: 565.7 (M + H)$^+$. |
| 171.0 | The racemic compound 169.0 was separated by supercritical fluid chromatography (250 × 21 m AS-H column on Thar 80 with 9 g/min MeOH + 41 g/min CO$_2$, 18% co-solvent at 50 g/min. Temperature = 22° C.; outlet pressure = 100 bar; wavelength = 295 nm; injection volume = 0.22 mL or 35 mg sample disolved in 4 mL of MeOH:DCM 1:1). This was the second isomer to elute under these conditions | 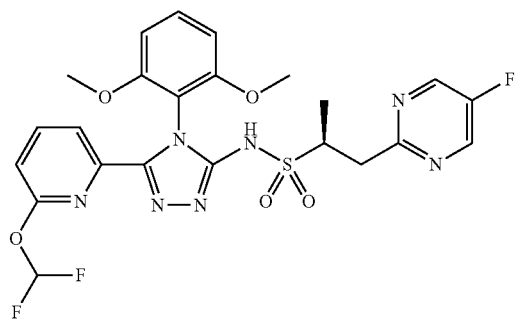 [SMILES: COc1cccc(OC)c1-n1c(NS(=O)(=O)[C@@H](C)Cc2ncc(F)cn2)nnc1-c1cccc(OC(F)F)n1]<br>OR<br>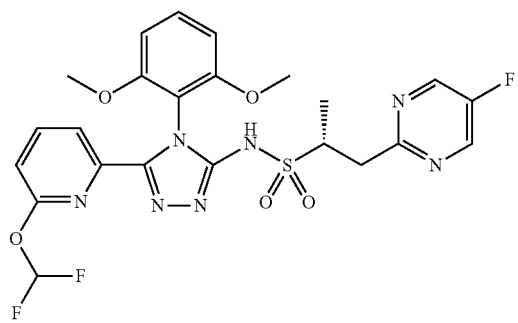 [SMILES: COc1cccc(OC)c1-n1c(NS(=O)(=O)[C@H](C)Cc2ncc(F)cn2)nnc1-c1cccc(OC(F)F)n1]<br>(2S)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide<br>$^1$H NMR (400 MHz, CDCl$_3$) δ: 8.53 (s, 2H), 7.85-7.92 (m, 1H), 7.80 (t, J = 7.63 Hz, 1H), 7.41 (t, J = 8.22 Hz, 1H), 6.86 (d, J = 7.04 Hz, 1H), 6.67 (d, J = 8.22 Hz, 2H), 5.75-6.17 (m, 1H), 3.80 (m, 1H), 3.73 (s, 3H), 3.70 (s, 3H), |

TABLE 10-continued

| Example | Reagents | Structure, Name and and Data |
|---|---|---|
| | | 3.64-3.69 (m, 1H), 3.09 (dd, J = 14.57, 9.88 Hz, 1H), 1.31 (d, J = 6.46 Hz, 3H). LCMS-ESI (POS.) m/z: 565.7 (M + H)⁺. |
| 172.0 | (1R,2S)-1-methoxy-1-(5-methylpyrimidin-2-yl)propane-2-sulfonamide (Example 14.0), 6-ethoxypicolinohydrazide (Example 3.46), 2-isothiocyanato-1,3-dimethoxybenzene (Example 1.0) | 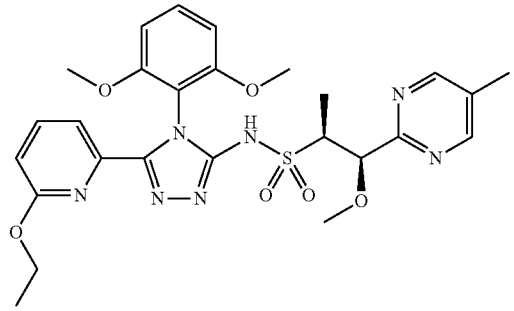 [SMILES: CCOc1cccc(-c2nnc(NS(=O)(=O)[C@@H](C)[C@H](OC)c3ncc(C)cn3)n2-c2c(OC)cccc2OC)n1]<br>(1R,2S)-N-(4-(2,6-dimethoxyphenyl)-5-(6-ethoxypyridin-2-yl)-4H-1,2,4-triazol-3-yl)-1-methoxy-1-(5-methylpyrimidin-2-yl)propane-2-sulfonamide<br>$^1$H NMR (500 MHz, CDCl$_3$) δ: 8.63 (s, 2H), 7.54-7.65 (m, 2H), 7.32 (t, J = 8.56 Hz, 1H), 6.67 (dd, J = 7.82, 1.22 Hz, 1H), 6.59 (dd, J = 8.56, 3.91 Hz, 2H), 4.98 (d, J = 4.89 Hz, 1H), 3.75 (qd, J = 6.97, 4.77 Hz, 1H), 3.71 (s, 3H), 3.69 (s, 3H), 3.43 (q, J = 7.09 Hz, 2H), 3.34 (s, 3H), 2.34 (s, 3H), 1.39 (d, J = 7.09 Hz, 3H), 1.08 (t, J = 7.09 Hz, 3H). LCMS-ESI (POS.) m/z: 570.2 (M + H)⁺. |
| 173.0 | (1R,2S)-1-methoxy-1-(5-methylpyrimidin-2-yl)propane-2-sulfonamide (Example 14.0), nicotinic hydrazide (comercially available from Acros Organics, NJ, USA), 2-isothiocyanato-1,3-dimethoxybenzene (Example 1.0) | 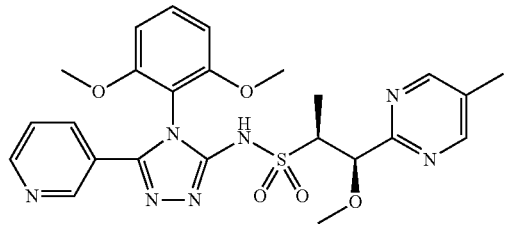 [SMILES: COc1cccc(OC)c1-n1c(NS(=O)(=O)[C@@H](C)[C@H](OC)c2ncc(C)cn2)nnc1-c1cccnc1]<br>(1R,2S)-N-(4-(2,6-dimethoxyphenyl)-5-(pyridin-3-yl)-4H-1,2,4-triazol-3-yl)-1-methoxy-1-(5-methylpyrimidin-2-yl)propane-2-sulfonamide<br>$^1$H NMR (500 MHz, CDCl$_3$) δ: 11.30 (br.s., 1H), 8.62 (td, J = 2.45, 1.47 Hz, 2H), 8.61 (d, J = 0.73 Hz, 2H), 7.78 (dt, J = 8.07, 1.96 Hz, 1H), 7.39 (t, J = 8.56 Hz, 1H), 7.29 (ddd, J = 7.95, 4.89, 0.86 Hz, 1H), 6.60 (d, J = 8.07 Hz, 2H), 4.97 (d, J = 4.65 Hz, 1H), 3.75-3.78 (m, 1H), 3.75 (s, 3H), 3.72 (s, 3H), 3.34 (s, 3H), 2.33 (s, 3H), 1.39 (d, J = 7.09 Hz, 3H). LCMS-ESI (POS.) m/z: 526.3 (M + H)⁺. |
| 174.0 | (1R,2S)-1-methoxy-1-(5-methylpyrimidin-2-yl)propane-2-sulfonamide (Example 14.0), 6-ethylpicolinohydrazide (Example 3.50), 2-isothiocyanato-1,3-dimethoxybenzene (Example 1.0) | 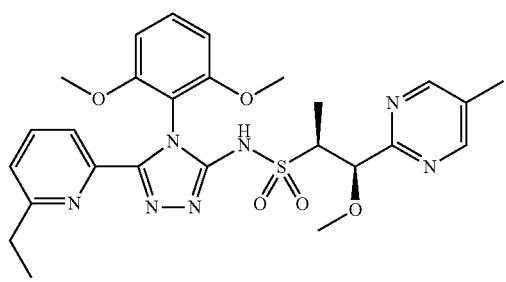 [SMILES: CCc1cccc(-c2nnc(NS(=O)(=O)[C@@H](C)[C@H](OC)c3ncc(C)cn3)n2-c2c(OC)cccc2OC)n1]<br>(1R,2S)-N-(4-(2,6-dimethoxyphenyl)-5-(6-ethylpyridin-2-yl)-4H-1,2,4-triazol-3-yl)-1-methoxy-1-(5-methylpyrimidin-2-yl)propane-2-sulfonamide<br>$^1$H NMR (500 MHz, CDCl$_3$) δ: 11.22 (br.s., |

| Example | Reagents | Structure, Name and and Data |
|---|---|---|
| | | 1H), 8.61 (s, 2H), 7.64-7.70 (m, 1H), 7.57-7.64 (m, 1H), 7.33 (t, J = 8.56 Hz, 1H), 7.08 (d, J = 7.58 Hz, 1H), 6.58 (d, J = 8.56 Hz, 2H), 4.97 (d, J = 4.89 Hz, 1H), 3.72-3.80 (m, 1H), 3.70 (s, 3H), 3.67 (s, 3H), 3.35 (s, 3H), 2.47 (q, J = 7.58 Hz, 2H), 2.33 (s, 3H), 1.40 (d, J = 7.09 Hz, 3H), 0.85-0.89 (m, 3H). LCMS-ESI (POS.) m/z: 554.0 (M + H)+. |
| 175.0 | (1R,2S)-1-((tert-butyldimethylsilyl)oxy)-1-(5-methylpyrimidin-2-yl)propane-2-sulfonamide (Example 11.0), 6-ethylpicolinohydrazide (Example 3.50), 2-isothiocyanato-1,3-dimethoxybenzene (Example 1.0) | 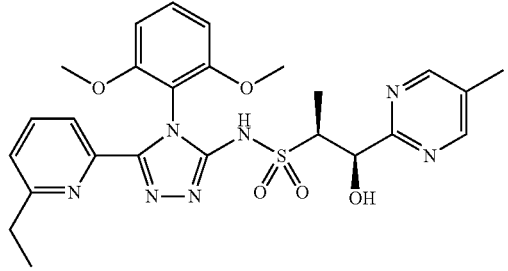 [SMILES: CCc1cccc(-c2nnc(NS(=O)(=O)[C@@H](C)[C@H](O)c3ncc(C)cn3)n2-c2c(OC)cccc2OC)n1]<br>(1R,2S)-N-(4-(2,6-dimethoxyphenyl)-5-(6-ethylpyridin-2-yl)-4H-1,2,4-triazol-3-yl)-1-hydroxy-1-(5-methylpyrimidin-2-yl)propane-2-sulfonamide<br>$^1$H NMR (500 MHz, CDCl$_3$) δ: 10.97 (br.s., 1H), 8.54 (s, 2H), 7.58-7.62 (m, 1H), 7.49-7.56 (m, 1H), 7.25 (t, J = 8.56 Hz, 1H), 6.98-7.02 (m, 1H), 6.55 (d, J = 8.56 Hz, 1H), 6.48 (dd, J = 8.56, 0.98 Hz, 1H), 5.53 (d, J = 0.98 Hz, 1H), 3.72-3.80 (m, 2H), 3.66 (s, 3H), 3.58 (s, 3H), 2.38 (q, J = 7.58 Hz, 2H), 2.26 (s, 3H), 1.13 (d, J = 6.85 Hz, 3H), 0.73-0.84 (m, 3H). LCMS-ESI (POS.) m/z: 540.0 (M + H)+. |
| 176.0 | (2S,3R)-3-(5-methylpyrimidin-2-yl)butane-2-sulfonamide (Example 10.0), 6-ethylpicolinohydrazide (Example 3.50), 2-isothiocyanato-1,3-dimethoxybenzene (Example 1.0) | 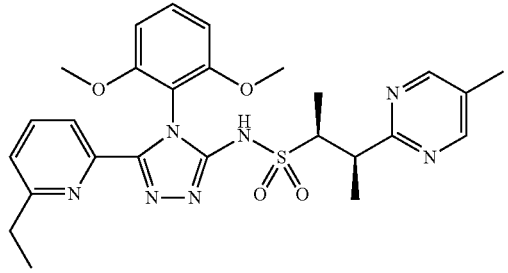 [SMILES: CCc1cccc(-c2nnc(NS(=O)(=O)[C@@H](C)[C@H](C)c3ncc(C)cn3)n2-c2c(OC)cccc2OC)n1]<br>(2S,3R)-N-(4-(2,6-dimethoxyphenyl)-5-(6-ethylpyridin-2-yl)-4H-1,2,4-triazol-3-yl)-3-(5-methylpyrimidin-2-yl)butane-2-sulfonamide<br>$^1$H NMR (500 MHz, CDCl$_3$) δ: 11.27 (br.s., 1H), 8.53 (s, 2H), 7.64-7.69 (m, 1H), 7.57-7.63 (m, 1H), 7.32 (t, J = 8.56 Hz, 1H), 7.08 (d, J = 7.58 Hz, 1H), 6.56 (td, J = 9.23, 0.86 Hz, 2H), 3.87-3.95 (m, 1H), 3.79 (quin, J = 6.85 Hz, 1H), 3.69 (s, 3H), 3.66 (s, 3H), 2.47 (q, J = 7.58 Hz, 2H), 2.29 (s, 3H), 1.39 (d, J = 7.09 Hz, 3H), 1.36 (d, J = 7.09 Hz, 3H), 0.87 (t, J = 7.58 Hz, 3H). LCMS-ESI (POS.) m/z: 538.0 (M + H)+. |
| 177.0 | (2S,3R)-3-(5-methylpyrimidin-2-yl)butane-2-sulfonamide (Example 10.1), 6-methoxy-4-methylpicolinohydrazide (Example 3.51), 2-isothiocyanato-1,3-dimethoxybenzene (Example 1.0) | 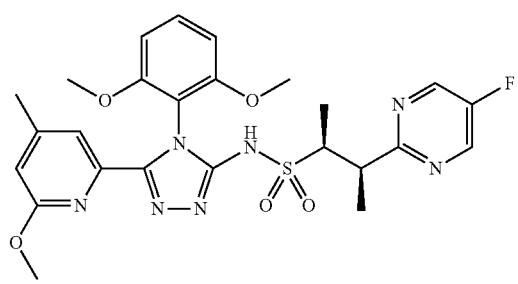 [SMILES: COc1cc(C)cc(-c2nnc(NS(=O)(=O)[C@@H](C)[C@H](C)c3ncc(F)cn3)n2-c2c(OC)cccc2OC)n1] |

| Example | Reagents | Structure, Name and and Data |
|---|---|---|
| | | (2S,3R)-N-(4-(2,6-dimethoxyphenyl)-5-(6-methoxy-4-methylpyridin-2-yl)-4H-1,2,4-triazol-3-yl)-3-(5-fluoropyrimidin-2-yl)butane-2-sulfonamide<br>¹H NMR (500 MHz, CDCl₃) δ: 11.03 (br.s., 1H), 8.54 (s, 2H), 7.45 (s, 1H), 7.30 (t, J = 8.44 Hz, 1H), 6.58 (t, J = 7.95 Hz, 2H), 6.51 (s, 1H), 3.80-3.88 (m, 2H), 3.71 (s, 3H), 3.68 (s, 3H), 3.14 (s, 3H), 2.33 (s, 3H), 1.37 (d, J = 6.58 Hz, 3H), 1.35 (d, J = 6.60 Hz, 3H). LCMS-ESI (POS.) m/z: 557.9 (M + H)⁺. |
| 178.0 | (2S,3R)-3-(5-methylpyrimidin-2-yl)butane-2-sulfonamide (Example 10.0), 6-methoxy-4-methylpicolinohydrazide (Example 3.51), 2-isothiocyanato-1,3-dimethoxybenzene (Example 1.0) | 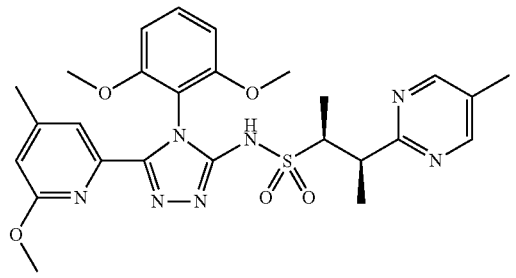 [SMILES: COc1cc(C)cc(-c2nnc(NS(=O)(=O)[C@@H](C)[C@H](C)c3ncc(C)cn3)n2-c2c(OC)cccc2OC)n1]<br>(2S,3R)-N-(4-(2,6-dimethoxyphenyl)-5-(6-methoxy-4-methylpyridin-2-yl)-4H-1,2,4-triazol-3-yl)-3-(5-fluoropyrimidin-2-yl)butane-2-sulfonamide<br>¹H NMR (500 MHz, CDCl₃) δ: 11.25 (br.s., 1H), 8.55 (s, 2H), 7.46 (d, J = 0.73 Hz, 1H), 7.30 (t, J = 8.56 Hz, 1H), 6.58 (ddd, J = 8.38, 7.27, 0.73 Hz, 2H), 6.47-6.52 (m, 1H), 3.91 (s, 1H), 3.75-3.82 (m, 1H), 3.71 (s, 3H), 3.68 (s, 3H), 3.14 (s, 3H), 2.32 (s, 3H), 2.30 (s, 3H), 1.39 (d, J = 7.09 Hz, 3H), 1.36 (d, J = 7.09 Hz, 3H). LCMS-ESI (POS.) m/z: 554.3 (M + H)⁺. |
| 179.0 | (1R,2S)-1-methoxy-1-(5-methylpyrimidin-2-yl)propane-2-sulfonamide (Example 14.0), 6-methoxy-4-methylpicolinohydrazide (Example 3.51), 2-isothiocyanato-1,3-dimethylbenzene (Example 1.0) | 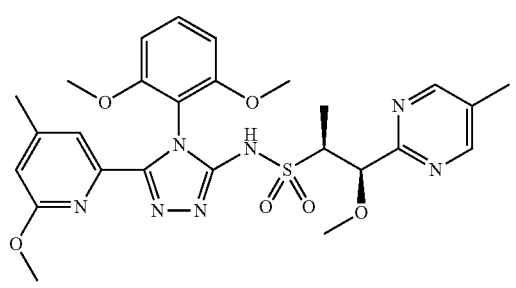 [SMILES: COc1cc(C)cc(-c2nnc(NS(=O)(=O)[C@@H](C)[C@H](OC)c3ncc(C)cn3)n2-c2c(OC)cccc2OC)n1]<br>(1R,2S)-N-(4-(2,6-dimethoxyphenyl)-5-(6-methoxy-4-methylpyridin-2-yl)-4H-1,2,4-triazol-3-yl)-1-methoxy-1-(5-methylpyrimidin-2-yl)propane-2-sulfonamide<br>¹H NMR (500 MHz, CDCl₃) δ: 11.19 (br.s., 1H), 8.60 (d, J = 0.73 Hz, 2H), 7.45 (d, J = 1.22 Hz, 1H), 7.30 (t, J = 8.56 Hz, 1H), 6.58 (d, J = 8.56 Hz, 2H), 6.47-6.53 (m, 1H), 4.97 (d, J = 4.65 Hz, 1H), 3.72-3.76 (m, 1H), 3.71 (s, 3H), 3.69 (s, 3H), 3.33 (s, 3H), 3.13 (s, 3H), 2.32 (s, 6H), 1.38 (d, J = 7.09 Hz, 3H). LCMS-ESI (POS.) m/z: 570.0 (M + H)⁺. |

TABLE 10-continued

| Example | Reagents | Structure, Name and and Data |
|---|---|---|
| 180.0 | (2S,3R)-3-(5-methylpyrimidin-2-yl)butane-2-sulfonamide (Example 10.0), 6-ethoxypicolinohydrazide (Example 3.46), 2-isothiocyanato-1,3-dimethoxybenzene (Example 1.0) | (2S,3R)-N-(4-(2,6-dimethoxyphenyl)-5-(6-ethoxypyridin-2-yl)-4H-1,2,4-triazol-3-yl)-3-(5-methylpyrimidin-2-yl)butane-2-sulfonamide<br>¹H NMR (500 MHz, CDCl₃) δ: 8.67 (s, 2H), 7.55-7.64 (m, 2H), 7.33 (t, J = 8.44 Hz, 1H), 6.68 (dd, J = 7.95, 1.10 Hz, 1H), 6.60 (dd, J = 8.56, 2.69 Hz, 2H), 3.83-3.93 (m, 1H), 3.72-3.78 (m, 1H), 3.71 (s, 3H), 3.69 (s, 3H), 3.43 (q, J = 6.77 Hz, 2H), 2.35 (s, 3H), 1.40 (d, J = 7.09 Hz, 3H), 1.38 (d, J = 7.09 Hz, 3H), 1.08 (t, J = 7.09 Hz, 3H). LCMS-ESI (POS.) m/z: 554.9 (M + H)⁺. |
| 181.0 | 2-(2-cyano-4-fluorophenyl)-ethanesulfonamide (Example 8.0), 5-chloronicotinohydrazide (Example 3.15) 2-isothioxycnato-1,3-dimethoxybenzene (Example 1.0), ercury acetate (comercially available from VWR International, Radnor, PA, USA) was used instead of silver nitrate, TFA (comercially available from Sigma-Aldrich Corp, St. Louis, MO, USA) was used instead of methanesulfonic acid. | N-(5-(5-chloro-3-pyridinyl)-4-(2,6-dimethoxyphenyl)-4H-1,2,4-triazol-3-yl)-2-(2-cyano-4-fluorophenyl)ethanesulfonamide<br>¹H NMR (400 MHz, CDCl₃) δ 8.58 (d, J = 2.3 Hz, 1H), 8.43 (d, J = 1.8 Hz, 1H), 8.02 (s, 1H), 7.81 (dd, J = 2.2, 2.2, 1H), 7.20-7.45 (m, 3H), 6.64 (d, J = 8.6 Hz, 2H), 3.76 (s, 6H), 3.19-3.46 (m, 4H). LCMS-ESI (POS.) m/z: 543.0 (M + H)⁺. |
| 182.0 | (2R,3S)-3-(5-fluoropyrimidin-2-yl)butane-2-sulfonamide and (2S,3R)-3-(5-fluoropyrimidin-2-yl)butane-2-sulfonamide (Example 10.0), Nicotinic hydrazide (Sigma-Aldrich Chemical Company, Inc.), 2-isothiocyanato-1,3-dimethoxybenzene (Example 1.0), ercury acetate (comercially available from VWR International, Radnor, PA, USA) was used instead of silver nitrate, TFA (comercially available from Sigma-Aldrich Corp, St. Louis, MO, USA) was used instead of methanesulfonic acid. | AND<br><br>(2R,3S)-N-(4-(2,6-dimethoxyphenyl)-5-(3-pyridinyl)-4H-1,2,4-triazol-3-yl)-3-(5-fluoro-2-pyrimidinyl)-2-butanesulfonamide and (2S,3R)-N-(4-(2,6-dimethoxyphenyl)-5-(3-pyridinyl)-4H-1,2,4-triazol-3-yl)-3-(5-fluoro-2-pyrimidinyl)-2-butanesulfonamide<br>LCMS-ESI (POS.) m/z: 514.1 (M + H)⁺. |

TABLE 10-continued

| Example | Reagents | Structure, Name and Data |
|---|---|---|
| 183.0 | The racemic Example 182.0 was separated by supercritical fluid chromatography (250 × 30 m AS-H column on Thar 80 with 16 mL/min 20 mM NH₃ in EtOH + 64 g/min CO₂, 20% co-solvent at 80 g/min. Outlet pressure = 100 bar; temperature = 21° C.; wavelength = 265 nm; injection volume = 0.5 mL, 11.4 mg/mL 2:1 MeOH:DCM). This was the first isomer to elute under these conditions. | OR<br><br>(2R,3S)-N-(4-(2,6-dimethoxyphenyl)-5-(3-pyridinyl)-4H-1,2,4-triazol-3-yl)-3-(5-fluoro-2-pyrimidinyl)-2-butanesulfonamide or (2S,3R)-N-(4-(2,6-dimethoxyphenyl)-5-(3-pyridinyl)-4H-1,2,4-triazol-3-yl)-3-(5-fluoro-2-pyrimidinyl)-2-butanesulfonamide<br>¹H NMR (400 MHz, CDCl₃) δ 8.61 (br. s., 2H), 8.53 (s, 2H), 7.74 (dt, J = 8.02, 1.96 Hz, 1H), 7.39 (t, J = 8.51 Hz, 1H), 7.23-7.27 (m, 1H), 6.55-6.64 (m, 2H), 3.79-3.89 (m, 2H), 3.73 (s, 3H), 3.71 (s, 3H), 1.36 (dd, J = 7.00 Hz, 6H). LCMS-ESI (POS.) m/z: 514.2 (M + H)⁺. |
| 184.0 | The racemic Example 182.0 was separated by supercritical fluid chromatography (250 × 30 m AS-H column on Thar 80 with 16 mL/min 20 mM NH₃ in EtOH + 64 g/min CO₂, 20% co-solvent at 80 g/min. Outlet pressure = 100 bar; temperature = 21° C.; wavelength = 265 nm; injection volume = 0.5 mL, 11.4 mg/mL 2:1 MeOH:DCM).<br>This was the second isomer to elute under these conditions. | OR<br><br>(2R,3S)-N-(4-(2,6-dimethoxyphenyl)-5-(3-pyridinyl)-4H-1,2,4-triazol-3-yl)-3-(5-fluoro-2-pyrimidinyl)-2-butanesulfonamide or (2S,3R)-N-(4-(2,6-dimethoxyphenyl)-5-(3-pyridinyl)-4H-1,2,4-triazol-3-yl)-3-(5-fluoro-2-pyrimidinyl)-2-butanesulfonamide<br>¹H NMR (400 MHz, CDCl₃) δ 8.62 (br. s., 2H), 8.53 (s, 2H), 7.73 (dt, J = 8.12, 1.81 Hz, 1H), 7.38 (t, J = 8.51 Hz, 1H), 7.22-7.26 (m, 1H), 6.59 (ddd, J = 8.46, 7.38, 0.78 Hz, 2H), 3.79-3.89 (m, 2H), 3.72 (s, 3H), 3.70 (s, 3H), 1.37 (d, J = 7.04 Hz, 3H), 1.35 (d, J = 6.85 Hz, 3H). LCMS-ESI (POS.) m/z: 514.2 (M + H)⁺. |

TABLE 10-continued

| Example | Reagents | Structure, Name and and Data |
|---|---|---|
| 185.0 | (2R,3S)-3-(5-fluoropyrimidin-2-yl)butane-2-sulfonamide (Example 10.1), 6-(2,2,2-trifluoroethoxy)picolinohydrazide (Example 3.21) 2-isothiocyanato-1,3-dimethoxybenzene (Example 1.0), ercury acetate (comercially available from VWR International, Radnor, PA, USA) was used instead of silver nitrate, TFA (comercially available from Sigma-Aldrich Corp, St. Louis, MO, USA) was used instead of methanesulfonic acid. | 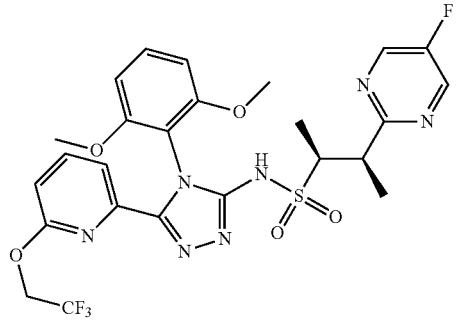 [SMILES: COc1cccc(OC)c1-n1c(NS(=O)(=O)[C@@H](C)[C@H](C)c2ncc(F)cn2)nnc1-c1cccc(OCC(F)(F)F)n1]<br>(2S,3R)-N-(4-(2,6-dimethoxyphenyl)-5-(6-(2,2,2-trifluoroethoxy)pyridin-2-yl)-4H-1,2,4-triazol-3-yl)-3-(5-fluoropyrimidin-2-yl)butane-2-sulfonamide<br>$^1$H NMR (400 MHz, CDCl$_3$) δ 8.54 (s, 2H), 7.70-7.78 (m, 2H), 7.36 (dd, J = 8.5, 8.5 Hz, 1H), 6.83 (d, J = 8.0 Hz, 1H), 6.63 (dd, J = 7.5, 7.5 Hz, 2H), 3.85-3.80 (m, 2H), 3.75-3.71 (m, 2H), 3.71 (s, 3H), 3.68 (s, 3H), 1.33-1.37 (m, 6H). LCMS-ESI (POS.) m/z: 612.0 (M + H)$^+$. |
| 186.0 | (2R,3S)-3-(5-fluoropyrimidin-2-yl)butane-2-sulfonamide (Example 10.1), 6-(2-((tert-butyldimethylsilyl)oxy)ethoxy) picolinohydrazide (Example 3.22), 2-isothiocyanato-1,3-dimethoxybenzene (Example 1.0), mercury acetate (comercially available from VWR International, Radnor, PA, USA) was used instead of silver nitrate, TFA (comercially available from Sigma-Aldrich Corp, St. Louis, MO, USA) was used instead of methanesulfonic acid. | 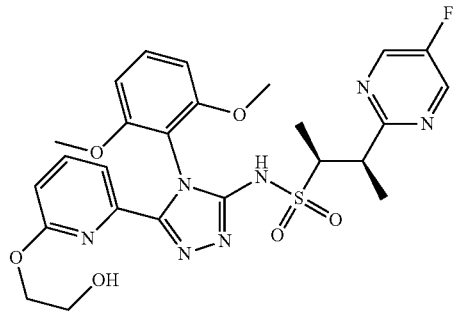 [SMILES: COc1cccc(OC)c1-n1c(NS(=O)(=O)[C@@H](C)[C@H](C)c2ncc(F)cn2)nnc1-c1cccc(OCCO)n1]<br>(2S,3R)-N-(4-(2,6-dimethoxyphenyl)-5-(6-(2-hydroxyethoxy)pyridin-2-yl)-4H-1,2,4-triazol-3-yl)-3-(5-fluoropyrimidin-2-yl)butane-2-sulfonamide<br>$^1$H NMR (400 MHz, CDCl$_3$) δ 8.52 (s, 2H), 7.57-7.65 (m, 2H), 7.33 (dd, J = 8.5, 8.5 Hz, 1H), 6.74 (dd, J = 8.0, 1.0 Hz, 1H), 6.60 (dd, J = 7.8, 6.7 Hz, 2H), 3.81-3.86 (m, 2H), 3.70 (s, 3H), 3.67 (s, 3H), 3.63-3.65 (m, 2H), 3.54-3.56 (m, 2H), 1.32-1.36 (m, 6H). LCMS-ESI (POS.) m/z: 574.1 (M + H)$^+$. |
| 187.0 | (1R,2S)-1-methoxy-1-(5-methylpyrimidin-2-yl)propane-2-sulfonamide (Example 14.0), trifluoroethoxy)picolinohydrazide (Example 3.21), 2-isothiocyanato-1,3-dimethoxybenzene (Example 1.0), silver(I) nitrate (Sigma Aldrich), ethanesulfonic acid, (Sigma Aldrich) | 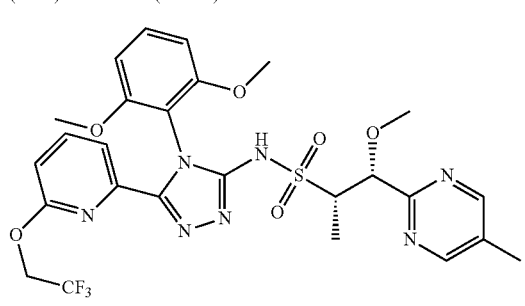<br>(1R,2S)-N-(4-(2,6-dimethoxyphenyl)-5-(6-(2,2,2-trifluoroethoxy)pyridin-2-yl)-4H-1,2,4-triazol-3-yl)-1-methoxy-1-(5-methylpyrimidin-2-yl)propane-2-sulfonamide<br>$^1$H NMR (400 MHz, CDCl$_3$) δ 8.98 (s, 2H), 7.69-7.78 (m, 2H), 7.36 (dd, J = 8.5, 8.5 Hz, 1H), 6.82 (d, J = 7.6 Hz, 1H), 6.66 (d, J = 8.2 Hz, 1H), 6.63 (d, J = 8.4 Hz, 1H), 4.99 (d, J = 5.9 Hz, 1H), 3.79-3.86 (m, 1H), 3.68-3.74 |

TABLE 10-continued

| Example | Reagents | Structure, Name and and Data |
|---|---|---|
| | | (obscured m, 2H), 3.72 (s, 3H), 3.70 (s, 3H), 3.36 (s, 3H), 2.47 (s, 3H), 1.38 (d, J = 6.8 Hz, 3H). LCMS-ESI (POS.) m/z: 624.2 (M + H)⁺. |
| 188.0 | (1R,2S)-1-methoxy-1-(5-methylpyrimidin-2-yl)propane-2-sulfonamide (Example 14.0), 6-(2-((tert-butyldimethylsilyl)oxy)-ethoxy)picolinohydrazide (Example 3.22), 2-isothiocyanato-1,3-dimethylbenzene (Example 1.0), silver(I) nitrate (Sigma Aldrich), ethanesulfonic acid (Sigma Aldrich). | 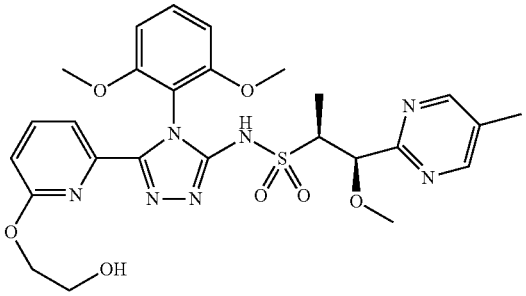 [SMILES: COc1cccc(OC)c1-n1c(NS(=O)(=O)[C@@H](C)[C@H](OC)c2ncc(C)cn2)nnc1-c1cccc(OCCO)n1]<br><br>(1R,2S)-N-(4-(2,6-dimethoxyphenyl)-5-(6-(2-hydroxyethoxy)pyridin-2-yl)-4H-1,2,4-triazol-3-yl)-1-methoxy-1-(5-methylpyrimidin-2-yl)propane-2-sulfonamide<br>¹H NMR (400 MHz, CDCl₃) δ 11.25 (br s, 1H), 8.58 (s, 2H), 7.58-7.65 (m, 2H), 7.32 (d, J = 8.5, 8.5 Hz, 1H), 6.74 (d, J = 7.6 Hz, 1H), 6.60 (d, J = 8.4 Hz, 2H), 4.96 9d, J = 4.3 Hz, 1H), 3.69-3.77 (obbscured m, 1H), 3.71 (s, 3H), 3.69 (s, 3H), 3.61-3.66 (m, 2H), 3.57-3.54 (m, 2H), 3.32 (s, 3H), 2.31 (s, 3H), 1.37 (d, J = 6.8 Hz, 3H). LCMS-ESI (POS.) m/z: 586.1 (M + H)⁺. |
| 189.0 | (1R,2S)-1-(6-chloropyridin-2-yl)-1-hydroxypropane-2-sulfonamide and (1S,2R)-1-(6-chloropyridin-2-yl)-1-hydroxypropane-2-sulfonamide (Example 262.0) micotinic hydrazide (ALFA AESAR), 2-isothiocyanato-1,3-dimethoxybenzene (Example 1.0), silver(I) nitrate (Sigma Aldrich), ethanesulfonic acid (Sigma Aldrich) | 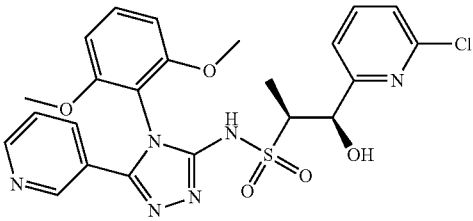<br><br>AND<br><br>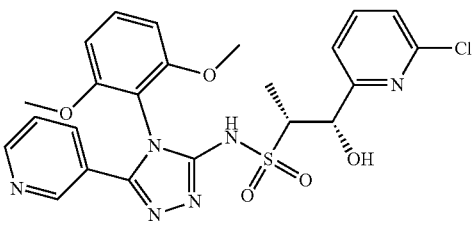 [SMILES: COc1cccc(OC)c1-n1c(NS(=O)(=O)[C@H](C)[C@@H](O)c2cccc(Cl)n2)nnc1-c1cccnc1]<br><br>(1S,2R)-1-(6-chloropyridin-2-yl)-N-(4-(2,6-dimethoxyphenyl)-5-(pyridin-3-yl)-4H-1,2,4-triazol-3-yl)-1-hydroxypropane-2-sulfonamide and (1R,2S)-1-(6-chloropyridin-2-yl)-N-(4-(2,6-dimethoxyphenyl)-5-(pyridin-3-yl)-4H-1,2,4-triazol-3-yl)-1-hydroxypropane-2-sulfonamide. LCMS-ESI (POS.) m/z: 531.0 (M + H)⁺. |

TABLE 10-continued

| Example | Reagents | Structure, Name and and Data |
|---|---|---|
| 190.0 | The racemic 189.0 was separated by supercritical fluid chromatography (250 × 21 m IC column on Thar 80 with 20.4 g/min MeOH + 20 mM NH₃ + 40 g/min CO₂, 34% co-solvent at 60 g/min. Outlet pressure = 100 bar; temperature = 24° C.; wavelength = 282 nm; injection volume = 0.4 mL, 7.8 mg/mL 4:1 MeOH:DCM). This was the first isomer to elute under these conditions. | 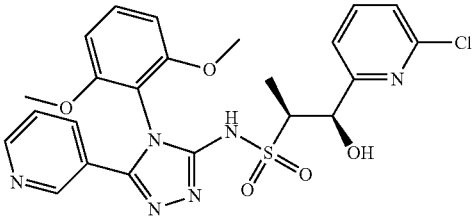 [SMILES: COc1cccc(OC)c1-n1c(NS(=O)(=O)[C@@H](C)[C@H](O)c2cccc(Cl)n2)nnc1-c1cccnc1]<br>OR<br>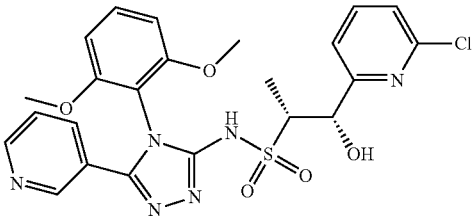 [SMILES: COc1cccc(OC)c1-n1c(NS(=O)(=O)[C@H](C)[C@@H](O)c2cccc(Cl)n2)nnc1-c1cccnc1]<br>(1S,2R)-1-(6-chloropyridin-2-yl)-N-(4-(2,6-dimethoxyphenyl)-5-(pyridin-3-yl)-4H-1,2,4-triazol-3-yl)-1-hydroxypropane-2-sulfonamide or (1R,2S)-1-(6-chloropyridin-2-yl)-N-(4-(2,6-dimethoxyphenyl)-5-(pyridin-3-yl)-4H-1,2,4-triazol-3-yl)-1-hydroxypropane-2-sulfonamide<br>¹H NMR (400 MHz, CDCl₃) δ 11.25 (br s, 1H), 8.63 (br s, 1H), 7.77 (d, J = 7.8 Hz, 1H), 7.64 (dd, J = 7.3, 7.3 Hz, 1H), 7.49 (d, J = 7.2 Hz, 1H), 7.42 (dd, J = 8.3, 8.3 Hz, 1H), 7.26-7.29 (obscured m, 1H), 7.19 (d, J = 7.8 Hz, 1H), 6.66 (d, J = 8.7 Hz, 1H), 6.61 (d, J = 8.6 Hz, 1H), 5.43 (s, 3H), 4.02 (br s, 1H), 33.77-3.83 (obscured m, 1H), 3.81 (s, 3H), 3.73 (s, 3H), 1.13 (d, J = 7.0 Hz, 3H). LCMS-ESI (POS.) m/z: 531.0 (M + H)⁺. |
| 191.0 | The racemic 189.0 was separated by supercritical fluid chromatography (250 × 21 m IC column on Thar 80 with 20.4 g/min MeOH + 20 mM NH₃ + 40 g/min CO₂, 34% co-solvent at 60 g/min. Outlet pressure = 100 bar; temperature = 24° C.; wavelength = 282 nm; injection volume = 0.4 mL, 7.8 mg/mL 4:1 MeOH:DCM). This was the second isomer to elute under these conditions. | 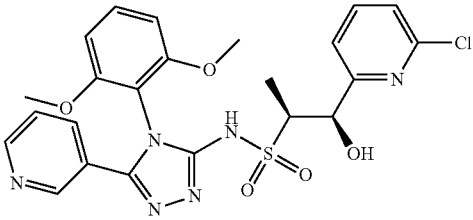 [SMILES: COc1cccc(OC)c1-n1c(NS(=O)(=O)[C@@H](C)[C@H](O)c2cccc(Cl)n2)nnc1-c1cccnc1]<br>OR<br>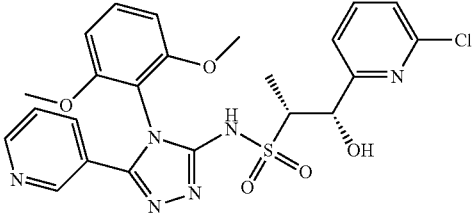 [SMILES: COc1cccc(OC)c1-n1c(NS(=O)(=O)[C@H](C)[C@@H](O)c2cccc(Cl)n2)nnc1-c1cccnc1]<br>(1S,2R)-1-(6-chloropyridin-2-yl)-N-(4-(2,6-dimethoxyphenyl)-5-(pyridin-3-yl)-4H-1,2,4-triazol-3-yl)-1-hydroxypropane-2-sulfonamide or (1R,2S)-1-(6-chloropyridin-2-yl)-N-(4-(2,6-dimethoxyphenyl)-5-(pyridin-3-yl)-4H-1,2,4-triazol-3-yl)-1-hydroxypropane-2-sulfonamide<br>¹H NMR (400 MHz, CDCl₃) δ 11.15 (br s, 1H), 8.63 (br s, 1H), 7.77 (d, J = 8.4 Hz, 1H), 7.64 (dd, J = 7.8, 7.8 Hz, 1H), 7.49 (d, J = 7.9 Hz, 1H), 7.42 (dd, J = 8.3, 8.3 Hz, 1H), 7.26-7.29 (obscured m, 1H), 7.19 (d, J = 8.0 Hz, 1H), 6.66 (d, J = 8.6 Hz, 1H), 6.60 (d, J = 8.1 Hz, |

TABLE 10-continued

| Example | Reagents | Structure, Name and and Data |
|---|---|---|
| | | 1H), 5.43 (s, 1H), 4.02 (br s, 1H), 3.77-3.83 (obscured m, 1H), 3.81 (s, 3H), 3.73 (s, 3H), 1.13 (d, J = 7.0 Hz, 3H). LCMS-ESI (POS.) m/z: 531.0 (M + H)+. |
| 192.0 | (2R,3S)-3-(5-fluoropyrimidin-2-yl)butane-2-sulfonamide (Example 10.1), 6-(2-hydroxy-2-methylpropoxy)picolinohydrazide (Example 3.23), 2-isothiocyanato-1,3-dimethoxybenzene (Example 1.0), silver(I) nitrate (Sigma Aldrich), ethanesulfonic acid (Sigma Aldrich) | 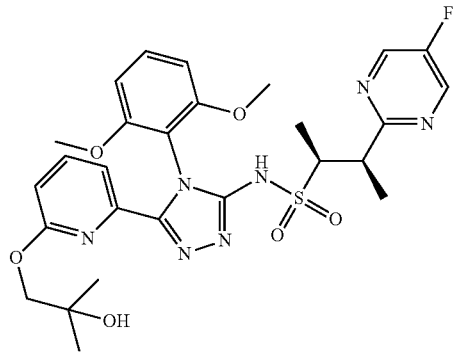 [SMILES: COc1cccc(OC)c1-n1c(NS(=O)(=O)[C@@H](C)[C@H](C)c2ncc(F)cn2)nnc1-c1cccc(OCC(C)(C)O)n1]<br>(2S,3R)-N-(4-(2,6-dimethoxyphenyl)-5-(6-(2-hydroxy-2-methylpropoxy)pyridin-2-yl)-4H-1,2,4-triazol-3-yl)-3-(5-fluoropyrimidin-2-yl)butane-2-sulfonamide<br>$^1$H NMR (400 MHz, CDCl$_3$) δ 11.28 (br s, 1H), 8.51 (s, 2H), 7.70 (d, J = 2.5 Hz, 1H), 7.43 (dd, J = 8.5, 8.5 Hz, 1H), 7.30 (dd, J = 9.5, 2.6 Hz, 1H), 6.64 (dd, J = 8.3, 8.3 Hz, 2H), 6.47 (d, J = 9.6 Hz, 1H), 3.88-3.97 (m, 2H), 3.76-3.85 (obscured m, 2H), 3.78 (s, 3H), 3.75 (s, 3H), 3.21 (br s, 1H), 1.34 (dd, J = 6.7, 6.7 Hz, 6H), 1.73 (d, J = 2.5 Hz, 6H). LCMS-ESI (POS.) m/z: 602.2 (M + H)+. |
| 193.0 | (1R,2S)-1-methoxy-1-(5-methylpyrimidin-2-yl)propane-2-sulfonamide (Example 14.0) 6-(2-hydroxy-2-methylpropoxy)picolinohydrazide (Example 3.23), 2-isothiocyanato-1,3-dimethylbenzene (Example 1.0), silver(I) nitrate (Sigma Aldrich), ethane sulfonic acid (Sigma Aldrich) | 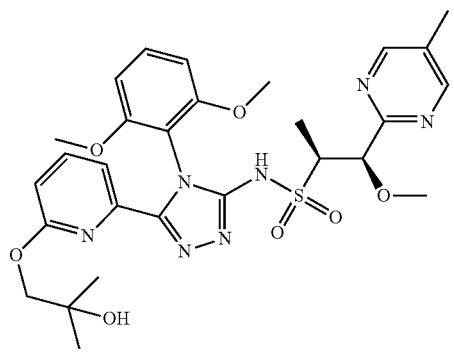 [SMILES: COc1cccc(OC)c1-n1c(NS(=O)(=O)[C@@H](C)[C@H](OC)c2ncc(C)cn2)nnc1-c1cccc(OCC(C)(C)O)n1]<br>(1R,2S)-N-(4-(2,6-dimethoxyphenyl)-5-(6-(2-hydroxy-2-methylpropoxy)pyridin-2-yl)-4H-1,2,4-triazol-3-yl)-1-methoxy-1-(5-methylpyrimidin-2-yl)propane-2-sulfonamide<br>$^1$H NMR (400 MHz, CDCl$_3$) δ 8.57 (s, 2H), 7.85 (br s, 1H), 7.42 (dd, J = 8.4, 8.3 Hz, 1H), 7.27 (d, J = 9.6 Hz, 1H), 6.64 (d, J = 8.4 Hz, 2H), 6.45 (d, J = 9.6 Hz, 1H), 4.95 (d, J = 4.1 Hz, 1H), 4.74 (s, 1H), 3.93-3.97 (m, 2H), 3.79 (s, 3H), 3.76 (s, 3H), 3.66-3.72 (m, 1H), 3.30 (s, 3H), 2.29 (s, 3H), 1.35 (d, J = 6.8 Hz, 3H), 1.14 (br s, 6H). LCMS-ESI (POS.) m/z: 614.2 (M + H)+. |

TABLE 10-continued

| Example | Reagents | Structure, Name and and Data |
|---|---|---|
| 194.0 | (2R,3S)-3-(5-fluoropyrimidin-2-yl)butane-2-sulfonamide (Example 10.1), 6-(3,3,3-trifluoro-2-hydroxy-2-(trifluoromethyl)propoxy)picolinohydrazide (Example 3.24), 2-isothiocyanato-1,3-dimethoxybenzene (Example 1.0), silver(I) nitrate (Sigma Aldrich), methanesulfonic acid (Sigma Aldrich) | 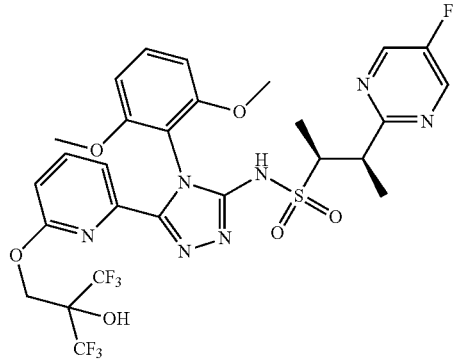 [SMILES: COc1cccc(OC)c1-n1c(NS(=O)(=O)[C@@H](C)[C@H](C)c2ncc(F)cn2)nnc1-c1cccc(OCC(O)(C(F)(F)F)C(F)(F)F)n1]<br>(2S,3R)-N-(4-(2,6-dimethoxyphenyl)-5-(6-(3,3,3-trifluoro-2-hydroxy-2-(trifluoromethyl)propoxy)pyridin-2-yl)-4H-1,2,4-triazol-3-yl)-3-(5-fluoropyrimidin-2-yl)butane-2-sulfonamide<br>$^1$H NMR (400 MHz, CDCl$_3$) δ 8.53 (s, 2H), 7.71 (dd, J = 7.9, 7.9 Hz, 1H), 7.43 (d, J = 7.1 Hz, 1H), 7.36 (dd, J = 8.3, 8.3 Hz, 1H), 6.88 (d, J = 8.2 Hz, 1H), 6.60 (dd, J = 7.6, 7.6 Hz, 2H), 4.1 (s, 2H), 3.79-3.88 (m, 2H), 3.69 (s, 3H), 3.67 (s, 3H), 1.37 (dd, J = 6.7, 6.7 Hz, 3H). LCMS-ESI (POS.) m/z: 710.2 (M + H)$^+$. |
| 195.0 | (1R,2S)-1-methoxy-1-(5-methylpyrimidin-2-yl)propane-2-sulfonamide (Example 14.0) 6-(methylamino)picolinohydrazide (Example 3.25), 2-isothiocyanato-1,3-dimethylbenzene (Example 1.0), silver(I) nitrate (Sigma Aldrich), ethanesulfonic acid (Sigma Aldrich) | 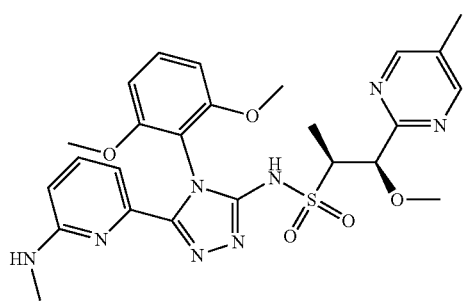 [SMILES: CNc1cccc(-c2nnc(NS(=O)(=O)[C@@H](C)[C@H](OC)c3ncc(C)cn3)n2-c2c(OC)cccc2OC)n1]<br>(1R,2S)-N-(4-(2,6-dimethoxyphenyl)-5-(6-(methylamino)pyridin-2-yl)-4H-1,2,4-triazol-3-yl)-1-methoxy-1-(5-methylpyrimidin-2-yl)propane-2-sulfonamide<br>$^1$H NMR (400 MHz, CDCl$_3$) δ 8.58 (s, 2H), 7.28-7.39 (m, 2H), 7.13 (d, J = 7.4 Hz, 1H), 6.57 (d, J = 8.6 Hz, 2H), 6.32 (d, J = 8.2 Hz, 1H), 4.96 (d, J = 4.7 Hz, 1H), 4.69 (d, J = 4.7 Hz, 1H), 4.21 (d, J = 4.7 Hz, 1H), 3.69-3.76 (m, 1H), 3.70 (s, 3H), 3.66 (s, 3H), 3.33 (s, 3H), 2.39 (d, J = 5.1 Hz, 3H), 2.31 (s, 3H), 1.38 (d, J = 7.0 Hz, 3H). LCMS-ESI (POS.) m/z: 555.2 (M + H)$^+$. |
| 196.0 | (1R,2S)-1-methoxy-1-(5-methylpyrimidin-2-yl)propane-2-sulfonamide (Example 14.0) 6-(2-methoxyethoxy)picolinohydrazide (Example 3.26), 2-isothiocyanato-1,3-dimethylbenzene (Example 1.0), silver(I) nitrate (Sigma Aldrich), ethane sulfonic acid. (Sigma Aldrich) | 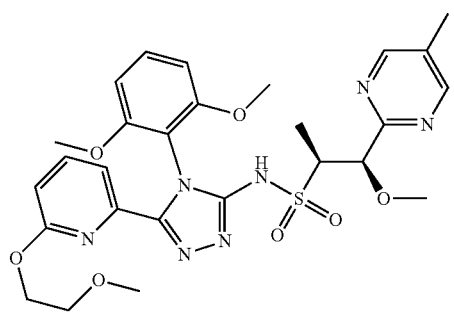 [SMILES: COCCOc1cccc(-c2nnc(NS(=O)(=O)[C@@H](C)[C@H](OC)c3ncc(C)cn3)n2-c2c(OC)cccc2OC)n1]<br>(1R,2S)-N-(4-(2,6-dimethoxyphenyl)-5-(6-(2-methoxyethoxy)pyridin-2-yl)-4H-1,2,4-triazol-3-yl)-1-methoxy-1-(5-methylpyrimidin-2- |

TABLE 10-continued

| Example | Reagents | Structure, Name and and Data |
|---|---|---|
| | | yl)propane-2-sulfonamide<br>$^1$H NMR (400 MHz, CDCl$_3$) δ 9.17 (d, J = 9.17 Hz, s 2H), 7.60-7.65 (m, 2H), 7.36 (dd, J = 8.4, 8.4 Hz, 1H), 6.76-6.80 (m, 1H), 6.68 (d, J = 8.6 Hz, 1H), 6.62 (d, J = 8.1 Hz, 1H), 5.09 (d, J = 5.7 Hz, 1H), 3.88-3.94 (m, 1H), 3.74 (s, 3H), 3.70 (s, 3H), 3.50-3.54 (, 2H), 3.40-3.46 (m, 2H), 3.41 (s, 3H), 3.36 (s, 3H), 2.38 (s, 3H), 1.38 (d, J = 7.0 Hz, 3H). LCMS-ESI (POS.) m/z: 600.2 (M + H)$^+$. |
| 197.0 | (1R,2S)-1-methoxy-1-(5-methylpyrimidin-2-yl)propane-2-sulfonamide (Example 14.0) 6-(dimethylamino)picolinohydrazide (Example 3.27), 2-isothiocyanato-1,3-dimethylbenzene (Example 1.0), silver(I) nitrate (Sigma Aldrich), ethane sulfonic acid (Sigma Aldrich) | 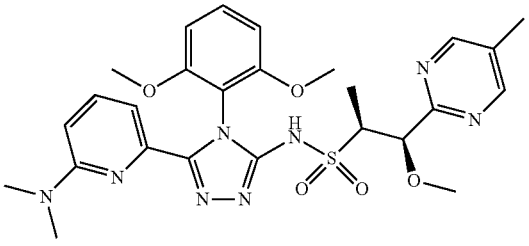<br>(1R,2S)-N-(4-(2,6-dimethoxyphenyl)-5-(6-(dimethylamino)pyridin-2-yl)-4H-1,2,4-triazol-3-yl)-1-methoxy-1-(5-methylpyrimidin-2-yl)propane-2-sulfonamide<br>$^1$H NMR (400 MHz, CDCl$_3$) δ 8.58 (s, 2H), 7.46 (dd, J = 8.5, 7.5 Hz, 2H), 7.27 (dd, J = 8.4, 8.4 Hz, 1H), 7.21 (d, J = 7.4 Hz, 1H), 6.57 (d, J = 8.4 Hz, 2H), 6.43 (d, J = 8.14 (Hz, 1H), 4.96 (d, J = 4.7 Hz, 1H), 3.70-3.76 (m, 1H), 3.69 (s, 3H), 3.67 (s, 3H), 3.33 (s, 3H), 2.60 (s, 3H), 3.33 (s, 3H), 2.6 (s, 6H), 2.31 (s, 3H), 1.38 (d, d = 6.8 Hz, 3H). LCMS-ESI (POS.) m/z: 569.2 (M + H)$^+$. |
| 198.0 | (2S,3R)-3-(5-methylpyrazin-2-yl)butane-2-sulfonamide (48 mg, 0.21 mol) (Example 10.2), 2-isothiocyanato-1,3-dimethoxybenzene (45 mg, 0.23 mol) (Example 1.0), silver(I) nitrate (Sigma Aldrich), ethane sulfonic acid (Sigma Aldrich) | 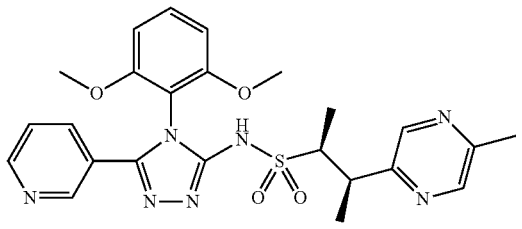 [SMILES: COc1cccc(OC)c1-n1c(NS(=O)(=O)[C@@H](C)[C@H](C)c2cnc(C)cn2)nnc1-c1cccnc1]<br>(2S,3R)-N-(4-(2,6-dimethoxyphenyl)-5-(pyridin-3-yl)-4H-1,2,4-triazol-3-yl)-3-(5-methylpyrazin-2-yl)butane-2-sulfonamide<br>$^1$H NMR (500 MHz, CD$_2$Cl$_2$) δ 8.69 (d, J = 1.47 Hz, 1H), 8.66 (dd, J = 5.07, 1.53 Hz, 1H), 8.43 (s, 1H), 8.30 (d, J = 1.22 Hz, 1H), 7.93 (dt, J = 8.13, 1.86 Hz, 1H), 7.44-7.51 (m, 2H), 6.67-6.71 (m, 2H), 3.75 (d, J = 1.10 Hz, 6H), 3.64 (qd, J = 7.00, 4.16 Hz, 1H), 3.52 (qd, J = 6.97, 5.01 Hz, 1H), 2.54 (s, 3H), 1.34 (d, J = 7.09 Hz, 3H), 1.30 (d, J = 6.97 Hz, 3H). LCMS-ESI (POS.) m/z: 510.1 (M + H)$^+$. |
| 199.0 | (2S,3R)-3-(5-methylpyrazin-2-yl)butane-2-sulfonamide (48 mg, 0.21 mol) (Example 10.3), 2-isothiocyanato-1,3-dimethoxybenzene (45 mg, 0.23 mol) (Example 1.0), silver(I) nitrate (Sigma Aldrich), ethane sulfonic acid. (Sigma Aldrich) | 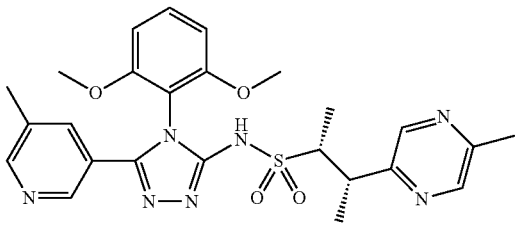 [SMILES: COc1cccc(OC)c1-n1c(NS(=O)(=O)[C@H](C)[C@@H](C)c2cnc(C)cn2)nnc1-c1cncc(C)c1]<br>(2S,3R)-N-(4-(2,6-dimethoxyphenyl)-5-(5-methylpyridin-3-yl)-4H-1,2,4-triazol-3-yl)-3-(5-methylpyrazin-2-yl)butane-2-sulfonamide<br>$^1$H NMR (500 MHz, CD$_2$Cl$_2$) δ 11.13 (br. s., 1H), |

TABLE 10-continued

| Example | Reagents | Structure, Name and and Data |
|---|---|---|
| | | 8.42 (d, J = 1.47 Hz, 1H), 8.34 (d, J = 0.73 Hz, 1H), 8.31 (d, J = 1.83 Hz, 1H), 8.29 (d, J = 1.35 Hz, 1H), 7.60 (td, J = 2.11, 0.79 Hz, 1H), 7.46 (t, J = 8.56 Hz, 1H), 6.67 (ddd, J = 8.60, 4.16, 1.10 Hz, 2H), 3.73 (s, 6H), 3.63-3.70 (m, 1H), 3.50 (qd, J = 7.03, 4.34 Hz, 1H), 2.49 (s, 3H), 2.27 (d, J = 0.61 Hz, 3H), 1.33 (d, J = 7.21 Hz, 3H), 1.28 (d, J = 6.97 Hz, 3H). LCMS-ESI (POS.) m/z: 524.2 (M + H)+. |
| 200.0 | Example 8.0 and 6-methoxypicolinohydrazide (comercially available from Aldrich) | 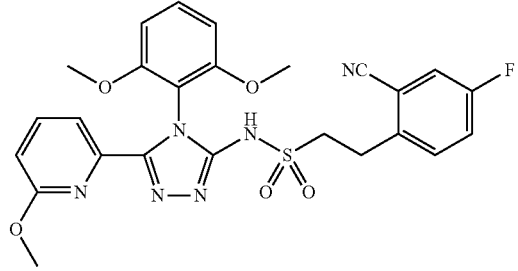 [SMILES: COc1cccc(-c2nnc(NS(=O)(=O)CCc3ccc(F)cc3C#N)n2-c2c(OC)cccc2OC)n1]  2-(2-cyano-4-fluorophenyl)-N-(4-(2,6-dimethoxyphenyl)-5-(6-methoxy-2-pyridinyl)-4H-1,2,4-triazol-3-yl)ethanesulfonamide  $^1$H NMR (500 MHz, CD$_3$OD) δ 7.73 (t, J = 7.83 Hz, 1H), 7.63 (d, J = 7.58 Hz, 1H), 7.52 (dd, J = 8.31, 2.69 Hz, 1H), 3.19 (s, 3H), 7.41-7.48 (m, 2H), 7.35-7.41 (m, 1H), 6.74-6.82 (m, 3H), 3.74 (s, 6H), 3.34-3.39 (m, 2H), 3.24-3.30 (m, 2H). LCMS-ESI (POS.) m/z: 539.2 (M + H)+. |
| 201.0 | (S)-2-(3,6-dimethyl-2-oxotetrahydropyrimidin-1(2H)-yl)ethanesulfonamide (made in an analogous fashion to that of 460.5 employing (S)-tert-butyl (3-aminobutyl)carbamate (0.053 g, 0.23 mol), 5-methylnicotinohydrazide (0.037 g, 0.25 mol), Example 1.0 (0.048 g, 0.25 mol) and TFA (0.104 mL, 1.35 mol) | 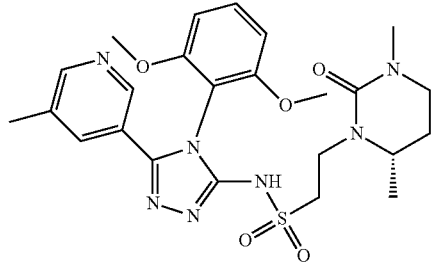 [SMILES: COc1cccc(OC)c1-n1c(NS(=O)(=O)CCN2C(=O)N(C)CC[C@@H]2C)nnc1-c1cncc(C)c1]  N-(4-(2,6-dimethoxyphenyl)-5-(5-methyl-3-pyridinyl)-4H-1,2,4-triazol-3-yl)-2-((6S)-3,6-dimethyl-2-oxotetrahydro-1(2H)-pyrimidinyl)ethanesulfonamide (0.011 g, 9.25% yield).  $^1$H NMR (500 MHz, CD$_2$Cl$_2$) δ = 8.42 (d, J = 1.7 Hz, 1H), 8.31 (d, J = 2.0 Hz, 1H), 7.58 (s, 1H), 7.45 (t, J = 8.4 Hz, 1H), 6.67 (dd, J = 2.2, 8.6 Hz, 2H), 3.94 (td, J = 6.6, 13.4 Hz, 1H), 3.76 (d, J = 4.6 Hz, 6H), 3.59-3.50 (m, 1H), 3.40-3.16 (m, 5H), 3.14-3.07 (m, 1H), 2.89 (s, 3H), 2.27 (s, 3H), 2.10-2.00 (m, 1H), 1.69-1.60 (m, 1H), 1.14 (d, J = 6.6 Hz, 3H). LCMS-ESI (POS.) m/z: 530.3 (M + H)+. |
| 202.0 | (S)-1-(5-fluoropyrimidin-2-yl)propane-2-sulfonamide and (R)-1-(5-fluoropyrimidin-2-yl)propane-2-sulfonamide (Example 9.0, 0.400 g, 1.82 mol), picolinohydrazide (0.25 g, 1.823 mol), Example 1.0 (0.392 g, 2.01 mol) and TFA (0.842 mL, 10.93 mol) | 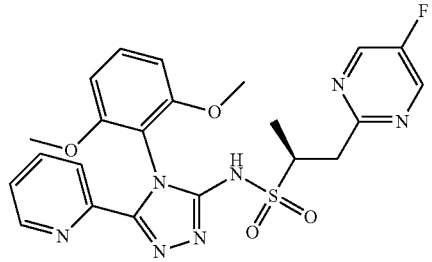 [SMILES: COc1cccc(OC)c1-n1c(NS(=O)(=O)[C@@H](C)Cc2ncc(F)cn2)nnc1-c1ccccn1]  AND |

| Example | Reagents | Structure, Name and and Data |
|---|---|---|
|  |  | 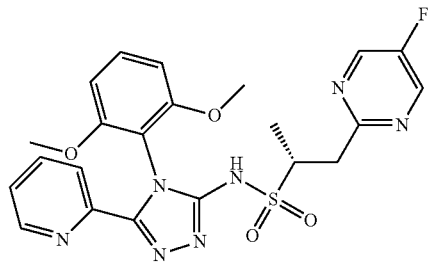 [SMILES: COc1cccc(OC)c1-n1c(NS(=O)(=O)[C@H](C)Cc2ncc(F)cn2)nnc1-c1ccccn1] (2R)-N-(4-(2,6-dimethoxyphenyl)-5-(2-pyridinyl)-4H-1,2,4-triazol-3-yl)-1-(5-fluoro-2-pyrimidinyl)-2-propanesulfonamide and (2S)-N-(4-(2,6-dimethoxyphenyl)-5-(2-pyridinyl)-4H-1,2,4-triazol-3-yl)-1-(5-fluoro-2-pyrimidinyl)-2-propanesulfonamide (0.245 g, 26.9% yield). $^{1}$H NMR (500 MHz, CD$_2$Cl$_2$) δ = 11.13 (br. s., 1H), 8.54 (s, 2H), 8.33-8.28 (m, 1H), 7.82 (d, J = 7.8 Hz, 1H), 7.74 (dt, J = 1.8, 7.8 Hz, 1H), 7.42 (t, J = 8.4 Hz, 1H), 7.27 (ddd, J = 1.2, 4.6, 7.6 Hz, 1H), 6.65 (dd, J = 1.7, 8.6 Hz, 2H), 3.70 (d, J = 9.8 Hz, 7H), 3.61 (dd, J = 3.9, 14.4 Hz, 1H), 3.03 (dd, J = 9.9, 14.5 Hz, 1H), 1.26 (d, J = 6.8 Hz, 3H). LCMS-ESI (POS.) m/z: 500.1 (M + H)$^+$. |
| 203.0 | (1S,2R)-1-methoxy-1-(5-methylpyrimidin-2-yl)propane-2-sulfonamide (Example 14.0, 336 mg, 1.37 mol), 5-methylnicotinohydrazide (207 mg, 1.37 mol), Example 1.0 (281 mg, 1.44 mol) and TFA (1018 μL, 13.70 mol) | 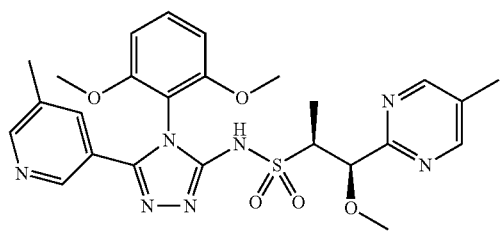 [SMILES: COc1cccc(OC)c1-n1c(NS(=O)(=O)[C@@H](C)[C@H](OC)c2ncc(C)cn2)nnc1-c1cncc(C)c1] (1R,2S)-N-(4-(2,6-dimethoxyphenyl)-5-(5-methyl-3-pyridinyl)-4H-1,2,4-triazol-3-yl)-1-methoxy-1-(5-methyl-2-pyrimiidnyl)-2-propanesulfonamide (0.27 g, 0.50 mol, 37% yield). $^{1}$H NMR (500 MHz, MeOH) δ = 8.64 (s, 2H), 8.43 (d, J = 1.2 Hz, 1H), 8.31 (d, J = 2.0 Hz, 1H), 7.73-7.67 (m, 1H), 7.49 (t, J = 8.6 Hz, 1H), 6.79 (d, J = 8.6 Hz, 2H), 4.99 (d, J = 3.7 Hz,1H), 3.79 (s, 3H), 3.76 (s, 3H), 3.27 (s, 3H), 2.34 (s, 3H), 2.30 (d, J = 0.7 Hz, 3H), 1.24 (d, J = 7.1 Hz, 3H). LCMS-ESI (POS.) m/z: 540.3 (M + H)$^+$. |
| 204.0 | Example 1.8 (0.071 g, 0.36 mol) and 2-(2-cyano-4-fluorophenyl)-ethanesulfonamide (Example 8.0, 0.075 g, 0.33 mol) 6-methoxypicolinohydrazide (Adesis, 0.055 g, 0.33 mol), TFA (0.16 mL, 2.01 mol) | 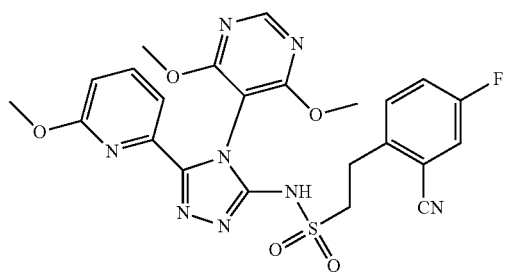 [SMILES: COc1cccc(-c2nnc(NS(=O)(=O)CCc3ccc(F)cc3C#N)n2-c2c(OC)ncnc2OC)n1] 2-(2-cyano-4-fluorophenyl)-N-(4-(2,6-dimethoxy-5-pyrimidinyl)-5-(6-methoxy-2-pyridinyl)-4H-1,2,4-triazol-3-yl)ethanesulfonamide (0.02 g, 11% yield). $^{1}$H NMR (500 MHz, CD$_2$Cl$_2$) δ = 10.93 (br. s., 1H), 8.48 (s, 1H), 7.70-7.63 (m, 2H), 7.38-7.32 (m, 2H), 7.29-7.23 (m, 1H), 6.77 (dd, J = 1.7, 7.3 Hz, 1H), 3.91 (s, 6H), 3.34-3.29 |

| Example | Reagents | Structure, Name and and Data |
|---|---|---|
| | | (m, 2H), 3.29-3.24 (m, 2H), 3.23 (s, 3H), 1.52 (s, 4H). LCMS-ESI (POS.) m/z: 541.1 (M + H)+. |

Example 205.0: Preparation of (2S)—N-(4-(2,6-dimethoxyphenyl)-5-(3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(3-pyridinyl)-4H-1,2,4-triazol-3-yl)-1-(5-fluoro-2-pyrimidinyl)-2-propanesulfonamide 205.0

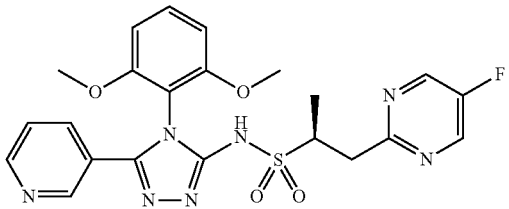

205.1

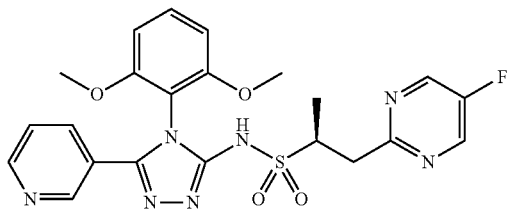

AND

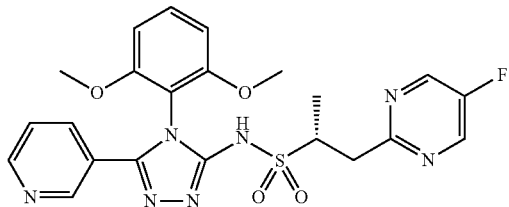

(2S)—N-(4-(2,6-dimethoxyphenyl)-5-(3-pyridinyl)-4H-1,2,4-triazol-3-yl)-1-(5-fluoro-2-pyrimidinyl)-2-propanesulfonamide and (2R)—N-(4-(2,6-dimethoxyphenyl)-5-(3-pyridinyl)-4H-1,2,4-triazol-3-yl)-1-(5-fluoro-2-pyrimidinyl)-2-propanesulfonamide, Example 205.1

To a mixture of N-((2,6-dimethoxyphenyl)carbamothioyl)-1-(5-fluoropyrimidin-2-yl)propane-2-sulfonamide (Example 431.0) (0.200 g, 0.48 mmol) and nicotinic hydrazide (0.199 g, 1.45 mmol, Sigma-Aldrich Chemical Company, Inc.) in DMF (2.0 mL) was added mercuric acetate (0.049 mL, 0.51 mmol, VWR International) at RT. The mixture was stirred at RT for 30 min, followed by dropwise addition of TFA (0.223 mL, 2.90 mmol, Sigma-Aldrich Corp). The resulting mixture was then stirred at 110° C. and monitored by LCMS. Upon reaction completion, the mixture was cooled to RT and directly subjected to reverse phase-HPLC purification to give the title compound 205.1 (187 mg, 0.37 mmol, 78%). LCMS-ESI (POS.) m/z: 500.1 (M+H)+.

OR

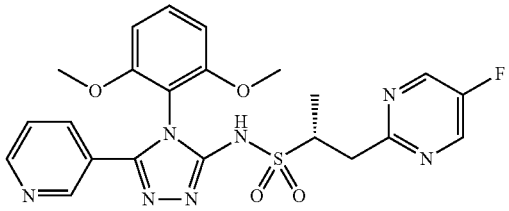

(2S)—N-(4-(2,6-dimethoxyphenyl)-5-(3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(3-pyridinyl)-4H-1,2,4-triazol-3-yl)-1-(5-fluoro-2-pyrimidinyl)-2-propanesulfonamide, Example 205.0

The racemic compound (Example 205.1) was separated by supercritical fluid chromatography (2×15 cm AD-H column with 60 mL/min 22% MeOH (0.1% NH$_3$)/CO$_2$. Outlet pressure=100 bar; temperature=23° C.; wavelength=220 nm; injection volume=0.6 mL, 9 mg/mL 2:1 MeOH:DCM). Two enantiomers were obtained. The title compound 205.0 was the first isomer to elute under these conditions. $^1$H NMR (400 MHz, CDCl$_3$) δ 8.62 (br. s., 2H), 8.54 (s, 2H), 7.71-7.77 (m, 1H), 7.39 (t, J=8.51 Hz, 1H), 7.24-7.29 (m, 1H), 6.61 (d, J=8.48 Hz, 2H), 3.76-3.90 (m, 1H), 3.74 (s, 3H), 3.72 (s, 3H), 3.64-3.70 (m, 1H), 3.10 (dd, J=14.67, 9.98 Hz, 1H), 1.32 (d, J=6.85 Hz, 3H). LCMS-ESI (POS.) m/z: 500.1 (M+H)+.

Example 206.0: Preparation of (2S)—N-(4-(2,6-dimethoxyphenyl)-5-(3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(3-pyridinyl)-4H-1,2,4-triazol-3-yl)-1-(5-fluoro-2-pyrimidinyl)-2-propanesulfonamide

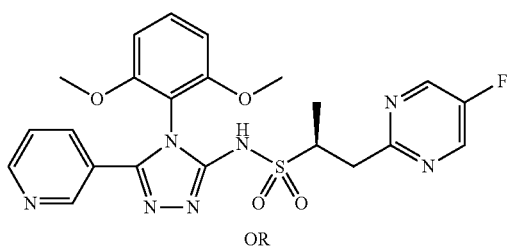

OR

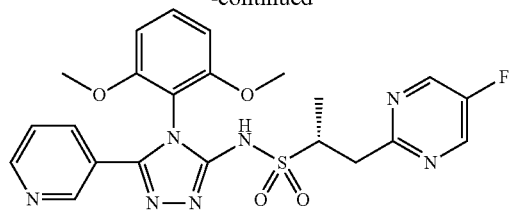

206.0

Example 206.0 is the enantiomer of Example 205.0. The title compound 206.0 was the second isomer to elute on subjecting 205.1 to the SFC conditions described in Example 205.0. $^1$H NMR (500 MHz, CDCl$_3$) δ 8.59-8.64 (m, 2H), 8.54 (s, 2H), 7.70-7.77 (m, 1H), 7.39 (t, J=8.56 Hz, 1H), 7.23-7.30 (m, 2H), 6.61 (dd, J=8.56, 1.47 Hz, 2H), 3.81 (ddd, J=9.84, 6.79, 4.40 Hz, 1H), 3.74 (s, 3H), 3.72 (s, 3H), 3.66-3.71 (m, 1H), 3.10 (dd, J=14.67, 10.03 Hz, 1H), 1.32 (d, J=6.85 Hz, 3H). LCMS-ESI (POS.) m/z: 500.1 (M+H)$^+$.

The compounds set forth in the following Table were synthesized following the procedure in Example 205.0 using the known starting material as described.

TABLE 11

| Example | Reagents | Structure, Name and data |
|---|---|---|
| 207.0 | (S)-N-((2,6-dimethoxyphenyl)-carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0) 5-methylnicotinohydrazide (Example 3.11) mercury (II) acetate (commercially available from VWR International, Radnor, PA, USA) TFA (commercially available from Sigma-Aldrich Corp, St. Louis, MO, USA) | AND<br><br>(S)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide and (R)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide LCMS-ESI (POS.) m/z: 514.1 (M + H)$^+$. |
| 208.0 | The racemic compound 207.0 was separated by supercritical fluid chromatography (250 x 30 mm IA column on Thar 80 with 21 g/min MeOH(NH$_3$) + 49 g/min CO$_2$, 30% co-solvent at 70 g/min. Outlet pressure = 100 bar; temperature = 22° C.; wavelength = 265 nm; injection volume = 0.8 mL of a solution from 110 mg sample dissolved in 10 mL of MeOH:DCM 6:4). This was the first isomer to elute under these conditions. | OR |

TABLE 11-continued

| Example | Reagents | Structure, Name and data |
|---|---|---|
| | | 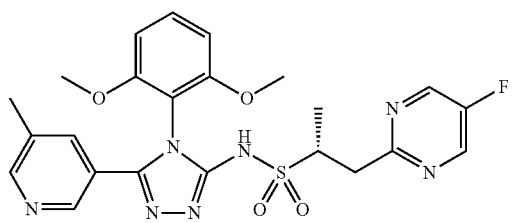 [SMILES: COc1cccc(OC)c1-n1c(NS(=O)(=O)[C@H](C)Cc2ncc(F)cn2)nnc1-c1cncc(C)c1](S)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide or (R)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide<br>$^1$H NMR (400 MHz, CDCl$_3$) δ 8.53 (s, 2H), 8.44 (s, 1H), 8.33 (s, 1H), 7.64 (s, 1H), 7.38 (t, J = 8.51 Hz, 1H). 6.60 (d, J = 8.61 Hz, 2H), 3.77-3.84 (m, 1H), 3.74 (s, 3H), 3.71 (s, 3H), 3.66-3.70 (m, 1H), 3.09 (dd, J = 14.67, 9.98 Hz, 1H), 2.30 (s, 3H), 1.30 (d, J = 6.85 Hz, 3 H). LCMS-ESI (POS.) m/z: 514.1 (M + H)$^+$. |
| 209.0 | The racemic compound 207.0 was separated by supercritical fluid chromatography (250 x 30 mm IA column on Thar 80 with 21 g/min MeOH(NH$_3$) + 49 g/min CO$_2$, 30% co-solvent at 70 g/min. Outlet pressure = 100 bar; temperature = 22° C.; wavelength = 265 nm; injection volume = 0.8 mL of a solution from 110 mg sample dissolved in 10 mL of MeOH:DCM 6:4). This was the second isomer to elute under these conditions. | 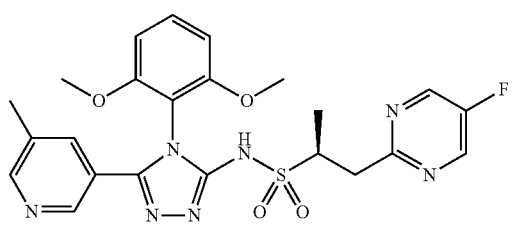OR<br>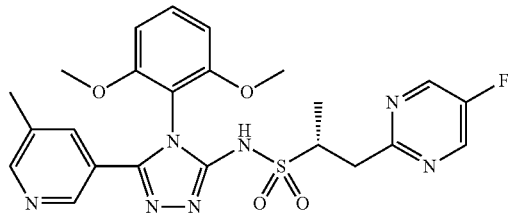 [SMILES: COc1cccc(OC)c1-n1c(NS(=O)(=O)[C@H](C)Cc2ncc(F)cn2)nnc1-c1cncc(C)c1](S)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide or (R)-N-(4-(2,6-dimethoxyphenyl)-5-(5-methylpyridin-3-yl)-4H-1,2,4-triazol-3-yl)-1-(5-fluoropyrimidin-2-yl)propane-2-sulfonamide<br>$^1$H NMR (400 MHz, CDCl$_3$) δ 8.53 (s, 2H), 8.41-8.48 (m, 1H), 8.33 (d, J = 1.56 Hz, 1H), 7.64 (s, 1H), 7.39 (t, J = 8.51 Hz, 1H), 6.60 (dd, J = 8.51, 0.88 Hz, 2H), 3.80 (ddd, J = 9.88, 6.75, 4.30 Hz, 1H), 3.74 (s, 3H), 3.72 (s, 3H), 3.65-3.70 (m, 1H), 3.09 (dd, J = 14.77, 9.88 Hz, 1H), 2.30 (s, 3H), 1.31 (d, J = 6.65 Hz, 3 H). LCMS-ESI (POS.) m/z: 514.1 (M + H)$^+$. |
| 210.0 | (S)-N-((2,6-dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0), 2-methylnicotinohydrazide (Example 3.12) mercury (II) acetate (commercially available from VWR International, Radnor, PA, USA) TFA (commercially available from Sigma-Aldrich Corp, St. Louis, MO, USA). | 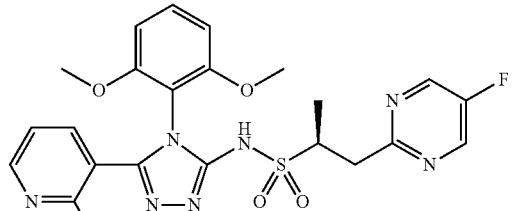and |

TABLE 11-continued

| Example | Reagents | Structure, Name and data |
|---|---|---|
| | | 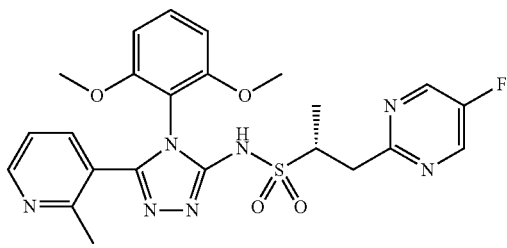 [SMILES: COc1cccc(OC)c1-n1c(NS(=O)(=O)[C@H](C)Cc2ncc(F)cn2)nnc1-c1cccnc1C]

(S)-N-(4-(2,6-dimethoxyphenyl)-5-(2-methylpyridin-3-yl)-
4H-1,2,4-triazol-3-yl)-1-(5-fluoropyrimidin-2-yl)propane-2-
sulfonamide and (R)-N-(4-(2,6-dimethoxyphenyl)-5-(2-
methylpyridin-3-yl)-4H-1,2,4-triazol-3-yl)-1-
(5-fluoropyrimidin-2-yl)propane-2-sulfonamide
LCMS-ESI (POS.) m/z: 514.0 (M + H)+. |
| 211.0 | The racemic 210.0 was separated by supercritical fluid chromatography (2 × 15 cm IA column with 60 mL/min 20% MeOH/CO$_2$. Outlet pressure = 100 bar; wavelength = 220 nm; injection volume = 10 mL, 11 mg/mL 1:1 MeOH:DCM). This was the first isomer to elute under these conditions. | 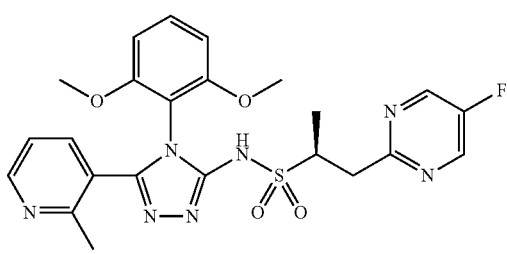

or

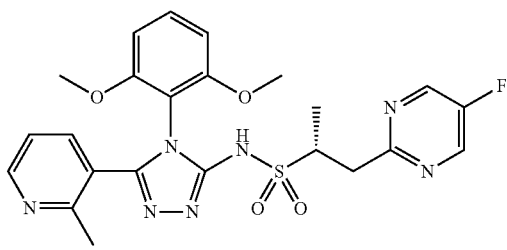 [SMILES: COc1cccc(OC)c1-n1c(NS(=O)(=O)[C@H](C)Cc2ncc(F)cn2)nnc1-c1cccnc1C]

(S)-N-(4-(2,6-dimethoxyphenyl)-5-(2-methylpyridin-3-yl)-
4H-1,2,4-triazol-3-yl)-1-(5-fluoropyrimidin-2-yl)propane-2-
sulfonamide or (R)-N-(4-(2,6-dimethoxyphenyl)-5-(2-
methylpyridin-3-yl)-4H-1,2,4-triazol-3-yl)-1-(5-fluoro-
pyrimidin-2-yl)propane-2-sulfonamide.
$^1$H NMR (400 MHz, CDCl$_3$) δ 8.53 (s, 2H), 8.47 (d, J = 4.11 Hz, 1H), 7.38 (d, J = 7.63 Hz, 1H), 7.24-7.30 (m, 1H), 7.00 (dd, J = 7.53, 4.99 Hz, 1H), 6.50 (d, J = 8.61 Hz, 2H), 3.80-3.85 (m, 1H), 3.74-3.77 (m, 1H), 3.73 (s, 3H), 3.71 (s, 3H), 3.11 (dd, J = 14.48, 10.17 Hz, 1H), 2.57 (s, 3H), 1.32 (d, J = 6.65 Hz, 3 H). LCMS-ESI (POS.) m/z: 514.1 (M + H)+. |
| 212.0 | The racemic 210.0 was separated by supercritical fluid chromatography (2 × 15 cm IA column with 60 mL/min 20% MeOH/CO$_2$. Outlet pressure = 100 bar; wavelength = 220 nm; injection volume = 10 mL, 11 mg/mL 1:1 MeOH:DCM). This was the second isomer to elute under these conditions. | 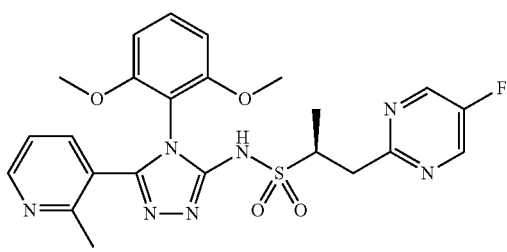

or |

TABLE 11-continued

| Example | Reagents | Structure, Name and data |
|---|---|---|
| | | 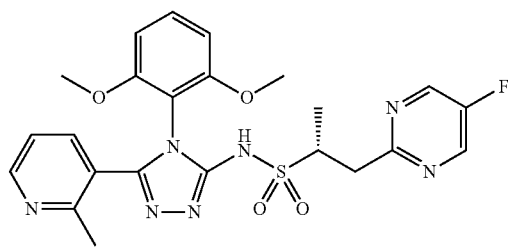 [SMILES: COc1cccc(OC)c1-n1c(NS(=O)(=O)[C@H](C)Cc2ncc(F)cn2)nnc1-c1cccnc1C]<br>(S)-N-(4-(2,6-dimethoxyphenyl)-5-(2-methylpyridin-3-yl)-4H-1,2,4-triazol-3-yl)-1-(5-fluoropyrimidin-2-yl)propane-2-sulfonamide or (R)-N-(4-(2,6-dimethoxyphenyl)-5-(2-methylpyridin-3-yl)-4H-1,2,4-triazol-3-yl)-1-(5-fluoro-pyrimidin-2-yl)propane-2-sulfonamide.<br>$^1$H NMR (400 MHz, CDCl$_3$) δ 8.53 (s, 2H), 8.43-8.50 (m, 1H), 7.38 (d, J = 7.24 Hz, 1H), 7.26 (t, J = 8.41 Hz, 2H), 6.91-7.09 (m, 1H), 6.50 (d, J = 8.61 Hz, 1H), 3.78-3.85 (m, 1H), 3.74-3.77 (m, 1H), 3.72 (s, 3H), 3.71 (s, 3H), 3.11 (dd, J = 14.09, 10.17 Hz, 1H), 2.57 (s, 3H), 1.32 (d, J = 6.26 Hz, 3 H). LCMS-ESI (POS.) m/z: 514.1 (M + H)$^+$. |
| 213.0 | (S)-N-((2,6-dimethoxyphenyl)carbamothioyl)-1-(5-fluoropyrimidin-2-yl )propane-2-sulfonamide and (R)-N-((2,6-dimethoxyphenyl)carbamothioyl)-1-(5-fluoropyrimidin-2-yl)propane-2-sulfonamide (Example 431.0) 6-methylnicotinohydrazide (Example 3.13) mercury (II) acetate (commercially available from VWR International, Radnor, PA, USA) TFA (commercially available from Sigma-Aldrich Corp, St. Louis, MO, USA). | 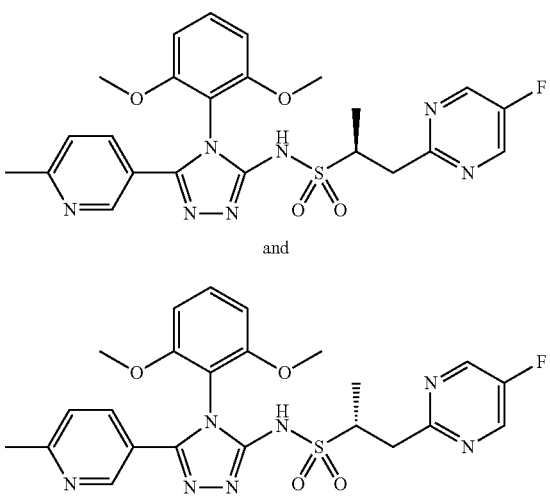<br>and<br>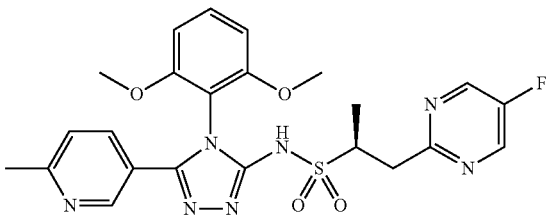 [SMILES: COc1cccc(OC)c1-n1c(NS(=O)(=O)[C@H](C)Cc2ncc(F)cn2)nnc1-c1ccc(C)nc1]<br>(2S)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide. LCMS-ESI (POS.) m/z: 514.1 (M + H)$^+$. |
| 214.0 | The racemic compound 213.0 was separated by supercritical fluid chromatography (2 x 15 cm IA column with 60 mL/min 25% MeOH(0.1% NH$_3$)/CO$_2$. Outlet pressure = 100 bar; wavelength = 220 nm; injection volume = 0.6 mL, 5 mg/mL 1:1 MeOH:DCM). This was the first isomer to elute under these conditions. | 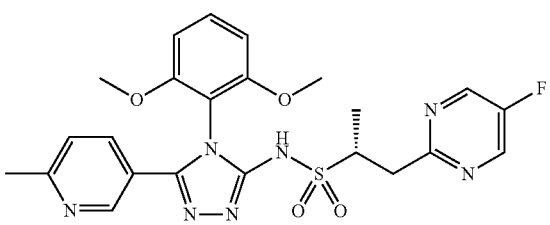 [SMILES: COc1cccc(OC)c1-n1c(NS(=O)(=O)[C@H](C)Cc2ncc(F)cn2)nnc1-c1ccc(C)nc1]<br>or |

| Example | Reagents | Structure, Name and data |
|---|---|---|
| | | (2S)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide.<br>$^1$H NMR (400 MHz, CDCl$_3$) δ 8.51 (s, 2H), 8.45 (d, J = 1.56 Hz, 1H), 7.66 (dd, J = 8.02, 2.15 Hz, 1H), 7.37 (t, J = 8.51 Hz, 1H), 7.11 (d, J = 8.22 Hz, 1H), 6.59 (dd, J = 8.51, 1.27 Hz, 2H), 3.79 (ddd, J = 10.17, 6.36, 4.21 Hz, 1H), 3.73 (s, 3H), 3.71 (s, 3H), 3.65-3.70 (m, 1H), 3.08 (dd, J = 14.57, 10.07 Hz, 1H), 2.53 (s, 3H), 1.30 (d, J = 6.85 Hz, 3 H). LCMS-ESI (POS.) m/z: 514.1 (M + H)$^+$. |
| 215.0 | The racemic compound 213.0 was separated by supercritical fluid chromatography (2 x 15 cm IA column with 60 mL/min 25% MeOH(0.1% NH$_3$)/CO$_2$. Outlet pressure = 100 bar; wavelength = 220 nm; injection volume = 0.6 mL, 5 mg/mL 1:1 MeOH:DCM). This was the second isomer to elute under these conditions. | or<br><br>(2S)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide.<br>$^1$H NMR (400 MHz, CDCl$_3$) δ 8.50-8.55 (m, 2H), 8.45 (s, 1H), 7.66 (dd, J = 8.12, 2.05 Hz, 1H), 7.38 (t, J = 8.51 Hz, 1H), 7.12 (d, J = 8.02 Hz, 1H), 6.60 (dd, J = 8.61, 1.17 Hz, 2H), 3.75-3.85 (m, 1H), 3.74 (s, 3H), 3.71 (s, 3H), 3.65-3.70 (m, 1H), 3.09 (dd, J = 14.57, 9.88 Hz, 1H), 2.54 (s, 3H), 1.30 (d, J = 6.65 Hz, 3 H). LCMS-ESI (POS.) m/z: 514.1 (M + H)$^+$. |
| 216.0 | (S)-N-((2,6-dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0) 4-methylnicotinohydrazide (Example 3.14) mercury (II) acetate (commercially available from VWR International, Radnor, PA, USA) (commercially available from Sigma-Aldrich Corp, St. Louis, MO, USA). | and |

TABLE 11-continued

| Example | Reagents | Structure, Name and data |
|---|---|---|
| | | (2S)-N-(4-(2,6-dimethoxyphenyl)-5-(4-methyl-3-pyridinyl)-4H-1,2,4-triazol-3-yl)-1-(5-fluoro-2-pyrimidinyl)-2-propane-sulfonamide and (2R)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide. LCMS-ESI (POS.) m/z: 514.1 (M + H)$^+$. |
| 217.0 | The racemic compound 216.0 was separated by chiral chromatography. (Run on Thar 80 SFC with 150 x 30 mm IA column with 24 g/min MeOH(+20 mM NH$_3$) + 56 g/min CO$_2$, 30% co-solvent at 80 g/min. Outlet pressure = 100 bar; Temp. = 22 C.; Wavelength = 280 nm. Injected 0.3 mL of a solution from 59 mg sample dissolved in 5.5 mL of MeOH(with 2 mL DCM), c = 10.7 mg/mL; 3.2 mg per injection. Cycle time 6 min, run time 12 min. This was the first isomer to elute. | 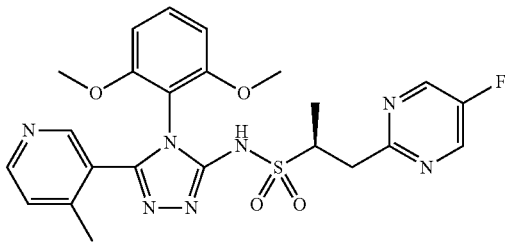 [SMILES: COc1cccc(OC)c1-n1c(NS(=O)(=O)[C@H](C)Cc2ncc(F)cn2)nnc1-c1cnccc1C]<br>or<br>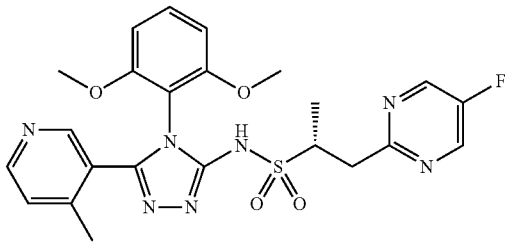<br>(2S)-N-(4-(2,6-dimethoxyphenyl)-5-(4-methyl-3-pyridinyl)-4H-1,2,4-triazol-3-yl)-1-(5-fluoro-2-pyrimidinyl)-2-propane-sulfonamide or (2R)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide.<br>$^1$H NMR (400 MHz, CDCl$_3$) δ 8.52 (s, 2H), 7.51-7.61 (m, 2H), 7.35 (t, J = 8.51 Hz, 1H), 7.09 (dd, J = 6.46, 1.96 Hz, 1H), 6.58 (dd, J = 8.51, 1.66 Hz, 2H), 3.77-3.86 (m, 1H), 3.72-3.75 (m, 1H), 3.70 (s, 3H), 3.68 (s, 3H), 3.10 (dd, J = 14.77, 9.88 Hz, 1H), 2.22 (s, 3H), 1.32 (d, J = 6.65 Hz, 3 H). LCMS-ESI (POS.) m/z: 514.1 (M + H)$^+$. |
| 218.0 | The racemic compound 216.0 was separated by chiral chromatography. (Run on Thar 80 SFC with 150 x 30 mm IA column with 24 g/min MeOH(+20 mM NH$_3$) + 56 g/min CO$_2$, 30% co-solvent at 80 g/min. Outlet pressure = 100 bar; Temp. = 22 C.; Wavelength = 280 nm. Injected 0.3 mL of a solution from 59 mg sample dissolved in 5.5 mL of MeOH(with 2 mL DCM), c = 10.7 mg/mL; 3.2 mg per injection. Cycle time 6 min, run time 12 min. This was the second isomer to elute. | 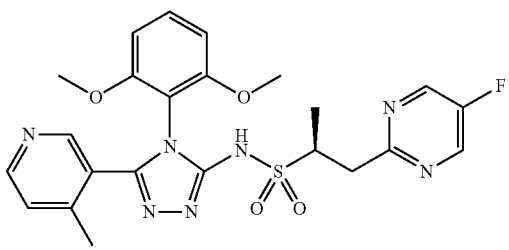<br>or<br>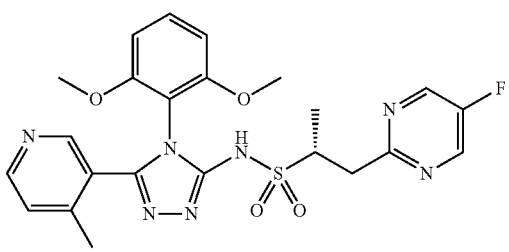<br>(2S)-N-(4-(2,6-dimethoxyphenyl)-5-(4-methyl-3-pyridinyl)-4H-1,2,4-triazol-3-yl)-1-(5-fluoro-2-pyrimidinyl)-2-propane-sulfonamide or (2R)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide. |

| Example | Reagents | Structure, Name and data |
|---|---|---|
| | | ¹H NMR (400 MHz, CDCl₃) δ 8.53 (s, 2H), 7.52-7.60 (m, 2H), 7.35 (t, J = 8.51 Hz, 1H), 7.09 (dd, J = 6.75, 1.66 Hz, 1H), 6.58 (dd, J = 8.51, 1.66 Hz, 2H), 3.77-3.87 (m, 1H), 3.72-3.75 (m, 1H), 3.70 (s, 3H), 3.68 (s, 3H), 3.10 (dd, J = 14.77, 9.88 Hz, 1H), 2.23 (s, 3H), 1.32 (d, J = 6.65 Hz, 3 H). LCMS-ESI (POS.) m/z: 514.1 (M + H)⁺. |
| 219.0 | (S)-N-((2,6-dimethoxyphenyl) carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0) 5-chloronicotinohydrazide (Example 3.15) mercury (II) acetate (commercially available from VWR International, Radnor, PA, USA) TFA (commercially available from Sigma-Aldrich Corp, St. Louis, MO, USA). | 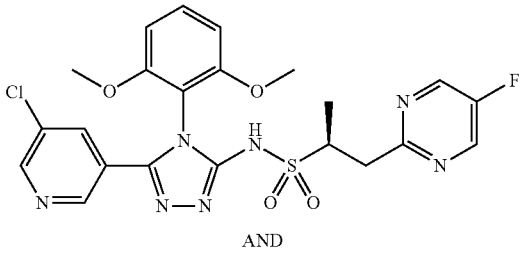 [SMILES: COc1cccc(OC)c1-n1c(NS(=O)(=O)[C@@H](C)Cc2ncc(F)cn2)nnc1-c1cncc(Cl)c1]

AND

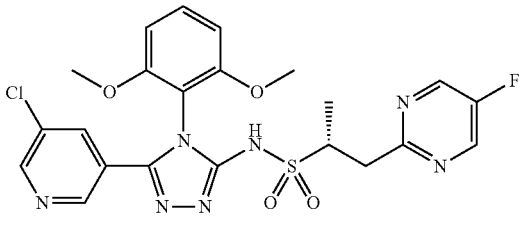 [SMILES: COc1cccc(OC)c1-n1c(NS(=O)(=O)[C@H](C)Cc2ncc(F)cn2)nnc1-c1cncc(Cl)c1]

(2S)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide and (2R)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide. LCMS-ESI (POS.) m/z: 534.2 (M + H)⁺. |
| 220.0 | The racemic compound 219.0 was separated by supercritical fluid chromatography (150 x 30 mm IA column on Thar 80 with 24 g/min MeOH(+20 mM NH₃) + 56 g/min CO₂, 30% co-solvent at 80 g/min. Outlet pressure = 100 bar; temperature = 22° C.; wavelength = 280 nm; injection volume = 0.3 mL of a solution of 59 mg sample dissolved in 5.5 mL MeOH + 2 mL DCM). This was the first isomer to elute under these conditions. | 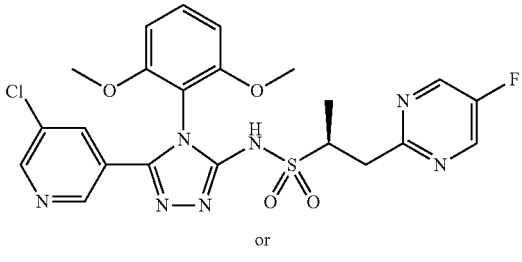 [SMILES: COc1cccc(OC)c1-n1c(NS(=O)(=O)[C@@H](C)Cc2ncc(F)cn2)nnc1-c1cncc(Cl)c1]

or

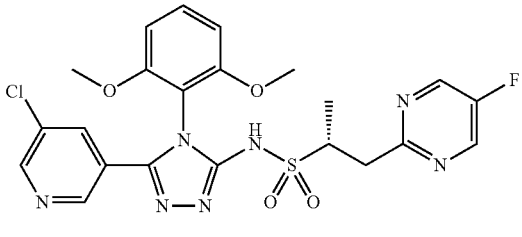 [SMILES: COc1cccc(OC)c1-n1c(NS(=O)(=O)[C@H](C)Cc2ncc(F)cn2)nnc1-c1cncc(Cl)c1]

(2S)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide.
¹H NMR (400 MHz, CDCl₃) δ 8.50-8.57 (m, 4H), 8.43 (d, J = 1.76 Hz, 1H), 7.81 (t, J = 2.15 Hz, 1H), 7.41 (t, J = 8.51 Hz, 1H), 6.62 (d, J = 8.61 Hz, 2H), 3.77-3.83 (m, 1H), 3.75 (s, 3H), 3.73 (s, 3H), 3.65-3.72 (m, 1H), 3.08 (dd, J = 14.67, 9.98 Hz, 1H), 1.29 (d, J = 6.65 Hz, 3 H). LCMS-ESI (POS.) m/z: 534.0 (M + H)⁺. |

TABLE 11-continued

| Example | Reagents | Structure, Name and data |
|---|---|---|
| 221.0 | The racemic compound 219.0 was separated by supercritical fluid chromatography (150 × 30 mm IA column on Thar 80 with 24 g/min MeOH(+20 mM NH$_3$) + 56 g/min CO$_2$, 30% co-solvent at 80 g/min. Outlet pressure = 100 bar; temperature = 22° C.; wavelength = 280 nm; injection volume = 0.3 mL of a solution of 59 mg sample dissolved in 5.5 mL MeOH + 2 mL DCM). This was the second isomer to elute under these conditions. | 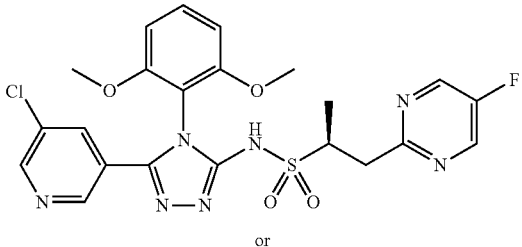 [SMILES: COc1cccc(OC)c1-n1c(NS(=O)(=O)[C@@H](C)Cc2ncc(F)cn2)nnc1-c1cncc(Cl)c1]<br>or<br>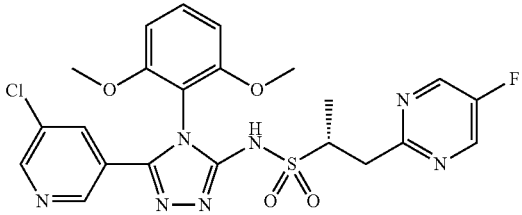 [SMILES: COc1cccc(OC)c1-n1c(NS(=O)(=O)[C@H](C)Cc2ncc(F)cn2)nnc1-c1cncc(Cl)c1]<br>(2S)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide or (2R)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide.<br>$^1$H NMR (400 MHz, CDCl$_3$) δ 8.54-8.61 (m, 1H), 8.52 (s, 2H), 8.43 (d, J = 1.76 Hz, 1H), 7.80 (t, J = 2.05 Hz, 1H), 7.40 (t, J = 8.51 Hz, 1H), 6.62 (d, J = 8.61 Hz, 2H), 3.78-3.84 (m, 1H), 3.75 (s, 3H), 3.72 (s, 3H), 3.65-3.71 (m, 1H), 3.08 (dd, J = 14.67, 9.98 Hz, 1H), 1.29 (d, J = 6.85 Hz, 3 H). LCMS-ESI (POS.) m/z: 534.0 (M + H)$^+$. |
| 222.0 | (S)-N-((2,6-dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0), 4-methylpicolinohydrazide Example 3.16, mercury (II) acetate (commercially available from VWR International, Radnor, PA, USA) TFA (commercially available from Sigma-Aldrich Corp, St. Louis, MO, USA). | 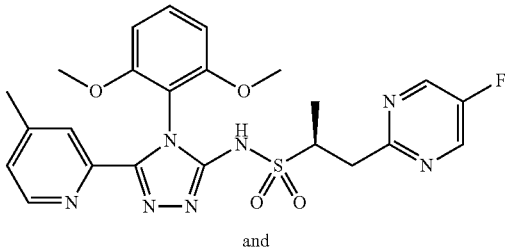 [SMILES: COc1cccc(OC)c1-n1c(NS(=O)(=O)[C@@H](C)Cc2ncc(F)cn2)nnc1-c1cc(C)ccn1]<br>and<br>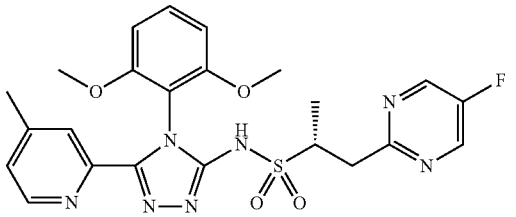<br>2S)-N-(4-(2,6-dimethoxyphenyl)-5-(4-methyl-2-pyridinyl)-4H-1,2,4-triazol-3-yl)-1-(5-fluoro-2-pyrimidinyl)-2-propane-sulfonamide and (2R)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide. LCMS ESI (POS.) m/z: 514.1 (M + H)$^+$. |
| 223.0 | The racemic compound 222.0 was separated by supercritical fluid chromatography (300 × 30 mm IA column on Thar 200 with 31 g/min MeOH(+20 mM NH$_3$) + 94 g/min CO$_2$, 25% co-solvent at 125 g/min. Wavelength = 276 nm; injection volume = 0.3 mL). This was the first isomer to elute under these conditions. | 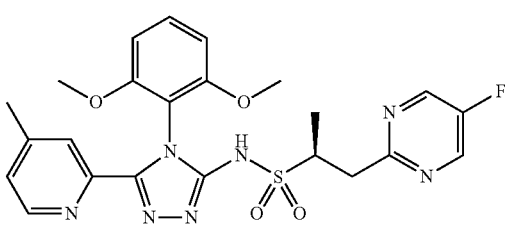<br>or |

TABLE 11-continued

| Example | Reagents | Structure, Name and data |
|---|---|---|
| | | 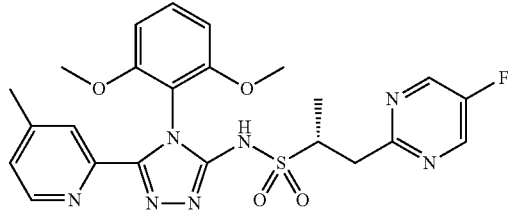<br>2S)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide.<br>$^{1}$H NMR (400 MHz, CDCl$_{3}$) δ 8.46-8.56 (m, 2H), 8.20 (d, J = 4.89 Hz, 1H), 7.59 (s, 1H), 7.34 (t, J = 8.51 Hz, 1H), 7.05 (d, J = 4.70 Hz, 1H), 6.58 (dd, J = 8.51, 1.86 Hz, 2H), 3.77-3.85 (m, 1H), 3.71-3.75 (m, 1H), 3.70 (s, 3H), 3.68 (s, 3H), 3.10 (dd, J = 14.77, 9.88 Hz, 1H), 2.34 (s, 3H), 1.32 (d, J = 6.65 Hz, 3 H). LCMS-ESI (POS.) m/z: 514.1 (M + H)$^{+}$. |
| 224.0 | The racemic compound 222.0 was separated by supercritical fluid chromatography (300 x 30 mm IA column on Thar 200 with 31 g/min MeOH(+20 mM NH$_{3}$) + 94 g/min CO$_{2}$, 25% co-solvent at 125 g/min. Wavelength = 276 nm; injection volume = 0.3 mL). This was the first isomer to elute under these conditions. | 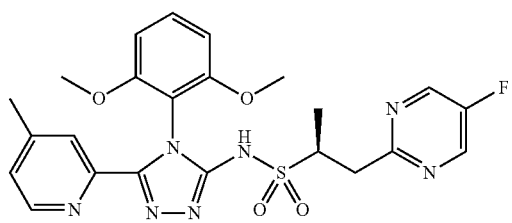<br>or<br>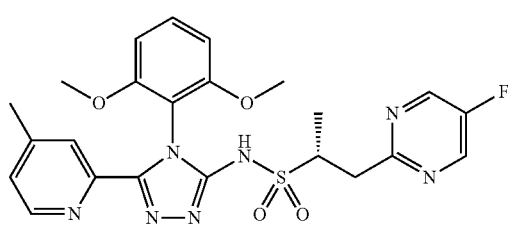<br>2S)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide.<br>$^{1}$H NMR (400 MHz , CDCl$_{3}$) δ 8.52 (s, 2H), 8.2 (d, J = 4.9 Hz, 1H), 7.59 (s, 1H), 7.34 (dd, J = 8.4, 8.4 Hz, 1H), 7.05 (d, J = 4.7 Hz, 1H), 6.58 (dd, J = 8.5, 1.9 Hz, 2H), 3.77-3.85 (m, 1H), 3.69-3.74 (obscured m, 1H), 3.70 (s, 3H), 3.68 (s, 3H), 3.1 (dd, J = 14.8, 9.9 Hz, 1H), 2.34 (s, 3H), 1.32 (d, J = 6.7 Hz, 3H). LCMS-ESI (POS.) m/z: 514.1 (M + H)$^{+}$. |
| 225.0 | (S)-N-((2,6-dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0), 5-fluoronocotinohydrazide Example 3.17, mercury (II) acetate (commercially available from VWR International, Radnor, PA, USA) TFA (commercially available from Sigma-Aldrich Corp, St. Louis, MO, USA). | 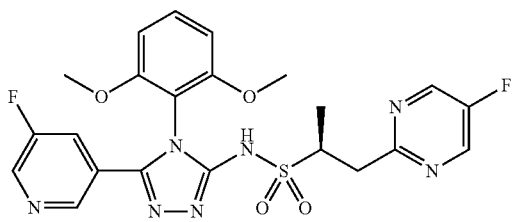 [SMILES: COc1cccc(OC)c1-n1c(NS(=O)(=O)[C@H](C)Cc2ncc(F)cn2)nnc1-c1cncc(F)c1]<br>and |

TABLE 11-continued

| Example | Reagents | Structure, Name and data |
|---|---|---|
| | | (2S)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide and (2R)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide. LCMS-ESI (POS.) m/z: 518.2 (M + H)+. |
| 226.0 | The racemic compound 225.0 was separated by supercritical fluid chromatography (2 x 15 cm IA column with 60 mL/min 20% MeOH/CO$_2$. Outlet pressure = 100 bar; wavelength = 220 nm; injection volume = 1 mL, 5 mg/mL MeOH). This was the first isomer to elute under these conditions. | (2S)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide.<br>$^1$H NMR (400 MHz, CDCl$_3$) δ 8.54 (s, 2H), 8.49 (d, J = 2.74 Hz, 1H), 8.44 (s, 1H), 7.47-7.54 (m, 1H), 7.42 (t, J = 8.51 Hz, 1H), 6.63 (dd, J = 8.51, 0.88 Hz, 2H), 3.78-3.84 (m, 1H), 3.76 (s, 3H), 3.74 (s, 3H), 3.69 (dd, J = 14.77, 4.21 Hz, 1H), 3.09 (dd, J = 14.77, 9.88 Hz, 1H), 1.31 (d, J = 6.85 Hz, 3 H). LCMS-ESI (POS.) m/z: 540.3 (M + H)+. |
| 227.0 | The racemic compound 225.0 was separated by supercritical fluid chromatography (2 x 15 cm IA column with 60 mL/min 20% MeOH/CO$_2$. Outlet pressure = 100 bar; wavelength = 220 nm; injection volume = 1 mL, 5 mg/mL MeOH). This was the second isomer to elute under these conditions. | |

| Example | Reagents | Structure, Name and data |
|---|---|---|
| | | (2S)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide or (2R)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide.<br>$^1$H NMR (400 MHz, CDCl$_3$) δ 8.54 (s, 2H), 8.49 (d, J = 2.35 Hz, 1H), 8.44 (s, 1H), 7.50 (d, J = 9.00 Hz, 1H), 7.42 (t, J = 8.51 Hz, 1H), 6.63 (dd, J = 8.61, 0.98 Hz, 2H), 3.78-3.84 (m, 1H), 3.76 (s, 3H), 3.74 (s, 3H), 3.69 (dd, J = 14.77, 4.01 Hz, 1H), 3.09 (dd, J = 14.67, 9.78 Hz, 1H), 1.31 (d, J = 6.65 Hz, 3 H). LCMS-ESI (POS.) m/z: 540.3 (M + H)$^+$. |
| 228.0 | (S)-N-((2,6-dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0), N-ethyl-6-(hydrazinecarbonyl)picolinamide (Example 3.19) mercury (II) acetate (commercially available from VWR International, Radnor, PA, USA) TFA (commercially available from Sigma-Aldrich Corp, St. Louis, MO, USA). | 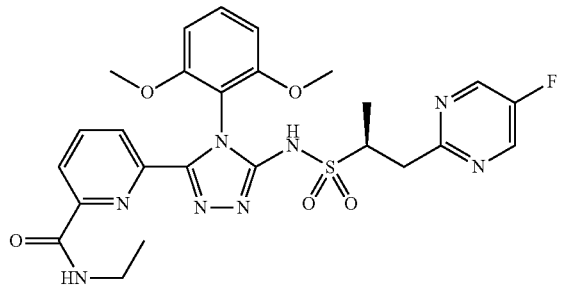 [SMILES: CCNC(=O)c1cccc(-c2nnc(NS(=O)(=O)[C@H](C)Cc3ncc(F)cn3)n2-c2c(OC)cccc2OC)n1]<br>and<br>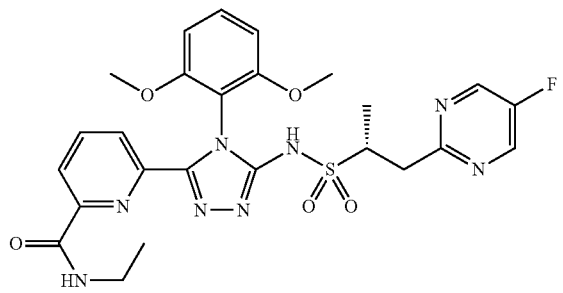 [SMILES: CCNC(=O)c1cccc(-c2nnc(NS(=O)(=O)[C@H](C)Cc3ncc(F)cn3)n2-c2c(OC)cccc2OC)n1]<br>6-(4-(2,6-dimethoxyphenyl)-5-(((((1S)-2-(5-fluoro-2-pyrimidinyl)-1-methylethyl)sulfonyl)amino)-4H-1,2,4-triazol-3-yl)-N-ethyl-2-pyridinecarboxamide and 6-(4-(2,6-dimethoxyphenyl)-5-(((((1R)-2-(5-fluoro-2-pyrimidinyl)-1-methylethyl)sulfonyl)amino)-4H-1,2,4-triazol-3-yl)-N-ethyl-2-pyridinecarboxamide.<br>LCMS-ESI (POS.) m/z: 571.2 (M + H)$^+$. |
| 229.0 | The racemic 228.0 was separated by supercritical fluid chromatography (2 x 15 cm IA column with 60 mL/min 28% MeOH (0.1% NH$_4$OH)/CO$_2$. Outlet pressure = 100 bar; wavelength = 220 nm; injection volume = 0.75 mL, 10 mg/mL MeOH). This was the first isomer to elute under these conditions. | 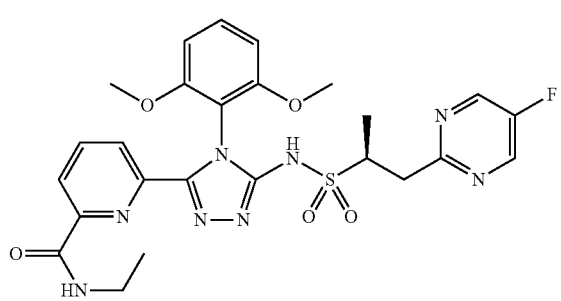<br>or |

TABLE 11-continued

| Example | Reagents | Structure, Name and data |
|---------|----------|--------------------------|
| | | 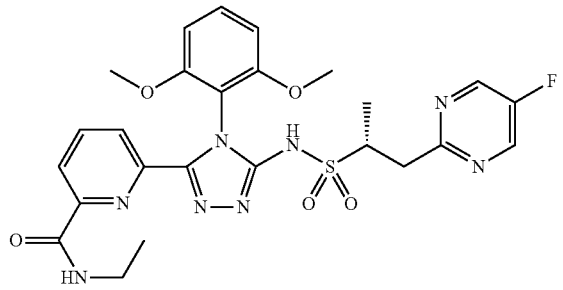
6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-ethyl-2-pyridinecarboxamide or 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-ethyl-2-pyridinecarboxamide.
$^1$H NMR (400 MHz, CDCl$_3$) δ 8.53 (s, 2H), 8.23 (dd, J = 8.02, 0.98 Hz, 1H), 8.16 (dd, J = 7.63, 0.98 Hz, 1H), 7.93 (t, J = 7.83 Hz, 1H), 7.45 (t, J = 8.41 Hz, 1H), 6.69 (dd, J = 8.61, 1.76 Hz, 2H), 6.49 (t, J = 6.16 Hz, 1H), 3.77-3.86 (m, 1H), 3.73 (s, 3H), 3.71 (s, 3H), 3.66-3.70 (m, 1H), 3.49 (s, 1H), 3.22 (quin, J = 7.04 Hz, 2H), 3.10 (dd, J = 14.87, 9.98 Hz, 1H), 1.32 (d, J = 6.65 Hz, 3H), 1.10 (t, J = 7.24 Hz, 3 H). LCMS-ESI (POS.) m/z: 570.8 (M + H)$^+$. |
| 230.0 | The racemic 228.0 was separated by supercritical fluid chromatography (2 × 15 cm IA column with 60 mL/min 28% MeOH (0.1% NH$_4$OH)/CO$_2$. Outlet pressure = 100 bar; wavelength = 220 nm; injection volume = 0.75 mL, 10 mg/mL MeOH). This was the second isomer to elute under these conditions | 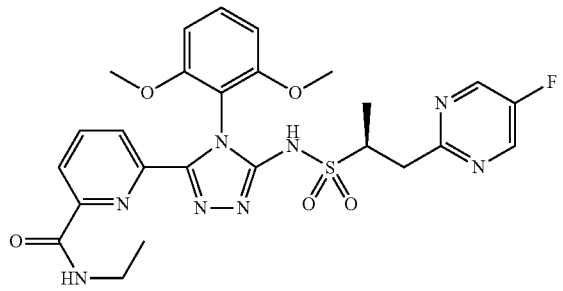
or
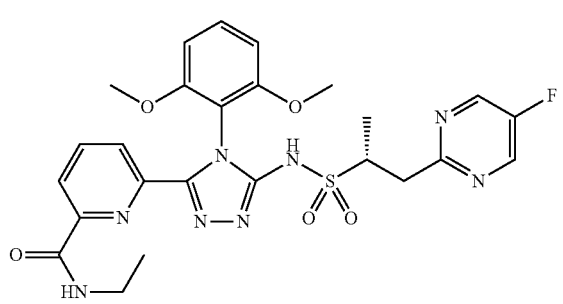 [SMILES: CCNC(=O)c1cccc(-c2nnc(NS(=O)(=O)[C@H](C)Cc3ncc(F)cn3)n2-c2c(OC)cccc2OC)n1]
6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-ethyl-2-pyridinecarboxamide or 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-ethyl-2-pyridinecarboxamide.
$^1$H NMR (400 MHz, CDCl$_3$) δ 8.53 (s, 2H), 8.22 (dd, J = 7.82, 0.98 Hz, 1H), 8.16 (dd, J = 7.73, 0.88 Hz, 1H), 7.84-7.98 (m, 1H), 7.45 (t, J = 8.51 Hz, 1H), 6.70 (dd, J = 8.51, 1.66 Hz, 2H), 6.49 (t, J = 6.06 Hz, 1H), 3.77-3.87 (m, 1H), 3.73 (s, 3H), 3.71 (s, 3H), 3.63-3.70 (m, 1H), 3.49 (s, 1H), 3.22 (quin, J = 6.99 Hz, 2H), 3.10 (dd, J = 14.77, 9.88 Hz, 1H), 1.32 (d, J = 6.85 Hz, 3H), 1.10 (t, J = 7.14 Hz, 3 H). LCMS-ESI (POS.) m/z: 570.8 (M + H)$^+$. |

TABLE 11-continued

| Example | Reagents | Structure, Name and data |
|---|---|---|
| 231.0 | (S)-N-((2,6-dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide (Example 431.0), 6-(hydrazinecarbonyl)-N,N-dimethyl-picolinamide (Example 3.20), mercury (II) acetate (commercially available from VWR International, Radnor, PA, USA) TFA (Sigma-Aldrich) | and<br><br>6-(4-(2,6-dimethoxyphenyl)-5-(((((1S)-2-(5-fluoro-2-pyrimidinyl)-1-methylethyl)sulfonyl)amino)-4H-1,2,4-triazol-3-yl)-N,N-dimethyl-2-pyridinecarboxamide and 6-(4-(2,6-dimethoxy-phenyl)-5-((((1R)-2-(5-fluoro-2-pyrimidinyl)-1-methylethyl) sulfonyl)amino)-4H-1,2,4-triazol-3-yl)-N,N-dimethyl-2-pyridinecarboxamide. LCMS-ESI (POS.) m/z: 571.2 (M + H)+. |
| 232.0 | The racemic 231.0 was separated by supercritical fluid chromatography (250 x 21 mm IC column on Thar 80 with 20.4 g/min MeOH + 20 mM NH3 + 40 g/min CO2, 34% co-solvent at 60 g/min. Outlet pressure = 100 bar; temperature = 24° C.; wavelength = 282 nm; injection volume = 0.4 mL, 7.8 mg/mL 4:1 MeOH:DCM). This was the first isomer to elute under these conditions. | or |

| Example | Reagents | Structure, Name and data |
| --- | --- | --- |
| | | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N,N-dimethyl-2-pyridinecarboxamide or 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N,N-dimethyl-2-pyridinecarboxamide.<br>$^1$H NMR (400 MHz, CDCl$_3$) δ 8.53 (s, 2H), 7.96 (dd, J = 8.02, 0.98 Hz, 1H), 7.84 (t, J = 7.82 Hz, 1H), 7.63 (dd, J = 7.73, 1.08 Hz, 1H), 7.34 (t, J = 8.51 Hz, 1H), 6.57 (dd, J = 8.61, 1.56 Hz, 2H), 3.76-3.86 (m, 1H), 3.69-3.74 (m, 1H), 3.68 (s, 3H), 3.66 (s, 3H), 3.10 (dd, J = 14.77, 9.88 Hz, 1H), 2.96 (s, 3H), 2.56 (s, 3H), 1.31 (d, J = 6.65 Hz, 3 H). LCMS-ESI (POS.) m/z: 570.8 (M + H)$^+$. |
| 233.0 | The racemic 231.0 was separated by supercritical fluid chromatography (250 x 21 mm IC column on Thar 80 with 20.4 g/min MeOH + 20 mM NH$_3$ + 40 g/min CO$_2$, 34% co-solvent at 60 g/min. Outlet pressure = 100 bar; temperature = 24° C.; wavelength = 282 nm; injection volume = 0.4 mL, 7.8 mg/mL 4:1 MeOH:DCM). This was the second isomer to elute under these conditions. | 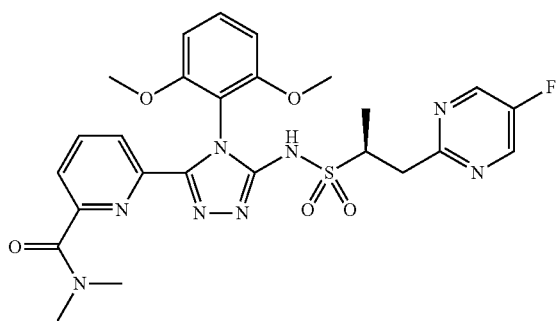 [SMILES: COc1cccc(OC)c1-n1c(NS(=O)(=O)[C@H](C)Cc2ncc(F)cn2)nnc1-c1cccc(C(=O)N(C)C)n1]<br>or<br>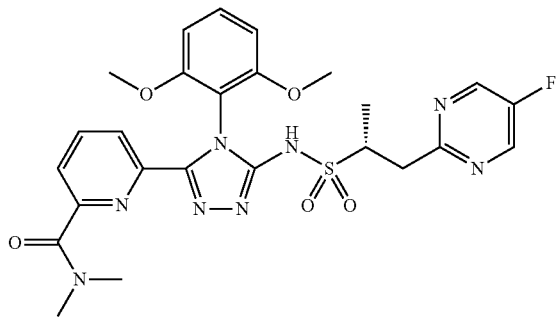 [SMILES: COc1cccc(OC)c1-n1c(NS(=O)(=O)[C@H](C)Cc2ncc(F)cn2)nnc1-c1cccc(C(=O)N(C)C)n1]<br>6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N,N-dimethyl-2-pyridinecarboxamide or 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N,N-dimethyl-2-pyridinecarboxamide.<br>$^1$H NMR (400 MHz, CDCl$_3$) δ 8.53 (s, 2H), 7.96 (dd, J = 7.92, 1.08 Hz, 1H), 7.84 (t, J = 7.82 Hz, 1H), 7.63 (dd, J = 7.73, 1.08 Hz, 1H), 7.34 (t, J = 8.51 Hz, 1H), 6.57 (dd, J = 8.51, 1.47 Hz, 2H), 3.76-3.85 (m, 1H), 3.69-3.75 (m, 1H), 3.68 (s, 3H), 3.66 (s, 3H), 3.10 (dd, J = 14.77, 9.88 Hz, 1H), 2.96 (s, 3H), 2.55 (s, 3H), 1.31 (d, J = 6.65 Hz, 3 H). LCMS-ESI (POS.) m/z: 570.8 (M + H)$^+$. |

Example 234.0: Preparation of (2S,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2S,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide

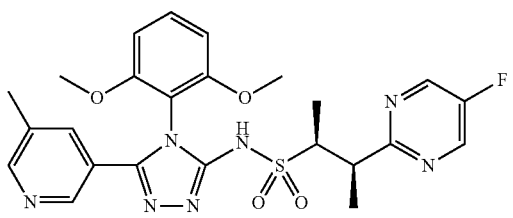

AND

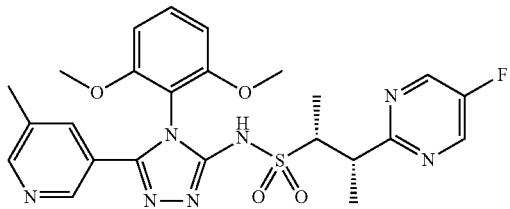

AND

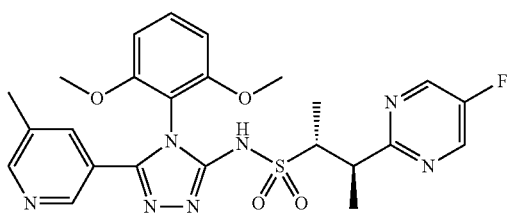

AND

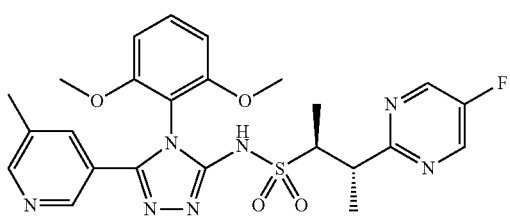

(2S,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide and (2R,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide and (2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide and (2S,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, Example 234.1

To a solution of 4-(2,6-dimethoxyphenyl)-5-(5-methyl-pyridin-3-yl)-4H-1,2,4-triazol-3-amine (0.696 g, 2.24 mmol) (Example 2.04) in THF (10 mL, 123 mmol) in an ice bath was added LHMDS 1.0M in THF (2.24 mL, 2.24 mmol) (Sigma Aldrich) dropwise. The mixture was stirred at 0° C. for 1 h, to which was added a solution of 432.0 (0.264 g, 1.12 mmol) in THF (5 mL). The resulting mixture was warmed to RT and stirred for 18 h. The mixture was concentrated and the residue was loaded onto a plug of silica gel and purified by chromatography through a Redi-Sep pre-packed silica gel column (24 g), eluting with a gradient of 0% to 100% EtOAc in hexanes, to give the title compound 234.1 (0.091 g, 0.172 mmol, 15% yield). LCMS-ESI (POS.) m/z: 528.1 (M+H)$^+$.

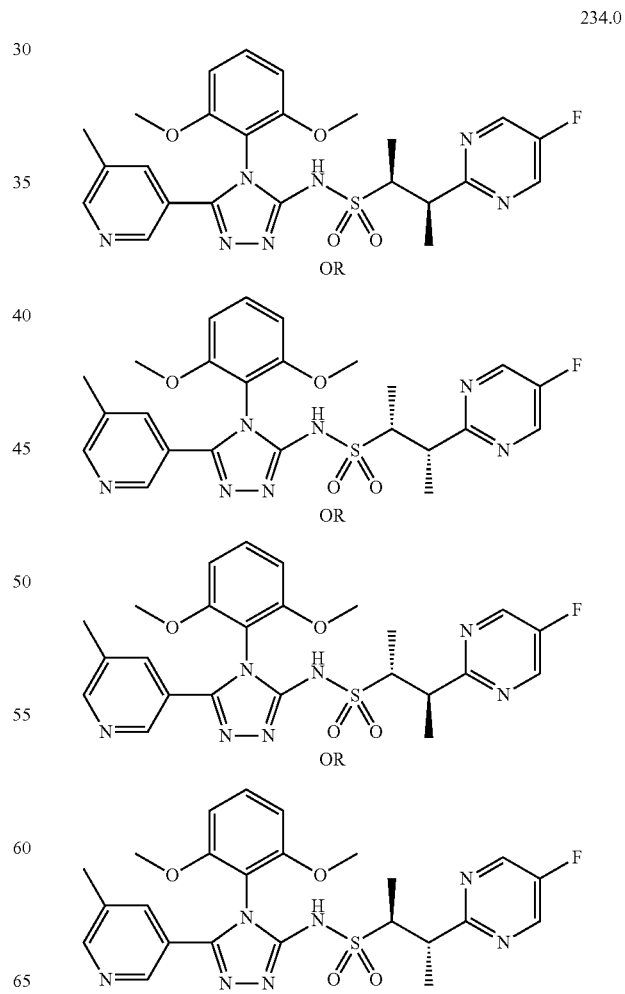

(2S,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2S,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, Example 234.0

The racemic mixture of 234.1 was purified via preparative SFC, requiring multiple purifications using methods including: (a) ChiralPak AS-H column (Sepax) (150×21 mm, 5 µm), 75:25 (Liquid $CO_2$: IPA (20 mM $NH_3$), Flow Rate: 70 mL/min; (b) chiralpak AD-H column (Sepax) (150×21 mm, 5 µm), 60:40 Liquid $CO_2$: IPA (20 mM $NH_3$); Flow Rate: 70 mL/min and (c) chiralpak AS-H column (250×21 mm, 5 µm), 88:12 (Liquid $CO_2$/MeOH (20 mM $NH_3$)), Flow Rate: 70 mL/min respectively. Four isomers were obtained. The title compound 234.0 was the first isomer to elute under these conditions. $^1$H NMR (400 MHz, CDCl$_3$) δ 8.53 (s, 2H), 8.44 (d, J=1.56 Hz, 1H), 8.33 (d, J=1.96 Hz, 1H), 7.62-7.67 (m, 1H), 7.39 (t, J=8.51 Hz, 1H), 6.56-6.64 (m, 2H), 3.79-3.88 (m, 2H), 3.74 (s, 3H), 3.71 (s, 3H), 2.30 (s, 3H), 1.36 (dd. J=8.31, 6.94 Hz, 6H). LCMS-ESI (POS.) m/z: 528.2 (M+H)$^+$.

Example 235.0: Preparation of (2S,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2S,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide

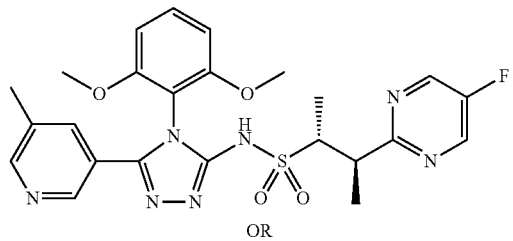

OR

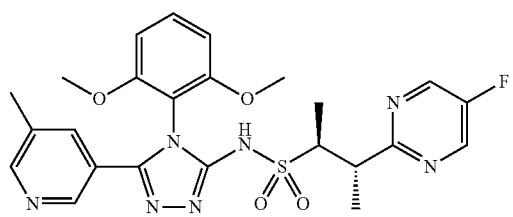

The title compound. Example 235.0, was the second isomer to elute on subjecting 234.1 to the SFC conditions described in Example 234.0. $^1$H NMR (400 MHz, CDCl$_3$) δ 8.53 (s, 2H), 8.44 (d, J=1.56 Hz, 1H), 8.33 (d, J=1.76 Hz, 1H), 7.64 (s, 1H), 7.39 (t, J=8.51 Hz, 1H), 6.55-6.64 (m, 2H), 3.80-3.89 (m, 2H), 3.74 (s, 3H), 3.71 (s, 3H), 2.30 (s, 3H), 1.36 (dd, J=8.22, 6.85 Hz, 6H). LCMS-ESI (POS.) m/z: 528.2 (M+H)$^+$.

Example 236.0: Preparation of (2S,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2S,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide 235.0

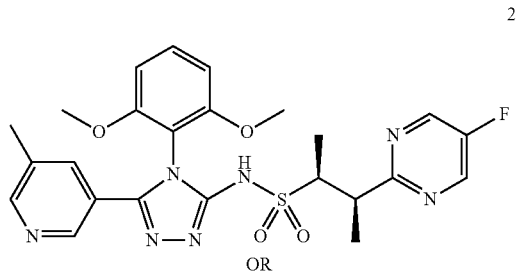

OR

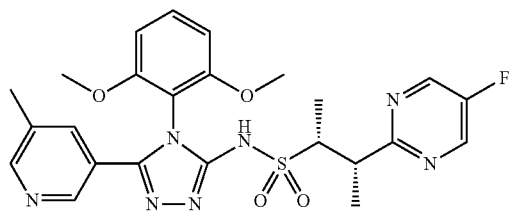

236.0

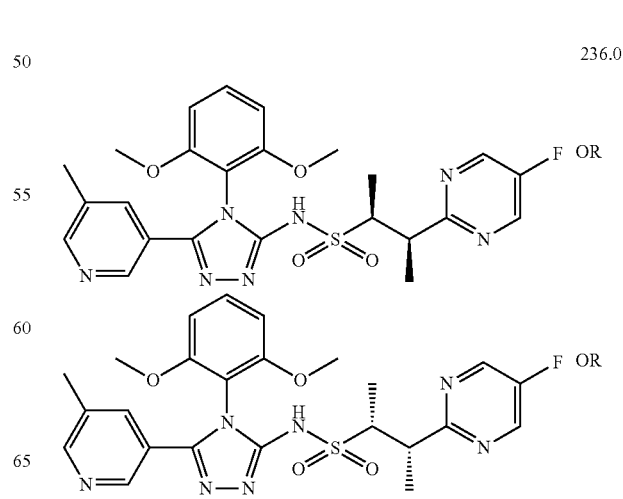

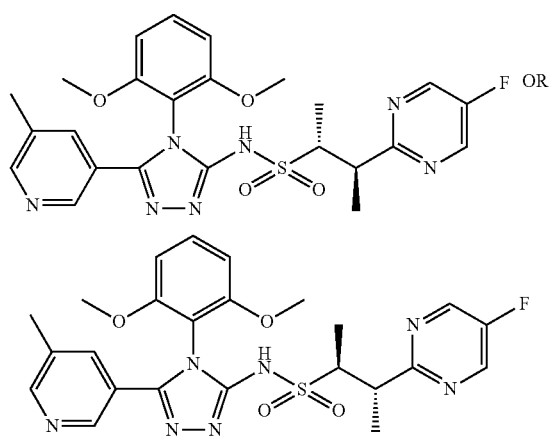

The title compound, Example 236.0, was the third isomer to elute on subjecting 234.1 to the SFC conditions described in 234.0. $^1$H NMR (400 MHz, CDCl$_3$) δ 8.53 (s, 2H), 8.44 (d, J=1.56 Hz, 1H), 8.33 (d, J=1.76 Hz, 1H), 7.63 (s, 1H), 7.39 (t, J=8.51 Hz, 1H), 6.61 (dd, J=8.51, 2.45 Hz, 2H), 3.75 (s, 3H), 3.74 (s, 3H), 3.52-3.69 (m, 2H), 2.30 (s, 3H), 1.50 (d, J=7.04 Hz, 3H), 1.25 (d, J=7.04 Hz, 3H). LCMS-ESI (POS.) m/z: 528.2 (M+H)$^+$.

Example 237.0: Preparation of (2S,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2R,3R)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide or (2S,3S)—N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide

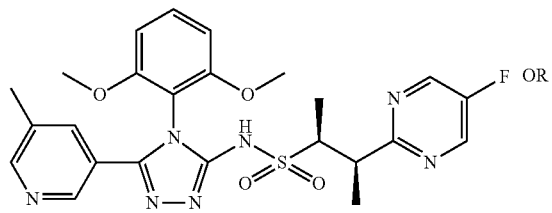

237.0

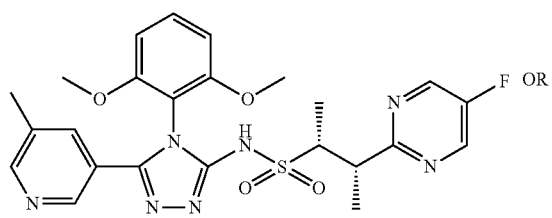

The title compound, Example 237.0, was the fourth isomer to elute on subjecting 234.1 to the SFC conditions described 234.0. $^1$H NMR (400 MHz, CDCl$_3$) δ 8.53 (s, 2H), 8.44 (d, J=1.37 Hz, 1H), 8.33 (d, J=1.56 Hz, 1H), 7.63 (s, 1H), 7.39 (t, J=8.51 Hz, 1H), 6.60 (dd, J=8.41, 2.54 Hz, 2H), 3.75 (s, 3H), 3.74 (s, 3H), 3.53-3.68 (m, 2H), 2.30 (s, 3H), 1.50 (d, J=6.85 Hz, 3H), 1.25 (d, J=6.85 Hz, 3H). LCMS-ESI (POS.) m/z: 528.2 (M+H)$^+$.

Example B

Example 238.0: Preparation of (2R,3S)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide

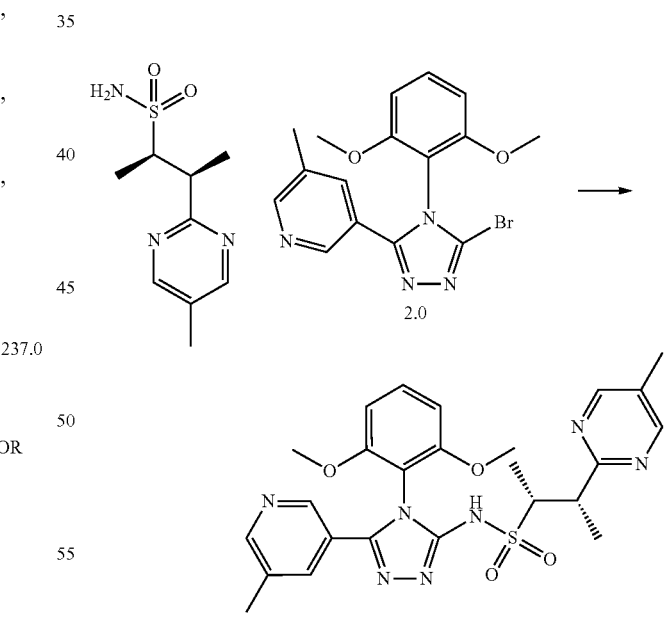

(2R,3S)—N-(4-(2,6-dimethoxyphenyl)-5-(5-methyl-pyridin-3-yl)-4H-1,2,4-triazol-3-yl)-3-(5-methylpyrimidin-2-yl)butane-2-sulfonamide, Example 238.0

A vial containing (2R,3S)-3-(5-methylpyrimidin-2-yl)butane-2-sulfonamide (378 mg, 1.65 mmol), 3-(5-bromo-4-(2, 6-dimethoxyphenyl)-4H-1,2,4-triazol-3-yl)-5-methylpyridine (Example 2.0, 809 mg, 2.16 mmol), copper(I) iodide (161 mg, 0.85 mmol), trans-N,N'-dimethyl-1,2-cyclohexanediamine (0.53 mL, 3.36 mmol), and cesium carbonate (1.36 g, 4.18 mmol) was degassed and then backfilled with house nitrogen. Evacuation and backfilling was repeated three times. Anhydrous 1,4-dioxane (3.3 mL) was added to the mixture and then the dark blue heterogeneous solution was heated on a pre-heated stirplate at 80° C. and monitored with LC-MS. After 20 h, the reaction was cooled to RT and then diluted with water. Aqueous solution of 1N HCl was carefully added to the dark blue homogeneous solution to pH~7. After extracting four times with DCM, the organics were combined then washed once with aqueous 1 M sodium thiosulfate. After drying the organic layer over anhydrous magnesium sulfate, filtration, and concentration under reduced pressure, the blue green residue was loaded onto a silica gel column (0-75% 3:1 EtOAc: EtOH in heptanes) to afford a white solid (2S,3R)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide 238.0 (401 mg). 1H NMR (500 MHz, DMSO-d₆) δ=13.37 (s, 1H), 8.63-8.55 (m, 2H), 8.47 (d, J=1.5 Hz, 1H), 8.19 (d, J=1.7 Hz, 1H), 7.65-7.58 (m, 1H), 7.53-7.47 (m, 1H), 6.85-6.80 (m, 2H), 3.70-3.65 (m, 7H), 3.60 (dq, J=3.4, 6.9 Hz, 1H), 2.25 (s, 3H), 2.23 (s, 3H), 1.24 (d, J=7.1 Hz, 3H), 1.10 (d, J=7.1 Hz, 3H). Mass Spectrum (pos.) m/z: 524.3 (M+H)+.

The compounds set forth in the following Table were synthesized following the procedure in Example B using the known starting material as described.

TABLE 12

| Example | Reagents | Structure, Name and Data |
|---|---|---|
| 239.0 240.0 | 2-(5-bromo-4-(2,6-dimethoxyphenyl)-4H-1,2,4-triazol-3-yl)-6-methoxypyridine (Example 2.2), (1S,2R)-1-(5-fluoropyrimidin-2-yl)-1-methoxypropane-2-sulfonamide and (1R,2S)-1-(5-fluoropyrimidin-2-yl)-1-methoxypropane-2-sulfonamide (Example22.0) Preparative SFC method: Column: Chiralpak AS (10 um) (250 x 21 mm, 5 μm), Mobile Phase: 80:20 (A:B), A: Liquid CO₂, B: EtOH. Flow Rate: 70 mL/min, 220 nm, 151 bar inlet pressure. | First eluting peak:<br><br>(1S,2R)-N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide<br>¹H NMR (500 MHz, CDCl₆) δ: 8.61 (s, 2H) 7.54-7.65 (m, 2H) 7.26-7.38 (m, 1H) 6.68 (d, J = 7.0 Hz, 1H) 6.59 (d, J = 8.6 Hz, 2H) 4.96 (d, J = 4.9 Hz, 1H) 3.65-3.80 (m, 7H) 3.33 (s, 3H) 3.16 (s, 3H) 1.39 (d, J = 7.0 Hz, 3H). LCMS-ESI (POS.) m/z: 560.2 (M + H)⁺.<br><br>Second eluting peak:<br><br>(1R,2S)-N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide<br>¹H NMR (500 MHz, CDCl₃) δ: 11.01 (br. s., 1H) 8.61 (s, 2H) 7.53-7.69 (m, 2H) 7.30 (t, J = 8.5 Hz, 1H) 6.69 (d, J = 7.6 Hz, 1H) 6.59 (d, J = 8.4 Hz, 2H) 4.98 (d, J = 4.9 Hz, 1H) 3.63-3.82 (m, 7H) 3.33 (s, 3H) 3.16 (s, 3H) 1.39 (d, J = 7.0 Hz, 3H). LCMS-ESI (POS.) m/z: 560.2 (M + H)⁺. |
| 241.0 242.0 | 3-(5-bromo-4-(2,6-dimethoxyphenyl)-4H-1,2,4-triazol-3-yl)-5-methylpyridine (Example 2.0), (1S,2R)-1-(5-fluoropyrimidin-2-yl)-1-methoxypropane-2-sulfonamide and (1R,2S)-1-(5-fluoropyrimidin-2-yl)-1-methoxypropane-2-sulfonamide (Example 22.0). Preparative SFC method: Column: Chiralpak AS-H (2 x 25 cm), 20% EtOH/CO₂, 100 bar, 60 mL/min, 220 nm, Inj vol.: 0.7 mL, 5 mg/mL, (1:1) EtOH:DCM. | First eluting peak: |

| Example | Reagents | Structure, Name and Data |
|---|---|---|
| | | (1S,2R)-N-(4-(2,6-dimethoxyphenyl)-5-(5-methylpyridin-3-yl)-4H-1,2,4-triazol-3-yl)-1-(5-fluoropyrimidin-2-yl)-1-methoxypropane-2-sulfonamide<br>$^1$H NMR (500 MHz, CDCl$_3$) δ: 8.61 (s, 2H), 8.44 (s, 1H), 8.33 (s, 1H), 7.64 (s, 1H), 7.38 (t, J = 8.6 Hz, 1H), 6.60 (d, J = 8.6 Hz, 2H), 4.99 (d, J = 4.9 Hz, 1H), 3.67-3.85 (m, 7H), 3.33 (s, 3H), 2.30 (s, 3H), 1.39 (d, J = 6.8 Hz, 3H). LCMS-ESI (POS.) m/z: 554.1 (M + H)$^+$. |
| | | Second eluting peak:<br>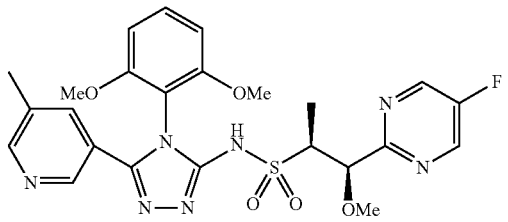<br>(1R,2S)-N-(4-(2,6-dimethoxyphenyl)-5-(5-methylpyridin-3-yl)-4H-1,2,4-triazol-3-yl)-1-(5-fluoropyrimidin-2-yl)-1-methoxypropane-2-sulfonamide<br>$^1$H NMR (500 MHz, CDCl$_3$) δ: 8.61 (s, 2H), 8.44 (br. s., 1H), 8.33 (br. s., 1H), 7.64 (s, 1H), 7.38 (t, J = 8.5 Hz, 1H), 6.60 (d, J = 8.6 Hz, 2H), 4.99 (d, J = 4.9 Hz, 1H), 3.69-3.78 (m, 7H), 3.33 (s, 3H), 2.30 (s, 3H), 1.39 (d, J = 7.0 Hz, 3H). LCMS-ESI (POS.) m/z: 554.1 (M + H)$^+$. |
| 243.0<br>244.0 | 3-(5-bromo-4-(2,6-dimethoxyphenyl)-4H-1,2,4-triazol-3-yl)pyridine (Example 2.1), (1S,2R)-1-(5-fluoropyrimidin-2-yl)-1-methoxypropane-2-sulfonamide and (1R,2S)-1-(5-fluoropyrimidin-2-yl)-1-methoxypropane-2-sulfonamide (Example 22.0). Preparative SFC method: Column: Chiralpak AS-H (2 x 25 cm), 20% EtOH/CO$_2$,100 bar, 60 mL/min, 220 nm, Inj vol.: 0.7 mL, 5 mg/mL, (1:1) EtOH:DCM. | First eluting peak:<br>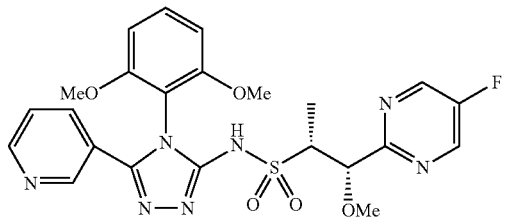<br>(1S,2R)-N-(4-(2,6-dimethoxyphenyl)-5-(pyridin-3-yl)-4H-1,2,4-triazol-3-yl)-1-(5-fluoropyrimidin-2-yl)-1-methoxypropane-2-sulfonamide.<br>$^1$H NMR (500 MHz, CDCl$_3$) δ: 8.51-8.70 (m, 4H), 7.73 (d, J = 8.0 Hz, 1H), 7.38 (t, J = 8.5 Hz, 1H), 7.22-7.27 (m, 1H), 6.60 (d, J = 8.4 Hz, 2H), 4.99 (d, J = 4.9 Hz, 1H), 3.73 (d, J = 11.0 Hz, 6H), 3.69-3.76 (m, 1H), 3.33 (s, 3H), 1.39 (d, J = 6.8 Hz, 3H). LCMS-ESI (POS.) m/z: 530.2 (M + H)$^+$. |
| | | Second eluting peak:<br>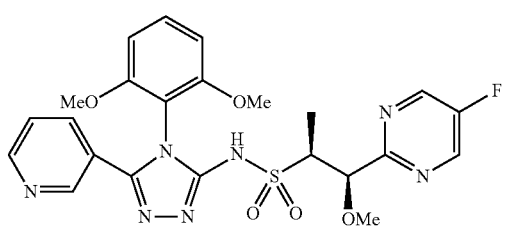<br>(1R,2S)-N-(4-(2,6-dimethoxyphenyl)-5-(pyridin-3-yl)-4H-1,2,4-triazol-3-yl)-1-(5-fluoropyrimidin-2-yl)-1-methoxypropane-2-sulfonamide<br>$^1$H NMR (500 MHz, CDCl$_3$) δ: 8.51-8.70 (m, 4H), 7.73 (d, J = 8.0 Hz, 1H), 7.38 (t, J = 8.5 Hz, 1H), 7.22-7.30 (m, 1H), 6.60 (d, J = 8.4 Hz, 2H), 4.99 (d, J = 4.9 Hz, 1H), 3.73 (d, J = 11.0 Hz, 6H), 3.69-3.76 (m, 1H), 3.33 (s, 3H), 1.39 (d, J = 6.8 Hz, 3H). LCMS-ESI (POS.) m/z: 530.2 (M + H)$^+$. |

TABLE 12-continued

| Example | Reagents | Structure, Name and Data |
|---|---|---|
| 245.0 246.0 | 2-(5-bromo-4-(2,6-dimethoxyphenyl)-4H-1,2,4-triazol-3-yl)-6-methylpyridine (Example 2.3), (1S,2R)-1-(5-fluoropyrimidin-2-yl)-1-methoxypropane-2-sulfonamide and (1R,2S)-1-(5-fluoropyrimidin-2-yl)-1-methoxypropane-2-sulfonamide (Example 22.0). Run on Thar 80 SFC with 250x30 mm AS-H column with 17 mL/min EtOH (neat) + 58 g/min CO₂, 22% co-solvent at 75 g/min. Temp. = 37° C., Outlet pressure = 100 bar, Wavelength = 281 nm. Injected 0.4 mL of 30 mg sample dissolved in 3.0 mL of MeOH:DCM 2:1; c = 10 mg/mL and 4.0 mg per injection. Cycle time 7.5 min, Run time 14 min. | First eluting peak:<br>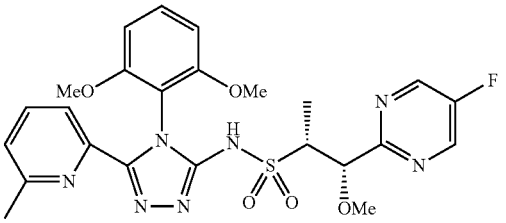<br>(1S,2R)-N-(4-(2,6-dimethoxyphenyl)-5-(6-methylpyridin-2-yl)-4H-1,2,4-triazol-3-yl)-1-(5-fluoropyrimidin-2-yl)-1-methoxypropane-2-sulfonamide<br>¹H NMR (500 MHz, CDCl₃) δ: 11.05 (br, s., 1H), 8.60 (s, 2H), 7.48-7.66 (m, 2H), 7.34 (t, J = 8.5 Hz, 1H), 7.09 (d, J = 7.0 Hz, 1H), 6.58 (d, J = 8.4 Hz, 2H), 4.98 (d, J = 5.1 Hz, 1H), 3.57-3.82 (m, 7H), 3.33 (s, 3H), 2.23 (s, 3H), 1.40 (d, J = 6.8 Hz, 3H). LCMS-ESI (POS.) m/z: 544.1 (M + H)⁺.<br><br>Second eluting peak:<br>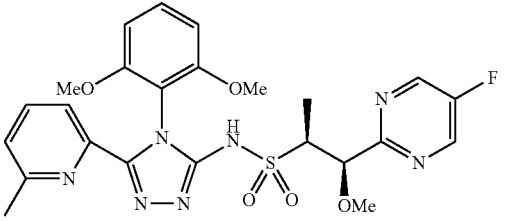<br>(1R,2S)-N-(4-(2,6-dimethoxyphenyl)-5-(6-methylpyridin-2-yl)-4H-1,2,4-triazol-3-yl)-1-(5-fluoropyrimidin-2-yl)-1-methoxypropane-2-sulfonamide<br>¹H NMR (500 MHz, CDCl₃) δ: 11.08 (br. s., 1H), 8.60 (s, 2H), 7.50-7.64 (m, 2H), 7.35 (t, J = 8.4 Hz, 1H), 7.08 (dd, J = 6.4, 2.4 Hz, 1H), 6.58 (d, J = 8.4 Hz, 2H), 4.99 (d, J = 5.1 Hz, 1H), 3.59-3.83 (m, 7H), 3.33 (s, 3H), 2.21 (s, 3H), 1.40 (d, J = 7.0 Hz, 3H). LCMS-ESI (POS.) m/z: 544.1 (M + H)⁺. |
| 247.0 | (1R,2S)-1-(4-cyanophenyl)-1-hydroxy-propane-2-sulfonamide and (1S,2R)-1-(4-cyanophenyl)-1-hydroxypropane-2-sulfonamide (Example 261.0), 3-(5-bromo-4-(2,6-dimethoxyphenyl)-4H-1,2,4-triazol-3-yl)-5-methylpyridine (Example 2.0). | 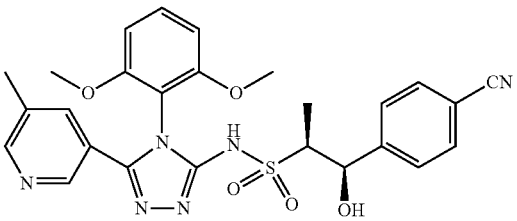 [SMILES: COc1cccc(OC)c1-n1c(NS(=O)(=O)[C@H](C)[C@@H](O)c2ccc(C#N)cc2)nnc1-c1cncc(C)c1]<br>and<br>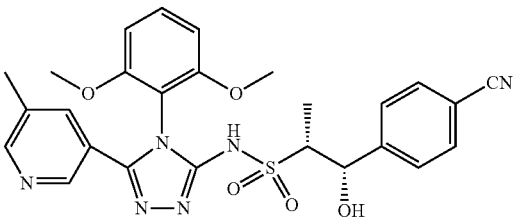 [SMILES: COc1cccc(OC)c1-n1c(NS(=O)(=O)[C@H](C)[C@@H](O)c2ccc(C#N)cc2)nnc1-c1cncc(C)c1]<br>(1R,2S)-1-(4-cyanophenyl)-N-(4-(2,6-dimethoxyphenyl)-5-(5-methyl-3-pyridinyl)-4H-1,2,4-triazol-3-yl)-1-hydroxy-2-propane-sulfonamide and (1S,2R)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide LCMS-ESI (POS.) m/z: 535.1 (M + H)⁺. |

TABLE 12-continued

| Example | Reagents | Structure, Name and Data |
|---|---|---|
| 248.0 | The racemic 247.0 was separated by supercritical fluid chromatography (2 × 15 cm IA column with 60 mL/min 20% MeOH(0.1% NH$_4$OH)/CO$_2$. Outlet pressure = 100 bar; wavelength = 220 nm; injection volume = 0.5 mL, 11 mg/mL 1:1 DCM:MeOH). This was the first isomer to elute under these conditions. | <br>(1R,2S)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide<br>$^1$H NMR (400 MHz, CDCl$_3$) δ 8.48 (br. s., 1H), 8.37 (br. s., 1H), 7.58-7.71 (m, 3H), 7.39-7.50 (m, 3H), 6.50-6.77 (m, 2H), 5.46-5.68 (m, 1H), 3.86 (s, 3H), 3.71 (s, 3H), 3.09-3.22 (m, 1H), 2.31 (s, 3H), 1.15 (d, J = 6.06 Hz, 3H). LCMS-ESI (POS.) m/z: 535.1 (M + H)$^+$. |
| 249.0 | The racemic 247.0 was separated by supercritical fluid chromatography (2 × 15 cm IA column with 60 mL/min 20% MeOH(0.1% NH$_4$OH)/CO$_2$. Outlet pressure = 100 bar; wavelength = 220 nm; injection volume = 0.5 mL, 11 mg/mL 1:1 DCM:MeOH). This was the second isomer to elute under these conditions. | <br>(1R,2S)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide<br>$^1$H NMR (400 MHz, CDCl$_3$) δ 8.48 (br. s., 1H), 8.36 (br. s., 1H), 7.58-7.69 (m, 3H), 7.39-7.50 (m, 3H), 6.70 (d, J = 8.41 Hz, 1H), 6.62 (d, J = 8.41 Hz, 1H), 5.55 (s, 1H), 3.87 (s, 3H), 3.72 (s, 3H), 3.11-3.22 (m, 1H), 2.31 (s, 3H), 1.15 (d, J = 6.46 Hz, 3H). LCMS-ESI (POS.) m/z: 535.1 (M + H)$^+$. |

TABLE 12-continued

| Example | Reagents | Structure, Name and Data |
|---|---|---|
| 250.0 | 3-(5-bromo-4-(2,6-dimethoxyphenyl)-4H-1,2,4-triazol-3-yl)-5-methylpyridine (Example 2.0), (1R,2S)-1-methoxy-1-(pyrimidin-2-yl)propane-2-sulfonamide (Example 14.4) | 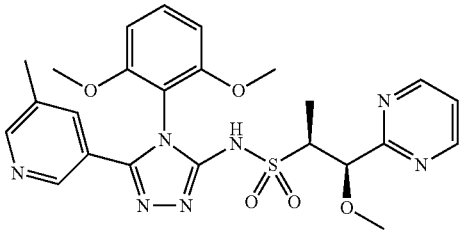 [SMILES: COc1cccc(OC)c1-n1c(NS(=O)(=O)[C@@H](C)[C@H](OC)c2ncccn2)nnc1-c1cncc(C)c1]<br>(1R,2S)-N-(4-(2,6-dimethoxyphenyl)-5-(5-methylpyridin-3-yl)-4H-1,2,4-triazol-3-yl)-1-methoxy-1-(pyrimidin-2-yl)propane-2-sulfonamide<br>$^1$H NMR (CDCl$_3$) δ: 11.22 (br. s., 1H), 8.77 (d, J = 4.8 Hz, 2H), 8.44 (d, J = 1.2 Hz, 1H), 8.34 (d, J = 1.6 Hz, 1H), 7.64 (s, 1H), 7.38 (t, J = 8.5 Hz, 1H), 7.22 (t, J = 4.8 Hz, 1H), 6.60 (d, J = 8.6 Hz, 2H), 5.02 (d, J = 4.4 Hz, 1H), 3.76-3.82 (m, 1H), 3.75 (s, 3H), 3.72 (s, 3H), 3.37 (s, 3H), 2.30 (s, 3H), 1.38 (d, J = 7.0 Hz, 3H). LCMS-ESI (POS.) m/z: 526.0 (M + H)$^+$. |
| 251.0<br>252.0 | 3-(5-bromo-4-(2,6-dimethoxyphenyl)-4H-1,2,4-triazol-3-yl)-5-methylpyridine (Example 2.0), (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamide (Example 15.0), Preparative SFC method: Column: Chiralpak AD-H (250 x 21 mm, 5 μm), Mobile Phase: 81:19 (A:B), A: Liquid CO$_2$, B: MeOH, Flow Rate: 70 mL/min, 220 nm, 179 bar inlet pressure. | First eluting peak:<br>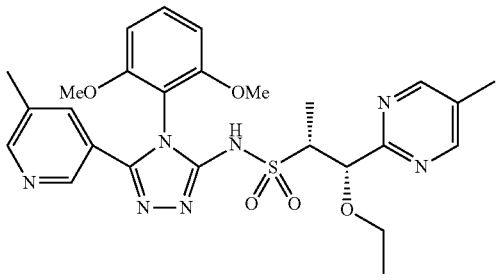<br>(1S,2R)-N-(4-(2,6-dimethoxyphenyl)-5-(5-methylpyridin-3-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 11.36 (br. s., 1H), 8.60 (s, 2H), 8.45 (s, 1H), 8.34 (s, 1H), 7.68 (s, 1H), 7.39 (t, J = 8.5 Hz, 1H), 6.61 (dd, J = 8.3, 6.0 Hz, 2H), 4.96-5.06 (m, 1H), 3.78-3.84 (m, 1H), 3.76 (s, 3H), 3.72 (s, 3H), 3.43-3.58 (m, 2H), 2.32 (s, 6H), 2.21-2.38 (m, 6H), 1.45 (d, J = 7.0 Hz, 3H), 1.15 (t, J = 7.0 Hz, 3H). LCMS-ESI (POS.) m/z: 554.0 (M + H)$^+$.<br><br>Second eluting peak:<br>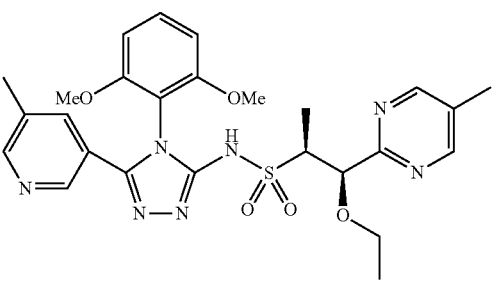 |

| Example | Reagents | Structure, Name and Data |
|---|---|---|
| | | (1R,2S)-N-(4-(2,6-dimethoxyphenyl)-5-(5-methylpyridin-3-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 11.36 (br. s., 1H), 8.60 (s, 2H), 8.45 (s, 1H), 8.34 (s, 1H), 7.68 (s, 2H), 7.39 (t, J = 8.5 Hz, 1H), 6.61 (dd, J = 8.4, 5.5 Hz, 2H), 4.97-5.03 (m, 1H), 3.78-3.84 (m, 1H), 3.76 (s, 3H), 3.72 (s, 3H), 3.44-3.60 (m, 2H), 2.32 (s, 6H), 1.45 (d, J = 7.0 Hz, 3H), 1.15 (t, J = 7.0 Hz, 3H). LCMS-ESI (POS.) m/z: 554.0 (M + H)$^+$. |
| 253.0<br>254.0 | 3-(5-bromo-4-(2,6-dimethoxyphenyl)-4H-1,2,4-triazol-3-yl)-5-methylpyridine (Example 2.0), (1S,2S)-1-ethoxy-1-(5-methylpyrimidin-2-yl)propane-2-sulfonamide and (1R,2R)-1-ethoxy-1-(5-methylpyrimidin-2-yl)propane-2-sulfonamide (Example 15.1), Preparative SFC method: Column: ChiralPak AD-H (Reversed) (250 x 21 mm, 5 μm), Mobile Phase: 80:20 (A:B), A: Liquid CO2, B: EtOH, Flow Rate: 70 mL/min, Column/Oven temp.: 40 C., 220 nm, 186 bar inlet pressure. | First eluting peak:<br>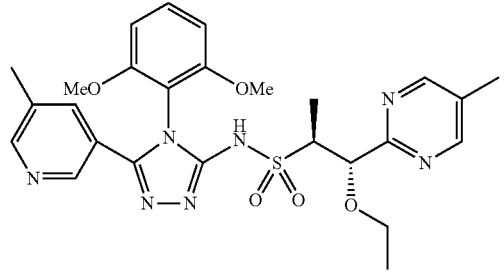<br>(1S,2S)-N-(4-(2,6-dimethoxyphenyl)-5-(5-methylpyridin-3-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.65 (s, 2H), 8.45 (d, J = 1.4 Hz, 1H), 8.36 (d, J = 1.8 Hz, 1H), 7.70 (br. s., 1H), 7.38 (t, J = 8.5 Hz, 1H), 6.55-6.67 (m, 2H), 4.80 (d, J = 4.9 Hz, 1H), 3.82 (s, 3H), 3.77 (dd, J = 6.9, 5.0 Hz, 1H), 3.70 (s, 3H), 3.51-3.59 (m, 1H), 3.34-3.43 (m, 1H), 2.34 (d, J = 10.8 Hz, 6H), 1.42 (d, J = 7.2 Hz, 3H), 1.08 (t, J = 6.9 Hz, 3H). LCMS-ESI (POS.) m/z: 554.2 (M + H)$^+$.<br><br>Second eluting peak:<br>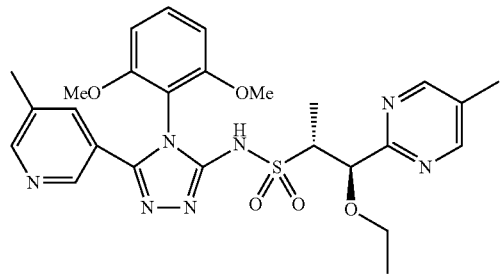<br>(1R,2R)-N-(4-(2,6-dimethoxyphenyl)-5-(5-methylpyridin-3-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ: 8.65 (s, 2H), 8.45 (d, J = 1.6 Hz, 1H), 8.36 (d, J = 1.8 Hz, 1H), 7.69 (br. s., 1H), 7.38 (t, J = 8.4 Hz, 1H), 6.56-6.67 (m, 2H), 4.80 (d, J = 4.9 Hz, 1H), 3.82 (s, 3H), 3.77 (dd, J = 7.1, 5.0 Hz, 1H), 3.70 (s, 3H), 3.52-3.59 (m, 1H), 3.34-3.43 (m, 1H), 2.34 (d, J = 11.0 Hz, 6H), 1.42 (d, J = 7.2 Hz, 3H), 1.08 (t, J = 7.0 Hz, 3H). LCMS-ESI (POS.) m/z: 554.2 (M + H)$^+$. |

Example C

Example 255.0: Preparation of (1S,2R)-(4-bromo-2-fluorophenyl)-1-hydroxypropane-2-sulfonamide and (1S,2S)-(4-bromo-2-fluorophenyl)-1-hydroxypropane-2-sulfonamide and (1R,2R)-(4-bromo-2-fluorophenyl)-1-hydroxypropane-2-sulfonamide and (1R,2S)-(4-bromo-2-fluorophenyl)-1-hydroxypropane-2-sulfonamide

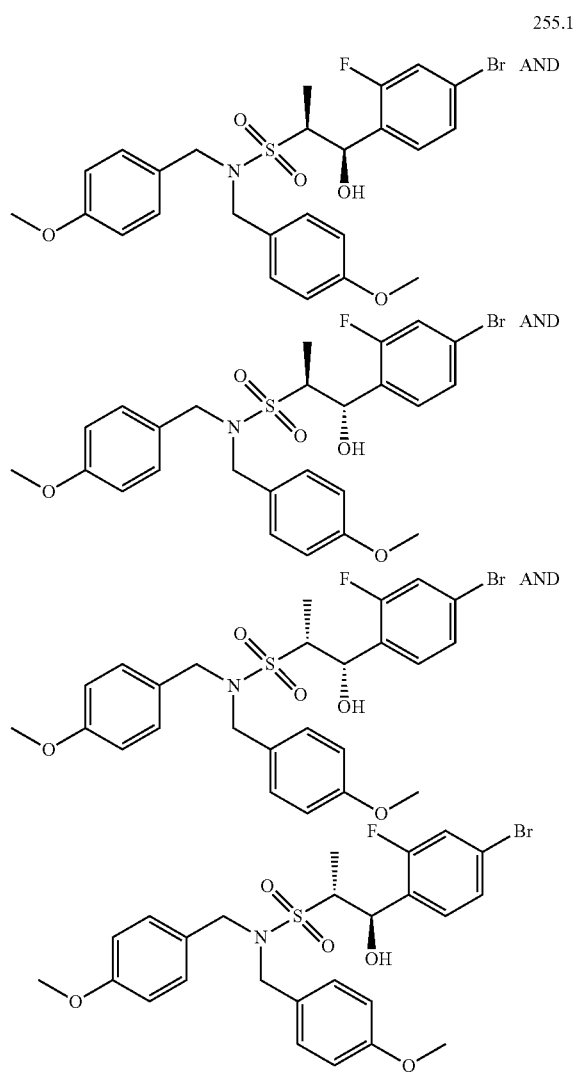

(1S,2R)-(4-bromo-2-fluorophenyl)-1-hydroxy-N,N-bis(4-methoxybenzyl)propane-2-sulfonamide and (1R,2R)-(4-bromo-2-fluorophenyl)-1-hydroxy-N,N-bis(4-methoxybenzyl)propane-2-sulfonamide and (1S,2S)-(4-bromo-2-fluorophenyl)-1-hydroxy-N,N-bis(4-methoxybenzyl)propane-2-sulfonamide and (1R,2S)-(4-bromo-2-fluorophenyl)-1-hydroxy-N,N-bis(4-methoxybenzyl)propane-2-sulfonamide, Example 255.1

A flask was charged with N,N-bis(4-methoxybenzyl)ethanesulfonamide 12.0 (600 mg, 1.72 mmol, Jubilant), azeotroped with toluene, added THF (7 mL) and cooled to −78° C. n-Butyl lithium (0.72 mL, 1.80 mmol) was added slowly and the mixture was stirred for 10 min. 4-Bromo-2-fluorobenzaldehyde (383 mg, 1.89 mmol) in THF (2 mL) was then added dropwise. The reaction was further stirred at −78° C. for 45 min and then the temperature of the reaction was raised to RT and stirred for another 3 h. The reaction was quenched with saturated NH$_4$C$_1$ and extracted with EtOAc. The EtOAc layer was dried, concentrated and purified by silica gel chromatography, eluting with a gradient of 0-40% EtOAc in hexanes to provide 1-(4-bromo-2-fluorophenyl)-1-hydroxy-N,N-bis(4-methoxybenzyl)propane-2-sulfonamide 255.1 (811 mg, 85%) as a racemic mixture of four isomers. LCMS-ESI (POS.) m/z: 573.9 (M+H)$^+$.

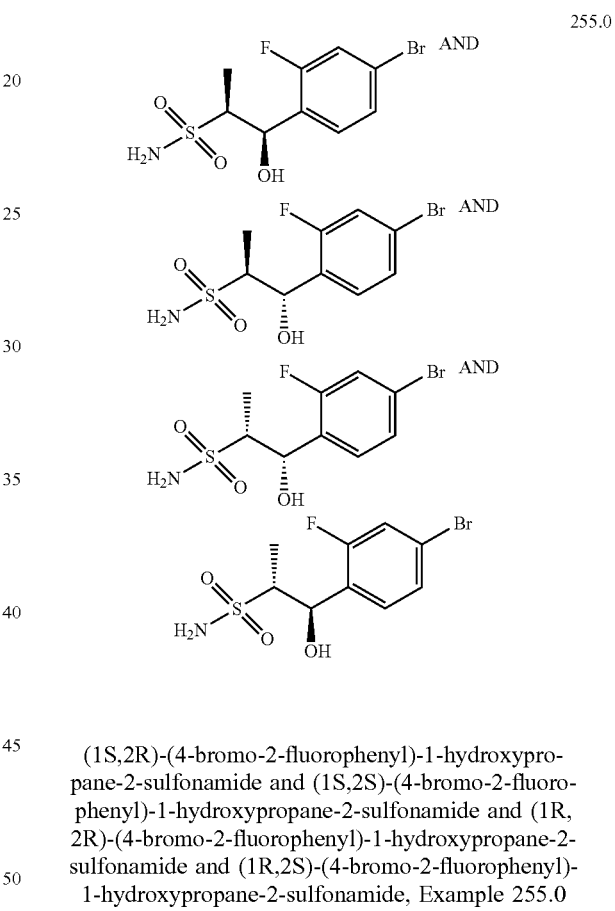

(1S,2R)-(4-bromo-2-fluorophenyl)-1-hydroxypropane-2-sulfonamide and (1S,2S)-(4-bromo-2-fluorophenyl)-1-hydroxypropane-2-sulfonamide and (1R,2R)-(4-bromo-2-fluorophenyl)-1-hydroxypropane-2-sulfonamide and (1R,2S)-(4-bromo-2-fluorophenyl)-1-hydroxypropane-2-sulfonamide, Example 255.0

To a flask charged with 1-(4-bromo-2-fluorophenyl)-1-hydroxy-N,N-bis(4-methoxybenzyl)propane-2-sulfonamide 255.1 (603 mg, 1.09 mmol) was added TFA (10.9 mL) followed by anisole (0.477 mL, 4.37 mmol). The resulting solution was stirred overnight and was then concentrated in vacuo and azeotroped with toluene to remove residual TFA. The material thus obtained was purified by silica gel chromatography, eluting with a gradient of 0-8% MeOH in DCM to provide 1-(4-bromo-2-fluorophenyl)-1-hydroxypropane-2-sulfonamide 255.0 (308 mg, 90%) as a white solid. LCMS-ESI (POS.) m/z: 336.0 (M+H)$^+$.

The compounds set forth in the following Table were synthesized following the procedure in Example C using the known starting material as described.

TABLE 13

| Example | Reagents | Structure, Name and Data |
|---|---|---|
| 256.0 | imidazo[1,2-a]pyridine-2-carbaldehyde and Example 5.0 | 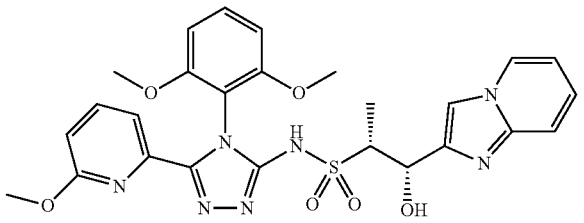<br><br>AND<br><br>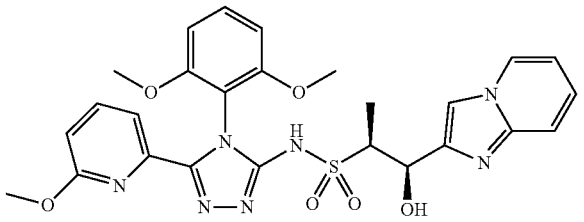 [SMILES: COc1cccc(-c2nnc(NS(=O)(=O)[C@@H](C)[C@H](O)c3cn4ccccc4n3)n2-c2c(OC)cccc2OC)n1]<br><br>(1S,2R)-N-(4-(2,6-dimethoxyphenyl)-5-(6-methoxypyridin-2-yl)-4H-1,2,4-triazol-3-yl)-1-hydroxy-1-(imidazo[1,2-a]pyridin-2-yl)propane-2-sulfonamide and (1R,2S)-N-(4-(2,6-dimethoxyphenyl)-5-(6-methoxypyridin-2-yl)-4H-1,2,4-triazol-3-yl)-1-hydroxy-1-(imidazo[1,2-a]pyridin-2-yl)propane-2-sulfonamide<br>$^1$H NMR (500 MHz, DMSO-$d_6$) δ 13.42 (br. s, 1H), 8.50 (d, J = 6.8 Hz, 1H), 7.75-7.84 (m, 2H), 7.59 (d, J = 7.3 Hz, 1H), 7.47 (d, J = 8.8 Hz, 1H), 7.41 (t, J = 8.4 Hz, 1H), 7.19 (ddd, J = 8.9, 6.8, 1.1 Hz, 1H), 6.81-6.87 (m, 2H), 6.78 (dd, J = 8.6, 2.9 Hz, 2H), 5.43 (s, 1H), 4.80 (br. s, 1H), 3.66 (s, 3H), 3.58-3.64 (m, 3H), 3.50 (qd, J = 7.0, 1.1 Hz, 1H), 3.10 (s, 3H), 1.03 (d, J = 7.1 Hz, 3 H). LCMS-ESI (POS.) m/z: 566.2 (M + H)$^+$. |
| 257.0 | imidazo[1,2-a]pyridine-2-carbaldehyde, Example 4.0 | 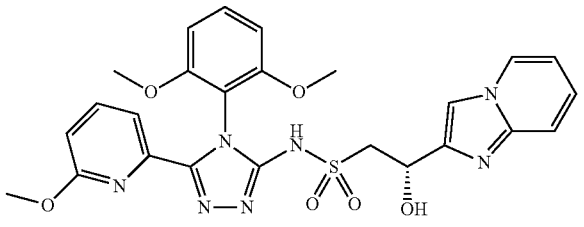<br><br>AND<br><br>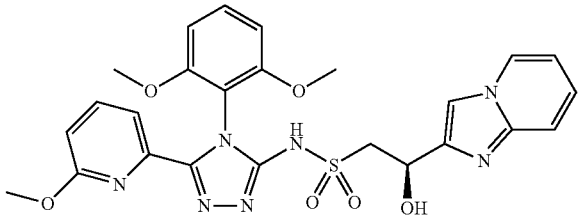 [SMILES: COc1cccc(-c2nnc(NS(=O)(=O)C[C@H](O)c3cn4ccccc4n3)n2-c2c(OC)cccc2OC)n1]<br><br>(S)-N-(4-(2,6-dimethoxyphenyl)-5-(6-methoxypyridin-2-yl)-4H-1,2,4-triazol-3-yl)-2-hydroxy-2-(imidazo[1,2-a]pyridin-2-yl)ethanesulfonamide and (R)-N-(4-(2,6-dimethoxyphenyl)-5-(6-methoxypyridin-2-yl)-4H-1,2,4-triazol-3-yl)-2-hydroxy-2-(imidazo[1,2-a]pyridin-2-yl)ethanesulfonamide<br>$^1$H NMR (500 MHz, CD$_3$OD) δ 8.33-8.40 (m, 1H), 7.77 (s, 1H), 7.67-7.73 (m, 1H), 7.56-7.64 (m, 1H), 7.45-7.51 (m, 1H), 7.40 (t, J = 8.6 Hz, 1H), 7.29 (ddd, J = 9.0, 6.8, 1.2 Hz, 1H), 6.89 (td, J = 6.8, 1.1 Hz, 1H), 6.70-6.79 (m, 3H), 5.33-5.39 (m, 1H), 3.71 (s, 3H), 3.72 (s, 3H), 3.64-3.69 (m, 1H), 3.46 (dd, J = 14.2, 9.3 Hz, 1H), 3.16 (s, 3 H). LCMS-ESI (POS.) m/z: 552.0 (M + H)$^+$. |

TABLE 13-continued

| Example | Reagents | Structure, Name and Data |
|---|---|---|
| 258.0 | 1-methyl-1H-imidazole-4-carbaldehyde, Example 5.0 | 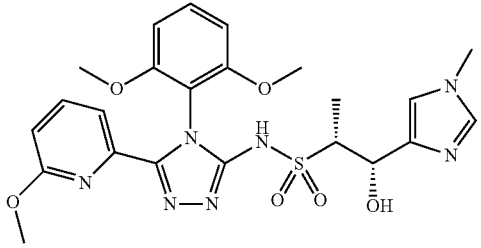<br>AND<br>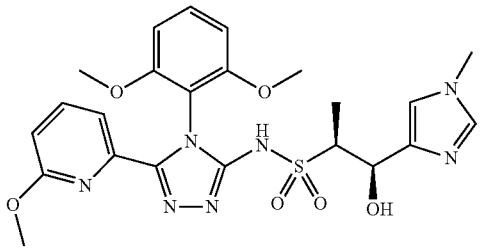 [SMILES: COc1cccc(-c2nnc(NS(=O)(=O)[C@@H](C)[C@H](O)c3cn(C)cn3)n2-c2c(OC)cccc2OC)n1]<br>(1S,2R)-N-(4-(2,6-dimethoxyphenyl)-5-(6-methoxypyridin-2-yl)-4H-1,2,4-triazol-3-yl)-1-hydroxy-1-(1-methyl-1H-imidazol-4-yl)propane-2-sulfonamide and (1R,2S)-N-(4-(2,6-dimethoxyphenyl)-5-(6-methoxypyridin-2-yl)-4H-1,2,4-triazol-3-yl)-1-hydroxy-1-(1-methyl-1H-imidazol-4-yl)propane-2-sulfonamide<br>$^1$H NMR (500 MHz, DMSO-$d_6$) δ 13.38 (br. s,1H), 7.80 (dd, J = 8.3, 7.3 Hz, 1H), 7.58 (dd, J = 7.5, 0.6 Hz, 1H), 7.47 (s, 1H), 7.40 (t, J = 8.6 Hz, 1H), 6.90 (s, 1H), 6.80-6.85 (m, 1H), 6.78 (dd, J = 8.6, 0.7 Hz, 2H), 5.17 (s, 1H), 4.38 (br. s, 1H), 3.65 (s, 3H), 3.63 (s, 3H), 3.60 (s, 3H), 3.30 (qd, J = 7.0, 1.2 Hz, 1H), 3.10 (s, 3H), 1.03 (d, J = 7.1 Hz, 3 H). LCMS-ESI (POS.) m/z: 530.2 (M + H)$^+$. |
| 259.0 | 1-methyl-1H-imidazole-4-carbaldehyde, Example 5.0 | 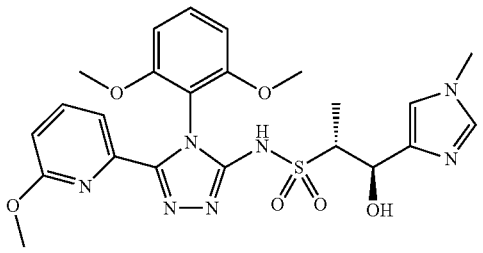<br>AND<br>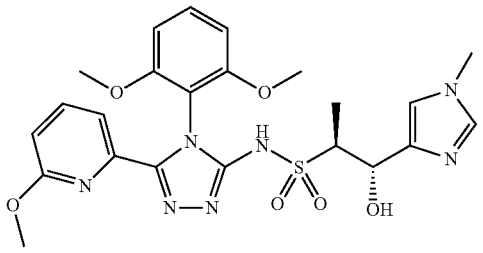 [SMILES: COc1cccc(-c2nnc(NS(=O)(=O)[C@@H](C)[C@@H](O)c3cn(C)cn3)n2-c2c(OC)cccc2OC)n1]<br>(1R,2R)-N-(4-(2,6-dimethoxyphenyl)-5-(6-methoxypyridin-2-yl)-4H-1,2,4-triazol-3-yl)-1-hydroxy-1-(1-methyl-1H-imidazol-4-yl)propane-2-sulfonamide and (1S,2S)-N-(4-(2,6-dimethoxyphenyl)-5-(6-methoxypyridin-2-yl)-4H-1,2,4-triazol-3-yl)-1-hydroxy-1-(1-methyl-1H-imidazol-4-yl)propane-2-sulfonamide<br>$^1$H NMR (500 MHz, DMSO-$d_6$) δ 7.74-7.84 (m, 1H), 7.59 (dd, J = 7.5, 0.6 Hz, 1H), 7.52 (s, 1H), 7.40 (t, J = 8.6 Hz, 1H), 6.99 (d, J = 1.2 Hz, 1H), 6.74-6.88 (m, 3H), 4.83 (br. s, 1H), 4.63 (d, J = 7.8 Hz, 1H), 3.67 (s, 3H), 3.68 (s, 3H), 3.61 (s, 3H), 3.21-3.29 (m, 1H), 3.10 (s, 3H), 0.95 (d, J = 7.1 Hz, 3 H). LCMS-ESI (POS.) m/z: 530.2 (M + H)$^+$. |

TABLE 13-continued

| Example | Reagents | Structure, Name and Data |
|---|---|---|
| 260.0 | 1,5-dimethyl-1H-pyrazole-3-carbaldehyde, Example 5.0 | 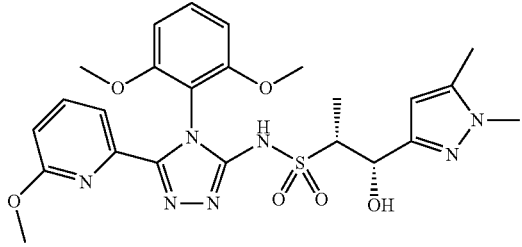  AND  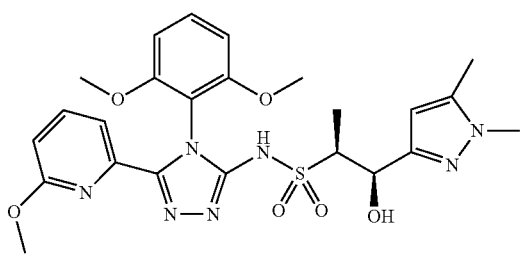 [SMILES: COc1cccc(-c2nnc(NS(=O)(=O)[C@@H](C)[C@H](O)c3cc(C)n(C)n3)n2-c2c(OC)cccc2OC)n1]  (1S,2R)-N-(4-(2,6-dimethoxyphenyl)-5-(6-methoxypyridin-2-yl)-4H-1,2,4-triazol-3-yl)-1-(1,5-dimethyl-1H-pyrazol-3-yl)-1-hydroxypropane-2-sulfonamide and (1R,2S)-N-(4-(2,6-dimethoxyphenyl)-5-(6-methoxypyridin-2-yl)-4H-1,2,4-triazol-3-yl)-1-(1,5-dimethyl-1H-pyrazol-3-yl)-1-hydroxypropane-2-sulfonamide  $^1$H NMR (500 MHz, DMSO-$d_6$) δ 13.35 (s, 1H), 7.76-7.85 (m, 1H), 7.58 (d, J = 7.3 Hz, 1H), 7.40 (t, J = 8.4 Hz, 1H), 6.75-6.86 (m, 3H), 5.94 (s, 1H), 5.14-5.22 (m, 1H), 4.44 (d, J = 3.7 Hz, 1H), 3.66 (s, 3H), 3.63 (s, 6H), 3.15-3.22 (m, 1H), 3.10 (s, 3H), 2.19 (s, 3H), 1.11 (d, J = 7.1 Hz, 3 H). LCMS-ESI (POS.) m/z: 544.1 (M + H)$^+$. |
| 261.0 | Example 12.0, 4-formylbenzonitrile. The syn and anti diastereomers were separated by purification on a Isco CombiFlash on a Redi 220 g silica gel column using 0-100% EtOAc/hexanes as the eluent after the aldol reaction. | 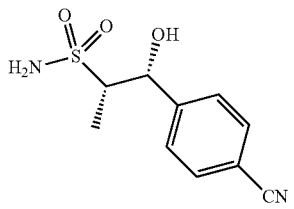  AND  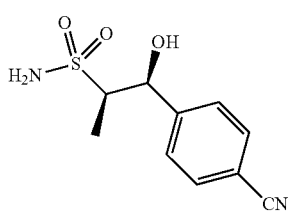 [SMILES: C[C@H]([C@@H](O)c1ccc(C#N)cc1)S(N)(=O)=O]  (1R,2S)-1-(4-cyanophenyl)-1-hydroxypropane-2-sulfonamide compound and (1S,2R)-1-(4-cyanophenyl)-1-hydroxypropane-2-sulfonamide  $^1$H NMR (400 MHz, CDCl$_3$) δ 7.73 (d, J = 8.41 Hz, 2H), 7.55 (d, J = 8.22 Hz, 2H), 4.71-4.79 (m, 2H), 3.29-3.36 (m, 1H), 1.31 (d, J = 7.04 Hz, 3 H). LCMS-ESI (POS.) m/z: 263.0 (M + Na)$^+$. |
| 262.0 | Example 12.0, 6-chloropicolinaldehyde | 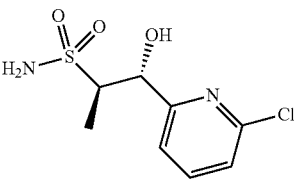  AND |

TABLE 13-continued

| Example | Reagents | Structure, Name and Data |
|---------|----------|--------------------------|
| | | 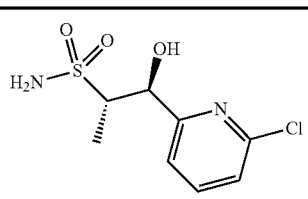<br>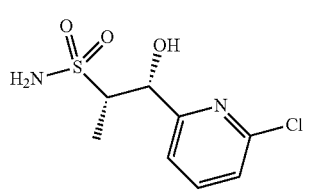<br>AND<br>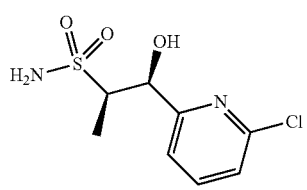<br>(1R,2S)-1-(6-chloropyridin-2-yl)-1-hydroxypropane-2-sulfonamide and (1S,2R)-1-(6-chloropyridin-2-yl)-1-hydroxypropane-2-sulfonamide and (1R,2R)-1-(6-chloropyridin-2-yl)-1-hydroxypropane-2-sulfonamide and (1S,2S)-1-(6-chloropyridin-2-yl)-1-hydroxypropane-2-sulfonamide<br>LCMS-ESI (POS.) m/z: 251.0 (M + H)$^+$. |

Example 263.0: Preparation of (2S,3R)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide

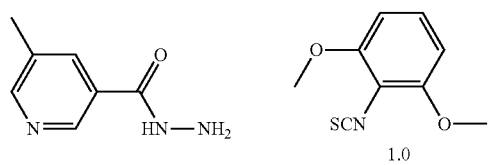

1.0

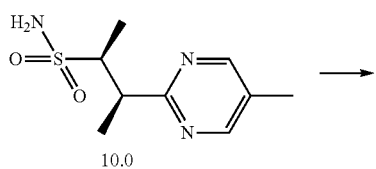

10.0

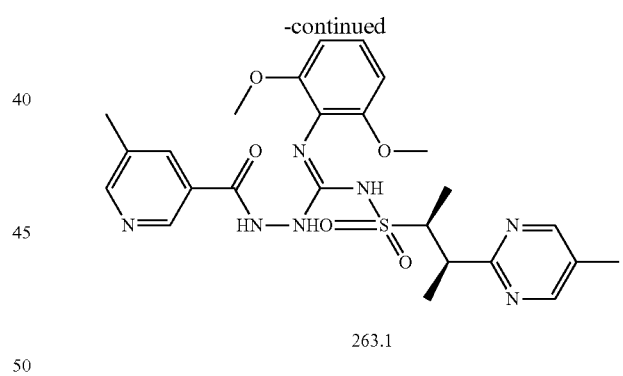

263.1

(Z)—V-(2,6-dimethoxyphenyl)-2-(5-methylnicotinoyl)-N-(((2S,3R)-3-(5-methylpyrimidin-2-yl)butan-2-yl)sulfonyl)hydrazinecarboximidamide, Example 263.1

To a flask containing Example 10.0 (1.10 g, 4.82 mmol) was added ACN (23 mL). After 3 min, Example 1.0 (981 mg, 5.03 mmol) was added carefully in portions. The mixture was cooled in an ice-bath to 10° C., and then cesium carbonate (2.07 g, 6.34 mmol) was added carefully in portions. Upon complete addition of cesium carbonate, the mixture was allowed to warm to 23° C. and monitored with LC-MS. After 22 h, the mixture was cooled in an ice-water bath. After 20 min, 5-methylnicotinohydrazide (773 mg, 4.86 mmol) (commercially available from Hellen Chemistry Co.) and then silver nitrate (1.65 g, 9.73 mmol) were carefully added in portions. The mixture was allowed to warm to 23° C. and monitored with LC-MS. After 30 additional min, the mixture was concentrated under reduced pressure. The black residue was diluted with chloroform and then loaded onto a silica gel column (0-85% 3:1 EtOAc: EtOH in heptanes). Fractions containing desired product were combined and then concentrated under reduced pressure to afford a light yellow film that solidified into an-off white sticky foam (Z)—N'-(2,6-dimethoxyphenyl)-2-(5-methylnicotinoyl)-N-(((2S,3R)-3-(5-methylpyrimidin-2-yl)butan-2-yl)sulfonyl)hydrazinecarboximidamide 263.1 (2.58 g, 4.76 mmol, 99% yield) that was used without further purification. Mass Spectrum (pos.) m/z: 542.2 (M+H)$^+$.

(d, J=1.7 Hz, 1H), 8.19 (d, J=2.0 Hz, 1H), 7.64-7.60 (m, 1H), 7.50 (t, J=8.6 Hz, 1H), 6.82 (dd, J=3.8, 8.4 Hz, 2H), 3.69-3.64 (m, 7H), 3.64-3.60 (m, 1H), 2.25 (s, 3H), 2.23 (s, 3H), 1.24 (d, J=7.1 Hz, 3H), 1.10 (d, J=7.1 Hz, 3H). MS (pos.) m/z: 524.2 (M+H)$^+$.

Example 264.0: Preparation of (R)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide and (S)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide

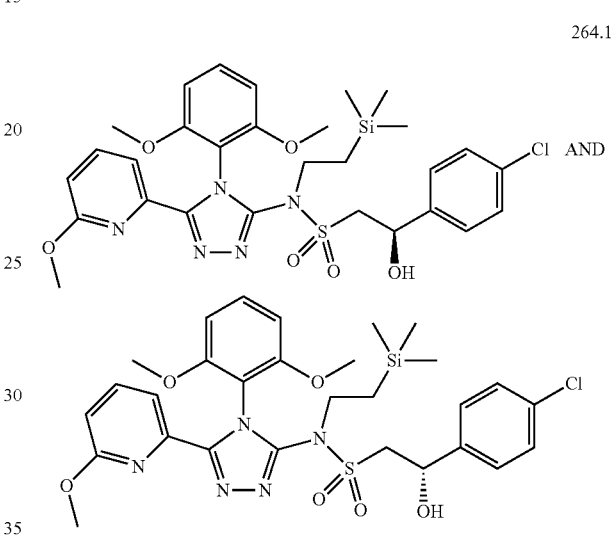

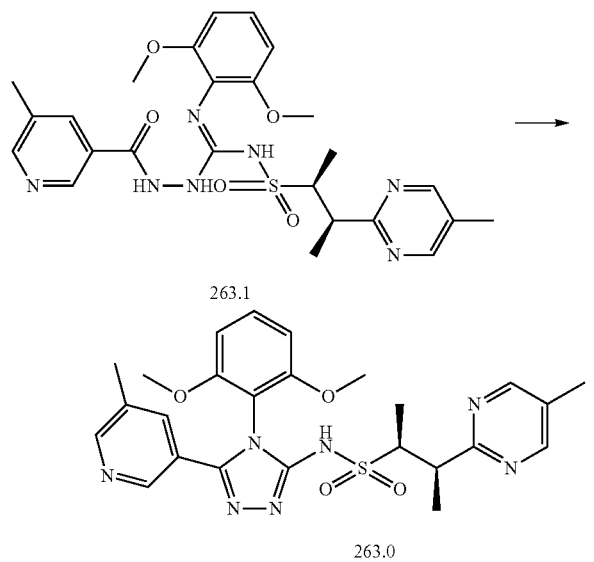

(2S,3R)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide, Example 263.0

(R)-2-(4-chlorophenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide and (S)-2-(4-chlorophenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide, Example 264.1

To a flask containing (Z)—N'-(2,6-dimethoxyphenyl)-2-(5-methylnicotinoyl)-N-(((2S,3R)-3-(5-methylpyrimidin-2-yl)butan-2-yl)sulfonyl)hydrazinecarboximidamide 263.1 (2.58 g, 4.76 mmol) in 1,4-dioxane (19 mL) was added methanesulfonic acid (0.93 mL, 14.3 mmol) dropwise. Upon complete addition of methanesulfonic acid, the mixture was heated on a preheated stir plate at 100° C. and monitored with LC-MS. After 7.5 h, the reaction was cooled to RT and then diluted with 15 mL of water. The pH was carefully adjusted with dropwise addition of saturated aqueous sodium bicarbonate solution to give a pH-7. The mixture was then extracted three times with DCM. The organic layers were combined and then concentrated under reduced pressure. The material thus obtained was absorbed onto a plug of silica gel and purified by chromatography through a Redi-Sep pre-packed silica gel column (80 g), eluting with a gradient of 0-75% (3:1 EtOAc: EtOH) in heptanes. Fractions containing desired product were combined then concentrated to afford a white solid as (2S,3R)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide 263.0 (1.63 g, 3.13 mmol, 66% yield). $^1$H NMR (500 MHz, DMSO-d$_6$) δ=13.36 (s, 1H), 8.59 (s, 2H), 8.47

N-(4-(2,6-dimethoxyphenyl)-5-(6-methoxypyridin-2-yl)-4H-1,2,4-triazol-3-yl)-N-(2-(trimethylsilyl)ethyl)methanesulfonamide (Example 4.0, 210 mg, 0.415 mmol) was azeotroped with toluene and then dissolved in THF (2 mL). The solution was then cooled to −78° C. To this was added dropwise butyllithium solution (2.5 M in hexanes (0.183 mL, 0.46 mmol, commercially available from Sigma-Aldrich Corp., St. Louis, Mo., USA) and stirred for 10 min at −78° C. A solution of 4-chlorobenzaldehyde (0.059 mL, 0.50 mmol, commercially available from Sigma-Aldrich Corp., St. Louis, Mo., USA) in THF (1 mL) was added dropwise and stirring was continued at −78° C. for 45 minute. The mixture was then allowed to warm to RT for 1 h. The reaction was quenched with saturated NH$_4$Cl (5 mL), diluted with water (10 mL) and DCM (10 mL). The two layers were separated. The aqueous layer was extracted with DCM (2×10 mL). The combined organic layers were dried over Na$_2$SO$_4$, filtered and concentrated in vacuo. The material thus obtained was absorbed onto a plug of silica gel and purified by chromatography through a Redi-Sep pre-packed silica gel column (12 g), eluting with a gradient of 0-50% EtOAc in hexanes, to provide the title compound 264.1 (247 mg, 0.38 mmol, 92% yield) as white solid. ¹H NMR (400 MHz, CD₂Cl₂) δ 7.63-7.67 (m, 1H) 7.59-7.62 (m, 1H) 7.40 (t, J=8.51 Hz, 1H) 7.26-7.31 (m, 2H) 7.09-7.14 (m, 2H) 6.71 (dd, J=8.02, 0.98 Hz, 1H) 6.68 (dd, J=8.61, 0.78 Hz, 1H) 6.64 (dd, J=8.61, 0.78 Hz, 1H) 4.88 (dd, J=9.59, 1.17 Hz, 1H) 4.43-4.57 (m, 3H) 3.72 (s, 3H) 3.68 (s, 3H) 3.16 (s, 3H) 2.86-2.99 (m, 2H) 1.34-1.44 (m, 2H) 0.11-0.14 (m, 9H). LCMS-ESI (POS.) m/z: 646.3 (M+H)⁺.

264.0

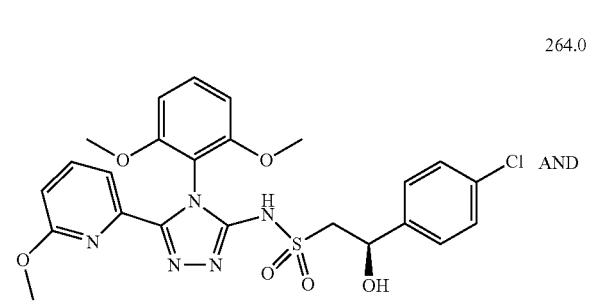

AND

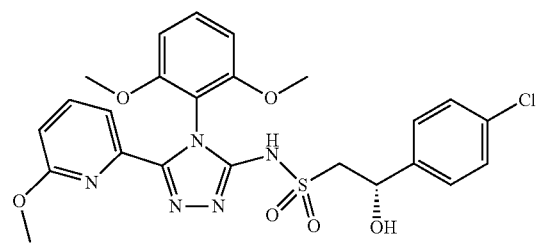

(R)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide and (S)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide, Example 264.0

A mixture of 264.1 (243 mg, 0.376 mmol) and tris(dimethylamino)sulfonium difluorotrimethylsilicate (311 mg, 1.13 mmol) (commercially available from Sigma-Aldrich Corp., St. Louis, Mo., USA) in DMF (2 mL) was heated at 60° C. for 16 h. The reaction was diluted with EtOAc (20 mL) and 0.1N HCl (aqueous) (20 mL). The organic layer was washed with more 0.1 N HCl (aqueous) (3×20 mL), dried over Na₂SO₄, filtered and concentrated in vacuo. The material thus obtained was absorbed onto a plug of silica gel and purified by chromatography through a Redi-Sep pre-packed silica gel column (12 g), eluting with a gradient of 0-100% (3:1 EtOAc: EtOH) in hexanes, to provide the title compound 264.0 (186 mg, 0.341 mmol, 91% yield) as white solid. ¹H NMR (400 MHz, DMSO-d₆) δ 13.43 (br. s., 1H) 7.81 (dd, J=8.22, 7.43 Hz, 1H) 7.58 (d, J=7.24 Hz, 1H) 7.42 (t, J=8.51 Hz, 1H) 7.33-7.38 (m, 2H) 7.26-7.31 (m, 2H) 6.79-6.85 (m, 3H) 5.38 (br. s., 1H) 4.93 (dd, J=6.85, 4.11 Hz, 1H) 3.66 (s, 3H) 3.66 (s, 3H) 3.24-3.30 (m, 1H) 3.13-3.21 (m, 1H) 3.11 (s, 3H). LCMS-ESI (POS.) m/z: 546.1 (M+H)⁺.

Example 265.0: Preparation of (R)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide or (S)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide 265.0

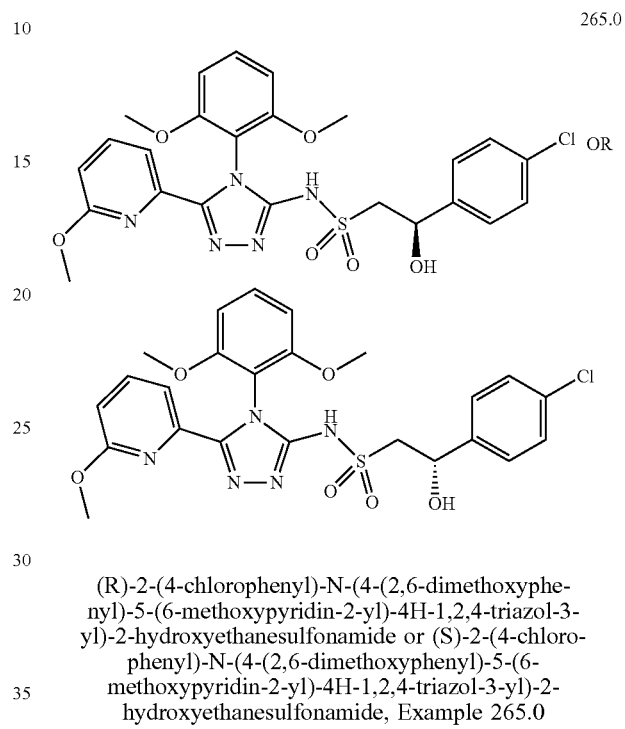

(R)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide or (S)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide, Example 265.0

The title compound 265.0 was the first isomer to elute on subjecting 264.0 to the following SFC conditions: OJ-H (2×25 cm) column, 20% MeOH/CO₂, 100 bar, 70 mL/min, wavelength=220 nm, inj vol.: 1 mL, 5 mg/mL solution of 264.0 in MeOH. ¹H NMR (400 MHz, DMSO-d₆) δ 7.78 (t, J=7.92 Hz, 1H), 7.58 (dd, J=7.34, 0.49 Hz, 1H), 7.33-7.42 (m, 3H), 7.27-7.32 (m, 2H), 6.75-6.84 (m, 3H), 5.45 (br. s., 1H), 4.94 (dd, J=7.73, 4.01 Hz, 1H), 3.65 (s, 3H), 3.64 (s, 3H) 3.15-3.29 (m, 2H), 3.09 (s, 3H). LCMS-ESI (POS.) m/z: 546.0 (M+H)⁺.

Example 266.0: Preparation of (R)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide or (S)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide 266.0

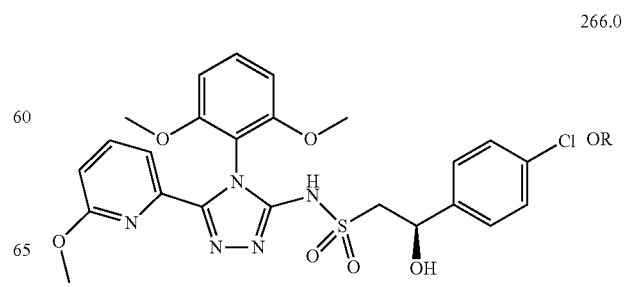

-continued

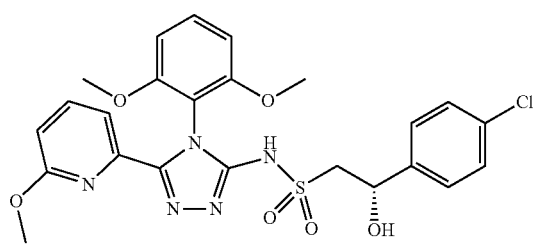

(R)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide or (S)-2-(4-chlorophenyl)-N-(4-(2,6-dimethoxyphenyl)-5-(6-methoxypyridin-2-yl)-4H-1,2,4-triazol-3-yl)-2-hydroxyethanesulfonamide, Example 266.0

Example 266.0 is the enantiomer of 265.0. 266.0 was the second isomer to elute on subjecting 264.0 to the SFC conditions described in 265.0. $^1$H NMR (400 MHz, DMSO-$d_6$) δ 7.76 (t, J=7.83 Hz, 1H) 7.58 (dd, J=7.43, 0.39 Hz, 1H) 7.33-7.40 (m, 3H) 7.28-7.32 (m, 2H) 6.74-6.81 (m, 3H) 5.49 (br. s., 1H) 4.94 (dd, J=7.73, 4.01 Hz, 1H) 3.65 (s, 3H) 3.63 (s, 3H) 3.16-3.28 (m, 2H) 3.09 (s, 3H). LCMS-ESI (POS.) m/z: 546.2 (M+H)$^+$.

Example 267.0: Preparation of (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide and (S)—N-(4-(2,6-(trimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide 267.1

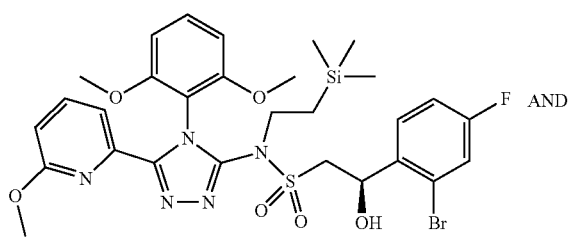

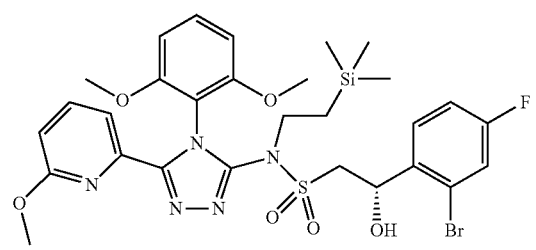

(R)-2-(2-bromo-4-fluorophenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide and (R)-2-(2-bromo-4-fluorophenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide, Example 267.1

The title compound was prepared from Example 4.0 (1.52 g, 3.01 mmol) and 2-bromo-4-fluorobenzaldehyde (commercially available from Oakwood Products, Inc.) (0.732 g, 3.61 mmol), using the procedure described in Example 264.0 to obtained the title compound 267.1 (1.77 g, 2.50 mmol, 83% yield) as a white solid. LCMS-ESI (POS.) m/z: 708.0 (M+H)$^+$.

267.2

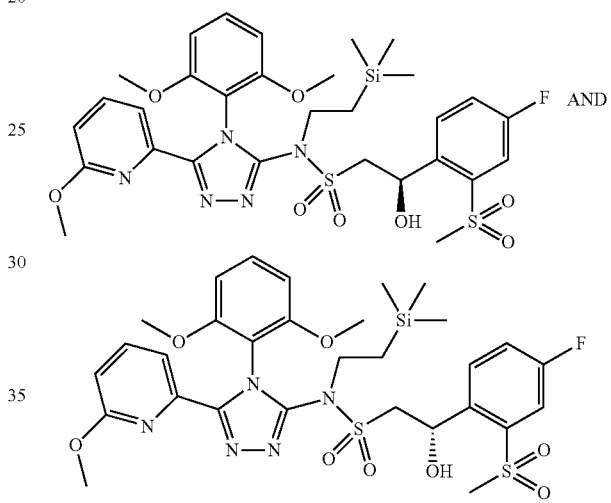

(R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxy-N-(2-(trimethylsilyl)ethyl)ethanesulfonamide and (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxy-N-(2-(trimethylsilyl)ethyl)ethanesulfonamide, Example 267.2

A mixture of sodium methanesulfinate (508 mg, 4.23 mmol, commercially available from Sigma-Aldrich Corp., St. Louis, Mo., USA), copper(i) iodide (81 mg, 0.42 mmol, commercially available from Strem Chemicals Inc., Newburyport, Mass., USA) and N, N'-dimethylethylenediamine (91 µL, 0.85 mmol, commercially available from Sigma-Aldrich Corp., St. Louis, Mo., USA) in DMSO (8.5 mL) was bubbled with nitrogen for 2 min. To the mixture was added 2-(2-bromo-4-fluorophenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide (267.1, 600 mg, 0.85 mmol), and N$_2$ was bubbled through the mixture for another minute. The mixture was then heated at 110° C. for 22 h. The reaction was cooled to RT, diluted with saturated NH$_4$C$_1$(aqueous) (80 mL) and EtOAc (80 mL). The two layers were separated. The organic layer was washed with saturated NH$_4$C$_1$ (3×80 mL), dried over Na₂SO₄, filtered and concentrated in vacuo. The material thus obtained was absorbed onto a plug of silica gel and purified by chromatography through a Redi-Sep pre-packed silica gel column (24 g), eluting with a gradient of 0-100% EtOAc in hexanes, to provide the title compound 267.2 (380 mg, 0.54 mmol, 63% yield) as white solid, LCMS-ESI (POS.) m/z: 708.2 (M+H)⁺; and a by-product N-(4-(2,6-dimethoxyphenyl)-5-(6-methoxypyridin-2-yl)-4H-1,2,4-triazol-3-yl)-2-(4-fluorophenyl)-2-hydroxy-N-(2-(trimethylsilyl)ethyl)ethanesulfonamide (Example 267.3) (118 mg, 0.19 mmol, 22% yield) as a white solid.

Example 268.0: Preparation of (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide

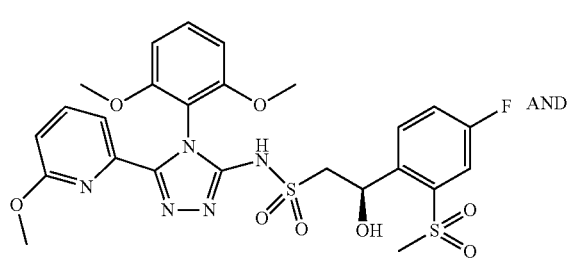

(R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide and (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide, Example 267.0

The title compound was prepared from 267.2 (150 mg, 0.212 mmol) using the procedure described in Example 264.0 to obtain the title compound Example 267.0 (45 mg, 0.074 mmol, 35% yield) as a white solid. ¹H NMR (400 MHz, DMSO-d₆) δ 13.45 (br. s, 1H) 7.85 (dd, J=8.41, 5.28 Hz, 1H) 7.81 (dd, J=8.41, 7.43 Hz, 1H) 7.56-7.63 (m, 3H) 7.41 (t, J=8.41 Hz, 1H) 6.76-6.85 (m, 3H) 5.82-5.88 (m, 1H) 3.68 (s, 3H) 3.63 (s, 3H) 3.34-3.45 (m, 2H) 3.19 (s, 3H) 3.10 (s, 3H). LCMS-ESI (POS.) m/z: 608.2 (M+H)⁺.

(R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide, Example 268.0

The title compound was the first isomer to elute under the following SFC conditions: Thar 80 SFC with 250×30 mm AS column with 24 g/min EtOH (neat)+56 g/min CO₂, 30% co-solvent at 80 g/min. Temperature.=23° C., Outlet pressure=100 bar, Wavelength=293 nm. Injected 0.35 mL of a solution of 40 mg sample 267.0 dissolved in 10 mL of MeOH, c=4.0 mg/mL and 1.4 mg per injection. Cycle time 8 min, run time=14 min. ¹H NMR (400 MHz, DMSO-d₆) δ 13.41 (br. s., 1H) 7.85 (dd, J=8.41, 5.48 Hz, 1H) 7.80 (dd, J=8.31, 7.53 Hz, 1H) 7.55-7.63 (m, 3H) 7.40 (t, J=8.51 Hz, 1H) 6.75-6.85 (m, 3H) 5.82-5.88 (m, 1H) 5.50 (br. s., 1H) 3.68 (s, 3H) 3.63 (s, 3H) 3.34-3.46 (m, 2H) 3.20 (s, 3H) 3.10 (s, 3H). LCMS-ESI (POS.) m/z: 608.2 (M+H)⁺.

Example 269.0: Preparation of (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide

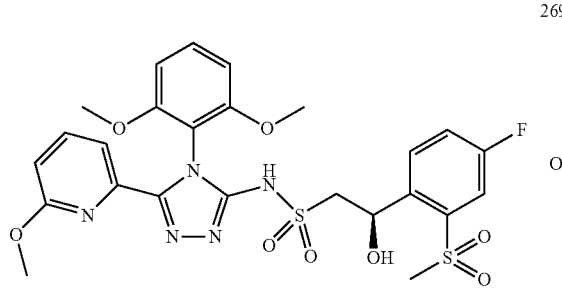

269.0

OR

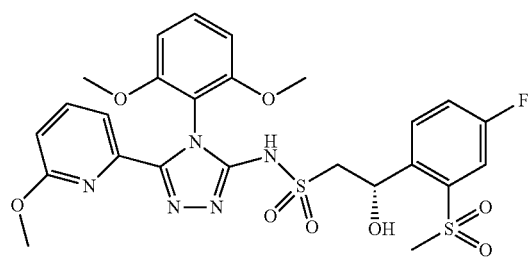

(R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxyethanesulfonamide, Example 269.0

Example 269.0 is the enantiomer of Example 268.0. Example 269.0 was the second isomer to elute on subjecting 267.0 to the SFC conditions described in 268.0. $^1$H NMR (400 MHz, DMSO-$d_6$) δ 13.45 (br. s., 1H) 7.85 (dd, J=8.51, 5.38 Hz, 1H) 7.80 (dd, J=8.31, 7.53 Hz, 1H) 7.55-7.63 (m, 3H) 7.40 (t, J=8.51 Hz, 1H) 6.75-6.85 (m, 3H) 5.82-5.88 (m, 1H) 5.50 (br. s., 1H) 3.68 (s, 3H) 3.63 (s, 3H) 3.34-3.46 (m, 2H) 3.20 (s, 3H) 3.10 (s, 3H). LCMS-ESI (POS.) m/z: 608.2 (M+H)$^+$.

Example 270.0: Preparation of (R)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide and (S)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide 270.1

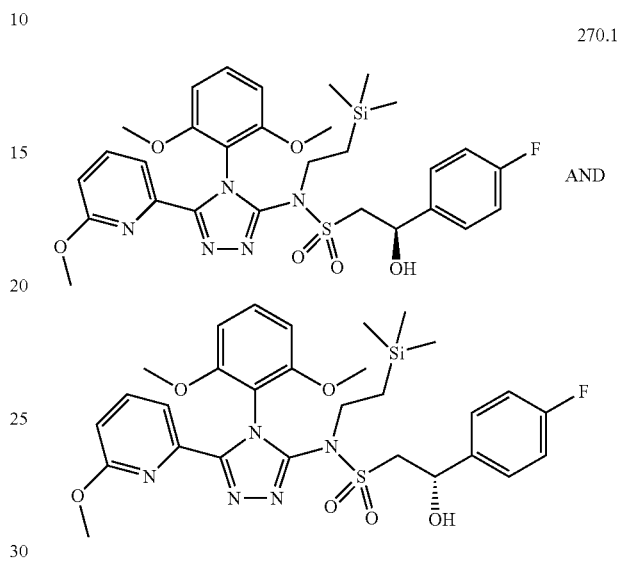

AND (R)—N-(4-(2,6-dimethoxyphenyl)-5-(6-methoxypyridin-2-yl)-4H-1,2,4-triazol-3-yl)-2-(4-fluorophenyl)-2-hydroxy-N-(2-(trimethylsilyl)ethyl)ethanesulfonamide and (R)—N-(4-(2,6-dimethoxyphenyl)-5-(6-methoxypyridin-2-yl)-4H-1,2,4-triazol-3-yl)-2-(4-fluorophenyl)-2-hydroxy-N-(2-(trimethylsilyl)ethyl)ethanesulfonamide, Example 270.1

The title compound was obtained as a by-product from synthesis of Example 267.2. LCMS-ESI (POS.) m/z: 630.2 (M+H)$^+$.

270.0

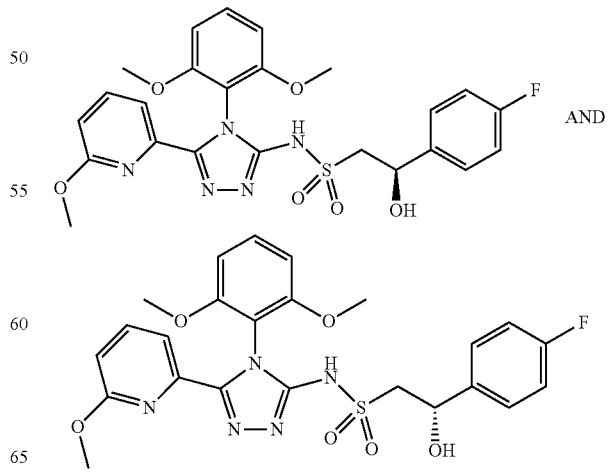

AND (R)—N-(4-(2,6-dimethoxyphenyl)-5-(6-methoxy-pyridin-2-yl)-4H-1,2,4-triazol-3-yl)-2-(4-fluorophe-nyl)-2-hydroxyethanesulfonamide and (S)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide, Example 270.0

The title compound was prepared from 270.1 (113 mg, 0.179 mmol) and tris(dimethylamino)sulfonium difluorot-rimethylsilicate (148 mg, 0.538 mmol, commercially available from Sigma-Aldrich Corp., St. Louis, Mo., USA) using the procedure described in Example 264.0. This provided the title compound 270.0 (64 mg, 0.12 mmol, 88% yield) as a white solid. $^1$H NMR (400 MHz, DMSO-$d_6$) δ 13.43 (br. s., 1H) 7.81 (dd, J=8.22, 7.43 Hz, 1H) 7.58 (d, J=7.43 Hz, 1H) 7.42 (t, J=7.78 Hz, 1H) 7.30 (t, J=6.14 Hz, 2H) 7.12 (t, J=8.38 Hz, 2H) 6.79-6.85 (m, 3H) 5.31 (br. s., 1H) 4.94 (br. s., 1H) 3.66 (s, 3H) 3.65 (s, 3H) 3.25-3.30 (m, 1H) 3.13-3.19 (m, 1H) 3.11 (s, 3H). LCMS-ESI (POS.) m/z: 530.2 (M+H)$^+$.

Example 271.0: Preparation of (R)—N-(4-(2,6-di-methoxyphenyl)-5-(6-methoxypyridin-2-yl)-4H-1,2,4-triazol-3-yl)-2-(4-fluorophenyl)-2-hydroxyethane-sulfonamide or (S)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide

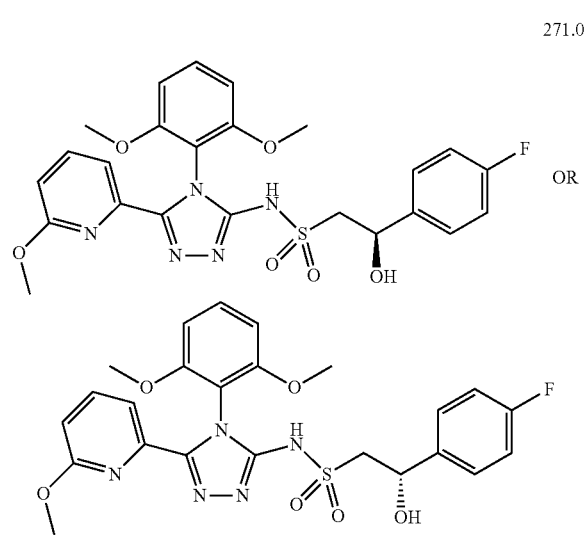

271.0

(R)—N-(4-(2,6-dimethoxyphenyl)-5-(6-methoxy-pyridin-2-yl)-4H-1,2,4-triazol-3-yl)-2-(4-fluorophe-nyl)-2-hydroxyethanesulfonamide or (S)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide, Example 271.0

The title compound was the first isomer to elute under the following SFC conditions: Thar 80 SFC with 250×30 mm AD column with 40 g/min EtOH (neat)+40 g/min CO$_2$, 50% co-solvent at 80 g/min. Temperature.=22° C., Outlet pressure=100 bar, Wavelength=295 nm. Injected 1.0 mL of a solution of 63 mg sample of Example 270.0 dissolved in 10 mL of MeOH, c=6.3 mg/mL and 6.3 mg per injection. Cycle time 8.2 min, run time=14 min. $^1$H NMR (400 MHz, DMSO-$d_6$) δ 13.43 (br. s., 1H) 7.80 (dd, J=8.22, 7.43 Hz, 1H) 7.58 (d, J=7.43 Hz, 1H) 7.42 (t, J=8.41 Hz, 1H) 7.27-7.33 (m, 2H) 7.09-7.15 (m, 2H) 6.78-6.85 (m, 3H) 5.32 (br. s., 1H) 4.94 (dd, J=7.63, 3.91 Hz, 1H) 3.66 (s, 3H) 3.65 (s, 3H) 3.24-3.30 (m, 1H) 3.16 (dd, J=13.89, 3.52 Hz, 1H) 3.10 (s, 3H). LCMS-ESI (POS.) m/z: 530.2 (M+H)$^+$.

Example 272.0: Preparation of (R)—N-(4-(2,6-di-methoxyphenyl)-5-(6-methoxypyridin-2-yl)-4H-1,2,4-triazol-3-yl)-2-(4-fluorophenyl)-2-hydroxyethane-sulfonamide or (S)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide

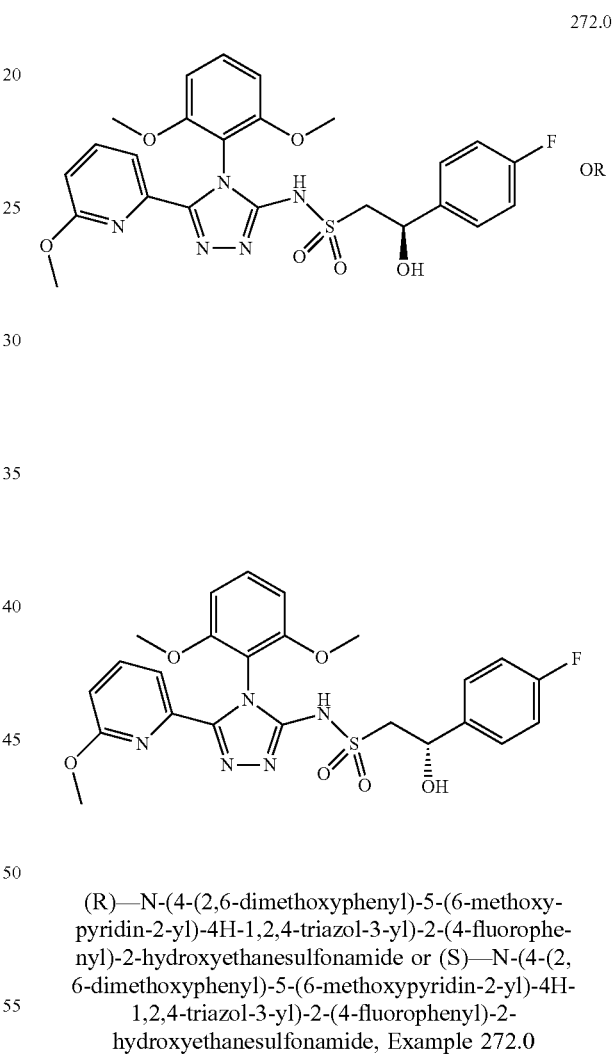

272.0

(R)—N-(4-(2,6-dimethoxyphenyl)-5-(6-methoxy-pyridin-2-yl)-4H-1,2,4-triazol-3-yl)-2-(4-fluorophe-nyl)-2-hydroxyethanesulfonamide or (S)—N-(4-(2,6-dimethoxyphenyl)-5-(6-methoxypyridin-2-yl)-4H-1,2,4-triazol-3-yl)-2-(4-fluorophenyl)-2-hydroxyethanesulfonamide, Example 272.0

Example 272.0 is the enantiomer of Example 271.0. The title compound was the second isomer to elute on subjecting 270.0 to the SFC conditions described in 271.0. $^1$H NMR (400 MHz, DMSO-$d_6$) δ 13.43 (br. s., 1H) 7.81 (dd, J=8.22, 7.43 Hz, 1H) 7.58 (d, J=7.04 Hz, 1H) 7.42 (t, J=8.51 Hz, 1H) 7.27-7.33 (m, 2H) 7.08-7.16 (m, 2H) 6.78-6.86 (m, 3H) 5.31 (br. s., 1H) 4.94 (dd, J=6.85, 3.72 Hz, 1H) 3.66 (s, 3H) 3.65 (s, 3H) 3.28 (m, J=6.46 Hz, 1H) 3.16 (dd, J=14.28, 4.11 Hz, 1H) 3.11 (s, 3H). LCMS-ESI (POS.) m/z: 530.2 (M+H)$^+$.

Example 273.0: Preparation of (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide and (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide

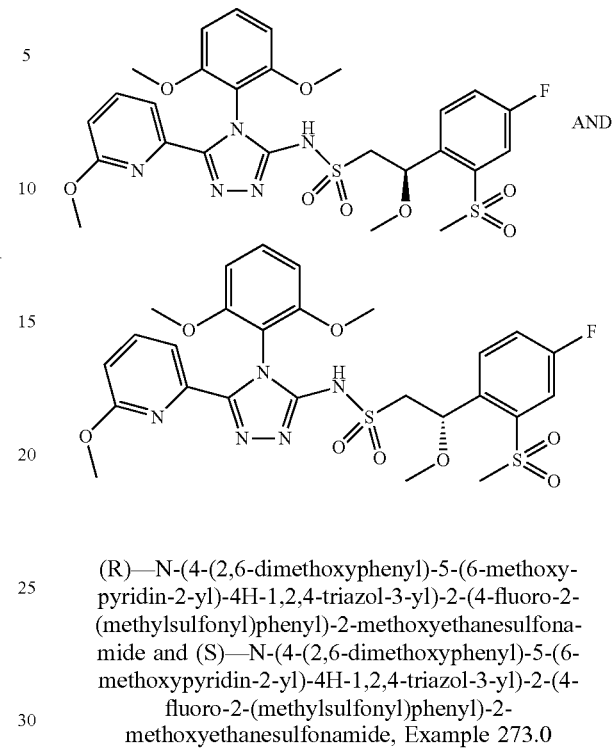

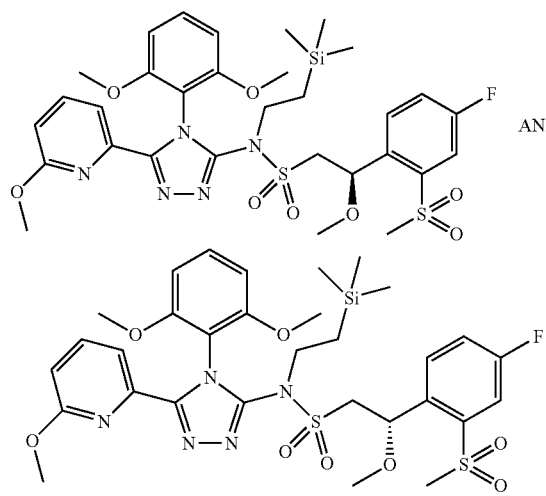

(R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxy-N-(2-(trimethylsilyl)ethyl)ethanesulfonamide and (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxy-N-(2-(trimethylsilyl)ethyl)ethanesulfonamide, Example 273.1

To a solution of N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-hydroxy-N-(2-(trimethylsilyl)ethyl)ethanesulfonamide 267.2 (224 mg, 0.32 mmol) in DMF (2.0 mL) at 0° C., was added sodium hydride (60% dispersion in mineral oil (15.2 mg, 0.38 mmol)) (commercially available from Sigma-Aldrich Corp., St. Louis, Mo., USA). The mixture was warmed to RT for 15 min. A solution of iodomethane (stabilized, 0.026 mL, 0.41 mmol), commercially available from Acros Organics, NJ, USA) in DMF (0.50 mL) was injected dropwise. After 30 min, the reaction was quenched by addition of aqueous saturated NH$_4$Cl (25 mL) and then it was extracted with EtOAc (25 mL). The organic layer was washed with brine (3×25 mL), dried over Na$_2$SO$_4$, filtered and concentrated in vacuo. The material thus obtained was absorbed onto a plug of silica gel and purified by chromatography through a Redi-Sep pre-packed silica gel column (12 g), eluting with a gradient of 0-50% EtOAc in hexanes, to provide the title compound 273.1 (166 mg, 0.23 mmol, 73% yield) as white solid. LCMS-ESI (POS.) m/z: 722.2 (M+H)$^+$.

(R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide and (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide, Example 273.0

The title compound was prepared from 273.1 (162 mg, 0.22 mmol) and tris(dimethylamino)sulfonium difluorotrimethylsilicate(IV) (185 mg, 0.67 mmol, commercially available from Sigma-Aldrich Corp., St. Louis, Mo., USA) using the procedure described in Example 264.0. This provided the title compound 273.0 (133 mg, 0.21 mmol, 95% yield) as a white solid. $^1$H NMR (400 MHz, DMSO-d$_6$) δ 13.40 (s, 1H) 7.76-7.82 (m, 2H) 7.60-7.68 (m, 2H) 7.57 (d, J=7.24 Hz, 1H) 7.41 (t, J=8.41 Hz, 1H) 6.78-6.84 (m, 3H) 5.52 (dd, J=7.34, 4.79 Hz, 1H) 3.67 (s, 3H) 3.66 (s, 3H) 3.48 (dd, J=14.48, 7.63 Hz, 1H) 3.36 (dd, J=14.38, 4.79 Hz, 1H) 3.19 (s, 3H) 3.10 (s, 3H) 3.03 (s, 3H). LCMS-ESI (POS.) m/z: 622.1 (M+H)$^+$.

Example 274.0: Preparation of (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide

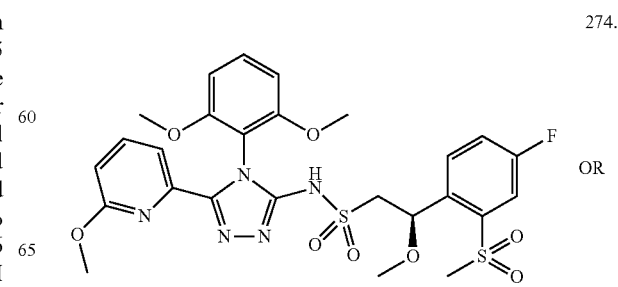

-continued

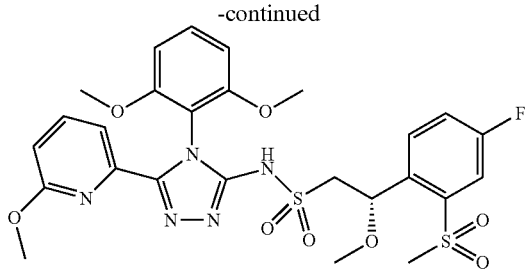

(R)—N-(4-(2,6-dimethoxyphenyl)-5-(6-methoxy-pyridin-2-yl)-4H-1,2,4-triazol-3-yl)-2-(4-fluoro-2-(methylsulfonyl)phenyl)-2-methoxyethanesulfona-mide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide, Example 274.0

The title compound was the first isomer to elute under the following SFC conditions: IA column (2×15 cm), 30% MeOH/CO$_2$, 100 bar, 60 mL/min, wavelength=220 nm. Injection vol.: 1.0 mL per injection of 4 mg/mL solution of 273.0 in 1:1 DCM: MeOH. $^1$H NMR (400 MHz, DMSO-d$_6$) δ 13.40 (s, 1H) 7.75-7.83 (m, 2H) 7.60-7.68 (m, 2H) 7.57 (dd, J=7.43, 0.78 Hz, 1H) 7.41 (t, J=8.51 Hz, 1H) 6.78-6.84 (m, 3H) 5.52 (dd, J=7.43, 4.70 Hz, 1H) 3.67 (s, 3H) 3.66 (s, 3H) 3.48 (dd, J=14.48, 7.43 Hz, 1H) 3.36 (dd, J=14.57, 4.79 Hz, 1H) 3.19 (s, 3H) 3.10 (s, 3H) 3.03 (s, 3H). LCMS-ESI (POS.) m/z: 622.1 (M+H)$^+$.

Example 275.0: Preparation of (R)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide 275.0

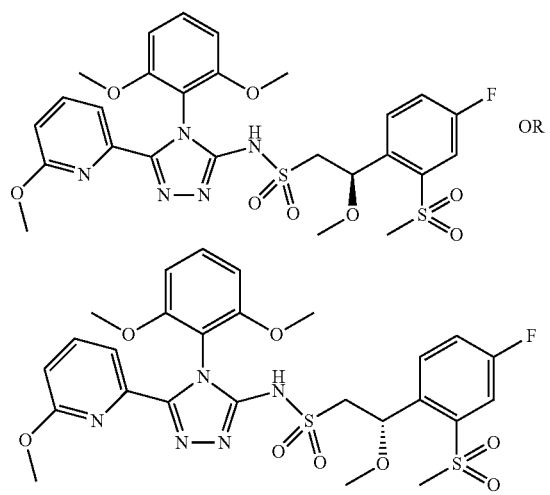

(R)—N-(4-(2,6-dimethoxyphenyl)-5-(6-methoxy-pyridin-2-yl)-4H-1,2,4-triazol-3-yl)-2-(4-fluoro-2-(methylsulfonyl)phenyl)-2-methoxyethanesulfona-mide or (S)—N-(4-(2,6-dimethoxyphenyl)-5-(6-methoxypyridin-2-yl)-4H-1,2,4-triazol-3-yl)-2-(4-fluoro-2-(methylsulfonyl)phenyl)-2-methoxyethanesulfonamide, Example 275.0

Example 275.0 is the enantiomer of 274.0. This compound was the second isomer to elute from the IA column under the condition described in Example 274.0. $^1$H NMR (400 MHz, DMSO-d$_6$) δ 13.40 (s, 1H) 7.76-7.82 (m, 2H) 7.60-7.67 (m, 2H) 7.57 (dd, J=7.43, 0.78 Hz, 1H) 7.41 (t, J=8.51 Hz, 1H) 6.77-6.84 (m, 3H) 5.52 (dd, J=7.43, 4.70 Hz, 1H) 3.67 (s, 3H) 3.66 (s, 3H) 3.48 (dd, J=14.48, 7.43 Hz, 1H) 3.36 (dd, J=14.57, 4.79 Hz, 1H) 3.19 (s, 3H) 3.10 (s, 3H) 3.03 (s, 3H). LCMS-ESI (POS.), m/z: 622.1 (M+H)$^+$.

Example 276.0: (R)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfona-mide and (S)-2-(2-cyano-4-fluorophenyl)-N-(4-(2,6-dimethoxyphenyl)-5-(6-methoxypyridin-2-yl)-4H-1, 2,4-triazol-3-yl)-2-methoxyethanesulfonamide 276.1

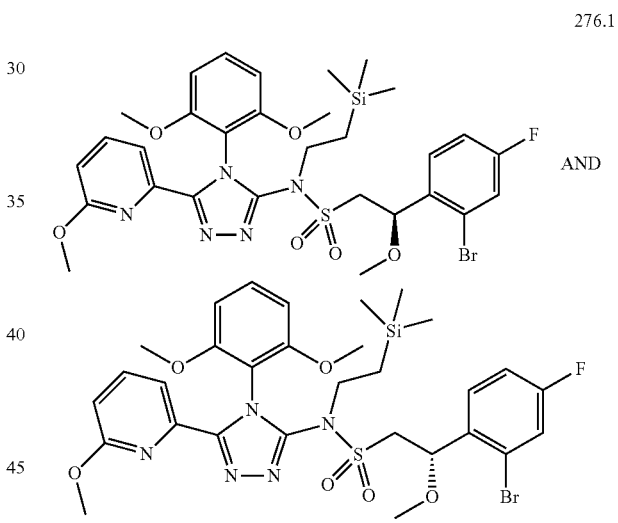

(R)-2-(2-bromo-4-fluorophenyl)-N-(4-(2,6-dime-thoxyphenyl)-5-(6-methoxypyridin-2-yl)-4H-1,2,4-triazol-3-yl)-2-methoxy-N-(2-(trimethylsilyl)ethyl)ethanesulfonamide and (S)-2-(2-bromo-4-fluorophenyl)-N-(4-(2,6-dimethoxyphenyl)-5-(6-methoxypyridin-2-yl)-4H-1,2,4-triazol-3-yl)-2-methoxy-N-(2-(trimethylsilyl)ethyl)ethanesulfonamide, Example 276.1

To a solution of 2-(2-bromo-4-fluorophenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide 267.1 (881 mg, 1.24 mmol) in DMF (6 mL) at 0° C., was added sodium hydride (60% dispersion in mineral oil (59.7 mg, 1.49 mmol), commercially available from Sigma-Aldrich Corp., St. Louis, Mo., USA). The mixture was warmed to RT for 15 min. To this mixture was added iodomethane (stabilized (0.100 mL, 1.62 mmol), commercially available from Acros Organics, NJ, USA) in DMF (1.5 mL) dropwise. After 50 min, the reaction was quenched with a saturated aqueous NH₄Cl solution (50 mL), diluted with EtOAc (50 mL). The layers were separated. The organic layer was washed with brine (3×50 mL), dried over Na₂SO₄, filtered and concentrated in vacuo. The material thus obtained was absorbed onto a plug of silica gel and purified by chromatography through a Redi-Sep pre-packed silica gel column (12 g), eluting with a gradient of 0-50% EtOAc in hexanes, to provide the title compound 276.1 (875 mg, 1.21 mmol, 97% yield) as a white solid. LCMS-ESI (POS.), m/z: 722.2 (M+H)⁺.

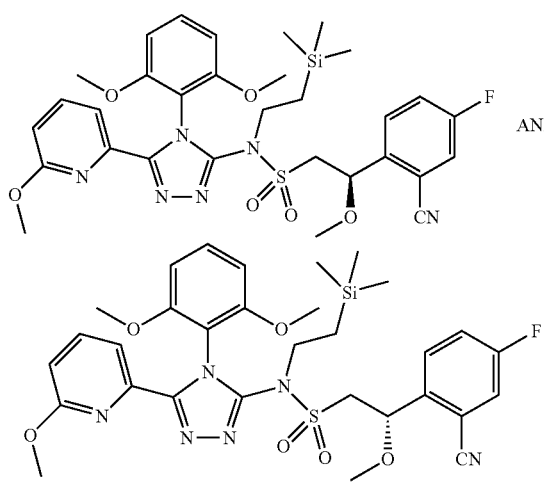

(R)-2-(2-cyano-4-fluorophenyl)-N-(4-(2,6-dimethoxyphenyl)-5-(6-methoxypyridin-2-yl)-4H-1,2,4-triazol-3-yl)-2-methoxy-N-(2-(trimethylsilyl)ethyl)ethanesulfonamide and (S)-2-(2-cyano-4-fluorophenyl)-N-(4-(2,6-dimethoxyphenyl)-5-(6-methoxypyridin-2-yl)-4H-1,2,4-triazol-3-yl)-2-methoxy-N-(2-(trimethylsilyl)ethyl)ethanesulfonamide, Example 276.2

A microwave tube was charged with 2-(2-bromo-4-fluorophenyl)-N-(4-(2,6-dimethoxyphenyl)-5-(6-methoxypyridin-2-yl)-4H-1,2,4-triazol-3-yl)-2-methoxy-N-(2-(trimethylsilyl)ethyl)ethanesulfonamide 276.1 (199 mg, 0.28 mmol), zinc cyanide (53.3 mg, 0.45 mmol, commercially available from Alfa Aesar, A Johnson Matthey Company, Ward Hill, Mass., USA) and DMF (3 mL), and then N₂ was bubbled through for 3 min. To the mixture was added tetrakis(triphenylphosphine)palladium(0) (63.6 mg, 0.055 mmol, commercially available from Strem Chemicals Inc., Newburyport, Mass., USA), and the mixture was degassed with nitrogen again. The reaction was heated at 120° C. for an h in the microwave. The reaction mixture was diluted with water (30 mL) and EtOAc (30 mL). The layers were separated. The organic layer was washed with brine (3×30 mL), dried over Na₂SO₄, filtered and concentrated in vacuo. The material thus obtained was absorbed onto a plug of silica gel and purified by chromatography through a Redi-Sep pre-packed silica gel column (12 g), eluting with a gradient of 0-70% EtOAc in hexanes, to provide the title compound 276.2 (141 mg, 0.211 mmol, 77% yield) as colorless film. LCMS-ESI (POS.), m/z: 669.2 (M+H)⁺.

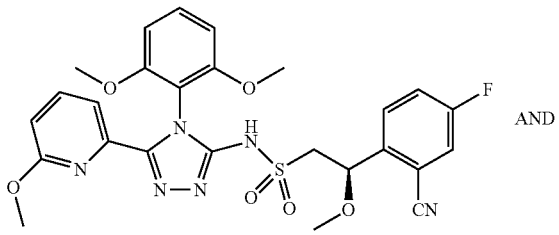

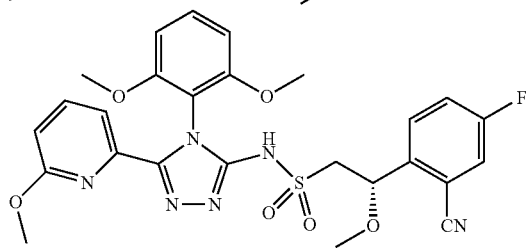

(R)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide and (S)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide, Example 276.0

The title compound was prepared from 276.2 (137 mg, 0.205 mmol) and tris(dimethylamino)sulfonium difluorotrimethylsilicate(IV) (169 mg, 0.615 mmol, commercially available from Sigma-Aldrich Corp., St. Louis, Mo., USA), using the procedure described in Example 264.0. This provided the title compound 267.0 (90 mg, 0.16 mmol, 77% yield) as a white solid. ¹H NMR (400 MHz, DMSO-d₆) δ 13.38 (s, 1H) 7.78-7.85 (m, 2H) 7.53-7.61 (m, 3H) 7.41 (t, J=8.51 Hz, 1H) 6.83 (dd, J=8.31, 0.68 Hz, 1H) 6.80 (d, J=8.41 Hz, 2H) 4.85 (dd, J=7.04, 5.48 Hz, 1H) 3.67 (s, 6H) 3.52 (dd, J=14.28, 7.24 Hz, 1H) 3.34 (dd, J=14.28, 5.28 Hz, 1H) 3.10 (s, 3H) 3.05 (s, 3H). LCMS-ESI (POS.), m/z: 569.2 (M+H)⁺.

Example 277.0: Preparation of (R)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide or (S)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide

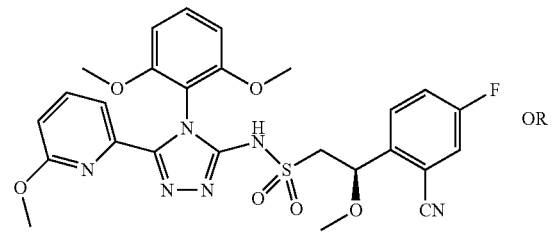

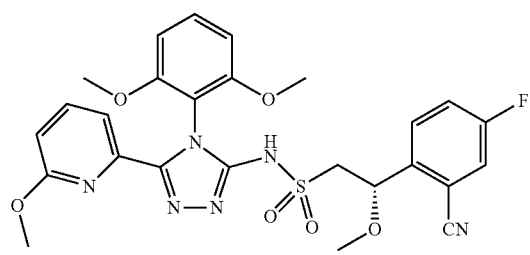

(R)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide or (S)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide, Example 277.0

The title compound 277.0 was the first isomer to elute under the following SFC conditions: Run on Thar 80 SFC with 250×30 mm CC4 column with 40 g/min MeOH (neat)+ 40 g/min CO$_2$, 50% co-solvent at 80 g/min. Temperature.=26° C., Outlet pressure=100 bar, Wavelength=297 nm. Injected 0.6 mL of a solution of 77 mg sample of 276.0 dissolved in 14 mL of MeOH:DCM, 8:6, c=5.5 mg/mL and 3.3 mg per injection. Cycle time 6.2 min, run time=15 min. LCMS-ESI (POS.), m/z: 569.2 (M+H)$^+$.

Example 278.0: Preparation of (R)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide or (S)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide 278.0

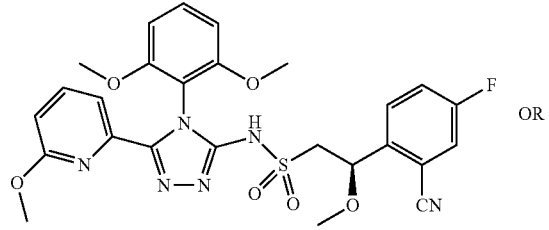

OR

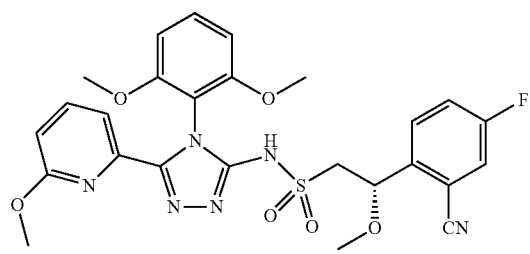

(R)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide or (S)-2-(2-cyano-4-fluorophenyl)-N-(4-(2,6-dimethoxyphenyl)-5-(6-methoxypyridin-2-yl)-4H-1,2,4-triazol-3-yl)-2-methoxyethanesulfonamide, Example 278.0

Example 278.0 is the enantiomer of Example 277.0. Example 278.0 was the second isomer to elute from CC4 column under the conditions described in Example 277.0. LCMS-ESI (POS.), m/z: 569.2 (M+H)$^+$.

Example 279.0: Preparation of (1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1R,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide 279.1

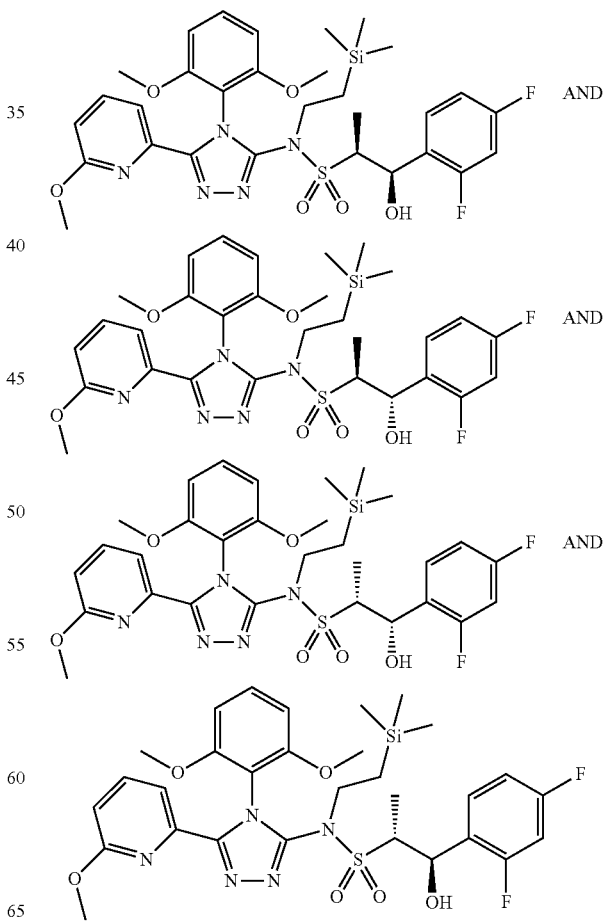

(1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide and (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide and (1R,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide and (1S,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide,
Example 279.1

N-(4-(2,6-dimethoxyphenyl)-5-(6-methoxypyridin-2-yl)-4H-1,2,4-triazol-3-yl)-N-(2-(trimethylsilyl)ethyl)ethanesulfonamide (Example 5.0) (311 mg, 0.598 mmol) was azeotroped with toluene and then dissolved in THF (3 mL). The solution was cooled to −78° C. To this was added n-butyllithium solution (2.5M in hexanes (0.24 mL, 0.60 mmol), commercially available from Sigma-Aldrich Corp., St. Louis, Mo., USA) dropwise, afterwhich the reaction mixture was stirred at −78° C. for 10 min. A solution of 2,4-difluorobenzaldehyde (102 mg, 0.718 mmol, commercially available from Fluka Chemie GmbH, Buchs, Switzerland) in THF (1.0 mL) was then injected dropwise. The reaction was stirred at −78° C. for 15 min and then was warmed to RT for 1 h. The reaction mixture was quenched with saturated NH$_4$C$_1$ (aqueous) and extracted with EtOAc. The organic extract was dried over Na$_2$SO$_4$, filtered and concentrated in vacuo. The residue thus obtained was absorbed onto a plug of silica gel and purified by chromatography through a Redi-Sep pre-packed silica gel column (24 g), eluting with a gradient of 0-100% EtOAc in hexanes, to provide the title compound 279.1 (266 mg, 0.402 mmol, 67% yield) as a colorless gum. LCMS-ESI (POS.) m/z: 662.3 (M+H)$^+$.

279.2

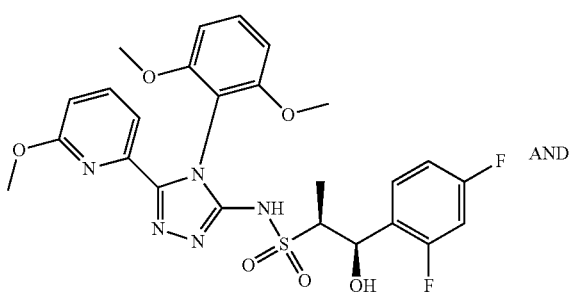

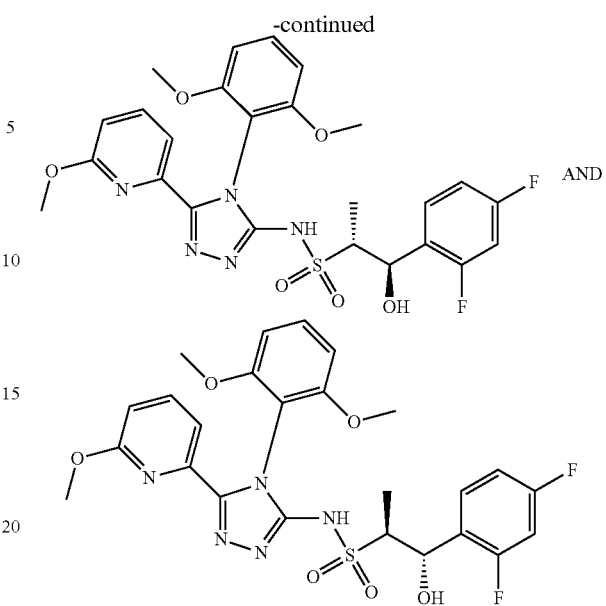

(1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide and (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide and (1R,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide and (1S,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide,
Example 279.2

A mixture of 279.1 (263 mg, 0.397 mmol) and tris(dimethylamino)sulfonium difluorotrimethylsilicate(IV) (438 mg, 1.59 mmol, commercially available from Sigma-Aldrich Corp., St. Louis, Mo., USA) in DMF (3 mL) was heated at 60° C. for 18 h. The reaction mixture was diluted with EtOAc (30 mL), washed with 0.1N HCl (30 mL) followed by brine (3×30 mL), dried over Na$_2$SO$_4$, filtered and concentrated in vacuo. The material thus obtained was absorbed onto a plug of silica gel and purified by chromatography through a Redi-Sep pre-packed silica gel column (12 g), eluting with a gradient of 0-50% EtOAc in DCM, to provide the title compound 279.2 (102 mg, 0.18 mmol, 46% yield) as a white solid. LCMS-ESI (POS.) m/z: 562.1 (M+H)$^+$.

279.0

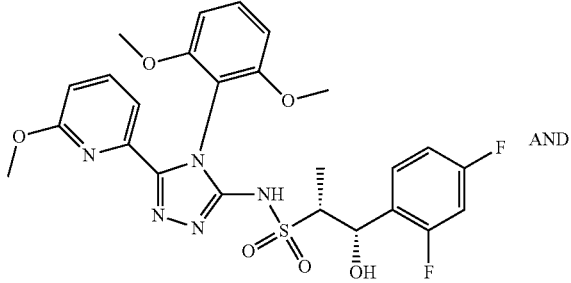

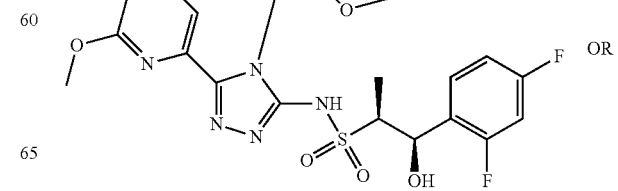

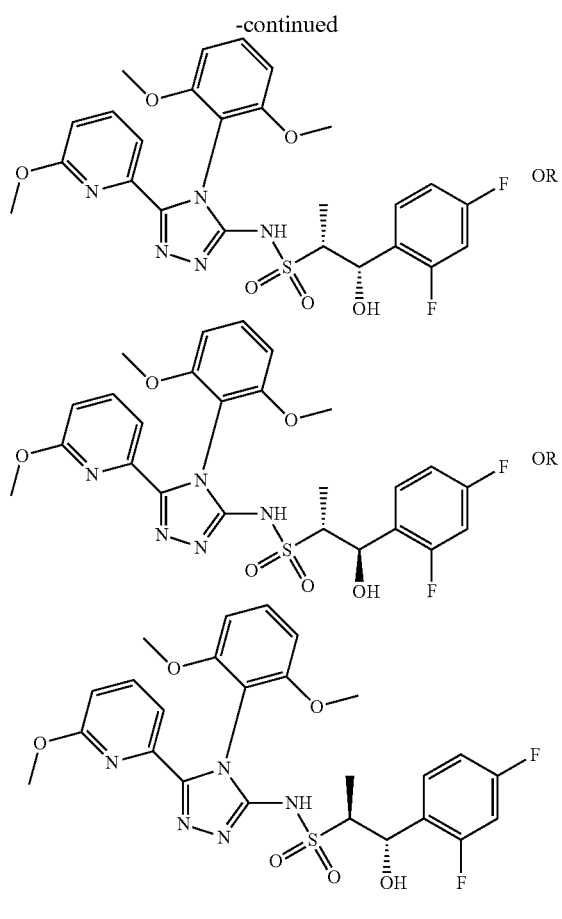

(1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide, Example 279.0

Example 279.0 was the first enantiomer to elute from an AD-H column under the following conditions: Run on Thar 80 SFC with 250×30 mm AD-H column with 32 g/min EtOH (neat)+48 g/min CO₂, 40% co-solvent at 80 g/min. Outlet pressure=100 bar; Temperature.=21° C.; Wavelength=215 nm. injected 0.5 mL of a solution of 279.2 dissolved in 1:1 MeOH/DCM (c=12.5 mg/mL, A drop of ammonia was used to dissolve the sample), 6.2 mg per injection. Cycle time 18 min, run time 22 min. ¹H NMR (400 MHz, DMSO-d₆) δ 13.36 (br. s., 1H) 7.76-7.82 (m, 1H) 7.58 (d, J=7.04 Hz, 1H) 7.44-7.49 (m, 1H) 7.40 (t, J=8.51 Hz, 1H) 7.17 (ddd, J=10.96, 9.10, 2.45 Hz, 1H) 7.07 (td, J=8.51, 2.35 Hz, 1H) 6.76-6.84 (m, 3H) 5.43 (s, 1H) 5.14 (br. s., 1H) 3.66 (s, 3H) 3.63 (s, 3H) 3.09 (s, 3H) 3.04 (q, J=6.91 Hz, 1H) 1.05 (d, J=6.8 Hz, 3H). LCMS-ESI (POS.) m/z: 562.1 (M+H)⁺.

Example 280: Preparation of (1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1R,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide 280.0

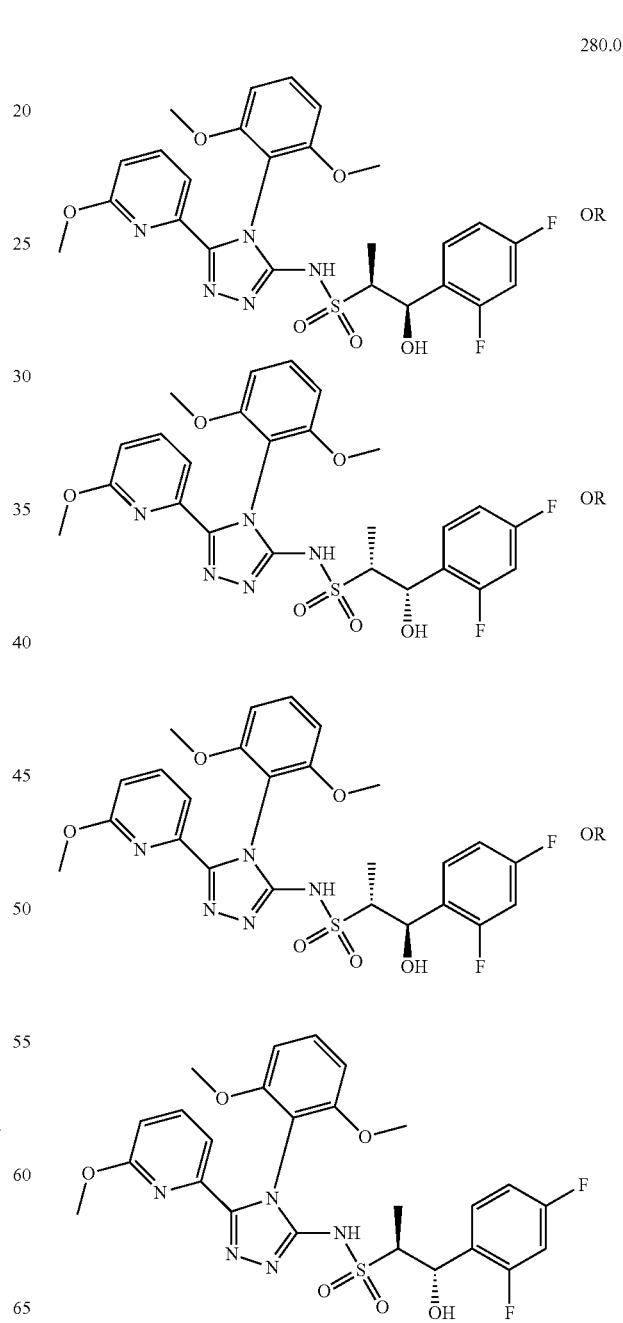

(1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide, Example 280.0

Example 280.0 is the enantiomer of 279.0. Example 280.0 was the fourth diasteromer to elute from AD-H column under the conditions described in Example 279.0. LCMS-ESI (POS), m/z: 562.1 (M+H)$^+$.

Example 281.0: Preparation of (1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide 281.0

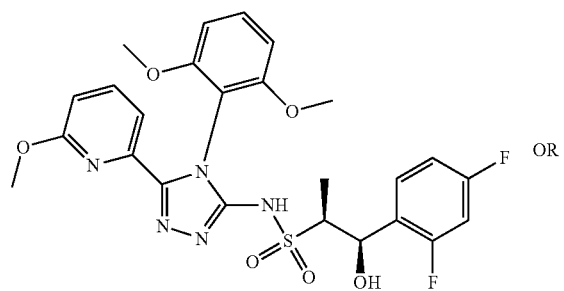

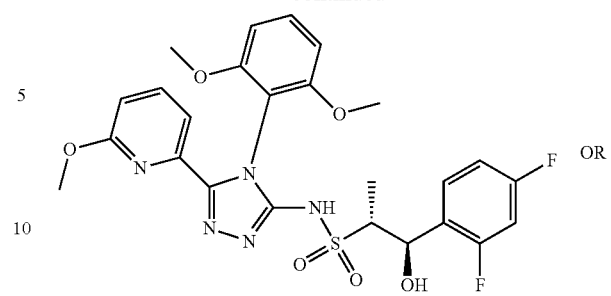

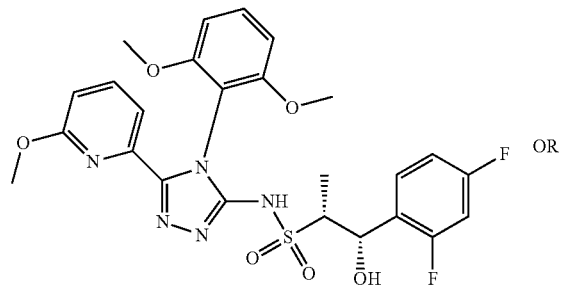

(1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(2,4-(difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide, Example 281.0

Example 281.0 was the second diastereomer to elute from the AD-H column under the conditions described in Example 279.0. $^1$H NMR (400 MHz, DMSO-d$_6$) δ 13.47 (br. s., 1H) 7.80 (t, J=7.87 Hz, 1H) 7.58 (d, J=7.25 Hz, 1H) 7.43-7.50 (m, 1H) 7.40 (t, J=8.51 Hz, 1H) 7.11-7.18 (m, 1H) 7.06 (td, J=8.56, 2.25 Hz, 1H) 6.76-6.84 (m, 3H) 5.27 (br. s., 1H) 5.04 (d, J=7.63 Hz, 1H) 3.67 (s, 3H) 3.64 (s, 3H) 3.27 (q, J=7.00 Hz, 1H) 3.10 (s, 3H) 0.91 (d, J=6.85 Hz, 3H). LCMS-ESI (POS), m/z: 562.3 (M+H)$^+$.

Example 282.0: Preparation of (1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1R,2R)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-(trimethoxyphenyl)-5-(6-methoxypyridin-2-yl)-4H-1,2,4-triazol-3-yl)-1-hydroxypropane-2-sulfonamide

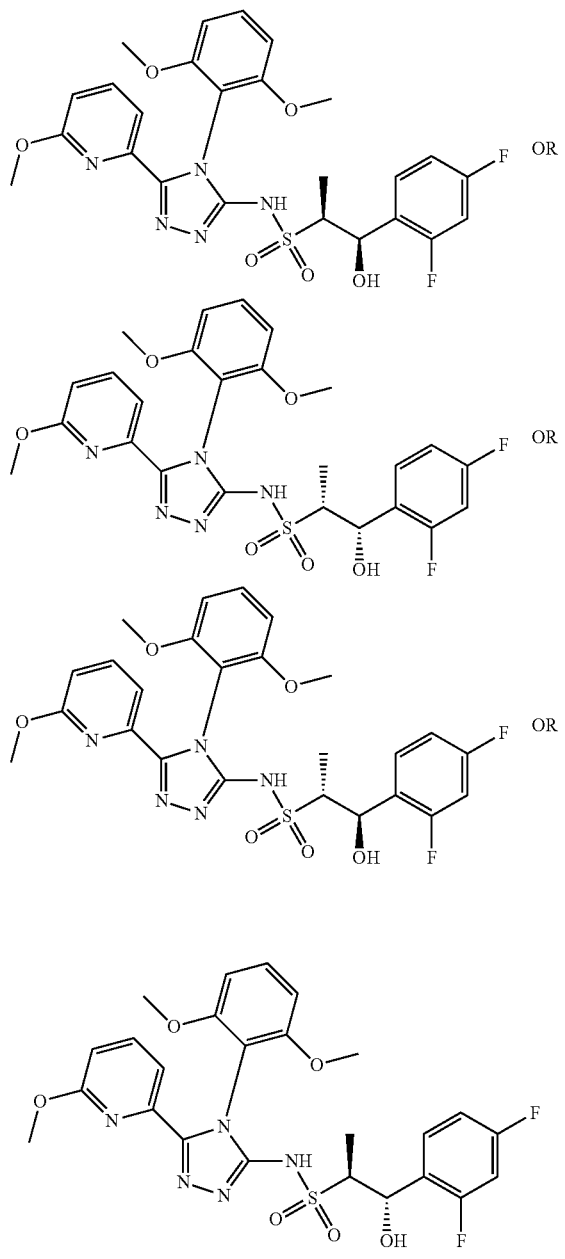

282.0

(1R,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(2,4-(difluorophenyl)-N-(4-(2,6-dimethoxyphenyl)-5-(6-methoxypyridin-2-yl)-4H-1,2,4-triazol-3-yl)-1-hydroxypropane-2-sulfonamide or (1S,2S)-1-(2,4-difluorophenyl)-N-(4-(2,6-dimethoxyphenyl)-5-(6-methoxypyridin-2-yl)-4H-1,2,4-triazol-3-yl)-1-hydroxypropane-2-sulfonamide, Example 282.0

Example 282.0 is the enantiomer of 281.0. Example 282.0 was the third diastereomer to elute from AD-H column under the conditions described in Example 279.0. LCMS-ESI (POS), m/z: 562.1 (M+H)$^+$.

Example 283.0: Preparation of (1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide and (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide and (1R,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide and (1S,2S)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide

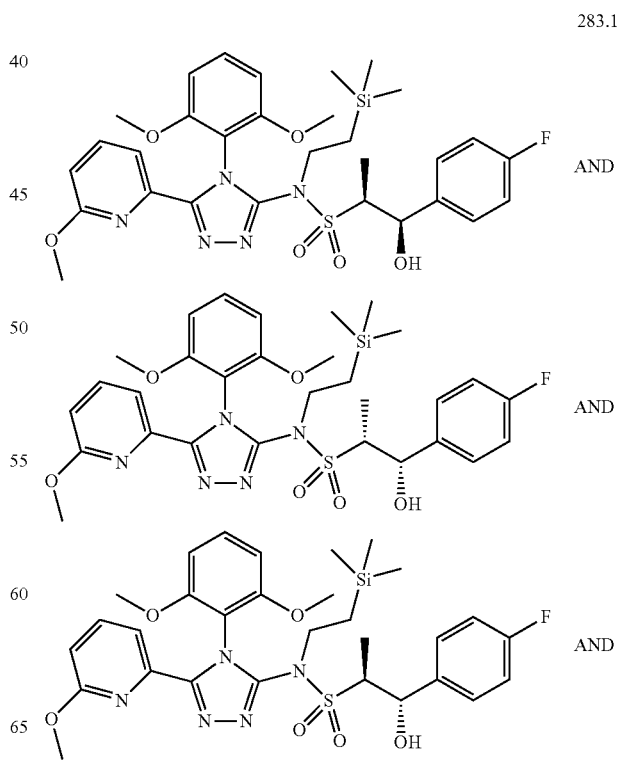

283.1

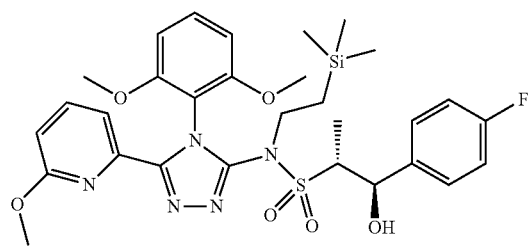

(1R,2R)—N-(4-(2,6-dimethoxyphenyl)-5-(6-methoxypyridin-2-yl)-4H-1,2,4-triazol-3-yl)-1-(4-fluorophenyl)-1-hydroxy-N-(2-(trimethylsilyl)ethyl)propane-2-sulfonamide and (1R,2S)—N-(4-(2,6-dimethoxyphenyl)-5-(6-methoxypyridin-2-yl)-4H-1,2,4-triazol-3-yl)-1-(4-fluorophenyl)-1-hydroxy-N-(2-(trimethylsilyl)ethyl)propane-2-sulfonamide and (1S,2R)—N-(4-(2,6-dimethoxyphenyl)-5-(6-methoxypyridin-2-yl)-4H-1,2,4-triazol-3-yl)-1-(4-fluorophenyl)-1-hydroxy-N-(2-(trimethylsilyl)ethyl)propane-2-sulfonamide and (1S,2S)—N-(4-(2,6-dimethoxyphenyl)-5-(6-methoxypyridin-2-yl)-4H-1,2,4-triazol-3-yl)-1-(4-fluorophenyl)-1-hydroxy-N-(2-(trimethylsilyl)ethyl)propane-2-sulfonamide, Example 283.1

The title compound was prepared from (Example 5.0) (401 mg, 0.77 mmol) and 4-fluorobenzaldehyde (115 mg, 0.93 mmol, commercially available from Sigma-Aldrich Corp., St. Louis, Mo., USA), using the procedure described in Example C. The title compound 283.1 (451 mg, 0.701 mmol, 91% yield) was obtained as an off-white solid. LCMS-ESI (POS), m/z: 644.3 (M+H)+.

283.0

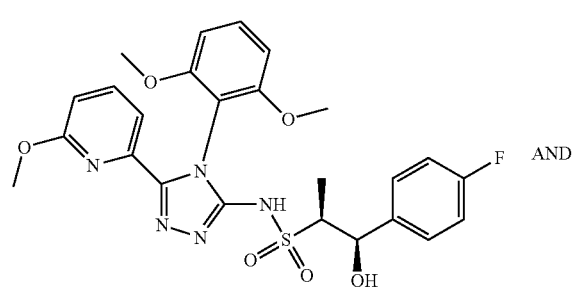 AND

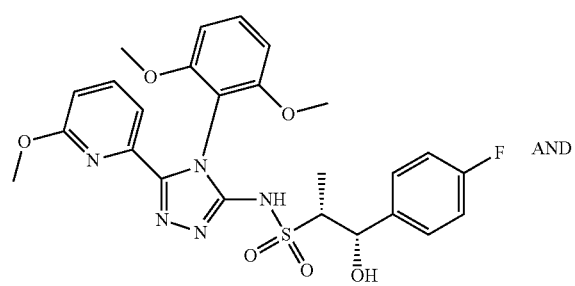 AND

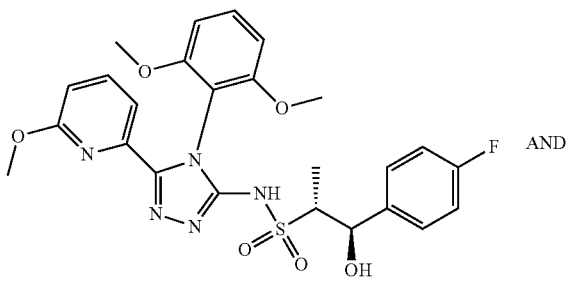 AND

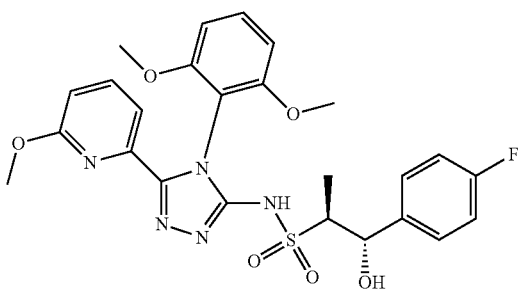

(1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide and (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide and (1R,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide and (1S,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide, Example 283.0

The title compound was prepared from 283.1 (445 mg, 0.69 mmol), using the procedure described in Example 279.2. This provided the title compound 283.0 (236 mg, 0.43 mmol, 63% yield) as a white crystalline solid. LCMS-ESI (POS), m/z: 544.2 (M+H)+.

Example 284.0: Preparation of (1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide

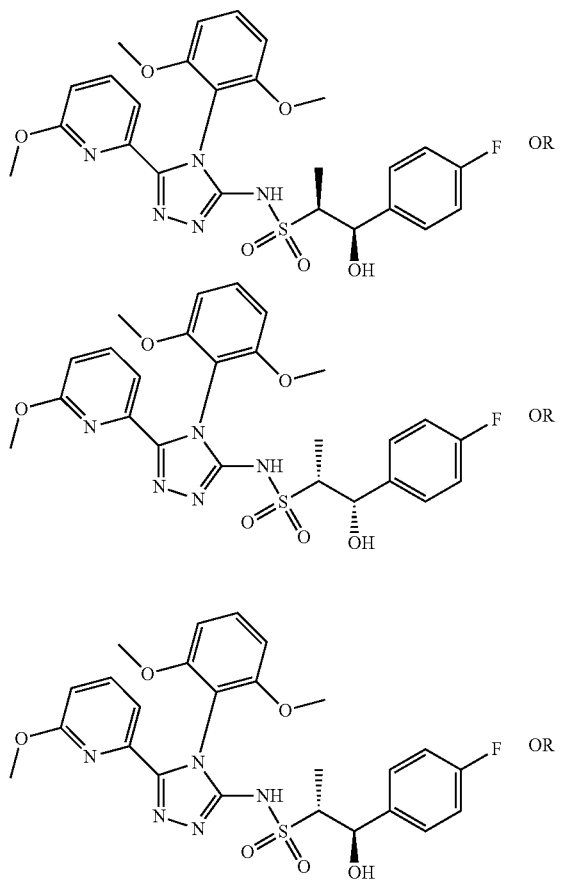

284.0

(1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide, Example 284.0

The mixture of four isomers (Example 283.0) was purified by SFC chiral separation in three steps and four pure enantiomers were obtained. Step 1. Separation of 284.0 (first eluent from OD-H column in analytical chiral HPLC) and 285.0 (2nd eluent from OD-H column in analytical chiral HPLC) from 286.0 (third eluent from OD-H column in analytical chiral HPLC) and 287.0 (fourth eluent from OD-H column in analytical chiral HPLC) by preparative method: OD-H column (2×25 cm 3×15 cm), 15% EtOH/CO$_2$, 100 bar, 65 mL/min, 220 nM. Injection vol. 0.75 mL, 4 mg/mL 1:4 DCM/MeOH. Step. 2. Separation of Example 286.0 from Example 287.0 by preparative method: IC-column (2×15 cm), 20% EtOH/CO$_2$, 100 bar, 65 mL/min, 220 nM. Step 3. Re-work of Example 285.0 by preparative method: AD-H column (2×15 cm), 35% EtOH/CO$_2$, 100 bar, 65 mL/min.

Example 284.0 was the first enantiomer to elute from OD-H column (Step 1.) as described above. $^1$H NMR (400 MHz, DMSO-d$_6$) δ 13.41 (s, 1H) 7.81 (dd, J=8.22, 7.43 Hz, 1H) 7.59 (dd, J=7.43, 0.39 Hz, 1H) 7.42 (t, J=8.51 Hz, 1H) 7.28 (dd, J=6.54 Hz, 2H) 7.14 (t, J=8.35 Hz, 2H) 6.83 (d, J=8.41 Hz, 1H) 6.80 (d, J=8.41 Hz, 2H) 5.24 (br. s., 1H) 4.90 (d, J=3.52 Hz, 1H) 3.65-3.68 (m, 3H) 3.64 (s, 3H) 3.10 (s, 3H) 3.02 (qd, J=6.91, 1.56 Hz, 1H) 1.02 (d, J=7.04 Hz, 3H). LCMS-ESI (POS.) m/z: 544.1 (M+H)$^+$.

Example 285.0: Preparation of (1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide

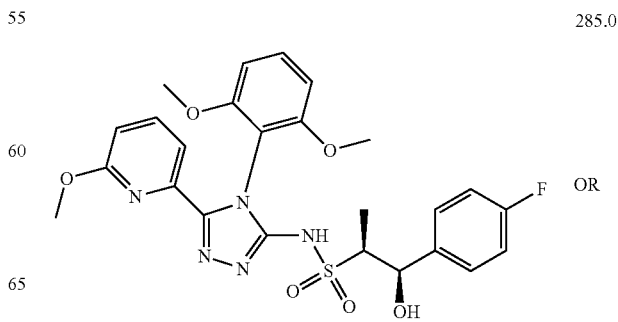

285.0

-continued

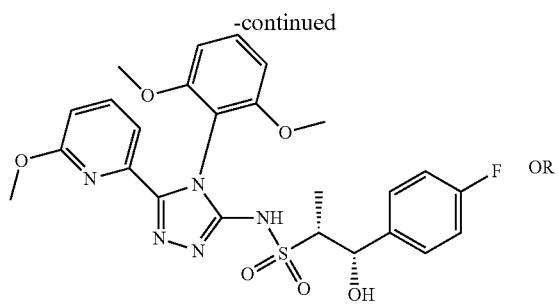

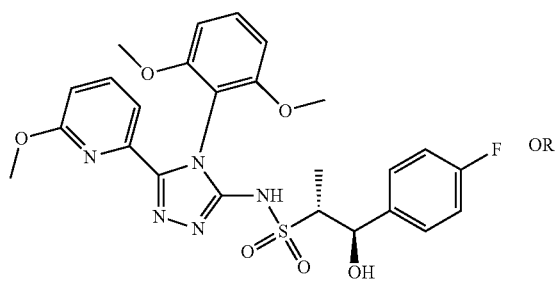

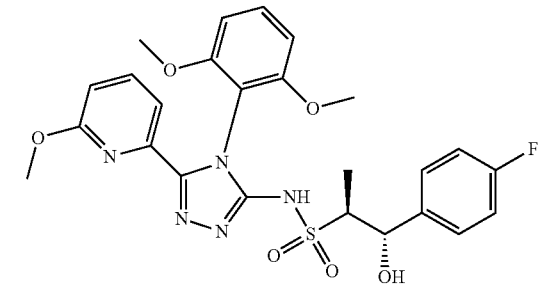

(1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide, Example 285.0

Example 285.0 is the enantiomer of 284.0. Example 285.0 was the second enantiomer to elute from OD-H column (Step L), and then repurified by AD-H column (Step 3.) as described above in Example 284.0. LCMS-ESI (POS.) m/z: 544.1 (M+H)$^+$.

Example 286.0: Preparation of (1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide 286.0

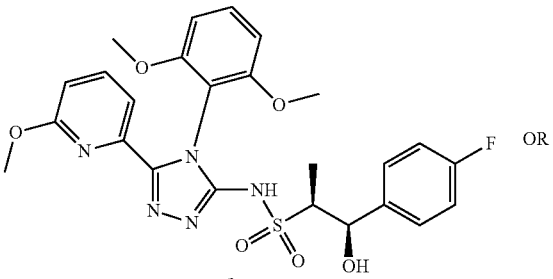

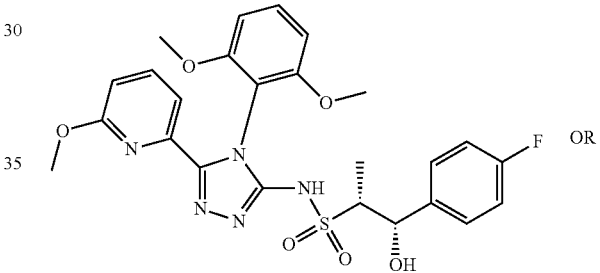

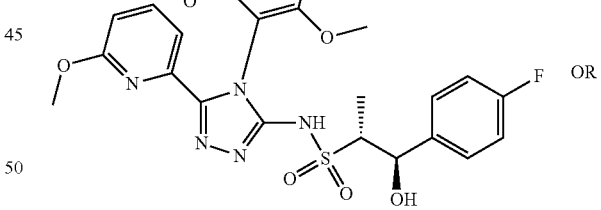

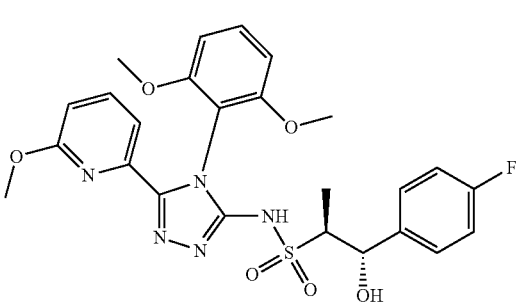

(1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide, Example 286.0

Example 286.0 was the first enantiomer to elute from the IC column (Step 2.) as described above in Example 284.0. $^1$H NMR (400 MHz, DMSO-$d_6$) δ 13.45 (s, 1H) 7.76-7.85 (m, 1H) 7.59 (d, J=7.17 Hz, 1H) 7.42 (t, J=8.25 Hz, 1H) 7.29 (dd. J=8.61, 5.67 Hz, 2H) 7.09 (t, J=8.22 Hz, 2H) 6.80-6.85 (m, 2H) 6.79 (d, J=2.93 Hz, 1H) 5.30 (br. s., 1H) 4.88 (dd. J=6.06, 1.96 Hz, 1H) 3.68 (s, 3H) 3.64 (s, 3H) 3.23-3.29 (m, 1H) 3.10 (s, 3H) 0.87 (d, J=7.04 Hz, 3H). LCMS-ESI (POS.) m/z: 544.2 (M+H)$^+$.

Example 287.0: Preparation of (1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide 287.0

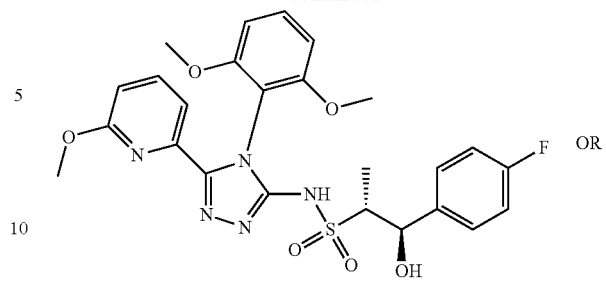

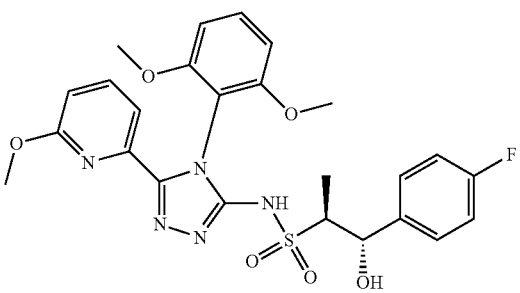

(1R,2S)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluorophenyl)-1-hydroxypropane-2-sulfonamide or (1R,2R)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide or (1S,2S)—N-(4-(2,6-(trimethoxyphenyl)-5-(6-methoxypyridin-2-yl)-4H-1,2,4-triazol-3-yl)-1-(4-fluorophenyl)-1-hydroxypropane-2-sulfonamide, Example 287.0

Example 287.0 is the enantiomer of 286.0. Example 287.0 was the second enantiomer to elute from IC column (Step 2.) described above in Example 284.0. LCMS-ESI (POS.) m/z: 544.2 (M+H)$^+$.

Example 288.0: Preparation of (1R,2S)—N-(4-(2,6-(trimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide and (1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide and (1R,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide and (1S,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide (1R,2R)-1-(2-bromo-4-fluorophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (1R,2S)-1-(2-bromo-4-fluorophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (1S,2R)-1-(2-bromo-4-fluorophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (1S,2S)-1-(2-bromo-4-fluorophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide, Example 288.1

The title compound was prepared from Example 5.0 (1.01 g, 1.94 mmol) and 2-bromo-4-fluorobenzaldehyde (0.473 g, 2.33 mmol, commercially available from Oakwood Products, Inc., West Columbia, S.C., USA) using the procedure described in Example C. This provided the title compound 288.1 (1.29 g, 1.79 mmol, 92% yield) as a white foam. LCMS-ESI (POS), m/z: 722.2 (M+H)$^+$.

288.1

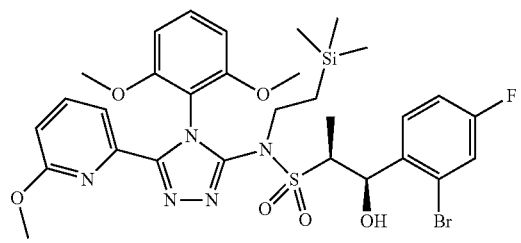

AND

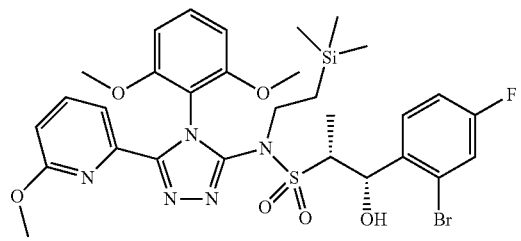

AND

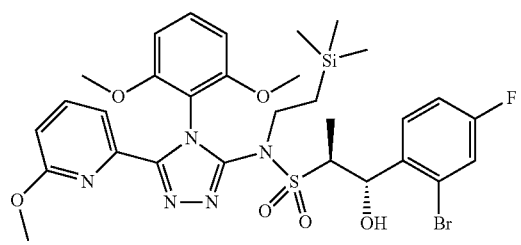

AND

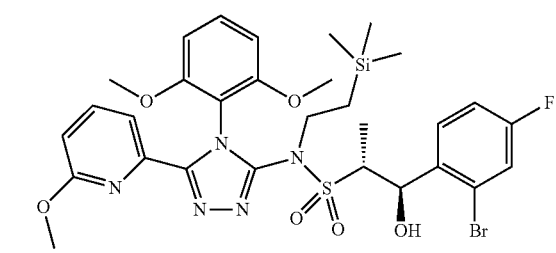

288.2

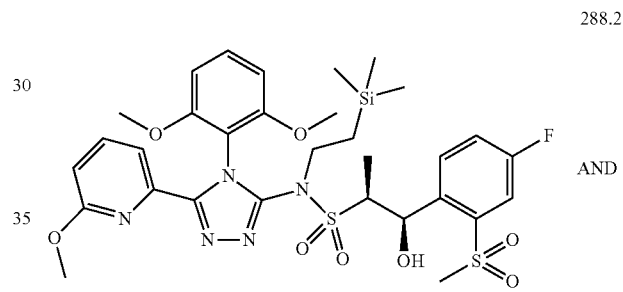

AND


AND


AND

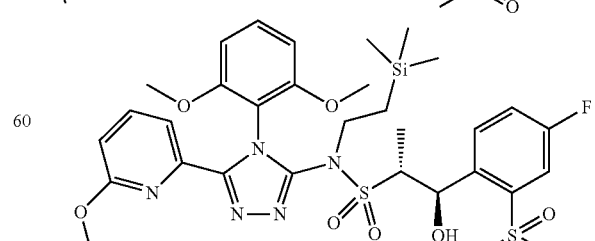

(1R,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxy-N-(2-(trimethylsilyl)ethyl)propane-2-sulfonamide and
(1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxy-N-(2-(trimethylsilyl)ethyl)propane-2-sulfonamide and
(1R,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxy-N-(2-(trimethylsilyl)ethyl)propane-2-sulfonamide and
(1S,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxy-N-(2-(trimethylsilyl)ethyl)propane-2-sulfonamide,
Example 288.2

A mixture of sodium methanesulfinate (332 mg, 2.77 mmol, commercially available from Sigma-Aldrich Corp., St. Louis, Mo., USA), copper(I) iodide (52.7 mg, 0.28 mmol, commercially available from Strem Chemicals Inc., Newburyport, Mass. USA) and N, N'-dimethylethylenediamine (59.6 μL, 0.55 mmol, commercially available from Sigma-Aldrich Corp., St. Louis, Mo., USA) in DMSO (5.5 mL) was bubbled with $N_2$ for 2 min. To the mixture was added 1-(2-bromo-4-fluorophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide 288.1 (400 mg, 0.55 mmol), and nitrogen was bubbled through the mixture for another minute. The mixture was then heated at 110° C. for 16 h. The reaction was quenched with saturated $NH_4C_1$ (35 mL) and extracted with EtOAc (35 mL). The organic extract was washed with saturated $NH_4Cl$ (3×30 mL), dried over $Na_2SO_4$, filtered and concentrated in vacuo. The residue was purified on a 24 g silica gel column, gradient eluenting with 0-50% EtOAc/Hexanes provided the title compound 288.2 (233 mg, 0.323 mmol, 58% yield) as a white solid. LCMS-ESI (POS), m/z: 722.2 (M+H)$^+$.

288.0

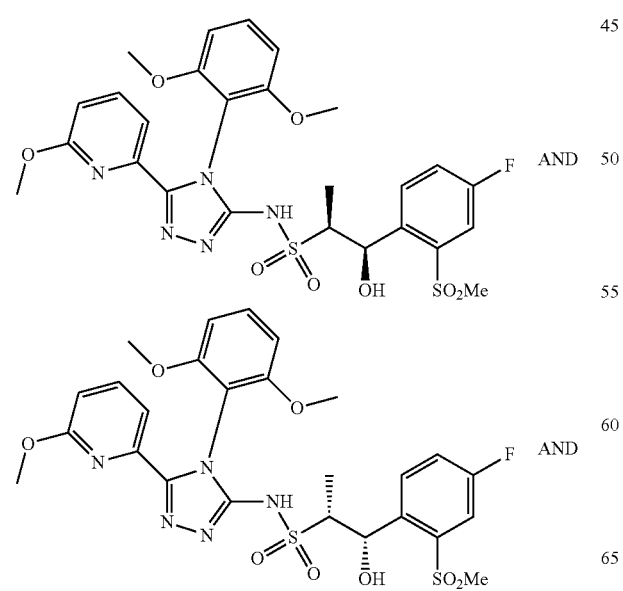

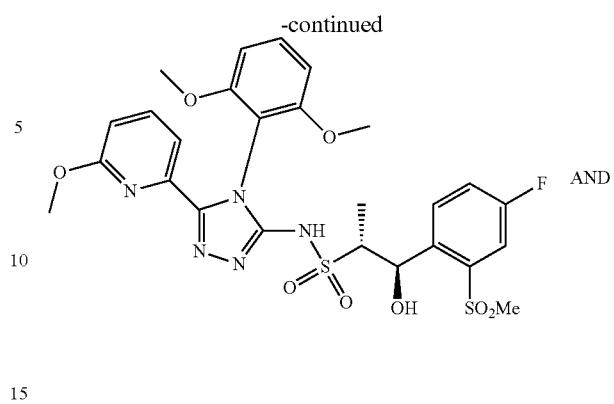

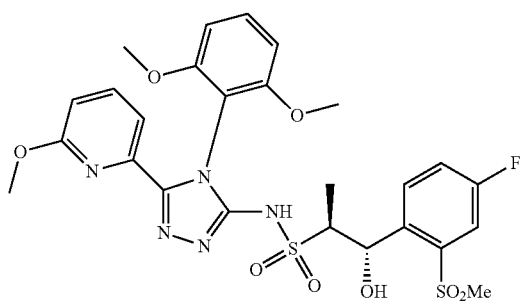

(1R,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide and (1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide and (1R,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide and (1S,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide, Example 288.0

The title compound was prepared from Example 288.2 (257 mg, 0.36 mmol) using the procedure described in Example 279.2. This provided the title compound 288.0 (160 mg, 0.26 mmol, 72% yield) as a white solid. LCMS-ESI (POS), m/z: 622.1 (M+H)$^+$. The mixture of four diastereomers 288.0 was purified by SFC chiral separation. Two major diastereomers were obtained pure, however the two minor diastereomers were accidentally lost during the chiral separation.

447

Example 289.0: Preparation of (1R,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide

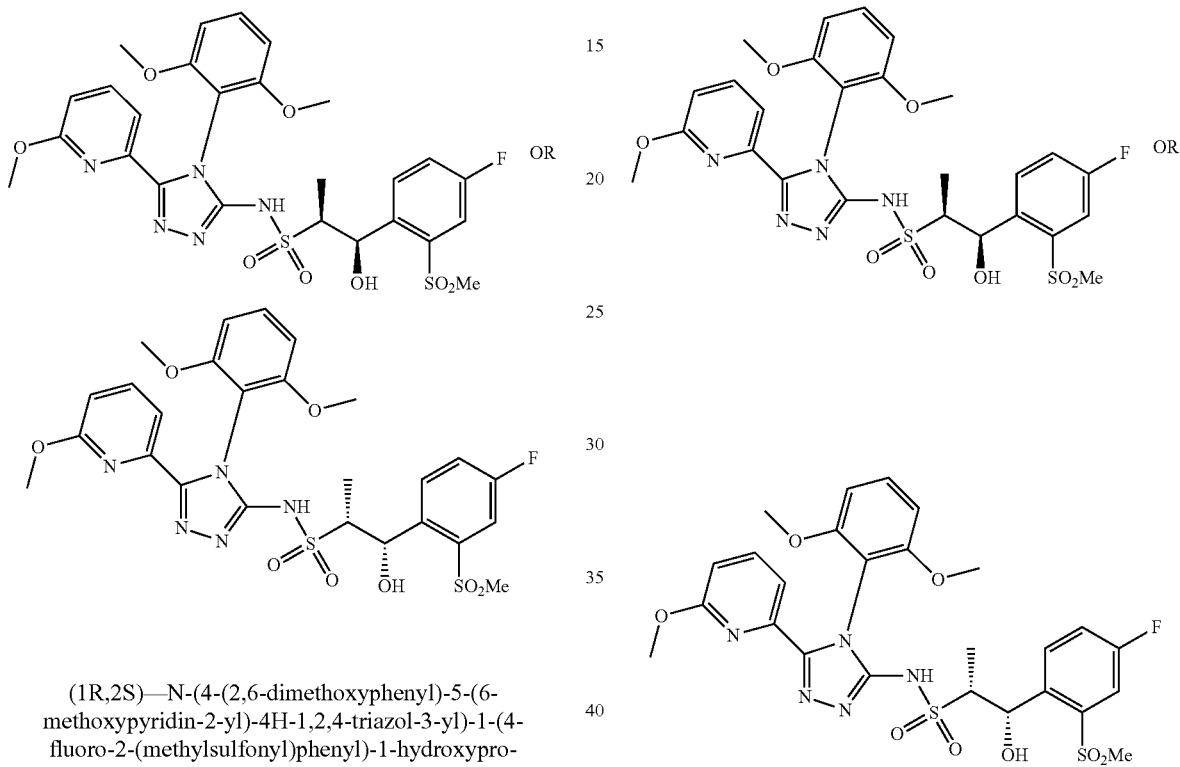

(1R,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide, Example 289.0

The title compound 289.0 was the first major isomer to elute under the following SFC conditions: IC (10 um, 21 mm×25 cm, S/N=2271) with 45% organic modifier modifier: 55% carbon dioxide. Organic modifier: MeOH with 20 mM ammonia. F=60 mL/min, T=40° C., BPR=100 bar, P=186 bar, 220 nm. Inj. Vol. 1.2 mL, c=1.8 mg/mL of 288.0 in MeOH/DCM (4:6). The compound was furthered purified as second eluent by OZ—H (10 um, 21 mm×25 cm, S/N=1051) with 45% organic modifier modifier: 55% carbon dioxide. Organic modifier: MeOH with 20 mM ammonia. F=60 mL/min, T=40° C., BPR=100 bar, P=206 bar, 220 nm. Inj. Vol. 1.2 mL, c=6.0 mg/mL in MeOH. $^1$H NMR (400 MHz, DMSO-$d_6$) δ 13.22 (br. s., 1H) 7.76-7.84 (m, 2H) 7.63 (dd, J=8.80, 2.74 Hz, 1H) 7.55-7.61 (m, 2H) 7.41 (t, J=8.17 Hz, 1H) 6.81 (d, J=8.02 Hz, 2H) 6.78 (d, J=8.61 Hz, 1H) 5.86 (br. s., 1H) 5.25 (br. s., 1H) 3.71 (s, 3H) 3.63 (s, 3H) 3.37-3.42 (m, 1H) 3.20 (s, 3H) 3.10 (s, 3H) 1.19 (d, J=6.85 Hz, 3H). LCMS-ESI (POS), m/z: 622.1 (M+H)$^+$.

448

Example 290.0: Preparation of (1R,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide (1R,2S)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide or (1S,2R)—N-(4-(2,6-dimethoxyphenyl)-5-(6-methoxypyridin-2-yl)-4H-1,2,4-triazol-3-yl)-1-(4-fluoro-2-(methylsulfonyl)phenyl)-1-hydroxypropane-2-sulfonamide, Example 290.0

Example 290.0 is the enantiomer of Example 289.0. Example 290.0 was the second major isomer to elute under the following SFC conditions: IC (10 um, 21 mm×25 cm, S/N=2271) with 45% organic modifier modifier: 55% carbon dioxide. Organic modifier: MeOH with 20 mM ammonia. F=60 mL/min, T=40 C, BPR=100 bar, P=186 bar, 220 nm. Inj. Vol. 1.2 mL, c=1.8 mg/mL in MeOH/DCM (4:6). $^1$H NMR (400 MHz, DMSO-$d_6$) δ 13.22 (br. s., 1H) 7.76-7.84 (m, 2H) 7.63 (dd, J=8.90, 2.84 Hz, 1H) 7.55-7.61 (m, 2H) 7.41 (t, J=8.51 Hz, 1H) 6.80 (d, J=8.22 Hz, 2H) 6.78 (d, J=8.61 Hz, 1H) 5.87 (br. s., 1H) 5.25 (br. s., 1H) 3.71 (s, 3H) 3.63 (s, 3H) 3.37-3.42 (m, 1H) 3.21 (s, 3H) 3.10 (s, 3H) 1.19 (d, J=6.85 Hz, 3H). LCMS-ESI (POS), m/z: 622.1 (M+H)$^+$.

Example 291.0: Preparation of [(1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide and (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide] or [(1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide]

291.1

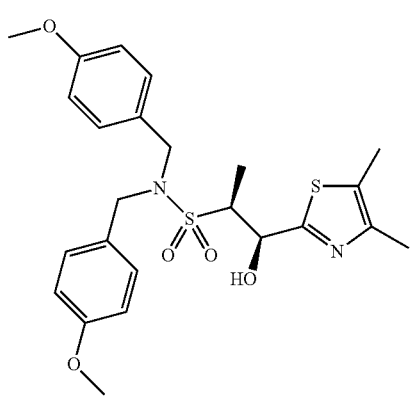

AND

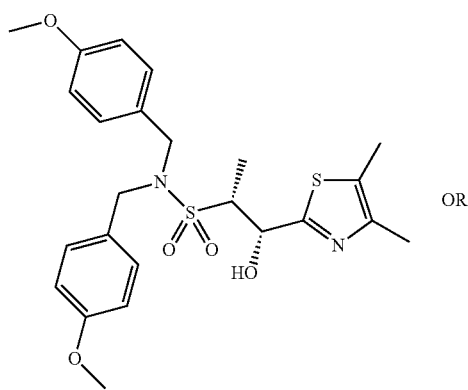

OR

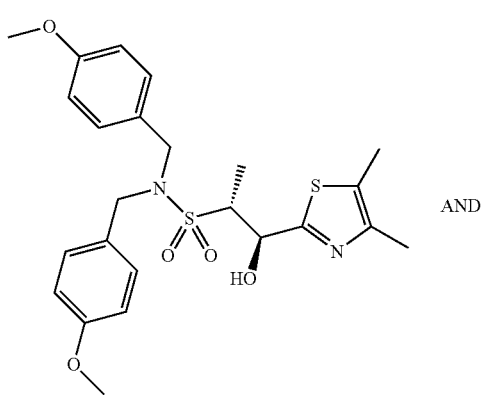

AND

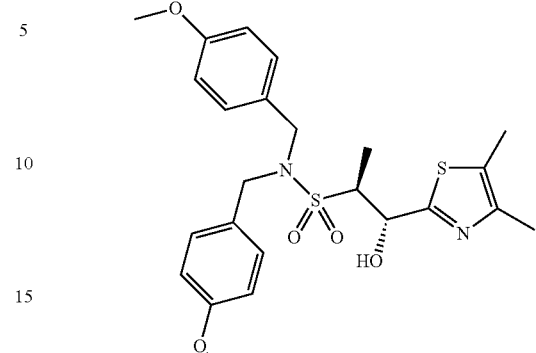

[(1S,2S)-1-(4,5-dimethylthiazol-2-yl)-1-hydroxy-N,N-bis(4-methoxybenzyl)propane-2-sulfonamide and (1R,2R)-1-(4,5-dimethylthiazol-2-yl)-1-hydroxy-N,N-bis(4-methoxybenzyl)propane-2-sulfonamide] or [(1S,2R)-1-(4,5-dimethylthiazol-2-yl)-1-hydroxy-N,N-bis(4-methoxybenzyl)propane-2-sulfonamide and (1R,2S)-1-(4,5-dimethylthiazol-2-yl)-1-hydroxy-N,N-bis(4-methoxybenzyl)propane-2-sulfonamide], Example 291.1

To a solution of N,N-bis(4-methoxybenzyl)ethanesulfonamide (4.70 g, 13.5 mmol) (Example 12.0) in THF (75 mL) in a 500 mL round bottomed flask at −78° C., was injected dropwise n-butyllithium (2.5M solution in hexanes (5.92 mL, 14.79 mmol)) (commercially available from Sigma-Aldrich Corp., St. Louis, Mo., USA). The resulting mixture was stirred for 20 min at −78° C. To this was added a solution of 4,5-dimethylthiazole-2-carbaldehyde (1.90 g, 13.5 mmol, commercially available from Sigma-Aldrich Corp., St. Louis, Mo., USA) in THF (25 mL) which was injected dropwise at −78° C. The reaction was stirred at −78° C. for 1 h. The reaction was then quenched with saturated aqueous $NH_4C_1$ (150 mL) and diluted with EtOAc (200 mL) and water (50 mL). The two layers were separated. The aqueous layer was further extracted with EtOAc (50 mL). The combined organic layers were dried over $Na_2SO_4$. The solution was filtered and concentrated in vacuo to give the initial material as light orange oil. The material thus obtained was absorbed onto a plug of silica gel and purified by chromatography through a Redi-Sep pre-packed silica gel column (220 g), eluting with a gradient of 0-100% EtOAc in hexanes, to provide the title compound 291.1 (3.33 g, 6.79 mmol, 51% yield) as an off-white solid, LCMS-ESI (POS.) m/z: 490.9 $(M+H)^+$.

291.2

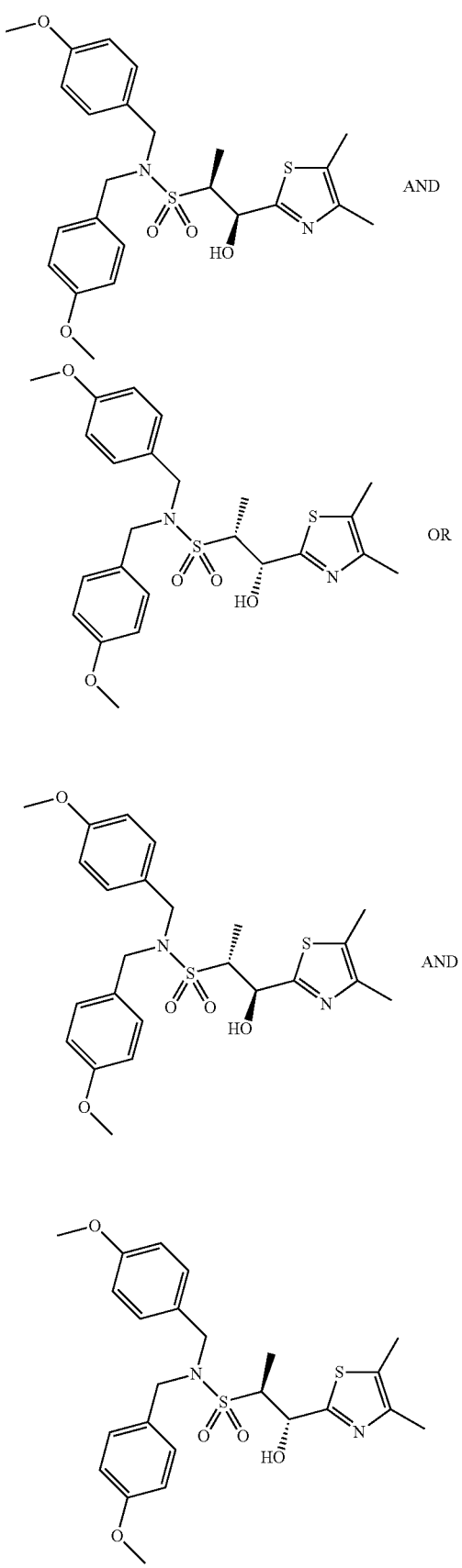

[(1S,2S)-1-(4,5-dimethylthiazol-2-yl)-1-hydroxy-N,N-bis(4-methoxybenzyl)propane-2-sulfonamide and (1R,2R)-1-(4,5-dimethylthiazol-2-yl)-1-hydroxy-N,N-bis(4-methoxybenzyl)propane-2-sulfonamide] or [(1S,2R)-1-(4,5-dimethylthiazol-2-yl)-1-hydroxy-N,N-bis(4-methoxybenzyl)propane-2-sulfonamide and (1R,2S)-1-(4,5-dimethylthiazol-2-yl)-1-hydroxy-N,N-bis(4-methoxybenzyl)propane-2-sulfonamide], Example 291.2

Example 291.2 (the diastereomer of 291.1) was further eluted with a gradient of 0-100% EtOAc in hexanes, to provide the title compound (1.61 g, 3.28 mmol, 24% yield) as an off-white solid, LCMS-ESI (POS.) m/z: 490.9 (M+H)⁺.

291.3

[(1S,2S)-1-(4,5-dimethylthiazol-2-yl)-1-hydroxypropane-2-sulfonamide and (1R,2R)-1-(4,5-dimethylthiazol-2-yl)-1-hydroxypropane-2-sulfonamide] or [(1S,2R)-1-(4,5-dimethylthiazol-2-yl)-1-hydroxypropane-2-sulfonamide and (1R,2S)-1-(4,5-dimethylthiazol-2-yl)-1-hydroxypropane-2-sulfonamide], Example 291.3

To a solution of 1-(4,5-dimethylthiazol-2-yl)-1-hydroxy-N,N-bis(4-methoxybenzyl)propane-2-sulfonamide, Example 291.1 (675 mg, 1.38 mmol) in DCM (5 mL), was added anhydrous anisole (0.598 mL, 5.50 mmol, commercially available from Sigma-Aldrich Corp., St. Louis, Mo., USA) followed by adding TFA (protein sequencer grade, 5.11 mL, 68.8 mmol, commercially available from Sigma-Aldrich Corp., St. Louis, Mo., USA) dropwise. The reaction mixture was then stirred at RT for 25 h. The reaction was concentrated in vacuo at 36° C. The material thus obtained was absorbed onto a plug of silica gel and purified by chromatography through a Redi-Sep pre-packed silica gel column (12 g), eluting with a gradient of 0-40% EtOAc:EtOH (3:1) in DCM, to provide an orange oil, which was triturated with diethyl ether (2 mL) to give the title compound 291.3 (318 mg, 1.27 mmol, 92% yield) as a white solid. ¹H NMR (500 MHz, DMSO-d₆) δ 6.73 (s, 2H) 6.35 (d, J=5.50

Hz, 1H) 5.38 (d, J=3.30 Hz, 1H) 3.51 (qd, J=6.70, 1.34 Hz, 1H) 2.29 (s, 3H) 2.20-2.22 (m, 3H) 1.13 (d, J=6.97 Hz, 3H). LCMS-ESI (POS.) m/z: 250.9 (M+H)+.

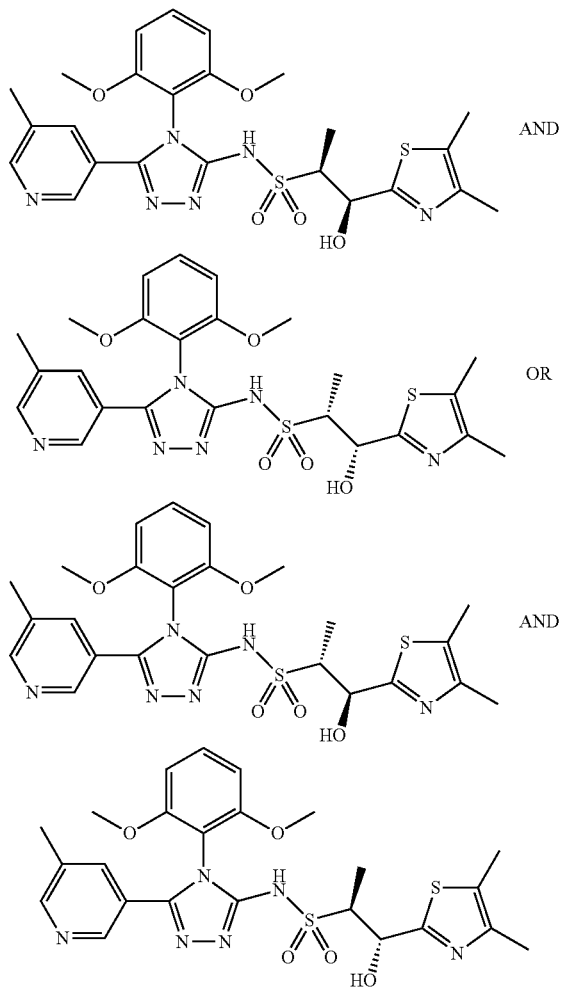

[(1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide and (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide] or [(1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide, Example 291.0

A suspension of 3-(5-bromo-4-(2,6-dimethoxyphenyl)-4H-1,2,4-triazol-3-yl)-5-methylpyridine (270 mg, 0.72 mmol) (Example 2.0), 1-(4,5-dimethylthiazol-2-yl)-1-hydroxypropane-2-sulfonamide (120 mg, 0.48 mmol) 291.3, cesium carbonate (469.2 mg, 1.44 mmol, commercially available from Sigma-Aldrich Corp., St. Louis, Mo., USA) and copper(i) iodide (110 mg, 0.58 mmol, commercially available from Strem Chemicals Inc., Newburyport, Mass., USA) in ACN (2.40 mL) was degassed in a N$_2$ stream. To the mixture was then added trans-N, N'-dimethyl-1,2-cyclohexanesdiamine (181 µL, 1.15 mmol) (commercially available from Sigma-Aldrich Corp., St. Louis, Mo., USA). The mixture was heated to 80° C. in a pre-heated heating block for 18 h. The reaction was diluted with saturated NH$_4$Cl (aqueous) (10 mL) and stirred vigorously for 10 min. The reaction mixture was then diluted with water (5 mL) and extracted with DCM (3×15 mL). The combined organic layers were dried over Na$_2$SO$_4$, filtered, and evaporated in vacuo. The material thus obtained was absorbed onto a plug of silica gel and purified by chromatography through a Redi-Sep pre-packed silica gel column (12 g), eluting with a gradient of 0-100% EtOAc:EtOH (3:1) in hexanes to provide enriched product, which was triturated by diethyl ether (2 mL) to provide the title compound 291.0 (73 mg, 0.13 mmol, 28% yield) as a white solid. $^1$H NMR (DMSO-d$_6$) δ: 13.49 (br. s., 1H), 8.48 (d, J=1.3 Hz, 1H), 8.20 (d, J=1.8 Hz, 1H), 7.63 (s, 1H), 7.50 (t, J=8.3 Hz, 1H), 6.82 (d, J=8.6 Hz, 2H), 5.35 (s, 1H), 3.69 (s, 3H), 3.66 (s, 3H), 3.41-3.47 (m, 1H), 2.28 (s, 3H), 2.25 (s, 3H), 2.20 (s, 3H), 1.06 (d, J=7.0 Hz, 3H). LCMS-ESI (POS.) m/z: 545.2 (M+H)+.

Example 292.0: Preparation of (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide] or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide

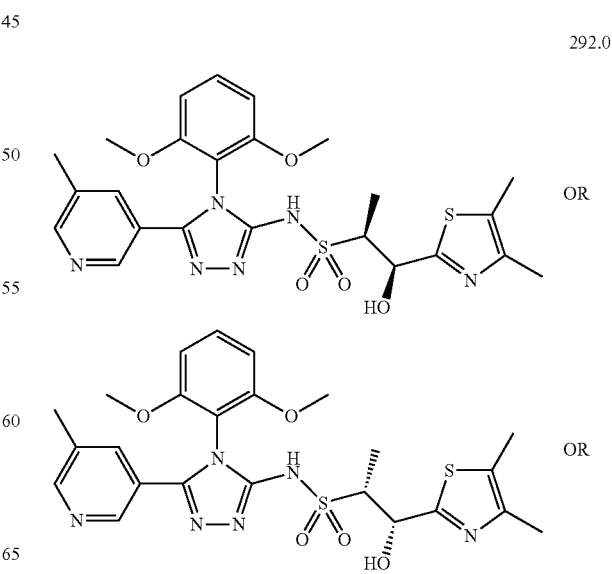

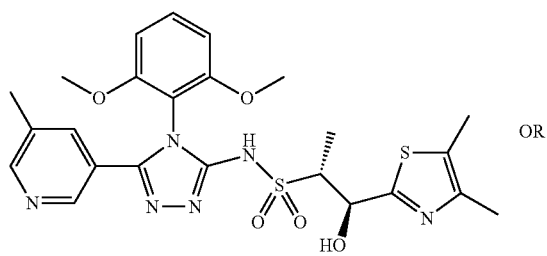

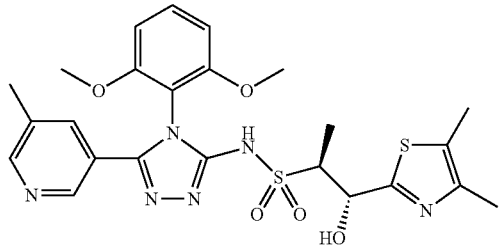

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide or (1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide] or (1S,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide or (1R,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide, Example 292.0

Purification of 291.0 resulted in the title compound 292.0 which was the first isomer to elute under the following SFC conditions: Run on Thar 80 SFC with 250×21 mm IA column with 24.0 mL/min MeOH (neat)+51.0 g/min CO₂, 32% co-solvent at 75 g/min. Temperature.=35° C., Outlet pressure=100 bar, Wavelength=260 nm. Injected 0.35 mL of sample solution (65 mg of 291.0 in 10.0 mL of MeOH); c=6.5 mg/mL and 2.28 mg per injection. Cycle time=4.5 min, run time 6.0 min. ¹H NMR (MeOH) δ: 8.43 (s, 1H), 8.31 (s, 1H), 7.71 (s, 1H), 7.50 (t, J=8.4 Hz, 1H), 6.80 (dd, J=8.4, 6.1 Hz, 2H), 5.52 (s, 1H), 3.77 (s, 3H), 3.74 (s, 3H), 3.59 (qd, J=7.0, 1.2 Hz, 1H), 2.33 (s, 3H), 2.30 (s, 3H), 2.26 (s, 3H), 1.19 (d, J=7.1 Hz, 3H). LCMS-ESI (POS.) m/z: 545.0 (M+H)⁺.

Example 293.0: Preparation of (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide 293.0

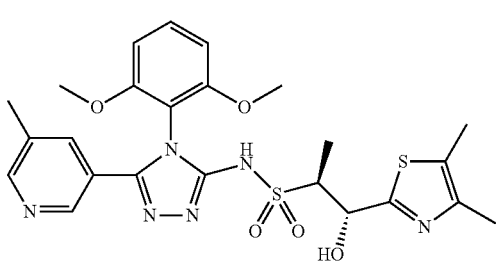

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide or (1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide or (1S,2R)—N-(4-(2,6-dimethoxyphenyl)-5-(5-methyl-pyridin-3-yl)-4H-1,2,4-triazol-3-yl)-1-(4,5-(dimeth-ylthiazol-2-yl)-1-hydroxypropane-2-sulfonamide or (1R,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide, Example 293.0

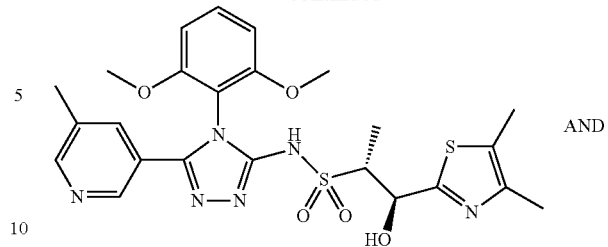

-continued

AND

Example 293.0 is the enantiomer of 292.0. Further purification of 291.0 resulted in 293.0 which was the second isomer to elute from the IA column on subjecting 291.0 to the SFC conditions described in Example 292.0. $^1$H NMR (MeOH) δ: 8.43 (s, 1H), 8.31 (s, 1H), 7.71 (s, 1H), 7.50 (t, J=8.3 Hz, 1H), 6.80 (dd. J=8.4, 5.9 Hz, 2H), 5.52 (s, 1H), 3.77 (s, 3H), 3.74 (s, 3H), 3.60 (qd, J=7.1, 1.3 Hz, 1H), 2.33 (s, 3H), 2.30 (s, 3H), 2.26 (s, 3H), 1.19 (d, J=7.0 Hz, 3H). LCMS-ESI (POS.) m/z: 545.2 (M+H)$^+$.

Example 294.0: Preparation of (1S,2S)—N-(4-(2,6-dimethoxyphenyl)-5-(5-methylpyridin-3-yl)-4H-1,2,4-triazol-3-yl)-1-(4,5-(dimethylthiazol-2-yl)-1-hydroxypropane-2-sulfonamide and (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1S,2R)—N-(4-(2,6-dimethoxyphenyl)-5-(5-methylpyridin-3-yl)-4H-1,2,4-triazol-3-yl)-1-(4,5-(dimethylthiazol-2-yl)-1-hydroxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide 294.0

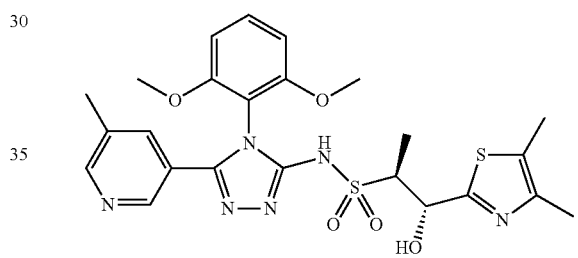

AND

[(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide and (1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide] or [(1S,2R)—N-(4-(2,6-dimethoxyphenyl)-5-(5-meth-ylpyridin-3-yl)-4H-1,2,4-triazol-3-yl)-1-(4,5-dimeth-ylthiazol-2-yl)-1-hydroxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfona-mide, Example 294.0

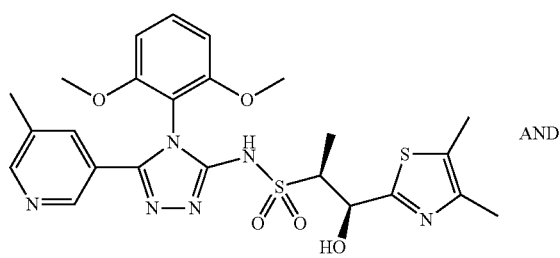

OR

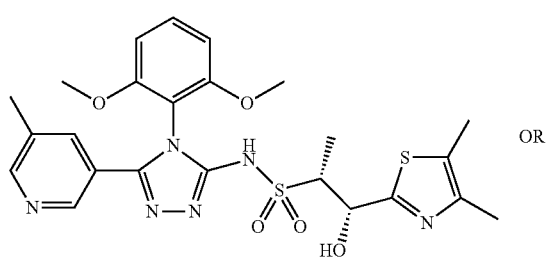

Example 294.0 is a diastereomers of 291.0. Example 294.0 was prepared from 291.2, using the procedure described in Example 291.0. $^1$H NMR (DMSO-d$_6$) δ: 13.54 (br. s., 1H), 8.50 (br. s., 1H), 8.22 (br. s., 1H), 7.63 (s, 1H), 7.51 (t, J=8.5 Hz, 1H), 6.84 (dd, J=8.6, 3.9 Hz, 2H), 4.91 (d, J=7.1 Hz, 1H), 3.74 (s, 3H), 3.73 (s, 3H), 3.20-3.26 (m, 1H), 2.30 (s, 3H), 2.26 (s, 3H), 2.21 (s, 3H), 1.06 (d, J=7.1 Hz, 3H). LCMS-ESI (POS.) m/z: 545.2 (M+H)$^+$.

Example 295.0: Preparation of (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-hydroxypropane-2-sulfonamide or (1S,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-hydroxypropane-2-sulfonamide or (1R,2S)—N-(4-(2,6-(trimethoxyphenyl)-5-(5-methylpyridin-3-yl)-4H-1,2,4-triazol-3-yl)-1-(4,5-dimethylthiazol-2-yl)-1-hydroxypropane-2-sulfonamide

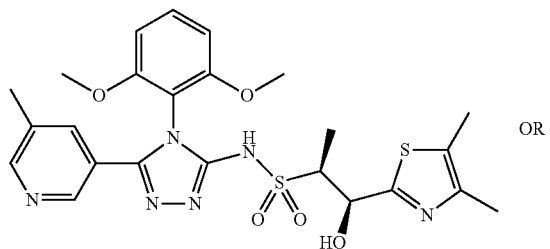

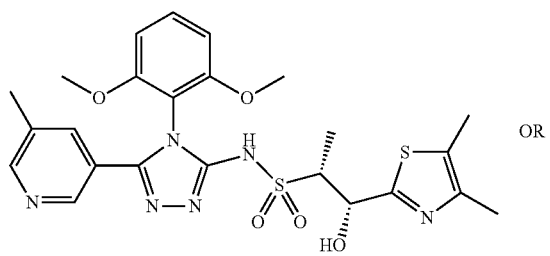

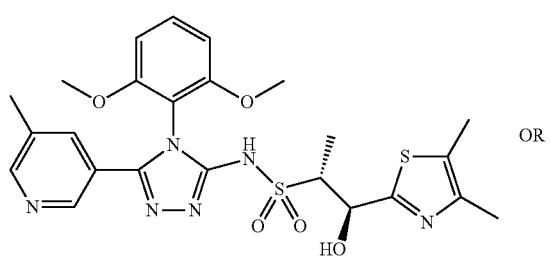

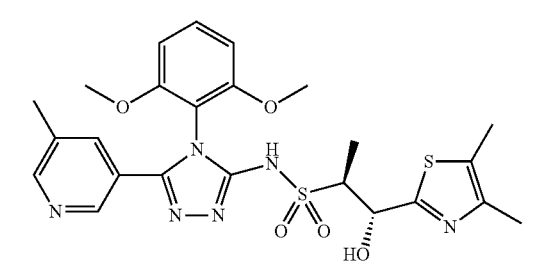

[(1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide] or [(1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide, Example 295.0

Example 295.0 is a diasteromer of Example 296.0. Purification of 294.0 resulted in the title compound 295.0 which was the first isomer to elute under the following SFC conditions: Stage L Run on Thar 200 SFC with 250×21 mm IA column with 24.0 mL/min MeOH (20 mM NH$_3$)+46.0 g/min CO$_2$, 35% co-solvent at 70 g/min. Temperature.=30° C., Outlet pressure=100 bar, Wavelength=263 nm. Injected 0.6 mL of 83 mg sample 294.0 dissolved in 15 mL 13:2 MeOH:DCM; c=5.53 mg/mL and 3.32 mg per injection. This material was re-purified on Thar 200 SFC with 250×21+150×21 mm IA columns with 18.0 mL/min MeOH (20 mM NH$_3$)+37.0 g/min CO$_2$, 32% co-solvent at 55 g/min. Temperature.=30° C., Outlet pressure=99-100 bar, Wavelength=263 nm. Injected 0.3 mL of 29 mg sample dissolved in 5 mL 4:1 MeOH:DCM; c=5.8 mg/mL and 1.74 mg per injection. $^1$H NMR (CD$_2$Cl$_2$) δ: 11.18 (br. s., 1H), 8.44 (d, J=1.5 Hz, 1H), 8.33 (d, J=1.7 Hz, 1H), 7.60 (dt, J=2.1, 1.0 Hz, 1H), 7.48 (t, J=8.4 Hz, 1H), 6.69 (dd, J=8.1, 5.1 Hz, 2H), 4.92 (d, J=8.7 Hz, 1H), 3.80 (s, 3H), 3.79 (s, 3H), 3.25-3.32 (m, 1H), 2.32 (s, 3H), 2.28 (s, 3H), 2.26 (s, 3H), 1.17 (d, J=7.0 Hz, 3H). LCMS-ESI (POS.) m/z: 545.3 (M+H)$^+$.

Example 296.0: Preparation of (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide

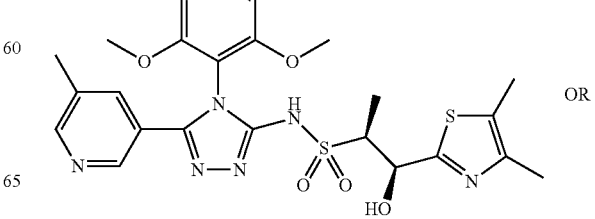

-continued

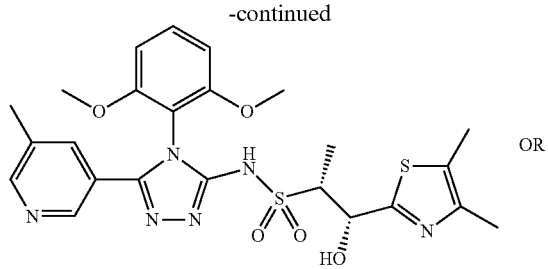

OR

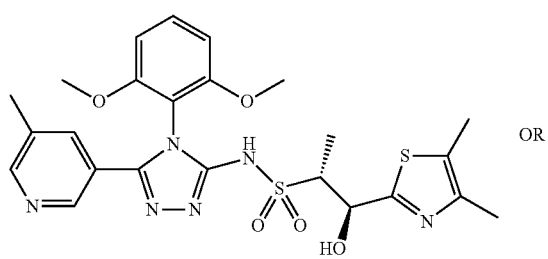

OR

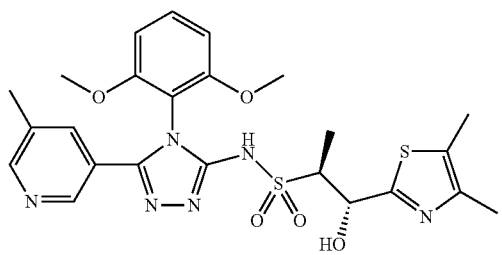

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide or (1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-hydroxypropane-2-sulfonamide or (1S,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-hydroxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-hydroxypropane-2-sulfonamide, Example 296.0

Example 296.0 is the enantiomer of 295.0. Further purification of Example 294.0 resulted in the 296.0 which was the second isomer to elute from the IA column on subjecting 294.0 to the SFC conditions described in 295.0. $^1$H NMR (CD$_2$Cl$_2$) δ: 11.13 (br. s., 1H), 8.44 (d, J=1.3 Hz, 1H), 8.33 (d, J=1.7 Hz, 1H), 7.59-7.61 (m, 1H), 7.48 (t, J=8.5 Hz, 1H), 6.69 (t, J=6.9 Hz, 2H), 4.91 (d, J=8.6 Hz, 1H), 3.80 (s, 3H), 3.79 (s, 3H), 3.25-3.32 (m, 1H), 2.32 (s, 3H), 2.28 (s, 3H), 2.26 (s, 3H), 1.17 (d, J=7.0 Hz, 3H). LCMS-ESI (POS.) m/z: 545.3 (M+H)$^+$.

Example 297.0: Preparation of (1S,2S)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide and (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide 297.1

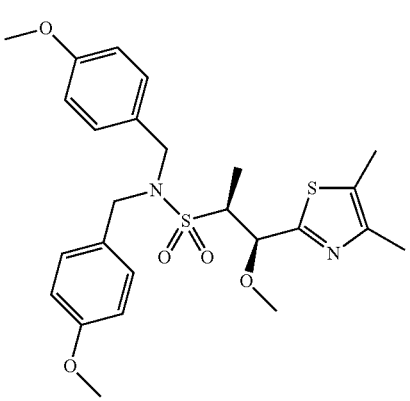

AND

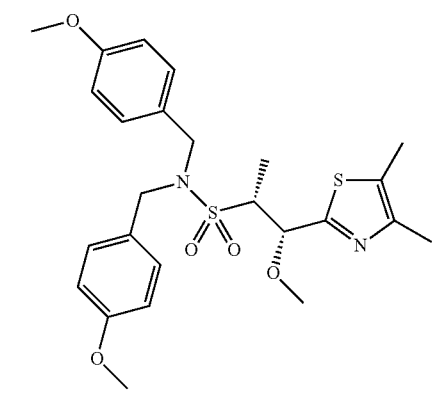

OR

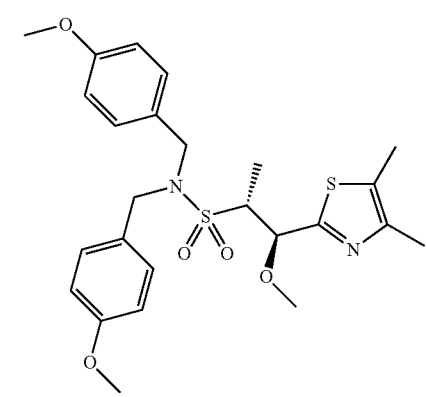

AND

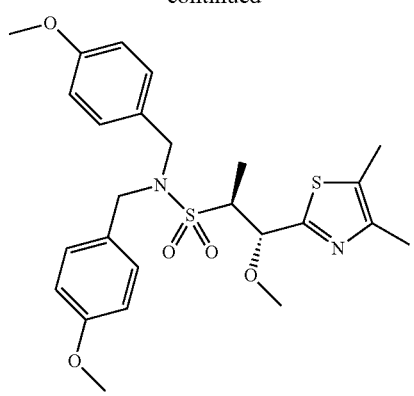

(1S,2S)-1-(4,5-dimethylthiazol-2-yl)-1-methoxy-N,
N-bis(4-methoxybenzyl)propane-2-sulfonamide and
(1R,2R)-1-(4,5-dimethylthiazol-2-yl)-1-methoxy-N,
N-bis(4-methoxybenzyl)propane-2-sulfonamide or
(1S,2R)-1-(4,5-dimethylthiazol-2-yl)-1-methoxy-N,
N-bis(4-methoxybenzyl)propane-2-sulfonamide and
(1R,2S)-1-(4,5-dimethylthiazol-2-yl)-1-methoxy-N,
N-bis(4-methoxybenzyl)propane-2-sulfonamide,
Example 297.1

1-(4,5-Dimethylthiazol-2-yl)-1-hydroxy-N,N-bis(4-methoxybenzyl)propane-2-sulfonamide (335 mg, 0.683 mmol) 291.1 (azeotroped with toluene before use) was dissolved in THF (3 mL), and the mixture was cooled to −78° C. To this was added potassium bis(trimethylsilyl) amide (1M in THF (0.82 mL, 0.82 mmol), commercially available from Sigma-Aldrich Corp., St. Louis, Mo., USA). The cold bath was then removed and the mixture was stirred for 25 min. The reaction mixture was re-cooled to −78° C. and a solution of iodomethane (0.064 mL, 1.02 mmol, commercially available from Sigma-Aldrich Corp., St. Louis, Mo., USA) in THF (1.0 mL) was added dropwise. The reaction was warmed to RT over 2 h. The reaction was quenched with a saturated $NH_4Cl$ solution (aqueous) (15 mL) and diluted with EtOAc (15 mL). The layers were separated and the organic layer was washed with brine (2×15 mL) and dried over $Na_2SO_4$. The solution was filtered and concentrated in vacuo to give the initial material as an orange oil. The material thus obtained was absorbed onto a plug of silica gel and purified by chromatography through a Redi-Sep pre-packed silica gel column (12 g), eluting with a gradient of 0-100% EtOAc in hexanes, to provide enriched title compound 297.1 (335 mg, 0.66 mmol, 97% yield) as a colorless gum, which was used directly for the next step without further purification. LCMS-ESI (POS.) m/z: 505.0 (M+H)$^+$.

297.2

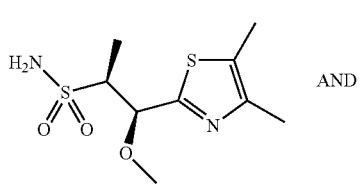

AND

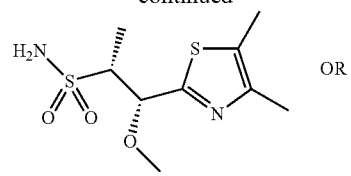

OR

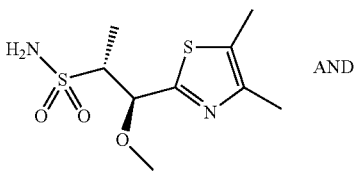

AND

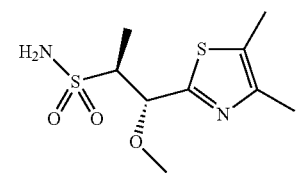

(1R,2R)-1-(4,5-dimethylthiazol-2-yl)-1-methoxypropane-2-sulfonamide and (1S,2S)-1-(4,5-dimethylthiazol-2-yl)-1-methoxypropane-2-sulfonamide or (1R,2S)-1-(4,5-dimethylthiazol-2-yl)-1-methoxypropane-2-sulfonamide and (1S,2R)-1-(4,5-dimethylthiazol-2-yl)-1-methoxypropane-2-sulfonamide, Example 297.2

To a solution of 1-(4,5-dimethylthiazol-2-yl)-1-methoxy-N,N-bis(4-methoxybenzyl)propane-2-sulfonamide 297.1 (330 mg, 0.58 mmol) in DCM (3 mL), was added anhydrous anisole (0.250 mL, 2.30 mmol)) (commercially available from Sigma-Aldrich Corp., St. Louis, Mo., USA) followed by addition of TFA (protein sequencer grade (2.14 mL, 28.8 mmol)) (commercially available from Sigma-Aldrich Corp., St. Louis, Mo., USA) dropwise. The reaction mixture was then stirred at RT for 2 d. The resulting mixture was then concentrated in vacuo at 36° C. The material thus obtained was absorbed onto a plug of silica gel and purified by chromatography through a Redi-Sep pre-packed silica gel column (12 g), eluting with a gradient of 0-100% B/A (B=3:1 EtOAc/EtOH, A=DCM), to provide an orange oil, which was triturated with diethyl ether (2 mL) to give the title compound 297.2 (135 mg, 0.51 mmol, 89% yield) as an off-white solid. LCMS-ESI (POS.) m/z: 265.1 (M+H)$^+$.

Example 297.0: Preparation of (1S,2S)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide and (1R,2R)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(4,5-dimethylthiazol-2-yl)-1-methoxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide and (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide, Example 297.0

The title compound 297.0 was prepared from 297.2 (76 mg, 0.29 mmol), using the procedure described in Example B. This provided Example 297.0 (134 mg, 0.20 mmol, 69% yield) as a white solid. $^1$H NMR (DMSO-$d_6$) δ: 13.49 (s, 1H), 8.48 (d, J=1.3 Hz, 1H), 8.21 (d, J=1.7 Hz, 1H), 7.64 (dt, J=2.0, 1.0 Hz, 1H), 7.50 (t, J=8.6 Hz, 1H), 6.83 (dd, J=8.6, 2.7 Hz, 2H), 5.01 (d, J=1.3 Hz, 1H), 3.70 (s, 3H), 3.69 (s, 3H), 3.28 (s, 3H), 3.25-3.31 (In, 1H), 2.30 (s, 3H), 2.25 (s, 3H), 2.22 (s, 3H), 1.08 (d, J=7.1 Hz, 3H). LCMS-ESI (POS.) m/z: 559.1 (M+H)$^+$.

Example 298.0: Preparation of (1S,2S)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2S)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide 297.0

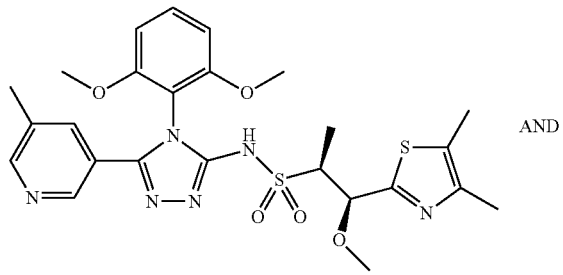

AND

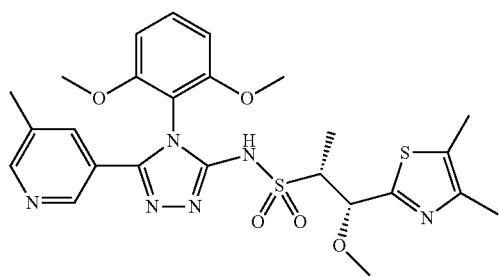

OR

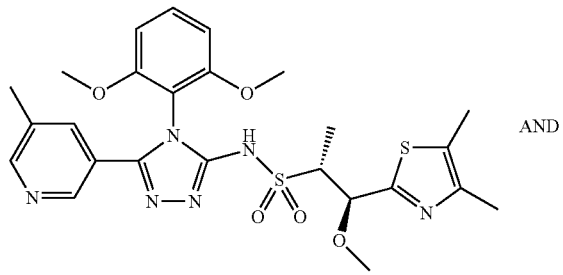

AND

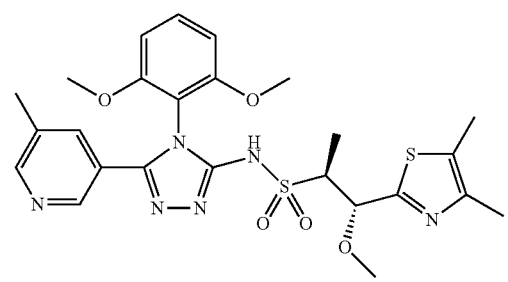

298.0

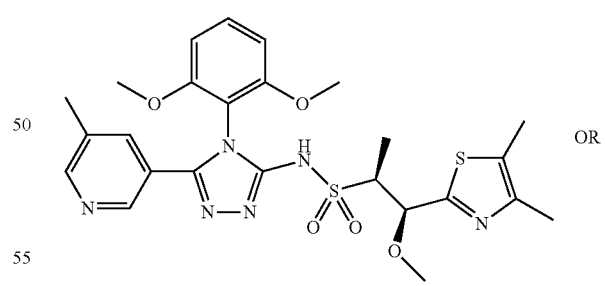

OR


OR

-continued

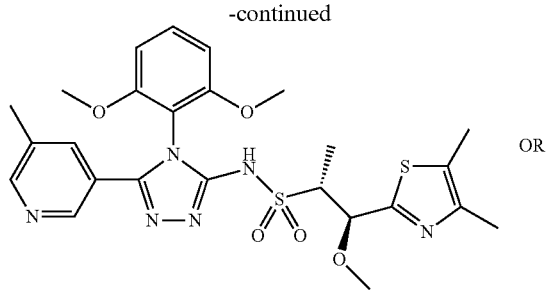

OR

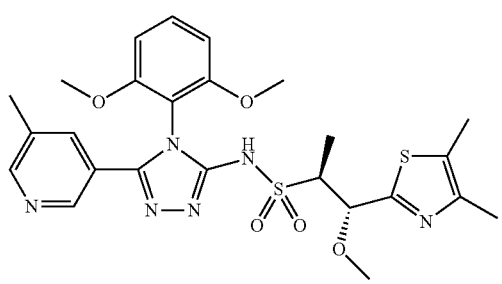

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or (1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or (1S,2R)—N-(4-(2,6-dimethoxyphenyl)-5-(5-methyl-pyridin-3-yl)-4H-1,2,4-triazol-3-yl)-1-(4,5-dimeth-ylthiazol-2-yl)-1-methoxypropane-2-sulfonamide or (1R,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide, Example 298.0

Purification of 297.0 resulted in the title compound 298.0 as the first isomer to elute under the following SFC conditions: AS-H (2×15 cm) 25% IPA (0.1% NH$_4$OH)/CO$_2$, 100 bar 60 mL/min, 220 nm. Inj vol.: 0.75 mL, 12 mg/mL, (2:1) MeOH:DCM solution of 297.0. $^1$H NMR (400 MHz, DMSO-d$_6$) δ. $^1$H NMR (CD$_2$Cl$_2$) δ: 11.23 (br. s., 1H), 8.42 (d, J=1.2 Hz, 1H), 8.32 (d, J=1.6 Hz, 1H), 7.61 (td, J=2.0, 0.7 Hz, 1H), 7.46 (t, J=8.5 Hz, 1H), 6.65-6.69 (m, 2H), 5.07 (d, J=2.2 Hz, 1H), 3.75 (s, 3H), 3.74 (s, 3H), 3.46 (qd, J=7.0, 2.4 Hz, 1H), 3.34 (s, 3H), 2.32 (s, 3H), 2.28 (d, J=0.5 Hz, 3H), 2.27 (d, J=0.6 Hz, 3H), 1.23 (d, J=7.1 Hz, 3H). LCMS-ESI (POS.) m/z: 559.1 (M+H)$^+$.

Example 299.0: Preparation of (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide 299.0

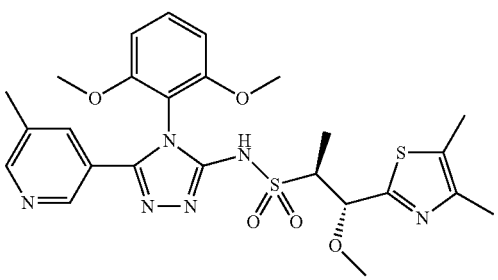

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or
(1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or
(1S,2R)—N-(4-(2,6-dimethoxyphenyl)-5-(5-methyl-pyridin-3-yl)-4H-1,2,4-triazol-3-yl)-1-(4,5-(dimeth-ylthiazol-2-yl)-1-methoxypropane-2-sulfonamide or
(1R,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide,
Example 299.0

Example 299.0 is the enantiomer of 298.0. Further purification of 297.0 resulted in the title compound. Example 299.0, as the second isomer to elute from AS-H column on subjecting 297.0 to the SFC conditions described in Example 298.0. $^1$H NMR (400 MHz, DMSO-d$_6$) δ ppm. $^1$H NMR (CD$_2$Cl$_2$) δ: 11.22 (br. s., 1H), 8.42 (d, J=1.5 Hz, 1H), 8.32 (d, J=1.8 Hz, 1H), 7.60 (dt, J=2.2, 1.3 Hz, 1H), 7.45 (t, J=8.5 Hz, 1H), 6.65-6.69 (In, 2H), 5.06 (d, J=2.3 Hz, 1H), 3.75 (s, 3H), 3.74 (s, 3H), 3.46 (qd, J=7.0, 2.4 Hz, 1H), 3.34 (s, 3H), 2.32 (s, 3H), 2.27 (d, J=0.5 Hz, 3H), 2.26 (d, J=0.6 Hz, 3H), 1.23 (d, J=7.1 Hz, 3H). LCMS-ESI (POS.) m/z: 559.1 (M+H)$^+$.

Example 300.0: Preparation of (1S,2S)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide and (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide and (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide

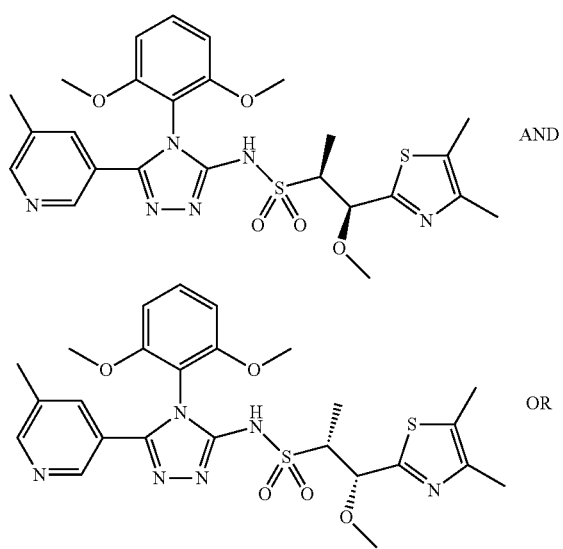

300.0

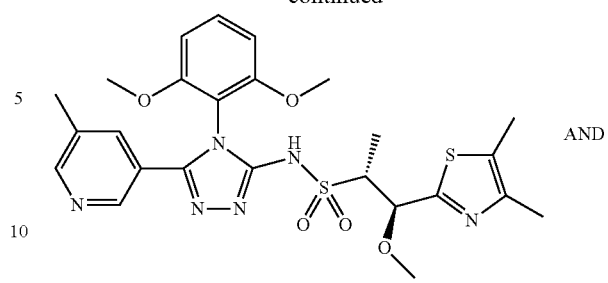

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide and
(1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or
(1S,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide and
(1R,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide,
Example 300.0

Example 300.0 was prepared starting from 291.2, using the procedure described in Example 297.0. $^1$H NMR (DMSO-d$_6$) δ: 13.35 (br. s., 1H), 8.48 (d, J=1.5 Hz, 1H), 8.20 (d, J=1.8 Hz, 1H), 7.62 (dt, J=7.5 Hz, 1H), 7.51 (t, J=8.5 Hz, 1H), 6.84 (dd, J=8.6, 2.1 Hz, 2H), 4.53 (d, J=8.1 Hz, 1H), 3.75 (s, 3H), 3.73 (s, 3H), 3.24 (dd, J=7.9, 7.3 Hz, 1H), 3.03 (s, 3H), 2.32 (s, 3H), 2.25 (s, 3H), 2.23 (s, 3H), 0.98 (d, J=7.1 Hz, 3H). LCMS-ESI (POS.) m/z: 559.1 (M+H)$^+$.

Example 301.0: Preparation of (1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2S)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide 301.0

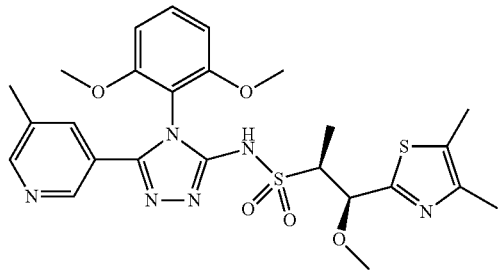

OR

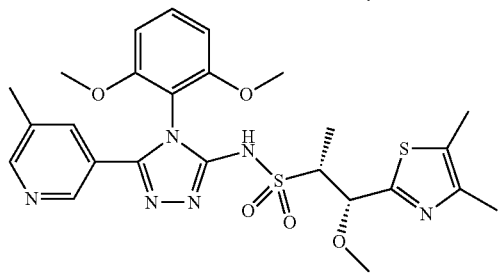

OR

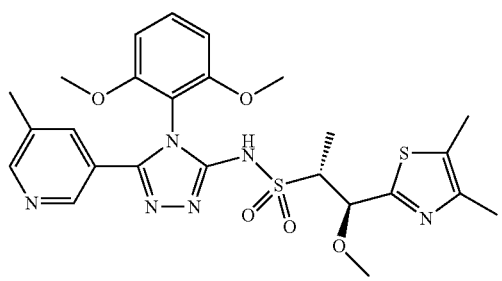

OR

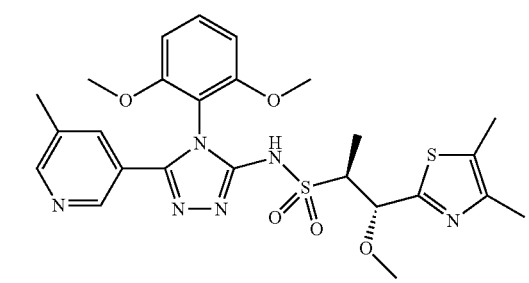

(1S,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2S)—N-(4-(2,6-dimethoxyphenyl)-5-(5-methylpyridin-3-yl)-4H-1,2,4-triazol-3-yl)-1-(4,5-dimethylthiazol-2-yl)-1-methoxypropane-2-sulfonamide, Example 301.0

Purification of Example 300.0 resulted in the title compound. Example 301.0, as the first isomer to elute under the following SFC conditions: Run on Thar 80 SFC with 250× 30 mm CC4 column with 37.60 mL/min MeOH (20 mM NH$_3$)+42.40 g/min CO$_2$, 47% co-solvent at 80 g/min. Temperature.=28° C., Outlet pressure=100 bar, Wavelength=264 nm. Injected 0.5 mL of 117 mg sample (300.0 dissolved in 10 mL of MeOH and 5 mL of DCM (2:1); c=7.8 mg/mL and 3.9 mg per injection. Cycle time 9.0 min, run time 15.5 min. $^1$H NMR (CD$_2$Cl$_2$) δ: 8.41 (d, J=1.5 Hz, 1H), 8.32 (d, J=1.7 Hz, 1H), 7.59 (s, 1H), 7.46 (t, J=8.5 Hz, 1H), 6.69 (dd. J=8.6, 4.3 Hz, 2H), 4.67 (d, J=7.0 Hz, 1H), 3.80 (s, 3H), 3.76 (s, 3H), 3.41-3.46 (m, 1H), 3.19 (s, 3H), 2.35 (s, 3H), 2.30 (s, 3H), 2.27 (s, 3H), 1.15 (d, J=7.1 Hz, 3H). LCMS-ESI (POS.) m/z: 559.1 (M+H)$^+$.

Example 303.0: Preparation of (1S,2S)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2S)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide 303.0

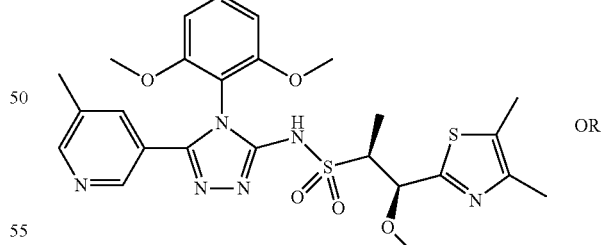

OR

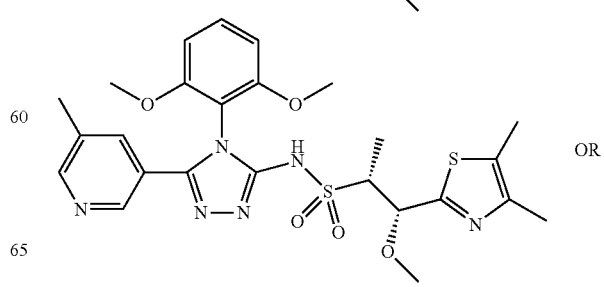

OR

-continued

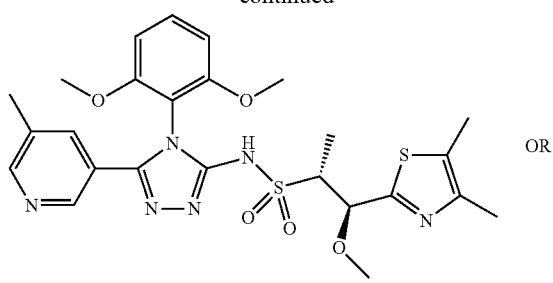

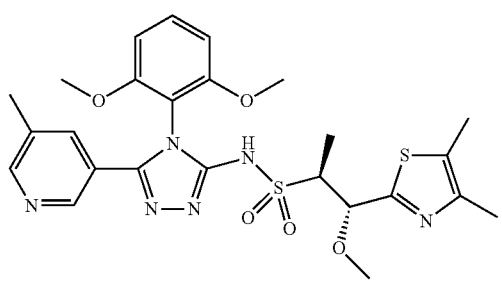

(1S,2S)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or (1R,2R)—N-(4-(2,6-dimethoxyphenyl)-5-(5-methyl-pyridin-3-yl)-4H-1,2,4-triazol-3-yl)-1-(4,5-dimethyl-thiazol-2-yl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(4,5-(dimethylthiazol-2-yl)-1-methoxypropane-2-sulfonamide or (1R,2S)—N-(4-(2,6-(trimethoxyphenyl)-5-(5-methylpyridin-3-yl)-4H-1,2,4-triazol-3-yl)-1-(4,5-dimethylthiazol-2-yl)-1-methoxypropane-2-sulfonamide, Example 303.0

Further purification of Example 300.0 resulted in Example 303.0 which was the second isomer to elute from the CC4 column on subjecting 300.0 to the SFC conditions described in Example 301.0. $^1$H NMR (CD$_2$Cl$_2$) δ: 11.68 (br. s., 1H), 8.42 (d, J=1.3 Hz, 1H), 8.32 (d, J=1.7 Hz, 1H), 7.60 (s, 1H), 7.47 (t J=8.5 Hz, 1H), 6.67-6.72 (m, 2H), 4.64 (d, J=7.8 Hz, 1H), 3.81 (s, 3H), 3.77 (s, 3H), 3.38-3.45 (m, 2H), 3.19 (s, 3H), 2.35 (s, 3H), 2.30 (s, 3H), 2.27 (s, 3H), 1.15 (d, J=7.1 Hz, 3H). LCMS-ESI (POS.) m/z: 559.1 (M+H)$^+$.

Example 304.0: Preparation of (1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide 304.1

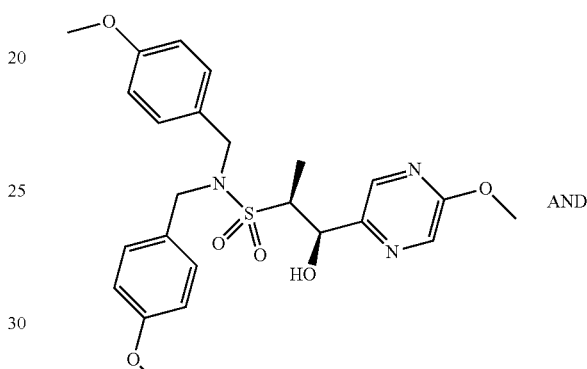

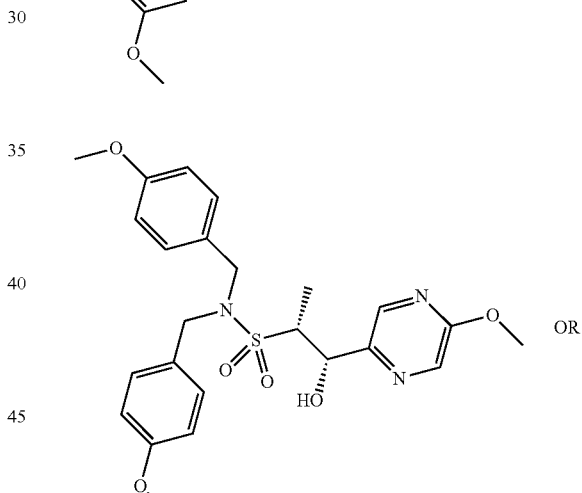

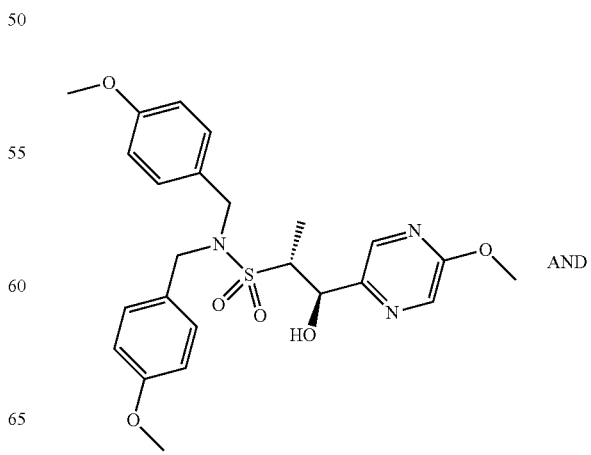

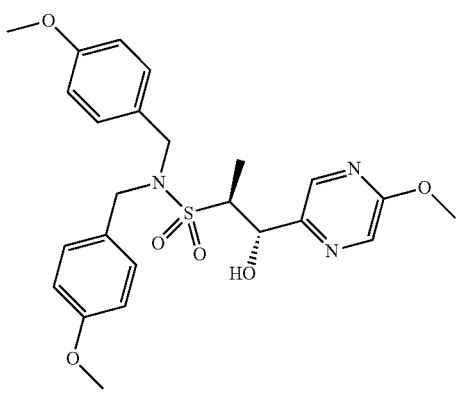

(1R,2S)-1-hydroxy-N,N-bis(4-methoxybenzyl)-1-(5-methoxypyrazin-2-yl)propane-2-sulfonamide and (1S,2R)-1-hydroxy-N,N-bis(4-methoxybenzyl)-1-(5-methoxypyrazin-2-yl)propane-2-sulfonamide or (1R,2R)-1-hydroxy-N,N-bis(4-methoxybenzyl)-1-(5-methoxypyrazin-2-yl)propane-2-sulfonamide and (1S,2S)-1-hydroxy-N,N-bis(4-methoxybenzyl)-1-(5-methoxypyrazin-2-yl)propane-2-sulfonamide, Example 304.1

To a solution of N,N-bis(4-methoxybenzyl)ethanesulfonamide (2.50 g, 7.15 mmol) (Example 12.0) in THF (30 mL) at −78° C., was added n-butyllithium solution (2.5M in hexanes (3.15 mL, 7.87 mmol), commercially available from Sigma-Aldrich Corp., St. Louis, Mo., USA) dropwise. The mixture was stirred at −78° C. for 20 min. To this was added dropwise a solution of 5-methoxypyrazine-2-carbaldehyde (0.988 g, 7.15 mmol, commercially available from Frontier Scientific Inc., Logan, Utah, USA) in THF (6.0 mL). The reaction was continued at −78° C. for 1 h. After the cold bath was removed for 10 min, the reaction was quenched with saturated aqueous NH$_4$Cl (75 mL), and diluted with EtOAc (100 mL) and water (25 mL). The layers were separated and the aqueous layer was extracted with more EtOAc (25 mL). The organic layers were combined and dried over Na$_2$SO$_4$. The solution was filtered and concentrated in vacuo to give the initial material as a light orange oil. The material thus obtained was absorbed onto a plug of silica gel and purified by chromatography through a Redi-Sep pre-packed silica gel column (220 g), eluting with a gradient of 0-100% EtOAc in hexanes, to provide the title compound 304.1 (1.46 g, 2.99 mmol, 42% yield) as a light yellow solid, LCMS-ESI (POS.) m/z: 488.3 (M+H)$^+$.

304.2

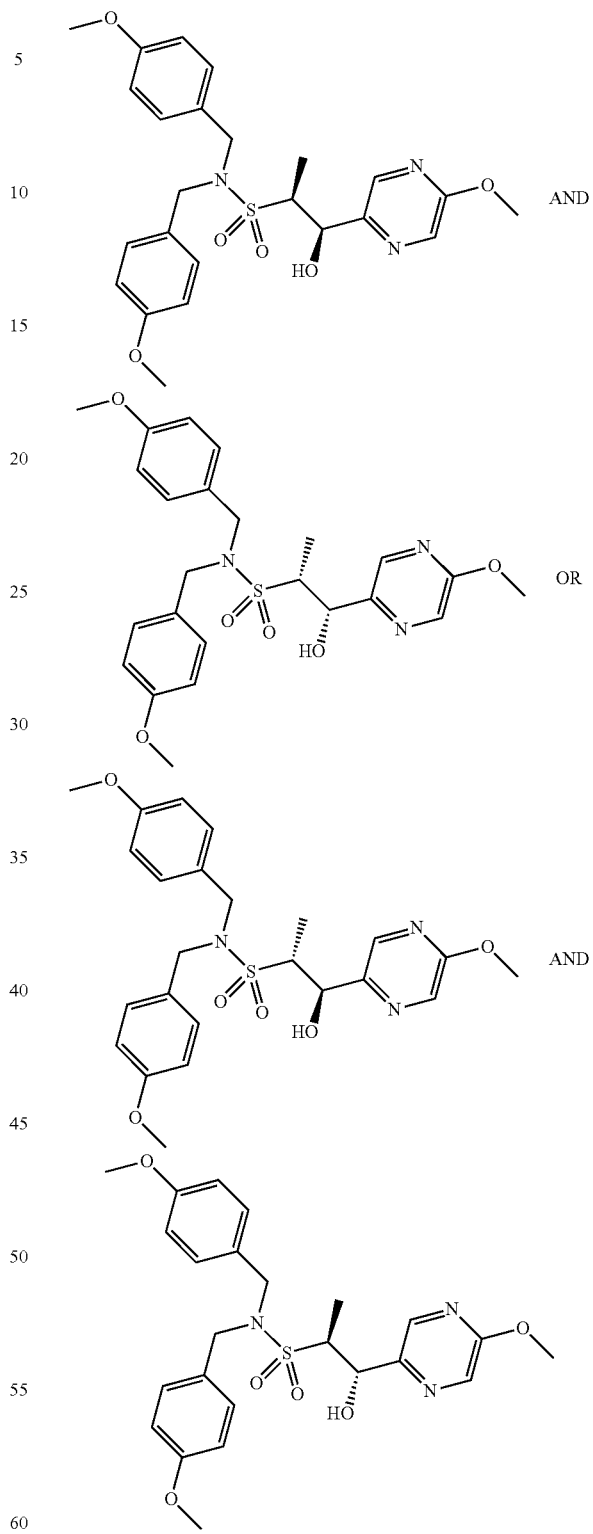

(1R,2S)-1-hydroxy-N,N-bis(4-methoxybenzyl)-1-(5-methoxypyrazin-2-yl)propane-2-sulfonamide and (1S,2R)-1-hydroxy-N,N-bis(4-methoxybenzyl)-1-(5-methoxy-pyrazin-2-yl)propane-2-sulfonamide or (1R,2R)-1-hydroxy-N,N-bis(4-methoxybenzyl)-1-(5-methoxypyrazin-2-yl)

propane-2-sulfonamide and (1S,2S)-1-hydroxy-N,N-bis(4-methoxybenzyl)-1-(5-methoxypyrazin-2-yl)propane-2-sulfonamide, Example 304.2

Further elution with a gradient of 0-100% EtOAc in hexanes provided the title compound 304.2, (0.663 g, 1.36 mmol, 19% yield) as an orange gum, LCMS-ESI (POS.) m/z: 488.3 (M+H)⁺.

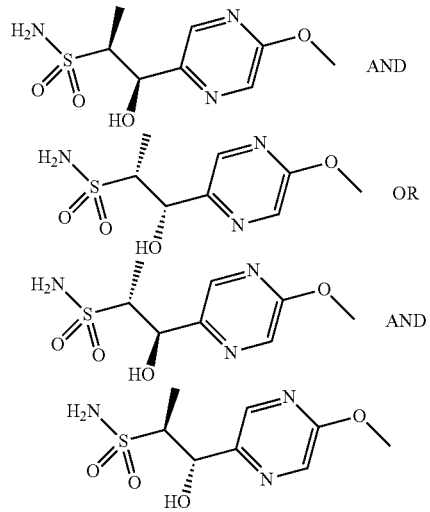

304.3

(1R,2S)-1-hydroxy-1-(5-methoxypyrazin-2-yl)propane-2-sulfonamide and (1S,2R)-1-hydroxy-1-(5-methoxypyrazin-2-yl)propane-2-sulfonamide or (1R,2R)-1-hydroxy-1-(5-methoxypyrazin-2-yl)propane-2-sulfonamide and (1S,2S)-1-hydroxy-1-(5-methoxypyrazin-2-yl)propane-2-sulfonamide, Example 304.3

To a solution of 1-hydroxy-N,N-bis(4-methoxybenzyl)-1-(5-methoxypyrazin-2-yl)propane-2-sulfonamide, Example 304.1 (558 mg, 1.144 mmol) in DCM (4 mL), was added anhydrous anisole (0.498 mL, 4.58 mmol, commercially available from Sigma-Aldrich Corp., St. Louis, Mo., USA) followed by adding TFA, (protein sequencer grade, 4.25 mL, 57.2 mmol, commercially available from Sigma-Aldrich Corp., St. Louis, Mo., USA) dropwise. The reaction mixture was stirred at RT for 39 h. The reaction was then concentrated in vacuo at 30° C. The material thus obtained was absorbed onto a plug of silica gel and purified by chromatography through a Redi-Sep pre-packed silica gel column (24 g), eluting with a gradient of 0-40% (3:1 EtOAc/EtOH) in DCM to provide the title compound 304.3 (123 mg, 0.50 mmol, 44% yield) as an off-white white solid. LCMS-ESI (POS.) m/z: 248.1 (M+H)⁺.

304.0

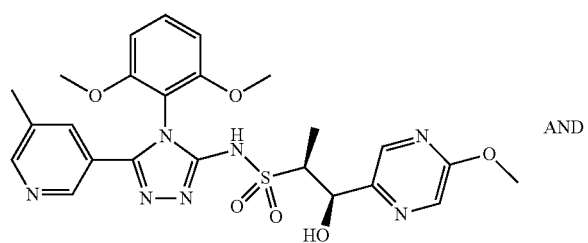

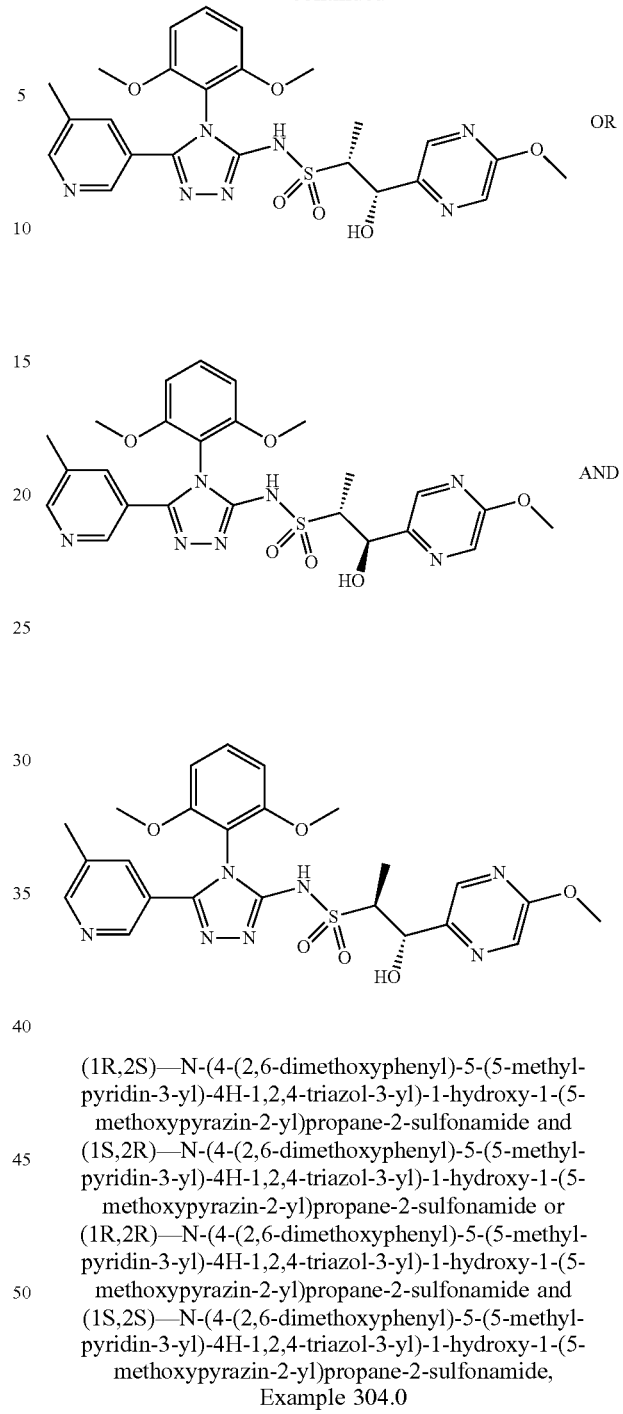

(1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide and
(1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or
(1R,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide and
(1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide,
Example 304.0

The title compound 304.0 was prepared from 3-(5-bromo-4-(2,6-dimethoxyphenyl)-4H-1,2,4-triazol-3-yl)-5-methylpyridine 2.0 (273 mg, 0.73 mmol) and 304.3 (120 mg, 0.49 mmol) using the procedure described in Example B. This provided the title compound Example 304.0 (115 mg, 0.18 mmol, 36% yield) as a white solid. ¹H NMR (CD₂Cl₂) δ: 8.55 (d, J=1.0 Hz, 1H), 8.48 (d, J=1.3 Hz, 1H), 8.24 (t, J=1.1 Hz, 1H), 8.13 (d, J=1.3 Hz, 1H), 7.99 (s, 1H), 7.52 (t, J=8.3 Hz, 1H), 6.68-6.78 (m, 2H), 5.42 (t, J=1.1 Hz, 1H), 3.95 (s, 3H), 3.85 (s, 3H), 3.76 (s, 3H), 3.61 (qd, J=7.0, 1.4 Hz, 1H), 2.42 (s, 3H), 1.11 (d, J=7.0 Hz, 3H). LCMS-ESI (POS.) m/z: 542.2 (M+H)⁺.

Example 305.0: Preparation of (1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide

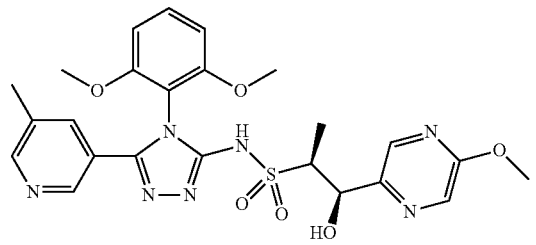

305.0 OR

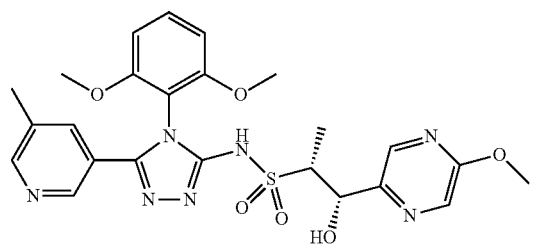

OR

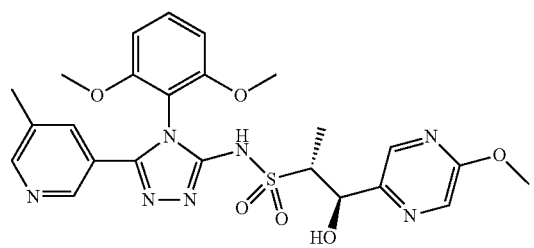

OR

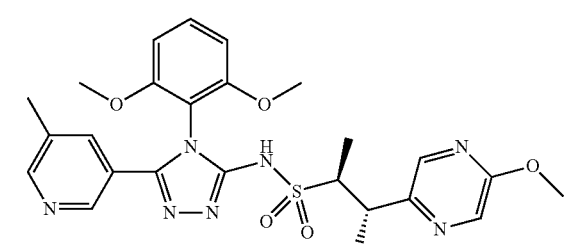

(1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide, Example 305.0

Purification of 304.0 resulted in the title compound 305.0 which was the first isomer to elute under the following SFC conditions: Run on Thar 80 SFC with 150×30 mm IA column with 28.0 mL/min MeOH (20 mm $NH_3$)+52.0 g/min $CO_2$, 35% co-solvent at 80 g/min. Temperature.=29° C., Outlet pressure=100 bar, Wavelength=277 nm. Injected 0.7 mL of sample solution (108 mg 304.0 dissolved in 13 mL of MeOH:DCM 8:5; c=8.31 mg/mL and 5.81 mg per injection). Cycle time 5.8 min, run time 10 min. $^1$H NMR ($CD_2Cl_2$) δ: 8.44 (d, J=1.5 Hz, 1H), 8.33 (d, J=1.7 Hz, 1H), 8.24 (s, 1H), 8.12 (d, J=1.2 Hz, 1H), 7.61 (s, 1H), 7.49 (t, J=8.5 Hz, 1H), 6.65-6.75 (m, 2H), 5.41 (s, 1H), 3.94 (s, 3H), 3.83 (s, 3H), 3.73 (s, 3H), 3.60 (qd, J=7.0, 1.3 Hz, 1H), 3.42 (s, 1H), 2.28 (s, 3H), 1.11 (d, J=7.1 Hz, 3H). LCMS-ESI (POS.) m/z: 542.3 $(M+H)^+$.

Example 306.0: Preparation of (1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide

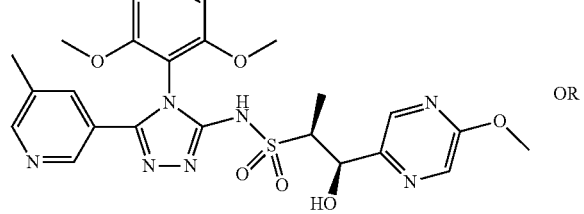

306.0 OR

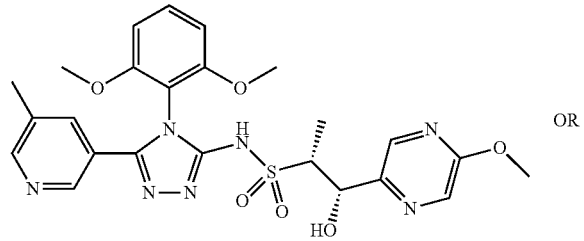

OR

-continued

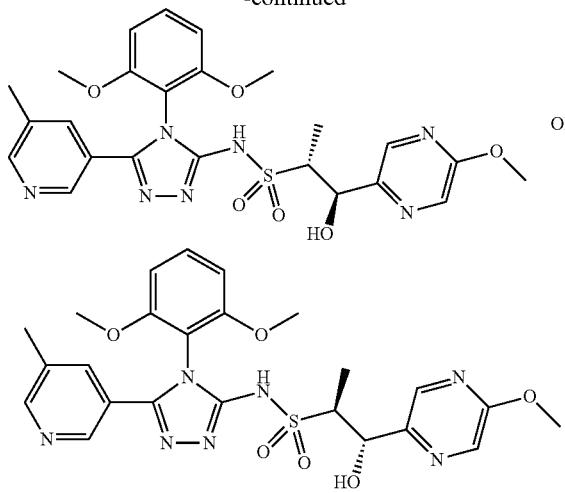

(1R,2S)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide, Example 306.0

Further purification of Example 304.0 resulted in Example 306.0 which was the second isomer to elute from IA column on subjecting Example 304.0 to the SFC conditions described in Example 305.0. $^1$H NMR (CD$_2$Cl$_2$) δ: 8.44 (d, J=1.5 Hz, 1H), 8.33 (d, J=1.8 Hz, 1H), 8.24 (t, J=1.2 Hz, 1H), 8.12 (d, J=1.3 Hz, 1H), 7.61 (td, J=2.0, 0.8 Hz, 1H), 7.49 (t, J=8.6 Hz, 1H), 6.65-6.75 (m, 2H), 5.41 (s, 1H), 3.94 (s, 3H), 3.83 (s, 3H), 3.73 (s, 3H), 3.60 (qd, J=7.0, 1.3 Hz, 1H), 2.28 (s, 3H), 1.11 (d, J=7.1 Hz, 3H). LCMS-ESI (POS.) m/z: 542.3 (M+H)$^+$.

Example 307.0: Preparation of (1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide

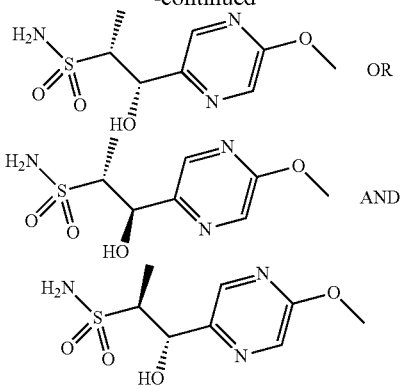

(1R,2S)-1-hydroxy-1-(5-methoxypyrazin-2-yl)propane-2-sulfonamide and (1S,2R)-1-hydroxy-1-(5-methoxypyrazin-2-yl)propane-2-sulfonamide or (1R,2R)-1-hydroxy-1-(5-methoxypyrazin-2-yl)propane-2-sulfonamide and (1S,2S)-1-hydroxy-1-(5-methoxypyrazin-2-yl)propane-2-sulfonamide, Example 307.1

To a solution of 1-hydroxy-N,N-bis(4-methoxybenzyl)-1-(5-methoxypyrazin-2-yl)propane-2-sulfonamide 304.2 (356 mg, 0.73 mmol) in DCM (2.5 mL), was added anhydrous anisole (0.317 mL, 2.92 mmol, commercially available from Sigma-Aldrich Corp., St. Louis, Mo., USA) followed by adding TFA (protein sequencer grade (2.71 mL, 36.5 mmol, commercially available from Sigma-Aldrich Corp., St. Louis, Mo., USA) dropwise. The reaction mixture was stirred at RT for 39 h. The reaction was then concentrated in vacuo at 30° C. The material thus obtained was absorbed onto a plug of silica gel and purified by chromatography through a Redi-Sep pre-packed silica gel column (12 g), eluting with a gradient of 0-40% B/A (B=3:1 EtOAc/EtOH, A=DCM), to provide an orange oil, which was trituated with diethyl ether (2 mL) to give the title compound 307.1 (108 mg, 0.437 mmol, 60% yield) as an orange gum. LCMS-ESI (POS.) m/z: 248.1 (M+H)$^+$.

307.0

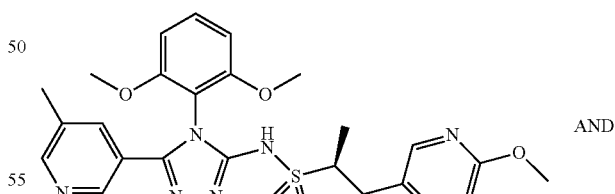

307.1

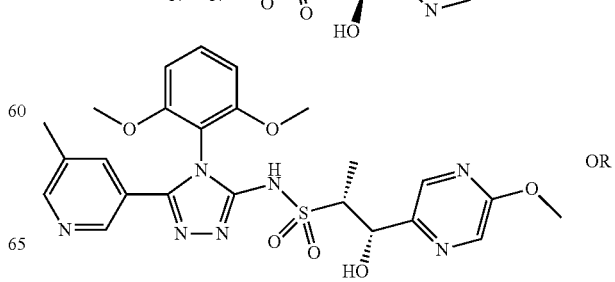

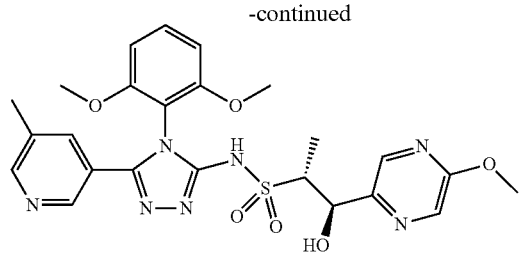

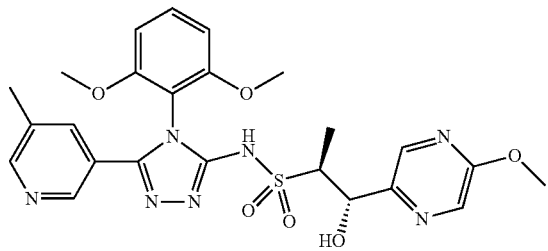

(1R,2S)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide and (1S,2R)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide or (1R,2R)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide and (1S,2S)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide, Example 307.0

The title compound 307.0 was prepared from 3-(5-bromo-4-(2,6-dimethoxyphenyl)-4H-1,2,4-triazol-3-yl)-5-methyl-pyridine (239 mg, 0.637 mmol) (Example 2.0) and 1-hydroxy-1-(5-methoxypyrazin-2-yl)propane-2-sulfonamide 307.1 (105 mg, 0.43 mmol) using the procedure described in Example B. This provided the title compound 307.0 (64 mg, 0.098 mmol, 23% yield) as a white solid. $^1$H NMR (CD$_2$Cl$_2$) δ: 8.59 (s, 1H), 8.50 (s, 1H), 8.16 (s, 1H), 8.11 (s, 1H), 8.08 (s, 1H), 7.52 (t, J=8.6 Hz, 1H), 6.70-6.75 (m, 2H), 4.87 (d, J=8.2 Hz, 1H), 3.95 (s, 3H), 3.81 (s, 3H), 3.80 (s, 3H), 3.53 (quin, J=7.1 Hz, 1H), 2.44 (s, 3H), 1.06 (d, J=7.0 Hz, 3H). LCMS-ESI (POS.) m/z: 542.0 (M+H)$^+$.

Example 308.0: Preparation of (1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide 308.0

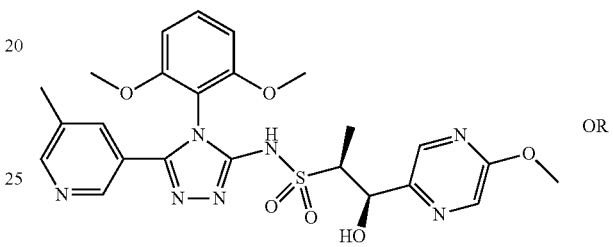

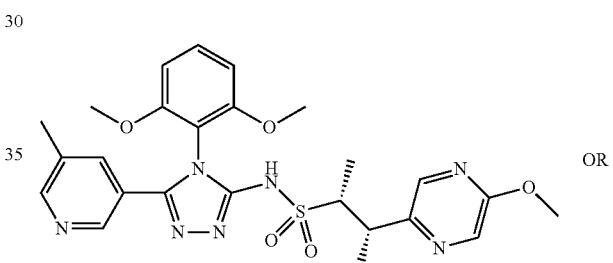

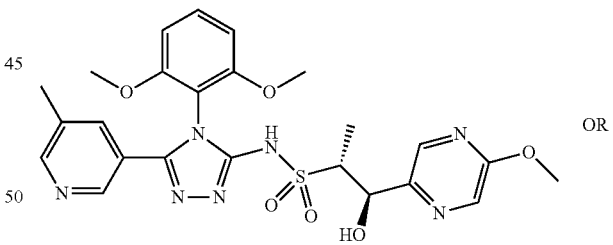

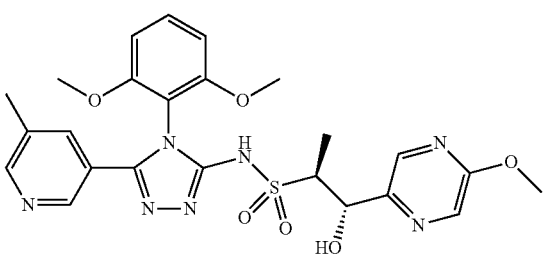

(1R,2S)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide, Example 308.0

Purification of 307.0 resulted in the title compound 308.0 which was the first isomer to elute under the following SFC conditions: Run on Thar 80 SFC with 250×21 mm IC column with 29.0 mL/min MeOH (20 mm NH$_3$)+52.0 g/min CO$_2$, 48% co-solvent at 60 g/min. Temperature.=28° C., Outlet pressure=100 bar, Wavelength=277 nm. Injected 0.3 mL of sample solution (57 mg sample 307.0 dissolved in 3 mL of MeOH:DCM 2:1; c=19.0 mg/mL and 5.7 mg per injection). Cycle time 6.4 min, run time 17 min. $^1$H NMR (CD$_2$Cl$_2$) δ: 8.44 (d, J=1.2 Hz, 1H), 8.33 (d, J=1.5 Hz, 1H), 8.15 (d, J=1.2 Hz, 1H), 8.09 (d, J=1.1 Hz, 1H), 7.60 (s, 1H), 7.47 (t, J=8.4 Hz, 1H), 6.68 (dd, J=8.6, 5.5 Hz, 2H), 4.85 (d, J=8.3 Hz, 1H), 3.94 (s, 3H), 3.77 (s, 3H), 3.77 (s, 3H), 3.47-3.54 (m, 1H), 2.28 (s, 3H), LOS (d, J=7.0 Hz, 3H). LCMS-ESI (POS.) m/z: 542.3 (M+H)$^+$.

Example 309.0: Preparation of (1R,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide

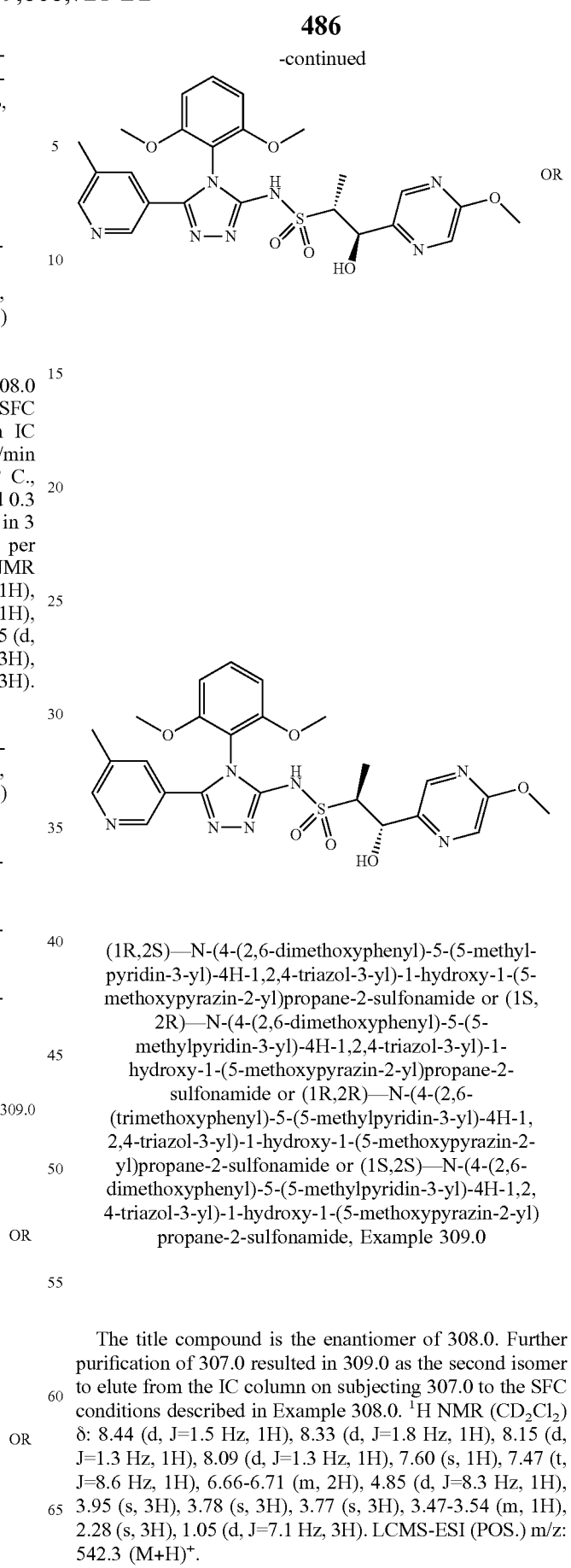

(1R,2S)—N-(4-(2,6-dimethoxyphenyl)-5-(5-methyl-pyridin-3-yl)-4H-1,2,4-triazol-3-yl)-1-hydroxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-hydroxy-1-(5-methoxypyrazin-2-yl)propane-2-sulfonamide, Example 309.0

The title compound is the enantiomer of 308.0. Further purification of 307.0 resulted in 309.0 as the second isomer to elute from the IC column on subjecting 307.0 to the SFC conditions described in Example 308.0. $^1$H NMR (CD$_2$Cl$_2$) δ: 8.44 (d, J=1.5 Hz, 1H), 8.33 (d, J=1.8 Hz, 1H), 8.15 (d, J=1.3 Hz, 1H), 8.09 (d, J=1.3 Hz, 1H), 7.60 (s, 1H), 7.47 (t, J=8.6 Hz, 1H), 6.66-6.71 (m, 2H), 4.85 (d, J=8.3 Hz, 1H), 3.95 (s, 3H), 3.78 (s, 3H), 3.77 (s, 3H), 3.47-3.54 (m, 1H), 2.28 (s, 3H), 1.05 (d, J=7.1 Hz, 3H). LCMS-ESI (POS.) m/z: 542.3 (M+H)$^+$.

Example 310.0: Preparation of (1R,2S)—N-(4-(2,6-(trimethoxyphenyl)-5-(5-methylpyridin-3-yl)-4H-1,2,4-triazol-3-yl)-1-methoxy-1-(5-methoxypyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide 310.1


AND

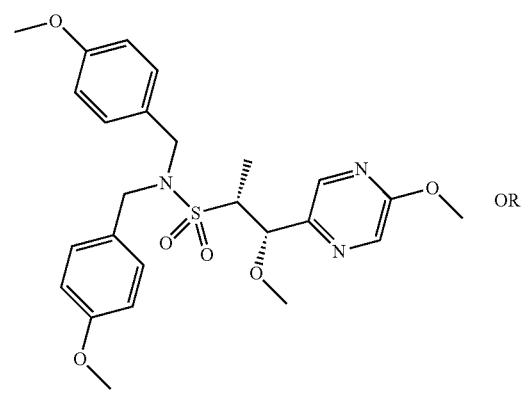

OR

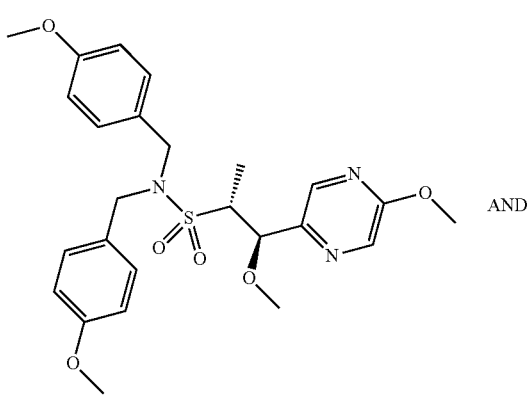

AND

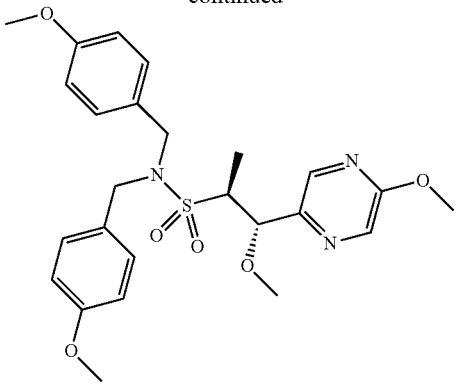

(1R,2S)-1-methoxy-N,N-bis(4-methoxybenzyl)-1-(5-methoxypyrazin-2-yl)propane-2-sulfonamide and (1S,2R)-1-methoxy-N,N-bis(4-methoxybenzyl)-1-(5-methoxypyrazin-2-yl)propane-2-sulfonamide or (1R,2R)-1-methoxy-N,N-bis(4-methoxybenzyl)-1-(5-methoxypyrazin-2-yl)propane-2-sulfonamide and (1S,2S)-1-methoxy-N,N-bis(4-methoxybenzyl)-1-(5-methoxypyrazin-2-yl)propane-2-sulfonamide, Example 310.1

(1R,2S)-1-hydroxy-N,N-bis(4-methoxybenzyl)-1-(5-methoxypyrazin-2-yl)propane-2-sulfonamide and (1S,2R)-1-hydroxy-N,N-bis(4-methoxybenzyl)-1-(5-methoxypyrazin-2-yl)propane-2-sulfonamide or (1R,2R)-1-hydroxy-N,N-bis(4-methoxybenzyl)-1-(5-methoxypyrazin-2-yl)propane-2-sulfonamide and (1S,2S)-1-hydroxy-N,N-bis(4-methoxybenzyl)-1-(5-methoxypyrazin-2-yl)propane-2-sulfonamide (760 mg, 1.56 mmol) Example 304.1 was (azeotroped with toluene before use) dissolved in THF (6 mL) and then cooled to −78° C. To this mixture was added potassium bis(trimethylsilyl)amide (1 M in THF, 1.87 mL, 1.87 mmol), commercially available from Sigma-Aldrich Corp., St. Louis, Mo., USA) dropwise. The mixture was stirred for 15 min at −78° C. A solution of iodomethane (0.145 mL, 2.34 mmol) in THF (1.00 mL, commercially available from Sigma-Aldrich Corp., St. Louis, Mo., USA) was then added dropwise. The reaction was warmed to RT for 1.5 h. The reaction was quenched with saturated NH$_4$Cl (aqueous) (25 mL) and diluted with EtOAc (25 mL). The layers were separated. The organic layer was washed with brine (2×25 mL) and then dried over Na$_2$SO$_4$. The solution was filtered and concentrated in vacuo to give the initial material as an orange oil. The material thus obtained was absorbed onto a plug of silica gel and purified by chromatography through a Redi-Sep pre-packed silica gel column (40 g), eluting with a gradient of 0-100% EtOAc in hexanes, to provide the title compound 310.1 (740 mg, 1.48 mmol, 95% yield) as an off-white solid. $^1$H NMR (500 MHz, CD$_2$Cl$_2$) δ 8.20 (d, J=1.35 Hz, 1H) 8.15 (dd, J=9.60 Hz, 1H) 7.15-7.18 (m, 4H) 6.81-6.85 (m, 4H) 4.97 (dd, J=2.63, 0.55 Hz, 1H) 4.36 (d, J=15.16 Hz, 2H) 4.24-4.27 (m, 1H) 4.19 (d, J=15.16 Hz, 2H) 3.97 (s, 3H) 3.78 (s, 6H) 3.43 (s, 3H) 1.22 (d, J=7.21 Hz, 3H). LCMS-ESI (POS.) m/z: 502.3 (M+H)$^+$.

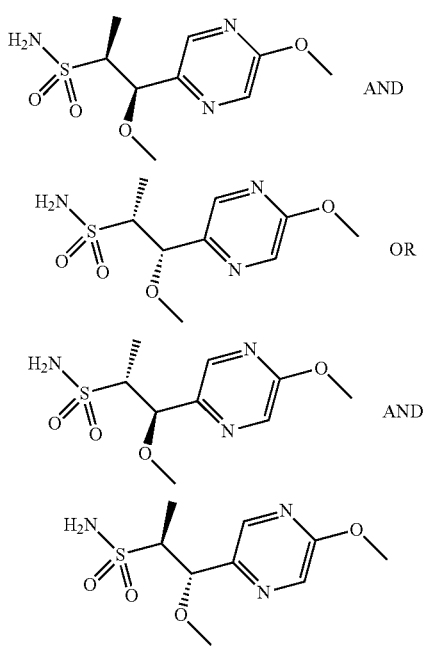

310.2

AND

OR

AND (1R,2S)-1-methoxy-1-(5-methoxypyrazin-2-yl)propane-2-sulfonamide and (1S,2R)-1-methoxy-1-(5-methoxypyrazin-2-yl)propane-2-sulfonamide or (1R,2R)-1-methoxy-1-(5-methoxypyrazin-2-yl)propane-2-sulfonamide and (1S,2S)-1-methoxy-1-(5-methoxypyrazin-2-yl)propane-2-sulfonamide, Example 310.2

To a solution of 310.1 (737 mg, 1.47 mmol) in DCM (5 mL), was added anhydrous anisole (0.639 mL, 5.88 mmol, commercially available from Sigma-Aldrich Corp., St. Louis, Mo., USA) followed by adding TFA (reagentplus, 5.46 mL, 73.5 mmol, commercially available from Sigma-Aldrich Corp., St. Louis, Mo., USA) dropwise. The reaction mixture was stirred at RT for 40 h. The reaction was then concentrated in vacuo at 30° C. The material thus obtained was absorbed onto a plug of silica gel and purified by chromatography through a Redi-Sep pre-packed silica gel column (24 g), eluting with a gradient of 0-40% B/A (B=3:1 EtOAc/EtOH, A=DCM), to provide to give the title compound 310.2 (236 mg, 0.90 mmol, 62% yield) as an off-white white solid. LCMS-ESI (POS.) m/z: 262.1 (M+H)$^+$.

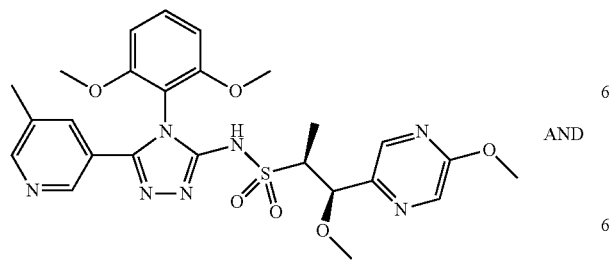

310.0

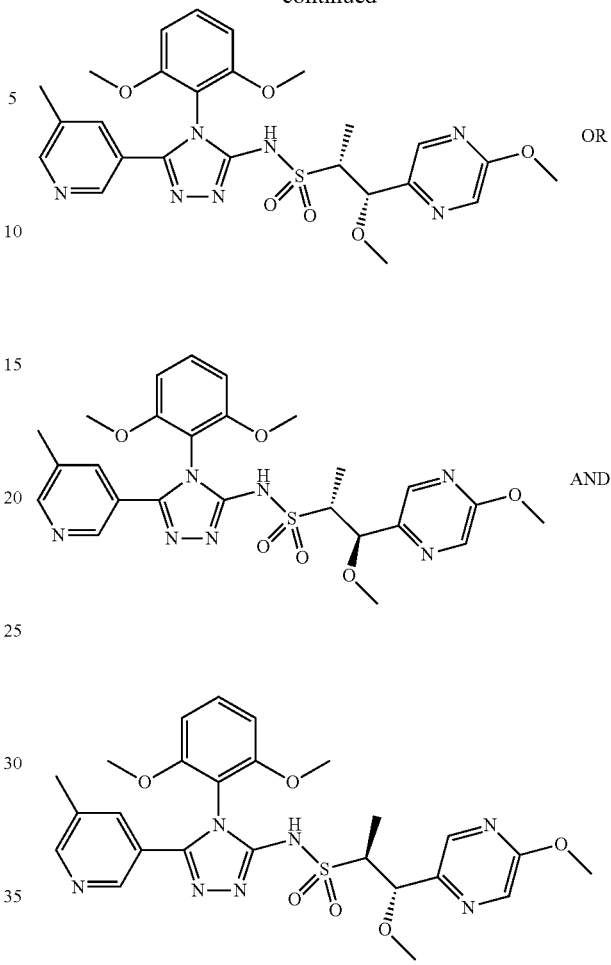

OR

AND (1R,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide, Example 310.0

The title compound 310.0 was prepared from 3-(5-bromo-4-(2,6-dimethoxyphenyl)-4H-1,2,4-triazol-3-yl)-5-methylpyridine 2.0 (226 mg, 0.603 mmol) and 310.2 (105 mg, 0.40 mmol) using the procedure described in Example B. This provided Example 310.0 (159 mg, 0.24 mmol, 59% yield) as an off-white solid. $^1$H NMR (CD$_2$Cl$_2$) δ: 8.53 (d, J=1.2 Hz, 1H), 8.45 (d, J=1.5 Hz, 1H), 8.17 (d, J=1.5 Hz, 1H), 8.09-8.12 (m, 1H), 7.95-7.98 (m, 1H), 7.49 (t, J=8.4 Hz, 1H), 6.68-6.73 (m, 2H), 4.94 (d, J=2.4 Hz, 1H), 3.96 (s, 3H), 3.78 (s, 3H), 3.76 (s, 3H), 3.39 (qd, J=7.1, 2.9 Hz, 1H), 3.26 (s, 3H), 2.40 (s, 3H), 1.20 (d, J=7.0 Hz, 3H). LCMS-ESI (POS.) m/z: 556.3 (M+H)$^+$.

Example 311.0: Preparation of (1R,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide

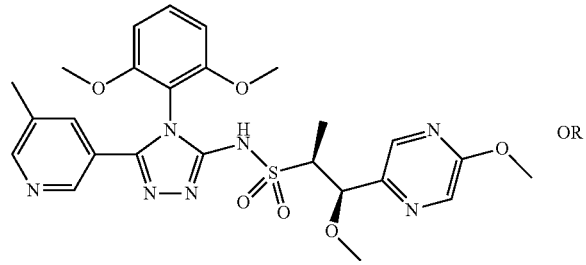

311.0

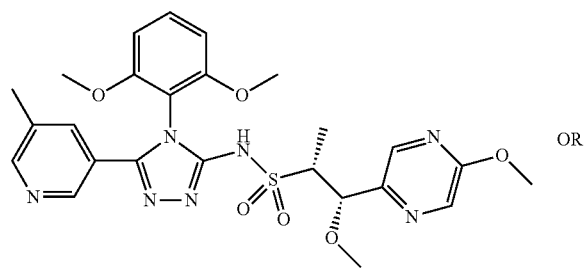

OR

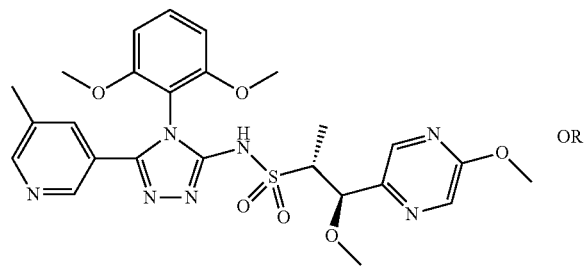

OR

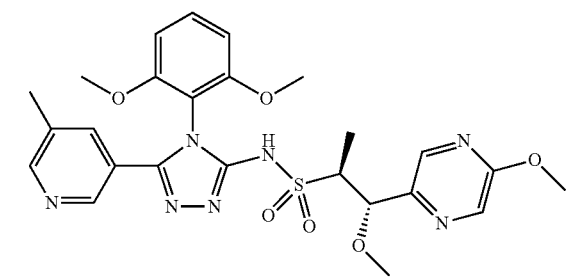

OR (1R,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide, Example 311.0

Purification of 310.0 resulted in the title compound which was the first isomer to elute under the following SFC conditions: Run on Thar 200 SFC with 30×250 mm CC4 column with 50 mL/min MeOH (20 mM NH$_3$)+50 g/min CO$_2$, 50% co-solvent at 100 g/min. Temperature.=30° C., Outlet pressure=100 bar, Wavelength=278 nm. Injected 3.0 mL of sample solution (115 mg 310.0 dissolved in 20 mL 1:1 iPrOH:DCM; c=5.75 mg/mL and 17.3 mg per injection). Cycle time 11 min, run time 13 min. $^1$H NMR (CD$_2$Cl$_2$) δ: 11.09 (br. s., 1H), 8.42 (d, J=1.5 Hz, 1H), 8.32 (d, J=1.8 Hz, 1H), 8.17 (d, J=1.3 Hz, 1H), 8.10 (s, 1H), 7.59-7.61 (m, 1H), 7.46 (t, J=8.5 Hz, 1H), 6.65-6.70 (m, 2H), 4.94 (d, J=2.9 Hz, 1H), 3.95 (s, 3H), 3.75 (s, 3H), 3.73 (s, 3H), 3.38 (qd, J=7.1, 2.9 Hz, 1H), 3.27 (s, 3H), 2.27 (s, 3H), 1.20 (d, J=7.1 Hz, 3H). LCMS-ESI (POS.) m/z: 556.3 (M+H)$^+$.

Example 312.0: Preparation of (1R,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1R,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide 312.0

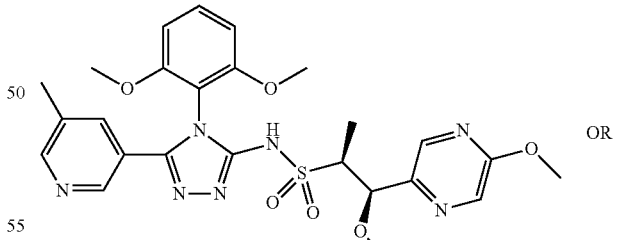

OR

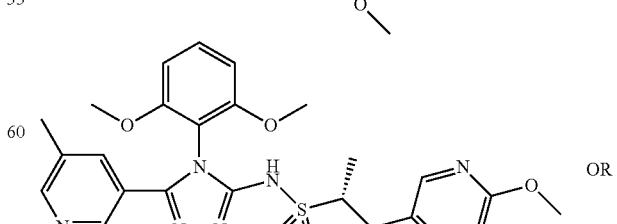

OR

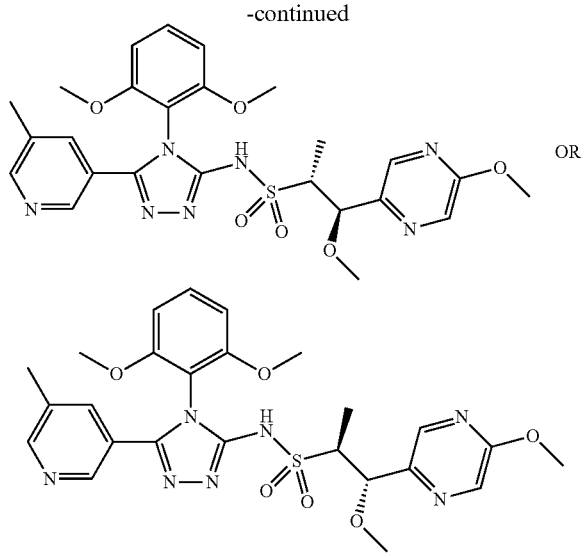

(1R,2S)—N-(4-(2,6-dimethoxyphenyl)-5-(5-methyl-pyridin-3-yl)-4H-1,2,4-triazol-3-yl)-1-methoxy-1-(5-methoxypyrazin-2-yl)propane-2-sulfonamide or (1S,2R)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide or (1R,2R)—N-(4-(2,6-(trimethoxyphenyl)-5-(5-methylpyridin-3-yl)-4H-1,2,4-triazol-3-yl)-1-methoxy-1-(5-methoxypyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-methoxy-1-(5-methoxypyrazin-2-yl)propane-2-sulfonamide, Example 312.0

Example 312.0 is the enantiomer of 311.0. Further purification of 310.0 resulted in the title compound which was the second isomer to elute from CC4 column on subjecting 310.0 to the SFC conditions described in 311.0. $^1$H NMR (CD$_2$Cl$_2$) δ: 11.13 (br. s., 1H), 8.42 (d, J=1.2 Hz, 1H), 8.32 (d, J=1.6 Hz, 1H), 8.17 (d, J=1.3 Hz, 1H), 8.09-8.12 (m, 1H), 7.60 (td, J=2.0, 0.7 Hz, 1H), 7.46 (t, J=8.6 Hz, 1H), 6.65-6.70 (m, 2H), 4.94 (d, J=2.6 Hz, 1H), 3.95 (s, 3H), 3.75 (s, 3H), 3.73 (s, 3H), 3.38 (qd, J=7.1, 2.9 Hz, 1H), 3.27 (s, 3H), 2.27 (s, 3H), 1.20 (d, J=7.1 Hz, 3H). LCMS-ESI (POS.) m/z: 556.3 (M+H)$^+$.

Example 313.0: Preparation of (2S,3R)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide

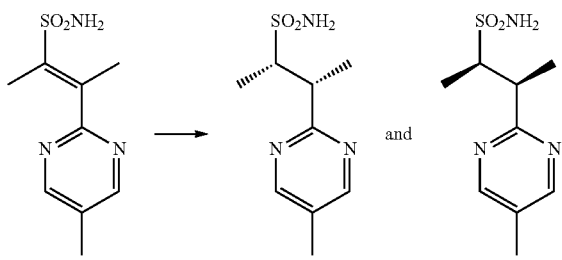

313.1

(2S,3R)-3-(5-methylpyrimidin-2-yl)butane-2-sulfonamide and (2R,3S)-3-(5-methylpyrimidin-2-yl)butane-2-sulfonamide, Example 313.1

To a 500-mL round-bottomed flask was added (E)-3-(5-methylpyrimidin-2-yl)but-2-ene-2-sulfonamide (Example 10.05, 2.5 g, 11.00 mmol), zinc trifluoromethanesulfonate (Sigma-Aldrich, 0.800 g, 2.20 mmol), and (R)-(–)-4, 12-bis(diphenylphosphino)[2.2]paracyclophane(1,5-cyclooctadiene)rhodium (Strem Chemicals Inc., 0.481 g, 0.55 mmol) in EtOH. The mixture was stirred under 1 atm H$_2$ for 16 h. The solid was then filtered. The solid was washed with 20% EtOAc in hexanes to give a mixture of (2S,3R)-3-(5-methylpyrimidin-2-yl)butane-2-sulfonamide and (2R,3S)-3-(5-methylpyrimidin-2-yl)butane-2-sulfonamide (1.39 g, 6.06 mmol, 55% yield).

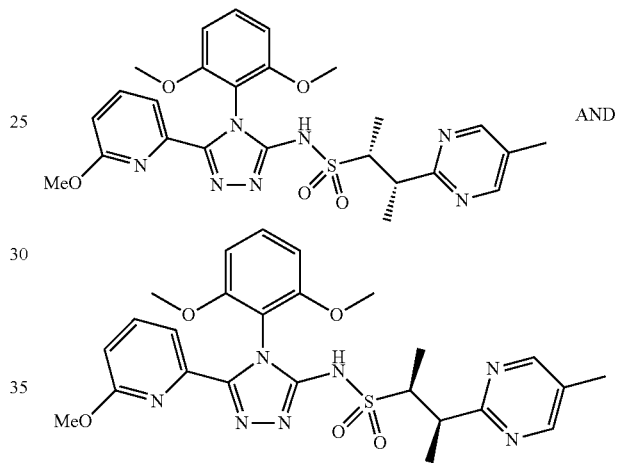

313.2

(2R,3S)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide and (2S,3R)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide, Example 313.2

To a 50 mL flask was added 2-isothiocyanato-1,3-dimethoxybenzene 1.0 (439 mg, 2.25 mmol), cesium carbonate (Sigma-Aldrich, 195 μL, 2.44 mmol) and (2R,3S)-3-(5-methylpyrimidin-2-yl)butane-2-sulfonamide and (2S,3R)-3-(5-methylpyrimidin-2-yl)butane-2-sulfonamide 313.2 (430 mg, 1.875 mmol) in DMF. The reaction mixture was stirred at RT for 16 h. To a 250-mL flask was added (2R,3S)—N-((2,6-dimethoxyphenyl)carbamothioyl)-3-(5-methylpyrimidin-2-yl)butane-2-sulfonamide and (2S,3R)—N-((2,6-dimethoxyphenyl)carbamothioyl)-3-(5-methylpyrimidin-2-yl)butane-2-sulfonamide (348 mg, 0.82 mmol), AcOH (Sigma-Aldrich, 189 μL, 3.28 mmol), 6-methoxypicolinohydrazide (Sigma-Aldrich, 164 mg, 0.98 mmol), 4 mL of DMF, and silver nitrate (Sigma-Aldrich, 251 mg, 1.48 mmol). The reaction mixture was stirred at RT over 30 min and then EtOAc was added. The reaction mixture was filtered to remove Ag$_2$S. The reaction mixture was concentrated in vacuo. Next, 1,4-dioxane and TFA (Sigma, Aldrich, 304 μL, 4.10 mmol) were added to the mixture and it was then heated at 110° C. for 16 h. The reaction was stopped and the solution was reduced to a small volume of solvent. The material thus obtained was purified by reverse-phase preparative HPLC using a Phenomenex Luna column, 5 micron, C$_8$(2), 100 Å, 150×21.2 mm, 0.1% TFA in CH$_3$CN/H$_2$O, gradient 0-70% over 25 min to provide (2R,3S)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide and (2S,3R)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide 313.2 (126 mg, 0.23 mmol, 28.5% yield) as a white solid.

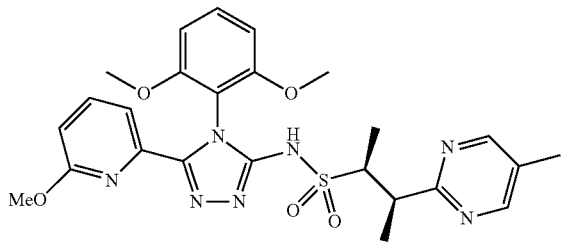

313.0

(2S,3R)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide, Example 313.0

The mixture obtained as described above in Example 313.2 was purified directly on 250 mm×20 mm AS-H×AS-H columns with 15% MeOH/100 bar CO$_2$ on Thar 80 SFC. The first eluting fraction (52.23 mg 99% ee) was (2S,3R)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide, 313.0 1H NMR (400 MHz, CDCl$_3$) δ 1.36 (d, J=7.04 Hz, 3H) 1.39 (d, J=7.04 Hz, 3H) 2.30 (s, 3H) 3.18 (s, 3H) 3.69 (s, 3H) 3.72 (s, 3H) 3.75-3.84 (m, 1H) 3.90 (dd, J=6.85, 5.67 Hz, 2H) 6.71 (dd, J=7.24, 1.96 Hz, 1H) 7.30 (m, 1H) 7.57-7.66 (m, 2H) 8.53 (s, 2H), MS ESI (pos.) m/z: 540.2 (M+H)$^+$.

Example 314.0: Preparation of (2R,3S)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide

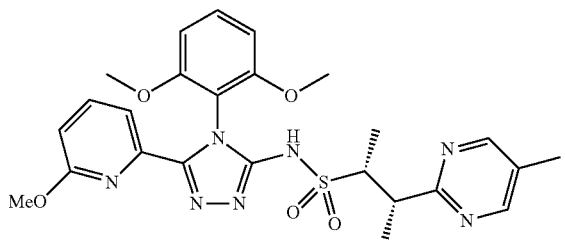

314.0

(2R,3S)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide, Example 314.0

The title compound was the second eluting fraction using the conditions described in Example 313.0 to deliver (2R,3S)—N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide 314.0 (19.96 mg, 96.1% ee). 1H NMR (400 MHz, CDCl$_3$) δ 1.36 (d, J=7.04 Hz, 3H) 1.39 (d, J=7.04 Hz, 3H) 2.30 (s, 3H) 3.18 (s, 3H) 3.69 (s, 3H) 3.72 (s, 3H) 3.75-3.84 (m, 1H) 3.90 (dd, J=6.85, 5.67 Hz, 1H) 6.60 (t, J=7.61 Hz, 2H) 6.71 (dd, J=7.24, 1.96 Hz, 1H) 7.30 (m, 1H) 7.57-7.66 (m, 2H) 8.53 (s, 2H), MS ESI (pos.) m/z: 540.2 (M+H)$^+$.

Example 315.0: Preparation of (2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide and (2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide

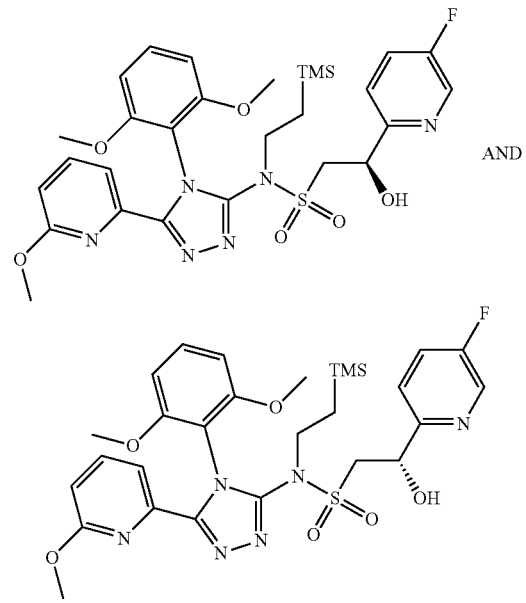

315.1

(R)—N-(4-(2,6-dimethoxyphenyl)-5-(6-methoxy-pyridin-2-yl)-4H-1,2,4-triazol-3-yl)-2-(5-fluoropyridin-2-yl)-2-hydroxy-N-(2-(trimethylsilyl)ethyl)ethanesulfonamide and (S)—N-(4-(2,6-dimethoxyphenyl)-5-(6-methoxypyridin-2-yl)-4H-1,2,4-triazol-3-yl)-2-(5-fluoropyridin-2-yl)-2-hydroxy-N-(2-(trimethylsilyl)ethyl)ethanesulfonamide, Example 315.1

A flask was charged with N-(4-(2,6-dimethoxyphenyl)-5-(6-methoxypyridin-2-yl)-4H-1,2,4-triazol-3-yl)-N-(2-(trimethylsilyl)ethyl)methanesulfonamide (4.0, 396 mg, 0.78 mmol) and was azeotroped with toluene. THF (3.5 mL) was added, and the reaction was cooled in a dry ice-acetone bath. A solution of n-butyllithium (2.5M, 0.313 mL, 0.78 mmol) was added, and the reaction was stirred for 10 min. Next, a THF (1.5 mL) solution of 5-fluoropicolinaldehyde (118 mg, 0.94 mmol) was added dropwise. The reaction was stirred in the dry ice-acetone bath for another 45 min and then warmed to RT and stirred for another 3 h. The reaction was quenched with saturated $NH_4Cl$ and extracted with EtOAc. The EtOAc layer was dried, concentrated in vacuo and purified by silica gel chromatography, eluting with a gradient of 0-40% EtOAc in hexanes to provide the title compound 315.1 (351 mg, 71%). LCMS-ESI (POS.) m/z: 631.0 $(M+H)^+$.

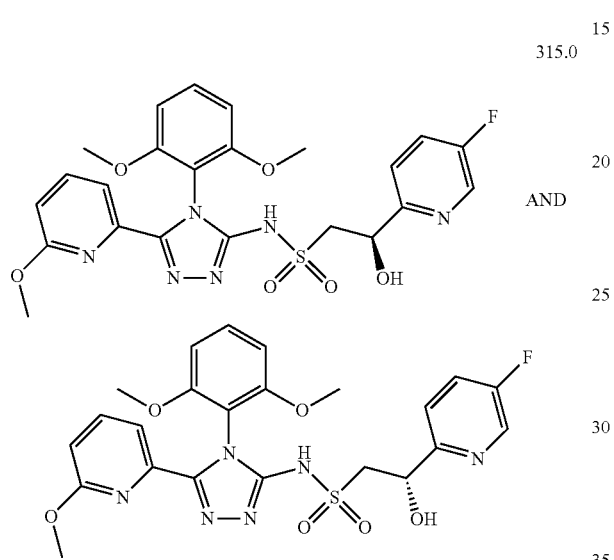

315.0

AND (2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide and (2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide, Example 315.0

A flask was charged with (R)—N-(4-(2,6-dimethoxyphenyl)-5-(6-methoxypyridin-2-yl)-4H-1,2,4-triazol-3-yl)-2-(5-fluoropyridin-2-yl)-2-hydroxy-N-(2-(trimethylsilyl)ethyl)ethanesulfonamide and (S)—N-(4-(2,6-dimethoxyphenyl)-5-(6-methoxypyridin-2-yl)-4H-1,2,4-triazol-3-yl)-2-(5-fluoropyridin-2-yl)-2-hydroxy-N-(2-(trimethylsilyl)ethyl)ethanesulfonamide (315.1, 199 mg, 0.32 mmol) and was azeotroped with toluene. Tris(dimethylamino)sulfonium difluorotrimethylsilicate (261 mg, 0.95 mmol) was added to the flask, followed by addition of DMF (2.5 mL). The reaction flask was heated to 70° C. for 1 h under nitrogen. The product initially obtained was directly purified on reverse phase HPLC column, using an Agilent SB $C_8$ column, 0.1% TFA in $CH_3CN/H_2O$, 20-80% gradient elution over 25 min. The desired fractions were combined and lyophilized to provide the TFA salt of the title compound 315.0 (138 mg, 68% yield) as a white solid. $^1H$ NMR (400 MHz, $CD_3OD$) δ 8.43 (d, J=2.74 Hz, 1H) 7.74 (dd, J=8.22, 7.43 Hz, 1H) 7.58-7.67 (m, 3H) 7.44 (t, J=8.41 Hz, 1H) 6.78 (td, J=8.36, 1.27 Hz, 3H) 5.21 (dd, J=8.61, 3.33 Hz, 1H) 3.75 (s, 3H) 3.74 (s, 3H) 3.65 (dd, J=14.28, 3.33 Hz, 1H) 3.33 (m, 1H) 3.19 (s, 3H). LCMS-ESI (POS.) m/z: 531.0 $(M+H)^+$.

Example 316.0: Preparation of (2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide

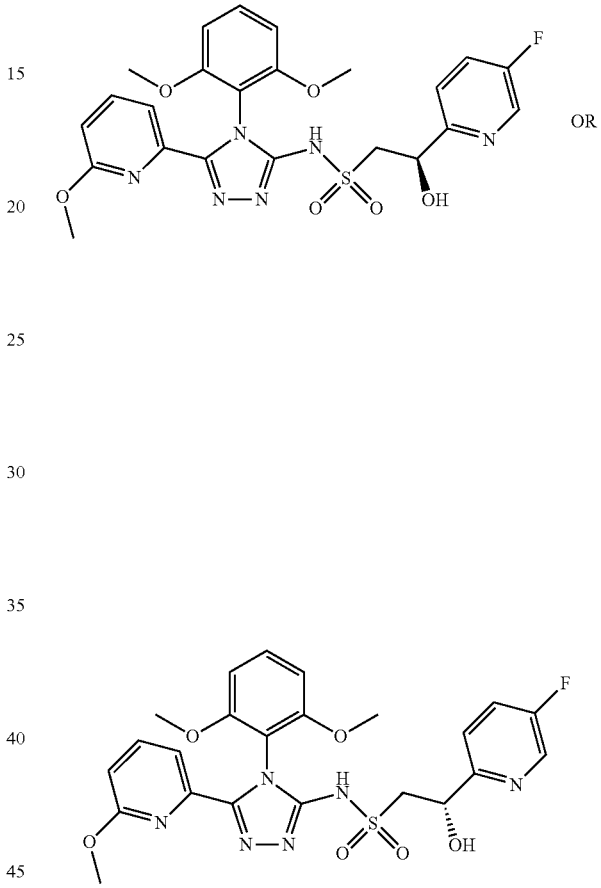

316.0

OR (2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide, Example 316.0

The racemate 315.0 was separated by supercritical fluid chromatography into two enantiomers. Chiral separation condition (Lotus Inc.): OZ—H (2×25 cm), 25% $IPA/CO_2$, 100 bar, 70 mL/min, 220 nm, inj vol.: 1 mL, 6 mg/mL MeOH provided the title compound 316.0 as the first peak off the chiral column. $^1H$ NMR (400 MHz, $CD_3OD$) δ 8.39 (d, J=2.15 Hz, 1H) 7.72 (t, J=7.80 Hz, 1H) 7.54-7.63 (m, 3H) 7.41 (t, J=8.33 Hz, 1H) 6.73-6.81 (m, 3H) 5.18 (dd, J=9.00, 3.13 Hz, 1H) 3.73 (s, 3H) 3.71 (s, 3H) 3.63 (dd, J=14.28, 3.13 Hz, 1H) 3.26-3.36 (m, 1H) 3.17 (s, 3H). LCMS-ESI (POS.) m/z: 531.0 $(M+H)^+$.

Example 317.0: Preparation of (2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide (2R)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide, Example 317.0

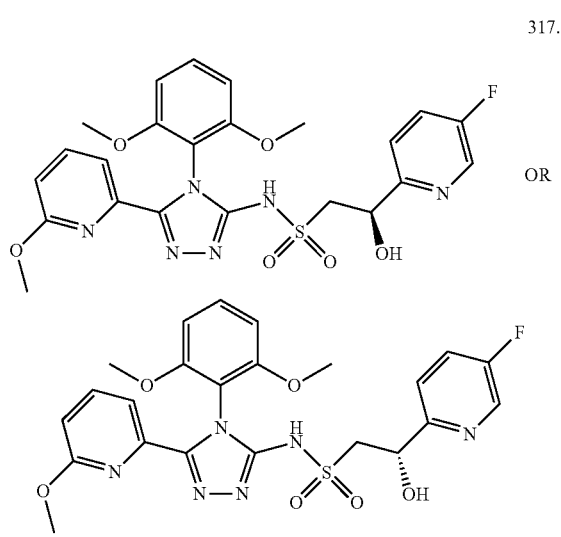

317.0

The title compound is the second peak off the chiral column on subjecting 315.0 to the SFC conditions described in Example 316.0. $^1$H NMR (400 MHz, CD$_3$OD) δ 8.39 (d, J=5.60 Hz, 1H) 7.72 (t, J=7.79 Hz, 1H) 7.54-7.63 (m, 3H) 7.41 (t, J=8.51 Hz, 1H) 6.70-6.83 (m, 3H) 5.18 (dd, J=8.80, 3.13 Hz, 1H) 3.73 (s, 3H) 3.71 (s, 3H) 3.63 (dd, J=14.28, 3.13 Hz, 1H) 3.27-3.35 (m, 1H) 3.17 (s, 3H). LCMS-ESI (POS.) m/z: 531.0 (M+H)$^+$.

The compounds set forth in the following Table were synthesized following the procedure in Example 315.0 using the known starting material as described.

TABLE 14

| Example | Reagents | Structure, Name and Data |
|---|---|---|
| 318.0 | N-(4-(2,6-dimethoxyphenyl)-5-(6-methoxypyridin-2-yl)-4H-1,2,4-triazol-3-yl)-N-(2-(trimethylsilyl)ethyl)ethanesulfonamide (Example 5.0), 4-cyanobenzaldehyde (Acros Organics), n-butyllithium solution, 1.6M in hexanes (Acros Organics). | 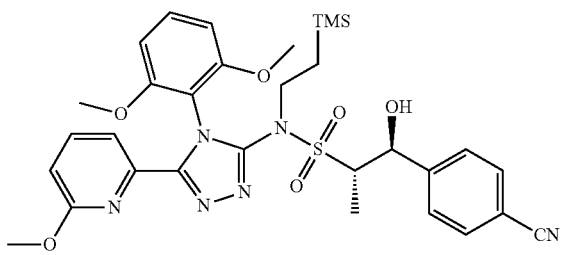 [SMILES: COc1cccc(-c2nnc(N(CC[Si](C)(C)C)S(=O)(=O)[C@@H](C)[C@@H](O)c3ccc(C#N)cc3)n2-c2c(OC)cccc2OC)n1]<br>AND<br><br>AND |

TABLE 14-continued

| Example | Reagents | Structure, Name and Data |
|---|---|---|
| | | 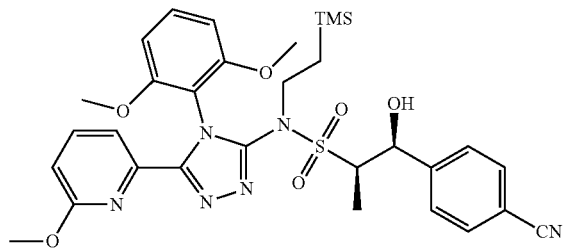<br>AND<br>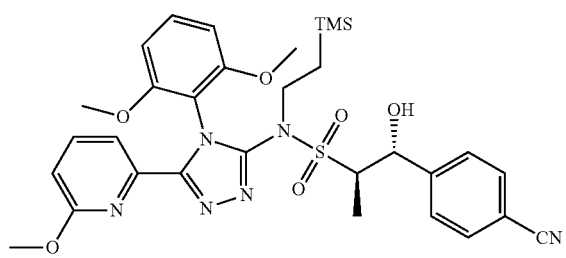 [SMILES: COc1cccc(-c2nnc(N(CC[Si](C)(C)C)S(=O)(=O)[C@H](C)[C@H](O)c3ccc(C#N)cc3)n2-c2c(OC)cccc2OC)n1]<br>(1R,2S)-1-(4-cyanophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (1R,2R)-1-(4-cyanophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (1S,2R)-1-(4-cyanophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (1S,2S)-1-(4-cyanophenyl)-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide<br>LCMS-ESI (POS.) m/z: 651.2 (M + H)$^+$. |
| 319.0 | Example 318.0, tris(dimethylamino)sulfonium difluorotrimethylsilicate (Sigma-Aldrich Chemical Company, Inc.). | 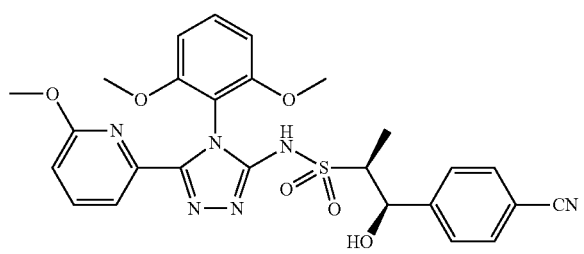 [SMILES: COc1cccc(-c2nnc(NS(=O)(=O)[C@@H](C)[C@H](O)c3ccc(C#N)cc3)n2-c2c(OC)cccc2OC)n1]<br>AND<br>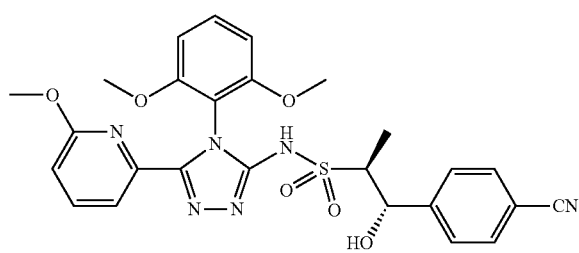 [SMILES: COc1cccc(-c2nnc(NS(=O)(=O)[C@@H](C)[C@@H](O)c3ccc(C#N)cc3)n2-c2c(OC)cccc2OC)n1]<br>AND |

| Example | Reagents | Structure, Name and Data |
|---|---|---|
| | | 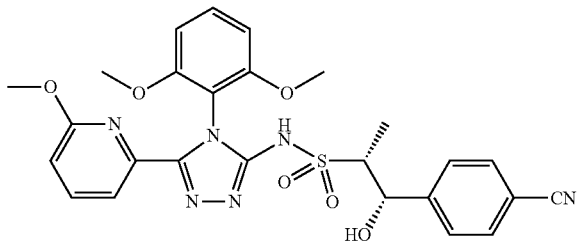 [SMILES: COc1cccc(-c2nnc(NS(=O)(=O)[C@H](C)[C@@H](O)c3ccc(C#N)cc3)n2-c2c(OC)cccc2OC)n1]
AND
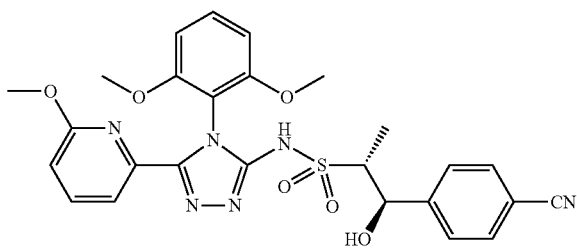 [SMILES: COc1cccc(-c2nnc(NS(=O)(=O)[C@H](C)[C@H](O)c3ccc(C#N)cc3)n2-c2c(OC)cccc2OC)n1]
(1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide and (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide and (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide and (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide
LCMS-ESI (POS.) m/z: 551.2 (M + H)$^+$. |
| 320.0 | The racemic Example 319.0 was separated by supercritical fluid chromatography (250 × 21 mm AD-H column with 70 mL/min 30% EtOH (20 mM NH$_3$)/CO$_2$. Outlet pressure = 100 bar; temperature = 40° C.; wavelength = 226 nm; injection volume = 18 mg/injection. This was the first isomer to elute under these conditions. | 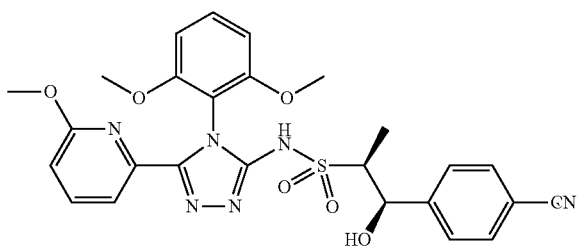 [SMILES: COc1cccc(-c2nnc(NS(=O)(=O)[C@@H](C)[C@H](O)c3ccc(C#N)cc3)n2-c2c(OC)cccc2OC)n1]
OR
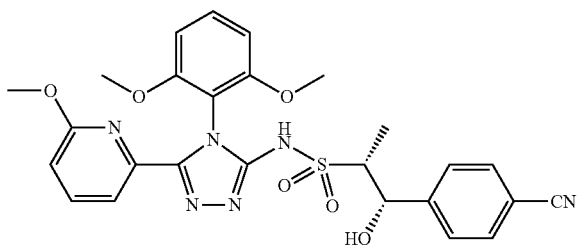 [SMILES: COc1cccc(-c2nnc(NS(=O)(=O)[C@H](C)[C@@H](O)c3ccc(C#N)cc3)n2-c2c(OC)cccc2OC)n1]
OR |

| Example | Reagents | Structure, Name and Data |
|---|---|---|
| | | 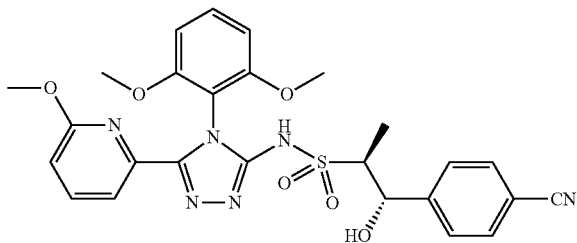 [SMILES: COc1cccc(-c2nnc(NS(=O)(=O)[C@@H](C)[C@@H](O)c3ccc(C#N)cc3)n2-c2c(OC)cccc2OC)n1]<br>OR<br>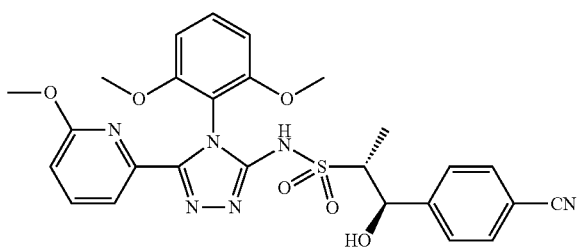 [SMILES: COc1cccc(-c2nnc(NS(=O)(=O)[C@H](C)[C@H](O)c3ccc(C#N)cc3)n2-c2c(OC)cccc2OC)n1]<br>(1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide<br>$^1$H NMR (400 MHz, CDCl$_3$) δ 7.60-7.65 (m, 4H), 7.46 (d, J = 8.02 Hz, 2H), 7.37 (t, J = 8.51 Hz, 1H), 6.73 (dd, J = 5.09, 4.11 Hz, 1H), 6.67-6.71 (m, 1H), 6.62 (dd, J = 8.61, 0.78 Hz, 1H), 5.55 (s, 1H), 3.98-4.10 (m, 1H), 3.85 (s, 3H), 3.68 (s, 3H), 3.17 (s, 3H), 3.11-3.16 (m, 1H), 1.15 (d, J = 7.04 Hz, 3H). LCMS-ESI (POS.) m/z: 551.2 (M + H)$^+$. |
| 321.0 | The racemic Example 319.0 was separated by supercritical fluid chromatography (250 × 21 mm AD-H column with 70 mL/min 30% EtOH (20 mM NH$_3$)/CO$_2$. Outlet pressure = 100 bar; temperature = 40° C.; wavelength = 226 nm; injection volume = 18 mg/injection. This was the second isomer to elute under these conditions. | 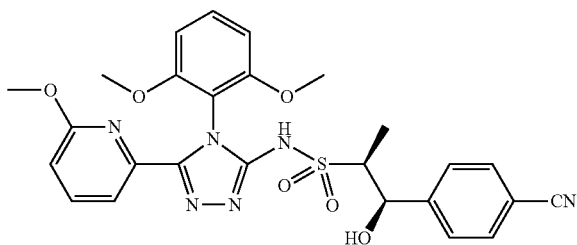 [SMILES: COc1cccc(-c2nnc(NS(=O)(=O)[C@@H](C)[C@H](O)c3ccc(C#N)cc3)n2-c2c(OC)cccc2OC)n1]<br>OR<br>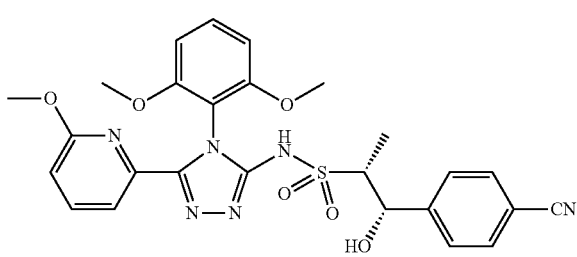<br>OR |

TABLE 14-continued

| Example | Reagents | Structure, Name and Data |
|---|---|---|

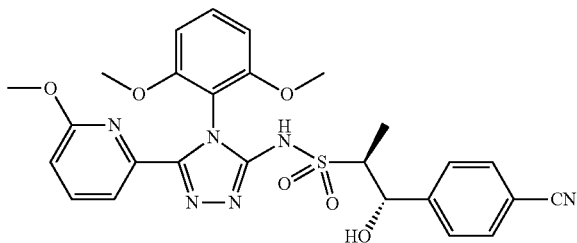 [SMILES: COc1cccc(-c2nnc(NS(=O)(=O)[C@@H](C)[C@@H](O)c3ccc(C#N)cc3)n2-c2c(OC)cccc2OC)n1]

OR

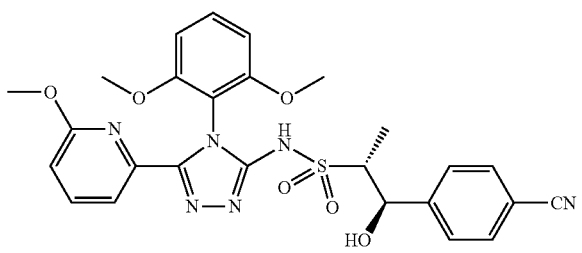 [SMILES: COc1cccc(-c2nnc(NS(=O)(=O)[C@H](C)[C@H](O)c3ccc(C#N)cc3)n2-c2c(OC)cccc2OC)n1]

(1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide
$^1$H NMR (400 MHz, CDCl$_3$) δ 7.59-7.65 (m, 4H), 7.42 (d, J = 8.41 Hz, 2H), 7.35 (t, J = 8.51 Hz, 1H), 6.70-6.75 (m, 1H), 6.60-6.67 (m, 2H), 4.88 (d, J = 9.00 Hz, 1H), 3.77 (s, 3H), 3.70 (s, 3H), 3.18-3.25 (m, 1H), 3.16 (s, 3H), 0.99 (d, J = 7.04 Hz, 3H).
LCMS-ESI (POS.) m/z: 551.2 (M + H)$^+$.

| | | |
|---|---|---|
| 322.0 | The racemic Example 319.0 was separated by supercritical fluid chromatography (250 × 21 mm AD-H column with 70 mL/min 30% EtOH (20 mM NH$_3$)/CO$_2$. Outlet pressure = 100 bar; temperature = 40° C.; wavelength = 226 nm; volume = 18 mg/injection. This was the third isomer to elute under these conditions. | 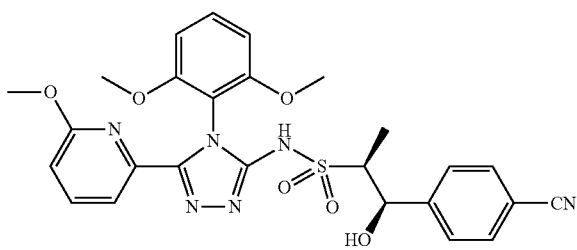 OR 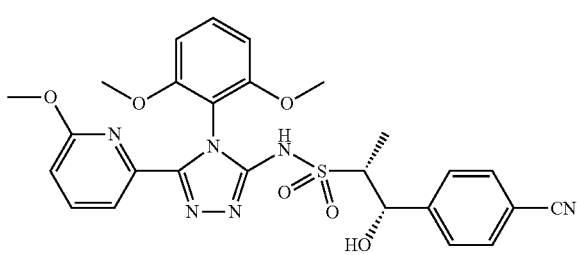 OR |

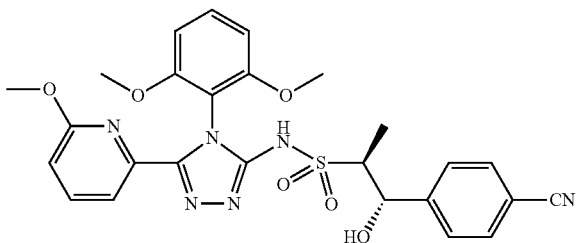

OR

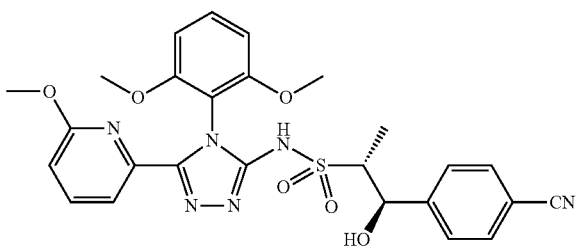

(1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide
$^1$H NMR (400 MHz, CDCl$_3$) δ 7.60-7.66 (m, 4H), 7.46 (d, J = 8.02 Hz, 2H), 7.37 (t, J = 8.51 Hz, 1H), 6.73 (t, J = 4.60 Hz, 1H), 6.69 (dd, J = 8.41, 0.78 Hz, 1H), 6.62 (dd, J = 8.61, 0.78 Hz, 1H), 5.55 (s, 1H), 3.85 (s, 3H), 3.68 (s, 3H), 3.16 (s, 3H), 3.13-3.16 (m, 1H), 1.15 (d, J = 6.85 Hz, 3H).
LCMS-ESI (POS.) m/z: 551.2 (M + H)$^+$.

| Example | Reagents | Structure, Name and Data |
|---|---|---|
| 323.0 | The racemic Example 319.0 was separated by supercritical fluid chromatography (250 × 21 mm AD-H column with 70 mL/min 30% EtOH (20 mM NH$_3$)/CO$_2$. Outlet pressure = 100 bar; temperature = 40° C.; wavelength = 226 nm; volume = 18 mg/injection. This was the fourth isomer to elute under these conditions. | |

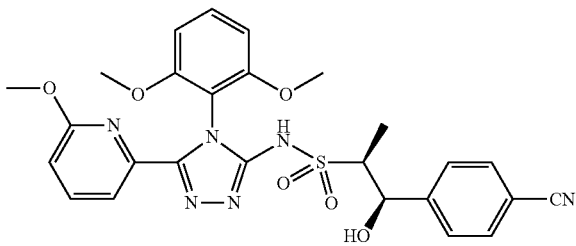 [SMILES: COc1cccc(-c2nnc(NS(=O)(=O)[C@@H](C)[C@H](O)c3ccc(C#N)cc3)n2-c2c(OC)cccc2OC)n1]

OR

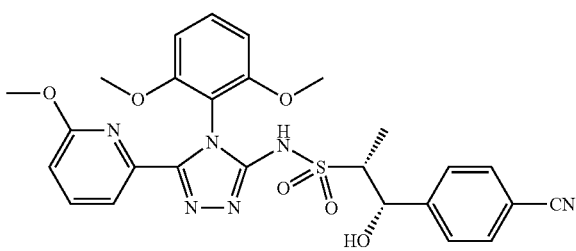 [SMILES: COc1cccc(-c2nnc(NS(=O)(=O)[C@H](C)[C@@H](O)c3ccc(C#N)cc3)n2-c2c(OC)cccc2OC)n1]

OR

| Example | Reagents | Structure, Name and Data |
|---|---|---|
| | | 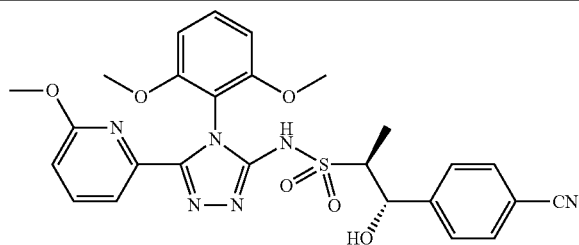 OR 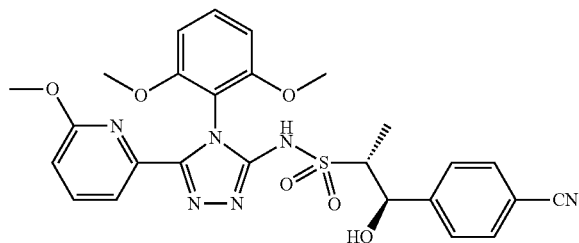 (1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide or (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide <br> $^1$H NMR (400 MHz, CDCl$_3$) δ 7.60-7.66 (m, 4H), 7.42 (d, J = 8.22 Hz, 2H), 7.35 (t, J = 8.51 Hz, 1H), 6.69-6.78 (m, 1H), 6.58-6.68 (m, 2H), 4.88 (d, J = 8.80 Hz, 1H), 3.77 (s, 3H), 3.70 (s, 3H), 3.18-3.25 (m, 1H), 3.16 (s, 3H), 0.99 (d, J = 7.04 Hz, 3H). <br> LCMS-ESI (POS.) m/z: 551.2 (M + H)$^+$. |
| 324.1 | N-(4-(2,6-dimethoxyphenyl)-5-(6-methoxypyridin-2-yl)-4H-1,2,4-triazol-3-yl)-N-(2-(trimethylsilyl)ethyl)ethanesulfonamide (Example 5.0), o-anisaldehyde (Sigma-Aldrich Chemical Company, Inc.), n-butyllithium solution, 1.6M in hexanes (Acros Organics). | 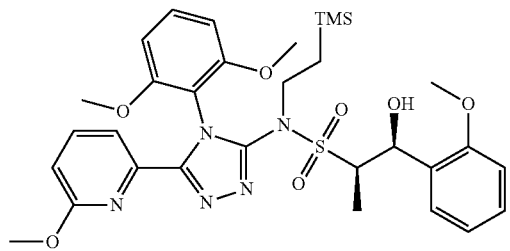 [SMILES: COc1cccc(-c2nnc(N(CC[Si](C)(C)C)S(=O)(=O)[C@H](C)[C@@H](O)c3ccccc3OC)n2-c2c(OC)cccc2OC)n1] AND 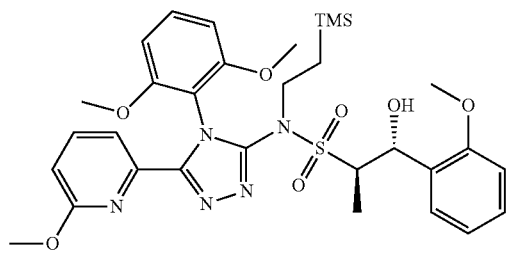 [SMILES: COc1cccc(-c2nnc(N(CC[Si](C)(C)C)S(=O)(=O)[C@H](C)[C@H](O)c3ccccc3OC)n2-c2c(OC)cccc2OC)n1] AND |

| Example | Reagents | Structure, Name and Data |
|---|---|---|
| | | 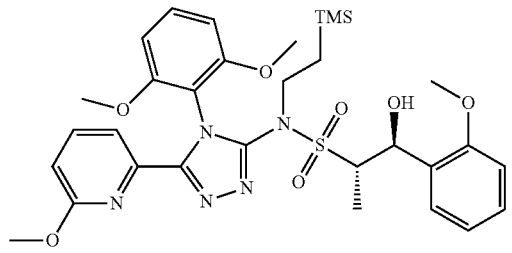 [SMILES: COc1cccc(-c2nnc(N(CC[Si](C)(C)C)S(=O)(=O)[C@@H](C)[C@@H](O)c3ccccc3OC)n2-c2c(OC)cccc2OC)n1] |
| | | AND |
| | | 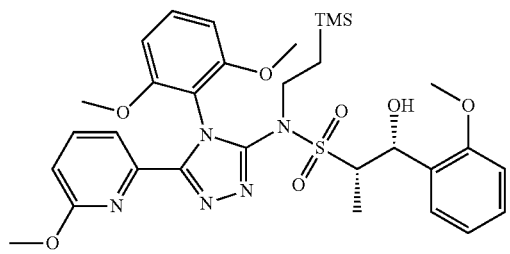 [SMILES: COc1cccc(-c2nnc(N(CC[Si](C)(C)C)S(=O)(=O)[C@@H](C)[C@H](O)c3ccccc3OC)n2-c2c(OC)cccc2OC)n1] |
| | | (1R)-N-(4-(2,6-dimethoxyphenyl)-5-(6-methoxypyridin-2-yl)-4H-1,2,4-triazol-3-yl)-1-hydroxy-1-(2-methoxyphenyl)-N-(2-(trimethylsilyl)ethyl)propane-2-sulfonamide and (1S)-N-(4-(2,6-dimethoxyphenyl)-5-(6-methoxypyridin-2-yl)-4H-1,2,4-triazol-3-yl)-1-hydroxy-1-(2-methoxyphenyl)-N-(2-(trimethylsilyl)ethyl)propane-2-sulfonamide and (1S)-N-(4-(2,6-dimethoxyphenyl)-5-(6-methoxypyridin-2-yl)-4H-1,2,4-triazol-3-yl)-1-hydroxy-1-(2-methoxyphenyl)-N-(2-(trimethylsilyl)ethyl)propane-2-sulfonamide and (1R)-N-(4-(2,6-dimethoxyphenyl)-5-(6-methoxypyridin-2-yl)-4H-1,2,4-triazol-3-yl)-1-hydroxy-1-(2-methoxyphenyl)-N-(2-(trimethylsilyl)ethyl)propane-2-sulfonamide LCMS-ESI (POS.) m/z: 656.2 (M + H)$^+$. |
| 324.2 | Example 324.1, tris(dimethylamino)sulfonium difluorotrimethylsilicate (Sigma-Aldrich Chemical-Company, Inc.). | 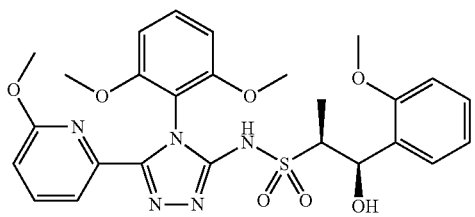 [SMILES: COc1cccc(-c2nnc(NS(=O)(=O)[C@@H](C)[C@H](O)c3ccccc3OC)n2-c2c(OC)cccc2OC)n1] |
| | | AND |
| | | 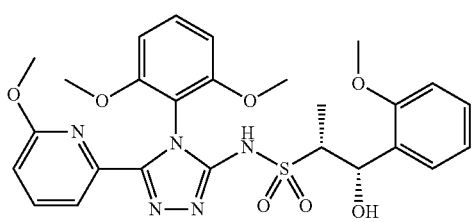 [SMILES: COc1cccc(-c2nnc(NS(=O)(=O)[C@H](C)[C@@H](O)c3ccccc3OC)n2-c2c(OC)cccc2OC)n1] |
| | | AND |

TABLE 14-continued

| Example | Reagents | Structure, Name and Data |
|---|---|---|

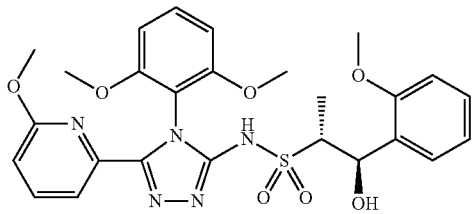 [SMILES: COc1cccc(-c2nnc(NS(=O)(=O)[C@H](C)[C@H](O)c3ccccc3OC)n2-c2c(OC)cccc2OC)n1]

AND

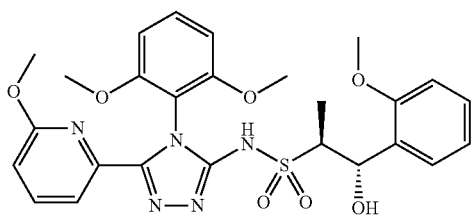 [SMILES: COc1cccc(-c2nnc(NS(=O)(=O)[C@@H](C)[C@@H](O)c3ccccc3OC)n2-c2c(OC)cccc2OC)n1]

(1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide and (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide and (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide and (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide
LCMS-ESI (POS.) m/z: 556.1 (M + H)+.

324.0    The Example 324.2 was separated by supercritical fluid chromatography (2 × 25 cm IC column with 60 mL/min 30% MeOH/CO$_2$. Outlet pressure = 100 bar; wavelength = 220 nm; injection volume = 1 mL, 4 mg/mL). This was the first isomer to elute under these conditions.

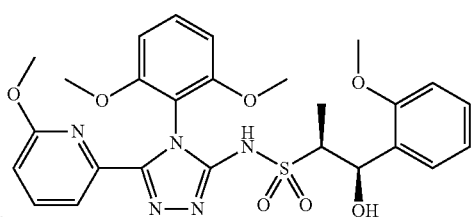 [SMILES: COc1cccc(-c2nnc(NS(=O)(=O)[C@@H](C)[C@H](O)c3ccccc3OC)n2-c2c(OC)cccc2OC)n1]

OR

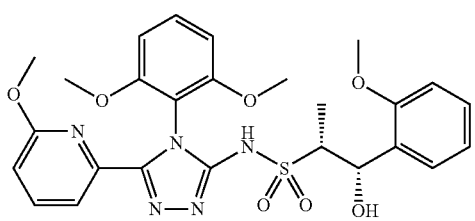 [SMILES: COc1cccc(-c2nnc(NS(=O)(=O)[C@H](C)[C@@H](O)c3ccccc3OC)n2-c2c(OC)cccc2OC)n1]

OR

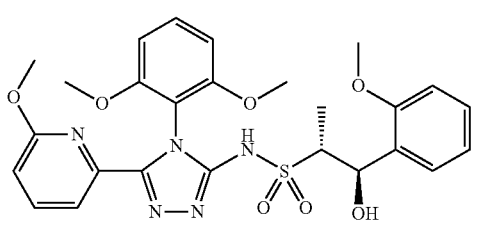 [SMILES: COc1cccc(-c2nnc(NS(=O)(=O)[C@H](C)[C@H](O)c3ccccc3OC)n2-c2c(OC)cccc2OC)n1]

OR

TABLE 14-continued

| Example | Reagents | Structure, Name and Data |
|---|---|---|
| | | 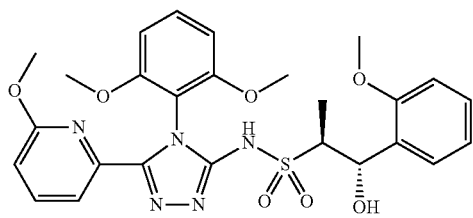 [SMILES: COc1cccc(-c2nnc(NS(=O)(=O)[C@@H](C)[C@@H](O)c3ccccc3OC)n2-c2c(OC)cccc2OC)n1]
(1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide
$^1$H NMR (400 MHz, CDCl$_3$) δ 7.53-7.66 (m, 2H), 7.44-7.51 (m, 1H), 7.30-7.39 (m, 1H), 7.17-7.26 (m, 1H), 6.89-6.98 (m, 1H), 6.82 (d, J = 8.02 Hz, 1H), 6.64-6.74 (m, 2H), 6.60 (d, J = 8.22 Hz, 1H), 5.76 (br. s., 1H), 3.84 (br. s., 3H), 3.78 (br. s., 3H), 3.67 (s, 3H), 3.39-3.49 (m, 1H), 3.17 (s, 3H), 1.16 (d, J = 6.85 Hz, 3H).
LCMS-ESI (POS.) m/z: 556.1 (M + H)$^+$. |
| 325.0 | The Example 324.2 was separated by supercritical fluid chromatography (2 × 25 cm IC column with 60 mL/min 30% MeOH/CO$_2$. Outlet pressure = 100 bar; wavelength = 220 nm; injection volume = 1 mL, 4 mg/mL). This was the second isomer to elute under these conditions. | 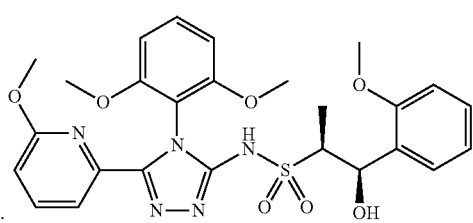
OR
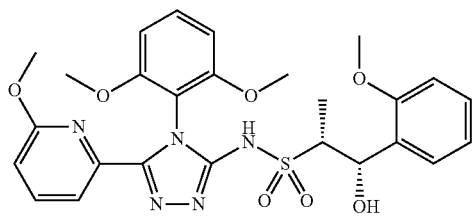 [SMILES: COc1cccc(-c2nnc(NS(=O)(=O)[C@H](C)[C@@H](O)c3ccccc3OC)n2-c2c(OC)cccc2OC)n1]
OR
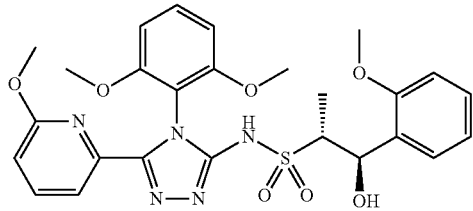 [SMILES: COc1cccc(-c2nnc(NS(=O)(=O)[C@H](C)[C@H](O)c3ccccc3OC)n2-c2c(OC)cccc2OC)n1]
OR |

| Example | Reagents | Structure, Name and Data |
|---|---|---|
| | | 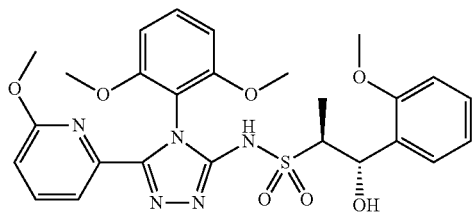 [SMILES: COc1cccc(-c2nnc(NS(=O)(=O)[C@@H](C)[C@@H](O)c3ccccc3OC)n2-c2c(OC)cccc2OC)n1]
(1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide
$^1$H NMR (400 MHz, CDCl$_3$) δ 7.56-7.66 (m, 2H), 7.44-7.52 (m, 1H), 7.31-7.38 (m, 1H), 7.19-7.26 (m, 1H), 6.92-7.00 (m, 1H), 6.79-6.88 (m, 1H), 6.65-6.75 (m, 2H), 6.60 (d, J = 8.41 Hz, 1H), 5.76 (s, 1H), 3.87 (br. s, 3H), 3.80 (s, 3H), 3.68 (s, 3H) 3.40-3.51 (m, 1H), 3.17 (s, 3H), 1.16 (d, J = 6.85 Hz, 3 H). LCMS-ESI (POS.) m/z: 556.2 (M + H)$^+$. |
| 326.0 | The Example 324.2 was separated by supercritical fluid chromatography (2 × 25 cm IC column with 60 mL/min 30% MeOH/CO$_2$. Outlet pressure = 100 bar; wavelength = 220 nm; injection volume = 1 mL, 4 mg/mL). This was the third isomer to elute under these conditions. | 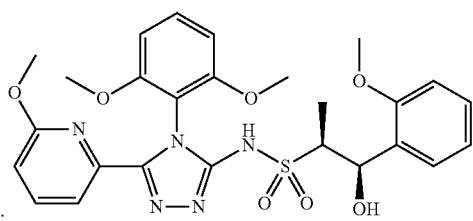
OR
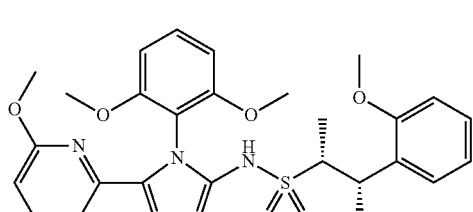
OR
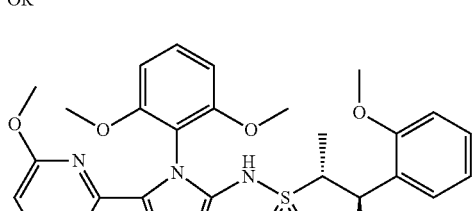
OR |

| Example | Reagents | Structure, Name and Data |
|---|---|---|
| | | 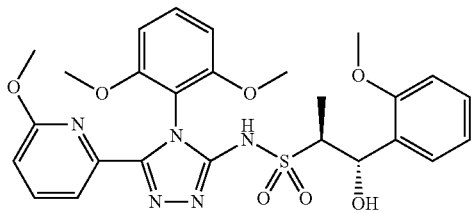 [SMILES: COc1cccc(-c2nnc(NS(=O)(=O)[C@@H](C)[C@@H](O)c3ccccc3OC)n2-c2c(OC)cccc2OC)n1]
(1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide
LCMS-ESI (POS.) m/z: 556.2 (M + H)+. |
| 327.0 | The Example 324.2 was separated by supercritical fluid chromatography (2 × 25 cm IC column with 60 mL/min 30% MeOH/CO2. Outlet pressure = 100 bar; wavelength = 220 nm; injection volume = 1 mL, 4 mg/mL). This was the fourth isomer to elute under these conditions. | 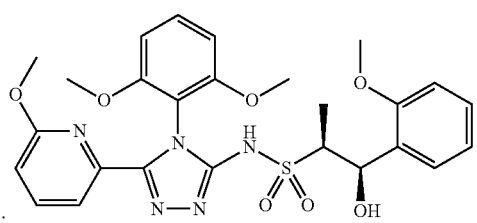
OR
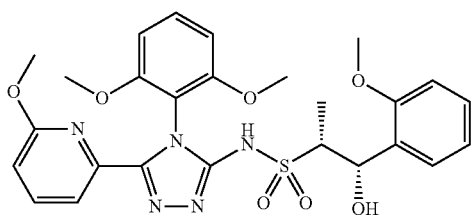 [SMILES: COc1cccc(-c2nnc(NS(=O)(=O)[C@H](C)[C@@H](O)c3ccccc3OC)n2-c2c(OC)cccc2OC)n1]
OR
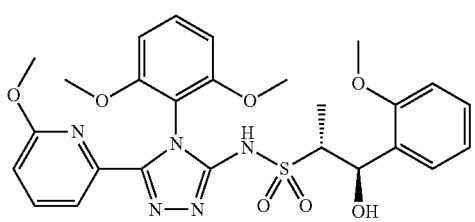 [SMILES: COc1cccc(-c2nnc(NS(=O)(=O)[C@H](C)[C@H](O)c3ccccc3OC)n2-c2c(OC)cccc2OC)n1]
OR
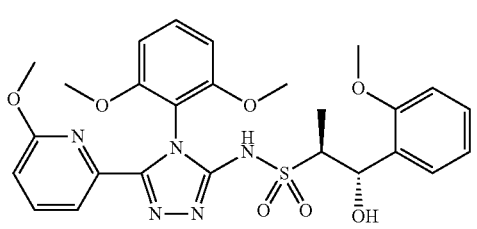 [SMILES: COc1cccc(-c2nnc(NS(=O)(=O)[C@@H](C)[C@@H](O)c3ccccc3OC)n2-c2c(OC)cccc2OC)n1]
(1R,2S)-N-(4-(2,6-dimethoxyphenyl)-5-(6-methoxy-2-pyridinyl)-4H-1,2,4-triazol-3-yl)-1- | hydroxy-1-(2-methoxyphenyl)-2-propanesulfonamide or (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide or (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide
LCMS-ESI (POS.) m/z: 556.1 (M + H)+.

Example 328.0: Preparation of (2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide and (2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide

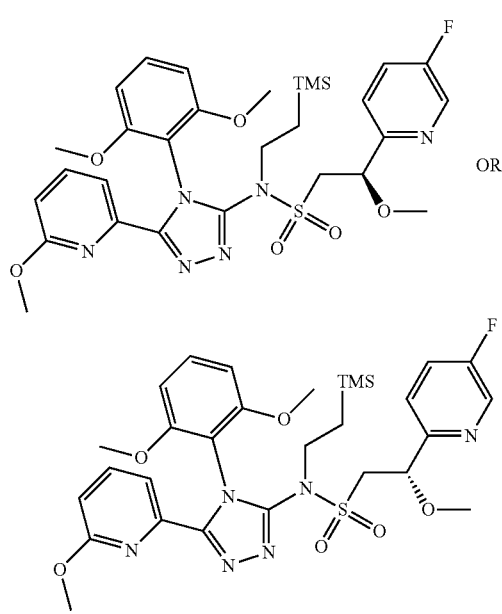

328.1

(R)—N-(4-(2,6-dimethoxyphenyl)-5-(6-methoxy-pyridin-2-yl)-4H-1,2,4-triazol-3-yl)-2-(5-fluoropyridin-2-yl)-2-methoxy-N-(2-(trimethylsilyl)ethyl)ethanesulfonamide and (S)—N-(4-(2,6-dimethoxyphenyl)-5-(6-methoxypyridin-2-yl)-4H-1,2,4-triazol-3-yl)-2-(5-fluoropyridin-2-yl)-2-methoxy-N-(2-(trimethylsilyl)ethyl)ethanesulfonamide, Example 328.1

A flask was charged with (R)—N-(4-(2,6-dimethoxyphenyl)-5-(6-methoxypyridin-2-yl)-4H-1,2,4-triazol-3-yl)-2-(5-fluoropyridin-2-yl)-2-hydroxy-N-(2-(trimethylsilyl)ethyl)ethanesulfonamide and (S)—N-(4-(2,6-dimethoxyphenyl)-5-(6-methoxypyridin-2-yl)-4H-1,2,4-triazol-3-yl)-2-(5-fluoropyridin-2-yl)-2-hydroxy-N-(2-(trimethylsilyl)ethyl)ethanesulfonamide (Example 315.1, 166 mg, 0.26 mmol) and was azeotroped with toluene. THF (3 mL) was added to the flask and then NaH (13.68 mg, 0.34 mmol) was added. After 11 min, MeI (0.023 mL, 0.37 mmol) was added. Stirring was continued at ambient temperature overnight. A significant amount of eliminated product was observed. A saturated solution of NH$_4$Cl was added, and the reaction was extracted with EtOAc. The EtOAc layer was dried with magnesium sulfate, filtered and concentrated in vacuo. The residue thus obtained was purified by silica gel chromatography eluting with gradient EtOAc in hexanes to provide the title compound 328.1 (60 mg, 35% yield) as a foamy solid.

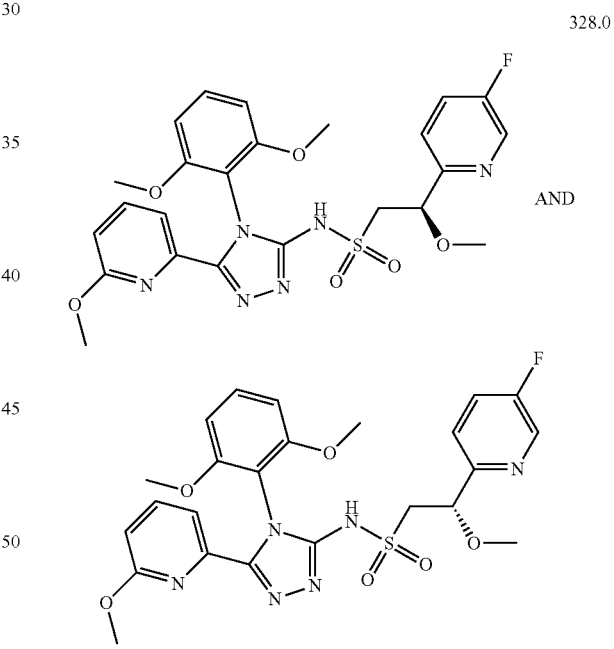

328.0

(2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide and (2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide, Example 328.0

The title compound 328.0 was prepared from 328.1 according to the procedure described in Example 315.0. $^1$H NMR (400 MHz, CD$_3$OD) δ 8.44 (d, J=2.93 Hz, 1H) 7.71

(dd, J=8.22, 7.43 Hz, 1H) 7.57-7.65 (m, 2H) 7.46-7.51 (m, 1H) 7.41 (t, J=8.27 Hz, 1H) 6.73-6.80 (m, 3H) 4.79-4.83 (m, 1H) 3.73 (s, 3H) 3.73 (s, 3H) 3.43-3.46 (m, 2H) 3.20 (s, 3H) 3.17 (s, 3H). LCMS-ESI (POS.) m/z: 545.0 (M+H)+.

Example 329.0: Preparation of (2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide

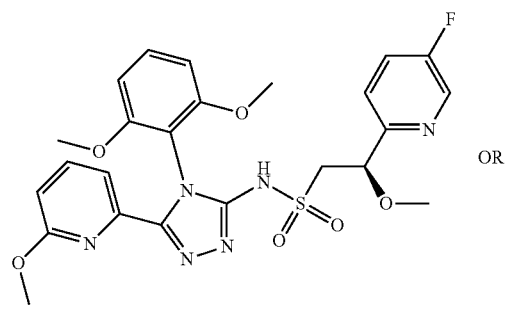

329.0

OR

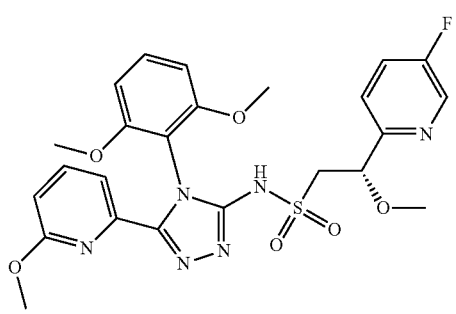

(2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide, Example 329.0

The racemate 328.0 was separated by supercritical fluid chromatography into two enantiomers by Lotus Inc. Separation condition: AS-H (2×15 cm) 25% EtOH/CO₂, 100 bar 60 mL/min, 220 nm inj vol.: 1 mL, 6 mg/mL MeOH. The title compound 329.0 was the first peak off the chiral column ¹H NMR (400 MHz, CD₃OD) δ 8.44 (d, J=2.93 Hz, 1H) 7.72 (dd, J=7.43, 0.39 Hz, 1H) 7.61 (m, 2H) 7.47-7.51 (m, 1H) 7.41 (t, J=8.23 Hz, 1H) 6.76 (m, 3H) 4.79-4.83 (m, 1H) 3.73-3.74 (m, 3H) 3.73 (s, 3H) 3.43-3.47 (m, 2H) 3.20 (s, 3H) 3.17 (s, 3H). LCMS-ESI (POS.) m/z: 545.0 (M+H)+.

Example 330.0: Preparation of (2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide

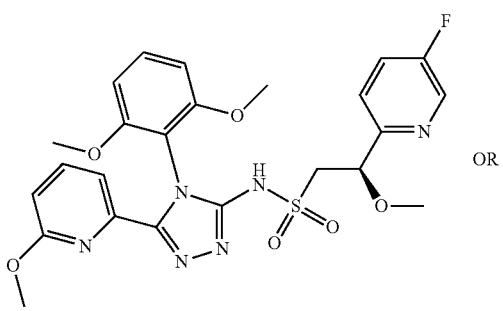

330.0

OR

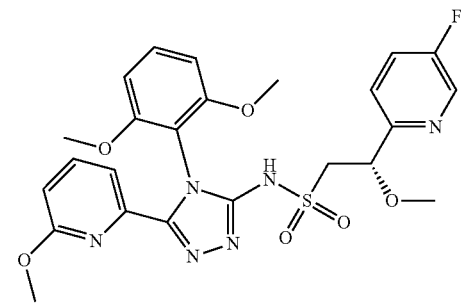

(2R)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide or (2S)—N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide, Example 330.0

The title compound was the second peak to elute off the chiral column on subjecting 328.0 to the SFC conditions described in Example 329.0. ¹H NMR (400 MHz, CD₃OD) δ 8.44 (d, J=2.74 Hz, 1H) 7.71 (dd, J=8.22, 7.43 Hz, 1H) 7.59-7.65 (m, 2H) 7.46-7.51 (m, 1H) 7.38-7.44 (m, 1H) 6.72-6.80 (m, 3H) 4.79-4.83 (m, 1H) 3.73 (s, 3H) 3.73 (s, 3H) 3.42-3.47 (m, 2H) 3.20 (s, 3H) 3.17 (s, 3H). LCMS-ESI (POS.) m/z: 545.0 (M+H)+.

Example 331.0: Preparation of (R)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide and (S)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide

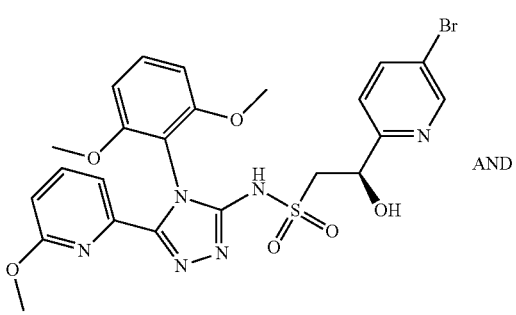

331.1

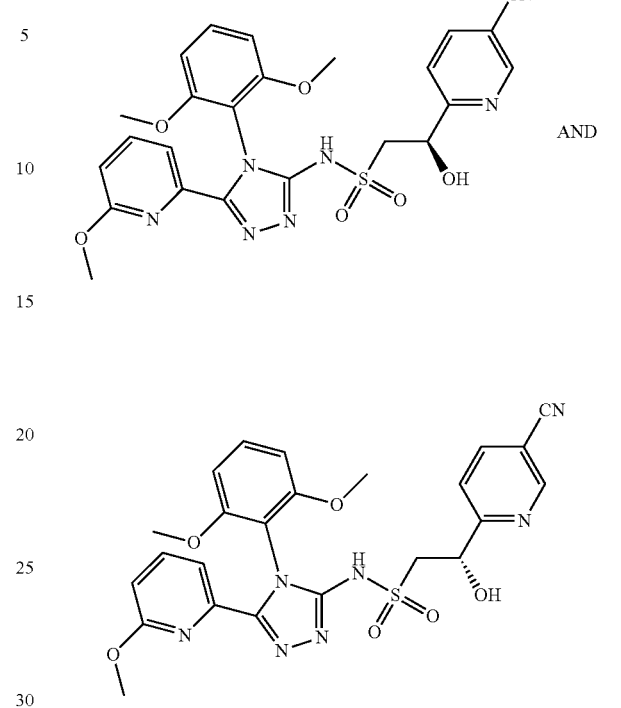

331.0

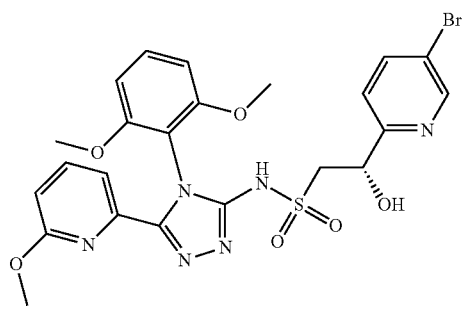

(R)-2-(5-bromopyridin-2-yl)-N-(4-(2,6-dimethoxyphenyl)-5-(6-methoxypyridin-2-yl)-4H-1,2,4-triazol-3-yl)-2-hydroxyethanesulfonamide and (S)-2-(5-bromopyridin-2-yl)-N-(4-(2,6-dimethoxyphenyl)-5-(6-methoxypyridin-2-yl)-4H-1,2,4-triazol-3-yl)-2-hydroxyethanesulfonamide, Example 331.1

The title compound was prepared following the same procedure as described in Example 315.0 employing 5-bromopicolinaldehyde. LCMS-ESI (POS.) m/z: 592.8 (M+H)⁺.

(R)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide and (S)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide, Example 331.0

A microwave tube was charged with (R)-2-(5-bromopyridin-2-yl)-N-(4-(2,6-dimethoxyphenyl)-5-(6-methoxypyridin-2-yl)-4H-1,2,4-triazol-3-yl)-2-hydroxyethanesulfonamide and (S)-2-(5-bromopyridin-2-yl)-N-(4-(2,6-dimethoxyphenyl)-5-(6-methoxypyridin-2-yl)-4H-1,2,4-triazol-3-yl)-2-hydroxyethanesulfonamide (331.1, 140 mg, 0.24 mmol), zinc cyanide (24.64 µL, 0.39 mmol), and tetrakis(triphenylphosphine)palladium(0) (54.7 mg, 0.047 mmol). Degassed DMF (1.9 mL) was added to the microwave tube, and the mixture was degassed again. The tube was heated in the microwave at 120° C. for 1 h. The reaction mixture was partitioned between EtOAc and water. The EtOAc layer was dried with magnesium sulfate, filtered and concentrated in vacuo. The material thus obtained was purified on reverse phase HPLC column, using an Agilent SB C₈ column, 0.1% TFA in CH₃CN/H₂O, 20-80% gradient elution over 25 min. The desired fractions were combined and lyophilized to provide the TFA salt of the title compound (40 mg, 26% yield) as a white solid. ¹H NMR (400 MHz, CDCl₃) δ 8.80 (d, J=2.15 Hz, 1H), 7.97 (dd, J=8.12, 2.05 Hz, 1H), 7.73 (d, J=8.22 Hz, 1H), 7.60-7.66 (m, 2H), 7.37 (t, J=8.41 Hz, 1H), 6.73 (dd, J=7.53, 1.47 Hz, 1H), 6.64 (dd, J=8.61, 5.48 Hz, 2H), 5.32 (dd, J=9.59, 1.37 Hz, 1H), 3.79 (dd, J=14.09, 1.96 Hz, 1H), 3.73 (s, 3H), 3.72 (s, 3H), 3.28 (dd, J=14.09, 9.78 Hz, 1H), 3.17 (s, 3H). LCMS-ESI (POS.) m/z: 538.0 (M+H)⁺.

Example 332.0: Preparation of (R)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide or (S)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide

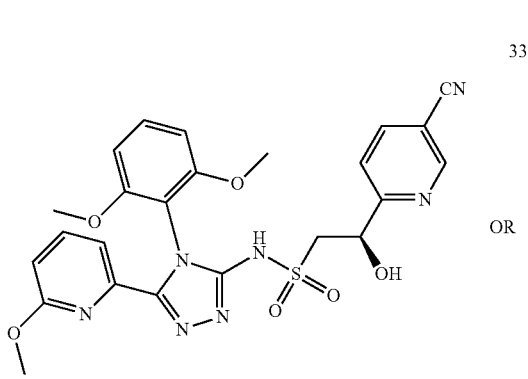

(R)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide or (S)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide, 332.0

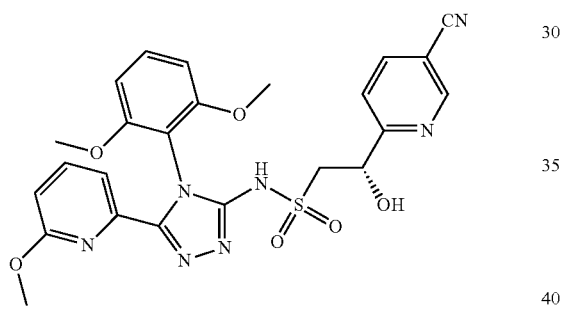

The racemate 331.0 was separated by supercritical fluid chromatography into two enantiomers by the following conditions: Run on Thar 80 SFC with 250×21 mm IC column with 27.5 g/min MeOH (neat)+27.5 g/min CO$_2$, 50% co-solvent at 55 g/min. Temperature.=24° C., Outlet pressure=100 bar, Wavelength=222 nm. Injected 1.2 mL of 32 mg sample dissolved in 13 mL of MeOH:DCM 7:6, c=2.46 mg/mL i.e. 2.95 mg per injection. Cycle time 10 min, run time=13 min. The title compound 332.0 was the first peak off chiral column. $^1$H NMR (400 MHz, DMSO-d$_6$) δ 8.95 (dd, J=2.15, 0.59 Hz, 1H), 8.30 (dd, J=8.22, 2.15 Hz, 1H), 7.80 (m, J=8.22 Hz, 1H), 7.67 (d, J=8.02 Hz, 1H), 7.58 (dd, J=7.43, 0.59 Hz, 1H), 7.40 (t, J=8.51 Hz, 1H), 6.82 (d, J=8.22 Hz, 1H), 6.78 (d, J=8.61 Hz, 2H), 5.06 (dd, J=8.31, 3.42 Hz, 1H), 3.64 (s, 3H), 3.63 (s, 3H), 3.55 (dd, J=14.18, 3.42 Hz, 1H), 3.24 (dd, J=13.89, 8.22 Hz, 1H), 3.10 (s, 3H). LCMS-ESI (POS.) m/z: 538.0 (M+H)$^+$.

Example 333.0: Preparation of (R)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide or (S)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide

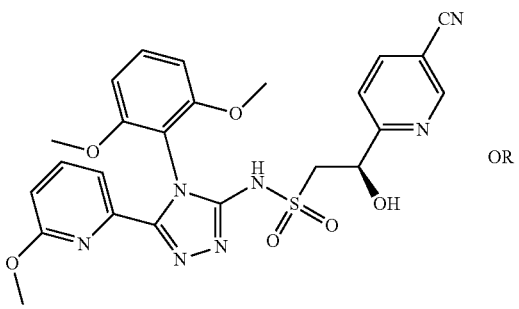

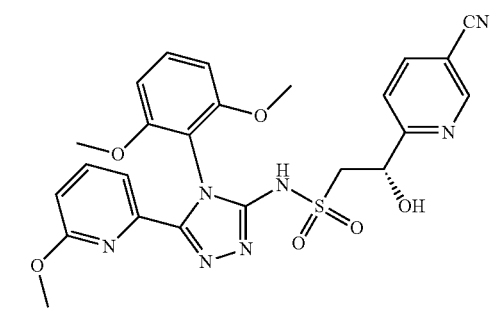

(R)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide or (S)-2-(5-cyanopyridin-2-yl)-N-(4-(2,6-dimethoxyphenyl)-5-(6-methoxypyridin-2-yl)-4H-1,2,4-triazol-3-yl)-2-hydroxyethanesulfonamide, Example 333.0

Example 333.0 was the second peak to elute off the chiral column on subjecting 331.0 to the SFC conditions described in Example 332.0. $^1$H NMR (400 MHz, CD$_2$Cl$_2$) δ 8.79 (br. s., 1H), 7.99 (dd, J=8.31, 1.86 Hz, 1H), 7.72 (d, J=8.22 Hz, 1H), 7.58-7.68 (m, 2H), 7.41 (t, J=8.51 Hz, 1H), 6.73 (dd, J=7.92, 0.88 Hz, 1H), 6.68 (dd, J=8.61, 4.89 Hz, 2H), 5.24 (d, J=9.98 Hz, 1H), 3.73-3.75 (m, 4H), 3.71 (s, 3H), 3.21 (dd, J=14.18, 9.88 Hz, 1H), 3.16 (s, 3H). LCMS-ESI (POS.) m/z: 538.0 (M+H)$^+$.

Example 334.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide Example 335.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide 334.0

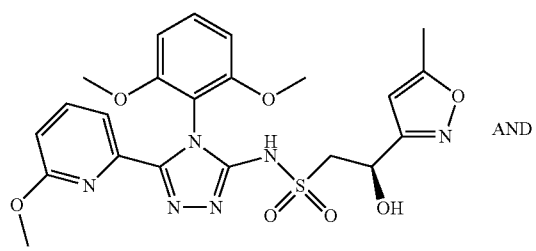

AND 335.0

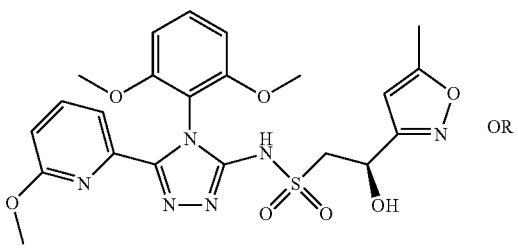

OR

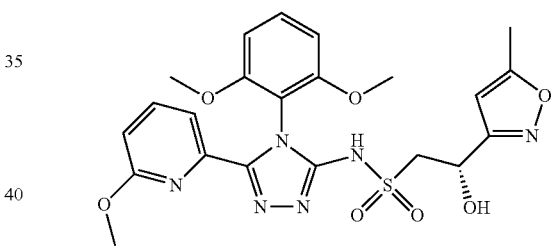

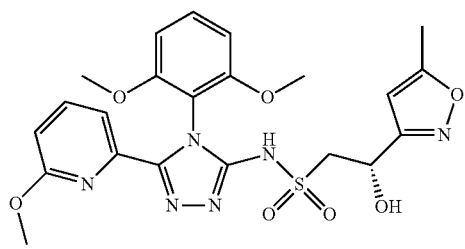

(2R)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide, Example 334.0

The title compound 334.0 was prepared according to the procedure of described in Example 315.0 employing 5-methylisoxazole-3-carbaldehyde. $^1$H NMR (400 MHz, CD$_3$OD) δ 7.71 (dd, J=8.22, 7.43 Hz, 1H), 7.61 (dd, J=7.43, 0.78 Hz, 1H), 7.41 (t, J=8.34 Hz, 1H), 6.73-6.78 (m, 3H), 6.16 (d, J=0.59 Hz, 1H), 5.20 (dd, J=7.82, 4.30 Hz, 1H), 3.73 (s, 3H), 3.72 (s, 3H), 3.41-3.46 (m, 2H), 3.17 (s, 3H), 2.40 (d, J=0.98 Hz, 3H). LCMS-ESI (POS.) m/z: 517.0 (M+H)$^+$.

(2R)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide, Example 335.0

The racemic compound 334.0 was separated by supercritical fluid chromatography. Separation conditions were as follows: Run on Thar 200 with 250×30 mm AD column with 40 g/min MeOH (20 mM NH$_3$)+60 g/min CO$_2$, 40% co-solvent at 100 g/min. Temperature 25° C., Wavelength 297 nm. Injected 0.5 mL of a solution of 110 mg sample dissolved in 12 mL MeOH:DCM 7:5; c=9.2 mg/mL; 4.6 mg/injection. Cycle time 5.3 min; run time=11 min. The title compound 335.0 was the first peak off the chiral column. $^1$H NMR (400 MHz, CD$_3$OD) δ 7.70 (t, J=7.76 Hz, 1H), 7.59 (d, J=7.43 Hz, 1H), 7.40 (t, J=8.51 Hz, 1H), 6.71-6.78 (m, 3H), 6.17 (s, 1H), 5.21 (dd, J=7.53, 4.60 Hz, 1H), 3.73 (s, 3H), 3.71 (s, 3H), 3.39-3.50 (m, 2H), 3.16 (s, 3H), 2.39 (s, 3H). LCMS-ESI (POS.) m/z: 517.0 (M+H)$^+$.

Example 336: Preparation of (2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide Example 337.0: Preparation of (2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide

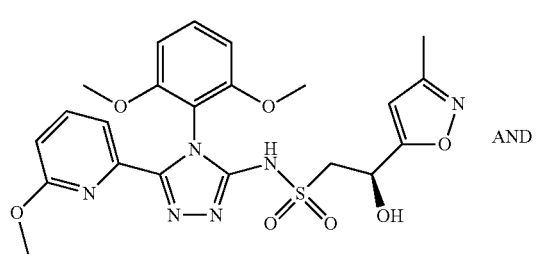

AND

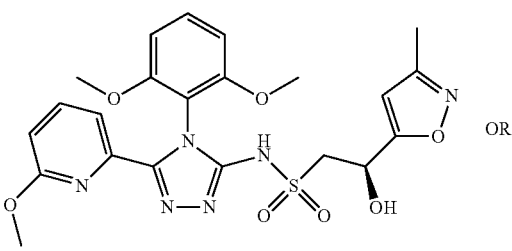

OR

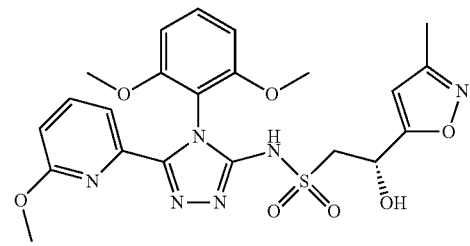

(2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide, Example 336.0

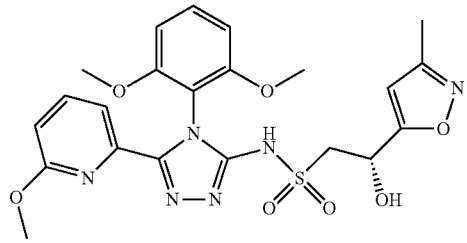

(2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide, Example 337.0

The title compound 336.0 was prepared according to the procedure of described in Example 315.0 employing 3-methylisoxazole-5-carbaldehyde. $^1$H NMR (400 MHz, CD$_3$OD) δ 7.72 (dd, J=8.31, 7.53 Hz, 1H), 7.61 (dd, J=7.43, 0.78 Hz, 1H), 7.41 (t, J=8.51 Hz, 1H), 6.76 (m, 3H), 6.21 (s, 1H), 5.21 (dd, J=8.12, 4.01 Hz, 1H), 3.73 (s, 3H), 3.72 (s, 3H), 3.38-3.51 (m, 2H), 3.17 (s, 3H), 2.25 (s, 3H). LCMS-ESI (POS.) m/z: 517.0 (M+H)$^+$.

The racemate 336.0 was separated by supercritical fluid chromatography into two enantiomers. Separation condition (by Lotus Inc.): AD-H (2×15 cm), 22% 1:1 ACN:MeOH/CO$_2$, 100 bar, 60 mL/min, 220 nm. inj vol.: 0.7 mL, 10 mg/mL 1:3 DCM:MeOH. The title compound 337.0 was the first peak off the chiral column. $^1$H NMR (400 MHz, CD$_3$OD) δ 7.71 (t, J=7.68 Hz, 1H), 7.61 (d, J=7.19 Hz, 1H), 7.41 (t, J=8.51 Hz, 1H), 6.73-6.79 (m, 3H), 6.21 (s, 1H), 5.21 (dd, J=8.22, 4.11 Hz, 1H), 3.73 (s, 3H), 3.71 (s, 3H), 3.38-3.52 (m, 2H), 3.17 (s, 3H), 2.25 (s, 3H). LCMS-ESI (POS.) m/z: 517.0 (M+H)$^+$.

Example 338.0: Preparation of (2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide Example 339.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide

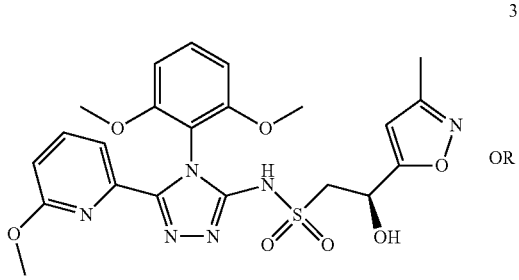

OR

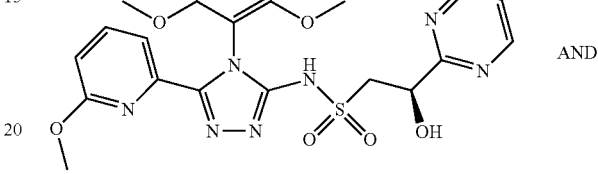

AND

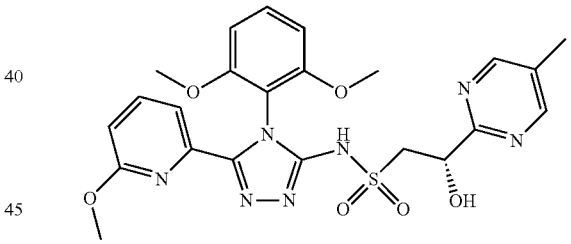

(2R)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide, Example 338.0

(2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide, Example 339.0

Example 338.0 was the second peak to elute off the chiral column on subjecting 336.0 to the SFC conditions described in Example 337.0. $^1$H NMR (400 MHz, CD$_3$OD) δ 7.71 (dd, J=8.22, 7.43 Hz, 1H) 7.61 (d, J=7.19 Hz, 1H) 7.41 (t, J=8.51 Hz, 1H) 6.73-6.79 (m, 3H) 6.21 (s, 1H) 5.21 (dd, J=8.12, 4.01 Hz, 1H) 3.73 (s, 3H) 3.71 (s, 3H) 3.38-3.52 (m, 2H) 3.17 (s, 3H) 2.25 (s, 3H). LCMS-ESI (POS.) m/z: 517.0 (M+H)$^+$.

The title compound 339.0 was prepared according to the procedure described in Example 315.0 employing 5-methylpyrimidine-2-carbaldehyde. $^1$H NMR (400 MHz, CD$_3$OD) δ 8.66 (s, 2H), 7.71 (t, J=7.89 Hz, 1H), 7.60 (d, J=7.26 Hz, 1H), 7.40 (t, J=8.26 Hz, 1H), 6.72-6.79 (m, 3H), 5.25 (dd, J=7.63, 4.11 Hz, 1H), 3.70-3.76 (m, 7H), 3.47 (dd, J=14.28, 7.83 Hz, 1H), 3.17 (s, 3H), 2.35 (s, 3H). LCMS-ESI (POS.) m/z: 528.0 (M+H)$^+$.

Example 340.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide

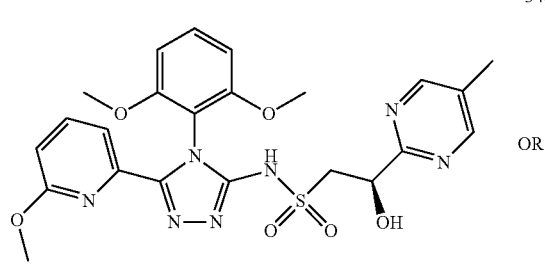

340.0

OR

Example 341.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide

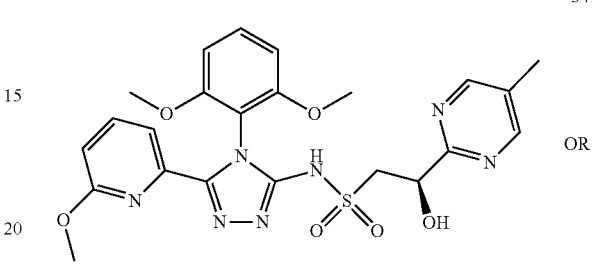

341.0

OR

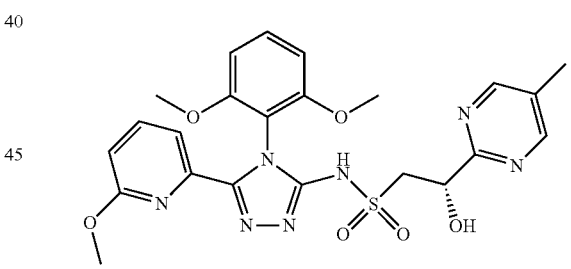

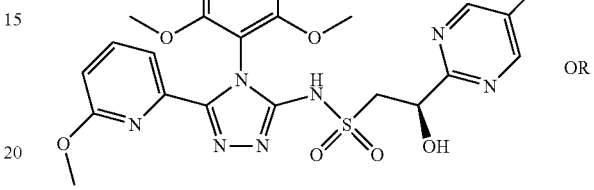

(2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide, Example 340.0

The racemate 339.0 was separated by supercritical fluid chromatography into two enantiomers by Lotus Inc. separation condition: AD-H (2×15 cm), 35% 1:1 ACN:MeOH/CO$_2$, 100 bar, 65 mL/min, 220 nm, inj vol.: 0.6 mL, 9 mg/mL 1:1 DCM:MeOH. The title compound 340.0 was the first peak off the chiral column $^1$H NMR (400 MHz, CD$_3$OD) δ 8.62 (s, 2H), 7.71 (t, J=7.83 Hz, 1H), 7.60 (d, J=7.29 Hz, 1H), 7.40 (t, J=8.51 Hz, 1H), 6.70-6.81 (m, 3H), 5.23 (dd, J=8.02, 4.11 Hz, 1H), 3.68-3.79 (m, 7H), 3.45 (dd, J=14.09, 8.02 Hz, 1H), 3.17 (s, 3H), 2.33 (s, 3H). LCMS-ESI (POS.) m/z: 528.0 (M+H)$^+$.

(2R)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide, Example 341.0

Example 341.0 was the second peak to elute off the chiral column on subjecting 339.0 to the SFC conditions described in Example 340.0. $^1$H NMR (400 MHz, CD$_3$OD) δ 8.62 (s, 2H), 7.71 (t, J=7.29 Hz, 1H), 7.60 (d, J=7.13 Hz, 1H), 7.40 (t, J=8.51 Hz, 1H), 6.72-6.78 (m, 3H), 5.23 (dd, J=7.92, 4.21 Hz, 1H), 3.73 (m, 7H), 3.46 (dd, J=14.28, 8.02 Hz, 1H), 3.17 (s, 3H), 2.33 (s, 3H). LCMS-ESI (POS.) m/z: 528.0 (M+H)$^+$.

Example 342.0: Preparation of (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide and (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide and (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide and (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide

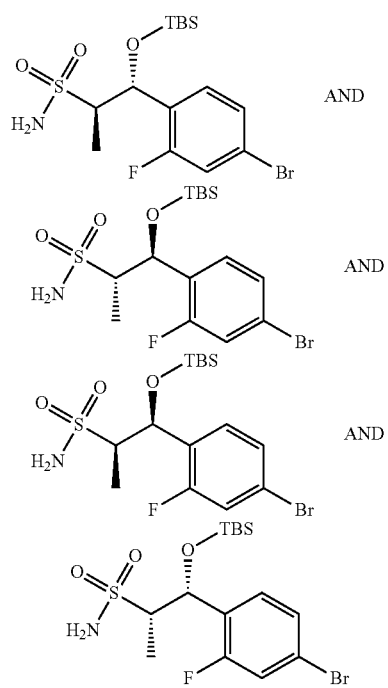

342.1

(1S,2S)-1-(4-bromo-2-fluorophenyl)-1-((tert-butyldimethylsilyl)oxy)propane-2-sulfonamide and (1R,2R)-1-(4-bromo-2-fluorophenyl)-1-((tert-butyldimethylsilyl)oxy)propane-2-sulfonamide and (1S,2R)-1-(4-bromo-2-fluorophenyl)-1-((tert-butyldimethylsilyl)oxy)propane-2-sulfonamide and (1R,2S)-1-(4-bromo-2-fluorophenyl)-1-((tert-butyldimethylsilyl)oxy)propane-2-sulfonamide, Example 342.1

(1S,2S)-1-(4-Bromo-2-fluorophenyl)-1-hydroxypropane-2-sulfonamide and (1R,2S)-1-(4-Bromo-2-fluorophenyl)-1-hydroxypropane-2-sulfonamide and (1S,2R)-1-(4-Bromo-2-fluorophenyl)-1-hydroxypropane-2-sulfonamide and (1R,2R)-1-(4-Bromo-2-fluorophenyl)-1-hydroxypropane-2-sulfonamide (prepared following the procedures described in Example C) (308 mg, 0.987 mmol) was azeotroped with toluene. Then DMAP (12.05 mg, 0.099 mmol) and tert-butylchlorodimethylsilane (178 mg, 1.18 mmol) were added, followed by DCM (8 mL) and TEA (0.358 mL, 2.57 mmol). The reaction was stirred at RT for 16 h. The reaction product was concentrated in vacuo and purified by chromatography through a Redi-Sep pre-packed gold silica gel column, eluting with a gradient of 0-20% EtOAc in hexanes to provide 342.1 (372 mg, 88%) as an oil. LCMS-ESI (POS.) m/z: 427.9 (M+H)+.

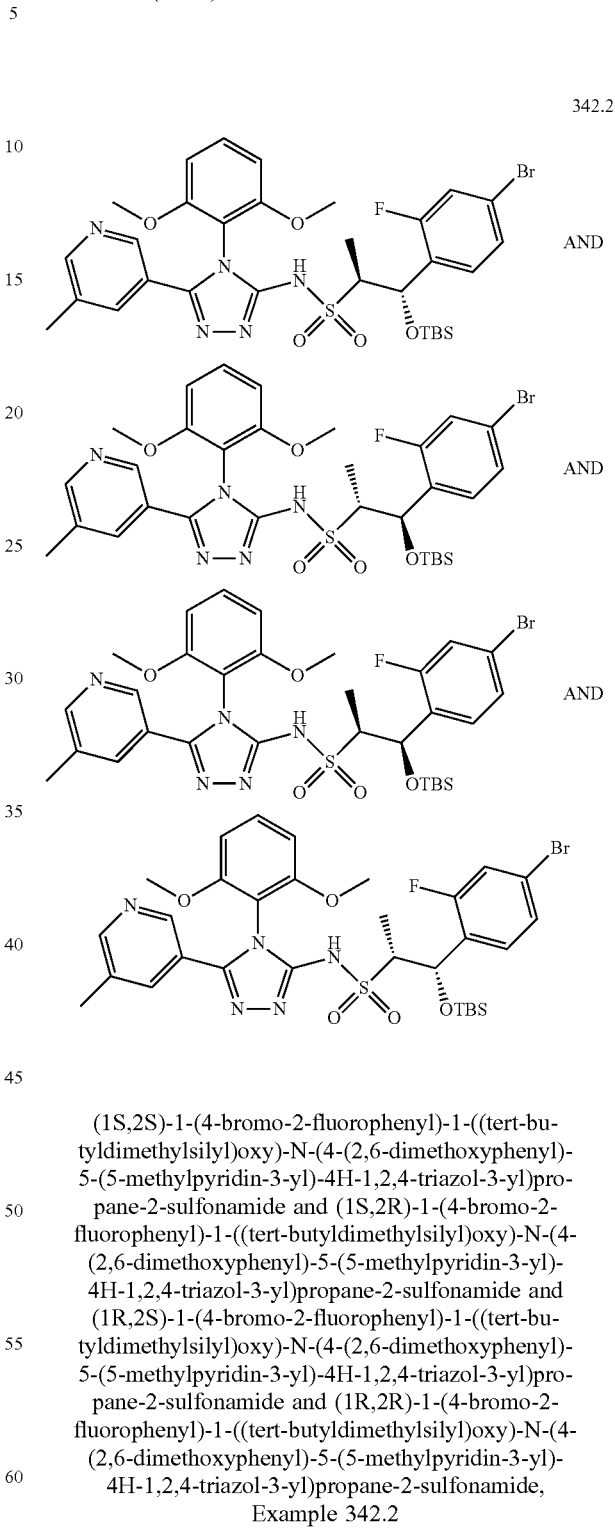

342.2

(1S,2S)-1-(4-bromo-2-fluorophenyl)-1-((tert-butyldimethylsilyl)oxy)-N-(4-(2,6-dimethoxyphenyl)-5-(5-methylpyridin-3-yl)-4H-1,2,4-triazol-3-yl)propane-2-sulfonamide and (1S,2R)-1-(4-bromo-2-fluorophenyl)-1-((tert-butyldimethylsilyl)oxy)-N-(4-(2,6-dimethoxyphenyl)-5-(5-methylpyridin-3-yl)-4H-1,2,4-triazol-3-yl)propane-2-sulfonamide and (1R,2S)-1-(4-bromo-2-fluorophenyl)-1-((tert-butyldimethylsilyl)oxy)-N-(4-(2,6-dimethoxyphenyl)-5-(5-methylpyridin-3-yl)-4H-1,2,4-triazol-3-yl)propane-2-sulfonamide and (1R,2R)-1-(4-bromo-2-fluorophenyl)-1-((tert-butyldimethylsilyl)oxy)-N-(4-(2,6-dimethoxyphenyl)-5-(5-methylpyridin-3-yl)-4H-1,2,4-triazol-3-yl)propane-2-sulfonamide, Example 342.2

The title compound was prepared following the procedure described in Example A with the initial stage heated at 70° C. overnight to provide 342.2 (149 mg 68%)). LCMS-ESI (POS.) m/z: 722.0 (M+H)+.

342.3

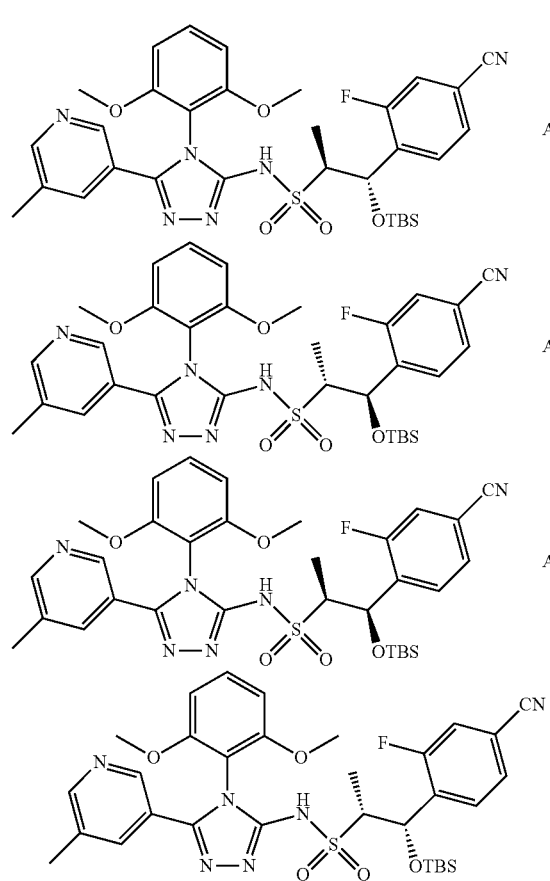

342.0

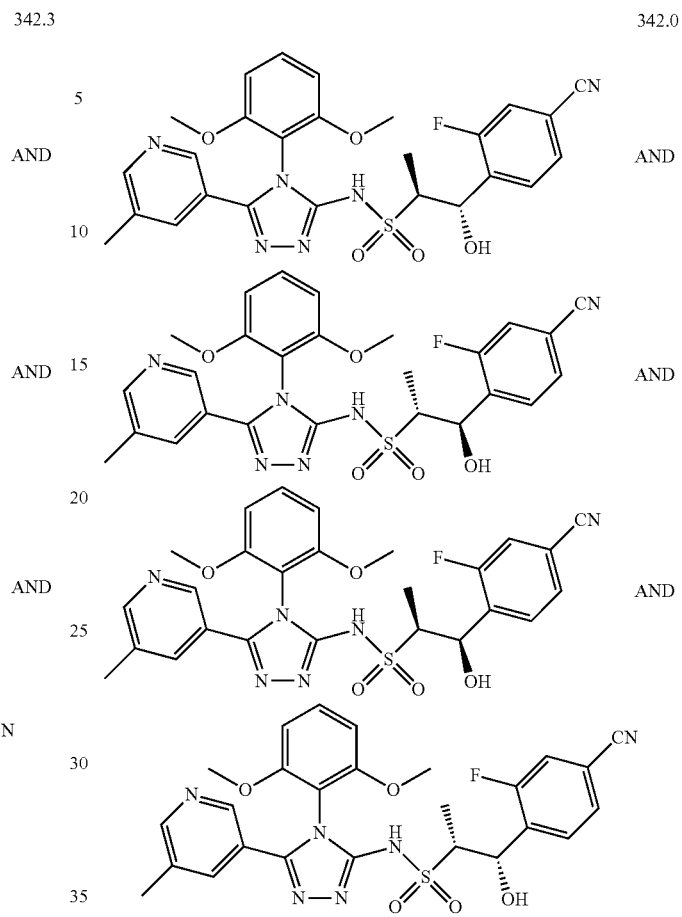

(1S,2S)-1-((tert-butyldimethylsilyl)oxy)-1-(4-cyano-2-fluorophenyl)-N-(4-(2,6-dimethoxyphenyl)-5-(5-methylpyridin-3-yl)-4H-1,2,4-triazol-3-yl)propane-2-sulfonamide and (1S,2R)-1-((tert-butyldimethylsilyl)oxy)-1-(4-cyano-2-fluorophenyl)-N-(4-(2,6-dimethoxyphenyl)-5-(5-methylpyridin-3-yl)-4H-1,2,4-triazol-3-yl)propane-2-sulfonamide and (1R,2S)-1-((tert-butyldimethylsilyl)oxy)-1-(4-cyano-2-fluorophenyl)-N-(4-(2,6-dimethoxyphenyl)-5-(5-methylpyridin-3-yl)-4H-1,2,4-triazol-3-yl)propane-2-sulfonamide and (1R,2R)-1-((tert-butyldimethylsilyl)oxy)-1-(4-cyano-2-fluorophenyl)-N-(4-(2,6-dimethoxyphenyl)-5-(5-methylpyridin-3-yl)-4H-1,2,4-triazol-3-yl)propane-2-sulfonamide,
Example 342.3

A microwave tube was charged with 342.2 (146 mg, 0.20 mmol), zinc cyanide (39.0 mg, 0.33 mmol, Alfa Aesar), and tetrakis(triphenylphosphine)palladium (46.8 mg, 0.041 mmol, Strem Chemicals Inc.). DMF (1.7 mL) degassed with Argon was added, and the mixture was further degassed with argon. The mixture was heated in the microwave at 120° C. for 1 h and then the reaction was diluted with water and extracted with DCM. The DCM layer was dried, concentrated, and purified by chromatography through a Redi-Sep pre-packed gold silica gel column, eluting with a gradient 0-8% MeOH in DCM to provide 342.3 (65 mg). LCMS-ESI (POS.) m/z: 667.1 (M+H)$^+$.

(1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide and (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide and (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide and (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide,
Example 342.0

A flask was charged with 342.3 (65 mg, 0.097 mmol) and to this was added tris(dimethylamino)sulfonium difluorotrimethylsilicate (IV) (81 mg, 0.292 mmol) followed by DMF (1.2 mL). The reaction was heated at 70° C. for 1 h. The reaction mixture was directly purified by reverse phase HPLC using an Agilent SB $C_8$ column, 0.1% TFA in $CH_3CN/H_2O$, gradient 30-80% over 25 min (collected the peaks that were visible at 220 nm). The desired fractions were lyophilized to give the title compound 342.0 (34.5 mg) as a TFA salt (white solid) in 6:1 diastereomeric ratio as determined by $^1$H NMR (400 MHz, $CD_3OD$) δ 8.49 (d, J=1.37 Hz, 1H), 8.37 (d, J=1.76 Hz, 1H), 7.79-7.85 (m, 1H), 7.62-7.74 (m, 1H), 7.47-7.61 (m, 3H), 6.78-6.86 (m, 2H), 5.64 (s, 1H), 3.81 (br. s, 3H), 3.77 (br. s, 3H), 3.21-3.27 (m, 1H), 2.29-2.37 (m, 3H), 1.01-1.21 (m, 3H). LCMS-ESI (POS.) m/z: 553.0 (M+H)⁺.

Example 343.0: Preparation of (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide 343.0

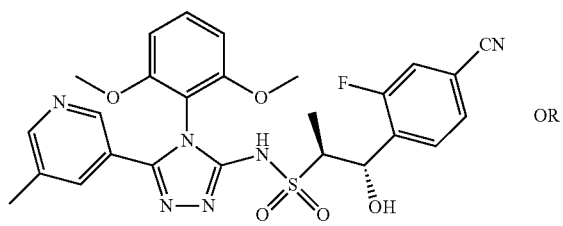

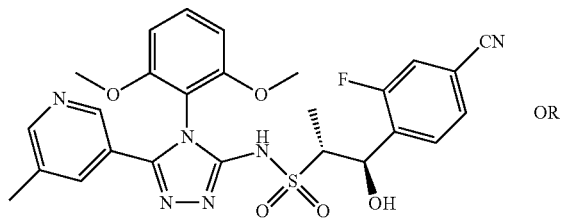

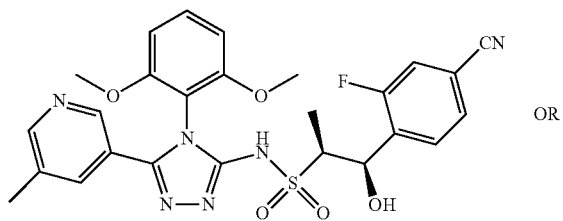

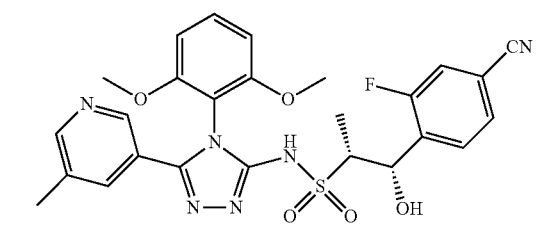

(1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, Example 343.0

The racemate 342.0 (with a 6:1 diastereomer ratio) was separated into four isomers by supercritical fluid chromatography with only the two isomers from the major diastereomer pair characterized. The peaks from the minor diastereomer pair were not characterized. The racemate 342.0 was purified using 2 stages. Peak 1 from the first purification contained 3 isomers and that was purified using a second stage. Stage1: Run on Thar 80 SFC with 250×30 mm AS-H column with 20 g/min MeOH (neat)+60 g/min CO₂, 25% co-solvent at 80 g/min. Temperature.=22° C., Outlet pressure=100 bar, Wavelength=227 nm. Injected 0.5 mL of a solution of 17 mg sample dissolved in 13 mL of MeOH (10% DCM) c=5.4 mg/mL and 2.7 mg per injection. Cycle time 7.0 min, run time=14 min. Peak 1 was dried down and concentrated and re-suspended in 5 mL of MeOH. Stage2: Run on Thar 80 SFC with 250×30 mm CC4 column with 38 g/min MeOH (neat)+41 g/min CO₂, 48% co-solvent at 80 g/min. Temperature.=22° C., Outlet pressure=100 bar, Wavelength=227 nm. Injected 0.3 mL Cycle time 5.50 min, run time=16.0 min. The title compound 343.0 was the first peak (faster-eluting) of the major diastereomer pair from the chiral column, which was also the major peak in stage 2 purification. ¹H NMR (400 MHz, CD₃OD) δ 8.40 (br. s., 1H), 8.30 (br. s., 1H), 7.66-7.74 (m, 2H), 7.57 (dd, J=7.92, 1.47 Hz, 1H), 7.46-7.53 (m, 2H), 6.74-6.85 (m, 2H), 5.69 (s, 1H), 3.77 (s, 3H), 3.75 (s, 3H), 3.32-3.30 (m, 1H), 2.27 (s, 3H) 1.17 (d, J=6.85 Hz, 3H). LCMS-ESI (POS.) m/z: 553.0 (M+H)⁺.

Example 344.0: Preparation of (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide 344.0

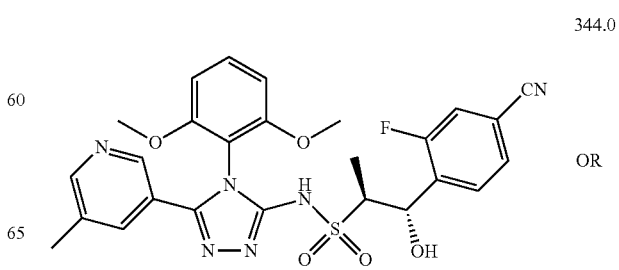

-continued


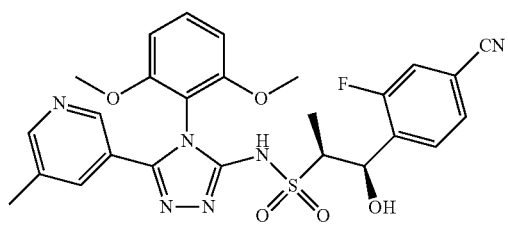

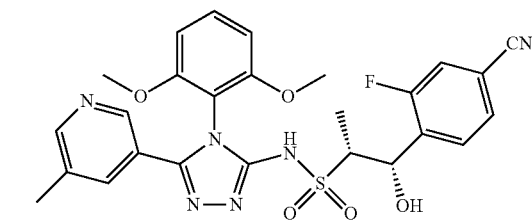

(1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide or (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, Example 344.0

Example 344.0 was the second peak (which is peak 2 from the stage 1 purification) from the chiral separation of the major diastereomer described in Example 343.0. $^1$H NMR (400 MHz, CD$_3$OD) δ 8.11-8.59 (m, 2H), 7.66-7.75 (m, 2H), 7.58 (dd, J=8.12, 1.27 Hz, 1H), 7.49-7.55 (In, 2H), 6.82 (dd. J=8.41, 5.87 Hz, 2H), 5.65 (s, 1H), 3.80 (s, 3H), 3.77 (s, 3H), 3.22-3.28 (m, 1H), 2.29-2.32 (m, 3H), 1.16-1.19 (m, 3H). LCMS-ESI (POS.) m/z: 553.0 (M+H)$^+$.

Example 345: Preparation of (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide 345.1

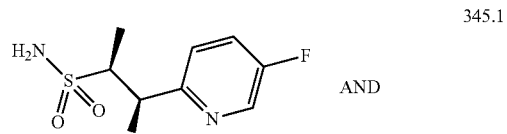

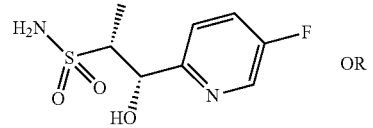

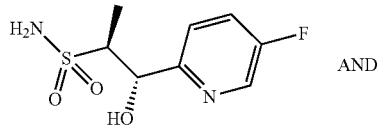

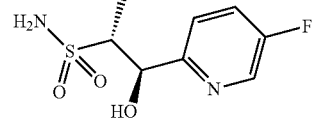

(1R,2S)-1-(5-fluoropyridin-2-yl)-1-hydroxypropane-2-sulfonamide and (1S,2R)-1-(5-fluoropyridin-2-yl)-1-hydroxypropane-2-sulfonamide or (1S,2S)-1-(5-fluoropyridin-2-yl)-1-hydroxypropane-2-sulfonamide and (1R,2R)-1-(5-fluoropyridin-2-yl)-1-hydroxypropane-2-sulfonamide, Example 345.1

The title compound 345.1 was prepared following the procedure in Example C using 12.0 and the 5-fluoropicolinaldehyde. The major diasteromeric pair of the aldol reaction step was isolated.

345.0

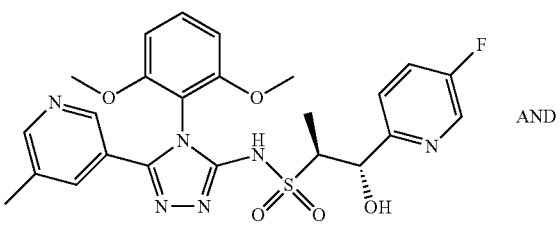

-continued

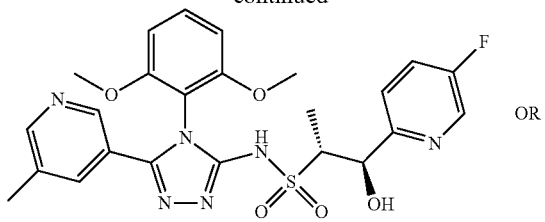

OR

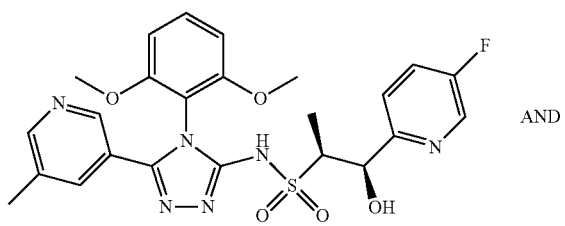

AND

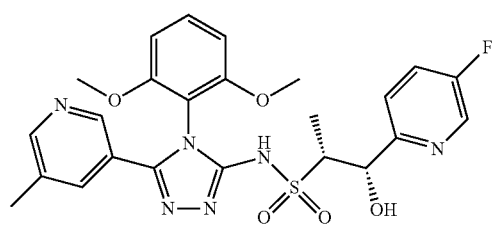

(1R,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2S)—N-(4-(2,6-(trimethoxyphenyl)-5-(5-methyl-3-pyridinyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, Example 345.0

The title compound 345.0 was prepared using the same procedure as described in Example A employing 345.1, 1.0 and 3.11. $^1$H NMR (400 MHz, CD$_3$OD) δ 8.51 (br. s, 1H), 8.34-8.43 (m, 2H), 7.81-7.86 (m, 1H), 7.58-7.63 (m, 2H), 7.53 (t, J=8.51 Hz, 1H), 6.77-6.86 (m, 2H), 5.35-5.41 (in. 1H), 3.79 (s, 3H), 3.76 (s, 3H), 3.58-3.65 (in. 1H), 2.32-2.35 (m, 3H), 1.10 (d, J=7.04 Hz, 3H). LCMS-ESI (POS.) m/z: 529.1 (M+H)$^+$.

Example 346.0: Preparation of (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide 346.0

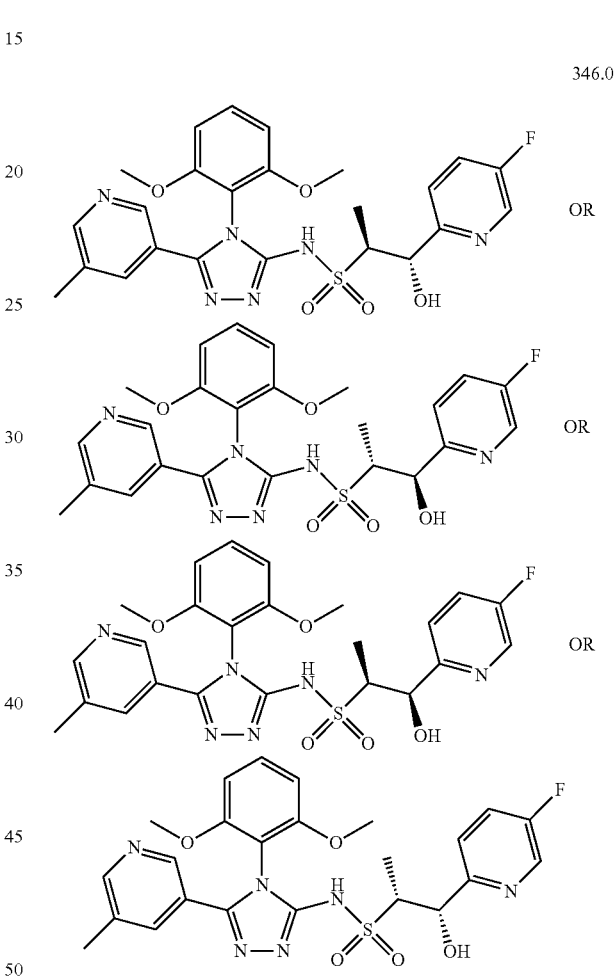

(1R,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, Example 346.0

The racemate 345.0 was chirally separated into two enantiomers by supercritical fluid chromatography. Separation condition: Run on Thar 200 with 250×30 mm AD-H column with 33 mL/min MeOH (neat)+77 g/min $CO_2$, 30% co-solvent at 110 g/min. Temperature 20° C., Wavelength 273 nm. Injected 1.5 mL of a solution of 192 mg sample dissolved in 12 mL 5:1 MeOH:DCM; c=16 mg/mL; 16.0 mg/injection. Cycle time 5.5 min, run time=11 min. The title compound 346.0 was the first peak off the chiral column. $^1$H NMR (400 MHz, $CD_3OD$) δ 8.42-8.45 (m, 1H), 8.40 (t, J=1.47 Hz, 1H), 8.32 (d, J=1.96 Hz, 1H), 7.68-7.74 (m, 1H), 7.59 (dd, J=6.75, 1.86 Hz, 2H), 7.51 (t, J=8.51 Hz, 1H), 6.76-6.84 (m, 1H), 5.38 (s, 1H), 3.78 (s, 3H), 3.76 (s, 3H), 3.62 (qd, J=7.01, 1.86 Hz, 1H), 2.26-2.35 (m, 3H), 1.10 (d, J=7.04 Hz, 3H). LCMS-ESI (POS.) m/z: 529.0 (M+H)$^+$.

Example 347.0: Preparation of (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide

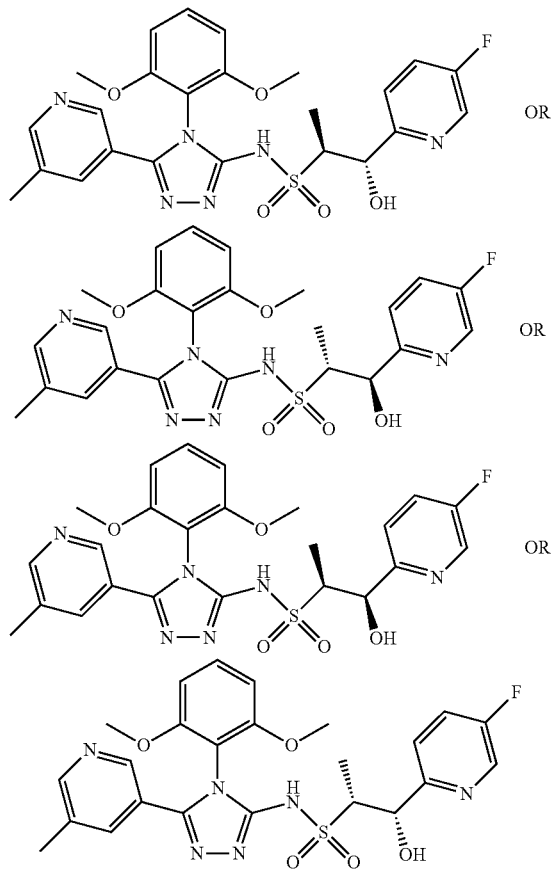

347.0

(1R,2S)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1S,2S)—N-(4-(2,6-(trimethoxyphenyl)-5-(5-methyl-3-pyridinyl)-4H-1,2,4-triazol-3-yl)-1-(5-fluoro-2-pyridinyl)-1-hydroxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, Example 347.0

The title compound 347.0 was the second peak to elute off the chiral column on subjecting 345.0 to the SFC conditions described in Example 346.0. $^1$H NMR (400 MHz, $CD_3OD$) δ 8.46-8.50 (m, 1H), 8.39-8.43 (m, 1H), 8.34-8.38 (m, 1H), 7.80 (d, J=0.78 Hz, 1H), 7.58-7.63 (m, 2H), 7.52 (t, J=8.51 Hz, 1H), 6.77-6.87 (m, 2H), 5.36-5.40 (m, 1H), 3.79 (s, 3H), 3.76 (s, 3H), 3.62 (qd, J=7.01, 2.05 Hz, 1H), 2.33 (s, 3H), 1.10 (d, J=7.04 Hz, 3H). LCMS-ESI (POS.) m/z: 529.0 (M+H)$^+$.

Example 348.0: Preparation of (2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide and (2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide

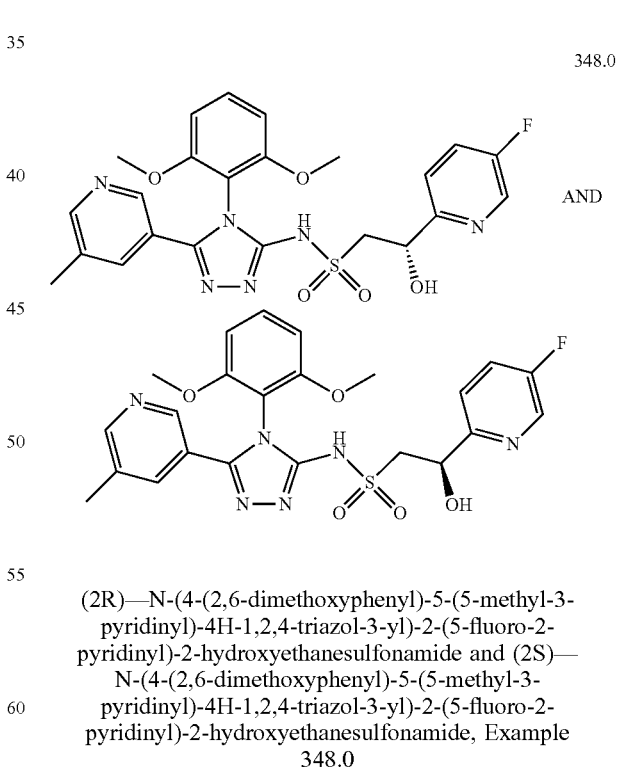

348.0

(2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide and (2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide, Example 348.0

The title compound 348.0 was prepared according to the procedures described in Examples A and C using 2.0, 1.0, 13.0 and 5-fluoropicolinaldehyde. $^1$H NMR (500 MHz, $CD_3OD$) δ 8.52 (br. s, 1H), 8.35-8.43 (m, 2H), 7.81-7.87 (m, 1H), 7.57-7.64 (m, 2H), 7.52 (t, J=8.56 Hz, 1H), 6.81 (dd, J=8.56, 2.20 Hz, 2H), 5.15-5.23 (m, 1H), 3.78 (s, 3H), 3.77 (s, 3H), 3.59-3.69 (m, 1H), 3.32-3.36 (m, 1H), 2.34 (s, 3H). LCMS-ESI (POS.) m/z: 515.0 (M+H)+.

Example 349.0: Preparation of (2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide 349.0

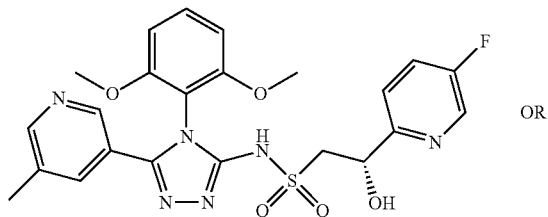

OR

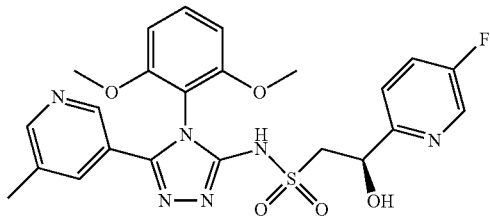

(2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide, Example 349.0

The racemate 348.0 was purified by supercritical fluid chromatography into two enantiomers (separation condition: IA (2×15 cm) column, 25% MeOH/CO2, 100 bar, 65 mL/min, 220 nm. Inj vol.: 0.5 mL, 1 mg/mL 1:1 DCM: MeOH.). The title compound 349.0 was the first peak off the chiral column. 1H NMR (400 MHz, DMSO-d6) δ 13.47 (br. s, 1H), 8.48 (d, J=3.32 Hz, 2H), 8.20 (s, 1H), 7.71 (td, J=8.81, 2.90 Hz, 1H), 7.58-7.61 (m, 1H), 7.50 (s, 2H), 6.82 (d, J=8.50 Hz, 2H), 5.51 (br. s, 1H), 4.96-5.07 (m, 1H), 3.70 (s, 3H), 3.68 (s, 3H), 3.53 (dd, J=14.10, 3.32 Hz, 1H), 3.22 (dd, J=14.10, 8.50 Hz, 1H), 3.17 (d, J=5.18 Hz, 1H), 2.22-2.26 (m, 3H). LCMS-ESI (POS.) m/z: 514.9 (M+H)+.

Example 350.0: Preparation of (2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide 350.0

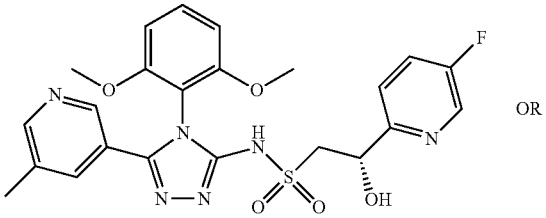

OR

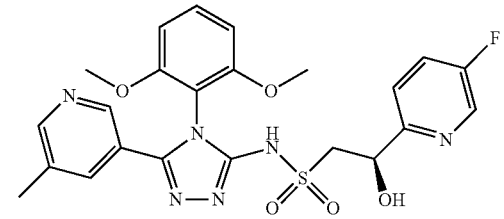

(2R)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide or (2S)—N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide, 350.0

Example 350.0 was the second peak to elute on subjecting 348.0 to the SFC conditions described in Example 349.0. 1H NMR (400 MHz, DMSO-d6) δ 13.38-13.55 (m, 1H), 8.44-8.51 (m, 2H), 8.20 (d, J=1.87 Hz, 1H), 7.71 (td, J=8.81, 2.90 Hz, 1H), 7.60 (s, 1H), 7.46-7.56 (m, 2H), 6.82 (d, J=8.50 Hz, 2H), 5.53 (br. s, 1H), 4.97-5.07 (m, 1H), 3.70 (s, 3H), 3.68 (s, 3H), 3.53 (dd, J=14.10, 3.32 Hz, 1H), 3.19-3.26 (m, 1H), 3.17 (d, J=5.18 Hz, 1H), 2.25 (s, 3H). LCMS-ESI (POS.) m/z: 514.9 (M+H)+.

Example 351.0: Preparation of (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide and (1S,2R)—N-(4-(2,6-(trimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide and (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide

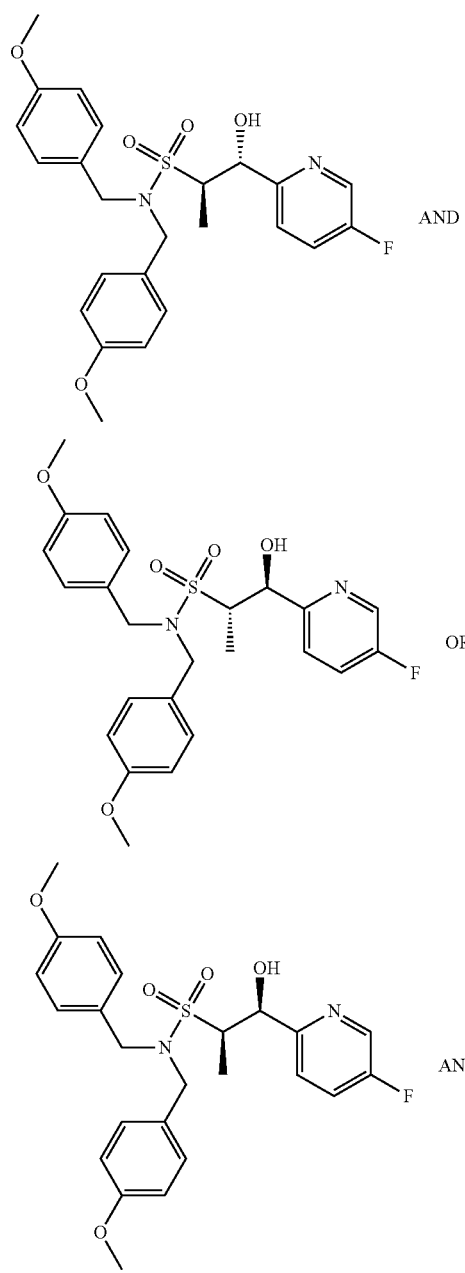

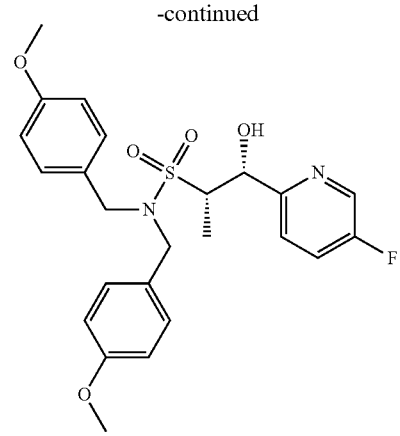

(1R,2R)-(5-fluoropyridin-2-yl)-1-hydroxy-N,N-bis(4-methoxybenzyl)propane-2-sulfonamide and (1S,2S)-(5-fluoropyridin-2-yl)-1-hydroxy-N,N-bis(4-methoxybenzyl)propane-2-sulfonamide or (1S,2R)-(5-fluoropyridin-2-yl)-1-hydroxy-N,N-bis(4-methoxybenzyl)propane-2-sulfonamide and (1R,2S)-(5-fluoropyridin-2-yl)-1-hydroxy-N,N-bis(4-methoxybenzyl)propane-2-sulfonamide, Example 351.1

The title compound was prepared following the procedure described in Example C. The title compound 351.1 is the major diastereomer isolated from the reaction. LCMS-ESI (POS.) m/z: 475.0 (M+H)$^+$.

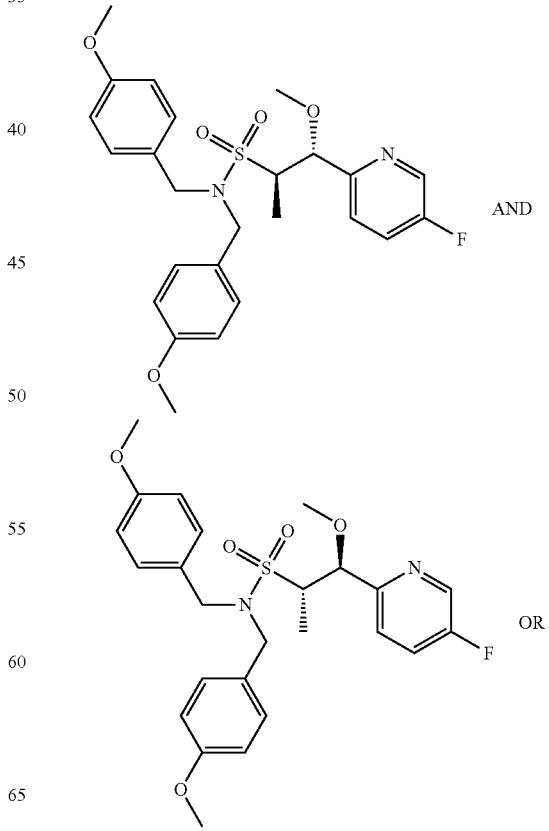

-continued

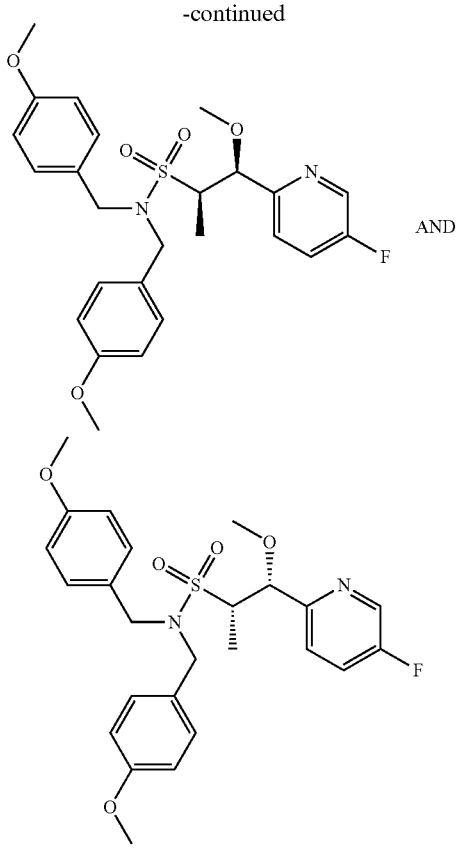

(1R,2R)-1-(5-fluoropyridin-2-yl)-1-methoxy-N,N-bis(4-methoxybenzyl)propane-2-sulfonamide and (1S,2S)-1-(5-fluoropyridin-2-yl)-1-methoxy-N,N-bis(4-methoxybenzyl)propane-2-sulfonamide or (1R,2S)-1-(5-fluoropyridin-2-yl)-1-methoxy-N,N-bis(4-methoxybenzyl)propane-2-sulfonamide and (1S,2R)-1-(5-fluoropyridin-2-yl)-1-methoxy-N,N-bis(4-methoxybenzyl)propane-2-sulfonamide, Example 351.2

(1R,2R)-(5-Fluoropyridin-2-yl)-1-hydroxy-N,N-bis(4-methoxybenzyl)propane-2-sulfonamide and (1S,2S)-(5-fluoropyridin-2-yl)-1-hydroxy-N,N-bis(4-methoxybenzyl)propane-2-sulfonamide or (1S,2R)-(5-fluoropyridin-2-yl)-1-hydroxy-N,N-bis(4-methoxybenzyl)propane-2-sulfonamide and (1R,2S)-(5-fluoropyridin-2-yl)-1-hydroxy-N,N-bis(4-methoxybenzyl)propane-2-sulfonamide (351.1, 943 mg, 1.99 mmol) was azeotroped with toluene. Methyltetrahydrofuran (20 mL) was added, and the reaction was cooled to −78° C. Potassium bis(trimethylsilyl)amide (1.0 M in THF, 2.39 mL, 2.39 mmol)) was then added. The resulting mixture was stirred for 10 min and then methyl iodide (373 μL, 5.96 mmol) was added dropwise at −78° C. The mixture was then stirred for 2 h at −78° C. Next, the reaction was warmed to −15° C. and stirred for 1 h. LCMS showed the reaction >95% completed. A saturated ammonium chloride solution was added to the cold solution, and the reaction was extracted with EtOAc and concentrated in vacuo. The residue was combined with a 500 mg scale reaction, conducted following the same procedure and purified together on a Redi-Sep pre-packed gold silica gel column with a gradient 0-45% EtOAc in hexanes to provide the title compound 351.2. (1.34 g, 90% yield). LCMS-ESI (POS.) m/z: 489.0 (M+H)$^+$.

351.0

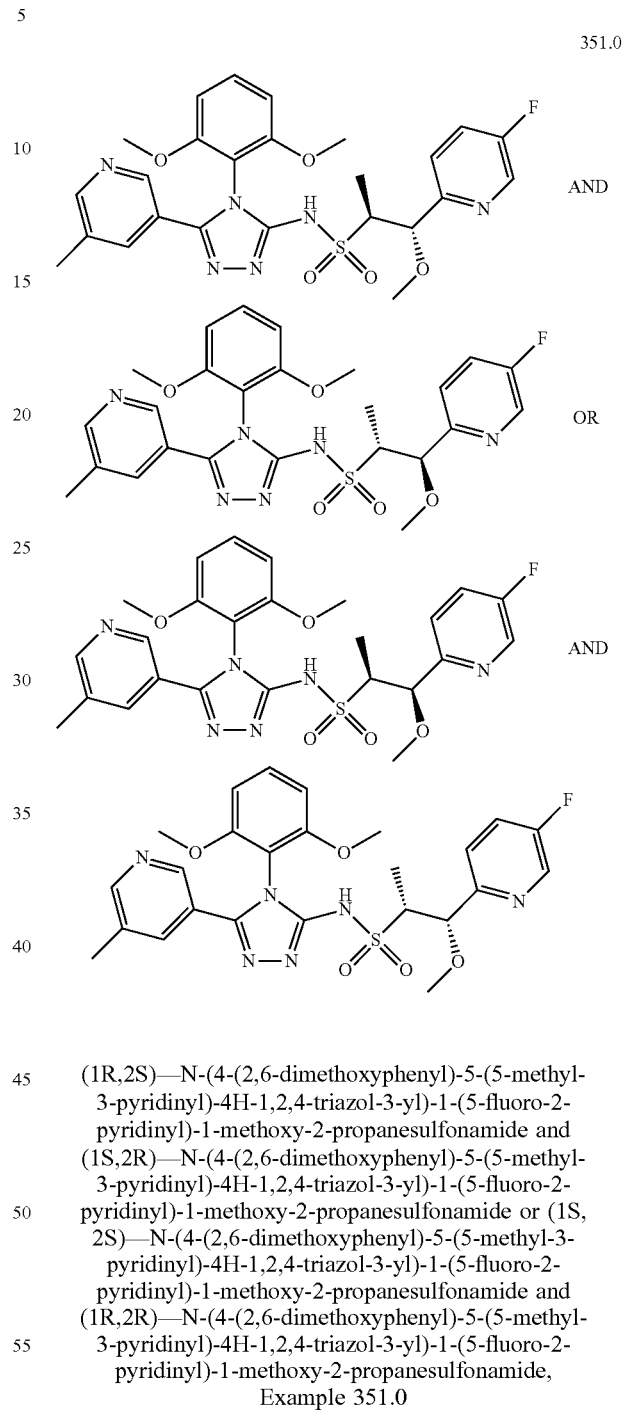

(1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide and (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide and (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, Example 351.0

The title compound 351.0 was prepared according to the procedures as described in Example C and the following procedures described in Example A to obtain 351.0. $^1$H NMR (400 MHz, CD$_2$Cl$_2$) δ 11.19 (br. s, 1H), 8.43 (d, J=2.93 Hz, 2H), 8.33 (d, J=1.56 Hz, 1H), 7.58-7.68 (m, 1H), 7.35-7.52 (m, 3H), 6.68 (dd, J=8.61, 4.11 Hz, 2H), 4.98 (d, J=2.54 Hz, 1H), 3.75 (s, 3H), 3.73 (s, 3H), 3.41 (qd, J=7.04, 2.54 Hz, 1H), 3.27 (s, 0.3H), 2.29 (s, 3H), 1.13 (d, J=7.04 Hz, 3H). LCMS-ESI (POS.) m/z: 543.0 (M+H)$^+$.

Example 352.0: Preparation of (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, Example 352.0

The racemate 351.0 was chirally separated into two enantiomers by supercritical fluid chromatography. Separation condition were as follows: Column: Chiralpak AD-H, 2.1×15 cm; Mobile phase: 50% IPA/50% $CO_2$; Flow rate: 80 g/min; SFC Outlet pressure: 100 bar; Wavelength: 274 nm; Sample dissolved to 25 mg/mL in 1:1 MeOH:DCM; introduced 1.0 mL sample solution, or 25 mg sample in each preparative injection. The title compound 352.0 was the first peak off the chiral column. $^1$H NMR (400 MHz, $CD_3OD$) δ 8.40-8.49 (m, 2H), 8.32 (d, J=1.57 Hz, 1H), 7.70-7.73 (m, 1H), 7.62 (td, J=8.61, 2.93 Hz, 1H), 7.44-7.53 (m, 2H), 6.79 (d, J=8.61 Hz, 2H), 4.95-5.03 (m, 1H), 3.78 (s, 3H), 3.75 (s, 3H), 3.40 (qd, J=7.04, 2.54 Hz, 1H), 3.26 (s, 3H), 2.30 (s, 3H), 1.14 (d, J=7.04 Hz, 3H). LCMS-ESI (POS.) m/z: 543.0 $(M+H)^+$.

Example 353.0: Preparation of (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2R)—N-(4-(2,6-(trimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide 352.0


OR

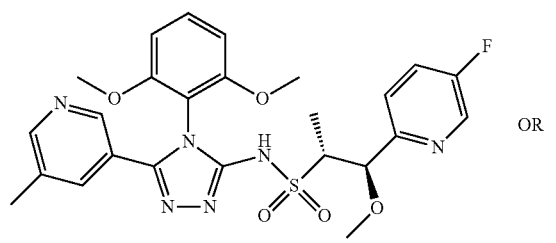

OR

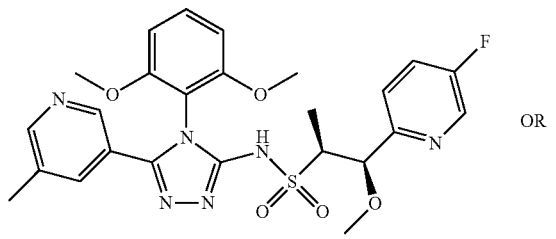

OR


353.0

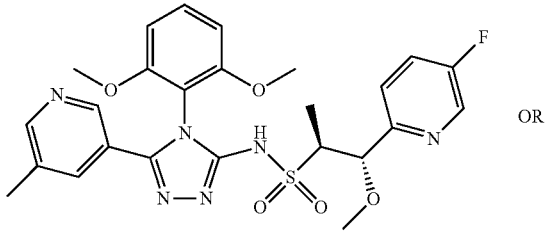

OR

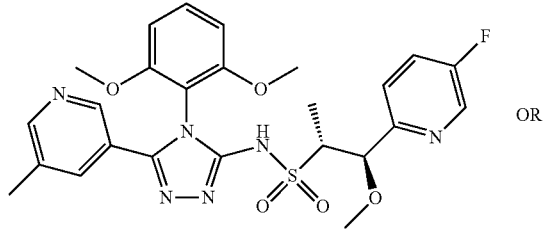

OR

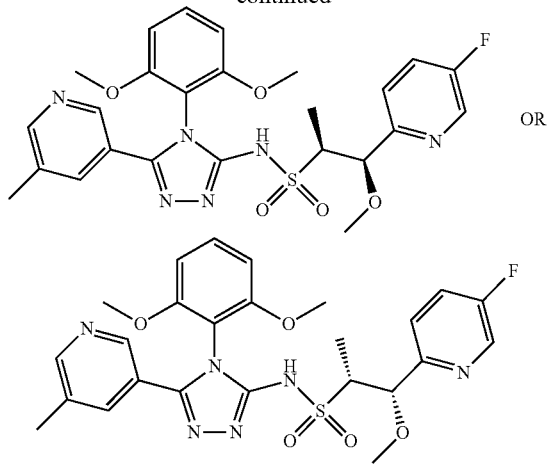

OR (1R,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1S,2S)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide or (1R,2R)—N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, Example 353.0

Example 353.0 was the second peak to elute off the column on subjecting 351.0 to the SFC conditions described in Example 352.0. $^1$H NMR (400 MHz, CD$_3$OD) δ 8.40-8.49 (m, 2H), 8.27-8.35 (m, 1H), 7.68-7.75 (m, 1H), 7.62 (td, J=8.61, 2.93 Hz, 1H), 7.41-7.53 (m, 2H), 6.79 (d, J=8.61 Hz, 2H), 5.00 (d, J=2.54 Hz, 1H), 3.78 (s, 3H), 3.75 (s, 3H), 3.40 (qd, J=7.01, 2.45 Hz, 1H), 3.26 (s, 3H), 2.30 (s, 3H), 1.14 (d, J=7.04 Hz, 3H). LCMS-ESI (POS.) m/z: 543.0 (M+H)$^+$.

Example 354.0: Preparation of (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide

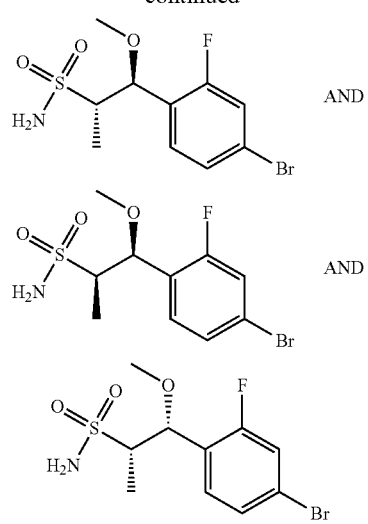

(1R,2S)-1-(4-bromo-2-fluorophenyl)-1-methoxypropane-2-sulfonamide and (1R,2R)-1-(4-bromo-2-fluorophenyl)-1-methoxypropane-2-sulfonamide and (1S,2S)-1-(4-bromo-2-fluorophenyl)-1-methoxypropane-2-sulfonamide and (1S,2R)-1-(4-bromo-2-fluorophenyl)-1-methoxypropane-2-sulfonamide, Example 354.1

The title compound was prepared following the procedure described in Example C using 5.0 and the 4-bromo-2-fluorobenzaldehyde. LCMS-ESI POS. m/z: 347.9 (M+Na)$^+$.

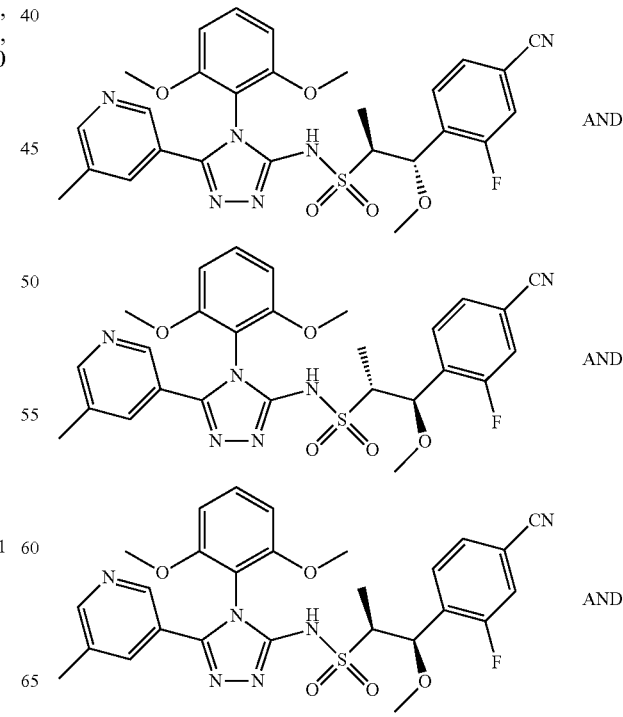

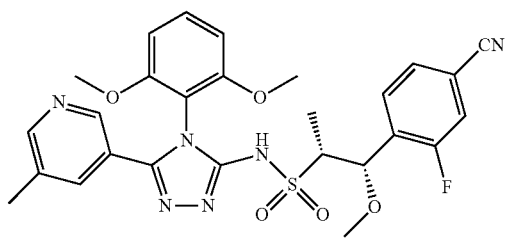

(1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide and
(1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide and
(1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide and
(1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide,
Example 354.0

The title compound was prepared employing 354.1, 1.0 and 3.11 and following the procedure described in Example A. The title compound 354.0 was obtained as a 3:1 mixture of diastereomers. $^1$H NMR (400 MHz, CD$_3$OD) δ 8.50 (s, 1H), 8.34-8.41 (m, 1H), 7.81-7.87 (m, 1H), 7.47-7.63 (m, 4H), 6.79-6.85 (m, 2H), 5.24 (d, J=2.54 Hz, 1H), 3.79 (In, J=9.80 Hz, 6H), 3.03-3.24 (m, 4H), 2.31-2.37 (m, 3H), 1.04-1.23 (m, 3H). LCMS-ESI (POS.) m/z: 567.0 (M+H)$^+$.

Example 355.0: Preparation of (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide 355.0

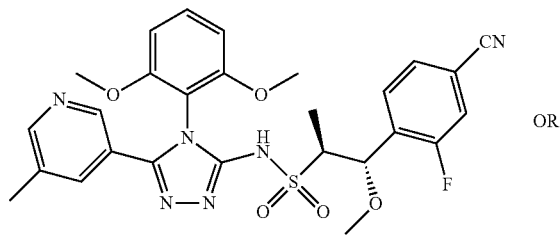

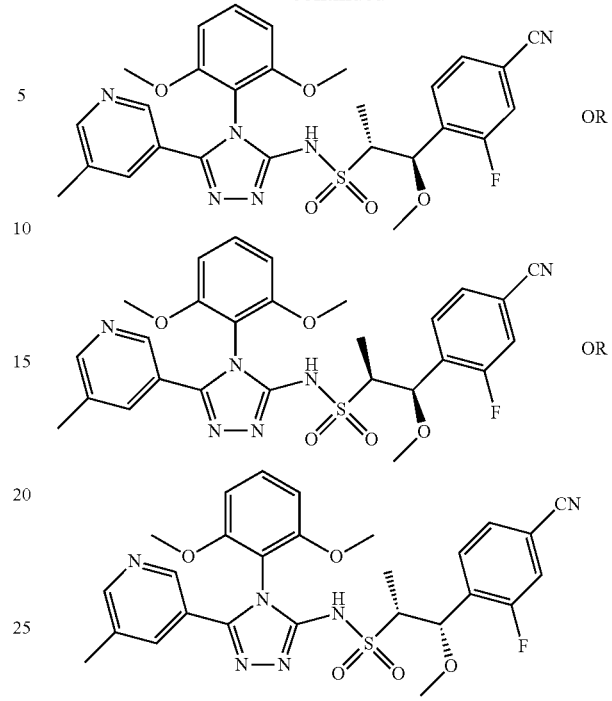

(1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or
(1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or
(1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or
(1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide,
Example 355.0

The racemic compound 354.0 was separated by supercritical fluid chromatography into four isomers. The fourth eluting peak did not have sufficient amount and was not characterized. Separation condition: Stage 1: Chiral purification (159 mg): Run on Thar 80 SFC with 400×mm AD-H column with 28 g/min EtOH (neat)+52 g/min CO$_2$, 35% co-solvent at 80 g/min. Temperature.=22° C., Outlet pressure=100 bar, Wavelength=275 nm. Injected 1.3 mL of 159 mg sample dissolved in 17 mL of MeOH:DCM 10:7; c=9.35 mg/mL and 12.15 mg per injection. Cycle time 11 min, run time 20 min. Stage 2: Chiral purification (94 mg): Run on Thar 80 SFC with 250×21+150×21 mm AD-H columns with 15 g/min EtOH (neat)+45 g/min CO$_2$, 25% co-solvent at 60 g/min. Temperature.=22° C., Outlet pressure=100 bar, Wavelength=275 nm. Injected 0.15 mL of 92 mg sample dissolved in 6 mL (5:1) MeOH:DCM; c=15.3 mg/mL, i.e. 2.3 mg per injection. Cycle time=10 min, run time=22 min. Stage 3: Chiral purification (20.5 mg): Run on Thar 80 SFC with 250×30 mm CC4 column with 40 g/min MeOH (20 mM NH$_3$)+40 g/min CO$_2$, 50% co-solvent at 80 g/min. Temperature.=22° C., Outlet pressure=100 bar, Wavelength=275 nm. Injected 0.3 mL of 20.5 mg sample dissolved in 4 mL MeOH; c=5.1 mg/mL, i.e. 1.5 mg per injection. Cycle time=4.7 min, run time=9.6 min. The title compound 355.0 was the first eluting peak of the major diastereomer from chiral separation (stage 2, peak 2). $^1$H NMR (400 MHz, CD$_3$OD) δ 8.43 (s, 1H), 8.32 (br. s, 1H), 7.71 (br. s., 1H), 7.45-7.64 (m, 4H), 6.80 (d, J=8.41 Hz, 2H), 5.18-5.30 (m, 1H), 3.79 (s, 3H), 3.77 (s, 3H), 3.12-3.23 (m, 4H), 2.30 (s, 3H), 1.19 (d, J=6.85 Hz, 3H) LCMS-ESI (POS.) m/z: 567.0 (M+H)$^+$.

Example 356.0: Preparation of (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide

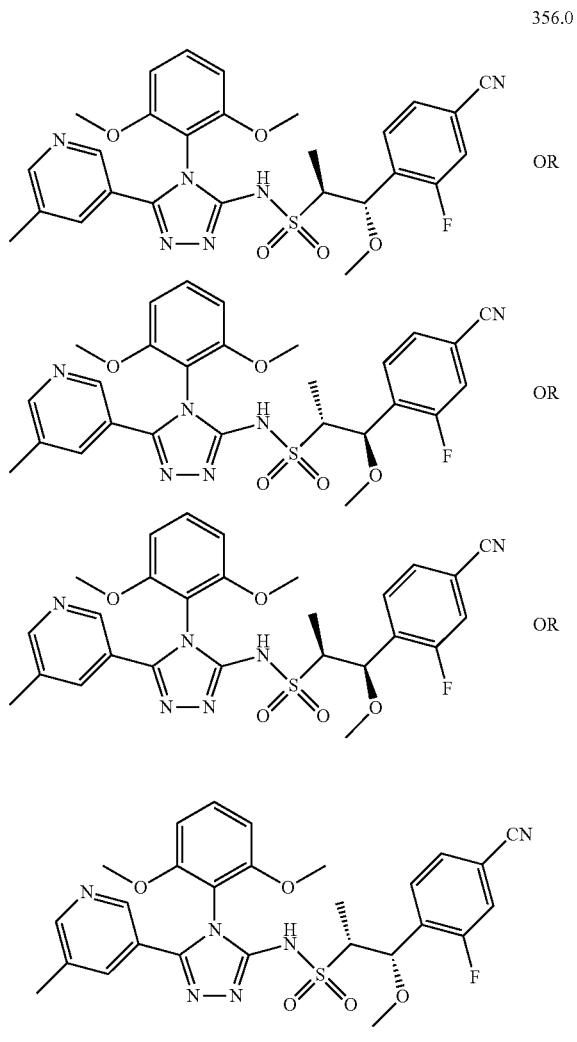

356.0

(1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, Example 356.0

Example 356.0 was the second peak of the major diastereomer from chiral separation (stage 1, peak 2) on subjecting 354.0 to the same SFC conditions described in Example 355.0. $^1$H NMR (400 MHz, CD$_3$OD) δ 8.43 (d, J=1.37 Hz, 1H), 8.32 (m, J=2.00 Hz, 1H), 7.71 (d, J=0.78 Hz, 1H), 7.53-7.62 (m, 3H), 7.50 (t, J=8.51 Hz, 1H), 6.81 (d, J=8.61 Hz, 2H), 5.24 (d, J=2.74 Hz, 1H), 3.15-3.22 (m, 4H), 2.26-2.33 (m, 3H), 1.19 (d, J=7.04 Hz, 3H). LCMS-ESI (POS.) m/z: 567.0 (M+H)$^+$.

Example 357.0: Preparation of (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide

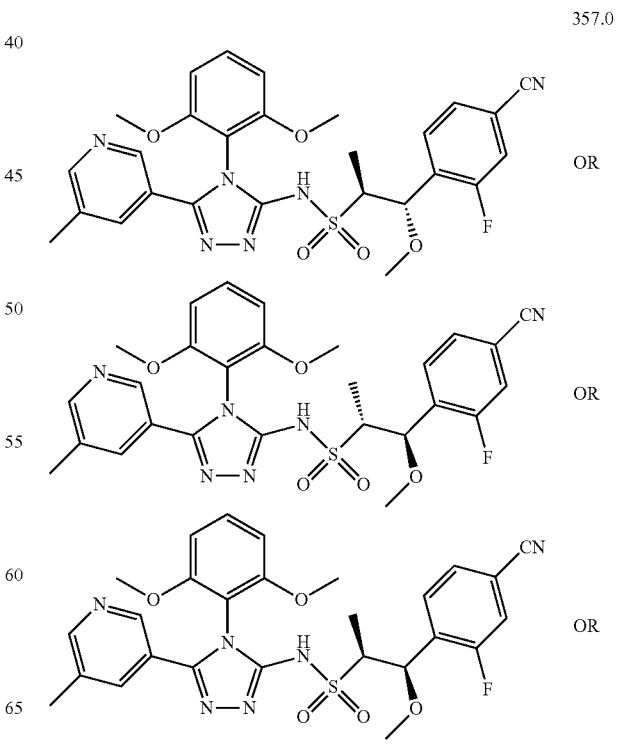

357.0

-continued

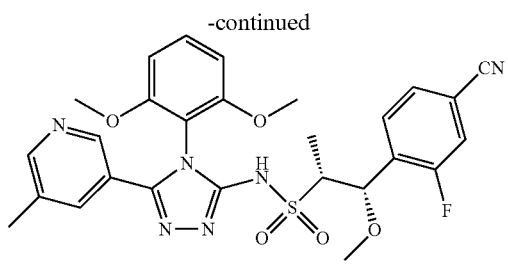

(1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, Example 357.0

Example 357.0 was the first peak of the minor diastereomer from chiral separation (stage 3, peak 2) on subjecting 354.0 to the same SFC conditions described in Example 355.0. $^1$H NMR (400 MHz, CD$_3$OD) δ 8.43 (br. s, 1H), 8.31 (br. s, 1H), 7.69 (s, 1H), 7.48-7.61 (m, 4H), 6.76-6.84 (m, 2H), 4.86-4.89 (m, 1H), 3.79 (s, 3H), 3.77 (s, 3H), 3.39-3.47 (m, 1H), 3.07 (s, 3H), 2.29 (s, 3H), 2.27-2.32 (m, 3H), 1.06 (d, J=7.05 Hz, 3H). LCMS-ESI (POS.) m/z: 567.0 (M+H)$^+$.

Example 358.0: Preparation of (1R,2R)—N-(4-(2,6-dimethoxyphenyl)-5-(5-methylpyridin-3-yl)-4H-1,2,4-triazol-3-yl)-1-(5-fluoropyrimidin-2-yl)-1-hydroxypropane-2-sulfonamide or (1S,2S)—N-(4-(2,6-dimethoxyphenyl)-5-(5-methylpyridin-3-yl)-4H-1,2,4-triazol-3-yl)-1-(5-fluoropyrimidin-2-yl)-1-hydroxypropane-2-sulfonamide (1R,2R)—N-(4-(2,6-dimethoxyphenyl)-5-(5-methylpyridin-3-yl)-4H-1,2,4-triazol-3-yl)-1-(5-fluoropyrimidin-2-yl)-1-hydroxypropane-2-sulfonamide or (1S,2S)—N-(4-(2,6-dimethoxyphenyl)-5-(5-methylpyridin-3-yl)-4H-1,2,4-triazol-3-yl)-1-(5-fluoropyrimidin-2-yl)-1-hydroxypropane-2-sulfonamide, Example 358.0

To a solution of 21.0 (88 mg, 0.14 mmol) in EtOH (1.4 mL) was added 12 N aqueous HCl solution (57 mL, 0.68 mmol). The reaction was stirred at RT until completion and then was partitioned between water and EtOAc (2×). The combined organic layers were dried over anhydrous magnesium sulfate and concentrated in vacuo. The residue was purified by silica gel chromatography (eluent: 0-5% IPA in DCM) to provide the racemic alcohol product (52 mg, 70% yield) as a white solid. Chiral supercritical fluid chromatography purification was then performed to separate the two enantiomeric products. Run on Thar 350 SFC with 250×30 mm AD-H column with 48 g/min IPA (neat)+72 g/min CO$_2$ (40% co-solvent) at 100 g/min. Outlet pressure=100 bar; Temp.=19° C.; Wavelength=215 nm. injected 0.8 mL of 50 mg sample in 8 mL (5:3) MeOH:DCM, i.e. 6.2 mg/mL, resulting in 5.0 mg per injection. Cycle time 8.3 min, run time 15 min. The first eluting peak was (13.0 mg): 358.0. $^1$H NMR (500 MHz, CDCl$_3$) δ: 11.03 (br. s., 1H), 8.59 (s, 2H), 8.48 (br. s., 1H), 8.35 (br. s., 1H), 7.73 (br. s., 1H), 7.43 (t, J=8.4 Hz, 1H), 6.64 (dd, J=8.2, 6.2 Hz, 2H), 5.07 (d, J=6.6 Hz, 1H), 3.69-3.84 (m, 7H), 2.34 (s, 3H), 1.29 (d, J=6.8 Hz, 3H). LCMS-ESI (POS.) m/z: 530.2 (M+H)$^+$.

Example 359.0: Preparation of (1R,2R)—N-(4-(2,6-dimethoxyphenyl)-5-(5-methylpyridin-3-yl)-4H-1,2,4-triazol-3-yl)-1-(5-fluoropyrimidin-2-yl)-1-hydroxypropane-2-sulfonamide or (1S,2S)—N-(4-(2,6-dimethoxyphenyl)-5-(5-methylpyridin-3-yl)-4H-1,2,4-triazol-3-yl)-1-(5-fluoropyrimidin-2-yl)-1-hydroxypropane-2-sulfonamide

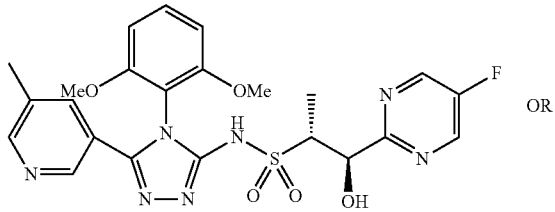

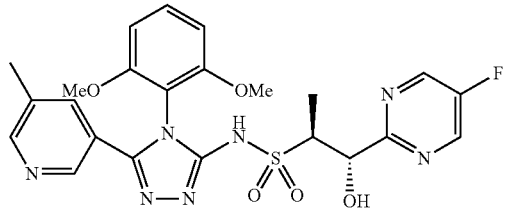

(1S,2S)—N-(4-(2,6-dimethoxyphenyl)-5-(5-methyl-pyridin-3-yl)-4H-1,2,4-triazol-3-yl)-1-(5-fluoropy-rimidin-2-yl)-1-hydroxypropane-2-sulfonamide or (1R,2R)—N-(4-(2,6-dimethoxyphenyl)-5-(5-methyl-pyridin-3-yl)-4H-1,2,4-triazol-3-yl)-1-(5-fluoropy-rimidin-2-yl)-1-hydroxypropane-2-sulfonamide, Example 359.0

Further elution under the conditions described in Example 358.0 delivered the second eluting peak 359.0 (11.3 mg). ¹H NMR (500 MHz, CDCl₃) δ: 11.03 (br. s., 1H), 8.59 (s, 2H), 8.48 (br. s., 1H), 8.35 (br. s., 1H), 7.76 (br. s., 1H), 7.43 (t, J=8.6 Hz, 1H), 6.65 (dd, J=8.3, 6.1 Hz, 2H), 5.07 (d, J=6.4 Hz, 1H), 3.70-3.85 (m, 7H), 2.36 (s, 3H), 1.29 (d, J=6.8 Hz, 3H). LCMS-ESI (POS.) m/z: 530.2 (M+H)⁺.

Example 360.0: Preparation of (1R,2R)—N-(4-(2,6-dimethoxyphenyl)-5-(5-methylpyridin-3-yl)-4H-1,2,4-triazol-3-yl)-1-(5-fluoropyrimidin-2-yl)-1-methoxypropane-2-sulfonamide or (1S,2S)—N-(4-(2,6-dimethoxyphenyl)-5-(5-methylpyridin-3-yl)-4H-1,2,4-triazol-3-yl)-1-(5-fluoropyrimidin-2-yl)-1-methoxypropane-2-sulfonamide chiral supercritical fluid chromatography purification was then performed to separate the two enantiomeric products. chiral purification (15 mg): Run on Thar 80 SFC with 250×30 mm CC4 column with 40 g/min MeOH (neat)+40 g/min CO₂, 50% co-solvent at 80 g/min. Temp.=25° C., Outlet pressure=100 bar, Wavelength=215 nm. Manually injected 0.5 mL of a solution of 15 mg sample dissolved in 3 mL of MeOH; c=5.0 mg/mL and 2.5 mg per injection. Run time=25 min. The first eluting peak was Example 360 (1.5 mg). ¹H NMR (500 MHz, CDCl₃) δ: 8.63 (s, 2H), 8.45 (s, 1H), 8.33 (s, 1H), 7.69 (br. s., 1H), 7.40 (t, J=8.4 Hz, 1H), 6.58-6.66 (m, 2H), 4.82 (d, J=6.6 Hz, 1H), 3.71-3.82 (m, 7H), 3.24 (s, 3H), 2.32 (s, 3H), 1.24 (d, J=7.1 Hz, 3H). LCMS-ESI (POS.) m/z: 544.1 (M+H)⁺.

Example 361.0: Preparation of (1R,2R)—N-(4-(2,6-dimethoxyphenyl)-5-(5-methylpyridin-3-yl)-4H-1,2,4-triazol-3-yl)-1-(5-fluoropyrimidin-2-yl)-1-methoxypropane-2-sulfonamide or (1S,2S)—N-(4-(2,6-dimethoxyphenyl)-5-(5-methylpyridin-3-yl)-4H-1,2,4-triazol-3-yl)-1-(5-fluoropyrimidin-2-yl)-1-methoxypropane-2-sulfonamide

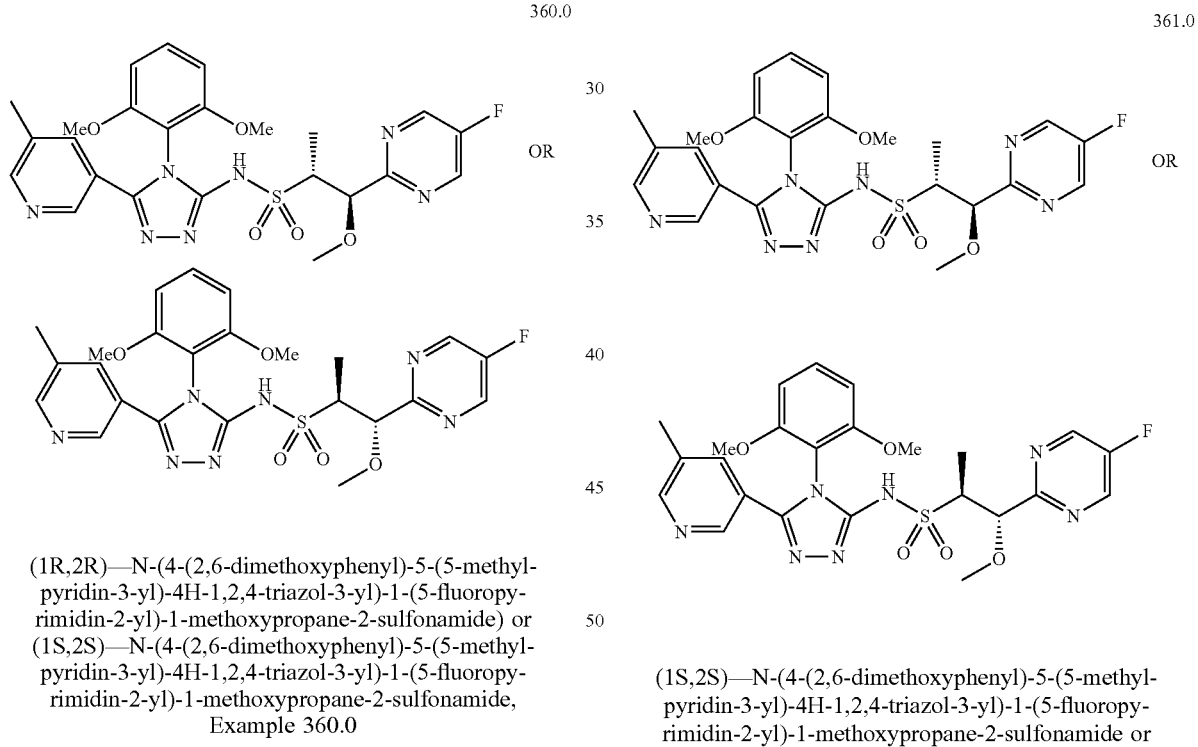

(1R,2R)—N-(4-(2,6-dimethoxyphenyl)-5-(5-methyl-pyridin-3-yl)-4H-1,2,4-triazol-3-yl)-1-(5-fluoropy-rimidin-2-yl)-1-methoxypropane-2-sulfonamide) or (1S,2S)—N-(4-(2,6-dimethoxyphenyl)-5-(5-methyl-pyridin-3-yl)-4H-1,2,4-triazol-3-yl)-1-(5-fluoropy-rimidin-2-yl)-1-methoxypropane-2-sulfonamide, Example 360.0

To a 1:1 mixture of the products described in Examples 359.0 and 358.0 (83 mg, 0.16 mmol) in THF (1.6 mL) was added sodium hydride, 60% dispersion in mineral oil (31 mg, 0.78 mmol) directly followed by iodomethane (20 µL, 0.31 mmol) via syringe. The reaction was stirred at RT for 5 h and then was quenched with a saturated aqueous ammonium chloride solution. The mixture was extracted with DCM (3×) and the combined organic layers were dried over anhydrous magnesium sulfate and concentrated in vacuo. The residue was purified by silica gel chromatography (eluent: 0-10% IPA in DCM) to provide the racemic methyl ether product (15 mg, 18% yield) as a white solid. A (1S,2S)—N-(4-(2,6-dimethoxyphenyl)-5-(5-methyl-pyridin-3-yl)-4H-1,2,4-triazol-3-yl)-1-(5-fluoropy-rimidin-2-yl)-1-methoxypropane-2-sulfonamide or (1R,2R)—N-(4-(2,6-dimethoxyphenyl)-5-(5-methyl-pyridin-3-yl)-4H-1,2,4-triazol-3-yl)-1-(5-fluoropy-rimidin-2-yl)-1-methoxypropane-2-sulfonamide, Example 361.0

Further elution under the conditions described in Example 360.0, delivered the second eluting peak 361.0 (4.4 mg): ¹H NMR (500 MHz, CDCl₃) δ: 8.63 (s, 2H), 8.45 (s, 1H), 8.33 (s, 1H), 7.68 (s, 1H), 7.40 (t, J=8.4 Hz, 1H), 6.59-6.67 (m, 2H), 4.82 (d, J=6.6 Hz, 1H), 3.69-3.83 (m, 7H), 3.24 (s, 3H), 2.32 (s, 3H), 1.23 (d, J=7.3 Hz, 3H). LCMS-ESI (POS.) m/z: 544.1 (M+H)⁺.

Example 362.0: Preparation of (1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide or (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide

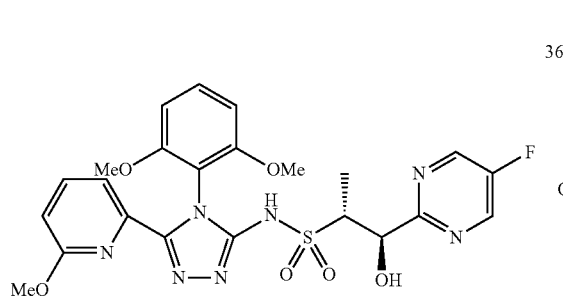

362.0

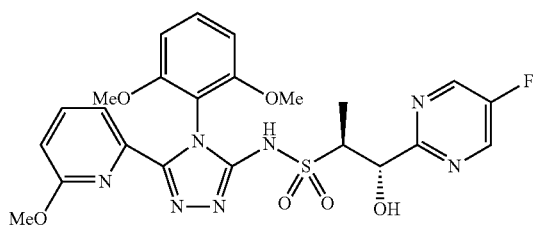

(1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide or (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide, Example 362.0

Following the procedure in Example A, 20.0 (700 mg, 2.00 mmol), 6-methoxypicolinohydrazide (402 mg, 2.40 mmol) and 1.0 (411 mg, 2.10 mmol) were coupled. After completion, the reaction mixture was then allowed to cool and was quenched directly with a 7 N solution of ammonia in MeOH (2.29 mL, 16.0 mmol). The resulting mixture was concentrated and the residue was purified by silica gel chromatography (eluent: pure hexanes grading to pure EtOAc) to provide the racemic alcohol product (551 mg, 51% yield) as a white solid. A 50 mg amount of the racemic alcohol was purified by chiral supercritical fluid chromatography to separate the two enantiomeric products. IC (2×15 cm) 40% EtOH/CO$_2$, 100 bar 60 mL/min, 220 nm. inj vol.: 1 mL, 5 mg/mL EtOH. The first eluting peak was assigned as Example 362.0 (18.0 mg). $^1$H NMR (500 MHz, CDCl$_3$) δ: 11.00 (s, 1H), 8.58 (s, 2H), 7.54-7.69 (m, 2H), 7.34 (t, J=8.6 Hz, 1H), 6.71 (dd, J=7.8, 1.2 Hz, 1H), 6.56-6.66 (m, 2H), 5.07 (dd, J=6.6, 5.1 Hz, 1H), 3.68-3.80 (m, 7H), 3.17 (s, 3H), 1.27 (d, J=7.1 Hz, 3H). LCMS-ESI (POS.) m/z: 546.0 (M+H)$^+$.

Example 363.0: Preparation of (1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide or (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide

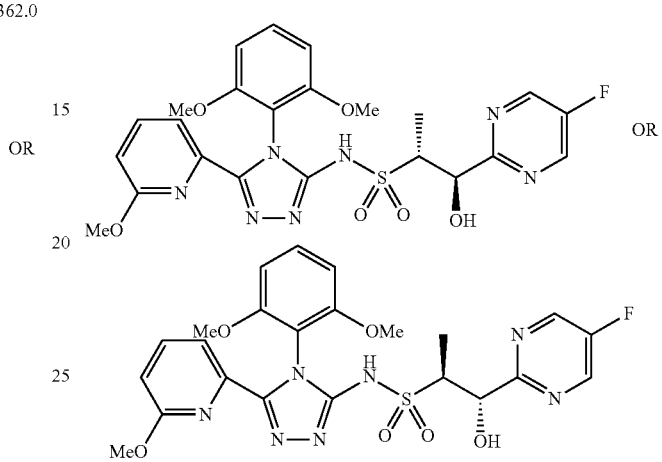

363.0

(1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide or (1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-hydroxypropane-2-sulfonamide, Example 363.0

Further elution under the conditions described in Example 362.0, delivered the second eluting peak which was assigned as Example 363.0 (16.1 mg). $^1$H NMR (500 MHz, CDCl$_3$) δ: 11.02 (br. s., 1H), 8.60 (s, 2H), 7.56-7.66 (m, 2H), 7.36 (t, J=8.4 Hz, 1H), 6.73 (dd, J=7.7, 1.3 Hz, 1H), 6.56-6.66 (m, 2H), 5.07 (d, J=6.6 Hz, 1H), 3.68-3.80 (m, 7H), 3.18 (s, 3H), 1.29 (d, J=7.1 Hz, 3H). LCMS-ESI (POS.) m/z: 546.0 (M+H)$^+$.

Example 364.0: Preparation of (1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide or (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide

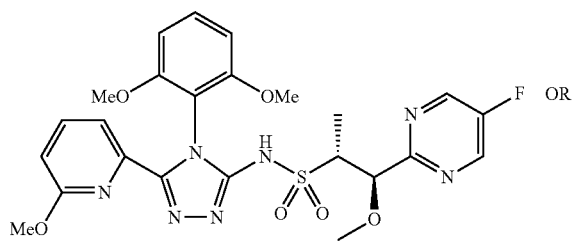

364.0

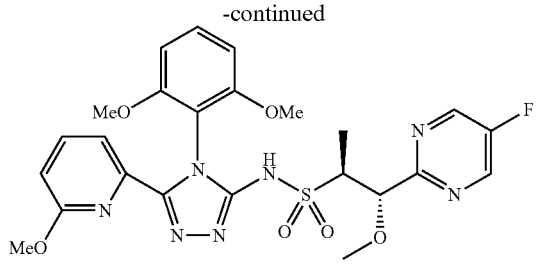

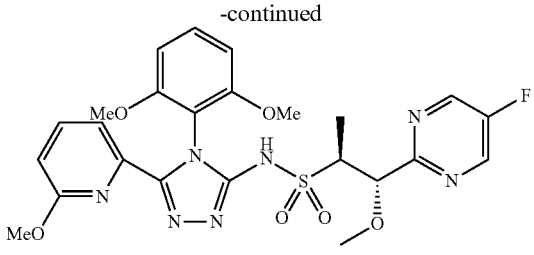

(1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide or (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide, 364.0

To a 1:1 mixture of the products described in Examples 362.0 and 363.0 (200 mg, 0.37 mmol) in THF (3.7 mL) was added sodium hydride (60% dispersion in mineral oil (73 mg, 1.83 mmol)) directly followed by iodomethane (69 µL, 1.10 mmol) via syringe. The reaction was stirred at RT for 16 h and then was quenched with a saturated aqueous ammonium chloride solution. The mixture was extracted with EtOAc (3×) and the combined organic layers were dried over anhydrous magnesium sulfate and concentrated in vacuo. The residue was purified by silica gel chromatography (eluent: 0-10% IPA in DCM) to provide initial product. The initial product was then repurified by reverse phase prep. HPLC (Sunfire 10 µM C18 column, eluent: 35-55% ACN in water over a 20 minute period where both solvents contained 0.1% TFA) to provide the racemic methyl ether product (51 mg, 25% yield) as a white solid. Chiral supercritical fluid chromatography purification was then performed to separate the two enantiomeric products. Preparative Method: Analytical Method: AS-H (2×25 cm) 20% MeOH/CO$_2$, 100 bar, 65 mL/min, 220 nm, inj vol.: 1 mL, 4 mg/mL 1:3 DCM:MeOH. The first eluting peak (364.0, 15.0 mg). $^1$H NMR (500 MHz, CDCl$_3$) δ: 11.30 (br. s., 1H), 8.64 (s, 2H), 7.58-7.69 (m, 2H), 7.33 (t, J=8.6 Hz, 1H), 6.71 (d, J=7.8 Hz, 1H), 6.57-6.66 (m, 2H), 4.84 (d, J=6.6 Hz, 1H), 3.74-3.82 (m, 4H), 3.71 (s, 3H), 3.25 (s, 3H), 3.18 (s, 3H), 1.23 (d, J=7.1 Hz, 3H). LCMS-ESI (POS.) m/z: 560.2 (M+H)$^+$.

Example 365.0: Preparation of (1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide or (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide 365.0

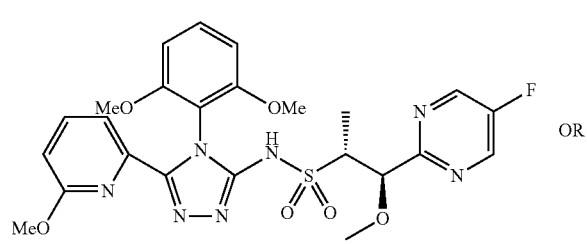

OR (1S,2S)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide or (1R,2R)—N-(4-(2,6-dimethoxyphenyl)-5-(6-methoxypyridin-2-yl)-4H-1,2,4-triazol-3-yl)-1-(5-fluoropyrimidin-2-yl)-1-methoxypropane-2-sulfonamide, Example 365.0

Further elution under the conditions described in Example 364.0 delivered the second eluting peak (365.0, 16.7 mg). $^1$H NMR (500 MHz, CDCl$_3$) δ: 8.63 (s, 2H), 7.55-7.67 (m, 2H), 7.31 (t, J=8.4 Hz, 1H), 6.69 (dd, J=7.7, 1.3 Hz, 1H), 6.56-6.65 (m, 2H), 4.83 (d, J=6.8 Hz, 1H), 3.72-3.81 (m, 4H), 3.69 (s, 3H), 3.23 (s, 3H), 3.17 (s, 3H), 1.22 (d, J=7.3 Hz, 3H). LCMS-ESI (POS.) m/z: 560.2 (M+H)$^+$.

Example 366.0: Preparation of (S)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide or (R)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide 366.0

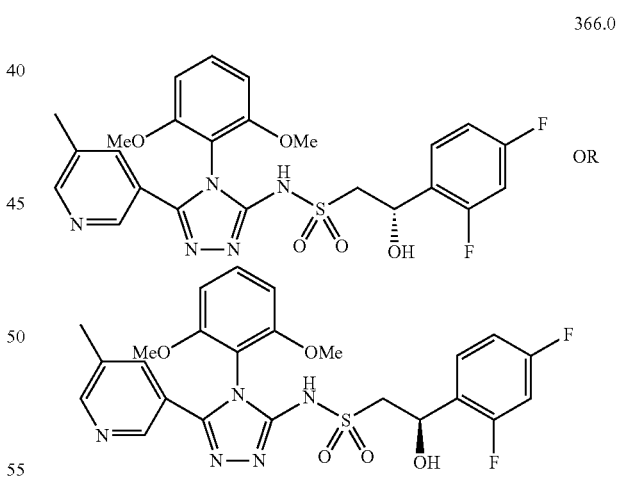

(S)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide or (R)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide, Example 366.0

Following the procedure in Example B; 23.0 (100 mg, 0.42 mmol) and 2.0 (190 mg, 0.51 mmol) were coupled to provide the racemic alcohol product (120 mg, 54% yield) as a white solid. A chiral supercritical fluid chromatography purification was then performed to separate the two enantiomeric products. Chiralpak AD-H, 5 uM, 250×20 mm, 35% IPA, 274-nm, 193 Bar. The first eluting peak (366.0, 42.7 mg). $^1$H NMR (500 MHz, CDCl$_3$) δ: 11.00 (br. s., 1H), 8.47 (br. s., 1H), 8.34 (br. s., 1H), 7.72 (s, 1H), 7.37-7.57 (m, 2H), 6.87 (t, J=8.4 Hz, 1H), 6.77 (t, J=10.0 Hz, 1H), 6.64 (t, J=9.3 Hz, 2H), 5.41 (dd, J=8.2, 2.7 Hz, 1H), 4.40 (br. s., 1H), 3.67-3.85 (m, 6H), 3.22-3.42 (m, 2H), 2.34 (s, 3H). LCMS-ESI (POS.) m/z: 532.1 (M+H)$^+$.

Example 367.0: Preparation of (S)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide or (R)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide

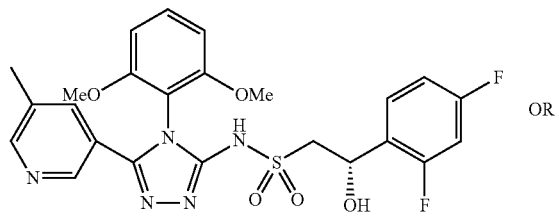

367.0

OR

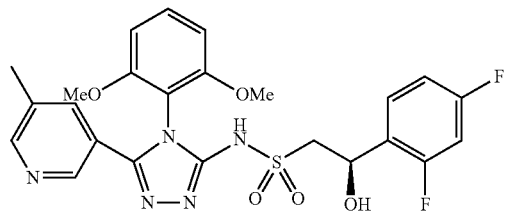

(S)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide or (R)-2-(2,4-difluorophenyl)-N-(4-(2,6-dimethoxyphenyl)-5-(5-methylpyridin-3-yl)-4H-1,2,4-triazol-3-yl)-2-hydroxyethanesulfonamide, Example 367.0

Further elution under the conditions described in Example 366.0, delivered the second eluting peak (367.0, 40.6 mg). $^1$H NMR (500 MHz, CDCl$_3$) δ: 10.99 (br. s., 1H), 8.47 (s, 1H), 8.34 (s, 1H), 7.71 (s, 1H), 7.34-7.56 (m, 2H), 6.87 (t, J=8.4 Hz, 1H), 6.77 (t, J=10.0 Hz, 1H), 6.64 (br. s., 1H), 5.42 (dd, J=8.3, 3.0 Hz, 1H), 4.40 (br. s., 1H), 3.68-3.85 (m, 6H), 3.23-3.40 (m, 2H), 2.33 (s, 3H). LCMS-ESI (POS.) m/z: 532.1 (M+H)$^+$.

Example 368.0: Preparation of 2-(4-chlorophenyl)-N-(4-(2,6-dimethoxyphenyl)-5-(2-pyridinyl)-4H-1,2,4-triazol-3-yl)ethanesulfonamide

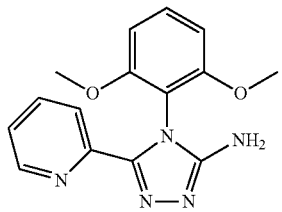

368.1

4-(2,6-dimethoxyphenyl)-5-(pyridin-2-yl)-4H-1,2,4-triazol-3-amine, Example 368.1

Employing a similar procedure to that used in the synthesis of Example 2.04, using picolinohydrazide yielded 368.1. LCMS-ESI (POS), m/z: 298.2 (M+H)$^+$.

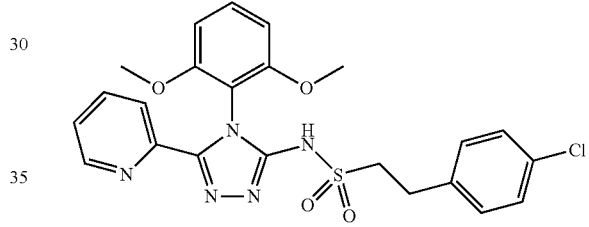

368.0

2-(4-chlorophenyl)-N-(4-(2,6-dimethoxyphenyl)-5-(2-pyridinyl)-4H-1,2,4-triazol-3-yl)ethanesulfonamide, Example 368.0

To a solution of 368.1 (22 mg, 0.074 mmol) and TEA (51.5 μL, 0.370 mmol) in DCM (370 μL) was added 2-(4-chlorophenyl)-ethanesulfonyl chloride (commercially available from SynChem Inc., 35.4 mg, 0.15 mmol). The reaction was stirred at RT. Next, a further two equivalents of sulfonyl chloride and one equivalent of TEA was added. After the reaction was complete, the mixture was diluted with DCM and washed with a saturated solution of NaHCO$_3$ and brine. The organic layers were dried on MgSO$_4$, filtered and evaporated to an orange oil. Purification of the residue by preparatory RP-HPLC (55% ACN, water, 0.1% TFA, isocratic elution) using Sunfire™ Prep C18 OBD column, 10 μm, 30×150 mm (Waters, Milford, Mass.) at 30 mLs/min provided the product. The material was isolated as the free base under standard conditions; yielding 368.0 (5 mg, 13%) as a white solid. $^1$H NMR (400 MHz, CD$_3$OD) δ: 8.34 (d, J=4.9 Hz, 1H), 7.79-7.86 (m, 1H), 7.72-7.78 (m, 1H), 7.44 (t, J=8.5 Hz, 1H), 7.34-7.39 (m, 1H), 7.25-7.31 (m, 2H), 7.15-7.21 (m, 2H), 6.74 (d, J=8.4 Hz, 2H), 3.69 (s, 6H), 3.22-3.28 (m, 2H), 2.98-3.06 (m, 2H). LCMS-ESI (POS.) m/z: 500.2 (M+H)$^+$.

Example 369.0: Preparation of 2-(4-chlorophenyl)-N-(4-(2,6-dimethoxyphenyl)-5-(3-pyridinyl)-4H-1,2,4-triazol-3-yl)ethanesulfonamide

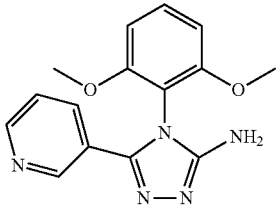

4-(2,6-dimethoxyphenyl)-5-(pyridin-3-yl)-4H-1,2,4-triazol-3-amine, Example 369.1

Employing a similar procedure to that used in the synthesis of Example 2.04, and employing nicotinohydrazide yielded Example 369.1. LCMS-ESI (POS), m/z: 298.1 (M+H)$^+$.

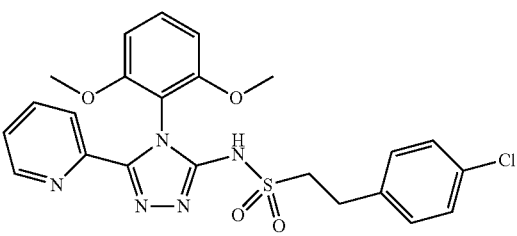

2-(4-chlorophenyl)-N-(4-(2,6-dimethoxyphenyl)-5-(3-pyridinyl)-4H-1,2,4-triazol-3-yl)ethanesulfonamide, Example 369.0

Employing 369.1 and the procedure described in Example 368.0 yielded 369.0 (50 mg, 22%) of as an off-white solid. $^1$H NMR (400 MHz, CD$_3$OD) δ: 8.54-8.67 (m, 2H), 7.87 (dt, J=8.0, 2.0 Hz, 1H), 7.51 (t, J=8.5 Hz, 1H), 7.46 (dd, J=8.0, 5.1 Hz, 1H), 7.22-7.32 (m, 2H), 7.16-7.20 (m, 2H), 6.81 (d, J=8.6 Hz, 2H), 3.76 (s, 6H), 3.22-3.28 (m, 2H), 2.98-3.06 (m, 2H). LCMS-ESI (POS.) m/z: 500.0 (M+H)$^+$.

Example 370.0: Preparation of 2-(4-chlorophenyl)-N-(4-(2,6-dimethoxyphenyl)-5-(6-methylpyridin-3-yl)-4H-1,2,4-triazol-3-yl)ethanesulfonamide

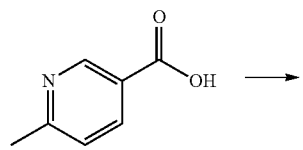

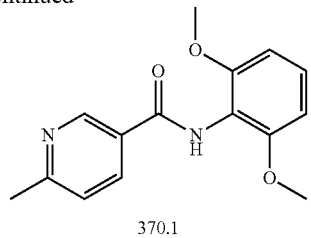

N-(2,6-dimethoxyphenyl)-6-methylnicotinamide, Example 370.1

To a stirred solution of 6-methylnicotinic acid (3.1 g, 22.8 mmol) and TEA (9.5 mL, 68.5 mmol) in DMF (76 mL) was added HATU (9.6 g, 25.1 mmol). After 3 min, 2,6-dimethoxyaniline (3.5 g, 22.9 mmol) was added. The resulting mixture was stirred at RT until LCMS analysis indicated that the reaction was complete. The reaction mixture was quenched using a mixture of saturated aqueous sodium bicarbonate and brine, then was extracted with EtOAc (4×). The combined organic layers were dried over anhydrous magnesium sulfate and concentrated in vacuo. The residue was purified by silica gel chromatography (eluent: 25-100% EtOAc/hexanes) to provide 370.1 (4.2 g, 68% yield) as a tan solid. LCMS-ESI (POS), m/z: 273.2 (M+H)$^+$.

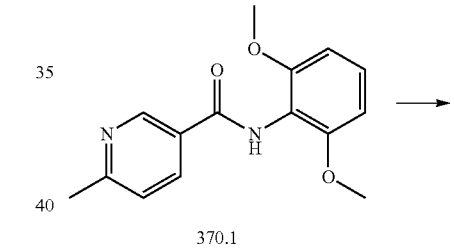

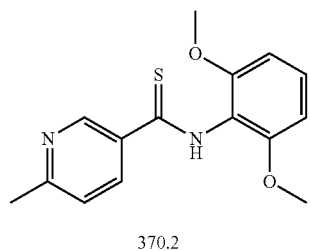

N-(2,6-dimethoxyphenyl)-6-methylpyridine-3-carbothioamide, Example 370.2

To a solution of 370.1 (4.2 g, 15.6 mmol) in dioxane (50 mL) was added hexamethyldisiloxane (10.7 mL, 49.9 mmol) and diphosphorus pentasulfide (694 mg, 3.1 mmol). The resulting slurry was heated at 100° C. for 16 h until LCMS analysis indicated that the reaction was complete. The reaction mixture was concentrated and partitioned between water and EtOAc (3×). The combined organic layers were dried over anhydrous sodium sulfate and concentrated in vacuo to provide 370.2 (4.5 g, 100% yield) as a yellow solid. LCMS-ESI (POS), m/z: 289.2 (M+H)$^+$.

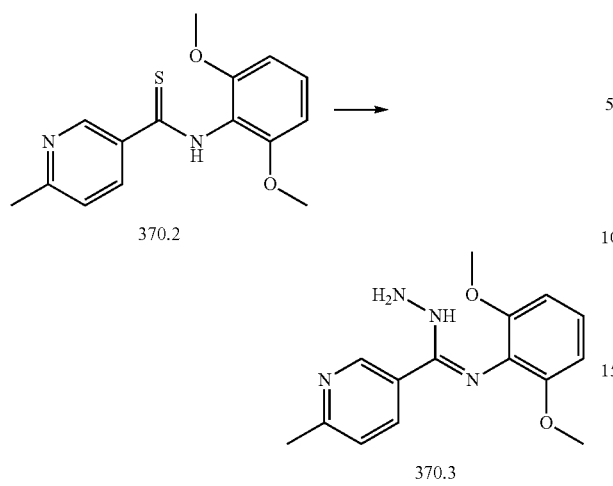

370.2

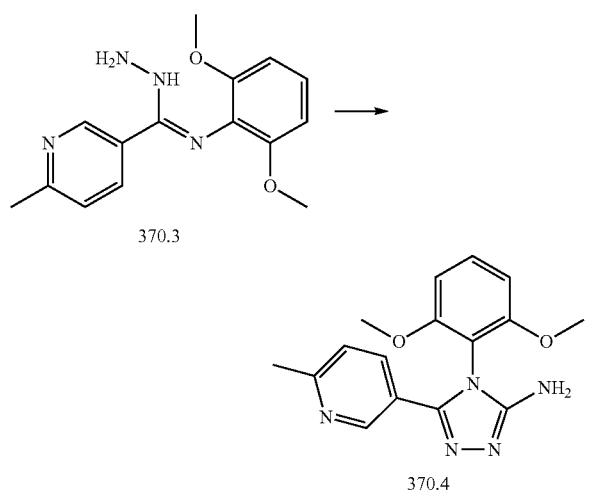

(Z)—N''-(2,6-dimethoxyphenyl)-6-methylnicotin-imidohydrazide, Example 370.3

To a solution of 370.2 (2.42 g, 8.39 mmol) in THF (56 mL) was added hydrazine hydrate solution (80 wt. %, 3.3 mL, 84 mmol). The resulting slurry was heated at reflux for 1 h until LCMS analysis indicated that the reaction was complete. The reaction mixture was partitioned between brine and EtOAc. The organic layer was dried over anhydrous sodium sulfate and concentrated in vacuo. The residue was purified by chromatography on a neutral alumina column (eluent: 0-10% MeOH in DCM) to provide 370.3 (1.29 g, 54% yield) as an off-white solid. LCMS-ESI (POS), m/z: 287.2 (M+H)$^+$.

4-(2,6-dimethoxyphenyl)-5-(6-methylpyridin-3-yl)-4H-1,2,4-triazol-3-amine, Example 370.4

To a solution of 370.3 (1.29 g, 4.51 mmol) in EtOH (15 mL) was added a cyanogen bromide solution (5 M, 2.70 mL, 13.5 mmol). The resulting red solution was heated at 60° C. for 4 h and then stirred at RT for 16 h. LCMS analysis indicated that the reaction was complete. The reaction mixture was quenched with saturated aqueous sodium bicarbonate and extracted with EtOAc (4×). The combined organic layers were dried over anhydrous sodium sulfate and concentrated in vacuo. The residue was purified by reverse phase preparative HPLC (Sunfire 5 μM C18 column, eluent: 5-40% ACN in water over a 35 minute period where both solvents contain 0.1% TFA) to provide 370.4 (428 mg, 31% yield) as a tan solid. LCMS-ESI (POS), m/z: 312.2 (M+H)$^+$.

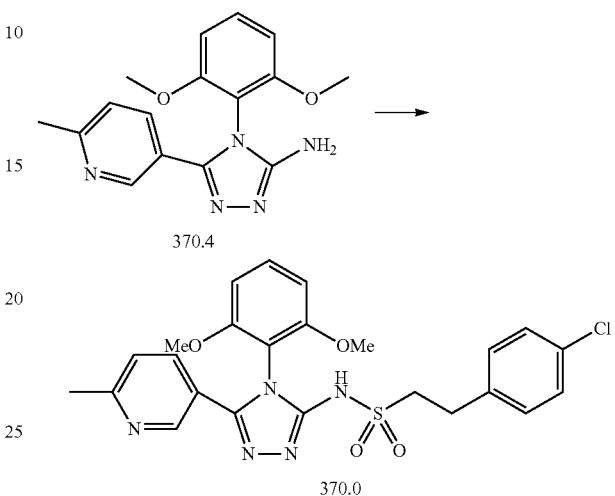

2-(4-chlorophenyl)-N-(4-(2,6-dimethoxyphenyl)-5-(6-methylpyridin-3-yl)-4H-1,2,4-triazol-3-yl)ethanesulfonamide, Example 370.0

To a solution of 370.4 (48 mg, 0.15 mmol) and TEA (107 μL, 0.77 mmol) in DCM (15 mL) was added 2-(4-chlorophenyl)ethanesulfonyl chloride (96 mg, 0.40 mmol). The resulting solution was stirred at RT for 2.5 d at which time LCMS analysis indicated partial conversion had occurred. The reaction mixture was partitioned between saturated aqueous sodium bicarbonate and EtOAc. The organic layer was dried over anhydrous sodium sulfate and concentrated in vacuo. The residue was purified by reverse phase preparatory HPLC (Sunfire 5 μM C18 column, eluent: 20-50% ACN in water over a 35 minute period where both solvents contain 0.1% TFA) to provide 370.0 (9.6 mg, 12% yield) as an off-white solid. $^1$H NMR (500 MHz, CD$_3$OD) δ: 8.53 (d, J=1.7 Hz, 1H), 7.96 (dd, J=8.3, 2.3 Hz, 1H), 7.52 (dt, J=8.5, 4.3 Hz, 2H), 7.28 (d, J=8.6 Hz, 2H), 7.17 (d, J=8.6 Hz, 2H), 6.82 (d, J=8.6 Hz, 2H), 3.77 (s, 6H), 3.20-3.28 (m, 2H), 2.94-3.07 (m, 2H), 2.61 (s, 3H). LCMS-ESI (POS.) m/z: 514.2 (M+H)$^+$.

Example 371.0: Preparation of (1R,2S)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide

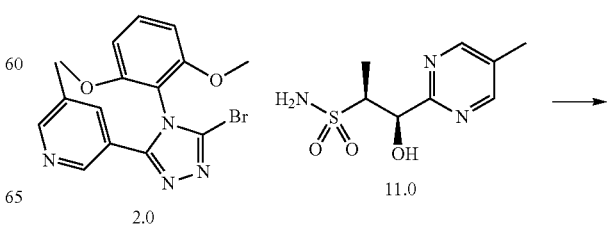

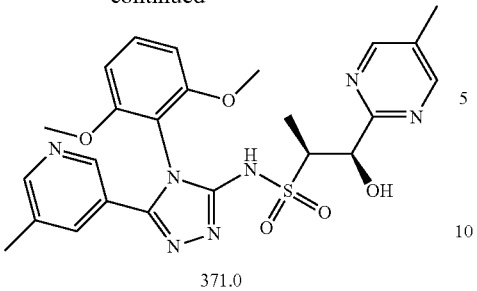

371.0

(1R,2S)—N-(4-(2,6-dimethoxyphenyl)-5-(5-methyl-pyridin-3-yl)-4H-1,2,4-triazol-3-yl)-1-hydroxy-1-(5-methylpyrimidin-2-yl)propane-2-sulfonamide, Example 371.0

A mixture of (1R,2S)-1-hydroxy-1-(5-methylpyrimidin-2-yl)propane-2-sulfonamide, 11.0 (253 mg, 1.09 mmol), 3-(5-bromo-4-(2,6-dimethoxyphenyl)-4H-1,2,4-triazol-3-yl)-5-methylpyridine, 2.0 (575 mg, 1.53 mmol) and dioxane (6 mL) was heated to 60° C. at which point the solution became homogenous. The solution was allowed to cool to RT and was treated with $Cs_2CO_3$ (918 mg, 2.82 mmol) and racemic-trans-N,N'-dimethylcyclohexanes-1,2-diamine (0.35 mL, 2.22 mmol). The solution was then purged with $N_2$ for 10 min and was then treated with copper(i) iodide (130 mg, 0.68 mmol) and stirred in an 80° C. oil bath. After 3 d, the reaction was cooled to RT and concentrated in vacuo. The material thus obtained was filtered through a syringe filter and then purified by reverse-phase preparative HPLC on a Phenomenex Gemini column (10 micron, C18, 110 Å, Axia, 100×50 mm) eluting at 90 mL/min with a linear gradient of 10-35% ACN (0.1% TFA) in water (0.1% TFA) over 20 min. The desired fractions were poured into 10% $Na_2CO_3$/DCM and extracted with $CHCl_3$:iPrOH (9:1) to give (1R,2S)—N-(4-(2,6-dimethoxyphenyl)-5-(5-methyl-pyridin-3-yl)-4H-1,2,4-triazol-3-yl)-1-hydroxy-1-(5-methylpyrimidin-2-yl)propane-2-sulfonamide (371.0, 60 mg, 10% yield). $^1$H NMR (CDCl$_3$) δ: 8.58 (s, 2H), 8.46 (d, J=1.6 Hz, 1H), 8.34 (d, J=1.9 Hz, 1H), 7.66 (s, J=3.1 Hz, 1H), 7.40 (t, J=8.6 Hz, 1H), 6.64 (d, J=8.5 Hz, 1H), 6.60 (d, J=8.5 Hz, 1H), 5.59 (s, 1H), 4.07 (br. s, 1H), 3.81-3.91 (m, 1H), 3.76 (s, 3H), 3.74 (s, 3H), 2.34 (s, 3H), 2.32 (s, 3H), 1.21 (d, J=7.0 Hz, 3H). LCMS-ESI (POS.) m/z: 526.2 (M+H)$^+$.

Example 372.0: Preparation of (1R)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide and (1S)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide 372.0

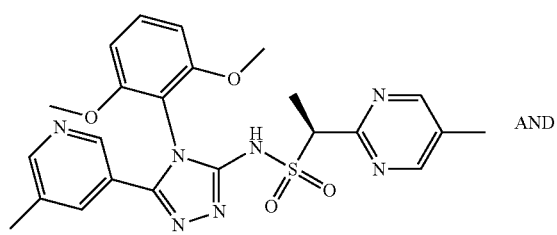

AND

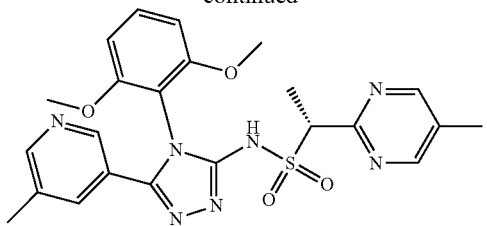

(1R)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide and (1S)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide, 372.0

Further elution under the conditions described in Example 371.0 yielded a by-product. The fractions were poured into 10% $Na_2CO_3$/DCM and extracted with $CHCl_3$:iPrOH (9:1) to give (1R)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide and (1S)—N-(4-(2,6-dimethoxyphenyl)-5-(5-methyl-3-pyridinyl)-4H-1,2,4-triazol-3-yl)-1-(5-methyl-2-pyrimidinyl)ethanesulfonamide 372.0. $^1$H NMR (CDCl$_3$) δ: 11.08 (br. s, 1H), 8.57 (s, 2H), 8.47 (s, J=3.8 Hz, 1H), 8.35 (d, J=1.8 Hz, 1H), 7.70 (s, 1H), 7.41 (t, J=8.5 Hz, 1H), 6.63 (d, J=8.5 Hz, 2H), 4.65 (q, J=6.9 Hz, 1H), 3.77 (s, 6H), 2.34 (s, 3H), 2.31 (s, 3H), 1.82 (d, J=7.0 Hz, 3H). LCMS-ESI (POS.) m/z: 496.2 (M+H)$^+$.

Example 373.0: Preparation of 4-(3-chloro-2,6-dimethoxyphenyl)-N-(2-(4-chlorophenyl)ethyl)-5-(5-methyl-3-pyridinyl)-4H-1,2,4-triazole-3-sulfonamide 373.1

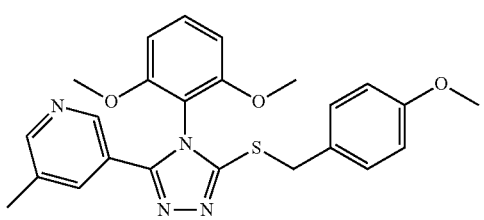

3-(4-(2,6-dimethoxyphenyl)-5-((4-methoxybenzyl)thio)-4H-1,2,4-triazol-3-yl)-5-methylpyridine, Example 373.1

To a solution of 3-(5-bromo-4-(2,6-dimethoxyphenyl)-4H-1,2,4-triazol-3-yl)-5-methylpyridine. Example 2.0 (231 mg, 0.62 mmol) in 1,2-dimethoxyethane (2.0 mL) was added palladium (II) acetate (11 mg, 0.049 mmol), (R)-(−)-1-[(S)-2-(dicyclohexylphosphino)ferrocenyl]ethyldi-t-butylphosphine (24.2 mg, 0.044 mmol, Strem Chemicals, Inc.), 4-methoxy-alpha-toluenethiol (0.10 mL, 0.65 mmol, tech., 90%, Sigma-Aldrich) and sodium tert-butoxide (2.0M in THF 0.63 mL, 1.26 mmol). The reaction mixture was stirred at 80° C. After 2 h, LC-MS showed starting material had been consumed. The reaction was allowed to cool to RT and diluted with water and extracted with EtOAc (3×20 mL). The combined EtOAc layers were concentrated in vacuo and adsorbed onto a plug of silica gel and chromatographed through a Redi-Sep® pre-packed silica gel column (12 g), eluting with 0-50% EtOAc:EtOH (3:1) in heptane, to provide the title compound (373.1, 26 mg, 9.42% yield) as an oil. ¹H NMR (CDCl₃) δ: 8.39 (d, J=1.3 Hz, 1H), 8.33 (d, J=1.8 Hz, 1H), 7.85 (s, 1H), 7.40 (t, J=8.3 Hz, 1H), 7.25-7.31 (m, 2H), 6.82 (d, J=8.6 Hz, 2H), 6.62 (d, J=8.5 Hz, 2H), 4.43 (s, 2H), 3.79 (s, 3H), 3.68 (s, 6H), 2.32 (s, 3H). LCMS-ESI (POS.) m/z: 449.1 (M+H)⁺.

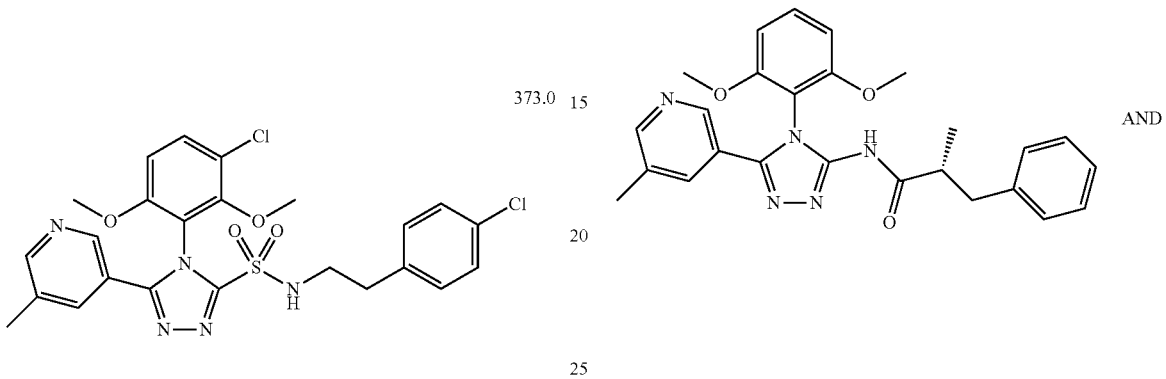

373.0

4-(3-chloro-2,6-dimethoxyphenyl)-N-(2-(4-chlorophenyl)ethyl)-5-(5-methyl-3-pyridinyl)-4H-1,2,4-triazole-3-sulfonamide, Example 373.0

To a 0° C. solution of 3-(4-(2,6-dimethoxyphenyl)-5-((4-methoxybenzyl)thio)-4H-1,2,4-triazol-3-yl)-5-methylpyridine (26 mg, 0.058 mmol) in a mixture of ACN/AcOH/H₂O (0.40 mL/0.015 mL/0.010 mL) was added portionwise 1,3-dichloro-5,5-dimethylhydantoin (25.6 mg, 0.13 mmol). After 3 h at 0° C., LC-MS showed the reaction to be incomplete. Thus, the reaction was treated with more 1,3-dichloro-5,5-dimethylhydantoin (13 mg) and stirred in the ice bath. After 45 min, the reaction was concentrated in vacuo, taken up in DCM (3 mL) and chilled in an ice bath. After stirring for 5 min, a 5% NaHCO₃ solution (3 mL) was added slowly and the solution stirred in the ice bath for 15 min. The organic layer was separated. The reaction was treated with 2-(4-chlorophenyl)ethylamine (8.11 μL, 0.058 mmol, Sigma-Aldrich) and TEA (8.06 μL, 0.058 mmol) and stirred at RT. After 16 h, the reaction was diluted with water and the aqueous layer was back extracted with DCM (10 mL). The combined DCM layers were concentrated in vacuo and adsorbed onto a plug of silica gel and chromatographed through a Redi-Sep® pre-packed silica gel column (4 g), eluting with 0-50% EtOAc:EtOH (3:1) in heptane. The material was repurified by reverse-phase preparative HPLC on a Phenomenex Luna column (5 micron, Phenyl-hexyl, 100 Å, 100×30 mm) eluting at 45 mL/min with a linear gradient of 10-90% ACN (0.1% TFA) in water (0.1% TFA) over 12 min to give the title compound (373.0, 12 mg, 31%) as a TFA salt after lyopholization. ¹H NMR (CDCl₃) δ: 8.60 (d, J=1.5 Hz, 1H), 8.47 (d, J=1.6 Hz, 1H), 8.23 (s, 1H), 7.53 (d, J=9.2 Hz, 1H), 7.30-7.35 (m, 2H), 7.18-7.23 (m, 2H), 6.83 (d, J=9.2 Hz, 1H), 5.20 (t, J=6.4 Hz, 1H), 3.83 (s, 3H), 3.76 (s, 3H), 3.62 (q, J=6.8 Hz, 2H), 2.97 (t, J=7.0 Hz, 2H), 2.49 (s, 3H). LCMS-ESI (POS.) m/z: 548.2, 550.1 (M+H)⁺.

Example 374.0: Preparation of (2R)—N-(4-(2,6-dimethoxyphenyl)-5-(5-methyl-3-pyridinyl)-4H-1,2,4-triazol-3-yl)-2-methyl-3-phenylpropanamide and (2S)—N-(4-(2,6-dimethoxyphenyl)-5-(5-methyl-3-pyridinyl)-4H-1,2,4-triazol-3-yl)-2-methyl-3-phenylpropanamide

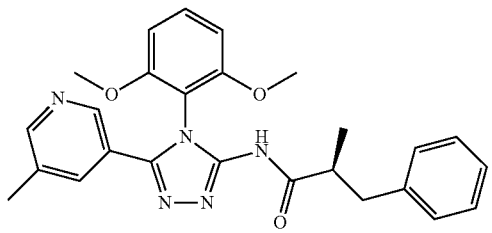

374.0

AND (2R)—N-(4-(2,6-dimethoxyphenyl)-5-(5-methyl-3-pyridinyl)-4H-1,2,4-triazol-3-yl)-2-methyl-3-phenylpropanamide and (2S)—N-(4-(2,6-dimethoxyphenyl)-5-(5-methyl-3-pyridinyl)-4H-1,2,4-triazol-3-yl)-2-methyl-3-phenylpropanamide, Example 374.0

To a solution of 4-(2,6-dimethoxyphenyl)-5-(5-methyl-pyridin-3-yl)-4H-1,2,4-triazol-3-amine. Example 2.04 (191 mg, 0.61 mmol) and DCM (5 mL) was added a mixture of (S)-2-methyl-3-phenylpropanoic acid and (R)-2-methyl-3-phenylpropanoic acid (100.9 mg, 0.61 mmol), HATU (304 mg, 0.80 mmol), and N,N-diisopropylethylamine (0.21 mL, 1.23 mmol). The reaction was stirred at RT. After 2 d, the reaction was diluted with DCM (10 mL) and washed with water (10 mL). The DCM layer was adsorbed onto a plug of silica gel and chromatographed through a Redi-Sep® pre-packed silica gel column (12 g), eluting with 0-70% EtOAc:EtOH (3:1) in heptane, to provide the title compound (374.0, 80 mg, 14% yield) as a white solid. ¹H NMR (CDCl₃) δ: 8.41 (d, J=1.5 Hz, 1H), 8.26 (s, 1H), 7.82 (m, 1H), 7.42 (t, J=8.5 Hz, 1H), 7.11-7.25 (m, 5H), 6.63 (dd, J=8.5, 5.0 Hz, 2H), 3.69 (s, 3H), 3.64 (s, 3H), 3.06 (br. s, 1H), 2.55 (dd, J=13.2, 8.1 Hz, 1H), 2.32 (s, 3H), 1.44-1.54 (m, 1H), 1.08 (d, J=6.6 Hz, 3H). LCMS-ESI (POS.) m/z: 458.1 (M+H)⁺.

Example 375.0: Preparation of (1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1S,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1S,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide

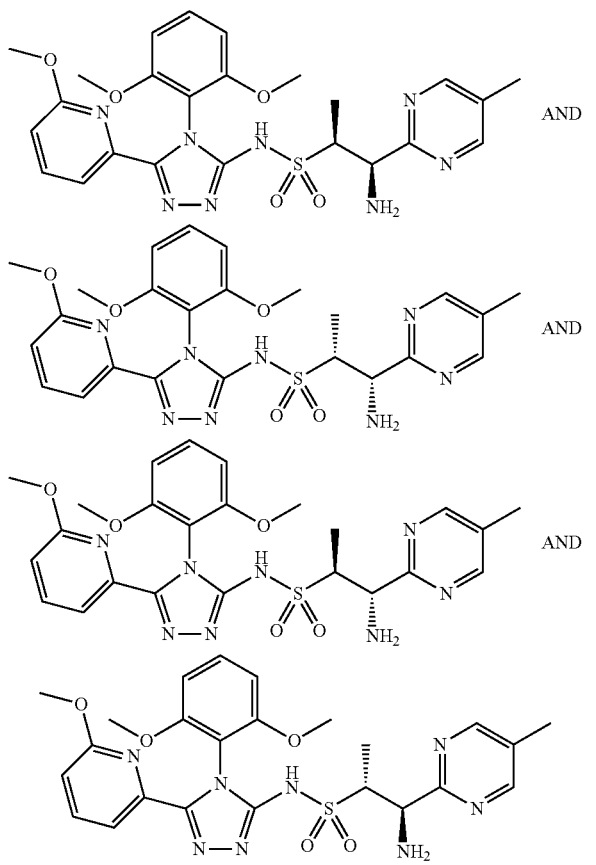

375.0

(1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1S,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1S,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide, Example 375.0

To a mixture of N-(4-(2,6-dimethoxyphenyl)-5-(6-methoxypyridin-2-yl)-4H-1,2,4-triazol-3-yl)-1-(5-methyl-pyrimidin-2-yl)-1-oxopropane-2-sulfonamide (421.1, 90 mg, 0.17 mmol) and ammonium acetate (120 mg, 1.55 mmol) in MeOH (0.75 mL) was added sodium cyanoborohydride (11 mg, 0.175 mmol). The reaction mixture was then stirred at 60° C. for 1.5 h. The solvent was removed and the residue was purified by chromatography through a Biotage 10 g ultra column, eluting with a gradient of 0-50% 3:1 EtOAc/EtOH in DCM to give the title compound 375.0 (59 mg, 0.11 mmol, 65.4% yield) as a white solid.

Example 376.0: Preparation of (1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1S,2S)-1-amino-N-(4-(2,6-dimethoxyphenyl)-5-(6-methoxypyridin-2-yl)-4H-1,2,4-triazol-3-yl)-1-(5-methylpyrimidin-2-yl) propane-2-sulfonamide or (1S,2R)-1-amino-N-(4-(2,6-(trimethoxyphenyl)-5-(6-methoxypyridin-2-yl)-4H-1,2,4-triazol-3-yl)-1-(5-methylpyrimidin-2-yl) propane-2-sulfonamide

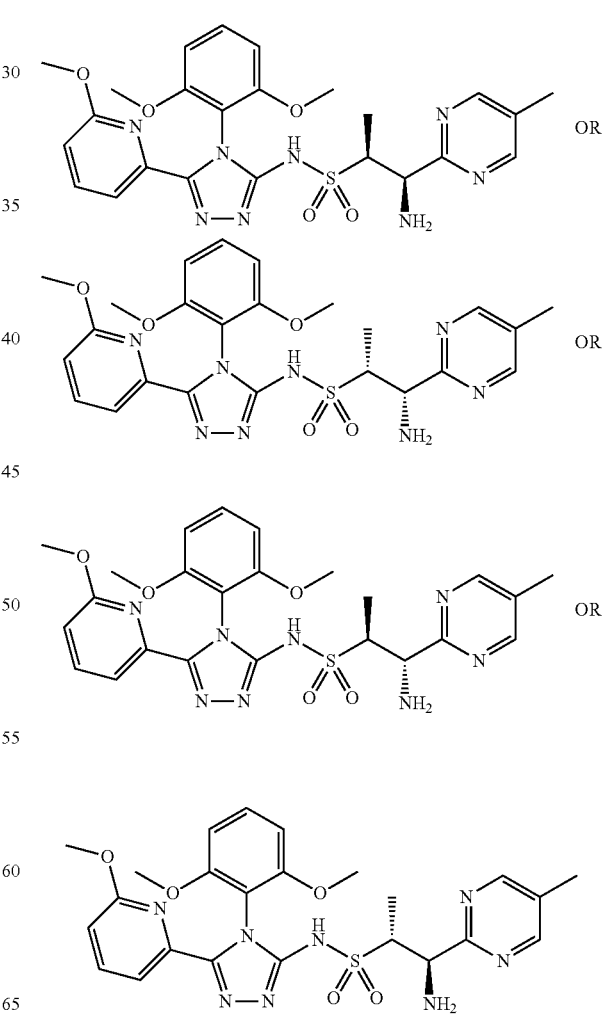

376.0

(1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1S,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1S,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide, Example 376.0

Chiral purification was performed on the mixture of diastereomers prepared in Example 375.0. The conditions were as follows: (AD-H (21×150 mm sn=3242, reversed) 5 um, organic modifier: 30% EtOH with 20 mM $NH_3$. F=70 mL/min, T=40° C., BPR=100 bar, 220 nm. P=179 bar) and delivered the pure enantiomers. The first eluting peak was Example 376.0. $^1$H NMR (CDCl$_3$) δ: 8.55 (s, 2H), 7.55-7.69 (m, 2H), 7.29-7.38 (m, 1H), 6.71 (dd. J=7.2, 1.8 Hz, 1H), 6.55-6.67 (m, 2H), 4.35 (d, J=7.9 Hz, 1H), 3.76 (s, 3H), 3.73 (s, 3H), 3.56-3.68 (m, 1H), 3.19 (s, 3H), 2.31 (s, 3H), 1.14 (d, J=6.1 Hz, 3H). LCMS-ESI (POS.) m/z: 541.0 (M+H)$^+$.

Example 377.0: Preparation of (1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1R,2R)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide or (1S,2S)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide or (1S,2R)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide

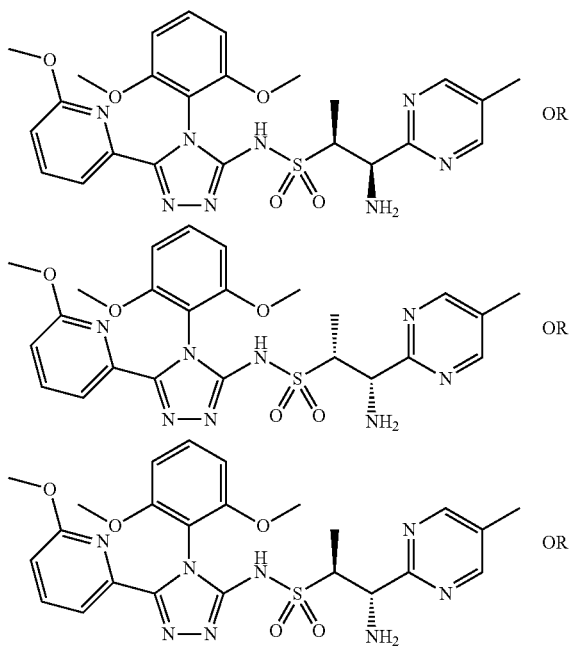

377.0

OR

OR

OR

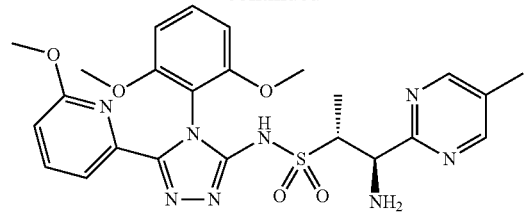

(1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1S,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1S,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide, Example 377.0

Chiral purification was performed on the mixture of four diastereomers described in Example 375.0 using the method described in Example 376.0. The second eluting peak was Example 377.0. $^1$H NMR (CDCl$_3$) δ: 8.55 (s, 2H), 7.55-7.69 (m, 2H), 7.29-7.38 (m, 1H), 6.71 (dd. J=7.2, 1.8 Hz, 1H), 6.55-6.67 (m, 2H), 4.35 (d, J=7.9 Hz, 1H), 3.76 (s, 3H), 3.73 (s, 3H), 3.56-3.68 (m, 1H), 3.19 (s, 3H), 2.31 (s, 3H), 1.14 (d, J=6.1 Hz, 3H). LCMS-ESI (POS.) m/z: 541.0 (M+H)$^+$.

Example 378.0: Preparation of (1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1R,2R)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide or (1S,2S)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide or (1S,2R)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide 378.0

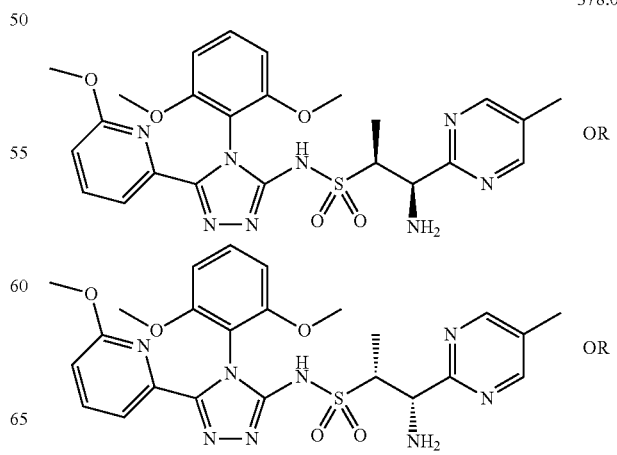

OR

OR

-continued

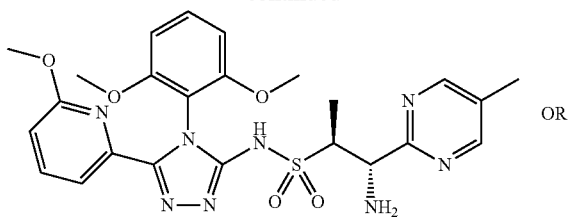

OR

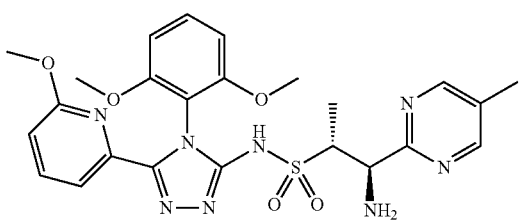

(1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or
(1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or
(1S,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or
(1S,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide,
Example 378.0

Chiral purification was performed on the mixture of diastereomers in Example 375.0 and provided Example 378.0 as the third eluting peak. The conditions were as follows: (AD-H (21×150 mm sn=3242, reversed) 5 um, organic modifier: 30% EtOH with 20 mM NH$_3$. F=70 mL/min, T=40 C, BPR=100 bar, 220 nm. P=179 bar). $^1$H NMR (CDCl$_3$) δ: 8.54 (s, 2H), 7.56-7.67 (m, 2H), 7.32 (t, J=8.5 Hz, 1H), 6.70 (dd, J=7.7, 1.3 Hz, 1H), 6.62 (dd, J=11.5, 8.4 Hz, 2H), 4.35 (d, J=7.8 Hz, 1H), 3.75 (s, 3H), 3.72 (s, 3H), 3.57-3.68 (m, 1H), 3.18 (s, 3H), 2.30 (s, 3H), 1.17-1.23 (m, 3H). LCMS-ESI (POS.) m/z: 541.0 (M+H)$^+$.

Example 379.0: Preparation of (1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or (1R,2R)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide or (1S,2S)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide or (1S,2R)-1-amino-N-(4-(2,6-(trimethoxyphenyl)-5-(6-methoxypyridin-2-yl)-4H-1,2,4-triazol-3-yl)-1-(5-methylpyrimidin-2-yl)propane-2-sulfonamide 379.0

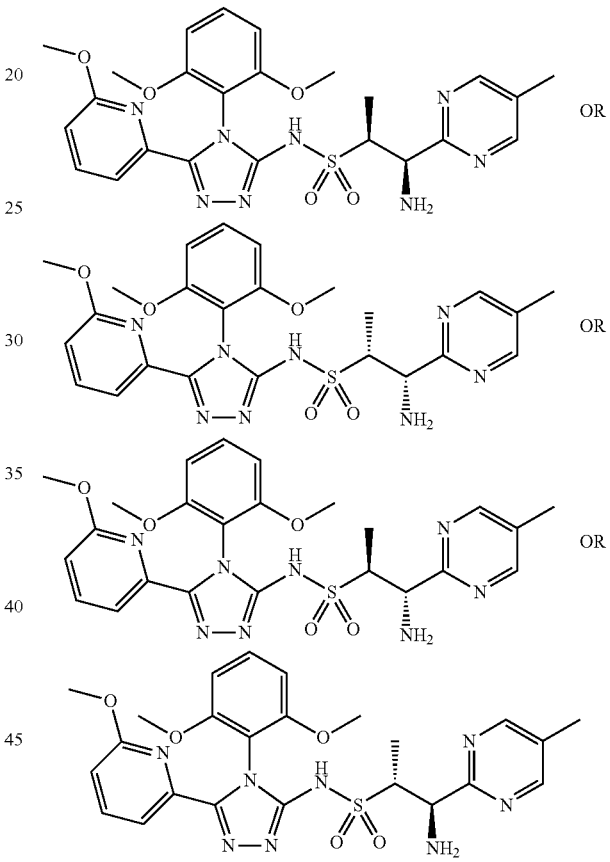

(1R,2S)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or
(1R,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide or
(1S,2S)-1-amino-N+1-(2,6-dimethoxyphenyl)-5-(6-methoxypyridin-2-yl)-4H-1,2,4-triazol-3-yl)-1-(5-methylpyrimidin-2-yl)propane-2-sulfonamide or
(1S,2R)-1-amino-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide,
Example 379.0

Chiral purification was performed on the mixture of diastereomers in Example 375.0 and provided Example 379.0 as the fourth eluting peak. The conditions were as follows: (AD-H (21×150 mm sn=3242, reversed) 5 um, organic modifier: 30% EtOH with 20 mM NH$_3$. F=70 mL/min, T=40 C, BPR=100 bar, 220 nm. P=179 bar). $^1$H NMR (CDCl$_3$) δ: 8.54 (s, 2H), 7.56-7.67 (m, 2H), 7.32 (t, J=8.5 Hz, 1H), 6.70 (dd, J=7.7, 1.3 Hz, 1H), 6.62 (dd, J=11.5, 8.4 Hz, 2H), 4.35 (d, J=7.8 Hz, 1H), 3.75 (s, 3H), 3.72 (s, 3H), 3.57-3.68 (m, 1H), 3.18 (s, 3H), 2.30 (s, 3H), 1.17-1.23 (m, 3H). LCMS-ESI (POS.) m/z: 541.0 (M+H)$^+$.

Example 381.0: Preparation of (R)—N-(4-(2,6-dimethoxyphenyl)-5-(5-methylpyridin-3-yl)-4H-1,2,4-triazol-3-yl)-2-hydroxy-2-(3-methyloxetan-3-yl)ethanesulfonamide and (S)—N-(4-(2,6-dimethoxyphenyl)-5-(5-methylpyridin-3-yl)-4H-1,2,4-triazol-3-yl)-2-hydroxy-2-(3-methyloxetan-3-yl)ethanesulfonamide 6.0

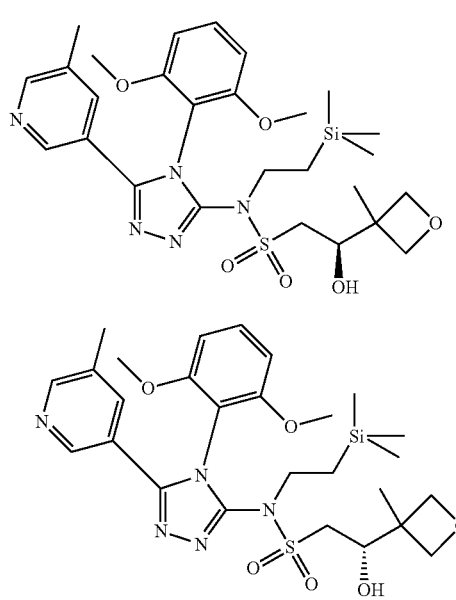

381.1

(R)—N-(4-(2,6-dimethoxyphenyl)-5-(5-methylpyridin-3-yl)-4H-1,2,4-triazol-3-yl)-2-hydroxy-2-(3-methyloxetan-3-yl)-N-(2-(trimethylsilyl)ethyl)ethanesulfonamide and (S)—N-(4-(2,6-dimethoxyphenyl)-5-(5-methylpyridin-3-yl)-4H-1,2,4-triazol-3-yl)-2-hydroxy-2-(3-methyloxetan-3-yl)-N-(2-(trimethylsilyl)ethyl)ethanesulfonamide, 381.1

In a 20-mL scintillation vial, 6.0 (0.200 g, 0.41 mmol) was dissolved into methyltetrahydrofuran (2 mL) and cooled in a dryice-acetone bath. n-Butyl lithium (2.5M in hexanes, 0.195 mL, 0.488 mmol) was then added dropwise, and the mixture was stirred at that temperature for 20 min. 3-Methyloxetane-3-carbaldehyde (0.039 mL, 0.45 mmol, Advanced ChemBlocks) was added dropwise and the reaction mixture was stirred as the cold bath slowly expired. After 5 h, the reaction was quenched by adding half-saturated aqueous ammonium chloride (0.3 mL). The mixture was partitioned between half-saturated aqueous ammonium chloride (10 mL) and EtOAc (10 mL). The aqueous phase was extracted with EtOAc (10 mL). The combined organic phases were dried by passing through a Chem Elute extraction cartridge eluting with EtOAc (2×20 mL). The organic was concentrated and purified by silica gel column chromatography (a gradient of 0-70% 3:1 EtOAc/EtOH in hexanes) to provide 381.1 (0.040 g, 0.067 mmol, 16.5% yield) as a yellow paste. LCMS-ESI (POS.) m/z: 590.0 (M+H)$^+$.

381.0

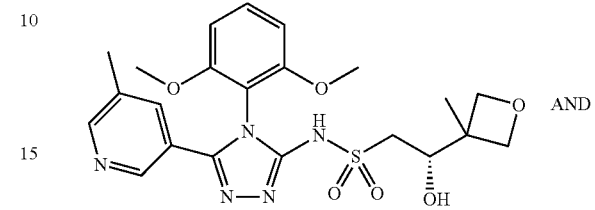

AND

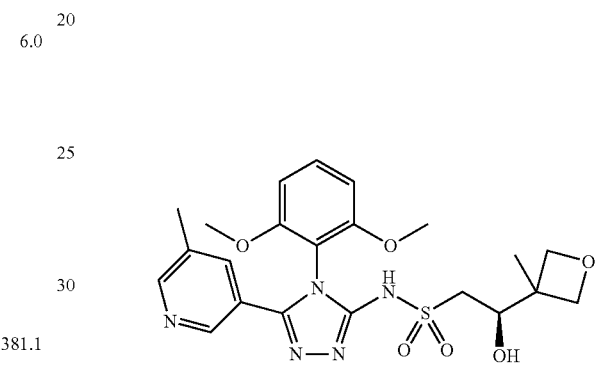

(R)—N-(4-(2,6-dimethoxyphenyl)-5-(5-methylpyridin-3-yl)-4H-1,2,4-triazol-3-yl)-2-hydroxy-2-(3-methyloxetan-3-yl)ethanesulfonamide and (S)—N-(4-(2,6-dimethoxyphenyl)-5-(5-methylpyridin-3-yl)-4H-1,2,4-triazol-3-yl)-2-hydroxy-2-(3-methyloxetan-3-yl)ethanesulfonamide, Example 381.0

To a stirred solution of 381.1 (0.038 g, 0.064 mmol) in DMF (1 mL), was added tris(dimethylamino)sulfur trimethylsilyl difluoride (0.035 g, 0.13 mmol, SynQuest Laboratories). The mixture was placed in a heating block at 110° C. and stirred under N$_2$ for 2 h. More tris(dimethylamino)sulfur trimethylsilyl difluoride (0.033 g, 0.12 mmol) was added at RT and then the mixture was stirred at 110° C. for 1.5 h. The reaction mixture was allowed to cool to RT and then partitioned between water (10 mL) and 10% IPA in chloroform (10 mL). The aqueous phase was extracted with 10% IPA in chloroform (10 mL). The combined organic phases were washed with water (20 mL) and saturated aqueous sodium chloride (20 mL). The organic phase was dried over sodium sulfate, filtered and concentrated. The residue was purified by silica gel column chromatography (a gradient of 0-50% 3:1 EtOAc/EtOH in DCM) and lyophilized to obtain 381.0 (7.4 mg, 0.015 mmol, 23% yield) as a white solid. $^1$H NMR (400 MHz, CDCl$_3$) δ: 11.03 (br. s., 1H), 8.52-8.28 (m, 2H), 7.64 (s, 1H), 7.42 (t, J=8.6 Hz, 1H), 6.63 (dd, J=4.9, 8.6 Hz, 2H), 4.61 (d, J=6.0 Hz, 1H), 4.45 (d, J=5.8 Hz, 1H), 4.42-4.36 (m, 1H), 4.33 (d, J=6.0 Hz, 1H), 4.27 (d, J=5.8 Hz, 1H), 3.82-3.79 (m, 1H), 3.78 (s, 3H), 3.74 (s, 3H), 3.05-2.97 (m, 2H), 2.31 (s, 3H), 1.29 (s, 3H). LCMS-ESI (POS.) m/z: 489.9 (M+H)$^+$.

Example 382.0: Preparation of (R)-2-cyclobutyl-N-(4-(2,6-dimethoxyphenyl)-5-(5-methylpyridin-3-yl)-4H-1,2,4-triazol-3-yl)-2-hydroxyethanesulfonamide and (S)-2-cyclobutyl-N-(4-(2,6-dimethoxyphenyl)-5-(5-methylpyridin-3-yl)-4H-1,2,4-triazol-3-yl)-2-hydroxyethanesulfonamide 382.1

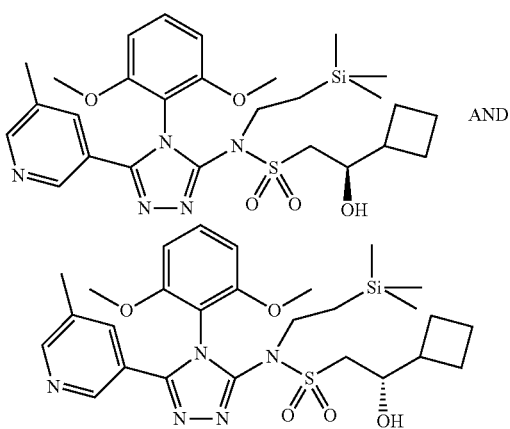

(R)-2-cyclobutyl-N-(4-(2,6-dimethoxyphenyl)-5-(5-methylpyridin-3-yl)-4H-1,2,4-triazol-3-yl)-2-hydroxy-N-(2-(trimethylsilyl)ethyl)ethanesulfonamide and (S)-2-cyclobutyl-N-(4-(2,6-dimethoxyphenyl)-5-(5-methylpyridin-3-yl)-4H-1,2,4-triazol-3-yl)-2-hydroxy-N-(2-(trimethylsilyl)ethyl)ethanesulfonamide, 382.1

This material was prepared in an analogous fashion to that described in Example 381.1, using 1-cyclobutane-aldehyde (commercially available from Astatech, Inc.). LCMS-ESI (POS.) m/z: 574.0 (M+H)$^+$.

382.0

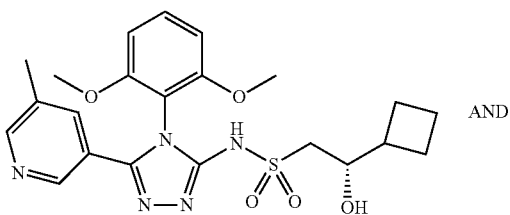

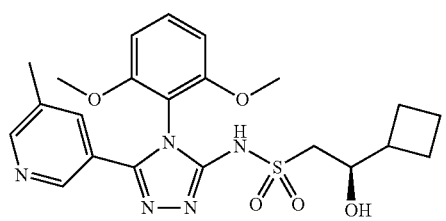

(R)-2-cyclobutyl-N-(4-(2,6-dimethoxyphenyl)-5-(5-methylpyridin-3-yl)-4H-1,2,4-triazol-3-yl)-2-hydroxyethanesulfonamide and (S)-2-cyclobutyl-N-(4-(2,6-dimethoxyphenyl)-5-(5-methylpyridin-3-yl)-4H-1,2,4-triazol-3-yl)-2-hydroxyethanesulfonamide, 382.0

The title compound was prepared in an analogous fashion to that described in Example 381.0, using 382.1. $^1$H NMR (400 MHz, CDCl$_3$) δ: 11.02 (br. s., 1H), 8.46 (d, J=1.5 Hz, 1H), 8.33 (d, J=1.8 Hz, 1H), 7.63 (d, J=0.7 Hz, 1H), 7.41 (t, J=8.5 Hz, 1H), 6.62 (dd, J=4.5, 8.5 Hz, 2H), 4.03 (t, J=8.0 Hz, 1H), 3.77 (s, 3H), 3.74 (s, 3H), 3.63 (br. s., 1H), 3.11-3.01 (m, 1H), 3.00-2.88 (m, 1H), 2.39-2.33 (m, 1H), 2.31 (s, 3H), 2.10-1.73 (m, 6H). LCMS-ESI (POS.) m/z: 474.0 (M+H)$^+$.

Example 383.0: Preparation of (R)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide and (S)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide racemate

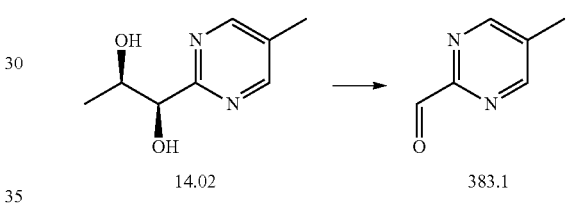

5-Methylpyrimidine-2-carbaldehyde, Example 383.1

A 500 mL round-bottomed flask was charged with Example 14.02 (racemate, 1.50 g, 8.93 mmol), dioxane (60 mL) and water (15 mL). The light yellow solution was cooled in an ice-water bath. Sodium periodate (4.81 g, 22.5 mmol) was added and the cold bath was removed. The white mixture was then stirred at RT for 1.5 h. DCM (100 mL) was added, and the mixture was filtered through a cake of MgSO$_4$. The filter cake was rinsed with additional DCM (400 mL). The filtrate was concentrated and then azeotroped with toluene (2×10 mL) to afford 383.1 (0.914 g, 7.48 mmol, 84% yield) as a white solid. LCMS-ESI (POS.) m/z: 123.1 (M+H)$^+$.

383.2

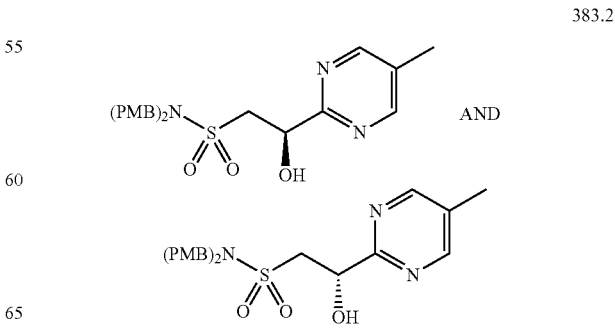

(R)-2-hydroxy-N,N-bis(4-methoxybenzyl)-2-(5-methylpyrimidin-2-yl)ethanesulfonamide and (S)-2-hydroxy-N,N-bis(4-methoxybenzyl)-2-(5-methylpyrimidin-2-yl)ethanesulfonamide, Example 383.2

A 250-mL round-bottomed flask was charged with 13.0 (2.50 g, 7.45 mmol) and THF (30 mL) and was cooled in a dry ice-acetone bath until the internal temperature reached −75° C. n-Butyllithium (2.5 M in hexanes, 3.28 mL, 8.20 mmol) was then added slowly keeping the internal temperature below −72° C. over 15 min. The mixture was then stirred in the cold bath for 20 min. 383.1 (0.910 g, 7.45 mmol) in THF (12 mL) was added slowly keeping the internal temperature below −71° C. over 15 min. The yellow mixture was stirred as the cold bath slowly expired and the temperature rose to RT overnight. The reaction was then quenched with 2 mL sat NH$_4$C$_1$ and then partitioned between half-saturated aqueous ammonium chloride (50 mL) and EtOAc (20 mL). The aqueous phase was extracted with EtOAc (40 mL). The combined organic phases were washed with water (50 mL) and saturated aqueous sodium chloride (50 mL). The organic phase was dried by passing through a Chem Elute extraction cartridge eluting with EtOAc (2×10 mL). The organic phase was concentrated and purified by silica gel column chromatography (a gradient of 0-50% 3:1 EtOAc/EtOH in hexanes) to afford 383.2 (1.45 g, 3.17 mmol, 43% yield) as an off-white solid. LCMS-ESI (POS.) m/z: 457.9 (M+H)$^+$.

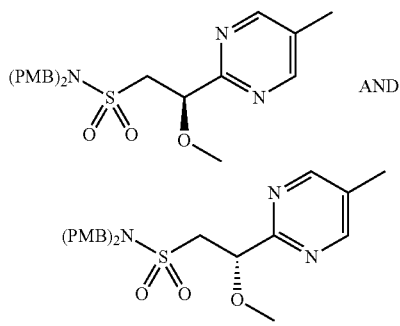

383.3

(R)-2-methoxy-N,N-bis(4-methoxybenzyl)-2-(5-methylpyrimidin-2-yl)ethanesulfonamide and (S)-2-methoxy-N,N-bis(4-methoxybenzyl)-2-(5-methylpyrimidin-2-yl)ethanesulfonamide, Example 383.3

A 250-mL round-bottomed flask was charged with 383.2 (1.44 g, 3.15 mmol) and methyltetrahydrofuran (40 mL) to give a light yellow suspension. The mixture was cooled in a dryice-acetone bath. When the internal temperature reached −71° C., KHMDS (1.0 M in THF, 3.46 mL, 3.46 mmol) was added slowly keeping the internal temperature below −69° C. over 8 min. The mixture was stirred in the cold bath allowing to warm up to −65° C. Methyl trifluoromethanesulfonate (Matrix Scientific, 0.520 mL, 4.72 mmol) was added slowly so that the internal temperature was below −64° C. over 8 min. The mixture was stirred at −67-68° C. for 20 min. The reaction was then quenched by adding 30 mL half-saturated NH$_4$Cl. The cold bath was removed and the mixture was allowed to warm to RT. EtOAc (20 mL) was added, and the layers were separated. The aqueous phase was extracted with EtOAc (20 mL). The combined organic phases were washed with water (70 mL) and saturated aqueous sodium chloride (70 mL). The organic phase was dried over sodium sulfate, filtered and concentrated in vacuo and purified by silica gel column chromatography (a gradient of 0-60% EtOAc in hexanes). The mixed fraction was repurified by silica gel column chromatography (a gradient of 0-50% acetone/hexanes) to afford 383.3 (0.225 g, 0.48 mmol, 15% yield) as a clear oil. LCMS-ESI (POS.) m/z: 471.9 (M+H)$^+$.

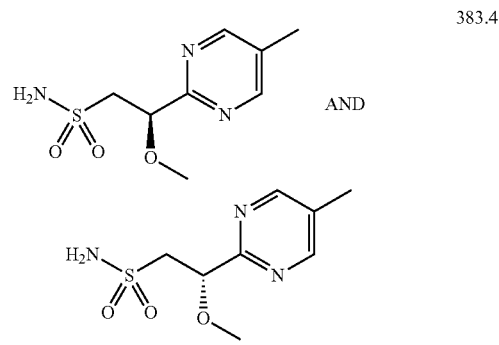

383.4

(R)-2-methoxy-2-(5-methylpyrimidin-2-yl)ethanesulfonamide and (S)-2-methoxy-2-(5-methylpyrimidin-2-yl)ethanesulfonamide, Example 383.4

A 20 mL scintillation vial was charged with 383.3 (0.224 g, 0.48 mmol), anisole (Aldrich, 0.20 mL, 1.83 mmol) and DCM (1 mL). TFA (1.0 mL, 13 mmol) was added, and the mixture was stirred at RT for 19 h. More TFA (0.5 mL) was added, and the stirring at RT continued for an additional 3.5 h. The mixture was then concentrated and purified by silica gel column chromatography (a gradient of 0-50% 3:1 EtOAc/EtOH) in DCM) to afford 383.4 (0.081 g, 0.35 mmol, 74% yield) as a clear paste. LCMS-ESI (POS.) m/z: 232.0 (M+H)$^+$.

383.0

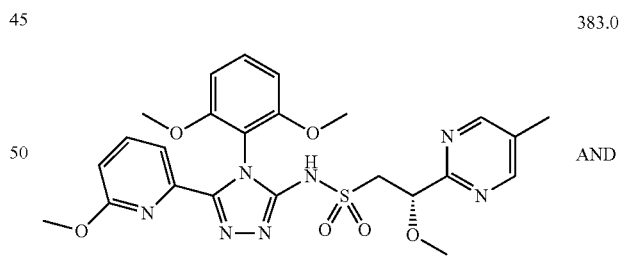

AND

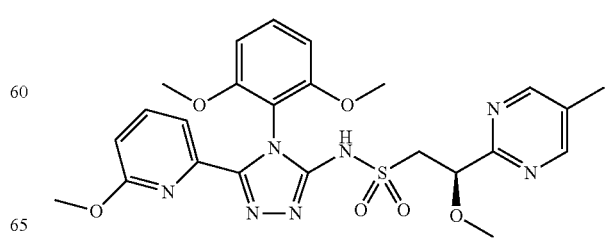

(R)—N-(4-(2,6-dimethoxyphenyl)-5-(6-methoxy-pyridin-2-yl)-4H-1,2,4-triazol-3-yl)-2-methoxy-2-(5-methylpyrimidin-2-yl)ethanesulfonamide and (S)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide, Example 383.0

The title compound was prepared following the procedure described in Example A using 383.4 (0.080 g, 0.35 mmol), 1.0 (0.0685 g, 0.351 mmol) and 6-methoxypicolinohydrazide (Adesis, Inc, 0.060 g, 0.36 mmol). This provided the title compound 383.0 (0.0723 g, 0.13 mmol, 53% yield) as a white solid. $^1$H NMR (CDCl$_3$) δ: 11.27 (br. s., 1H), 8.61 (s, 2H), 7.55-7.67 (m, 2H), 7.28-7.34 (m, 1H), 6.70 (dd, J=7.3, 1.8 Hz, 1H), 6.60 (d, J=8.5 Hz, 2H), 4.94 (t, J=6.2 Hz, 1H), 3.64-3.85 (m, 8H), 3.32 (s, 3H), 3.18 (s, 3H), 2.33 (s, 3H). LCMS-ESI (POS.) m/z: 542.0 (M+H)$^+$.

Example 384.0: Preparation of (R)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide or (S)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide

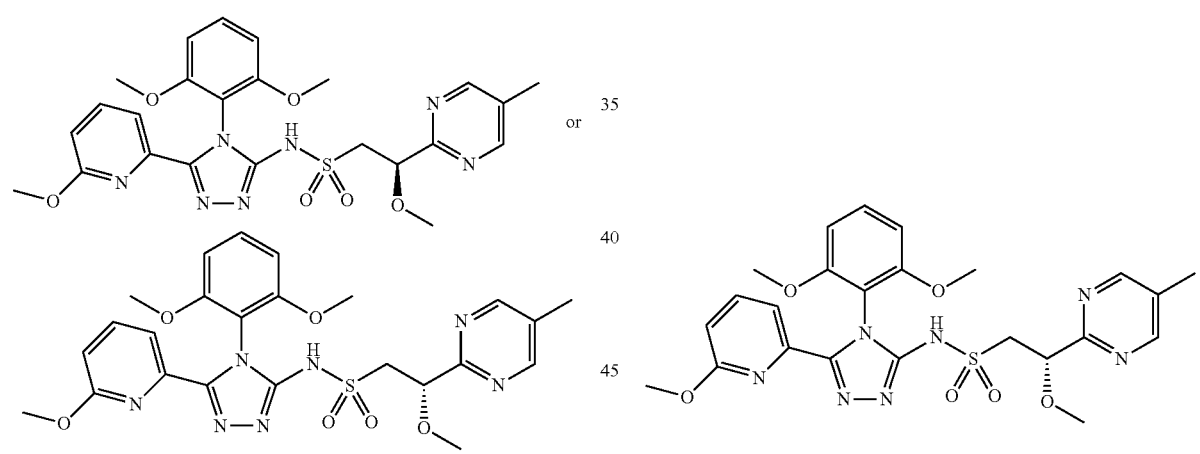

384.0 or (R)—N-(4-(2,6-dimethoxyphenyl)-5-(6-methoxy-pyridin-2-yl)-4H-1,2,4-triazol-3-yl)-2-methoxy-2-(5-methylpyrimidin-2-yl)ethanesulfonamide or (S)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide, Example 384.0

Example 383.0 was separated by SFC chromatography (Chiralpak AS-H 21.2×250 mm, 30% MeOH (20 mM NH$_3$) in CO$_2$, Flow rate at 70 mL/min) to deliver two enantiomers. Example 384.0 was the first eluting peak: $^1$H NMR (CDCl$_3$) δ: 8.61 (s, 2H), 7.56-7.65 (m, 2H), 7.31 (t, J=8.5 Hz, 1H), 6.70 (dd, J=7.5, 1.5 Hz, 1H), 6.60 (d, J=8.4 Hz, 2H), 4.94 (t, J=6.2 Hz, 1H), 3.74-3.79 (m, 1H), 3.71-3.73 (m, 6H), 3.66-3.71 (m, 1H), 3.32 (s, 3H), 3.17 (s, 3H), 2.33 (s, 3H). LCMS-ESI (POS.) m/z: 541.9 (M+H)$^+$.

Example 385.0: Preparation of (R)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide or (S)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide

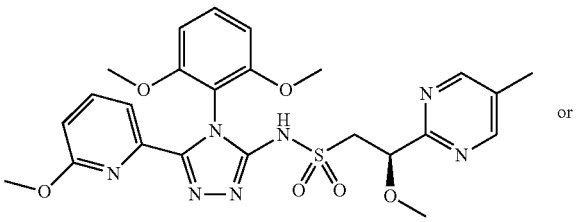

385.0 or (R)—N-(4-(2,6-dimethoxyphenyl)-5-(6-methoxy-pyridin-2-yl)-4H-1,2,4-triazol-3-yl)-2-methoxy-2-(5-methylpyrimidin-2-yl)ethanesulfonamide or (S)—N-(4-(2,6-dimethoxyphenyl)-5-(6-methoxypyridin-2-yl)-4H-1,2,4-triazol-3-yl)-2-methoxy-2-(5-methylpyrimidin-2-yl)ethanesulfonamide, Example 385.0

Example 383.0 was separated by SFC chromatography (Chiralpak AS-H 21.2×250 mm, 30% MeOH (20 mM NH$_3$) in CO$_2$, Flow rate at 70 mL/min) to deliver two enantiomers. Example 385.0 was the second eluting peak: $^1$H NMR (400 MHz, CDCl$_3$) δ: 8.61 (s, 2H), 7.65-7.57 (m, 2H), 7.31 (t, J=8.4 Hz, 1H), 6.70 (dd, J=1.5, 7.5 Hz, 1H), 6.60 (d, J=8.6 Hz, 2H), 4.94 (t, J=6.2 Hz, 1H), 3.79-3.74 (m, 1H), 3.73 (s, 3H), 3.72 (s, 3H), 3.71-3.65 (m, 1H), 3.32 (s, 3H), 3.17 (s, 3H), 2.33 (s, 3H). One proton was not observed. LCMS-ESI (POS.) m/z: 542.0 (M+H)$^+$.

Example 386.0: Preparation of (1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide and (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide 386.0

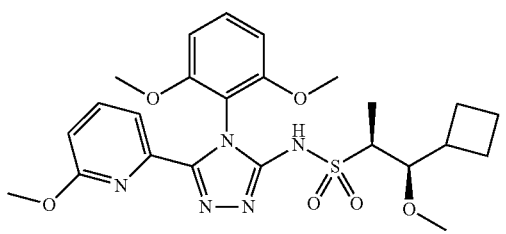

AND

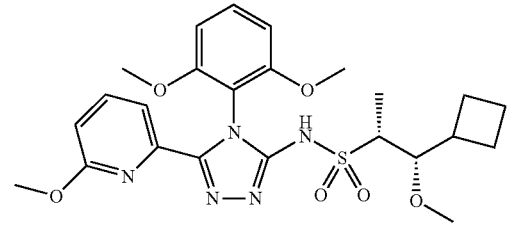

OR

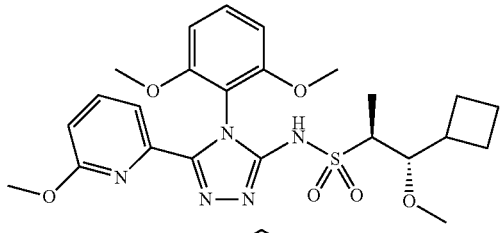

AND

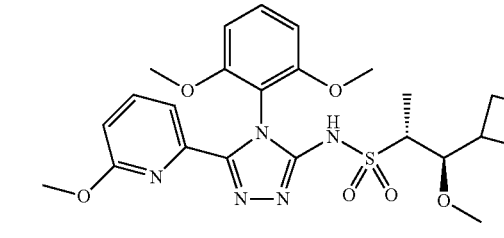

(1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide, Example 386.0

Example 386.0 was prepared following the procedure described in Example A using 1.0, 3.18 and 24.0. This delivered Example 386.0. $^1$H NMR (CDCl$_3$) δ: 10.92 (br. s., 1H), 7.56-7.66 (m, 2H), 7.33 (t, J=8.5 Hz, 1H), 6.70 (dd. J=7.2, 1.9 Hz, 1H), 6.61 (dd. J=8.5, 4.7 Hz, 2H), 3.73 (s, 3H), 3.70 (s, 3H), 3.56-3.60 (m, 1H), 3.36 (s, 3H), 3.31 (dd, J=7.1, 3.1 Hz, 1H), 3.17 (s, 3H), 2.72 (d, J=4.2 Hz, 1H), 1.88-2.14 (m, 2H), 1.65-1.83 (m, 4H), 1.22 (d, J=7.2 Hz, 3H). LCMS-ESI (POS.) m/z: 518.0 (M+H)$^+$.

Example 387.0: Preparation of (1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide 387.0

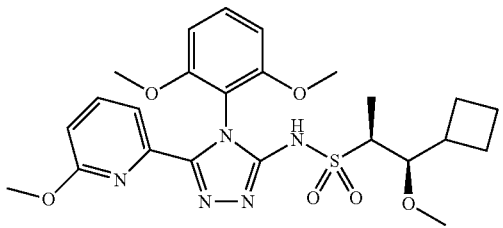

OR

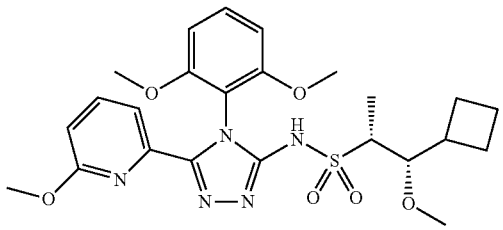

OR

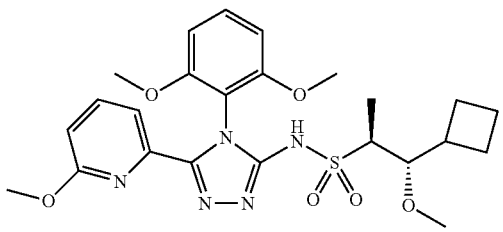

OR

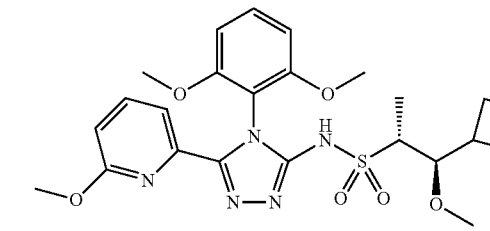

(1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide, Example 387.0

Example 386.0 was purified by chiral SFC (OX, 21 mm×15 cm, 5 mm, 40% MeOH with 20 mM NH₃ 60% carbon dioxide. F=70 mL/min) to afford the two enantiomers. The first eluting peak was assigned as Example 387.0. $^1$H NMR (400 MHz, CDCl$_3$) δ: 10.96 (br. s., 1H), 7.67-7.56 (m, 2H), 7.33 (t J=8.5 Hz, 1H), 6.70 (dd, J=2.3, 6.9 Hz, 1H), 6.65-6.56 (m, 2H), 3.73 (s, 3H), 3.70 (s, 3H), 3.61-3.54 (m, 1H), 3.36 (s, 3H), 3.30 (dd, J=3.1, 7.1 Hz, 1H), 3.17 (s, 3H), 2.81-2.65 (m, 1H), 2.15-1.87 (m, 2H), 1.85-1.65 (m, 4H), 1.22 (d, J=7.2 Hz, 3H). LCMS-ESI (POS.) m/z: 518.0 (M+H)$^+$.

Example 388.0: Preparation of (1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide

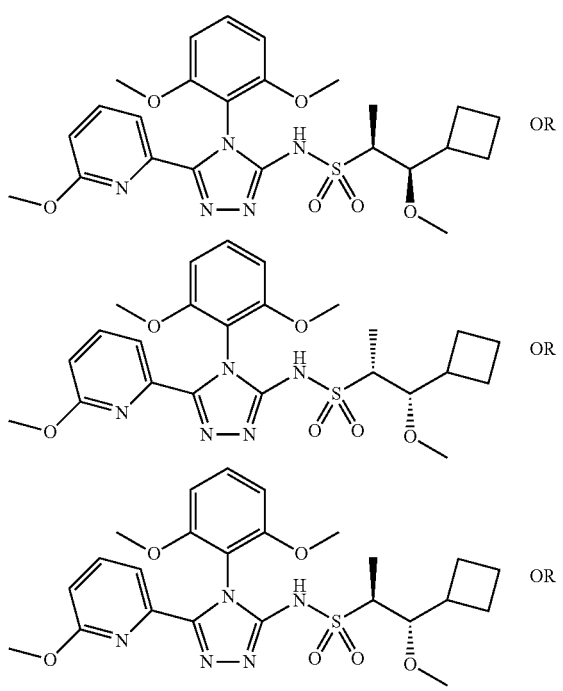

388.0

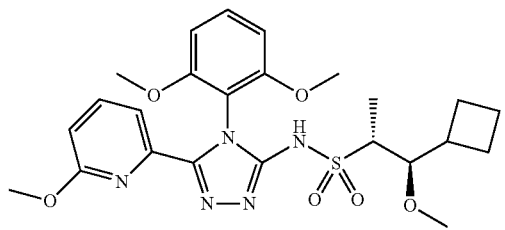

(1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide, Example 388.0

Example 386.0 was purified by chiral SFC (OX, 21 mm×15 cm, 5 mm, 40% MeOH with 20 mM NH₃ 60% carbon dioxide. F=70 mL/min) to afford the two enantiomers. The second eluting peak was Example 388.0. $^1$H NMR (300 MHz, CDCl$_3$) δ: 10.96 (br. s., 1H), 7.67-7.56 (m, 2H), 7.33 (t, J=8.5 Hz, 1H), 6.70 (dd. J=2.2, 6.9 Hz, 1H), 6.61 (dd. J=4.6, 8.6 Hz, 2H), 3.73 (s, 3H), 3.70 (s, 3H), 3.57 (t, J=3.7 Hz, 1H), 3.36 (s, 3H), 3.30 (dd. J=3.1, 7.2 Hz, 1H), 3.17 (s, 3H), 2.82-2.64 (m, 1H), 2.14-1.99 (m, 1H), 1.98-1.86 (m, 1H), 1.83-1.64 (m, 4H), 1.22 (d, J=7.2 Hz, 3H). LCMS-ESI (POS.) m/z: 518.0 (M+H)$^+$.

Example 389.0: Preparation of (1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1R,2R)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide 389.0

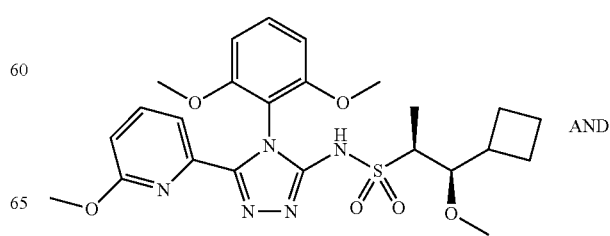

-continued

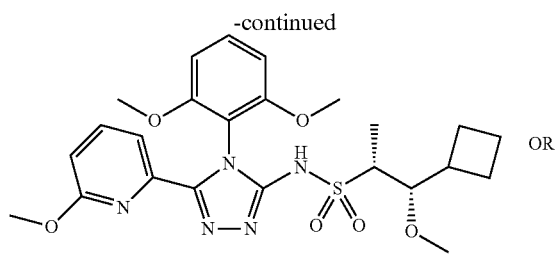

OR

AND

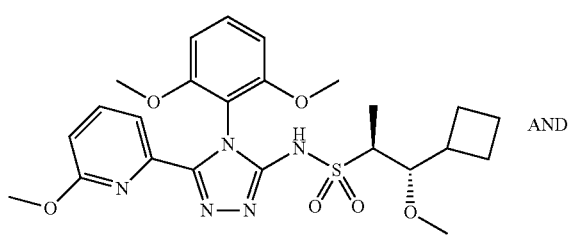

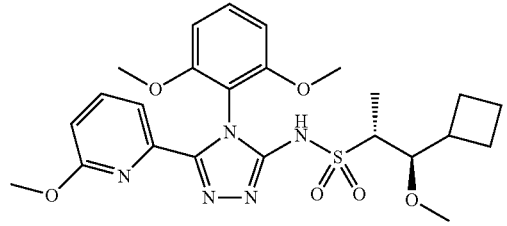

(1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide and (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide, Example 389.0

The title compound 389.0 was prepared in an analogous fashion to that of Example 386.0 starting from 24.02. $^1$H NMR (300 MHz, CDCl$_3$) δ: 10.99 (br. s., 1H), 7.66-7.56 (m, 2H), 7.34-7.28 (m, 1H), 6.70 (dd, J=2.0, 7.1 Hz, 1H), 6.60 (d, J=8.5 Hz, 2H), 3.84 (dd, J=1.5, 8.8 Hz, 1H), 3.72 (s, 3H), 3.71 (s, 3H), 3.33 (s, 3H), 3.17 (s, 3H), 2.93-2.83 (m, 1H), 2.47-2.32 (m, 1H), 2.16-2.02 (m, 1H), 2.00-1.69 (m, 5H), 1.27 (d, J=7.0 Hz, 3H). LCMS-ESI (POS.) m/z: 518.0 (M+H)$^+$.

Example 390.0: Preparation of (1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide 390.0

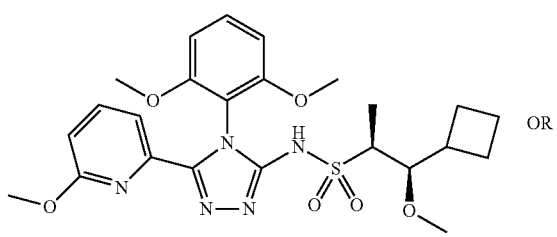
OR

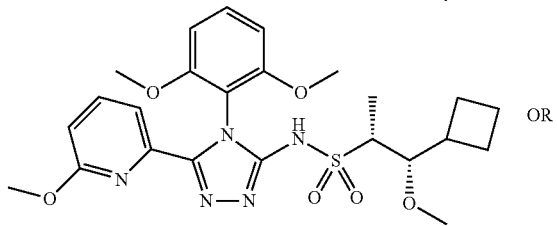
OR

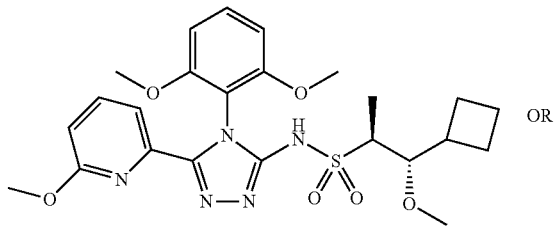
OR

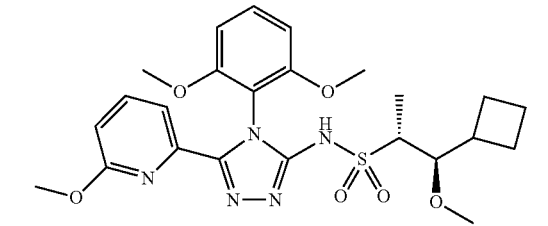
OR

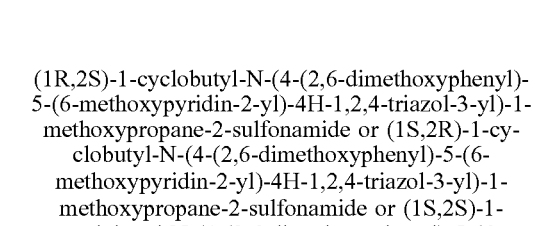

(1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide, Example 390.0

Example 389.0 was purified by chiral SFC (OX, 21 mm×15 cm, 5 mm, 50% MeOH with 20 mM NH$_3$ 50% carbon dioxide. F=70 mL/min) to afford two enantiomers, the first eluting peak is Example 390.0. $^1$H NMR (300 MHz, CDCl$_3$) δ: 11.01 (br. s., 1H), 7.65-7.55 (m, 2H), 7.34-7.27 (m, 1H), 6.70 (dd, J=2.2, 6.9 Hz, 1H), 6.59 (d, J=8.5 Hz, 2H), 3.83 (dd, J=1.5, 8.8 Hz, 1H), 3.72 (s, 3H), 3.71 (s, 3H), 3.33 (s, 3H), 3.17 (s, 3H), 2.94-2.82 (m, 1H), 2.48-2.31 (m, 1H), 2.17-2.02 (m, 1H), 2.00-1.67 (m, 5H), 1.27 (d, J=7.0 Hz, 3H). LCMS-ESI (POS.) m/z: 518.0 (M+H)$^+$.

Example 391.0: Preparation of (1R,2S)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-(trimethoxyphenyl)-5-(6-methoxypyridin-2-yl)-4H-1,2,4-triazol-3-yl)-1-methoxypropane-2-sulfonamide 391.0

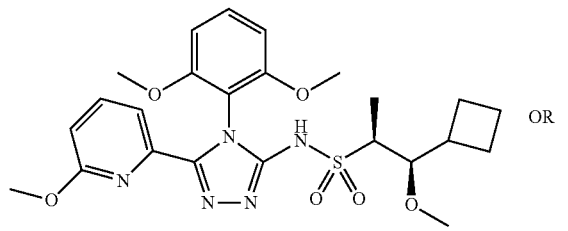

OR

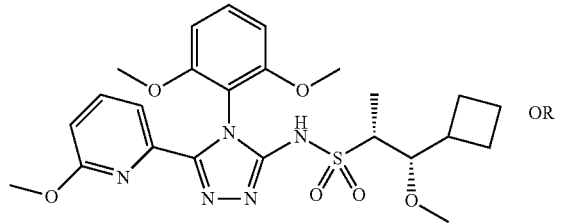

OR


OR

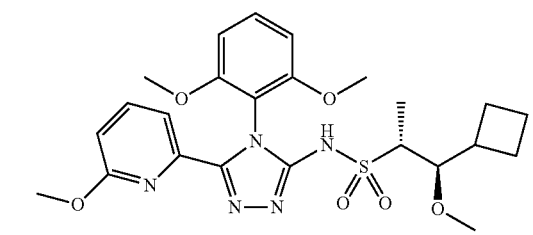

(1R,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1S,2S)-1-cyclobutyl-N-(4-(2,6-dimethoxyphenyl)-5-(6-methoxypyridin-2-yl)-4H-1,2,4-triazol-3-yl)-1-methoxypropane-2-sulfonamide or (1R,2R)-1-cyclobutyl-N-(4-(2,6-dimethoxyphenyl)-5-(6-methoxypyridin-2-yl)-4H-1,2,4-triazol-3-yl)-1-methoxypropane-2-sulfonamide, Example 391.0

Example 389.0 was purified by chiral SFC (OX, 21 mm×15 cm, 5 mm, 50% MeOH with 20 mM NH$_3$ 50% carbon dioxide. F=70 mL/min) to afford two enantiomers, the second eluting peak is Example 391.0. $^1$H NMR (300 MHz, CDCl$_3$) δ: 11.54-10.52 (m, 1H), 7.66-7.56 (m, 2H), 7.34-7.27 (m, 1H), 6.70 (dd. J=2.2, 7.0 Hz, 1H), 6.59 (d, J=8.5 Hz, 2H), 3.83 (dd. J=1.5, 8.8 Hz, 1H), 3.72 (s, 3H), 3.71 (s, 3H), 3.33 (s, 3H), 3.17 (s, 3H), 2.88 (dq, J=1.5, 7.1 Hz, 1H), 2.48-2.30 (m, 1H), 2.16-2.01 (m, 1H), 2.00-1.70 (m, 5H), 1.27 (d, J=7.2 Hz, 3H). LCMS-ESI (POS.) m/z: 518.0 (M+H)$^+$.

Example 392.0: Preparation of (S)—N-(4-(2,6-dimethoxyphenyl)-5-(5-methylpyridin-3-yl)-4H-1,2,4-triazol-3-yl)-2-(5-fluoropyrimidin-2-yl)ethane-1-sulfamide 392.0

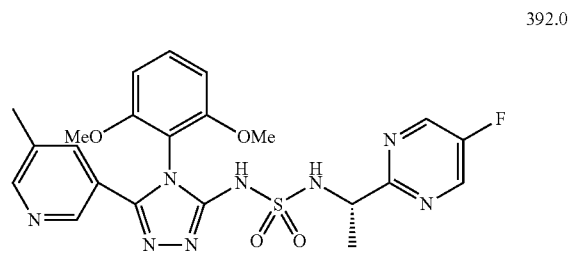 [SMILES: COc1cccc(OC)c1-n1c(NS(=O)(=O)N[C@@H](C)c2ncc(F)cn2)nnc1-c1cncc(C)c1]

(S)—N-(4-(2,6-dimethoxyphenyl)-5-(5-methylpyridin-3-yl)-4H-1,2,4-triazol-3-yl)-2-(5-fluoropyrimidin-2-yl)ethane-1-sulfamide, Example 392.0

Following the procedure in Example B, 17.0 (75 mg, 0.34 mmol) and 2.0 (105 mg, 0.28 mmol) were coupled. After purification by silica gel chromatography, an additional purification by achiral supercritical fluid chromatography was performed to provide 392.0 (1.3 mg, 1% yield) as a white solid. $^1$H NMR (500 MHz, CD$_3$OD) δ: 8.66 (s, 2H), 8.41 (s, 1H), 8.27 (s, 1H), 7.65 (s, 1H), 7.46 (t, J=8.5 Hz, 1H), 6.75 (dd, J=8.2, 6.1 Hz, 2H), 4.67 (q, J=7.0 Hz, 1H), 3.77 (s, 3H), 3.72 (s, 3H), 2.29 (s, 3H), 1.47 (d, J=7.0 Hz, 3H). LCMS-ESI (POS.) m/z: 515.2 (M+H)$^+$.

Example 393.0: Preparation of (1S,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide 393.1

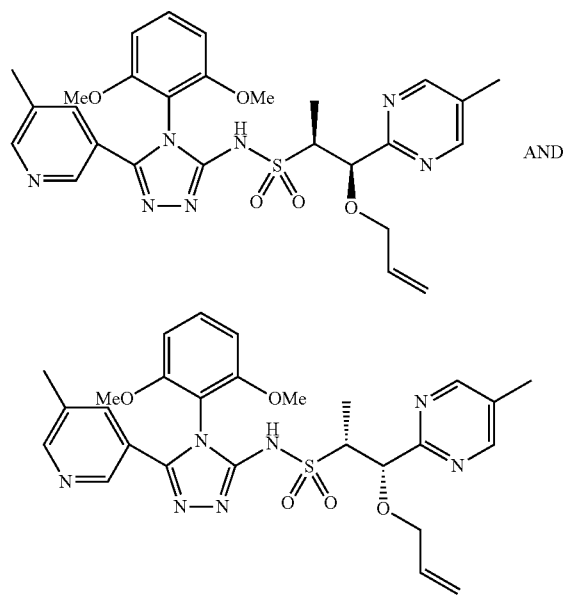

(1S,2R)-1-(allyloxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1R,2S)-1-(allyloxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide, Example 393.1

Following the procedure in Example B, 25.0 (370 mg, 1.36 mmol) and 2.0 (715 mg, 1.91 mmol) were coupled to provide 393.1 (553 mg, 72% yield) as a yellow solid. LCMS-ESI (POS.) m/z: 566.0 (M+H)$^+$.

393.2

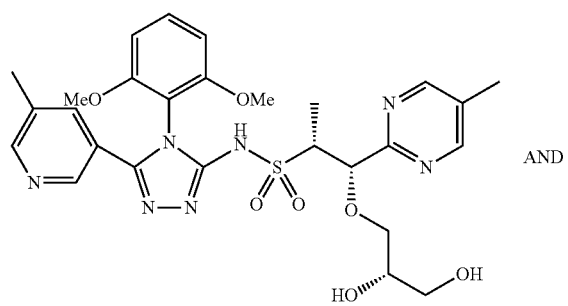

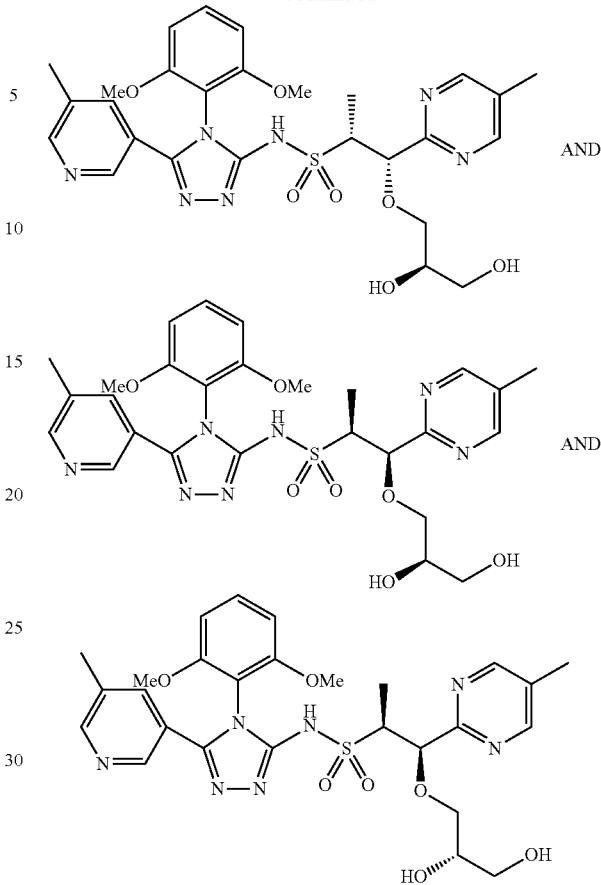

(1S,2R)-1-((S)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1S,2R)-1-((R)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1R,2S)-1-((R)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1R,2S)-1-((S)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide, Example 393.2

To a solution of 393.1 (530 mg, 0.94 mmol) in a mixture of acetone (11.4 mL) and water (4 mL) was added osmium tetroxide (4 wt. % solution in water (286 µL, 0.05 mmol)) and 4-methylmorpholine-N-oxide (384 mg, 3.28 mmol). The resulting orange slurry was stirred at RT for 23.5 h and then was partially concentrated on a rotary evaporator to remove the acetone. The aqueous residue was diluted with water and extracted with DCM (4×). The combined organic layers were dried over anhydrous sodium sulfate and concentrated in vacuo. The residue was purified by silica gel chromatography (eluent: 0-5% MeOH in DCM over a 35 min period) to provide 393.2 (451 mg, 81% yield) as a light tan solid. LCMS-ESI (POS.) m/z: 599.9 (M+H)$^+$.

393.0

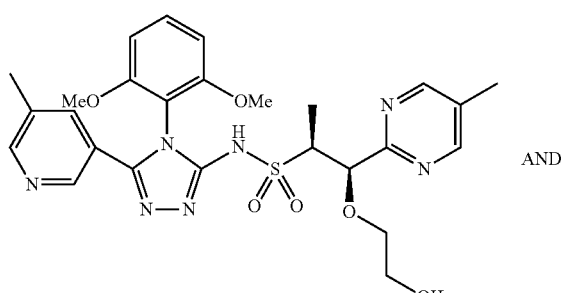

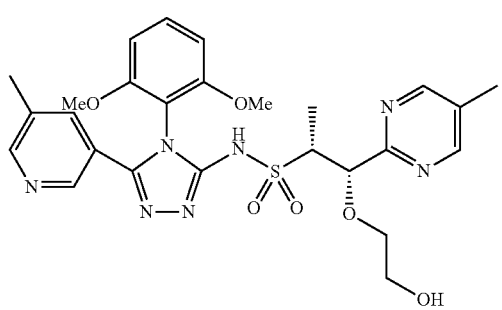

(1S,2R)—N-(4-(2,6-dimethoxyphenyl)-5-(5-methyl-pyridin-3-yl)-4H-1,2,4-triazol-3-yl)-1-(2-hydroxy-ethoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide, Example 393.0

To a solution of 393.2 (540 mg, 0.90 mmol) in a mixture of THF (12 mL) and water (4 mL) was added sodium periodate (539 mg, 2.52 mmol). The resulting yellow slurry was stirred at RT for 1.5 h and then was filtered, rinsing the filtrate with DCM. The mixture was partially concentrated on a rotary evaporator to remove the organic solvents, then was diluted with water and extracted with DCM (3×). The combined organic layers were dried over anhydrous sodium sulfate and concentrated in vacuo to afford the aldehyde as a tan solid. To an ice-cooled solution of the aldehyde thus obtained in MeOH (15 mL) was added sodium borohydride (153 mg, 4.05 mmol). Gas evolution was observed. The resulting yellow solution was stirred at 0° C. for 3 h and then additional sodium borohydride (306 mg, 9.10 mmol) was added. After stirring for another 1.3 h at 0° C., the reaction was quenched with 1 N HCl solution (20 mL). The mixture was partially concentrated on the rotary evaporator to remove the MeOH, then was extracted with DCM (3×). The combined organic layers were dried over anhydrous sodium sulfate and concentrated in vacuo. The residue was purified by silica gel chromatography (eluent: 0-15% MeOH in DCM over a 35 min period) to provide the racemic alcohol product 393.0 (220 mg, 43% yield) as a white solid.

Example 394.0: Preparation of (1S,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide 394.0

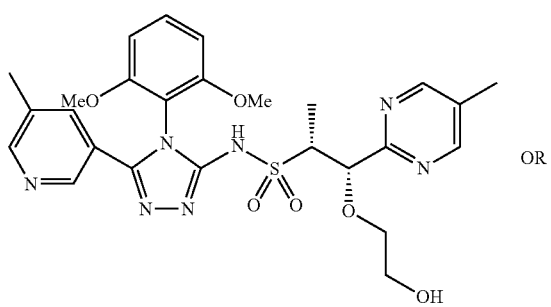

OR

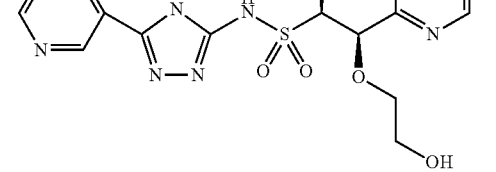

(1S,2R)—N-(4-(2,6-dimethoxyphenyl)-5-(5-methyl-pyridin-3-yl)-4H-1,2,4-triazol-3-yl)-1-(2-hydroxy-ethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide, Example 394.0

Chiral supercritical fluid chromatography purification of 393.0 was undertaken to separate the two enantiomeric products. Chiralpak ASH, 250×30 mm, 5 uM, 30% MeOH at 120 mL/min, 274-nm. The first eluting peak was Example 394.0 (108.5 mg): $^1$H NMR (500 MHz, CDCl$_3$) δ: 11.22 (br. s., 1H), 8.58 (s, 2H), 8.45 (s, 1H), 8.34 (s, 1H), 7.68 (s, 1H), 7.39 (t, J=8.5 Hz, 1H), 6.61 (d, J=8.6 Hz, 2H), 5.32 (d, J=1.4 Hz, 1H), 3.85-3.95 (in. 1H), 3.74-3.83 (m, 1H), 3.75 (s, 3H), 3.73 (s, 3H), 3.53-3.68 (m, 3H), 2.33 (s, 3H), 2.32 (s, 3H), 1.28 (d, J=7.0 Hz, 3H). LCMS-ESI (POS.) m/z: 570.0 (M+H)$^+$.

Example 395.0: Preparation of (1S,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide

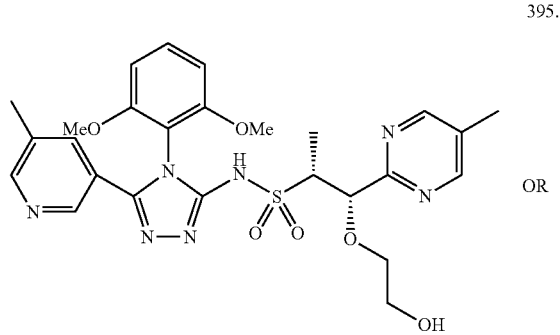

395.0

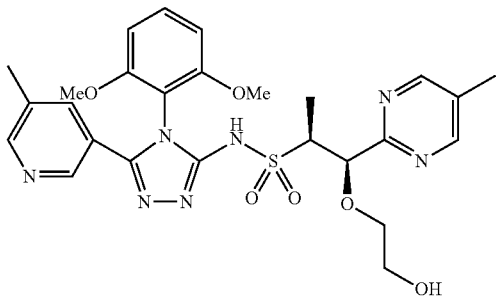

(1S,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide, Example 395.0

Chiral supercritical fluid chromatography purification of 393.0 was undertaken to separate the two enantiomeric products as described in Example 394.0. The second eluting peak was Example 395.0 (111 mg). $^1$H NMR (500 MHz, CDCl$_3$) δ: 11.24 (br. s., 1H), 8.58 (s, 2H), 8.47 (s, 1H), 8.35 (s, 1H), 7.77 (s, 1H), 7.40 (t, J=8.5 Hz, 1H), 6.62 (d, J=8.6 Hz, 2H), 6.57-6.66 (m, 2H), 5.32 (s, 1H), 3.86-3.96 (m, 1H), 3.74-3.83 (m, 1H), 3.76 (s, 3H), 3.74 (s, 3H), 3.55-3.68 (m, 3H), 2.35 (s, 3H), 2.33 (s, 3H), 1.28 (d, J=7.0 Hz, 3H). LCMS-ESI (POS.) m/z: 570.0 (M+H)$^+$.

Example 396.0: Preparation of (1S,2R)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide

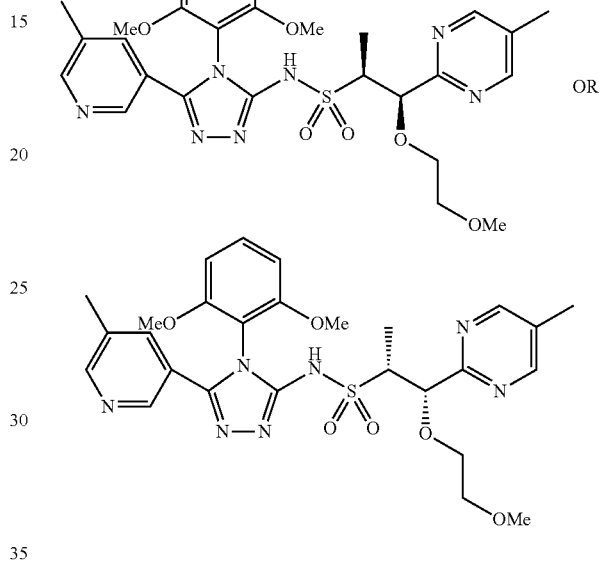

396.0

(1S,2R)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide, Example 396.0

To a −78° C. solution of 394.0 (59 mg, 0.10 mmol) in THF (3.2 mL) was added potassium bis(trimethylsilyl)amide (1.0 M solution in THF (218 μL, 0.22 mmol)) slowly via syringe. After stirring for 15 min at −78° C., the reaction was warmed to −35° C. and stirred for an additional 5 min. The reaction was then recooled to −78° C. and methyl trifluoromethanesulfonate (12 μL, 0.11 mmol) was added slowly via syringe. The resulting yellow solution was stirred at −78° C. for 25 min and then additional methyl trifluoromethanesulfonate (6 μL, 0.05 mmol) was added. After an additional 15 min at −78° C., the reaction was quenched with a 2.5:1 mixture of saturated aqueous ammonium chloride and water (7 mL) and was extracted with DCM (4×). The combined organic layers were dried over anhydrous sodium sulfate and concentrated. The residue was purified by silica gel chromatography (eluent: 0-13% MeOH in DCM over a 45 min period) to provide 396.0 (23.7 mg, 39% yield) as a white solid. $^1$H NMR (500 MHz, CDCl$_3$) δ: 11.71 (br. s., 1H), 8.60 (s, 2H), 8.46 (s, 1H), 8.34 (s, 1H), 7.79 (br. s., 1H), 7.40 (t, J=8.5 Hz, 1H), 6.62 (d, J=9.4 Hz, 2H), 5.13 (d, J=4.7 Hz, 1H), 3.75-3.86 (m, 2H), 3.79 (s, 3H), 3.78 (s, 3H), 3.53-3.65 (m, 3H), 3.39 (s, 3H), 2.35 (s, 3H), 2.33 (s, 3H), 1.40 (d, J=7.2 Hz, 3H). LCMS-ESI (POS.) m/z: 584.0 (M+H)$^+$.

Example 397.0: Preparation of (1S,2R)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide

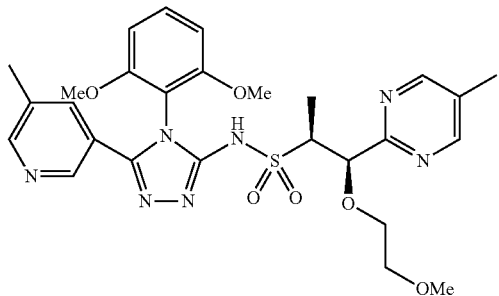

397.0

OR

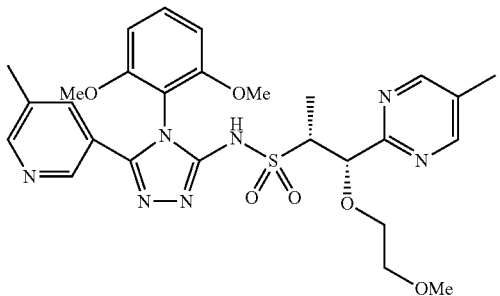

(1R,2S)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide, Example 397.0

To a −78° C. solution of 395.0 (40.9 mg, 0.07 mmol) in THF (3 mL) was added potassium bis(trimethylsilyl)amide (1 M solution in THF (151 µL, 0.15 mmol)) slowly via syringe. After stirring for 40 min at −78° C., the reaction was warmed to −35° C. and stirred for an additional 7 min. The reaction was then recooled to −78° C. and methyl trifluoromethanesulfonate (9 µL, 0.08 mmol) was added slowly via syringe. The resulting yellow solution was stirred at −78° C. for 2.25 h and then additional methyl trifluoromethanesulfonate (3 µL, 0.03 mmol) was added. After an additional 60 min at −78° C., the reaction was quenched with a 2.5:1 mixture of saturated aqueous ammonium chloride and water (7 mL) and was extracted with DCM (4×). The combined organic layers were dried over anhydrous sodium sulfate and concentrated in vacuo. The residue was purified by silica gel chromatography (eluent: 0-8% MeOH in DCM over a 45 min period) to provide initial product. The initial product was then further purified by reverse phase preparative HPLC (Luna 5 µM C18 column, eluent: 20-60% ACN in water over a 40 min period where both solvents contain OA % TFA) to provide 397.0 (16.5 mg, 39% yield) as a white solid. $^1$H NMR (500 MHz, CDCl$_3$) δ: 8.72 (s, 2H), 8.63 (s, 1H), 8.43 (s, 1H), 8.17 (s, 1H), 7.45 (t, J=8.5 Hz, 1H), 6.67 (dd, J=8.6, 3.9 Hz, 2H), 5.19 (d, J=4.7 Hz, 1H), 3.79 (s, 3H), 3.78 (s, 3H), 3.68-3.75 (m, 1H), 3.48-3.63 (m, 3H), 3.36 (s, 3H), 2.49 (s, 3H), 2.39 (s, 3H), 1.37 (d, J=7.0 Hz, 3H). LCMS-ESI (POS.) m/z: 584.0 (M+H)$^+$.

Example 398.0: Preparation of (1R,2S)—N-(4-(2,6-dimethoxyphenyl)-5-(5-methylpyridin-3-yl)-4H-1,2,4-triazol-3-yl)-1-(2-methoxyethoxy)-N-methyl-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(2-methoxyethoxy)-N-methyl-1-(5-methylpyrimidin-2-yl)propane-2-sulfonamide or (1R,2S,Z)—N-(4-(2,6-dimethoxyphenyl)-1-methyl-3-(5-methylpyridin-3-yl)-1H-1,2,4-triazol-5(4H)-ylidene)-1-(2-methoxyethoxy)-1-(5-methylpyrimidin-2-yl)propane-2-sulfonamide or (1S,2R,Z)—N-(4-(2,6-dimethoxyphenyl)-1-methyl-3-(5-methylpyridin-3-yl)-1H-1,2,4-triazol-5(4H)-ylidene)-1-(2-methoxyethoxy)-1-(5-methylpyrimidin-2-yl)propane-2-sulfonamide 398.0

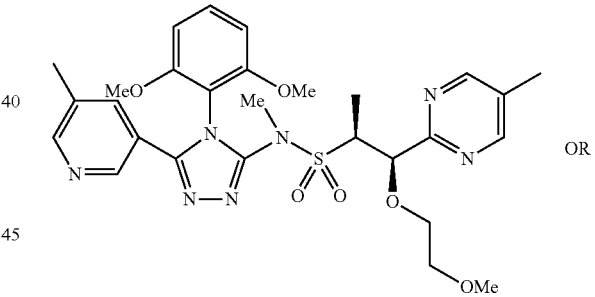

OR

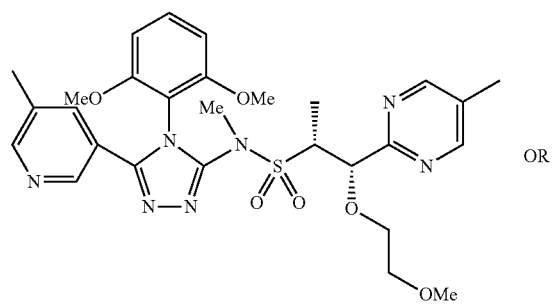

OR

-continued

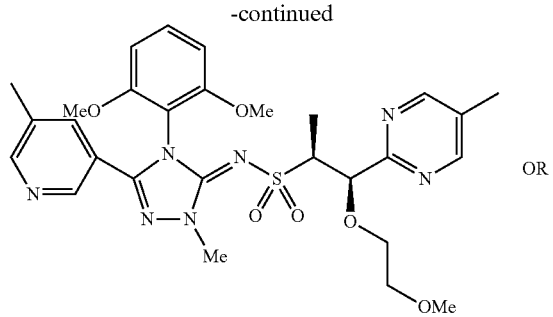

OR

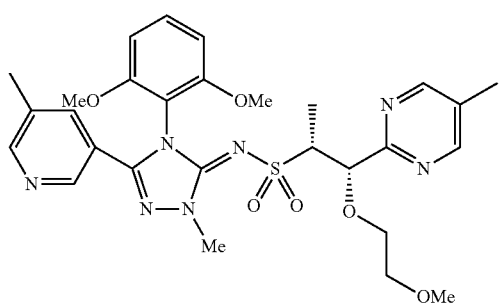

(1R,2S)—N-(4-(2,6-dimethoxyphenyl)-5-(5-methyl-pyridin-3-yl)-4H-1,2,4-triazol-3-yl)-1-(2-methoxyethoxy)-N-methyl-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(2-methoxyethoxy)-N-methyl-1-(5-methylpyrimidin-2-yl)propane-2-sulfonamide or (1R,2S,Z)—N-(4-(2,6-(trimethoxyphenyl)-1-methyl-3-(5-methylpyridin-3-yl)-1H-1,2,4-triazol-5(4H)-ylidene)-1-(2-methoxyethoxy)-1-(5-methylpyrimidin-2-yl)propane-2-sulfonamide or (1S,2R,Z)—N-(4-(2,6-dimethoxyphenyl)-1-methyl-3-(5-methylpyridin-3-yl)-1H-1,2,4-triazol-5(4H)-ylidene)-1-(2-methoxyethoxy)-1-(5-methylpyrimidin-2-yl)propane-2-sulfonamide, Example 398.0

Further elution under the conditions described in Example 397.0 provided a by-product 398.0 (12.5 mg, 29% yield) as a white solid. $^1$H NMR (500 MHz, CDCl$_3$) δ: 8.74 (s, 2H), 8.63 (s, 1H), 8.45 (s, 1H), 8.13 (s, 1H), 7.44 (t, J=8.5 Hz, 1H), 6.64 (dd. J=15.1, 8.6 Hz, 2H), 4.90 (d, J=6.7 Hz, 1H), 4.00 (s, 3H), 3.82 (s, 3H), 3.74 (s, 3H), 3.57-3.70 (m, 2H), 3.41-3.57 (m, 3H), 3.27 (s, 3H), 2.48 (s, 3H), 2.38 (s, 3H), 1.30 (d, J=6.8 Hz, 3H). LCMS-ESI (POS.) m/z: 598.0 (M+H)$^+$.

Example 399.0: Preparation of (1S,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide and (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide 399.0

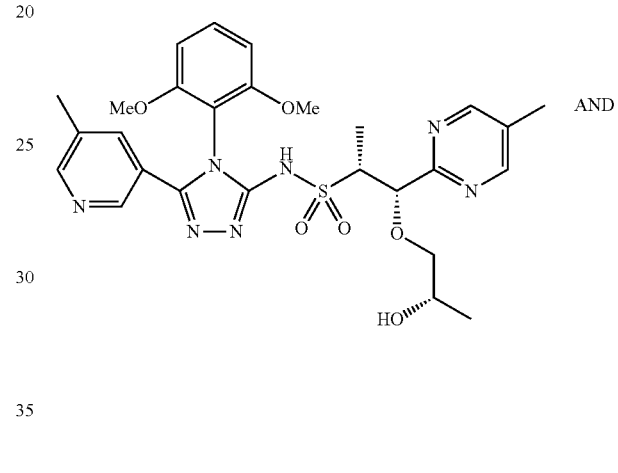

AND

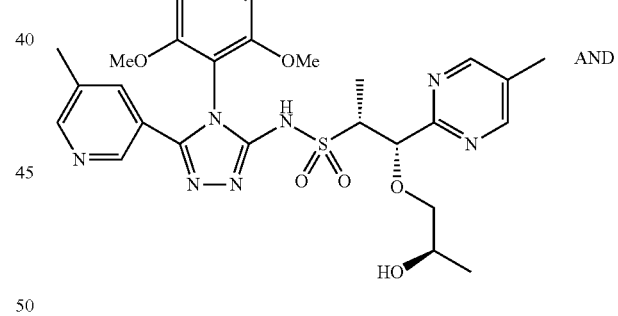

AND

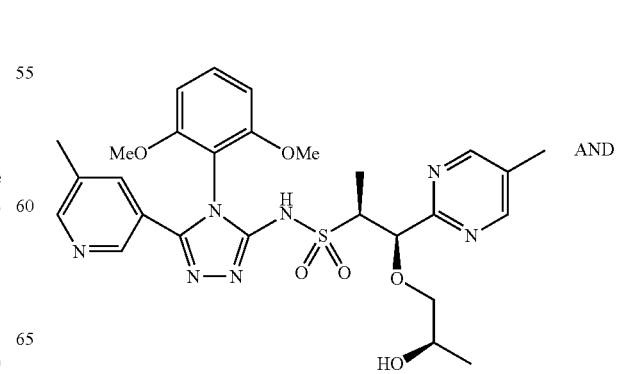

AND

-continued

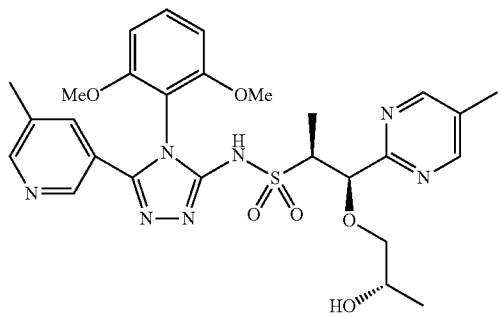

(1S,2R)—N-(4-(2,6-dimethoxyphenyl)-5-(5-methyl-pyridin-3-yl)-4H-1,2,4-triazol-3-yl)-1-((S)-2-hydroxypropoxy)-1-(5-methylpyrimidin-2-yl)propane-2-sulfonamide and (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide and (1R,2S)—N-(4-(2,6-dimethoxyphenyl)-5-(5-methyl-pyridin-3-yl)-4H-1,2,4-triazol-3-yl)-1-((R)-2-hydroxypropoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide, Example 399.0

To a solution of 393.2 (685 mg, 1.14 mmol) in a mixture of THF (15 mL) and water (5 mL) was added sodium periodate (684 mg, 3.20 mmol). The resulting light yellow slurry was stirred at RT for 60 min and then was filtered, rinsing the filtrate with DCM. The mixture was partially concentrated on a rotary evaporator to remove the organic solvents, then was diluted with water and extracted with DCM (4×). The combined organic layers were dried over anhydrous sodium sulfate and concentrated to afford the aldehyde as a white solid. To a −78° C. solution of the aldehyde in THF (40 mL) was added methylmagnesium bromide (1.4 M solution in a mixture of 3:1 toluene/THF (3.26 mL, 4.6 mmol)). The resulting yellow solution was stirred at −78° C. for 1 h and then was warmed to 0° C. and stirred for an additional 1.75 h. After this time period, the reaction was warmed to RT and stirred for another 18 h. The reaction was quenched with saturated aqueous ammonium chloride (50 mL), and then was extracted with chloroform (4×). The combined organic layers were dried over anhydrous sodium sulfate and concentrated. The residue was purified by silica gel chromatography (eluent: 0-12% MeOH in DCM over a 40 min period) to provide the alcohol product as a diastereomeric mixture 399.0, (157 mg, 24% yield).

Example 400.0: Preparation of (1S,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methyl-pyridin-3-yl)-4H-1,2,4-triazol-3-yl)-1-((S)-2-hydroxypropoxy)-1-(5-methylpyrimidin-2-yl)propane-2-sulfonamide

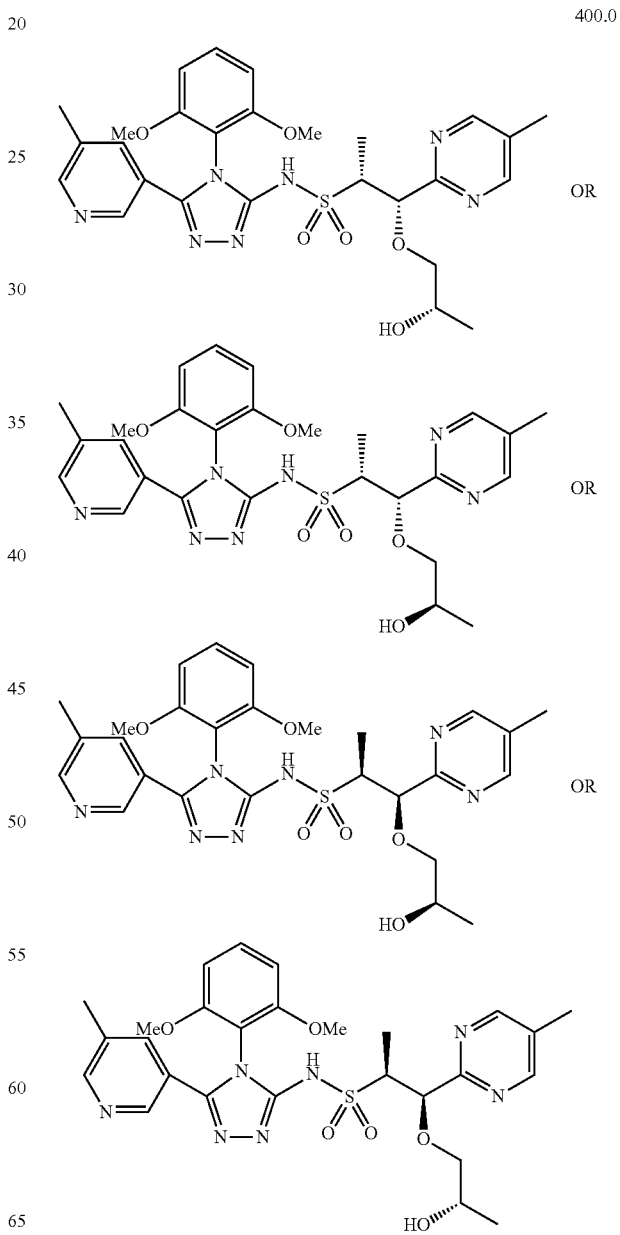

400.0

(1S,2R)—N-(4-(2,6-dimethoxyphenyl)-5-(5-methyl-pyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methyl-pyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide, Example 400.0

A chiral supercritical fluid chromatography purification of 399.0 was performed to separate all four product isomers. The sample was purified via preparative SFC. Multiple purifications were required to separate all the isomers as described. The material was purified by chiral supercritical fluid chromatography purification of 399.0 on AD-H at 213 bar to give three eluting peaks. The third eluting peak was repurified by chiral supercritical fluid chromatography purification on an-OX-H column at 186 bar to resolve the final two stereoisomers. The first eluting peak is Example 400.0 (6.3 mg). $^1$H NMR (500 MHz, CDCl$_3$) δ: 8.57 (s, 2H), 8.44 (d, J=1.4 Hz, 1H), 8.33 (d, J=1.8 Hz, 1H), 7.63 (s, 1H), 7.37 (t, J=8.5 Hz, 1H), 6.60 (d, J=8.6 Hz, 2H), 5.32 (s, 1H), 3.87-4.03 (m, 2H), 3.73 (s, 3H), 3.72 (s, 3H), 3.65 (dd, J=10.6, 2.0 Hz, 1H), 3.24 (t, J=10.0 Hz, 1H), 2.32 (s, 3H), 2.30 (s, 3H), 1.27 (d, J=6.8 Hz, 3H), 1.00 (d, J=6.5 Hz, 3H). LCMS-ESI (POS.) m/z: 584.2 (M+H)$^+$.

Example 401.0: Preparation of (1S,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide 401.0

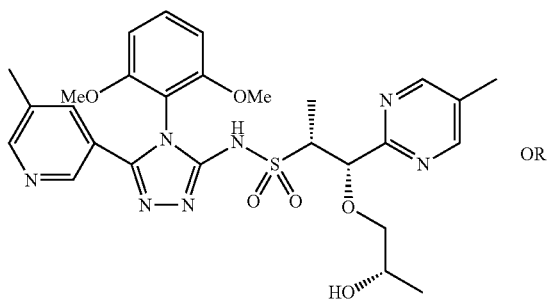

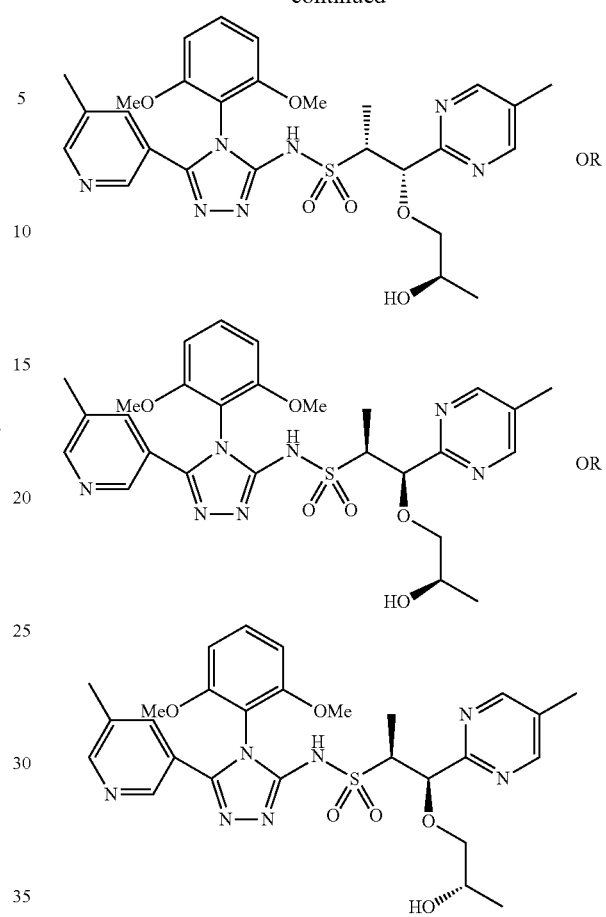

(1S,2R)—N-(4-(2,6-dimethoxyphenyl)-5-(5-methyl-pyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methyl-pyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide, Example 401.0

A chiral supercritical fluid chromatography purification of 399.0 was performed to separate all four product enantiomers as described in Example 400.0. The second eluting peak is Example 401.0 (29 mg). $^1$H NMR (500 MHz, CDCl$_3$) δ: 11.32 (br. s., 1H), 8.58 (s, 2H), 8.46 (br. s., 1H), 8.34 (br. s., 1H), 7.74 (br. s., 1H), 7.40 (t, J=8.5 Hz, 1H), 6.62 (dd, J=8.6 Hz, 1.0 Hz, 2H), 5.27 (d, J=1.8 Hz, 1H), 3.74-3.94 (m, 3H), 3.75 (s, 3H), 3.74 (s, 3H), 3.11 (t, J=9.8 Hz, 1H), 2.34 (s, 3H), 2.33 (s, 3H), 1.29 (d, J=7.0 Hz, 3H), 1.02 (d, J=6.3 Hz, 3H). LCMS-ESI (POS.) m/z: 584.2 (M+H)$^+$.

Example 402.0: Preparation of (1S,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide (1S,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide, Example 402.0

A chiral supercritical fluid chromatography purification of 399.0 was performed to separate all four product enantiomers as described in Example 400.0. The third eluting peak is Example 402.0 (5.1 mg). $^1$H NMR (500 MHz, CDCl$_3$) δ: 8.57 (s, 2H), 8.43 (s, 1H), 8.33 (d, J=1.8 Hz, 1H), 7.64 (s, 1H), 7.37 (t, J=8.5 Hz, 1H), 6.60 (d, J=8.6 Hz, 2H), 5.30 (s, 1H), 3.88-4.05 (m, 2H), 3.73 (s, 3H), 3.72 (s, 3H), 3.65 (dd. J=10.6, 2.2 Hz, 1H), 3.24 (t, J=9.9 Hz, 1H), 2.32 (s, 3H), 2.30 (s, 3H), 1.27 (d, J=6.8 Hz, 3H), 1.01 (d, J=6.5 Hz, 3H). LCMS-ESI (POS.) m/z: 584.2 (M+H)$^+$.

Example 403.0: Preparation of (1S,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide

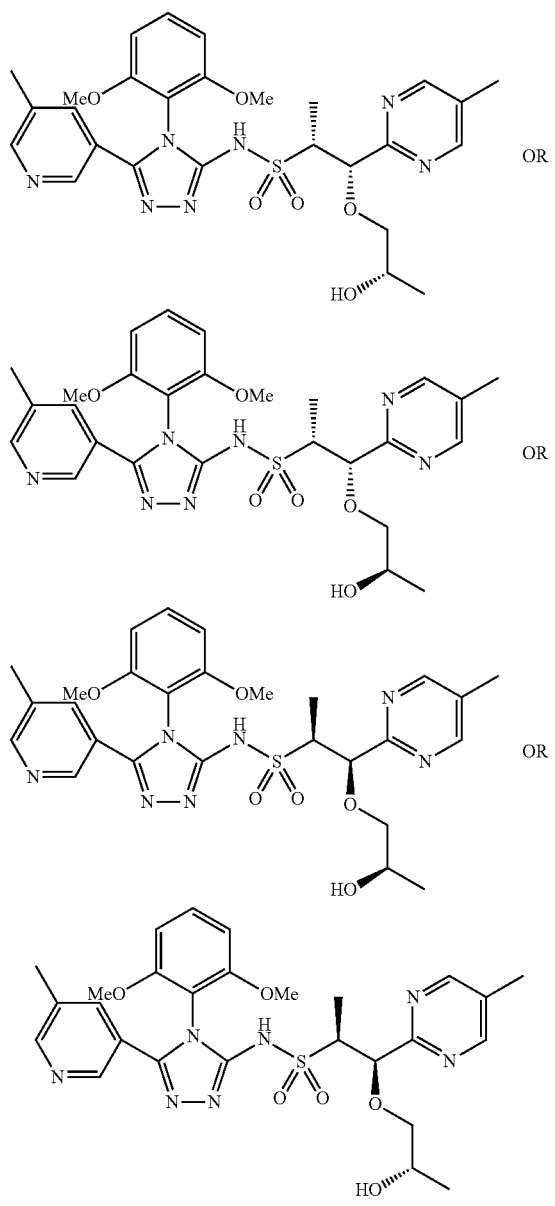

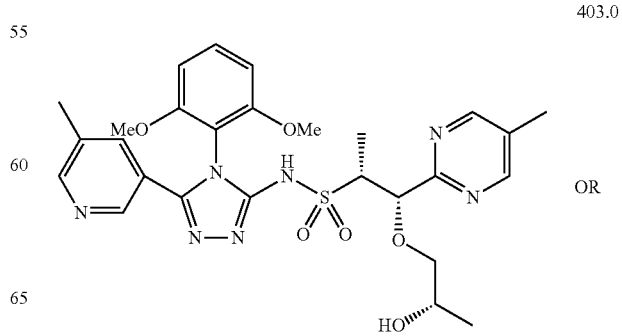

-continued

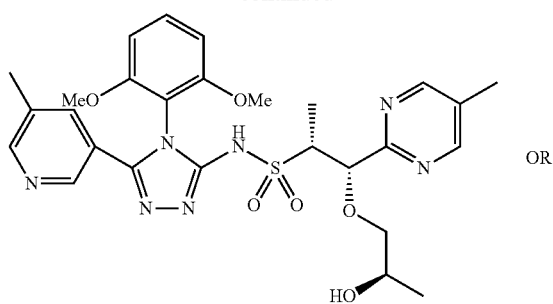

OR

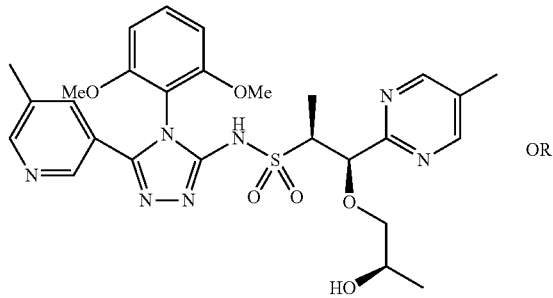

OR

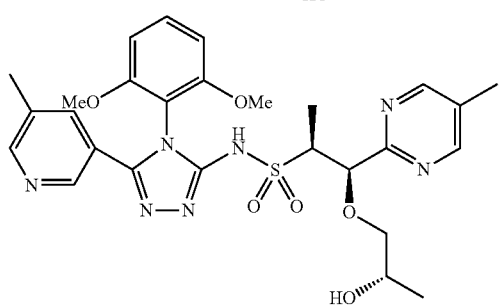

(1S,2R)—N-(4-(2,6-dimethoxyphenyl)-5-(5-methyl-pyridin-3-yl)-4H-1,2,4-triazol-3-yl)-1-((S)-2-hydroxypropoxy)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methyl-pyridin-3-yl)-4H-1,2,4-triazol-3-yl)-1-((R)-2-hydroxypropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide, Example 403.0

A chiral supercritical fluid chromatography purification of 399.0 was performed to separate all four product enantiomers as described in Example 400.0. The fourth eluting peak is Example 403.0 (25.3 mg). $^1$H NMR (500 MHz, CDCl$_3$) δ: 11.31 (br. s., 1H), 8.58 (s, 2H), 8.46 (br. s., 1H), 8.34 (br. s., 1H), 7.72 (br. s., 1H), 7.40 (t, J=8.5 Hz, 1H), 6.61 (d, J=8.6 Hz, 2H), 5.27 (d, J=1.6 Hz, 1H), 3.74-3.94 (m, 3H), 3.75 (s, 3H), 3.74 (s, 3H), 3.11 (t, J=9.7 Hz, 1H), 2.33 (s, 6H), 1.28 (d, J=7.0 Hz, 3H), 1.02 (d, J=6.5 Hz, 3H). LCMS-ESI (POS.) m/z: 584.2 (M+H)$^+$.

Example 404.0: Preparation of (1S,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide 404.1

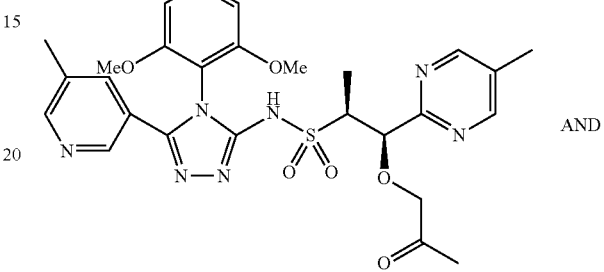

AND

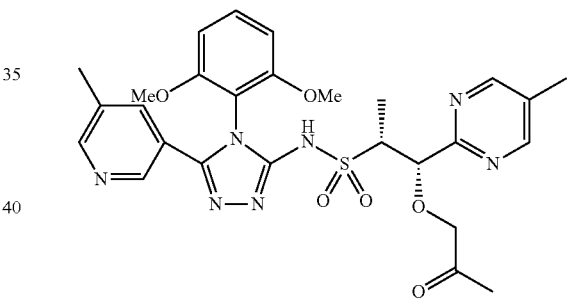

(1S,2R)—N-(4-(2,6-dimethoxyphenyl)-5-(5-methyl-pyridin-3-yl)-4H-1,2,4-triazol-3-yl)-1-(5-methylpyrimidin-2-yl)-1-(2-oxopropoxy)propane-2-sulfonamide and (1R,2S)—N-(4-(2,6-dimethoxyphenyl)-5-(5-methylpyridin-3-yl)-4H-1,2,4-triazol-3-yl)-1-(5-methylpyrimidin-2-yl)-1-(2-oxopropoxy)propane-2-sulfonamide, Example 404.1

To a solution of a mixture of 399.0 (57.7 mg, 0.10 mmol) in DCM (5 mL) was added Dess-Martin periodinane (335 mg, 0.79 mmol). The resulting colorless solution was stirred at RT for 1.25 h and was then was quenched by addition of saturated aqueous sodium thiosulfate solution (10 mL) and saturated aqueous sodium bicarbonate solution (10 mL). The mixture was stirred for 7 min and was then extracted with DCM (4×). The combined organic layers were dried over anhydrous sodium sulfate and concentrated. The residue was purified by silica gel chromatography (eluent: pure DCM grading to 12% MeOH in DCM over a 45 min period) to provide 404.1 (39.3 mg, 68% yield) as a white solid. LCMS-ESI (POS.) m/z: 582.0 (M+H)$^+$.

404.0

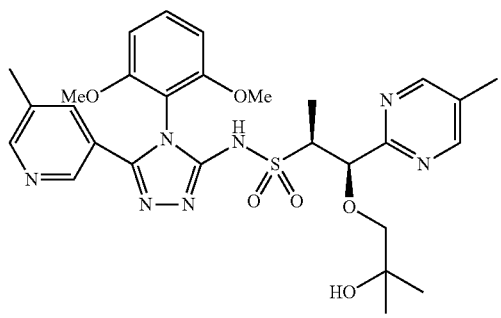

AND

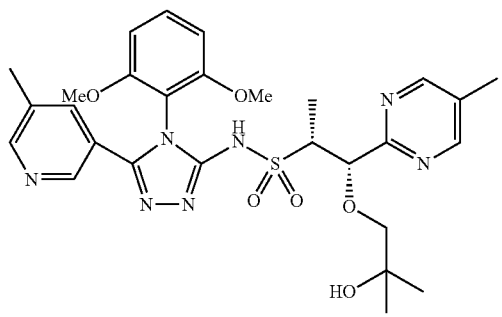

(1S,2R)—N-(4-(2,6-dimethoxyphenyl)-5-(5-methyl-pyridin-3-yl)-4H-1,2,4-triazol-3-yl)-1-(2-hydroxy-2-methylpropoxy)-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide, Example 404.0

To a −78° C. solution of 404.1 (39.3 mg, 0.07 mmol) in THF (15 mL) was added methylmagnesium bromide (1.4 M solution in 3:1 toluene/THF (290 μL, 0.41 mmol)) dropwise via syringe. The resulting light yellow solution was stirred at −78° C. for 7.25 h and was then was quenched with saturated aqueous ammonium chloride solution (10 mL). The resulting mixture was extracted with chloroform (4×), and the combined organic layers were dried over anhydrous sodium sulfate and concentrated in vacuo. The residue was purified by silica gel chromatography (eluent: 1-12% MeOH in DCM over a 45 min period) to provide the racemic alcohol product 404.0 (20.3 mg, 50% yield) as a white solid.

Example 405.0: Preparation of (1S,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2S)—N-(4-(2,6-dimethoxyphenyl)-5-(5-methyl-pyridin-3-yl)-4H-1,2,4-triazol-3-yl)-1-(2-hydroxy-2-methylpropoxy)-1-(5-methylpyrimidin-2-yl)propane-2-sulfonamide 405.0

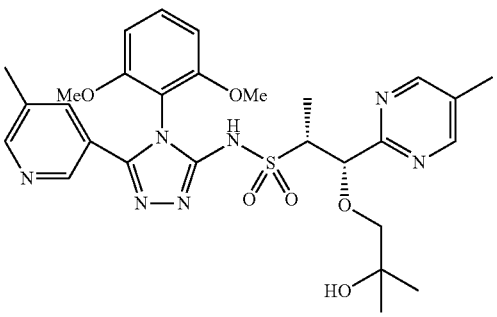

OR (1S,2R)—N-(4-(2,6-dimethoxyphenyl)-5-(5-methyl-pyridin-3-yl)-4H-1,2,4-triazol-3-yl)-1-(2-hydroxy-2-methylpropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide, Example 405.0

A chiral supercritical fluid chromatography purification of 404.0 was performed to separate the two enantiomeric products. The first eluting peak was Example 405.0 (6.0 mg). $^1$H NMR (500 MHz, CDCl$_3$) δ: 8.57 (s, 2H), 8.43 (s, 1H), 8.32 (d, J=1.4 Hz, 1H), 7.63 (s, 1H), 7.37 (t, J=8.5 Hz, 1H), 6.59 (d, J=8.6 Hz, 2H), 5.27 (d, J=2.5 Hz, 1H), 3.88 (qd, J=6.9, 2.5 Hz, 1H), 3.71 (s, 3H), 3.71 (s, 3H), 3.39-3.52 (m, 2H), 2.32 (s, 3H), 2.30 (s, 3H), 1.33 (d, J=7.0 Hz, 3H), 1.20 (s, 3H), 1.16 (s, 3H). LCMS-ESI (POS.) m/z: 598.1 (M+H)$^+$.

Example 406.0: Preparation of (1S,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide

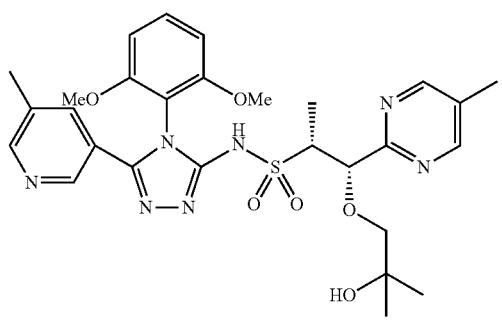

406.0

OR

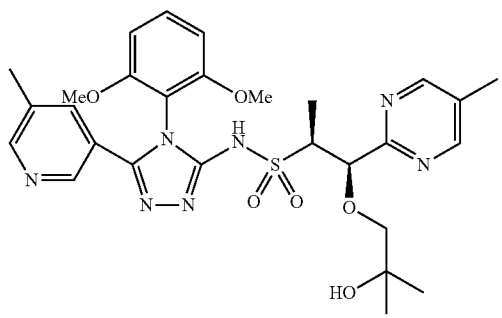

(1S,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide, Example 406.0

A chiral supercritical fluid chromatography purification of 404.0 was performed to separate the two enantiomeric products. The second eluting peak was Example 406.0 (7.0 mg). $^1$H NMR (500 MHz, CDCl$_3$) δ: 8.57 (s, 2H), 8.43 (s, 1H), 8.32 (s, 1H), 7.63 (s, 1H), 7.37 (t, J=8.5 Hz, 1H), 6.59 (d, J=8.6 Hz, 2H), 5.28 (d, J=2.5 Hz, 1H), 3.88 (qd, J=6.9, 2.6 Hz, 1H), 3.72 (s, 3H), 3.71 (s, 3H), 3.38-3.52 (m, 2H), 2.32 (s, 3H), 2.30 (s, 3H), 1.33 (d, J=7.0 Hz, 3H), 1.20 (s, 3H), 1.16 (s, 3H). LCMS-ESI (POS.) m/z: 598.1 (M+H)$^+$.

Example 407.0: Preparation of (1S,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide

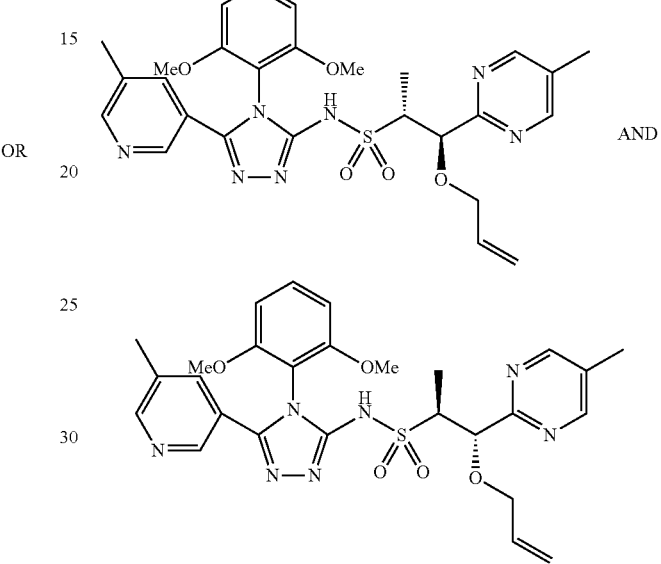

407.1

AND

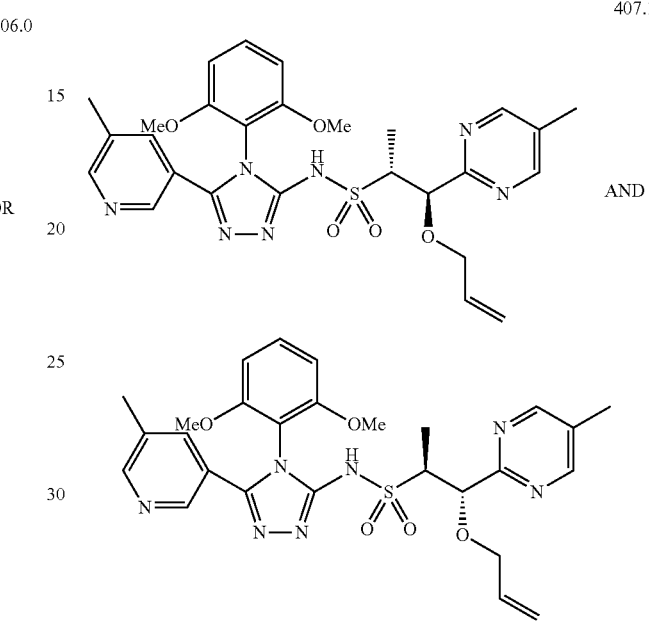

(1S,2S)-1-(allyloxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1R,2R)-1-(allyloxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide, Example 407.1

Following the procedure in Example B, 26.0 (391 mg, 1.44 mmol) and 2.0 (757 mg, 2.02 mmol) were coupled to provide 407.1 (600 mg, 74% yield) as a yellow solid. LCMS-ESI (POS.) m/z: 566.0 (M+H)$^+$.

407.2

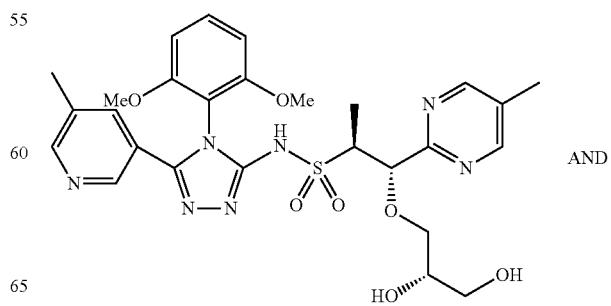

AND

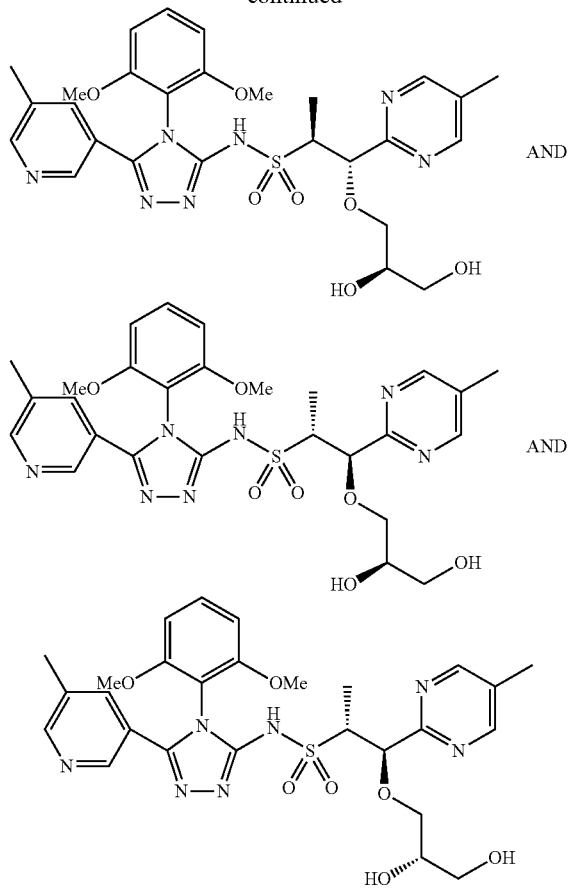

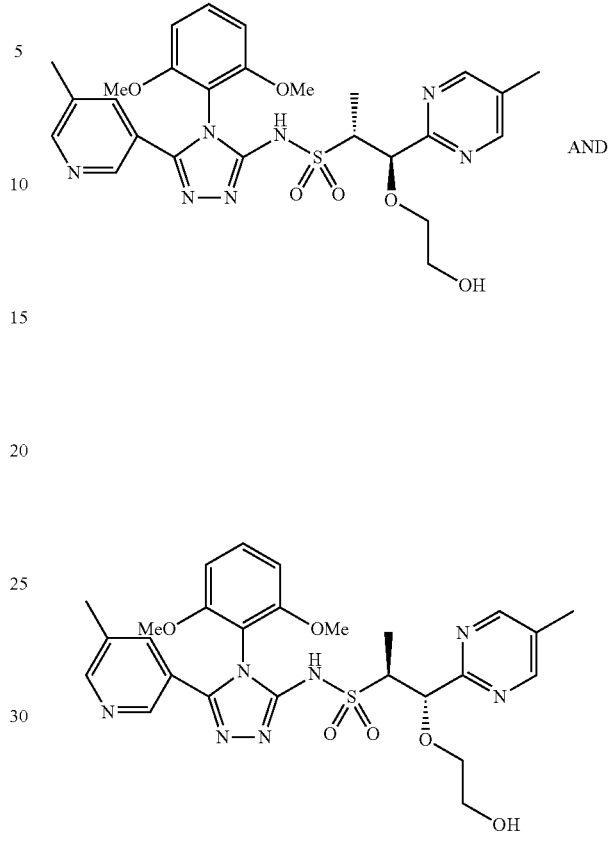

(1S,2S)-1-((S)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1S,2S)-1-((R)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1R,2R)-1-((R)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide and (1R,2R)-1-((S)-2,3-dihydroxypropoxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide, Example 407.2

To a solution of 407.1 (600 mg, 1.06 mmol) in a mixture of acetone (12 mL) and water (4 mL) was added osmium tetroxide (4 wt. % solution in water (389 µL, 0.06 mmol)) and 4-methylmorpholine-N-oxide (435 mg, 3.71 mmol). The resulting orange slurry was stirred at RT for 28 h and then was partially concentrated on a rotary evaporator to remove the acetone. The aqueous residue was diluted with water and extracted with DCM (7×). The combined organic layers were dried over anhydrous sodium sulfate and concentrated in vacuo. The residue was purified by silica gel chromatography (eluent: 0-15% MeOH in DCM over a 35 min period) to provide 407.2 (505 mg, 79% yield) as a light tan solid. LCMS-ESI (POS.) m/z: 599.9 (M+H)$^+$.

407.0

(1S,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide, Example 407.0

To a solution of Example 407.2 (199 mg, 0.33 mmol) in a mixture of THF (6 mL) and water (2 mL) was added sodium periodate (199 mg, 0.93 mmol). The resulting yellow slurry was stirred at RT for 1 h and then was filtered, rinsing the filtrate with DCM. The mixture was partially concentrated on a rotary evaporator to remove the organic solvents, then was diluted with water and extracted with DCM (4×). The combined organic layers were dried over anhydrous sodium sulfate and concentrated to afford the aldehyde as a yellow solid. To an ice-cooled solution of the aldehyde in MeOH (6 mL) was added sodium borohydride (126 mg, 3.32 mmol). Gas evolution was observed. The resulting yellow solution was stirred at 0° C. for 35 min and then was quenched with 1 N HCl solution (7 mL). The mixture was partially concentrated on the rotary evaporator to remove the MeOH, and then was extracted with DCM (5×). The combined organic layers were dried over anhydrous sodium sulfate and concentrated in vacuo. The residue was purified by silica gel chromatography (eluent: 0-15% MeOH in DCM over a 40 min period) to provide the racemic alcohol product 407.0 (115 mg, 61% yield) as an off-white solid.

Example 408.0: Preparation of (1S,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide Example 409.0: Preparation of (1S,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide

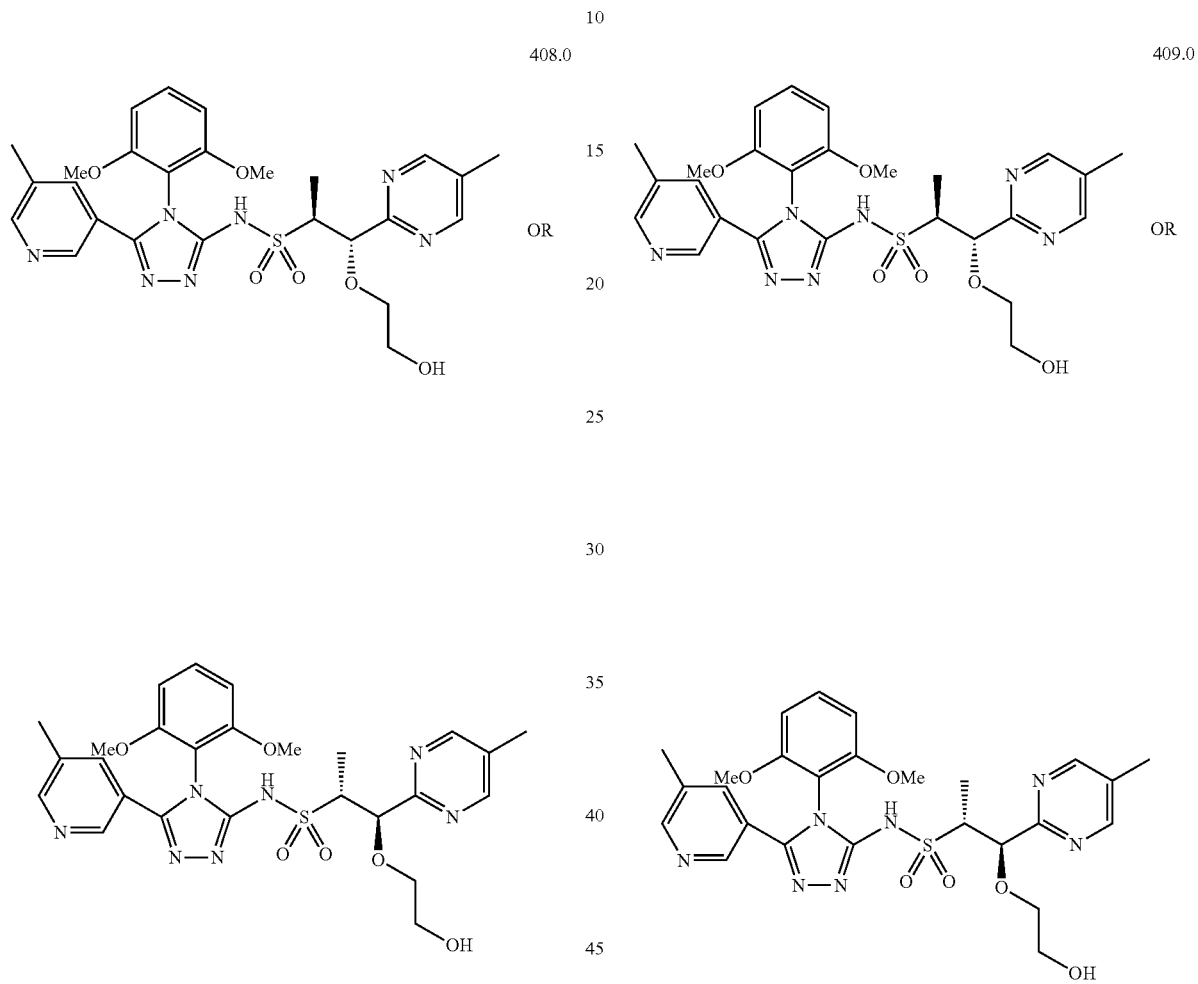

(1S,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide, Example 408.0

(1S,2S)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxyethoxy)-1-(5-methylpyrimidin-2-yl)propane-2-sulfonamide, Example 409.0

A chiral supercritical fluid chromatography purification of 407.0 was performed to separate the two enantiomeric products. The first eluting peak was Example 408.0 (41 mg). $^1$H NMR (500 MHz, CDCl$_3$) δ: 11.78 (br. s., 1H), 8.62 (s, 2H), 8.46 (s, 1H), 8.36 (s, 1H), 7.72 (br. s., 1H), 7.40 (t, J=8.6 Hz, 1H), 6.63 (t, J=7.6 Hz, 2H), 4.75 (d, J=7.2 Hz, 1H), 3.82 (s, 3H), 3.81-3.90 (m, 1H), 3.75 (s, 3H), 3.43-3.61 (In, 4H), 2.34 (d, J=8.4 Hz, 6H), 1.24 (d, J=7.0 Hz, 3H). LCMS-ESI (POS.) m/z: 570.0 (M+H)$^+$.

A chiral supercritical fluid chromatography purification of 407.0 was performed to separate the two enantiomeric products. The second eluting peak was Example 409.0 (32 mg). $^1$H NMR (500 MHz, CDCl$_3$) δ: 11.79 (br. s., 1H), 8.62 (s, 2H), 8.46 (s, 1H), 8.36 (s, 1H), 7.74 (br. s., 1H), 7.40 (t, J=8.4 Hz, 1H), 6.63 (t, J=7.8 Hz, 2H), 4.75 (d, J=7.2 Hz, 1H), 3.82 (s, 3H), 3.80-3.89 (m, 1H), 3.76 (s, 3H), 3.44-3.60 (m, 4H), 2.35 (d, J=6.2 Hz, 6H), 1.24 (d, J=7.0 Hz, 3H). LCMS-ESI (POS.) m/z: 570.0 (M+H)$^+$.

Example 410.0: Preparation of (1S,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide

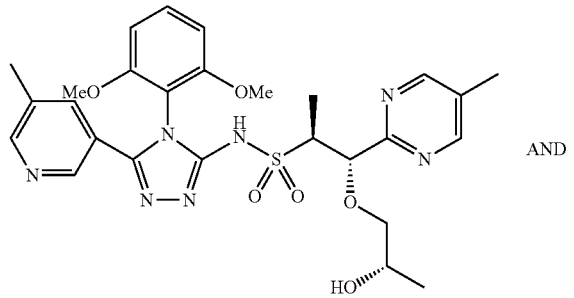

410.1

AND

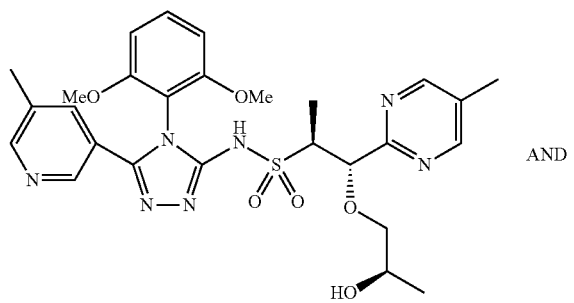

AND

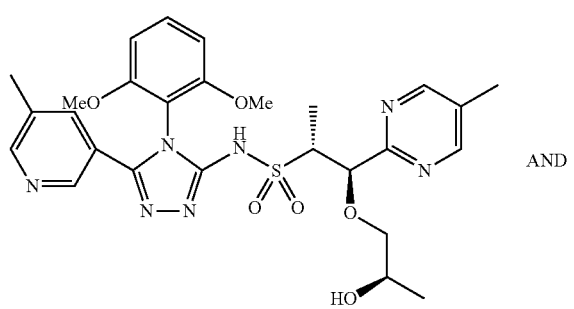

AND

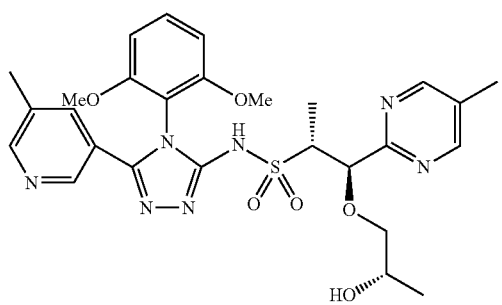

(1S,2S)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide and (1S,2S)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-((R)-2-hydroxypropoxy)-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-((S)-2-hydroxypropoxy)-1-(5-methylpyrimidin-2-yl)propane-2-sulfonamide, Example 410.1

To a solution of 407.2 (281 mg, 0.47 mmol) in a mixture of THF (6 mL) and water (2 mL) was added sodium periodate (281 mg, 1.31 mmol). The resulting tan slurry was stirred at RT for 55 min and then was filtered, rinsing the filtrate with DCM. The mixture was partially concentrated to remove the organic solvents and then was diluted with water and extracted with DCM (4×). The combined organic layers were dried over anhydrous sodium sulfate and concentrated to afford the aldehyde as a tan solid. To a −78° C. solution of the aldehyde in THF (12 mL) was added methylmagnesium bromide (1.4 M solution in 3:1 toluene/THF (838 µL, 1.17 mmol)) via syringe. The resulting orange solution was stirred at −78° C. for 70 min and was then warmed to 0° C. and stirred for an additional 50 min. The reaction mixture was recooled to −78° C. and additional methylmagnesium bromide (1.4 M solution in 3:1 toluene/THF (670 µL, 0.94 mmol)) and THF (5 mL) were added. After 30 min at −78° C., the reaction was warmed to RT and stirred for an additional 15 h. The reaction was quenched with saturated aqueous ammonium chloride solution (30 mL) and was extracted with chloroform (4×). The combined organic layers were dried over anhydrous sodium sulfate and concentrated in vacuo. The residue was purified by silica gel chromatography (eluent: 0-15% MeOH in DCM over a 35 min period) to provide 410.1 (140 mg, 51% yield) as a colorless oil. LCMS-ESI (POS.) m/z: 584.0 (M+H)$^+$.

410.2

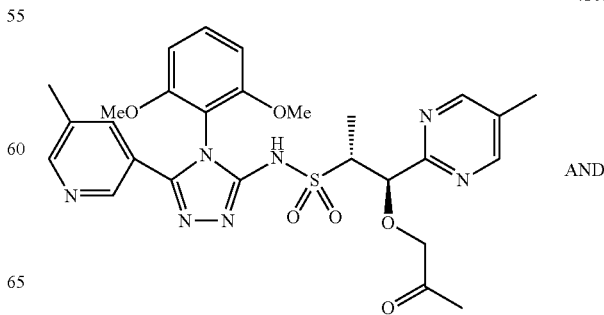

AND

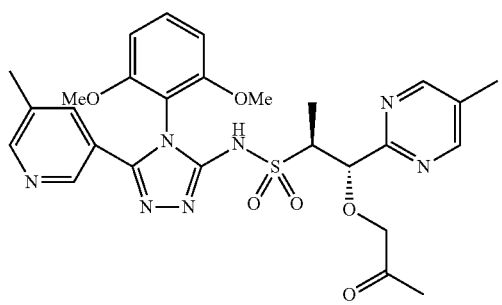

(1S,2S)—N-(4-(2,6-dimethoxyphenyl)-5-(5-methyl-pyridin-3-yl)-4H-1,2,4-triazol-3-yl)-1-(5-methylpyrimidin-2-yl)-1-(2-oxopropoxy)propane-2-sulfonamide and (1R,2R)—N-(4-(2,6-dimethoxyphenyl)-5-(5-methylpyridin-3-yl)-4H-1,2,4-triazol-3-yl)-1-(5-methylpyrimidin-2-yl)-1-(2-oxopropoxy)propane-2-sulfonamide, Example 410.2

To a solution of Example 410.1 (140 mg, 0.19 mmol) in DCM (9 mL) was added Dess-Martin periodinane (416 mg, 0.98 mmol). The resulting light yellow solution was stirred at RT for 6 h and then was quenched by addition of saturated aqueous sodium thiosulfate solution (5 mL) and saturated aqueous sodium bicarbonate solution (5 mL). The mixture was stirred for 10 min and then was extracted with DCM (4×). The combined organic layers were dried over anhydrous sodium sulfate and concentrated. The residue was purified by silica gel chromatography (eluent: 0-15% MeOH in DCM over a 35 min period) to provide 410.2 (112 mg, 100% yield) as a white solid. LCMS-ESI (POS.) m/z: 581.9 (M+H)$^+$.

(1S,2S)—N-(4-(2,6-dimethoxyphenyl)-5-(5-methyl-pyridin-3-yl)-4H-1,2,4-triazol-3-yl)-1-(2-hydroxy-2-methylpropoxy)-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide, Example 410.0

To a −78° C. solution of 410.2 (112 mg, 0.19 mmol) in THF (20 mL) was added methylmagnesium bromide (1.4 M solution in 3:1 toluene/THF (550 μL, 0.77 mmol)) dropwise via syringe. The resulting light yellow solution was stirred at −78° C. for 4.25 h and then was warmed to 0° C. and stirred for an additional 2 h. After this time period, the reaction was warmed to RT and stirred for another 7 h. The reaction was quenched with saturated aqueous ammonium chloride solution (20 mL) and was extracted with chloroform (4×). The combined organic layers were dried over anhydrous sodium sulfate and concentrated. The residue was purified by silica gel chromatography (eluent: 1-15% MeOH in DCM over a 35 min period) to provide the racemic alcohol product 410.0 (27.5 mg, 24% yield) as a white solid.

Example 411.0: Preparation of (1S,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2R)—N-(4-(2,6-dimethoxyphenyl)-5-(5-methyl-pyridin-3-yl)-4H-1,2,4-triazol-3-yl)-1-(2-hydroxy-2-methylpropoxy)-1-(5-methylpyrimidin-2-yl)propane-2-sulfonamide

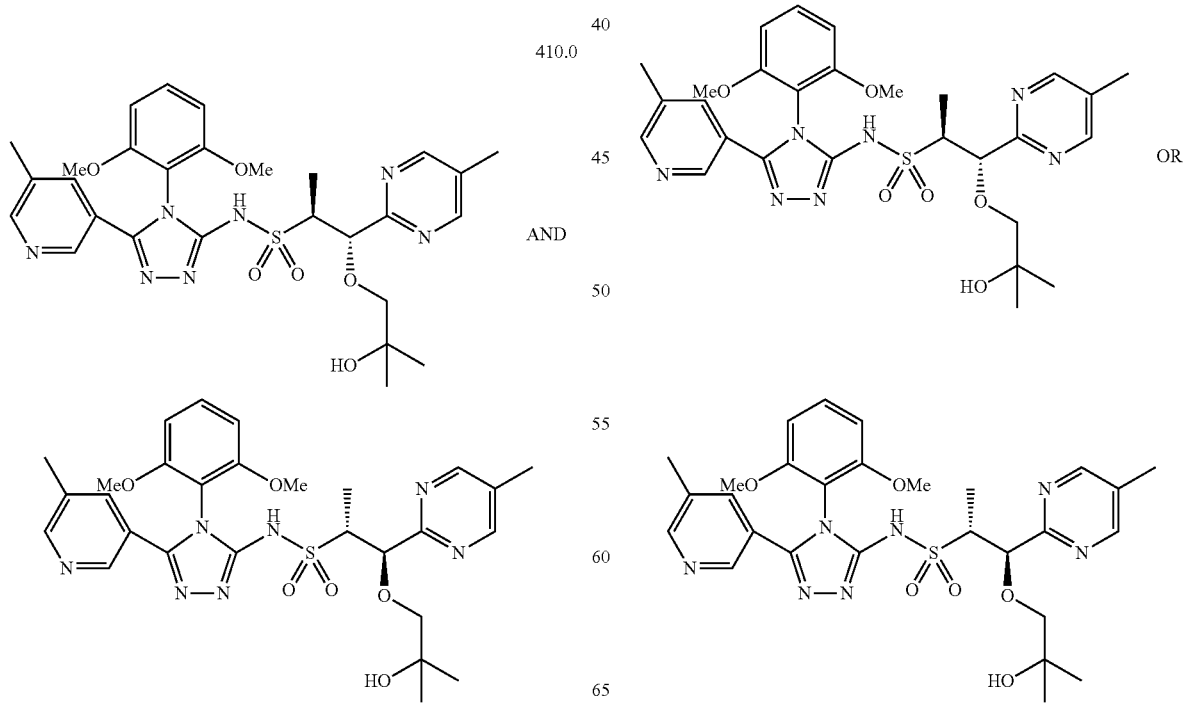

(1S,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide, Example 411.0

A chiral supercritical fluid chromatography purification of 410.0 was performed to separate the two enantiomeric products in Example 410.0. Chiralpak ADH (250×20 mm), 20% EtOH, 70 mL/min, 274-nm. The first eluting peak was Example 411.0 (6.8 mg). $^1$H NMR (500 MHz, CDCl$_3$) δ: 8.63 (s, 2H), 8.47 (s, 1H), 8.34 (d, J=1.6 Hz, 1H), 7.79 (br. s., 1H), 7.40 (t, J=8.6 Hz, 1H), 6.63 (dd, J=16.2, 8.2 Hz, 2H), 4.77 (d, J=7.4 Hz, 1H), 3.84 (s, 3H), 3.82-3.91 (m, 1H), 3.72 (s, 3H), 3.31 (d, J=9.0 Hz, 1H), 3.18 (d, J=9.2 Hz, 1H), 2.35 (s, 6H), 1.23 (d, J=7.0 Hz, 3H), 1.13 (d, J=6.3 Hz, 6H). LCMS-ESI (POS.) m/z: 598.1 (M+H)$^+$.

Example 412.0: Preparation of (1S,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide

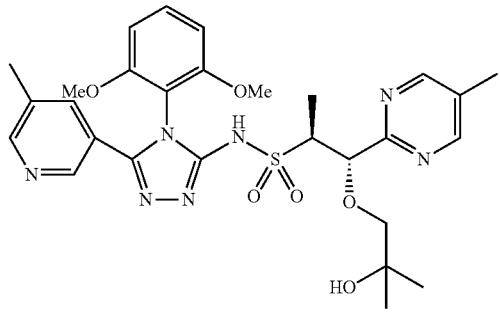

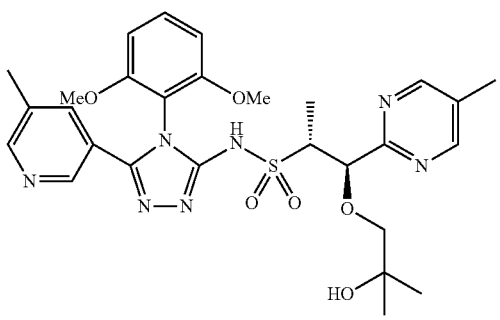

(1S,2S)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-hydroxy-2-methylpropoxy)-1-(5-methylpyrimidin-2-yl)propane-2-sulfonamide, Example 412.0

A chiral supercritical fluid chromatography purification of 410.0 was performed to separate the two enantiomeric products as described in Example 411.0. The second eluting peak was Example 412.0 (7.8 mg). $^1$H NMR (500 MHz, CDCl$_3$) δ: 8.63 (s, 2H), 8.46 (s, 1H), 8.34 (d, J=1.6 Hz, 1H), 7.74 (br. s., 1H), 7.39 (t, J=8.5 Hz, 1H), 6.62 (dd, J=16.1, 8.3 Hz, 2H), 4.77 (d, J=7.4 Hz, 1H), 3.83 (s, 3H), 3.81-3.89 (m, 1H), 3.72 (s, 3H), 3.31 (d, J=9.2 Hz, 1H), 3.18 (d, J=9.2 Hz, 1H), 2.35 (d, J=5.5 Hz, 6H), 1.23 (d, J=7.2 Hz, 3H), 1.13 (d, J=6.1 Hz, 6H). LCMS-ESI (POS.) m/z: 598.1 (M+H)$^+$.

Example 413.0: Preparation of 1S,2S)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide

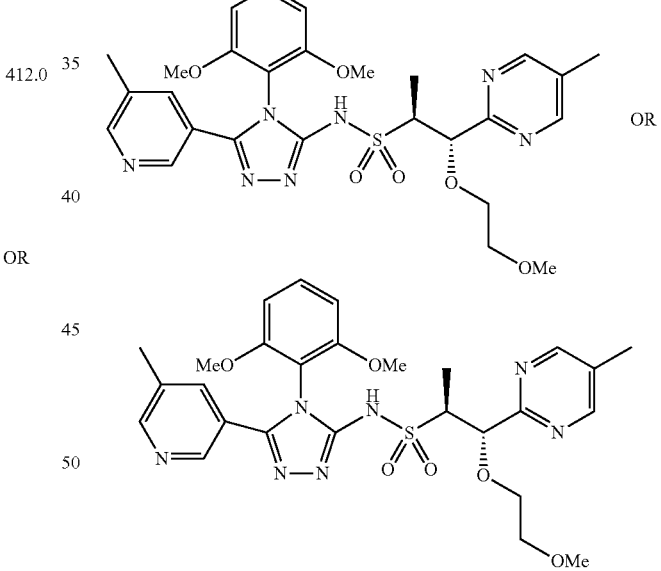

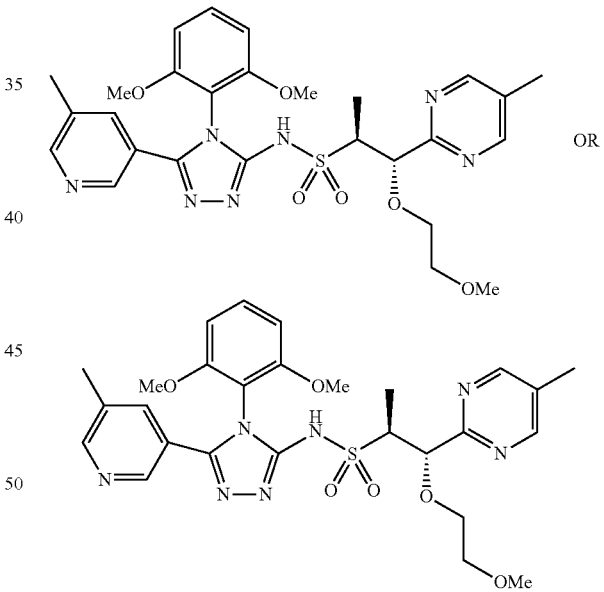

(1S,2S)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide or (1R,2R)—N-(4-(2,6-dimethoxyphenyl)-5-(5-methylpyridin-3-yl)-4H-1,2,4-triazol-3-yl)-1-(2-methoxyethoxy)-1-(5-methylpyrimidin-2-yl)propane-2-sulfonamide, Example 413.0

To a −78° C. solution of 408.0 (7.3 mg, 0.013 mmol) in THF (2.6 mL) was added potassium bis(trimethylsilyl)amide (1.0 M solution in THF (29 µL, 0.03 mmol)) slowly via syringe. After stirring for 10 min at −78° C., the reaction was warmed to −35° C. and stirred for an additional 7 min. The reaction was then recooled to −78° C. and methyl trifluoromethanesulfonate (2.3 µL, 0.02 mmol) was added slowly via syringe. The resulting yellow solution was stirred at −78° C. for 2.75 h and then was quenched with a 2.5:1 mixture of saturated aqueous ammonium chloride and water (7 mL) and was extracted with DCM (3×). The combined organic layers were dried over anhydrous sodium sulfate and concentrated in vacuo. The residue was purified by reverse phase preparative HPLC (Luna 5 µM C18 column, eluent: 20-60% ACN in water over a 35 minute period where both solvents contain 0.1% TFA) to provide 413.0 (3.9 mg, 52% yield) as a white solid. $^1$H NMR (500 MHz, CDCl$_3$) δ: 8.69 (s, 2H), 8.60 (s, 1H), 8.41 (s, 1H), 8.12 (s, 1H), 7.44 (t, J=8.5 Hz, 1H), 6.65 (dd, J=19.2, 8.4 Hz, 2H), 4.86 (d, J=5.9 Hz, 1H), 3.84 (s, 3H), 3.82-3.91 (m, 2H), 3.73 (s, 3H), 3.59-3.69 (m, 2H), 3.46-3.58 (m, 2H), 3.38 (s, 3H), 2.46 (s, 3H), 2.37 (s, 3H), 1.31 (d, J=6.7 Hz, 3H). LCMS-ESI (POS.) m/z: 584.2 (M+H)$^+$.

Example 414.0: Preparation of (1S,2R)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide and (1R,2S)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide 414.1

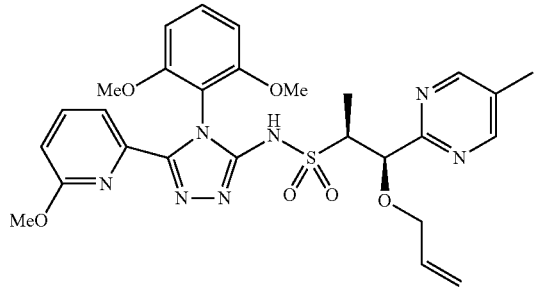

AND

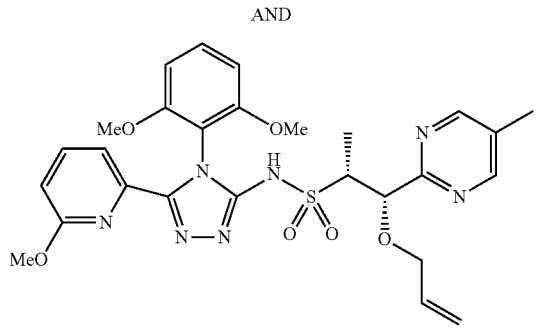

(1S,2R)-1-(allyloxy)-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1R,2S)-1-(allyloxy)-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide, Example 414.1

Following the procedure in Example A, 25.0 (209 mg, 0.77 mmol), 6-methoxypicolino hydrazide (135 mg, 0.81 mmol) and Example 1.0 (152 mg, 0.79 mmol) were coupled to provide 414.1 (234 mg, 52% yield) as a white solid. LCMS-ESI (POS.) m/z: 582.2 (M+H)$^+$.

414.2

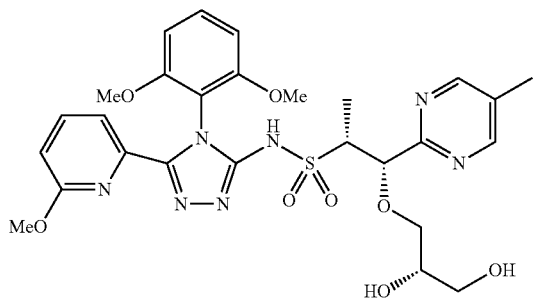

AND

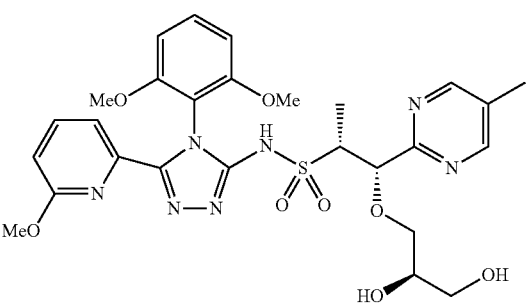

AND

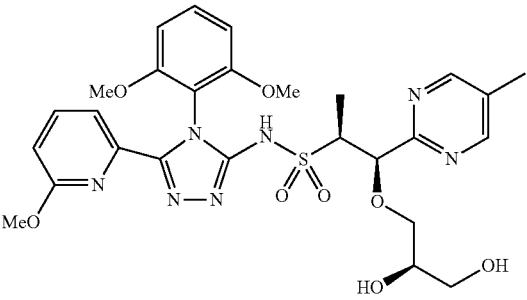

AND

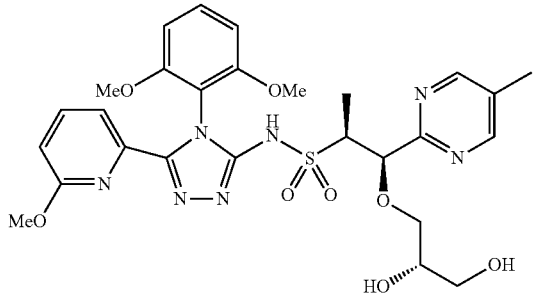

(1S,2R)-1-((S)-2,3-dihydroxypropoxy)-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1S,2R)-1-((R)-2,3-dihydroxypropoxy)-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1R,2S)-1-((R)-2,3-dihydroxypropoxy)-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide and (1R,2S)-1-((S)-2,3-dihydroxypropoxy)-N-(4-(2,6-dimethoxyphenyl)-5-(6-methoxypyridin-2-yl)-4H-1,2,4-triazol-3-yl)-1-(5-methylpyrimidin-2-yl)propane-2-sulfonamide, Example 414.2

To a solution of 414.1 (234 mg, 0.40 mmol) in a mixture of acetone (9 mL) and water (3 mL) was added a catalytic amount of solid osmium tetroxide and 4-methylmorpholine-N-oxide (165 mg, 1.41 mmol). The resulting brown solution was stirred at RT for 26 h and then was partially concentrated on a rotary evaporator to remove the acetone. The aqueous residue was diluted with water and extracted with chloroform (5×). The combined organic layers were dried over anhydrous sodium sulfate and concentrated. The residue was purified by silica gel chromatography (eluent: 3-15% MeOH in DCM over a 35 min period) to provide 414.2 (116 mg, 37% yield) as a colorless oil. LCMS-ESI (POS.) m/z: 616.1 (M+H)$^+$.

(1S,2R)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide and (1R,2S)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide, Example 414.0

To a solution of 414.2 (116 mg, 0.17 mmol) in a mixture of THF (6 mL) and water (2 mL) was added sodium periodate (133 mg, 0.62 mmol). The white slurry was stirred at RT for 2.5 h and then was filtered, rinsing the filtrate with DCM. The mixture was partially concentrated on a rotary evaporator to remove the organic solvents, then was diluted with water and extracted with DCM (4×). The combined organic layers were dried over anhydrous sodium sulfate and concentrated to afford the aldehyde as a white solid. To an ice-cooled solution of the aldehyde in MeOH (5 mL) was added sodium borohydride (52 mg, 1.37 mmol). Gas evolution was observed. The resulting yellow solution was stirred at 0° C. for 30 min and then additional sodium borohydride (117 mg, 3.08 mmol) was added. After stirring for an additional 40 min at 0° C., the reaction was quenched with 1 N HCl solution (8 mL). The mixture was partially concentrated on the rotary evaporator to remove the MeOH, and then was extracted with DCM (4×). The combined organic layers were dried over anhydrous sodium sulfate and concentrated in vacuo. The residue was purified by silica gel chromatography (eluent: 0-12% MeOH in DCM over a 45 min period) to provide the racemic alcohol product 414.0 (71 mg, 71% yield) as a white solid.

Example 415.0: Preparation of (1S,2R)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide

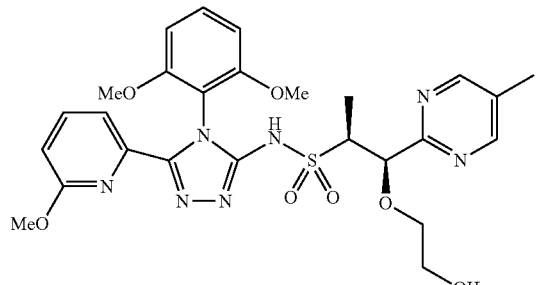

414.0

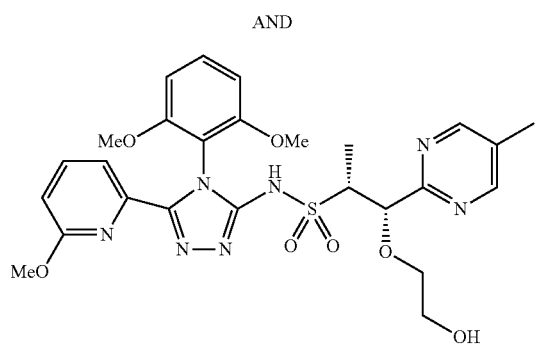

AND

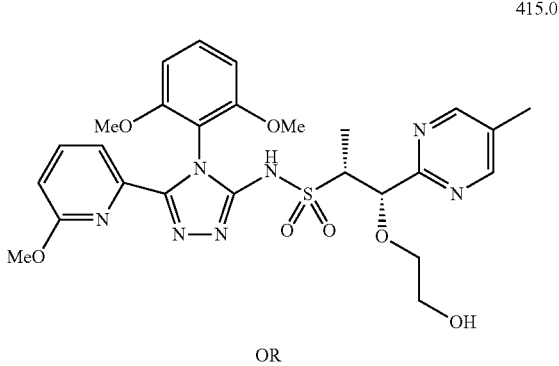

415.0

OR

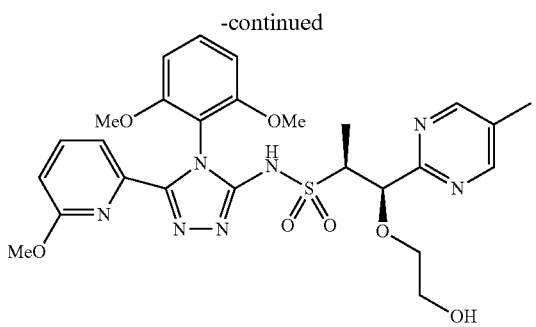

(1S,2R)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide, Example 415.0

A chiral supercritical fluid chromatography purification of 414.0 was performed to separate the two enantiomeric products. Preparative SFC method #1: Column. Chiralpak AS-H (Reversed) (250×21 mm, 5 μm), Mobile Phase: 67:33 (A:B), A: Liquid CO₂, B: MeOH, Flow Rate: 70 mL/min, 220 nm, 213 bar inlet pressure, Preparative SFC method #2 (Re-purification of the peak 1 fraction): Column: Whelk 0-1 (250×21 mm, 5 μm), Mobile Phase: 70:30 (A:B), A: Liquid CO₂, B: MeOH, Flow Rate: 70 mL/min, 220 nm, 165-172 bar inlet pressure. The first eluting peak was Example 415.0 (22.8 mg): $^1$H NMR (500 MHz, CDCl₃) δ: 8.65 (s, 2H), 7.56-7.66 (m, 2H), 7.32 (t, J=8.5 Hz, 1H), 6.70 (dd, J=7.4, 1.8 Hz, 1H), 6.57-6.64 (m, 2H), 5.35 (d, J=2.3 Hz, 1H), 3.85-3.95 (m, 1H), 3.71 (s, 3H), 3.70 (s, 3H), 3.59-3.75 (m, 3H), 3.51-3.57 (m, 1H), 3.17 (s, 3H), 2.36 (s, 3H), 1.28 (d, J=6.8 Hz, 3H). LCMS-ESI (POS.) m/z: 586.1 (M+H)⁺.

Example 416.0: Preparation of (1S,2R)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide 416.0

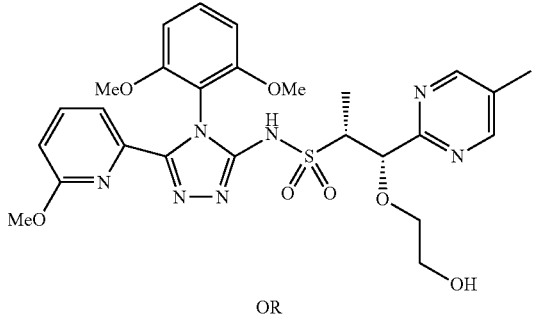

OR

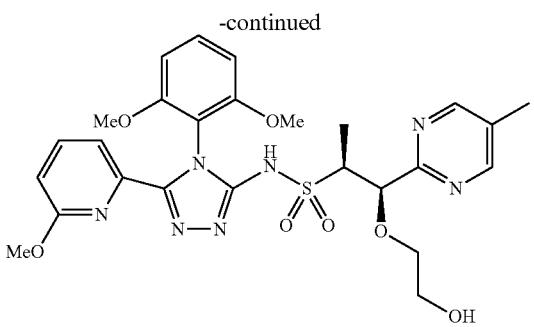

(1S,2R)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide or (1R,2S)—N-(4-(2,6-dimethoxyphenyl)-5-(6-methoxypyridin-2-yl)-4H-1,2,4-triazol-3-yl)-1-(2-hydroxyethoxy)-1-(5-methylpyrimidin-2-yl)propane-2-sulfonamide, Example 416.0

A chiral supercritical fluid chromatography purification of 414.0 was performed to separate the two enantiomeric products as described in Example 415.0. The second eluting peak was Example 416.0 (27.3 mg). $^1$H NMR (500 MHz, CDCl₃) δ: 8.67 (s, 2H), 7.54-7.67 (m, 2H), 7.32 (t, J=8.5 Hz, 1H), 6.70 (dd, J=7.4, 1.8 Hz, 1H), 6.57-6.64 (m, 2H), 5.36 (br. s., 1H), 3.86-3.95 (m, 1H), 3.72 (s, 3H), 3.70 (s, 3H), 3.59-3.77 (m, 3H), 3.51-3.57 (m, 1H), 3.17 (s, 3H), 2.36 (s, 3H), 1.28 (d, J=6.8 Hz, 3H). LCMS-ESI (POS.) m/z: 586.1 (M+H)⁺.

Example 417.0: Preparation of (2S)—N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide and (2R)—N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide 417.0

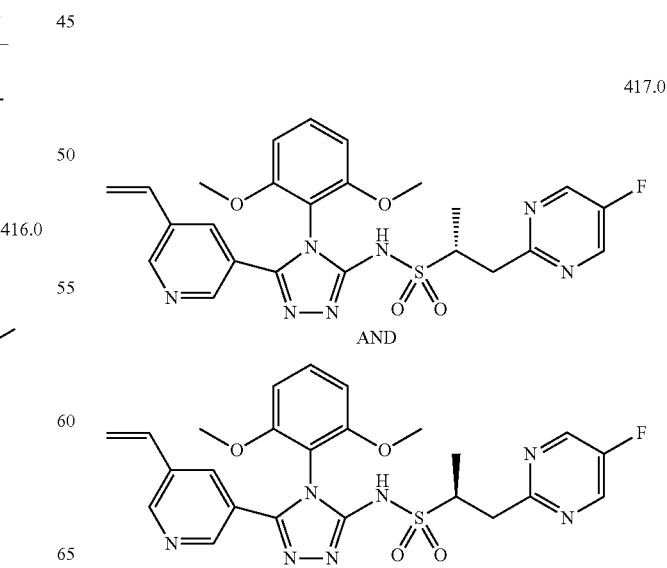

AND (2S)—N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide and (2R)—N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide, Example 417.0

A 10-mL round bottom flask was charged with compound 146.0 (0.231 g, 0.40 mmol), vinylboronic acid pinacol ester (0.143 mL, 0.80 mmol, commercially available from Sigma-Aldrich Corp, St. Louis, Mo., USA), tricyclohexylphosphine (0.022 g, 0.080 mmol, commercially available from Sigma-Aldrich Corp, St. Louis, Mo., USA), and tris(dibenzylideneacetone)dipalladium (0.037 g, 0.040 mmol, commercially available from Strem Chemicals, Inc. Newburyport, Mass., USA) and backfilled with argon. 1,4-Dioxane (3 mL) and aqueous 1.3 M potassium phosphate (0.922 mL, 1.198 mmol) were added to the reaction mixture by syringe. The resulting reaction was heated at 90° C. and monitored with TLC and LC-MS. After 18 h, the reaction was cooled to RT and then concentrated under reduced pressure. The residue was diluted with EtOAc and dried over $MgSO_4$. The material thus obtained was absorbed onto a plug of silica gel and purified by chromatography through a Redi-Sep pre-packed silica gel column (12 g), eluting with a gradient of 0-100% EtOAc in heptanes, to provide the title compound 417.0, (0.106 g, 0.20 mmol, 50% yield) as white solid. $^1$H NMR (400 MHz, $CDCl_3$) δ: 8.61 (br. s., 1H), 8.54 (s, 2H), 8.47 (s, 1H), 7.88 (s, 1H), 7.42 (t, J=8.51 Hz, 1H), 6.55-6.72 (m, 3H), 5.73 (d, J=17.61 Hz, 1H), 5.44 (d, J=10.96 Hz, 1H), 3.82 (ddd, J=9.88, 6.65, 4.40 Hz, 1H), 3.76 (s, 3H), 3.74 (s, 3H), 3.70 (dd, J=14.87, 4.69 Hz, 1H), 3.10 (dd, J=14.77, 9.88 Hz, 1H), 1.32 (d, J=6.85 Hz, 3H). LCMS-ESI (POS.) m/z: 525.8 $(M+H)^+$.

Example 418.0: Preparation of (2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide and (2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide

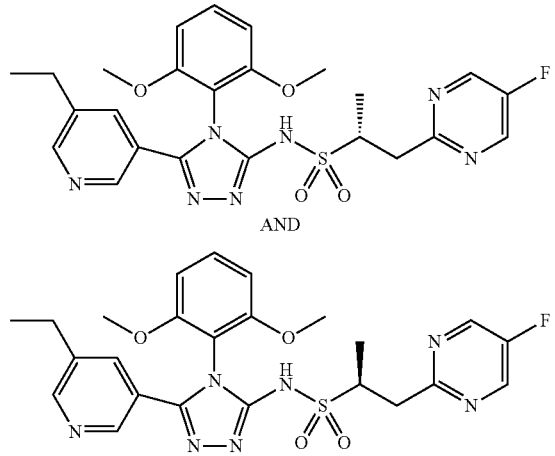

(2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide and (2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide, Example 418.0

To a round-bottomed flask was added compound 417.0 (0.065 g, 0.12 mmol) and palladium on activated carbon (0.013 g, 6.18 μmop (commercially available from Sigma-Aldrich Corp, St. Louis, Mo., USA). A mixture of EtOH (2.5 mL) and DCM (2.5 mL) was added, and the reaction mixture was stirred overnight under an atmosphere of $H_2$. The reaction mixture was filtered through a syringe filter (Whatman 0.45 μm PTFE w/GMF). The filtrate was concentrated in vacuo to give the initial material. The material thus obtained was absorbed onto a plug of silica gel and purified by chromatography through a Redi-Sep pre-packed silica gel column (12 g), eluting with a gradient of 0-100% EtOAc in heptanes, to provide the title compound 418.0 (0.034 g, 0.064 mmol, 52% yield). LCMS-ESI (POS.) m/z: 527.8 $(M+H)^+$.

Example 419.0: Preparation of (2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide

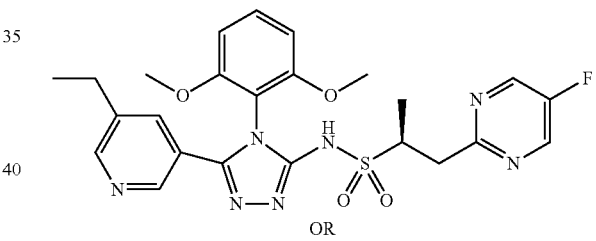

OR

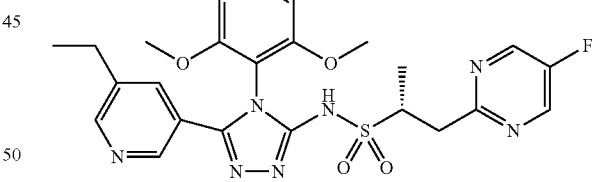

(2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide, Example 419.0

The racemic compound 418.0 was separated by supercritical fluid chromatography (250×21 mm IA column on Thar 80 with 18 g/min MeOH (+20 mM $NH_3$)+37 g/min $CO_2$, 33% co-solvent at 55 g/min. Temperature=24° C.; outlet pressure=100 bar; wavelength=215 nm; injection volume=0.2 mL of 20 mg sample dissolved in 4 mL MeOH (25% DCM). Two enantiomers were obtained. The title compound was the first isomer to elute under these conditions. ¹H NMR (400 MHz, CDCl₃) δ: 8.54 (s, 1H), 8.46 (d, J=1.96 Hz, 1H), 8.41 (d, J=2.15 Hz, 1H), 7.59 (t, J=2.15 Hz, 1H), 7.57-7.61 (m, 1H), 7.39 (t, J=8.51 Hz, 1H), 6.61 (d, J=8.46 Hz, 2H), 3.77-3.85 (m, 1H), 3.74 (s, 3H), 3.72 (s, 3H), 3.69 (d, J=3.72 Hz, 1H), 3.10 (dd, J=14.77, 9.88 Hz, 1H), 2.61 (q, J=7.63 Hz, 2H), 1.32 (d, J=6.85 Hz, 3H), 1.15 (t, J=7.63 Hz, 3H). LCMS-ESI (POS.) m/z: 527.8 (M+H)⁺.

Example 420.0: Preparation of (2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide Example 421.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide

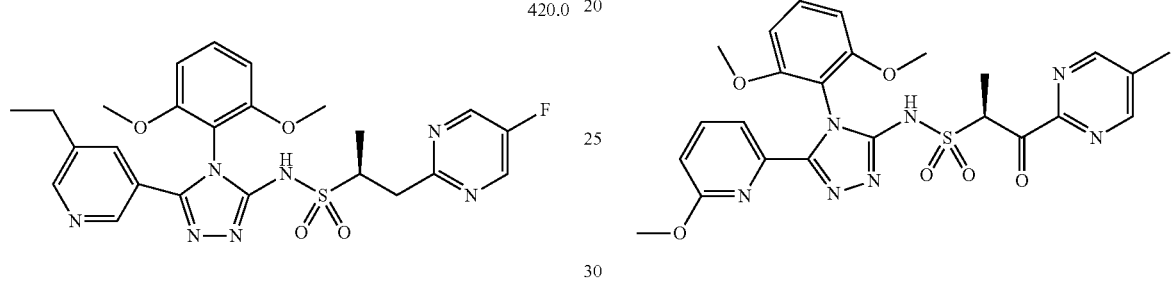

420.0

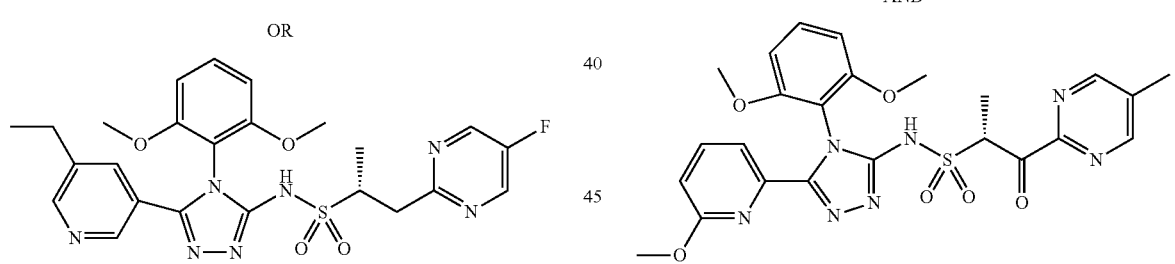

421.1

(2S)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide, Example 420.0

(S)—N-(4-(2,6-dimethoxyphenyl)-5-(6-methoxypyridin-2-yl)-4H-1,2,4-triazol-3-yl)-1-(5-methylpyrimidin-2-yl)-1-oxopropane-2-sulfonamide and (R)—N-(4-(2,6-dimethoxyphenyl)-5-(6-methoxypyridin-2-yl)-4H-1,2,4-triazol-3-yl)-1-(5-methylpyrimidin-2-yl)-1-oxopropane-2-sulfonamide, Example 421.1

The title compound was the second isomer to elute on subjecting compound 418.0 to the SFC conditions described in Example 419.0. ¹H NMR (400 MHz, CDCl₃) δ: 8.54 (s, 2H), 8.39-8.48 (m, 2H), 7.59 (t, J=2.15 Hz, 1H), 7.39 (t, J=8.51 Hz, 1H), 6.61 (dd, J=8.51, 0.88 Hz, 2H), 3.81 (ddd, J=9.88, 6.75, 4.30 Hz, 1H), 3.74 (s, 3H), 3.72 (s, 3H), 3.69 (d, J=4.50 Hz, 1H), 3.10 (dd, J=14.77, 9.88 Hz, 1H), 2.61 (q, J=7.76 Hz, 2H), 1.32 (d, J=6.85 Hz, 3H), 1.15 (t, J=7.63 Hz, 3H). LCMS-ESI (POS.) m/z: 527.8 (M+H)⁺.

Following the general procedure Example A, using 19.0, 1.0, and 3.18 delivered 421.1. ¹H NMR (CDCl₃) δ: 8.67-8.76 (m, 2H), 7.47 (dd, J=8.3, 7.5 Hz, 1H), 7.29-7.35 (m, 1H), 6.56-6.68 (m, 3H), 6.43-6.54 (m, 1H), 4.41 (q, J=6.9 Hz, 1H), 3.75-3.80 (m, 3H), 3.67-3.75 (m, 3H), 3.12 (s, 3H), 2.40-2.48 (m, 3H), 1.38 (d, J=7.0 Hz, 3H). One exchangeable proton was not observed. MS-ESI (POS.) m/z: 539.9 (M+H)⁺.

421.0

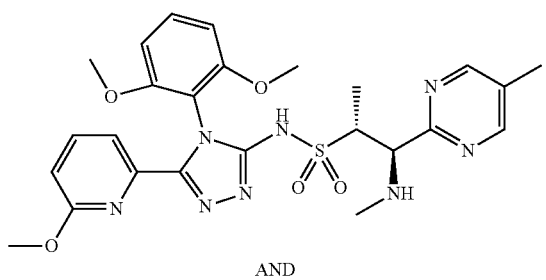

AND

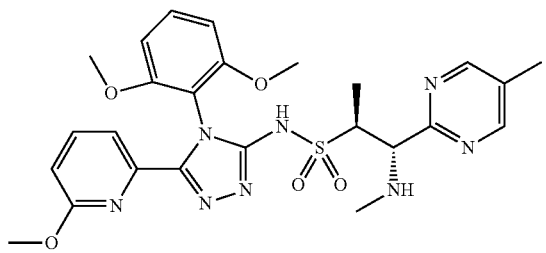

AND

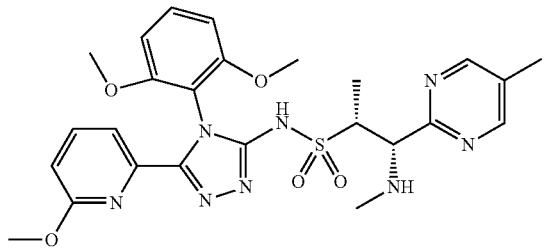

AND

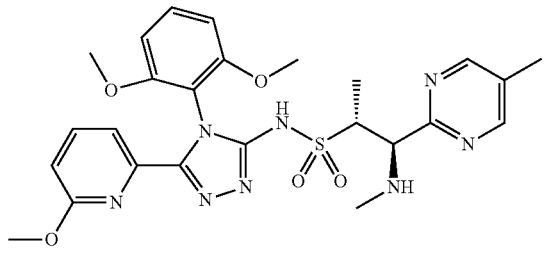

(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 421.0

To a solution of 421.1 (0.150 g, 0.278 mmol) in MeOH (2.0 mL) was added methylamine (0.30 mL, 2.86 mmol, Aldrich, St. Louis, Mo.), 2 drops AcOH, and sodium borocyanohydride (0.040 g, 0.61 mmol, Aldrich, St. Louis, Mo.). The resulting mixture was heated at 60° C. under N₂ for 18 hours. To the reaction mixture was added sodium triacetoxyborohydride (0.120 g, 0.57 mmol, Aldrich, St. Louis, Mo.) and the reaction was heated for another 18 h. The reaction was cooled to RT and concentrated. The residue was partitioned between EtOAc (60 mL) and saturated aqueous NaHCO₃ (30 mL). The aqueous layer was extracted with 10% iPrOH in CHCl₃ (50 mL). The combined organic layers were dried over MgSO₄, filtered, and concentrated. The product thus obtained 421.0 was purified by column chromatography (40 g of silica, 0-4% MeOH in DCM) to obtain two diastereomers.

Example 422.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide 422.0

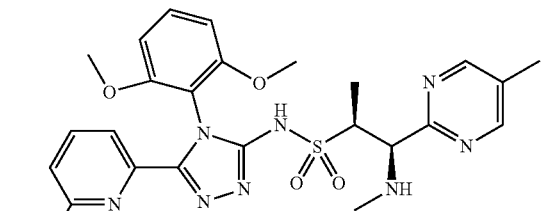

AND

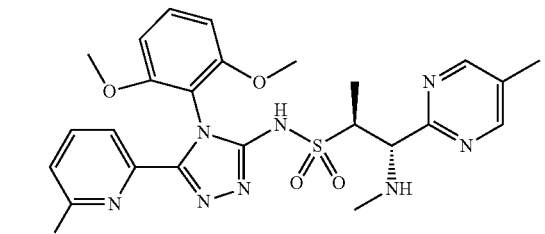

OR

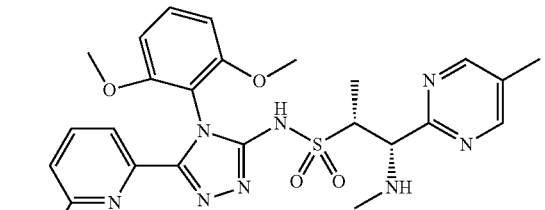

AND


(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 422.0

As described in Example 421.0, the diastereomers were separated by silica gel purification to give the first eluting diastereomer which is the title compound. $^1$H NMR (CDCl$_3$) δ: 8.57 (s, 2H), 7.55-7.66 (m, 2H), 7.29-7.36 (m, 1H), 6.65-6.73 (m, 1H), 6.60 (dd, J=8.5, 4.7 Hz, 2H), 4.55 (d, J=3.1 Hz, 1H), 3.72 (s, 3H), 3.71 (s, 3H), 3.63 (qd, J=7.1, 3.0 Hz, 1H), 3.17 (s, 3H), 2.31 (d, J=2.6 Hz, 6H), 1.29 (s, 3H). Two exchangeable protons were not observed. MS-ESI (POS.) m/z: 555.0 (M+H)$^+$.

Example 423.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide 423.0

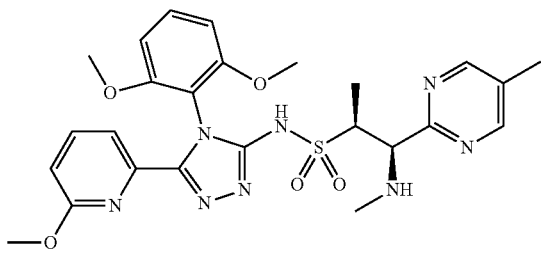

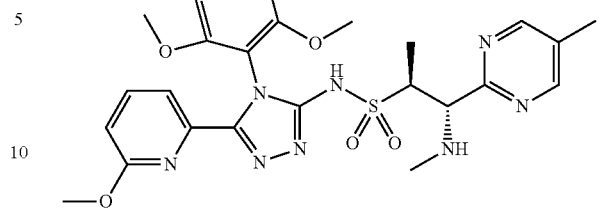

AND

OR

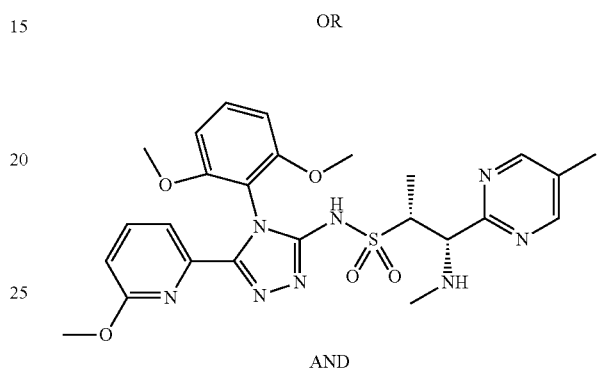

AND

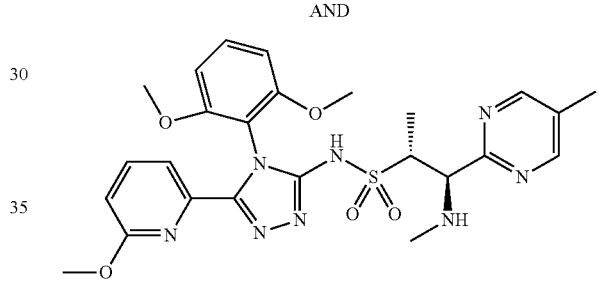

(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 423.0

As described in Example 421.0, the diastereomers were separated by silica gel purification to give the second eluting diastereomer which is Example 423.0. $^1$H NMR (CDCl$_3$) δ: 8.52-8.60 (m, 2H), 7.54-7.66 (in. 2H), 7.29-7.35 (in. 1H), 6.69 (dd, J=7.0, 2.2 Hz, 1H), 6.60 (d, J=8.6 Hz, 2H), 4.08 (d, J=8.8 Hz, 1H), 3.76 (s, 3H), 3.73 (s, 3H), 3.65 (dd, J=8.8, 7.0 Hz, 1H), 3.18 (s, 3H), 2.28-2.35 (m, 3H), 2.13-2.20 (in. 3H), 1.11 (d, J=7.0 Hz, 3H). Two exchangeable protons were not observed. MS-ESI (POS.) m/z: 554.9 (M+H)$^+$.

Example 424.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide 424.0

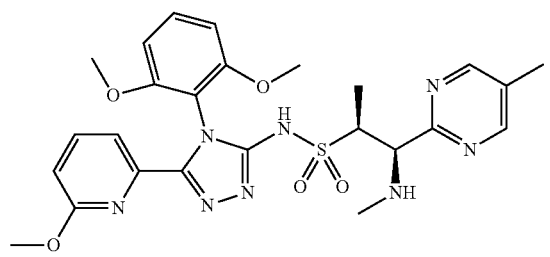

OR

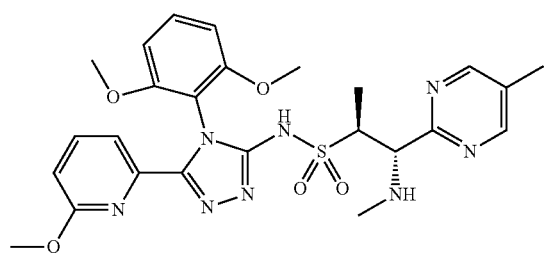

OR

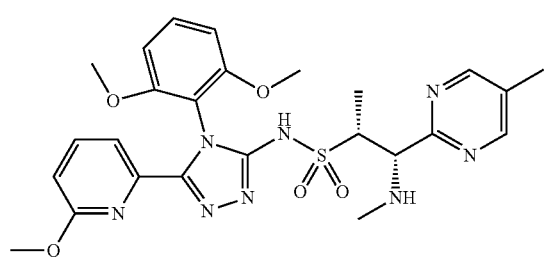

OR

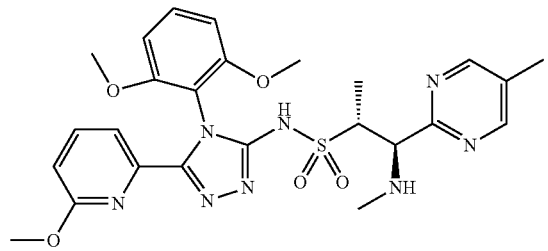

(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 424.0

The first eluting mixture of diastereomers 422.0 was resolved using preparative SFC (OX column (5 um, 21 mm×25 cm, 5 um S/N=2121 regular direction) eluting with 50% liquid $CO_2$ in 50% MeOH with 0.2% isopropylamine at a flow rate of 50 mL/min) to give two products in greater than 99.5% enantiomeric excess; the first eluting peak was Example 424.0. $^1$H NMR ($CDCl_3$) δ: 8.57 (s, 2H), 7.58-7.65 (m, 2H), 7.29-7.35 (m, 1H), 6.66-6.74 (m, 1H), 6.60 (t, J=7.4 Hz, 2H), 4.56 (d, J=3.1 Hz, 1H), 3.64-3.57 (m, 7H), 3.17 (s, 3H), 2.32 (s, 3H), 2.31 (s, 3H), 1.25-1.34 (m, 4H). One exchangeable proton was not observed. MS-ESI (POS.) m/z: 555.2 $(M+H)^+$.

Example 425.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide 425.0

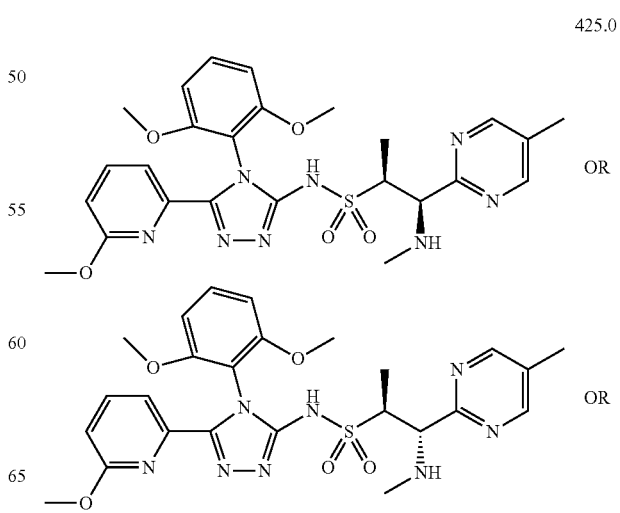

-continued

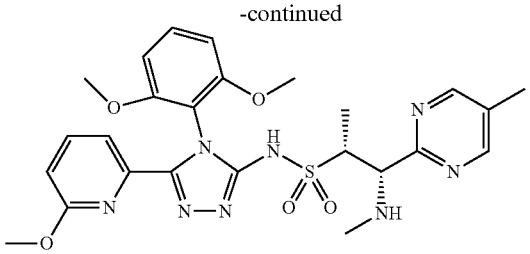

(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 425.0

The second eluting peak from the procedure described in Example 424.0 was Example 425.0. $^1$H NMR (CDCl$_3$) δ: 8.57 (s, 2H), 7.57-7.65 (in. 2H), 7.29-7.35 (m, 1H), 6.65-6.74 (m, 1H), 6.55-6.65 (m, 2H), 4.56 (d, J=3.1 Hz, 1H), 3.72 (s, 3H), 3.71 (s, 3H), 3.60-3.68 (m, 1H), 3.17 (s, 3H), 2.32 (m, 6H), 1.29 (d, J=7.2 Hz, 4H). One exchangeable proton was not observed. MS-ESI (POS.) m/z: 554.8 (M+H)$^+$.

Example 426.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide 426.0

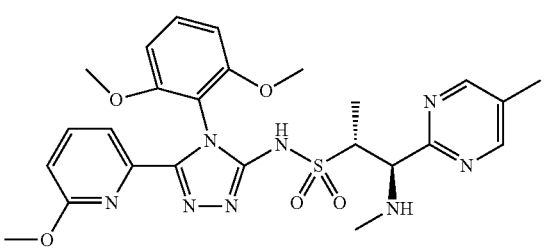

(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 426.0

The second mixture of diastereomers 423.0 was resolved using preparative SFC (OX column (5 um, 21 mm×25 cm, 5 um S/N=2121 regular direction) eluting with 50% liquid $CO_2$ in 50% MeOH with 0.2% isopropylamine at a flow rate of 50 mL/min) to give two products in greater than 99.5% enantiomeric excess. The first eluting peak was Example 426.0. $^1$H NMR (CDCl$_3$) δ: 8.57 (s, 2H), 7.55-7.64 (m, 2H), 7.29-7.35 (m, 1H), 6.65-6.72 (m, 1H), 6.60 (d, J=8.5 Hz, 2H), 4.08 (d, J=8.9 Hz, 1H), 3.76 (s, 3H), 3.72 (s, 3H), 3.56-3.70 (m, 1H), 3.18 (s, 3H), 2.32 (s, 3H), 2.17 (s, 3H), 1.23-1.28 (m, 1H), 1.10 (d, J=7.0 Hz, 3H). One exchangeable proton was not observed. MS-ESI (POS.) m/z: 555.0 (M+H)$^+$.

Example 427.0: Preparation of (1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide

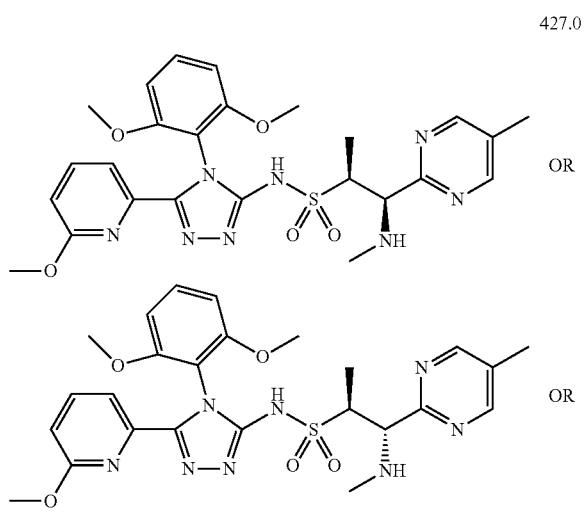

427.0

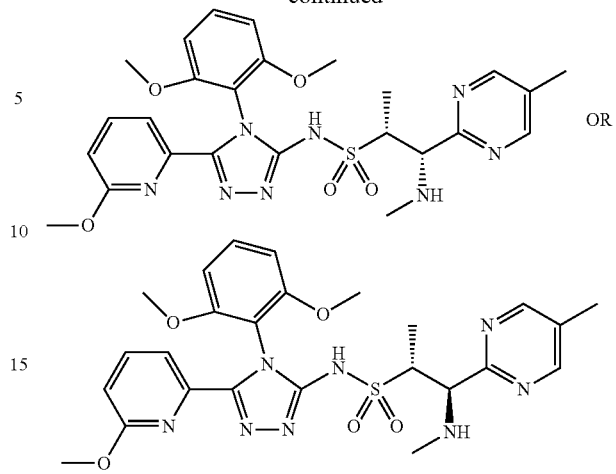

(1R,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-(methylamino)-1-(5-methylpyrimidin-2-yl)propane-2-sulfonamide, Example 427.0

The second eluting peak from the procedure described in Example 426.0 delivered 427.0. $^1$H NMR (CDCl$_3$) δ: 8.57 (s, 2H), 7.55-7.64 (m, 2H), 7.29-7.35 (m, 1H), 6.69 (dd, J=6.9, 2.2 Hz, 1H), 6.60 (d, J=8.5 Hz, 2H), 4.03-4.11 (m, 1H), 3.76 (s, 3H), 3.72 (s, 3H), 3.57-3.68 (m, 1H), 3.18 (s, 3H), 2.32 (s, 3H), 2.17 (s, 3H), 1.17 (d, J=6.3 Hz, 3H). One exchangeable proton was not observed. MS-ESI (POS.) m/z: 555.0 (M+H)$^+$.

Example 428.0: Preparation of (1R,2S)—N-(4-(2,6-dimethoxyphenyl)-5-(5-methylpyridin-3-yl)-4H-1,2,4-triazol-3-yl)-1-methoxy-1-(5-phenylpyrimidin-2-yl)propane-2-sulfonamide 428.1

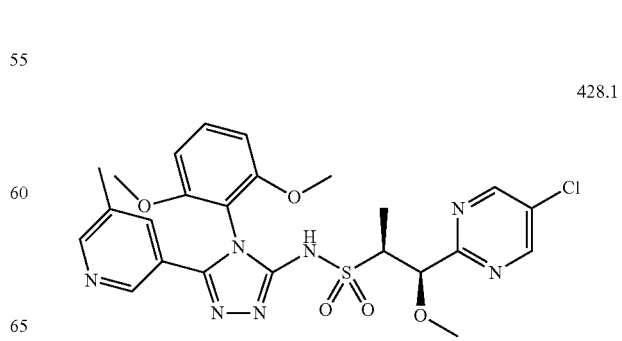

(1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide Example 428.1

Following the general procedure Example A, using 14.3, 1.0 and 3.11 delivered 428.1. $^1$H NMR (CDCl$_3$) δ: 11.08 (br. s., 1H), 8.61-8.82 (m, 2H), 8.44 (d, J=1.5 Hz, 1H), 8.33 (d, J=1.9 Hz, 1H), 7.57-7.70 (m, 1H), 7.34-7.47 (m, 1H), 6.55-6.66 (m, 2H), 4.91-5.03 (m, 1H), 3.69-3.78 (m, 7H), 3.26-3.40 (m, 3H), 2.30 (s, 3H), 1.32-1.46 (m, 3H). MS-ESI (POS.) m/z: 559.9 (M+H)$^+$.

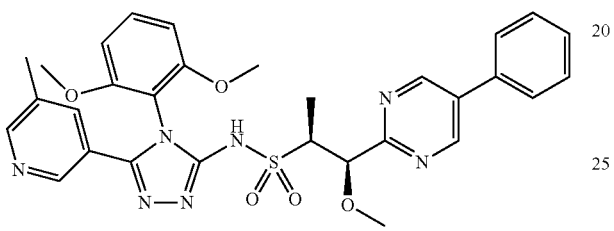

428.0

(1R,2S)—N-(4-(2,6-dimethoxyphenyl)-5-(5-methylpyridin-3-yl)-4H-1,2,4-triazol-3-yl)-1-methoxy-1-(5-phenylpyrimidin-2-yl)propane-2-sulfonamide, Example 428.0

To a 25 mL round bottomed flask was added (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide (428.1, 0.050 g, 0.089 mmol), phenylboronic acid (0.035 g, 0.287 mmol, Aldrich, St. Louis, Mo.), potassium phosphate (0.060 g, 0.283 mmol, Aldrich, St. Louis, Mo.), (AmPhos) 1,1-bis[(di-t-butyl-p-methylaminophenyl]palladium(II) chloride (8.0 mg, 0.011 mmol, Aldrich, St. Louis, Mo.), 1,4-dioxane (2.0 mL), and water (0.70 mL). The resulting mixture was bubbled with Argon for a couple min and then a condenser was attached and the mixture was heated at 85° C. under N$_2$ for 20 h. The reaction was then cooled to RT and partitioned between water (10 mL) and 10% iPrOH in CHCl$_3$ (20 mL). The aqueous layer was extracted with 10% iPrOH in CHCl$_3$ (15 mL). The combined organic layers were dried over MgSO$_4$, filtered, and concentrated in vacuo. The residue was purified by column chromatography (40 g of silica, 2-5% MeOH in DCM) to afford (1R,2S)—N-(4-(2,6-dimethoxyphenyl)-5-(5-methylpyridin-3-yl)-4H-1,2,4-triazol-3-yl)-1-methoxy-1-(5-phenylpyrimidin-2-yl)propane-2-sulfonamide (428.0, 0.040 g). $^1$H NMR (CDCl$_3$) δ: 11.21 (br. s., 1H), 8.92-9.01 (m, 2H), 8.44 (d, J=1.5 Hz, 1H), 8.28-8.38 (m, 1H), 7.65 (s, 1H), 7.57-7.62 (m, 2H), 7.45-7.56 (m, 3H), 7.39 (t, J=8.6 Hz, 1H), 6.61 (d, J=8.5 Hz, 2H), 5.08 (d, J=4.4 Hz, 1H), 3.78-3.87 (m, 1H), 3.70-3.78 (m, 6H), 3.40 (s, 3H), 2.30 (s, 3H), 1.41-1.45 (m, 3H). MS-ESI (POS.) m/z: 602.0 (M+H)$^+$.

Example 429.0: Preparation of (1R,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide

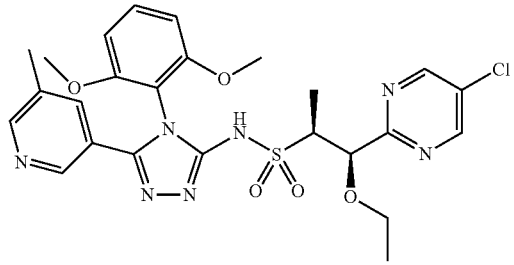

429.0

(1R,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide, Example 429.0

Following the general procedure Example A, using 14.7, 1.0, and 3.11 delivered 429.0. $^1$H NMR (CDCl$_3$) δ: 11.08 (s, 1H), 8.70 (s, 2H), 8.44 (s, 1H), 8.33 (s, 1H), 7.63 (s, 1H), 7.39 (t, J=8.5 Hz, 1H), 6.60 (dd, J=8.5, 4.1 Hz, 2H), 5.00 (d, J=5.8 Hz, 1H), 3.77-3.85 (m, 1H), 3.67-3.77 (m, 6H), 3.39-3.59 (m, 2H), 2.30 (s, 3H), 1.44 (d, J=7.0 Hz, 3H), 1.07-1.19 (m, 3H). MS-ESI (POS.) m/z: 573.9 (M+H)$^+$.

Example 430.0: Preparation of (1R,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide

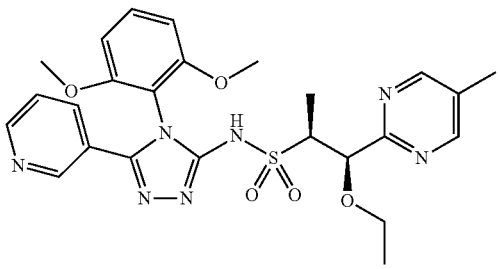

430.0

(1R,2S)-1-(5-chloropyrimidin-2-A-N-(4-(2,6-dimethoxyphenyl)-5-(pyridin-3-yl)-4H-1,2,4-triazol-3-yl)-1-ethoxypropane-2-sulfonamide, Example 430.0

Following the general procedure Example A, using 14.7, and 1.0 and nicotinohydrazide delivered 430.0. $^1$H NMR (CDCl$_3$) δ: 11.10 (s, 1H), 8.71 (s, 2H), 8.58-8.65 (m, 2H), 7.73 (dt, J=8.0, 2.0 Hz, 1H), 7.39 (t, J=8.5 Hz, 1H), 7.24 (d, J=5.7 Hz, 1H), 6.60 (dd, J=8.6, 4.8 Hz, 2H), 5.00 (d, J=5.8 Hz, 1H), 3.77-3.84 (m, 1H), 3.74-3.77 (m, 3H), 3.71 (s, 3H), 3.39-3.61 (m, 2H), 1.42-1.49 (m, 3H), 1.10-1.19 (m, 3H). MS-ESI (POS.) m/z: 559.8 (M+H)$^+$.

Example 431.0: Preparation of (S)—N-((2,6-dimethoxyphenyl)carbamothioyl)-1-(5-fluoropyrimidin-2-yl)propane-2-sulfonamide and (R)—N-((2,6-dimethoxyphenyl)carbamothioyl)-1-(5-fluoropyrimidin-2-yl)propane-2-sulfonamide

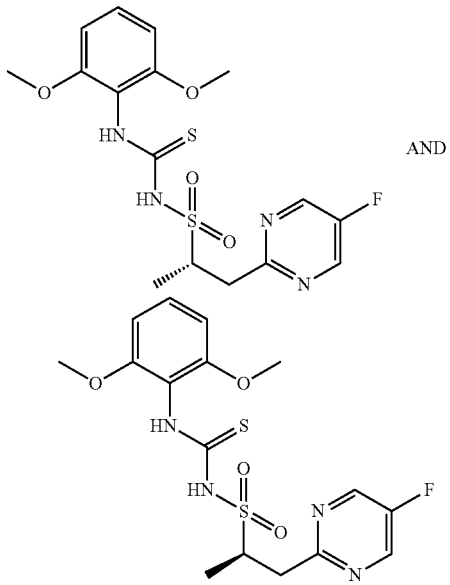

431.0

AND (S)—N-((2,6-dimethoxyphenyl)carbamothioyl)-1-(5-fluoropyrimidin-2-yl)propane-2-sulfonamide and (R)—N-((2,6-dimethoxyphenyl)carbamothioyl)-1-(5-fluoropyrimidin-2-yl)propane-2-sulfonamide, Example 431.0

To a solution of 9.0 (1.8 g, 8.21 mmol) in DMF (10 mL) was added cesium carbonate (0.99 mL, 12.32 mmol) in portions. The mixture was stirred at RT for 5 min before 2-isothiocyanato-1,3-dimethoxybenzene 1.0 (1.68 g, 8.62 mmol) was added in portions. The resulting mixture was then stirred at RT and monitored by LCMS. Upon reaction completion, 20 mL of water was added and the mixture was acidified by addition of aqueous HCl solution (2.0N, 6.16 mL, 12.32 mmol) to pH 5. The precipitate that formed was collected, washed with water three times, and dried under vacuum to give 431.0 (3.37 g, 8.13 mmol, 99% yield). LCMS-ESI (POS.) m/z: 415.1 (M+H)⁺.

Example 432.0: Preparation of (2S,3S)-3-(5-fluoropyrimidin-2-yl)butane-2-sulfonyl fluoride and (2R,3R)-3-(5-fluoropyrimidin-2-yl)butane-2-sulfonyl fluoride and (2S,3R)-3-(5-fluoropyrimidin-2-yl)butane-2-sulfonyl fluoride and (2R,3S)-3-(5-fluoropyrimidin-2-yl)butane-2-sulfonyl fluoride 432.0

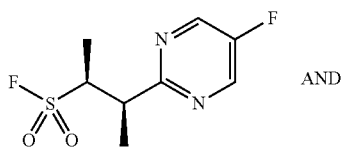

AND

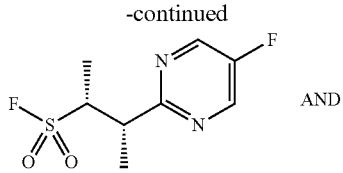

AND

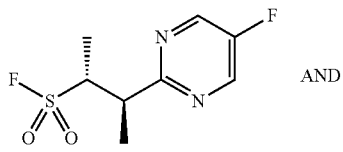

AND

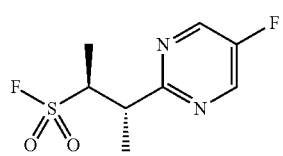

(2S,3S)-3-(5-fluoropyrimidin-2-yl)butane-2-sulfonyl fluoride and (2R,3R)-3-(5-fluoropyrimidin-2-yl) butane-2-sulfonyl fluoride and (2S,3R)-3-(5-fluoropyrimidin-2-yl)butane-2-sulfonyl fluoride and (2R,3S)-3-(5-fluoropyrimidin-2-yl)butane-2-sulfonyl fluoride, Example 432.0

To a solution of (2S,3S)-3-(5-fluoropyrimidin-2-yl)butane-2-sulfonic acid and (2R,3S)-3-(5-fluoropyrimidin-2-yl) butane-2-sulfonic acid and (2R,3R)-3-(5-fluoropyrimidin-2-yl)butane-2-sulfonic acid and (2S,3R)-3-(5-fluoropyrimidin-2-yl)butane-2-sulfonic acid (0.389 g, 1.66 mmol) (Prepared using the general procedures described in Example 7.0 and 10.0) in DCM (8 mL, 1.66 mmol) was added dropwise (diethylamino)sulfur trifluoride (0.44 mL, 3.32 mmol, commercially available from Sigma-Aldrich Chemical Company, Inc.) at 0° C. The mixture was stirred at RT for 18 h. The mixture was cooled by an ice bath and silica gel was added to quench the reaction. The mixture was concentrated and the residue was directly loaded onto a plug of silica gel and purified by chromatography through a Redi-Sep pre-packed silica gel column, eluting with a gradient of 0-100% EtOAc in hexanes, to give 432.0 (0.264 g, 1.12 mmol, 67% yield). LCMS-ESI (POS.) m/z: 237.1 (M+H)⁺.

Example 433.0: Preparation of (2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide and (2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide and (2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide and (2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide (2R,3S)—N-(4-(2,6-dimethoxyphenyl)-5-(6-methoxypyridin-2-yl)-4H-1,2,4-triazol-3-yl)-3-hydroxy-4,4-dimethyl-N-(2-(trimethylsilyl)ethyl)pentane-2-sulfonamide and (2R,3R)—N-(4-(2,6-dimethoxyphenyl)-5-(6-methoxypyridin-2-yl)-4H-1,2,4-triazol-3-yl)-3-hydroxy-4,4-dimethyl-N-(2-(trimethylsilyl)ethyl)pentane-2-sulfonamide and (2S,3S)—N-(4-(2,6-dimethoxyphenyl)-5-(6-methoxypyridin-2-yl)-4H-1,2,4-triazol-3-yl)-3-hydroxy-4,4-dimethyl-N-(2-(trimethylsilyl)ethyl)pentane-2-sulfonamide and (2S,3R)—N-(4-(2,6-dimethoxyphenyl)-5-(6-methoxypyridin-2-yl)-4H-1,2,4-triazol-3-yl)-3-hydroxy-4,4-dimethyl-N-(2-(trimethylsilyl)ethyl)pentane-2-sulfonamide, Example 433.1

To a stirred solution of 5.0 (200 mg, 0.39 mmol) in THF (1.9 mL) at −78° C. was added n-butyllithium (2.5M, 231 µL, 0.58 mmol). The reaction was stirred for 10 min and then pivaldehye (0.064 mL, 0.58 mmol) was added and the reaction stirred for 1 h at −78° C. Next, a saturated solution of ammonium chloride was added to quench the reaction and the resulting mixture was warmed to RT. The reaction mixture was extracted with EtOAc. The material thus obtained was purified on silica gel eluting with 0-20% EtOAc in hexane to give the desired compound 433.1 (0.165 g, 0.27 mmol, 71% yield). LCMS-ESI (POS.) m/z: 606.3 (M+H)+.

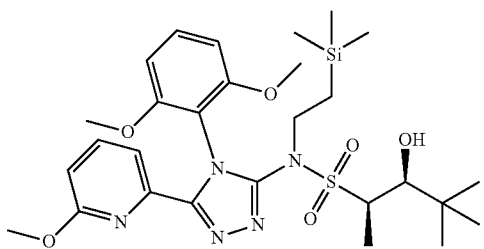

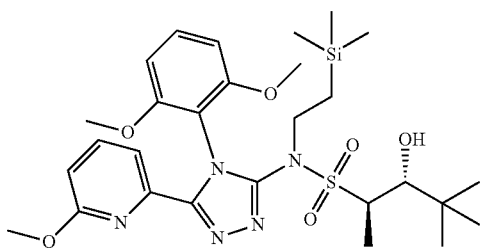



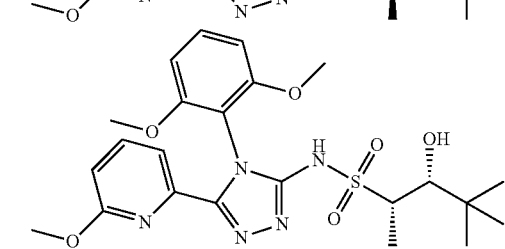

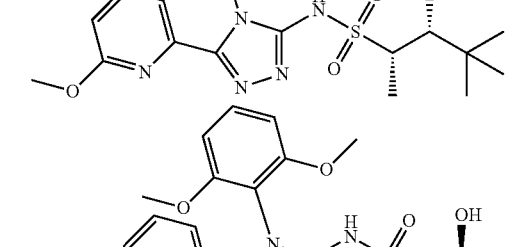

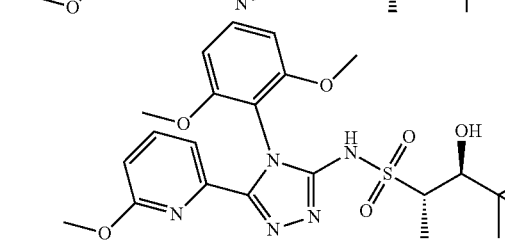

(2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide and (2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide and (2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide and (2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, Example 433.0

To a vial containing 433.1 (0.165 g, 0.27 mmol) was added DMF (1.36 mL) followed by tris(dimethylamino)sulfonium difluorotrimethylsilicate, TASF (0.225 g, 0.82 mmol). The mixture was carefully heated at 60° C. with stirring. After 4 h, the mixture was cooled to RT and water was added. The reaction mixture was extracted with EtOAc and concentrated in vacuo. The product thus obtained was purified on silica gel eluting with 0-70% of EtOAc in heptanes to afford 433.0 as a white solid (38.6 mg, 0.076 mmol, 28% yield) as a racemic mixture of diastereomers in a ratio of 2.6:1 (as determined by $^1$H NMR, syn: anti). $^1$H NMR (500 MHz, CD$_2$Cl$_2$) δ=10.98 (br. s., 1H), 7.67-7.61 (m, 1H), 7.61-7.57 (m, 1H), 7.43-7.36 (m, 1H), 6.73-6.70 (m, 1H), 6.70-6.65 (m, 2H), 4.12 (d, J=4.9 Hz, 0.28H), 3.93 (dd, J=0.7, 2.4 Hz, 0.72H), 3.77 (s, 2.16H), 3.72 (d, J=1.7 Hz, 1.68H), 3.69 (s, 2.16H), 3.36 (dd, J=4.9, 6.8 Hz, 0.28H), 3.20-3.16 (m, 0.72H), 3.15 (s, 3H), 3.12 (t, J=7.0 Hz, 0.28H), 2.72 (d, J=2.4 Hz, 0.72H), 1.40 (d, J=6.8 Hz, 0.84H), 1.33 (d, J=7.1 Hz, 2.16H), 0.93 (s, 2.52H), 0.91 (s, 6.48H). LCMS-ESI (POS.) m/z: 506.3 (M+H)$^+$.

Example 434.0: Preparation of (2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide

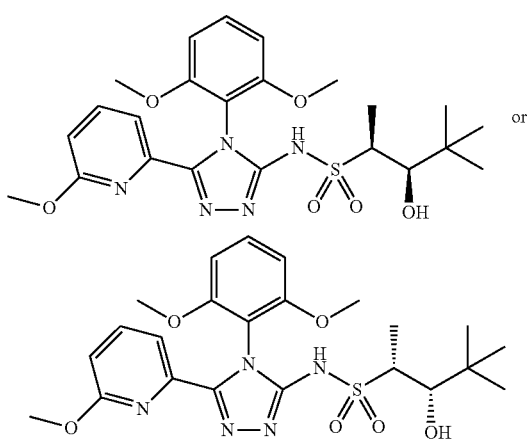

434.0

(2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, Example 434.0

The mixture of diastereomers 433.0 was purified on an AD-H column eluting with isocratic 20% EtOH (+20 mM NH$_3$) to give the first eluting peak as 434.0 (99% ee, 0.035 g, 0.069 mmol). $^1$H NMR (500 MHz, CD$_2$Cl$_2$) δ=7.67-7.59 (m, 2H), 7.40 (t, J=8.4 Hz, 1H), 6.71 (dd, J=1.1, 7.9 Hz, 1H), 6.70-6.65 (m, 2H), 3.95 (s, 1H), 3.76 (s, 3H), 3.70 (s, 3H), 3.21-3.16 (m, 1H), 3.15 (s, 3H), 2.87-2.71 (m, 1H), 1.34 (d, J=7.1 Hz, 3H), 0.91 (s, 9H). LCMS-ESI (POS.) m/z: 506.3 (M+H)$^+$.

Example 435.0: Preparation of (2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide

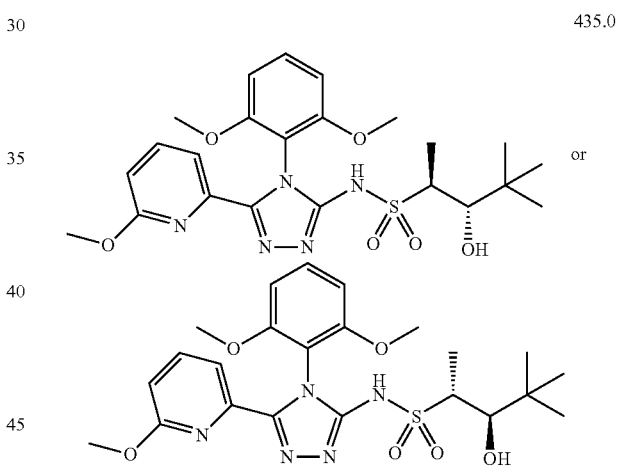

435.0

(2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, Example 435.0

The mixture of diastereomers 433.0 was purified on a AD-H column eluting with isocratic 20% EtOH (+20 mM NH$_3$) to give the second eluting peak as 435.0 (98% ee, 0.008 g, 0.016 mmol). $^1$H NMR (500 MHz, CD$_2$Cl$_2$) δ=11.19-10.85 (m, 1H), 7.67-7.62 (m, 1H), 7.61-7.58 (m, 1H), 7.39 (t, J=8.6 Hz, 1H), 6.71 (dd, J=1.0, 8.1 Hz, 1H), 6.67 (d, J=8.6 Hz, 2H), 4.13 (d, J=4.4 Hz, 1H), 3.72 (s, 3H), 3.72 (s, 3H), 3.36 (dd, J=4.3, 6.7 Hz, 1H), 3.15 (s, 3H), 3.14-3.10 (m, 1H), 1.41 (d, J=7.1 Hz, 3H), 0.93 (s, 9H). LCMS-ESI (POS.) m/z: 506.3 (M+H)$^+$.

Example 436.0: Preparation of (2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide Example 437.0: Preparation of (2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide

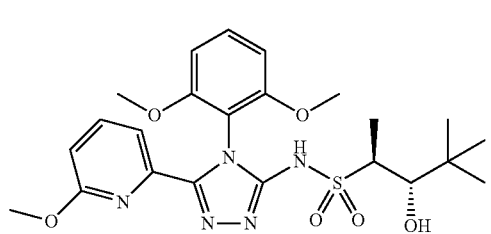

436.0 or

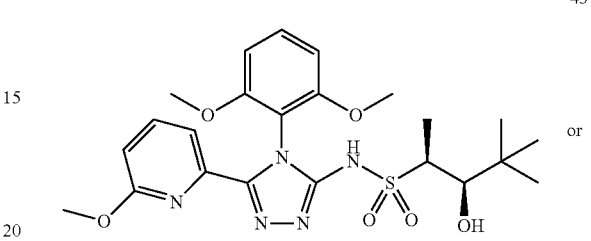

437.0 or

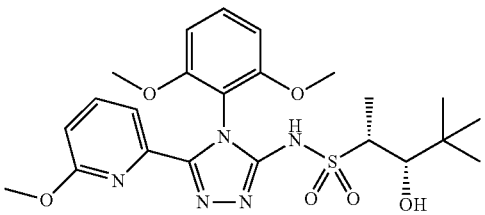

(2S,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, Example 436.0

(2S,3R)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide or (2R,3S)—N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, Example 437.0

The mixture of diastereomers 433.0 was purified on an AD-H column eluting with isocratic 20% EtOH (+20 mM NH$_3$) to give the a mixture of two diastereomers eluting as overlapping peaks (elution third and forth peaks respectively). The mixture was further purified on a AD-H column eluting with isocratic 30% MeOH (+20 mM NH$_3$) to give the second eluting peak as 436.0 (95.2% ee, 0.0104 g, 0.021 mmol). $^1$H NMR (500 MHz, CD$_2$Cl$_2$) δ=7.65-7.58 (m, 2H), 7.38 (t, J=8.4 Hz, 1H), 6.70 (d, J=8.1 Hz, 1H), 6.66 (d, J=8.6 Hz, 2H), 3.71 (s, 6H), 3.36 (d, J=6.6 Hz, 1H), 3.19-3.09 (m, 4H), 1.40 (d, J=7.1 Hz, 3H), 0.93 (s, 9H). LCMS-ESI (POS.) m/z: 506.3 (M+H)$^+$.

The mixture of diastereomers 433.0 was purified on a AD-H column eluting with isocratic 20% EtOH (+20 mM NH$_3$) to give the a mixture of two diastereomers eluting as overlapping peaks (elution third and forth peaks respectively). The mixture was further purified on a AD-H column eluting with isocratic 30% MeOH (+20 mM NH$_3$) to give the first eluting peak as 437.0 (95.2% ee, 0.0104 g, 0.021 mmol). $^1$H NMR (500 MHz, CD$_2$Cl$_2$) δ=7.67-7.58 (m, 2H), 7.39 (t, J=8.6 Hz, 1H), 6.71 (dd, J=1.2, 7.8 Hz, 1H), 6.67 (t, J=9.0 Hz, 2H), 3.95 (s, 1H), 3.76 (s, 3H), 3.70 (s, 3H), 3.19 (q, J=6.8 Hz, 1H), 3.15 (s, 3H), 1.34 (d, J=6.8 Hz, 3H), 0.91 (s, 9H). LCMS-ESI (POS.) m/z: 506.3 (M+H)$^+$.

Example 438.0: Preparation of (2R,3S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide and (2S,3S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide and (2R,3R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide and (2S,3R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide (2R,3S)-1-cyclopropyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2R,3R)-1-cyclopropyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2S,3S)-1-cyclopropyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2S,3R)-1-cyclopropyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide, Example 438.1

To a stirred solution of N-(4-(2,6-dimethoxyphenyl)-5-(6-methoxypyridin-2-yl)-4H-1,2,4-triazol-3-yl)-N-(2-(trimethylsilyl)ethyl)ethanesulfonamide 5.0 (200 mg, 0.39 mmol) in THF (1924 µL) −78° C. was added n-butyllithium (2.5 M, 231 µL, 0.58 mmol). The reaction was stirred for 10 min and then cyclopropanecarbaldehyde (0.040 g, 0.58 mmol) was added and the reaction stirred for 1 h at −78° C. Next, a saturated solution of ammonium chloride was added to quench the reaction, and the reaction was warmed to RT. The reaction mixture was extracted with EtOAc. The material thus obtained was purified on silica gel eluting with 0-20% EtOAc in hexane to give the desired compound 438.1. (0.135 g, 0.23 mmol, 60% yield). LCMS-ESI (POS.) m/z: 590.3 (M+H)$^+$.

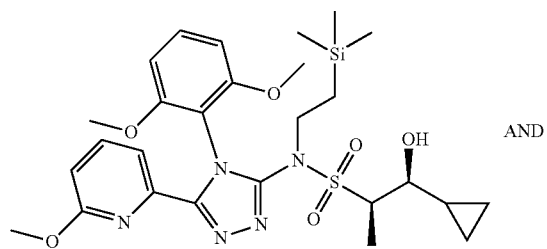

433.0

AND

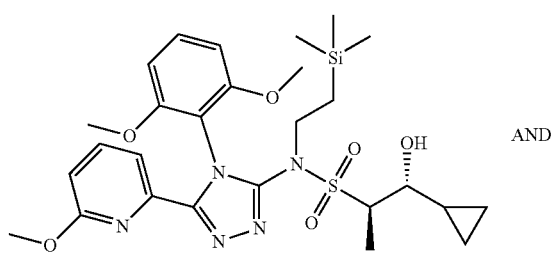

AND

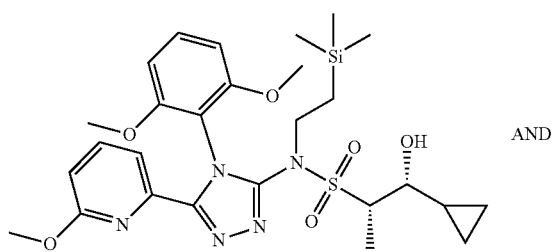

AND

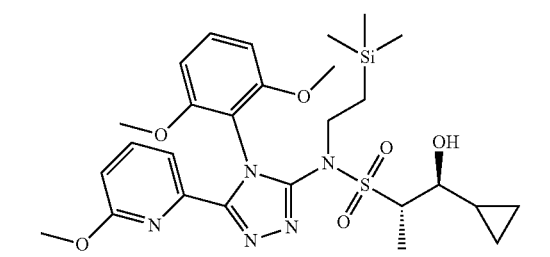

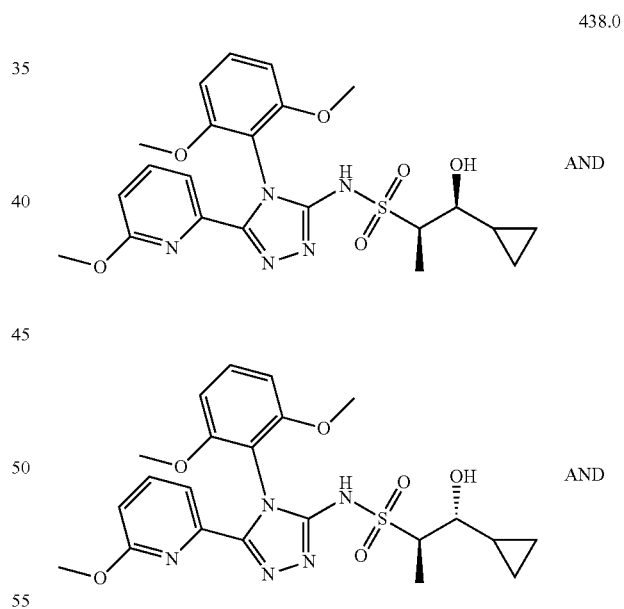

438.0

AND

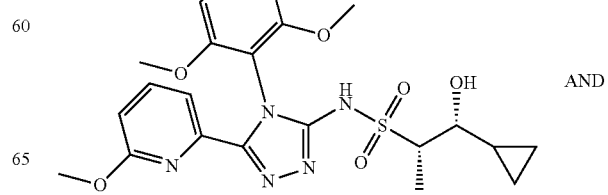

AND

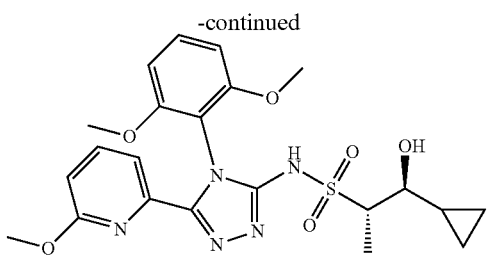

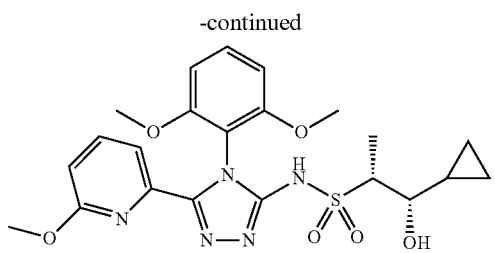

(2R,3S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide and (2S,3S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide and (2R,3R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide and (2S,3R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, Example 438.0

To a vial containing 438.1 (0.165 g, 0.27 mmol) was added DMF (1.14 mL) followed by tris(dimethylamino)sulfonium difluorotrimethylsilicate, TASF (0.189 g, 0.69 mmol). The mixture was carefully heated to 60° C. and stirring was continued. After 4 h, the mixture was cooled to RT and water was added. The reaction mixture was extracted with EtOAc and concentrated in vacuo. The initially obtained product was purified on silica gel eluting with 0-70% of EtOAc in heptane to afford 438.0 as a white solid (100 mg, 0.20 mmol, 89% yield) as a racemic mixture of diastereomers in a ratio of ~2:1 (as determined by 1H NMR, syn: anti). $^1$H NMR (500 MHz, CD$_2$Cl$_2$) δ=10.96 (br. s., 1H), 7.67-7.61 (m, 1H), 7.61-7.57 (m, 1H), 7.39 (t, J=8.4 Hz, 1H), 6.71 (dd, J=1.0, 8.3 Hz, 1H), 6.70-6.64 (m, 2H), 4.02 (d, J=2.0 Hz, 0.3H), 3.77 (s, 2H), 3.73 (s, 1H), 3.71 (s, 1H), 3.70 (s, 2H), 3.46-3.42 (m, 0.7H), 3.20-3.16 (m, 0.3H), 3.16-3.13 (m, 3H), 3.12 (d, J=1.2 Hz, 0.7H), 3.10 (dd, J=1.1, 7.0 Hz, 1H), 1.40-1.36 (m, 3H), 0.92-0.81 (m, 1H), 0.59-0.29 (m, 3H), 0.18-0.10 (m, 1H). LCMS-ESI (POS.) m/z: 490.3 (M+H)$^+$.

Example 439.0: Preparation of (1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide 439.0

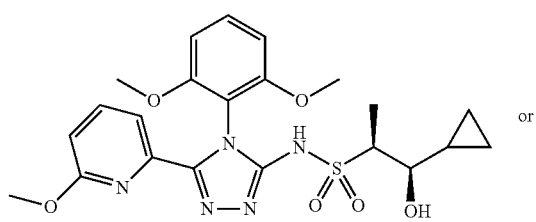

or (1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, Example 439.0

The mixture of diastereomers 438.0 was purified on a Thar 350 SFC with 250×30 mm IC columns at 55 g/min MeOH(+20 mM NH$_3$)+45 g/min CO$_2$, 55% co-solvent, at 100 g/min. Outlet pressure=100 bar; Temperature.=22° C.; Wavelength=297 nm. Injected 0.4 mL of 100 mg sample in 11 mL (6:5) MeOH:DCM (9.1 mg/mL), i.e. 3.6 mg per injection to give the first eluting peak as 439.0 (99% ee, 0.024 g, 0.048 mmol). $^1$H NMR (500 MHz, CD$_2$Cl$_2$) δ=10.95 (br. s., 1H), 7.67-7.57 (m, 2H), 7.39 (t, J=8.4 Hz, 1H), 6.72 (dd, J=1.0, 8.1 Hz, 1H), 6.67 (ddd, J=0.9, 8.5, 15.8 Hz, 2H), 3.77 (s, 3H), 3.70 (s, 3H), 3.44 (dd, J=1.1, 8.4 Hz, 1H), 3.15 (s, 3H), 3.09 (dq, J=1.2, 7.0 Hz, 1H), 1.38 (d, J=7.1 Hz, 3H), 0.86 (tq, J=5.1, 8.1 Hz, 2H), 0.57-0.51 (m, 1H), 0.45-0.33 (m, 2H), 0.18-0.09 (m, 1H). LCMS-ESI (POS.) m/z: 490.3 (M+H)$^+$.

Example 440.0: Preparation of (1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide 440.0

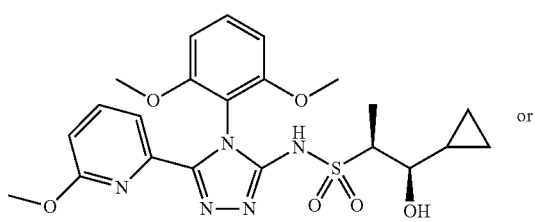

or

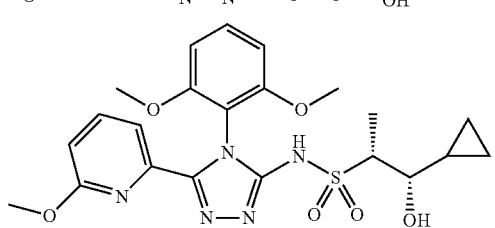

(1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, Example 440.0

The mixture of diastereomers 438.0 was purified on a Thar 350 SFC with 250×30 mm IC columns at 55 g/min MeOH(+20 mM NH$_3$)+45 g/min CO$_2$, 55% co-solvent, at 100 g/min. Outlet pressure=100 bar; Temperature.=22° C.; Wavelength=297 nm. Injected 0.4 mL of 100 mg sample in 11 mL (6:5) MeOH:DCM (9.1 mg/mL), i.e. 3.6 mg per injection to give the fourth eluting peak as 440.0 (98% ee, 0.024 g, 0.048 mmol). $^1$H NMR (500 MHz, CD$_2$Cl$_2$) δ=10.95 (br. s., 1H), 7.67-7.57 (m, 2H), 7.39 (t, J=8.6 Hz, 1H), 6.72 (dd, J=1.0, 8.1 Hz, 1H), 6.70-6.63 (m, 2H), 3.77 (s, 3H), 3.70 (s, 3H), 3.44 (dd, J=1.0, 8.3 Hz, 1H), 3.15 (s, 3H), 3.12-3.05 (m, 1H), 1.38 (d, J=7.1 Hz, 3H), 0.91-0.79 (m, 4H), 0.57-0.51 (m, 1H), 0.44-0.34 (m, 2H), 0.18-0.11 (m, 1H). LCMS-ESI (POS.) m/z: 490.3 (M+H)$^+$. The minor diastereomers were not isolated.

Example 441.0: Preparation of (2R,3S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide and (2S,3S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide and (2R,3R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide and (2S,3R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide

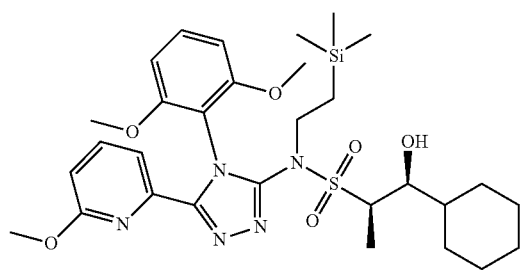

AND

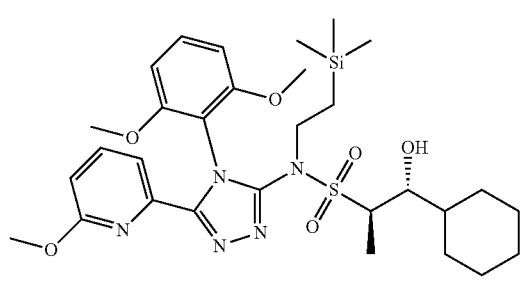

AND

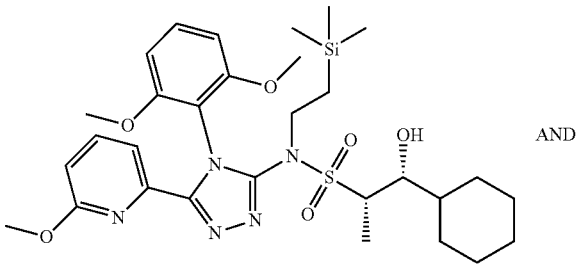

5.0

AND

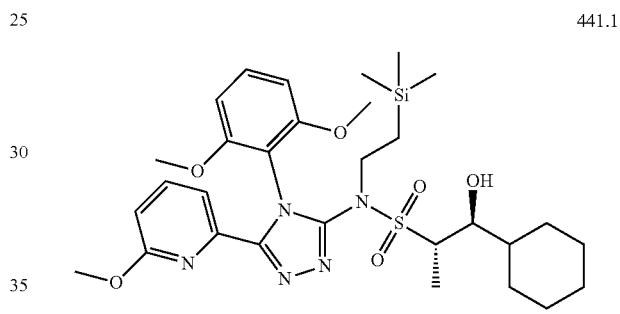

441.1

(2R,3S)-1-cyclohexpyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2R,3R)-1-cyclohexpyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2S,3S)-1-cyclohexpyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2S,3R)-1-cyclohexpyl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide, Example 441.1

To a stirred solution of N-(4-(2,6-dimethoxyphenyl)-5-(6-methoxypyridin-2-yl)-4H-1,2,4-triazol-3-yl)-N-(2-(trimethylsilyl)ethyl)ethanesulfonamide 5.0 (200 mg, 0.39 mmol) in THF (1.92 mL) at −78° C. was added n-butyllithium (2.5 M, 231 μL, 0.577 mmol). The reaction was stirred for 10 min, afterwhich cyclohexanescarbaldehyde (0.040 g, 0.577 mmol) was added and the reaction stirred for 1 h at −78° C. Next, a saturated solution of ammonium chloride was added to quench and the reaction was warmed to RT. The reaction mixture was extracted with EtOAc. The material thus obtained was purified on silica gel eluting with 0-20% EtOAc in hexane to give the desired compound 441.1. (0.169 g, 0.27 mmol, 70% yield). LCMS-ESI (POS.) m/z: 632.3 (M+H)$^+$.

441.0

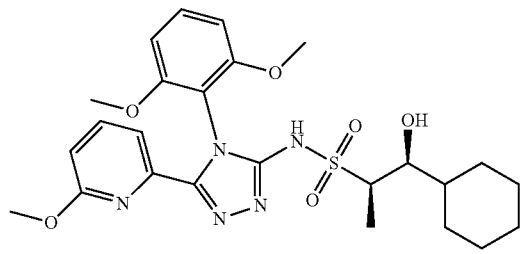

AND

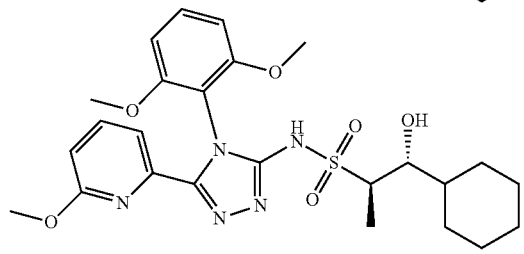

AND

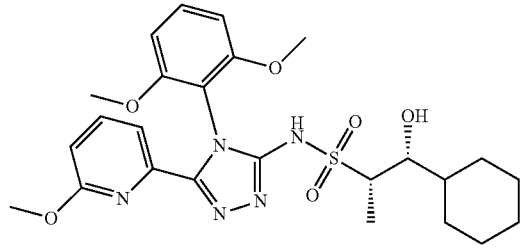

AND

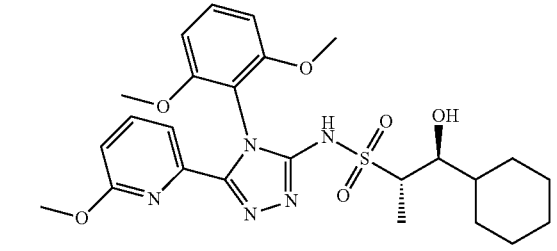

(2R,3S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide and (2S,3S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide and (2R,3R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide and (2S,3R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, Example 441.0

To a vial containing 441.1 (0.169 g, 0.27 mmol) was added DMF (1.34 mL) followed by tris(dimethylamino)sulfonium difluorotrimethylsilicate, TASF (0.221 g, 0.80 mmol). The mixture was carefully heated to 60° C. and stirring was continued. After 4 h, the mixture was cooled to RT and water was added. The reaction mixture was then extracted with EtOAc and concentrated in vacuo. The product was purified on silica gel eluting with 0-70% of EtOAc in heptane to afford 441.0 as a white solid (110 mg, 0.207 mmol, 77% yield) and a mixture of diastereomers in a ratio of ~3.3:1 (as determined by 1H NMR, syn:anti). $^1$H NMR (500 MHz, CD$_2$Cl$_2$) δ=10.98 (br. s., 1H), 7.67-7.61 (m, 1H), 7.61-7.57 (m, 1H), 7.42-7.35 (m, 1H), 6.71 (dd, J=0.7, 8.1 Hz, 1H), 6.69-6.63 (m, 2H), 3.83 (dd, J=0.9, 9.2 Hz, 0.8H), 3.76 (s, 2.4H), 3.72 (d, J=5.1 Hz, 1.2H), 3.70 (s, 2.4H), 3.58 (d, J=8.6 Hz, 0.2H), 3.15 (s, 3H), 3.11-3.05 (m, 1H), 2.05 (d, J=13.0 Hz, 1H), 1.79-1.67 (m, 2H), 1.63 (d, J=10.5 Hz, 1H), 1.54-1.40 (m, 2H), 1.33-1.08 (m, 6H), 0.89 (dquin, J=3.4, 12.6 Hz, 2H). LCMS-ESI (POS.) m/z: 532.3 (M+H)$^+$.

Example 442.0: Preparation of (1R,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide 442.0

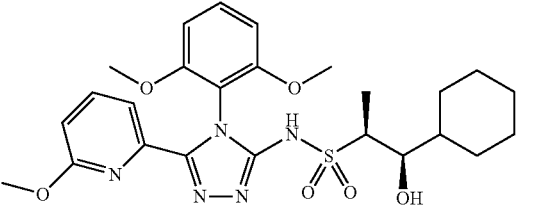

or

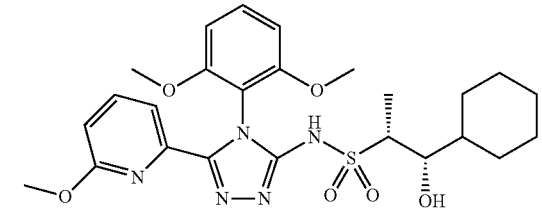

(1R,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide or (1S,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, Example 442.0

The mixture of diastereomers 441.0 was purified on a SFC instrument on a AS-H column at 25% MeOH/CO$_2$, 100 bar; 70 mL/min, 220 nm; to give the first eluting peak 442.0 (99% ee, 0.037 g, 0.070 mmol). $^1$H NMR (500 MHz, CD$_2$Cl$_2$) δ=7.66-7.59 (m, 2H), 7.39 (t, J=8.6 Hz, 1H), 6.71 (dd, J=1.5, 7.6 Hz, 1H), 6.69-6.63 (m, 2H), 3.86 (d, J=9.3 Hz, 1H), 3.75 (s, 3H), 3.70 (s, 3H), 3.15 (s, 3H), 3.10 (q, J=6.8 Hz, 1H), 2.07 (d, J=13.0 Hz, 1H), 1.76-1.67 (m, 2H), 1.63 (d, J=11.0 Hz, 1H), 1.51 (d, J=12.5 Hz, 1H), 1.35-1.10 (m, 7H), 0.97-0.83 (m, 2H). LCMS-ESI (POS.) m/z: 532.3 (M+H)$^+$.

Example 443.0: Preparation of (1R,2S)-1-cyclo-
hexyl-N-(4-(2,6-dimethoxyphenyl)-5-(6-methoxy-2-
pyridinyl)-4H-1,2,4-triazol-3-yl)-1-hydroxy-2-pro-
panesulfonamide or (1S,2R)-1-cyclohexyl-N-(4-(2,
6-dimethoxyphenyl)-5-(6-methoxy-2-pyridinyl)-4H-
1,2,4-triazol-3-yl)-1-hydroxy-2-propanesulfonamide Example 444.0: Preparation of (1S,2S)—N-(4-(2,6-
dimethoxyphenyl)-5-(6-methoxy-2-pyridinyl)-4H-1,
2,4-triazol-3-yl)-1-hydroxy-1-(tetrahydro-2H-pyran-
4-yl)-2-propanesulfonamide and (1R,2R)—N-(4-(2,
6-dimethoxyphenyl)-5-(6-methoxy-2-pyridinyl)-4H-
1,2,4-triazol-3-yl)-1-hydroxy-1-(tetrahydro-2H-
pyran-4-yl)-2-propanesulfonamide and (1R,2S)—N-
(4-(2,6-dimethoxyphenyl)-5-(6-methoxy-2-
pyridinyl)-4H-1,2,4-triazol-3-yl)-1-hydroxy-1-
(tetrahydro-2H-pyran-4-yl)-2-propanesulfonamide
and (1S,2R)—N-(4-(2,6-dimethoxyphenyl)-5-(6-
methoxy-2-pyridinyl)-4H-1,2,4-triazol-3-yl)-1-hy-
droxy-1-(tetrahydro-2H-pyran-4-yl)-2-propanesulfo-
namide

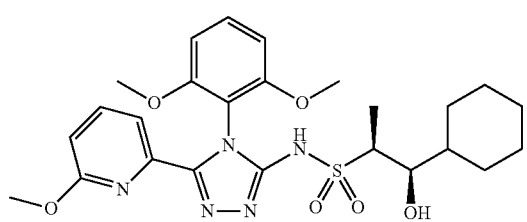

443.0 or

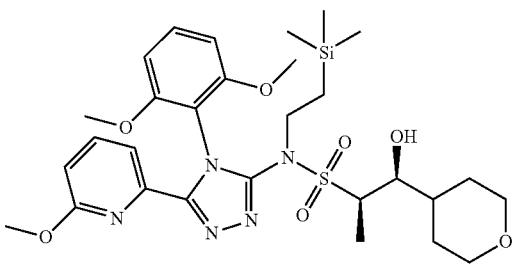

AND

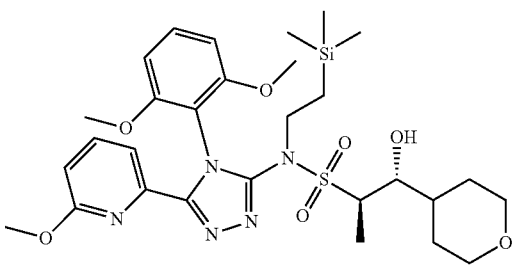

AND (1R,2S)-1-cyclohexyl-N-(4-(2,6-dimethoxyphenyl)-
5-(6-methoxy-2-pyridinyl)-4H-1,2,4-triazol-3-yl)-1-
hydroxy-2-propanesulfonamide or (1S,2R)-1-cyclo-
hexyl-N-(4-(2,6-dimethoxyphenyl)-5-(6-methoxy-2-
pyridinyl)-4H-1,2,4-triazol-3-yl)-1-hydroxy-2-
propanesulfonamide, Example 443.0

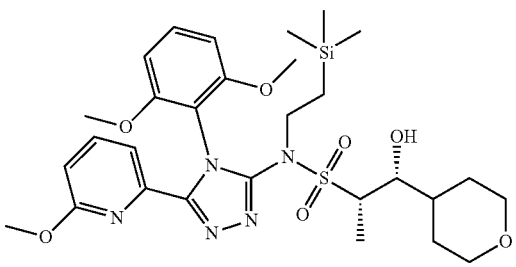

AND

The mixture of diastereomers 441.0 was purified on a SFC instrument on a AS-H column at 25% MeOH/CO$_2$, 100 bar; 70 mL/min, 220 nm; to give the fourth eluting peak as 443.0 (99% ee, 0.036 g, 0.068 mmol). $^1$H NMR (500 MHz, CD$_2$Cl$_2$) δ=7.67-7.59 (m, 2H), 7.39 (t, J=8.6 Hz, 1H), 6.71 (dd. J=1.3, 7.5 Hz, 1H), 6.67 (t, J=8.4 Hz, 2H), 3.86 (d, J=9.3 Hz, 1H), 3.76 (s, 3H), 3.70 (s, 3H), 3.15 (s, 3H), 3.11 (q, J=6.8 Hz, 1H), 2.07 (d, J=12.7 Hz, 1H), 1.71 (d, J=11.2 Hz, 2H), 1.63 (d, J=11.2 Hz, 1H), 1.51 (d, J=12.5 Hz, 1H), 1.36-1.10 (m, 7H), 0.97-0.83 (m, 2H). LCMS-ESI (POS.) m/z: 532.3 (M+H)$^+$.

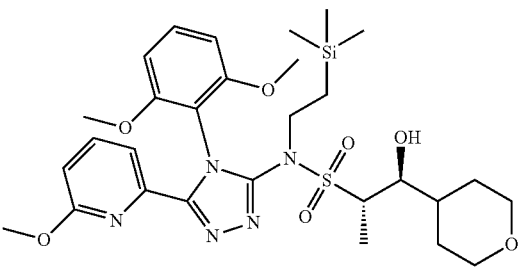

677

(2R,3S)-1-tetrahydro-2H-pyran-4-yl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2R,3R)-1-tetrahydro-2H-pyran-4-yl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2S,3S)-1-tetrahydro-2H-pyran-4-yl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide and (2S,3R)-1-tetrahydro-2H-pyran-4-yl-N-(4-(2,6-dimethoxyphenyl)-5-(6-methoxypyridin-2-yl)-4H-1,2,4-triazol-3-yl)-1-hydroxy-N-(2-(trimethylsilyl)ethyl)propane-2-sulfonamide, Example 444.1

To a stirred solution of N-(4-(2,6-dimethoxyphenyl)-5-(6-methoxypyridin-2-yl)-4H-1,2,4-triazol-3-yl)-N-(2-(trimethylsilyl)ethyl)ethanesulfonamide 5.0 (200 mg, 0.389 mmol) in THF (1.92 mL) at −78° C. was added n-butyllithium (2.5M, 231 µL, 0.58 mmol). The reaction was stirred for 10 min and then 4-formyltetrahydropyran (Frontier Scientific, 0.066 g, 0.577 mmol) was added and the reaction stirred for 1 h at −78° C. Next, a saturated solution of ammonium chloride was added to quench the reaction, and the reaction was warmed to RT. The reaction mixture was extracted with EtOAc. The material thus obtained was purified on silica gel eluting with 0-20% EtOAc in hexane to give the desired compound 444.1 (0.17 g, 0.27 mmol, 70% yield). LCMS-ESI (POS.) m/z: 634.4 (M+H)+.

444.0

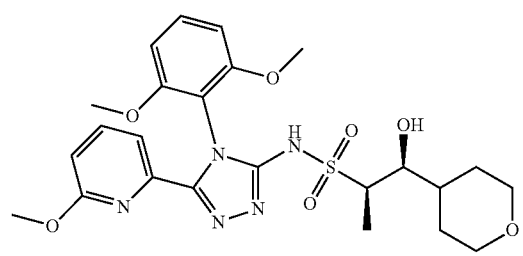

AND

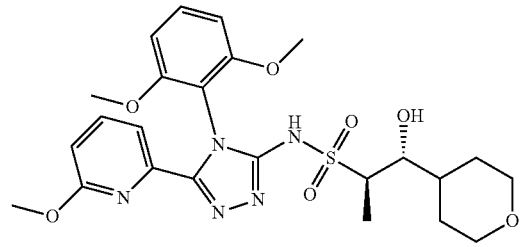

AND

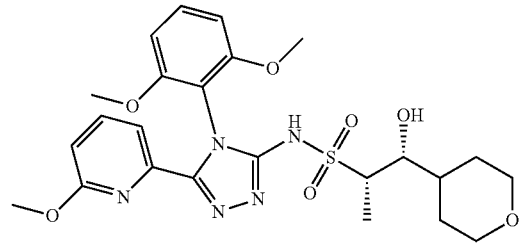

AND

678

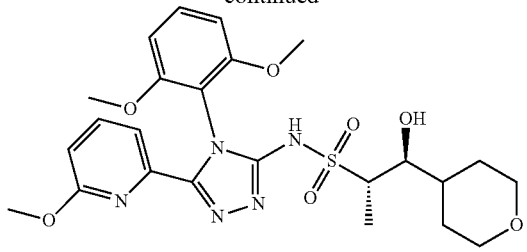

(2R,3S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide and (2S,3S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide and (2R,3R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide and (2S,3R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, Example 444.0

To a vial containing 444.1 (0.17 g, 0.27 mmol) was added DMF (1.34 mL) followed by tris(dimethylamino)sulfonium difluorotrimethylsilicate, TASF (0.222 g, 0.81 mmol). The mixture was carefully heated to 60° C. and stirring was continued. After 4 h, the mixture was cooled to RT and water was added. The reaction mixture was extracted with EtOAc and concentrated in vacuo. The residue was purified on silica gel eluting with 0-70% EtOAc in heptanes to afford 444.0 as a white solid (100 mg, 0.19 mmol, 70% yield) and a mixture of diastereomers in a ratio of ~3.3:1 (as determined by $^1$H NMR, syn:anti $^1$H NMR (400 MHz, CD$_2$Cl$_2$) δ=10.98 (br. s., 1H), 7.68-7.56 (m, 2H), 7.43-7.35 (m, 1H), 6.74-6.70 (m, 1H), 6.72 (dd, J=1.0, 8.0 Hz, 1H), 6.69-6.63 (m, 2H), 4.03-3.85 (m, 3H), 3.76 (s, 2.3H), 3.73 (s, 0.7H), 3.71 (s, 0.7H), 3.70 (s, 2.3H), 3.59-3.52 (m, 0.3H), 3.30 (tt, J=2.7, 11.8 Hz, 2H), 3.21 (d, J=1.4 Hz, 0.7H), 3.15 (s, 3H), 3.10-2.99 (m, 1H), 1.95-1.86 (m, 1H), 1.82-1.63 (m, 1H), 1.61-1.46 (m, 1H), 1.36-1.16 (m, 5H). LCMS-ESI (POS.) m/z: 534.2 (M+H)+.

Example 445.0: Preparation of (1S,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide 445.0

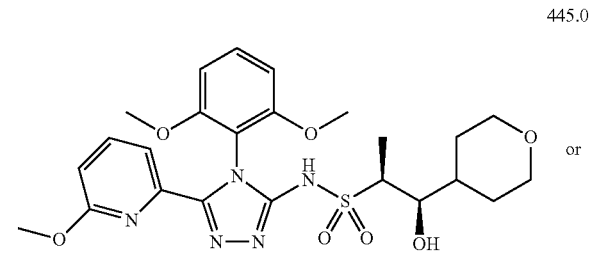

or

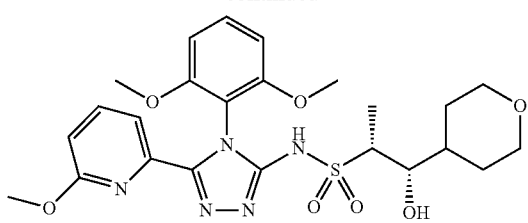

(1S,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, Example 445.0

The mixture of diastereomers 444.0 was purified on an SFC instrument on a IA-H column at 25% MeOH/CO$_2$, 100 bar; 60 mL/min, 220 nm; to give the first eluting peak, which was a mixture of two diastereomers. This mixture was further purified on a SFC instrument on a AS-H column at 25% EtOH/CO$_2$, 100 bar; 65 mL/min, 220 nm; to give the second eluting peak as 445.0 (99% ee, 0.035 g, 0.066 mmol). $^1$H NMR (400 MHz, CD$_2$Cl$_2$) δ=7.39 (t, J=8.5 Hz, 1H), 6.71 (dd, J=1.0, 8.0 Hz, 1H), 6.69-6.63 (m, 2H), 3.95-3.89 (m, 2H), 3.89-3.85 (m, 1H), 3.76 (s, 3H), 3.70 (s, 3H), 3.35-3.25 (m, 2H), 3.18-3.12 (m, 3H), 3.07-2.99 (m, 1H), 1.91 (dd, J=1.9, 13.6 Hz, 1H), 1.61-1.47 (m, 2H), 1.37-1.20 (m, 5H). LCMS-ESI (POS.) m/z: 534.2 (M+H)$^+$.

Example 446.0: Preparation of (1S,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide 446.0

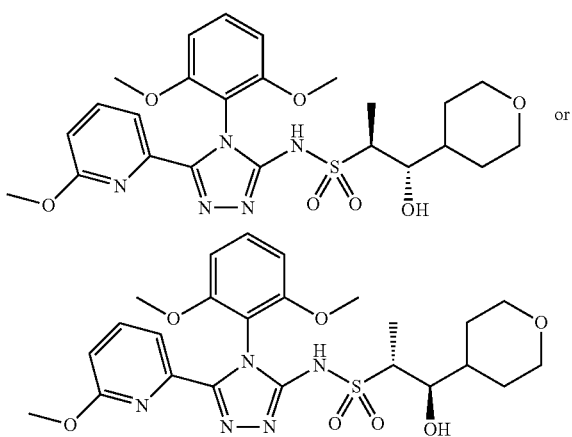

(1S,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, Example 446.0

The mixture of diastereomers 444.0 was purified on a SFC instrument on a IA-H column at 25% MeOH/CO$_2$, 100 bar; 60 mL/min, 220 nm; to give the first eluting peak, which was a mixture of two diastereomers. This mixture was further purified on an SFC instrument on a AS-H column at 25% EtOH/CO$_2$, 100 bar; 65 mL/min, 220 nm; to give the second eluting peak as 446.0 (99% ee, 0.023 g, 0.043 mmol). $^1$H NMR (400 MHz, CD$_2$Cl$_2$) δ=7.68-7.56 (m, 2H), 7.39 (t, J=8.5 Hz, 1H), 6.72 (dd, J=1.0, 8.0 Hz, 1H), 6.69-6.63 (m, 2H), 3.97-3.87 (m, 2H), 3.73 (s, 3H), 3.71 (s, 3H), 3.56 (dd, J=3.4, 8.1 Hz, 1H), 3.38-3.24 (m, 2H), 3.15 (s, 3H), 3.08 (quin, J=7.2 Hz, 1H), 1.83-1.65 (m, 2H), 1.59 (dq, J=4.5, 12.3 Hz, 1H), 1.43-1.32 (m, 2H), 1.32-1.28 (m, 3H). LCMS-ESI (POS.) m/z: 534.2 (M+H)$^+$.

Example 447.0: Preparation of (1S,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide

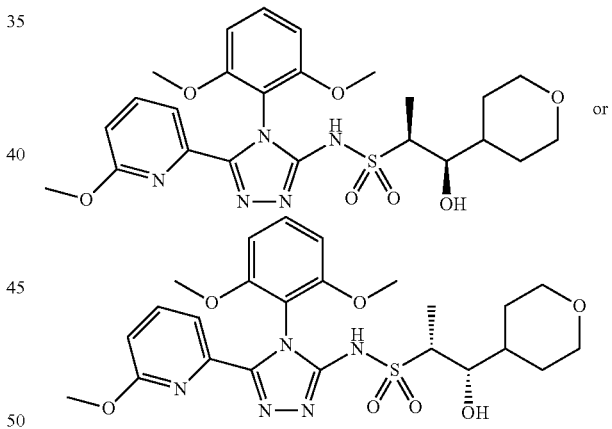

(1S,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, Example 447.0

The mixture of diastereomers 444.0 was purified on an SFC instrument on a IA-H column at 25% MeOH/CO$_2$, 100 bar; 60 mL/min, 220 nm; to give the second eluting peak as 447.0 (98% ee, 0.035 g, 0.066 mmol). $^1$H NMR (400 MHz, CD$_2$Cl$_2$) δ=7.67-7.56 (m, 1H), 7.67-7.56 (m, 2H), 7.37 (t, J=8.5 Hz, 1H), 6.73-6.61 (m, 3H), 3.97-3.84 (m, 3H), 3.74 (s, 3H), 3.70 (s, 3H), 3.36-3.23 (m, 2H), 3.15 (s, 3H), 3.10-2.96 (m, 2H), 1.92 (d, J=13.1 Hz, 1H), 1.54 (d, J=9.2 Hz, 1H), 1.42-1.14 (m, 6H). LCMS-ESI (POS.) m/z: 534.2 (M+H)+.

Example 448.0: Preparation of (1S,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide 448.0

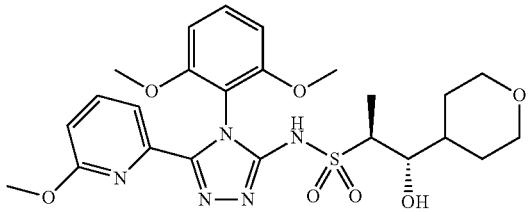

or

(1S,2S)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, Example 448.0

The mixture of diastereomers 444.0 was purified on an SFC instrument on a IA-H column at 25% MeOH/CO$_2$, 100 bar; 60 mL/min, 220 nm; to give the third eluting peak as 448.0 (97% ee, 0.010 g, 0.019 mmol). $^1$H NMR (400 MHz, CD$_2$Cl$_2$) δ=7.61 (d, J=9.4 Hz, 2H), 7.38 (t, J=8.4 Hz, 1H), 6.74-6.61 (m, 3H), 3.91 (d, J=10.6 Hz, 2H), 3.71 (d, J=4.5 Hz, 6H), 3.58 (dd, J=3.3, 7.0 Hz, 1H), 3.38-3.25 (m, 3H), 3.15 (s, 3H), 3.11 (d, J=7.2 Hz, 1H), 1.83-1.51 (m, 3H), 1.47-1.35 (m, 2H), 1.28 (d, J=6.8 Hz, 3H). LCMS-ESI (POS.) m/z: 534.2 (M+H)+.

Example 449.0: Preparation of (2S,3R)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide and (2R,3S)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide 449.0

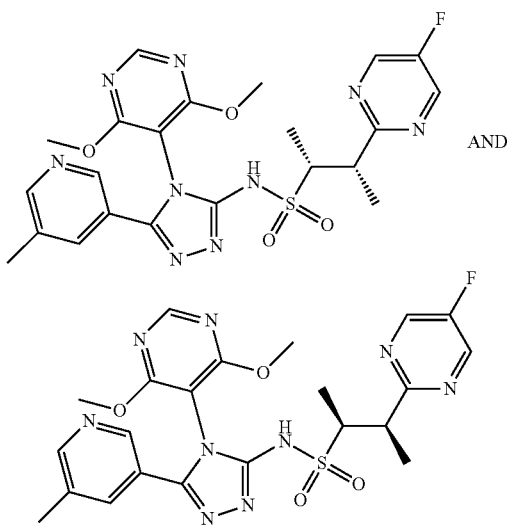

(2S,3R)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide and (2R,3S)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide, Example 449.0

To a solution of 5-isothiocyanato-4,6-dimethoxypyrimidine (0.047 g, 0.24 mmol) and 10.1 (80% ee, 0.05 g, 0.214 mmol) in ACN (0.43 mL) was added cesium carbonate (0.091 g, 0.28 mmol). The reaction was stirred at 23° C. for 16 h. To the reaction mixture was added silver(I) nitrate (0.073 g, 0.43 mmol) and 5-methylnicotinohydrazide (0.032 g, 0.21 mmol). The reaction was stirred for a further 10 mins at 23° C. The reaction was then filtered through a plug of silica gel and concentrated in vacuo. The material thus obtained was placed in 1,4-dioxane (2.14 mL) and TFA (0.099 mL, 1.28 mmol) was added. The resulting mixture was stirred at 90° C. for 16 h. The reaction was then concentrated in vacuo and neutralised by the addition of an aqueous solution of sodium bicarbonate. The resulting mixture was extracted with EtOAc, dried over magnesium sulfate, filtered and concentrated in vacuo. The material thus obtained was purified on silica gel eluting with 0-50% EtOAc/EtOH (3/1) in hexanes to give 449.0 (80% ee, 0.041 g, 36% yield). $^1$H NMR (500 MHz, CD$_2$Cl$_2$) δ=11.07 (br. s., 1H), 8.55 (s, 2H), 8.51-8.47 (m, 2H), 8.36 (d, J=2.0 Hz, 1H), 7.61 (dt, J=0.9, 2.1 Hz, 1H), 3.95 (s, 3H), 3.93 (s, 3H), 3.81-3.69 (m, 2H), 2.32 (d, J=0.7 Hz, 3H), 1.35 (d, J=7.1 Hz, 3H), 1.32 (d, J=6.8 Hz, 3H). LCMS-ESI (POS.) m/z: 530.3 (M+H)+.

Example 450.0: Preparation of (2S,3R)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide

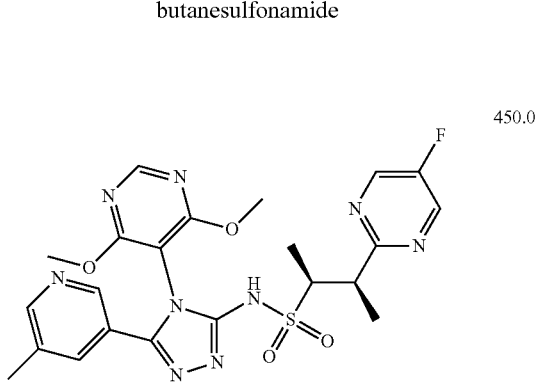

450.0

(2S,3R)—N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide, Example 450.0

The mixture of diastereomers 449.0 was purified on a Thar 80 SFC with 250×21 mm AD-H column with 14 g/min EtOH (20 mM Ammonia)+40 g/min $CO_2$, 27% co-solvent at 55 g/min. Temperature.=22° C., Outlet pressure=100 bar, Wavelength=215 nm. Injected 0.3 mL of 40 mg sample dissolved in 4 mL of MeOH/DCM (50% DCM), c=10 mg/mL i.e. 3 mg per injection. Cycle time 5.5 min, run time=12 min to give 450.0 (99% ee, 19.0 mg, 0.036 mmol). $^1$H NMR (400 MHz, $CD_2Cl_2$) δ=11.08-10.83 (m, 1H), 8.55 (s, 2H), 8.51-8.47 (m, 2H), 8.36 (d, J=2.0 Hz, 1H), 7.61 (dt, J=0.8, 2.2 Hz, 1H), 3.95 (s, 3H), 3.93 (s, 3H), 3.82-3.67 (m, 2H), 2.32 (d, J=0.8 Hz, 3H), 1.35 (d, J=6.8 Hz, 3H), 1.32 (d, J=6.8 Hz, 3H). LCMS-ESI (POS.) m/z: 530.3 $(M+H)^+$.

Example 451.0: Preparation of (2S,3R)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butanesulfonamide and (2R,3S)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butanesulfonamide

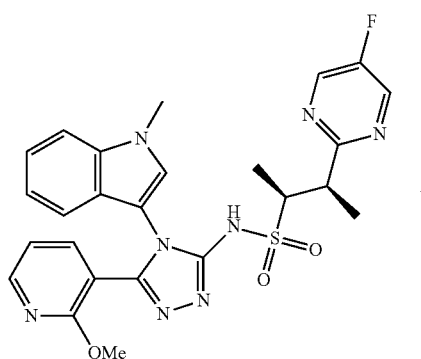

451.0

AND

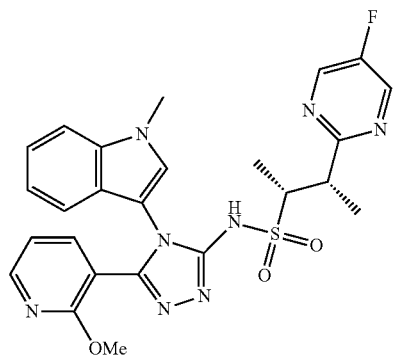

(2S,3R)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butanesulfonamide and (2R,3S)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butanesulfonamide, Example 451.0

To a solution of 1.3 (0.05 g, 0.27 mmol) and 10.1 (80% ee, 0.062 g, 0.27 mmol) in ACN (0.531 mL) was added cesium carbonate (0.113 g, 0.35 mmol). The reaction was stirred at 23° C. for 16 h. To the reaction mixture was added silver(I) nitrate (0.090 g, 0.53 mmol) and 6-methoxypicolinohydrazide (0.044 g, 0.27 mmol). Stirring was continued for 10 mins at 23° C. The reaction was filtered through a plug of silica gel and concentrated in vacuo. The reaction mixture was then placed in 1,4-dioxane (2.65 mL) and TFA (0.123 mL, 1.59 mmol) was added. The reaction was stirred at 90° C. for 16 h. Next, an aqueous solution of sodium hydrogen bicarbonate was added to the reaction mixture. The mixture was extracted with EtOAc and the organic layers were concentrated in vacuo. The material thus obtained was purified on silica gel eluting with EtOAc/EtOH (3/1) in hexanes to give 451.0 (80% ee, 0.082 g, 58% yield). $^1$H NMR (500 MHz, $CD_2Cl_2$) δ=11.22-10.98 (m, 1H), 8.51 (s, 2H), 7.63-7.58 (m, 1H), 7.55-7.51 (m, 1H), 7.41-7.36 (m, 1H), 7.30 (d, J=8.1 Hz, 1H), 7.26 (ddd, J=1.0, 7.2, 8.3 Hz, 1H), 7.23 (s, 1H), 7.07 (ddd, J=0.9, 7.1, 7.9 Hz, 1H), 6.65 (dd, J=0.7, 8.3 Hz, 1H), 3.84-3.79 (m, 3H), 3.75-3.67 (m, 2H), 2.83 (s, 3H), 1.30 (d, J=6.4 Hz, 3H), 1.27 (d, J=6.8 Hz, 3H). LCMS-ESI (POS.) m/z: 537.2 $(M+H)^+$.

Example 452.0: Preparation of (2S,3R)—N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide and (2R,3S)—N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide

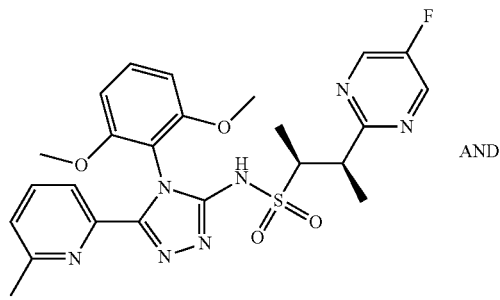

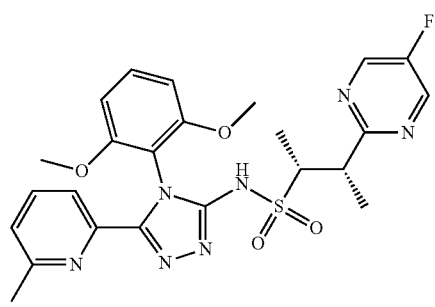

(2S,3R)—N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide and (2R,3S)—N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide, Example 452.0

To a solution of 1.0 (0.046 g, 0.24 mmol) and 10.1 (80% ee, 0.05 g, 0.21 mmol) in ACN (0.43 mL) was added cesium carbonate (0.091 g, 0.279 mmol). The reaction was stirred at 23° C. for 16 h. To the reaction mixture was added silver(I) nitrate (0.073 g, 0.43 mmol), 6-methylpicolinohydrazide (0.032 g, 0.21 mmol). Stirring was continued for 10 min at 23° C. Next, the reaction was filtered through a plug of silica gel and concentrated in vacuo. The material thus obtained was dissolved in 1,4-dioxane (2.1 mL), and TFA (0.165 mL, 2.14 mmol) was added. The reaction was stirred at 90° C. for 16 h. An aqueous solution of sodium hydrogen bicarbonate was then added to the reaction mixture. The mixture was extracted with EtOAc and the organic layers were concentrated in vacuo and purified on silica gel eluting with 0-60% EtOAc/EtOH (3/1) in heptanes to give 452.0 (80% ee, 0.02 g, 17.6% yield). $^1$H NMR (500 MHz, $CD_2Cl_2$) δ=11.03 (br. s., 1H), 8.54 (s, 2H), 7.65-7.57 (m, 2H), 7.42 (t, J=8.4 Hz, 1H), 7.14-7.08 (m, 1H), 6.68-6.60 (m, 2H), 3.78-3.72 (m, 2H), 3.71-3.70 (m, 3H), 3.71 (s, 3H), 3.68 (s, 3H), 2.16 (s, 3H), 1.34 (d, J=7.1 Hz, 3H), 1.31 (d, J=6.8 Hz, 3H). LCMS-ESI (POS.) m/z: 528.2 (M+H)$^+$.

Example 453.0: Preparation of (2S,3R)—N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide

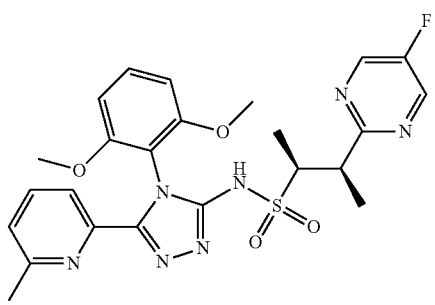

(2S,3R)—N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide, Example 453.0

To a solution of 1.0 (0.088 g, 0.450 mmol) and 10.1 (99% ee, 0.1 g, 0.43 mmol) in ACN (0.86 mL) was added cesium carbonate (0.182 g, 0.56 mmol). The reaction was stirred at 23° C. for 16 h. To the reaction mixture was added silver(I) nitrate (0.146 g, 0.86 mmol) and 6-methylpicolinohydrazide (0.065 g, 0.43 mmol). Stirring was continued for 10 min at 23° C. Next, the reaction was filtered through a plug of silica gel and concentrated in vacuo. The material thus obtained was dissolved in 1,4-dioxane (1.23 mL,) and methane sulfonic acid (0.083 mL, 1.29 mmol) was added. The reaction was then stirred at 90° C. for 3 h. The pH was then carefully adjusted with dropwise addition of a saturated aqueous sodium bicarbonate solution to pH-7. After extracting three times with DCM, the organic layers were combined and then dried over anhydrous magnesium sulfate. The product thus obtained was loaded onto a silica gel column then purified (0-80% EtOAc/EtOH (3/1) in hexanes) to give a white solid 453.0 (0.026 g, 0.049 mmol, 12% yield). LCMS-ESI (POS.) m/z: 528.2 (M+H)$^+$.

Example 454.0: Preparation of (2S,3R)—N-(5-(6-chloro-2-pyridinyl)-4-(2,6-dimethoxyphenyl)-4H-1,2,4-triazol-3-yl)-3-(5-fluoro-2-pyrimidinyl)-2-butanesulfonamide

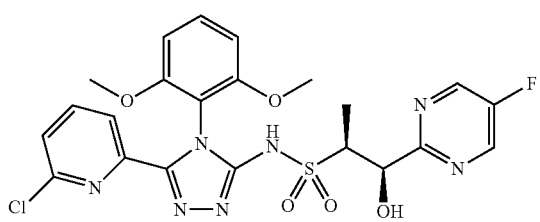

(Z)-2-(6-chloropicolinoyl)-N'-(2,6-dimethoxyphenyl)-N-(((2S,3R)-3-(5-fluoropyrimidin-2-yl)butan-2-yl)sulfonyl)hydrazinecarboximidamide, Example 454.0

The title compound was prepared following Example A using 1.0, 10.1 (0.15 g, 0.350 mmol) and 6-chloropicolinohydrazide (0.060 g, 0.350 mmol) to give a white solid 454.0 (0.05 g, 0.091 mmol, 33% yield). $^1$H NMR (400 MHz, CD$_2$Cl$_2$) δ=11.20-11.00 (m, 1H), 8.54 (s, 2H), 7.80 (dd, J=0.8, 7.6 Hz, 1H), 7.70 (t, J=7.8 Hz, 1H), 7.45 (t, J=8.5 Hz, 1H), 7.30 (dd, J=0.9, 7.9 Hz, 1H), 6.68 (dd, J=6.7, 7.7 Hz, 2H), 3.78-3.75 (m, 1H), 3.74 (s, 3H), 3.71 (s, 3H), 3.80-3.70 (m, 8H), 1.34 (d, J=6.8 Hz, 3H), 1.31 (d, J=6.8 Hz, 3H). LCMS-ESI (POS.) m/z: 548.2 (M+H)$^+$.

Example 455.0: Preparation of (2S,3R)—N-(4-(2,6-dimethoxyphenyl)-5-(6-phenyl-2-pyridinyl)-4H-1,2,4-triazol-3-yl)-3-(5-fluoro-2-pyrimidinyl)-2-butanesulfonamide

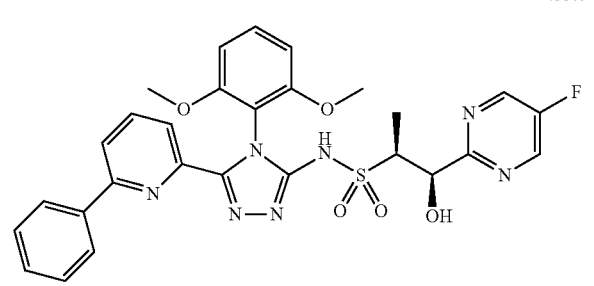

455.0

(2S,3R)—N-(4-(2,6-dimethoxyphenyl)-5-(6-phenyl-2-pyridinyl)-4H-1,2,4-triazol-3-yl)-3-(5-fluoro-2-pyrimidinyl)-2-butanesulfonamide, Example 455.0

454.0 (0.033 g, 0.060 mmol), phenylboronic acid (0.015 g, 0.12 mmol), tricyclohexylphosphine (3.38 mg, 0.012 mmol), and Pd$_2$(dba)$_3$ (5.51 mg, 6.02 μmop were added to a vial which was then degassed and backfilled with nitrogen. To the vial were added 1,4-dioxane (1.0 mL) and aqueous potassium phosphate tribasic (0.015 mL, 0.181 mmol) by syringe. The resulting reaction was heated at 100° C. for 2 h. The reaction mixture was then cooled to RT. The organics were concentrated under reduced pressure. The residue was filtered through a plug of silica gel, then loaded onto a silica gel column (0-20% EtOAc in heptanes) to afford 455.0 (0.0041 g, 6.77 μmol, 11.2% yield). $^1$H NMR (500 MHz, CD$_2$Cl$_2$) δ=10.98 (br. s., 1H), 8.53 (s, 2H), 7.78 (dd, J=7.6, 8.3 Hz, 1H), 7.56 (dd, J=0.7, 7.6 Hz, 1H), 7.31-7.24 (m, 3H), 7.18-7.13 (m, 1H), 6.95 (dd, J=0.7, 8.3 Hz, 1H), 6.76-6.70 (m, 2H), 6.47-6.40 (m, 2H), 3.75-3.64 (m, 2H), 3.55 (s, 3H), 3.52 (s, 3H), 1.31 (d, J=6.8 Hz, 3H), 1.27 (d, J=6.6 Hz, 3H). LCMS-ESI (POS.) m/z: 590.0 (M+H)$^+$.

Example 456.0: Preparation of (2S,3R)—N-(4-(2,6-dimethoxyphenyl)-5-(1-oxido-6-phenyl-2-pyridinyl)-4H-1,2,4-triazol-3-yl)-3-(5-fluoro-2-pyrimidinyl)-2-butanesulfonamide

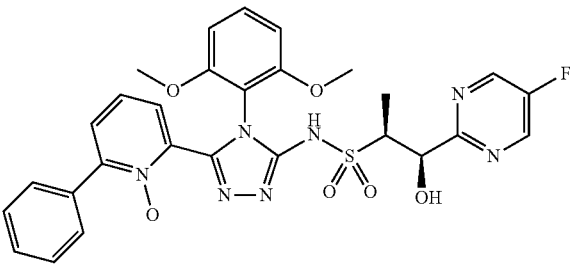

456.0

(2S,3R)—N-(4-(2,6-dimethoxyphenyl)-5-(1-oxido-6-phenyl-2-pyridinyl)-4H-1,2,4-triazol-3-yl)-3-(5-fluoro-2-pyrimidinyl)-2-butanesulfonamide, Example 456.0

Further elution under the conditions described in 455.0 gave 456.0 (0.0057 g, 9.67 μmol, 16% yield). $^1$H NMR (500 MHz, CD$_2$Cl$_2$) δ=11.29-10.92 (m, 1H), 8.55 (s, 2H), 7.95 (dd, J=0.7, 7.8 Hz, 1H), 7.84 (t, J=7.9 Hz, 1H), 7.77 (dd, J=0.9, 7.9 Hz, 1H), 7.49 (t, J=8.6 Hz, 1H), 7.38-7.32 (m, 3H), 7.32-7.27 (m, 2H), 6.76-6.70 (m, 2H), 3.80-3.72 (m, 2H), 3.70 (s, 3H), 3.66 (s, 3H), 1.35 (d, J=6.8 Hz, 3H), 1.32 (d, J=6.6 Hz, 3H). LCMS-ESI (POS.) m/z: 606.2 (M+H)$^+$.

Example 457.0: Preparation of (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide and (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide

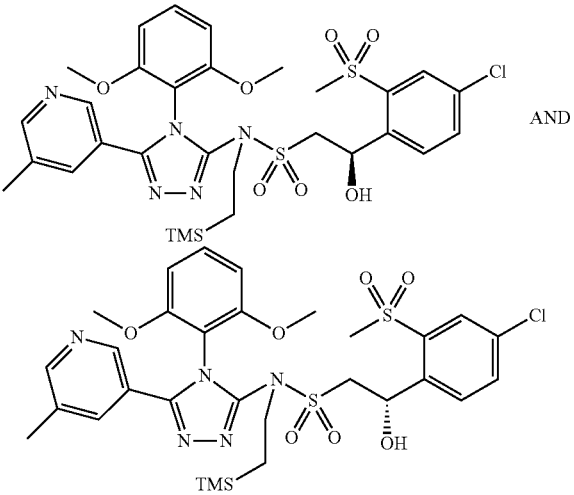

457.1

AND (2R)-2-(4-chloro-2-(methylsulfonyl)phenyl)-N-(4-(2,6-dimethoxyphenyl)-5-(5-methylpyridin-3-yl)-4H-1,2,4-triazol-3-yl)-2-hydroxy-N-(2-(trimethylsilyl)ethyl)ethanesulfonamide and (2S)-2-(4-chloro-2-(methylsulfonyl)phenyl)-N-(4-(2,6-dimethoxyphenyl)-5-(5-methylpyridin-3-yl)-4H-1,2,4-triazol-3-yl)-2-hydroxy-N-(2-(trimethylsilyl)ethyl)ethanesulfonamide, Example 457.1

To a 50-mL round-bottomed flask was added 6.0 (276 mg, 0.56 mmol) in THF (5 mL). tert-Butyllithium (1.7 M solution in pentane (0.398 mL, 0.676 mmol)) was added dropwise via syringe under N₂ at −78° C. with stirring. The solution was then stirred at −78° C. for 10 min and then 4-chloro-2-(methylsulfonyl)benzaldehyde (commercially available from Matrix Scientific, SC, USA) (136 mg, 0.62 mmol) in THF (1.5 mL) was added dropwise via syringe under N₂ at −78° C. with stirring. The reaction mixture was allowed to warm to 23° C. over 2 h before being quenched with saturated aqueous NH₄Cl. The reaction mixture was diluted with water and extracted with EtOAc. The organic layers were combined and washed with brine and dried over Na₂SO₄. The solution was filtered and concentrated in vacuo to give the initial material as a light-yellow oil, which was purified by silica gel chromatography (a gradient of 0% to 100% EtOAc in DCM) to provide 457.1 (160 mg, 0.226 mmol, 40.1% yield) as a light-yellow solid. LCMS-ESI (POS), m/z: 708.2 (M+H)⁺.

457.0

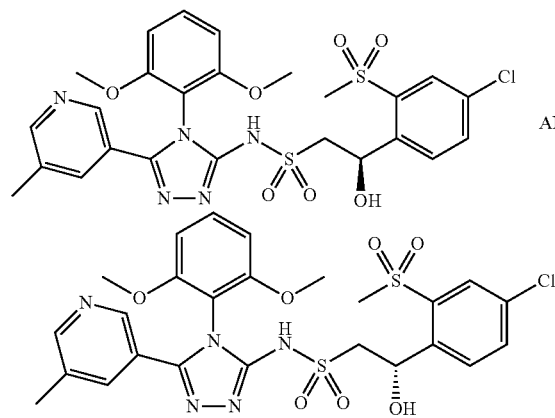

(2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide and (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, Example 457.0

The title compound was prepared from 457.1 by deprotection as described in Example 264.0. The title compound 457.0 was obtained as a TFA salt. ¹H NMR (500 MHz, CD₃OD) δ 8.54 (s, 1H), 8.40 (s, 1H), 7.97 (d, J=2.45 Hz, 1H), 7.84-7.88 (m, 2H), 7.74 (dd, J=8.44, 2.32 Hz, 1H), 7.55 (t, J=8.34 Hz, 1H), 6.82-6.87 (m, 2H), 6.01 (dd, J=7.82, 4.40 Hz, 1H), 3.84 (s, 3H), 3.79 (s, 3H), 3.54-3.60 (m, 1H), 3.45-3.52 (m, 1H), 3.13 (s, 3H), 2.37 (s, 3H). LCMS-ESI (POS), m/z: 608.2 (M+H)⁺.

Example 458.0: Preparation of (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide 458.0

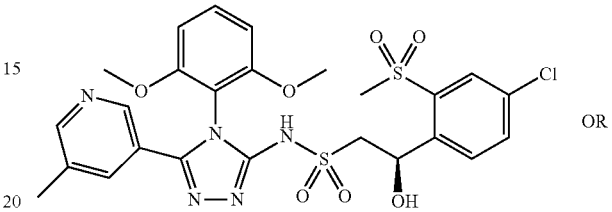

OR

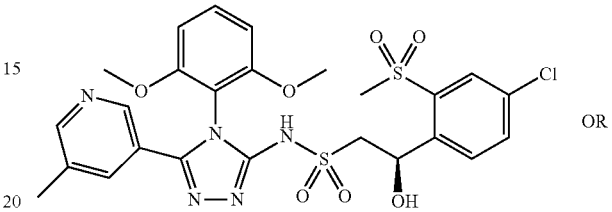

(2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, Example 458.0

The title compound was the first isomer to elute from a CC4 column on subjecting 457.0 to the following SFC conditions: Run on Thar 80 SFC with 250×30+150×30 mm CC4 column with 44 g/min MeOH (+20 mM NH₃)+36 g/min CO₂, 55% co-solvent at 80 g/min. Temperature.=27° C., Outlet pressure 99 bar, Wavelength=277 nm. Injected 1.0 mL of 80 mg sample dissolved in 5 mL of MeOH; c=16.0 mg/mL and 16.0 mg per injection. Cycle time=8.0 min, run time 22.0 min. ¹H NMR (500 MHz, CD₃OD) δ 8.41 (br. s., 1H), 8.30 (br. s., 1H), 7.97 (d, J=2.4 Hz, 1H), 7.86 (d, J=8.3 Hz, 1H), 7.74 (dd, J=8.4, 2.3 Hz, 1H), 7.69 (s, 1H), 7.50 (t, J=8.6 Hz, 1H), 6.81 (dd. J=14.5, 8.4 Hz, 2H), 6.03 (t, J=6.0 Hz, 1H), 3.81 (s, 3H), 3.76 (s, 3H), 3.51-3.59 (m, 2H), 3.16 (s, 3H), 2.31 (s, 3H) LCMS-ESI (POS), m/z: 608.2 (M+H)⁺.

Example 459.0: Preparation of (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide

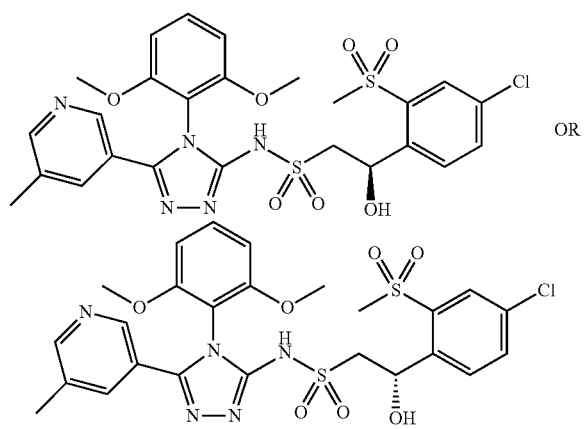

459.0

OR (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, Example 459.0

Example 459.0 was the second isomer to elute from the CC4 column on subjecting 457.0 under the SFC conditions described in Example 458.0. LCMS-ESI (POS), m/z: 608.2 (M+H)$^+$.

Example 460.0: Preparation of N-(4-(2,6-dimethoxyphenyl)-5-(5-methyl-3-pyridinyl)-4H-1,2,4-triazol-3-yl)-2-06R)-3,6-dimethyl-2-oxotetrahydro-1 (2H)-pyrimidinyl)ethanesulfonamide N,N-bis(4-methoxybenzyl)ethenesulfonamide, Example 460.1

To a 1 L round bottomed flask was added bis(4-methoxybenzyl)amine 12.01 (23.16 g, 90 mmol) and TEA (anhydrous (43.8 mL, 315 mmol)) in DCM (200 mL). At 0° C. (ice bath), 2-chloro-1-ethanesulfonyl chloride (10.41 mL, 99 mmol) in DCM (100 mL) was added dropwise with stirring. The reaction mixture was stirred at 0° C. for 3 h after completion of the addition. LCMS analysis indicated the reaction was complete. The reaction mixture was diluted with water and extracted with DCM. The organic extract was washed with brine and dried over Na$_2$SO$_4$. The solution was filtered and concentrated in vacuo to give the initial material as a light-yellow oil, which was purified by silica gel chromatography (a gradient of 0-60% EtOAc in hexanes), to provide 460.1 (23 g, 66.2 mmol, 74% yield) as a white solid. LCMS-ESI (POS), m/z: 370.1 (M+Na)$^+$.

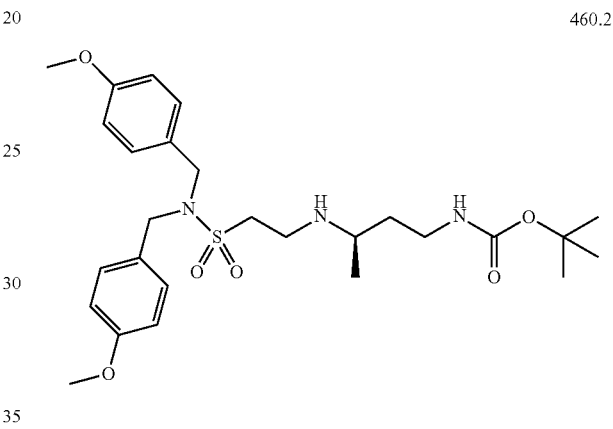

460.2

(R)-tert-butyl (3-((2-(N,N-bis(4-methoxybenzyl)sulfamoyl)ethyl)amino)butyl)carbamate, Example 460.2

To a 250-mL round-bottomed flask was added 460.1 (0.463 g, 1.33 mmol) and (R)-tert-butyl (3-aminobutyl)carbamate (commercially available from J & W PharmLab LLC, PA, USA) (0.251 g, 1.33 mmol) in MeOH (8 mL). The reaction mixture was stirred at 60° C. under N$_2$ for 16 h. The reaction mixture solution was concentrated in vacuo to afford the initial material of 460.2 as a colorless film, which was directly used in the next step without purification. LCMS-ESI (POS), m/z: 536.3 (M+H)$^+$.

460.1

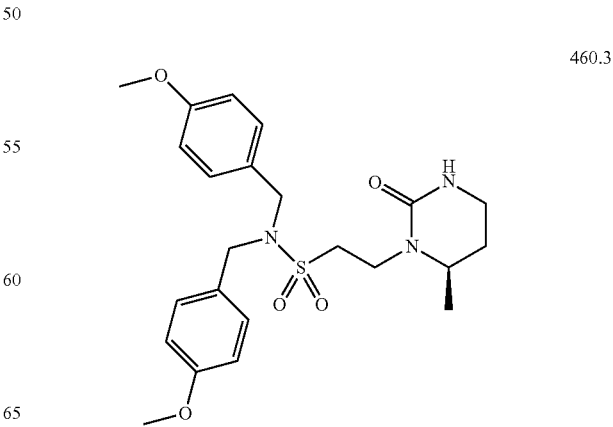

460.3

(R)—N,N-bis(4-methoxybenzyl)-2-(6-methyl-2-oxotetrahydropyrimidin-1(2H)-yl)ethanesulfonamide, Example 460.3

To a 250-mL flask was added 460.2 (0.714 g, 1.33 mmol) in DCM (6 mL). Hydrochloric acid (4.0M solution in 1,4-dioxane, 5.00 mL, 20.0 mmol) was added at 23° C. with stirring. The reaction mixture was then stirred at 23° C. for 20 min. LCMS analysis indicated the reaction was complete. The reaction solution was then concentrated in vacuo. The residue was co-evaporated with toluene in vacuo two times before the following step. To a 250-mL round-bottomed flask was added the initial product and DIEA (1.04 mL, 6.66 mmol) in 1,4-dioxane (30 mL). 1,1'-Carbonyldiimidazole (0.4 M in DCM) (3.67 mL, 1.47 mmol) was added dropwise with stirring. The resulting solution was stirred at 23° C. for 15 h. LCMS indicated formation of the desired product along with un-cyclized intermediate. The reaction mixture was stirred at 90° C. for 90 min. LCMS analysis then showed that the reaction was complete. The reaction mixture was diluted with water and extracted with DCM. The organic extract was washed with brine and dried over Na$_2$SO$_4$. The solution was filtered and concentrated in vacuo to give the initial material as a light-yellow oil, which was purified by silica gel chromatography (a gradient of 0-100% EtOAc in DCM, with 24% EtOH in EtOAc), to provide 460.3 (0.42 g, 0.910 mmol, 68.3% yield) as an off-white solid. LCMS-ESI (POS), m/z: 462.2 (M+H)$^+$.

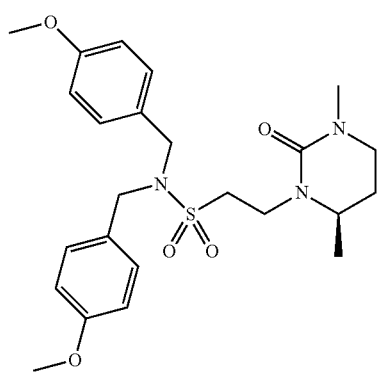

(R)-2-(3,6-dimethyl-2-oxotetrahydropyrimidin-1(2H)-yl)-N,N-bis(4-methoxybenzyl)ethanesulfonamide, Example 460.4

To a 100-mL round bottomed flask was added 460.3 (350 mg, 0.758 mmol) in THF (7 mL). Potassium bis(trimethylsilyl)amide (1.0 M in THF, 1.14 mL, 1.14 mmol)) was added at −78° C. with stirring under N$_2$. The reaction mixture was stirred at −78° C. for 5 min and then iodomethane (0.061 mL, 0.986 mmol) was added. The reaction mixture was then stirred and allowed to warm to 23° C. over 3 h. LCMS analysis indicated the reaction was complete. The reaction mixture was diluted with saturated aqueous NaHCO$_3$ at −78° C. and then extracted with EtOAc. The organic extract was washed with brine and dried over Na$_2$SO$_4$. The solution was filtered and concentrated in vacuo to give the initial material as a light-yellow oil, which was purified by silica gel chromatography (a gradient of 0-100% EtOAc in DCM), to provide 460.4 (300 mg, 0.631 mmol, 83% yield) as an off-white solid. 1H NMR (500 MHz, CDCl$_3$) δ 1.17 (d, J=6.60 Hz, 3H), 1.58-1.72 (m, 1H), 2.05-2.21 (m, 1H), 2.93 (s, 3H), 3.04-3.17 (m, 2H), 3.28-3.45 (m, 3H), 3.59-3.69 (m, 1H), 3.80 (s, 6H), 3.91-4.03 (m, 1H), 4.16-4.32 (m, 4H), 6.79-6.91 (m, 4H), 7.12-7.25 (m, 4H). LCMS-ESI (POS), m/z: 476.1 (M+H)$^+$.

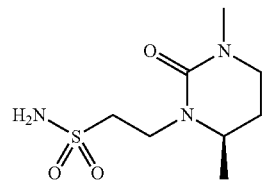

(R)-2-(3,6-dimethyl-2-oxotetrahydropyrimidin-1(2H)-yl)ethanesulfonamide, Example 460.5

To a 250-mL round bottomed flask was added 460.4 (350 mg, 0.74 mmol) in TFA (7 mL). Anisole (0.320 mL, 2.94 mmol) was added at 23° C. with stirring under N$_2$. The reaction mixture was stirred at 23° C. for 19 h. LCMS analysis indicated the reaction was complete. The reaction mixture was concentrated in vacuo and the material thus obtained was purified by silica gel column chromatography using a gradient of 0-100% EtOAc in DCM, to provide 460.5 (180 mg, 0.77 mmol, 100% yield) as a colorless oil. LCMS-ESI (POS), m/z: 236.1 (M+H)$^+$. Note: The purification was conducted on a CombiFlash equipped with an ELSD detector.

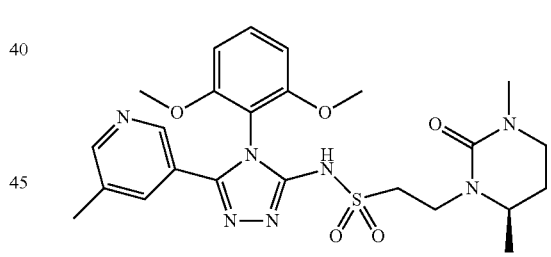

N-(4-(2,6-dimethoxyphenyl)-5-(5-methyl-3-pyridinyl)-4H-1,2,4-triazol-3-yl)-2-06R)-3,6-dimethyl-2-oxotetrahydro-1 (2H)-pyrimidinyl)ethanesulfonamide, Example 460.0

The title compound was prepared from 460.5, 1.0 and 5-methylnicotinohydrazide using the procedure described in Example A. $^1$H NMR (500 MHz, CD$_3$OD) δ 8.50 (s, 1H), 8.37 (s, 1H), 7.81 (br. s., 1H), 7.53 (t, J=8.6 Hz, 1H), 6.83 (dd, J=8.6, 1.7 Hz, 2H), 3.84-3.92 (m, 1H), 3.82 (s, 3H), 3.81 (s, 3H), 3.57-3.65 (m, 1H), 3.44 (td, J=12.0, 4.4 Hz, 1H), 3.35-3.40 (m, 2H), 3.13-3.27 (m, 2H), 2.90 (s, 3H), 2.35 (s, 3H), 2.00-2.12 (m, 1H), 1.64-1.73 (m, 1H), 1.16 (d, J=6.6 Hz, 3H). LCMS-ESI (POS), m/z: 530.2 (M+H)$^+$.

Example 461.0: Preparation of 2-(2-cyano-4-fluoro-phenyl)-N-(4-(2,6-dimethoxyphenyl)-5-(6-oxo-1,6-dihydro-2-pyridinyl)-4H-1,2,4-triazol-3-yl)ethanesulfonamide

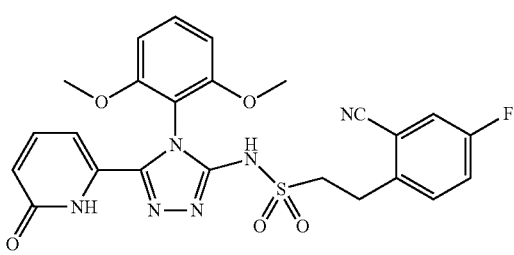

461.0

2-(2-cyano-4-fluorophenyl)-N-(4-(2,6-dimethoxyphenyl)-5-(6-oxo-1,6-dihydro-2-pyridinyl)-4H-1,2,4-triazol-3-yl)ethanesulfonamide, Example 461.0

A glass microwave reaction vessel was charged with 200.0 (50 mg) and pyridine HCl salt (1.5 g, commercially available from Aldrich). The reaction mixture was stirred and heated in a Discover model microwave reactor (CEM, Matthews, N.C.) at 120° C. for 60 min. After this period, LCMS indicated formation of the desired product. The reaction mixture was diluted with water and extracted with DCM. The organic extract was washed with brine and dried over $Na_2SO_4$. The solution was filtered and concentrated in vacuo to give the initial material as a orange oil. The material thus obtained was purified by reverse-phase preparative HPLC using 0.1% TFA in $CH_3CN/H_2O$, gradient 20-80% over 30 min to provide the title compound 461.0 (5 mg, 10% yield) as a white powder. $^1$H NMR (500 MHz, $CD_3OD$) δ 7.49-7.57 (m, 2H), 7.44-7.49 (m, 1H), 7.35-7.44 (m, 2H), 6.84 (d, J=8.6 Hz, 2H), 6.60 (d, J=9.3 Hz, 1H), 6.15 (d, J=5.4 Hz, 1H), 3.82 (s, 6H), 3.35-3.41 (m, 2H), 3.23-3.30 (m, 2H). LCMS-ESI (POS), m/z, 525.0 (M+H)$^+$.

Example 462.0: Preparation of (3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide and (3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide

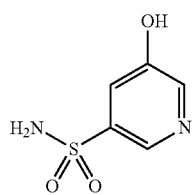

462.1

5-hydroxypyridine-3-sulfonamide, Example 462.1

To a 100-mL round-bottomed flask was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-i-isopropyl-biphenyl (commercially available from Strem Chemicals, Inc., MA, USA, 0.079 g, 0.16 mmol) and $Pd_2(dba)_3$ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under $N_2$ for 17 h. LCMS analysis indicated the reaction was complete. The reaction mixture was allowed to cool to RT. The reaction mixture was diluted with 1 N HCl and washed with $Et_2O$. The aqueous phase was concentrated in vacuo to afford the title compound 462.1 (0.387 g, 2.22 mmol, 100% yield) as a white solid, which was directly used in the next step without further purification. LCMS-ESI (POS), m/z: 175.1 (M+H)$^+$.

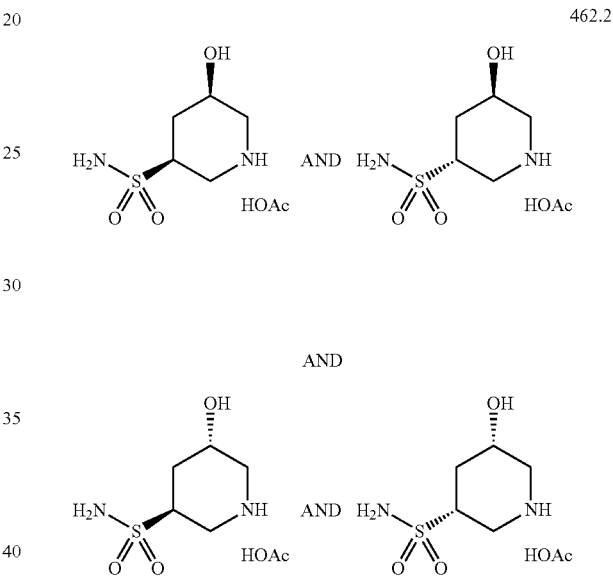

462.2

(3R,5R)-5-hydroxypiperidine-3-sulfonamide acetate and (3S,5R)-5-hydroxypiperidine-3-sulfonamide acetate and (3R,5S)-5-hydroxypiperidine-3-sulfonamide acetate and (3S,5S)-5-hydroxypiperidine-3-sulfonamide acetate, Example 462.2

To a 1-L hydrogenation flask was added 462.1 (6.46 g, 37.1 mmol) and AcOH (250 mL, 4330 mmol). Water (20 mL) was added as co-solvent. The mixture was bubbled with $N_2$ for 2 min before platinum (IV) oxide hydrate (8.42 g, 37.1 mmol) was added under $N_2$ flow. The flask was set up on a Parr shaker, vacuumed and back-filled with $N_2$ two times, and then placed under vacuum and back-filled with hydrogen gas (tank). The reaction mixture was stirred at 23° C. under 50 psi of hydrogen gas for 24 h. LCMS analysis indicated that the reaction was complete. Celite® brand filter agent (20 g) was added to the mixture with stirring. The solid was removed by filtration after 10 min of stirring. The filter cake was rinsed with MeOH. The combined organics were concentrated in vacuo to afford 462.2 (8.91 g, 100% yield) as a light-yellow oil, which was directly used in the next step without purification. LCMS-ESI (POS), m/z: 181.1 (M+H)$^+$.

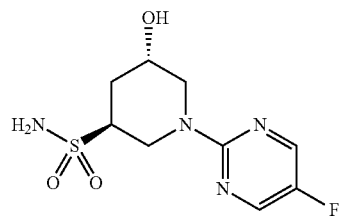 AND 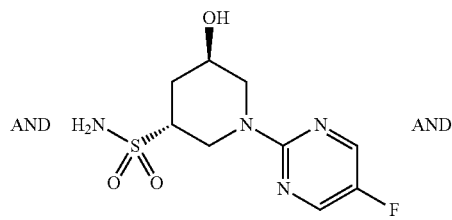 AND

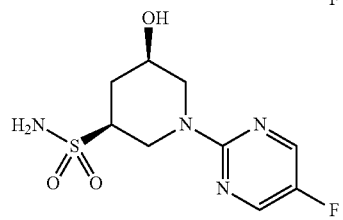 AND 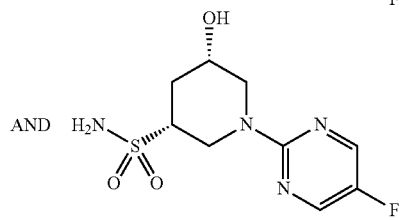 AND 462.3

(3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 462.3

To a 500-mL round-bottomed flask was added 462.2 (8.91 g, 37.1 mmol) and Hunig's base (32.3 mL, 185 mmol) in DMF (80 mL). 2-Chloro-5-fluoro-pyrimidine (18.32 mL, 148 mmol) was then added with stirring. The reaction mixture was stirred at 120° C. for 18 h. LCMS analysis indicated the reaction was complete. The reaction mixture was allowed to cool to RT and then was diluted with water and extracted with DCM. The organic layers were washed with brine and dried over Na$_2$SO$_4$. The solution was filtered and concentrated in vacuo to give the initial material as an orange oil. The material thus obtained was purified by silica gel chromatography (a gradient of 0-100% EtOAc in DCM), to provide 462.3 (3.7 g, 10.93 mmol, 36% yield) as a light-yellow solid. LCMS-ESI (POS), m/z: 277.0 (M+H)$^+$.

463.0

(3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide and (3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide, Example 462.0

The title compound was prepared from 462.3, 1.0, and 3.4 using the procedure described in Example A. The title compound 462.0 was isolated as the major diastereomers and as a TFA salt. $^1$H NMR (500 MHz, CD$_3$OD) δ 8.30 (s, 2H), 7.72 (t, J=7.8 Hz, 1H), 7.61 (d, J=7.6 Hz, 1H), 7.47 (t, J=8.6 Hz, 1H), 7.25 (d, J=7.8 Hz, 1H), 6.77 (dd, J=8.6, 4.2 Hz, 2H), 5.07-5.15 (m, 1H), 4.81-4.86 (m, 1H), 3.73-3.79 (m, 6H), 3.55-3.64 (m, 1H), 3.06-3.15 (m, 1H), 2.88 (dd, J=13.0, 11.5 Hz, 1H), 2.47-2.58 (m, 2H), 2.23 (s, 3H), 1.62-1.73 (m, 1H). LCMS-ESI (POS), m/z: 571.3 (M+H)$^+$.

Example 463.0: Preparation of (3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide 463.0

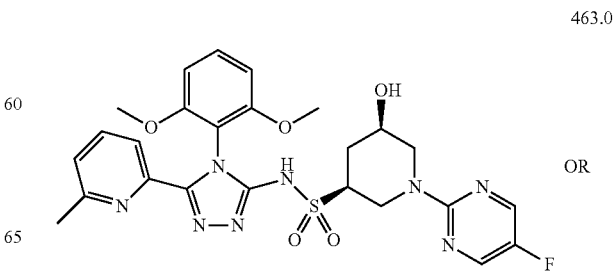

OR

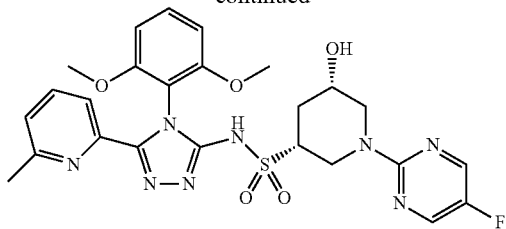

(3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide, Example 463.0

The title compound was the first isomer to elute from an AS-H column on subjecting 462.0 under the following SFC conditions. Run on Thar 80 SFC with 250×30 mm AS-H column with 44 g/min MeOH (neat)+36 g/min CO₂, 55% co-solvent at 80 g/min. Temperature.=27° C., Outlet pressure=100 bar, Wavelength=240 nm. Injected 1.0 mL of a solution of 66 mg sample dissolved in 8 mL of MeOH; c=8.25 mg/mL and 8.25 mg per injection. Cycle time 6.0 min, run time=9 min. ¹H NMR (500 MHz, CD₃OD) δ 8.29 (s, 2H), 7.70 (t, J=7.8 Hz, 1H), 7.60 (d, J=7.8 Hz, 1H), 7.46 (t, J=8.4 Hz, 1H), 7.23 (d, J=7.8 Hz, 1H), 6.77 (dd, J=8.6, 3.9 Hz, 2H), 5.09-5.13 (m, 1H), 4.84 (dd, J=12.6, 4.8 Hz, 1H), 3.76 (s, 3H), 3.75 (s, 3H), 3.56-3.62 (m, 1H), 3.09-3.15 (m, 1H), 2.91 (s, 1H), 2.88-2.89 (m, 1H), 2.54 (dd, J=12.5, 10.5 Hz, 2H), 2.22 (s, 3H), 1.61-1.75 (m, 1H). LCMS-ESI (POS), m/z: 571.3 (M+H)⁺.

Example 464.0: Preparation of (3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide 464.0

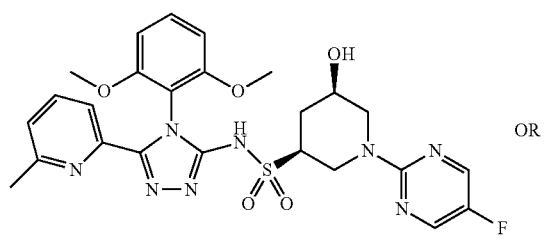

OR

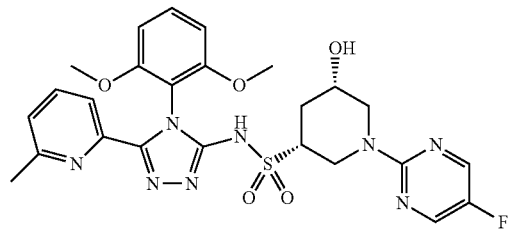

(3R,5S)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide, Example 464.0

The title compound was the second isomer to elute from an AS-H column on subjecting 462.0 under the SFC conditions described in Example 463.0. ¹H NMR (500 MHz, CD₃OD) δ 8.29 (s, 2H), 7.69 (t, J=7.7 Hz, 1H), 7.59 (d, J=7.8 Hz, 1H), 7.46 (t, J=8.4 Hz, 1H), 7.23 (d, J=7.6 Hz, 1H), 6.76 (dd, J=8.3, 3.9 Hz, 2H), 5.05-5.17 (m, 1H), 4.77-4.87 (m, 1H), 3.76 (s, 3H), 3.75 (s, 3H), 3.55-3.63 (m, 1H), 3.10-3.19 (m, 1H), 2.85-2.92 (m, 1H), 2.49-2.57 (m, 2H), 2.22 (s, 3H), 1.68 (q, J=12.0 Hz, 1H). LCMS-ESI (POS), m/z: 571.3 (M+H)⁺.

Example 465.0: Preparation of (3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide and (3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide 465.0

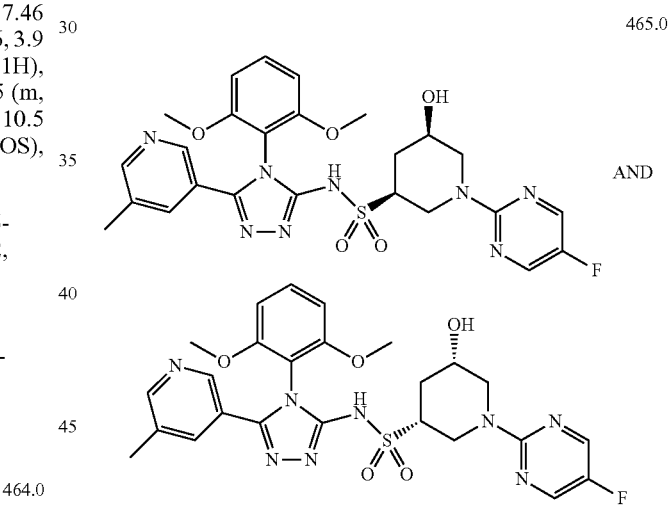

(3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide and (3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, Example 465.0

The title compound was prepared from 462.3, 1.0 and 5-methylnicotinohydrazide (commercially available from Hellen Chemistry Co., Beijing, China) using the procedures described in Example A. The title compound 465.0 was isolated as the major diastereomers and as a TFA salt. ¹H NMR (500 MHz, CDCl₃) δ 8.52 (s, 1H), 8.38 (s, 1H), 8.20 (s, 2H), 7.85 (s, 1H), 7.45 (t, J=8.56 Hz, 1H), 6.66 (dd. J=8.68, 3.06 Hz, 2H), 4.92 (dd, J=13.45, 3.67 Hz, 1H), 4.61 (dd. J=13.08, 4.52 Hz, 1H), 3.72-3.85 (m, 7H), 3.31 (dd, J=13.20, 10.03 Hz, 1H), 3.12-3.22 (m, 1H), 2.93 (dd, J=12.59, 9.41 Hz, 1H), 2.54 (d, J=12.72 Hz, 1H), 2.40 (s, 3H), 1.86-1.96 (m, 1H). LCMS-ESI (POS), m/z: 571.3 (M+H)$^+$.

Example 466.0: Preparation of (3R,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide and (3S,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide 466.0

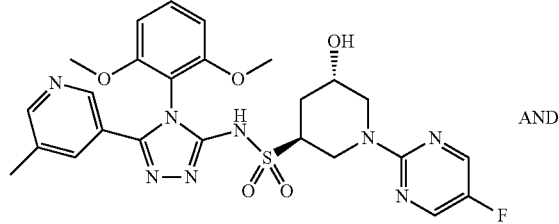

AND

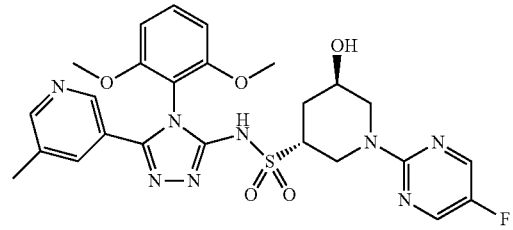

(3R,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide and (3S,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, Example 466.0

The title compound was isolated as the minor mixture of diasteromers and as a TFA salt using the conditions described in 465.0. $^1$H NMR (500 MHz, CD$_3$OD) δ 8.53 (br. s., 1H), 8.41 (br. s., 1H), 8.26 (s, 2H), 7.88 (s, 1H), 7.54 (t, J=8.44 Hz, 1H), 6.84 (dd, J=8.56, 4.89 Hz, 2H), 5.00 (dt, J=12.96, 1.83 Hz, 1H), 4.61 (d, J=13.69 Hz, 1H), 4.14 (br. s., 1H), 3.78-3.85 (m, 6H), 3.41-3.51 (m, 1H), 3.05-3.20 (m, 2H), 2.37 (s, 3H), 2.27 (d, J=13.45 Hz, 1H), 1.91-2.00 (m, 1H). LCMS-ESI (POS), m/z: 571.3 (M+H)$^+$.

Example 467.0: Preparation of (3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide 467.0

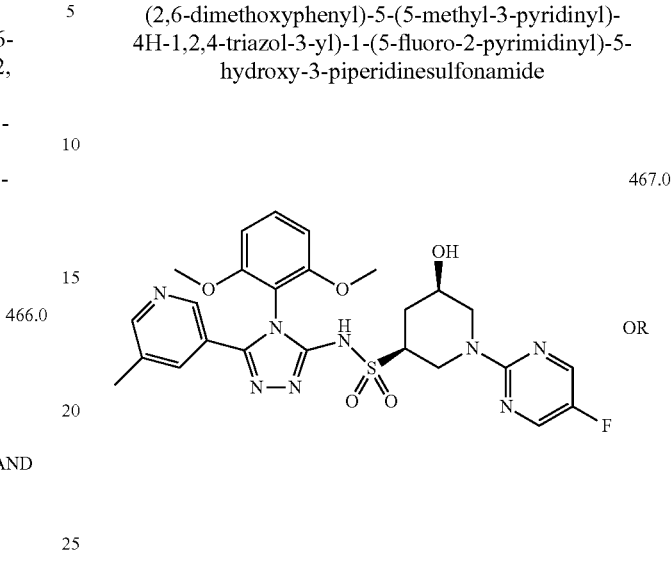

OR

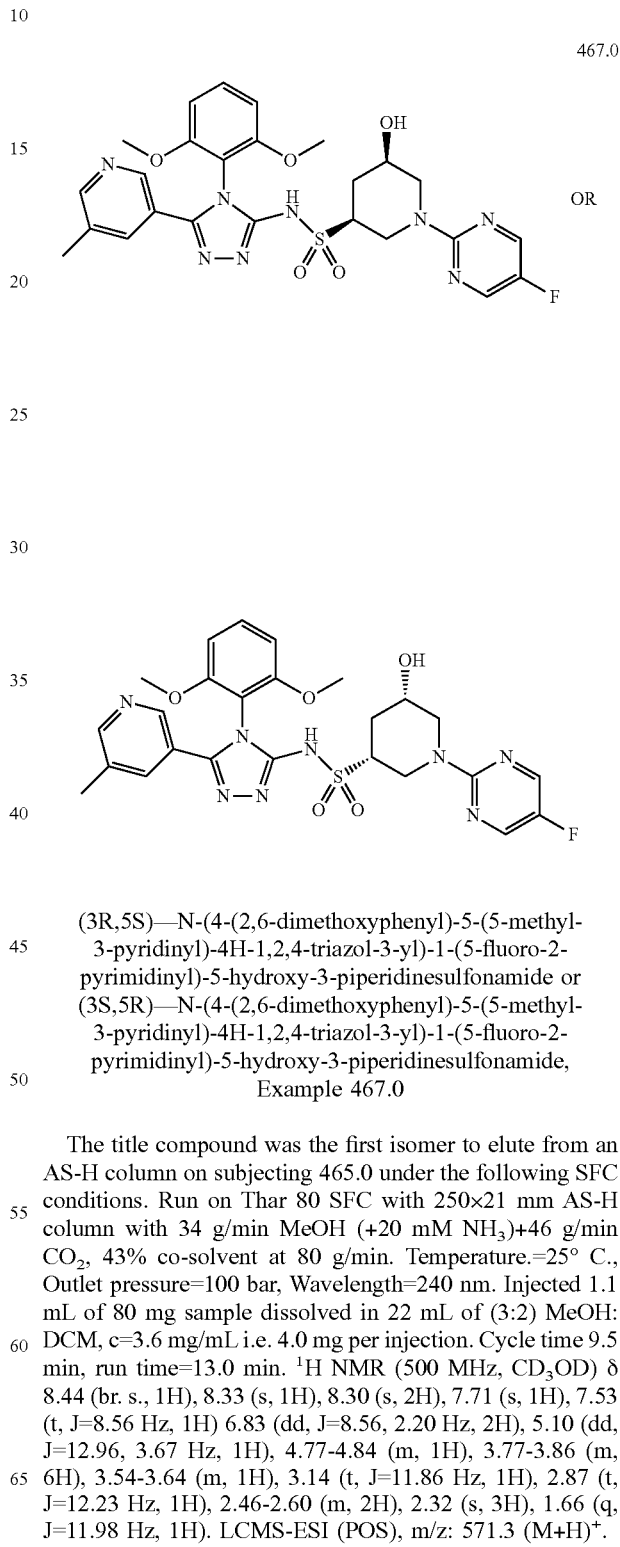

(3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, Example 467.0

The title compound was the first isomer to elute from an AS-H column on subjecting 465.0 under the following SFC conditions. Run on Thar 80 SFC with 250×21 mm AS-H column with 34 g/min MeOH (+20 mM NH$_3$)+46 g/min CO$_2$, 43% co-solvent at 80 g/min. Temperature.=25° C., Outlet pressure=100 bar, Wavelength=240 nm. Injected 1.1 mL of 80 mg sample dissolved in 22 mL of (3:2) MeOH:DCM, c=3.6 mg/mL i.e. 4.0 mg per injection. Cycle time 9.5 min, run time=13.0 min. $^1$H NMR (500 MHz, CD$_3$OD) δ 8.44 (br. s., 1H), 8.33 (s, 1H), 8.30 (s, 2H), 7.71 (s, 1H), 7.53 (t, J=8.56 Hz, 1H) 6.83 (dd, J=8.56, 2.20 Hz, 2H), 5.10 (dd, J=12.96, 3.67 Hz, 1H), 4.77-4.84 (m, 1H), 3.77-3.86 (m, 6H), 3.54-3.64 (m, 1H), 3.14 (t, J=11.86 Hz, 1H), 2.87 (t, J=12.23 Hz, 1H), 2.46-2.60 (m, 2H), 2.32 (s, 3H), 1.66 (q, J=11.98 Hz, 1H). LCMS-ESI (POS), m/z: 571.3 (M+H)$^+$.

Example 468.0: Preparation of (3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide

Example 469.0: Preparation of (3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide and (3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide 468.0

OR

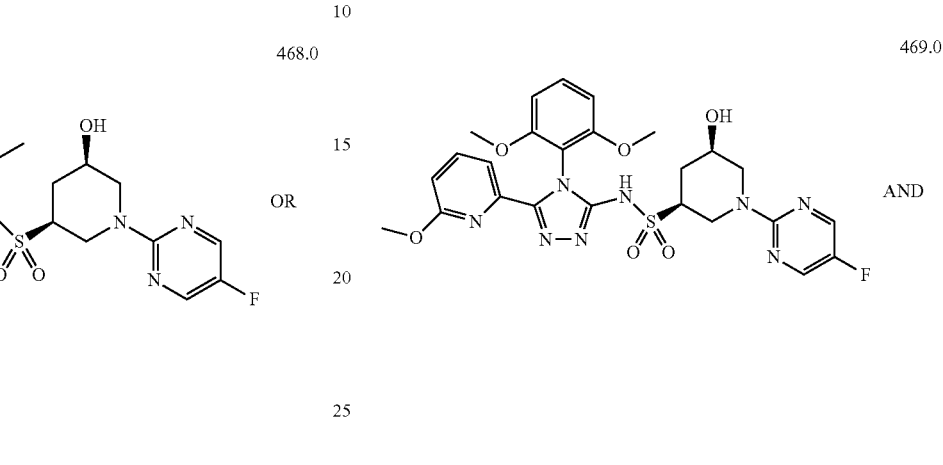

469.0

AND

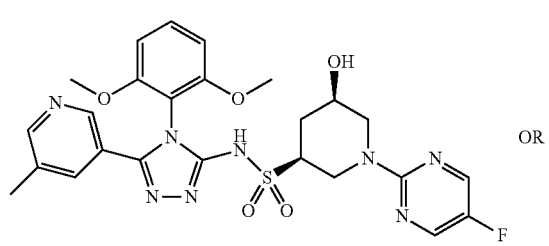

Preparation of (3R,5S)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, Example 468.0

The title compound was the second isomer to elute from the AS-H column on subjecting 465.0 under the SFC conditions described in Example 467.0. $^1$H NMR (500 MHz, CD$_3$OD) δ 8.44 (br. s., 1H), 8.33 (s, 1H), 8.30 (s, 2H), 7.71 (s, 1H), 7.53 (t, J=8.56 Hz, 1H) 6.83 (dd, J=8.56, 2.20 Hz, 2H), 5.10 (dd, J=12.96, 3.67 Hz, 1H), 4.77-4.84 (m, 1H), 3.77-3.86 (m, 6H), 3.54-3.64 (m, 1H), 3.14 (t, J=11.86 Hz, 1H), 2.87 (t, J=12.23 Hz, 1H), 2.46-2.60 (m, 2H), 2.32 (s, 3H), 1.66 (q, J=11.98 Hz, 1H). LCMS-ESI (POS), m/z: 571.3 (M+H)$^+$.

(3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide and (3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, Example 469.0

The title compound was prepared from 462.3, 1.0 and 6-methoxy-pyridine-2-carboxylic acid hydrazide (commercially available from Sigma-Aldrich Chemical Company, Inc., MO, USA) using the procedures described in Example A. The title compound 469.0 was isolated as a mixture of the major diasteromers and as a TFA salt. $^1$H NMR (500 MHz, CD$_3$OD) δ 8.30 (s, 2H), 7.70-7.77 (m, 1H), 7.63 (d, J=7.34 Hz, 1H), 7.44 (t, J=8.44 Hz, 1H), 6.73-6.85 (m, 3H), 5.05-5.14 (m, 1H), 4.80-4.87 (m, 1H), 3.72-3.81 (m, 6H), 3.54-3.64 (m, 1H), 3.20 (s, 3H), 3.09 (tt, J=11.92, 3.73 Hz, 1H), 2.86 (dd, J=12.84, 11.62 Hz, 1H), 2.46-2.59 (m, 2H), 1.66 (q, J=12.15 Hz, 1H). LCMS-ESI (POS), m/z: 587.2 (M+H)$^+$.

Example 470.0: Preparation of (3R,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide and (3S,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide

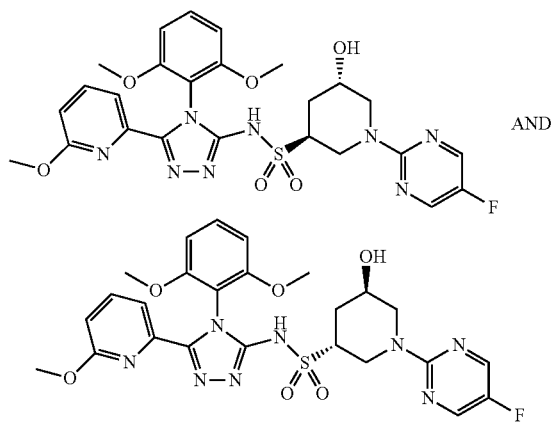

470.0

(3R,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide and (3S,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, Example 470.0

The title compound was isolated as a mixture of the minor diastereomers and as a TFA salt as described in 469.0. $^1$H NMR (500 MHz, CD$_3$OD) δ 8.21-8.33 (m, 2H), 7.70-7.78 (m, 1H), 7.58-7.66 (m, 1H), 7.40-7.48 (m, 1H), 6.73-6.84 (m, 3H), 4.97-5.05 (m, 1H), 4.61 (d, J=13.69 Hz, 1H), 4.13 (br. s., 1H), 3.70-3.82 (m, 6H), 3.45 (tt, J=11.07, 3.97 Hz, 1H), 3.19 (s, 3H), 3.03-3.17 (m, 2H), 2.27 (d, J=13.69 Hz, 1H), 1.90-2.00 (m, 1H). LCMS-ESI (POS), m/z: 587.2 (M+H)$^+$.

Example 471.0: Preparation of (3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide

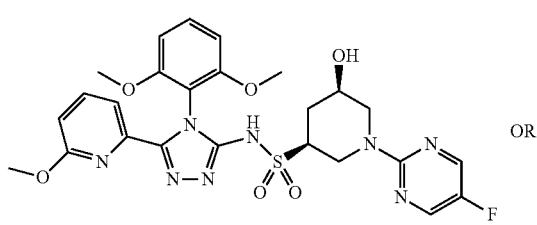

471.0

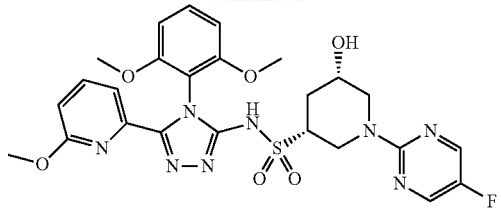

(3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, Example 471.0

The title compound was the first isomer to elute from an AS column on subjecting 469.0 under the following SFC conditions. Run on Thar 200 with 250×21 mm AS column with 25 g/min MeOH (20 mM NH$_3$)+25 g/min CO$_2$, 50% co-solvent at 100 g/min. Temperature 21° C., Wavelength 297 nm. Injected 2.5 mL of a solution of 70 mg sample dissolved in 10 mL MeOH; c=7.0 mg/mL; 17.5 mg/injection. Run time=9 min. $^1$H NMR (500 MHz, CD$_3$OD) δ 8.29 (s, 2H), 7.68-7.77 (m, 1H), 7.59-7.66 (m, 1H), 7.43 (t, J=8.44 Hz, 1H), 6.79 (dd, J=8.44, 3.79 Hz, 2H), 6.76 (d, J=8.07 Hz, 1H), 5.05-5.15 (m, 1H), 4.81-4.86 (m, 1H), 3.77 (s, 3H), 3.76 (s, 3H), 3.54-3.64 (m, 1H), 3.17-3.22 (m, 3H), 3.06-3.16 (m, 1H), 2.86 (dd, J=12.84, 11.37 Hz, 1H), 2.47-2.58 (m, 2H), 1.66 (q, J=11.98 Hz, 1H). LCMS-ESI (POS), m/z: 587.2 (M+H)$^+$.

Example 472.0: Preparation of (3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide

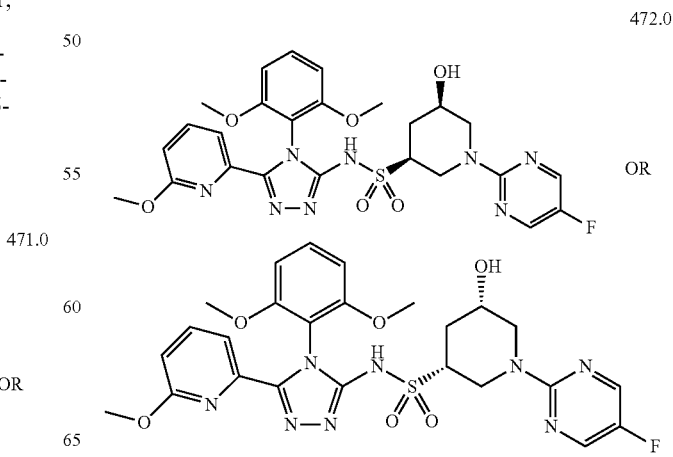

472.0

(3R,5S)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide or (3S,5R)—N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, Example 472.0

The title compound was the second isomer to elute from the AS-H column on subjecting 469.0 under the SFC conditions described in Example 471.0. $^1$H NMR (500 MHz, CD$_3$OD) δ 8.29 (s, 2H), 7.68-7.77 (m, 1H), 7.59-7.66 (m, 1H), 7.43 (t, J=8.44 Hz, 1H), 6.79 (dd. J=8.44, 3.79 Hz, 2H), 6.76 (d, J=8.07 Hz, 1H), 5.05-5.15 (m, 1H), 4.81-4.86 (m, 1H), 3.77 (s, 3H), 3.76 (s, 3H), 3.54-3.64 (m, 1H), 3.17-3.22 (m, 3H), 3.06-3.16 (m, 1H), 2.86 (dd, J=1284, 11.37 Hz, 1H), 2.47-2.58 (m, 2H), 1.66 (q J=11.98 Hz, 1H). LCMS-ESI (POS), m/z: 587.2 (M+H)$^+$.

Example 473.0: Preparation of (1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide and (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide and (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide and (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide 473.1

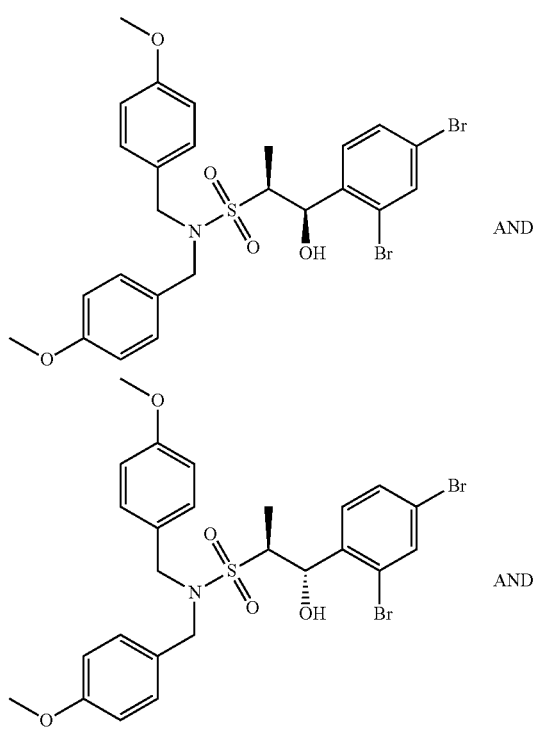

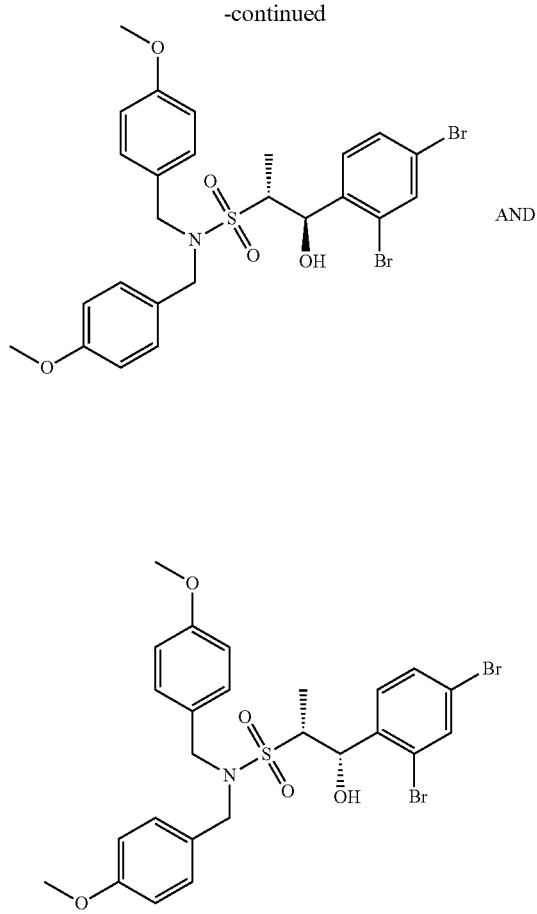

(1R,2S)-1-(2,4-dibromophenyl)-1-hydroxy-N,N-bis(4-methoxybenzyl)propane-2-sulfonamide and (1S,2S)-1-(2,4-dibromophenyl)-1-hydroxy-N,N-bis(4-methoxybenzyl)propane-2-sulfonamide and (1R,2R)-1-(2,4-dibromophenyl)-1-hydroxy-N,N-bis(4-methoxybenzyl)propane-2-sulfonamide and (1S,2R)-1-(2,4-dibromophenyl)-1-hydroxy-N,N-bis(4-methoxybenzyl)propane-2-sulfonamide, Example 473.1

To a 250-mL round-bottomed flask was added 12.0 (3.06 g, 8.76 mmol) in Me-THF (21.9 mL). n-Butyllithium (2.5 M solution in hexanes, 4.20 mL, 10.51 mmol) was added under N$_2$ at −78° C. with stirring. The reaction mixture was stirred at −78° C. for 10 min and then left at RT with stirring for 20 min. 2,4-Dibromobenzaldehyde (2.54 g, 9.63 mmol) in Me-THF (21.89 mL) was added dropwise under N$_2$ at −78° C. with stirring. The reaction mixture was then stirred at −78° C. for 1 h. LCMS analysis indicated formation of the desired product. The reaction was quenched with saturated aqueous NH$_4$C$_1$. The reaction mixture was diluted with saturated NH$_4$C$_1$ and extracted with EtOAc. The organic layer was washed with brine and dried over Na$_2$SO$_4$. The solution was filtered and concentrated in vacuo to give the initial material as a light-yellow solid which was purified by silica gel chromatography (a gradient of 0-100% EtOAc in DCM), to provide the title compound 473.1 (4.9 g, 7.99 mmol, 91% yield) as a white solid. LCMS-ESI (POS), m/z: 634.0 (M+Na)$^+$.

473.2

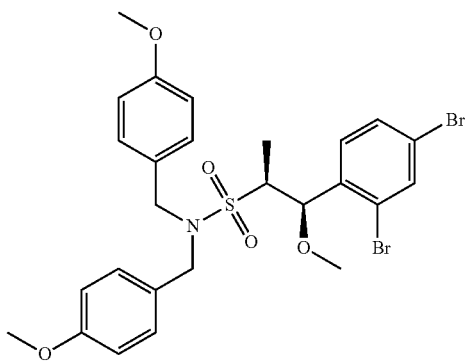
AND

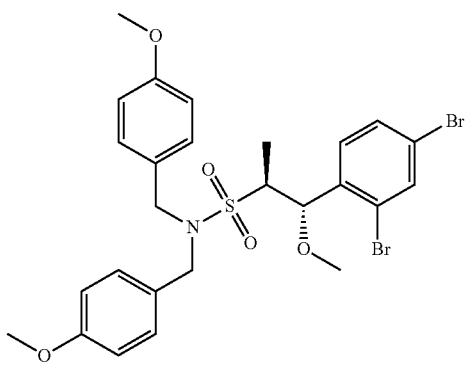
AND

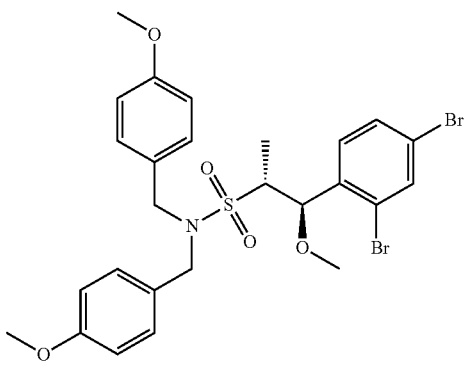
AND

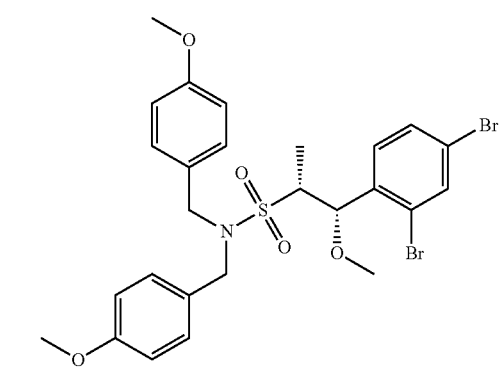

(1R,2S)-1-(2,4-dibromophenyl)-1-methoxy-N,N-bis(4-methoxybenzyl)propane-2-sulfonamide and (1R,2R)-1-(2,4-dibromophenyl)-1-methoxy-N,N-bis(4-methoxybenzyl)propane-2-sulfonamide and (1S,2S)-1-(2,4-dibromophenyl)-1-methoxy-N,N-bis(4-methoxybenzyl)propane-2-sulfonamide and (1S,2R)-1-(2,4-dibromophenyl)-1-methoxy-N,N-bis(4-methoxybenzyl)propane-2-sulfonamide, Example 473.2

To a 250-mL round-bottomed flask was added 473.1 (4.9 g, 7.99 mmol) in Me-THF (53.3 mL). Potassium bis(trimethylsilyl)amide (1 M in THF, 8.79 mL, 8.79 mmol) was added under N₂ at −78° C. with stirring. The reaction mixture was stirred at −78° C. for 10 min and then left at RT for 5 min. Iodomethane (0.546 mL, 8.79 mmol) was added dropwise under N₂ at −78° C. with stirring. The reaction mixture was then stirred at −78° C. for 30 min and then the dry ice-acetone bath was removed and the mixture was left to stir at RT for 10 min. LCMS analysis indicated formation of the desired product but the reaction was not complete. The reaction mixture was then stirred at 23° C. for 16 h. The reaction mixture was next cooled to −78° C. and quenched with saturated aqueous NaHCO₃. The reaction mixture was diluted with water and extracted with EtOAc. The organic layer was washed with brine and dried over Na₂SO₄. The solution was filtered and concentrated in vacuo to give the initial material as a light-yellow oil, which was purified by silica gel chromatography (0-100% EtOAc in hexanes), to provide the title compound 473.2 (5.0 g, 7.97 mmol, 100% yield) as white solid. LCMS-ESI (POS), m/z: 626.0 (M+H)⁺.

473.3

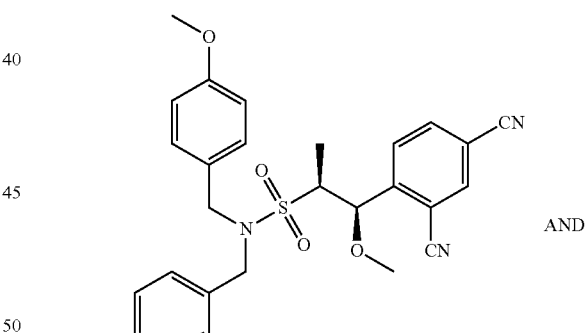
AND

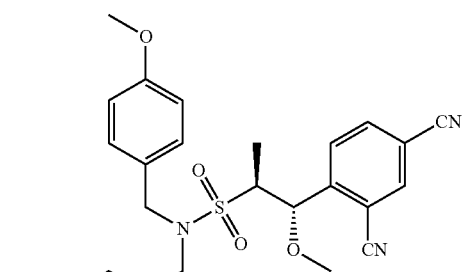
AND

-continued

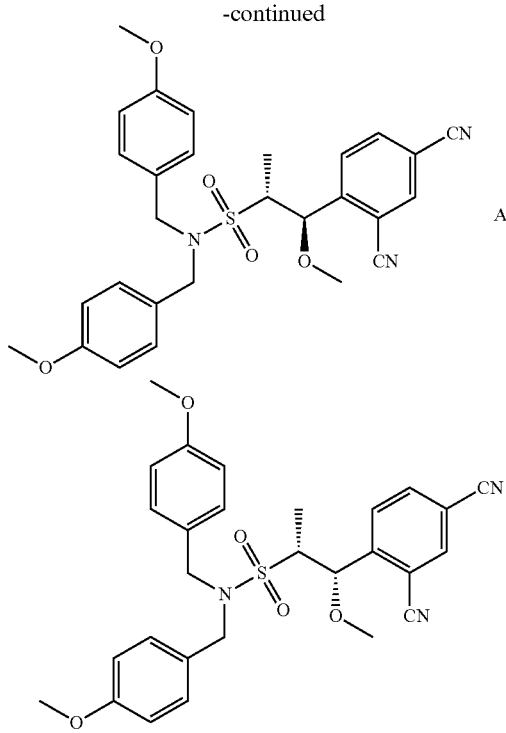

(1R,2S)-1-(2,4-dicyanophenyl)-1-methoxy-N,N-bis(4-methoxybenzyl)propane-2-sulfonamide and (1R,2R)-1-(2,4-dicyanophenyl)-1-methoxy-N,N-bis(4-methoxybenzyl)propane-2-sulfonamide and (1S,2S)-1-(2,4-dicyanophenyl)-1-methoxy-N,N-bis(4-methoxybenzyl)propane-2-sulfonamide and (1S,2R)-1-(2,4-dicyanophenyl)-1-methoxy-N,N-bis(4-methoxybenzyl)propane-2-sulfonamide, Example 473.3

To a 250-mL round-bottomed flask was added 472.2 (5.0 g, 7.97 mmol) in DMA (53.1 mL). Under $N_2$, zinc cyanide (2.06 g, 17.53 mmol) and bis(tri-tert-butylphosphine)palladium (0) (0.815 g, 1.59 mmol) were added. The reaction mixture was then stirred at 100° C. for 15 h. The reaction mixture was cooled and filtered. The solution was concentrated in vacuo at 75° C. The material thus obtained was purified by silica gel chromatography (a gradient of 0-100% EtOAc in DCM), to provide 473.3 (4 g, 7.70 mmol, 97% yield) as a white solid. LCMS-ESI (POS), m/z: 542.2 (M+Na)$^+$.

473.4

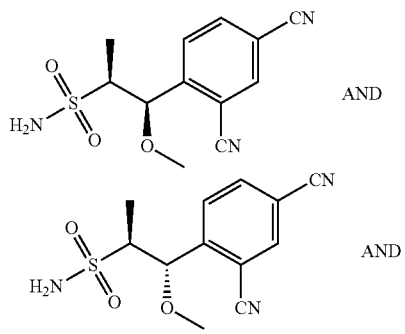

-continued

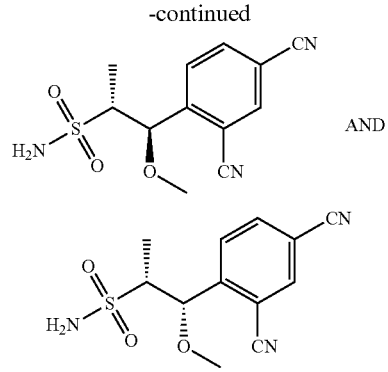

(1R,2S)-1-(2,4-dicyanophenyl)-1-methoxypropane-2-sulfonamide and (1R,2R)-1-(2,4-dicyanophenyl)-1-methoxypropane-2-sulfonamide and (1S,2S)-1-(2,4-dicyanophenyl)-1-methoxypropane-2-sulfonamide and (1S,2R)-1-(2,4-dicyanophenyl)-1-methoxypropane-2-sulfonamide, Example 473.4

To a 250-mL round-bottomed flask was added 473.3 (4 g, 7.70 mmol) and anisole (4.18 mL, 38.5 mmol) in TFA (42.8 mL, 7.70 mmol). The reaction mixture was stirred at 23° C. for 15 h. The reaction mixture was concentrated in vacuo. The material thus obtained was purified by silica gel chromatography (a gradient of 0-100% EtOAc in DCM), to provide 473.4 (1.6 g, 5.73 mmol, 74% yield) as a white solid. LCMS-ESI (POS), m/z: 302.1 (M+Na)$^+$.

473.0

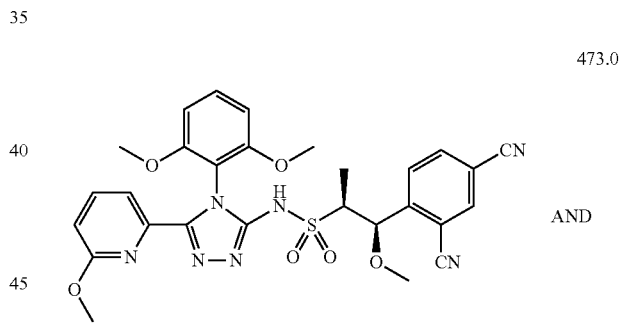

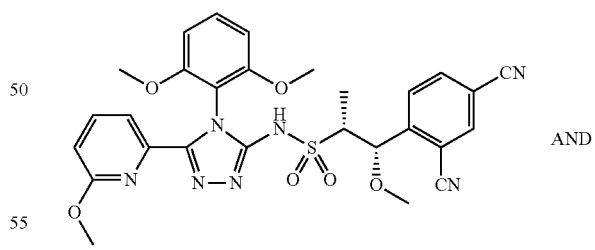


-continued

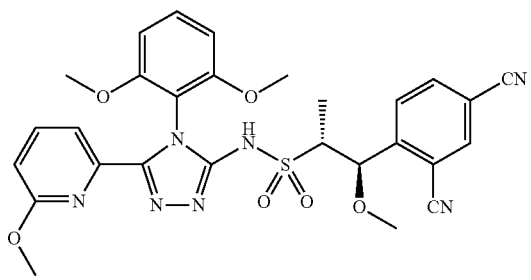

(1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide and (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide and (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide and (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, Example 473.0

The title compound was prepared from 473.4, 1.0 and 6-methoxy-pyridine-2-carboxylic acid hydrazide (commercially available from Sigma-Aldrich Chemical Company, Inc., MO, USA) using the procedures as described in Example A. The title compound 473.0 was isolated as a mixture of four diasteromers, which were completely separated in two stages of an SFC chiral separation under the following conditions: Stage 1 (a pair of major diasteromers, the first and the fourth peak on LUX-2 column, were obtained as optically pure product under the following conditions): Run on Thar 200 with 150×30 mm LUX-2 column with 72 mL/min MeOH (20 mM NH$_3$)+50 g/min CO$_2$, 60% co-solvent at 120 g/min. Temperature 20° C., Wavelength 293 nm. Injected 4.5 mL of a solution of 299 mg sample dissolved in 32 mL 5:3 MeOH:DCM; c=9.3 mg/mL; 42 mg/injection. Cycle time 8.5 min, run time=11 min. Stage 2 (the pair of minor diasteromers, two peaks in the middle from above conditions were separated under the following conditions): Run on Thar 200 with 150×30 mm CC4 column with 58 mL/min MeOH (20 mM NH$_3$)+63 g/min CO$_2$, 48% co-solvent at 120 g/min. Temperature 20° C., Wavelength 293 nm. Injected 0.8 mL of a solution of 18.0 mg sample dissolved in 2.5 mL MeOH; c=7.2 mg/mL; 5.76 mg/injection. Run time=4 min.

Example 474.0: Preparation of (1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide

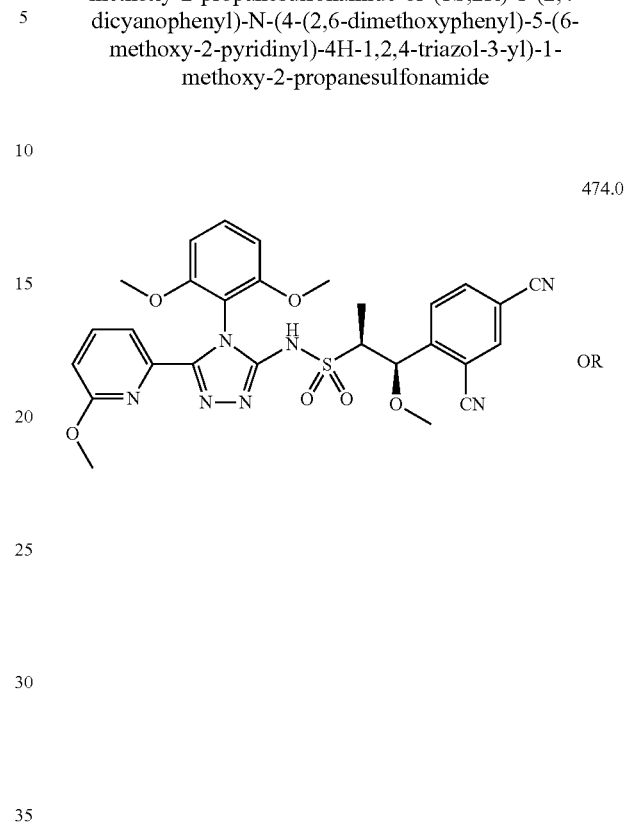

474.0

OR

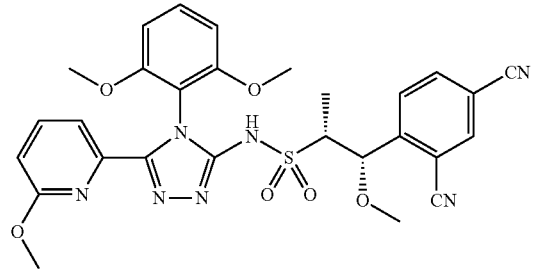

(1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, Example 474.0

The title compound was the first isomer to elute from the LUX-2 column by SFC chiral separation of 473.0 under the conditions described in Example 473.0. $^1$H NMR (500 MHz, CD$_3$OD) δ 8.19 (d, J=1.5 Hz, 1H), 8.00 (dd, J=8.2, 1.6 Hz, 1H), 7.73 (t, J=7.8 Hz, 1H), 7.63 (dd, J=7.8, 3.2 Hz, 2H), 7.43 (t, J=8.4 Hz, 1H), 6.80 (dd, J=8.6, 1.7 Hz, 2H), 6.76 (d, J=8.1 Hz, 1H), 5.11 (d, J=4.4 Hz, 1H), 3.77 (s, 3H), 3.75 (s, 3H), 3.42 (dd, J=7.0, 4.3 Hz, 1H), 3.19 (s, 6H), 1.27 (d, J=6.8 Hz, 3H). LCMS-ESI (POS), m/z: 590.2 (M+H)$^+$.

Example 475.0: Preparation of (1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide

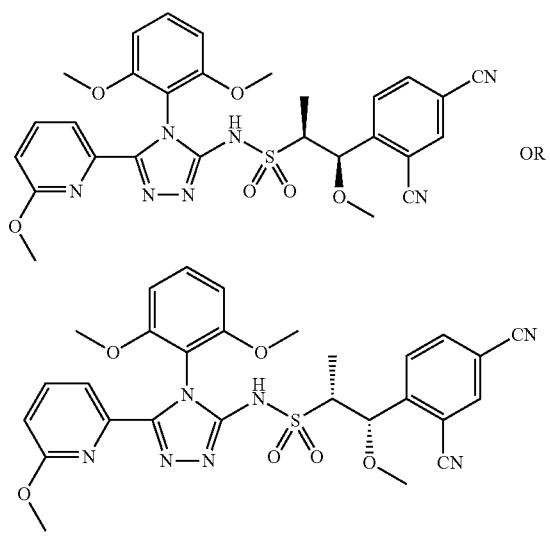

475.0

(1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, Example 475.0

The title compound was the fourth isomer to elute from the LUX-2 column by SFC chiral separation of 473.0 under the conditions described in Example 473.0. LCMS-ESI (POS), m/z: 590.2 (M+H)+.

Example 476.0: Preparation of (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide

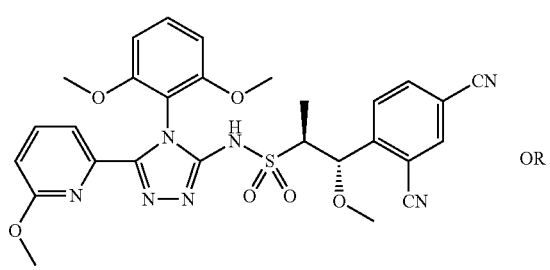

476.0

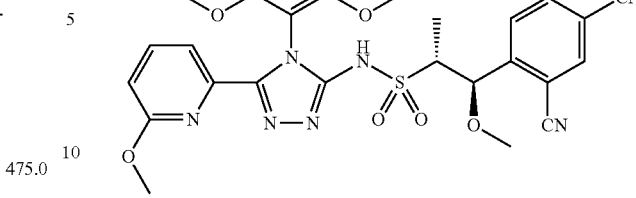

(1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, Example 476.0

The title compound was the second isomer to elute from the LUX-2 column by SFC chiral separation of 473.0 under the conditions described in Example 473.0. ¹H NMR (500 MHz, CD₃OD) δ 8.20 (d, J=1.5 Hz, 1H), 8.01 (dd, J=8.3, 1.7 Hz, 1H), 7.69-7.78 (m, 2H), 7.61 (d, J=7.5 Hz, 1H), 7.43 (t, J=8.4 Hz, 1H), 6.73-6.81 (m, 3H), 4.93 (d, J=7.3 Hz, 1H), 3.75 (d, J=12.5 Hz, 6H), 3.53-3.66 (m, 1H), 3.19 (s, 3H), 3.15 (s, 3H), 1.13 (d, J=7.1 Hz, 3H). LCMS-ESI (POS), m/z: 590.2 (M+H)+.

Example 477.0: Preparation of (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide 477.0

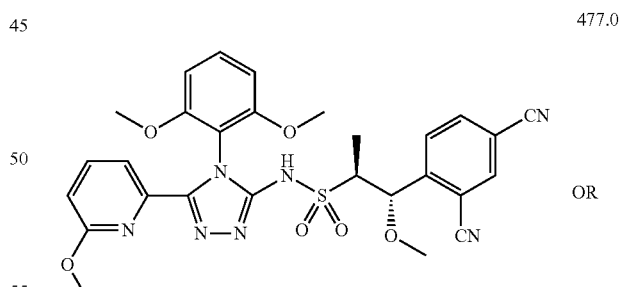

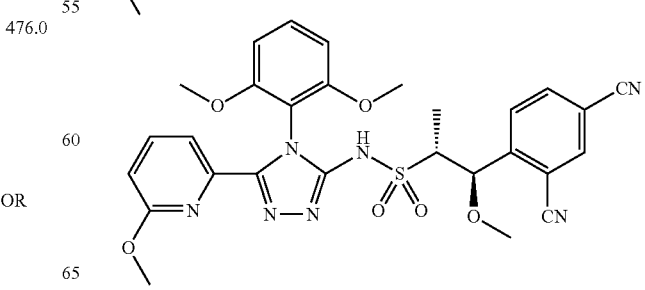

(1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide or (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, Example 477.0

The title compound was the third isomer to elute from the LUX-2 column by SFC chiral separation of 473.0 under the conditions described in Example 473.0. ¹H NMR (500 MHz, CD₃OD) δ 8.20 (d, J=1.5 Hz, 1H), 8.01 (dd, J=8.3, 1.7 Hz, 1H), 7.69-7.78 (m, 2H), 7.61 (d, J=7.5 Hz, 1H), 7.43 (t, J=8.4 Hz, 1H), 6.73-6.81 (m, 3H), 4.93 (d, J=7.3 Hz, 1H), 3.75 (d, J=12.5 Hz, 6H), 3.53-3.66 (m, 1H), 3.19 (s, 3H), 3.15 (s, 3H), 1.13 (d, J=7.1 Hz, 3H). LCMS-ESI (POS), m/z: 590.2 (M+H)⁺.

Example 478.0: Preparation of (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide and (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide 478.0

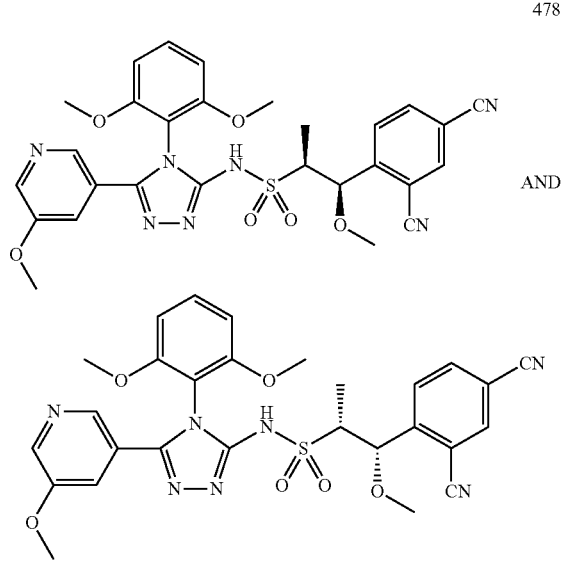

AND (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide and (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide, Example 478.0

The title compound was prepared from 473.4, 1.0 and 5-methylnicotinohydrazide (commercially available from Bellen Chemistry Co., Beijing, China) using the procedures described in Example A. The title compound 478.0 was isolated as a racemic mixture of the two major diastereomers. ¹H NMR (400 MHz, CD₃OD) δ 8.43-8.48 (m, 1H), 8.34 (d, J=1.6 Hz, 1H), 8.20 (d, J=1.4 Hz, 1H), 8.03 (d, J=7.6 Hz, 1H), 7.72-7.74 (m, 1H), 7.69 (d, J=7.9 Hz, 1H), 7.53 (t, J=8.4 Hz, 1H), 6.83 (dd, J=8.6, 2.5 Hz, 2H), 5.17 (d, J=3.9 Hz, 1H), 3.83 (s, 3H), 3.79-3.82 (m, 3H), 3.37-3.47 (m, 1H), 3.21 (s, 3H), 2.33 (s, 3H), 1.27 (d, J=7.0 Hz, 3H). LCMS-ESI (POS), m/z: 574.3 (M+H)⁺.

Example 479.0: Preparation of (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide 479.0

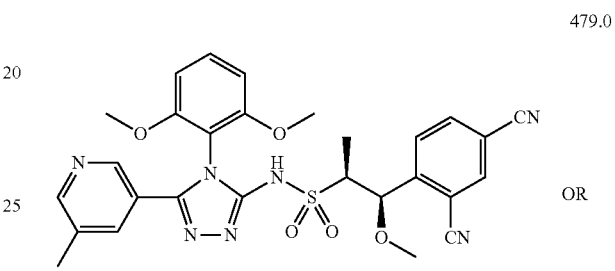

OR

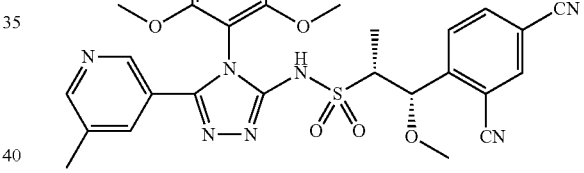

(1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide, Example 479.0

The title compound was the first isomer to elute from an OD-H column on subjecting 478.0 to the following SFC conditions: Run on Thar 80 SFC with 250×30 mm OD-H column with 16 g/min MeOH (+20 mM NH₃)+64 g/min CO₂, 20% co-solvent at 80 g/min. Temperature.=22° C., Outlet pressure=100 bar, Wavelength=215 nm. Injected 0.3 mL of 177 mg sample dissolved in 10 mL MeOH (30% DCM); c=17.7 mg/mL and 5.3 mg per injection. Cycle time 14.5 min, run time=22 min. ¹H NMR (500 MHz, CD₃OD) δ 8.46 (s, 1H), 8.34 (d, J=1.6 Hz, 1H), 8.20 (d, J=1.4 Hz, 1H), 8.03 (d, J=7.5 Hz, 1H), 7.72-7.75 (m, 1H), 7.69 (d, J=8.4 Hz, 1H), 7.53 (t, J=8.3 Hz, 1H), 6.83 (dd, J=8.6, 2.5 Hz, 2H), 5.17 (d, J=3.9 Hz, 1H), 3.83 (s, 3H), 3.78-3.82 (m, 3H), 3.37-3.48 (m, 1H), 3.21 (s, 3H), 2.33 (s, 3H), 1.27 (d, J=7.0 Hz, 3H). LCMS-ESI (POS), m/z: 574.3 (M+H)⁺.

Example 480.0: Preparation of (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide

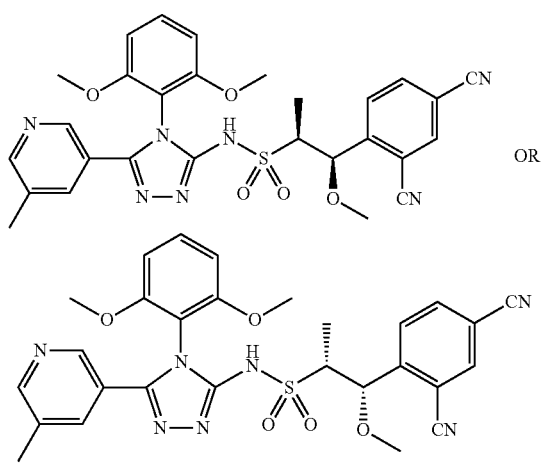

(1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide or (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide, Example 480.0

The title compound was the second isomer to elute from the OD-H column on subjecting 478.0 under the SFC conditions described in Example 479.0. LCMS-ESI (POS), m/z: 574.3 (M+H)$^+$.

Example 481.0: Preparation of (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide and (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide

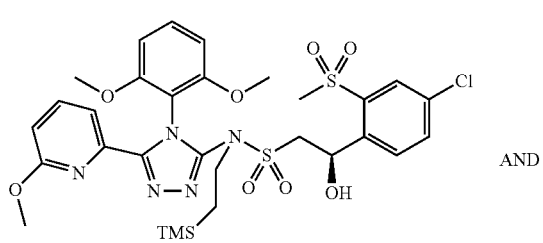

481.1

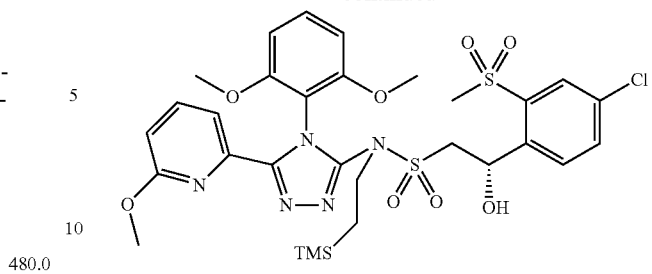

(S)-2-(4-chloro-2-(methylsulfonyl)phenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide and (R)-2-(4-chloro-2-(methylsulfonyl)phenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide, Example 481.1

To a 50-mL round-bottomed flask was added 4.0 (464 mg, 0.92 mmol) in THF (5 mL). n-Butyllithium solution (2.5 M in hexanes, 0.440 mL, 1.101 mmol) was added dropwise via syringe under N$_2$ at −78° C. with stirring. The flask was then removed from the acetone-dry ice bath and the solution was stirred at RT for 5 min. Next, 4-chloro-2-(methylsulfonyl)benzaldehyde (221 mg, 1.01 mmol) in THF (3 mL) was added dropwise via syringe under N$_2$ at −78° C. with stirring. The reaction mixture was then stirred at −78 to 23° C. for 2 h in total before being quenched with saturated aqueous NH$_4$C$_1$. The reaction mixture was diluted with water and extracted with EtOAc. The organic extract was washed with brine and dried over Na$_2$SO$_4$. The solution was filtered and concentrated in vacuo to give the initial material as a light-yellow oil, which was purified by silica gel chromatography (a gradient of 0-100% EtOAc in DCM), to provide the title compound 481.1 (298 mg, 0.41 mmol, 44.8% yield) as a light-yellow solid. LCMS-ESI (POS), m/z: 724.1 (M+H)$^+$.

481.2

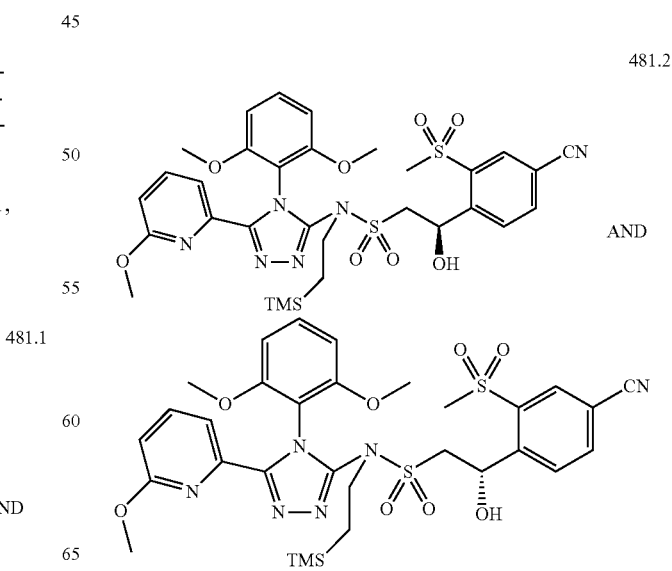

(S)-2-(4-cyano-2-(methylsulfonyl)phenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide and (R)-2-(4-cyano-2-(methylsulfonyl)phenyl)-N-(4-(2,6-dimethoxyphenyl)-5-(6-methoxypyridin-2-yl)-4H-1,2,4-triazol-3-yl)-2-hydroxy-N-(2-(trimethylsilyl)ethyl)ethanesulfonamide, Example 481.2

To a 50-mL round-bottomed flask under an atmosphere of N₂ was added 481.1 (298 mg, 0.41 mmol), zinc cyanide (48.3 mg, 0.41 mmol) and bis(tri-tert-butylphosphine)palladium(0) (42.1 mg, 0.082 mmol) in DMA (5 mL). The reaction mixture was stirred at 110° C. for 15 h. LCMS analysis indicated the reaction was complete. The reaction mixture was diluted with water and extracted with EtOAc. The organic extract was washed with brine and dried over Na₂SO₄. The solution was filtered and concentrated in vacuo to give the initial material as a light-yellow oil, which was purified by silica gel chromatography (a gradient of 0-100% EtOAc in DCM) provided 481.2 (280 mg, 0.39 mmol, 95% yield) as a light-yellow semi-solid. LCMS-ESI (POS), m/z: 715.3 (M+H)⁺.

481.0

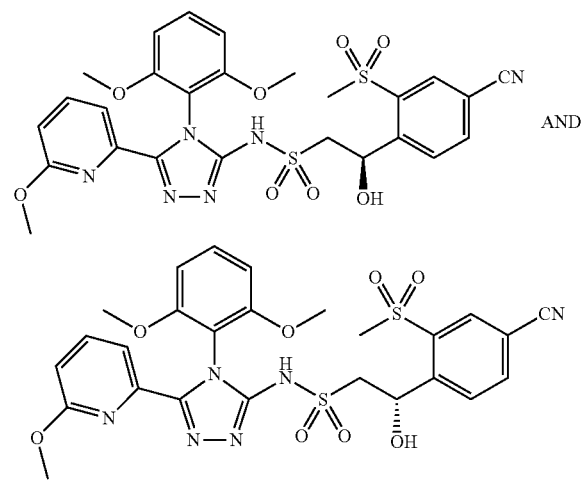

(2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide and (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide, Example 481.0

The title compound was prepared from 481.2 by deprotection as described in Example 264.0. ¹H NMR (400 MHz, CDCl₃) δ 8.30 (d, J=1.7 Hz, 1H), 7.93 (d, J=8.1 Hz, 1H), 7.87 (dd, J=8.1, 1.7 Hz, 1H), 7.57-7.62 (m, 2H), 7.33 (t, J=8.4 Hz, 1H), 6.67-6.71 (m, 1H), 6.62 (d, J=8.6 Hz, 1H), 6.60 (d, J=8.6 Hz, 1H), 5.97 (dd, J=8.9, 2.6 Hz, 1H), 3.74 (s, 3H), 3.66 (s, 3H), 3.53 (dd, J=13.9, 2.4 Hz, 1H), 3.32 (dd, J=13.9, 9.0 Hz, 1H), 3.12 (s, 3H), 3.10 (s, 3H). LCMS-ESI (POS), m/z: 615.2 (M+H)⁺.

Example 482.0: Preparation of (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide or (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide 482.0

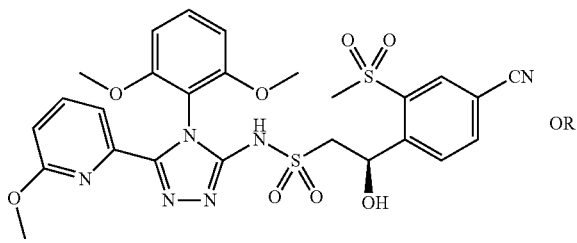

OR

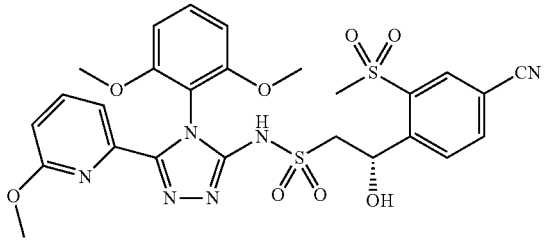

(2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide or (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide, Example 482.0

The title compound was the first isomer to elute from an OD column on subjecting 481.0 to the following SFC conditions: Run on Thar 200 SFC with 250×21 mm OD column with 26.25 g/min MeOH (20 mM NH₃)+49 g/min CO₂, 35% co-solvent at 75 g/min. Temperature.=23° C., Outlet pressure=100 bar, Wavelength=296 nm. Injected 1.2 mL of 32 mg sample dissolved in 5 mL MeOH, c=6.4 mg/mL and 7.68 mg per injection. Run time=6 min, cycle time=4 min. ¹H NMR (400 MHz, CD₃OD) δ 8.31 (d, J=1.0 Hz, 1H), 8.02-8.08 (m, 2H), 7.73 (t, J=7.8 Hz, 1H), 7.62 (d, J=7.3 Hz, 1H), 7.45 (t, J=8.5 Hz, 1H), 6.74-6.84 (m, 3H), 6.06 (dd, J=7.4, 4.9 Hz, 1H), 3.78-3.81 (m, 3H), 3.72 (s, 3H), 3.49-3.66 (m, 2H), 3.20 (s, 3H), 3.16 (s, 3H). LCMS-ESI (POS), m/z: 615.2 (M+H)⁺.

Example 483.0: Preparation of (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide or (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide

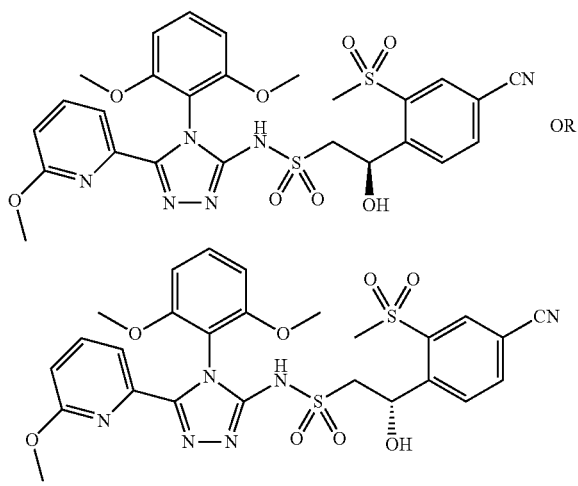

483.0

(2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide or (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide, Example 483.0

The title compound was the second isomer to elute from the OD column on subjecting 481.0 to the SFC conditions described in Example 482.0.

Example 484.0: Preparation of (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide and (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide 484.1

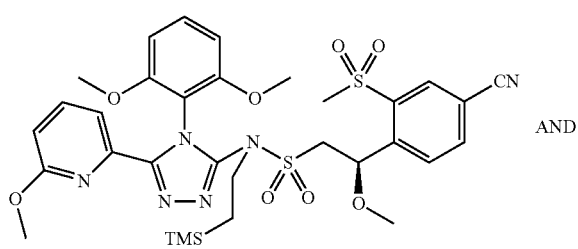

AND

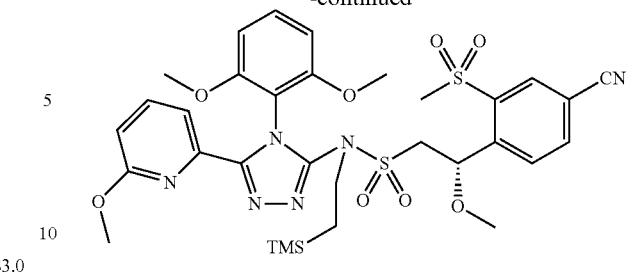

(S)-2-(4-cyano-2-(methylsulfonyl)phenyl)-N-(4-(2,6-dimethoxyphenyl)-5-(6-methoxypyridin-2-yl)-4H-1,2,4-triazol-3-yl)-2-methoxy-N-(2-(trimethylsilyl)ethyl)ethanesulfonamide and (R)-2-(4-cyano-2-(methylsulfonyl)phenyl)-N-(4-(2,6-dimethoxyphenyl)-5-(6-methoxypyridin-2-yl)-4H-1,2,4-triazol-3-yl)-2-methoxy-N-(2-(trimethylsilyl)ethyl)ethanesulfonamide, Example 484.1

To a 25-mL round-bottomed flask was added Example 481.2 (140 mg, 0.20 mmol) in DMF (2.5 mL). Sodium hydride (60% dispersion in mineral oil, 11.8 mg, 0.29 mmol) was added with stirring at 0° C. The reaction mixture was stirred at 0° C. for 10 min before iodomethane (0.018 mL, 0.29 mmol) was added with stirring. The reaction mixture was allowed to warm to 23° C. over 2.5 h. LCMS analysis indicated the reaction was complete. The reaction mixture was then diluted with water and extracted with EtOAc. The organic extract was washed with brine and dried over $Na_2SO_4$. The solution was filtered and concentrated in vacuo to give 484.1 (122 mg, 85% yield) as a light-yellow thick oil, which was used directly in the next step without purification. LCMS-ESI (POS), m/z: 729.2 $(M+H)^+$.

484.0

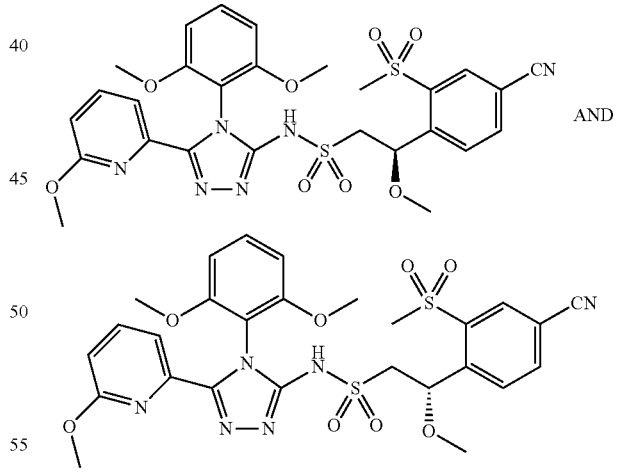

(2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide and (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide, Example 484.0

The title compound was prepared from 484.1 by deprotection as described in Example 264.0. $^1$H NMR (500 MHz, CDCl$_3$) δ 10.94 (br. s., 1H), 8.35 (d, J=1.7 Hz, 1H), 7.93 (dd, J=8.3, 1.7 Hz, 1H), 7.84 (d, J=8.3 Hz, 1H), 7.63-7.67 (m, 1H), 7.62 (t, J=7.0 Hz, 1H), 7.41 (t, J=8.5 Hz, 1H), 6.75 (td, J=8.4 Hz, 2H), 6.63 (d, J=8.3 Hz, 1H), 5.79 (dd, J=7.6, 5.38 Hz, 1H), 3.84 (s, 3H), 3.62-3.71 (m, 4H), 3.53 (dd, J=14.3, 7.7 Hz, 1H), 3.23-3.29 (m, 3H), 3.18-3.20 (m, 3H), 3.01 (s, 3H). LCMS-ESI (POS), m/z: 629.2 (M+H)$^+$.

Example 485.0: Preparation of (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide or (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide

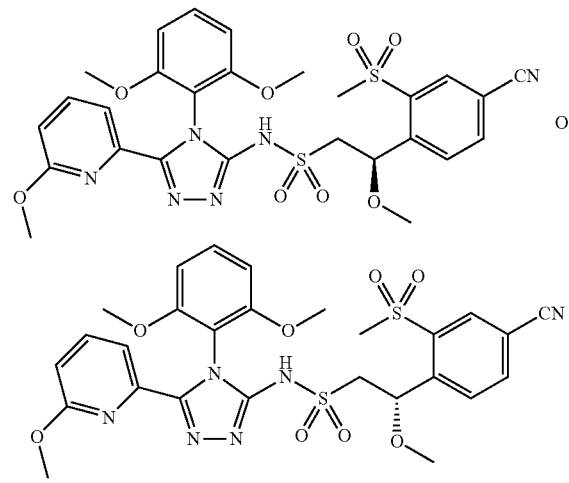

485.0

(2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide or (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide, Example 485.0

The title compound was the first isomer to elute from an IA column on subjecting 484.0 to the following SFC conditions: Run on Thar 200 SFC with 250×21 mm IA column with 40 g/min MeOH (20 mM NH$_3$)±40 g/min CO$_2$, 50% co-solvent at 80 g/min. Temperature.=22° C., Outlet pressure=100 bar, Wavelength=297 nm. Injected 1 mL of 35 mg sample dissolved in 8 mL (1:1) MeOH:DCM, c=4.4 mg/mL and 4.4 mg per injection. Cycle time=4 min, run time=6 min. $^1$H NMR (500 MHz, CDOD) δ 8.33 (d, J=1.6 Hz, 1H), 8.08 (dd, J=8.1, 1.7 Hz, 1H), 7.95 (d, J=8.2 Hz, 1H), 7.73 (dd, J=8.2, 7.6 Hz, 1H), 7.62 (d, J=7.5 Hz, 1H), 7.45 (t, J=8.5 Hz, 1H), 6.74-6.84 (m, 3H), 5.74 (dd, J=6.8, 5.6 Hz, 1H), 3.78 (s, 3H), 3.74 (s, 3H), 3.48-3.64 (m, 2H), 3.20 (d, J=6.1 Hz, 6H), 3.16 (s, 3H). LCMS-ESI (POS), m/z: 629.2 (M+H)$^+$.

Example 486.0: Preparation of (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide or (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide

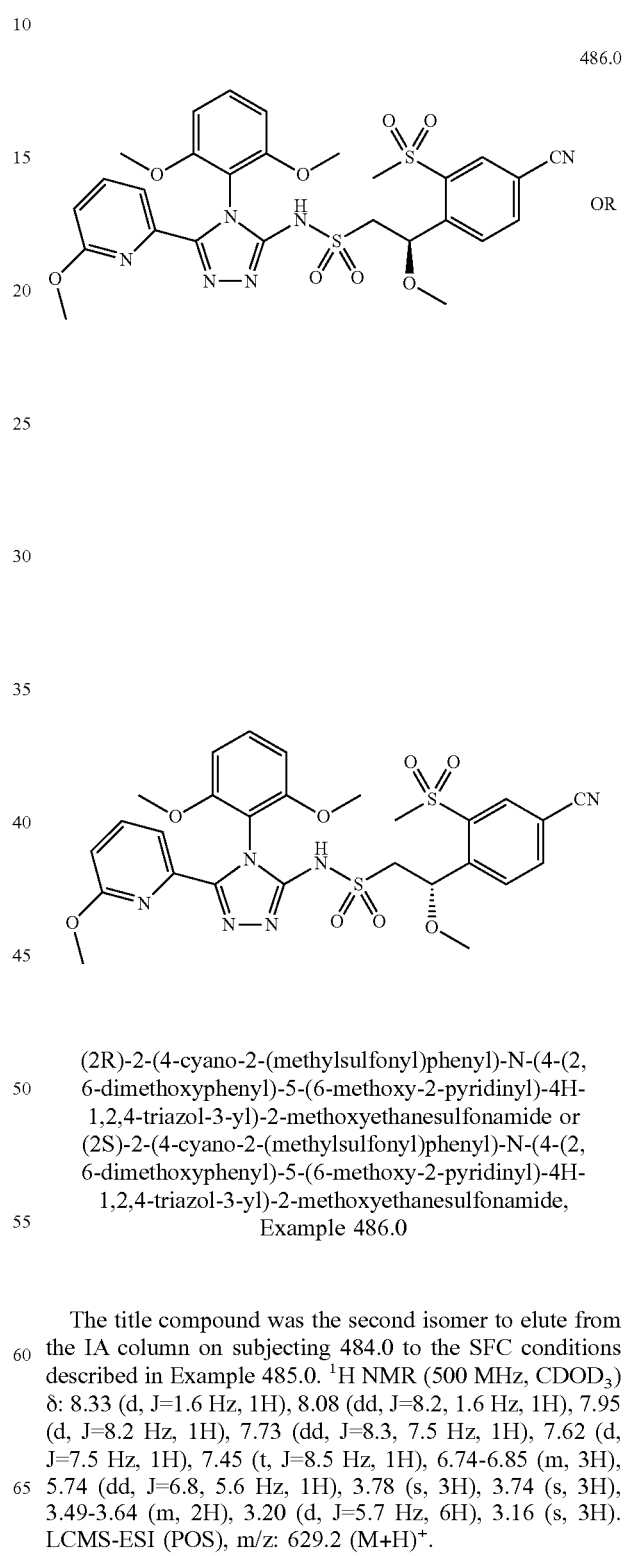

486.0

(2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide or (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide, Example 486.0

The title compound was the second isomer to elute from the IA column on subjecting 484.0 to the SFC conditions described in Example 485.0. $^1$H NMR (500 MHz, CDOD$_3$) δ: 8.33 (d, J=1.6 Hz, 1H), 8.08 (dd, J=8.2, 1.6 Hz, 1H), 7.95 (d, J=8.2 Hz, 1H), 7.73 (dd, J=8.3, 7.5 Hz, 1H), 7.62 (d, J=7.5 Hz, 1H), 7.45 (t, J=8.5 Hz, 1H), 6.74-6.85 (m, 3H), 5.74 (dd, J=6.8, 5.6 Hz, 1H), 3.78 (s, 3H), 3.74 (s, 3H), 3.49-3.64 (m, 2H), 3.20 (d, J=5.7 Hz, 6H), 3.16 (s, 3H). LCMS-ESI (POS), m/z: 629.2 (M+H)$^+$.

Example 487.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide

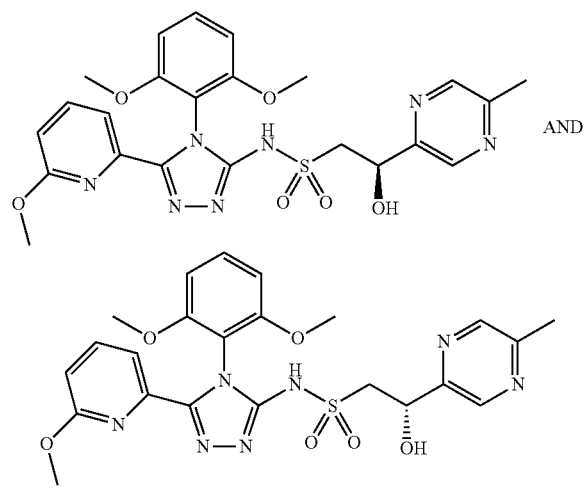

487.0

AND (2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide, Example 487.0

The title compound was prepared following the procedure in Example C using 4.0 and 5-methyl-2-pyrazinecarbaldehyde (commercially available from ChemBridge Corporation, San Diego, Calif.).

Example 488.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide 488.0

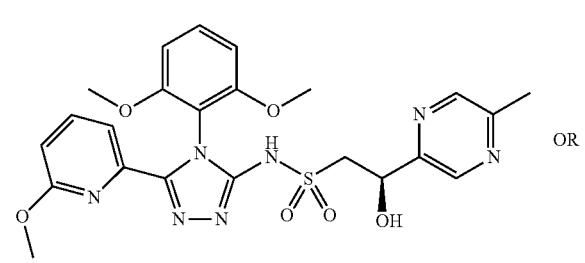

OR

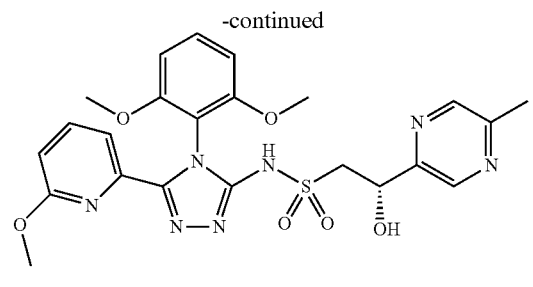

(2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide, Example 488.0

The enantiomers of 487.0 were separated by a SFC chiral separation. Example 488.0 was the first isomer to elute from a CC4 column using the following SFC conditions: Run on Thar 200 SFC with 250×30 mm CC4 column with 58 g/min MeOH (20 mM $NH_3$)+42 g/min $CO_2$, 58% co-solvent at 100 g/min. Temperature.=22° C., Outlet pressure=100 bar, Wavelength=276 nm. Injected 3 mL of 47 mg sample dissolved in 8 mL (5:3) MeOH:DCM, c=5.9 mg/mL and 17.7 mg per injection. Run time=14 min; fractions manually collected. $^1$H NMR (500 MHz, $CD_3OD$) δ 8.55 (s, 1H), 8.49 (s, 1H), 7.73 (t, J=7.8 Hz, 1H), 7.63 (d, J=7.3 Hz, 1H), 7.44 (t, J=8.6 Hz, 1H), 6.75-6.81 (m, 3H), 5.23 (dd, J=8.3, 3.9 Hz, 1H), 3.76 (s, 3H), 3.74 (s, 3H), 3.71 (d, J=3.9 Hz, 1H), 3.68 (d, J=3.9 Hz, 1H), 3.42 (dd, J=14.2, 8.3 Hz, 1H), 3.19 (s, 3H), 2.56 (s, 3H). LCMS-ESI (POS), m/z: 528.2 $(M+H)^+$.

Example 489.0: Preparation of (2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide 489.0

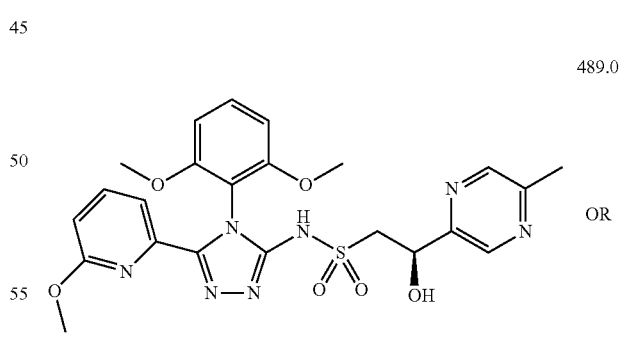

OR

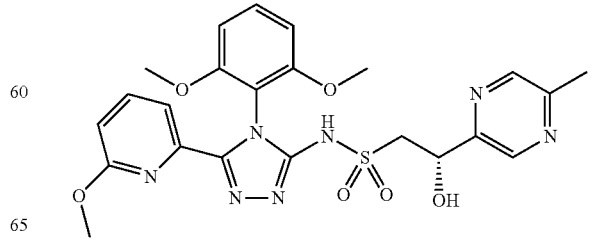

(2R)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide, Example 489.0

The title compound was the second isomer to elute from the CC4 column using the SFC conditions described in Example 488.0. $^1$H NMR (500 MHz, CD$_3$OD) δ 8.55 (s, 1H), 8.49 (s, 1H), 7.73 (t, J=7.8 Hz, 1H), 7.63 (d, J=7.5 Hz, 1H), 7.44 (t, J=8.3 Hz, 1H), 6.75-6.81 (m, 3H), 5.23 (dd, J=8.3, 3.9 Hz, 1H), 3.76 (s, 3H), 3.74 (s, 3H), 3.69 (dd, J=14.2, 3.9 Hz, 1H), 3.42 (dd, J=14.2, 8.3 Hz, 1H), 3.19 (s, 3H), 2.56 (s, 3H). LCMS-ESI (POS), m/z: 528.2 (M+H)$^+$.

Example 490.0: Preparation of (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide and (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide 490.0

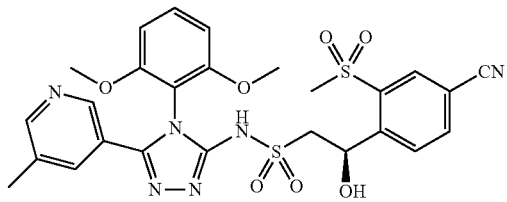

AND

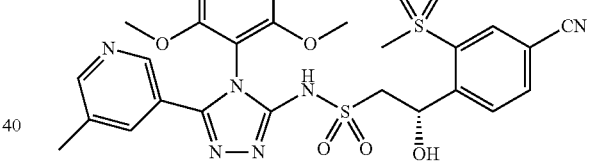

(2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide and (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, Example 490.0

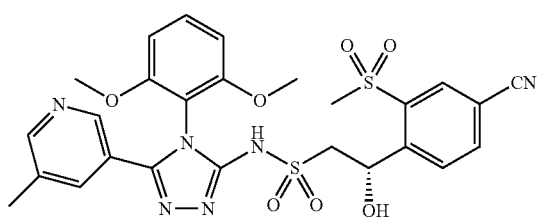

The title compound was prepared following the procedure described in Example 481.0, using 6.0.

Example 491.0: Preparation of (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide 491.0

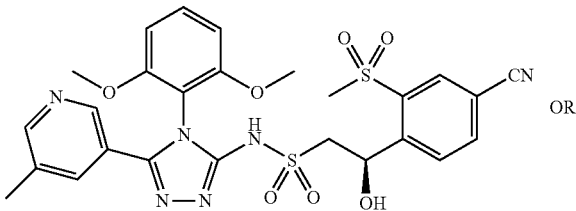

OR (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, Example 491.0

The enantiomers prepared in Example 490.0 were separated by an SFC chiral separation. Example 491.0 was the second isomer to elute from an IC column using the following SFC conditions. Run on Thar 350 SFC with 150×50 mm IC column with 110 mL/min MeOH (neat)+90 g/min CO$_2$, 55% co-solvent at 200 g/min. Temperature.=19° C., Outlet pressure=100 bar, Wavelength=276 nm. Injected 4.8 mL of 200 mg sample dissolved in 16 mL (3:1) MeOH:DCM; c=12.5 mg/mL, i.e. 60 mg per injection. Cycle time=14.5 min, run time=16 min. $^1$H NMR (500 MHz, CD$_3$OD) δ 8.45 (br. s., 1H), 8.26-8.36 (m, 2H), 8.03-8.09 (m, 2H), 7.71 (s, 1H), 7.54 (t, J=8.6 Hz, 1H), 6.85 (d, J=8.1 Hz, 1H), 6.81 (d, J=8.3 Hz, 1H), 6.07 (dd, J=7.3, 4.9 Hz, 1H), 3.83 (s, 3H), 3.77 (s, 3H), 3.62 (dd, J=14.31, 4.77 Hz, 1H), 3.53 (dd, J=14.3, 7.5 Hz, 1H), 3.16 (s, 3H), 2.32 (s, 3H). LCMS-ESI (POS), m/z: 599.2 (M+H)$^+$.

Example 492.0: Preparation of (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide

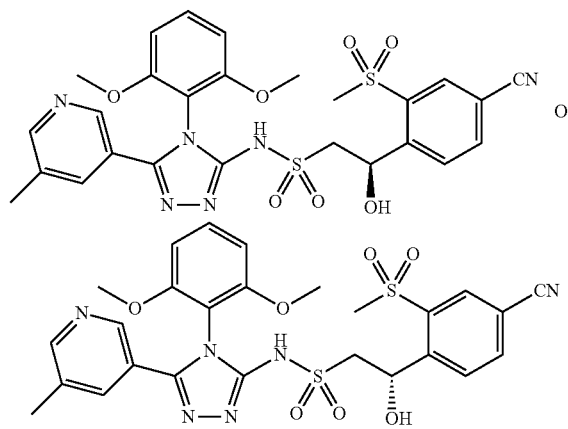

(2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide or (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, Example 492.0

The title compound was the first isomer to elute from the IC column using the SFC conditions described in Example 491.0. $^1$H NMR (500 MHz, CD$_3$OD) δ 8.45 (br. s., 1H), 8.27-8.35 (m, 2H), 8.01-8.10 (m, 2H), 7.71 (s, 1H), 7.53 (t, J=8.5 Hz, 1H), 6.85 (d, J=8.3 Hz, 1H), 6.81 (d, J=8.4 Hz, 1H), 6.07 (dd, J=7.5, 4.9 Hz, 1H), 3.83 (s, 3H), 3.77 (s, 3H), 3.62 (dd, J=14.2, 4.8 Hz, 1H), 3.53 (dd, J=14.2, 7.5 Hz, 1H), 3.16 (s, 3H), 2.32 (s, 3H). LCMS-ESI (POS), m/z: 599.2 (M+H)$^+$.

Example 493.0: Preparation of (2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide

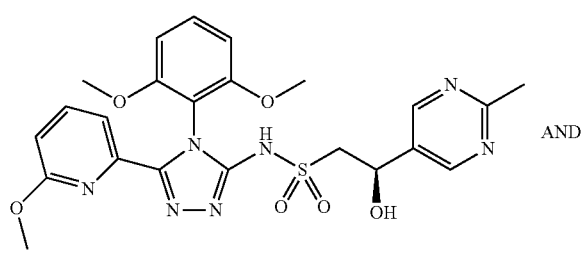

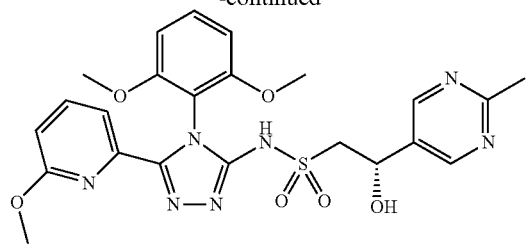

(2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide and (2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide, Example 493.0

The title compound was prepared following the procedure in Example C using 4.0 and 2-methyl-pyrimidine-5-carbaldehyde (commercially available from AstaTech, Inc., Bristol, Pa.).

Example 494.0: Preparation of (2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide

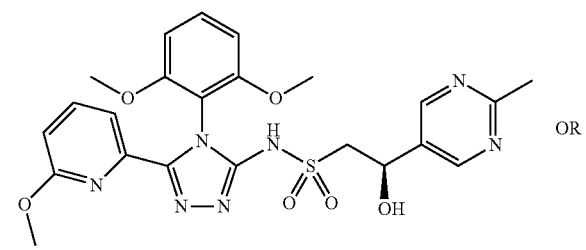

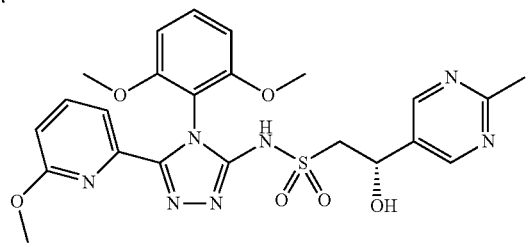

(2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide, Example 494.0

The enantiomers prepared in Example 493.0 were separated by SFC chiral separation as described. Example 494.0 was the first isomer to elute from an AD-H column using the following SFC conditions. Run on Thar 200 SFC with 250×30 mm AD-H column with 45 mL/min MeOH (20 mm $NH_3$)+45 g/min $CO_2$, 50% co-solvent at 90 g/min. Temperature=20° C., Outlet pressure=100 bar, Wavelength=296 nm. Injected 3.0 mL of 251 mg sample dissolved in 15 mL 2:1 MeOH:DCM, c=16.7 mg/mL and 50.1 mg per injection. Fractions were collected manually $^1$H NMR (500 MHz, $CD_3OD$) δ 8.64 (s, 2H), 7.73 (dd, J=8.3, 7.6 Hz, 1H), 7.63 (dd, J=7.3, 0.7 Hz, 1H), 7.45 (t, J=8.6 Hz, 1H), 6.81 (d, J=8.6 Hz, 2H), 6.76 (dd, J=8.3, 0.7 Hz, 1H), 5.14 (dd, J=7.1, 5.4 Hz, 1H), 3.77 (s, 3H), 3.75 (s, 3H), 3.50-3.59 (m, 1H), 3.40-3.49 (m, 1H), 3.19 (s, 3H), 2.69 (s, 3H). LCMS-ESI (POS), m/z: 528.2 $(M+H)^+$.

Example 495.0: Preparation of (2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide

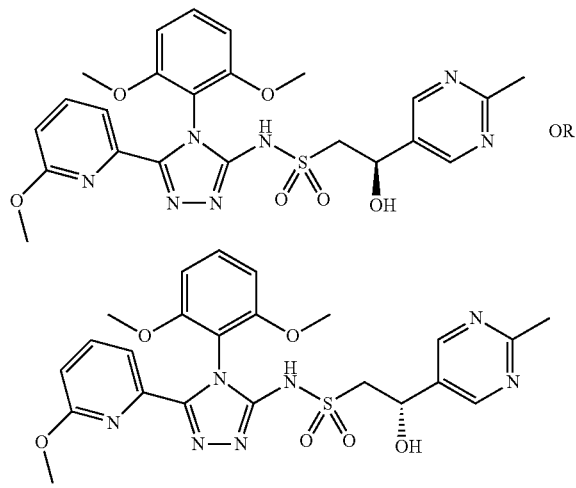

495.0

(2R)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide or (2S)—N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide. Example 495.0

The title compound was the second isomer to elute from the AD-H column using the SFC conditions described in Example 494.0. $^1$H NMR (500 MHz, $CD_3OD$) δ 8.64 (s, 2H), 7.73 (dd, J=8.3, 7.5 Hz, 1H), 7.63 (d, J=7.4 Hz, 1H), 7.45 (t, J=8.5 Hz, 1H), 6.81 (d, J=8.6 Hz, 2H), 6.76 (dd, J=8.3, 0.7 Hz, 1H), 5.14 (dd, J=7.1, 5.5 Hz, 1H), 3.77 (s, 3H), 3.76 (s, 3H), 3.55 (dd, J=14.2, 7.2 Hz, 1H), 3.45 (dd, J=14.1, 5.4 Hz, 1H), 3.19 (s, 3H), 2.69 (s, 3H). LCMS-ESI (POS), m/z: 528.2 $(M+H)^+$.

Example 496.0: Preparation of (1R,2S)—N-(4-(2,6-(trimethoxyphenyl)-5-(6-methoxy-2-pyridinyl)-4H-1,2,4-triazol-3-yl)-1-hydroxy-1-(2-methyl-5-pyrimidinyl)-2-propanesulfonamide and (1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide and (1S,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide and (1R,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide

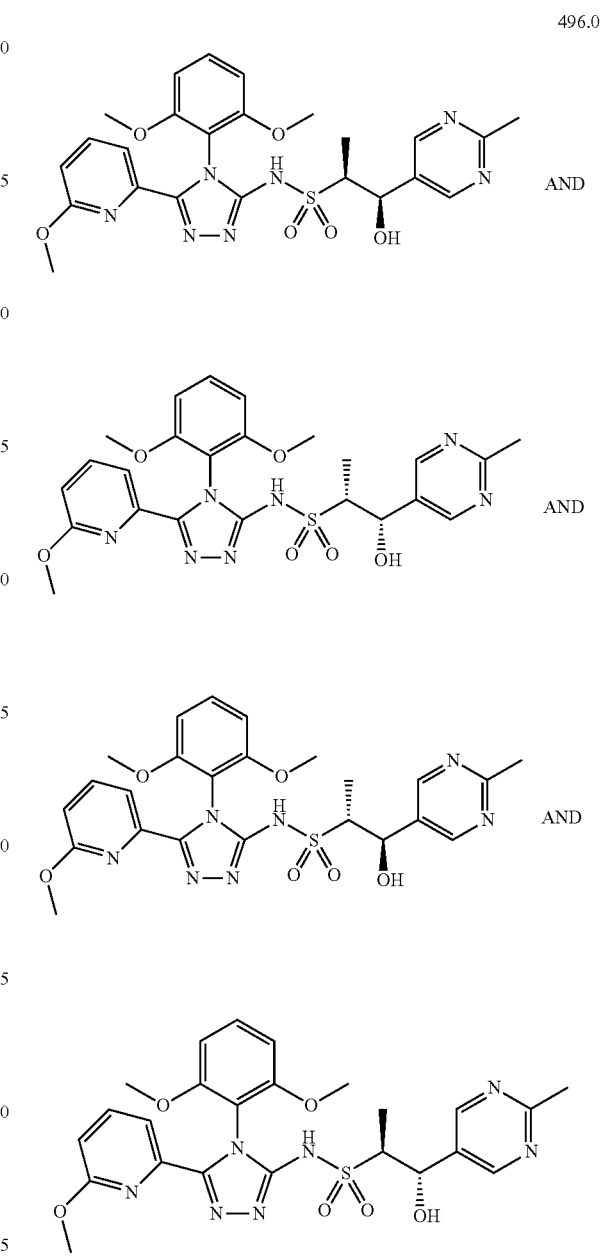

496.0

(1R,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide and (1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide and (1S,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide and (1R,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, Example 496.0

The title compound was prepared following the procedure in Example C using 5.0 and 2-methyl-pyrimidine-5-carbaldehyde (commercially available from AstaTech, Inc., Bristol, Pa.). LCMS-ESI (POS), m/z: 542.2 (M+H)$^+$.

Example 497.0: Preparation of (1R,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide 497.0

OR

OR

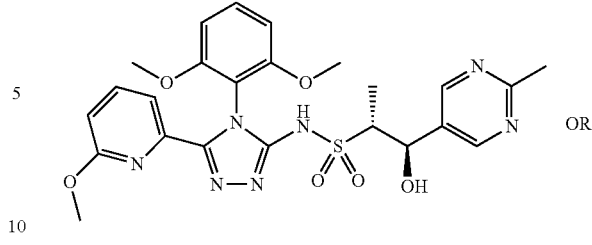
OR

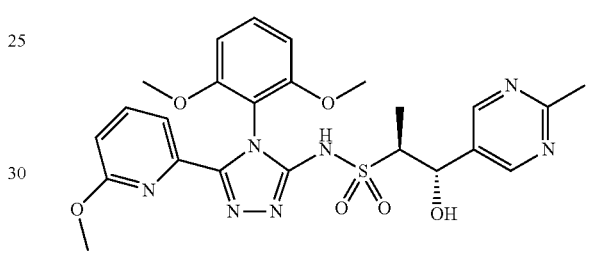

(1R,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, Example 497.0

The enantiomers of Example 496.0 were separated by SFC chiral separation as described below. The title compound was the first isomer to elute on injecting 496.0 to an AD-H column using the following SFC conditions. Run on Thar 200 SFC with 400×30 mm AD-H column with 36 mL/min EtOH (20 mm NH$_3$)+74 g/min CO$_2$, 33% cosolvent at 110 g/min. Temperature.=20° C., Outlet pressure=100 bar, Wavelength=297 nm. Injected 0.5 mL of 395 mg sample dissolved in 14 mL 2:1 MeOH:DCM, c=28.2 mg/mL and 14.1 mg per injection. Cycle time 12 min, run time 18 min. $^1$H NMR (500 MHz, CDCl$_3$) δ 8.62 (s, 2H), 7.61-7.69 (m, 2H), 7.39 (t, J=8.5 Hz, 1H), 6.72-6.76 (m, 1H), 6.69 (d, J=8.4 Hz, 1H), 6.63 (d, J=8.3 Hz, 1H), 5.55 (s, 1H), 3.84 (s, 3H), 3.70 (s, 3H), 3.17 (s, 3H), 3.12-3.16 (m, 1H), 2.75 (s, 3H), 1.22 (d, J=7.0 Hz, 3H). LCMS-ESI (POS), m/z: 542.2 (M+H)$^+$.

Example 498.0: Preparation of (1R,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2S)—N-(4-(2,6-(trimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1R,2R)—N-(4-(2,6-(trimethoxyphenyl)-5-(6-methoxy-2-pyridinyl)-4H-1,2,4-triazol-3-yl)-1-hydroxy-1-(2-methyl-5-pyrimidinyl)-2-propanesulfonamide 498.0

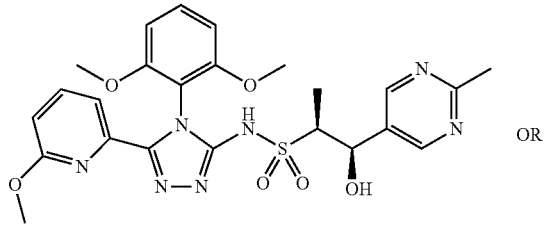

OR

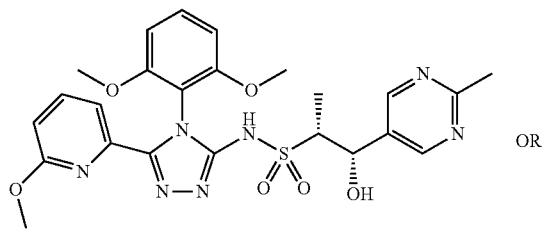

OR

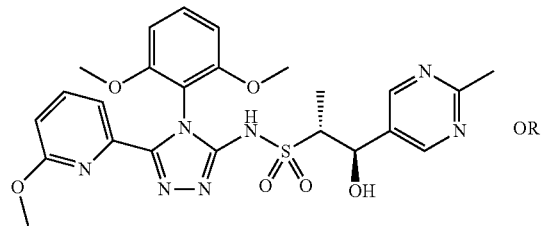

OR

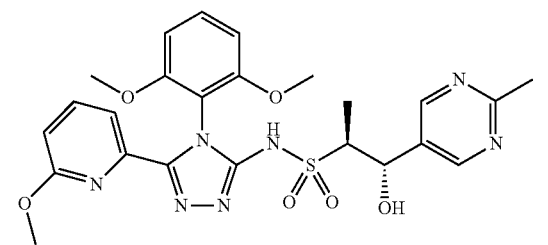

(1R,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide.
Example 498.0

The title compound was the fourth isomer to elute on injecting 496.0 to the AD-H column using the SFC conditions described in Example 497.0. $^1$H NMR (CD$_2$Cl$_2$) δ: 8.49 (s, 2H), 7.51-7.60 (In, 2H), 7.34 (t, J=8.5 Hz, 1H), 6.65 (ddd, J=8.3, 5.7, 0.9 Hz, 2H), 6.59 (dd. J=8.5, 0.8 Hz, 1H), 5.39 (s, 1H), 3.75 (s, 3H), 3.62 (s, 3H), 3.07 (s, 3H), 3.02 (dd. J=7.0, 1.3 Hz, 1H), 2.59 (s, 3H), 1.10 (d, J=7.0 Hz, 3H). LCMS-ESI (POS), m/z: 542.2 (M+H)$^+$.

Example 499.0: Preparation of (1R,2S)—N-(4-(2,6-(trimethoxyphenyl)-5-(6-methoxy-2-pyridinyl)-4H-1,2,4-triazol-3-yl)-1-methoxy-1-(2-methyl-5-pyrimidinyl)-2-propanesulfonamide and (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide and (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide and (1R,2R)—N-(4-(2,6-(trimethoxyphenyl)-5-(6-methoxy-2-pyridinyl)-4H-1,2,4-triazol-3-yl)-1-methoxy-1-(2-methyl-5-pyrimidinyl)-2-propanesulfonamide 499.0

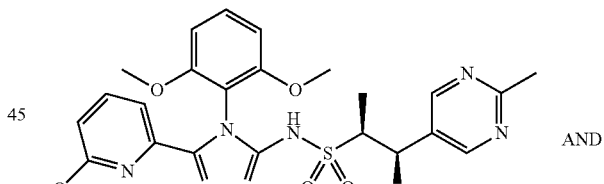

AND

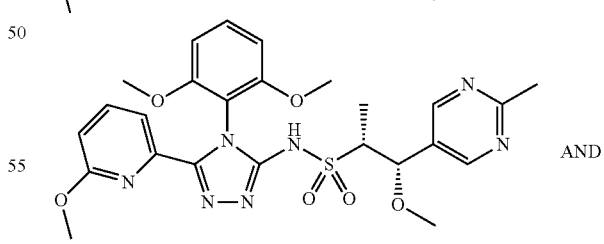

AND

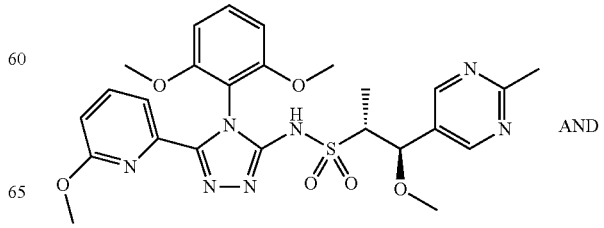

AND

739

-continued

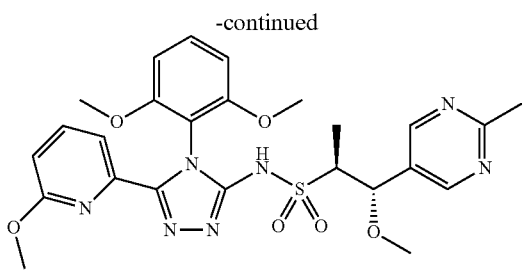

(1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide and (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide and (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide and (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, Example 499.0

The title compound was prepared following the procedure in Example C, using 4.0 and 2-methyl-pyrimidine-5-carbaldehyde (commercially available from AstaTech, Inc., Bristol, Pa.). LCMS-ESI (POS), m/z: 556.0 (M+H)$^+$.

Example 500.0: Preparation of (1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide 500.0

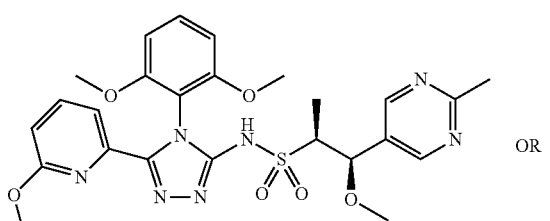

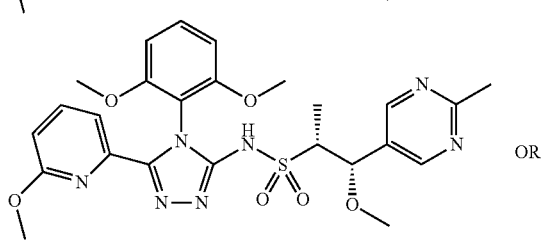

740

-continued

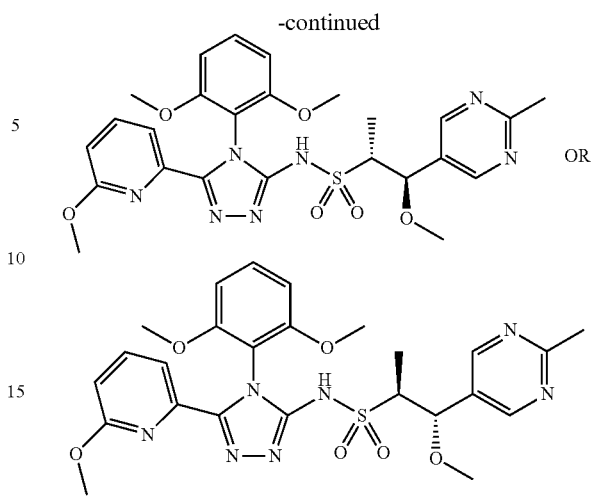

(1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, Example 500.0

The enantiomers of Example 499.0 were separated by SFC chiral separation as described. The title compound was the third peak on IC column (the third isomer to elute on injecting of 499.0 to IC column) under the SFC condition as described below. Run on Thar 350 SFC with 30×150+30×250 mm IC columns in series with 50 mL/min EtOH (20 mM NH$_3$)+50 g/min CO$_2$, 50% co-solvent at 50 g/min. Temperature.=24° C., Outlet pressure=100 bar, Wavelength=297 nm. Injected 2.0 mL of 435 mg sample dissolved in 20 mL 1:1 MeOH:DCM; c=21.8 mg/mL, and 43.6 mg per injection. Cycle time 13.5 min, run time 18 min. The third peak 500.0 and the fourth peak 501.0 were obtained pure while the first and the second peak were partially overlapped. The mixture of the first and the second peak isomers were separated on OD-H column on the Stage 2 purification as described below. Run on Thar 350 SFC with 21×150+21×250 mm OD-H columns in series with 15.40 mL/min MeOH (20 mM NH$_3$)+54.00 g/min CO$_2$, 22% co-solvent at 70 g/min. Temperature.=24° C., Outlet pressure=100 bar, Wavelength=297 nm. Injected 4.8 mL of 117 mg sample dissolved in 10 mL 1:1 MeOH:DCM; c=1.17 mg/mL, and 5.617 mg per injection. $^1$H NMR (500 MHz, CD$_3$OD) δ 8.48 (s, 2H), 7.74 (dd, J=8.3, 7.6 Hz, 1H), 7.61-7.67 (m, 1H), 7.47 (t, J=8.4 Hz, 1H), 6.81-6.89 (m, 2H), 6.77 (dd, J=8.3, 0.7 Hz, 1H), 4.61 (d, J=4.9 Hz, 1H), 3.79 (s, 3H), 3.77 (s, 3H), 3.21-3.29 (m, 1H), 3.19 (s, 3H), 3.19 (s, 3H), 2.70 (s, 3H), 1.34 (d, J=7.1 Hz, 3H). LCMS-ESI (POS), m/z: 555.9 (M+H)$^+$.

Example 501.0: Preparation of (1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide 501.0

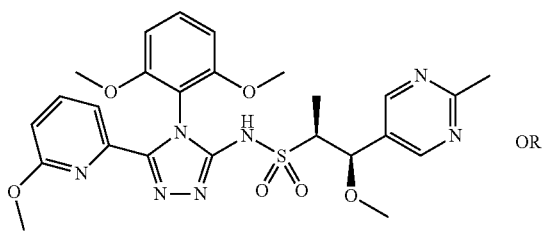

OR

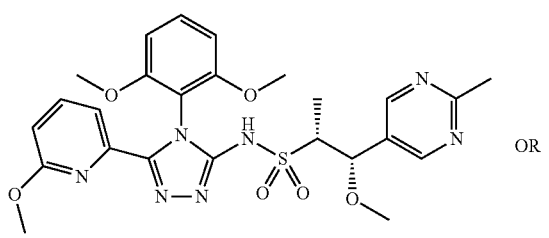

OR

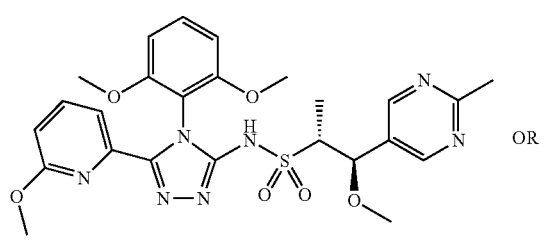

OR

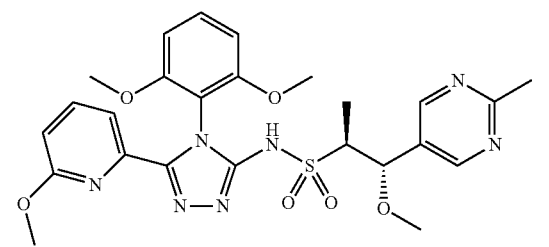

OR (1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-(trimethoxyphenyl)-5-(6-methoxy-2-pyridinyl)-4H-1,2,4-triazol-3-yl)-1-methoxy-1-(2-methyl-5-pyrimidinyl)-2-propanesulfonamide, 501.0

The title compound was the fourth isomer to elute on injecting 499.0 to IC column using the SFC conditions described in Example 500.0. $^1$H NMR (500 MHz, CD$_3$OD) δ 8.48 (br. s., 2H), 7.74 (t, J=7.9 Hz, 1H), 7.64 (d, J=7.5 Hz, 1H), 7.47 (t, J=8.4 Hz, 1H), 6.84 (t, J=7.6 Hz, 2H), 6.77 (d, J=8.2 Hz, 1H), 4.60-4.66 (m, 1H), 3.79 (s, 3H), 3.77 (s, 3H), 3.22-3.30 (m, 1H), 3.19 (s, 3H), 3.18 (s, 3H), 2.70 (s, 3H), 1.34 (d, J=7.0 Hz, 3H). LCMS-ESI (POS), m/z: 555.9 (M+H)$^+$.

Example 502.0: Preparation of (1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-(trimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide 502.0

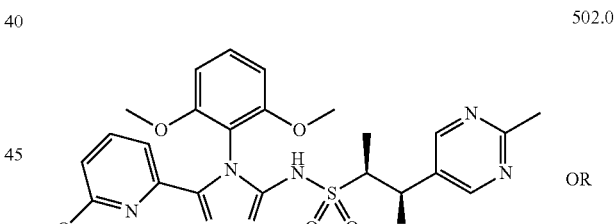

OR

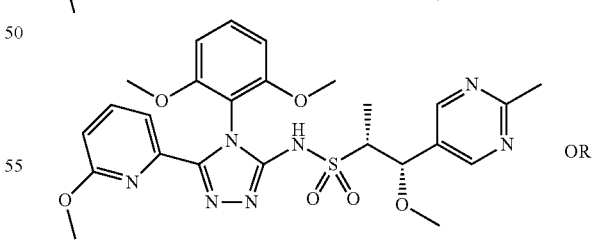

OR

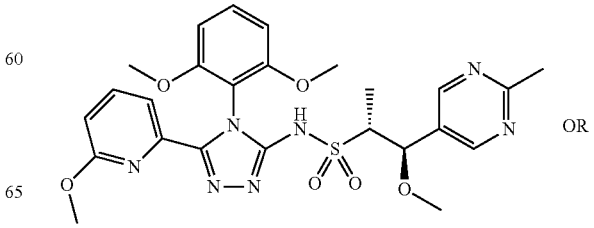

OR

743

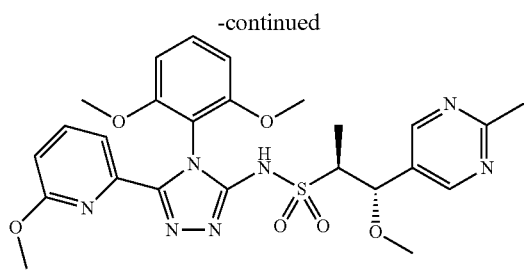

(1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, Example 502.0

The title compound was the first peak to elute on the OD column. It was obtained from the second stage purification of 499.0 on OD column under the SFC condition as described in the Example 500.0. $^1$H NMR (500 MHz, CD$_3$OD) δ 8.48 (s, 2H), 7.74 (t, J=7.8 Hz, 1H), 7.65 (d, J=7.0 Hz, 1H), 7.47 (t, J=8.5 Hz, 1H), 6.84 (t, J=7.2 Hz, 2H), 6.77 (d, J=8.2 Hz, 1H), 4.61 (d, J=4.9 Hz, 1H), 3.79 (s, 3H), 3.77 (s, 3H), 3.21-3.28 (m, 1H), 3.19 (s, 3H), 3.18 (s, 3H), 2.70 (s, 3H), 1.34 (d, J=6.8 Hz, 3H). LCMS-ESI (POS), m/z: 556.0 (M+H)$^+$.

Example 503.0: Preparation of (1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-(trimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide 503.0

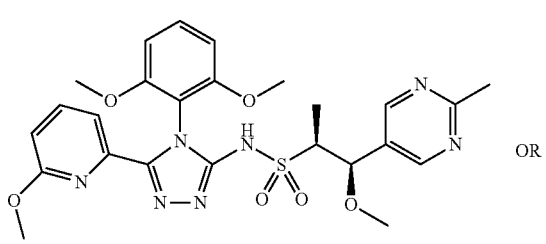 OR

744

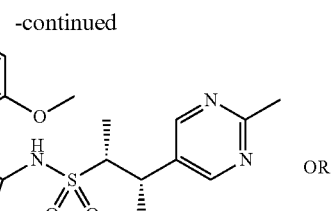 OR

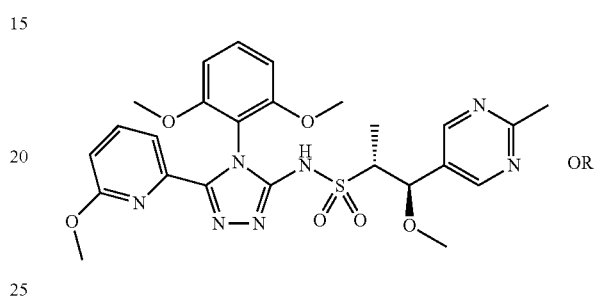 OR (1R,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide or (1R,2R)—N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, Example 503.0

The title compound was the second peak to elute on the OD column. It was obtained from the second stage purification of 499.0 on OD column under the SFC condition as described in the Example 500.0. $^1$H NMR (500 MHz, CD$_3$CN) δ 8.53 (s, 2H), 7.75 (t, J=7.7 Hz, 1H), 7.59-7.64 (m, 1H), 7.45 (t, J=8.0 Hz, 1H), 6.75-6.82 (m, 3H), 4.67 (d, J=5.6 Hz, 1H), 3.75 (s, 3H), 3.70-3.73 (m, 3H), 3.52-3.60 (m, 1H), 3.18 (s, 3H), 3.16 (s, 3H), 2.66 (s, 3H), 1.11 (d, J=7.1 Hz, 3H). LCMS-ESI (POS), m/z: 556.0 (M+H)$^+$.

Example 504.0: Preparation of (2E)-N-(4-(2,6-dimethoxyphenyl)-5-(5-methyl-3-pyridinyl)-4H-1,2,4-triazol-3-yl)-3-(5-fluoro-2-pyrimidinyl)-2-butene-2-sulfonamide

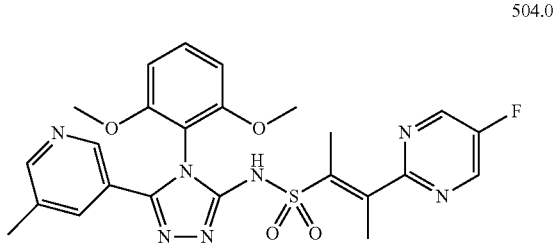 [SMILES: COc1cccc(OC)c1-n1c(NS(=O)(=O)/C(C)=C(\C)c2ncc(F)cn2)nnc1-c1cncc(C)c1]

504.0

(2E)-N-(4-(2,6-dimethoxyphenyl)-5-(5-methyl-3-pyridinyl)-4H-1,2,4-triazol-3-yl)-3-(5-fluoro-2-pyrimidinyl)-2-butene-2-sulfonamide, Example 504.0

The title compound was prepared following the procedure in Example B, using 2.0 and 10.05. $^1$H NMR (500 MHz, DMSO-$d_6$) δ 13.50 (s, 1H), 8.96 (d, J=0.7 Hz, 2H), 8.49 (d, J=1.7 Hz, 1H), 8.22 (d, J=2.0 Hz, 1H), 7.58-7.67 (m, 1H), 7.46-7.55 (m, 1H), 6.83 (d, J=8.6 Hz, 2H), 3.71 (s, 6H), 2.30 (d, J=1.7 Hz, 3H), 2.26 (s, 3H), 1.84 (d, J=1.5 Hz, 3H). LCMS-ESI (POS), m/z: 525.8 (M+H)$^+$.

Example 505.0: Preparation of (2E)-N-(4-(2,6-dimethoxyphenyl)-5-(6-methoxy-2-pyridinyl)-4H-1,2,4-triazol-3-yl)-3-(5-fluoro-2-pyrimidinyl)-2-butene-2-sulfonamide

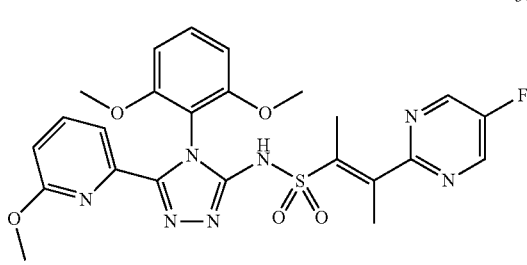

505.0

(2E)-N-(4-(2,6-dimethoxyphenyl)-5-(6-methoxy-2-pyridinyl)-4H-1,2,4-triazol-3-yl)-3-(5-fluoro-2-pyrimidinyl)-2-butene-2-sulfonamide, Example 505.0

The title compound was prepared following the procedure in Example B, using 2.2 and 10.05. $^1$H NMR (500 MHz, DMSO-$d_6$) δ 13.42 (s, 1H), 8.95 (d, J=0.7 Hz, 2H), 7.81 (dd, J=8.3, 7.6 Hz, 1H), 7.60 (dd, J=7.3, 0.7 Hz, 1H), 7.41 (t, J=8.4 Hz, 1H), 6.84 (d, J=7.8 Hz, 1H), 6.79 (d, J=8.6 Hz, 2H), 3.65 (s, 6H), 3.11 (s, 3H) 2.30 (d, J=1.5 Hz, 3H) 1.82 (d, J=1.5 Hz, 3H). LCMS-ESI (POS), m/z: 541.8 (M+H)$^+$.

Example 506.0: Preparation of (2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide 506.0

(2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide, Example 506.0

The title compound was prepared following the procedure in Example B, using 2.0 and 10.3. $^1$H NMR (500 MHz, CD$_2$Cl$_2$) δ 8.43-8.58 (m, 3H) 8.25 (s, 1H) 8.04 (s, 1H) 7.43 (t, J=8.56 Hz, 1H), 6.64 (t, J=8.80 Hz, 2H), 3.69 (s, 3H), 3.70 (s, 3H), 3.42-3.59 (m, 2H), 2.52 (s, 3H), 2.36 (s, 3H), 1.26 (t, J=7.34 Hz, 6H). LCMS-ESI (POS), m/z: 523.9 (M+H)$^+$.

Example 507.0: Preparation of (2S,3R)—N-(4-(2,6-dimethoxyphenyl)-5-(6-methoxy-2-pyridinyl)-4H-1,2,4-triazol-3-yl)-3-(5-methyl-2-pyrazinyl)-2-butanesulfonamide

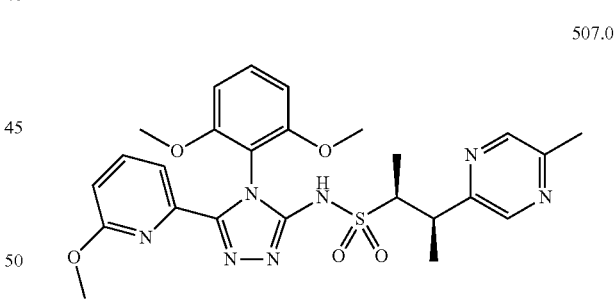

507.0

(2S,3R)—N-(4-(2,6-dimethoxyphenyl)-5-(6-methoxy-2-pyridinyl)-4H-1,2,4-triazol-3-yl)-3-(5-methyl-2-pyrazinyl)-2-butanesulfonamide, Example 507.0

The title compound was prepared following the procedure in Example B, using 2.2 and 10.3. $^1$H NMR (500 MHz, CD$_2$Cl$_2$) δ 8.64 (s, 1H), 8.31 (s, 1H), 7.55-7.76 (m, 2H), 7.44 (t, J=8.4 Hz, 1H), 6.59-6.84 (m, 3H), 3.75 (m, 6H), 3.47-3.66 (m, 2H), 3.19 (s, 3H), 2.65 (s, 3H), 1.39 (d, J=9.2, Hz, 3H), 1.37 (d, J=7.0 Hz, 3H). LCMS-ESI (POS), m/z: 539.9 (M+H)$^+$.

Example 508.0: Preparation of (1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide and (1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide and (1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide and (1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide 508.0

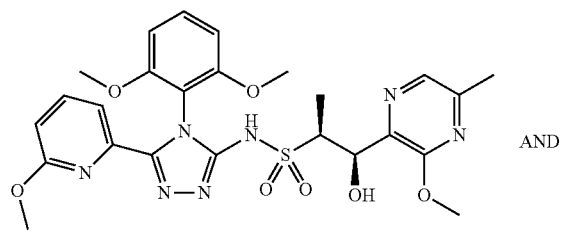

AND

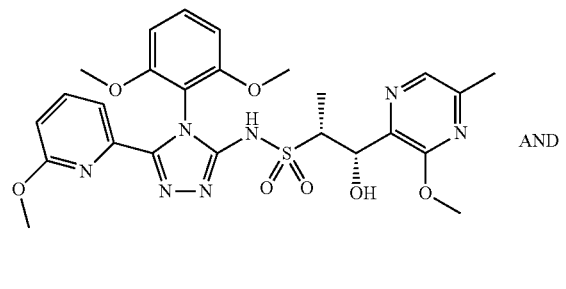

AND

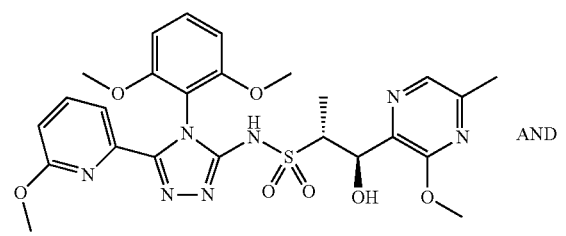

AND

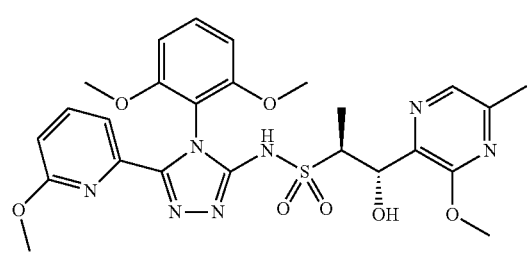

(1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide and (1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide and (1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide and (1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, Example 508.0

The title compound was prepared following the procedure in Example C, using 5.0 and 3-methoxy-5-methyl-pyrazinecarboxaldehyde (commercially available from ACES Pharma, Inc., Princeton, N.J.). The major and minor diastereomer were separated as described in the following Examples.

Example 509.0: Preparation of (1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide

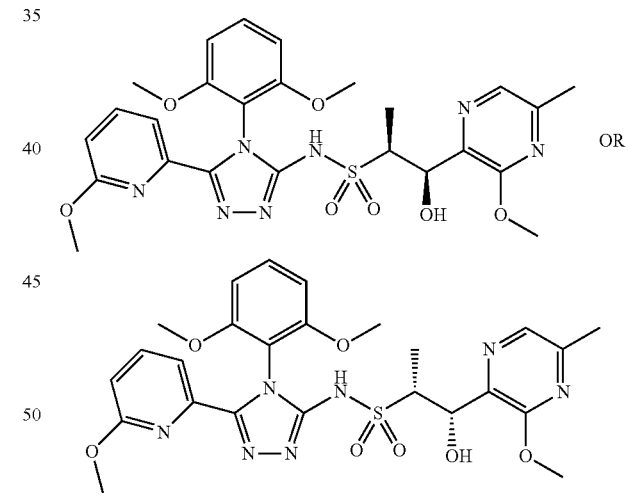

509.0

(1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, Example 509.0

The title compound was the first peak to elute on an IC column on subjecting the mixture of major diastereomers from Example 508.0. The IC column separation conditions were as follows. Run on Thar 80 SFC with 250×21 mm IC column with 41 mL/min MeOH (20 mM $NH_3$)+34 g/min $CO_2$, 55% co-solvent at 75 g/min. Temperature.=35° C., Outlet pressure=100 bar, Wavelength=299 nm. Injected 1.5 mL of 110 mg sample dissolved in 20 mL of MeOH:DCM 3:1; c=5.5 mg/mL and 8.25 mg per injection. Cycle time=3.75 min, run time 8 min. $^1$H NMR (500 MHz, $CD_3OD$) δ 8.01 (s, 1H), 7.73 (dd, J=8.2, 7.5 Hz, 1H), 7.63 (dd, J=7.6, 0.7 Hz, 1H), 7.42 (t, J=8.6 Hz, 1H), 6.72-6.81 (m, 3H), 5.58 (d, J=2.9 Hz, 1H), 3.91 (s, 3H), 3.73 (s, 3H), 3.71 (s, 3H), 3.59-3.66 (m, 1H), 3.19 (s, 3H), 2.46 (s, 3H), 1.24 (d, J=7.1 Hz, 3H). LCMS-ESI (POS), m/z: 572.3 $(M+H)^+$.

Example 510.0: Preparation of (1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide 510.0

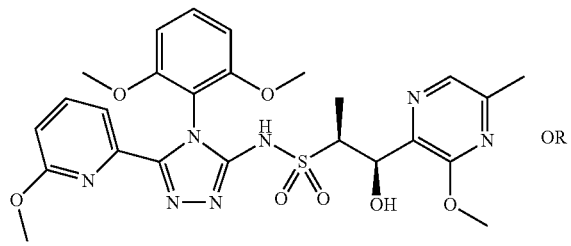

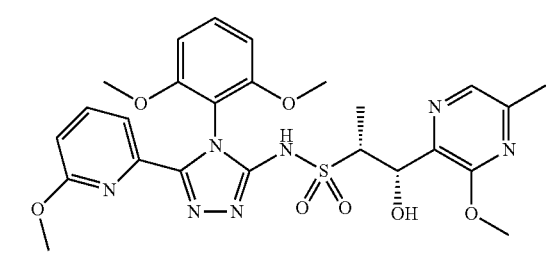

(1S,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, Example 510.0

The title compound was the second peak to elute on the IC column as the condition described in Example 509.0. $^1$H NMR (500 MHz, $CD_3OD$) δ 8.01 (s, 1H), 7.73 (dd, J=8.2, 7.5 Hz, 1H), 7.63 (dd, J=7.6, 0.7 Hz, 1H), 7.42 (t, J=8.6 Hz, 1H), 6.72-6.81 (m, 3H) 5.58 (d, J=2.9 Hz, 1H), 3.91 (s, 3H), 3.73 (s, 3H), 3.71 (s, 3H) 3.64-3.60 (m, 1H), 3.19 (s, 3H), 2.46 (s, 3H), 1.24 (d, J=7.1 Hz, 3H). LCMS-ESI (POS), m/z: 572.3 $(M+H)^+$.

Example 511.0: Preparation of (1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide 511.0

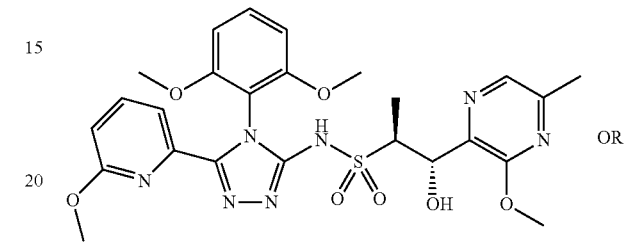

(1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, Example 511.0

The mixture of minor diastereomers from Example 508.0 were separated. The title compound was the first peak to elute on a CC4 column under the following conditions. Run on Thar 200 SFC with 250×30 mm CC4 column with 66 mL/min MeOH (20 mM $NH_3$)+54 g/min $CO_2$, 55% co-solvent at 120 g/min. Temperature.=30° C., Outlet pressure=100 bar, Wavelength=296 nm. Injected 3.0 mL of 116 mg sample dissolved in 20 mL MeOH; c=5.8 mg/mL and 17.4 mg per injection. Cycle time=9 min, run time=15 min. $^1$H NMR (500 MHz, $CD_3OD$) δ 8.02 (s, 1H), 7.67-7.76 (m, 1H), 7.58-7.65 (m, 1H), 7.41 (t, J=8.6 Hz, 1H), 6.77 (dd, J=8.6, 2.5 Hz, 2H), 6.73 (d, J=8.3 Hz, 1H), 5.20 (d, J=8.6 Hz, 1H), 3.98 (s, 3H), 3.73-3.76 (m, 1H), 3.75 (s, 3H), 3.73 (s, 3H), 3.18 (s, 3H), 2.46 (s, 3H), 1.07 (d, J=6.9 Hz, 3H). LCMS-ESI (POS), m/z: 572.1 $(M+H)^+$.

Example 512.0: Preparation of 1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide Example 513.0: Preparation of (1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide and (1S,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide

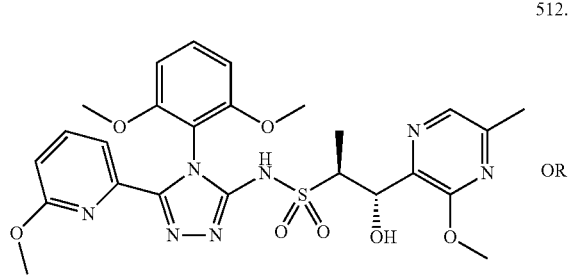

512.0

OR

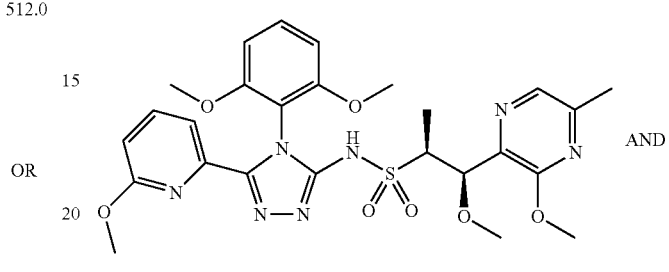

513.0

AND

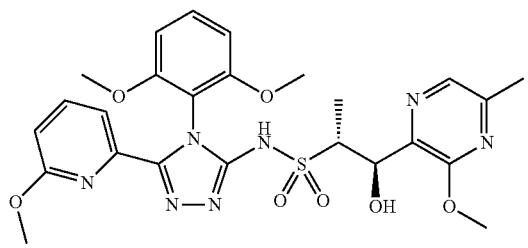

(1S,2S)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide or (1R,2R)—N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, Example 512.0

The title compound was the second peak to elute on the CC4 column as described in Example 511.0. $^1$H NMR (500 MHz, CD$_3$OD) δ 8.02 (s, 1H), 7.78-7.70 (m, 1H), 7.64 (m, 1H), 7.43 (t, J=8.4 Hz, 1H), 6.82-6.74 (m, 3H), 5.18 (d, J=8.3 Hz, 1H), 3.98 (s, 3H), 3.77 (s, 3H), 3.75 (s, 3H), 3.63-3.72 (m, 1H), 3.19 (s, 3H), 2.46 (s, 3H), 1.09 (d, J=6.9 Hz, 3H). LCMS-ESI (POS), m/z: 572.2 (M+H)$^+$.

(1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide and (1S,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, Example 513.0

The title compound was prepared following the procedure in Example C using 5.0 and 3-methoxy-5-methyl-pyrazinecarboxaldehyde (commercially available from ACES Pharma, Inc., Princeton, N.J.). The ether formation was accomplished following the procedure described in Example 22.0. The product was isolated as a mixture of the major diastereomers. $^1$H NMR (500 MHz, CDCl$_3$) δ 11.09 (br. s., 1H), 8.04 (s, 1H), 7.54-7.69 (m, 2H), 7.32 (t, J=8.6 Hz, 1H), 6.71 (dd, J=7.5, 1.6 Hz, 1H), 6.61 (dt, J=4.7, 4.0 Hz, 2H), 5.20 (d, J=4.4 Hz, 1H), 3.94 (s, 3H), 3.73 (s, 3H), 3.68 (s, 3H), 3.62 (qd, J=7.0, 4.7 Hz, 1H), 3.24-3.30 (m, 3H), 3.17 (s, 3H), 2.45 (s, 3H), 1.40 (d, J=7.1 Hz, 3H). LCMS-ESI (POS), m/z: 586.2 (M+H)$^+$.

Example 514.0: Preparation of (1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide and (1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide Example 515.0: Preparation of (1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide 514.0

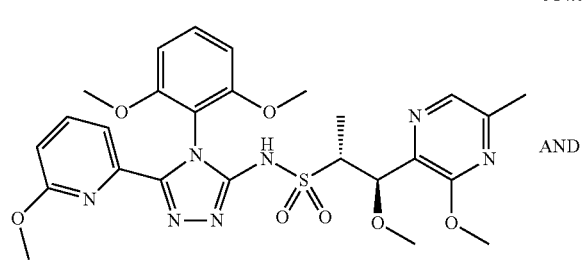

AND 515.0

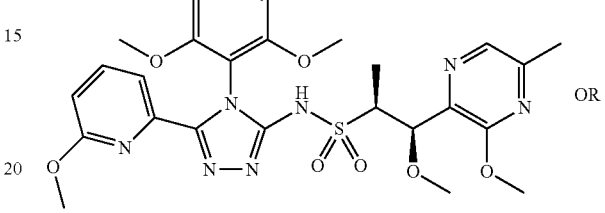

OR

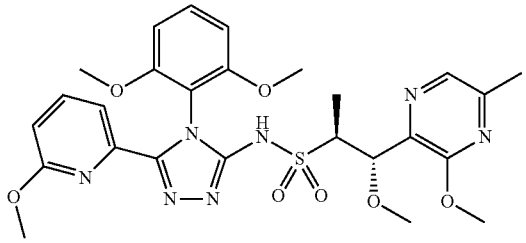

(1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide and (1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, Example 514.0

Further elution of the reaction described in Example 513.0, gave the title compound as a mixture of the minor diasteromers. $^1$H NMR (500 MHz, CD$_3$OD) δ 8.07 (s, 1H), 7.70-7.76 (m, 1H), 7.63 (dd, J=7.5, 0.9 Hz, 1H), 7.43 (t, J=8.6 Hz, 1H), 6.80 (d, J=8.6 Hz, 2H), 6.76 (dd, J=8.3, 0.7 Hz, 1H), 4.89 (d, J=8.8 Hz, 1H), 3.98 (s, 3H), 3.78 (s, 3H), 3.75 (s, 3H), 3.69-3.74 (m, 1H), 3.19 (s, 3H), 3.08 (s, 3H), 2.48 (s, 3H), 1.03 (d, J=7.09 Hz, 3H). LCMS-ESI (POS), m/z: 586.1 (M+H)$^+$.

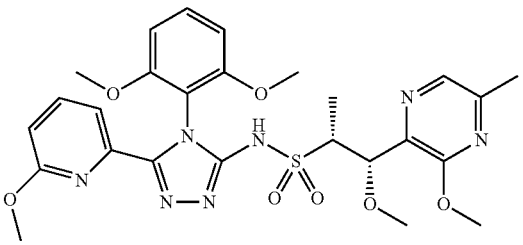

(1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, Example 515.0

The title compound was the first peak to elute on subjecting 513.0 to the following conditions using a CC4 column Run on Thar 80 SFC with 250×30 mm CC4 column with 36 mL/min MeOH (20 mM NH$_3$)+44 g/min CO$_2$, 45% co-solvent at 80 g/min. Temperature.=38° C., Outlet pressure=100 bar, Wavelength=296 nm. Injected 1.0 mL of 110 mg sample dissolved in 30 mL of 1:1 MeOH:DCM; c=3.7 mg/mL and 3.7 mg per injection. Cycle time 7 min, run time 13 min. $^1$H NMR (500 MHz, CDCl$_3$) δ 8.04 (s, 1H), 7.57-7.66 (m, 2H), 7.32 (t, J=8.6 Hz, 1H), 6.71 (dd, J=7.5, 1.6 Hz, 1H), 6.61 (dd, J=8.6, 4.2 Hz, 2H), 5.20 (d, J=4.4 Hz, 1H), 3.94 (s, 3H), 3.73 (s, 3H), 3.68 (s, 3H), 3.63 (qd, J=7.0, 4.5 Hz, 1H), 3.27 (s, 3H), 3.18 (s, 3H), 2.46 (s, 3H), 1.40 (d, J=7.1 Hz, 3H). LCMS-ESI (POS), m/z: 586.2 (M+H)$^+$.

Example 516.0: Preparation of (1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2R)—N-(4-(2,6-(trimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide Example 517.0: Preparation of (1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide

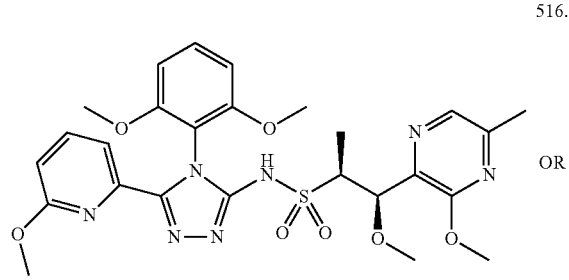

516.0 OR

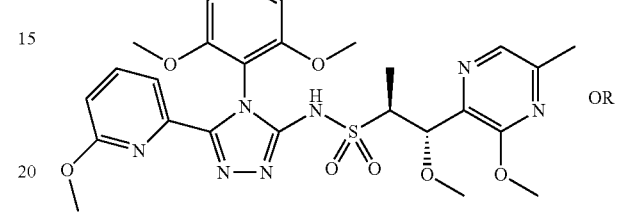

517.0 OR

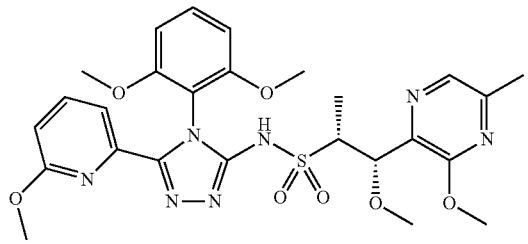

(1R,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, Example 516.0

The title compound was the second peak to elute on the CC4 column as described in Example 515.0. ¹H NMR (500 MHz, CDCl₃) δ 8.04 (s, 1H), 7.58-7.65 (m, 2H), 7.32 (t, J=8.5 Hz, 1H), 6.71 (dd, J=7.6, 1.4 Hz, 1H), 6.61 (dd, J=8.5, 4.3 Hz, 2H), 5.20 (d, J=4.5 Hz, 1H), 3.94 (s, 3H), 3.73 (s, 3H), 3.69 (s, 3H), 3.61-3.66 (m, 1H), 3.27 (s, 3H), 3.18 (s, 3H), 2.46 (s, 3H), 1.40 (d, J=7.0 Hz, 3H). LCMS-ESI (POS), m/z: 586.2 (M+H)⁺.

(1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, Example 517.0

The title compound was the first peak to elute on subjecting 514.0 to the following conditions on an IC column. Run on Thar 80 SFC with 250×21 mm IC column with 21 mL/min MeOH (20 mM NH₃)+39 g/min CO₂, 35% co-solvent at 60 g/min. Temperature.=28° C., Outlet pressure=100 bar, Wavelength=215 nm. Injected 0.3 mL of 66 mg sample dissolved in 15 mL of 2:1 MeOH:DCM; c=4.4 mg/mL and 1.3 mg per injection. Cycle time 9 min, run time 19 min. ¹H NMR (500 MHz, CDCl₃) δ 8.05 (s, 1H), 7.56-7.69 (m, 2H), 7.32 (t, J=8.44 Hz, 1H), 6.70 (dd, J=7.34, 1.96 Hz, 1H), 6.56-6.66 (m, 2H), 4.91 (d, J=8.07 Hz, 1H), 3.97 (s, 3H), 3.86 (quin, J=7.34 Hz, 1H), 3.78 (s, 3H), 3.71 (s, 3H), 3.18 (s, 3H), 3.16 (s, 3H), 2.48 (s, 3H), 1.16 (d, J=7.09 Hz, 3H). LCMS-ESI (POS), m/z: 586.2 (M+H)⁺.

Example 518.0: Preparation of (1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide Example 519.0: Preparation of (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide and (2S)-2-(5-chloro-1,3-thiazol-2-yl)-N-(4-(2,6-(trimethoxyphenyl)-5-(6-methoxy-2-pyridinyl)-4H-1,2,4-triazol-3-yl)-2-hydroxyethanesulfonamide 518.0

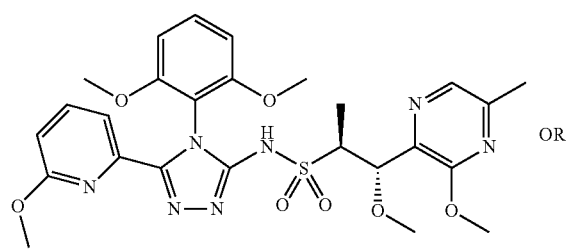

OR

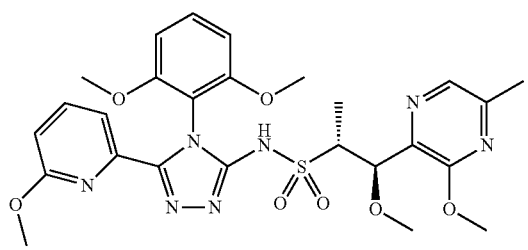

(1R,2R)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide or (1S,2S)—N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamidepropanesulfonamide, Example 518.0

The title compound was the second peak to elute on the IC column as described in Example 517.0. 1H NMR (500 MHz, CDCl3) δ ppm 8.05 (br. s, 1H), 7.60-7.62 (m, 2H), 7.31 (t, J=8.44 Hz, 1H), 6.70 ((br. s, 1H), 6.61 (t, J=8.7 Hz, 2H), 4.91 (d, J=7.8 Hz, 1H), 3.98 (s, 3H), 3.86-3.89 (m, 1H), 3.77 (s, 3H), 3.70 (s, 3H), 3.18 (s, 6H), 2.47 (s, 3H), 1.17 (br. s, 3H). LCMS-ESI (POS), m/z: 586.1 (M+H)+.

519.0

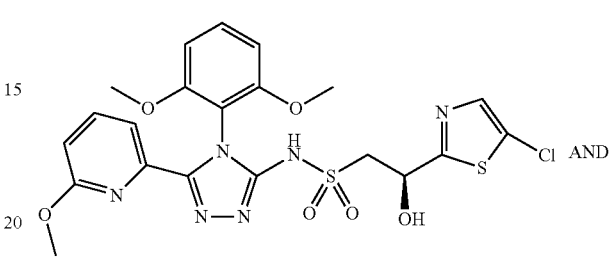

AND

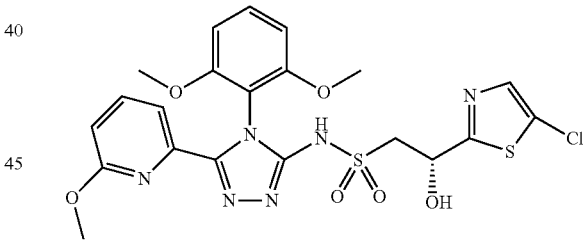

(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide and (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide, Example 519.0

The title compound was prepared following the procedure in Example C using 4.0 and 5-chlorothiazole-2-carboxaldehyde (commercially available from Acros Organics). 1H NMR (500 MHz, CD3OD) δ 7.70-7.76 (m, 1H), 7.63 (dd. J=7.6, 0.7 Hz, 1H), 7.60 (s, 1H), 7.42 (t, J=8.4 Hz, 1H), 6.73-6.81 (m, 3H), 5.31 (dd, J=9.4, 2.3 Hz, 1H), 3.68-3.75 (m, 7H), 3.30-3.36 (m, 2H), 3.17 (s, 3H). LCMS-ESI (POS), m/z: 553.0 (M+H)+.

Example 520.0: Preparation of (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide Example 521.0: Preparation of (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide

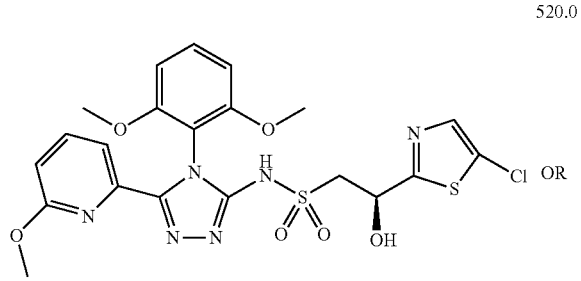

520.0

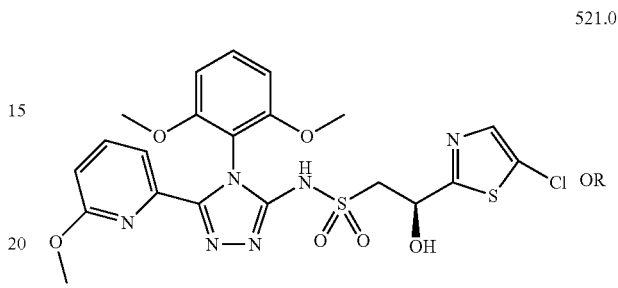

521.0

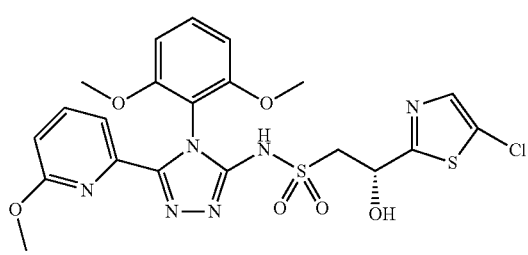

(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide, Example 520.0

The title compound was obtained from the enantiomeric mixture of Example 519.0 and was the first isomer to elute from an IC column using following SFC conditions. Run on Thar 80 SFC with 250×21 mm IC column with 26.25 mL/min EtOH (20 mM NH$_3$)+48.7 g/min CO$_2$, 35% co-solvent at 75 g/min. Temperature.=29° C., Outlet pressure=100 bar, Wavelength=297 nm. Injected 1.0 mL of 133 mg sample dissolved in 15 mL of MeOH; c=8.9 mg/mL and 8.9 mg per injection. Cycle time 6 min, run time 9 min. $^1$H NMR (500 MHz, CDCl$_3$) δ 7.63-7.68 (m, 2H), 7.52 (s, 1H), 7.38 (t, J=8.3 Hz, 1H), 6.70-6.79 (m, 1H), 6.64 (ddd, J=12.7, 8.6, 0.7 Hz, 2H), 5.39 (dd, J=10.3, 1.7 Hz, 1H), 3.80 (dd, J=14.1, 1.6 Hz, 1H), 3.76 (s, 3H), 3.72 (s, 3H), 3.30 (dd, J=14.2, 10.3 Hz, 1H), 3.17 (s, 3H). LCMS-ESI (POS), m/z: 553.0 (M+H)$^+$.

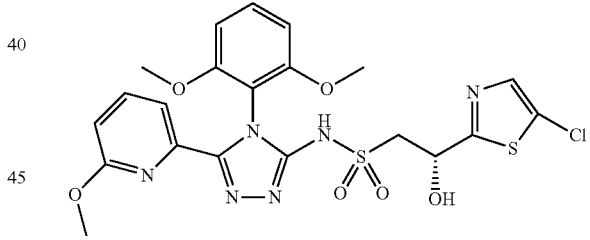

(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide, Example 521.0

The title compound was the second isomer to elute from the IC column using the SFC conditions described in Example 520.0. $^1$H NMR (500 MHz, CDCl$_3$) δ 7.63-7.68 (m, 2H), 7.52 (s, 1H), 7.38 (t, J=8.3 Hz, 1H), 6.70-6.79 (m, 1H), 6.64 (ddd, J=12.7, 8.56, 0.7 Hz, 2H), 5.39 (dd, J=10.3, 1.7 Hz, 1H), 3.80 (dd, J=14.1, 1.6 Hz, 1H), 3.76 (s, 3H), 3.72 (s, 3H), 3.30 (dd, J=14.2, 10.3 Hz, 1H), 3.17 (s, 3H). LCMS-ESI (POS), m/z: 553.0 (M+H)$^+$.

Example 522.0: Preparation of (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide and (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide

Example 523.0: Preparation of (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide

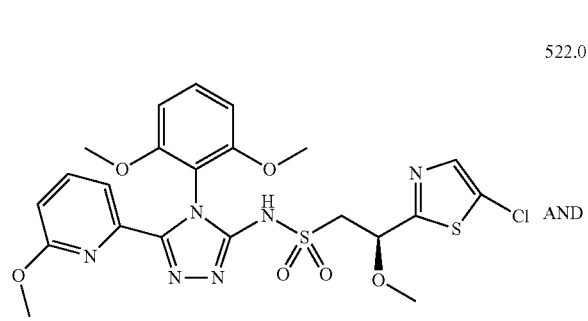

522.0

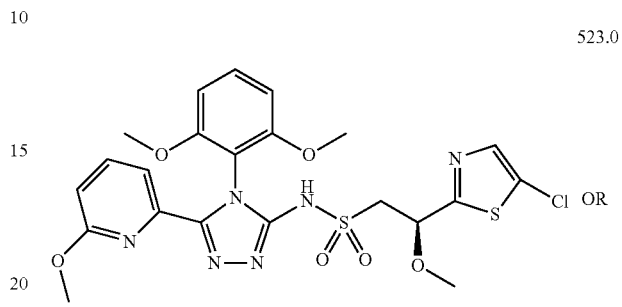

523.0

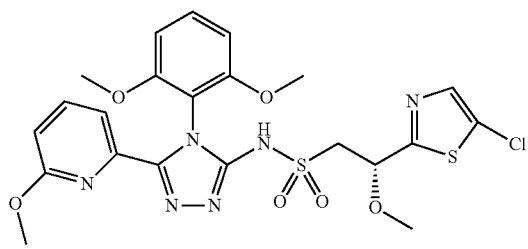

(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide and (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide, Example 522.0

(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide, Example 523.0

The title compound was prepared following the procedure in Example C using 4.0 and 5-chlorothiazole-2-carboxaldehyde (commercially available from Acros Organics). The ether formation was accomplished following the procedure described in Example 22.0. $^1$H NMR (500 MHz, CD$_3$OD) δ 7.68-7.75 (m, 1H), 7.59-7.64 (m, 2H), 7.40 (t, J=8.6 Hz, 1H), 6.75 (td, J=8.3, 0.7 Hz, 3H), 4.95 (dd, J=8.8, 3.4 Hz, 1H), 3.72 (d, J=2.5 Hz, 6H), 3.51-3.56 (m, 1H), 3.42-3.50 (m, 1H), 3.34 (s, 3H), 3.16 (s, 3H). LCMS-ESI (POS), m/z: 567.0 (M+H)$^+$. The enantiomers were separated by SFC chiral separation as described in Example 523.0.

The title compound was the first isomer to elute on subjecting 522.0 to the following separation conditions. Run on Thar 80 SFC with 150×20 mm AD-H column with 60 mL/min 15% (2:1) MeOH:ACN (0.1% NH$_4$OH)/CO$_2$. Temperature.=29° C., Outlet pressure=100 bar, Wavelength=220 nm. Injected 0.75 mL of sample solution at 5 mg/mL (2:1) MeOH:DCM. $^1$H NMR (500 MHz, CDCl$_3$) δ 7.55 (s, 1H), 7.45-7.52 (m, 2H), 7.22 (t, J=8.44 Hz, 1H), 6.55 (dd, J=8.31, 2.93 Hz, 3H), 4.96 (dd, J=8.31, 3.42 Hz, 1H), 3.71 (dd, J=14.18, 3.18 Hz, 1H), 3.60 (m, 6H), 3.54 (dd, J=14.31, 8.44 Hz, 1H), 3.37 (s, 3H), 3.12 (s, 3H). LCMS-ESI (POS), m/z: 567.0 (M+H)$^+$.

Example 524.0: Preparation of (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide

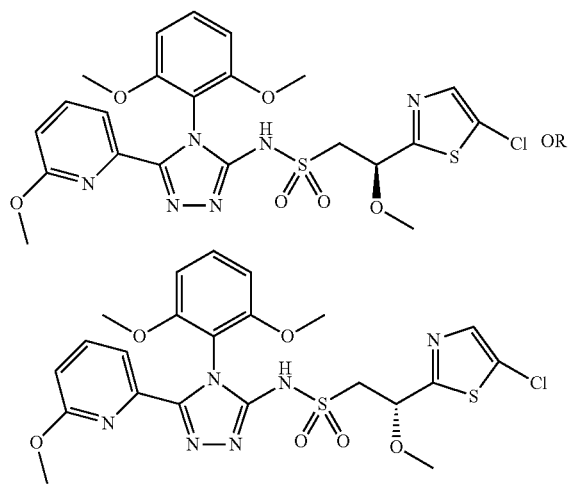

524.0

(2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide or (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide, Example 524.0

The title compound was the second isomer to elute from the AD-H column using the SFC conditions described in Example 523.0.

Example 525.0: Preparation of (2S,3R)—N-(4-((R)-2,4-dimethoxypyridin-3-yl)-5-(6-methoxypyridin-2-yl)-4H-1,2,4-triazol-3-yl)-3-(5-fluoropyrimidin-2-yl)butane-2-sulfonamide and (2S,3R)—N-(4-((S)-2,4-dimethoxypyridin-3-yl)-5-(6-methoxypyridin-2-yl)-4H-1,2,4-triazol-3-yl)-3-(5-fluoropyrimidin-2-yl)butane-2-sulfonamide (1:1 mixture of atropisomers)

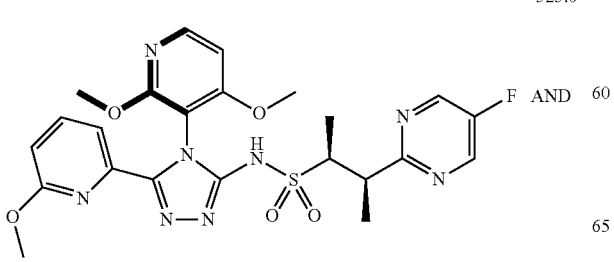

525.0

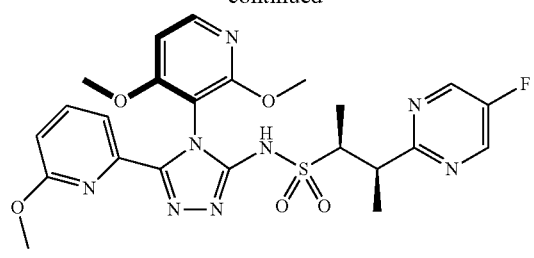

(2S,3R)—N-(4-((R)-2,4-dimethoxypyridin-3-yl)-5-(6-methoxypyridin-2-yl)-4H-1,2,4-triazol-3-yl)-3-(5-fluoropyrimidin-2-yl)butane-2-sulfonamide and (2S,3R)—N-(4-((S)-2,4-dimethoxypyridin-3-yl)-5-(6-methoxypyridin-2-yl)-4H-1,2,4-triazol-3-yl)-3-(5-fluoropyrimidin-2-yl)butane-2-sulfonamide (1:1 mixture of atropisomers, Example 525.0

The title compound was prepared following the procedure in Example A using the 10.1, 2,4-dimethoxypyridin-3-amine (Commercially available from SynChem, converted to the isothiocyanate through chemistry described in Example 1.3) and 6-methoxy-pyridine-2-carboxylic acid hydrazide (commercially available from Sigma-Aldrich Chemical Company, Inc.). LCMS-ESI (POS), m/z: 545.1 (M+H)$^+$.

Example 526.0: Preparation of (2S,3R)—N-(4-((R)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide and (2S,3R)—N-(4-((S)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide (1:1 mixture of atropisomers)

526.0

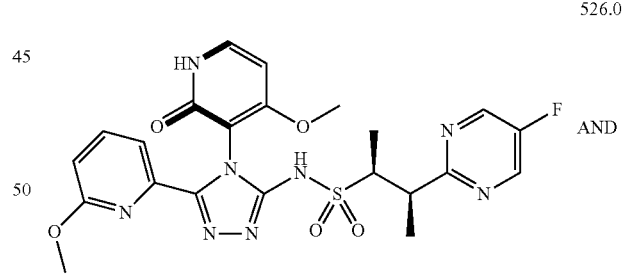

AND

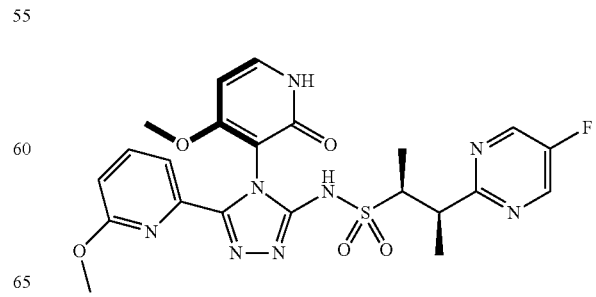

(2S,3R)—N-(4-((R)-4-methoxy-2-oxo-1,2-dihydro-pyridin-3-yl)-5-(6-methoxypyridin-2-yl)-4H-1,2,4-triazol-3-yl)-3-(5-fluoropyrimidin-2-yl)butane-2-sulfonamide compound and (2S,3R)—N-(4-((S)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide (1:1 mixture of atropisomers), Example 526.0

The title compound was obtained as a by-product during the preparation of 525.0. ¹H NMR (500 MHz, CD₃OD) δ 8.64-8.70 (m, 2H), 7.72-7.79 (m, 1H), 7.68 (dd, J=7.3, 0.7 Hz, 1H), 7.62 (d, J=7.6 Hz, 1H), 6.82 (dt, J=8.3, 0.7 Hz, 1H), 6.55 (dd, J=7.6, 2.5 Hz, 1H), 3.89 (d, J=4.4 Hz, 3H), 3.79-3.87 (m, 2H), 3.48 (d, J=0.7 Hz, 3H), 1.38-1.43 (m, 3H), 1.36 (t, J=6.6 Hz, 3H). LCMS-ESI (POS), m/z: 531.0 (M+H)⁺.

Example 527.0: Preparation of (2S,3R)—N-(4-((R)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide or (2S,3R)—N-(4-((S)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide (mixture of atropisomers)

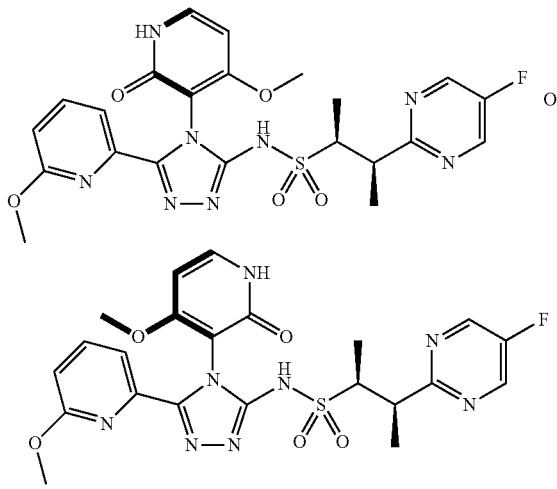

527.0

(2S,3R)—N-(4-((R)-4-methoxy-2-oxo-1,2-dihydro-pyridin-3-yl)-5-(6-methoxypyridin-2-yl)-4H-1,2,4-triazol-3-yl)-3-(5-fluoropyrimidin-2-yl)butane-2-sulfonamide compound or (2S,3R)—N-(4-((S)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide, Example 527.0

The title compound was the first isomer to elute from a CC4 column on subjecting 526.0 under the following SFC conditions. Run on Thar 80 SFC with 250×30 mm CC4 column with 48 mL/min MeOH (neat)+32 g/min CO₂, 60% co-solvent at 80 g/min. Temperature.=29° C., Outlet pressure=100 bar, Wavelength=297 nm. Injected 1.8 mL of 22 mg sample dissolved in 5 mL of 4:1 MeOH:DCM; c=4.4 mg/mL and 7.9 mg per injection. Fractions collected manually ¹H NMR (500 MHz, CD₃OD) δ 8.64 (d, J=0.7 Hz, 2H), 7.70-7.77 (m, 1H), 7.66 (dd, J=7.6, 0.7 Hz, 1H), 7.60 (d, J=7.6 Hz, 1H), 6.76-6.84 (m, 1H), 6.53 (d, J=7.6 Hz, 1H), 3.86 (s, 3H), 3.75-3.85 (m, 2H), 3.46 (s, 3H), 1.38 (d, J=6.9 Hz, 3H), 1.34 (d, J=6.6 Hz, 3H). LCMS-ESI (POS), m/z: 531.2 (M+H)⁺.

Example 528.0: Preparation of (2S,3R)—N-(4-((R)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide or (2S,3R)—N-(4-((S)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide (mixture of atropisomers)

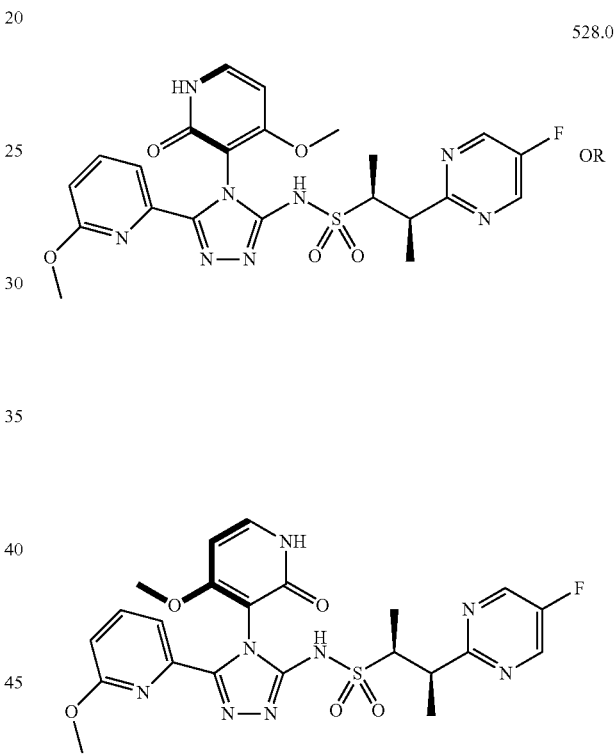

528.0

(2S,3R)—N-(4-((R)-4-methoxy-2-oxo-1,2-dihydro-pyridin-3-yl)-5-(6-methoxypyridin-2-yl)-4H-1,2,4-triazol-3-yl)-3-(5-fluoropyrimidin-2-yl)butane-2-sulfonamide compound or (2S,3R)—N-(4-((S)-4-methoxy-2-oxo-1,2-dihydropyridin-3-yl)-5-(6-methoxypyridin-2-yl)-4H-1,2,4-triazol-3-yl)-3-(5-fluoropyrimidin-2-yl)butane-2-sulfonamide, Example 528.0

The title compound was the second isomer to elute from the CC4 column on subjecting 526.0 to the SFC conditions described in Example 527.0. ¹H NMR (500 MHz, CD₃OD) δ 8.65 (s, 2H), 7.70-7.77 (m, 1H), 7.66 (dd, J=7.3, 0.7 Hz, 1H), 7.60 (d, J=7.3 Hz, 1H), 6.80 (d, J=8.1 Hz, 1H), 6.53 (d, J=7.6 Hz, 1H), 3.87 (s, 3H), 3.82 (d, J=6.4 Hz, 2H), 3.47 (s, 3H), 1.38 (d, J=6.9 Hz, 3H), 1.33 (d, J=6.9 Hz, 3H). LCMS-ESI (POS), m/z: 531.1 (M+H)⁺.

Example 529.0: Preparation of (1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide and (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide 529.1

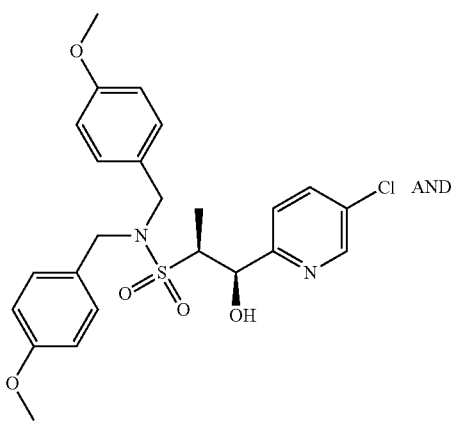

AND

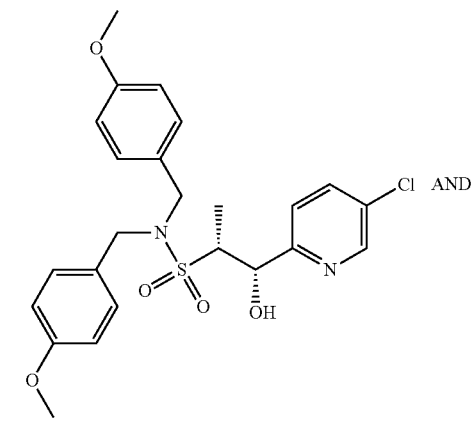

AND

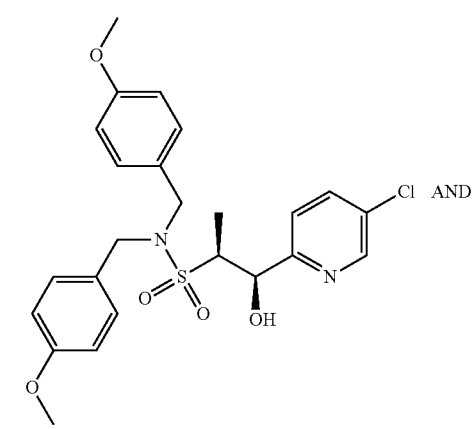

AND

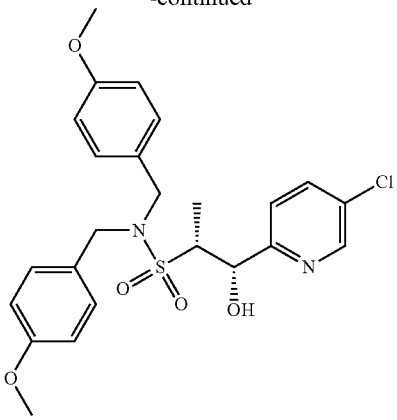

(1R,2S)-1-(5-chloropyridin-2-yl)-1-hydroxy-N,N-bis(4-methoxybenzyl)propane-2-sulfonamide and (1S,2R)-1-(5-chloropyridin-2-yl)-1-hydroxy-N,N-bis(4-methoxybenzyl)propane-2-sulfonamide and (1S,2S)-1-(5-chloropyridin-2-yl)-1-hydroxy-N,N-bis(4-methoxybenzyl)propane-2-sulfonamide and (1R,2R)-1-(5-chloropyridin-2-yl)-1-hydroxy-N,N-bis(4-methoxybenzyl)propane-2-sulfonamide, Example 529.1

To a 250-mL round-bottomed flask was added N,N-bis(4-methoxybenzyl)ethanesulfonamide (3.46 g, 9.90 mmol) in THF (49.5 mL). N-butyllithium solution (2.5 M in hexanes, 4.36 mL, 10.89 mmol) was added dropwise via syringe under a stream of $N_2$ at −78° C. with stirring. The reaction mixture was stirred at this temperature for 5 min and then 5-chloro-2-pyridinecarbaldehyde (1.40 g, 9.90 mmol) in THF (16.50 mL) was added dropwise via syringe under a stream of $N_2$ at −78° C. with stirring. The reaction mixture was then stirred at −78° C. for 10 min before the dry-ice bath was removed. The reaction mixture was stirred at RT for 10 min before being quenched with saturated aqueous $NH_4C_1$ (10 mL). The reaction mixture was then diluted with water and extracted with EtOAc. The organic layer was washed with a saturated solution of NaCl and dried over $Na_2SO_4$. The solution was filtered and concentrated in vacuo to give the initial material as a light-yellow oil. The material thus obtained was absorbed onto a plug of silica gel and purified by chromatography through a Redi-Sep pre-packed silica gel column (80 g) (Gold), eluting with a gradient of 0-100% EtOAc in hexanes (with 26% EtOH in EtOAc), to provide enriched material as an orange oil. The enriched material was absorbed onto a plug of silica gel and purified by chromatography through a Redi-Sep pre-packed silica gel column (80 g), eluting with a gradient of 20-100% EtOAc in hexanes, to provide (1R,2S)-1-(5-chloropyridin-2-yl)-1-hydroxy-N,N-bis(4-methoxybenzyl)propane-2-sulfonamide and (1S,2R)-1-(5-chloropyridin-2-yl)-1-hydroxy-N,N-bis(4-methoxybenzyl)propane-2-sulfonamide as the first stereoisomer to be eluted from the silica gel column, (syn isomers, 3.16 g, 6.44 mmol, 65.0% yield) as yellow solid. LCMS-ESI (POS.) m/z: 491.1 (M+H)$^+$. The second eluting compound was (1S,2S)-1-(5-chloropyridin-2-yl)-1-hydroxy-N,N-bis(4-methoxybenzyl)propane-2-sulfonamide and (1R,2R)-1-(5-chloropyridin-2-yl)-1-hydroxy-N,N-bis(4-methoxybenzyl)propane-2-sulfonamide from the silica gel column, anti isomer 1-(5-chloropyridin-2-yl)-1-hydroxy-N,N-bis(4-methoxybenzyl)propane-2-sulfonamide (anti isomers, 1.54 g, 3.14 mmol, 32% yield) as light-yellow solid. LCMS-ESI (POS.) m/z: 491.1 (M+H)⁺.

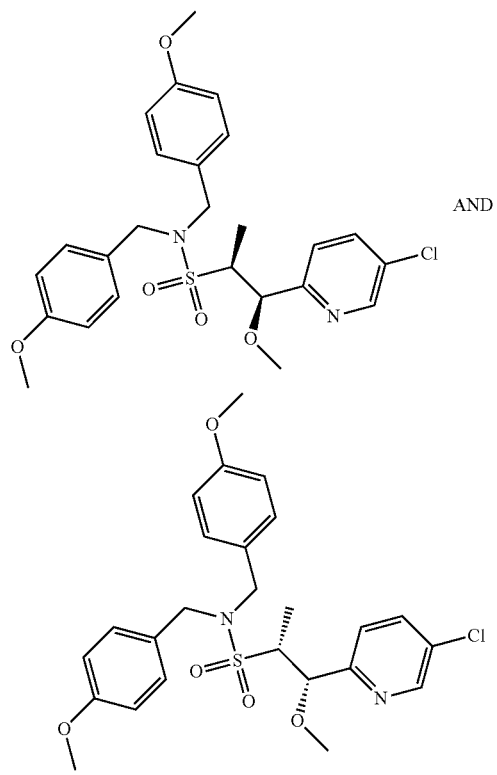

(1R,2S)-1-(5-chloropyridin-2-yl)-1-methoxy-N,N-bis(4-methoxybenzyl)propane-2-sulfonamide and (1S,2R)-1-(5-chloropyridin-2-yl)-1-methoxy-N,N-bis(4-methoxybenzyl)propane-2-sulfonamide, Example 529.2

To a 25-mL vial was added syn isomer (1R,2S)-1-(5-chloropyridin-2-yl)-1-hydroxy-N,N-bis(4-methoxybenzyl)propane-2-sulfonamide and (1S,2R)-1-(5-chloropyridin-2-yl)-1-hydroxy-N,N-bis(4-methoxybenzyl)propane-2-sulfonamide (3.16 g, 6.44 mmol) in THF (64.4 mL). Under N₂, potassium bis(trimethylsilyl)amide (1.0 M in THF, 9.65 mL, 9.65 mmol) was added at −78° C. with stirring. The reaction mixture was stirred at −78° C. for 60 min and then methyl trifluoromethanesulfonate (2.19 mL, 19.31 mmol) was added. The reaction mixture was stirred at −78° C. for 30 min. The reaction mixture was diluted with a saturated solution of NaHCO₃ and water and extracted with EtOAc. The organic layer was washed with a saturated solution of NaCl and dried over Na₂SO₄. The solution was filtered and concentrated in vacuo to give the initial material as a light-yellow oil. The material thus obtained was absorbed onto a plug of silica gel and purified by chromatography through a Redi-Sep pre-packed silica gel column (80 g), eluting with a gradient of 0-100% EtOAc in hexanes, to afford the desired product; syn isomer (1R,2S)-1-(5-chloropyridin-2-yl)-1-methoxy-N,N-bis(4-methoxybenzyl)propane-2-sulfonamide and (1S,2R)-1-(5-chloropyridin-2-yl)-1-methoxy-N,N-bis(4-methoxybenzyl)propane-2-sulfonamide (3.2 g, 6.34 mmol, 98% yield) as light-yellow solid. LCMS-ESI (POS.) m/z: 505.1 (M+H)⁺.

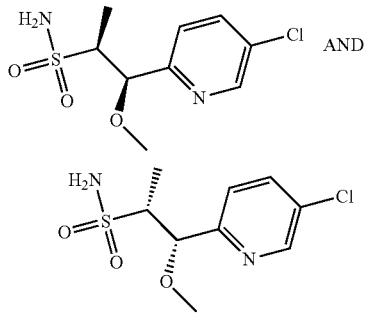

(1R,2S)-1-(5-chloropyridin-2-yl)-1-methoxypropane-2-sulfonamide compound and (1S,2R)-1-(5-chloropyridin-2-yl)-1-methoxypropane-2-sulfonamide, Example 529.3

To a 250-mL flask was added 529.2 (3.2 g, 6.34 mmol) and anisole (anhydrous, 2.75 mL, 25.3 mmol) in TFA (42.2 mL)). The reaction mixture was stirred at 23° C. for 20 h. The reaction mixture was concentrated in vacuo to give the product as an orange oil. The material obtained was absorbed onto a plug of silica gel and purified by chromatography through a Redi-Sep pre-packed silica gel column (80 g), eluting with a gradient of 0% to 100% EtOAc in DCM, to provide enriched material as an orange oil. The enriched material was absorbed onto a plug of silica gel and purified by chromatography through a Redi-Sep pre-packed silica gel column (80 g), eluting with a gradient of 0-100% EtOAc in hexanes (with 26% EtOH in EtOAc), to provide the title compound (1.44 g, 5.44 mmol, 86% yield) as light yellow solid. 1H NMR (500 MHz, CD₃OD) δ 8.56 (d, J=2.4 Hz, 1H), 7.91 (dd, J=8.6, 2.4 Hz, 1H), 7.47-7.53 (m, 1H), 4.99 (d, J=2.7 Hz, 1H), 3.46 (qd, J=7.1, 2.8 Hz, 1H), 3.41 (s, 3H), 1.22 (d, J=7.1 Hz, 3H). LCMS-ESI (POS.) m/z: 265.0 (M+H)⁺.

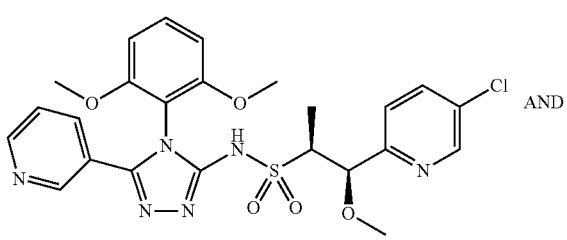

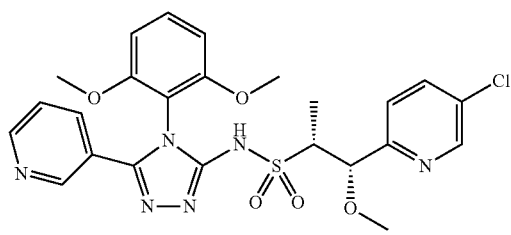

(1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide and (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide, Example 529.0

The title compound was prepared following the procedure in Example A, using 1.0, 529.3, and nicotinic acid hydrazide (commercially available from Acros organics). $^1$H NMR (500 MHz, CD$_3$OD) δ 8.61 (br. s., 2H), 8.55 (dd, J=2.5, 0.7 Hz, 1H), 7.83-7.96 (m, 2H), 7.47-7.55 (m, 2H), 7.44 (d, J=8.6 Hz, 1H), 6.80 (dd, J=8.6, 1.5 Hz, 2H), 4.98 (d, J=2.5 Hz, 1H), 3.79 (s, 3H), 3.75 (s, 3H), 3.36-3.46 (m, 1H), 3.26 (s, 3H), 1.13 (d, J=7.1 Hz, 3H). LCMS-ESI (POS), m/z: 545.0 (M+H)$^+$.

Example 530.0: Preparation of (1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide

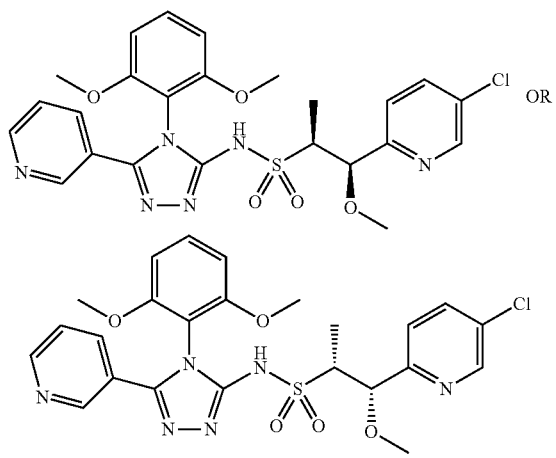

530.0

(1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide, Example 530.0

Example 530.0 was the first isomer to elute from the AS-H column on subjecting 529.0 under the following SFC conditions: Run on Thar 80 SFC with 250×30 mm AS-H column with 18.9 mL/min IPA (+20 mM NH$_3$)+51.1 g/min CO$_2$, 27% co-solvent at 70.0 g/min. Temperature.=29° C., Outlet pressure=100 bar, Wavelength=216 nm. Injected 0.5 mL of 32.0 mg sample dissolved in 5 mL of MeOH/DCM (4:1); c=6.4 mg/mL and 3.2 mg per injection. Cycle time 18.5 min, run time 20.0 min. $^1$H NMR (500 MHz, CD$_3$OD) δ 8.58 (br. s., 2H), 8.54 (d, J=2.4 Hz, 1H), 7.82-7.82 (m, 1H), 7.80-7.92 (m, 2H), 7.49 (t, J=8.6 Hz, 1H), 7.40-7.46 (m, 2H), 6.79 (dd, J=8.7, 1.1 Hz, 2H), 4.99 (d, J=2.5 Hz, 1H), 3.78 (s, 3H), 3.75 (s, 3H), 3.38-3.45 (m, 1H), 3.26 (s, 3H), 1.13 (d, J=7.1 Hz, 3H). LCMS-ESI (POS), m/z: 545.3 (M+H)$^+$.

Example 531.0: Preparation of (1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide

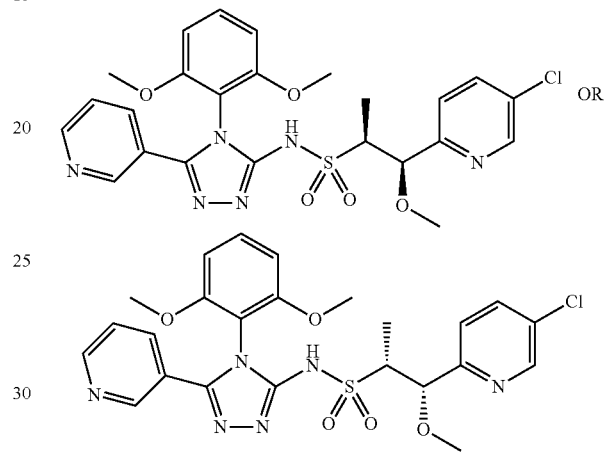

531.0

(1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide, Example 531.0

The title compound was the second isomer to elute from the AS-H column on subjecting 529.0 to the SFC conditions described in Example 530.0. LCMS-ESI (POS), m/z: 545.3 (M+H)$^+$.

Example 532.0: Preparation of (1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide and (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide

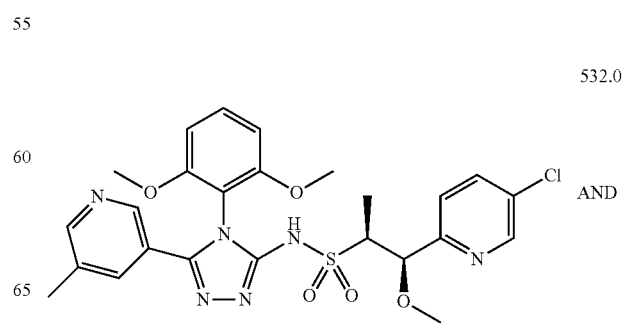

532.0

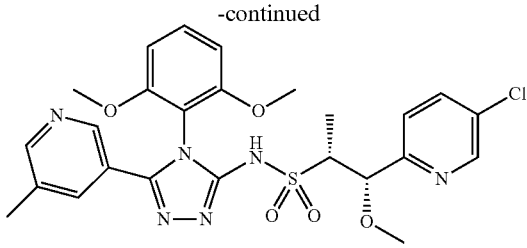

(1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide and (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 532.0

The title compound was prepared following the procedure in Example A using 1.0, 529.3 and 5-methylnicotinic acid hydrazide (commercially available from Bellen Chemistry Co, Ltd., Beijing, China). $^1$H NMR (500 MHz, CD$_3$OD) δ 8.55 (d, J=2.5 Hz, 1H), 8.52 (br. s., 1H), 8.40 (br. s., 1H), 7.83-7.94 (m, 2H), 7.52 (t, J=8.6 Hz, 1H), 7.44 (d, J=8.6 Hz, 1H), 6.81 (dd. J=8.7, 1.34 Hz, 2H), 4.98 (d, J=2.5 Hz, 1H), 3.79 (s, 3H), 3.77 (s, 3H), 3.41 (qd, J=7.1, 2.6 Hz, 1H), 3.26 (s, 3H), 2.35 (s, 3H), 1.13 (d, J=7.1 Hz, 3H). LCMS-ESI (POS), m/z: 559.0 (M+H)$^+$.

Example 533.0: Preparation of (1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide

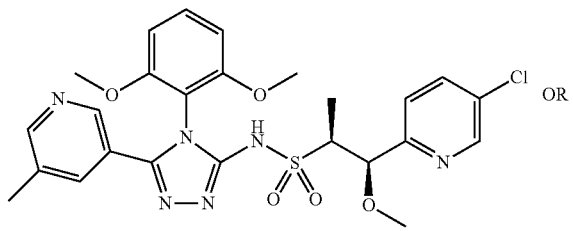

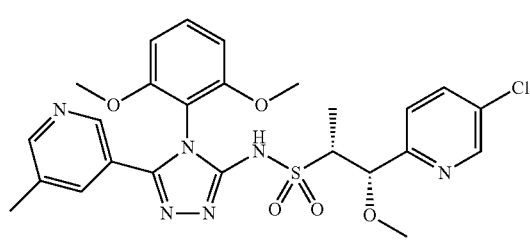

(1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 533.0

The title compound was the first isomer to elute from an AS-H column on subjecting 532.0 under the flowing SFC conditions: Run on Thar 200 SFC with 30×250 mm AS-H column with 30 mL/min IPA (20 mM NH$_3$)+90 g/min CO$_2$, 25% co-solvent at 120 g/min. Temperature.=30° C., Outlet pressure=100 bar, Wavelength=271 nm. Injected 1.0 mL of 178 mg sample dissolved in 20 mL 1:1 MeOH:DCM; c=8.9 mg/mL, i.e. 8.9 mg per injection. Cycle time 11.5 min, run time 15 min (Cycle time was increased to avoid the collection of TFA present in the sample). $^1$H NMR (500 MHz, CD$_3$OD) δ 8.56 (d, J=2.5 Hz, 1H), 8.45 (br. s., 1H), 8.34 (s, 1H), 7.89 (dd, J=8.3, 2.5 Hz, 1H), 7.74 (d, J=0.7 Hz, 1H), 7.51 (t, J=8.6 Hz, 1H), 7.46 (d, J=8.3 Hz, 1H), 6.77-6.86 (m, 2H), 5.01 (d, J=2.5 Hz, 1H), 3.80 (s, 3H), 3.77 (s, 3H), 3.43 (qd, J=7.0, 2.7 Hz, 1H), 3.28 (s, 3H), 2.32 (s, 3H), 1.15 (d, J=7.1 Hz, 3H). LCMS-ESI (POS), m/z: 559.0 (M+H)$^+$.

Example 534.0: Preparation of (1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide

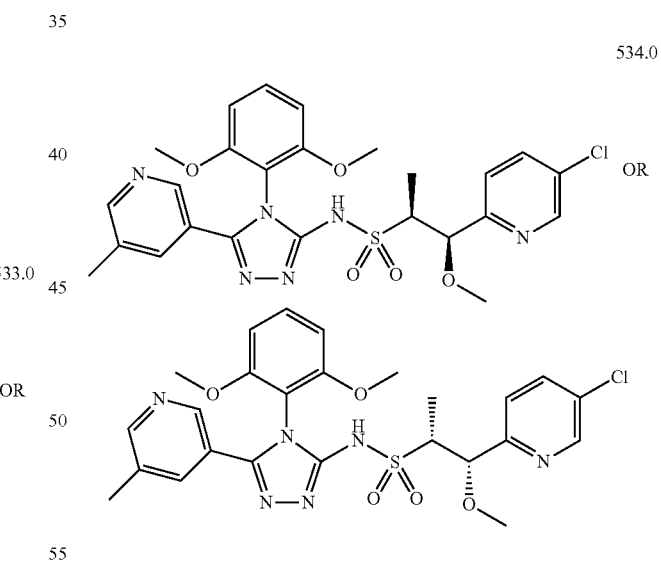

(1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 534.0

The title compound was the second isomer to elute from the AS-H column on subjecting 532.0 to the SFC conditions described in Example 533.0. $^1$H NMR (500 MHz, CD$_3$OD)

δ 8.56 (d, J=2.5 Hz, 1H) 8.45 (br. s., 1H) 8.34 (s, 1H) 7.89 (dd, J=8.3, 2.5 Hz, 1H) 7.74 (d, J=0.7 Hz, 1H) 7.51 (t, J=8.6 Hz, 1H) 7.46 (d, J=8.3 Hz, 1H) 6.77-6.86 (m, 2H) 5.01 (d, J=2.5 Hz, 1H) 3.80 (s, 3H) 3.77 (s, 3H) 3.43 (qd, J=7.0, 2.7 Hz, 1H) 3.28 (s, 3H) 2.32 (s, 3H) 1.15 (d, J=7.1 Hz, 3H). LCMS-ESI (POS), m/z: 559.0 (M+H)+.

Example 535.0: Preparation of (1R,2S)—N-(4-(2,6-dimethoxyphenyl)-5-(5-methylpyridin-3-yl)-4H-1,2,4-triazol-3-yl)-1-methoxy-1-(5-(prop-1-yn-1-yl)pyrimidin-2-yl)propane-2-sulfonamide

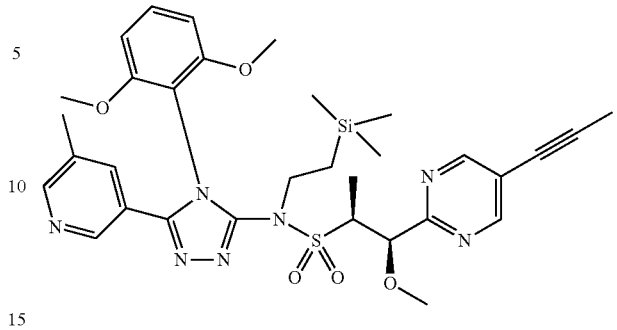

(1R,2S)—N-(4-(2,6-dimethoxyphenyl)-5-(5-methylpyridin-3-yl)-4H-1,2,4-triazol-3-yl)-1-methoxy-1-(5-(prop-1-yn-1-yl)pyrimidin-2-yl)-N-(2-(trimethylsilyl)ethyl)propane-2-sulfonamide, Example 535.2

To a solution of (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxy-N-(2-(trimethylsilyl)ethyl)propane-2-sulfonamide, Example 535.1 (0.110 g, 0.17 mmol) in 1,4-dioxane (5.0 mL) was added tributyl(prop-1-yn-1-yl)stannane (0.180 g, 0.55 mmol) and bis(tri-t-butylphosphine)palladium (24.0 mg, 0.046 mmol). The reaction mixture was heated at 100° C. under N₂ for 20 h. The solvent was concentrated in vacuo. The product thus obtained was purified by column chromatography (40 g of silica, 0-4% MeOH in DCM) to afford (1R,2S)—N-(4-(2,6-dimethoxyphenyl)-5-(5-methylpyridin-3-yl)-4H-1,2,4-triazol-3-yl)-1-methoxy-1-(5-(prop-1-yn-1-yl)pyrimidin-2-yl)-N-(2-(trimethylsilyl)ethyl)propane-2-sulfonamide as a yellow paste (0.090 g). ¹H NMR (CDCl₃) δ: 8.67 (s, 2H), 8.43 (s, 1H), 8.35 (s, 1H), 7.63 (s, 1H), 7.35 (t, J=8.5 Hz, 1H), 6.58 (t, J=8.3 Hz, 2H), 4.75 (d, J=4.8 Hz, 1H), 4.43 (dt, J=6.6, 5.1 Hz, 2H), 3.76-3.83 (m, 3H), 3.72 (s, 3H), 3.48-3.60 (m, 1H), 3.29 (s, 3H), 2.30 (s, 3H), 2.10 (s, 3H), 1.40 (d, J=8.2 Hz, 2H), 1.23 (d, J=7.0 Hz, 3H), 0.11 (s, 9H). LCMS-ESI (POS.) m/z: 664.0 (M+H)+.

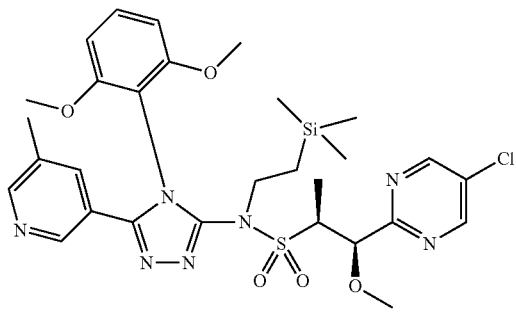

(1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxy-N-(2-(trimethylsilyl)ethyl)propane-2-sulfonamide, Example 535.1

To a stirred solution of (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide, Example 428.1 (0.175 g, 0.31 mmol) and 2-(trimethylsilyl)ethanol (0.100 mL, 0.70 mmol) in toluene (4.0 mL) was added cyanomethylenetri-n-butylphosphorane (0.160 mL, 0.66 mmol) dropwise via a syringe. After the addition, a condensor was attached and the reaction mixture was heated at 90° C. under N₂ for 2 h. The reaction was cooled to RT and solvent was concentrated. The product thus obtained was purified by column chromatography (40 g of silica, 0 to 4% MeOH in DCM) to afford (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxy-N-(2-(trimethylsilyl)ethyl)propane-2-sulfonamide as a brown foam (0.180 g). ¹H NMR (CDCl₃) δ: 8.61-8.70 (m, 2H), 8.43 (d, J=1.5 Hz, 1H), 8.35 (d, J=1.9 Hz, 1H), 7.60-7.66 (m, 1H), 7.37 (t, J=8.5 Hz, 1H), 6.60 (t, J=8.7 Hz, 2H), 4.66 (d, J=6.0 Hz, 1H), 4.31-4.49 (m, 2H), 3.80 (s, 3H), 3.69-3.75 (m, 3H), 3.48-3.61 (m, 1H), 3.27 (s, 3H), 2.30 (s, 3H), 1.37 (dd, J=9.6, 7.6 Hz, 2H), 1.25 (d, J=6.9 Hz, 3H), 0.07-0.14 (m, 9H). MS-ESI (POS.) m/z: 659.8 (M+H)+

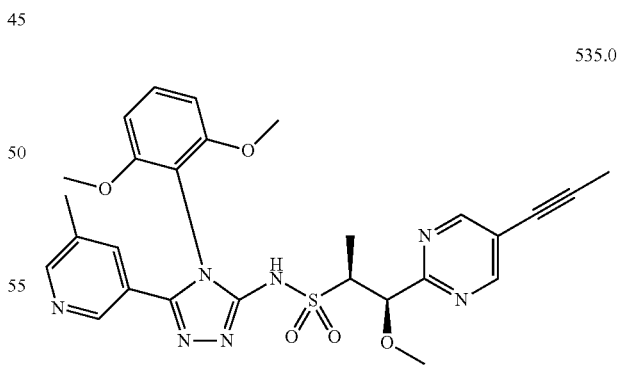

(1R,2S)—N-(4-(2,6-dimethoxyphenyl)-5-(5-methylpyridin-3-yl)-4H-1,2,4-triazol-3-yl)-1-methoxy-1-(5-(prop-1-yn-1-yl)pyrimidin-2-yl)propane-2-sulfonamide, Example 535.0

To a 50 mL round bottom flask was added (1R,2S)—N-(4-(2,6-dimethoxyphenyl)-5-(5-methylpyridin-3-yl)-4H-1, 2,4-triazol-3-yl)-1-methoxy-1-(5-(prop-1-yn-1-yl)pyrimidin-2-yl)-N-(2-(trimethylsilyl)ethyl)propane-2-sulfonamide, Example 535.2 (0.090 g, 0.14 mmol) in DMF (3.0 mL) was added tris(dimethylamino)sulfur (trimethylsilyl)difluoride (0.118 g, 0.43 mmol). The reaction mixture was heated at 110° C. under N₂ for 2 h. The reaction was cooled to RT and partitioned between EtOAc (60 mL) and water (30 mL). The aqueous layer was extracted with EtOAc (40 mL), 10% iPrOH in CHCl₃ (2×30 mL). The combined organic layers were dried over MgSO₄, filtered, and concentrated in vacuo. The residue was purified by column chromatography (40 g of silica, 5-40% acetone in hexanes) to afford (1R,2S)—N-(4-(2,6-dimethoxyphenyl)-5-(5-methylpyridin-3-yl)-4H-1,2,4-triazol-3-yl)-1-methoxy-1-(5-(prop-1-yn-1-yl)pyrimidin-2-yl)propane-2-sulfonamide as a yellow solid (0.030 g). ¹H NMR (CDCl₃) δ: 8.70-8.76 (m, 2H), 8.45 (d, J=1.6 Hz, 1H), 8.35 (d, J=1.8 Hz, 1H), 8.09 (t, J=1.8 Hz, 1H), 7.99 (d, J=7.9 Hz, 1H), 7.40-7.49 (m, 1H), 6.60 (d, J=8.5 Hz, 2H), 5.01 (d, J=4.4 Hz, 1H), 3.69-3.78 (m, 7H), 3.33-3.38 (m, 3H), 2.31 (s, 3H), 2.11 (s, 3H), 1.37 (d, J=7.0 Hz, 3H). LCMS-ESI (POS.) m/z: 564.0 (M+H)⁺.

Example 536.0: Preparation of (2S,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2R,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2R,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide 536.1

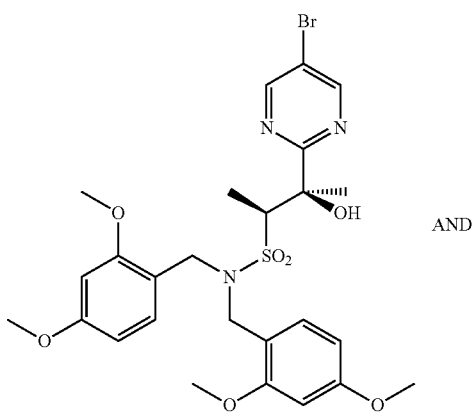

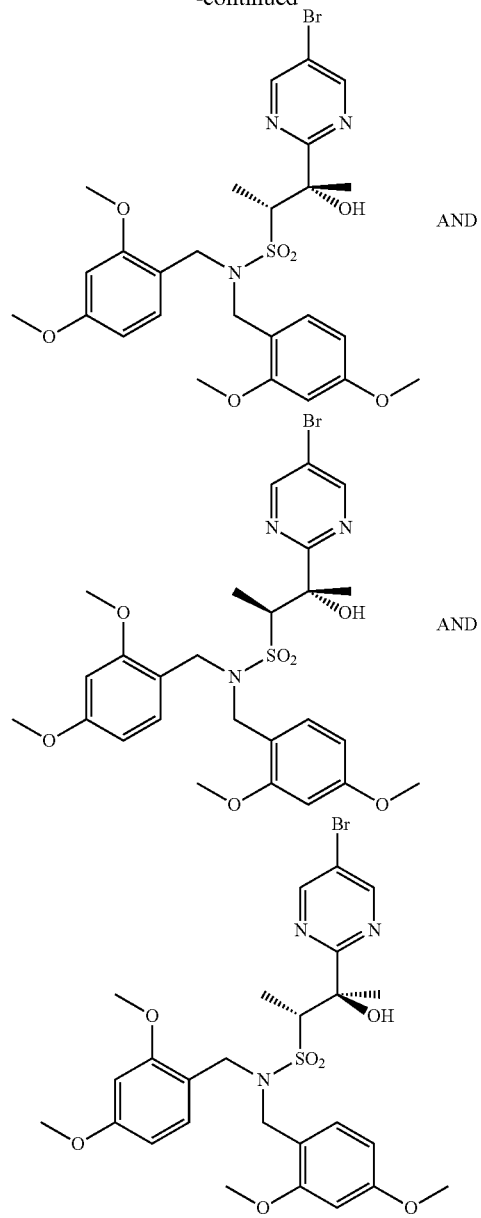

(2S,3R)-3-(5-bromopyrimidin-2-yl)-N,N-bis(2,4-dimethoxybenzyl)-3-hydroxybutane-2-sulfonamide and (2R,3R)-3-(5-bromopyrimidin-2-yl)-N,N-bis(2,4-dimethoxybenzyl)-3-hydroxybutane-2-sulfonamide and (2R,3S)-3-(5-bromopyrimidin-2-yl)-N,N-bis(2,4-dimethoxybenzyl)-3-hydroxybutane-2-sulfonamide and (2S,3S)-3-(5-bromopyrimidin-2-yl)-N,N-bis(2,4-dimethoxybenzyl)-3-hydroxybutane-2-sulfonamide 536.1

At −78° C., n-butyllithium (4.38 mL, 10.94 mmol) was added to a THF (99 mL) solution containing N,N-bis(2,4-dimethoxybenzyl)ethanesulfonamide (4.07 g, 9.95 mmol, prepared in a similar manner to that described in Example 12.0). The resulting mixture was stirred for 30 min at −78° C. Next, a THF solution of 1-(5-bromopyrimidin-2-yl)ethanone (2, 9.95 mmol) was added at −78° C. The reaction was continued at −78° C. and allowed to slowly warm to RT and stirred overnight. The reaction was then quenched with a saturated ammonium chloride solution and extracted with EtOAc (3×100 mL). After concentration, the reaction was purified on silica eluting with a hexanes/EtOAc gradient (0-100%). Desired fractions with 536.1 were then combined and concentrated in vacuo to yield the title compound (45% yield), LCMS m/z: 610.0 (M+H)⁺.

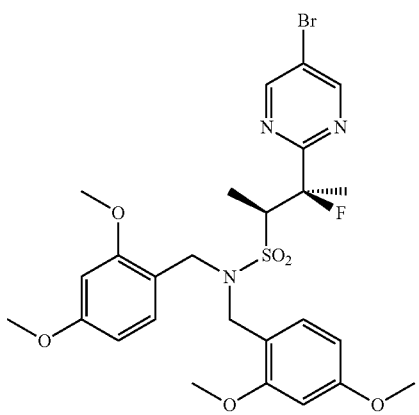

AND

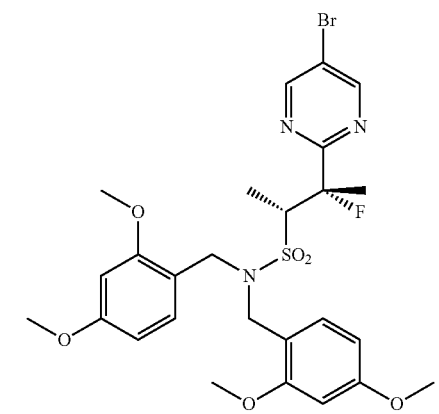

AND

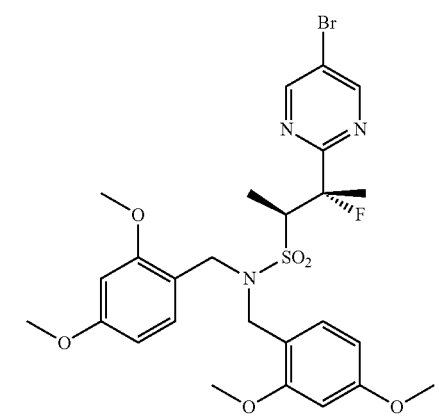

AND

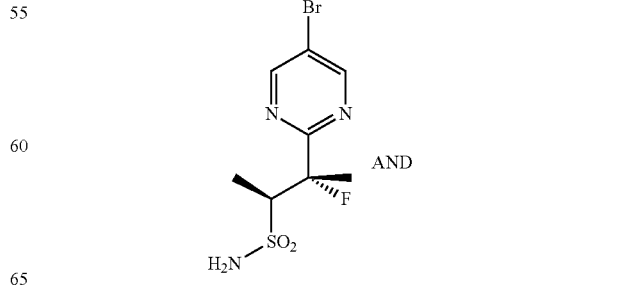

(2S,3R)-3-(5-bromopyrimidin-2-yl)-N,N-bis(2,4-dimethoxybenzyl)-3-fluorobutane-2-sulfonamide and (2R,3R)-3-(5-bromopyrimidin-2-yl)-N,N-bis(2,4-dimethoxybenzyl)-3-fluorobutane-2-sulfonamide and (2R,3S)-3-(5-bromopyrimidin-2-yl)-N,N-bis(2,4-dimethoxybenzyl)-3-fluorobutane-2-sulfonamide and (2S,3S)-3-(5-bromopyrimidin-2-yl)-N,N-bis(2,4-dimethoxybenzyl)-3-fluorobutane-2-sulfonamide Example 536.2

At 23° C., DAST (2.052 mL, 15.53 mmol) was added to a DCM (38.8 mL) solution containing 536.1 (4.74 g, 7.76 mmol). The resulting mixture was stirred at 23° C. for 1 h. TLC indicated that the reaction complete. MeOH (1 mL) was added, and the mixture was concentrated in vacuo. The reaction was purified on silica gel eluting with a hexanes/EtOAc gradient (0-100%). Desired fractions containing 536.2 were combined and concentrated in vacuo. (1.4 g, 29% yield), LCMS m/z: 612.0 (M+H)⁺.

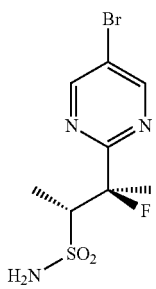

536.3

(2S,3R)-3-(5-bromopyrimidin-2-yl)-3-fluorobutane-2-sulfonamide and (2R,3R)-3-(5-bromopyrimidin-2-yl)-3-fluorobutane-2-sulfonamide and (2R,3S)-3-(5-bromopyrimidin-2-yl)-3-fluorobutane-2-sulfonamide and (2S,3S)-3-(5-bromopyrimidin-2-yl)-3-fluorobutane-2-sulfonamide Example 536.3

At 0° C., TFA (1.26 mL, 16.33 mmol) was added to a flask containing triethylsilane (2.61 mL, 16.33 mmol) and 3-(5-bromopyrimidin-2-yl)-N,N-bis(2,4-dimethoxybenzyl)-3-fluorobutane-2-sulfonamide (536.2, 1.0 g, 1.63 mmol). The resulting mixture was stirred for 3 h at 0° C. The resulting mixture was then partitioned with saturated aqueous sodium bicarbonate and DCM and the organic layers were concentrated in vacuo. The reaction was purified on silica gel eluting with a MeOH/DCM stepwise gradient (0-20%). The desired fractions containing 536.3 were then combined and concentrated in vacuo to provide the title compound (95%). LCMS m/z: 311.9 (M+H)+.

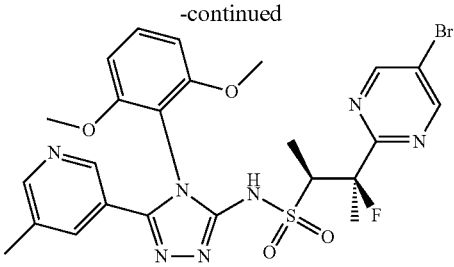

(2S,3R)-3-(5-bromopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2R,3R)-3-(5-bromopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2R,3S)-3-(5-bromopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2S,3S)-3-(5-bromopyrimidin-2-yl)-N-(4-(2,6-dimethoxyphenyl)-5-(5-methylpyridin-3-yl)-4H-1,2,4-triazol-3-yl)-3-fluorobutane-2-sulfonamide Example 536.4

The title compound was prepared following the procedure in Example A using 1.0, 536.4 and 5-methylnicotinic acid hydrazide. The reaction product was purified via reverse phase HPLC (Phenomenex Gemini-C18 column, 50×250 mm, 10 μm, 10-70% water/ACN gradient over 30 min., with 0.1% TFA, flow rate 100 mL/min). Desired fractions containing 536.4 were combined and lyophilized to give pure product. LCMS m/z: 606.0 (M+H)+.

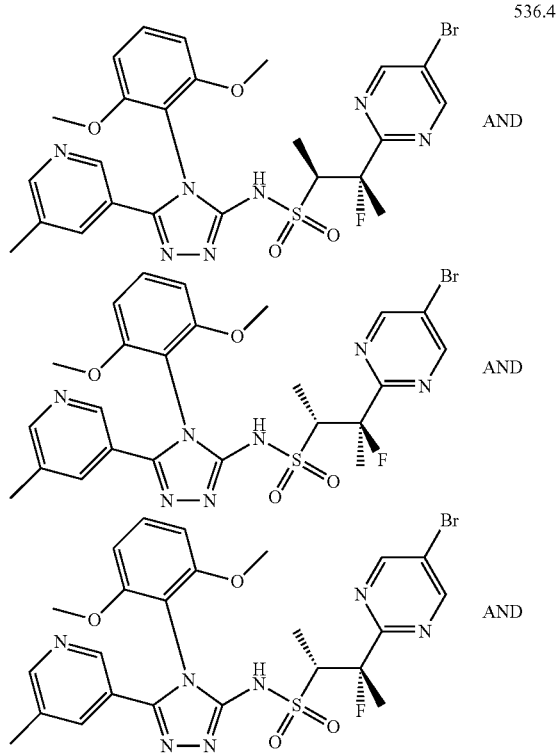

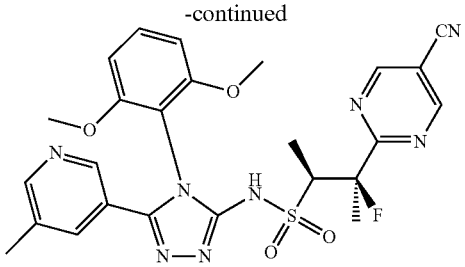

(2S,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2R,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2R,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide
Example 536.0

A glass microwave reaction vessel was charged with 536.4, (200 mg, 0.330 mmol), zinc cyanide (0.105 mL, 1.65 mmol), and tetrakis(triphenylphosphine)palladium (38.1 mg, 0.033 mmol) in 2-Me-THF. The reaction mixture was stirred and heated in a microwave reactor (CEM, Matthews, N.C.) at 120° C. for 30 min. The reaction was purified via reverse phase HPLC (Agilent SB-C$_8$ column, 30×250 mm, 5 μm, 10-95% water/ACN gradient over 25 min., with 0.1% TFA, flow rate 50 mL/min). Desired fractions with 536.0, were combined and lyophilized to give pure product. Final chiral separation was performed using SFC. Only 2 of the four isomers were isolated.

Example 537.0: Preparation of (2S,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2S,3R)-3-(5-Cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide 537.0

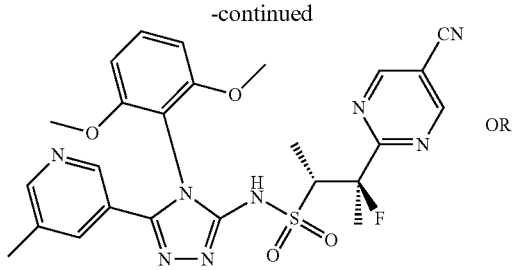

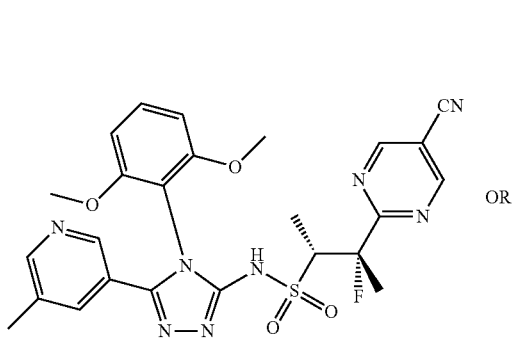

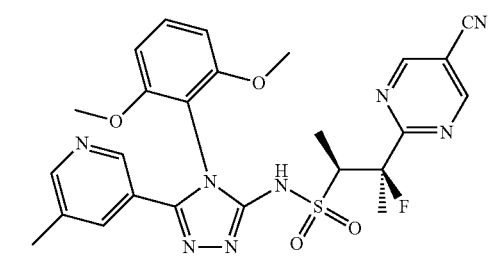

(2S,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3R)-3-(5-Cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3S)-3-(5-Cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2S,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide,
Example 537.0

The title compound was the first peak to elute by chiral separation of Example 536.0 by chiral separation using SFC using a column AD 35% IPA isocratic. $^1$H NMR (400 MHz, CD$_3$OD) δ 9.17 (s, 2H), 8.45 (In, 1H), 8.33 (s, 1H), 7.72 (s, 1H), 7.46-7.60 (m, 1H), 6.83 (d, J=8.8 Hz, 2H), 4.35 (m, 1H), 3.82 (s, 3H), 3.81 (s, 3H), 2.32 (s, 3H), 1.89 (d, J=24.1 Hz, 3H), 1.49 (d, J=6.9 Hz, 3H). LCMS ESI (pos.) m/z: 553.0 (M+H)$^+$.

Example 538.0: Preparation of (2S,3S)-3-(5-cyano-pyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3S)-3-(5-Cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2S,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide

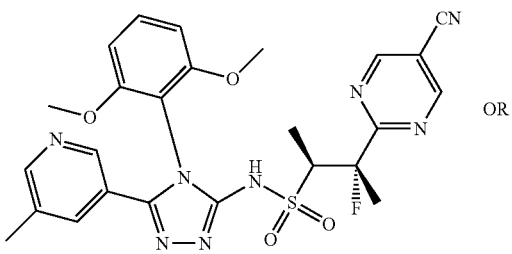

OR

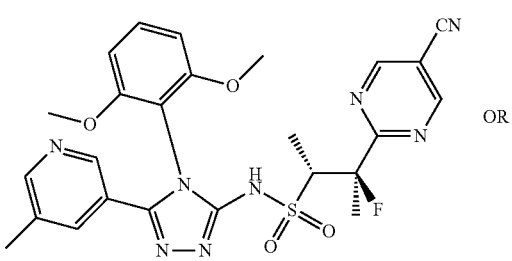

OR

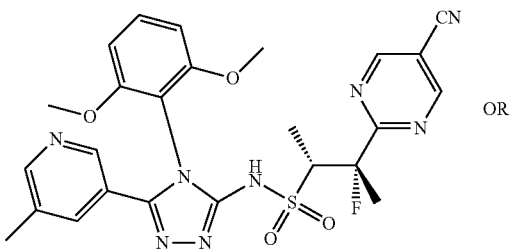

OR

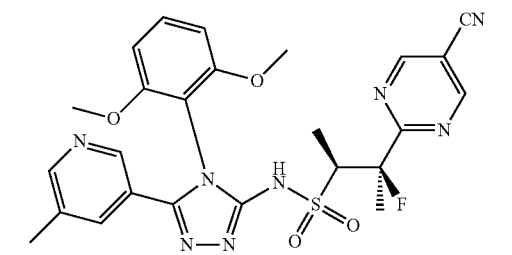

(2S,3S)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3R)-3-(5-Cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2R,3S)-3-(5-Cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide or (2S,3R)-3-(5-cyanopyrimidin-2-yl)-N-(4-(2,6-dimethoxyphenyl)-5-(5-methylpyridin-3-yl)-4H-1,2,4-triazol-3-yl)-3-fluorobutane-2-sulfonamide, Example 538.0

The title compound was the second peak to elute by chiral separation of Example 536.0 by chiral separation using SFC using a column AD 35% IPA isocratic. $^1$H NMR (400 MHz, CD$_3$OD) δ 9.17 (s, 2H), 8.46 (d, J=1.4 Hz, 1H), 8.33 (d, J=2.0 Hz, 1H), 7.72 (m, 1H), 7.54 (t, J=8.5 Hz, 1H), 6.84 (d, J=8.6 Hz, 2H), 4.35 (dd, J=10.6, 7.0 Hz, 1H), 3.82 (s, 3H), 3.81 (s, 3H), 2.32 (s, 3H), 1.88 (d, J=24.1 Hz, 3H), 1.49 (dd, J=7.0, 1.0 Hz, 3H). MS ESI (pos.) m/z: 553.0 (M+H)$^+$.

Example 539.0: Preparation of (1R,2S)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide and (1S,2S)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide

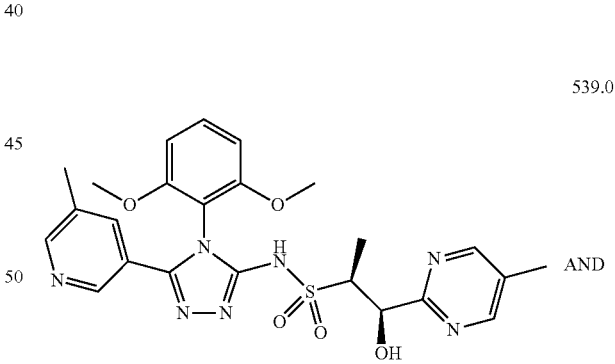

AND

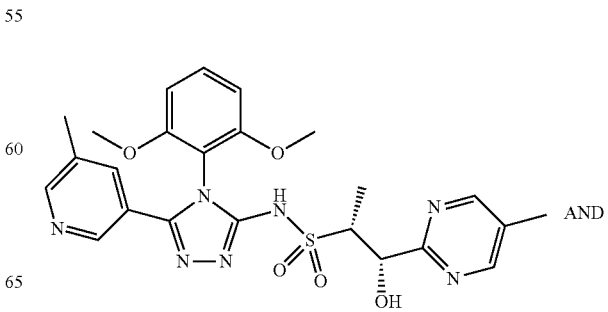

AND

-continued

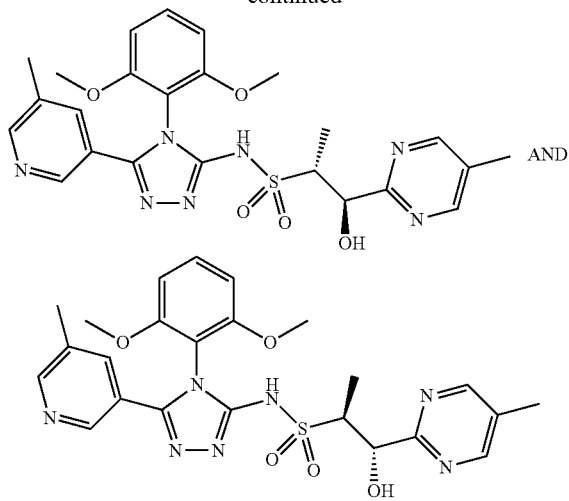

(1R,2S)—N-(4-(2,6-dimethoxyphenyl)-5-(5-methyl-pyridin-3-yl)-4H-1,2,4-triazol-3-yl)-1-hydroxy-1-(5-methylpyrimidin-2-yl)propane-2-sulfonamide and
(1R,2R)—N-(4-(2,6-dimethoxyphenyl)-5-(5-methyl-pyridin-3-yl)-4H-1,2,4-triazol-3-yl)-1-hydroxy-1-(5-methylpyrimidin-2-yl)propane-2-sulfonamide and
(1S,2S)—N-(4-(2,6-dimethoxyphenyl)-5-(5-methyl-pyridin-3-yl)-4H-1,2,4-triazol-3-yl)-1-hydroxy-1-(5-methylpyrimidin-2-yl)propane-2-sulfonamide and
(1S,2R)—N-(4-(2,6-dimethoxyphenyl)-5-(5-methyl-pyridin-3-yl)-4H-1,2,4-triazol-3-yl)-1-hydroxy-1-(5-methylpyrimidin-2-yl)propane-2-sulfonamide,
Example 539.0

At 23° C. and under argon, copper(I) iodide (0.082 g, 0.430 mmol) was added to a dioxane (1.72 mL) solution containing N1,N2-dimethylcyclohexane-1,2-diamine (0.245 g, 1.721 mmol), 1-hydroxy-1-(5-methylpyrimidin-2-yl)propane-2-sulfonamide 11.0 (0.199 g, 0.86 mmol), and 2.0. The resulting mixture was stirred overnight at 80° C. The reaction was then partitioned with EtOAc/water, washed with brine, dried over sodium sulfate, and concentrated in vacuo. The reaction was purified via reverse phase HPLC (Phenomenex Gemini-C18 column, 50×250 mm, 10 μm, 10-95% water/ACN gradient over 30 min., with 0.1% TFA, flow rate 100 mL/min). Desired fractions were combined and lyophilized to give pure product. Final chiral separation was performed using SFC. Only 2 of the four isomers were isolated.

Example 540.0: Preparation of (1S,2R)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide Chiral separation of the mixture of enantiomers (Example 539.0) was performed by preparative SFC using the following conditions: Run on Thar 200 with 250×30 mm AD-H column with 43 g/min EtOH (neat) and 52 g/min CO₂, 40% co-solvent at 95 g/min. Wavelength 275 nm. Injected 0.65 mL of a solution of 149 mg sample dissolved in 13 mL (11:2 MeOH:DCM); c=11.5 mg/mL, 7.5 mg/injection. Cycle time 6.5 min, run time 12 min delivered Example 540.0.

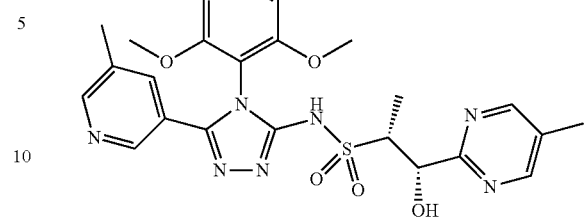

(1S,2R)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide
Example 540.0

The title compound was the first peak to elute by SFC using the conditions described. $^1$H NMR (500 MHz, CD$_3$OD) δ 8.65 (s, 2H), 8.44 (d, J=1.5 Hz, 1H), 8.33 (d, J=1.7 Hz, 1H), 7.72 (m, 1H), 7.51 (t, J=8.6 Hz, 1H), 6.81 (d, J=8.6 Hz, 2H), 5.42 (d, J=2.7 Hz, 1H), 3.73-3.77 (m, 7H), 2.34 (s, 3H), 2.31 (s, 3H), 1.20 (m, 3H). MS ESI (pos.) m/z: 526.0 (M+H)$^+$. SFC: Run on Thar 200 with 250×30 mm AD-H column with 43 g/min EtOH (neat) and 52 g/min CO$_2$, 40% co-solvent at 95 g/min.

Example 541.0: Preparation of (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide

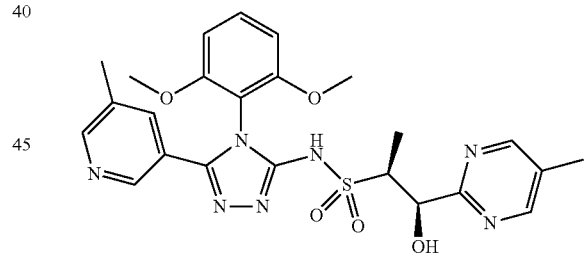

(1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide
Example 541.1

The title compound was the second peak to elute by SFC using the conditions described in Example 540.0. $^1$H NMR (300 MHz, CDCl$_3$) δ 8.58 (s, 2H), 8.46 (d, J=1.6 Hz, 1H), 8.34 (d, J=1.9 Hz, 1H), 7.66 (s, J=3.1 Hz, 1H), 7.40 (t, J=8.6 Hz, 1H), 6.64 (d, J=8.5 Hz, 1H), 6.60 (d, J=8.5 Hz, 1H), 5.59 (s, 1H), 4.07 (br. s, 1H), 3.81-3.91 (m, 1H), 3.76 (s, 3H), 3.74 (s, 3H), 2.34 (s, 3H), 2.32 (s, 3H), 1.21 (d, J=7.0 Hz, 3H). MS ESI (pos.) m/z: 526.2 (M+H)$^+$. SFC: Run on Thar 200 with 250×30 mm AD-H column with 43 g/min EtOH (neat) and 52 g/min CO$_2$, 40% co-solvent at 95 g/min.

Example 542.0: Preparation of (1S,2R)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide and (1S,2S)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide 542.0

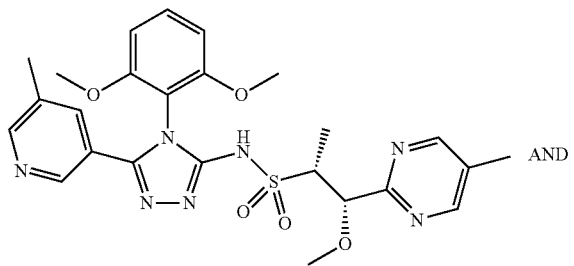
AND

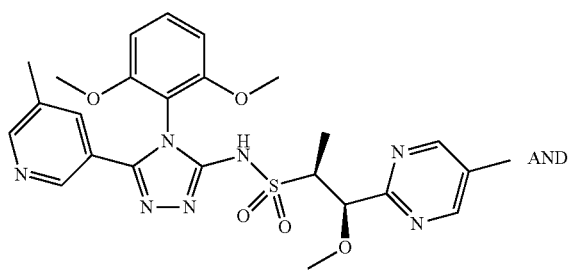
AND

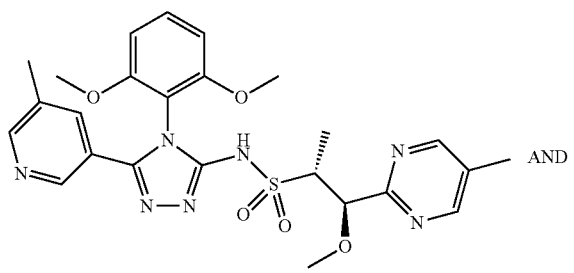
AND

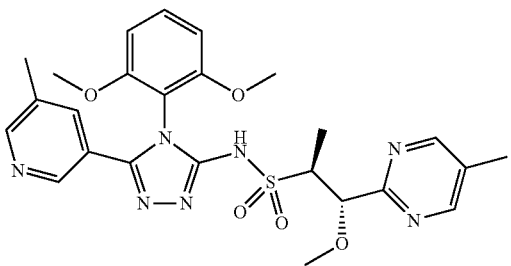

(1S,2R)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide and (1R,2R)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide and (1S,2S)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide and (1R,2S)—N-(4-(2,6-dimethoxyphenyl)-5-(5-methylpyridin-3-yl)-4H-1,2,4-triazol-3-yl)-1-methoxy-1-(5-methylpyrimidin-2-yl)propane-2-sulfonamide, Example 542.0

At 23° C. under argon, copper(I) iodide (0.178 g, 0.933 mmol) was added to a dioxane (3.73 mL) solution containing N1,N2-dimethylcyclohexane-1,2-diamine (0.531 g, 3.73 mmol), racemic 1-methoxy-1-(5-methylpyrimidin-2-yl)propane-2-sulfonamide (0.686 g, 2.80 mmol), and 2.0. The resulting mixture was stirred overnight at 80° C. The reaction was then partitioned with EtOAc/water, washed with brine, dried over sodium sulfate, and concentrated. The reaction was purified via reverse phase HPLC (Phenomenex Gemini-C18 column, 50×250 mm, 10 μm, 10-95% water/ACN gradient over 30 min., with 0.1% TFA, flow rate 100 mL/min). Desired fractions were combined and lyophilized to give pure product.

Example 543.0: Preparation of (1S,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide Final chiral resolution was performed on Example 542.0 using SFC. SFC conditions AS-H (2×25 cm) 15% MeOH/CO₂, 100 bar 60 mL/min, 220 nm. inj vol.: 0.75 mL, 10 mg/mL MeOH for 543.0 and 544.0. IA (2×15 cm) 15% MeOH/CO₂, 100 bar 60 mL/min, 220 nm. inj vol.: 0.75 mL, 5 mg/mL MeOH for 545.0 and 546.0.

543.0

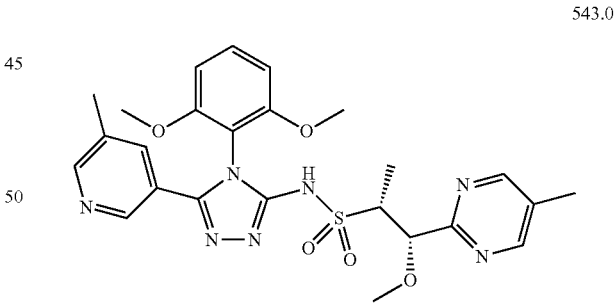

(1S,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide
Example 543.0

The title compound was the first peak to elute by SFC using the conditions described above. ¹H NMR (400 MHz, CD₃OD) δ 8.67 (s, 2H), 8.46 (s, 1H), 8.34 (s, 1H), 7.74 (s, 1H), 7.52 (t, J=8.3 Hz, 1H), 6.82 (d, J=8.6 Hz, 2H), 5.01 (d, J=3.5 Hz, 1H), 3.81 (s, 3H), 3.78 (s, 3H), 3.58 (dd, J=7.0, 3.7 Hz, 1H), 3.29 (s, 3H), 2.36 (s, 3H), 2.32 (s, 3H), 1.26 (d, J=4.0 Hz, 3H). MS ESI (pos.) m/z: 540.0 (M+H)+. SFC AS-H (2×25 cm) 15% MeOH/CO₂.

Example 544.0: Preparation of (1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide

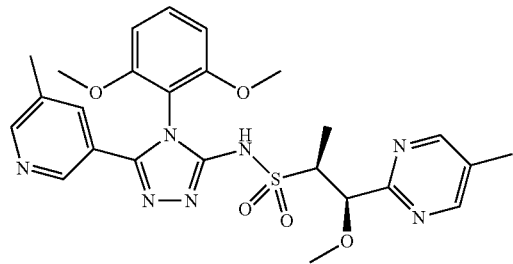

544.0

(1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide
Example 544.0

The title compound was the second peak to elute by SFC using the conditions described in 543.0. ¹H NMR (400 MHz, CD₃OD) δ 8.66 (s, 2H), 8.47 (s, 1H), 8.35 (s, 1H), 7.77 (s, 1H), 7.52 (dd, J=8.3, 8.3 Hz, 1H), 6.82 (d, J=8.4 Hz, 2H), 5.01 (d, J=3.5 Hz, 1H), 3.81 (s, 3H), 3.78 (s, 3H), 3.56-3.60 (m, 1H), 3.29 (s, 3H), 2.36 (s, 3H), 2.33 (s, 3H), 1.26 (d, J=7.0 Hz, 3H). MS ESI (pos.) m/z: 540.0 (M+H)+. SFC AS-H (2×25 cm) 15% MeOH/CO₂.

Example 545.0: Preparation of (1R,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide or (1S,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide

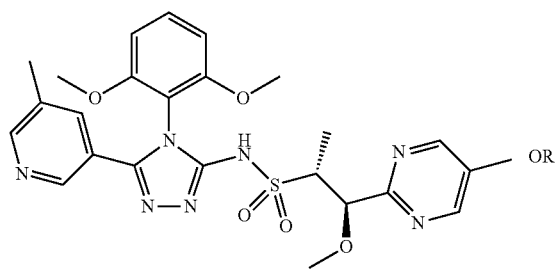

545.0

-continued

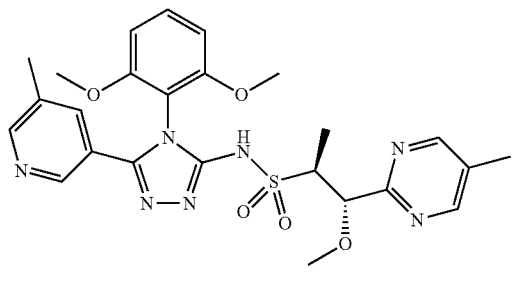

(1R,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide or (1S,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide
Example 545.0

The title compound was the first peak to elute by SFC using the conditions described in 543.0. ¹H NMR (400 MHz, CD₃OD) δ 8.69 (s, 2H), 8.46 (br s, 1H), 8.35 (br s, 1H), 7.75 (s, 1H), 7.52 (dd, J=8.3, 8.3 Hz, 1H), 6.81-6.84 (m, 2H), 4.63 (d, J=8.2 Hz, 1H), 3.85 (s, 3H), 3.81 (s, 3H), 3.61-3.69 (m, 1H), 3.12 (s, 3H), 2.37 (s, 3H), 2.32 (s, 3H), 1.05 (d, J=7.2 Hz, 3H). MS ESI (pos.) m/z: 540.0 (M+H)+. SFC IA (2×15 cm) 15% MeOH/CO₂.

Example 546.0: Preparation of (1R,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide or (1S,2S)—N-(4-(2,6-(trimethoxyphenyl)-5-(5-methyl-3-pyridinyl)-4H-1,2,4-triazol-3-yl)-1-methoxy-1-(5-methyl-2-pyrimidinyl)-2-propanesulfonamide 546.0

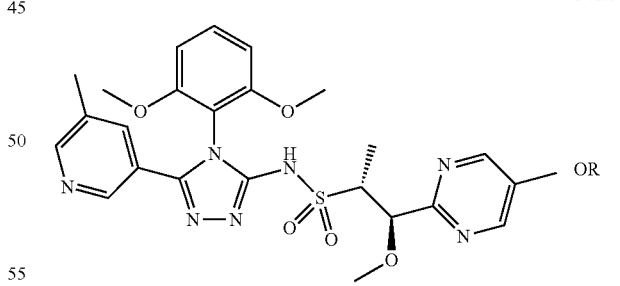

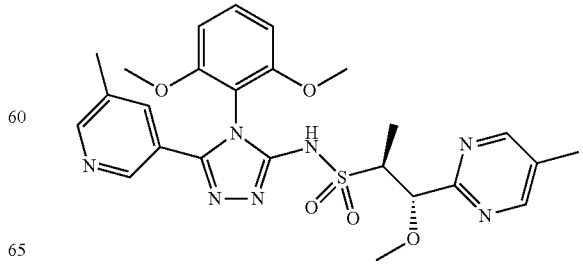

(1R,2R)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide or (1S,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide Example 546.0

The title compound was the second peak to elute by SFC using the conditions described in 543.0. $^1$H NMR (500 MHz, CD$_3$OD) δ 8.69 (s, 2H), 8.46 (br s, 1H), 8.34 (br s, 1H), 7.73 (s, 1H), 7.52 (dd, J=8.6, 8.6 Hz, 1H), 6.83 (dd. J=8.4, 3.1 Hz, 2H), 4.63 (d, J=8.4 Hz, 1H), 3.86 (s, 3H), 3.81 (s, 3H), 3.62-3.69 (m, 1H), 3.12 (s, 3H), 2.38 (s, 3H), 2.32 (s, 3H), 1.05 (d, J=7.2 Hz, 3H). MS ESI (pos.) m/z: 540.0 (M+H)$^+$. SFC IA (2×15 cm) 15% MeOH/CO$_2$.

Example 547.0: Preparation of (1R,2S)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide and (1S,2S)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide

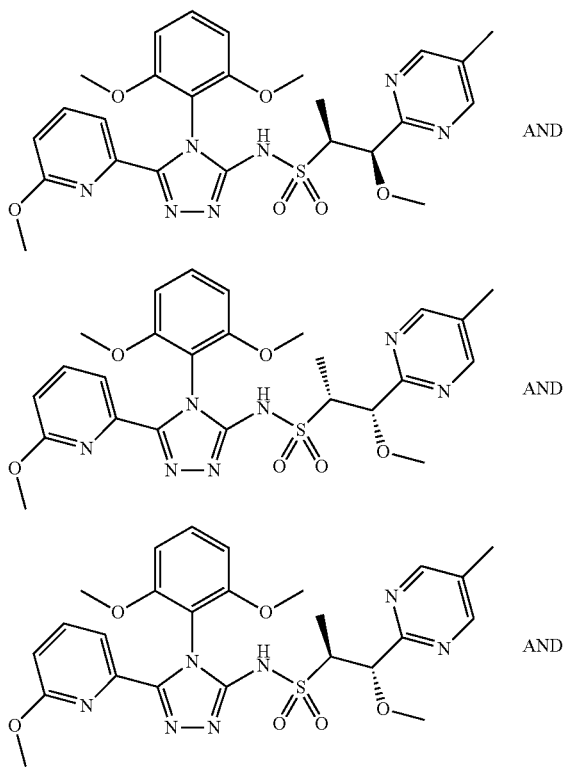

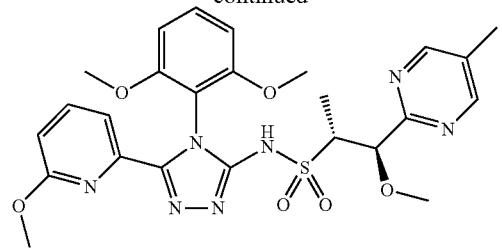

(1R,2S)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide and (1S,2S)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-methoxy-1-(5-methylpyrimidin-2-yl)propane-2-sulfonamide, Example 547.0

The title compound was prepared following the procedure described in Example A using 1.0, 6-methoxypicolinoyl) hydrazine carboxylic acid, and TFA (0.419 mL, 5.44 mmol). The racemic tail group was prepared using the general procedure described in Example C.

Example 548.0: Preparation of (1S,2R)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide Final chiral purification was performed on Example 547.0 using SFC (only 2 of the 4 isomers isolated). SFC AS-H (2×25 cm) 20% EtOH/CO$_2$, 100 bar 65 mL/min, 220 nm. inj vol.: 2 mL, 3 mg/mL 1:1 DCM:MeOH.

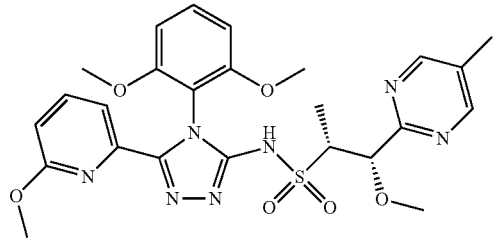

(1S,2R)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide, Example 548.0

The title compound was the first peak to elute by SFC using the conditions described above. $^1$H NMR (400 MHz, CD$_3$OD) δ 8.66 (d, J=0.8 Hz, 2H), 7.73 (dd, J=7.4, 7.4 Hz, 1H), 7.63 (d, J=7.1 Hz, 1H), 7.42 (dd, J=8.5, 8.5 Hz, 1H), 6.75-6.79 (m, 3H), 5.01 (d, J=3.7 Hz, 1H), 3.75 (s, 3H), 3.73 (s, 3H), 3.56-3.62 (m, 1H), 3.29 (s, 3H), 3.19 (s, 3H), 2.36

(s, 3H), 1.26 (d, J=7.0 Hz, 3H). MS ESI (pos.) m/z: 556.0 (M+H)⁺. SFC AS-H (2×25 cm) 20% EtOH/CO$_2$.

Example 549.0: Preparation of (1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide

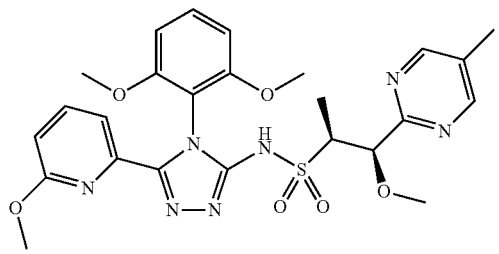

549.0

(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide, Example 549.0

The title compound was the second peak to elute by SFC using the conditions described in 548.0. $^1$H NMR (400 MHz, CD$_3$OD) δ 8.66 (s, 2H), 7.73 (dd, J=7.6, 7.6 Hz, 1H), 7.63 (d, J=7.0 Hz, 1H), 7.42 (dd, J=8.5, 8.5 Hz, 1H), 6.75-6.79 (m, 3H), 5.01 (d, J=3.7 Hz, 1H), 3.75 (s, 3H), 3.73 (s, 3H), 3.56-3.62 (m, 1H), 3.29 (s, 3H), 3.20 (s, 3H), 2.36 (s, 3H), 1.26 (d, J=7.0 Hz, 3H). MS ESI (pos.) m/z: 556.0 (M+H)⁺. SFC AS-H (2×25 cm) 20% EtOH/CO$_2$.

Example 550.0: Preparation of 2-(5-cyanopyridin-2-yl)-N-(4-(2,6-dimethoxyphenyl)-5-(6-methoxypyridin-2-yl)-4H-1,2,4-triazol-3-yl)ethanesulfonamide

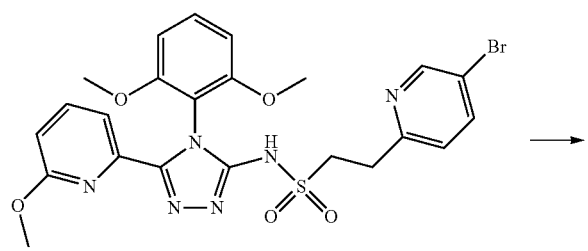

550.0

2-(5-cyanopyridin-2-yl)-N-(4-(2,6-dimethoxyphenyl)-5-(6-methoxypyridin-2-yl)-4H-1,2,4-triazol-3-yl)ethanesulfonamide, Example 550.0

A glass microwave reaction vessel was charged with 2-(5-bromopyridin-2-yl)-N-(4-(2,6-dimethoxyphenyl)-5-(6-methoxypyridin-2-yl)-4H-1,2,4-triazol-3-yl)ethanesulfonamide (0.30 g, 0.521 mmol), tetrakis(triphenylphosphine)palladium (0.060 g, 0.052 mmol), and zinc cyanide (0.245 g, 2.09 mmol) in DMF (1.0 mL). The reaction mixture was stirred and heated in a Discover model microwave reactor (CEM, Matthews, N.C.) at 120° C. for 60 min. The reaction was purified via reverse phase HPLC (Agilent SB-C$_8$ column, 30×250 mm, 5 µm, 10-95% water/ACN gradient over 25 min., with 0.1% TFA, flow rate 50 mL/min). Desired fractions were combined and lyophilized to give pure product. $^1$H NMR (400 MHz, CDCl$_3$) δ 8.79 (d, J=1.6 Hz, 1H), 7.85 (dd, J=8.0, 2.2 Hz, 1H), 7.57-7.65 (m, 2H), 7.31-7.35 (m, 2H), 6.71 (d, J=7.5 Hz, 1H), 6.60 (d, J=8.4 Hz, 2H), 3.69 (m, 6H), 3.49-3.53 (m, 2H), 3.34-3.38 (m, 2H), 3.16 (s, 3H). MS ESI (pos.) m/z: 521.9 (M+H)⁺.

Example 551.0: Preparation of (1S,2R)-1-(5-cyanopyridin-2-yl)-N-(4-(2,6-dimethoxyphenyl)-5-(5-methylpyridin-3-yl)-4H-1,2,4-triazol-3-yl)-1-methoxypropane-2-sulfonamide and (1R,2R)-1-(5-cyanopyridin-2-yl)-N-(4-(2,6-dimethoxyphenyl)-5-(5-methylpyridin-3-yl)-4H-1,2,4-triazol-3-yl)-1-methoxypropane-2-sulfonamide and (1S,2S)-1-(5-cyanopyridin-2-yl)-N-(4-(2,6-dimethoxyphenyl)-5-(5-methylpyridin-3-yl)-4H-1,2,4-triazol-3-yl)-1-methoxypropane-2-sulfonamide and (1R,2S)-1-(5-cyanopyridin-2-yl)-N-(4-(2,6-dimethoxyphenyl)-5-(5-methylpyridin-3-yl)-4H-1,2,4-triazol-3-yl)-1-methoxypropane-2-sulfonamide

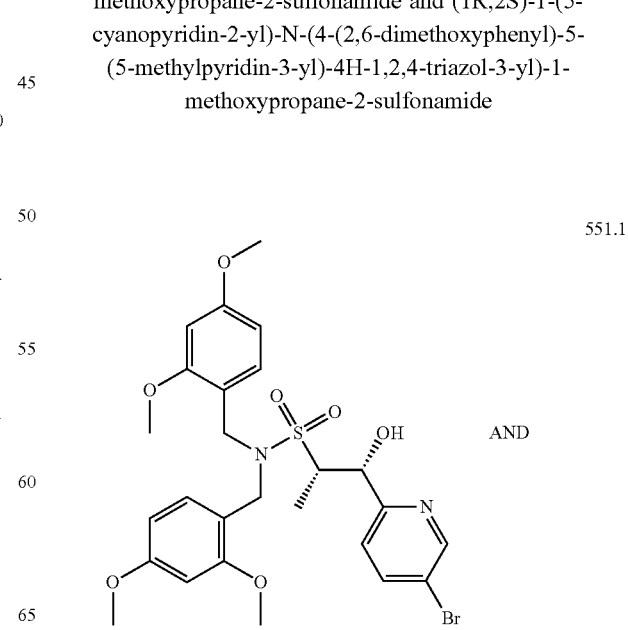

551.1

-continued


AND

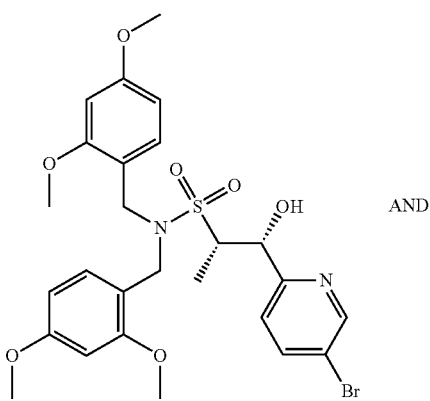

AND

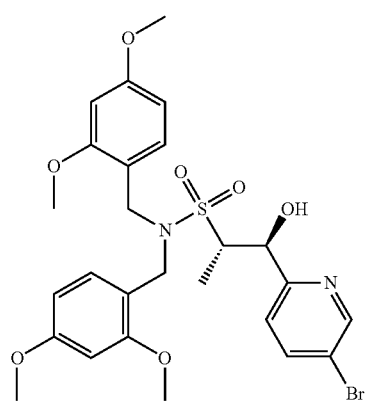

(1R,2S)-1-(5-bromopyridin-2-yl)-N,N-bis(2,4-dimethoxybenzyl)-1-hydroxypropane-2-sulfonamide and
(1R,2R)-1-(5-bromopyridin-2-yl)-N,N-bis(2,4-dimethoxybenzyl)-1-hydroxypropane-2-sulfonamide and
(1S,2S)-1-(5-bromopyridin-2-yl)-N,N-bis(2,4-dimethoxybenzyl)-1-hydroxypropane-2-sulfonamide and
(1S,2R)-1-(5-bromopyridin-2-yl)-N,N-bis(2,4-dimethoxybenzyl)-1-hydroxypropane-2-sulfonamide,
Example 551.1

To a −78° C. solution of N,N-bis(2,4-dimethoxybenzyl)ethanesulfonamide (6.95 g, 16.97 mmol) in THF (40 mL) was added n-BuLi (2.5 M in hexanes, 7 mL, 17.50 mmol) dropwise over 10 min. The temperature was kept below −68° C. during the addition. After 15 min of stirring, a solution of 5-bromo-2-formylpyridine (3.2 g, 17.20 mmol) in THF (10 mL) was added dropwise over 3 min. The resulting mixture was stirred overnight allowing the reaction to slowly warm to RT overnight. The reaction was quenched with a saturated solution of $NH_4C_1$. The mixture was then diluted with EtOAc and a saturated solution of ammonium chloride. The aqueous solution was extracted with EtOAc twice and then the combined organic layers were washed with brine and concentrated in vacuo. The material obtained was absorbed onto a plug of silica gel and purified by chromatography through a Redi-Sep pre-packed silica gel column (220 g), eluting with a gradient of 0-100% EtOAc in hexanes; the product eluted between 40-60% EtOAc. MS ESI (pos.) m/z: 616.9 (M+Na)⁺.

551.2

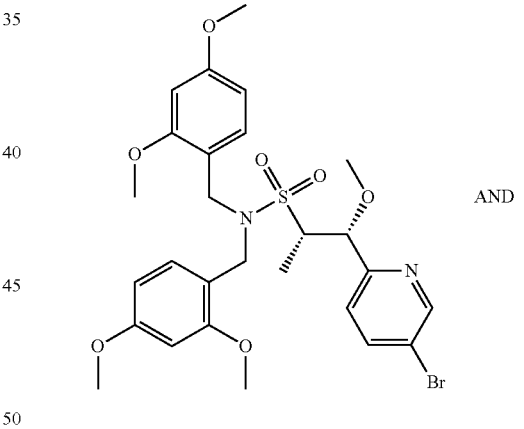

AND

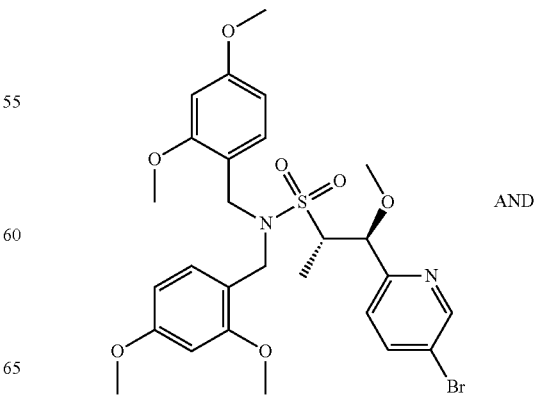

AND

-continued

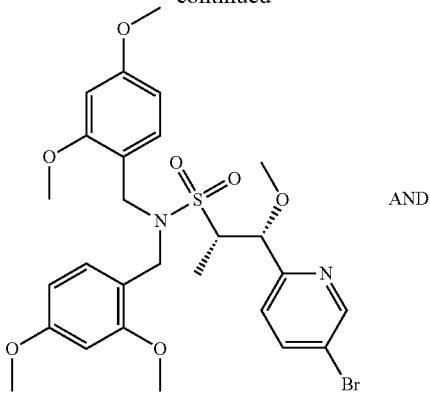

AND

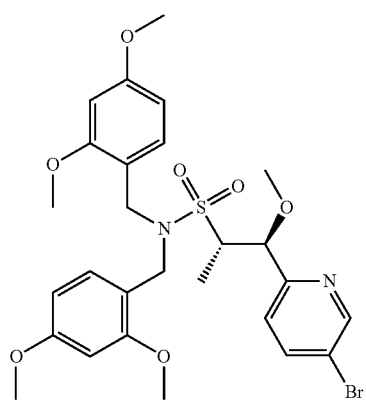

(1R,2S)-1-(5-bromopyridin-2-yl)-N,N-bis(2,4-dimethoxybenzyl)-1-methoxypropane-2-sulfonamide and (1S,2S)-1-(5-bromopyridin-2-yl)-N,N-bis(2,4-dimethoxybenzyl)-1-methoxypropane-2-sulfonamide and (1R,2R)-1-(5-bromopyridin-2-yl)-N,N-bis(2,4-dimethoxybenzyl)-1-methoxypropane-2-sulfonamide and (1S,2R)-1-(5-bromopyridin-2-yl)-N,N-bis(2,4-dimethoxybenzyl)-1-methoxypropane-2-sulfonamide Example 551.2

To a 0° C. solution of 551.1 (1.92 g, 3.22 mmol) in DMF (8 mL) was added sodium hydride, 60% dispersion in mineral oil (407 mg, 10.18 mmol). After 25 min, the cooling bath was removed. Next, iodomethane (1.01 mL, 16.12 mmol) was added, and the resulting mixture was stirred at RT overnight. The reaction was quenched with water and then diluted with diethyl ether. After extracting the aqueous phase three times with diethyl ether, the combined organic layers were washed with brine, dried over $Na_2SO_4$, and then concentrated in vacuo. This material was carried directly into the next step.

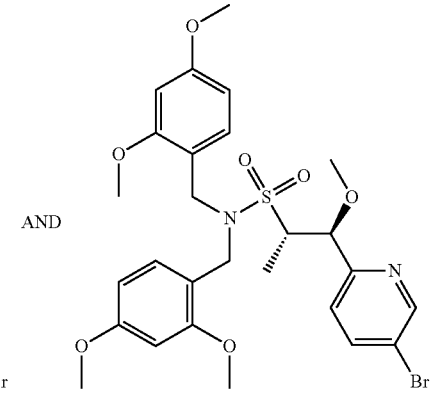

AND

-continued

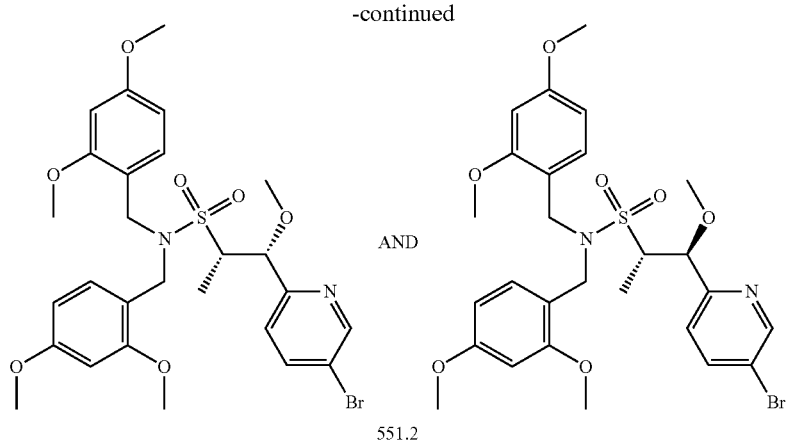

551.2

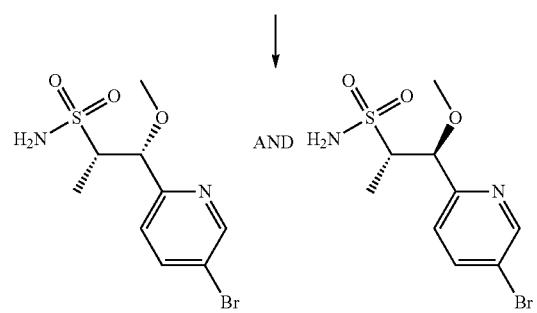

AND

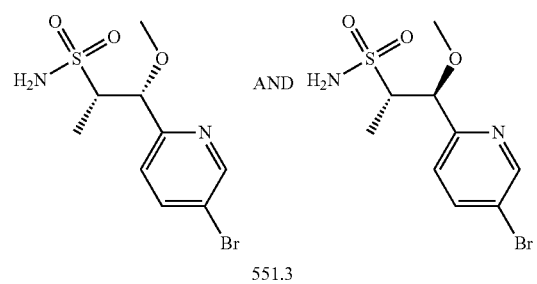

551.3

(1R,2S)-1-(5-bromopyridin-2-yl)-1-methoxypropane-2-sulfonamide and (1R,2R)-1-(5-bromopyridin-2-yl)-1-methoxypropane-2-sulfonamide and (1S,2S)-1-(5-bromopyridin-2-yl)-1-methoxypropane-2-sulfonamide and (1S,2R)-1-(5-bromopyridin-2-yl)-1-methoxypropane-2-sulfonamide, Example 551.3

To a solution of the 551.2 (2.2 g) in DCM (15 mL) was added triethylsilane (1.8 mL, 11.27 mmol), followed by TFA (4 mL, 51.9 mmol). The resulting solution was stirred at RT. The reaction was concentrated in vacuo and then dried on HVAC. The material obtained was partitioned between a saturated sodium bicarbonate solution and DCM. The aqueous layer was extracted with DCM (×3). The organic layers were combined and concentrated in vacuo. The material obtained was absorbed onto a plug of silica gel and purified by chromatography through a Redi-Sep pre-packed silica gel column (40 g), eluting with a gradient of 0-8% MeOH in DCM, to provide 551.3 (690 mg, 2.23 mmol, 69% yield) as a sticky yellow solid. MS ESI (pos.) m/z: 308.9 (M+H)$^+$.

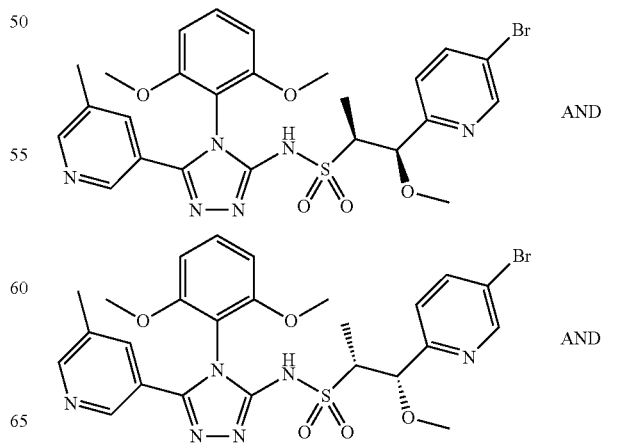

551.4

AND

AND

803
-continued

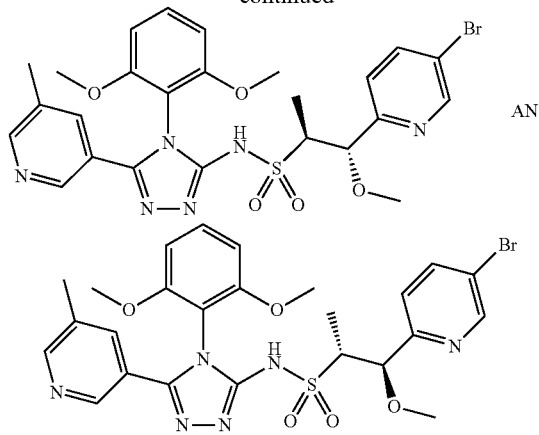

(1R,2S)-1-(5-bromopyridin-2-yl)-N-(4-(2,6-dime-
thoxyphenyl)-5-(5-methylpyridin-3-yl)-4H-1,2,4-
triazol-3-yl)-1-methoxypropane-2-sulfonamide bis
(2,2,2-trifluoroacetate) and (1R,2R)-1-(5-
bromopyridin-2-yl)-N-(4-(2,6-dimethoxyphenyl)-5-
(5-methylpyridin-3-yl)-4H-1,2,4-triazol-3-yl)-1-
methoxypropane-2-sulfonamide bis(2,2,2-
trifluoroacetate) and (1S,2S)-1-(5-bromopyridin-2-
yl)-N-(4-(2,6-dimethoxyphenyl)-5-(5-methylpyridin-
3-yl)-4H-1,2,4-triazol-3-yl)-1-methoxypropane-2-
sulfonamide bis(2,2,2-trifluoroacetate) and (1S,2R)-
1-(5-bromopyridin-2-yl)-N-(4-(2,6-
dimethoxyphenyl)-5-(5-methylpyridin-3-yl)-4H-1,2,
4-triazol-3-yl)-1-methoxypropane-2-sulfonamide
bis(2,2,2-trifluoroacetate) Example 551.4

The title compound was prepared following the procedure described in Example A using 1.0, 551.3 and 3.11. MS ESI (pos.) m/z: 602.9 (M+H)⁺.

551.0

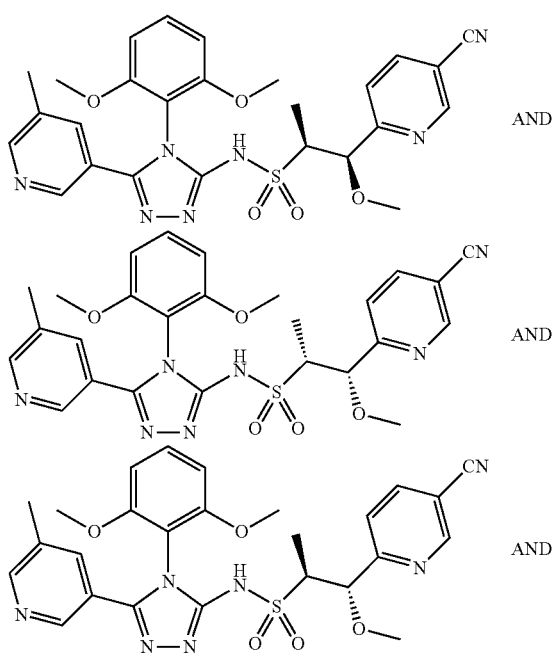

804
-continued

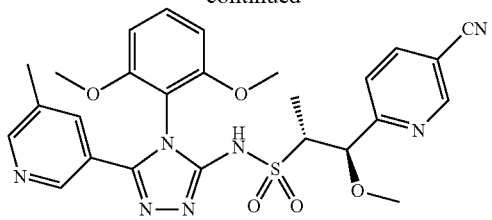

(1S,2R)-1-(5-cyanopyridin-2-yl)-N-(4-(2,6-dime-
thoxyphenyl)-5-(5-methylpyridin-3-yl)-4H-1,2,4-
triazol-3-yl)-1-methoxypropane-2-sulfonamide and
(1R,2R)-1-(5-cyanopyridin-2-yl)-N-(4-(2,6-dime-
thoxyphenyl)-5-(5-methylpyridin-3-yl)-4H-1,2,4-
triazol-3-yl)-1-methoxypropane-2-sulfonamide and
(1S,2S)-1-(5-Cyanopyridin-2-yl)-N-(4-(2,6-dime-
thoxyphenyl)-5-(5-methylpyridin-3-yl)-4H-1,2,4-
triazol-3-yl)-1-methoxypropane-2-sulfonamide and
(1R,2S)-1-(5-cyanopyridin-2-yl)-N-(4-(2,6-dime-
thoxyphenyl)-5-(5-methylpyridin-3-yl)-4H-1,2,4-
triazol-3-yl)-1-methoxypropane-2-sulfonamide,
Example 551.0

To a solution of 551.4 (293 mg, 0.352 mmol) in DMF (3 mL) was added tetrakis(triphenylphosphine)palladium (58.9 mg, 0.051 mmol) and zinc cyanide (56.7 mg, 0.48 mmol). Argon was then bubbled through the mixture for one minute and then the microwave vial was sealed. The resulting mixture was heated in a microwave for 60 min at 120° C. The reaction mixture was filtered, then purified by reverse-phase preparative HPLC using an Agilent SB C₈ column, 0.1% TFA in CH₃CN/H₂O, gradient 10-60% over 25 min (collected the peaks that were visible at 220 nm). Lyophilized the fractions overnight.

Example 552.0: Preparation of (1S,2R)-1-(5-cyano-
2-pyridinyl)-N-(4-(2,6-dimethoxyphenyl)-5-(5-
methyl-3-pyridinyl)-4H-1,2,4-triazol-3-yl)-1-
methoxy-2-propanesulfonamide or (1S,2S)-1-(5-
cyano-2-pyridinyl)-N-(4-(2,6-dimethoxyphenyl)-5-
(5-methyl-3-pyridinyl)-4H-1,2,4-triazol-3-yl)-1-
methoxy-2-propanesulfonamide or (1R,2R)-1-(5-
cyano-2-pyridinyl)-N-(4-(2,6-dimethoxyphenyl)-5-
(5-methyl-3-pyridinyl)-4H-1,2,4-triazol-3-yl)-1-
methoxy-2-propanesulfonamide or (1R,2S)-1-(5-
cyano-2-pyridinyl)-N-(4-(2,6-dimethoxyphenyl)-5-
(5-methyl-3-pyridinyl)-4H-1,2,4-triazol-3-yl)-1-
methoxy-2-propanesulfonamide 552.0

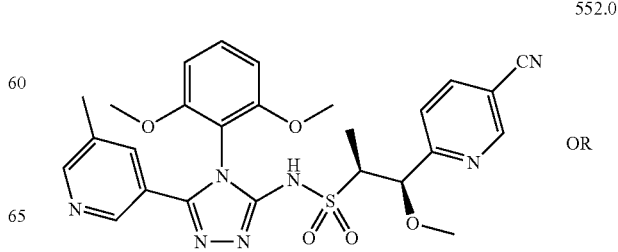

-continued

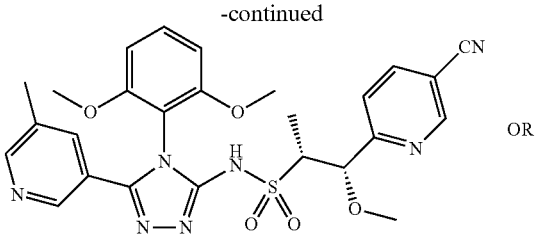

OR

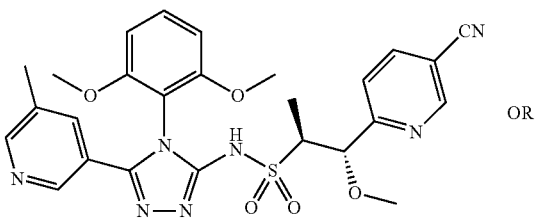

OR

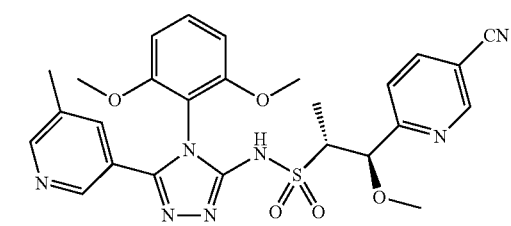

Final chiral separations were performed on Example 552.0 using SFC. SFC conditions (2 stage separation): Stage 1 IA (2×15 cm); 30% IPA/CO$_2$, 100 bar; 60 mL/min, 220 nm; inj vol.: 1 mL, 11 mg/mL 1:1 DCM:MeOH. Stage 2, OJ-H (2×25 cm); 15% EtOH/CO$_2$, 100 bar; 60 mL/min, 220 nm; inj vol.: 1 mL.

(1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 552.0

The title compound was purified by SFC using the conditions described above. $^1$H NMR (500 MHz, CDCl$_3$) δ 11.14 (s, 1H), 8.78-8.94 (m, 1H), 8.41-8.53 (m, 1H), 8.24-8.41 (m, 1H), 7.91-8.06 (m, 1H), 7.72-7.81 (m, 1H), 7.60 (d, J=8.07 Hz, 1H), 7.43 (s, 1H), 6.57-6.71 (m, 2H), 5.10 (d, J=2.69 Hz, 1H), 81s3 3.78 (s, 3H), 3.56-3.63 (m, 1H), 3.36 (s, 3H), 2.31-2.40 (m, 3H), 1.21 (d, J=7.09 Hz, 3H), MS ESI (pos.) m/z: 550.1 (M+H)$^+$.

Example 553.0: Preparation of (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide 553.0

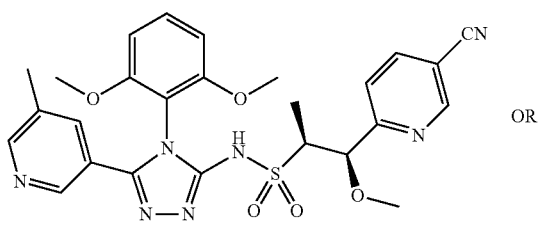

OR

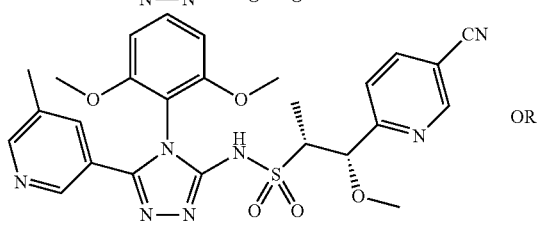

OR

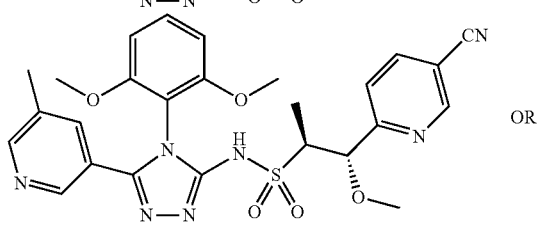

OR

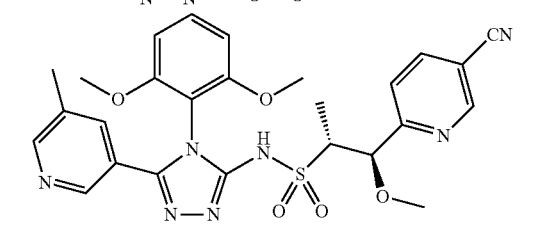

(1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 553.0

The title compound was purified by SFC using the conditions described in Example 552.0. $^1$H NMR (500 MHz, CDCl₃) δ 11.10-11.26 (m, 1H), 8.77-8.59 (m, 1H), 8.40-8.56 (m, 1H), 8.22-8.39 (m, 1H), 7.87-8.00 (m, 1H), 7.70-7.82 (m, 1H), 7.55-7.66 (m, 1H), 7.47 (t, J=8.44 Hz, 1H), 6.57-6.74 (m, 2H), 4.79 (d, J=5.87 Hz, 1H), 3.81 (s, 3H), 3.74 (s, 3H), 3.57-3.68 (m, 1H), 3.26 (s, 3H), 2.37 (s, 3H), 1.23 (d, J=7.09 Hz, 3H), MS ESI (pos.) m/z: 550.0 (M+H)⁺.

Example 554.0: Preparation of (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide

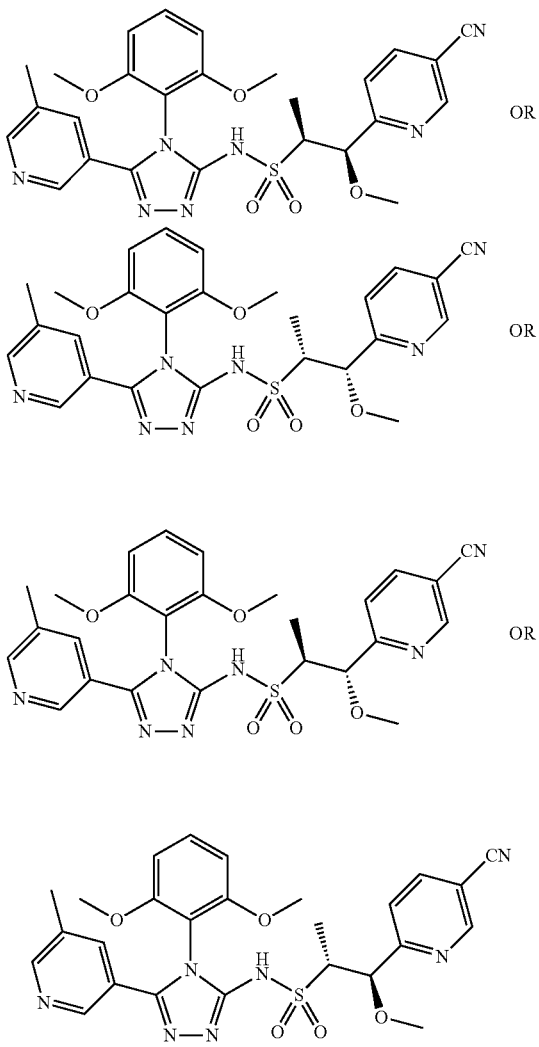

554.0

(1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 554.0

The title compound was purified by SFC using the conditions described in Example 552.0. ¹H NMR (500 MHz, CDCl₃) δ 11.10-11.26 (m, 1H), 8.77-8.59 (m, 1H), 8.40-8.56 (m, 1H), 8.22-8.39 (m, 1H), 7.87-8.00 (m, 1H), 7.70-7.82 (m, 1H), 7.55-7.66 (m, 1H), 7.47 (t, J=8.44 Hz, 1H), 6.57-6.74 (m, 2H), 4.79 (d, J=5.87 Hz, 1H), 3.81 (s, 3H), 3.74 (s, 3H), 3.57-3.68 (m, 1H), 3.26 (s, 3H), 2.37 (s, 3H), 1.23 (d, J=7.09 Hz, 3H); MS ESI (pos.) m/z: 550.0 (M+H)⁺.

Example 555.0: Preparation of (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-(trimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide

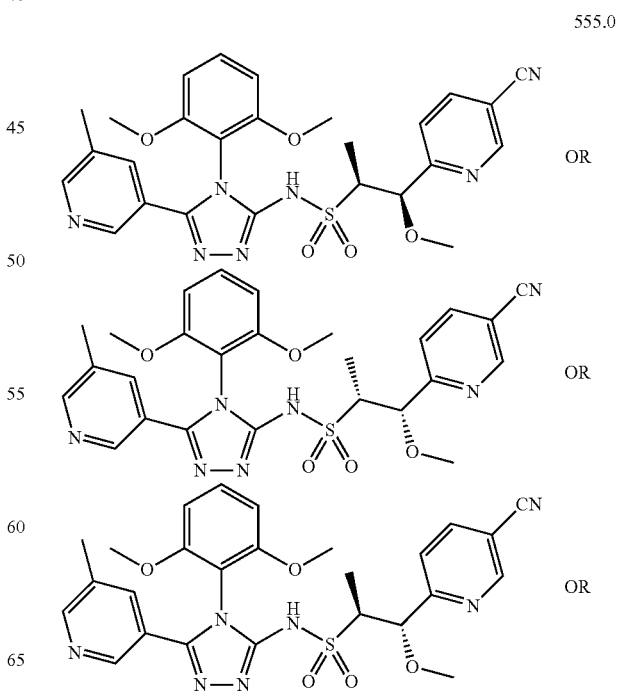

555.0

-continued

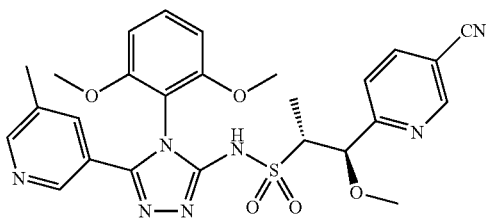

(1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, Example 555.0

The title compound was purified by SFC using the conditions described in Example 552.0. $^1$H NMR (500 MHz, CDCl$_3$) δ 11.14 (br. s., 1H), 8.86 (d, J=1.47 Hz, 1H), 8.43-8.60 (m, 1H), 8.27-8.42 (m, 1H), 7.89-8.06 (m, 1H), 7.70-7.81 (m, 1H), 7.55-7.65 (m, 1H), 7.42 (s, 1H), 6.63 (t, J=8.31 Hz, 2H), 5.10 (d, J=2.69 Hz, 1H), 3.78 (s, 3H), 3.75 (s, 3H), 3.55-3.63 (m, 1H), 3.36 (s, 3H), 2.35 (s, 3H), 1.20 (d, J=7.09 Hz, 3H) MS ESI (pos.) m/z: 550.0 (M+H)$^+$.

Example 556.0: Preparation of (1S,2R)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide and (1S,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide and (1R,2R)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide and (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide 556.0

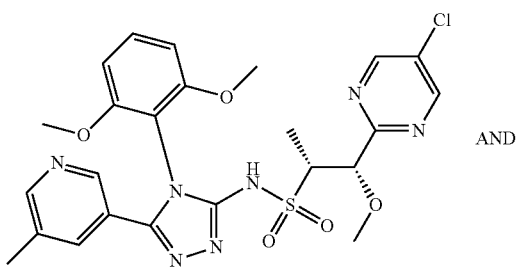

-continued

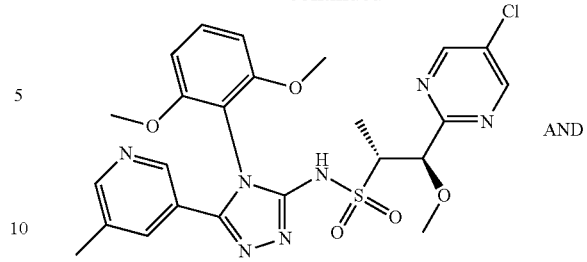
AND

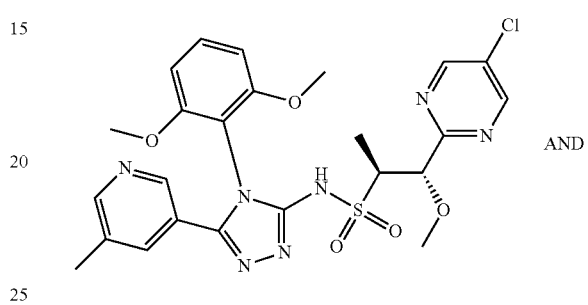
AND

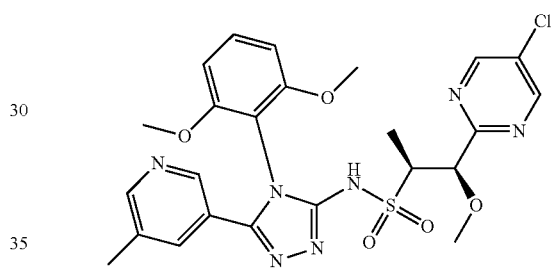

(1S,2R)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide and (1S,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide and (1R,2R)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide and (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide, Example 556.0

At 80° C., copper(I) iodide (0.065 g, 0.34 mmol) was added to a dioxane (1.37 mL) solution containing racemic 1-(5-chloropyrimidin-2-yl)-1-methoxypropane-2-sulfonamide (prepared following Example C using the appropriate aldehyde and 12.0, 0.181 g, 0.68 mmol), cesium carbonate (0.556 g, 1.71 mmol), and N1,N2-dimethylcyclohexane-1,2-diamine (0.194 g, 1.365 mmol). The resulting mixture was stirred overnight at 80° C. The reaction was then partitioned with EtOAc/water, washed with brine, dried over sodium sulfate, and concentrated in vacuo. The reaction was purified via reverse phase HPLC (Agilent SB-C$_8$ column, 30×250 mm, 5 μm, 10-95% water/ACN gradient over 25 min., with 0.1% TFA, flow rate 50 mL/min). Desired fractions were combined and lyophilized to give pure product.

Example 557.0: Preparation of (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide

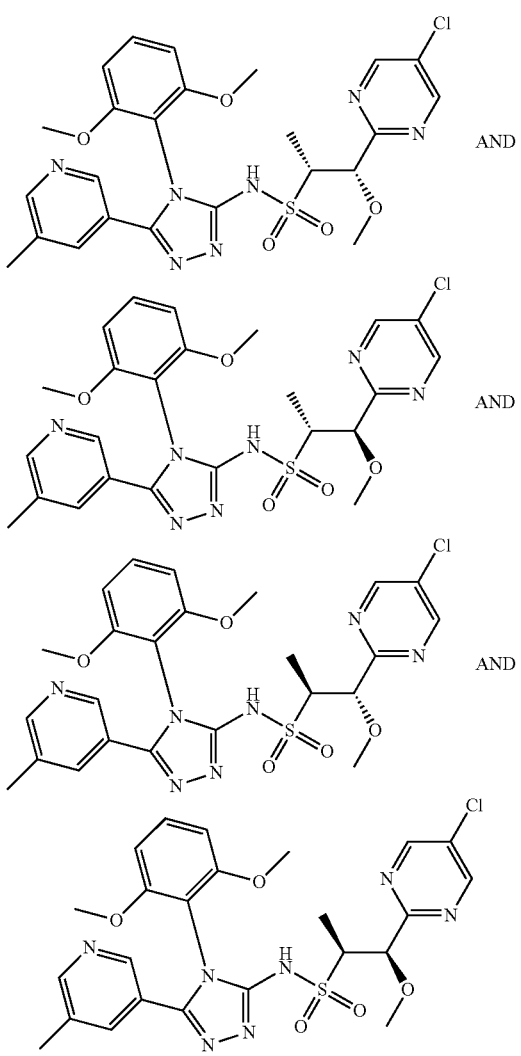

557.0

Final chiral purification was performed using SFC. Separation conditions for 557.0 and 558.0 (stage 1) chiral purification (299 mg): Run on Thar 200 SFC with 250×30 mm CC4 column with 50 g/min MeOH (neat)+50 g/min $CO_2$, 50% co-solvent at 100 g/min. Temperature.=25° C., Outlet pressure=100 bar, Wavelength=270 nm. Injected 0.6 mL of 299 mg sample dissolved in 10.0 mL MeOH, c=25 mg/mL, i.e. 15.0 mg per injection. Cycle time 8.0 min, run time=16 min.

Separation conditions for 559.0 and 560.0 (stage 2) chiral purification (51.6 mg): Run on Thar 200 SFC with 250×30 mm AS-H column with 20.8 g/min MeOH (neat)+139 g/min $CO_2$, 13% co-solvent at 160 g/min. Temperature.=20° C., Outlet pressure=100 bar, Wavelength=270 nm. Injected 1.2 mL of 51.6 mg sample dissolved in 8.0 mL MeOH, c=6.45 mg/mL, i.e. 7.74 mg per injection. Cycle time 8 min, run time=13 min.

(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, Example 557.0

The title compound was the first peak to elute by SFC using the conditions described above. $^1$H NMR (400 MHz, $CD_3OD$) δ 8.63 (s, 2H), 8.56 (br s, 1H), 8.43 (d, J=1.6 Hz, 1H), 7.99 (br s, 1H), 7.48 (dd, J=8.5, 8.5 Hz, 1H), 6.78 (d, J=8.6 Hz, 2H), 4.96 (d, J=3.5 Hz, 1H), 3.76 (s, 3H), 3.73 (s, 3H), 3.50-3.56 (m, 1H), 3.23 (s, 3H), 2.13 (s, 3H), 1.20 (d, J=7.0 Hz, 3H). MS ESI (pos.) m/z: 560.0 (M+H)$^+$. SFC with 250×30 mm CC4 column with 50 g/min MeOH (neat)+50 g/min $CO_2$, 50% co-solvent at 100 g/min.

Example 558.0: Preparation of (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide

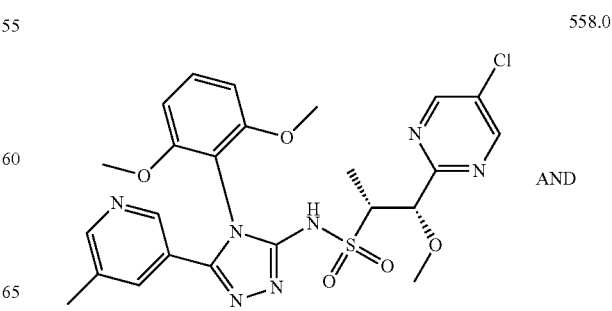

558.0

-continued

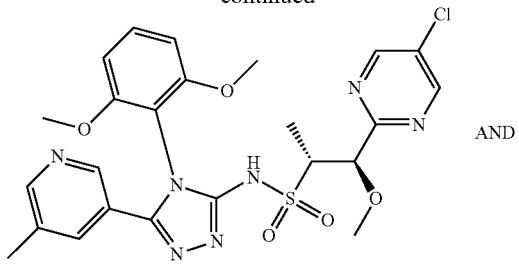

AND

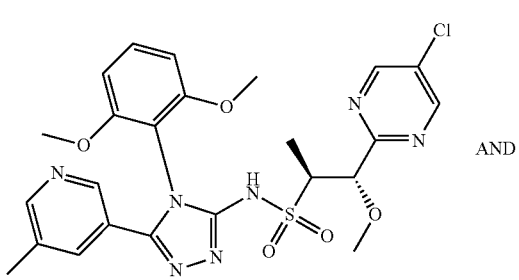

AND (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide,
Example 558.0

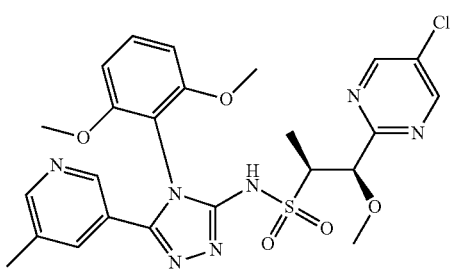

The title compound was the second peak to elute by SFC using the conditions described in 557.0. $^1$H NMR (400 MHz, CD$_3$OD) δ 8.86 (s, 2H), 8.48 (br s, 1H), 8.36 (br s, 1H), 7.76 (s, 1H), 7.52 (dd. J=8.6, 8.6 Hz, 1H), 6.83 (d, J=8.3 Hz, 2H), 4.66 (d, J=8.1 Hz, 1H), 3.84 (s, 3H), 3.81 (s, 3H), 3.62-3.69 (m, 1H), 3.14 (s, 3H), 2.33 (s, 3H), 1.09 (d, J=7.1 Hz, 3H). MS ESI (pos.) m/z: 559.9 (M+H)$^+$. SFC with 250×30 mm CC4 column with 50 g/min MeOH (neat)+50 g/min CO$_2$, 50% co-solvent at 100 g/min.

Example 559.0: Preparation of (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2S)-1-(5-chloro-2-pyrimidinyl)-N-(4-(2,6-trimethoxyphenyl)-5-(5-methyl-3-pyridinyl)-4H-1,2,4-triazol-3-yl)-1-methoxy-2-propanesulfonamide 559.0

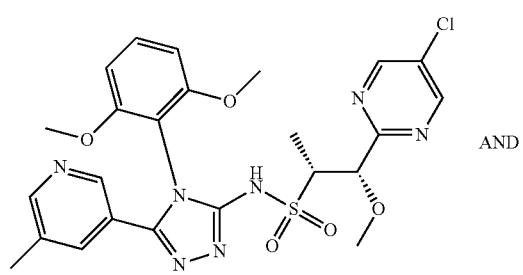

AND

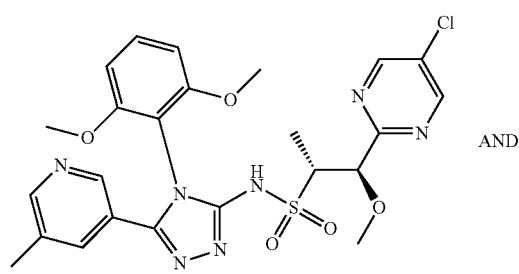

AND

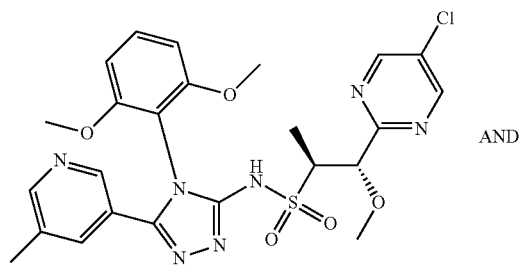

AND

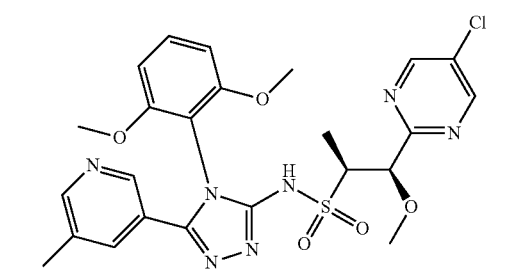

(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide,
Example 559.0

The title compound was the first peak (stage 2) to elute by SFC using the conditions described in 557.0. $^1$H NMR (500 MHz, CD$_3$OD) δ 8.84 (s, 2H), 8.64 (s, 1H), 8.33 (s, 1H), 7.72 (s, 1H), 7.51 (dd, J=8.3, 8.3 Hz, 1H), 6.81 (d, J=8.6 Hz, 2H), 4.59 (d, J=3.9 Hz, 1H), 3.80 (s, 3H), 3.78 (s, 3H), 3.62-3.68 (m, 1H), 3.30 (s, 3H), 2.32 (s, 3H), 1.28 (d, J=7.0 Hz, 3H). MS ESI (pos.) m/z: 559.9 (M+H)$^+$. SFC with 250×30 mm AS-H column with 20.8 g/min MeOH (neat)+ 139 g/min CO$_2$, 13% co-solvent at 160 g/min.

Example 560.0: Preparation of (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(5-chloro-2-pyrimidinyl)-N-(4-(2,6-trimethoxyphenyl)-5-(5-methyl-3-pyridinyl)-4H-1,2,4-triazol-3-yl)-1-methoxy-2-propanesulfonamide or (1R,2S)-1-(5-chloro-2-pyrimidinyl)-N-(4-(2,6-trimethoxyphenyl)-5-(5-methyl-3-pyridinyl)-4H-1,2,4-triazol-3-yl)-1-methoxy-2-propanesulfonamide 560.0

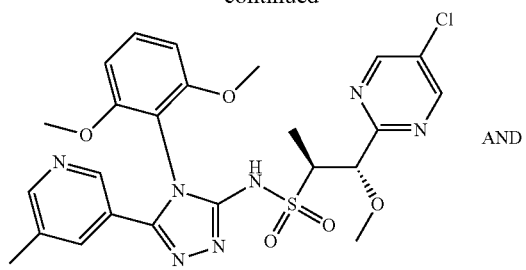

AND

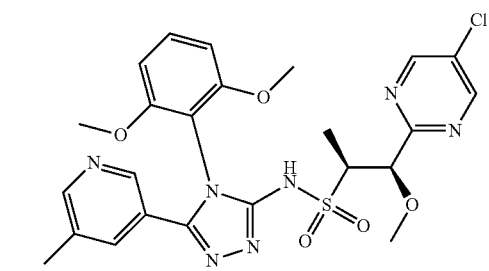

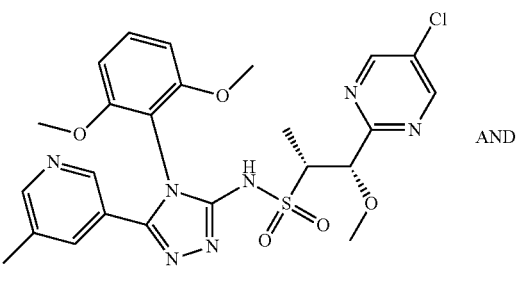

AND (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or
(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide,
Example 560.0

The title compound was the second peak (stage 2) to elute by SFC using the conditions described in 557.0. $^1$H NMR (500 MHz, CD$_3$OD) δ 8.85 (s, 2H), 8.42 (s, 1H), 8.72 (s, 1H), 7.70 (s, 1H), 7.5 (dd, J=8.6, 8.6 Hz, 1H), 6.81 (dd, J=8.6, 2.9 Hz, 2H), 4.69 (d, J=7.8 Hz, 1H), 3.83 (s, 3H), 3.79 (s, 3H), 3.66-3.72 (m, 1H), 3.15 (s, 3H), 2.31 (s, 3H), 1.09 (d, J 7.1 Hz, 3H). MS ESI (pos.) m/z: 560.0 (M+H)$^+$. SFC with 250×30 mm AS-H column with 20.8 g/min MeOH (neat)+139 g/min CO$_2$, 13% co-solvent at 160 g/min.

Example 561.0: Preparation of (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide and (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide and (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide and (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide 561.0

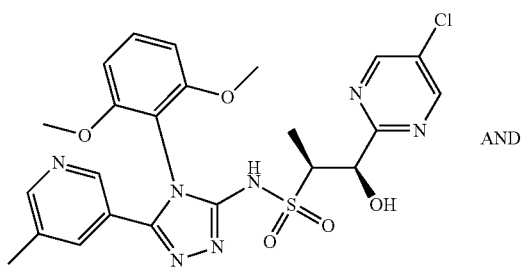

AND

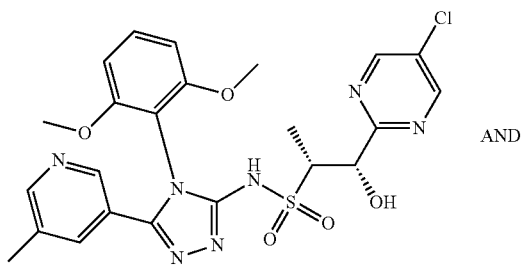

AND

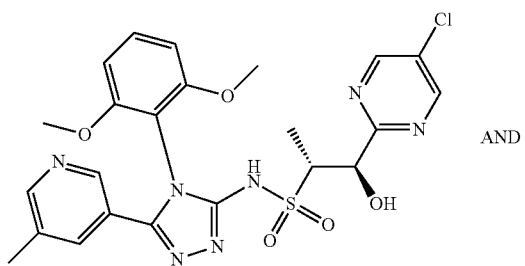

AND

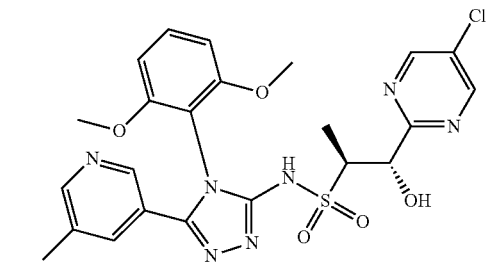

At 80° C., copper(I) iodide (0.039 g, 0.20 mmol) was added to a dioxane (0.82 mL) solution containing 1-(5-chloropyrimidin-2-yl)-1-hydroxypropane-2-sulfonamide (prepared following Example C using the appropriate aldehyde and 12.0, (0.103 g, 0.41 mmol)), cesium carbonate (0.332 g, 1.02 mmol), and N1,N2-dimethylcyclohexane-1,2-diamine (0.116 g, 0.82 mmol) and 2.0. The resulting mixture was stirred overnight at 80° C. The reaction was then partitioned with EtOAc and water, washed with brine, dried over sodium sulfate, and concentrated in vacuo. The reaction was purified via reverse phase HPLC (Agilent SB-C8 column, 30×250 mm, 5 µm, 10-95% water/ACN gradient over 25 min., with 0.1% TFA, flow rate 50 mL/min). Desired fractions were combined and lyophilized to give pure product.

Example 562.0: Preparation of (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide 562.0

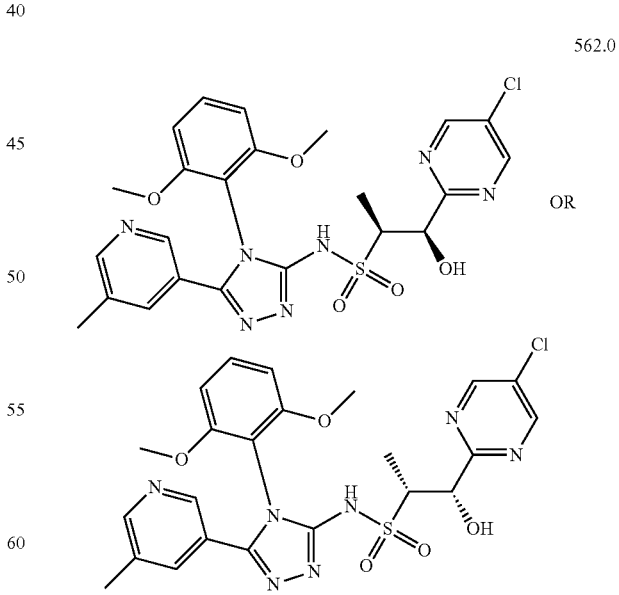

Final chiral separation was performed using SFC. Purification: Preparative SFC: AD-H (5 um, 21 mm×25 cm, S/N=3242) with 50% organic modifier modifier: 50% carbon dioxide. Organic modifier: IPA without any ammonia.

F=60 mL/min, T=40° C., BPR=100 bar, P=213 bar, 220 nm. All the sample (~132 mg) was dissolved in 12 mL MeOH, 11 mg/mL, 1.2 mL injection Two major peaks were collected and named as peak 1 and peak 2, respectively.

(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, Example 562.0

The title compound was the first peak to elute by SFC using the conditions described above. $^1$H NMR (400 MHz, CD$_3$OD) δ 8.83 (s, 2H), 8.45 (d, J=1.5 Hz, 1H), 8.34 (d, J=1.9 Hz, 1H), 7.72 (br s, 1H), 7.52 (dd, J=8.6, 8.6 Hz, 1H), 6.82 (d, J=8.7 Hz, 2H), 5.38 (d, J=3.5 Hz, 1H), 3.79 (s, 3H), 3.79 (s, 3H), 3.73-3.78 (m, 1H), 2.32 (s, 3H), 1.27 (d, J=6.8 Hz, 3H). MS ESI (pos.) m/z: 545.9 (M+H)$^+$. Preparative SFC: AD-H (5 um, 21 mm×25 cm, S/N=3242) with 50% organic modifier modifier: 50% carbon dioxide. Organic modifier: IPA without any ammonia. F=60 mL/min, T=40° C., BPR=100 bar, P=213 bar, 220 nm.

Example 563.0: Preparation of (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(5-chloro-2-pyrimidinyl)-N-(4-(2,6-(trimethoxyphenyl)-5-(5-methyl-3-pyridinyl)-4H-1,2,4-triazol-3-yl)-1-hydroxy-2-propanesulfonamide

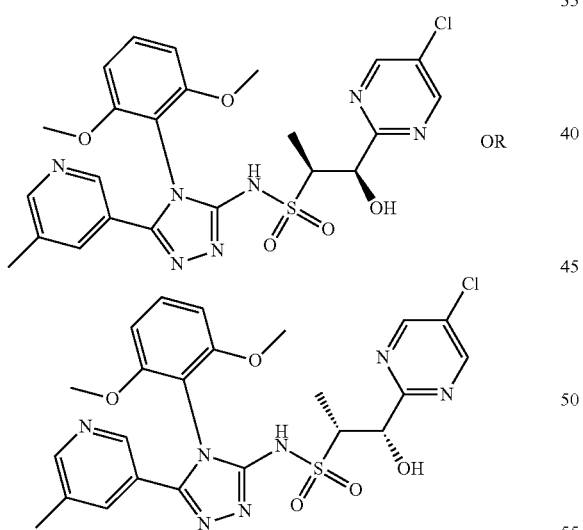

563.0

OR (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide or (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, Example 563.0

The title compound was the second peak to elute by SFC using the conditions described in 562.0. $^1$H NMR (400 MHz, CD$_3$OD) δ 8.83 (s, 2H), 8.45 (d, J=1.5 Hz, 1H), 8.34 (d, J=1.7 Hz, 1H), 7.72 (s, 1H), 7.52 (dd. J=8.5, 8.5 Hz, 1H), 6.82 (d, J=8.5 Hz, 2H), 5.38 (d, J=3.5 Hz, 1H), 3.79 (s, 3H), 3.79 (s, 3H), 3.73-3.78 (m, 1H), 2.32 (s, 3H), 1.27 (d, J=6.8 Hz, 3H). MS ESI (pos.) m/z: 545.9 (M+H)$^+$. AD-H (5 um, 21 mm×25 cm. S/N=3242) with 50% organic modifier modifier: 50% carbon dioxide. Organic modifier: IPA without any ammonia. F=60 mL/min, T=40° C., BPR=100 bar, P=213 bar, 220 nm.

Example 564.0: Preparation of (1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide and (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide (1S,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide and (1R,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide

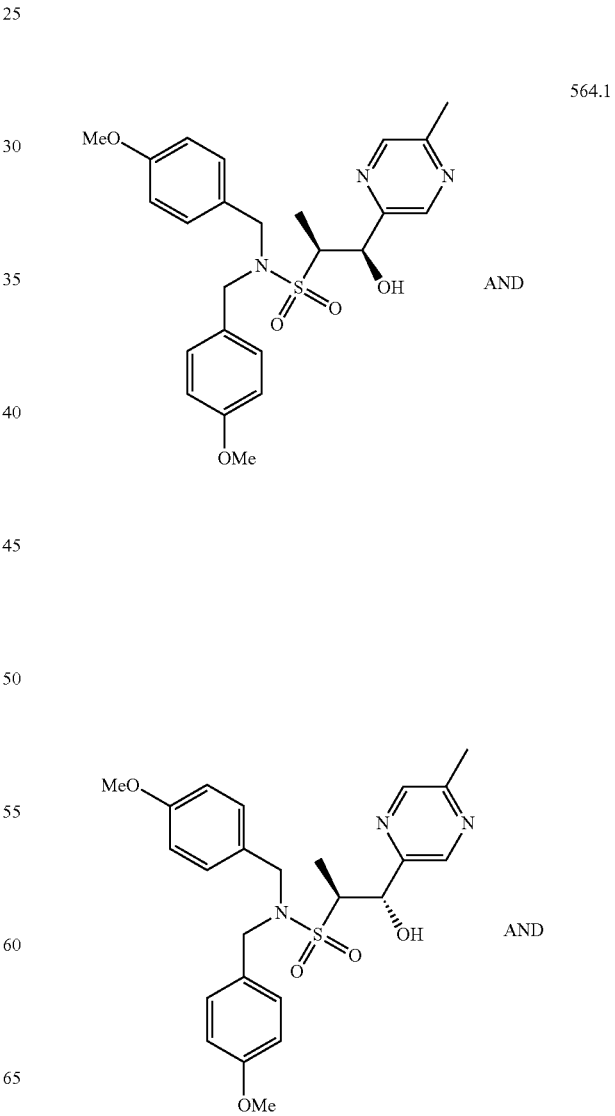

564.1

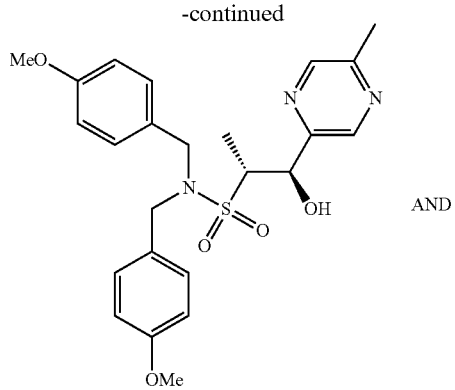

AND

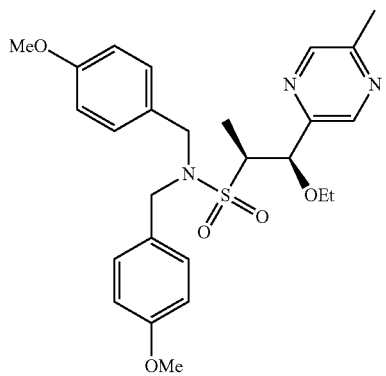

AND

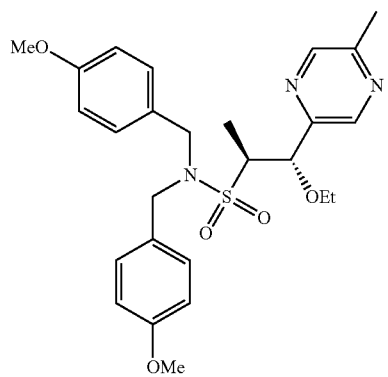

AND

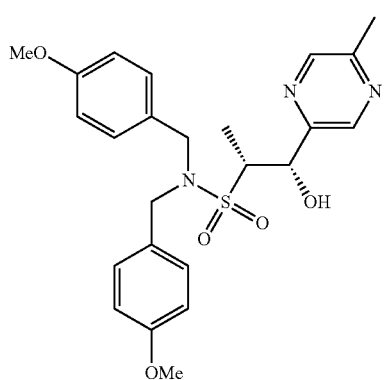

(1R,2R)-1-hydroxy-N,N-bis(4-methoxybenzyl)-1-(5-methylpyrazin-2-yl)propane-2-sulfonamide and (1S,2R)-1-hydroxy-N,N-bis(4-methoxybenzyl)-1-(5-methylpyrazin-2-yl)propane-2-sulfonamide and (1S,2S)-1-hydroxy-N,N-bis(4-methoxybenzyl)-1-(5-methylpyrazin-2-yl)propane-2-sulfonamide and (1R,2S)-1-hydroxy-N,N-bis(4-methoxybenzyl)-1-(5-methylpyrazin-2-yl)propane-2-sulfonamide and Example 564.1

At −78° C., a n-butyllithium solution (2.5 M in hexanes, 10.25 mL, 25.6 mmol) was added to a 2-methyltetrahydrofuran (107 mL) solution containing N,N-bis(4-methoxybenzyl)ethanesulfonamide (7.46 g, 21.36 mmol). The resulting mixture was stirred for 15 min at −78° C. Next, a 2-methyltetrahydrofuran solution containing 5-methyl-2-pyrazinecarbaldehyde (2.66 mL, 25.6 mmol) was added at −78° C. and then the reaction was allowed to slowly warm to RT and stirred overnight. The reaction was quenched with a saturated ammonium chloride solution and partitioned. The remaining residue was purified on silica eluting with a DCM/EtOAc gradient (0-50%). Desired fractions were then combined and concentrated in vacuo. MS ESI (pos.) m/z: 472.2 (M+H)+.

564.2

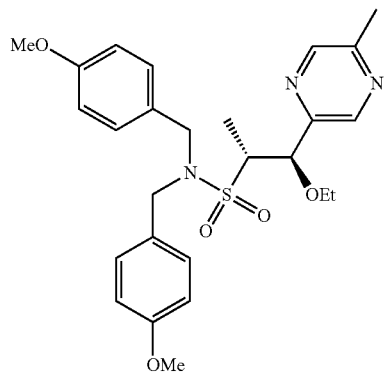

AND

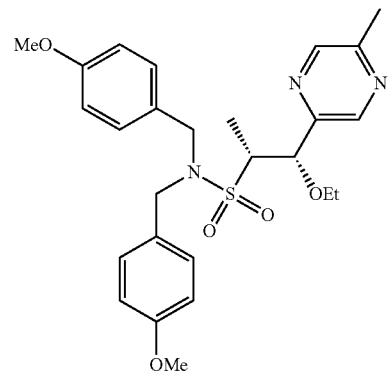

(1R,2R)-1-ethoxy-N,N-bis(4-methoxybenzyl)-1-(5-methylpyrazin-2-yl)propane-2-sulfonamide and (1R,2S)-1-ethoxy-N,N-bis(4-methoxybenzyl)-1-(5-methylpyrazin-2-yl)propane-2-sulfonamide and (1S,2R)-1-ethoxy-N,N-bis(4-methoxybenzyl)-1-(5-methylpyrazin-2-yl)propane-2-sulfonamide and (1S,2S)-1-ethoxy-N,N-bis(4-methoxybenzyl)-1-(5-methylpyrazin-2-yl)propane-2-sulfonamide, Example 564.2

At −78° C., potassium bis(trimethylsilyl)amide, (1.0 Mm THF, 2.51 mL, 2.51 mmol) was added to a 2-methyltetrahydrofuran (20.93 mL) solution containing 564.1 (0.987 g, 2.09 mmol). Next, ethyl trifluoromethanesulphonate (0.814 mL, 6.28 mmol) was added and the resulting mixture was stirred for 1 h at −78° C. The reaction was quenched at −78° C. with a saturated NH$_4$Cl solution and the mixture was then warmed to RT, extracted with EtOAc and concentrated in vacuo. The reaction was purified on silica eluting with a hexanes/EtOAc gradient (0-100%). Desired fractions were then combined and concentrated in vacuo. MS ESI (pos.) m/z: 500.3 (M+H)$^+$.

564.3

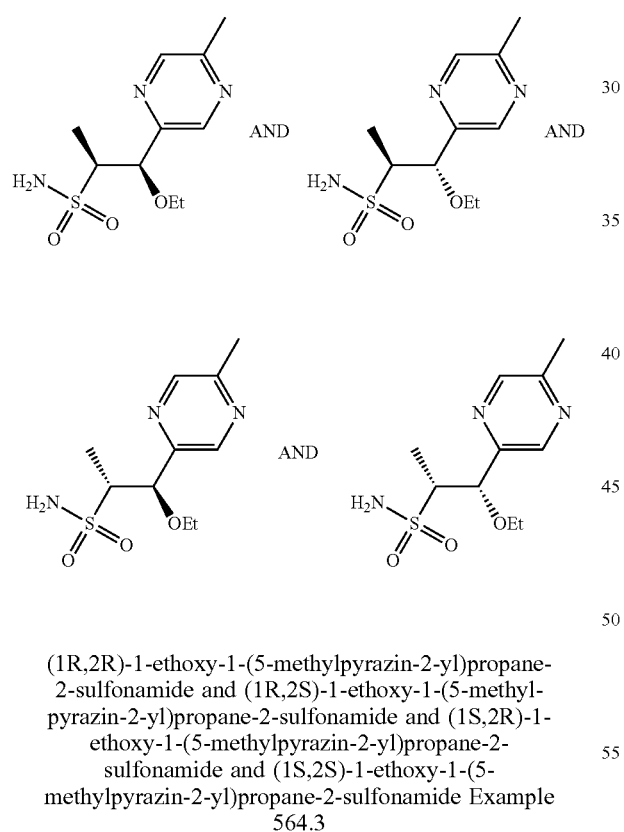

(1R,2R)-1-ethoxy-1-(5-methylpyrazin-2-yl)propane-2-sulfonamide and (1R,2S)-1-ethoxy-1-(5-methylpyrazin-2-yl)propane-2-sulfonamide and (1S,2R)-1-ethoxy-1-(5-methylpyrazin-2-yl)propane-2-sulfonamide and (1S,2S)-1-ethoxy-1-(5-methylpyrazin-2-yl)propane-2-sulfonamide Example 564.3

At 23° C., TFA (0.086 mL, 1.12 mmol) was added to a DCM solution containing anisole (0.122 mL, 1.12 mmol) and 564.2 (0.56 g, 1.12 mmol). The resulting mixture was stirred overnight at 23° C. The solvent was evaporated, and the material was purified on silica gel eluting with a MeOH/DCM stepwise gradient (0-20%). Desired fractions were then combined and concentrated in vacuo. MS ESI (pos.) m/z: 260.2 (M+H)$^+$.

564.0

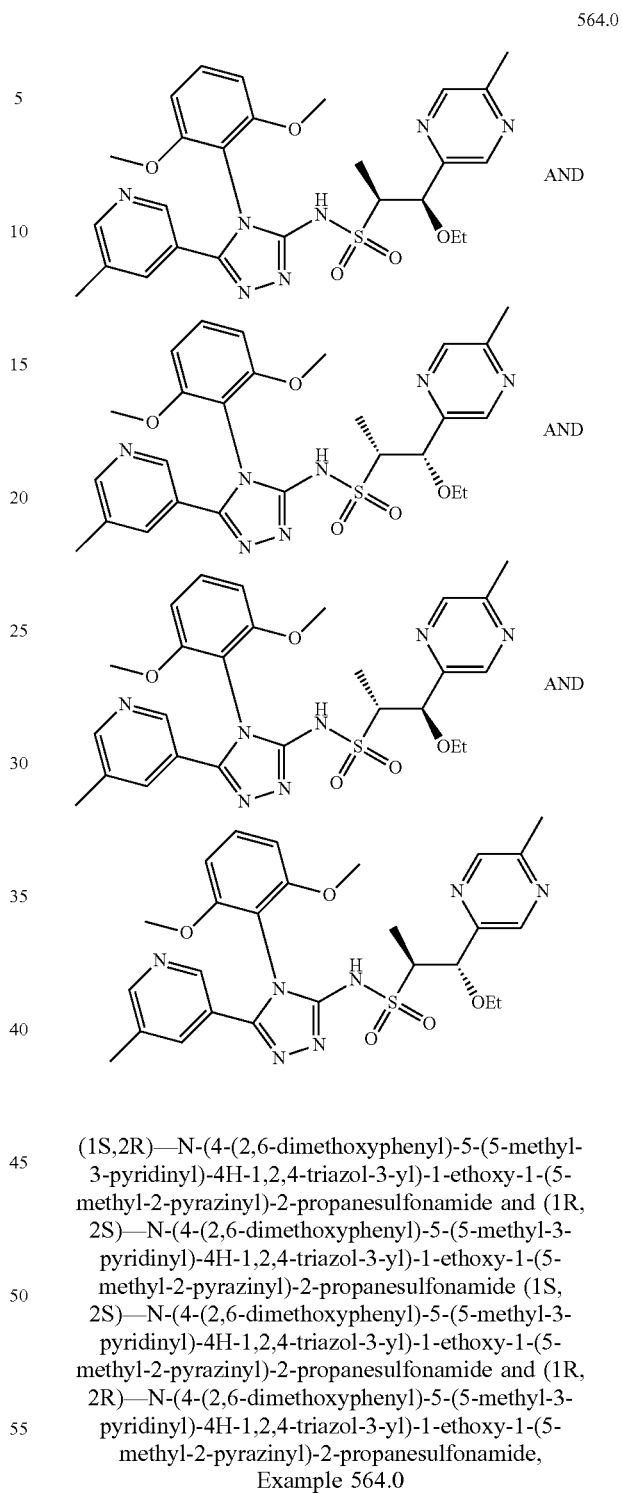

(1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide and (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide (1S,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide and (1R,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, Example 564.0

To a vial containing 564.3 (0.112 g, 0.43 mmol), 3-(5-bromo-4-(2,6-dimethoxyphenyl)-4H-1,2,4-triazol-3-yl)-5-methylpyridine 2.0 (0.194 g, 0.52 mmol), copper(I) iodide (0.040 g, 0.21 mmol), cesium carbonate (0.329 g, 1.01 mmol), and trans-N,N-dimethyl-1,2-cyclohexanesdiamine (0.129 mL, 0.82 mmol) was added degassed, anhydrous 1,4-dioxane (0.864 mL). Argon was bubbled through the reaction solution. After 15 min, the dark blue heterogeneous solution was heated on a pre-heated stir plate at 80° C. After 17 h, LCMS showed that the reaction was complete. The reaction was cooled to RT, then an aqueous solution of sodium thiosulfate was carefully added to the mixture. After extracting three times with DCM, the organics were combined and then dried over anhydrous magnesium sulfate. After filtration and concentration, the residue was purified on silica gel eluting with (0-20% DCM/MeOH) to give 564.0.

Example 565.0: Preparation of (1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide

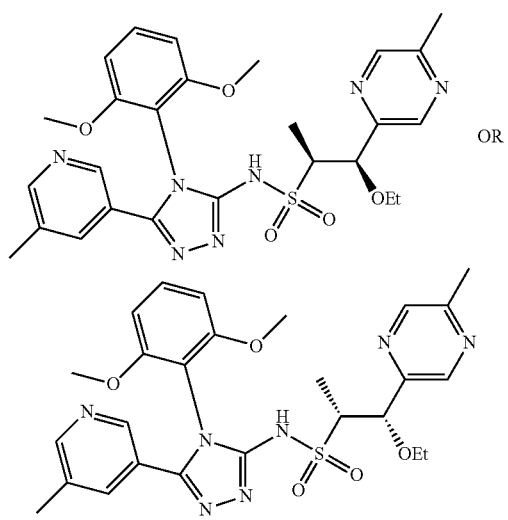

565.0

Final chiral separation was performed using SFC. Preparative SFC method: Column: Chiralpak OX-H (250×21 mm, 5 μm), Mobile Phase: 60:40 (CO₂: EtOH), Flow Rate: 65 mL/min, 220 nm, 30.3 mg/injection.

(1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide Example 565.0

The title compound was the first peak to elute by SFC using the conditions described above. $^1$H NMR (500 MHz, CD$_3$OD) δ 8.54 (s, 1H), 8.48 (br s, 2H), 8.36 (s, 1H), 7.74 (s, 1H), 7.54 (dd, J=8.6, 8.6 Hz, 1H), 6.84 (dd, J=8.5, 4.0 Hz, 2H), 5.09 (d, J=3.3 Hz, 1H), 3.83 (s, 3H), 3.79 (s, 3H), 3.45-3.52 (m, 3H), 2.55 (s, 3H), 2.30 (s, 3H), 1.26 (d, J=7.0 Hz, 3H), 1.16 (dd, J=7.0, 7.0 Hz, 3H). MS ESI (pos.) m/z: 554.3 (M+H)$^+$. Preparative SFC method: Column: Chiralpak OX-H (250×21 mm, 5 μm), Mobile Phase: 60:40 (CO$_2$: EtOH).

Example 566.0: Preparation of (1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide

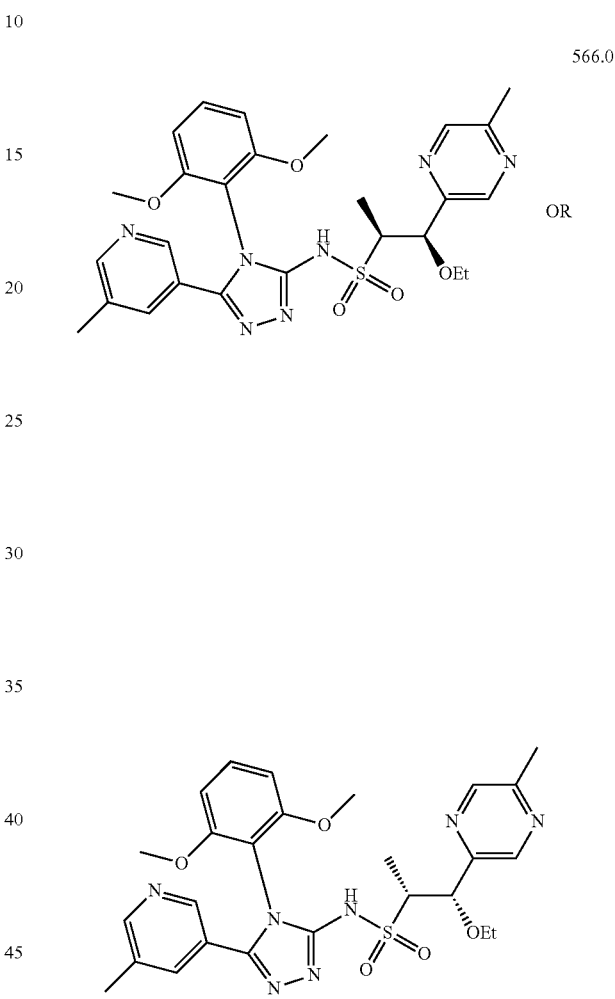

566.0

(1S,2R)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, Example 566.0

The title compound was the second peak to elute by SFC using the conditions described in 565.0. $^1$H NMR (500 MHz, CD$_3$OD) δ 8.59 (s, 1H), 8.53 (s, 1H), 8.47 (s, 2H), 7.99 (s, 1H), 7.55 (dd, J=8.5, 8.5 Hz, 1H), 6.85 (dd, J=8.5, 4.0 Hz, 2H), 5.07 (d, J=3.1 Hz, 1H), 3.83 (s, 3H), 3.79 (s, 3H), 3.45-3.55 (m, 3H), 2.55 (s, 3H), 2.30 (s, 3H), 1.25 (d, J=7.0, 3H), 1.15 (dd, J=6.9, 6.9 Hz, 3H). MS ESI (pos.) m/z: 554.2 (M+H)$^+$. Preparative SFC method: Column: Chiralpak OX-H (250×21 mm, 5 μm), Mobile Phase: 60:40 (CO$_2$: EtOH).

Example 567.0: Preparation of (1R,2S)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide and (1R,2R)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide 567.1

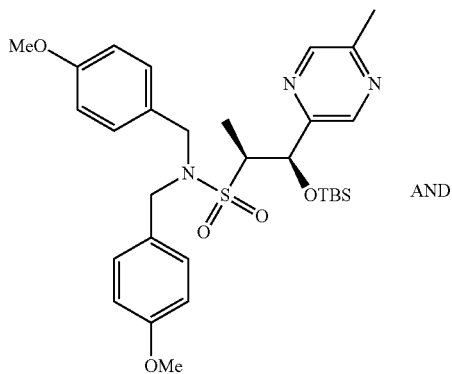

AND

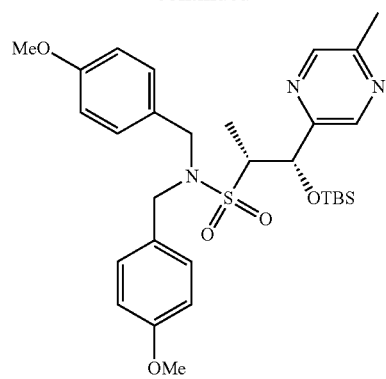

(1R,2R)-1-((tert-butyldimethylsilyl)oxy)-N,N-bis(4-methoxybenzyl)-1-(5-methylpyrazin-2-yl)propane-2-sulfonamide and (1S,2R)-1-((tert-butyldimethylsilyl)oxy)-N,N-bis(4-methoxybenzyl)-1-(5-methylpyrazin-2-yl)propane-2-sulfonamide and (1R,2S)-1-((tert-butyldimethylsilyl)oxy)-N,N-bis(4-methoxybenzyl)-1-(5-methylpyrazin-2-yl)propane-2-sulfonamide and (1S,2S)-1-((tert-butyldimethylsilyl)oxy)-N,N-bis(4-methoxybenzyl)-1-(5-methylpyrazin-2-yl)propane-2-sulfonamide, Example 567.1

To a stirred solution of 1-hydroxy-N,N-bis(4-methoxybenzyl)-1-(5-methylpyrazin-2-yl)propane-2-sulfonamide 564.1 (2.0 g, 4.24 mmol) in DCM (21.2 mL) at 0° C. was added tert-butyldimethylsilyl trifluoromethanesulfonate (1.07 mL, 4.67 mmol) followed by TEA (0.65 mL, 4.67 mmol). The mixture was allowed to warm to RT over 1 h. The reaction was then concentrated in vacuo, and purified on silica gel eluting with 0-100% EtOAc in hexanes to give the desired compound 567.1. MS ESI (pos.) m/z: 586.2 (M+H)$^+$.

567.2

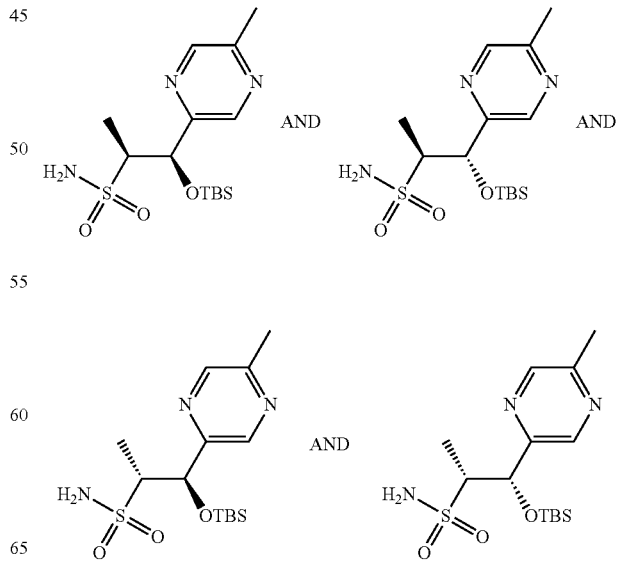

(1S,2R)-1-((tert-butyldimethylsilyl)oxy)-1-(5-methylpyrazin-2-yl)propane-2-sulfonamide and (1R,2R)-1-((tert-butyldimethylsilyl)oxy)-1-(5-methylpyrazin-2-yl)propane-2-sulfonamide and (1S,2S)-1-((tert-butyldimethylsilyl)oxy)-1-(5-methylpyrazin-2-yl)propane-2-sulfonamide and (1R,2S)-1-((tert-butyldimethylsilyl)oxy)-1-(5-methylpyrazin-2-yl)propane-2-sulfonamide Example 567.2

A 500-mL round-bottomed flask was charged with -1-((tert-butyldimethylsilyl)oxy)-N,N-bis(4-methoxybenzyl)-1-(5-methylpyrazin-2-yl)propane-2-sulfonamide (5.24 g, 8.94 mmol), anisole (4.0 mL, 36.6 mmol) and DCM (20 mL). TFA (21 mL, 273 mmol) was added and the mixture was stirred at RT until the reaction was complete. Toluene (10 mL) was then added to the mixture and the mixture was concentrated down to ~20 mL and then partitioned between a saturated aqueous sodium bicarbonate solution (20 mL) and EtOAc (20 mL). The organic phase was washed with a saturated aqueous sodium chloride solution (20 mL). The organic phase was then dried by passing through a Chem Elute extraction cartridge eluting with EtOAc (2×20 mL). The organic solution was concentrated to give a pale yellow oil. The yellow oil was purified by Biotage (SNAP100, Ultra, eluent: (3:1 EtOAc/EtOH) in hexanes 0-60%). The mixed fractions were re-purified (SNAP50, HP, eluent: EtOAc/hexanes 20-80%). The corresponding fractions were combined and concentrated in vacuo to give a white solid (2.82 g). $^1$H NMR (300 MHz, CDCl$_3$) δ 8.63 (d, J=1.17 Hz, 1H), 8.39 (s, 1H), 5.52 (d, J=2.78 Hz, 1H), 4.66 (s, 2H), 3.50 (dq, J=2.92, 6.97 Hz, 1H), 2.59 (s, 3H), 1.35 (d, J=6.87 Hz, 3H), 0.97 (s, 9H), 0.19 (s, 3H), −0.15 (s, 3H).

567.3

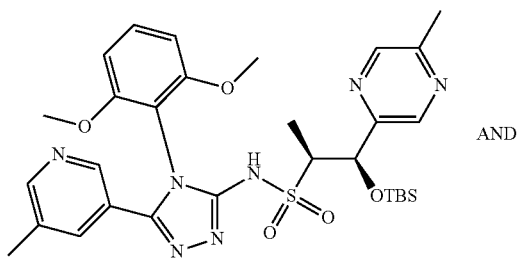

AND

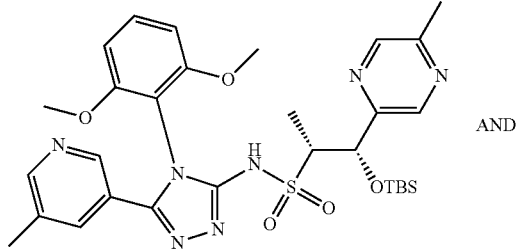

AND

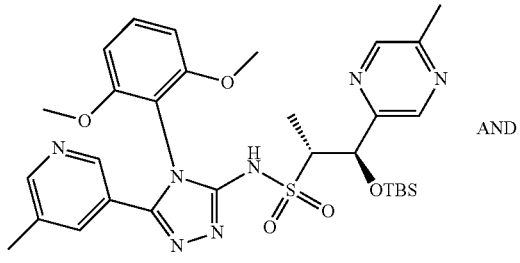

AND

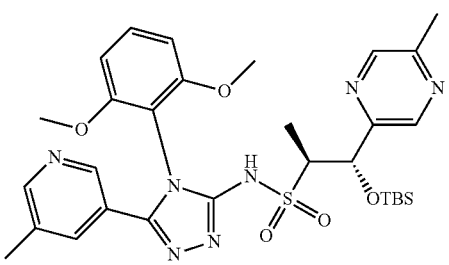

(1R,2R)-1-((tert-butyldimethylsilyl)oxy)-N-(4-(2,6-dimethoxyphenyl)-5-(5-methylpyridin-3-yl)-4H-1,2,4-triazol-3-yl)-1-(5-methylpyrazin-2-yl)propane-2-sulfonamide and (1S,2R)-1-((tert-butyldimethylsilyl)oxy)-N-(4-(2,6-dimethoxyphenyl)-5-(5-methylpyridin-3-yl)-4H-1,2,4-triazol-3-yl)-1-(5-methylpyrazin-2-yl)propane-2-sulfonamide and (1R,2S)-1-((tert-butyldimethylsilyl)oxy)-N-(4-(2,6-dimethoxyphenyl)-5-(5-methylpyridin-3-yl)-4H-1,2,4-triazol-3-yl)-1-(5-methylpyrazin-2-yl)propane-2-sulfonamide and (1S,2S)-1-((tert-butyldimethylsilyl)oxy)-N-(4-(2,6-dimethoxyphenyl)-5-(5-methylpyridin-3-yl)-4H-1,2,4-triazol-3-yl)-1-(5-methylpyrazin-2-yl)propane-2-sulfonamide, Example 567.3

Following the procedure of Example C. Examples 567.2 and 2.0 were mixed in degassed 1,4-dioxane and heated in a sealed tube at 80° C. overnight. The reaction mixture was then partitioned with water/EtOAc and the organics were concentrated in vacuo. The reaction was purified via reverse phase HPLC (Agilent SB-C$_8$ column, 30×250 mm, 5 μm, 10-95% water/ACN gradient over 25 min., with 0.1% TFA, flow rate 50 mL/min). Desired fractions were combined and lyophilized to give pure product 567.3. MS ESI (pos.) m/z: 640.2 (M+H)$^+$.

567.0

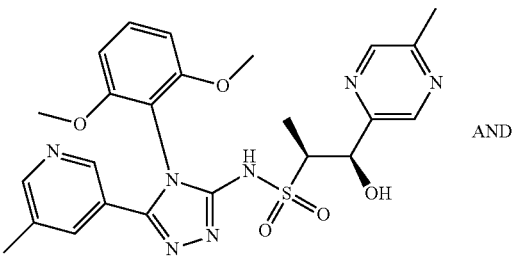

AND

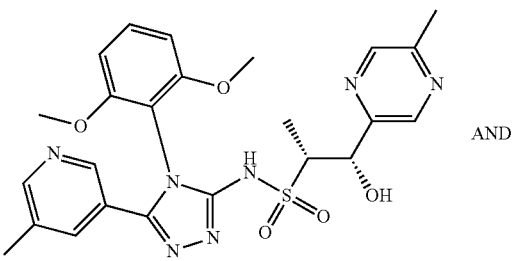

AND

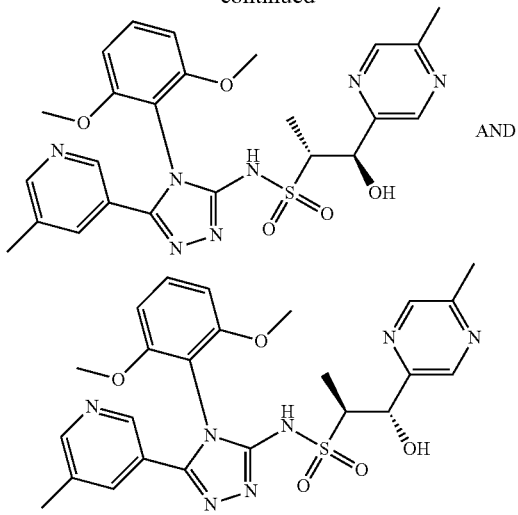

(1R,2S)—N-(4-(2,6-dimethoxyphenyl)-5-(5-methyl-pyridin-3-yl)-4H-1,2,4-triazol-3-yl)-1-hydroxy-1-(5-methylpyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide and (1R,2R)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(5-methylpyrazin-2-yl)propane-2-sulfonamide, Example 567.0

At 23° C., tetrabutylammonium fluoride solution (1.0 M in THF, 1.48 mL, 1.48 mmol) was added to a THF (4.92 mL) solution containing 567.3 (0.315 g, 0.49 mmol). The resulting mixture was stirred overnight at 23° C. The reaction was then concentrated and purified via reverse phase HPLC (Phenomenex Gemini-C18 column, 50×250 mm, 10 μm, 10-95% water/ACN gradient over 30 min., with 0.1% TFA, flow rate 100 mL/min). Desired fractions were combined and lyophilized to give pure product.

Example 568.0: Preparation of (1S,2R)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide

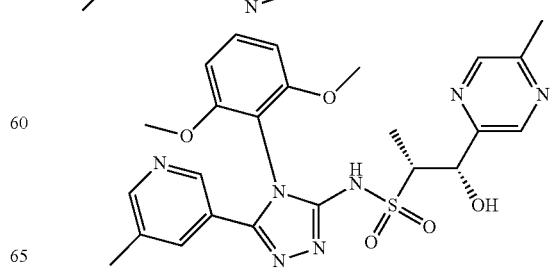

568.0

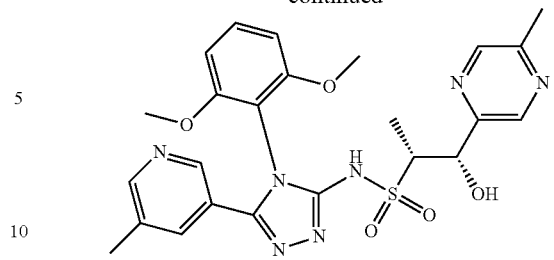

Final chiral separation was performed using SFC. Preparative SFC method: Column: Chiralpak OX-H (250×21 mm, 5 μm), Mobile Phase: 60:40 ($CO_2$:EtOH), Flow Rate: 70 mL/min, 220 nm, 42.8 mg/injection.

(1S,2R)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide, Example 568.0

The title compound was the first peak to elute by SFC using the conditions described above. $^1$H NMR (500 MHz, $CD_3OD$) δ 8.59 (s, 1H), 8.51 (s, 1H), 8.47 (s, 1H), 8.36 (s, 1H), 7.74 (s, 1H), 7.56 (dd, J=8.5, 8.5 Hz, 1H), 6.85 (dd, J=8.0, 8.0 Hz, 2H), 5.43 (br s, 1H), 3.82 (s, 3H), 3.79 (s, 3H), 3.64-3.70 (m, 1H), 2.58 (s, 3H), 2.34 (s, 3H), 1.19 (d, J=7.0 Hz, 3H). MS ESI (pos.) m/z: 526.1 (M+H)$^+$. SFC method: Column: Chiralpak OX-H (250×21 mm, 5 μm), Mobile Phase: 60:40 ($CO_2$:EtOH), Flow Rate: 70 mL/min, 220 nm, 42.8 mg/injection.

Example 569.0: Preparation of (1S,2R)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide

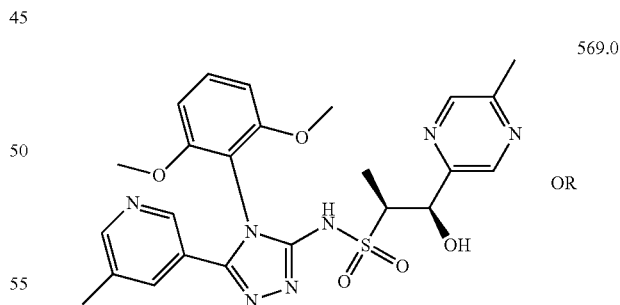

569.0

(1S,2R)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide Example 569.0

The title compound was the second peak to elute by SFC using the conditions described in 568.0. $^1$H NMR (500 MHz, CD$_3$OD) δ 8.59 (s, 1H), 8.51 (s, 1H), 8.47 (s, 1H), 8.36 (s, 1H), 7.75 (s, 1H), 7.55 (dd, J=8.5, 8.5 Hz, 1H), 6.85 (dd, J=7.6, 7.6 Hz, 2H), 5.43 (br s, 1H), 3.82 (s, 3H), 3.80 (s, 3H), 3.65-3.71 (m, 1H), 2.58 (s, 3H), 2.34 (s, 3H), 1.19 (d, J=6.8 Hz, 3H). MS ESI (pos.) m/z: 526.1 (M+H)$^+$. SFC method: Column: Chiralpak OX-H (250×21 mm, 5 μm), Mobile Phase: 60:40 (CO$_2$:EtOH), Flow Rate: 70 mL/min, 220 nm, 42.8 mg/injection.

Example 570.0: Preparation of (1R,2S)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide and (1R,2R)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide 570.0

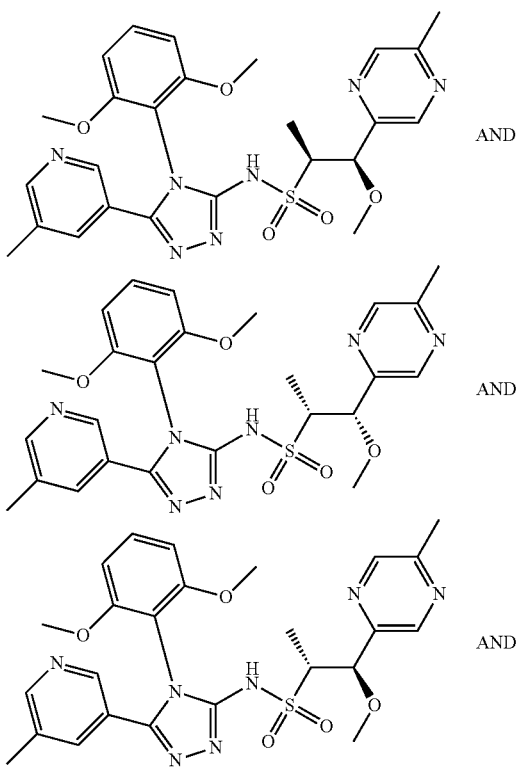

(1R,2S)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide and (1R,2R)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide and (1S,2R)—N-(4-(2,6-dimethoxyphenyl)-5-(5-methylpyridin-3-yl)-4H-1,2,4-triazol-3-yl)-1-methoxy-1-(5-methylpyrazin-2-yl)propane-2-sulfonamide, Example 570.0

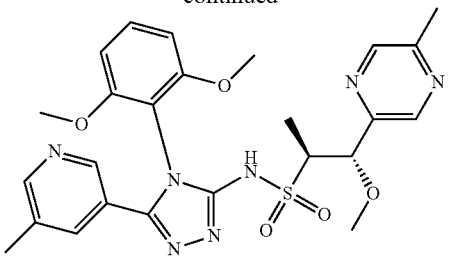

At 80° C., copper(I) iodide (0.089 g, 0.469 mmol) was added to a 1,4-dioxane (1.88 mL) solution containing (1R,2R)-1-methoxy-1-(5-methylpyrazin-2-yl)propane-2-sulfonamide and (1R,2S)-1-methoxy-1-(5-methylpyrazin-2-yl)propane-2-sulfonamide and (1S,2R)-1-methoxy-1-(5-methylpyrazin-2-yl)propane-2-sulfonamide and (1S,2S)-1-methoxy-1-(5-methylpyrazin-2-yl)propane-2-sulfonamide (prepared following procedures used to make 564.3 (in general using Example C using the appropriate aldehyde and 12.0 (0.230 g, 0.934 mmol), cesium carbonate (0.764 g, 2.34 mmol), and N1,N2-dimethylcyclohexanes-1,2-diamine (0.267 g, 1.88 mmol). The resulting mixture was stirred overnight at 80° C. The reaction was then partitioned with EtOAc/water, the organic layer was washed with brine, dried over sodium sulfate and concentrated in vacuo. The reaction was purified via reverse phase HPLC (Agilent SB-C$_8$ column, 30×250 mm, 5 μm, water/ACN gradient over 25 min., with 0.1% TFA, flow rate 50 mL/min). Desired fractions were combined and lyophilized to give pure product.

Example 571.0: Preparation of (1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide 571.0

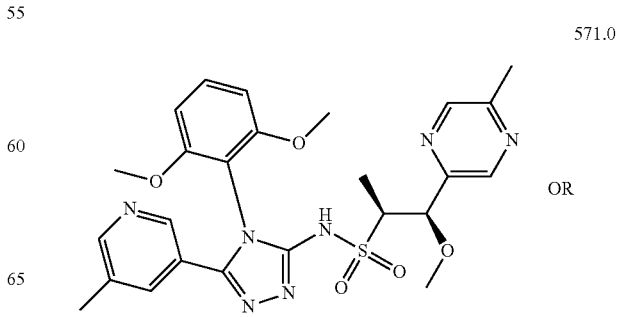

-continued

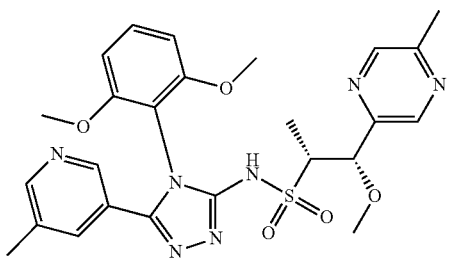

Final chiral separation was performed using SFC. Purification: Preparative SFC: OX (5 um, 21 mm×25 cm, S/N=2121) with 50% organic modifier modifier: 50% carbon dioxide. Organic modifier: EtOH without any ammonia. F=60 mL/min, T=40° C., BPR=100 bar, P=200 bar, 234 nm. All the sample (~490 mg) was dissolved in 17 nL MeOH (7 mL)/DCM (10 mL)), 30 mg/mL, 1.2 mL injection.

(1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide Example 571.0

The title compound was the first peak to elute by SFC using the conditions described above. $^1$H NMR (500 MHz, CD$_3$OD) δ 8.55 (s, 1H), 8.48 (d, J=1.4 Hz, 2H), 8.36 (d, J=2.0 Hz, 1H), 7.75 (d, J=3.6 Hz, 1H), 7.54 (dd, J=8.5, 8.5 Hz, 1H), 6.84 (d, J=8.6 Hz, 2H), 4.99 (d, J=3.1 Hz, 1H), 3.82 (s, 3H), 3.80 (s, 3H), 3.47-3.54 (m, 1H), 3.31 (s, 3H), 2.59 (s, 3H) 2.33 (s, 3H), 1.24 (d, J=6.8 Hz, 3H). MS ESI (pos.) m/z: 540.2 (M+H)$^+$. Preparative SFC: OX (5 um, 21 mm×25 cm, S/N=2121) with 50% organic modifier modifier: 50% carbon dioxide Organic modifier: EtOH without any ammonia.

Example 572.0: Preparation of (1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide -continued

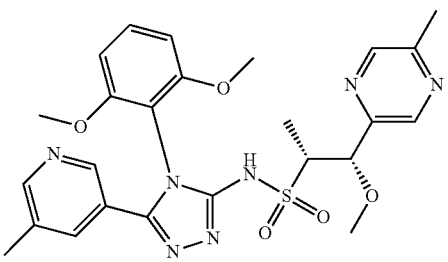

(1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide Example 572.0

The title compound was the second peak to elute by SFC using the conditions described in 571.0. $^1$H NMR (500 MHz, CD$_3$OD) δ 8.55 (s, 1H), 8.46 (s, 2H), 8.36 (s, 1H), 7.75 (s, 1H), 7.54 (dd, J=8.6, 8.6 Hz, 1H), 6.85 (d, J=8.4 Hz, 2H), 4.98 (d, J=3.1 Hz, 1H), 3.83 (s, 3H), 3.81 (s, 3H), 3.45-3.51 (m, 1H), 3.31 (s, 3H), 2.59 (s, 3H) 2.34 (s, 3H), 1.24 (d, J=6.8 Hz, 3H). MS ESI (pos.) m/z: 540.2 (M+H)$^+$. Preparative SFC: OX (5 um, 21 mm×25 cm, S/N=2121) with 50% organic modifier modifier: 50% carbon dioxide Organic modifier: EtOH without any ammonia.

Example 573.0: Preparation of (1R,2S)—N-(4-(2,6-(trimethoxyphenyl)-5-(6-methoxypyridin-2-yl)-4H-1,2,4-triazol-3-yl)-1-methoxy-1-(5-methylpyrazin-2-yl)propane-2-sulfonamide and (1S,2S)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide and (1R,2R)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide and (1S,2R)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide 572.0

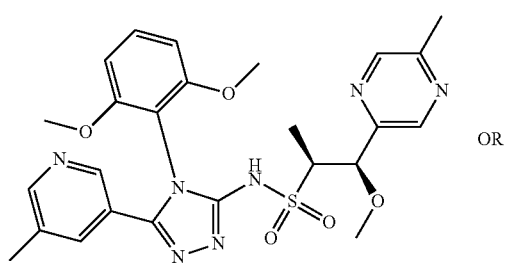

OR 573.0

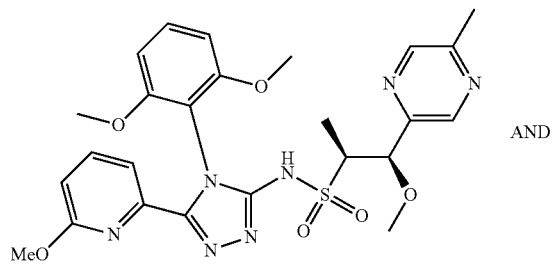

AND

-continued

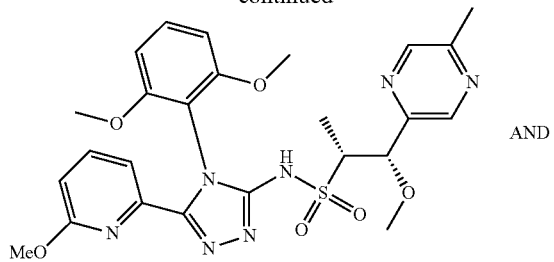

AND

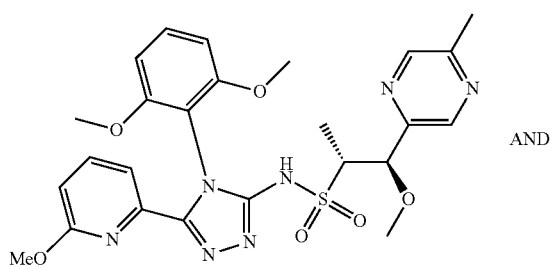

AND

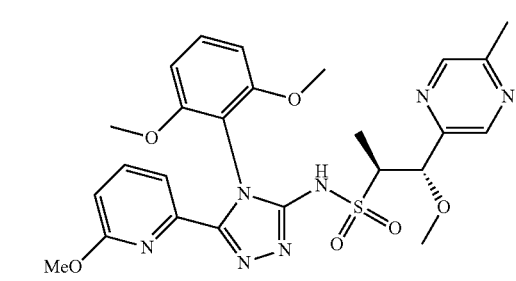

(1R,2S)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide and (1S,2S)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide and (1R,2R)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide and (1S,2R)—N-(4-(2,6-dimethoxyphenyl)-5-(6-methoxypyridin-2-yl)-4H-1,2,4-triazol-3-yl)-1-methoxy-1-(5-methylpyrazin-2-yl)propane-2-sulfonamide, Example 573.0

This compound was prepared following the procedure of Example A and employing 1.0, and the general procedures found in 564.3 and 6-methoxypicolinohydrazide. The reaction was purified via reverse phase HPLC (Agilent SB-C8 column, 30×250 mm, 5 μm, 10-95% water/ACN gradient over 25 min., with 0.1% TFA, flow rate 50 mL/min). Desired fractions were combined and lyophilized to give pure product.

Example 574.0: Preparation of (1R,2S)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide 574.0

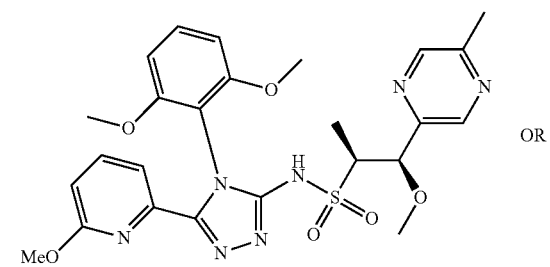

OR

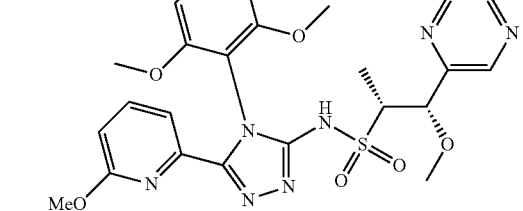

Final chiral separation was performed using SFC. Purification: Preparative SFC: OX (5 um, 21 mm×25 cm, S/N=2121) with 50% organic modifier modifier: 50% carbon dioxide. Organic modifier: EtOH without any ammonia. F=60 mL/min, T=40° C., BPR=100 bar, P=200 bar, 220 nm. All sample (~260 mg) dissolved in 8 mL MeOH/DCM (1/1, v/v), 32 mg/mL, 1.0 mL injection.

(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide Example 574.0

The title compound was the first peak to elute by SFC using the conditions described above. $^1$H NMR (500 MHz, CD$_3$OD) δ 8.55 (d, J=1.0 Hz, 1H), 8.43 (d, J=1.4 Hz, 1H), 7.75 (dd, J=7.8, 7.8 Hz, 1H), 7.65 (dd, J=7.4, 0.8 Hz, 1H), 7.45 (dd, J=8.5, 8.5 Hz, 1H), 6.77-6.82 (m, 3H), 4.95 (d, J=3.3 Hz, 1H), 3.77 (s, 3H), 3.76 (s, 3H), 3.45-3.51 (m, 1H), 3.30 (s, 3H), 3.21 (s, 3H), 2.59 (s, 3H), 1.19 (d, J=6.1 Hz, 3H). MS ESI (pos.) m/z: 556.3 (M+H)$^+$. OX (5 um, 21 mm×25 cm, S/N=2121) with 50% organic modifier modifier: 50% carbon dioxide. Organic modifier: EtOH without any ammonia.

Example 575.0: Preparation of (1R,2S)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide

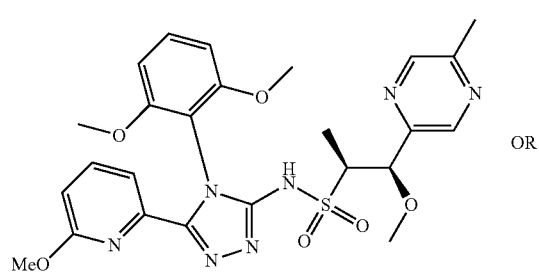

OR

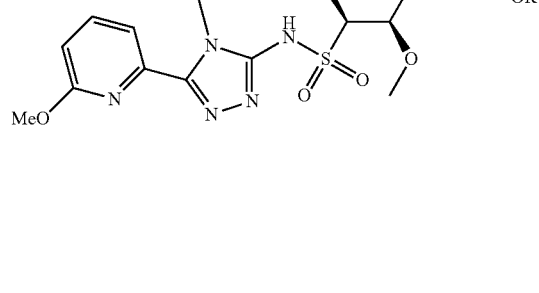

(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide Example 575.0

The title compound was the second peak to elute by SFC using the conditions described in 574.0. $^1$H NMR (500 MHz, CD$_3$OD) δ 8.55 (d, J=1 Hz, 1H), 8.43 (d, J=1.2 Hz, 1H), 7.75 (dd, J=8.2, 7.4 Hz, 1H), 7.66 (dd, J=7.4, 0.8 Hz, 1H), 7.45 (dd, J=8.5, 8.5 Hz, 1H), 6.77-6.82 (m, 3H), 4.95 (d, J=3.3 Hz, 1H), 3.77 (s, 3H), 3.76 (s, 3H), 3.44-3.51 (In, 1H), 3.30 (s, 3H), 3.21 (s, 3H), 2.59 (s, 3H), 1.19 (d, J=6.1 Hz, 3H). MS ESI (pos.) m/z: 556.3 (M+H)$^+$. OX (5 um, 21 mm×25 cm. S/N=2121) with 50% organic modifier modifier: 50% carbon dioxide. Organic modifier: EtOH without any ammonia.

Example 576.0: Preparation of (1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide and (1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide and (1R,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide and (1S,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide 576.0

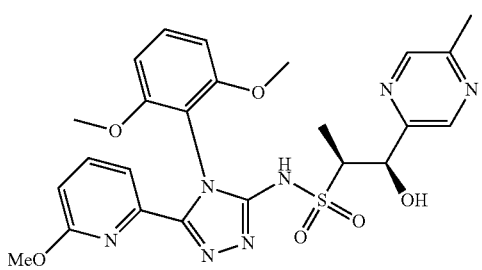

AND

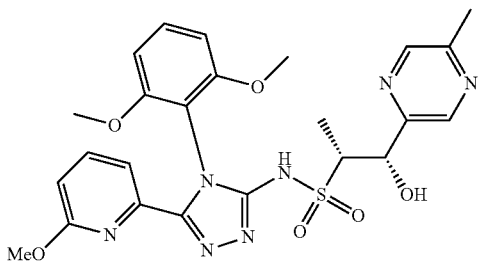

AND

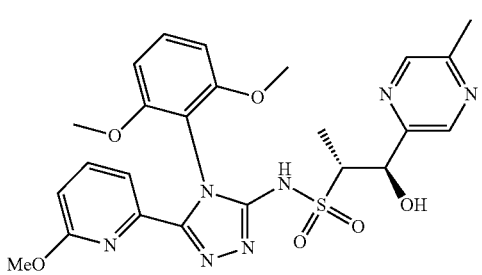

AND

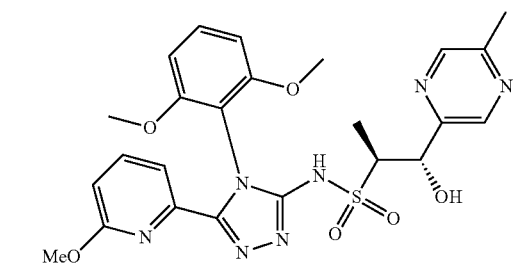

(1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide and (1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide and (1R,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide and (1S,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide, Example 576.0

The title compound was made following Example A employing 1.0 and the general procedures found in 564.3 and 6-methoxypicolinohydrazide. The reaction was purified via reverse phase HPLC (Agilent SB-C₈ column, 30×250 mm, 5 μm, 10-95% water/ACN gradient over 25 min., with 0.1% TFA, flow rate 50 mL/min). Desired fractions were combined and lyophilized to give pure product.

Example 577.0: Preparation of (1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide 577.0

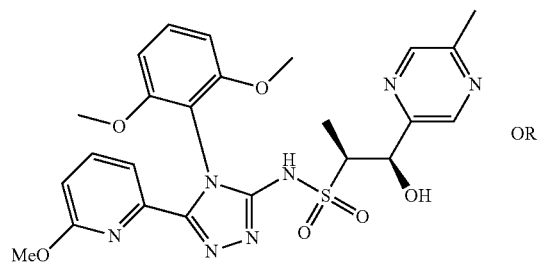

OR

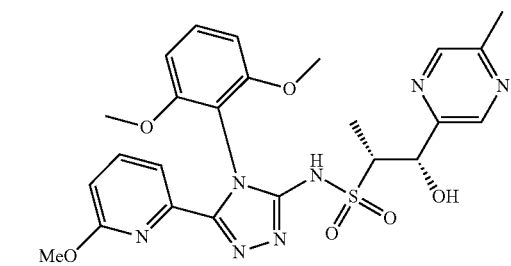

Final chiral separation was performed using SFC. Preparative SFC method: Column: Chiralpak AS-H (250×21 mm, 5 μm), Mobile Phase: 75:25 (CO₂: MeOH) Flow Rate: 70 mL/min, 220 nm, 32.2 mg/injection.

(1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide Example 577.0

The title compound was the first peak to elute by SFC using the conditions described above. ¹H NMR (500 MHz, CD₃OD) δ 8.57 (s, 1H), 8.51 (s, 1H), 7.75 (dd, J=7.8, 7.8 Hz, 1H), 7.66 (d, J=7.4 Hz, 1H), 7.47 (dd, J=8.5, 8.5 Hz, 1H), 6.77-6.84 (m, 3H), 5.40 (br s, 1H), 3.79 (s, 3H), 3.75 (s, 3H), 3.63-3.69 (m, 1H), 3.21 (s, 3H), 2.58 (s, 3H), 1.19 (d, J=7.0 Hz, 3H). MS ESI (pos.) m/z: 542.2 (M+H)⁺. SFC: Column: Chiralpak AS-H (250×21 mm, 5 μm), Mobile Phase: 75:25 (CO₂:MeOH).

Example 578.0: Preparation of (1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide 578.0

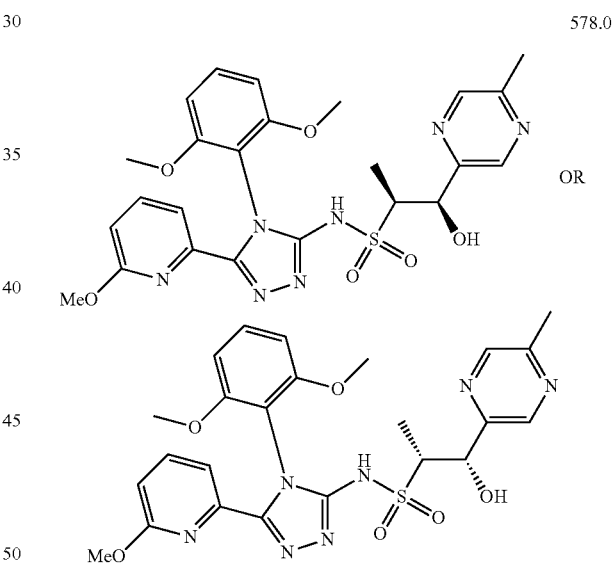

(1R,2S)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide or (1S,2R)—N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide Example 578.0

The title compound was the second peak to elute by SFC using the conditions described in 577.0. ¹H NMR (500 MHz, CD₃OD) δ 8.56 (s, 1H), 8.51 (s, 1H), 7.76 (dd, J=7.8, 7.8 Hz, 1H), 7.66 (d, J=7.4 Hz, 1H), 7.47 (dd, J=8.4, 8.4 Hz, 1H), 6.77-6.84 (m, 3H), 5.40 (br s, 1H), 3.79 (s, 3H), 3.75 (s, 3H), 3.63-3.69 (m, 1H), 3.21 (s, 3H), 2.58 (s, 3H), 1.18 (d, J=7.0

Hz, 3H). MS ESI (pos.) m/z: 542.2 (M+H)⁺. SFC: Column: Chiralpak AS-H (250×21 mm, 5 μm), Mobile Phase: 75:25 (CO₂:MeOH).

Example 579.0: Preparation of (1S,2R)—N-(4-(2,6-(trimethoxyphenyl)-5-(3-pyridinyl)-4H-1,2,4-triazol-3-yl)-1-methoxy-1-(5-methyl-2-pyrazinyl)-2-propanesulfonamide and (1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide and (1R,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide and (1S,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide 579.0

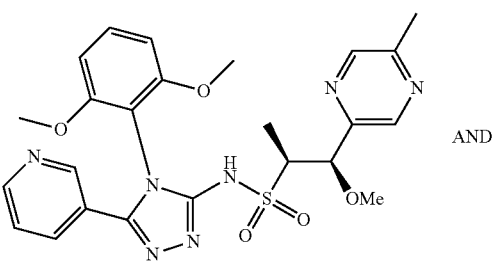
AND

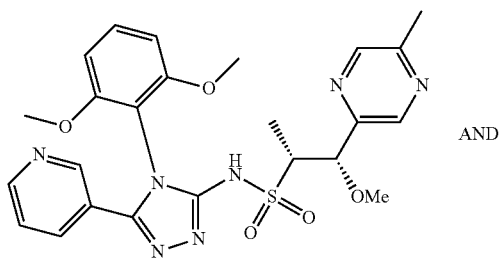
AND

AND

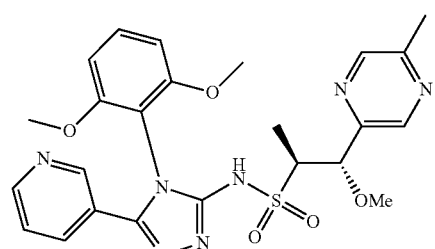

(1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide and (1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide and (1R,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide and (1S,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide, Example 579.0

The title compound was prepared following Example A employing 1.0 and the general procedures found in 564.3 and nicotinic hydrazide. The reaction was purified via reverse phase HPLC (Agilent SB-C₈ column, 30×250 mm, 5 μm, 10-95% water/ACN gradient over 25 min., with 0.1% TFA, flow rate 50 mL/min). Desired fractions were combined and lyophilized to give pure product.

Example 580.0: Preparation of (1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide and (1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide 580.0

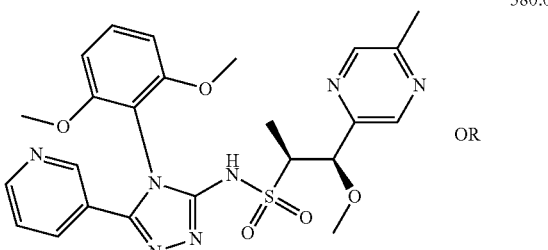
OR

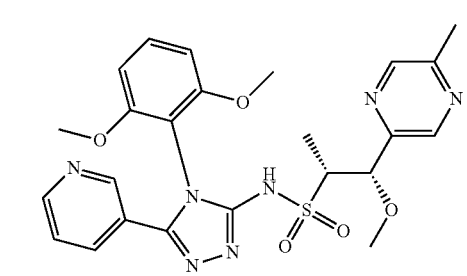

Final chiral separation was performed using SFC. Preparative SFC with 21×250 mm, 5 um OZ-H column. The mobile phase was 27 mL/min MeOH (neat)+33 g/min CO₂, 45% co-solvent at a total flowrate of 60 g/min (206 bar backpressure). Detection was performed by UV at 272 nm. The sample (344 mg) was dissolved in 30 mL MeOH (11.5 mg/mL) with an injection size of 1.8 mL (i.e. 20.7 mg/injection). Cycle time 7 min, run time 11 min.

(1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide Example 580.0

The title compound was the first peak to elute by SFC using the conditions described above. $^1$H NMR (500 MHz, CD$_3$OD) δ 8.62 (br s, 2H), 8.55 (s, 1H), 8.47 (s, 1H), 7.89 (d, J=8.0 Hz, 1H), 7.54 (dd, J=8.3, 8.3 Hz, 1H), 7.47 (dd, J=6.3, 6.3 Hz, 1H), 6.84 (d, J=8.6 Hz, 2H), 4.99 (d, J=3.1 Hz, 1H), 3.82 9s, 3H), 3.80 (s, 3H), 3.45-3.51 (m, 1H), 3.32 (s, 3H), 2.59 (s, 3H), 1.24 (d, J=6.6 Hz, 3H). MS ESI (pos.) m/z: 526.2 (M+H)$^+$. Preparative SFC with 21×250 mm, 5 um OZ-H column. The mobile phase was 27 mL/min MeOH (neat)+33 g/min CO$_2$, 45% co-solvent at a total flowrate of 60 g/min (206 bar backpressure).

Example 581.0: Preparation of (1S,2R)—N-(4-(2,6-(trimethoxyphenyl)-5-(3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide

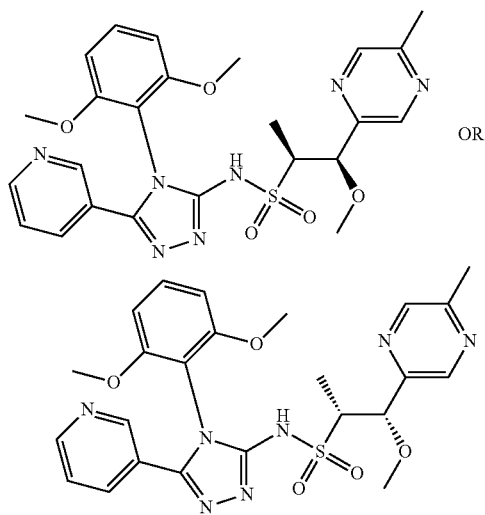

581.0

OR (1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide Example 581.0

The title compound was the second peak to elute by SFC using the conditions described in 580.0. $^1$H NMR (500 MHz, CD$_3$OD) δ 8.62 (br s, 2H), 8.55 (s, 1H), 8.46 (s, 1H), 7.88 (d, J=8.0 Hz, 1H), 7.69 (d, J=6.7 Hz, 1H), 7.54 (dd, J=8.5, 8.5 Hz, 1H), 7.42-7.48 (m, 2H), 6.84 (d, J=8.6 Hz, 2H), 4.99 (d, J=2.9 Hz, 1H), 3.82 (s, 3H), 3.80 (s, 3H), 3.45-3.51 (m, 1H), 3.31 (s, 3H), 2.59 (s, 3H), 1.24 (d, J=7.0 Hz, 3H). MS ESI (pos.) m/z: 526.1 (M+H)$^+$. Preparative SFC with 21×250 mm, 5 um OZ-H column. The mobile phase was 27 mL/min MeOH (neat)+33 g/min CO$_2$, 45% co-solvent at a total flow rate of 60 g/min (206 bar backpressure).

Example 582.0: Preparation of (1S,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide and (1R,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide

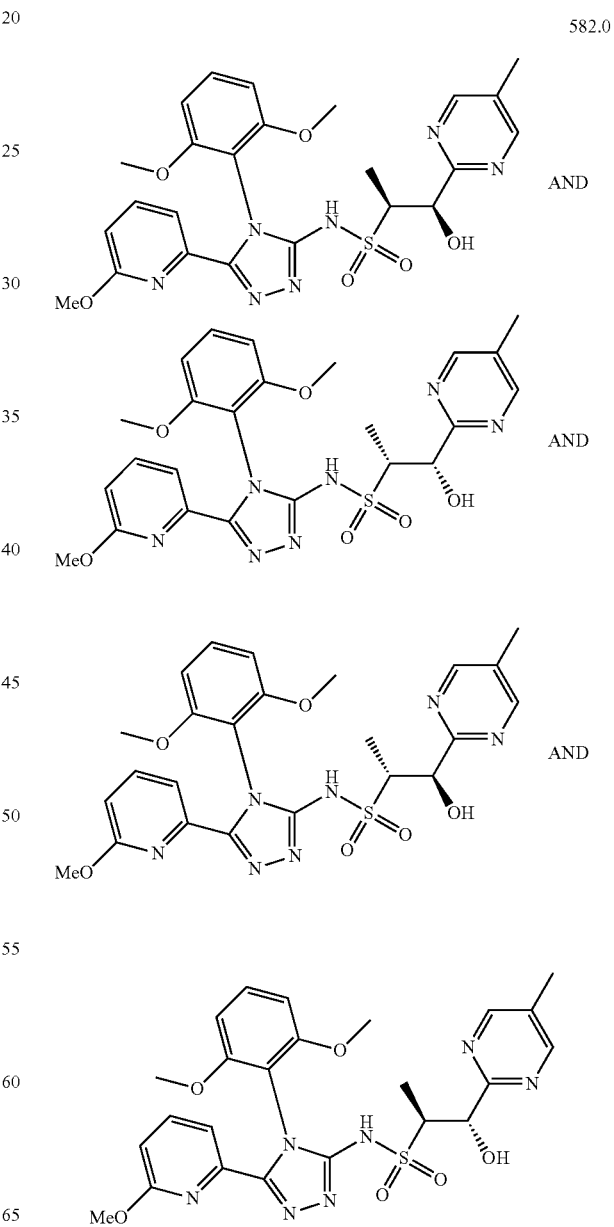

582.0

AND

AND

AND (1S,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide and (1R,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide, Example 582.0

The title compound was prepared following Example A employing 1.0, 11.0, and 6-methoxypicolinohydrazide. The reaction was purified via reverse phase HPLC (Phenomenex Gemini-C18 column, 30×250 mm, 10 µm, 10-95% water/ACN gradient over 25 min., with 0.1% TFA, flow rate 50 mL/min). Desired fractions were combined and lyophilized to give pure product.

Example 583.0: Preparation of (1S,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide or (1R,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide 583.0

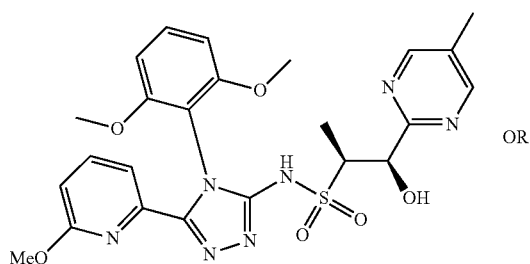

OR

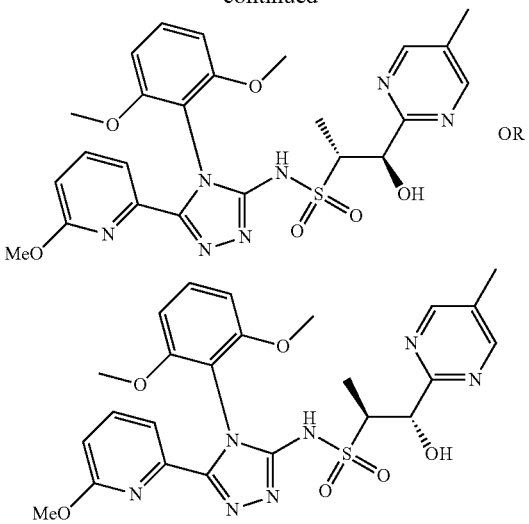

(1S,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide or (1R,2S)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide or (1R,2R)—N-(4-(2,6-dimethoxyphenyl)-5-(6-methoxypyridin-2-yl)-4H-1,2,4-triazol-3-yl)-1-hydroxy-1-(5-methylpyrimidin-2-yl)propane-2-sulfonamide Example 583.0

The mixture of compounds from Example 582.0 was separated using chiral separation conditions to provide Example 583.0. $^{1}$H NMR (500 MHz, CD$_{3}$OD) δ 8.67 (s, 2H), 7.75 (dd, J=7.9, 7.9 Hz, 1H), 7.65 (d, J=7.2 Hz, 1H), 7.44 (dd, J=8.5, 8.5 Hz, 1H), 6.77-6.79 (m, 3H), 5.44 (d, J=2.5 Hz, 1H), 3.76 (obscured m, 1H), 3.75 (s, 3H), 3.35 (s, 3H), 3.21 (s, 3H), 2.37 (s, 3H), 1.21 (d, J=6.8 Hz, 3H). MS ESI (pos.) m/z: 542.0 (M+H)$^{+}$.

Example 584.0: Preparation of (2S,3R)—N-(4-(2,6-dimethoxyphenyl)-5-(pyridin-3-yl)-4H-1,2,4-triazol-3-yl)-3-(5-methylpyrimidin-2-yl)butane-2-sulfonamide and (2R,3S)—N-(4-(2,6-dimethoxyphenyl)-5-(pyridin-3-yl)-4H-1,2,4-triazol-3-yl)-3-(5-methylpyrimidin-2-yl)butane-2-sulfonamide 584.0

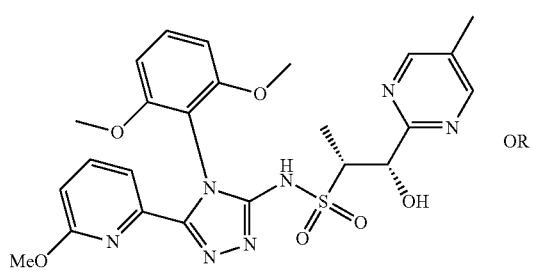

OR

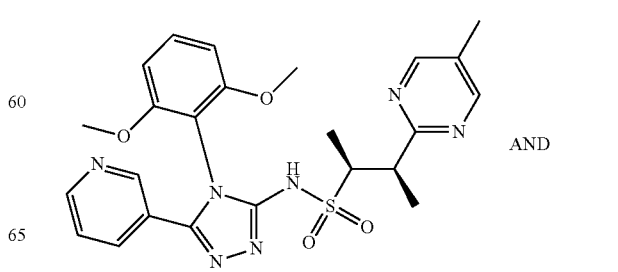

AND

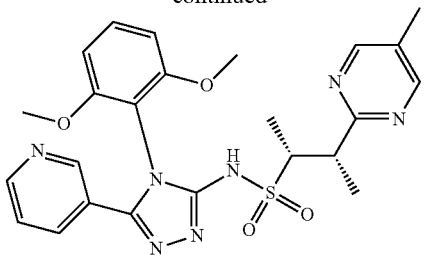

(2S,3R)—N-(4-(2,6-dimethoxyphenyl)-5-(pyridin-3-yl)-4H-1,2,4-triazol-3-yl)-3-(5-methylpyrimidin-2-yl)butane-2-sulfonamide and (2R,3S)—N-(4-(2,6-dimethoxyphenyl)-5-(pyridin-3-yl)-4H-1,2,4-triazol-3-yl)-3-(5-methylpyrimidin-2-yl)butane-2-sulfonamide, Example 584.0

The title compound was prepared following Example A employing 1.0, racemic 10.0 and nicotinic hydrazide. The reaction was purified via reverse phase HPLC (Agilent SB-C₈ column, 30×250 mm, 5 μm, 10-95% water/ACN gradient over 25 min., with 0.1% TFA, flow rate 50 mL/min). Desired fractions were combined and lyophilized to give pure product.

Example 585.0: Preparation of (2R,3S)—N-(4-(2,6-dimethoxyphenyl)-5-(3-pyridinyl)-4H-1,2,4-triazol-3-yl)-3-(5-methyl-2-pyrimidinyl)-2-butanesulfonamide

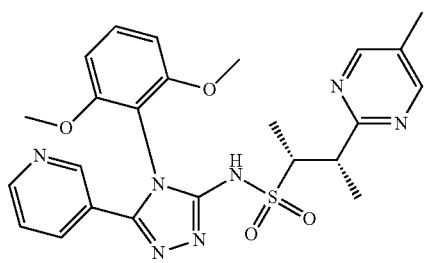

585.0

Final chiral separation was performed using SFC. Chiral separation of 344 mg of products performed on ATO DAS Berger MG2 "Robogram" preparative SFC with 21×250 mm, 5 um OZ-H column. The mobile phase was 27 mL/min MeOH (neat)+33 g/min CO₂, 45% co-solvent at a total flowrate of 60 g/min (206 bar backpressure). Detection was performed by UV at 272 nm. Sample (344 mg) was dissolved in 30 mL MeOH (11.5 mg/mL) with an injection size of 1.8 mL (i.e. 20.7 mg/injection). Cycle time 7 min, run time 11 min.

(2R,3S)—N-(4-(2,6-dimethoxyphenyl)-5-(3-pyridinyl)-4H-1,2,4-triazol-3-yl)-3-(5-methyl-2-pyrimidinyl)-2-butanesulfonamide Example 585.0

The title compound was the first peak to elute by SFC using the conditions described above. ¹H NMR (500 MHz, CDCl₃) δ 11.4 (br. s, 1H), 8.63 (br s, 2H), 8.56 (s, 2H), 7.78 (d, J=7.8 Hz, 1H), 7.39 (dd, J=8.5, 8.5 Hz, 1H), 7.28 (obscured m, 1H), 6.6 (ddd, J=7.8, 7.8 Hz, 2H), 3.88-3.94 (m, 1H), 3.74-3.81 (obscured m, 1H), 3.74 (s, 3H), 2.30 (s, 3H), 1.39 (d, J=7.2 Hz, 3H), 1.37 (d, J=7.0 Hz, 3H). MS ESI (pos.) m/z: 510 (M+H)⁺. Preparative SFC with 21×250 mm, 5 um OZ-H column. The mobile phase was 27 mL/min MeOH (neat)+33 g/min CO₂, 45% co-solvent at a total flowrate of 60 g/min (206 bar backpressure).

Example 586.0: Preparation of (2S,3R)—N-(4-(2,6-dimethoxyphenyl)-5-(3-pyridinyl)-4H-1,2,4-triazol-3-yl)-3-(5-methyl-2-pyrimidinyl)-2-butanesulfonamide

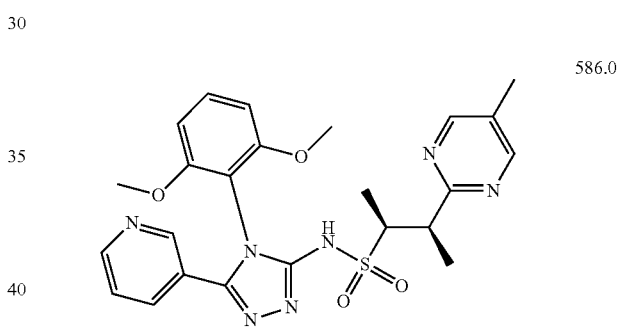

586.0

(2S,3R)—N-(4-(2,6-dimethoxyphenyl)-5-(3-pyridinyl)-4H-1,2,4-triazol-3-yl)-3-(5-methyl-2-pyrimidinyl)-2-butanesulfonamide Example 586.0

The title compound was the second peak to elute by SFC using the conditions described in 585.0. ¹H NMR (500 MHz, CDCl₃) δ 11.38 (br s, 1H), 8.63 (br s, 2H), 8.54 (s, 2H), 7.76 (d, J=8.0 Hz, 1H), 7.38 (dd, J=8.5, 8.5 Hz, 1H), 7.28 (obscured m, 1H), 6.6 (dd, J=7.8, 7.8 Hz, 2H), 3.87-3.94 (m, 1H), 3.74-3.81 (m, 1H), 3.74 (s, 3H), 3.71 (s, 3H), 2.30 (s, 3H), 1.39 (d, J=7.0 Hz, 3H), 1.36 (d, J=7.0 Hz, 3H). MS ESI (pos.) m/z: 510 (M+H)⁺. Preparative SFC with 21×250 mm, 5 um OZ-H column. The mobile phase was 27 mL/min MeOH (neat)+33 g/min CO₂, 45% co-solvent at a total flowrate of 60 g/min (206 bar backpressure). Peak 2.

Example 587.0: Preparation of (1R,2S)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide and (1S,2S)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide and (1R,2R)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide and (1S,2R)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide 587.0

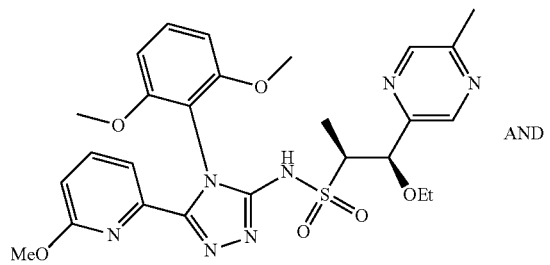

AND

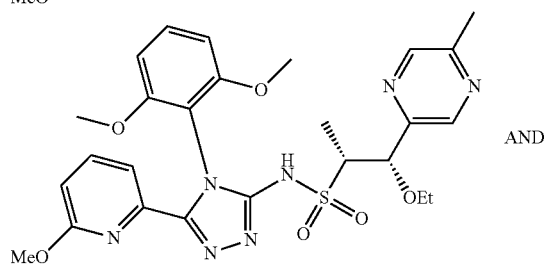

AND

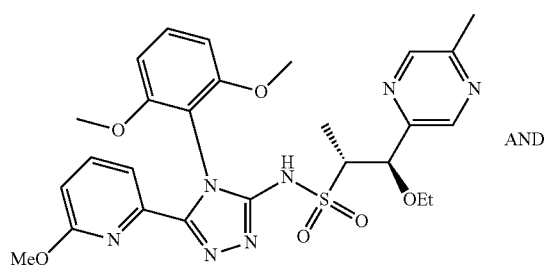

AND

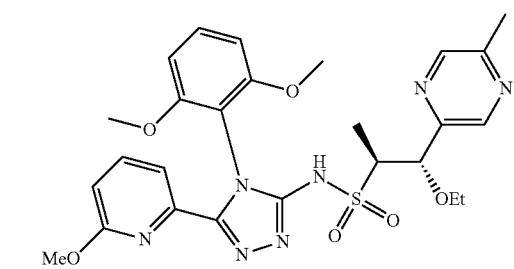

(1R,2S)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide and (1S,2S)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide and (1R,2R)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide and (1S,2R)—N-(4-(2,6-dimethoxyphenyl)-5-(6-methoxypyridin-2-yl)-4H-1,2,4-triazol-3-yl)-1-ethoxy-1-(5-methylpyrazin-2-yl)propane-2-sulfonamide, Example 587.0

The title compound was prepared following Example A employing 1.0, 564.3 and 6-methoxypicolinohydrazide. The reaction was purified via reverse phase HPLC (Agilent SB-C$_8$ column, 30×250 mm, 5 μm, 10-95% water/ACN gradient over 25 min., with 0.1% TFA, flow rate 50 mL/min). Desired fractions were combined and lyophilized to give pure product.

Example 588.0: Preparation of (1S,2R)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide

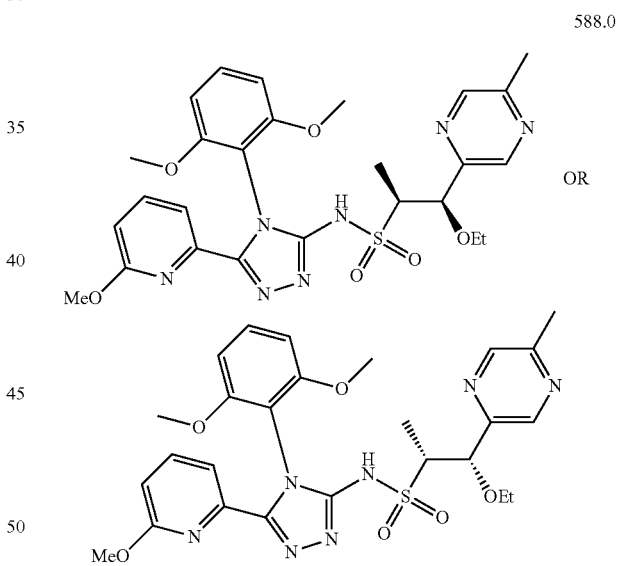

588.0

Final chiral separation was performed using SFC. Preparative SFC method: Column: OZ-H (250×21 mm, 5 μm), Mobile Phase: 65:35 (CO$_2$:MeOH); Flow Rate: 70 mL/min; 220 nm; 200-206 bar inlet pressure.

(1S,2R)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide Example 588.0

The title compound was the first peak to elute by SFC using the conditions described above. $^1$H NMR (500 MHz, CDCl$_3$) δ 8.52 (s, 1H), 8.44 (s, 1H), 7.58-7.63 (m, 2H), 7.31 (dd, J=8.4, 8.4 Hz, 1H), 6.7 (dd, J=7.6, 1.5 Hz, 1H), 6.6 (d, J=8.3 Hz, 2H), 5.1 (d, J=3.4 Hz, 1H), 3.70 (s, 3H), 3.68 (s, 3H), 3.46-3.56 (m, 3H), 3.16 (s, 3H), 2.58 (s, 3H), 1.27 (d, J=6.8 Hz, 3H), 1.14 (dd, J=6.8, 6.8 Hz, 3H). MS ESI (pos.) m/z: 569.9 (M+H)$^+$. Preparative SFC method: Column: OZ-H (250×21 mm, 5 μm), Mobile Phase: 65:35 (CO$_2$:MeOH); Flow Rate: 70 mL/min.

Example 589.0: Preparation of (1S,2R)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide 589.0

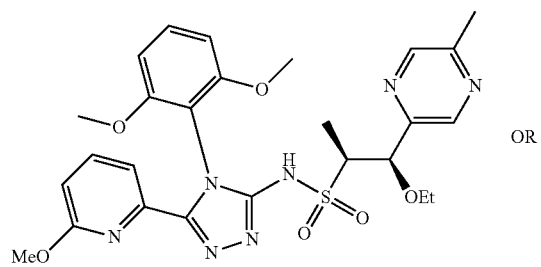

OR

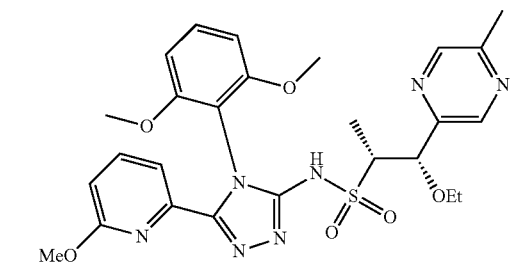

(1S,2R)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide, Example 589.0

The title compound was the second peak to elute by SFC using the conditions described in 588.0. $^1$H NMR (500 MHz, CDCl$_3$) δ 11.07 (br s, 1H), 8.52 (s, 1H), 8.45 (s, 1H), 7.56-7.63 (m, 2H), 7.32 (dd, J=8.4, 8.4 Hz, 1H), 6.7 (dd, J=7.8, 1.2 Hz, 1H), 6.6 (d, J=8.6 Hz, 2H), 5.1 (d, J=3.4 Hz, 1H), 3.70 (s, 3H), 3.69 (s, 3H), 3.47-3.59 (m, 3H), 3.16 (s, 3H), 2.59 (s, 3H), 1.28 (d, J=7.1 Hz, 3H), 1.14 (dd, J=7.0, 7.0 Hz, 3H). (M+H)$^+$ m/z: 569.9 (M+H)$^+$. Preparative SFC method: Column: OZ-H (250×21 mm, 5 μm), Mobile Phase: 65:35 (CO$_2$:MeOH); Flow Rate: 70 mL/min.

Example 590.0: Preparation of (1S,2S)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide and (1S,2R)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide and (1R,2S)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide and (1R,2R)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide 590.0

AND

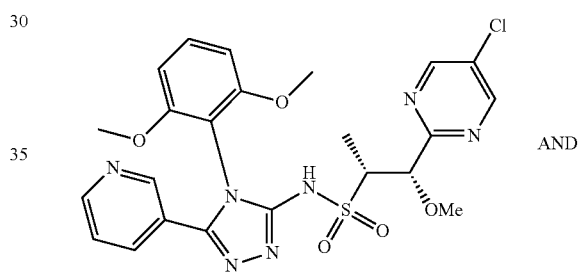

AND

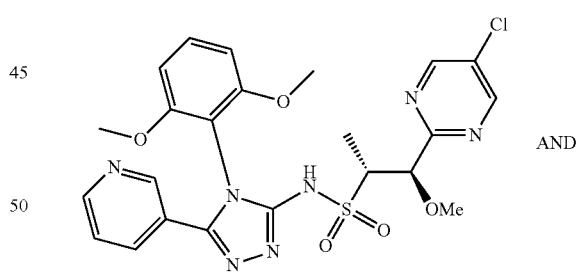

AND

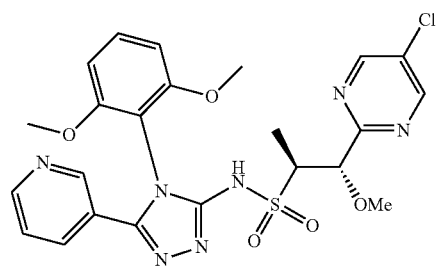

(1S,2S)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide and (1S,2R)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide and (1R,2S)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide and (1R,2R)-1-(5-chloropyrimidin-2-yl)-N-(4-(2,6-dimethoxyphenyl)-5-(pyridin-3-yl)-4H-1,2,4-triazol-3-yl)-1-methoxypropane-2-sulfonamide, Example 590.0

The title compound was prepared following Example A employing 1.0, racemic 14.3 (prepared using Example C) and nicotinic hydrazide. The reaction was purified via reverse phase HPLC (Phenomenex Gemini-C18 column, 30×250 mm, 10 μm, 10-95% water/ACN gradient over 25 min., with 0.1% TFA, flow rate 50 mL/min). Desired fractions were combined and lyophilized to give pure product.

Example 591.0: Preparation of (1R,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide

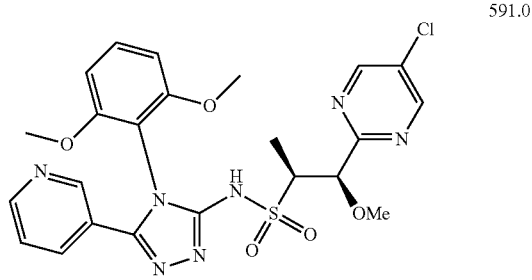 [SMILES: COc1cccc(OC)c1-n1c(NS(=O)(=O)[C@@H](C)[C@H](OC)c2ncc(Cl)cn2)nnc1-c1cccnc1]

591.0

(1R,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide Example 591.0

Final chiral separation was performed using SFC. Preparative SFC 2 stages. Method 1: Column: CC4-NT Mobile Phase: 60:40 ($CO_2$:MeOH); Method 2: Column: AS; Mobile Phase: 85:15 ($CO_2$:MeOH).

The title compound was the first peak (stage 1) to elute by SFC using the conditions described above. $^1$H NMR (500 MHz, CDCl$_3$) δ 11.19 (br s, 1H), 8.72 (s, 2H), 8.64 (br s, 2H), 7.79 (d, J=8.1 Hz, 1H), 7.40 (dd, J=8.6, 8.6 Hz, 1H), 7.32 (br s, 1H), 6.61 (d, J=8.1 Hz, 2H), 4.97 (d, J=4.9 Hz, 1H), 3.75 (s, 3H), 3.72 (br s, 3H), 3.71 (obscured m, 1H), 3.34 (s, 3H), 1.38 (d, J=6.8 Hz, 3H). MS ESI (pos.) m/z: 545.8 (M+H)$^+$. SFC: Method 1: Column: CC4-NT Mobile Phase: 60:40 ($CO_2$:MeOH); Method 2: Column. AS; Mobile Phase: 85:15 ($CO_2$:MeOH).

Example 592.0: Preparation of (1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide

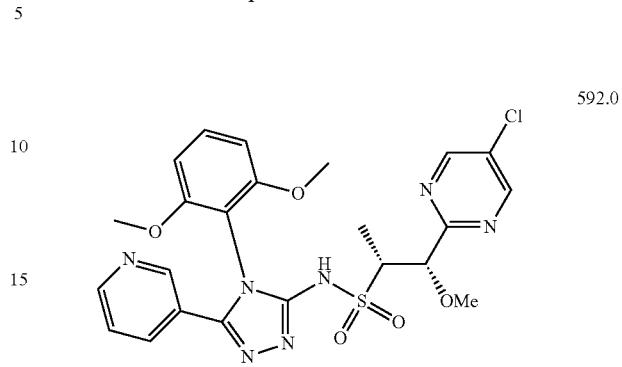

592.0

(1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide Example 592.0

The title compound was the first peak (stage 2) to elute by SFC using the conditions described in 591.0. $^1$H NMR (500 MHz, CDCl$_3$) δ 8.72 (s, 2H), 8.62 (br s, 2H), 7.76 (d, J=7.9 Hz, 1H), 7.40 (dd, J=8.4, 8.4 Hz, 1H), 7.29 (obscured m, 1H), 6.61 (m, 2H), 4.97 (d, J=4.6 Hz, 1H), 3.75 (s, 3H), 3.72 (s, 3H), 3.71 (obscured m, 1H), 3.34 (s, 3H), 1.38 (d, J=6.8 Hz, 3H). MS ESI (pos.) m/z: 545.9 (M+H)$^+$. SFC: Method 1: Column: CC4-NT Mobile Phase: 60:40 ($CO_2$:MeOH); Method 2: Column: AS; Mobile Phase: 85:15 ($CO_2$:MeOH).

Example 593.0: Preparation of (1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide

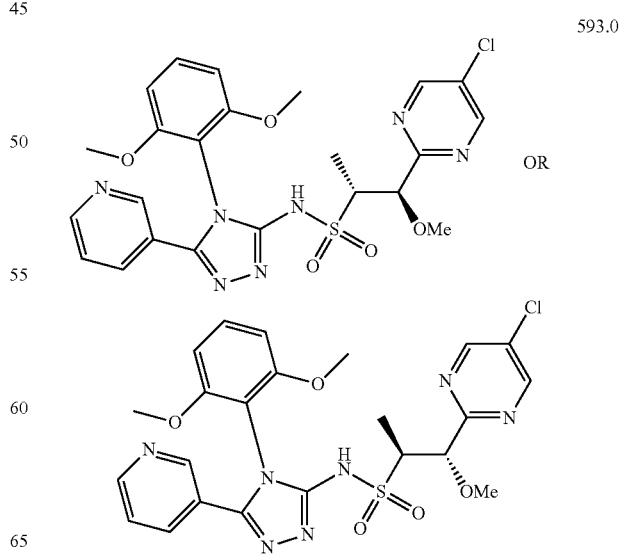

593.0

(1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide Example 593.0

The title compound was the second peak (stage 2) to elute by SFC using the conditions described in 591.0. $^1$H NMR (500 MHz, CDCl$_3$) δ 11.43 (br s, 1H), 8.74 (s, 2H), 8.63 (br s, 2H), 7.78 (d, J=7.1 Hz, 1H), 0.40 (dd, J=8.4, 8.4 Hz, 1H), 7.30 (br s, 1H), 6.63 (d, J=8.6 Hz, 1H), 6.61 (d, J=8.3 Hz, 1H), 4.77 (d, J=6.6 Hz, 1H), 3.80 (s, 3H), 3.77 (obscured m, 1H), 3.72 (s, 3H), 3.26 (s, 3H), 1.25 (d, J=7.1 Hz, 3H). MS ESI (pos.) m/z: 545.9 (M+H)$^+$. SFC: Method 1: Column: CC4-NT Mobile Phase: 60:40 (CO$_2$:MeOH); Method 2: Column: AS; Mobile Phase: 85:15 (CO$_2$:MeOH).

Example 594.0: Preparation of (1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide or (1R,2R)-1-(5-chloro-2-pyrimidinyl)-N-(4-(2,6-(trimethoxyphenyl)-5-(3-pyridinyl)-4H-1,2,4-triazol-3-yl)-1-methoxy-2-propanesulfonamide

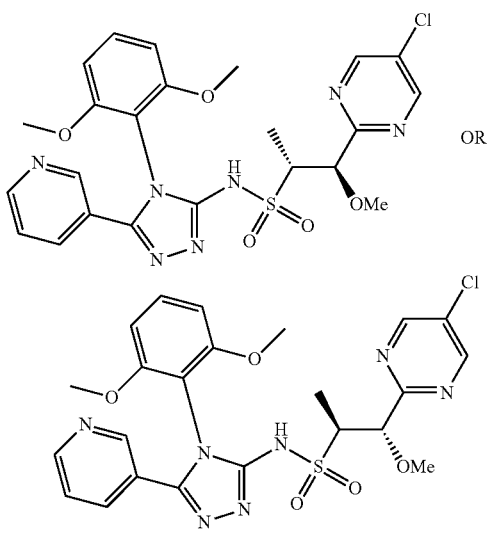

(1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide Example 594.0

The title compound was the third peak (stage 1) to elute by SFC using the conditions described in 591.0. $^1$H NMR (500 MHz, CDCl$_3$) δ 8.75 (s, 2H), 8.70 (br s, 2H), 811 (d, J=7.6 Hz, 1H), 7.59 (br s, 1H), 7.45 (dd, J=8.6, 8.6 Hz, 1H), 6.64-6.68 (m, 2H), 4.75 (d, J=6.4 Hz, 1H), 3.83 (s, 3H), 3.79 (obscured m, 1H), 3.76 (s, 3H), 3.26 (s, 3H), 1.27 (d, J=7.1 Hz, 3H). MS ESI (pos.) m/z: 545.8.0 (M+H)$^+$. SFC purification 2 stages: Stage 1, 40% MeOH; CC4-NT. Stage 2, AS; 15% IPA.

Example 595.0: Preparation of (1S,2S)-1-(5-chloro-pyrimidin-2-yl)-N-(4-(2,6-dimethoxyphenyl)-5-(6-methoxypyridin-2-yl)-4H-1,2,4-triazol-3-yl)-1-methoxypropane-2-sulfonamide and (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide and (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide and (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide

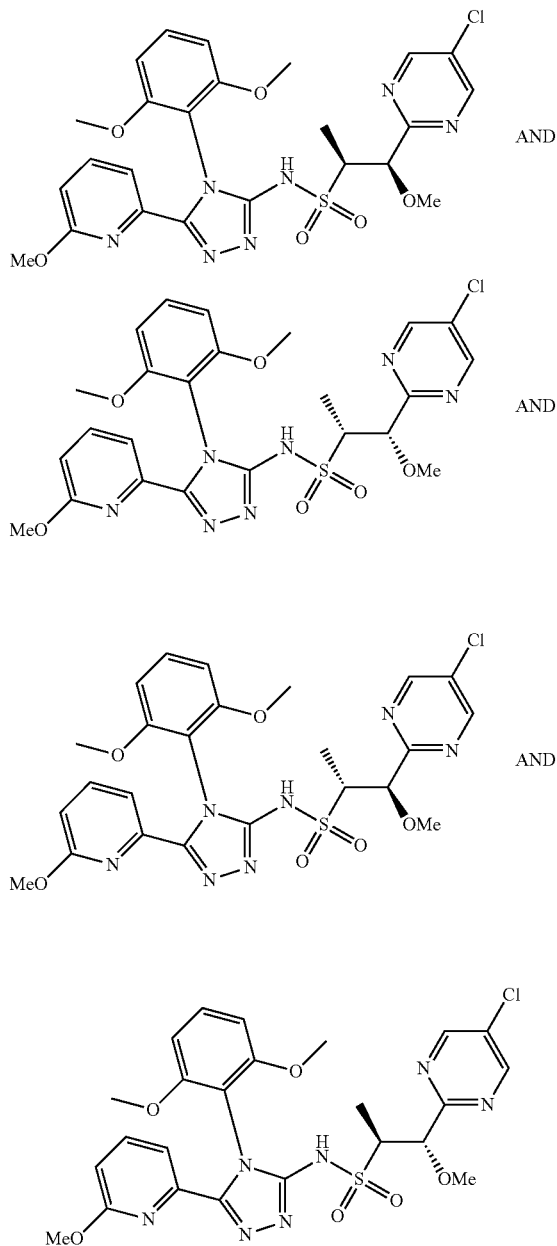

(1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide and (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide and (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide and (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide, Example 595.0

The title compound was prepared following Example A employing 1.0, racemic 14.3 (prepared using Example C) and 6-methoxypicolinohydrazide to provide the desired product. The reaction was purified via reverse phase HPLC (Phenomenex Gemini-C18 column, 30×250 mm, 10 μm. 10-95% water/ACN gradient over 25 min., with 0.1% TFA, flow rate 50 mL/min). Desired fractions were combined and lyophilized to give pure product.

Example 596.0: Preparation of (1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide 596.0

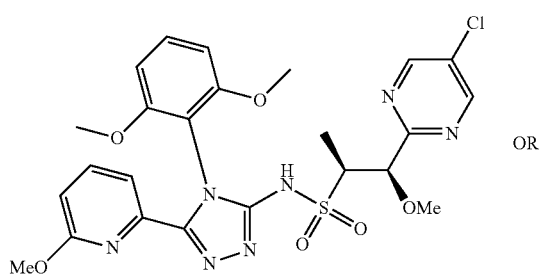

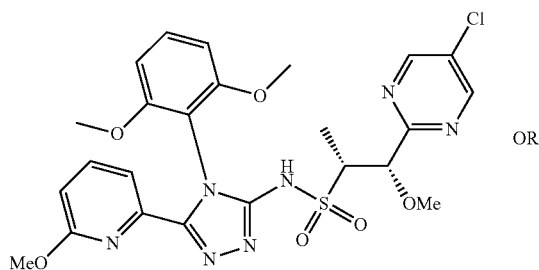

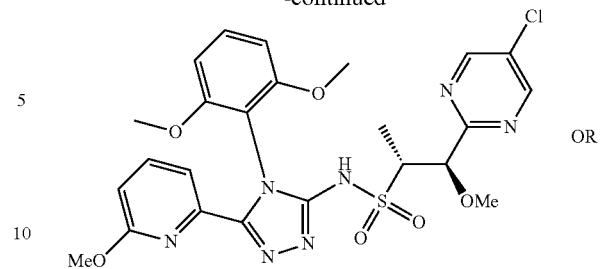

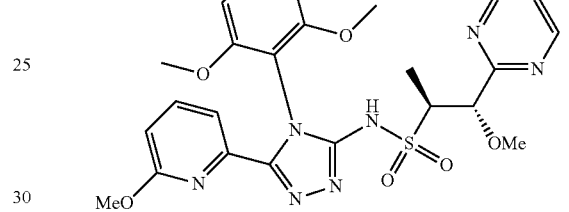

Final chiral separation was performed using SFC. Preparative separation conditions for 595.0 (107 mg): Run on Thar 200 with 250×30 mm CC4 column using 88 g/min CO₂ and 42 g/min MeOH (neat), 35% co-solvent at 130 g/min. Temperature 39° C., pressure 100 bar, wavelength 297 nm. 107 mg of sample was dissolved in 12 mL of MeOH:DCM (2/1, v/v), c=8.9 mg/mL. Injected 0.7 mL solution, 6.2 mg/injection. Cycle time 11 min., run time 25 min.

(1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide Example 596.0

The title compound was the first peak to elute by SFC using the conditions described above. $^1$H NMR (500 MHz, CDCl$_3$) δ 8.72 (s, 2H), 7.58-7.64 (m, 2H), 7.32 (dd, J=8.4, 8.4 Hz, 1H), 6.7 (dd, J=7.8, 1.2 Hz, 1H), 6.6 (d, J=8.6 Hz, 2H), 4.97 (d, J=4.9 Hz, 1H), 3.72 (obscured m, 1H), 3.71 (s, 3H), 3.69 (s, 3H), 3.34 (s, 3H), 3.16 (s, 3H), 1.38 (d, J=7.1 Hz, 3H). MS ESI (pos.) m/z: 576.0 (M+H)$^+$. SFC: 250×30 mm CC4 column using 88 g/min CO$_2$ and 42 g/min MeOH (neat), 35% co-solvent at 130 g/min. Temperature 39° C., pressure 100 bar, wavelength 297 nm.

Example 597.0: Preparation of (1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide

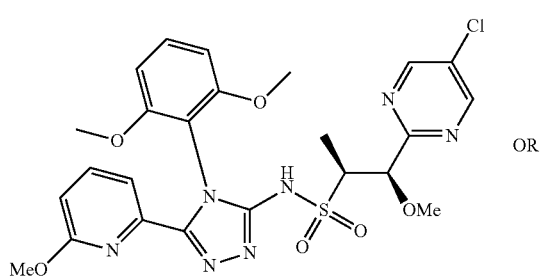

597.0

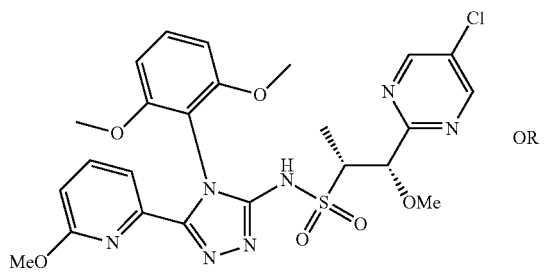

OR

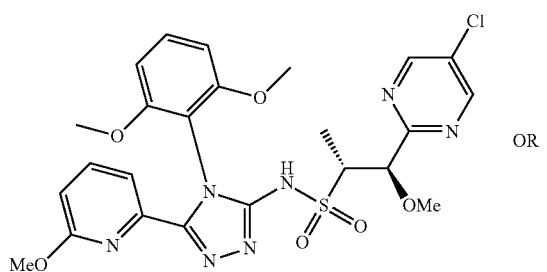

OR

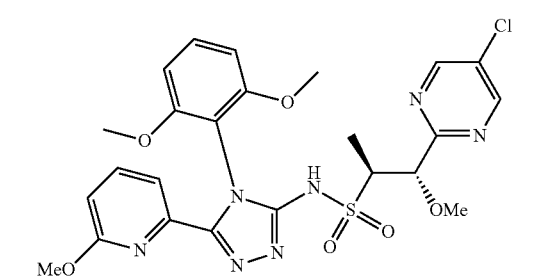

OR (1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide Example 597.0

The title compound was the second peak to elute by SFC using the conditions described in Example 596.0. $^1$H NMR (500 MHz, CDCl$_3$) δ 8.72 (s, 2H), 7.58-7.64 (m, 2H), 7.31 (dd, J=8.6, 8.6 Hz, 1H), 6.7 (dd, J=7.8, 1.5 Hz, 1H), 6.6 (d, J=8.6 Hz, 2H), 4.97 (d, J=4.9 Hz, 1H), 3.73 (obscured in, 1H), 3.71 (s, 3H), 3.69 (s, 3H), 3.34 (s, 3H), 3.16 (s, 3H), 1.39 (d, J=7.1 Hz, 3H). MS ESI (pos.) m/z: 575.8 (M+H)$^+$. SFC: 250×30 mm CC4 column using 88 g/min CO$_2$ and 42 g/min MeOH (neat), 35% co-solvent at 130 g/min. Temperature 39° C., pressure 100 bar, wavelength 297 nm.

Example 598.0: Preparation of (1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide

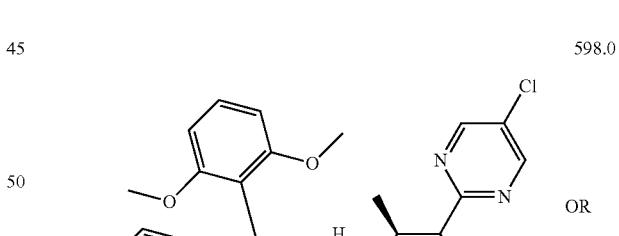

598.0

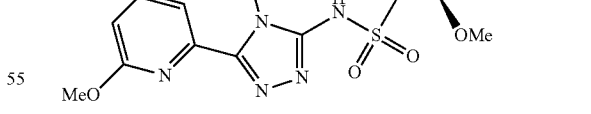

OR

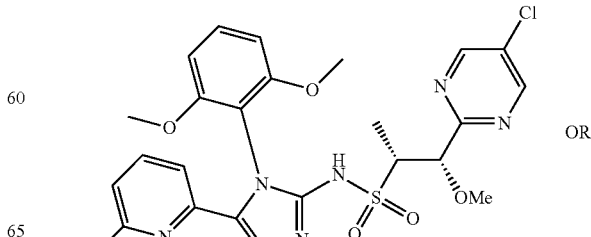

OR

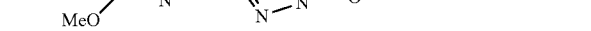

-continued

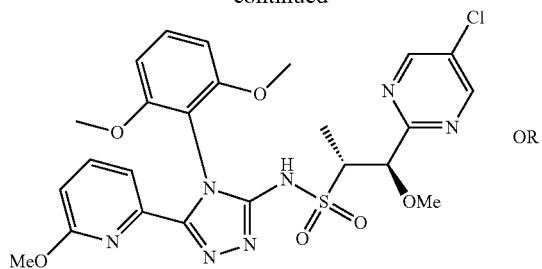

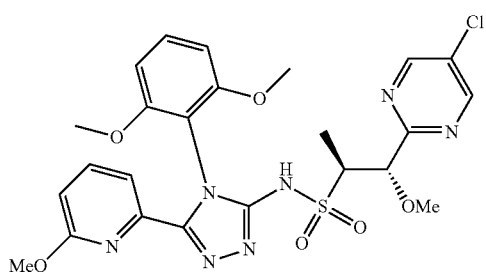

(1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide
Example 598.0

The title compound was the third peak to elute by SFC using the conditions described in Example 596.0. $^1$H NMR (500 MHz, CDCl$_3$) δ 8.75 (s, 2H), 7.58-7.64 (m, 2H), 7.32 (dd, J=8.4, 8.4 Hz, 1H), 6.70 (dd, J=7.6, 1.2 Hz, 1H), 6.59-6.62 (m, 2H), 4.78 (d, J=6.4 Hz, 1H), 3.79 (obscured m, 1H), 3.77 (s, 3H), 3.69 (s, 3H), 3.26 (s, 3H), 3.17 (s, 3H), 1.25 (d, J=7.1 Hz, 3H). MS ESI (pos.) m/z: 575.9 (M+H)$^+$. Preparative separation conditions 250×30 mm CC4 column using 88 g/min CO$_2$ and 42 g/min MeOH (neat), 35% co-solvent at 130 g/min. Temperature 39° C., pressure 100 bar, wavelength 297 nm.

Example 599.0: Preparation of (1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-(trimethoxyphenyl)-5-(6-methoxypyridin-2-yl)-4H-1,2,4-triazol-3-yl)-1-methoxypropane-2-sulfonamide 599.0

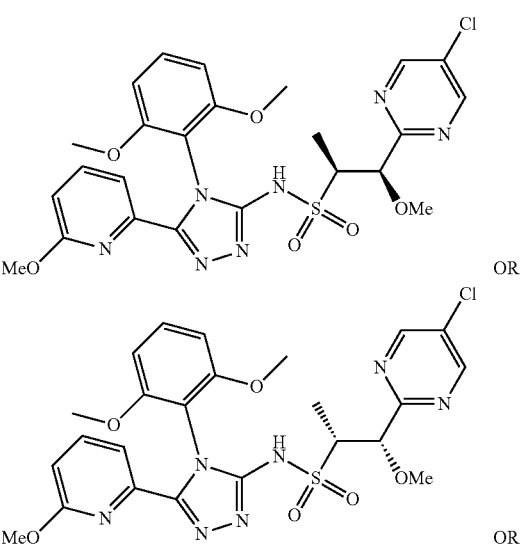

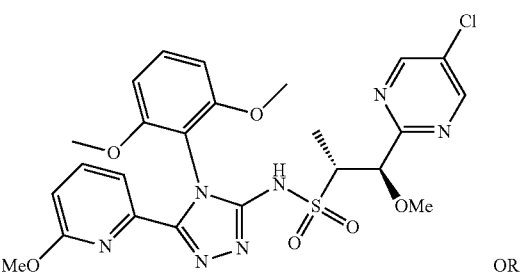

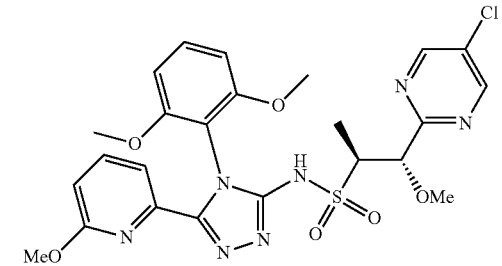

(1S,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1S,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide or (1R,2R)-1-(5-chloropyrimidin-2-yl)-N-(4-(2,6-dimethoxyphenyl)-5-(6-methoxypyridin-2-yl)-4H-1,2,4-triazol-3-yl)-1-methoxypropane-2-sulfonamide Example 599.0

The title compound was the fourth peak to elute by SFC using the conditions described in Example 596.0. $^1$H NMR (500 MHz, CDCl$_3$) δ 8.75 (s, 2H), 7.58-7.63 (m, 2H), 7.32 (dd, J=8.6, 8.6 Hz, 1H), 6.7 (dd, J=7.6, 1.5 Hz, 1H), 6.59-6.62 (m, 2H), 4.78 (d, J=6.4 Hz, 1H), 3.76 (obscured m, 1H), 3.77 (s, 3H), 3.69 (s, 3H), 3.25 (s, 3H), 3.17 (s, 3H), 1.25 (d, J=7.1 Hz, 3H). MS ESI (pos.) m/z: 575.9 (M+H)$^+$. Preparative separation conditions 250×30 mm CC4 column using 88 g/min CO$_2$ and 42 g/min MeOH (neat), 35% co-solvent at 130 g/min. Temperature 39° C., pressure 100 bar, wavelength 297 nm.

Example 600.0: Preparation of (1R,2S)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide and (1S,2S)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide and (1R,2R)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide and (1S,2R)—N+1-(2,6-dimethoxyphenyl)-5-(pyridin-3-yl)-4H-1,2,4-triazol-3-yl)-1-ethoxy-1-(5-methylpyrazin-2-yl)propane-2-sulfonamide 600.0

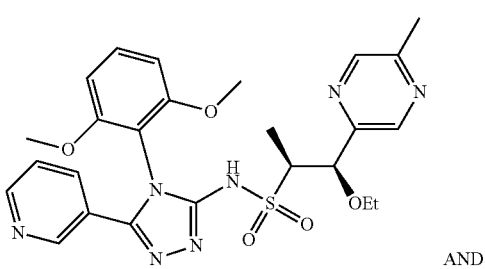

AND

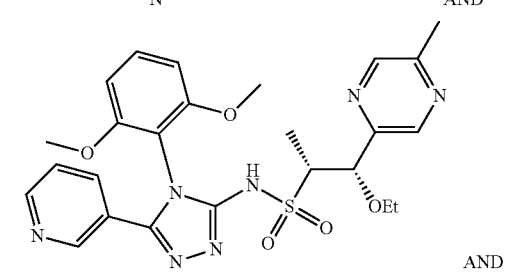

AND

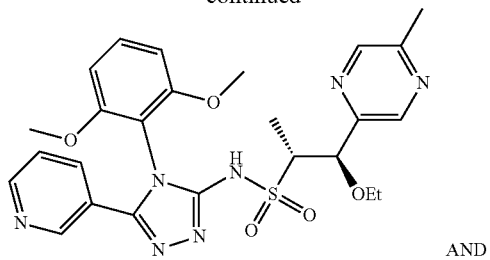

AND

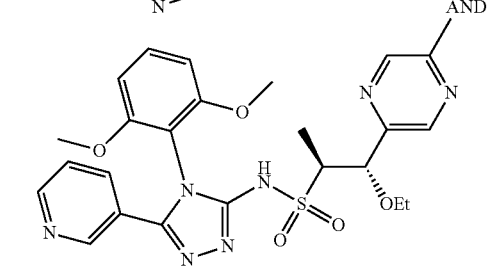

(1R,2S)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide and (1S,2S)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide and (1R,2R)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide and (1S,2R)—N-(4-(2,6-dimethoxyphenyl)-5-(pyridin-3-yl)-4H-1,2,4-triazol-3-yl)-1-ethoxy-1-(5-methylpyrazin-2-yl)propane-2-sulfonamide, Example 600.0

The title compound was prepared following Example A employing 1.0, 564.3 and nicotinic hydrazide. The reaction was purified via reverse phase HPLC (Agilent SB-C$_8$ column, 30×250 mm, 5 μm, 10-95% water/ACN gradient over 25 min, with 0.1% TFA, flow rate 50 mL/min). Desired fractions were combined and lyophilized to give pure product.

Example 601.0: Preparation of (1S,2R)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide 601.0

[structure]

OR

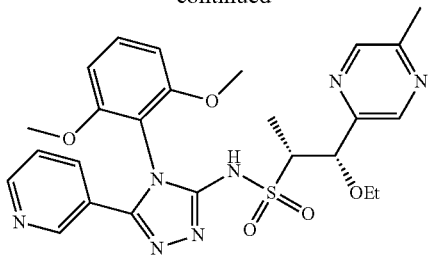

Final chiral separation was performed using SFC. Preparative SFC method: Column: Chiralcel OX-H (250×21 mm, 5 μm) Mobile Phase: 60:40 (CO₂: MeOH); Flow Rate: 70 mL/min; 220 nm; 200 bar inlet pressure.

(1S,2R)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide Example 601.0

The title compound was the first peak to elute by SFC using the conditions described above. ¹H NMR (500 MHz, CDCl₃) δ 11.19 (br s, 1H), 8.62 (br s, 2H), 8.54 (s, 1H), 8.42 (s, 1H), 7.75 (ddd, J=8.1, 1.2, 1.2 Hz, 1H), 7.39 (dd, J=8.4, 8.4 Hz, 1H), 7.28 (obscured m, 1H), 6.6 (d, J=8.6 Hz, 2H), 5.13 (d, J=3.2 Hz, 1H), 3.73 (s, 3H), 3.71 (s, 3H), 3.47-3.59 (m, 3H), 2.57 (s, 3H), 1.27 (d, J=7.1 Hz, 3H), 1.14 (dd, J=7.1, 7.1 Hz, 3H). MS ESI (pos.) m/z: 540.0 (M+H)⁺. Preparative SFC method: Column: Chiralcel OX-H (250×21 mm, 5 μm) Mobile Phase: 60:40 (CO₂:MeOH); Flow Rate: 70 mL/min; peak 1.

Example 602.0: Preparation of (1S,2R)—N-(4-(2,6-(trimethoxyphenyl)-5-(3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide 602.0

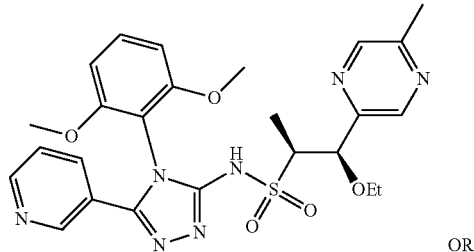

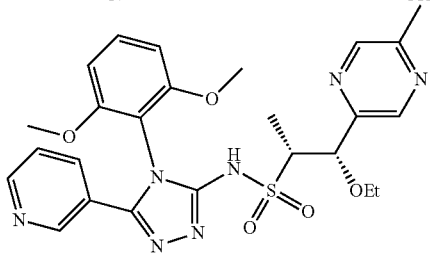

(1S,2R)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide or (1R,2S)—N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide Example 602.0

The title compound was the second peak to elute by SFC using the conditions described in Example 601.0. ¹H NMR (500 MHz, CDCl₃) δ 11.22 (br s, 1H), 8.62 (br s, 2H), 8.54 (s, 1H), 8.41 (s, 1H), 7.75 (d, J=7.9 Hz, 1H), 7.39 (dd, J=8.6, 8.6 Hz, 1H), 7.28 (obscured dd, J=5.9, 5.9 Hz, 1H), 6.6 (d, J=8.6 Hz, 2H), 5.13 (d, J=3.2 Hz, 1H), 3.73 (s, 3H), 3.71 (s, 3H), 3.47-3.59 (m, 3H), 2.57 (s, 3H), 1.27 (d, J=6.8 Hz, 3H), 1.14 (dd, J=7.0, 7.0 Hz, 3H). MS ESI (pos.) m/z: 540.0 (M+H)⁺. Preparative SFC method: Column: Chiralcel OX-H (250×21 mm, 5 μm) Mobile Phase: 60:40 (CO₂:MeOH); Flow Rate: 70 mL/min.

Example 603.0: Preparation of (1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide and (1R,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide and (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide and (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide 603.1

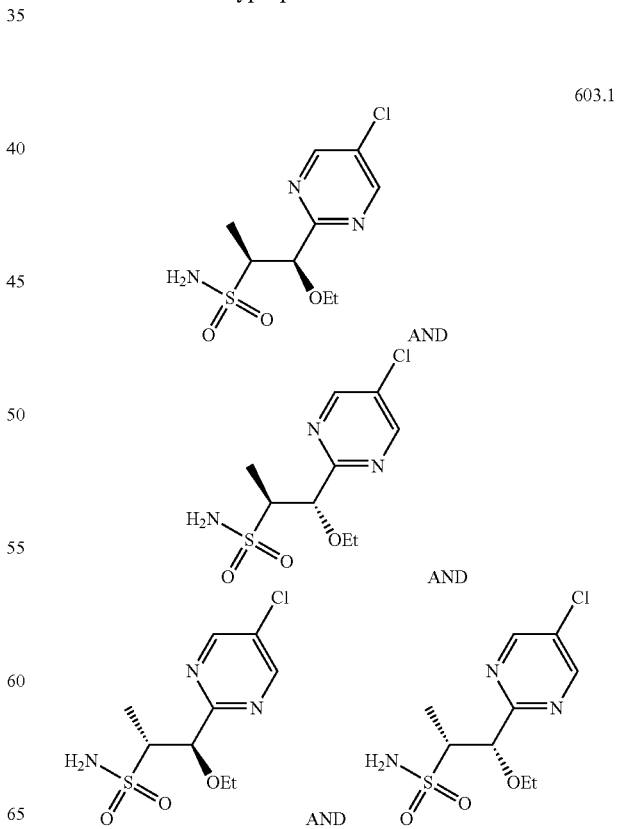

(1S,2R)-1-(5-chloropyrimidin-2-yl)-1-ethoxypropane-2-sulfonamide and (1R,2R)-1-(5-chloropyrimidin-2-yl)-1-ethoxypropane-2-sulfonamide and (1S,2S)-1-(5-chloropyrimidin-2-yl)-1-ethoxypropane-2-sulfonamide and (1R,2S)-1-(5-chloropyrimidin-2-yl)-1-ethoxypropane-2-sulfonamide, Example 603.1

At −78° C., KHMDS (1.0 M, 5.39 mL, 5.39 mmol) was added to a 2-methyltetrahydrofuran (75 mL) solution containing 1-(5-chloropyrimidin-2-yl)-1-hydroxy-N,N-bis(4-methoxybenzyl)propane-2-sulfonamide (prepared following Example C utilizing the appropriate aldehyde and 12.0 (2.41 g, 4.90 mmol)). The resulting mixture was stirred for 5 min at −78° C. and then ethyl trifluoromethanesulphonate (0.635 mL, 4.90 mmol) was added. After 45 min of stirring, LCMS indicated that the reaction was complete. A saturated solution of NH$_4$C$_1$ was added at −78° C. and the reaction was warmed to RT. The reaction was then partitioned with EtOAc and water, washed with brine, dried over sodium sulfate, and concentrated in vacuo. The reaction was purified on silica eluting with a hexanes/EtOAc gradient (0-100%). The desired fractions were combined and concentrated in vacuo. The residue was then dissolved in anisole (2 mL) and DCM (10 mL) and treated with TFA (10 mL). After stirring at RT overnight, the reaction was concentrated to dryness. The residue was purified on silica eluting with a MeOH in DCM stepwise gradient (0-20%). Desired fractions were then combined and concentrated in vacuo. MS ESI (pos.) m/z: 280.1 (M+H)$^+$.

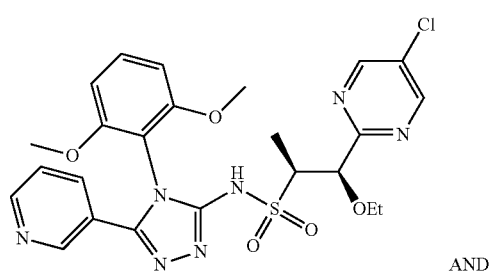

603.0

AND

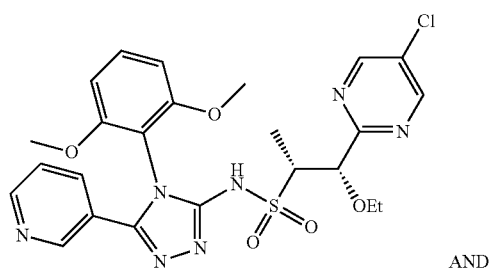

AND

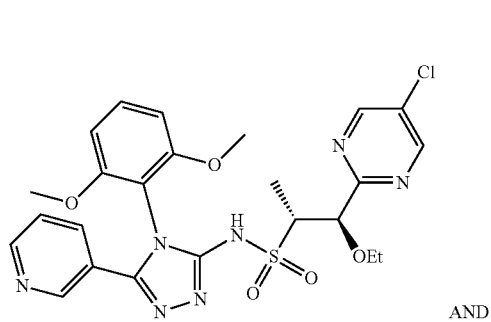

AND

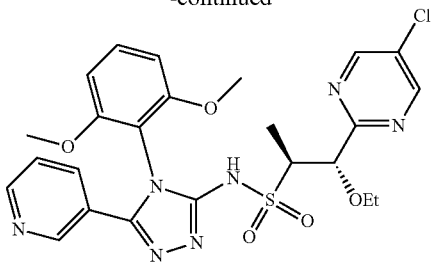

(1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide and (1R,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide and (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide and (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide, Example 603.0

Following Example A employing 1.0, 603.1 and nicotinic hydrazide provided the desired product. The reaction was purified via reverse phase HPLC (Agilent SB-C$_8$ column, 30×250 mm, 5 μm, 10-95% water/ACN gradient over 25 min., with 0.1% TFA, flow rate 50 mL/min). Desired fractions were combined and lyophilized to give pure product.

Example 604.0: Preparation of (1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide

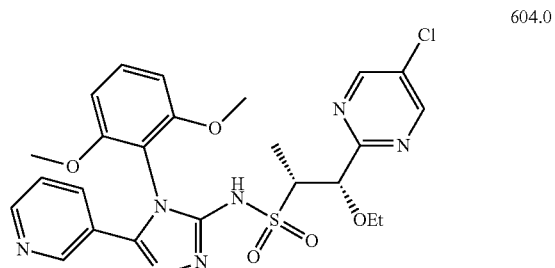

604.0

OR

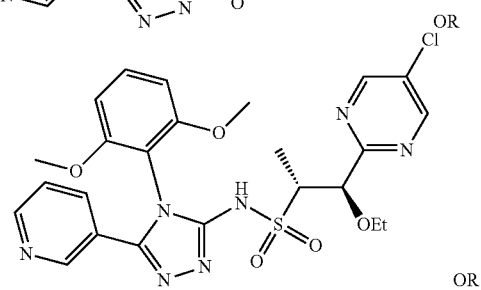

OR

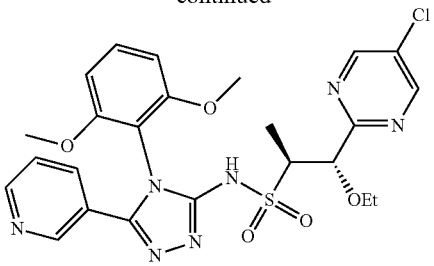

Final chiral separation was performed using SFC. SFC purification methods 3 stages: Stage 1: AS (10 um); 85% CO₂/15% MeOH; 70 mL/min; 220 nm. Stage 2: AD-H; 25% MeOH/75% CO₂; 70 mL/min.; 220 nm. Stage 3: OX-H; 40% MeOH/60% CO₂; 70 mL/min.; 220 nm.

(1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide Example 604.0

The title compound was the first peak (stage 1) to elute by SFC using the conditions described above. ¹H NMR (500 MHz, CDCl₃) δ 11.17 (br s, 1H), 8.70 (s, 2H), 8.62 (obscured dd, J=5.8, 1.9 Hz, 1H), 8.61 (s, 1H), 7.73 (ddd, J=8.1, 1.9, 1.9 Hz, 1H), 7.39 (dd, J=8.4, 8.4 Hz, 1H), 7.26-7.28 (obscured m, 1H), 6.60 (dd, J=8.8, 8.8 Hz, 2H), 5.0 (d, J=5.9 Hz, 1H), 3.78 (obscured m, 1H), 3.75 (s, 3H), 3.70 (s, 3H), 3.45-3.56 (m, 2H), 1.44 (d, J=6.8 Hz, 3H), 1.14 (dd, J=7.0, 7.0 Hz, 3H). MS ESI (pos.) m/z: 560.9 (M+H)⁺. SFC purification methods 3 stages: Stage 1: AS (10 um); 85% CO₂\15% MeOH; 70 mL/min; 220 nm. Stage 2: AD-H; 25% MeOH/75% CO₂; 70 mL/min.; 220 nm. Stage 3: OX-H; 40% MeOH/60% CO₂; 70 mL/min.; 220 nm.

Example 605.0: Preparation of (1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide

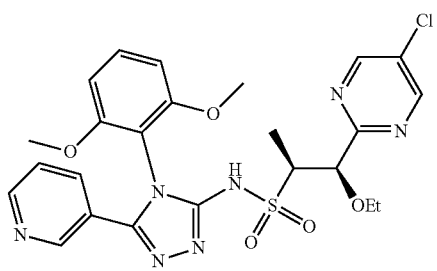

(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, Example 605.0

The title compound was the second peak (stage 3) to elute by SFC using the conditions described in Example 604.0. ¹H NMR (500 MHz, CDCl₃) δ 11.16 (br s 1H), 8.70 (s, 2H), 8.62 (br s, 2H), 7.75 (ddd, J=8.1, 1.8, 1.8 Hz, 1H), 7.39 (dd, J=8.6, 8.6 Hz, 1H), 7.28 (obscured m, 1H), 6.61 (dd, J=8.7, 8.7 Hz, 2H), 5.0 (d, J=5.9 Hz, 1H), 3.78 (obscured m, 1H), 3.75 (s, 3H), 3.71 (s, 3H), 3.46-3.51 (m, 2H), 1.44 (d, J=7.1 Hz, 3H), 1.14 (dd, J=7.0, 7.0 Hz, 3H). MS ESI (pos.) m/z: 560.9 (M+H)⁺. SFC purification methods 3 stages: Stage 1: AS (10 um); 85% CO₂\15% MeOH; 70 mL/min; 220 nm. Stage 2: AD-H; 25% MeOH/75% CO₂; 70 mL/min.; 220 nm. Stage 3: OX-H; 40% MeOH/60% CO₂; 70 mL/min.; 220 nm.

Example 606.0: Preparation of (1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide

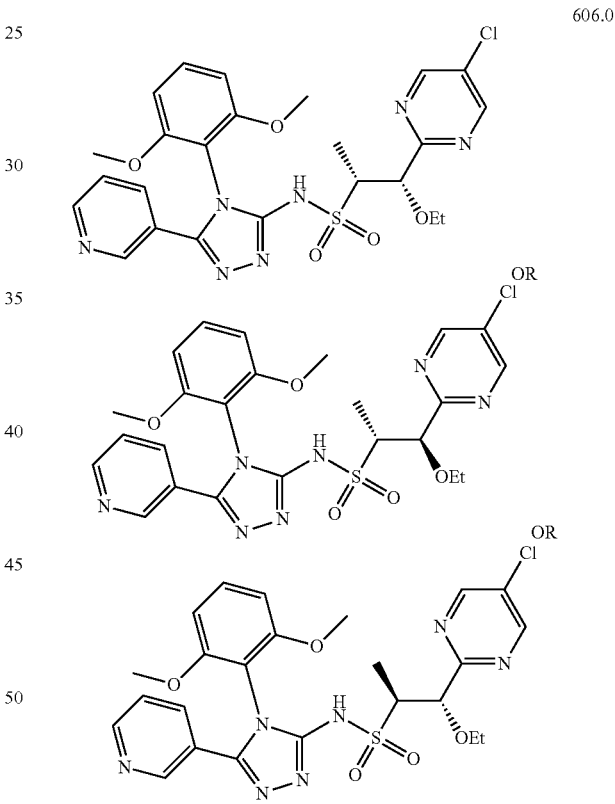

(1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide Example 606.0

The title compound was the first peak (stage 2) to elute by SFC using the conditions described in Example 604.0. ¹H NMR (500 MHz, CDCl$_3$) δ 11.78 (br s, 1H), 8.75 (s, 2H), 8.62 (br s, 2H), 7.73 (ddd, J=7.9, 1.8, 1.8 Hz, 1H), 7.3 (dd, J=8.4, 8.4 Hz, 1H), 7.28 (obscured m, 1H), 6.63 (d, J=8.3 Hz, 1H), 6.58 (d, J=8.3 Hz, 1H), 4.84 (d, J=5.1 Hz, 1H), 3.80 (s, 3H), 7.38 (obscured m, 1H), 3.69 (s, 3H), 3.50-3.56 (m, 1H), 3.38-3.44 (m, 1H), 1.38 (d, J=6.8 Hz, 3H), 1.09 (dd, J=7.0, 7.0 Hz, 3H). MS ESI (pos.) m/z: 560.9 (M+H)$^+$. SFC purification methods 3 stages: Stage 1: AS (10 um); 85% CO$_2$\15% MeOH; 70 mL/min; 220 nm. Stage 2: AD-H; 25% MeOH/75% CO$_2$; 70 mL/min.; 220 nm. Stage 3: OX-H; 40% MeOH/60% CO$_2$; 70 mL/min.; 220 nm.

Example 607.0: Preparation of (1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide (1S,2S)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or or (1S,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(pyridin-3-yl)-4H-1,2,4-triazol-3-yl)-1-ethoxypropane-2-sulfonamide Example 607.0

The title compound was the second peak (stage 2) to elute by SFC using the conditions described in Example 604.0. $^1$H NMR (500 MHz, CDCl$_3$) δ 11.78 (br s, 1H), 8.75 (s, 2H), 8.62 (br s, 2H), 7.74 (d, J=8.1 Hz, 1H), 7.38 (dd, J=8.6, 8.6 Hz, 1H), 7.28 (obscured m, 1H), 6.63 (d, J=8.3 Hz, 1H), 6.58 (d, J=8.3 Hz, 1H), 4.84 (d, J=5.1 Hz, 1H), 3.80 (s, 3H), 3.79 (obscured m, 1H), 3.69 (s, 3H), 3.51-3.56 (m, 1H), 3.38-3.44 (m, 1H), 1.38 (d, J=7.1 Hz, 3H), 1.09 (dd, J=7.0, 7.0 Hz, 3H). MS ESI (pos.) m/z: 560.9 (M+H)$^+$. SFC purification methods 3 stages: Stage 1: AS (10 um); 85% CO$_2$\ 15% MeOH; 70 mL/min; 220 nm. Stage 2: AD-H; 25% MeOH/75% CO$_2$; 70 mL/min.; 220 nm. Stage 3: OX-H; 40% MeOH/60% CO$_2$; 70 mL/min.; 220 nm.

Example 608.0: Preparation of (1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide and (1R,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide and (1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide and (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide

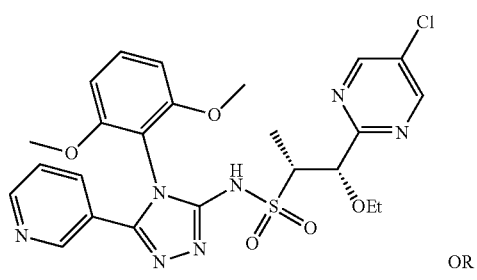

607.0

OR

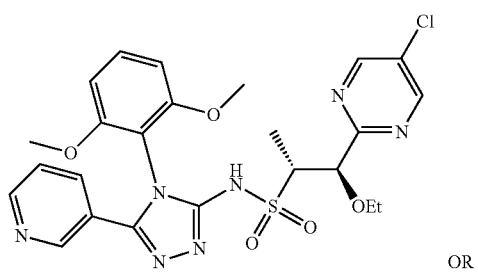

OR

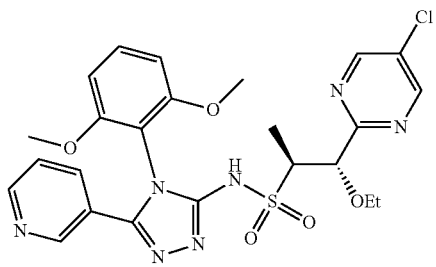

608.0

AND

AND

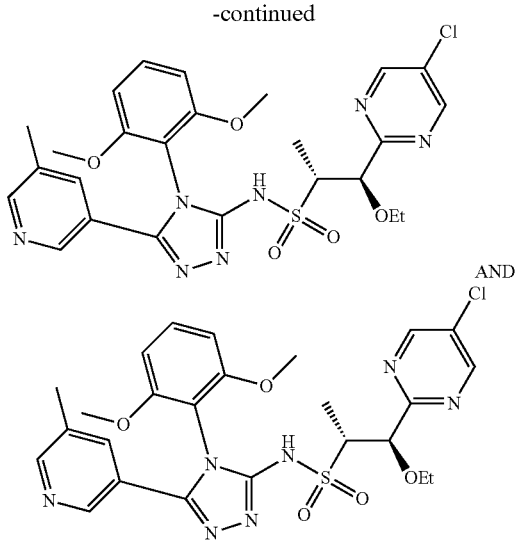

(1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide and
(1R,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide and
(1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide and
(1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide,
Example 608.0

Following Example B employing 2.0 and 603.1 provided the desired product. The residue was purified on silica gel eluting with (0-20% DCM/MeOH). The material was further purified via reverse phase HPLC (Agilent SB-C₈ column, 30×250 mm, 5 μm, 10-95% water/ACN gradient over 25 min., with 0.1% TFA, flow rate 50 mL/min). Desired fractions were combined and lyophilized to give pure product.

Example 609.0: Preparation of (1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide

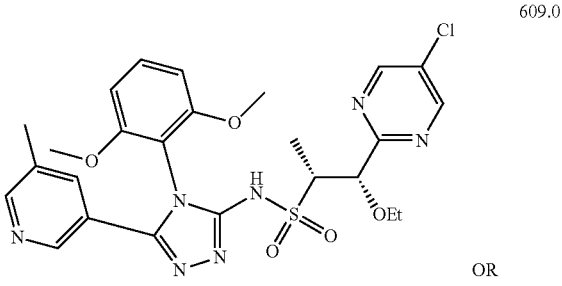

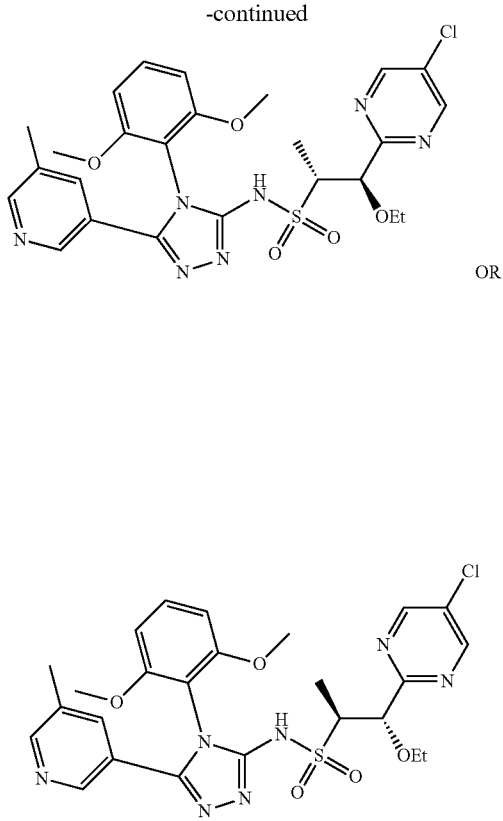

Final chiral separation was performed using SFC. SFC purification 3 stages: Stage 1, Achiral column preparative SFC method: Column: Pyridine (250×21 mm, 5 μm), Mobile Phase: 89:11 (A:B), A: Liquid CO₂, B: MeOH, Flow Rate: 70 mL/min, Oven/Column Temp.: 40 C, Outlet Pressure: 100 bar. Stage 2 Chiral column preparative SFC Column: Chiralpak AD-H (250×21 mm, 5 μm), Mobile Phase: 76:24 (A:B), A: Liquid CO₂, B: EtOH, Flow Rate: 70 mL/min, Oven/Column Temp.: 40 C, Outlet Pressure: 100 bar. Stage 3 Chiral column preparative SFC, Column: Chiralcel OX-H (250×21 mm, 5 μm), Mobile Phase: 65:35 (A:B), A: Liquid CO₂, B: MeOH, Flow Rate: 70 mL/min, Oven/Column Temp.: 40 C, Outlet Pressure: 100 bar.

(1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide.
Example 609.0

The title compound was purified by SFC using the conditions described above. $^1$H NMR (500 MHz, CDCl₃) δ 11.20 (s, 1H), 8.70 (s, 2H), 8.44 (br s, 1H), 8.32 (br s, 1H), 7.65 (s, 1H), 7.38 (dd, J=8.4, 8.4 Hz, 1H), 6.60 (dd, J=8.4, 8.4 Hz, 2H), 4.99 (d, J=5.9 Hz, 1H), 3.77 (obscured m, 1H), 3.76 (s, 3H), 3.71 (s, 3H), 3.45-3.56 (m, 2H), 2.30 (s, 3H), 1.43 (d, J=7.1 Hz, 3H), 1.14 (dd, J=7.0, 7.0 Hz, 3H). MS ESI (pos.) m/z: 574.1 (M+H)⁺.

Example 610.0: Preparation of (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide

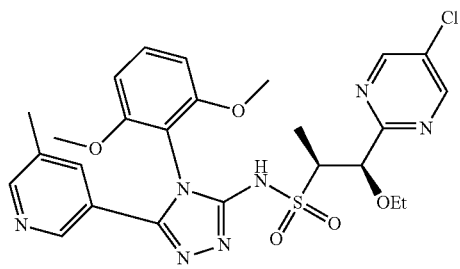

(1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide
Example 610.0

The title compound was purified by SFC using the conditions described in Example 609.0. $^1$H NMR (500 MHz, CDCl$_3$) δ 11.19 (br s, 1H), 8.70 (s, 2H), 8.44 (s, 1H), 8.32 (s, 1H), 7.64 (s, 1H), 7.38 (dd, J=8.4, 8.4 Hz, 1H), 6.60 (dd, J=8.4, 8.4 Hz, 2H), 4.99 (d, J=5.9 Hz, 1H), 3.77 (obscured in, 1H), 3.75 (s, 3H), 3.71 (s, 3H), 3.45-3.556 (m, 2H), 2.30 (s, 3H), 1.43 (d, J=6.8 Hz, 3H), 1.14 (dd, J=7.0, 7.0 Hz, 3H). MS ESI (pos.) m/z: 574.1 (M+H)$^+$.

Example 611.0: Preparation of (1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1S,2R)-1-(5-chloropyrimidin-2-yl)-N-(4-(2,6-(trimethoxyphenyl)-5-(5-methylpyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide

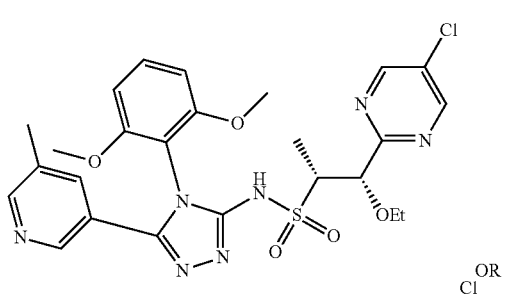

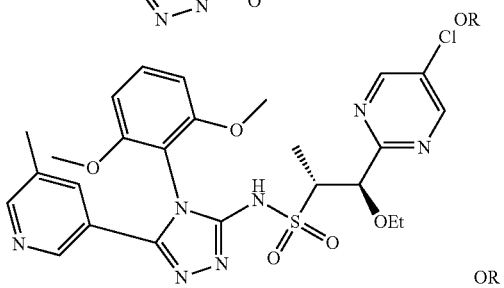

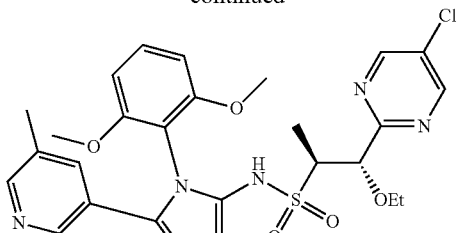

(1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide
Example 611.0

The title compound was purified by SFC using the conditions described in Example 609.0. $^1$H NMR (500 MHz, CDCl$_3$) δ ppm 11.78 (br s, 1H), 8.74 (s, 2H), 8.44 (br s, 1H), 8.33 (br s, 1H), 7.62 (s, 1H), 7.38 (dd, J=8.0, 8.0 Hz, 1H), 6.63 (d, J=8.3 Hz, 1H), 6.58 (d, J=7.7 Hz, 1H), 4.84 (d, J=5.4 Hz, 1H), 3.80 (s, 3H), 3.78 (obscured in, 1H), 3.70 (s, 3H), 3.52 (obscured m, 1H), 3.38-3.44 (m, 1H), 2.30 (s, 3H), 1.37 (d, J=7.1 Hz, 3H), 1.09 (t, J=6.9 Hz, 3H). MS ESI (pos.) m/z: 574.2 (M+H)$^+$.

Example 612.0: Preparation of (1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide

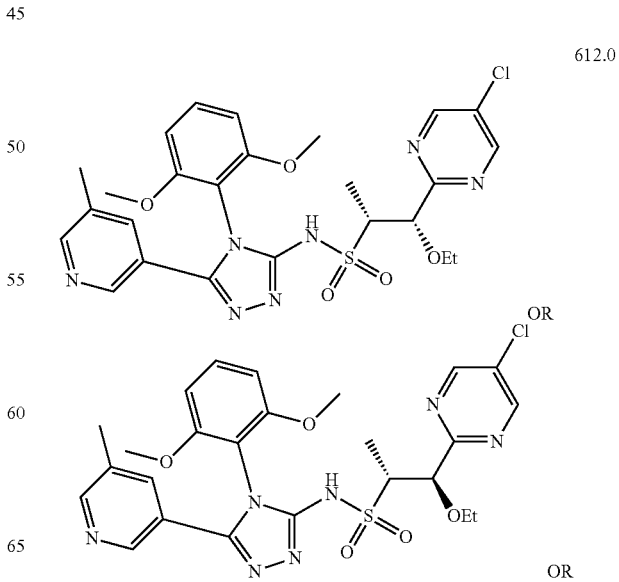

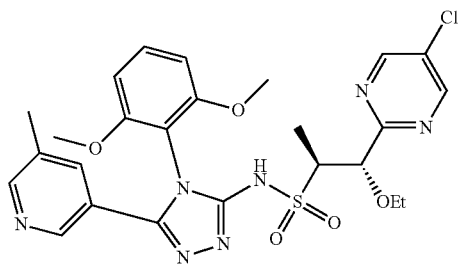

(1S,2S)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1S,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(5-methylpyridin-3-yl)-4H-1,2,4-triazol-3-yl)-1-ethoxypropane-2-sulfonamide Example 612.0

The title compound was purified by SFC using the conditions described in Example 609.0. $^1$H NMR (500 MHz, CDCl$_3$) δ 11.82 (br s, 1H), 8.74 (s, 2H), 8.44 (br s, 1H), 8.33 (br s, 1H), 7.61 (s, 1H), 7.37 (dd, J=8.1, 8.1 Hz, 1H), 6.62 (d, J=8.2 Hz, 1H), 6.58 (d, J=8.1 Hz, 1H), 4.83 (d, J=5.1 Hz, 1H), 3.79 (s, 3H), 3.77 (obscured m, 1H), 3.69 (s, 3H), 3.52 (obscured m, 1H), 3.39-3.43 (m, 1H), 2.30 (s, 3H), 1.36 (d, J=7.1 Hz, 3H), 1.09 (dd, J=7.0, 7.0 Hz, 3H). MS ESI (pos.) m/z: 574.1 (M+H)$^+$.

Example 613.0: Preparation of (1S,2R)—N-(4-(2,6-dimethoxyphenyl)-5-(pyridin-3-yl)-4H-1,2,4-triazol-3-yl)-1-hydroxy-1-(5-methylpyrazin-2-yl)propane-2-sulfonamide and (1R,2S)—N-(4-(2,6-dimethoxyphenyl)-5-(pyridin-3-yl)-4H-1,2,4-triazol-3-yl)-1-hydroxy-1-(5-methylpyrazin-2-yl)propane-2-sulfonamide

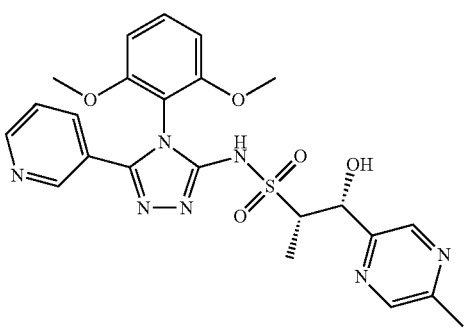

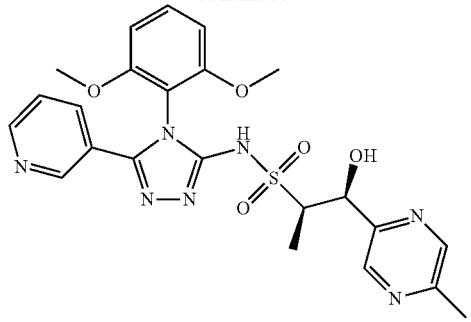

(1S,2R)—N-(4-(2,6-dimethoxyphenyl)-5-(pyridin-3-yl)-4H-1,2,4-triazol-3-yl)-1-hydroxy-1-(5-methylpyrazin-2-yl)propane-2-sulfonamide and (1R,2S)—N-(4-(2,6-dimethoxyphenyl)-5-(pyridin-3-yl)-4H-1,2,4-triazol-3-yl)-1-hydroxy-1-(5-methylpyrazin-2-yl)propane-2-sulfonamide, Example 613.0

Following Example A employing 1.0, 567.2 (the major syn diastereomers were used) and nicotinic hydrazide provided the desired TBS protected product. Removal of the TBS protecting group was conducted as follows. At 23° C., TBAF (3 eq.) were added to a THF solution (0.5 M) containing the corresponding TBS protected alcohol (1 eq.). The resulting mixture was stirred overnight at 23° C. The material was then concentrated and purified via reverse phase HPLC (Agilent SB-C$_8$ column, 30×250 mm, 5 μm, 10-95% water/ACN gradient over 25 min., with 0.1% TFA, flow rate 50 mL/min). Desired fractions were combined and lyophilized to give pure product.

Example 614.0: Preparation of (1S,2R)—N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide

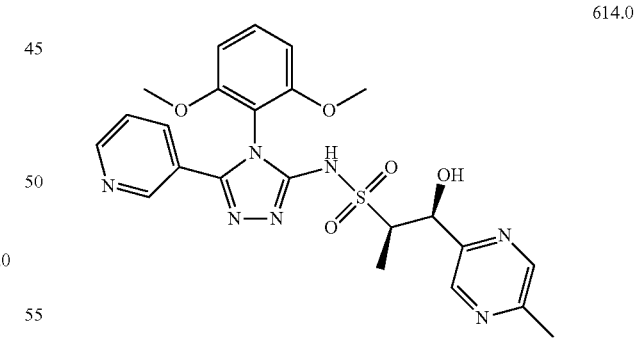

Final chiral separation was performed using SFC. SFC method: 25% MeOH, AD-H (250×20 mm i.d), 70 mL/min, 179 Bar, 270-nm.

(1S,2R)—N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide Example 614.0

The title compound was the first peak to elute by SFC using the conditions described above. $^1$H NMR (500 MHz, CDCl₃) δ 11.13 (br s, 1H), 8.72 (m, 2H), 8.69 (s, 1H), 8.48 (s, 1H), 8.03 (d, J=7.9 Hz, 1H), 7.54-7.48 (m, 2H), 6.75 (d, J=8.3 Hz, 1H), 6.66 (d, J=8.2 Hz, 1H), 5.56 (s, 1H), 3.87 (s, 3H), 3.77 (obscured m, 1H), 3.76 (s, 3H), 2.62 (s, 3H), 1.15 (d, J=7.0 Hz, 3H). MS ESI (pos.) m/z: 512.2 (M+H)⁺. SFC method: 25% MeOH, AD-H (250×20 mm i.d), 70 mL/min, 179 Bar, 270 nm.

Example 615.0: Preparation of (1R,2S)—N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide

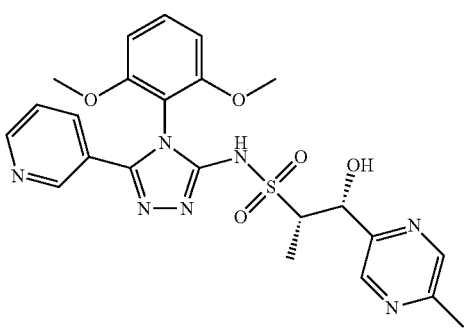

615.0

(1R,2S)—N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide Example 615.0

The title compound was the second peak to elute by SFC using the conditions described in Example 614.0. ¹H NMR (500 MHz, CDCl₃) δ 11.14 (br s, 1H), 8.75 (d, J=1.5 Hz, 1H), 8.72-8.74 (m, 1H), 8.70 (br s, 1H), 8.52 (br s, 1H), 8.08 (dd, J=8.1, 1.7 Hz, 1H), 7.57 (dd, J=6.7, 6.7 Hz, 1H), 7.51 (dd, J=8.4, 8.4 Hz, 1H), 6.75 (d, J=8.3 Hz, 1H), 6.67 (dd, J=8.6, 0.7 Hz, 1H), 5.56 (s, 1H), 3.88 (s, 3H), 3.78 (obscured m, 1H), 3.76 (s, 3H), 2.63 (s, 3H), 1.15 (d, J=6.8 Hz, 3H). MS ESI (pos.) m/z: 512.2 (M+H)⁺. SFC method: 25% MeOH, AD-H (250×20 mm i.d), 70 mL/min, 179 Bar, 270 nm.

Example 616.0: Preparation of (1R,2S)—N-(4-(2,6-dimethoxyphenyl)-5-(pyridin-3-yl)-4H-1,2,4-triazol-3-yl)-1-hydroxy-1-(5-methylpyrimidin-2-yl)propane-2-sulfonamide

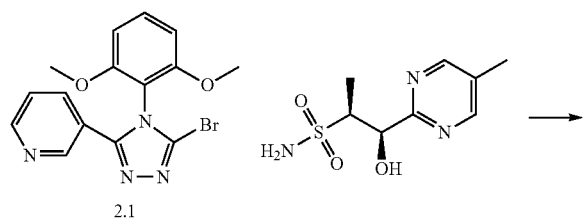

2.1

616.0

(1R,2S)—N-(4-(2,6-dimethoxyphenyl)-5-(pyridin-3-yl)-4H-1,2,4-triazol-3-yl)-1-hydroxy-1-(5-methylpyrimidin-2-yl)propane-2-sulfonamide, Example 616.0

To a vial containing (1R,2S)-1-hydroxy-1-(5-methylpyrimidin-2-yl)propane-2-sulfonamide (0.188 g, 0.81 mmol), 3-(5-bromo-4-(2,6-dimethoxyphenyl)-4H-1,2,4-triazol-3-yl)pyridine (0.352 g, 0.98 mmol), copper(I) iodide (0.076 g, 0.40 mmol), cesium carbonate (0.620 g, 1.90 mmol), and trans-N,N'-dimethyl-1,2-cyclohexanediamine (0.244 mL, 1.55 mmol) was added degassed, anhydrous 1,4-dioxane (1.63 mL). Argon was bubbled through the reaction solution. After 15 min, the dark blue heterogeneous solution was heated on a pre-heated stir plate at 80° C. After 17 h, LCMS shows the reaction was complete. The reaction was then cooled to RT and then an aqueous solution of sodium thiosulfate was carefully added to the mixture. After extracting three times with DCM, the organic layers were combined and then dried over anhydrous magnesium sulfate and concentrated in vacuo. The reaction was purified via reverse phase HPLC (Phenomenex Gemini-C18 column, 30×250 mm, 10 μm, 10-95% water/ACN gradient over 25 min., with 0.1% TFA, flow rate 50 mL/min). The desired fractions were combined and lyophilized to give pure product. ¹H NMR (500 MHz, CDCl₃) δ 8.66 (dd, J=5.0, 1.6 Hz, 1H), 8.65 (dd, J=2.2, 0.7 Hz, 1H), 8.61 (s, 2H), 7.95 (d, J=8.1 Hz, 2H), 7.42 (dd, J=8.4, 8.4 Hz, 1H), 6.67 (d, J=8.4 Hz, 1H), 6.62 (d, J=8.4 Hz, 1H), 5.57 (s, 1H), 3.84-3.89 (m, 1H), 3.78 (s, 3H), 3.74 (s, 3H), 2.34 (s, 3H), 1.19 (d, J=6.8 Hz, 3H). MS ESI (pos.) m/z: 511.9 (M+H)⁺.

Example 617.0: Preparation of (1R,2R)-1-isopropoxy-1-(5-methylpyrimidin-2-yl)propane-2-sulfonamide and (1S,2S)-1-isopropoxy-1-(5-methylpyrimidin-2-yl)propane-2-sulfonamide

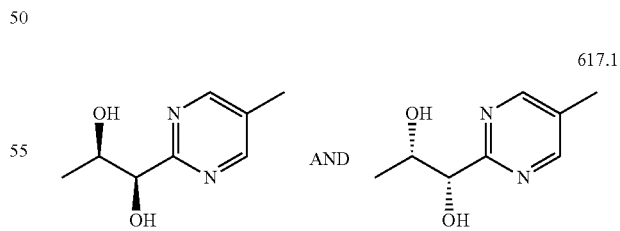

617.1

(1R,2R)-1-(5-methylpyrimidin-2-yl)propane-1,2-diol and (1S,2S)-1-(5-methylpyrimidin-2-yl)propane-1,2-diol To a solution of (E)-5-methyl-2-(prop-1-en-1-yl)pyrimidine (5.68 g, 42.3 mmol) and 4-methylmorpholine-4-oxide (7.44 g, 63.5 mmol) in acetone (60 mL) and water (6 mL)

was added osmium tetroxide (4 wt. %, in water, 0.673 mL, 0.110 mmol). The reaction was stirred at RT under N₂ for 19 h. The reaction mixture was then passed through a Varian Chem-Elut cartridge to remove water and concentrated in vacuo. Water was still present, the residue was dissolved in DCM, dried (Na₂SO₄), and concentrated in vacuo. The residue was purified by flash chromatography (Biotage 100 g ultra column, 0-10% MeOH/DCM) to give the title compound 617.1 (5.1 g, 30.3 mmol, 71.6% yield) as a tan solid. LCMS-ESI (POS.) m/z: 169.1 (M+H)⁺.

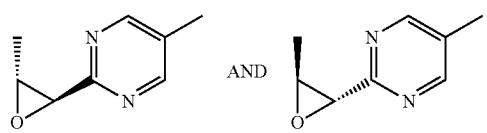

617.2

5-methyl-2-(2R,3R)-3-methyloxiran-2-yl)pyrimidine and 5-methyl-2-(2S,3S)-3-methyloxiran-2-yl)pyrimidine To a solution of 617.1 (5.1 g, 30.3 mmol) and DCM (100 mL) with a RT water bath for cooling, was added 1,1,1-trimethoxyethane (7.72 mL, 60.6 mmol), followed by chlorotrimethylsilane (7.70 mL, 60.6 mmol) dropwise over 10 min. After 6.5 h, additional 1,1,1-trimethoxyethane (5 mL) and chlorotrimethylsilane (5 mL) were added. The reaction was stirred for an additional 17 h and LCMS showed 78% conversion. The reaction was treated with more 1,1,1-trimethoxyethane (3 mL) and chlorotrimethylsilane (3 mL) and stirred for another 24 h. The reaction was concentrated in vacuo. The residue was taken up in MeOH (80 mL) and treated with potassium carbonate (8.38 g, 60.6 mmol). After stirring for 2 h, the solids formed were filtered off and the filtrate concentrated in vacuo. The residue was purified by flash column chromatography (Biotage 100 g ultra column, 0-100% EtOAc/hexanes) to afford 617.2 (3.35 g, 22.3 mmol, 74% yield) as a clear, light-yellow oil. LCMS-ESI (POS.) m/z: 151.2 (M+H)⁺.

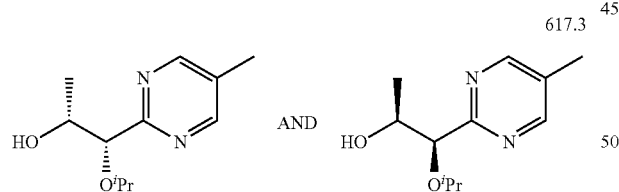

617.3

(1R,2S)-1-isopropoxy-1-(5-methylpyrimidin-2-yl)propan-2-ol and (1S,2R)-1-isopropoxy-1-(5-methylpyrimidin-2-yl)propan-2-ol To a flask containing a solution of 617.2 (128 mg, 0.85 mmol) in DCM/iPrOH (1/1.2 mL) at 0° C. under N₂ was added BF₃·OEt₂ (0.054 mL, 0.43 mmol). After stirring for 45 min at 0° C., the reaction was warmed to RT and then heated at 40° C. with stirring for 18 h. LCMS shows complete conversion to 3:2 ratio of products corresponding to mass of desired products with the major, more polar peak the desired 1-isopropoxy product as shown. The reaction was allowed to cool to RT, concentrated in vacuo and loaded onto a plug of silica gel with DCM, and purified by flash chromatography (Biotage 50 g ultra column, 5-80% 3:1 EtOAc:EtOH/hexane). The major, more polar product 617.3 (83 mg, 0.40 mmol, 46% yield) was isolated as a white sticky solid. LCMS-ESI (POS.) m/z: 211.1 (M+H)⁺.

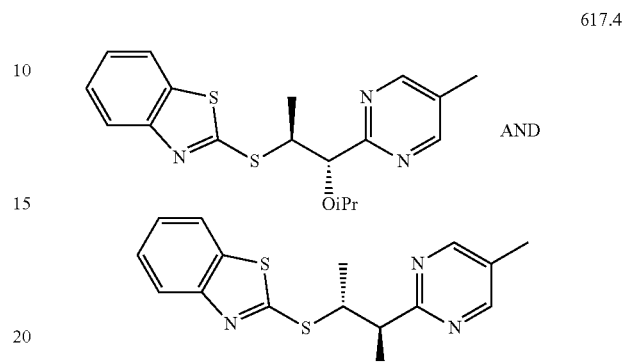

617.4

2-(((1R,2R)-1-isopropoxy-1-(5-methylpyrimidin-2-yl)propan-2-yl)thio)benzo[d]thiazole and 2-0(1S,2S)-1-isopropoxy-1-(5-methylpyrimidin-2-yl)propan-2-yl)thio)benzo[d]thiazole To a flask containing triphenylphosphine (160 mg, 0.61 mmol) in toluene (0.8 mL) under N₂ at 0° C. was added diethyl azodicarboxylate (40 wt. % solution in toluene, 270 µL, 0.59 mmol). The reaction mixture was stirred for 10 min and then 617.3 (83 mg, 0.40 mmol) in toluene (0.8 mL) was added and the reaction was stirred for another 10 min. Benzo[d]thiazole-2-thiol (99 mg, 0.59 mmol) was added, and the reaction mixture was allowed to warm to RT with stirring for 16 h. The reaction was directly loaded onto a plug of silica gel and purified by flash column chromatography (Biotage 50 g ultra, 0-35% EtOAc:hexanes) to give 617.4 (87 mg, 0.242 mmol, 61% yield) as a clear, colorless oil. LCMS-ESI (POS.) m/z: 360.2 (M+H)⁺.

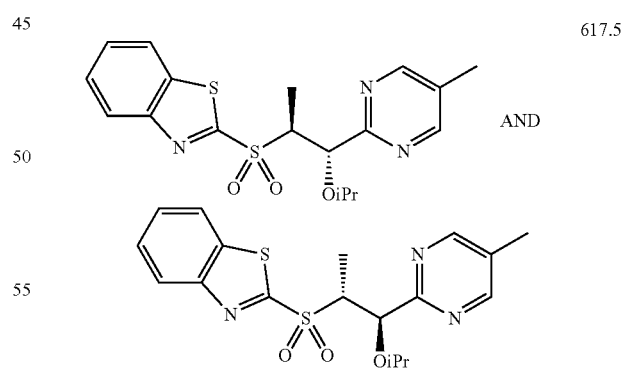

617.5

2-(((1R,2R)-1-isopropoxy-1-(5-methylpyrimidin-2-yl)propan-2-yl)sulfonyl)benzo[d]thiazole and 2-(((1S,2S)-1-isopropoxy-1-(5-methylpyrimidin-2-yl)propan-2-yl)sulfonyl)benzo[d]thiazole A solution of 617.4 (1.1 g, 3.1 mmol) in DCM (9.5 mL) at 0° C. was treated with 3-chloroperoxybenzoic acid (77% max., 1.54 g, 6.9 mmol). The reaction mixture was then stirred at 0° C. for 1 h before the cold bath was removed. After stirring at RT for 18 h, the reaction was quenched with a saturated aqueous sodium bisulfite (12 mL) solution and a saturated aqueous sodium bicarbonate (10 mL) solution, and then the reaction mixture was stirred for 10 min. The reaction product was then extracted with EtOAc (2×40 mL) and the organic layers combined, washed with saturated aqueous NaHCO$_3$ (10 mL), brine (10 mL), dried (Na$_2$SO$_4$) and concentrated in vacuo to give a white sticky solid. Purification by flash chromatography (Biotage100 g ultra, 0-100% 3:1 EtOAc:EtOH/hexane) gave 617.5 (0.81 g, 2.1 mmol, 68% yield) as a white foam. LCMS-ESI (POS.) M/Z: 392.2 (M+H)$^+$.

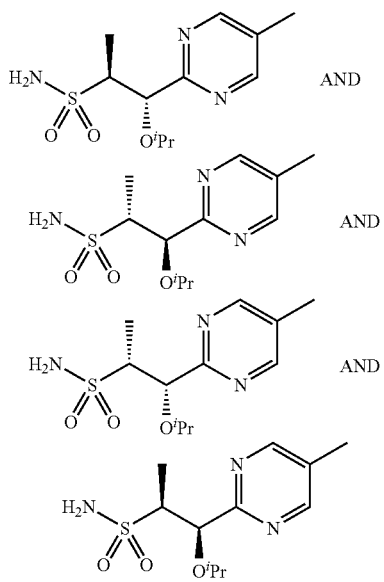

617.0

(1R,2R)-1-isopropoxy-1-(5-methylpyrimidin-2-yl)propane-2-sulfonamide and (1S,2S)-1-isopropoxy-1-(5-methylpyrimidin-2-yl)propane-2-sulfonamide and (1S,2R)-1-isopropoxy-1-(5-methylpyrimidin-2-yl)propane-2-sulfonamide and (1R,2S)-1-isopropoxy-1-(5-methylpyrimidin-2-yl)propane-2-sulfonamide A solution of 2-(((1R,2R)-1-isopropoxy-1-(5-methylpyrimidin-2-yl)propan-2-yl)sulfonyl)benzo[d]thiazole and 2-(((1S,2S)-1-isopropoxy-1-(5-methylpyrimidin-2-yl)propan-2-yl)sulfonyl)benzo[d]thiazole (0.85 g, 2.17 mmol) in MeOH (7.2 mL) at 0° C. was treated with potassium carbonate (0.6 g, 4.34 mmol). The reaction mixture was then stirred at 0° C. under N$_2$ and was then allowed to slowly warm to RT overnight with stirring. The reaction mixture was concentrated in vacuo, and the residue was suspended in water (15 mL), followed by addition of (aminooxy)sulfonic acid (0.491 g, 4.34 mmol) and potassium acetate (0.213 g, 2.17 mmol). The reaction mixture was then stirred at RT for 2 h. LC/MS indicated desired product formation as two peaks with 1:1 ratio. The resulting mixture was extracted with EtOAc (3×50 mL). The combined organic layers were dried over Na$_2$SO$_4$, filtered, and concentrated in vacuo. The residue was purified by column chromatography (Biotage 50 g ultra column, 2-6% MeOH in DCM) to provide 617.0 (0.53 g, 1.93 mmol, 89% yield) as a colorless oil. NMR showed the desired product, but with complete epimerization. LCMS ESI (POS.) m/z: 274.2 (M+H)$^+$.

The compounds set forth in the following Table were synthesized following the procedure in Example 205.0 using the known starting material as described.

TABLE 15

| Example | Reagents | Structure, Name and Data |
|---|---|---|
| 618.0 | (N-((2,6-dimethoxyphenyl)-carbamothioyl)-1-(5-fluoropyrimidin-2-yl)propane-2-sulfonamide (Example 431.1), 6-methylnicotinohydrazide (Example3.13), mercury (II) acetate (commercially available from VWR International, Radnor, PA, USA) TFA (commercially available from Sigma-Aldrich Corp, St. Louis, MO, USA). | and |

TABLE 15-continued

| Example | Reagents | Structure, Name and Data |
|---|---|---|
| | | (S)-N-(4-(2,6-dimethoxyphenyl)-5-(6-methylpyridin-2-yl)-4H-1,2,4-triazol-3-yl)-1-(5-fluoropyrimidin-2-yl)propane-2-sulfonamide and (R)-N-(4-(2,6-dimethoxyphenyl)-5-(6-methylpyridin-2-yl)-4H-1,2,4-triazol-3-yl)-1-(5-fluoropyrimidin-2-yl)propane-2-sulfonamide<br>LCMS-ESI (POS.) m/z: 514.1 (M + H)+. |
| 619.0 | The racemic 618.0 was separated by supercritical fluid chromatography (2 × 15 cm IA column with 60 mL/min 20% MeOH/CO$_2$. Outlet pressure = 100 bar; wavelength = 220 nm; injection volumn = 10 mL, 11 mg/mL 1:1 MeOH:DCM). This was the first isomer to elute under these conditions. | 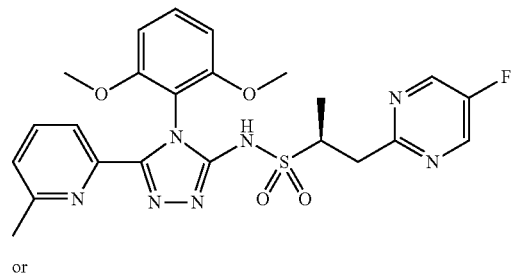<br>or<br>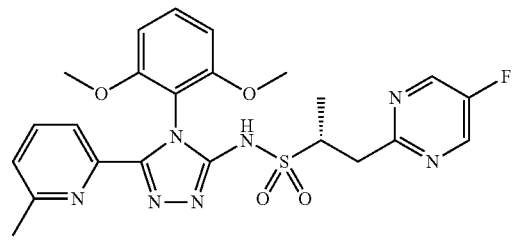 [SMILES: COc1cccc(OC)c1-n1c(NS(=O)(=O)[C@H](C)Cc2ncc(F)cn2)nnc1-c1cccc(C)n1]<br>(S)-N-(4-(2,6-dimethoxyphenyl)-5-(6-methylpyridin-2-yl)-4H-1,2,4-triazol-3-yl)-1-(5-fluoropyrimidin-2-yl)propane-2-sulfonamide or (R)-N-(4-(2,6-dimethoxyphenyl)-5-(6-methylpyridin-2-yl)-4H-1,2,4-triazol-3-yl)-1-(5-fluoropyrimidin-2-yl)propane-2-sulfonamide<br>$^1$H NMR (400 MHz, CDCl$_3$) δ: 8.52 (s, 2H), 7.53-7.59 (m, 2H), 7.35 (dd, J = 8.5, 8.5 Hz, 1H), 7.08-7.10 (m, 1H), 6.58 (d, J = 8.3 Hz, 2H), 3.73-3.83 (m, 1H), 3.69-3.73 (obscured m, 1H), 3.70 (s, 3H), 3.68 (s, 3H), 3.10 (dd, J = 14.8, 9.9 Hz, 1H), 2.22 (s, 3H), 1.32 (d, J = 6.7 Hz, 3H). MS ESI (pos.) m/z = 514.1 [M + H]. |
| 620.0 | The racemic intermediate 618.0 was separated by supercritical fluid chromatography (2 × 15 cm IA column with 60 mL/min 20% MeOH/CO$_2$. Outlet pressure = 100 bar; wavelength = 220 nm; injection volumn = 10 mL, 11 mg/mL 1:1 MeOH:DCM). This was the second isomer to elute under these conditions. | 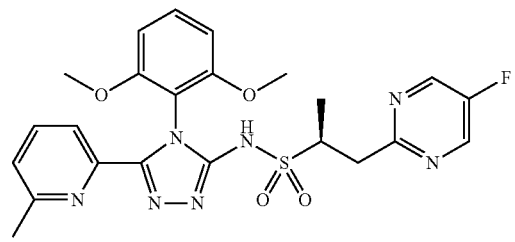 [SMILES: COc1cccc(OC)c1-n1c(NS(=O)(=O)[C@@H](C)Cc2ncc(F)cn2)nnc1-c1cccc(C)n1]<br>or<br>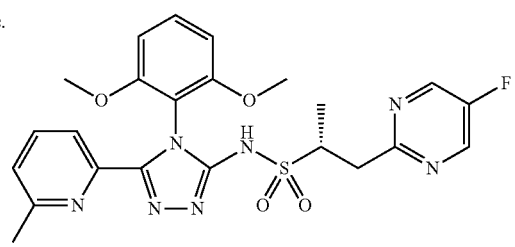<br>(S)-N-(4-(2,6-dimethoxyphenyl)-5-(6-methylpyridin-2-yl)-4H-1,2,4-triazol-3-yl)-1-(5-fluoropyrimidin-2-yl)propane-2-sulfonamide or (R)-N-(4-(2,6-dimethoxyphenyl)-5-(6-methylpyridin-2-yl)-4H-1,2,4- |

TABLE 15-continued

| Example | Reagents | Structure, Name and Data |
|---|---|---|
| | | triazol-3-yl)-1-(5-fluoropyrimidin-2-yl)propane-2-sulfonamide<br>$^1$H NMR (400 MHz, CDCl$_3$) δ: 11.1 br s, 1H), 8.53 (s, 2H), 7.53-7.59 (m, 2H), 7.35 (dd, J= 8.3, 8.3 Hz, 1H), 7.09 (dd, J = 6.7, 1.7 Hz, 1H), 6.58 (d, J = 8.9 Hz, 2H), 3.77-3.85 (m, 1H), 3.69-3.74 (obscured m, 1H), 3.70 (s, 3H), 3.68 (s, 3H), 3.10 (dd, J = 14.8, 9.9 Hz, 1H), 2.23 (s, 3H), 1.32 (d, J = 6.7 Hz, 3H).<br>MS ESI (pos.) m/z = 514.1 [M + H]. |

The compounds set forth in the following Table were synthesized following the procedure in Example A using the known starting material as described.

TABLE 16

| Example | Reagents | Structure, Name and Data |
|---|---|---|
| 621.0 | 2-(2-cyano-4-fluorophenyl)ethane-sulfonamide, (Example 8.0). 5-methylnicotinohydrazide (Example 3.11), 2-isothiocyanato-1,3-dimethoxybenzene (Example 1.0), mercury acetate (commercially available from VWR International, Radnor, PA, USA) was used instead of silver nitrate, TFA (commercially available). | 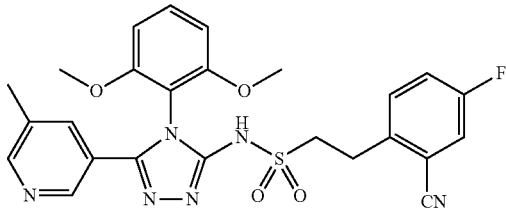 [SMILES: COc1cccc(OC)c1-n1c(NS(=O)(=O)CCc2ccc(F)cc2C#N)nnc1-c1cncc(C)c1]<br>2-(2-cyano-4-fluorophenyl)-N-(4-(2,6-(dimethoxyphenyl)-5-(5-methyl-3-pyridinyl)-4H-1,2,4-triazol-3-yl)ethanesulfonamide<br>$^1$H NMR (400 MHz, CDCl$_3$) δ: 11.18 (br s, 1H), 8.45 (d, J= 1.6 Hz, 1H), 8.33 (d, J = 2.0 Hz, 1H), 7.62 (m, 1H), 7.4237-7.37 (m, 2H), 7.29 (dd, J = 8.0, 2.7 Hz, 1H), 7.24-7.19 (td, J = 8.3, 8.3, 2.7 Hz, 1H), 6.61 (d, J = 8.6 Hz, 2H), 3.74 (s, 6H), 3.31-3.36 (m, 4H), 2.30 (s, 3H).<br>MS ESI (pos.) m/z = 523.1 [M + H]. |

Example 622.0: Preparation of (2R,3S)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide

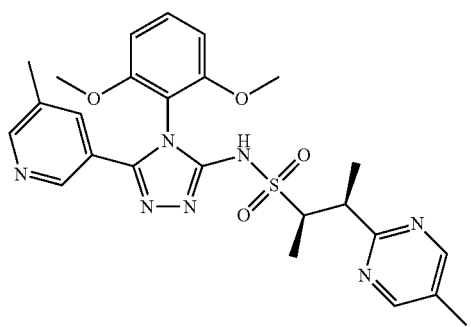

622.0

(2R,3S)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide, Example 622.0

A vial containing (2R,3S)-3-(5-methylpyrimidin-2-yl)butane-2-sulfonamide (346 mg, 1.51 mmol), 3-(5-bromo-4-(2,6-dimethoxyphenyl)-4H-1,2,4-triazol-3-yl)-5-methylpyridine (749 mg, 2.00 mmol), copper(II) triflate (289 mg, 0.80 mmol), trans-N,N'-dimethyl-1,2-cyclohexanediamine (0.48 mL, 3.04 mmol), and potassium carbonate (540 mg, 3.91 mmol) was degassed and then backfilled with nitrogen. Anhydrous 1,4-dioxane (3.0 mL) was added to the mixture and the dark blue heterogeneous solution was then heated on a pre-heated stirplate at 80° C. and monitored with LC-MS. After 21 h, the reaction was cooled to RT and then diluted with water. An aqueous solution of 1N HCl was carefully added to the dark blue homogeneous solution to adjust the pH to pH~7. After extracting four times with DCM, the organic layers were combined and then washed once with aqueous 1 M sodium thiosulfate. After drying the organic layer over anhydrous magnesium sulfate, filtration, and concentration in vacuo, the blue green residue was loaded onto a silica gel column (0-70% 3:1 EtOAc: EtOH in heptanes) to afford a white solid. The solid was recrystallized from EtOH to afford (2R,3S)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide (306 mg).

¹H NMR (500 MHz, DMSO-d₆) δ=13.36 (s, 1H), 8.62-8.56 (m, 2H), 8.47 (d, J=1.5 Hz, 1H), 8.19 (d, J=2.0 Hz, 1H), 7.62 (dt, J=0.9, 2.1 Hz, 1H), 7.54-7.45 (m, 1H), 6.87-6.78 (m, 2H), 3.71-3.63 (m, 7H), 3.63-3.57 (m, 1H), 2.25 (s, 3H), 2.23 (s, 3H), 1.24 (d, J=7.1 Hz, 3H), 1.10 (d, J=6.8 Hz, 3H). MS (pos.) m/z: 524.3 (M+H)⁺.

Example 623.0: Preparation of (1R,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1S,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1S,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1R,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide 623.1

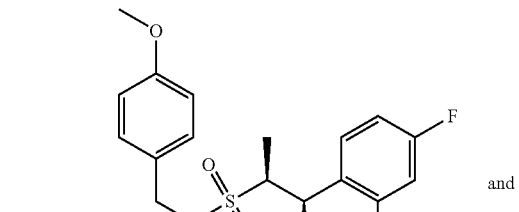
and

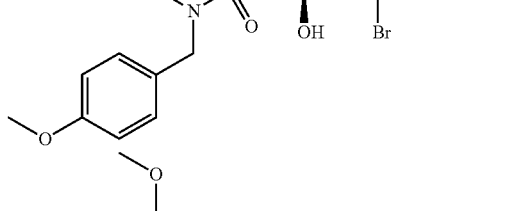
and

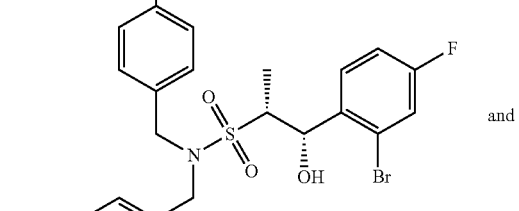
and

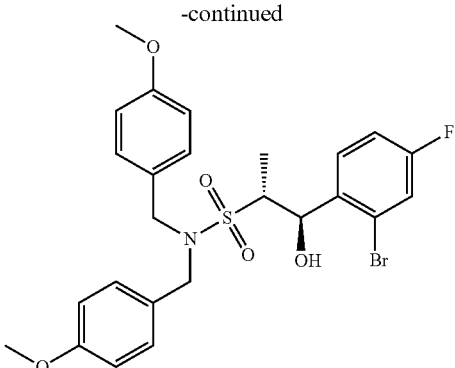

(1R,2R)-1-(2-bromo-4-fluorophenyl)-1-hydroxy-N,N-bis(4-methoxybenzyl)propane-2-sulfonamide and (1R,2S)-1-(2-bromo-4-fluorophenyl)-1-hydroxy-N,N-bis(4-methoxybenzyl)propane-2-sulfonamide and (1S,2R)-1-(2-bromo-4-fluorophenyl)-1-hydroxy-N,N-bis(4-methoxybenzyl)propane-2-sulfonamide and (1S,2S)-1-(2-bromo-4-fluorophenyl)-1-hydroxy-N,N-bis(4-methoxybenzyl)propane-2-sulfonamide, Example 623.1

N,N-bis(4-methoxybenzyl)ethanesulfonamide (14.3 g, 40.9 mmol) was azeotroped with toluene. THF (160 mL) was added, and the mixture was cooled to −78° C. n-Butyllithium (2.5M in hexanes, 18.01 mL, 45.0 mmol) was injected dropwise, and the mixture was stirred for 15 min. A solution of 2-bromo-4-fluorobenzaldehyde (from Oakwood Products, Inc., 9.97 g, 49.1 mmol) in THF (40.0 mL) was injected dropwise over period of 15 min. The mixture was kept at −78° C. for 30 min and then the cooling bath was removed and stirring was continued for 1 h. The reaction mixture was re-cooled to −78° C. and quenched with a saturated NH₄Cl solution (200 mL) and stored at −18° C. overnight. DCM (200 mL) was added and the layers were separated. The mixture was further extracted with DCM (3×50 mL) and the organic layers were combined, dried over Na₂SO₄, filtered and concentrated in vacuo. Purification on a 330 g silica gel column, gradient eluenting with 0-100% EtOAc/hexanes provided 623.1, 1-(2-bromo-4-fluorophenyl)-1-hydroxy-N,N-bis(4-methoxybenzyl)propane-2-sulfonamide (19.6 g, 35.5 mmol, 87% yield) as white solid. LCMS-ESI (POS.) M/Z: 574.0 (M+Na)⁺.

623.2

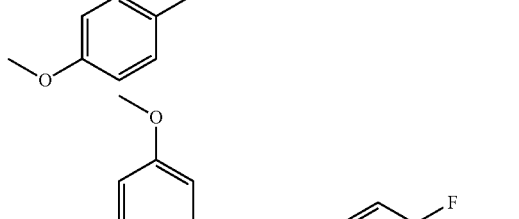
and

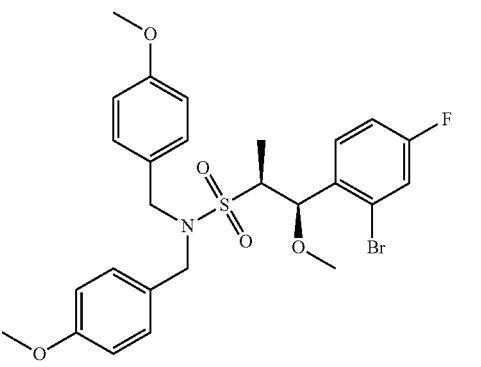
and

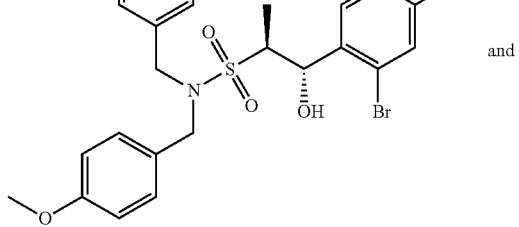

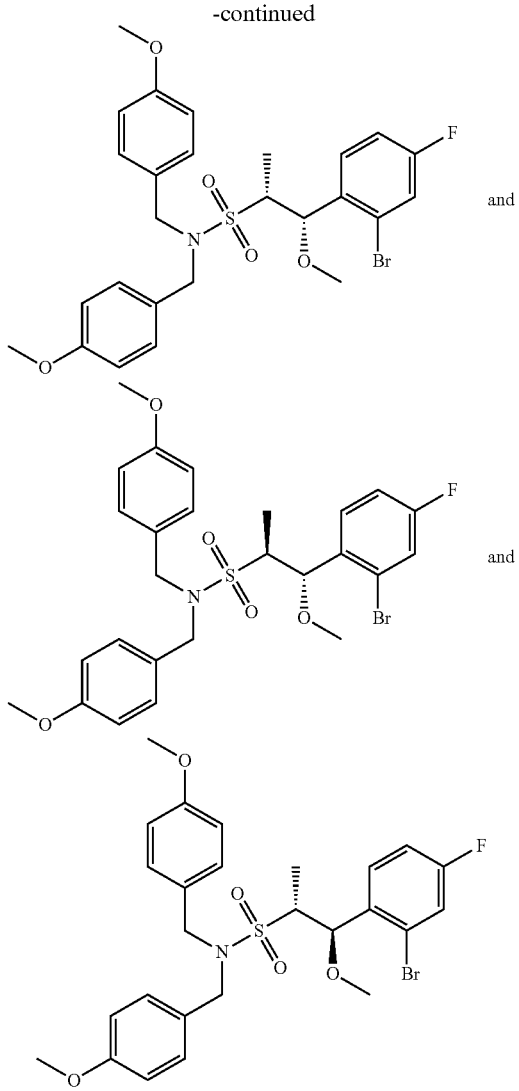

(1R,2S)-1-(2-bromo-4-fluorophenyl)-1-methoxy-N,
N-bis(4-methoxybenzyl)propane-2-sulfonamide and
(1S,2R)-1-(2-bromo-4-fluorophenyl)-1-methoxy-N,
N-bis(4-methoxybenzyl)propane-2-sulfonamide and
(1S,2S)-1-(2-bromo-4-fluorophenyl)-1-methoxy-N,
N-bis(4-methoxybenzyl)propane-2-sulfonamide and
(1R,2R)-1-(2-bromo-4-fluorophenyl)-1-methoxy-N,
N-bis(4-methoxybenzyl)propane-2-sulfonamide,
Example 623.2

To a 500-mL round-bottomed flask was added 623.1 (5.06 g, 9.16 mmol) in 2-methyltetrahydrofuran (50 mL). Potassium bis(trimethylsilyl)amide in THF (1.0 M, 10.08 mL, 10.08 mmol) was injected dropwise under $N_2$ at −78° C. with stirring. The reaction mixture was stirred at −78° C. for 15 min. Iodomethane (stabilized, 0.626 mL, 10.08 mmol) was then added dropwise under $N_2$ at −78° C. with stirring. The reaction mixture was stirred at −78° C. for 15 min and then the dry ice-acetone bath was removed. The reaction was allowed to stir at at RT and was monitored by LCMS. After 2.5 h, the reaction was quenched with a saturated aqueous $NH_4Cl$ solution (50 mL) and diluted with water (100 mL) and extracted with EtOAc (2×100 mL). The organic extract was dried over $Na_2SO_4$. The solution was filtered and concentrated in vacuo to give the initial material as a light-yellow solid. The material thus obtained was absorbed onto a plug of silica gel and purified by chromatography through a Redi-Sep pre-packed silica gel column (330 g), eluting with a gradient of 0-30% EtOAc in DCM, to provide 623.2 1-(2-bromo-4-fluorophenyl)-1-methoxy-N,N-bis(4-methoxybenzyl)propane-2-sulfonamide (4.75 g, 8.39 mmol, 92% yield) as white solid. LCMS-ESI (POS.) m/z: 588.0 $(M+Na)^+$.

623.3

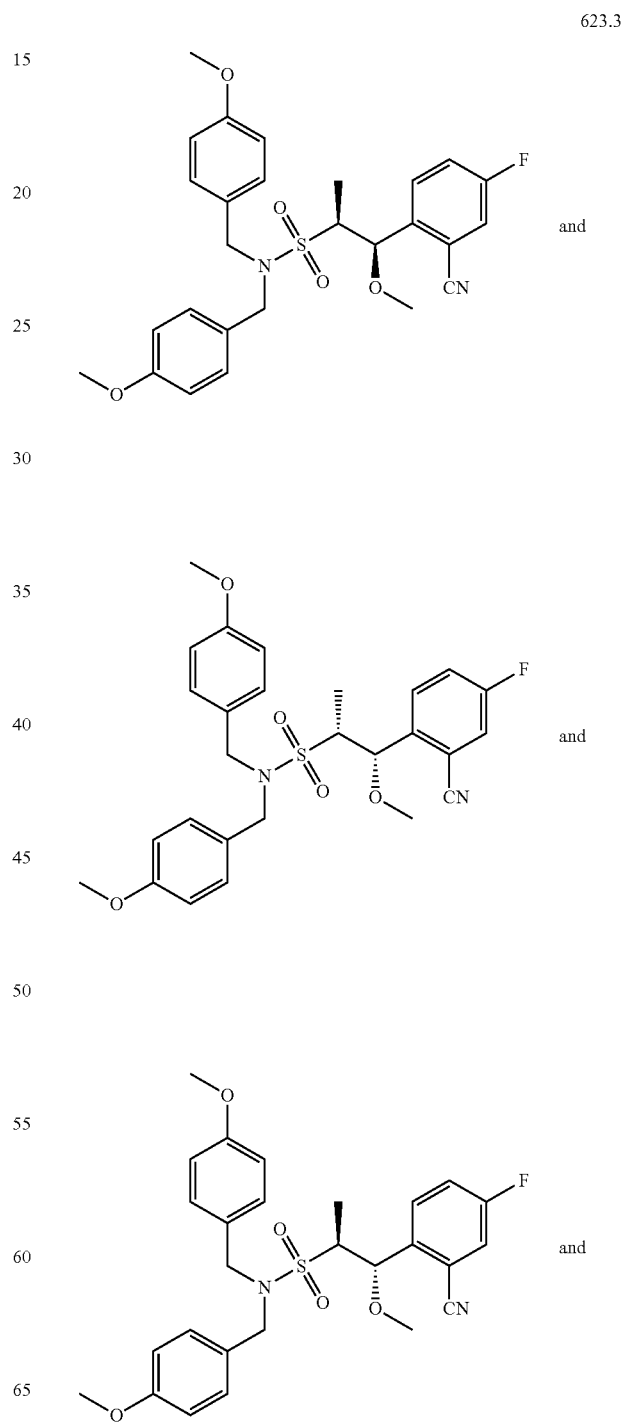

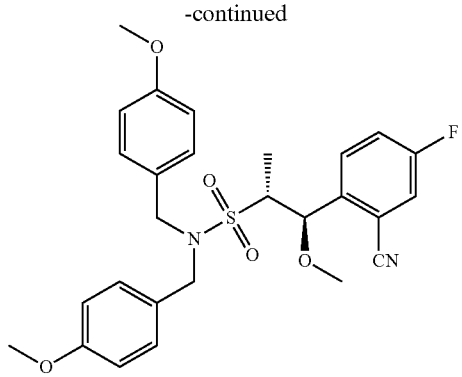

(1R,2R)-1-(2-cyano-4-fluorophenyl)-1-methoxy-N,
N-bis(4-methoxybenzyl)propane-2-sulfonamide and
(1R,2S)-1-(2-cyano-4-fluorophenyl)-1-methoxy-N,
N-bis(4-methoxybenzyl)propane-2-sulfonamide and
(1S,2R)-1-(2-cyano-4-fluorophenyl)-1-methoxy-N,
N-bis(4-methoxybenzyl)propane-2-sulfonamide and
(1S,2S)-1-(2-cyano-4-fluorophenyl)-1-methoxy-N,
N-bis(4-methoxybenzyl)propane-2-sulfonamide,
Example 623.3

A 60 mL vial with septa was charged with 623.2 (1.5 g, 2.65 mmol), zinc cyanide (0.466 g, 3.97 mmol) and DMA (17 mL). The mixture was degassed with N$_2$. Tetrakis(triphenylphosphine)palladium (0.61 g, 0.53 mmol) was added and the mixture was degassed again. The reaction mixture was then heated under nitrogen at 100° C. for 19 h. The reaction mixture was cooled to RT and then it was diluted with water (150 mL) and EtOAc (150 mL). The organic layer was washed with brine (3×150 mL), dried over Na$_2$SO$_4$, filtered and concentrated. The material thus obtained was absorbed onto a plug of silica gel (40 g), eluting with a gradient of 0-100% EtOAc in hexanes to provide 623.3; 1-(2-cyano-4-fluorophenyl)-1-methoxy-N,N-bis(4-methoxybenzyl)propane-2-sulfonamide (1.35 g, 2.63 mmol, 99% yield) as a pale yellow gum. LCMS-ESI (POS.) m/z: 535.2 (M+Na)$^+$.

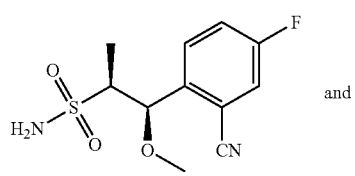

and

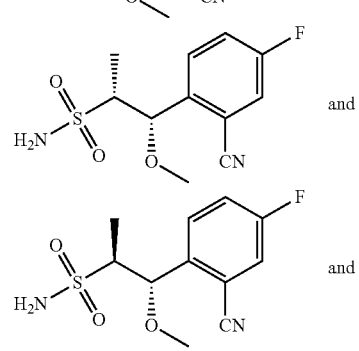

and

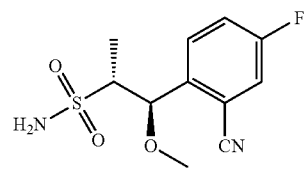

(1R,2R)-1-(2-cyano-4-fluorophenyl)-1-methoxypropane-2-sulfonamide and (1R,2S)-1-(2-cyano-4-fluorophenyl)-1-methoxypropane-2-sulfonamide and (1S,2R)-1-(2-cyano-4-fluorophenyl)-1-methoxypropane-2-sulfonamide and (1S,2S)-1-(2-cyano-4-fluorophenyl)-1-methoxypropane-2-sulfonamide,
Example 623.4

Example 623.3 (1.35 g, 2.63 mmol) was treated with anisole (anhydrous, 1.15 mL, 10.53 mmol) and TFA (9.78 mL, 132 mmol) at RT and monitored by LCMS. After 4 h, the reaction was concentrated in vacuo. The mixture was absorbed onto a plug of silica gel and purified by chromatography through a Redi-Sep pre-packed silica gel column (40 g), eluting with a gradient of 0-100% EtOAc in hexane, to provide 623.4 (0.68 g, 2.49 mmol, 95% yield) as a white solid. LCMS-ESI (POS.) m/z: 295.1 (M+Na)$^+$.

623.0

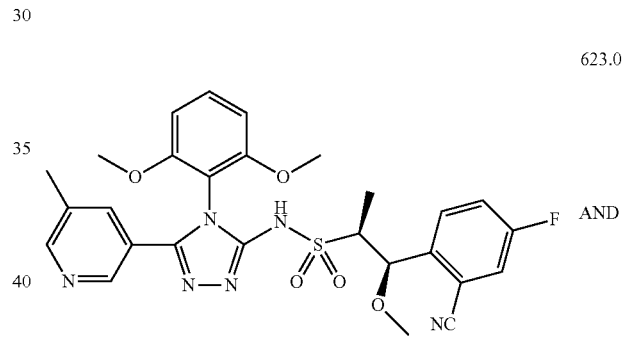

AND

OR

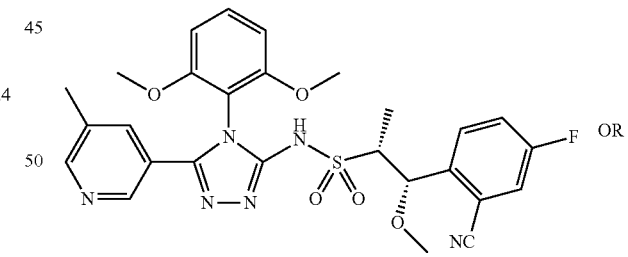

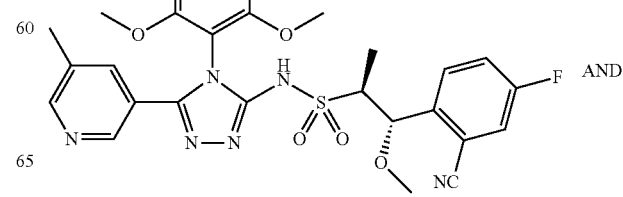

AND

-continued

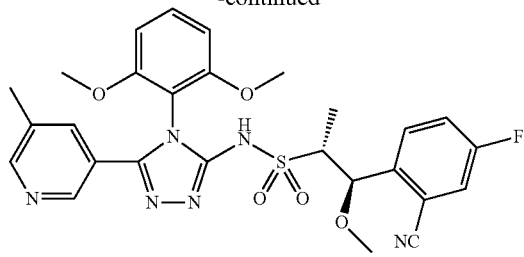

(1R,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1S,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide or (1R,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide and (1S,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide, Example 623.0

A mixture of 623.4 1-(2-cyano-4-fluorophenyl)-1-methoxypropane-2-sulfonamide (110 mg, 0.405 mmol) and 3-(5-bromo-4-(2,6-dimethoxyphenyl)-4H-1,2,4-triazol-3-yl)-5-methylpyridine (152 mg, 0.405 mmol) was azeotroped with toluene in a 40-mL vial on rota vapor at 50° C. To the mixture was added 1,4-dioxane (2.03 mL), cesium carbonate (330 mg, 1.01 mmol) and (1R,2R)-(−)-N,N″-dimethylcyclohexane-1,2-diamine (128 μL, 0.81 mmol). The reaction was degassed with argon. To the mixture was added copper(I) iodide (77 mg, 0.401 mmol). The mixture was heated at 90° C. overnight. The reaction was quenched with a saturated an aqueous solution of $NH_4C_1$ (15 mL) and extracted with DCM (3×15 mL), dried over $Na_2SO_4$, filtered and concentrated in vacuo. The material thus obtained was absorbed onto a plug of silica gel and purified by chromatography through a Redi-Sep pre-packed silica gel column (12 g), eluting with a gradient of 0-100% MeOH in DCM, to provide the initial product. The mixture of diastereomers was purified by reverse-phase preparative HPLC using a Capcell Pak C18 (UG120 5 um, 30×250 mm), 0.1% TFA in $CH_3CN/H_2O$, gradient 5-95% over 35 min to provide a separated pair of diastereomers 623.0 as an off-white solid (43 mg, TFA salt). $^1H$ NMR (400 MHz, $CD_3CN$) δ 1.38-1.55 (m, 3H) 2.36 (s, 3H) 3.14 (s, 3H) 3.67-3.88 (m, 7H) 4.31 (d, J=4.11 Hz, 1H) 6.79 (d, J=8.41 Hz, 1H) 6.82 (d, J=8.61 Hz, 1H) 7.10 (dd, J=9.00, 2.74 Hz, 1H) 7.25 (td, J=8.51, 2.74 Hz, 1H) 7.44 (dd, J=8.41, 5.48 Hz, 1H) 7.54 (t, J=8.61 Hz, 1H) 7.87 (s, 1H) 8.45 (br. s., 1H) 8.55 (br. s., 1H). LCMS-ESI (POS.) M/Z: 567.2 $(M+H)^+$.

The compounds set forth in the following Table were synthesized following the procedure in Example B using the known starting material as described.

TABLE 17

| Example | Reagents | Structure, Name and Data |
|---------|----------|--------------------------|
| 624.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-pyridine, (Example 2.1). The racemic mixture was purified by preparative SFC method #1 (Purification #1): Column: ChiralPak AD-H (Reversed) (250 × 21 mm, 5 μm) Mobile Phase: 80:20 (A:B) A: Liquid $CO_2$, B: EtOH (20 mM $NH_3$), Flow Rate: 70 mL/min, Column/Oven temp.: 40° C., 220 nm, 179-186 bar inlet pressure. Then by Preparative SFC method #2 (Purification #2): Column: ChiralPak AD-H (Reversed) (250 × 21 mm, 5 μm) Mobile Phase: 82:18 (A:B), A: Liquid $CO_2$, B: EtOH (20 mM $NH_3$), Flow Rate: 70 mL/min, Column/Oven temp.: 40° C., 220 nm, 179 bar inlet pressure to deliver the second eluting peak. | or<br><br>(1S,2R)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide or (1R,2S)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide.<br>$^1H$ NMR ($CDCl_3$) δ 11.41 (br. s., 1 H), 8.56-8.73 (m, 4 H), 7.73 (dt, J = 8.04, 1.97 Hz, 1 H), 7.39 (t, J = 8.55 Hz, 1 H), 7.18-7.28 (m, 1 H), 6.61 (t, J = 7.75 Hz, 2 H), 5.03 (d, J = 6.43 Hz, 1 H), 3.63-3.88 (m, 8 H), 2.33 (s, 3 H), |

| Example | Reagents | Structure, Name and Data |
|---|---|---|
| | | 1.48 (d, J = 7.02 Hz, 3 H), 1.14-1.23 (m, 3 H), 1.01 (d, J = 6.14 Hz, 3 H). LCMS ESI (POS.) m/z: 554.0 [M + H]. |
| 625.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-pyridine (Example 2.1). The racemic mixture was purified by preparative SFC method (Purification #1): Column: ChiralPak AD-H (Reversed) (250 × 21 mm, 5 μm) Mobile Phase: 80:20 (A:B) A: Liquid $CO_2$, B: EtOH (20 mM $NH_3$), Flow Rate: 70 mL/min, Column/Oven temp.: 40° C., 220 nm, 179-186 bar inlet pressure. Then by Preparative SFC method #2 (Purification #2): Column: ChiralPak AD-H (Reversed) (250 × 21 mm, 5 μm) Mobile Phase: 82:18 (A:B), A: Liquid $CO_2$, B: mM $NH_3$), Flow Rate: 70 mL/min, Column/Oven temp.: 40° C., 220 nm, 179 bar inlet pressure, to deliver peak 3. | 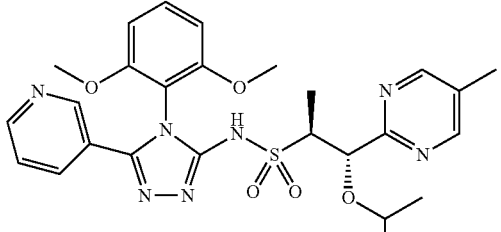 or 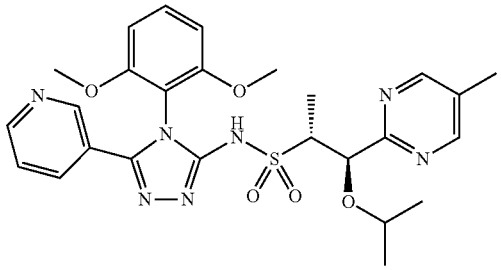 [SMILES: COc1cccc(OC)c1-n1c(NS(=O)(=O)[C@H](C)[C@H](OC(C)C)c2ncc(C)cn2)nnc1-c1cccnc1]<br><br>(1R,2R)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide.<br>$^1$H NMR (CDCl$_3$) δ 12.90 (br. s., 1 H), 8.56-8.72 (m, 4 H), 7.71 (dt, J = 7.97, 2.01 Hz, 1 H), 7.37 (t, J = 8.55 Hz, 1 H), 7.17-7.27 (m, 1 H), 6.51-6.70 (m, 2 H), 4.92 (d, J = 4.09 Hz, 1 H), 3.83 (s, 3 H), 3.76 (dd, J = 7.09, 4.17 Hz, 1 H), 3.69 (s, 3 H), 3.61 (dt, J = 12.20, 6.03 Hz, 1 H), 2.37 (s, 3 H), 1.48 (d, J = 7.16 Hz, 3 H), 1.15 (d, J = 5.99 Hz, 3 H), 1.03 (d, J = 5.99 Hz, 3 H).<br>LCMS ESI (POS.) m/z = 554.0 [M + H]. |
| 626.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-pyridine (Example 2.1). The racemic mixture was purified by preparative SFC method #1 (Purification #1): Column: ChiralPak AD-H (Reversed) (250 × 21 mm, 5 μm) Mobile Phase: 80:20 (A:B) A: Liquid $CO_2$, B: EtOH (20 mM $NH_3$), Flow Rate: 70 mL/min, Column/Oven temp.: 40° C., 220 nm, 179-186 bar inlet pressure. Then by Preparative SFC method #2 (Purification #2): Column: ChiralPak AD-H (Reversed) (250 × 21 mm, 5 μm) Mobile Phase: 82:18 (A:B), A: Liquid $CO_2$, B: EtOH (20 mM $NH_3$), Flow Rate: 70 mL/min, Column/Oven temp.: 40° C., 220 nm, 179 bar inlet pressure, to deliver peak 4. | 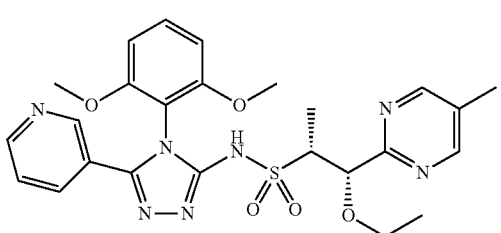 or 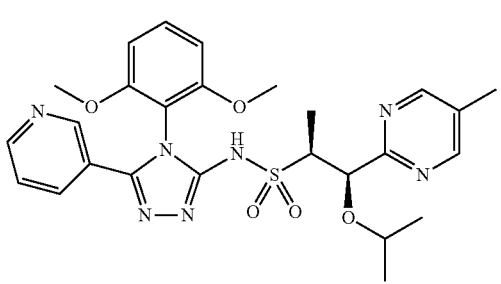 [SMILES: COc1cccc(OC)c1-n1c(NS(=O)(=O)[C@@H](C)[C@H](OC(C)C)c2ncc(C)cn2)nnc1-c1cccnc1] |

//

TABLE 17-continued

| Example | Reagents | Structure, Name and Data |
|---------|----------|--------------------------|
| | | (1S,2R)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide or (1R,2S)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide.<br>$^1$H NMR (CDCl$_3$) δ 8.61-8.71 (m, 4 H), 7.86-7.95 m. 1 H), 7.36-7.47 (m, 2 H), 6.57-6.68 (m, 2 H), 5.04 (d, J = 6.43 Hz, 1 H), 3.64-3.83 (m, 8 H), 2.35 (s, 3 H), 1.47 (d, J = 7.02 Hz, 3 H), 1.17 (d, J = 5.99 Hz, 3 H), 1.00 (d, J = 6.14 Hz, 3 H).<br>LCMS ESI (POS.) m/z = 554.0 [M + H]. |
| 627.0 | 1-isopropoxy-1-(5-methylpyrimidin-2-yl)propane-2-sulfonamide (Example 617.0), 3-(5-bromo-4-(2,6-dimethoxyphenyl)-4H-1,2,4-triazol-3-yl)-pyridine (Example 2.1). The racemic mixture was purified by preparative SFC method #1 (Purification #1): Column: ChiralPak AD-H (Reversed) (250 × 21 mm, 5 μm) Mobile Phase: 80:20 (A:B) A: Liquid CO$_2$, B: EtOH (20 mM NH$_3$), Flow Rate: 70 mL/min, Column/Oven temp.: 40° C., 220 nm, 179-186 bar inlet pressure. Then by Preparative SFC method #2 (Purification #2): Column: ChiralPak AD-H (Reversed) (250 × 21 mm, 5 μm) Mobile Phase: 82:18 (A:B), A: Liquid CO$_2$, B: EtOH (20 mM NH$_3$), Flow Rate: 70 mL/min, Column/Oven temp.: 40° C., 220 nm, 179 bar inlet pressure, to deliver peak 1. | 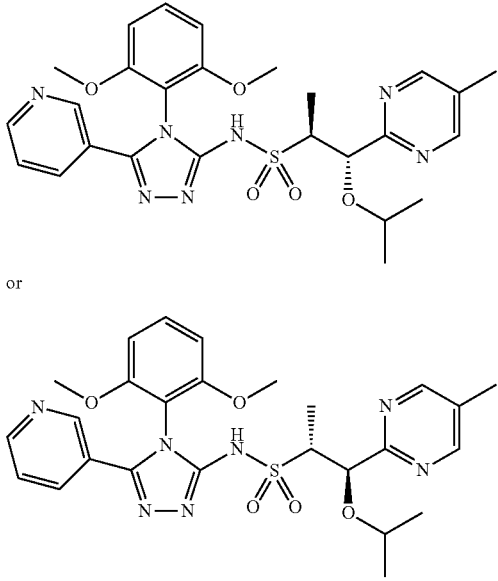<br>or<br><br>(1R,2R)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide or (1S,2S)-N-(4-(2,6-dimethoxyphenyl)-5-(pyridin-3-yl)-4H-1,2,4-triazol-3-yl)-1-isopropoxy-1-(5-methylpyrimidin-2-yl)propane-2-sulfonamide.<br>$^1$H NMR (CDCl$_3$) δ 12.90 (br. s., 1 H) 8.56-8.72 (m, 4 H), 7.71 (dt, J = 7.97, 2.01 Hz, 1 H), 7.37 (t, J = 8.55 Hz, 1 H), 7.17-7.27 (m, 1 H), 6.51-6.70 (m, 2 H), 4.92 (d, J = 4.09 Hz, 1 H), 3.83 (s, 3 H), 3.76 (dd, J = 7.09, 4.17 Hz, 1 H) 3.69 (s, 3 H), 3.61 (dt, J = 12.20, 6.03 Hz, 1 H), 2.37 (s, 3 H), 1.48 (d, J = 7.16 Hz, 3 H), 1.15 (d, J = 5.99 Hz, 3 H), 1.03 (d, J = 5.99 Hz, 3 H).<br>LCMS ESI (POS.) m/z = 554.0 [M + H]. |

The compounds set forth in the following Table were synthesized following the procedure in Example A using the known starting material as described.

TABLE 18

| Example | Reagents | Structure, Name and Data |
|---|---|---|
| 628.0 | (1R,2S)-1-methoxy-1-(5-methylpyrimidin-2-yl)propane-2-sulfonamide (Example 14.0), picolinhydrazide (Enamine), 5-isothiocyanato-4,6-dimethoxypyrimidine (Example 1.1) | (1R,2S)-N-(4-(4,6-dimethoxy-5-pyrimidinyl)-5-(2-pyridinyl)-4H-1,2,4-trizaol-3-yl)-1-methoxy-1-(5-methyl-2-pyrimidinyl)-2-propanesulfonamide<br>$^1$H NMR (500 MHz, DMSO-$d_6$) δ 13.50 (1 H, s) 8.65 (2 H, s) 8.63 (1 H, s) 8.32 (1 H, d, J = 4.41 Hz) 8.00-8.04 (1 H, m) 7.95 (1 H, td, J = 7.79, 1.62 Hz) 7.45 (1 H, td, J = 6.16, 0.84 Hz) 4.83 (1 H, d, J = 3.44 Hz) 3.84 (3 H, s) 3.83 (3 H, s) 3.41-3.48 (1 H, m) 3.15 (3 H, s) 2.27 (3 H, s) 1.16 (3 H, d, J = 7.01 Hz).<br>LCMS-ESI (POS.) m/z: 528.1 (M + H)$^+$. |
| 629.0 | (1R,2S)-1-methoxy-1-(5-methylpyrimidin-2-yl)propane-2-sulfonamide (Example 14.0), picolinhydrazide (Enamine), 2-isothiocyanato-1,3-dimethoxybenzene (Example 1.0), | (1R,2S)-N-(4-(2,6-dimethoxyphenyl)-5-(2-pyridinyl)-4H-1,2,4-triazol-3-yl)-1-(5-methyl-2-pyrimidinyl)-2-propanesulfonamide<br>$^1$H NMR (400 MHz, DMSO-$d_6$) δ 13.25 (1 H, s) 8.65 (2 H, d, J = 0.62 Hz) 8.30 (1 H, d, J = 4.35 Hz) 7.85-7.93 (1 H, m) 7.78-7.84 (1 H, m) 7.36-7.45 (2 H, m) 6.75 (2 H, d, J = 8.50 Hz) 4.83 (1 H, d, J = 3.63 Hz) 3.62 (6 H, d, J = 8.40 Hz) 3.44 (1 H, br dd, J = 7.00, 3.63 Hz) 3.16 (3 H, s) 1.15 (3 H, d, J = 7.05 Hz).<br>LCMS-ESI (POS.) m/z: 526.2 (M + H)$^+$. |
| 630.0 | (1R,2R)-1-methoxy-1-(4-methylthiazol-2-yl)propane-2-sulfonamide and (1R,2R)-1-methoxy-1-(4-methylthiazol-2-yl)propane-2-sulfonamide (prepared in an ana637.0logeous fashion to Example 11.04 and Example 14.05 employing 4-methylthiazole-2-carbaldehyde), 2-isothiocyanato-1,3-dimethoxybenzene (Example 1.0), 5-methylnicotinohydrazide, Example 3.11 | AND |

TABLE 18-continued

| Example Reagents | Structure, Name and Data |
|---|---|

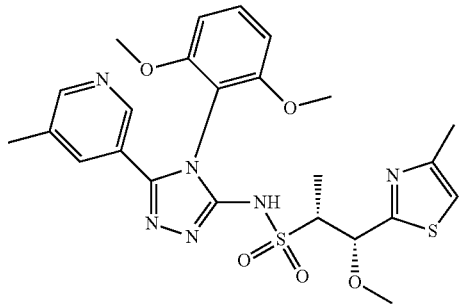 [SMILES: COc1cccc(OC)c1-n1c(NS(=O)(=O)[C@H](C)[C@@H](OC)c2nc(C)cs2)nnc1-c1cncc(C)c1]

(1R,2R)-N-(4-(2,6-dimethoxyphenyl)-5-
(5-methylpyridin-3-yl)-4H-1,2,4-triazol-3-yl)-1-
methoxy-1-(4-methylthiazol-2-yl)propane-2-
sulfonamide and (1S,2S)-N-(4-(2,6-
dimethoxyphenyl)-5-(5-methylpyridin-3-yl)-
4H-1,2,4-triazol-3-yl)-1-methoxy-1-(4-
methylthiazol-2-yl)propane-2-sulfonamide
$^1$H NMR (400 MHz, CD$_2$Cl$_2$) δ 1.22-1.32 (m, 3 H),
2.31 (s, 3 H) 2.42 (d, J = 0.88 Hz, 3 H) 3.41 (s, 3 H)
3.49-3.61 (m, 1 H) 3.77 (s, 3 H), 3.78 (s, 3 H),
5.19 (d, J = 2.23 Hz, 1 H), 6.70 (dd, J = 8.55, 3.63 Hz,
2 H) 6.90 (d, J = 0.98 Hz, 1 H) 7.48 (t,
J = 8.53 Hz, 1 H) 7.62-7.66 (m, 1 H)
8.33-8.40 (m, 1 H) 8.43-8.49 (m,
1 H) 11.26 (br s, 1 H).
LCMS-ESI (pos.) m/z: 545.2 (M + H)$^+$.

Example 631.0: Preparation of (2S,3R)—N-(4-(2,6-(trimethoxyphenyl)-5-(5-methyl-3-pyridinyl)-4H-1,2,4-triazol-3-yl)-N-methyl-3-(5-methyl-2-pyrimidinyl)-2-butanesulfonamide or (2S,3R,Z)—N-(4-(2,6-(trimethoxyphenyl)-1-methyl-3-(5-methylpyridin-3-yl)-1H-1,2,4-triazol-5(4H)-ylidene)-3-(5-methylpyrimidin-2-yl)butane-2-sulfonamide (2S,3R)—N-(4-(2,6-dimethoxyphenyl)-5-(5-methyl-3-pyridinyl)-4H-1,2,4-triazol-3-yl)-N-methyl-3-(5-methyl-2-pyrimidinyl)-2-butanesulfonamide or (2S,3R,Z)—N-(4-(2,6-dimethoxyphenyl)-1-methyl-3-(5-methylpyridin-3-yl)-1H-1,2,4-triazol-5(4H)-ylidene)-3-(5-methylpyrimidin-2-yl)butane-2-sulfonamide, Example 631.0

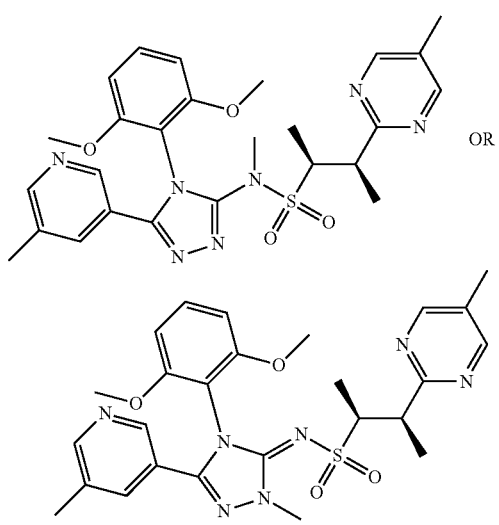

631.0

To a vial containing (2S,3R)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide (0.054 g, 0.103 mmol) in DMF (0.26 mL) was added methyl iodide (6.4 µL, 0.103 mmol) followed by cesium carbonate (0.037 g, 0.113 mmol). The mixture was stirred at 23° C. for 1 h and monitored with LC-MS. The mixture was then concentrated under reduced pressure, and the residue was loaded onto a silica gel column and purified (0-100% of (EtOAc/EtOH (3/1) in hexane)) to afford 631.0 as a white solid (0.019 g, 0.034 mmol, 33% yield). $^1$H NMR (400 MHz, CD$_2$Cl$_2$) δ 1.06 (d, J=6.89 Hz, 3H), 1.17 (d, J=7.05 Hz, 3H), 2.27 (s, 3H) 2.30 (s, 3H) 3.55-3.68 (m, 2H) 3.77 (s, 3H) 3.81 (s, 3H), 4.03 (s, 3H), 6.62-6.68 (m, 2H) 7.42 (t, J=8.53 Hz, 1H) 7.60-7.64 (m, 1H) 8.34 (d, J=1.81 Hz, 1H) 8.44 (m, 1H), 8.48 (s, 2H). LCMS-ESI (pos.) m/z: 538.2 (M+H)$^+$.

The compounds set forth in the following Table were synthesized following the procedure in Example A using the known starting material as described.

TABLE 19

| Example | Reagents | Structure, Name and Data |
|---|---|---|
| 632.0 | (1S,2R)-1-methoxy-1-(5-methyloxazol-2-yl)propane-2-sulfonamide and (1R,2S)-1-methoxy-1-(5-methyloxazol-2-yl)propane-2-sulfonamide (prepared in an analogous fashion to Example 11.04 and Example 14.05 employing 5-methyloxazole-2-carbaldehyde), 2-isothiocyanato-1,3-dimethoxybenzene (Example 1.0), 5-methylnicotinohydrazide, Example 3.11. The racemic mixture was purified by preparative SFC method: Column: ChiralPak AD-H 40% IPA to deliver peak 1. | OR<br><br>(1S,2R)-N-(4-(2,6-dimethoxyphenyl)-5-(5-methylpyridin-3-yl)-4H-1,2,4-triazol-3-yl)-1-methoxy-1-(5-methyloxazol-2-yl)propane-2-sulfonamide or (1R,2S)-N-(4-(2,6-dimethoxyphenyl)-5-(5-methylpyridin-3-yl)-4H-1,2,4-triazol-3-yl)-1-methoxy-1-(5-methyloxazol-2-yl)propane-2-sulfonamide<br>$^1$H NMR (500 MHz, DMSO-$d_6$) δ 1.42 (d, J = 6.95 Hz, 3 H) 2.18 (d, J = 1.09 Hz, 3 H) 2.31 (s, 3 H) 3.30 (s, 3 H) 3.52 (dd, J = 6.97, 4.38 Hz, 1 H) 3.79 (m, 6 H) 4.86 (d, J = 4.30 Hz, 1 H) 6.71 (d, J = 8.55 Hz, 2H) 7.42 (s, 1 H) 7.50 (t, J = 8.53 Hz, 1 H) 7.64 (s, 1 H) 8.30-8.60 (br s, 2H) 11.27 (br s, 1 H). LCMS-ESI (POS.) m/z: 529.2 (M + H)$^+$. |
| 633.0 | (1S,2R)-1-methoxy-1-(5-methyloxazol-2-yl)propane-2-sulfonamide and (1R,2S)-1-methoxy-1-(5-methyloxazol-2-yl)propane-2-sulfonamide (prepared in an analogous fashion to Example 11.04 and Example 14.05 employing 5-methyloxazole-2-carbaldehyde), 2-isothiocyanato-1,3-dimethoxybenzene (Example 1.0), 5-methylnicotinohydrazide, Example 3.11. The racemic mixture was purified by preparative SFC method: Column: ChiralPak AD-H 40% IPA to deliver peak 1. | OR<br><br>(1S,2R)-N-(4-(2,6-dimethoxyphenyl)-5-(5-methylpyridin-3-yl)-4H-1,2,4-triazol-3-yl)-1-methoxy-1-(5-methyloxazol-2-yl)propane-2-sulfonamide or (1R,2S)-N-(4-(2,6- |

TABLE 19-continued

| Example | Reagents | Structure, Name and Data |
|---|---|---|
| | | dimethoxyphenyl)-5-(5-methylpyridin-3-yl)-4H-1,2,4-triazol-3-yl)-1-methoxy-1-(5-methyloxazol-2-yl)propane-2-sulfonamide<br>$^1$H NMR (500 MHz, DMSO-$d_6$) δ 1.42 (d, J = 6.95 Hz, 3 H) 2.18 (d, J = 1.09 Hz, 3 H) 2.31 (s, 3 H) 3.30 (s, 3 H) 3.52 (dd, J = 6.97, 4.38 Hz, 1 H) 3.79 (m, 6 H) 4.86 (d, J = 4.30 Hz, 1 H) 6.71 (d, J = 8.55 Hz, 2 H) 7.42 (s, 1 H) 7.50 (t, J = 8.53 Hz, 1 H) 7.64 (s, 1 H) 8.30-8.60 (br s, 2H) 11.27 (br s, 1 H). LCMS-ESI (POS.) m/z: 529.2 (M + H)$^+$. |
| 634.0 | The racemic mixture Example 630.0 was purified by preparative SFC method: Column: ChiralPak AS-H (Reversed) (2 × 15 cm) Mobile Phase: 78:22 (A:B) A: Liquid CO$_2$, B: iPrOH (0.1% DEA), Flow Rate: 60 mL/min, 220 nm, 100 bar to deliver peak 1. | 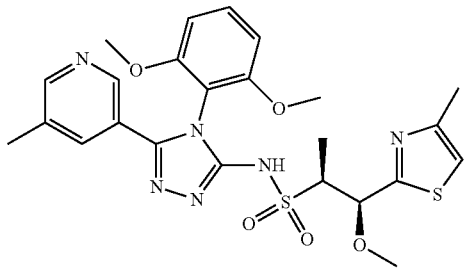 [SMILES: COc1cccc(OC)c1-n1c(NS(=O)(=O)[C@@H](C)[C@H](OC)c2nc(C)cs2)nnc1-c1cncc(C)c1]<br><br>OR<br><br>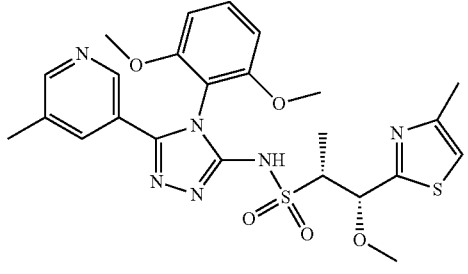 [SMILES: COc1cccc(OC)c1-n1c(NS(=O)(=O)[C@H](C)[C@@H](OC)c2nc(C)cs2)nnc1-c1cncc(C)c1]<br><br>(1R,2R)-N-(4-(2,6-dimethoxyphenyl)-5-(5-methylpyridin-3-yl)-4H-1,2,4-triazol-3-yl)-1-methoxy-1-(4-methylthiazol-2-yl)propane-2-sulfonamide or (1S,2S)-N-(4-(2,6-dimethoxyphenyl)-5-(5-methylpyridin-3-yl)-4H-1,2,4-triazol-3-yl)-1-methoxy-1-(4-methylthiazol-2-yl)propane-2-sulfonamide<br>$^1$H NMR (400 MHz, CD$_2$Cl$_2$) δ 1.23-1.25 (m, 3 H), 2.29 (s, 3 H) 2.42 (s, 3 H) 3.44 (s, 3 H), 3.61 (qd, J = 7.01, 1.58 Hz, 1 H), 3.76 (d, J = 3.27 Hz, 6 H), 5.14 (br s, 1H), 5.22 (m, 1 H) 6.70 (dd, J = 8.29, 3.01 Hz, 2H) 6.90 (s, 1 H) 7.47 (t, J = 8.42 Hz, 1 H) 7.62 (s, 1 H) 8.37 (br s, 1 H) 8.43 (br s, 1 H). LCMS-ESI (pos.) m/z: 545.0 (M + H)$^+$. |
| 635.0 | The racemic mixture Example 630.0 was purified by preparative SFC method: Column: ChiralPak AS-H (Reversed) (2 × 15 cm) Mobile Phase: 78:22 (A:B) A: Liquid CO$_2$, B: iPrOH (0.1% DEA), Flow Rate: 60 mL/min, 220 nm, 100 bar to deliver the second eluting peak. | 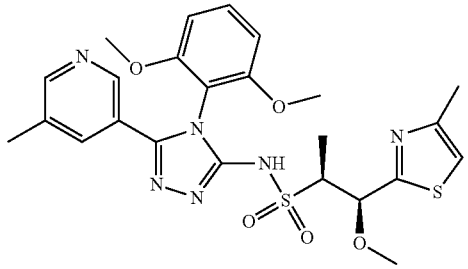 [SMILES: COc1cccc(OC)c1-n1c(NS(=O)(=O)[C@@H](C)[C@H](OC)c2nc(C)cs2)nnc1-c1cncc(C)c1] |

TABLE 19-continued

| Example | Reagents | Structure, Name and Data |
|---------|----------|--------------------------|

OR

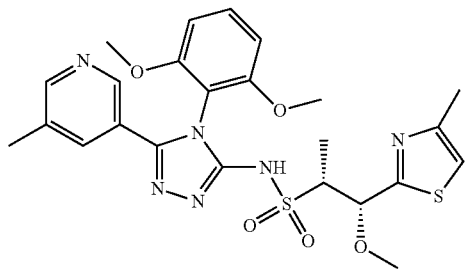 [SMILES: COc1cccc(OC)c1-n1c(NS(=O)(=O)[C@H](C)[C@@H](OC)c2nc(C)cs2)nnc1-c1cncc(C)c1]

(1R,2R)-N-(4-(2,6-dimethoxyphenyl)-5-(5-methylpyridin-3-yl)-4H-1,2,4-triazol-3-yl)-1-methoxy-1-(4-methylthiazol-2-yl)propane-2-sulfonamide or (1S,2S)-N-(4-(2,6-dimethoxyphenyl)-5-(5-methylpyridin-3-yl)-4H-1,2,4-triazol-3-yl)-1-methoxy-1-(4-methylthiazol-2-yl)propane-2-sulfonamide
$^1$H NMR (400 MHz, CD$_2$Cl$_2$) δ 1.22-1.32 (m, 3 H), 2.28 (s, 3 H) 2.42 (s, 3 H) 3.35 (s, 1 H) 3.45 (s, 8 H) 3.56-3.70 (m, 1 H), 3.75 (d, J = 3.47 Hz, 6 H) 4.82 (br s, 1 H) 5.19-5.27 (m, 1 H) 6.70 (dd, J = 8.40, 2.28 Hz, 2 H) 6.90 (s, 1 H) 7.46 (t, J = 8.47 Hz, 1 H) 7.61 (s, 1 H) 8.36 (br s, 1 H) 8.42 (br s, 1H). LCMS-ESI (pos.) m/z: 545.2 (M + H)$^+$.

30

The compounds set forth in the following Table were synthesized following the procedure in Example 741.0 using the known starting material as described.

TABLE 20

| Example | Reagents | Structure, Name and Data |
|---------|----------|--------------------------|
| 636.0 | (1R,2S)-1-methoxy-1-(5-methylpyrimidin-2-yl)propane-2-sulfonamide (Example 14.0), 3-isothiocyanato-2,4-dimethoxypyridine (Example 771.1), 6-methoxypicolinohydrazide, Example 3.18. | 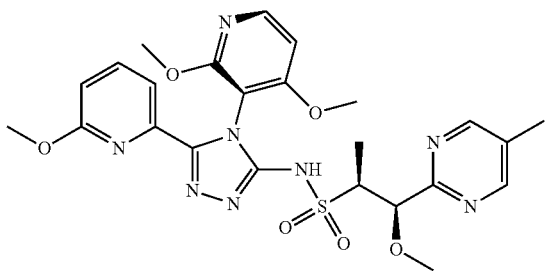 |

AND

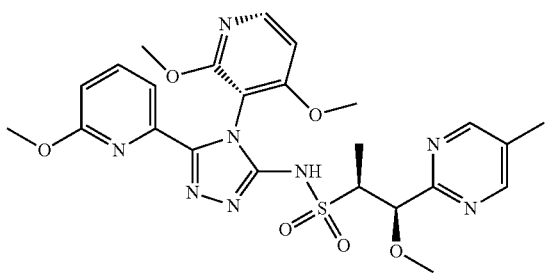

(1R,2S,P)-N-(4-(2,4-dimethoxypyridin-3-yl)-5-(6-methoxypyridin-2-yl)-4H-1,2,4-triazol-3-yl)-1-methoxy-1-(5-methylpyrimidin-2-yl)propane-2-sulfonamide and (1R,2S,M)-N-(4-(2,4-dimethoxypyridin-3-yl)-5-(6-methoxypyridin-2-yl)-4H-1,2,4-triazol-3-yl)-1-methoxy-1-(5-

| Example | Reagents | Structure, Name and Data |
|---|---|---|
| | | methylpyrimidin-2-yl)propane-2-sulfonamide<br>$^1$H NMR (400 MHz, CD$_2$Cl$_2$) δ 1.32 (m, 3 H) 2.32 (s, 3 H) 3.22 (s, 3 H) 3.29 (d, J = 2.59 Hz, 3 H) 3.62-3.70 (m, 1 H) 3.80-3.89 (m, 6 H) 4.94 (dd, J = 4.17, 1.32 Hz, 1 H) 6.71-6.78 (m, 2 H) 7.66-7.71 (m, 2 H) 8.18 (dd, J = 5.96, 1.61 Hz, 1 H) 8.60 (s, 2 H). LCMS-ESI (POS.) m/z: 557.2 (M + H)$^+$. |
| 637.0 | (1R,2S)-1-methoxy-1-(1-methyl-1H-1,2,4-triazol-5-yl)propane-2-sulfonamide and (1S,2R)-1-methoxy-1-(1-methyl-1H-1,2,4-triazol-5-yl)propane-2-sulfonamide (prepared in an analogous fashion to Example 11.04 and Example 14.05 employing 1-methyl-1H-1,2,4-triazole-5-carbaldehyde), 2-isothiocyanato-1,3-dimethoxybenzene (Example 1.0), 5-methylnicotinohydrazide, Example 3.11. | AND<br><br>(1S,2R)-N-(4-(2,6-dimethoxyphenyl)-5-(5-methylpyridin-3-yl)-4H-1,2,4-triazol-3-yl)-1-methoxy-1-(1-methyl-1H-1,2,4-triazol-5-yl)propane-2-sulfonamide and (1R,2S)-N-(4-(2,6-dimethoxyphenyl)-5-(5-methylpyridin-3-yl)-4H-1,2,4-triazol-3-yl)-1-methoxy-1-(1-methyl-1H-1,2,4-triazol-5-yl)propane-2-sulfonamide<br>$^1$H NMR (400 MHz, CD$_2$Cl$_2$) δ 1.46 (d, J = 7.00 Hz, 3 H) 2.32 (s, 10 H) 3.25 (s, 3 H) 3.59 (dd, J = 6.92, 6.04 Hz, 1 H) 3.79 (d, J = 3.63 Hz, 6H) 3.87 (s, 3 H) 4.94 (d, J = 5.91 Hz, 1 H) 6.71 (dd, J = 8.55, 2.23 Hz, 2 H) 7.50 (t, J = 8.55 Hz, 1 H) 7.66 (s, 1 H) 7.83 (s, 1 H) 8.36 (d, J = 1.81 Hz, 1 H) 8.47 (d, J = 1.45 Hz, 1 H) 11.42 (br s, 1 H). LCMS-ESI (POS.) m/z: 529.2 (M + H)$^+$. |

The compounds set forth in the following Table were synthesized following the procedure in Example A using the known starting material as described.

TABLE 21

| Example | Reagents | Structure, Name and Data |
|---|---|---|
| 638.0 | (1R,2S)-1-ethoxy-1-(5-fluoropyrimidin-2-yl)propane-2-sulfonamide (Example 10.1), 6-(2-methoxyethoxy)-picolinohydrazide (Example 3.26), 2-isothiocyanato-1,3-dimethoxybenzene (Example 1.0) | 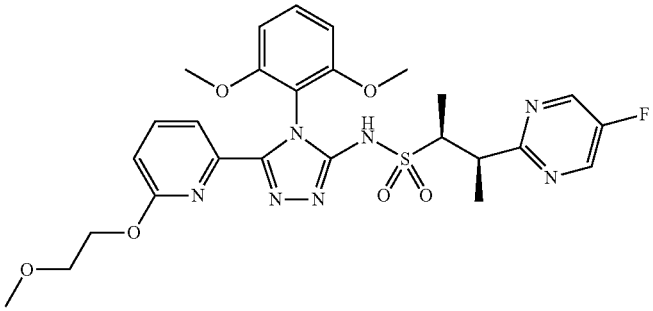 [SMILES: COCCOc1cccc(-c2nnc(NS(=O)(=O)[C@@H](C)[C@H](C)c3ncc(F)cn3)n2-c2c(OC)cccc2OC)n1]<br>(2S,3R)-N-(4-(2,6-dimethoxyphenyl)-5-(6-(2-methoxyethoxy)pyridin-2-yl)-4H-1,2,4-triazol-3-yl)-3-(5-fluoropyrimidin-2-yl)butane-2-sulfonamide<br>$^1$H NMR (400 MHz, CDCl$_3$) δ 11.0 (br s, 1H), 8.53 (s, 2H), 7.60-7.65 (m, 2H), 7.33 (dd, J = 8.5, 8.5 Hz, 1H), 6.77 (dd, J = 6.8, 2.2 Hz, 1H), 6.58-6.62 (m, 2H), 3.81-3.87 (m, 2H), 3.70 (s, 3H), 3.68 (s, 3H), 3.51-3.55 (m, 2H), 3.40-3.43 (m, 2H), 3.37 (s, 3H), 1.36 (d, J = 6.8 Hz, 3H), 1.34 (d, J = 6.8 Hz, 3H).<br>LCMS-ESI (pos.) m/z: 587.6 (M + H)$^+$. |
| 639.0 | (1R,2S)-1-ethoxy-1-(5-fluoropyrimidin-2-yl)propane-2-sulfonamide (Example 10.1), 6-(3,3,3-trifluoro-2-hydroxy-2-(trifluoromethyl)propoxy) picolinohydrazide (Example 3.24), 2-isothiocyanato-1,3-dimethoxybenzene (Example 1.0)<br>The mixture of the products were purified by supercritical fluid chromatography using the following method. ID (5 μm, 21 mm × 25 cm, S/n = 3041, 50/50/50, regular direction, p = 200 bar) with 20% organic modifier: 80% carbon dioxide; Organic modifier: MeOH with 20 mM ammonia. F = 70 mL/min, T = 40° C., BPR = 100 bar, P = 172 bar, 220 nm. All sample (70 mg) dissolved in 4 mL MeOH and 1 mL DCM, 14 mg/mL), 0.6 mL (8 mg) injection.<br>Three peaks were collected. This was the second peak to elute under these conditions. | 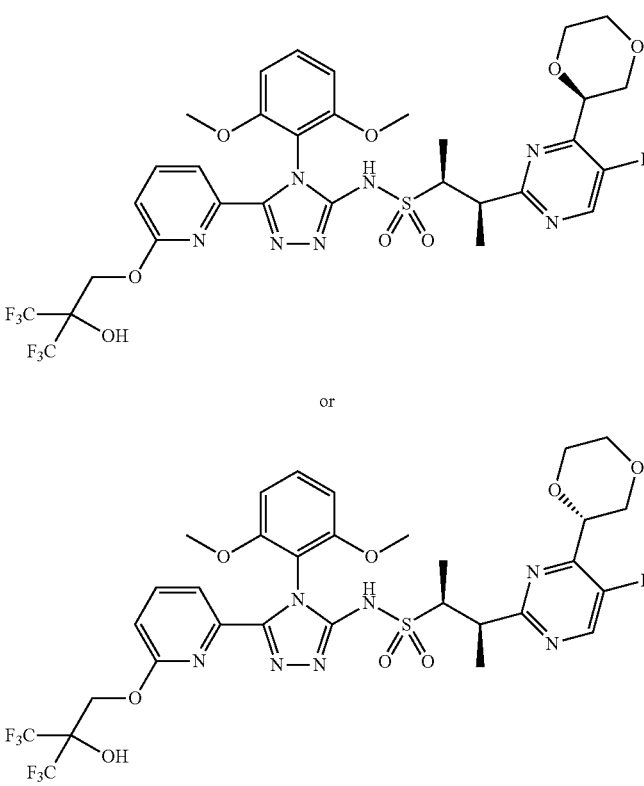<br>or<br><br>(2S,3R)-3-(4-((R)-1,4-dioxan-2-yl)-5-fluoropyrimidin-2-yl)-N-(4-(2,6-dimethoxyphenyl)-5-(6-(3,3,3-trifluoro-2-hydroxy-2-(trifluoromethyl)propoxy)pyridin-2-yl)-4H-1,2,4-triazol-3-yl)butane-2-sulfonamide or (2S,3R)-3-(4-((S)-1,4-dioxan-2-yl)-5-fluoropyrimidin-2-yl)-N-(4-(2,6-dimethoxyphenyl)-5-(6-(3,3,3-trifluoro-2-hydroxy-2-(trifluoromethyl)propoxy)pyridin-2-yl)-4H-1,2,4-triazol-3-yl)butane-2-sulfonamide<br>$^1$H NMR (400 MHz, CDCl$_3$) δ 8.51 (d, J = 1.6 Hz, 1H), 7.7 (t, J = 7.9, 7.9 Hz, 1H), 7.34-7.37 (m, 2H), 6.89 (d, J = 7.8 Hz, 1H), 6.56-6.65 (m, 2H), 5.02 (dd, J = 9.8, 2.0 Hz, 1H), 4.12-4.17 (m, 3H), 3.95-3.99 (m, 2H), 3.68-3.93 (m, 5H), 3.75 (s, 3H), 3.63 (s, |

TABLE 21-continued

| Example | Reagents | Structure, Name and Data |
|---|---|---|
| | | 3H), 1.40 (d, J = 7.3 Hz, 3H), 1.38 (d, J = 7.3 Hz, 3H). LCMS-ESI (pos.) m/z: 796.2 (M + H)+. |
| 640.0 | 1R,2S)-1-ethoxy-1-(5-fluoropyrimidin-2-yl)propane-2-sulfonamide (Example 10.1), 6-(3,3,3-trifluoro-2-hydroxy-2-(trifluoromethyl)propoxy) picolinohydrazide (Example 3.24), 2-isothiocyanato-1,3-dimethoxybenzene (Example 1.0) The mixture of the products were purified by supercritical fluid chromatography using the following method. ID (5 um, 21 mm × 25 cm, S/N = 3041, 50/50/50, regular direction, P = 200 bar) with 20% organic modifier: 80% carbon dioxide; Organic modifier: MeOH with 20 mM ammonia. F = 70 mL/min, T = 40° C., BPR = 100 bar, P = 172 bar, 220 nm. All sample (70 mg) dissolved in 4 mL MeOH and 1 mL DCM, 14 mg/mL), 0.6 mL (8 mg) injection. Three peaks were collected. This was the third peak to elute under these conditions. | 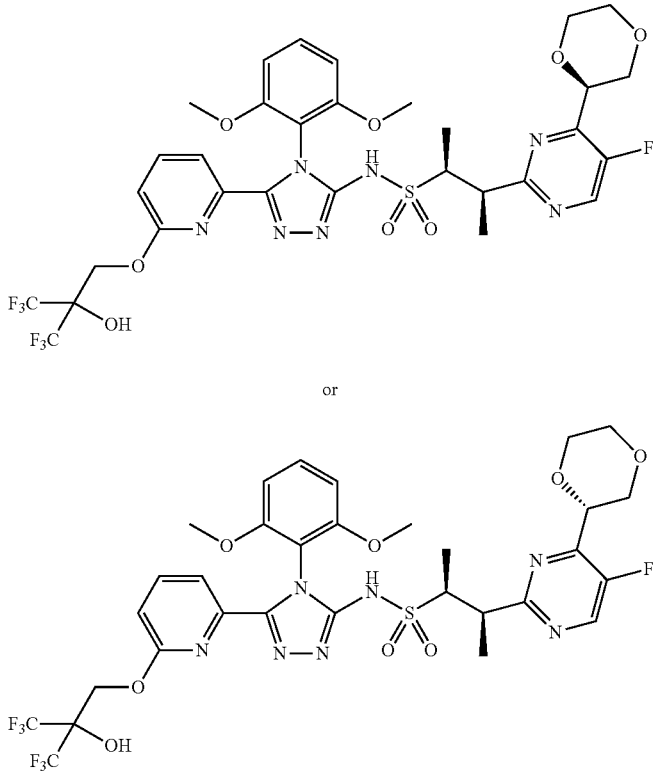 or 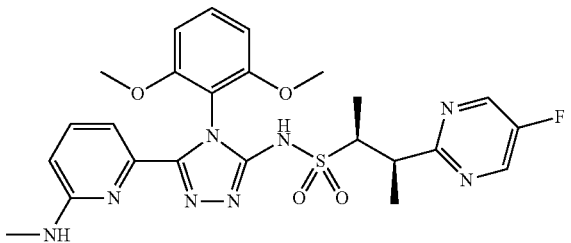 (2S,3R)-3-(4-((R)-1,4-dioxan-2-yl)-5-fluoropyrimidin-2-yl)-N-(4-(2,6-dimethoxyphenyl)-5-(6-(3,3,3-trifluoro-2-hydroxy-2-(trifluoromethyl)propoxy)pyridin-2-yl)-4H-1,2,4-triazol-3-yl)butane-2-sulfonamide or (2S,3R)-3-(4-((S)-1,4-dioxan-2-yl)-5-fluoropyrimidin-2-yl)-N-(4-(2,6-dimethoxyphenyl)-5-(6-(3,3,3-trifluoro-2-hydroxy-2-(trifluoromethyl)propoxy)pyridin-2-yl)-4H-1,2,4-triazol-3-yl)butane-2-sulfonamide <br> 1H NMR (400 MHz, CDCl3) δ 10.09 (br s, 1H) 8.50 (d, J = 1.8 Hz, 1H), 7.7 (d, J = 7.5, 7.5 Hz, 1H), 7.34-7.39 (m, 2H), 6.89 (d, J = 8.4 Hz, 1H), 6.61 (dd, J = 8.6, 3.9 Hz, 2H), 5.01 (dd, J = 9.9, 2.0 Hz, 1H), 4.13-4.17 (m, 3H), 3.74-4.00 (obscured m, 5H), 3.70 (s, 3H), 3.68 (s, 3H), 1.40 (d, J = 7.0 Hz, 3H), 1.37 (d, J = 7.0 Hz, 3H). LCMS-ESI (pos.) m/z: 796.2 (M + H)+. |
| 641.0 | (1R,2S)-1-ethoxy-1-(5-fluoropyrimidin-2-yl)propane-2-sulfonamide (Example 10.1), 6-(methylamino)picolinohydrazide (Example 3.25), 2-isothiocyanato-1,3-dimethoxybenzene (Example 1.0) | (2S,3R)-N-(4-(2,6-dimethoxyphenyl)-5-(6-(methylamino)pyridin-2-yl)-4H-1,2,4-triazol-3-yl)-3-(5-fluoropyrimidin-2-yl)butane-2-sulfonamide <br> 1H NMR (400 MHz, CDCl3) ) δ 11.0 (br s, 1H), 8.52 (s, 2H), 7.38 (dd, J = 8.2, 7.4 Hz, 1H), 7.31 (t, J = 8.5, 8.5 Hz, 1H), 7.13 (d, J = 7.2 Hz, 1H), 6.57 (dd, J = 7.6, 7.6 Hz, 2H), 6.32 (d, J = 8.0 Hz, 1H), 4.18 (br | s, 1H), 3.80-3.87 (m, 2H), 3.70 (s, 3H), 3.67 (s, 3H), 2.40 (d, J = 3.9 Hz, 3H), 1.36 (d, J = 6.8 Hz, 3H), 1.34 (d, J = 6.7 Hz, 3H). LCMS-ESI (pos.) m/z: 543.2 (M + H)+.

Example 642.0: Preparation of (1R,2S)-1-(5-bromo-6-methylpyridin-2-yl)-N-(4-(2,6-dimethoxyphenyl)-5-(pyridin-3-yl)-4H-1,2,4-triazol-3-yl)-1-hydroxy-propane-2-sulfonamide and (1S,2R)-1-(5-bromo-6-methylpyridin-2-yl)-N-(4-(2,6-dimethoxyphenyl)-5-(pyridin-3-yl)-4H-1,2,4-triazol-3-yl)-1-hydroxypropane-2-sulfonamide

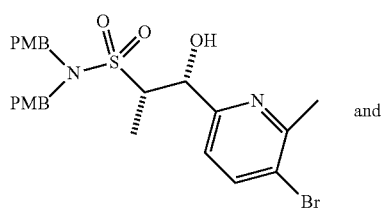

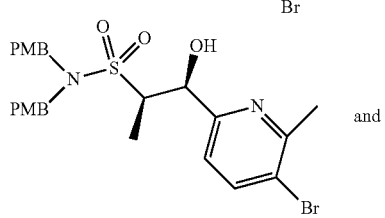

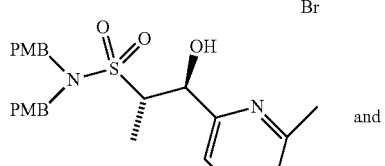

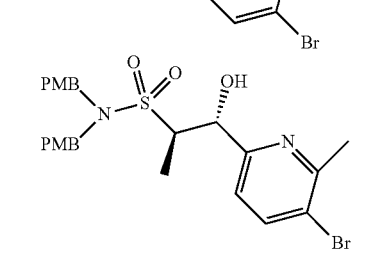

(1R,2R)-1-(5-bromo-6-methylpyridin-2-yl)-1-hydroxy-N,N-bis(4-methoxybenzyl)propane-2-sulfonamide compound and (1R,2S)-1-(5-bromo-6-methylpyridin-2-yl)-1-hydroxy-N,N-bis(4-methoxybenzyl)propane-2-sulfonamide and (1S,2R)-1-(5-bromo-6-methylpyridin-2-yl)-1-hydroxy-N,N-bis(4-methoxybenzyl)propane-2-sulfonamide and (1S,2S)-1-(5-bromo-6-methylpyridin-2-yl)-1-hydroxy-N,N-bis(4-methoxybenzyl)propane-2-sulfonamide, Example 642.1

To a solution of N,N-bis(4-methoxybenzyl)ethanesulfonamide (3.39 g, 9.70 mmol) in THF (24 mL) was added dropwise, n-butyllithium (1.6M in hexanes, 6.36 mL, 10.18 mmol) at −78° C. The resulting mixture was stirred at the same temperature for 30 minutes, and a solution of 3-bromo-2-methyl-pyridine-6-carbaldehyde (2.0 g, 9.70 mmol) in THF (8 mL) was added dropwise. The resulting mixture was warmed to RT and stirred for 24 hours. The mixture was then quenched with saturated aqueous NH$_4$Cl solution (50 mL) and the resulting mixture was extracted with EtOAc (80 mL×3). The combined extracts were dried (Na$_2$SO$_4$) and concentrated, and the the residue was purified by Isco CombiFlash on a 120 g silica gel column using 0-100% EtOAc gradient in heptane as the eluent to give Example 642.1 (2.87 g). LCMS (pos.) m/z: 550.0 (M+H)+.

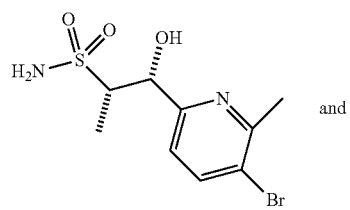

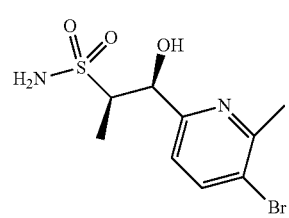

(1R,2S)-1-(5-bromo-6-methylpyridin-2-yl)-1-hydroxypropane-2-sulfonamide compound and (1S,2R)-1-(5-bromo-6-methylpyridin-2-yl)-1-hydroxypropane-2-sulfonamide, Example 642.2

To a mixture of Example 642.1 (2.77 g, 5.04 mmol) and anisole, 99% (5.48 mL, 50.4 mmol) was slowly added TFA (14.98 mL, 202 mmol) at RT. The resulting mixture was allowed to stir at RT for 24 hours. The mixture was concentrated in vacuo, and the residue was purified by Isco CombiFlash on a GraceResolv 220 g silica gel column using 0-100% EtOAc gradient in heptane as the eluent to give Example 642.2 (853 mg). $^1$H NMR (400 MHz, CDCl$_3$) δ 8.06 (d, J=8.2 Hz, 1H), 7.30 (d, J=8.4 Hz, 1H), 5.76 (br s, 2H), 5.59 (d, J=2.5 Hz, 1H), 5.04 (br s, 1H), 3.55-3.61 (m, 1H), 2.76 (s, 3H), 1.22 (d, J=7.3 Hz, 3H). LCMS-ESI (pos.) m/z: 310.0 (M+H)+

921

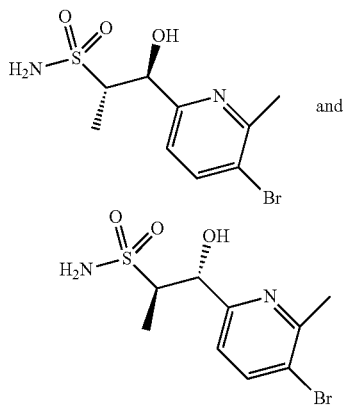

and 642.3

(1R,2R)-1-(5-bromo-6-methylpyridin-2-yl)-1-hydroxypropane-2-sulfonamide compound and (1S,2S)-1-(5-bromo-6-methylpyridin-2-yl)-1-hydroxypropane-2-sulfonamide, Example 642.3

Further elution using the conditions described in Example 642.2 delivered Example 642.3 (497 mg). $^1$H NMR (400 MHz, CDCl$_3$) δ 7.91 (d, J=8.0 Hz, 1H), 7.18 (d, J=8.2 Hz, 1H), 5.51 (br s, 3H), 4.99 (d, J=7.8 Hz, 1H), 3.53-3.60 (m, 1H), 2.67 (s, 3H), 1.25 (d, J=7.2 Hz, 3H). LCMS (pos.) m/z: 310.0 (M+H)$^+$.

The compounds set forth in the following Table were synthesized following the procedure in Example A using the known starting material as described.

TABLE 22

| Example | Reagents | Structure, Name and Data |
|---|---|---|
| 642.0 | 2-isothiocyanato-1,3-dimethoxybenzene (Example 1.0), (1R,2S)-1-(5-bromo-6-methylpyridin-2-yl)-1-hydroxypropane-2-sulfonamide and (1S,2R)-1-(5-bromo-6-methylpyridin-2-yl)-1-hydroxypropane-2-sulfonamide (Example 642.2), nicotinic hydrazide (Alfa Aesar) | [structures shown] and [structure shown]<br><br>(1R,2S)-1-(5-bromo-6-methylpyridin-2-yl)-N-(4-(2,6-dimethoxyphenyl)-5-(pyridin-3-yl)-4H-1,2,4-triazol-3-yl)-1-hydroxypropane-2-sulfonamide and (1S,2R)-1-(5-bromo-6-methylpyridin-2-yl)-N-(4-(2,6-dimethoxyphenyl)-5-(pyridin-3-yl)-4H-1,2,4-triazol-3-yl)-1-hydroxypropane-2-sulfonamide<br>$^1$H NMR (400 MHz, CDCl$_3$) δ 8.93 (s, 1H), 8.79 (s, 1H), 8.35 (d, J = 7.8 Hz, 1H), 8.23 (d, J = 8.4 Hz, 1H), 7.80-7.84 (m, 1H), 7.6 (d, J = 8.2 Hz, 1H), 7.48 (t, J = 8.5, 8.5 Hz, 1H), 6.69 (t, J = 8.4, 8.4 Hz, 2H), 5.69 (br s, 1H), 3.86-3.92 (m, 1H), 3.79 (s, 3H), 3.78 (s, 3H), 2.92 (s, 3H), 1.25 (d, J = 6.8 Hz, 3H).. LCMS-ESI (pos.) m/z: 590.1 (M + H)$^+$. |

Example 643.0: Preparation of (1R,2S)-1-(5-bromo-6-methylpyridin-2-yl)-N-(4-(2,6-dimethoxyphenyl)-5-(pyridin-3-yl)-4H-1,2,4-triazol-3-yl)-1-hydroxypropane-2-sulfonamide and (1S,2R)-1-(5-bromo-6-methylpyridin-2-yl)-N-(4-(2,6-dimethoxyphenyl)-5-(pyridin-3-yl)-4H-1,2,4-triazol-3-yl)-1-hydroxypropane-2-sulfonamide

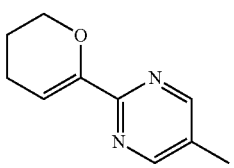

643.1

2-(3,4-Dihydro-2H-pyran-6-yl)-5-methylpyrimidine, Example 643.1

A mixture of 2-chloro-5-methylpyrimidine (1.2 g, 9.33 mmol), 3,4-dihydro-2h-pyran-6-boronic acid pinacol ester (2.94 mL, 14.0 mmol), tricyclohexylphosphine (0.524 g, 1.87 mmol) and tris-(dibenzylideneacetone) dipalladium (0) (0.855 g, 0.93 mmol) in a flask was degassed and backfilled with argon. To this mixture were added 1,4-dioxane (16 mL) and potassium phosphate tribasic (6.45 g, 28.0 mmol) in water (2.0 mL). A stream of argon was bubbled through the resulting mixture for an additional 5 minutes, and the mixture was stirred at 100° C. under a balloon of argon for 24 hours. The mixture was cooled to RT, filtered, and washed with EtOAc. The filtrate was concentrated in vacuo, and the residue was purified by Isco CombiFlash on a RediSep 80 g silica gel column using 0-100% EtOAc gradient in heptane as the eluent to give Example 643.1 (1.62 g). $^1$H NMR (400 MHz, CDCl$_3$) δ 8.48 (s, 2H), 6.26 (t, J=4.1, 4.1 Hz, 1H), 4.21-4.24 (m, 2H), 2.20-2.26 (obscured m, 2H), 2.25 (s, 3H), 1.9 (dd, J=5.6, 4.8 Hz, 2H). LCMS (pos.) m/z: 177.1 (M+H)$^+$.

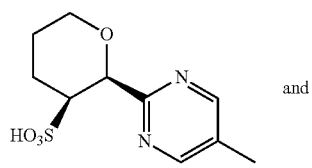

643.2

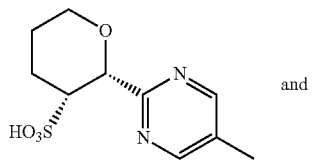

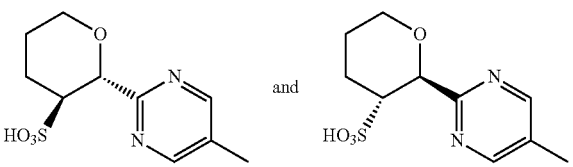

(2R,3R)-2-(5-methylpyrimidin-2-yl)tetrahydro-2H-pyran-3-sulfonic acid and (2R,3S)-2-(5-methylpyrimidin-2-yl)tetrahydro-2H-pyran-3-sulfonic acid and (2S,3R)-2-(5-methylpyrimidin-2-yl)tetrahydro-2H-pyran-3-sulfonic acid and (2S,3S)-2-(5-methylpyrimidin-2-yl)tetrahydro-2H-pyran-3-sulfonic acid, Example 643.2

To a solution of Example 643.1 (1.62 g, 9.19 mmol) in THF (15 mL) was added a solution of sodium bisulfite (7.55 g, 27.6 mmoL) in 5 mL of water at RT. The resulting mixture was then allowed to stir under a balloon of argon at 80° C. for 48 hours. The mixture was cooled to RT and concentrated in vacuo. To the residue was added water (30 mL) and the mixture was adjusted to pH=~2. The mixture was then extracted with DCM. The aqueous solution was lyophilized to give a white solid. The solid was triturated with EtOH. The resulting suspension was filtered through a pad of Celite® brand filter agent and washed with EtOH several times. The filtrate was concentrated to give Example 643.2 (2.48 g). LCMS (pos.) m/z: 259.0 (M=H)$^+$.

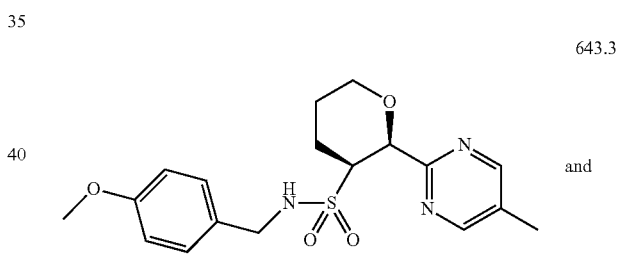

643.3

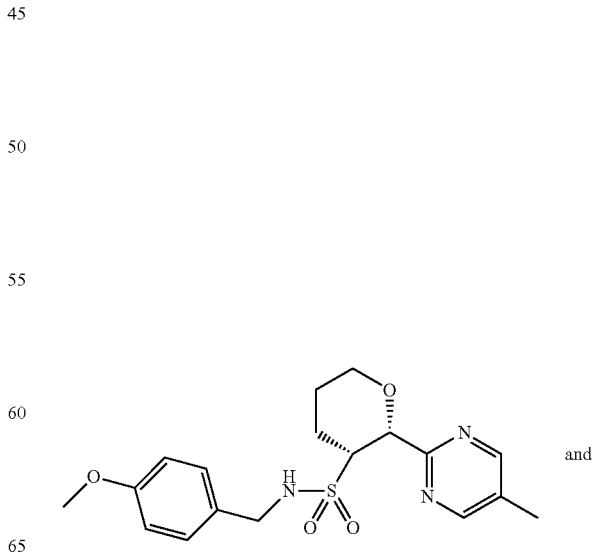

-continued

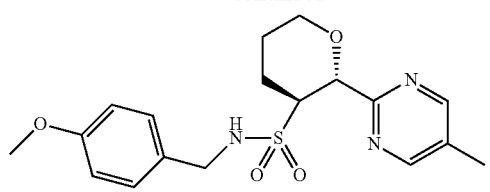 and

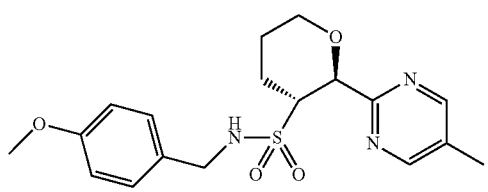

(2R,3R)—N-(4-methoxybenzyl)-2-(5-methylpyrimidin-2-yl)tetrahydro-2H-pyran-3-sulfonamide and
(2R,3S)—N-(4-methoxybenzyl)-2-(5-methylpyrimidin-2-yl)tetrahydro-2H-pyran-3-sulfonamide and
(2S,3R)—N-(4-methoxybenzyl)-2-(5-methylpyrimidin-2-yl)tetrahydro-2H-pyran-3-sulfonamide and
(2S,3S)—N-(4-methoxybenzyl)-2-(5-methylpyrimidin-2-yl)tetrahydro-2H-pyran-3-sulfonamide
Example 643.3

To a stirred suspension of Example 643.2 (1.39 g, 5.38 mmol) in DCM (27 mL) was added dropwise oxalyl chloride (1.433 mL, 16.14 mmol) at RT, followed by dropwise addition of DMF (5 drops). The resulting mixture was allowed to stir at RT and monitored by LCMS. Upon completion, the mixture was concentrated, and the residue was azeotroped with toluene and dried under vacuum overnight. DCM (26 mL) was added to the residue and the mixture was cooled to 0° C. Next, 4-methoxybenzylamine (2.095 mL, 16.14 mmol) was added dropwise, followed by TEA (3.74 mL, 26.9 mmol). The resulting mixture was allowed to stir at RT and monitored by LCMS. Upon completion, the mixture was concentrated and directly loaded onto a silica cartridge and then purified by Isco CombiFlash on a RediSep 40 g silica gel column using 0-100% EtOAc gradient in heptane as the eluent to give Example 643.3. LCMS (pos.) m/z: 378.0 (M+H)$^+$.

643.4

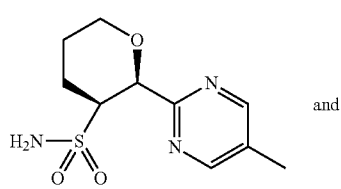 and

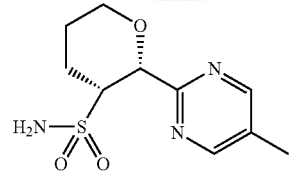 and

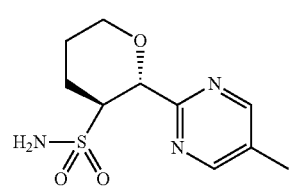 and

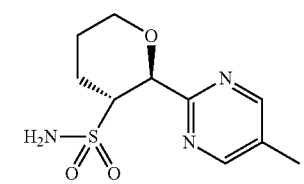

(2R,3R)-2-(5-methylpyrimidin-2-yl)tetrahydro-2H-pyran-3-sulfonamide and (2R,3S)-2-(5-methylpyrimidin-2-yl)tetrahydro-2H-pyran-3-sulfonamide and (2S,3R)-2-(5-methylpyrimidin-2-yl)tetrahydro-2H-pyran-3-sulfonamide and (2S,3S)-2-(5-methylpyrimidin-2-yl)tetrahydro-2H-pyran-3-sulfonamide,
Example 643.4

To a solution of Example 643.3 (0.449 g, 1.19 mmol) in DCM (6 mL) was added anisole (0.650 mL, 5.95 mmol) and TFA (1.83 mL, 23.8 mmol) respectively. The resulting mixture was allowed to stir at RT and monitored by LCMS. Upon completion, the mixture was concentrated and the residue was directly loaded onto silica and then purified by Isco CombiFlash on a RediSep 24 g gold silica gel column using 0-5% MeOH gradient in DCM as the eluent to give Example 643.4 (244 mg). LCMS (pos.) m/z: 258.0 (M+H)$^+$.

The compounds set forth in the following Table were synthesized following the procedure in Example B using the known starting material as described.

TABLE 23

| Example | Reagents | Structure, Name and Data |
|---|---|---|
| 643.5 | (2R,3R)-2-(5-methylpyrimidin-2-yl)tetrahydro-2H-pyran-3-sulfonamide compound and (2R,3S)-2-(5-methylpyrimidin-2-yl)tetrahydro-2H-pyran-3-sulfonamide and (2S,3R)-2-(5-methylpyrimidin-2-yl)tetrahydro-2H-pyran-3-sulfonamide and (2S,3S)-2-(5-methylpyrimidin-2-yl)tetrahydro-2H-pyran-3-sulfonamide (Example 643.4), 3-(5-bromo-4-(2,6-dimethoxyphenyl)-4H-1,2,4-triazol-3-yl)-5-methylpyridine (Example 2.0), trans-n,n'-dimethyl-1,2-cyclohexanediamine (Sigma-Aldrich Chemical Company, Inc.), cesium carbonate (Sigma-Aldrich Chemical Company, Inc.), copper (I) iodide (Strem Chemicals, Inc.) | 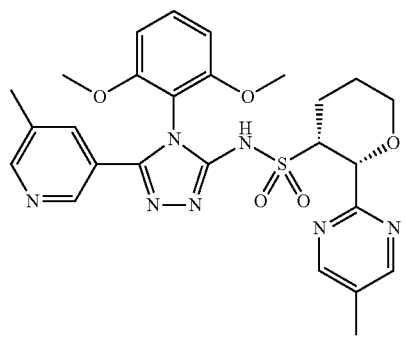 [SMILES: COc1cccc(OC)c1-n1c(NS(=O)(=O)[C@@H]2CCCO[C@@H]2c2ncc(C)cn2)nnc1-c1cncc(C)c1]<br>and<br>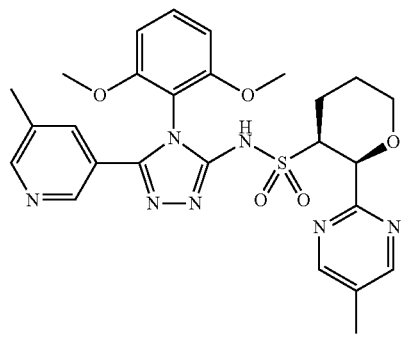 [SMILES: COc1cccc(OC)c1-n1c(NS(=O)(=O)[C@H]2CCCO[C@H]2c2ncc(C)cn2)nnc1-c1cncc(C)c1]<br>and<br>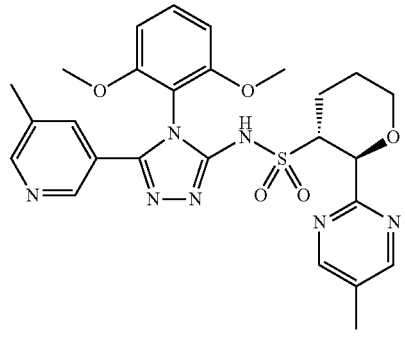 [SMILES: COc1cccc(OC)c1-n1c(NS(=O)(=O)[C@@H]2CCCO[C@H]2c2ncc(C)cn2)nnc1-c1cncc(C)c1]<br>and<br>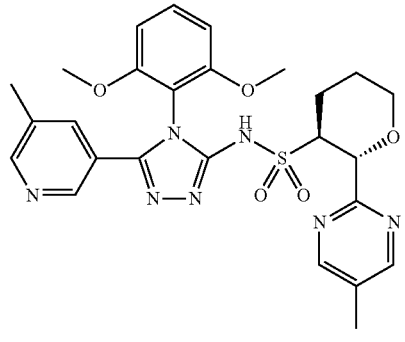 [SMILES: COc1cccc(OC)c1-n1c(NS(=O)(=O)[C@H]2CCCO[C@@H]2c2ncc(C)cn2)nnc1-c1cncc(C)c1]<br>(2R,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide and (2S,3S)-N-(4-(2,6-dimethoxyphenyl)-5-(5-methylpyridin-3-yl)-4H- |

| Example | Reagents | Structure, Name and Data |
|---|---|---|
| | | 1,2,4-triazol-3-yl)-2-(5-methylpyrimidin-2-yl)tetrahydro-2H-pyran-3-sulfonamide and (2S,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide and (2R,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide<br>LCMS-ESI (pos.) m/z: 552.2 (M + H)⁺. |
| 643.0 | Example 643.5 was separated by supercritical fluid chromatography by the following method: AD (10 μm, 21 mm × 25 cm, 50/50/50 p = 144). Organic modifier: 35% Isopropanol with 20 mM NH₃. F = 70 mL/min, T = 40° C., BPR = 100 bar, 220 nm. P = 144 bar. All sample (89 mg) dissolved in 5 mL of MeOH/DCM 1/1, 1.2 mL inj. Four peaks were collected; this was the first isomer to elute under these conditions. | 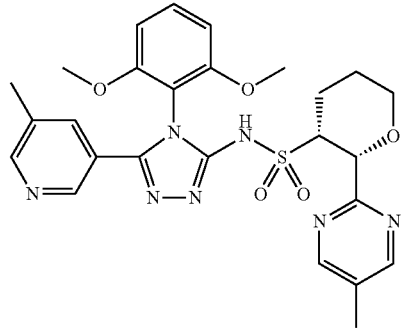 [SMILES: COc1cccc(OC)c1-n1c(NS(=O)(=O)[C@@H]2CCCO[C@@H]2c2ncc(C)cn2)nnc1-c1cncc(C)c1]<br>or<br>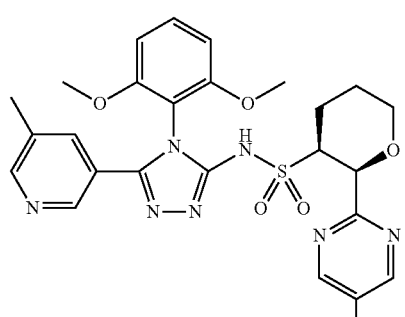<br>or<br>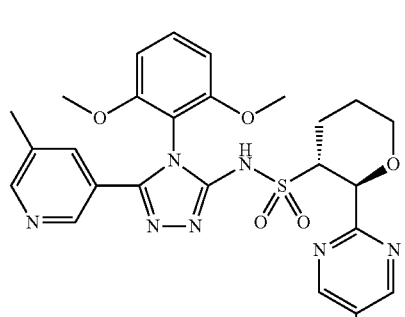<br>or |

TABLE 23-continued

| Example | Reagents | Structure, Name and Data |
|---------|----------|--------------------------|
| | | 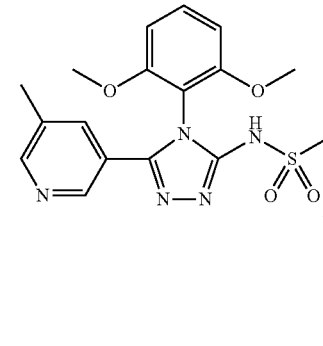
(2R,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide
$^1$H NMR (400 MHz, CDCl$_3$) δ 8.71 (d, J = 1.5 Hz, 2H), 8.45 (s, 1H), 8.37 (s, 1H), 7.65 (s, 1H), 7.51 (dd, J = 8.0, 8.0 Hz, 1H), 6.71-6.74 (m, 2H), 5.0 (d, J = 2.7 Hz, 1H), 4.17-4.21 (m, 1H), 3.79 (s, 3H), 3.77 (s, 3H), 3.70-3.75 (m, 2H), 2.53-2.65 (m, 2H), 2.40 (s, 3H), 2.31 (s, 3H), 2.11-2.19 (m, 1H), 1.37-1.40 (m, 1H). LCMS-ESI (pos.) m/z: 552.2 (M + H)$^+$. |
| 644.0 | Example 643.5 was separated by supercritical fluid chromatography by the following method: AD (10 μm, 21 mm × 25 cm, 50/50/50 p = 144). Organic modifier: 35% Isopropanol with 20 mM NH$_3$. F = 70 mL/min, T = 40° C., BPR = 100 bar, 220 nm. P = 144 bar. All sample (89 mg) dissolved in 5 mL of MeOH/DCM 1/1, 1.2 mL inj. Four peaks were collected; this was the second isomer to elute under these conditions. | 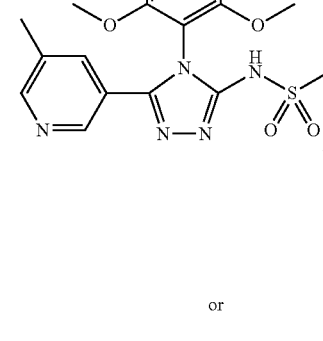
or
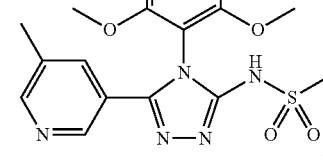
or |

TABLE 23-continued

| Example | Reagents | Structure, Name and Data |
|---|---|---|
| | | 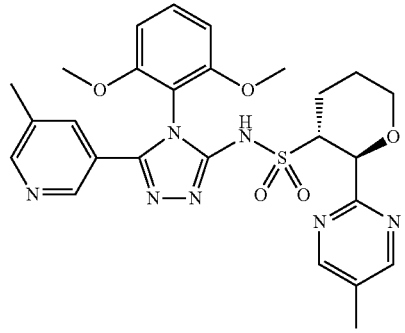 [SMILES: COc1cccc(OC)c1-n1c(NS(=O)(=O)[C@@H]2CCCO[C@H]2c2ncc(C)cn2)nnc1-c1cncc(C)c1]

or

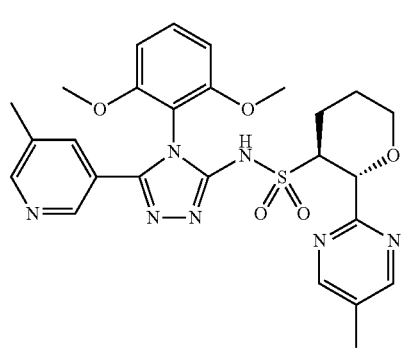 [SMILES: COc1cccc(OC)c1-n1c(NS(=O)(=O)[C@H]2CCCO[C@@H]2c2ncc(C)cn2)nnc1-c1cncc(C)c1]

(2R,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide
$^1$H NMR (400 MHz, CDCl$_3$) δ 8.71 (s, 2H), 8.45 (d, J = 1.5 Hz, 1H), 8.37 (d, J = 1.7 Hz, 1H), 7.65 (s, 1H), 7.51 (dd, J = 8.0, 8.0 Hz, 1H), 6.71-6.74 (m, 2H), 5.0 (d, J = 2.9 Hz, 1H), 4.17-4.21 (m, 1H), 3.79 (s, 3H), 3.77 (s, 3H), 3.72-3.75 (m, 2H), 2.52-2.61 (m, 2H), 2.39 (s, 3H), 2.31 (s, 3H), 2.11-2.19 (m, 1H), 1.37-1.40 (m, 1H). LCMS-ESI (pos.) m/z: 552.2 (M + H)$^+$. |
| 645.0 | Example 643.5 was separated by supercritical fluid chromatography by the following method: AD (10 μm, 21 mm × 25 cm, 50/50/50 p = 144). Organic modifier: 35% Isopropanol with 20 mM NH$_3$. F = 70 mL/min, T = 40° C., BPR = 100 bar, 220 nm. P = 144 bar, All sample (89 mg) dissolved in 5 mL of MeOH/DCM 1/1, 1.2 mL inj. Four peaks were collected; this was the third isomer to elute under these conditions. | 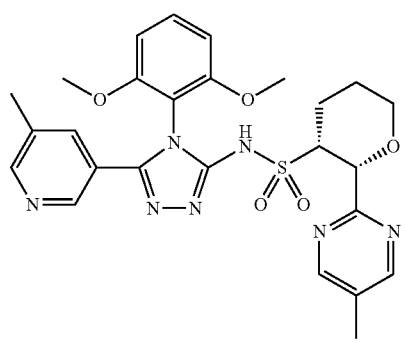 [SMILES: COc1cccc(OC)c1-n1c(NS(=O)(=O)[C@@H]2CCCO[C@@H]2c2ncc(C)cn2)nnc1-c1cncc(C)c1]

or |

| Example | Reagents | Structure, Name and Data |
|---|---|---|
| | | 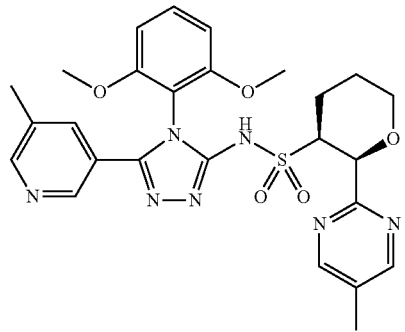 [SMILES: COc1cccc(OC)c1-n1c(NS(=O)(=O)[C@H]2CCCO[C@H]2c2ncc(C)cn2)nnc1-c1cncc(C)c1] |
| | | or |
| | | 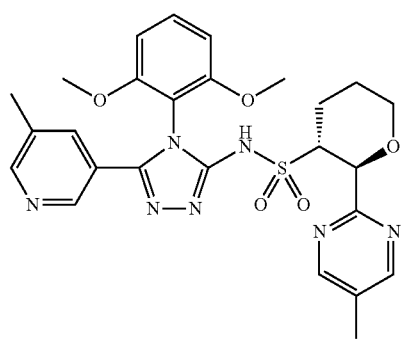 [SMILES: COc1cccc(OC)c1-n1c(NS(=O)(=O)[C@@H]2CCCO[C@H]2c2ncc(C)cn2)nnc1-c1cncc(C)c1] |
| | | or |
| | | 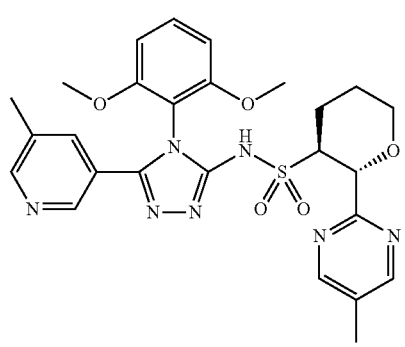 [SMILES: COc1cccc(OC)c1-n1c(NS(=O)(=O)[C@H]2CCCO[C@@H]2c2ncc(C)cn2)nnc1-c1cncc(C)c1] |
| | | (2R,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide <br> $^1$H NMR (400 MHz, CDCl$_3$) δ 8.63 (d, J = 0.7 Hz, 2H), 8.47 (s, 1H), 8.37 (s, 1H), 7.64 (s, 1H), 7.52 (dd, J = 8.0, 8.0 Hz, 1H), 6.71-6.75 (m, 2H), 4.74 (d, J = 8.0 Hz, 1H), 4.03-4.06 (m, 1H), 3.82-3.85 (obscured m, 1H), 3.84 (s, 3H), 3.77 (s, 3H), 3.51-3.56 (m, 1H), 2.39-2.42 (m, 1H), 2.34 (s, 3H), 2.31 (s, 3H), 1.97-2.05 (m, 1H), 1.78-1.90 (m, 2H). LCMS-ESI (pos.) m/z: 552.2 (M + H)$^+$. |

TABLE 23-continued

| Example | Reagents | Structure, Name and Data |
|---|---|---|
| 646.0 | Example 643.5 was separated by supercritical fluid chromatography by the following method: AD (10 μm, 21 mm × 25 cm, 50/50/50 p = 144), Organic modifier: 35% Isopropanol with 20 mM NH$_3$. F = 70 mL/min, T = 40° C., BPR = 100 bar, 220 nm. P = 144 bar, All sample (89 mg) dissolved in 5 mL of MeOH/DCM 1/1, 1.2 mL inj. Four peaks were collected; this was the fourth isomer to elute under these conditions. | or<br><br>or<br><br>or<br><br>(2R,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(5-methylpyridin-3-yl)-4H-1,2,4-triazol-3-yl)-2-(5-methylpyrimidin-2- |

| Example | Reagents | Structure, Name and Data |
|---|---|---|
| | | yl)tetrahydro-2H-pyran-3-sulfonamide or (2S,3R)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(5-methylpyridin-3-yl)-4H-1,2,4-triazol-3-yl)-2-(5-methylpyrimidin-2-yl)tetrahydro-2H-pyran-3-sulfonamide<br>$^1$H NMR (400 MHz, CDCl$_3$) δ 11.5 (br s, 1H), 8.63 (d, J = 0.7 Hz, 2H), 8.47 (br s, 1H), 8.36 (br s, 1H), 7.63 (s, 1H), 7.52 (dd, J = 8.0, 8.0 Hz, 1H), 6.71-6.76 (m, 2H), 4.74 (d, J = 8.0 Hz, 1H), 4.03-4.06 (m, 1H), 3.82-3.85 (obscured m, 1H), 3.84 (s, 3H), 3.77 (s, 3H), 3.51-3.56 (m, 1H), 2.39-2.42 (m, 1H), 2.35 (s, 3H), 2.31 (s, 3H), 1.97-2.05 (m, 1H), 1.77-1.90 (m, 2H). LCMS-ESI (pos.) m/z: 552.2 (M + H)$^+$. |

Example 647.0: Preparation of (2S,3S)—N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide and (2R,3R)—N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide and (2S,3R)—N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide and (2R,3S)—N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide (2R,3R)-3-(4-methyl-1H-pyrazol-1-yl)butan-2-ol and (2R,3S)-3-(4-methyl-1H-pyrazol-1-yl)butan-2-ol and (2S,3R)-3-(4-methyl-1H-pyrazol-1-yl)butan-2-ol and (2S,3S)-3-(4-methyl-1H-pyrazol-1-yl)butan-2-ol, Example 647.1

To a stirred mixture of 4-methylpyrazole (0.250 mL, 3.04 mmol) and 2,3-dimethyloxirane (0.44 g, 6.1 mmol) in DMF (3.0 mL) in a Chem Glass 15×45 mm vial with red pressure cap was added cesium carbonate (1.49 g, 4.57 mmol) in portions. The mixture was capped and stirred at 80° C. for 24 hours. The mixture was then directly loaded onto a silica cartridge and purified by Isco CombiFlash on a RediSep 24 g silica gel column using 0-10% MeOH gradient in DCM as the eluent to give Example 647.1 (470 mg). LCMS (pos.) m/z: 155.2 (M+H)$^+$.

2-(((2R,3R)-3-(4-methyl-1H-pyrazol-1-yl)butan-2-yl)thio)benzo[d]thiazole and 2-(((2R,3S)-3-(4-methyl-1H-pyrazol-1-yl)butan-2-yl)thio)benzo[d]thiazole and 2-(((2S,3R)-3-(4-methyl-1H-pyrazol-1-yl)butan-2-yl)thio)benzo[d]thiazole and 2-(((2S,3S)-3-(4-methyl-1H-pyrazol-1-yl)butan-2-yl)thio)benzo[d]thiazole, Example 647.2

To a stirred solution of triphenylphosphine (1.2 g, 4.57 mmol) in toluene (15 mL) under N$_2$ at 0° C. was added diethyl azodicarboxylate (40% in toluene, 1.39 mL, 3.05 mmol). The mixture was stirred at the same temperature for 10 minutes and Example 647.1 (0.470 g, 3.05 mmol) was added. The mixture was stirred for an additional 10 minutes and 2-mercaptobenzothiazole (0.538 mL, 4.57 mmol) in toluene (5.0 mL) was added. The mixture was warmed to RT and stirred for 24 hours. The resulting mixture was concentrated in vacuo and the residue was directly loaded onto a silica cartridge, purified by Isco CombiFlash on a 40 g silica gel column using 0-100% EtOAc gradient in heptane as the eluent to give Example 647.2 (1.06 g). LCMS (pos.) m/z: 304.0 (M+H)+.

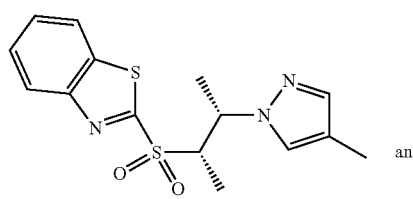

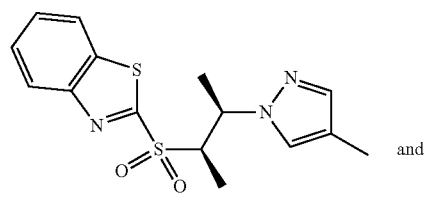


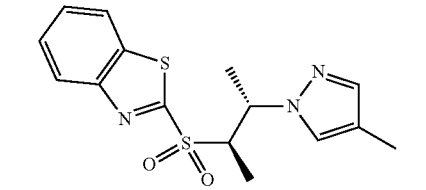

2-(((2R,3R)-3-(4-methyl-1H-pyrazol-1-yl)butan-2-yl)sulfonyl)benzo[d]thiazole and 2-(((2R,3S)-3-(4-methyl-1H-pyrazol-1-yl)butan-2-yl)sulfonyl)benzo[d]thiazole and 2-(((2S,3R)-3-(4-methyl-1H-pyrazol-1-yl)butan-2-yl)sulfonyl)benzo[d]thiazole and 2-(((2S,3S)-3-(4-methyl-1H-pyrazol-1-yl)butan-2-yl)sulfonyl)benzo[d]thiazole, Example 647.3

To a solution of Example 647.2 (1.06 g, 2.1 mmol) in DCM (11 mL) was added mCPBA (0.939 g, 4.19 mmol) slowly at 0° C. The resulting mixture was then stirred at RT and monitored by LCMS. Upon completion, sodium thiosulfate (3.31 g, 21.0 mmol) was added slowly in portions to quench the reaction, and the mixture was then stirred at RT for an additional 30 minutes. The resulting product was loaded directly onto a silica cartridge and purified by Isco CombiFlash on a RediSep 40 g silica gel column using 0-100% EtOAc gradient in hexane as the eluent to give Example 647.3 (638 mg). LCMS (pos.) m/z: 336.2 (M+H)+.

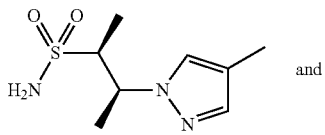

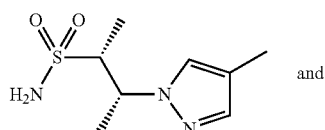

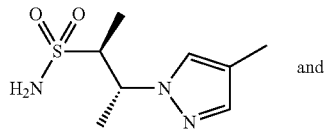

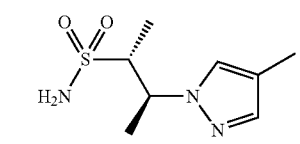

(2R,3R)-3-(4-methyl-1H-pyrazol-1-yl)butane-2-sulfonamide and (2R,3S)-3-(4-methyl-1H-pyrazol-1-yl)butane-2-sulfonamide and (2S,3R)-3-(4-methyl-1H-pyrazol-1-yl)butane-2-sulfonamide and (2S,3S)-3-(4-methyl-1H-pyrazol-1-yl)butane-2-sulfonamide, Example 647.4

To a stirred solution of 647.4 (0.638 g, 1.90 mmol) in MeOH (10 mL) was slowly added potassium carbonate (0.230 mL, 3.80 mmol) at 0° C. The resulting mixture was warmed to RT and stirred for 24 hours. The mixture was concentrated, and the residue was dried under vacuum. Water (9.51 mL, 1.90 mmol) was added to the residue, and the mixture was stirred and treated with amidoperoxymonosulfuric acid (0.452 g, 3.99 mmol) and potassium acetate (0.21 g, 2.09 mmol) respectively. The resulting mixture was stirred at RT for 24 hours, and then 20 mL of saturated aqueous NaCl solution was added. The resulting mixture was extracted with 30% iPrOH/chloroform (30 mL×2) and DCM (30 mL×2). The combined extracts were dried with anhydrous sodium sulfate and concentrated. The residue was purified by Isco CombiFlash on a RediSep 24 g silica gel column using 0-10% MeOH gradient in DCM as the eluent to give Example 647.4, (334 mg). LCMS (pos.) m/z: 218.1 (M+H).

The compounds set forth in the following Table were synthesized following the procedure in Example B using the known starting material as described.

TABLE 24

| Example | Reagents | Structure, Name and Data |
|---------|----------|--------------------------|
| 647.0 | (2R,3R)-3-(4-methyl-1H-pyrazol-1-yl)butane-2-sulfonamide and (2R,3S)-3-(4-methyl-1H-pyrazol-1-yl)butane-2-sulfonamide and (2S,3R)-3-(4-methyl-1H-pyrazol-1-yl)butane-2-sulfonamide and (2S,3S)-3-(4-methyl-1H-pyrazol-1-yl)butane-2-sulfonamide (Example 647.4). 3-(5-bromo-4-(2,6-dimethoxyphenyl)-4H-1,2,4-triazol-3-yl)-5-methylpyridine (Example 2.0), trans-n,n'-dimethyl-1,2-cyclohexanediamine (Sigma-Aldrich Chemical Company, Inc.), cesium carbonate (Sigma-Aldrich Chemical Company, Inc.), copper (i) iodide (Strem Chemicals, Inc.) | 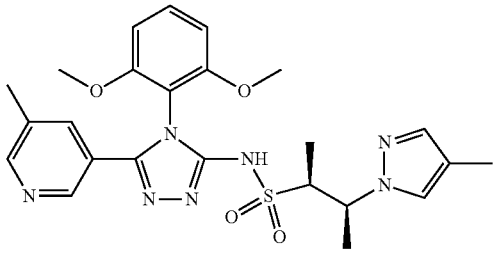 [SMILES: COc1cccc(OC)c1-n1c(NS(=O)(=O)[C@@H](C)[C@H](C)n2cc(C)cn2)nnc1-c1cncc(C)c1] and 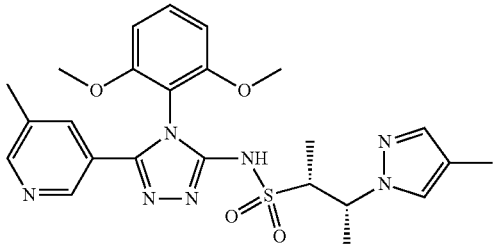 and 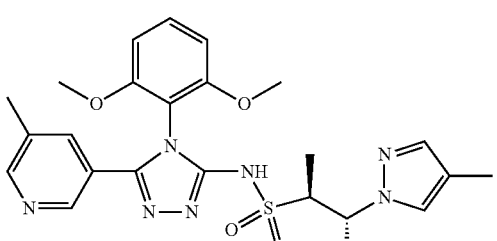 and 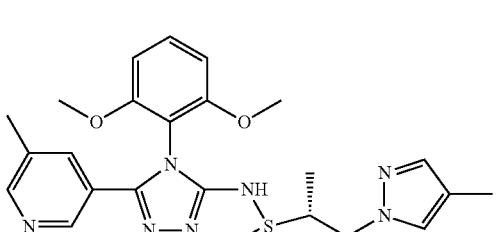 (2S,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide and (2R,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide and (2S,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide and (2R,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide LCMS-ESI (pos.) m/z: 512.2 (M + H)+. |

TABLE 24-continued

| Example | Reagents | Structure, Name and Data |
|---|---|---|
| 648.0 | (2R,3R)-2-(5-methylpyrimidin-2-yl)tetrahydro-2H-pyran-3-sulfonamide compound and (2R,3S)-2-(5-methylpyrimidin-2-yl)tetrahydro-2H-pyran-3-sulfonamide and (2S,3R)-2-(5-methylpyrimidin-2-yl)tetrahydro-2H-pyran-3-sulfonamide and (2S,3S)-2-(5-methylpyrimidin-2-yl)tetrahydro-2H-pyran-3-sulfonamide (Example 643.4), 2-(5-bromo-4-(2,6-dimethoxyphenyl)-4H-1,2,4-triazol-3-yl)-6-methoxypyridine (Example 2.2), (2R,3R)-2-(5-methylpyrimidin-2-yl)tetrahydro-2H-pyran-3-sulfonamide compound and (2R,3S)-2-(5-methylpyrimidin-2-yl)tetrahydro-2H-pyran-3-sulfonamide and (2S,3R)-2-(5-methylpyrimidin-2-yl)tetrahydro-2H-pyran-3-sulfonamide and (2S,3S)-2-(5-methylpyrimidin-2-yl)tetrahydro-2H-pyran-3-sulfonamide (Example 643.4), trans-n,n'-dimethyl-1,2-cyclohexanediamine (Sigma-Aldrich Chemical Company, Inc.), cesium carbonate (Sigma-Aldrich Chemical Company, Inc.), copper (i) iodide (Strem Chemicals, Inc.) | 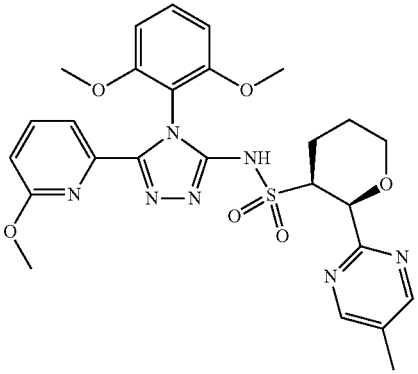 [SMILES: COc1cccc(-c2nnc(NS(=O)(=O)[C@H]3CCCO[C@H]3c3ncc(C)cn3)n2-c2c(OC)cccc2OC)n1]<br><br>and<br><br>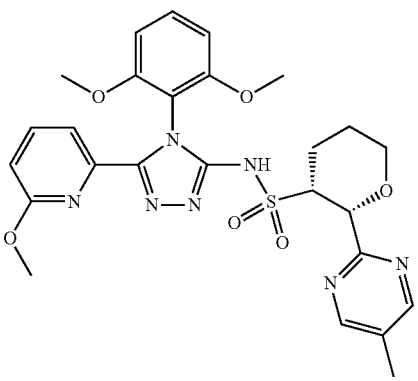 [SMILES: COc1cccc(-c2nnc(NS(=O)(=O)[C@@H]3CCCO[C@@H]3c3ncc(C)cn3)n2-c2c(OC)cccc2OC)n1]<br><br>and<br><br>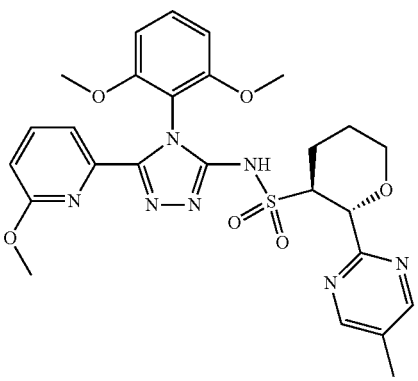 [SMILES: COc1cccc(-c2nnc(NS(=O)(=O)[C@H]3CCCO[C@@H]3c3ncc(C)cn3)n2-c2c(OC)cccc2OC)n1]<br><br>and |

TABLE 24-continued

| Example | Reagents | Structure, Name and Data |
|---------|----------|--------------------------|

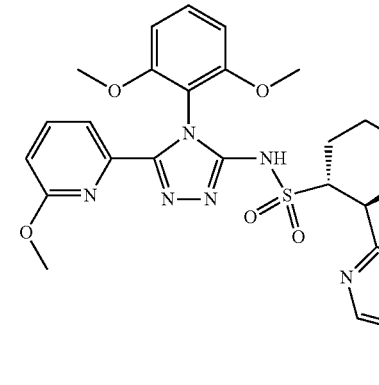

(2S,3S)-N-(4-(2,6-dimethoxyphenyl)-5-(6-
methoxypyridin-2-yl)-4H-1,2,4-triazol-3-yl)-2-
(5-methylpyrimidin-2-yl)tetrahydro-2H-pyran-3-
sulfonamide and (2R,3R)-N-(4-(2,6-
dimethoxyphenyl)-5-(6-methoxypyridin-2-yl)-
4H-1,2,4-triazol-3-yl)-2-(5-methylpyrimidin-2-
yl)tetrahydro-2H-pyran-3-sulfonamide and
(2R,3S)-N-(4-(2,6-dimethoxyphenyl)-5-(6-
methoxypyridin-2-yl)-4H-1,2,4-triazol-3-yl)-2-
(5-methylpyrimidin-2-yl)tetrahydro-2H-pyran-3-
sulfonamide and (2S,3R)-N-(4-(2,6-
dimethoxyphenyl)-5-(6-methoxypyridin-2-yl)-
4H-1,2,4-triazol-3-yl)-2-(5-methylpyrimidin-2-
yl)tetrahydro-2H-pyran-3-sulfonamide.
LCMS-ESI (pos.) m/z: 568.2 (M + H)$^+$.

649.0   2R,3R)-3-(4-methyl-1H-pyrazol-1-
        yl)butane-2-sulfonamide compound
        with (2R,3S)-3-(4-methyl-1H-
        pyrazol-1-yl)butane-2-sulfonamide
        and (2S,3R)-3-(4-methyl-1H-
        pyrazol-1-yl)butane-2-sulfonamide
        and (2S,3S)-3-(4-methyl-1H-
        pyrazol-1-yl)butane-2-sulfonamide
        (Example 647.4). 2-(5-bromo-4-
        (2,6-dimethoxyphenyl)-4H-1,2,4-
        triazol-3-yl)-6-methoxypyridine
        (Example 2.2). trans-n,n'-dimethyl-
        1,2-cyclohexanediamine (Sigma-
        Aldrich Chemical Company, Inc.),
        cesium carbonate (Sigma-Aldrich
        Chemical Company, Inc.), copper (i)
        iodide (Strem Chemicals, Inc.)

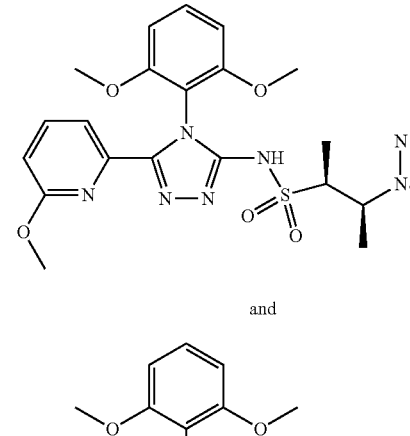

and

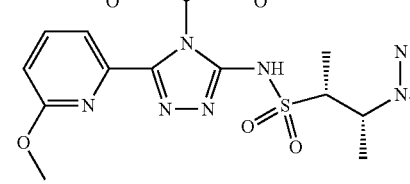

and

TABLE 24-continued

| Example | Reagents | Structure, Name and Data |
|---|---|---|
| | | 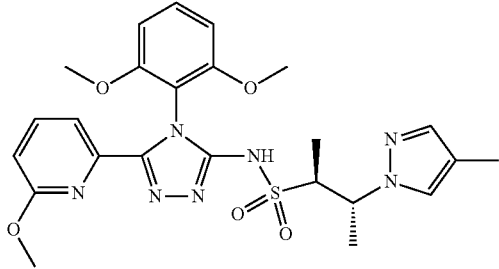 [SMILES: COc1cccc(-c2nnc(NS(=O)(=O)[C@@H](C)[C@@H](C)n3cc(C)cn3)n2-c2c(OC)cccc2OC)n1]

and

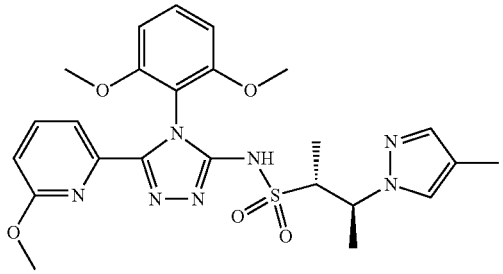 [SMILES: COc1cccc(-c2nnc(NS(=O)(=O)[C@H](C)[C@H](C)n3cc(C)cn3)n2-c2c(OC)cccc2OC)n1]

(2S,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide and (2R,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide and (2S,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide and (2R,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide.
LCMS-ESI (pos.) m/z: 528.2 (M + H)$^+$. |
| 650.0 | Example 647.0 was separated by supercritical fluid chromatography by the following method: 1st Step Preparative SFC Purification: IE (21 × 150 mm, 5 μm), Organic modifier: 50% EtOH with 20 mM NH$_3$. F = 50 mL/min, T = 40° C., BPR = 100 bar, 220 nm. 2nd Step Preparative SFC Purification: AD-H (21 × 250 mm, 5 μm), Organic modifier: 25% EtOH with 20 mM NH$_3$. F = 70 mL/min, T = 40° C., BPR = 100 bar, 220 nm. Four peaks were collected; this was the first isomer to elute under these conditions. | 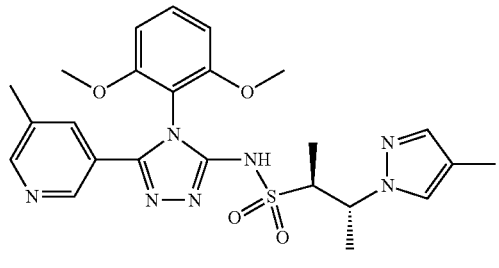 [SMILES: COc1cccc(OC)c1-n1c(NS(=O)(=O)[C@@H](C)[C@@H](C)n2cc(C)cn2)nnc1-c1cncc(C)c1]

or

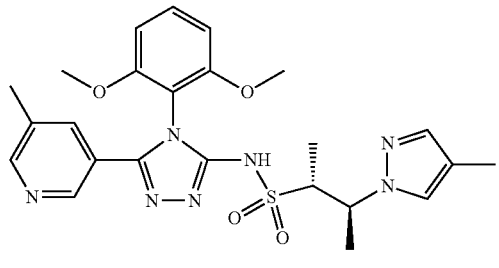 [SMILES: COc1cccc(OC)c1-n1c(NS(=O)(=O)[C@H](C)[C@H](C)n2cc(C)cn2)nnc1-c1cncc(C)c1]

or |

| Example | Reagents | Structure, Name and Data |
|---|---|---|
| | | 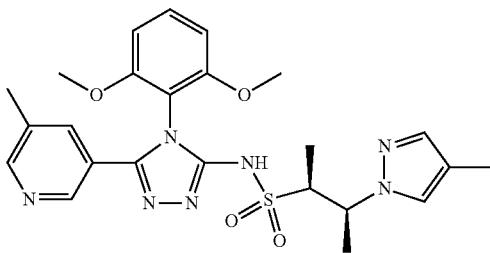 [SMILES: COc1cccc(OC)c1-n1c(NS(=O)(=O)[C@@H](C)[C@H](C)n2cc(C)cn2)nnc1-c1cncc(C)c1]<br>or<br><br>(2S,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2S,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide<br>$^1$H NMR (400 MHz, CDCl$_3$) δ 8.44 (s, 1H), 8.32 (s, 1H), 7.63 (s, 1H), 7.4 (dd, J = 8.5, 8.5 Hz, 1H), 7.30 (s, 1H), 7.16 (s, 1H), 6.61 (d, J = 8.6 Hz, 2H), 4.62-4.69 (m, 1H), 3.74 (s, 3H), 3.73 (s, 3H), 3.34-3.41 (m, 1H), 2.30 (s, 3H), 2.05 (s, 3H), 1.69 (d, J = 6.8 Hz, 3H), 1.07 (d, J = 7.0 Hz, 3H). LCMS-ESI (pos.) m/z: 512.2 (M + H)$^+$. |
| 651.0 | Example 647.0 was separated by supercritical fluid chromatography by the following method: 1st Step Preparative SFC Purification: IE (21 × 150 mm, 5 µm), Organic modifier: 50% EtOH with 20 mM NH$_3$. F = 50 mL/min, T = 40° C., BPR = 100 bar, 220 nm. 2nd Step Preparative SFC Purification: AD-H (21 × 250 mm, 5 µm), Organic modifier: 25% EtOH with 20 mM NH$_3$. F = 70 mL/min, T = 40° C., BPR = 100 bar, 220 nm.<br>Four peaks were collected; this was the second isomer to elute under these conditions. | 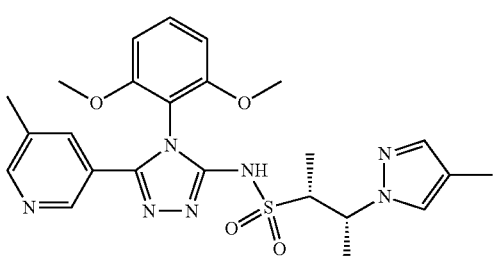<br>or |

| Example | Reagents | Structure, Name and Data |
|---|---|---|
| | | 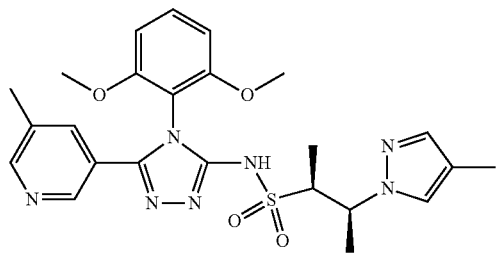 [SMILES: COc1cccc(OC)c1-n1c(NS(=O)(=O)[C@@H](C)[C@H](C)n2cc(C)cn2)nnc1-c1cncc(C)c1]
or
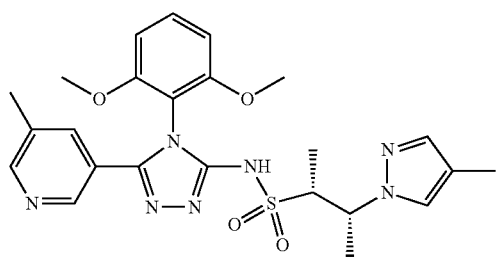 [SMILES: COc1cccc(OC)c1-n1c(NS(=O)(=O)[C@H](C)[C@@H](C)n2cc(C)cn2)nnc1-c1cncc(C)c1]
(2S,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide compound with methane (1:1) or (2S,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide
$^1$H NMR (400 MHz, CDCl$_3$) δ 8.44 (s, 1H), 8.32 (s, 1H), 7.63 (s, 1H), 7.4 (dd, J = 8.5, 8.5 Hz, 1H), 7.30 (s, 1H), 7.16 (s, 1H), 6.61 (d, J = 8.6 Hz, 2H), 4.62-4.69 (m, 1H), 3.74 (s, 3H), 3.73 (s, 3H), 3.34-3.41 (m, 1H), 2.30 (s, 3H), 2.05 (s, 3H), 1.69 (d, J = 6.8 Hz, 3H), 1.07 (d, J = 7.0 Hz, 3H). LCMS-ESI (pos.) m/z: 512.2 (M + H)$^+$. |
| 652.0 | Example 647.0 was separated by supercritical fluid chromatography by the following method: 1st Step Preparative SFC Purification: IE (21 × 150 mm, 5 μm), Organic modifier: 50% EtOH with 20 mM NH$_3$. F = 50 mL/min, T = 40° C., BPR = 100 bar, 220 nm. 2nd Step Preparative SFC Purification: AD-H (21 × 250 mm, 5 um), Organic modifier: 25% EtOH with 20 mM NH$_3$. F = 70 mL/min, T = 40° C., BPR = 100 bar, 220 nm. Four peaks were collected; this was the third isomer to elute under these conditions. | 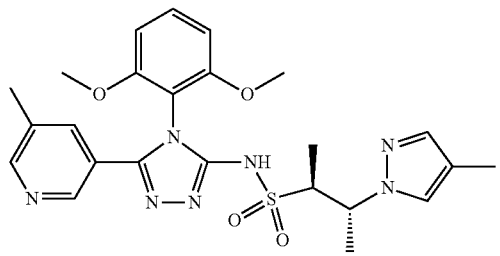 [SMILES: COc1cccc(OC)c1-n1c(NS(=O)(=O)[C@@H](C)[C@@H](C)n2cc(C)cn2)nnc1-c1cncc(C)c1]
or
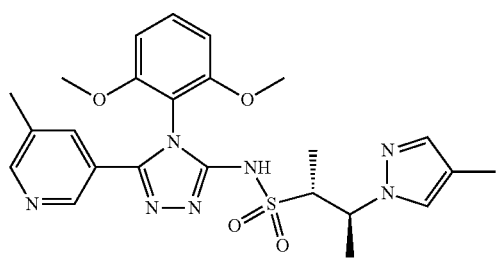 [SMILES: COc1cccc(OC)c1-n1c(NS(=O)(=O)[C@H](C)[C@H](C)n2cc(C)cn2)nnc1-c1cncc(C)c1]
or |

| Example | Reagents | Structure, Name and Data |
|---|---|---|
| | | 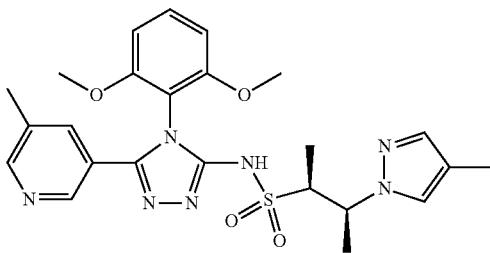 [SMILES: COc1cccc(OC)c1-n1c(NS(=O)(=O)[C@@H](C)[C@H](C)n2cc(C)cn2)nnc1-c1cncc(C)c1]

or

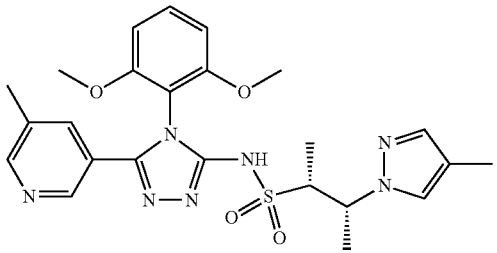 [SMILES: COc1cccc(OC)c1-n1c(NS(=O)(=O)[C@H](C)[C@@H](C)n2cc(C)cn2)nnc1-c1cncc(C)c1]

(2S,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide compound with methane (1:1) or (2S,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide
$^1$H NMR (400 MHz, CDCl$_3$) δ 8.45 (s, 1H), 8.33 (s, 1H), 7.64 (s, 1H), 7.39 (dd, J = 8.5, 8.5 Hz, 1H), 7.31 (s, 1H), 7.19 (s, 1H), 6.60 (dd, J = 8.6, 1.2 Hz, 2H), 5.01-5.07 (m, 1H), 3.73 (s, 3H), 3.72 (s, 3H), 3.51-3.58 (m, 1H), 2.30 (s, 3H), 2.06 (s, 3H), 1.55 (d, J = 7.0 Hz, 3H), 1.30 (d, J = 7.0 Hz, 3H). LCMS-ESI (pos.) m/z: 512.2 (M + H)$^+$. |
| 653.0 | Example 647.0 was separated by supercritical fluid chromatography by the following method: 1st Step Preparative SFC Purification: IE (21 × 150 mm, 5 μm), Organic modifier: 50% EtOH with 20 mM NH$_3$. F = 50 mL/min, T = 40° C., BPR = 100 bar, 220 nm. 2nd Step Preparative SFC Purification: AD-H (21 × 250 mm, 5 um), Organic modifier: 25% EtOH with 20 mM NH3. F = 70 mL/min, T = 40° C., BPR = 100 bar, 220 nm.
Four peaks were collected; this was the fourth isomer to elute under these conditions. | 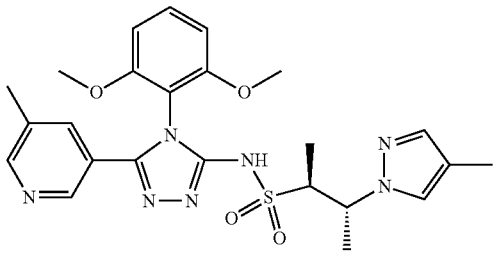 [SMILES: COc1cccc(OC)c1-n1c(NS(=O)(=O)[C@@H](C)[C@@H](C)n2cc(C)cn2)nnc1-c1cncc(C)c1]

or

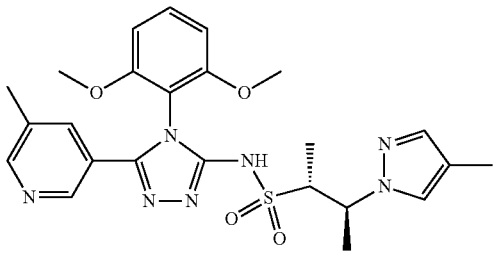 [SMILES: COc1cccc(OC)c1-n1c(NS(=O)(=O)[C@H](C)[C@H](C)n2cc(C)cn2)nnc1-c1cncc(C)c1]

or |

TABLE 24-continued

| Example | Reagents | Structure, Name and Data |
|---|---|---|
| | | 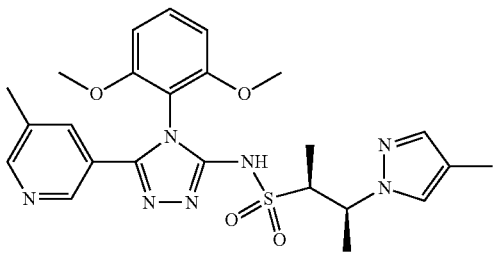 [SMILES: COc1cccc(OC)c1-n1c(NS(=O)(=O)[C@@H](C)[C@H](C)n2cc(C)cn2)nnc1-c1cncc(C)c1]

or

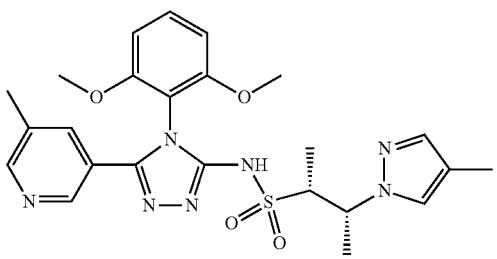 [SMILES: COc1cccc(OC)c1-n1c(NS(=O)(=O)[C@H](C)[C@@H](C)n2cc(C)cn2)nnc1-c1cncc(C)c1]

(2S,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide compound with methane (1:1) or (2S,3S)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(5-methylpyridin-3-yl)-4H-1,2,4-triazol-3-yl)-3-(4-methyl-1H-pyrazol-1-yl)butane-2-sulfonamide
$^1$H NMR (400 MHz, CDCl$_3$) δ 8.44 (s, 1H), 8.33 (s, 1H), 7.64 (s, 1H), 7.38 (dd, J = 8.5, 8.5 Hz, 1H), 7.30 (s, 1H), 7.18 (s, 1H), 6.59 (dd, J = 8.5, 1.7 Hz, 2H), 5.01-5.07 (m, 1H), 3.72 (s, 3H), 3.71 (s, 3H), 3.51-3.58 (m, 1H), 2.29 (s, 3H), 2.05 (s, 3H), 1.54 (d, J = 7.0 Hz, 3H), 1.28 (d, J = 7.0 Hz, 3H). LCMS-ESI (pos.) m/z: 512.2 (M + H)$^+$. |
| 654.0 | Example 648.0 was separated by supercritical fluid chromatography by the following method: AD-H (21 × 150 mm, 5 µm), Organic modifier: 30% EtOH with 20 mM NH$_3$. 70% Carbon Dioxide, F = 70 mL/min, T = 40° C., BPR = 100 bar, 220 nm. P = 186 bar, All samples dissolved in 15 mL MeOH/DCM 1/1, 0.7 mL inj<br>Four peaks were collected; this was the first isomer to elute under these conditions. | 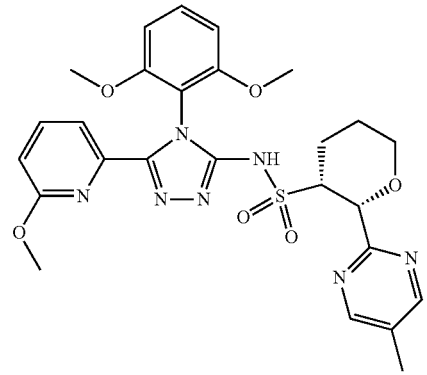 [SMILES: COc1cccc(-c2nnc(NS(=O)(=O)[C@@H]3CCCO[C@@H]3c3ncc(C)cn3)n2-c2c(OC)cccc2OC)n1]

or |

TABLE 24-continued

| Example | Reagents | Structure, Name and Data |
|---|---|---|

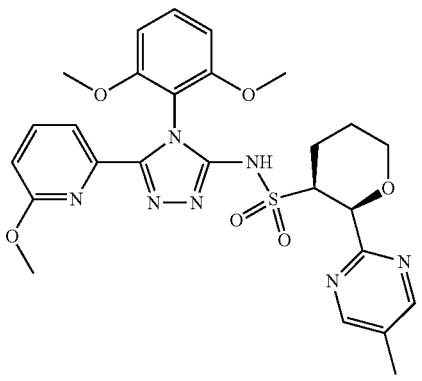 [SMILES: COc1cccc(-c2nnc(NS(=O)(=O)[C@H]3CCCO[C@H]3c3ncc(C)cn3)n2-c2c(OC)cccc2OC)n1]

or

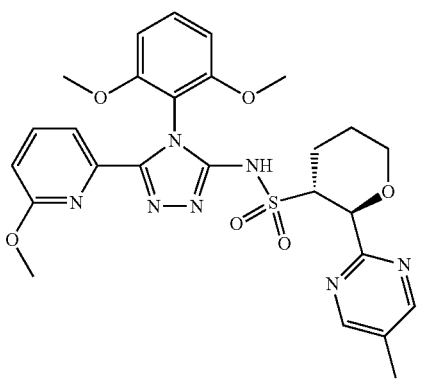 [SMILES: COc1cccc(-c2nnc(NS(=O)(=O)[C@@H]3CCCO[C@H]3c3ncc(C)cn3)n2-c2c(OC)cccc2OC)n1]

or

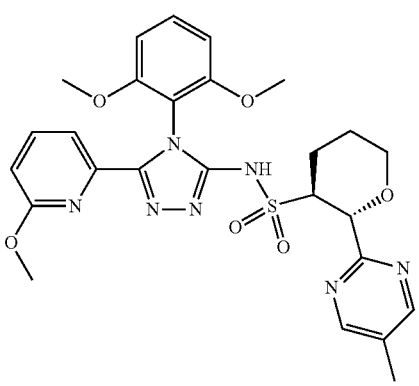 [SMILES: COc1cccc(-c2nnc(NS(=O)(=O)[C@H]3CCCO[C@@H]3c3ncc(C)cn3)n2-c2c(OC)cccc2OC)n1]

(2R,3R)-N-(4-(2,6-dimethoxyphenyl)-5-(6-
methoxypyridin-2-yl)-4H-1,2,4-triazol-3-yl)-2-
(5-methylpyrimidin-2-yl)tetrahydro-2H-pyran-3-
sulfonamide or (2S,3S)-N-(4-(2,6-
dimethoxyphenyl)-5-(6-methoxypyridin-2-yl)-
4H-1,2,4-triazol-3-yl)-2-(5-methylpyrimidin-2-
yl)tetrahydro-2H-pyran-3-sulfonamide or
(2S,3R)-N-(4-(2,6-dimethoxyphenyl)-5-(6-
methoxypyridin-2-yl)-4H-1,2,4-triazol-3-yl)-2-
(5-methylpyrimidin-2-yl)tetrahydro-2H-pyran-3-
sulfonamide or (2R,3S)-N-(4-(2,6-
dimethoxyphenyl)-5-(6-methoxypyridin-2-yl)-
4H-1,2,4-triazol-3-yl)-2-(5-methylpyrimidin-2-
yl)tetrahydro-2H-pyran-3-sulfonamide
$^{1}$H NMR (400 MHz, CDCl$_{3}$) δ 13.1 (br s, 1H),
8.67 (s, 2H), 7.59-7.65 (m, 2H), 7.29 (dd, J =
8.0, 8.0 Hz, 1H), 6.68 (dd, J = 7.8, 1.2 Hz, 1H),
6.59 (dd, J = 8.6, 8.6 Hz, 2H), 5.00 (d, J = 2.7

TABLE 24-continued

| Example | Reagents | Structure, Name and Data |
|---|---|---|
| | | Hz, 1H), 4.22 (dd, J = 11.2, 4.0 Hz, 1H), 3.81-3.85 (m, 1H), 3.66-3.73 (obscured m, 1H), 3.70 (s, 3H), 3.68 (s, 3H), 3.17 (s, 3H), 2.62-2.69 (m, 2H), 2.35 (s, 3H), 2.06-2.16 (m, 1H), 1.32-1.38 (m, 1H). LCMS-ESI (pos.) m/z: 568.1 (M + H)+. |
| 655.0 | Example 648.0 was separated by supercritical fluid chromatography by the following method: AD-H (21 × 150 mm, 5 μm), Organic modifier: 30% EtOH with 20 mM NH3. 70% Carbon Dioxide, F = 70 mL/min, T = 40° C., BPR = 100 bar, 220 nm. P = 186 bar, All samples dissolved in 15 mL MeOH/DCM 1/1, 0.7 mL inj. Four peaks were collected; this was the second isomer to elute under these conditions. | 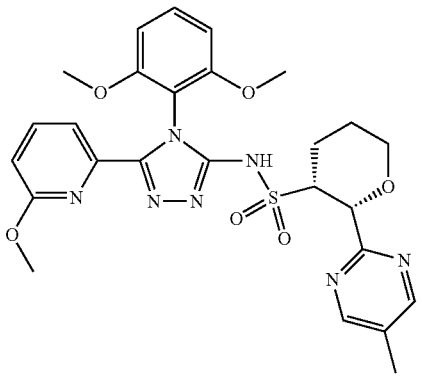 [SMILES: COc1cccc(-c2nnc(NS(=O)(=O)[C@@H]3CCCO[C@@H]3c3ncc(C)cn3)n2-c2c(OC)cccc2OC)n1]<br>or<br>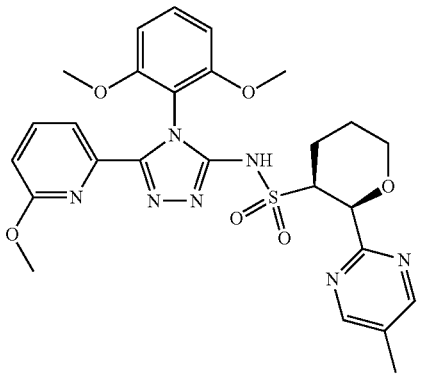 [SMILES: COc1cccc(-c2nnc(NS(=O)(=O)[C@H]3CCCO[C@H]3c3ncc(C)cn3)n2-c2c(OC)cccc2OC)n1]<br>or<br>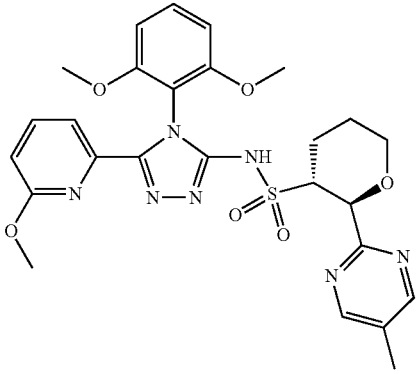 [SMILES: COc1cccc(-c2nnc(NS(=O)(=O)[C@@H]3CCCO[C@H]3c3ncc(C)cn3)n2-c2c(OC)cccc2OC)n1]<br>or |

| Example | Reagents | Structure, Name and Data |
|---|---|---|
| | | 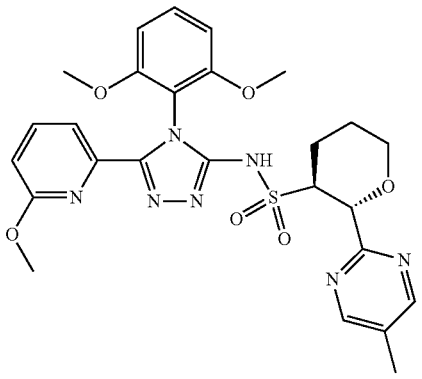 [SMILES: COc1cccc(-c2nnc(NS(=O)(=O)[C@H]3CCCO[C@@H]3c3ncc(C)cn3)n2-c2c(OC)cccc2OC)n1] (2R,3R)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2S,3R)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide $^1$H NMR (400 MHz, CDCl$_3$) δ 8.67 (s, 2H), 7.58-7.65 (m, 2H), 7.29 (dd, J = 8.0, 8.0 Hz, 1H), 6.67 (dd, J = 7.7, 1.3 Hz, 1H), 6.57-6.61 (m, 2H), 5.00 (d, J = 2.9 Hz, 1H), 4.22 (dd, J = 11.2, 4.0 Hz, 1H), 3.66-3.74 (m, 1H), 3.70 (s, 3H), 3.68 (s, 3H), 3.16 (s, 3H), 2.63-2.68 (m, 2H), 2.34 (s, 3H), 2.06-2.14 (m, 1H), 1.31-1.37 (m, 1H). LCMS-ESI (pos.) m/z: 568.1 (M + H)$^+$. |
| 656.0 | Example 648.0 was separated by supercritical fluid chromatography by the following method: AD-H (21 × 150 mm, 5 μm), Organic modifier: 30% EtOH with 20 mM NH$_3$. 70% Carbon Dioxide, F = 70 mL/min, T = 40° C., BPR = 100 bar, 220 nm. P = 186 bar, All samples dissolved in 15 mL MeOH/DCM 1/1, 0.7 mL inj Four peaks were collected; this was the third isomer to elute under these conditions. | 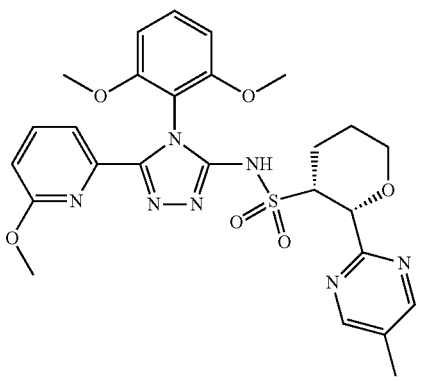 [SMILES: COc1cccc(-c2nnc(NS(=O)(=O)[C@@H]3CCCO[C@@H]3c3ncc(C)cn3)n2-c2c(OC)cccc2OC)n1] or |

TABLE 24-continued

| Example | Reagents | Structure, Name and Data |
|---|---|---|

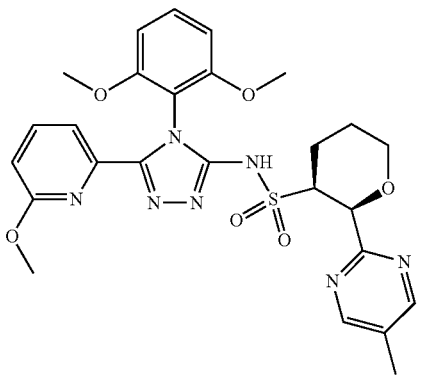 [SMILES: COc1cccc(-c2nnc(NS(=O)(=O)[C@H]3CCCO[C@H]3c3ncc(C)cn3)n2-c2c(OC)cccc2OC)n1]

or

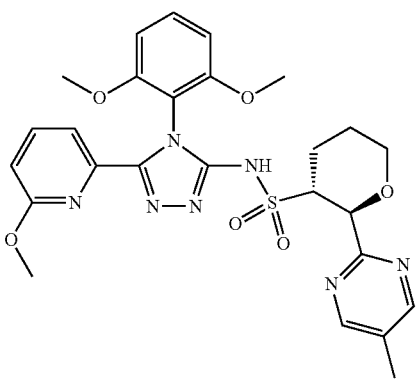 [SMILES: COc1cccc(-c2nnc(NS(=O)(=O)[C@@H]3CCCO[C@H]3c3ncc(C)cn3)n2-c2c(OC)cccc2OC)n1]

or

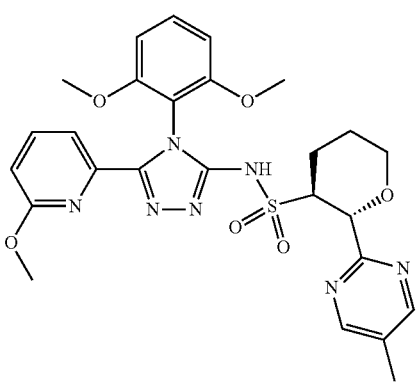 [SMILES: COc1cccc(-c2nnc(NS(=O)(=O)[C@H]3CCCO[C@@H]3c3ncc(C)cn3)n2-c2c(OC)cccc2OC)n1]

(2R,3R)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2S,3R)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide
$^1$H NMR (400 MHz, CDCl$_3$) δ 11.42 (br s, 1H), 8.62 (s, 2H), 7.58-7.64 (m, 2H), 7.32 (dd, J = 8.5, 8.5 Hz, 1H), 6.70 (dd, J = 7.7, 1.5 Hz, 1H), 6.58-6.64 (m, 2H), 4.81 (d, J = 10.0 Hz, 1H),

| Example | Reagents | Structure, Name and Data |
|---|---|---|
| | | 4.08-4.12 (m, 1H), 3.79-3.86 (m, 1H), 3.77 (s, 3H), 3.67 (s, 3H), 3.51-3.68 (m, 1H), 3.18 (s, 3H), 2.45-2.49 (m, 1H), 2.32 (s, 3H), 2.00-2.10 (m, 1H), 1.86-1.97 (m, 1H), 1.73-1.80 (m, 1H). LCMS-ESI (pos.) m/z: 568.1 (M + H)+. |
| 657.0 | Example 648.0 was separated by supercritical fluid chromatography by the following method: AD-H 21 × 150 mm, 5 μm), Organic modifier: 30% EtOH with 20 mM NH3. 70% Carbon Dioxide, F = 70 mL/min, T = 40° C., BPR = 100 bar, 220 nm. P = 186 bar, All samples dissolved in 15 mL MeOH/DCM 1/1, 0.7 mL inj<br>Four peaks were collected; this was the fourth isomer to elute under these conditions. | 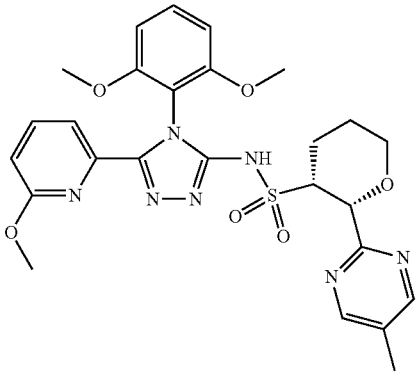 [SMILES: COc1cccc(-c2nnc(NS(=O)(=O)[C@@H]3CCCO[C@@H]3c3ncc(C)cn3)n2-c2c(OC)cccc2OC)n1]<br>or<br>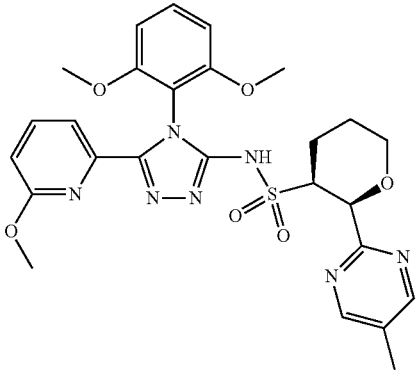 [SMILES: COc1cccc(-c2nnc(NS(=O)(=O)[C@H]3CCCO[C@H]3c3ncc(C)cn3)n2-c2c(OC)cccc2OC)n1]<br>or<br>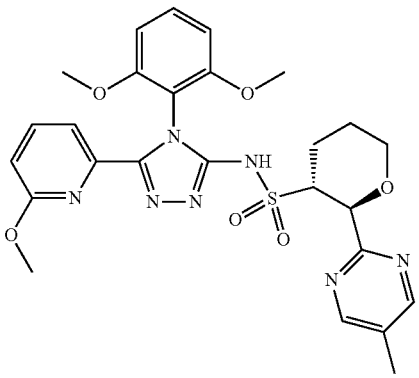 [SMILES: COc1cccc(-c2nnc(NS(=O)(=O)[C@@H]3CCCO[C@H]3c3ncc(C)cn3)n2-c2c(OC)cccc2OC)n1]<br>or |

TABLE 24-continued

| Example | Reagents | Structure, Name and Data |
|---|---|---|
| | | 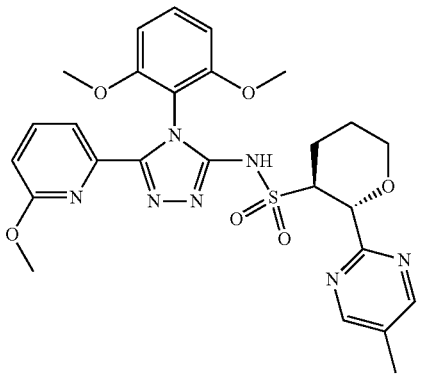 [SMILES: COc1cccc(-c2nnc(NS(=O)(=O)[C@H]3CCCO[C@@H]3c3ncc(C)cn3)n2-c2c(OC)cccc2OC)n1]
(2R,3R)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2S,3S)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2S,3R)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide or (2R,3S)-N-(4-(2,6-dimethoxyphenyl)-5-(6-methoxypyridin-2-yl)-4H-1,2,4-triazol-3-yl)-2-(5-methylpyrimidin-2-yl)tetrahydro-2H-pyran-3-sulfonamide
$^1$H NMR (400 MHz, CDCl$_3$) δ 11.43 (br s, 1H), 8.62 (s, 2H), 7.58-7.62 (m, 2H), 7.32 (dd, J = 8.5, 8.5 Hz, 1H), 6.70 (dd, J = 7.6, 1.4 Hz, 1H), 6.58-6.64 (m, 2H), 4.81 (d, J = 10.0 Hz, 1H), 4.08-4.12 (m, 1H), 3.80-3.86 (m, 1H), 3.77 (s, 3H), 3.67 (s, 3H), 3.51-3.68 (m, 1H), 3.18 (s, 3H), 2.45-2.48 (m, 1H), 2.32 (s, 3H), 2.00-2.10 (m, 1H), 1.86-1.97 (m, 1H), 1.73-1.80 (m, 1H). LCMS-ESI (pos.) m/z: 568.1 (M + H)$^+$. |
| 658.0 | Example 649.0 was separated by supercritical fluid chromatography by the following method: Column: Chiralcel OX-H (Reversed) (250 × 21 mm, 5 μm) Mobile Phase: 73:27 (A:B), A: Liquid CO$_2$ B: EtOH (20 mM NH$_3$) Flow Rate: 70 mL/min Column/Oven temp.: 40° C., 220 nm 172-179 bar inlet pressure Four peaks were collected; this was the first isomer to elute under these conditions. | 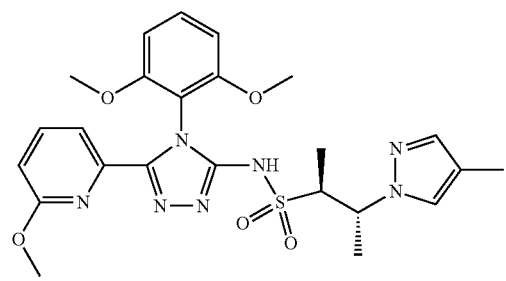 [SMILES: COc1cccc(-c2nnc(NS(=O)(=O)[C@@H](C)[C@@H](C)n3cc(C)cn3)n2-c2c(OC)cccc2OC)n1]
or
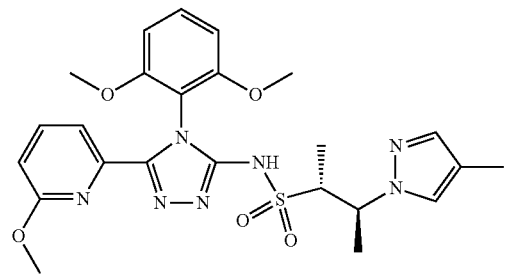 [SMILES: COc1cccc(-c2nnc(NS(=O)(=O)[C@H](C)[C@H](C)n3cc(C)cn3)n2-c2c(OC)cccc2OC)n1]
or |

TABLE 24-continued

| Example | Reagents | Structure, Name and Data |
|---|---|---|
| | | <br>or<br>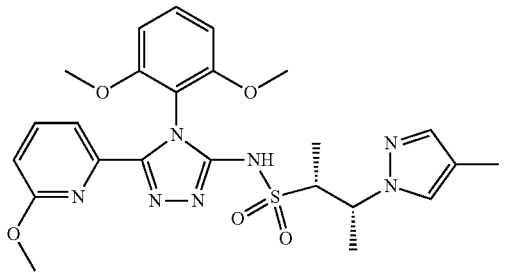 [SMILES: COc1cccc(-c2nnc(NS(=O)(=O)[C@H](C)[C@@H](C)n3cc(C)cn3)n2-c2c(OC)cccc2OC)n1]<br>(2S,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2S,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide<br>$^1$H NMR (400 MHz, CDCl$_3$) δ 7.59-7.63 (obscured m, 1H), 7.60 (s, 1H), 7.32 (obscured dd, J = 8.0, 8.0 Hz, 1H), 7.30 (s, 1H), 7.15 (s, 1H), 6.67-6.71 (m, 1H), 6.60 (d, J = 8.4 Hz, 2H), 4.60-4.67 (m, 1H), 3.70 (s, 3H), 3.69 (s, 3H), 3.32-3.39 (m, 1H), 3.16 (s, 3H), 2.04 (s, 3H), 1.68 (d, J = 6.8 Hz, 3H), 1.06 (d, J = 7.0 Hz, 3H). LCMS-ESI (pos.) m/z: 528.2 (M + H)$^+$. |
| 659.0 | Example 649.0 was separated by supercritical fluid chromatography by the following method:<br>Column: Chiralcel OX-H (Reversed) (250 × 21 mm, 5 μm)<br>Mobile Phase: 73:27 (A:B) A: Liquid CO$_2$ B: EtOH (20 mM NH$_3$)<br>Flow Rate: 70 mL/min<br>Column/Oven temp.: 40° C. 220 nm<br>172-179 bar inlet pressure<br>Four peaks were collected; this was the second isomer to elute under these conditions. | 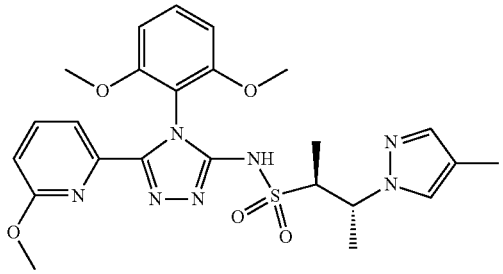 [SMILES: COc1cccc(-c2nnc(NS(=O)(=O)[C@@H](C)[C@@H](C)n3cc(C)cn3)n2-c2c(OC)cccc2OC)n1]<br>or |

TABLE 24-continued

| Example | Reagents | Structure, Name and Data |
|---------|----------|--------------------------|

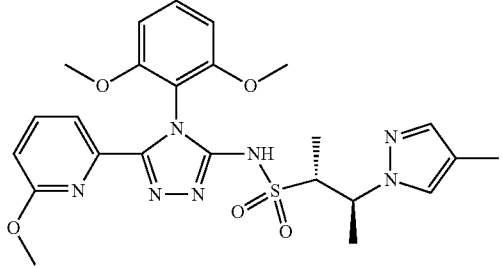 [SMILES: COc1cccc(-c2nnc(NS(=O)(=O)[C@H](C)[C@H](C)n3cc(C)cn3)n2-c2c(OC)cccc2OC)n1]

or

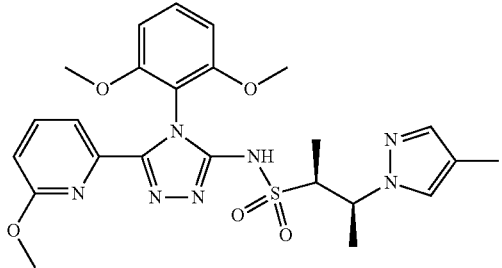 [SMILES: COc1cccc(-c2nnc(NS(=O)(=O)[C@@H](C)[C@H](C)n3cc(C)cn3)n2-c2c(OC)cccc2OC)n1]

or

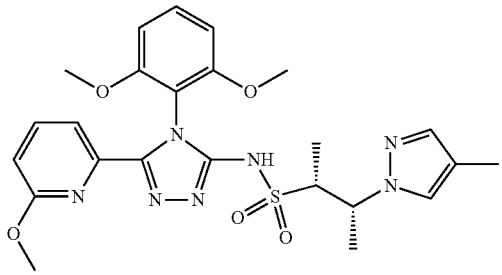 [SMILES: COc1cccc(-c2nnc(NS(=O)(=O)[C@H](C)[C@@H](C)n3cc(C)cn3)n2-c2c(OC)cccc2OC)n1]

(2S,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2S,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide $^1$H NMR (400 MHz, CDCl$_3$) δ 7.59-7.63 (m, 1H), 7.60 (s, 1H), 7.32 (dd, J = 8.0, 8.0 Hz, 1H), 7.30 (s, 1H), 7.15 (br s, 1H), 6.67-6.72 (m, 1H), 6.60 (d, J = 8.4 Hz, 2H), 4.60-4.67 (m, 1H), 3.70 (s, 3H), 3.69 (s, 3H), 3.32-3.39 (m, 1H), 3.16 (s, 3H), 2.04 (s, 3H), 1.68 (d, J = 6.8 Hz, 3H), 1.06 (d, J = 7.0 Hz, 3H). LCMS-ESI (pos.) m/z: 528.2 (M + H)$^+$.

TABLE 24-continued

| Example | Reagents | Structure, Name and Data |
|---|---|---|
| 660.0 | Example 649.0 was separated by supercritical fluid chromatography by the following method: Column: Chiralcel OX-H (Reversed) (250 × 21 mm, 5 μm) Mobile Phase: 73:27 (A:B), A: Liquid $CO_2$, B: EtOH (20 mM $NH_3$) Flow Rate: 70 mL/min Column/Oven temp.: 40° C., 220 nm, 172-179 bar inlet pressure Four peaks were collected; this was the third isomer to elute under these conditions. | or<br><br>or<br><br>or<br><br>(2S,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2S,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide<br>$^1$H NMR (400 MHz, CDCl$_3$) δ 7.58-7.63 (m, 1H), 7.60 (s, 1H), 7.31 (dd, J = 8.0, 8.0 Hz, 1H), 7.30 (s, 1H), 7.17 (s, 1H), 6.69 (dd, J = 3.9, 3.9 Hz, 1H), 6.57-6.60 (m, 2H), 5.00-5.06 (m, 1H), |

TABLE 24-continued

| Example | Reagents | Structure, Name and Data |
|---|---|---|
| | | 3.68 (s, 3H), 3.68 (s, 3H), 3.49-3.55 (m, 1H), 3.15 (s, 3H), 2.05 (s, 3H), 1.53 (d, J = 7.0 Hz, 3H), 1.29 (d, J = 7.0 Hz, 3H). LCMS-ESI (pos.) m/z: 528.2 (M + H)+. |
| 661.0 | Example 649.0 was separated by supercritical fluid chromatography by the following method: Column: Chiralcel OX-H (Reversed) (250 × 21 mm, 5 μm) Mobile Phase: 73:27 (A:B), A: Liquid $CO_2$, B: EtOH (20 mM $NH_3$) Flow Rate: 70 mL/min Column/Oven temp.: 40° C., 220 nm, 172-179 bar inlet pressure Four peaks were collected; this was the fourth isomer to elute under these conditions. | 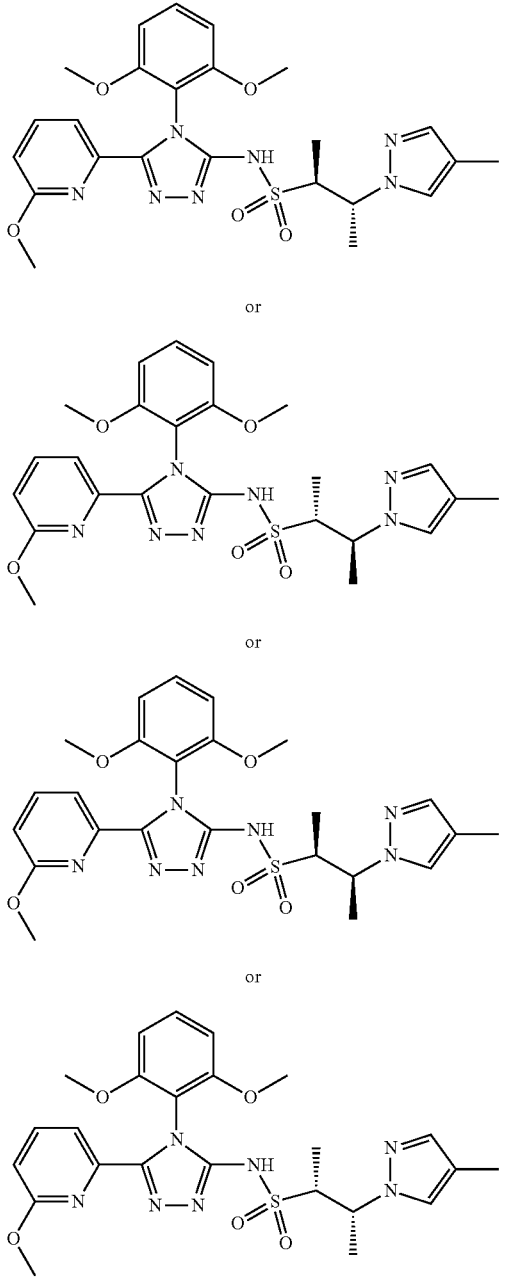

(2S,3R)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2S,3S)-N-(4-(2,6-dimethoxyphenyl)-5-(6-methoxypyridin-2-yl)-4H-1,2,4-triazol-3-yl)-3-(4-methyl-1H-pyrazol-1-yl)butane-2-sulfonamide or (2R,3R)-N-(4-(2,6-dimethoxyphenyl)-5-(6-methoxypyridin-2-yl)-4H-1,2,4-triazol-3-yl)-3-(4-methyl-1H- |

TABLE 24-continued

| Example | Reagents | Structure, Name and Data |
|---------|----------|--------------------------|
| | | pyrazol-1-yl)butane-2-sulfonamide<br>$^1$H NMR (400 MHz, CDCl$_3$) δ 7.59-7.64 (m, 1H), 7.60 (s, 1H), 7.31 (dd, J = 8.0, 8.0 Hz, 1H), 7.30 (s, 1H), 7.18 (br s, 1H), 6.68-6.72 (m, 1H), 6.57-6.60 (m, 2H), 5.00-5.06 (m, 1H), 3.69 (s, 3H), 3.68 (s, 3H), 3.50-3.56 (m, 1H), 3.15 (s, 3H), 2.05 (s, 3H), 1.53 (d, J = 7.0 Hz, 3H), 1.29 (d, J = 7.0 Hz, 3H). LCMS-ESI (pos.) m/z: 528.2 (M + H)$^+$. |

The compounds set forth in the following Table were synthesized following the procedure in Example A using the known starting material as described.

TABLE 25

| Example | Reagents | Structure, Name and Data |
|---------|----------|--------------------------|
| 662.0 | 6-(methylamino)picolinohydrazide (Example 3.25), 2-isothiocyanato-1,3-dimethoxybenzene (Example 1.0), (S)-1-(5-fluoropyrimidin-2-yl)propane-2-sulfonamide and (R)-1-(5-fluoropyrimidin-2-yl)propane-2-sulfonamide (Example 9.0) The racemic products were separated by supercritical fluid chromatography by the following method:<br>Column: Chiralcel OX-H (Reversed) (250 × 21 mm, 5 [m) Mobile Phase: 60:40 (A:B) A: Liquid CO2; B: EtOH (20 mM NH3); Flow Rate: 70 mL/min Column/Oven temp.: 40° C.; 66.1 220 nm<br>4.9 mg/injection; 193-200 bar inlet pressure.<br>Two peaks were collected; this was the first isomer to elute under these conditions. | 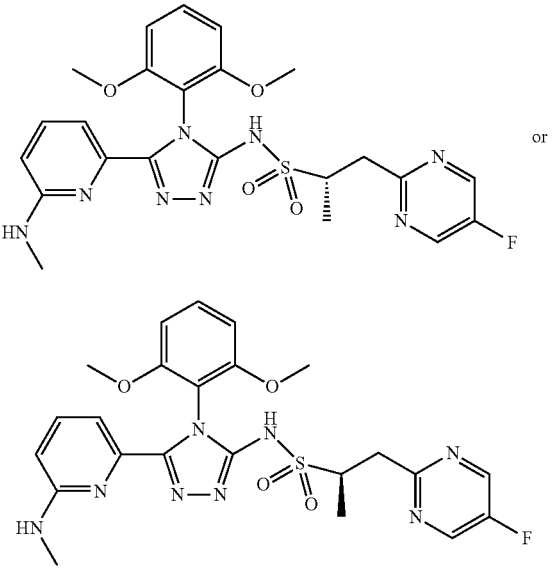<br><br>(R)-N-(4-(2,6-dimethoxyphenyl)-5-(6-(methylamino)pyridin-2-yl)-4H-1,2,4-triazol-3-yl)-1-(5-fluoropyrimidin-2-yl)propane-2-sulfonamide compound or (S)-N-(4-(2,6-dimethoxyphenyl)-5-(6-(methylamino)pyridin-2-yl)-4H-1,2,4-triazol-3-yl)-1-(5-fluoropyrimidin-2-yl)propane-2-sulfonamide<br>$^1$H NMR (400 MHz, CDCl$_3$) δ 8.52 (s, 2H), 7.40 (t, J = 7.8, 7.8 Hz, 1H), 7.32 (t, J = 8.4 Hz, 1H), 7.14 (d, J = 7.4 Hz, 1H), 6.59 (dd, J = 8.5, 2.4 Hz, 2H), 6.33 (d, J = 8.4 Hz, 1H), 4.15 (br s, 1H), 3.75-3.83 (m, 1H), 3.71 (s, 3H), 3.70 (s, 3H), 3.09 (dd, J = 14.7, 9.8 Hz, 1H), 2.41 (d, J = 5.1 Hz, 3H), 1.31 (d, J = 6.7 Hz, 3H). LCMS-ESI (pos.) m/z: 529.1 (M + H)$^+$. |

TABLE 25-continued

| Example | Reagents | Structure, Name and Data |
|---|---|---|
| 663.0 | 6-(methylamino)picolinohydrazide (Example 3.25), 2-isothiocyanato-1,3-dimethoxybenzene (Example 1.0), (S)-1-(5-fluoropyrimidin-2-yl)propane-2-sulfonamide and (R)-1-(5-fluoropyrimidin-2-yl)propane-2-sulfonamide (Example 9.0) The racemic products were separated by supercritical fluid chromatography by the following method: Column: Chiralcel OX-H (Reversed) (250 × 21 mm, 5 [m) Mobile Phase: 60:40 (A:B) A: Liquid CO2; B: EtOH (20 mM NH3); Flow Rate: 70 mL/min Column/Oven temp.: 40° C.; 220 nm 4.9 mg/injection; 193-200 bar inlet pressure. Two peaks were collected; this was the second isomer to elute under these conditions. | 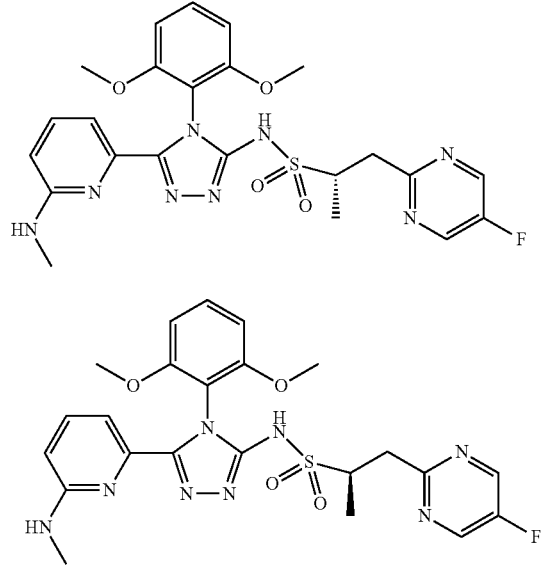<br>(R)-N-(4-(2,6-dimethoxyphenyl)-5-(6-(methylamino)pyridin-2-yl)-4H-1,2,4-triazol-3-yl)-1-(5-fluoropyrimidin-2-yl)propane-2-sulfonamide compound or (S)-N-(4-(2,6-dimethoxyphenyl)-5-(6-(methylamino)pyridin-2-yl)-4H-1,2,4-triazol-3-yl)-1-(5-fluoropyrimidin-2-yl)propane-2-sulfonamide<br>$^1$H NMR (400 MHz, CDCl$_3$) δ 11.0 (br s, 1H), 8.53 (s, 2H), 7.40 (dd, J = 8.0 Hz, 1H), 7.32 (dd, J = 8.4 Hz, 1H), 7.14 (d, J = 7.4 Hz), 6.59 (dd, J = 8.4, 2.2 Hz, 2H), 6.33 (d, J = 8.2 Hz, 8.2 Hz, 1H), 4.15 (br s, 1H), 3.75-3.82 (m, 1H), 3.71 (s, 3H), 3.70 (s, 3H), 3.09 (dd, J = 14.7, 9.8 Hz, 1H), 2.41 (d, J = 5.1 Hz, 3H), 1.31 (d, J = 6.8 Hz, 3H). LCMS-ESI (pos.) m/z: 529.1 (M + H)$^+$. |

Example 664.0: Preparation of (1R,2S,P)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide 664.0

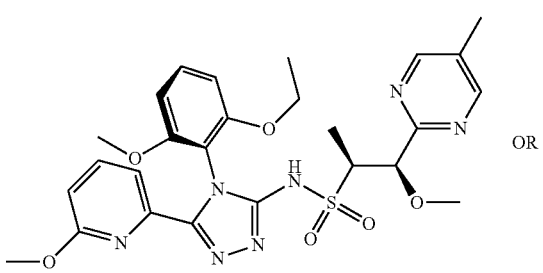

OR

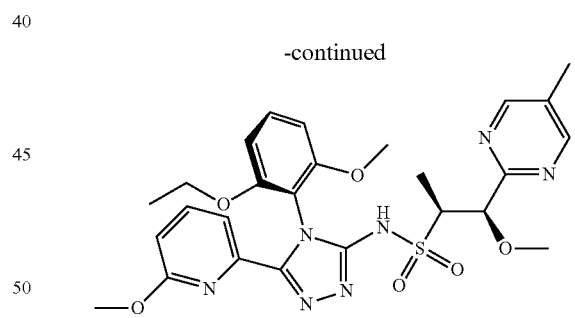

(1R,2S,P)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide, Example 664

A chiral supercritical fluid chromatography purification of Example 43.0 (45 mg, 1:1 ratio of P and M atropisomers) was performed to separate the two atropisomeric products. Preparative SFC method: Column: Chiralpak AD-H (150× 21 mm, 5 μm), Mobile Phase: 85:15 (A:B), A: Liquid CO$_2$, B: EtOH, Flow Rate: 70 mL/min, 220 nm, 213 bar inlet pressure and provided two peaks of >99.5% ee: The first eluting peak (10 mg) was Example 664.0, (1R,2S,P)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide. $^1$H NMR (400 MHz, CD$_3$CN) δ 8.59 (s, 2H), 7.71 (dd, J=8.3, 7.5 Hz, 1H), 7.57 (d, J=7.4 Hz, 1H), 7.37 (t, J=8.5 Hz, 1H), 6.64-6.80 (m, 3H), 4.82 (d, J=4.3 Hz, 1H), 3.98 (dq, J=9.7, 6.9 Hz, 1H), 3.84 (dq, J=9.7, 7.0 Hz, 1H), 3.73 (s, 3H), 3.48-3.60 (m, 1H), 3.21 (s, 3H), 3.17 (s, 3H), 2.28 (s, 3H), 1.20-1.30 (m, 3H), 1.07-1.13 (m, 1H), 1.02 (t, J=6.9 Hz, 3H). LCMS-ESI (POS.) m/z: 570.2 (M+H)$^+$.

Example 665.0: Preparation of (1R,2S,P)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide

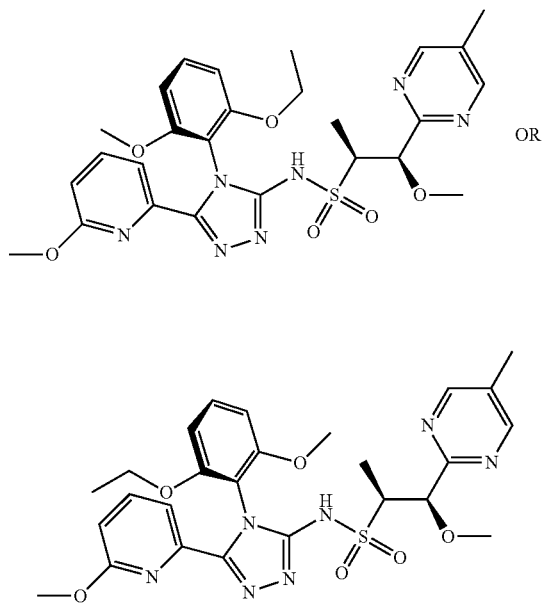

665.0

OR

The second eluting peak (10 mg) was Example 665.0, (1R,2S,M)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,P)—N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide. $^1$H NMR (400 MHz, CD$_3$CN) δ 8.61 (s, 2H), 7.69-7.80 (m, 1H), 7.60 (d, J=7.4 Hz, 1H), 7.40 (t, J=8.5 Hz, 1H), 6.66-6.83 (m, 3H), 4.86 (d, J=4.3 Hz, 1H), 3.97-4.08 (m, 1H), 3.88 (dq, J=9.7, 7.0 Hz, 1H), 3.72 (s, 3H), 3.55 (dq, J=7.0, 4.3 Hz, 1H), 3.20 (s, 3H), 3.17 (s, 3H), 2.30 (s, 3H), 1.24-1.29 (m, 3H), 1.07-1.11 (m, 4H). LCMS-ESI (POS.) m/z: 570.2 (M+H)$^+$.

Example 666.0: Preparation of (1R,2S,P)—N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide

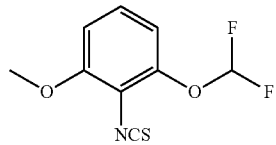

666.1

1-(difluoromethoxy)-2-isothiocyanato-3-methoxybenzene, Example 666.1

Step 1: 3-methoxy-2-nitrophenol

To a flask containing 1-fluoro-3-methoxy-2-nitrobenzene (1.00 g, 5.84 mmol, Apollo Scientific) and 2-(methylsulfonyl)ethanol (0.77 g, 6.19 mmol, Aldrich) under N$_2$ was added DMSO (5 mL) and potassium t-butoxide (6.19 mL, 6.19 mmol, 1.0 M in THF). The reaction was stirred under N$_2$ at RT for 20 h. An additional portion of 2-(methylsulfonyl)ethanol (0.77 g, 6.19 mmol) and potassium t-butoxide (6.19 mL, 6.19 mmol) was added, and the reaction was stirred for an additional 3.5 h. The reaction was then quenched with 1 N HCl (20 mL) to pH<1, and extracted with EtOAc (2×25 mL). The combined organic fractions were washed with 1 N NaOH (2×50 mL), and the aqueous layers were combined and acidified to pH 1 with 5 N HCl, and extracted with EtOAc (2×25 mL). The combined organic layers were dried (MgSO$_4$), and concentrated to give the product as an orange oil. Purification by automated flash chromatography (40 g SiO$_2$, 0-100% EtOAc/hexanes) gave 3-methoxy-2-nitrophenol (0.88 g, 5.20 mmol, 89% yield) as a dark orange oil. $^1$H NMR (300 MHz, CDCl$_3$) δ 7.42 (t, J=8.5 Hz, 1H), 6.73 (dd, J=8.5, 1.2 Hz, 1H), 6.56 (dd, J=8.5, 1.0 Hz, 1H), 3.96 (s, 3H). LCMS-ESI (POS.) m/z: 170.2 (M+H)$^+$; m/z: 152.2 (M−H$_2$O)$^+$.

Step 2: 1-(difluoromethoxy)-3-methoxy-2-nitrobenzene

To a round bottom flask containing 3-methoxy-2-nitrophenol (310 mg, 1.833 mmol) was added DMF (5 mL), cesium carbonate (1194 mg, 3.67 mmol), and sodium 2-chloro-2,2-difluoroacetate (559 mg, 3.67 mmol). The reaction was heated in a 100° C. oil bath under N$_2$ for 4 h. The reaction was then cooled to RT, diluted with water (50 mL) and extracted with EtOAc (3×25 mL). The organic layers were combined, dried (MgSO$_4$), and concentrated. Purification by automated flash chromatography (80 g SiO$_2$ 0-100% EtOAc/hexanes) gave 1-(difluoromethoxy)-3-methoxy-2-nitrobenzene (398 mg, 1.82 mmol, 99% yield) as an orange oil. $^1$H NMR (300 MHz, CDCl$_3$) δ 7.43 (t, J=8.6 Hz, 1H), 7.01-6.87 (m, 2H), 6.55 (t, J=72.5 Hz, 1H), 3.94 (s, 3H).

Step 3: 2-(difluoromethoxy)-6-methoxyaniline

To a round bottom flask containing 1-(difluoromethoxy)-3-methoxy-2-nitrobenzene (398 mg, 1.816 mmol) was added iron powder (507 mg, 9.08 mmol) and ammonium chloride (97 mg, 1.816 mmol). EtOH (20 mL) and H$_2$O (2 mL) were added, and the resulting mixture was heated in an oil bath at 80° C. under N$_2$ for 2 h. The suspension was filtered and the filtrate concentrated. Purification by automated flash chromatography (12 g SiO$_2$, 0-40% 3:1 EtOAc: EtOH/heptane) gave 2-(difluoromethoxy)-6-methoxyaniline (260 mg, 1.38 mmol, 76% yield) as a clear, colorless oil. $^1$H NMR (300 MHz, CDCl$_3$) δ 6.75-6.64 (m, 3H), 6.48 (t, J=74.6 Hz, 1H), 3.88 (s, 3H). LCMS-ESI (POS.) m/z: 190.1 (M+H)$^+$.

Step 4: 1-(difluoromethoxy)-2-isothiocyanato-3-methoxybenzene

To a 50 mL round bottom flask with 2-(difluoromethoxy)-6-methoxyaniline (260 mg, 1.375 mmol) in DCM (10 mL) at RT was added 1,1'-thiocarbonylbis(pyridin-2(1H)-one) (319 mg, 1.38 mmol). The reaction was stirred at RT under N$_2$ for 20 h. The reaction mixture was then concentrated to give an orange solid as Example 666.1 which was used without further purification.

The compounds set forth in the following Table were synthesized following the procedure in Example A using the known starting material as described.

TABLE 26

| Example | Reagents | Structure, Name and Data |
|---|---|---|
| 666.0 | (1R,2S)-1-methoxy-1-(5-methylpyrimidin-2-yl)propane-2-sulfonamide (Intermediate 14.0), 6-methoxypicolinohydrazide (Intermediate 3.18), 1-(difluoromethoxy)-2-isocyanato-3-methoxybenzene (Example 666.1) | 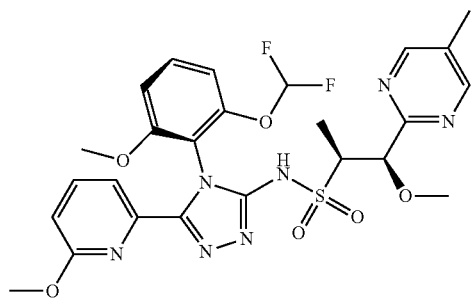<br>AND<br>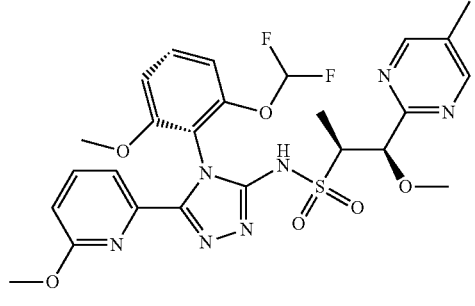<br>(1R,2S,P)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide<br>$^1$H NMR (300 MHz, CDCl$_3$) (1:1 ratio of P and M atropisomers) δ 8.72 (s, 4H), 7.56-7.73 (m, 4H), 7.39 (t, J = 8.5 Hz, 2H), 6.79-6.98 (m, 4H), 6.68-6.77 (m, 2H), 6.24-6.85 (m, 2H), 4.98 (dd, J = 6.7, 4.5 Hz, 2H), 3.72 (s, 3H), 3.70 (s, 3H), 3.66-3.77 (m, 2H), 3.29 (s, 3H), 3.27 (s, 3H), 3.15 (s, 6H), 2.38 (s, 6H), 1.33 (dd, J = 7.0, 3.8 Hz, 6H). LCMS-ESI (POS.) m/z: 592.1 (M + H)$^+$. |

TABLE 26-continued

| Example | Reagents | Structure, Name and Data |
|---|---|---|
| 667.0 | (1R,2S)-1-methoxy-1-(5-methylpyrimidin-2-yl)propane-2-sulfonamide (Intermediate 14.0), nicotinohydrazide (Aldrich), 1-(difluoromethoxy)-2-isocyanato-3-methoxybenzene (Example 666.1) | 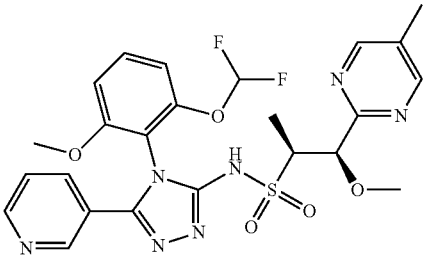<br>AND<br>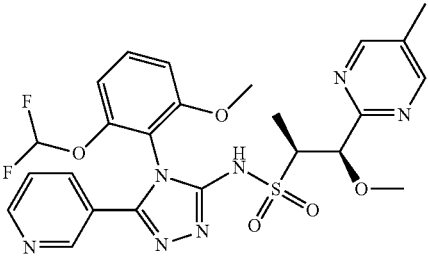 [SMILES: COc1cccc(OC(F)F)c1-n1c(NS(=O)(=O)[C@@H](C)[C@H](OC)c2ncc(C)cn2)nnc1-c1cccnc1]<br>(1R,2S,P)-N-(4-(2-(difluoromethoxy)-6-methoxyphenyl)-5-(3-pyridinyl)-4H-1,2,4-triazol-3-yl)-1-methoxy-1-(5-methyl-2-pyrimidinyl)-2-propanesulfonamide and (1R,2S,M)-N-(4-(2-(difluoromethoxy)-6-methoxyphenyl)-5-(3-pyridinyl)-4H-1,2,4-triazol-3-yl)-1-methoxy-1-(5-methyl-2-pyrimidinyl)-2-propanesulfonamide<br>$^1$H NMR (300 MHz, CDCl$_3$) (1:1 ratio of P and M atropisomers) $^1$H NMR (CDCl$_3$) δ 8.60-8.69 (m, 8H), 7.77-7.87 (m, 2H), 7.48 (t, J = 8.5 Hz, 2H), 7.35 (dd, J = 8.0, 5.0 Hz, 2H), 6.83-7.00 (m, 4H), 6.33-6.89 (m, 2H), 4.95 (dd, J = 7.7, 4.5 Hz, 2H), 3.77 (s, 3H), 3.73 (s, 3H), 3.66-3.81 (m, 2H) 3.33 (s, 3H), 3.31 (s, 3H), 2.35 (s, 6H), 1.37 (dd, J = 7.0, 5.0 Hz, 6H). LCMS-ESI (POS.) m/z: 562.1 (M + H)$^+$. |
| 668.0 | (1R,2S)-1-methoxy-1-(5-methylpyrimidin-2-yl)propane-2-sulfonamide (Intermediate 14.0), 5-methylnicotinohydrazide (JPM2 Pharmaceuticals), 1-(difluoromethoxy)-2-isocyanato-3-methoxybenzene (Example 666.1) | 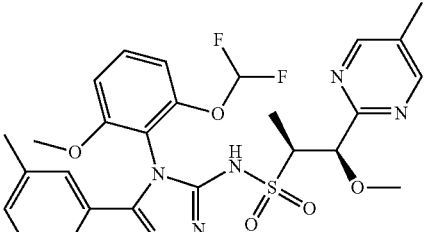<br>AND<br>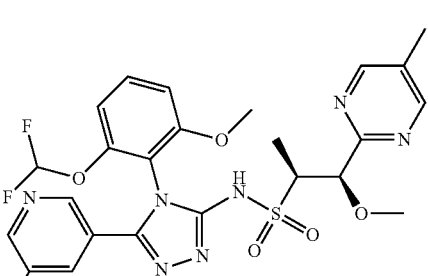<br>(1R,2S,P)-N-(4-(2-(difluoromethoxy)-6-methoxyphenyl)-5-(5-methyl-3-pyridinyl)-4H-1,2,4-triazol-3-yl)-1-methoxy-1-(5-methyl-2-pyrimidinyl)-2-propanesulfonamide and (1R,2S,M)-N-(4-(2-(difluoromethoxy)-6-methoxyphenyl)-5-(5-methyl-3- |

| Example | Reagents | Structure, Name and Data |
|---|---|---|
| | | pyridinyl)-4H-1,2,4-triazol-3-yl)-1-methoxy-1-(5-methyl-2-pyrimidinyl)-2-propanesulfonamide<br>$^1$H NMR (300 MHz, CDCl$_3$) (1:1 ratio of P and M atropisomers) δ 8.67 (s, 4H), 8.55 (d, J = 1.2 Hz, 2H), 8.43 (s, 2H), 7.95 (s, 2H), 7.51 (t, J = 8.6 Hz, 2H), 6.83-6.98 (m, 4H), 6.33-6.90 (m, 2H), 4.96 (dd, J = 6.1, 4.5 Hz, 2H), 3.82 (s, 3H), 3.78 (s, 3H), 3.68-3.78 (m, 2H), 3.31 (s, 3H), 3.30 (s, 3H), 2.42 (s, 6H), 2.36 (s, 6H), 1.36 (d, J = 6.9 Hz, 3H), 1.35 (d, J = 7.0 Hz, 3H). LCMS-ESI (POS.) m/z: 576.0 (M + H)$^+$. |
| 669.0 | (1R,2S)-1-methoxy-1-(5-methylpyrimidin-2-yl)propane-2-sulfonamide (Intermediate 14.0), nicotinohydrazide (Aldrich), 1,3-bis(difluoromethoxy)-2-isocyanatobenzene (Intermediate 1.5) | 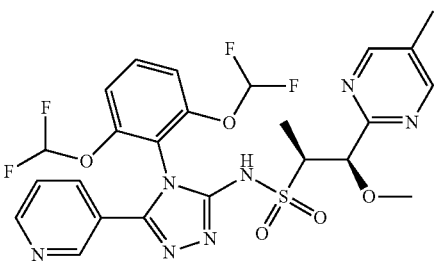 [SMILES: CO[C@H](c1ncc(C)cn1)[C@H](C)S(=O)(=O)Nc1nnc(-c2cccnc2)n1-c1c(OC(F)F)cccc1OC(F)F]<br>(1R,2S)-N-(4-(2,6-bis(difluoromethoxy)phenyl)-5-(3-pyridinyl)-4H-1,2,4-triazol-3-yl)-1-methoxy-1-(5-methyl-2-pyrimidinyl)-2-propanesulfonamide<br>$^1$H NMR (300 MHz, CDCl$_3$) δ 8.68 (dd, J = 5.0, 1.6 Hz, 1H), 8.60-8.65 (m, 3H), 7.78 (dt, J = 8.1, 1.9 Hz, 1H), 7.51-7.63 (m, 1H), 7.34 (dd, J = 8.0, 4.9 Hz, 1H), 7.21 (t, J = 8.0 Hz, 2H), 6.25-6.87 (m, 2H), 4.92 (d, J = 4.5 Hz, 1H), 3.63-3.77 (m, 1H), 3.31 (s, 3H), 2.34 (s, 3H), 1.35 (d, J = 7.0 Hz, 3H). LCMS-ESI (POS.) m/z: 598.1 (M + H)$^+$. |
| 670.0 | (1R,2S)-1-methoxy-1-(5-methylpyrimidin-2-yl)propane-2-sulfonamide (Intermediate 14.0), 5-methylnicotinohydrazide (JPM2 Pharmaceuticals), 1,3-bis(difluoromethoxy)-2-isocyanatobenzene (Intermediate 1.5) | 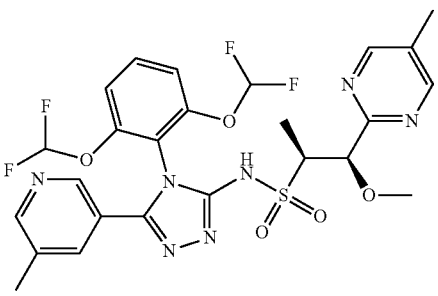 [SMILES: CO[C@H](c1ncc(C)cn1)[C@H](C)S(=O)(=O)Nc1nnc(-c2cncc(C)c2)n1-c1c(OC(F)F)cccc1OC(F)F]<br>(1R,2S)-N-(4-(2,6-bis(difluoromethoxy)phenyl)-5-(5-methyl-3-pyridinyl)-4H-1,2,4-triazol-3-yl)-1-methoxy-1-(5-methyl-2-pyrimidinyl)-2-propanesulfonamide<br>$^1$H NMR (300 MHz, CDCl$_3$) δ 8.61 (s, 2H), 8.50 (s, 1H), 8.33 (d, J = 1.8 Hz, 1H), 7.66 (s, 1H), 7.57 (t, J = 8.5 Hz, 1H), 7.16-7.25 (m, 2H), 6.22-6.97 (m, 2H), 4.91 (d, J = 4.4 Hz, 1H), 3.70 (dd, J = 7.0, 4.5 Hz, 1H), 3.31 (s, 3H), 2.34 (s, 6H), 1.35 (d, J = 7.0 Hz, 3H). LCMS-ESI (POS.) m/z: 612.0 (M + H)$^+$. |

Example 671.0: Preparation of (2R,3R)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide and (2S,3S)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide

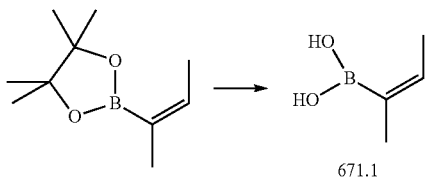

671.1

(E)-But-2-en-2-ylboronic acid, Example 671.1

To a stirred solution of (E)-2-butene-2-boronic acid pinacolester (5.0 g, 0.0274 mol) in acetone (25.0 mL) and water (25.0 mL) at RT, was added sodium periodate (5.87 g, 0.027 mol) and ammonium acetate (2.11 g, 0.0274 mol). The resulting mixture was stirred at RT for 4 hours. The reaction was then partially concentrated in vacuo to remove the acetone and was diluted with MTBE (50.0 mL). The resulting two phases were separated and the aqueous layer was extracted with MTBE (2×25.0 mL). The combined organic phases were dried over sodium sulfate and concentrated under vacuum to afford the desired product (E)-but-2-en-2-ylboronic acid, Example 671.1 in 44% yield.

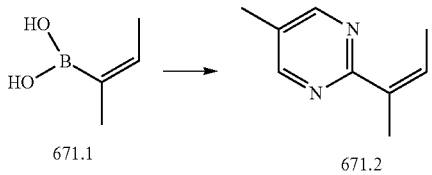

671.1    671.2

(Z)-2-(But-2-en-2-yl)-5-methylpyrimidine, Example 671.2

A round bottom flask was charged with IPA (600 mL) and purged with argon for 1-2 h at 25-30° C. 2-Chloro-5-methylpyrimidine (30.0 g, 0.233 mol) was charged into the flask, and the mixture was stirred for 5-10 min followed by addition of potassium phosphate tribasic (98.9 g, 466 mol), (E)-but-2-en-2-ylboronic acid Example 671.1 (34.9 g, 0.349 mol), 2-dicyclohexylphosphino-2',4',6'-triisopropylbiphenyl (4.2 g, 8.8 mmol) and $Pd_2(dba)_3$ (2.13 g, 2.32 mmol). The reaction was stirred for 10-15 min under argon atmosphere and then heated to 75-80° C. for 12-16 h. The reaction was cooled to 0-5° C. Water (300.0 mL) and MTBE (180.0 mL) were then added slowly. The aqueous and organic layers were separated. The aqueous layer was extracted with MTBE (60.0 mL). The combined organic layers were washed with brine (60.0 mL) twice. The organic layer was concentrated in vacuo to afford the initial product which was diluted with heptane (150.0 mL) and MTBE (75.0 mL). The above mixture, was extracted three times with aq. hydrochloric acid. The combined aqueous layers were washed with heptane (30.0 mL), made basic with sodium hydroxide solution until pH 10 was obtained, and extracted with heptane (90.0 mL). The aqueous and organic layers were separated and the aqueous layer was extracted with heptane (30.0 mL). The combined organic layers were washed with brine (60.0 mL), dried over sodium sulfate, and concentrated in vacuo to afford (Z)-2-(but-2-en-2-yl)-5-methylpyrimidine, Example 671.2 in 68% yield.

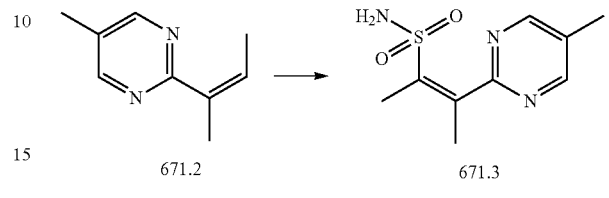

671.2    671.3

(Z)-3-(5-Methylpyrimidin-2-yl)but-2-ene-2-sulfonamide, Example 671.3

This compound was prepared in an analogous manner starting from (Z)-2-(but-2-en-2-yl)-5-methylpyrimidine, Example 671.2, according to the procedures described in Examples 10.02 through 10.05. in 22% overall yield. LCMS-ESI (POS.) m/z: 228.3 (M+H)⁺.

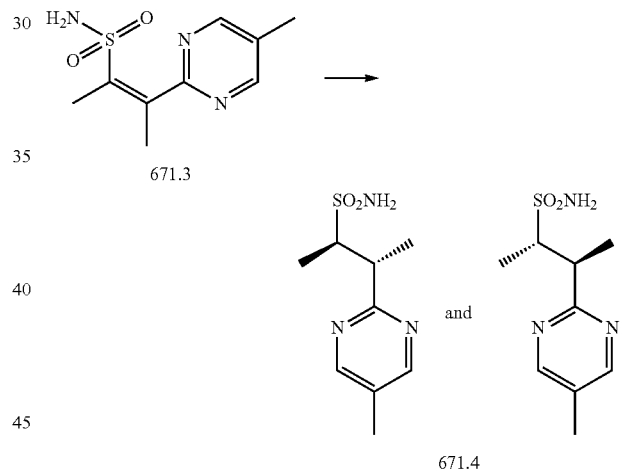

671.4

(2R,3R)-3-(5-Methylpyrimidin-2-yl)butane-2-sulfonamide and (2S,3S)-3-(5-methylpyrimidin-2-yl)butane-2-sulfonamide, Example 671.4

A Parr shaker flask was charged with MeOH (30.0 mL) and (Z)-3-(5-methylpyrimidin-2-yl)but-2-ene-2-sulfonamide, Example 671.3 (0.5 g, 1.0 eq). The resulting clear solution was purged with nitrogen gas before 10% palladium on carbon (0.05 g) was added. The reaction was hydrogenated under 50 psi of hydrogen pressure for 8 h. The reaction mixture was then filtered through a short pad of Celite® brand filter aid and the filtrate was concentrated in vacuo to afford the title compounds (2R,3R)-3-(5-methylpyrimidin-2-yl)butane-2-sulfonamide and (2S,3S)-3-(5-methylpyrimidin-2-yl)butane-2-sulfonamide, Example 671.4 as a racemic mixture in 20% yield. LCMS-ESI (POS), m/z: 230.2 (M+H)⁺.

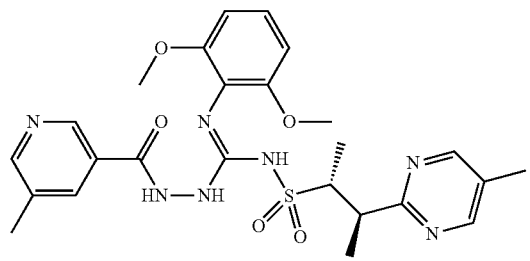

and

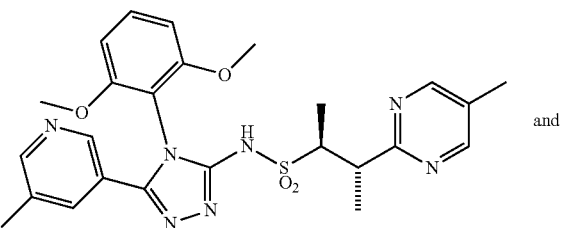

and

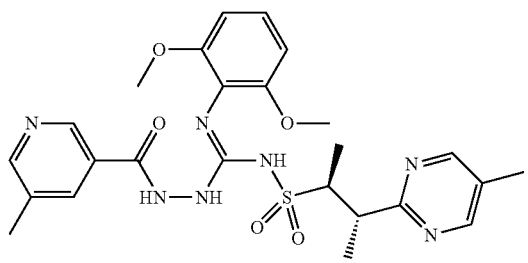

(Z)—N'-(2,6-Dimethoxyphenyl)-2-(5-methylnicotinoyl)-N-(((2R,3R)-3-(5-methylpyrimidin-2-yl)butan-2-yl)sulfonyl)hydrazinecarboximidamide and (Z)—N'-(2,6-dimethoxyphenyl)-2-(5-methylnicotinoyl)-N-(02S,3S)-3-(5-methylpyrimidin-2-yl)butan-2-yl) sulfonyl)hydrazinecarboximidamide, Example 671.5

A racemic mixture of (2R,3R)-3-(5-methylpyrimidin-2-yl)butane-2-sulfonamide and (2S,3S)-3-(5-methylpyrimidin-2-yl)butane-2-sulfonamide, Example 671.4 (88 mg, 0.38 mmol) was combined with 2-isothiocyanato-1,3-dimethoxybenzene, Intermediate 1.0 (76 mg, 0.38 mmol), cesium carbonate (150 mg, 0.46 mmol) and NMP (6.0 mL). The mixture was heated in a heat block set to to 45° C. After 17 hours, an additional portion of cesium carbonate (100 mg, 0.31 mmol) was added and the heat block was set to 60° C. After heating for an additional 1 hr and 45 min., the reaction was allowed to cool to room temperature before 5-methylnicotinohydrazide (65.3 mg, 0.422 mmol) followed by EDCI, (88 mg, 0.461 mmol) were added in one portion. The reaction was stirred for 2 h before an additional amount of 5-methylnicotinohydrazide (65 mg, 0.42 mmol) and EDCI, (88 mg, 0.46 mmol) were added. After stirring 17 h at RT, water (10 mL) was added and the pH of the reaction was adjusted to pH 4 with phosphoric acid and extracted twice with EtOAc. The combined organic layer were concentrated and purified by chromatography through a RediSep-Sep pre-packed silica gel column, eluting with a gradient of 5-20% MeOH/EtOAc, to provide the title compound (Z)—N'-(2,6-dimethoxyphenyl)-2-(5-methylnicotinoyl)-N-(((2R,3R)-3-(5-methylpyrimidin-2-yl)butan-2-yl)sulfonyl)hydrazinecarboximidamide and (Z)—N'-(2,6-dimethoxyphenyl)-2-(5-methylnicotinoyl)-N-(((2S,3S)-3-(5-methylpyrimidin-2-yl)butan-2-yl)sulfonyl)hydrazinecarboximidamide, Example 671.5 (130 mg, 0.24 mmol, 63% yield) as an off-white solid. LCMS-ESI (POS.) m/z: 542.2 (M+H)+.

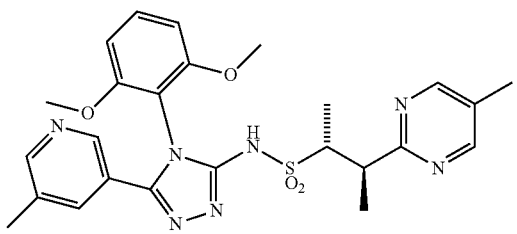

(2R,3R)—N-(4-(2,6-Dimethoxyphenyl)-5-(5-methyl-3-pyridinyl)-4H-1,2,4-triazol-3-yl)-3-(5-methyl-2-pyrimidinyl)-2-butanesulfonamide and (2S,3S)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide, Example 671.0

IPA (0.5 mL) and water (0.5 mL) were added to (Z)—N'-(2,6-dimethoxyphenyl)-2-(5-methylnicotinoyl)-N-(((2R,3R)-3-(5-methylpyrimidin-2-yl)butan-2-yl)sulfonyl)hydrazinecarboximidamide and (Z)—N'-(2,6-dimethoxyphenyl)-2-(5-methylnicotinoyl)-N-(((2S,3S)-3-(5-methylpyrimidin-2-yl)butan-2-yl) sulfonyl)hydrazinecarboximidamide, Example 671.5 (0.055 g, 0.102 mmol). To the resulting slurry was added 1 N aqueous NaOH (0.122 mL, 0.122 mmol) to afford a yellow solution that was transferred to a vial and sealed with a screw cap. The capped vial was placed on a heating block set at 70° C. After 28 h, the vial was allowed to cool to room temperature. 2 M aqueous citric acid (0.036 mL, 0.072 mmol) was added, and the white precipitate was filtered, washed with water, and dried to afford the title compound (2R,3R)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide and (2S,3S)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide, Example 671.0 (0.028 g, 0.053 mmol, 53% yield) as a racemic mixture. $^1$H NMR (400 MHz, CDCl$_3$) δ 11.87 (br. s., 1H), 8.54 (s, 2H), 8.45 (s, 1H), 8.35 (s, 1H), 7.68 (s, 1H), 7.39 (t, J=8.20 Hz, 1H), 6.61 (dd, J=8.61, 3.33 Hz, 2H), 3.76 (s, 3H), 3.75 (s, 3H), 3.52-3.64 (m, 2H), 2.32 (s, 3H), 2.30 (s, 3H), 1.52 (d, J=6.65 Hz, 3H), 1.26 (d, J=6.65 Hz, 3H). LCMS-ESI (POS.) m/z: 524.2 (M+H)+.

Example 672.0: Preparation of (2S,3R)—N-(4-(2,6-dimethoxyphenyl)-5-(pyridin-3-yl)-4H-1,2,4-triazol-3-yl)-3-(5-methoxypyrimidin-2-yl)butane-2-sulfonamide 2,2,2-trifluoroacetate

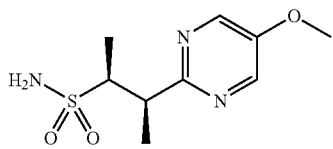

672.1

(2S,3R)-3-(5-methoxypyrimidin-2-yl)butane-2-sulfonamide, Example 672.1

A round bottom flask was charged with (2S,3R)-3-(5-fluoropyrimidin-2-yl)butane-2-sulfonamide (575 mg, 2.47 mmol, Example 10.1), MeOH (7 mL), and potassium carbonate (679 mg, 4.91 mmol). The reaction was stirred at RT. After 48 h, the reaction was heated to 50° C. and stirred for 24 h. The temperature was then raised to 65° C. and the mixture was stirred for 48 h. The reaction was allowed to cool to RT and filtered. The solids were rinsed with MeOH (2×5 mL). The filtrate was concentrated in vacuo and adsorbed onto a plug of silica gel and chromatographed through a RediSep® pre-packed silica gel column (Gold, 24 g), eluting with 0-40% EtOAc:EtOH (3:1) in heptanes. The chromatography solvents were contaminated with water. The organic layer from several fractions were concentrated in vacuo to give a mixture of starting material and the title compound (56 mg, 0.23 mmol, 9% yield) as an off-white solid. The fractions with a water layer were combined and the aqueous layer was saturated with NaCl and extracted with $CHCl_3$:IPA (9:1, 3×15 mL). The combined organic layers were dried over $MgSO_4$ and concentrated in vacuo to give more title compound (114 mg). The material was carried forward as is. LCMS-ESI (POS.) m/z: 246.1 $(M+H)^+$.

The compounds set forth in the following Table were synthesized following the procedure in Example A using the known starting material as described.

TABLE 27

| Example | Reagents | Structure, Name and Data |
|---|---|---|
| 672.0 | (2S,3R)-3-(5-methoxypyrimidin-2-yl)butane-2-sulfonamide (Example 672.1), 2-isothiocyanato-1,3-dimethoxybenzene (Example 1.0), nicotinohydrazide (Aldrich) | (2S,3R)-N-(4-(2,6-dimethoxyphenyl)-5-(pyridin-3-yl)-4H-1,2,4-triazol-3-yl)-3-(5-methoxypyrimidin-2-yl)butane-2-sulfonamide 2,2,2-trifluoroacetate <br> $^1$H NMR (300 MHz, $CDCl_3$) δ 8.67-8.71 (m, 2H), 8.44 (s, 2H), 7.97 (d, J = 7.9 Hz, 1H), 7.39-7.49 (m, 2H), 6.64 (dd, J = 8.4, 5.5 Hz, 2H), 3.94 (s, 3H), 3.84-3.91 (m, 1H), 3.76-3.81 (m, 4H), 3.74 (s, 3H), 1.40 (d, J = 2.9 Hz, 3H), 1.38 (d, J = 2.9 Hz, 3H). LCMS-ESI (pos.) m/z: 526.2 $(M + H)^+$. |
| 673.0 | (1R,2S)-1-methoxy-1-(5-methylpyrimidin-2-yl)propane-2-sulfonamide (Example 14.0), 2,6-dimethylphenyl isothiocyanate (Oakwood Products, Inc.), 5-methylnicotinohydrazide (Bellen Chemistry Co.) | (1R,2S)-N-(4-(2,6-dimethylphenyl)-5-(5-methyl-3-pyridinyl)-4H-1,2,4-triazol-3-yl)-1-methoxy-1-(5-methyl-2-pyrimidinyl)-2-propanesulfonamide 2,2,2-trifluoroacetate. $^1$H NMR (300 MHz, $CDCl_3$) δ 8.68 (s, 2H), 8.56 (s, 1H), 8.34 (s, 1H), 7.75 (s, 1H), 7.32-7.43 (m, 1H), 7.23 (d, J = 7.5 Hz, 2H), 5.05 (d, J = 3.4 Hz, 1H), 3.71 (dd, J = 6.7, 3.7 Hz, 1H), 3.29 (s, 3H), 2.35-2.39 (m, 6H), 2.18 (s, 3H), 2.13 (s, 3H), 1.34 (d, J = 6.9 Hz, 3H). LCMS-ESI (pos.) m/z: 508.3 $(M + H)^+$. |

Example 674.0: Preparation of (1R,2S,P)—N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide 2,2,2-trifluoroacetate and (1R,2S,M)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide 2,2,2-trifluoroacetate

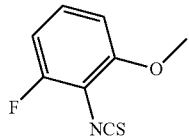

674.1

1-fluoro-2-isothiocyanato-3-methoxybenzene, Example 674.1

To a solution of 2-fluoro-6-methoxy-phenylamine (240 mg, 1.7 mmol, Indofine Chemical Co.) and DCM (15 mL) was added 1,1'-thiocarbonyldi-2(1H)-pyridone (434 mg, 1.87 mmol). The resulting mixture was stirred at RT. After 16 h, the reaction was concentrated to ½ volume and absorbed onto a plug of silica gel and chromatographed through a GraceResolv Silica gel column (12 g), eluting with 0-20% EtOAc in heptanes, to provide the title compound (340 mg, 1.86 mmol, 109% yield), as a white solid. The material thus obtained was carried forward without further purification. $^1$H NMR (300 MHz, DMSO-$d_6$) δ 7.36 (q, J=8.1 Hz, 1H), 6.94-7.05 (m, 2H), 3.92 (s, 3H).

The compounds set forth in the following Table were synthesized following the procedure in Example A using the known starting material as described.

TABLE 28

| Example | Reagents | Structure, Name and Data |
|---------|----------|--------------------------|
| 674.0 | (1R,2S)-1-methoxy-1-(5-methylpyrimidin-2-yl)propane-2-sulfonamide (Example 14.0), 1-fluoro-2-isothiocyanato-3-methoxybenzene (Example 674.1), 6-methoxypicolinohydrazide (Example 3.18) | (1R,2S,P)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide 2,2,2-trifluoroacetate and (1R,2S,M)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide 2,2,2-trifluoroacetate. $^1$H NMR (300 MHz, CDCl$_3$) δ 8.70 (s, 1H), 8.69 (s, 1H), 7.66 (d, J = 1.6 Hz, 1H), 7.65 (s, 1H), 7.37 (td, J = 8.5, 6.4 Hz, 1H), 6.84 (t, J = 8.6 Hz, 1H), 6.71-6.80 (m, 2H), 5.02 (d, J = 4.5 Hz, 0.5H), 4.99 (d, J = 4.8 Hz, 0.5H), 3.74-3.82 (m, 1H), 3.73 (s, 1.5H), 3.72 (s, 1.5H), 3.34 (s, 1.5H), 3.31 (s, 1.5H), 3.19 (s, 1.5H), 3.18 (s, 1.5H), 2.38 (s, 1.5H), 2.37 (s, 1.5H), 1.39 (d, J = 6.3 Hz, 1.5H), 1.36 (d, J = 6.7 Hz, 1.5H). LCMS-ESI (pos.) m/z: 544.1 (M + H)$^+$. |

TABLE 28-continued

| Example | Reagents | Structure, Name and Data |
|---|---|---|
| 675.0 | (1R,2S)-1-methoxy-1-(5-methylpyrimidin-2-yl)propane-2-sulfonamide (Example 14.0), 2,6-dichlorophenyl isothiocyanate (Oakwood Products, Inc.), 5-methylnicotinohydrazide (Bellen Chemistry Co.) | 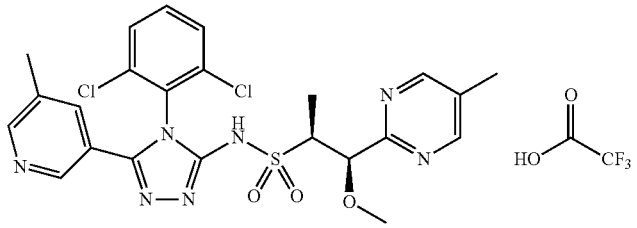 [SMILES: CO[C@H](c1ncc(C)cn1)[C@H](C)S(=O)(=O)Nc1nnc(-c2cncc(C)c2)n1-c1c(Cl)cccc1Cl ; O=C(O)C(F)(F)F]<br>(1R,2S)-N-(4-(2,6-dichlorophenyl)-5-(5-methyl-3-pyridinyl)-4H-1,2,4-triazol-3-yl)-1-methoxy-1-(5-methyl-2-pyrimidinyl)-2-propanesulfonamide 2,2,2-trifluoroacetate $^1$H NMR (300 MHz, CDCl$_3$) δ 8.68 (s, 2H), 8.58 (d, J = 1.3 Hz, 1H), 8.36 (d, J = 1.8 Hz, 1H), 7.90 (s, 1H), 7.39-7.64 (m, 3H), 5.02 (d, J = 4.5 Hz, 1H), 3.77 (dd, J = 7.0, 4.5 Hz, 1H), 3.32-3.38 (m, 3H), 2.42 (s, 3H), 2.37 (s, 3H), 1.41 (d, J = 7.0 Hz, 3H). LCMS-ESI (pos.) m/z: 548.2 (M + H)$^+$. |

Example 676.0: Preparation of N-(4-(2,6-dimethoxyphenyl)-5-(6-methoxy-2-pyridinyl)-4H-1,2,4-triazol-3-yl)-2-(5-fluoro-2-pyrimidinyl)ethanesulfonamide 2,2,2-trifluoroacetate

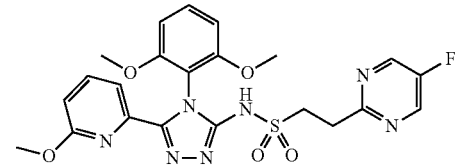

2-(5-fluoropyrimidin-2-yl)ethanesulfonyl chloride, Example 676.1

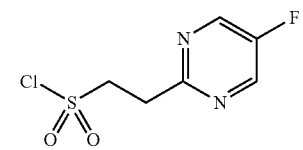

N-(4-(2,6-dimethoxyphenyl)-5-(6-methoxy-2-pyridinyl)-4H-1,2,4-triazol-3-yl)-2-(5-fluoro-2-pyrimidinyl)ethanesulfonamide 2,2,2-trifluoroacetate, Example 676.0

To a suspension of 2-(5-fluoropyrimidin-2-yl)ethanesulfonic acid (1.71 g, 8.30 mmol, Example 7.02) in DCM (30 mL) was added oxalyl chloride, (2M in DCM, 6.22 mL, 12.45 mmol). The suspension was stirred at RT. After stirring for 3 d, the material thus obtained was used in the next step without any further characterization.

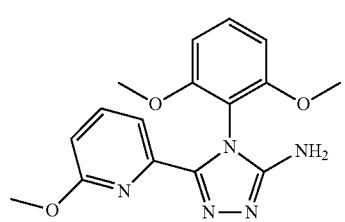

4-(2,6-dimethoxyphenyl)-5-(6-methoxypyridin-2-yl)-4H-1,2,4-triazol-3-amine, Example 676.2

Example 676.2 was prepared in an analogous fashion to that of Example 2.04, using 6-methoxypicolinohydrazide (Example 3.18

To a suspension of 4-(2,6-dimethoxyphenyl)-5-(6-methoxypyridin-2-yl)-4H-1,2,4-triazol-3-amine (39 mg, 0.12 mmol, Example 676.2) in DCM (30 mL) was added TEA (0.066 mL, 0.48 mmol). To this solution was added 2-(5-fluoropyrimidin-2-yl)ethanesulfonyl chloride (50 mg, 0.22 mmol). The suspension was stirred at RT. After 24 h, the reaction was treated with more 2-(5-fluoropyrimidin-2-yl)ethanesulfonyl chloride (50 mg) and TEA (0.100 mL). After a further 24 h, the reaction was poured into water and extracted with DCM (10 mL). The combined DCM layers were concentrated in vacuo and purified by reverse-phase preparative HPLC (Shimadzu) on a Phenomenex Luna column (5 micron, C18, 110 Å, Axia, 150×21.2 mm) eluting at 30 mL/min with a linear gradient of 30-60% MeCN (0.1% TFA) in water (0.1% TFA) over 20 min to give the title compound (1.2 mg, 1.91 μmol, 2% yield), as a white solid. $^1$H NMR (300 MHz, CDCl$_3$) δ 8.53 (s, 2H), 7.58-7.66 (m, 2H), 7.30-7.36 (m, 1H), 6.72 (dd, J=7.7, 1.5 Hz, 1H), 6.61 (d, J=8.6 Hz, 2H), 3.71 (m, 6H), 3.57-3.64 (m, 2H), 3.45-3.52 (m, 2H), 3.18 (s, 3H). LCMS-ESI (pos.) m/z: 516.0 (M+H)$^+$.

The compounds set forth in the following Table were synthesized following the procedure in Example A using the known starting material as described.

TABLE 29

| Example | Reagents | Structure, Name and Data |
|---|---|---|
| 677.0 | (1R,2S)-1-methoxy-1-(5-methylpyrimidin-2-yl)propane-2-sulfonamide (Example 14.0), 2,6-difluorophenyl isothiocyanate (Oakwood Products, Inc.), 5-methylnicotinohydrazide (Bellen Chemistry Co.) | 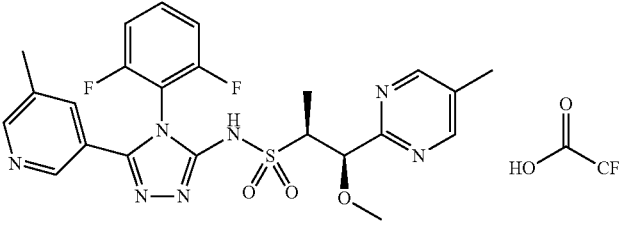<br>(1R,2S)-N-(4-(2,6-difluorophenyl)-5-(5-methylpyridin-3-yl)-4H-1,2,4-triazol-3-yl)-1-methoxy-1-(5-methylpyrimidin-2-yl)propane-2-sulfonamide 2,2,2-trifluoroacetate.<br>$^1$H NMR (300 MHz, CDCl$_3$) δ 8.65 (s, 2H), 8.57 (s, 1H), 8.38 (s, 1H), 7.81 (s, 1H), 7.50-7.63 (m, 1H), 7.12 (td, J = 8.3, 3.4 Hz, 2H), 5.01 (d, J = 4.4 Hz, 1H), 3.72-3.82 (m, 1H), 3.36 (s, 3H), 2.41 (s, 3H), 2.36 (s, 3H), 1.40 (d, J = 7.0 Hz, 3H). LCMS-ESI (pos.) m/z: 516.2 (M + H)$^+$. |
| 678.0 | The racemic compound 674.0 was separated by supercritical fluid chromatography. Column: Chiralpak IF (250 × 21 mm, 5 μm), Mobile Phase: 50:50 (A:B), A: Liquid CO$_2$, B: MeOH (20 mM NH$_3$), Flow Rate: 70 mL/min, Column/Oven temp.: 30° C., Detection = 220 nm, 213 bar inlet pressure. This was the second isomer to elute under these conditions. | 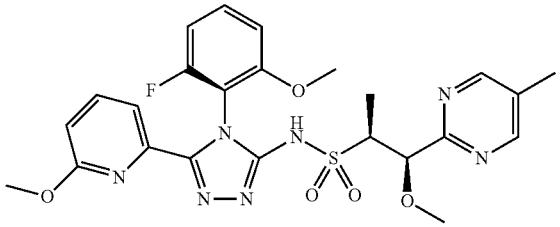<br>OR<br>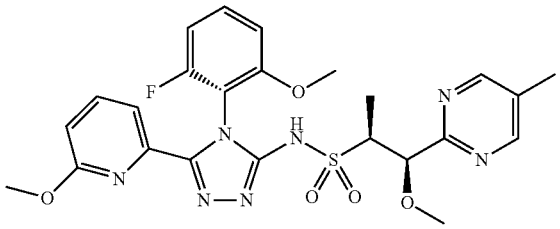<br>(1R,2S,P)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide.<br>$^1$H NMR (400 MHz, CDCl$_3$) δ 11.19 (br. s., 1H), 8.62 (s, 2H), 7.64 (d, J = 2.2 Hz, 1H), 7.63 (s, 1H), 7.34 (td, J = 8.5, 6.4 Hz, 1H), 6.82 (t, J = 8.4 Hz, 1H), 6.70-6.78 (m, 2H), 4.98 (d, J = 4.5 Hz, 1H), 3.71-3.80 (m, 1H), 3.69 (s, 3H), 3.34 (s, 3H), 3.17 (s, 3H), 2.33 (s, 3H), 1.39 (d, J = 7.0 Hz, 3H). LCMS-ESI (pos.) m/z: 544.2 (M + H)$^+$. |
| 679.0 | The racemic compound 674.0 was separated by supercritical fluid chromatography. Column: Chiralpak IF (250 × 21 mm, 5 μm), Mobile Phase: 50:50 (A:B), A: Liquid CO$_2$, B: MeOH (20 mM NH$_3$), Flow Rate: 70 mL/min, Column/Oven temp.: 30° C., Detection = 220 nm, 213 bar inlet pressure. This was the first isomer to elute under these conditions. | 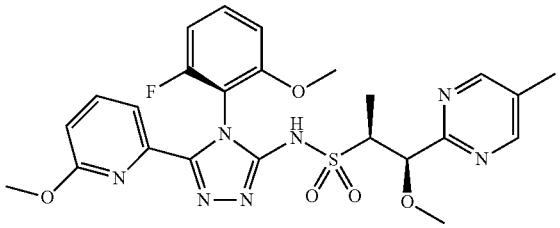<br>OR |

TABLE 29-continued

| Example | Reagents | Structure, Name and Data |
|---|---|---|
| | | 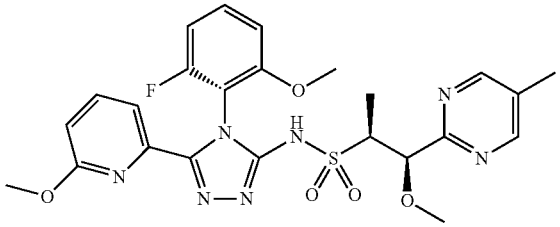<br>(1R,2S,P)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide.<br>1H NMR (400 MHz, CDCl$_3$) δ 11.22 (br. s., 1H), 8.60 (s, 2H), 7.62-7.66 (m, 2H), 7.34 (td, J = 8.5, 6.4 Hz, 1H), 6.77-6.84 (m, 1H), 6.69-6.77 (m, 2H), 4.96 (d, J = 4.7 Hz, 1H), 3.72-3.80 (m, 1H), 3.71 (s, 3H), 3.34 (s, 3H), 3.16 (s, 3H), 2.32 (s, 3H), 1.39 (d, J = 7.0 Hz, 3H). LCMS-ESI (pos.) m/z: 544.1 (M + H)$^+$. |
| 680.0 | (2R,3S)-3-(5-chloropyrimidin-2-yl)butane-2-sulfonamide and (2S,3R)-3-(5-chloropyrimidin-2-yl)butane-2-sulfonamide (racemate of Example 696.1), 2-isothiocyanato-1,3-dimethoxybenzene (Example 1.0), 5-methylnicotinohydrazide (Bellen Chemistry Co.) | 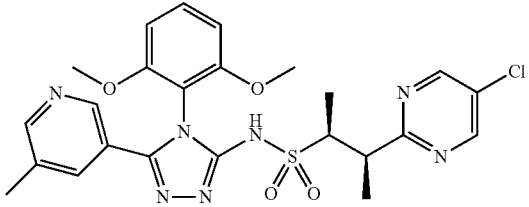<br>AND<br>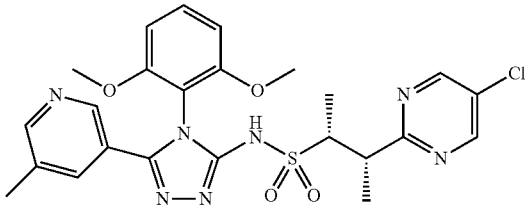 [SMILES: COc1cccc(OC)c1-n1c(NS(=O)(=O)[C@H](C)[C@@H](C)c2ncc(Cl)cn2)nnc1-c1cncc(C)c1]<br>(2R,3S)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide and (2S,3R)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide.<br>$^1$H NMR (400 MHz, CDCl$_3$) δ 11.08 (br. s., 1H), 8.62 (s, 2H), 8.45 (s, 1H), 8.32 (s, 1H), 7.74 (s, 1H), 7.39 (t, J = 8.5 Hz, 1H), 6.60 (t, J = 7.4 Hz, 2H), 3.75-3.89 (m, 2H), 3.74 (s, 3H), 3.72 (s, 3H), 2.33 (s, 3H), 1.36 (d, J = 5.7 Hz, 3H), 1.35 (d, J = 5.7 Hz, 3H). LCMS-ESI (pos.) m/z: 544.2 (M + H)$^+$. |
| 681.0 | (2R,3S)-3-(5-chloropyrimidin-2-yl)butane-2-sulfonamide and (2S,3R)-3-(5-chloropyrimidin-2-yl)butane-2-sulfonamide (Example 10.4), 2-isothiocyanato-1,3-dimethoxybenzene (Example 1.0), nicotinohydrazide (Aldrich) | 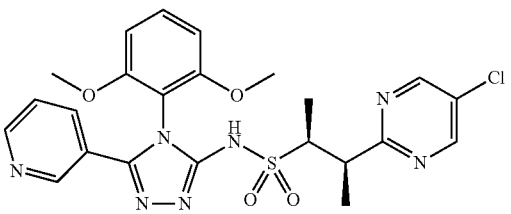<br>AND |

TABLE 29-continued

| Example | Reagents | Structure, Name and Data |
|---|---|---|
| | | 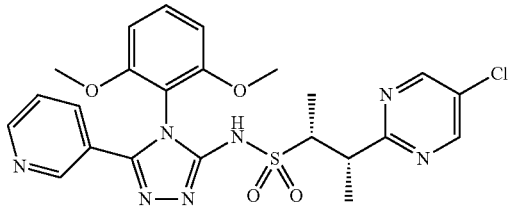(2R,3S)-3-(5-chloropyrimidin-2-yl)-N-(4-(2,6-dimethoxyphenyl)-5-(pyridin-3-yl)-4H-1,2,4-triazol-3-yl)butane-2-sulfonamide and (2S,3R)-3-(5-chloropyrimidin-2-yl)-N-(4-(2,6-dimethoxyphenyl)-5-(pyridin-3-yl)-4H-1,2,4-triazol-3-yl)butane-2-sulfonamide.<br>$^1$H NMR (400 MHz, CDCl$_3$) δ 11.09 (br. s., 1H), 8.59-8.65 (m, 4H), 7.85 (d, J = 7.2 Hz, 1H), 7.40 (t, J = 8.6 Hz, 1H), 7.31-7.37 (m, 1H), 6.61 (t, J = 7.7 Hz, 2H), 3.75-3.90 (m, 2H), 3.74 (s, 3H), 3.71 (s, 3H), 1.37 (d, J = 5.3 Hz, 3H), 1.35 (d, J = 5.3 Hz, 3H).<br>LCMS-ESI (pos.) m/z: 530.2 (M + H)$^+$. |
| 682.0 | (2S,3R)-3-(5-methoxypyrimidin-2-yl)butane-2-sulfonamide (Example 672.1), 2-isothiocyanato-1,3-dimethoxybenzene (Example 1.0), 5-methylnicotinohydrazide (Bellen Chemistry Co.) | 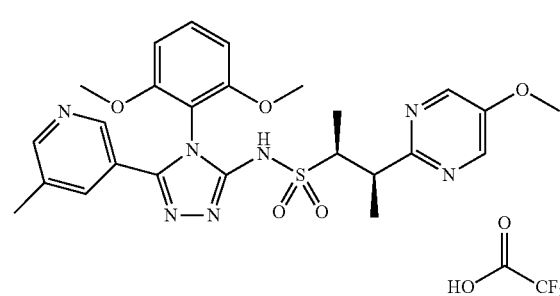(2S,3R)-N-(4-(2,6-dimethoxyphenyl)-5-(5-methyl-3-pyridinyl)-4H-1,2,4-triazol-3-yl)-3-(5-methoxy-2-pyrimidinyl)-2-butanesulfonamide 2,2,2-trifluoroacetate.<br>$^1$H NMR (300 MHz, CDCl$_3$) δ 8.56 (s, 1H), 8.44 (s, 2H), 8.41 (s, 1H), 8.00 (s, 1H), 7.44 (t, J = 8.5 Hz, 1H), 6.65 (dd, J = 8.4, 4.9 Hz, 2H), 3.94 (s, 3H), 3.83-3.92 (m, 1H), 3.72-3.82 (m, 7H), 2.43 (s, 3H), 1.39 (d, J = 3.1 Hz, 3H), 1.37 (d, J = 3.1 Hz, 3H).<br>LCMS-ESI (pos.) m/z: 540.0 (M + H)$^+$. |
| 683.0 | The racemic compound 681.0 was separated by supercritical fluid chromatography. Column: AS-H (21 × 150 mm, 5 μm) with 20% MeOH (no amine additive), 80% carbon dioxide.<br>Flow Rate: 120 mL/min<br>Column/Oven temp.: 40° C.<br>BPR = 100 bar, 220 nm, P = 140 bar. This was the second isomer to elute under these conditions. | 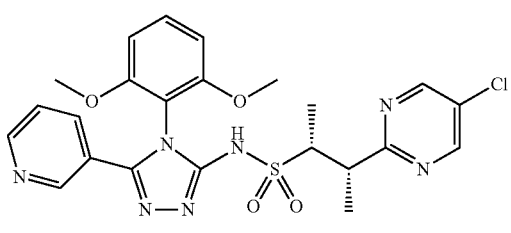 [SMILES: COc1cccc(OC)c1-n1c(NS(=O)(=O)[C@H](C)[C@@H](C)c2ncc(Cl)cn2)nnc1-c1cccnc1]OR<br>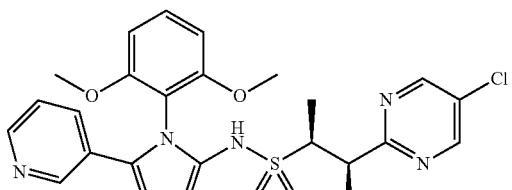(2R,3S)-3-(5-chloropyrimidin-2-yl)-N-(4-(2,6-dimethoxyphenyl)-5-(pyridin-3-yl)-4H-1,2,4-triazol-3-yl)butane-2-sulfonamide or (2S,3R)-3-(5-chloropyrimidin-2-yl)-N-(4-(2,6-dimethoxyphenyl)-5-(pyridin-3-yl)-4H-1,2,4-triazol-3-yl)butane-2- |

TABLE 29-continued

| Example | Reagents | Structure, Name and Data |
|---|---|---|
| | | sulfonamide.<br>¹H NMR (300 MHz, CDCl₃) δ 11.11 (br. s., 1H), 8.61-8.67 (m, 4H), 7.81 (d, J = 5.3 Hz, 1H), 7.41 (t, J = 8.6 Hz, 1H), 7.32 (dd, J = 7.7, 5.3 Hz, 1H), 6.63 (d, J = 4.5 Hz, 1H), 6.61 (d, J = 4.5 Hz, 1H), 3.77-3.92 (m, 2H), 3.75 (s, 3H), 3.73 (s, 3H), 1.39 (d, J = 3.7 Hz, 3H), 1.37 (d, J = 3.7 Hz, 3H). LCMS-ESI (pos.) m/z: 530.0 (M + H)⁺. |
| 684.0 | (1R,2S)-1-methoxy-1-(5-methylpyrimidin-2-yl)propane-2-sulfonamide (Example 14.0), 2,6-difluorophenyl isothiocyanate (Oakwood Products, Inc.), 6-methoxypicolinohydrazide (Example 3.18) | 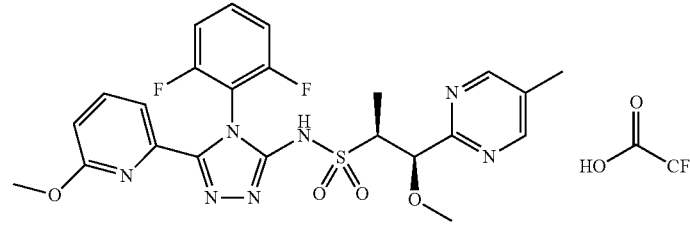<br>(1R,2S)-N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide.<br>¹H NMR (300 MHz, CDCl₃) δ 8.71 (s, 2H), 7.65-7.72 (m, 2H), 7.44 (tt, J = 8.6, 6.1 Hz, 1H), 7.07 (t, J = 8.7 Hz, 2H), 6.75-6.81 (m, 1H), 5.01 (d, J = 4.5 Hz, 1H), 3.75 (qd, J = 7.0, 4.7 Hz, 1H), 3.33 (s, 3H), 3.19 (s, 3H), 2.39 (s, 3H), 1.37 (d, J = 7.0 Hz, 3H). LCMS-ESI (pos.) m/z: 532.1(M + H)⁺. |
| 685.0 | The racemic compound 680.0 was separated by supercritical fluid chromatography. Column: 250 × 30 mm AS-H column with 15.40 mL/min MeOH (neat) + 54.60 g/min CO₂, 22% co-solvent at 70 g/min. Temp = 28° C., Outlet pressure = 100 bar, Wavelength = 271 nm. This was the second isomer to elute under these conditions. | 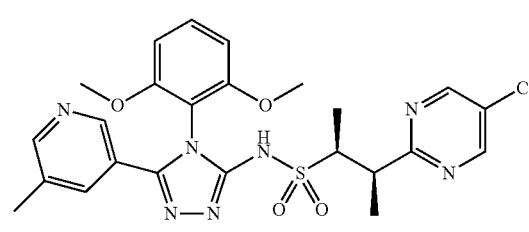<br>OR<br>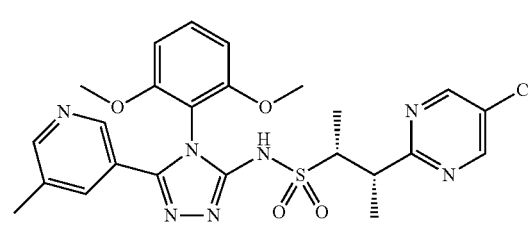<br>(2R,3S)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide or (2S,3R)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide.<br>¹H NMR (300 MHz, CDCl₃) δ 11.10 (br. s., 1H), 8.64 (s, 2H), 8.47 (s, 1H), 8.35 (s, 1H), 7.76 (s, 1H), 7.41 (t, J = 8.6 Hz, 1H), 6.64 (d, J = 4.4 Hz, 1H), 6.61 (d, J = 4.4 Hz, 1H), 3.77-3.92(m, 2H), 3.76 (s, 3H), 3.74 (s, 3H), 2.35 (s, 3H), 1.39 (d, J = 4.2 Hz, 3H), 1.36 (d, J = 4.1 Hz, 3H). LCMS-ESI (pos.) m/z: 544.1 (M + H)⁺. |

TABLE 29-continued

| Example | Reagents | Structure, Name and Data |
|---|---|---|
| 686.0 | The racemic compound 680.0 was separated by supercritical fluid chromatography. Column: 250 × 30 mm AS-H column with 15.40 mL/minMeOH (neat) + 54.60 g/min CO₂, 22% co-solvent at 70 g/min. Temp = 28° C., Outlet pressure = 100 bar, Wavelength = 271 nm. This was the first isomer to elute under these conditions. | 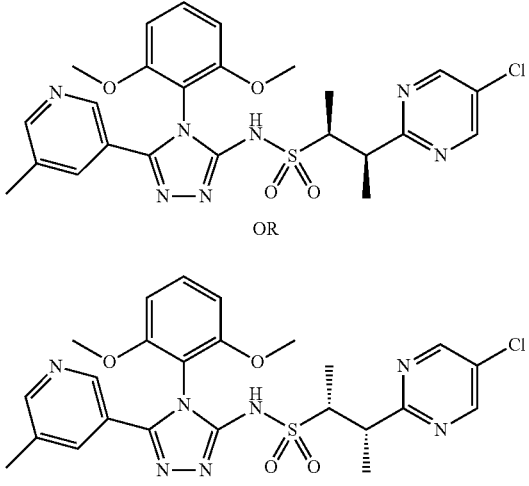    OR<br><br>(2R,3S)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide or (2S,3R)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide.<br>¹H NMR (300 MHz, CDCl₃) δ 11.10 (br. s., 1H), 8.64 (s, 2H), 8.47 (s, 1H), 8.34 (s, 1H), 7.71 (s, 1H), 7.40 (t, J = 8.6 Hz, 1H), 6.63 (d, J = 4.2 Hz, 1H), 6.60 (d, J = 4.2 Hz, 1H), 3.77-3.92(m, 2H), 3.75 (s, 3H), 3.73 (s, 3H), 2.33 (s, 3H), 1.38 (d, J = 7.0 Hz, 3H), 1.36 (d, J = 7.0 Hz, 3H). LCMS-ESI (pos.) m/z: 544.1 (M + H)⁺. |
| 687.0 | (1R,2S)-1-methoxy-1-(5-methoxypyrimidin-2-yl)propane-2-sulfonamide (Example 14.9), 2-isothiocyanato-1,3-dimethoxybenzene (Example 1.0), 5-methylnicotinohydrazide (Bellen Chemistry Co.) | 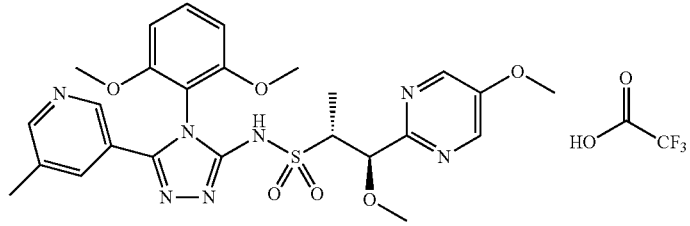<br><br>(1R,2R)-N-(4-(2,6-dimethoxyphenyl)-5-(5-methyl-3-pyridinyl)-4H-1,2,4-triazol-3-yl)-1-methoxy-1-(5-methoxy-2-pyrimidinyl)-2-propanesulfonamide 2,2,2-trifluoroacetate.<br>¹H NMR (300 MHz, CDCl₃) δ 8.55 (s, 1H), 8.48 (s, 2H), 8.43 (s, 1H), 7.98 (s, 1H), 7.44 (t, J = 8.6 Hz, 1H), 6.66 (t, J = 7.7 Hz, 2H), 4.74 (d, J = 6.6 Hz, 1H), 3.97 (s, 3H), 3.85 (s, 3H), 3.72-3.83 (m, 4H), 3.23 (s, 3H), 2.42 (s, 3H), 1.24 (d, J = 7.0 Hz, 3H). LCMS-ESI (pos.) m/z: 556.2 (M + H)⁺. |
| 688.0 | (2S,3R)-3-(5-methylpyrimidin-2-yl)butane-2-sulfonamide (Example 10.0) 1-fluoro-2-isothiocyanato-3-methoxybenzene (Example 1.9), , 5-methylnicotinohydrazide (Bellen Chemistry Co.) | 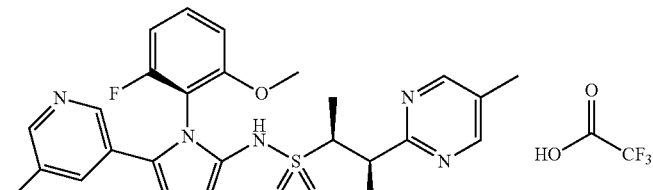<br><br>AND |

TABLE 29-continued

| Example | Reagents | Structure, Name and Data |
|---------|----------|--------------------------|

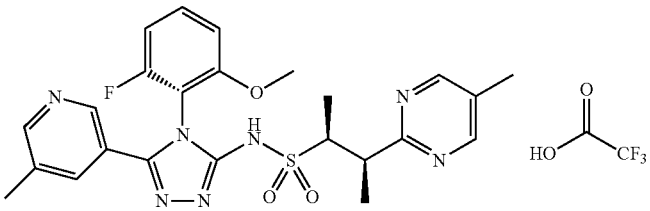

(2S,3R,P)-N-(4-(2-fluoro-6-methoxyphenyl)-5-(5-methyl-3-pyridinyl)-4H-1,2,4-triazol-3-yl)-3-(5-methyl-2-pyrimidinyl)-2-butanesulfonamide 2,2,2-trifluoroacetate and (2S,3R,M)-N-(4-(2-fluoro-6-methoxyphenyl)-5-(5-methyl-3-pyridinyl)-4H-1,2,4-triazol-3-yl)-3-(5-methyl-2-pyrimidinyl)-2-butanesulfonamide 2,2,2-trifluoroacetate.
$^1$H NMR (300 MHz, CDCl$_3$) δ 8.74 (s, 2H), 8.62 (s, 1H), 8.46 (s, 0.5H), 8.42 (s, 0.5H), 8.05 (s, 1H), 7.45-7.58 (m, 1H), 6.83-6.97 (m, 2H), 3.93 (t, J = 7.2 Hz, 1H), 3.85 (s, 1.5H), 3.79 (s, 1.5H), 3.73 (dd, J = 12.1, 7.6 Hz, 1H), 2.47 (s, 3H), 2.42 (s, 3H), 1.45 (d, J = 7.0 Hz, 3H), 1.42 (d, J = 7.0 Hz, 3H). LCMS-ESI (pos.) m/z: 512.2 (M + H)$^+$.

689.0  (1R,2S)-1-methoxy-1-(5-methylpyrimidin-2-yl)propane-2-sulfonamide (Example 14.0), 1-fluoro-2-isothiocyanato-3-methoxybenzene (Example 1.9), 5-methylnicotinohydrazide (Bellen Chemistry Co.)

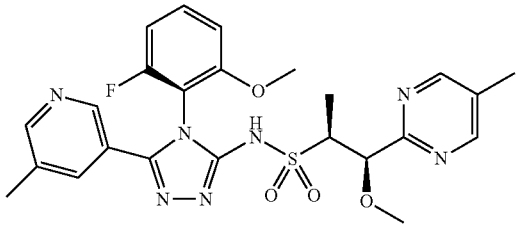

AND

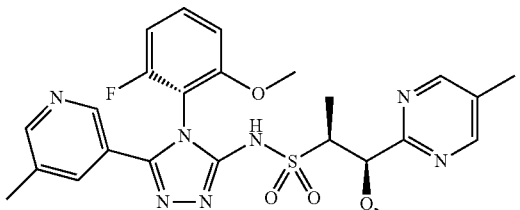

(1R,2S,P)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide and (1R,2S,M)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide.
$^1$H NMR (300 MHz, CDCl$_3$) δ 11.34 (br. s., 0.5H), 11.31 (br. s., 0.5H), 8.62 (s, 2H), 8.50 (s, 1H), 8.36 (s, 1H), 7.72 (s, 1H), 7.45 (q, J = 7.7 Hz, 1H), 6.78-6.90 (m, 2H), 4.96-5.01 (m, 1H), 3.72-3.82 (m, 4H), 3.36 (s, 3H), 2.35 (s, 3H), 2.34 (s, 3H), 1.41 (d, J = 7.0 Hz, 3H). LCMS-ESI (pos.) m/z: 528.2 (M + H)$^+$.

TABLE 29-continued

| Example | Reagents | Structure, Name and Data |
|---|---|---|
| 690.0 | The racemic compound 666.0 was separated by supercritical fluid chromatography. Column: Chiralpak AD-H (Reversed) (250 × 21 mm, 5 μm), Mobile Phase: 80:20 (A:B), A: Liquid CO$_2$, B: EtOH (20 mM NH$_3$), Flow Rate: 70 mL/min, Column/Oven temp.: 40° C., Detection = 226 mn 165-172 bar inlet pressure. This was the second isomer to elute under these conditions. | 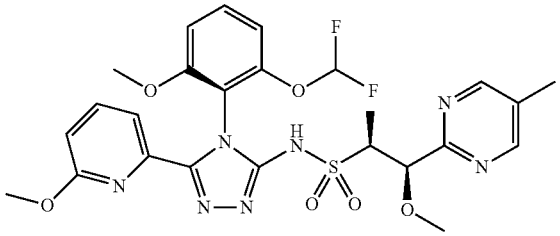<br>OR<br>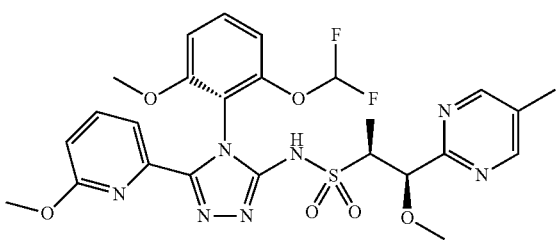<br>(1R,2S,P)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide.<br>$^1$H NMR (300 MHz, CDCl$_3$) δ 11.34 (br. s., 1H), 8.60 (s, 2H), 7.61-7.67 (m, 2H), 7.37 (t, J = 8.5 Hz, 1H), 6.89 (d, J = 8.4 Hz, 1H), 6.81-6.86 (m, 1H), 6.37-6.76 (m, 2H), 4.95 (d, J = 4.5 Hz, 1H), 3.67-3.74 (m, 4H), 3.33 (s, 3H), 3.14 (s, 3H), 2.32 (s, 3H), 1.35 (d, J = 7.0 Hz, 3H). LCMS-ESI (pos.) m/z: 592.1 (M + H)$^+$. |
| 691.0 | The racemic compound 666.0 was separated by supercritical fluid chromatography. Column: Chiralpak AD-H (Reversed) (250 × 21 mm, 5 μm), Mobile Phase: 80:20 (A:B) A: Liquid CO$_2$, B: EtOH (20 mM NH$_3$), . flow Rate: 70 mL/min, Column/Oven temp.: 40° C., Detection = 226 nm, 165-172 bar inlet pressure. This was the first isomer to elute under these conditions. | 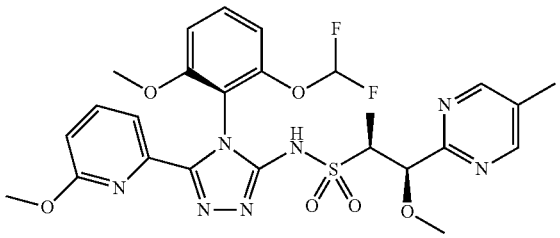<br>OR<br>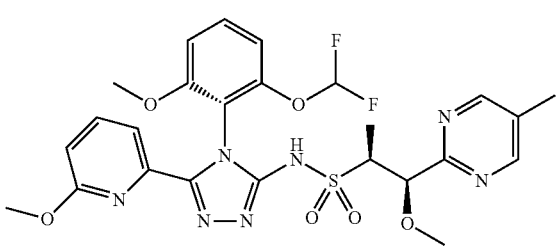<br>(1R,2S,P)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide or (1R,2S,M)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide.<br>1H NMR (300 MHz, CDCl$_3$) δ 11.32 (br. s., 1H), 8.64 (s, 2H), 7.66 (d, J = 4.4 Hz, 2H), 7.40 (t, J = 8.4 |

TABLE 29-continued

| Example | Reagents | Structure, Name and Data |
|---|---|---|
| | | Hz, 1H), 6.93 (d, J = 5.7 Hz, 1H), 6.36-6.88 (m, 3H), 4.94 (d, J = 4.8 Hz, 1H), 3.68-3.81 (m, 4H), 3.33 (s, 3H), 3.16 (s, 3H), 2.35 (s, 3H), 1.39 (d, J = 7.0 Hz, 3H). LCMS-ESI (pos.) m/z: 592.2 (M + H)+. |
| 692.0 | The racemic compound 689.0 was separated by supercritical fluid chromatography. IC Column (30 × 150 mm, 5 μm) with 45% MeOH, 55% carbon dioxide. Flow Rate: 120 mL/min, Column/Oven temp.: 40° C., BPR = 110 bar, P = 200 bar, Detection = 220 nm. This was the second isomer to elute under these conditions. | 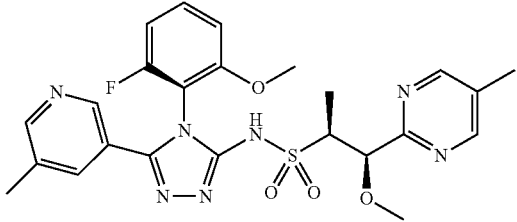<br>OR<br>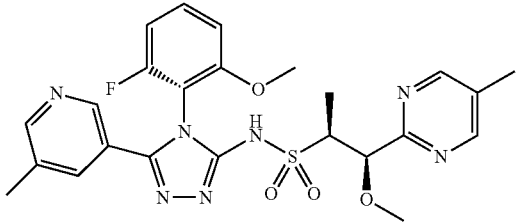<br>(1R,2S,P)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide or (1R,2S,M)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide.<br>¹H NMR (300 MHz, CDCl₃) δ 11.34 (br. s., 1H), 8.62 (s, 2H), 8.51 (s, 1H), 8.37 (s, 1H), 7.79 (s, 1H), 7.42-7.51 (m, 1H), 6.84-6.91 (m, 1H), 6.82 (d, J = 9.0 Hz, 1H), 4.99 (d, J = 4.4 Hz, 1H), 3.72-3.81 (m, 4H), 3.36 (s, 3H), 2.38 (s, 3H), 2.35 (s, 3H), 1.41 (d, J = 7.0 Hz, 3H). LCMS-ESI (pos.) m/z: 528.2 (M + H)+. |
| 693.0 | The racemic compound 689.0 was separated by supercritical fluid chromatography. IC Column (30 × 150 mm, 5 μm) with 45% MeOH, 55% carbon dioxide.<br>Flow Rate: 120 mL/min<br>Column/Oven temp.: 40° C.<br>BPR = 110 bar, P = 200 bar, Detection = 220 nm. This was the first isomer to elute under these conditions. | 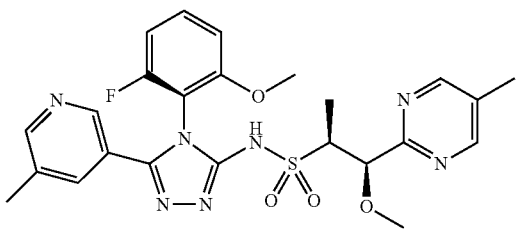<br>OR<br>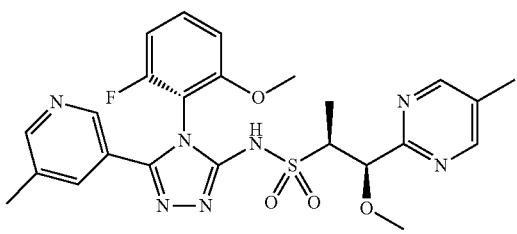<br>(1R,2S,P)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide or (1R,2S,M)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide.<br>¹H NMR (300 MHz, CDCl₃) δ 11.35 (br. s., 1H), |

TABLE 29-continued

| Example | Reagents | Structure, Name and Data |
|---|---|---|
| | | 8.62 (s, 2H), 8.49 (s, 1H), 8.35 (s, 1H), 7.69 (s, 1H), 7.35-7.52 (m, 1H), 6.78-6.89 (m, 2H), 4.98 (d, J = 4.4 Hz, 1H), 3.73-3.83 (m, 4H), 3.37 (s, 3H), 2.32-2.36 (m, 6H), 1.41 (d, J = 7.0 Hz, 3H). LCMS-ESI (pos.) m/z: 528.2 (M + H)+. |
| 694.0 | The racemic compound 681.0 was separated by supercritical fluid chromatography. Column: AS-H (21 × 150 mm, 5 μm) with 20% MeOH (no amine additive), 80% carbon dioxide. Flow Rate: 120 mL/min. Column/Oven temp.: 40° C. BPR = 100 bar, P = 140 bar, Detection = 220 nm. This was the first isomer to elute under these conditions. | 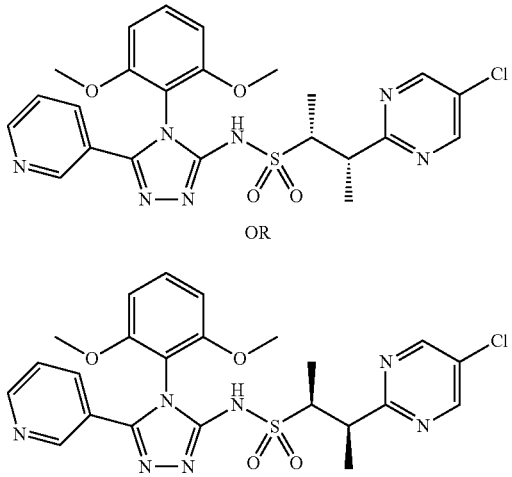<br>OR<br><br>(2R,3S)-3-(5-chloropyrimidin-2-yl)-N-(4-(2,6-dimethoxyphenyl)-5-(pyridin-3-yl)-4H-1,2,4-triazol-3-yl)butane-2-sulfonamide or (2S,3R)-3-(5-chloropyrimidin-2-yl)-N-(4-(2,6-dimethoxyphenyl)-5-(pyridin-3-yl)-4H-1,2,4-triazol-3-yl)butane-2-sulfonamide $^1$H NMR (300 MHz, CDCl$_3$) δ 11.13 (br. s., 1H), 8.60-8.67 (m, 4H), 7.77 (dt, J = 8.0, 1.9 Hz, 1H), 7.40 (t, J = 8.5 Hz, 1H), 7.25-7.31 (m, 1H), 6.63 (d, J = 4.7 Hz, 1H), 6.60 (d, J = 4.5 Hz, 1H), 3.77-3.92 (m, 2H), 3.75 (s, 3H), 3.72 (s, 3H), 1.38 (d, J = 3.70 Hz, 3H), 1.36 (d, J = 3.70 Hz, 3H). LCMS-ESI (pos.) m/z: 530.0 (M + H)+. |

Example 695.0: Preparation of (1R,2S)—N-(4-(2,6-dimethoxyphenyl)-5-(6-methoxypyridin-2-yl)-4H-1,2,4-triazol-3-yl)-1-(2-methoxyethoxy)-1-(5-methyl-pyrimidin-2-yl)propane-2-sulfonamide

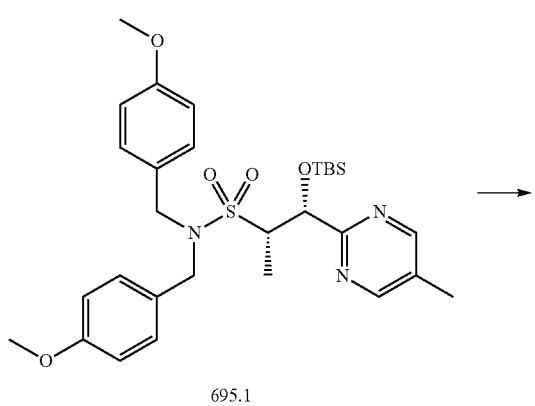

695.1

(1R,2S)-1-hydroxy-N,N-bis(4-methoxybenzyl)-1-(5-methylpyrimidin-2-yl)propane-2-sulfonamide, Example 695.2

To a solution of 695.1 (Prepared in an analogous fashion to that of Example 18.0, 4.14 g, 7.1 mmol) in THF (90 mL) was added TBAF, (1.0 M solution in THF, 7.8 mL, 7.8 mmol) via syringe. The resulting light yellow solution was stirred for 2.5 h, after which more TBAF, (1.0 M solution in THF, 3.5 mL, 3.5 mmol) was added via syringe. After an additional 2.25 h, the reaction mixture was quenched with 1 N HCl solution (50 mL) and extracted with EtOAc (2×). The combined organic layers were washed with water (8×), dried over anhydrous sodium sulfate and concentrated. The residue was purified by silica gel chromatography (eluent: 30% EtOAc in hexanes grading pure EtOAc over a 35 min period) to provide 695.2 (1.76 g, 53% yield) as a white solid. LCMS-ESI (POS.) m/z: 472.1 (M+H)+.

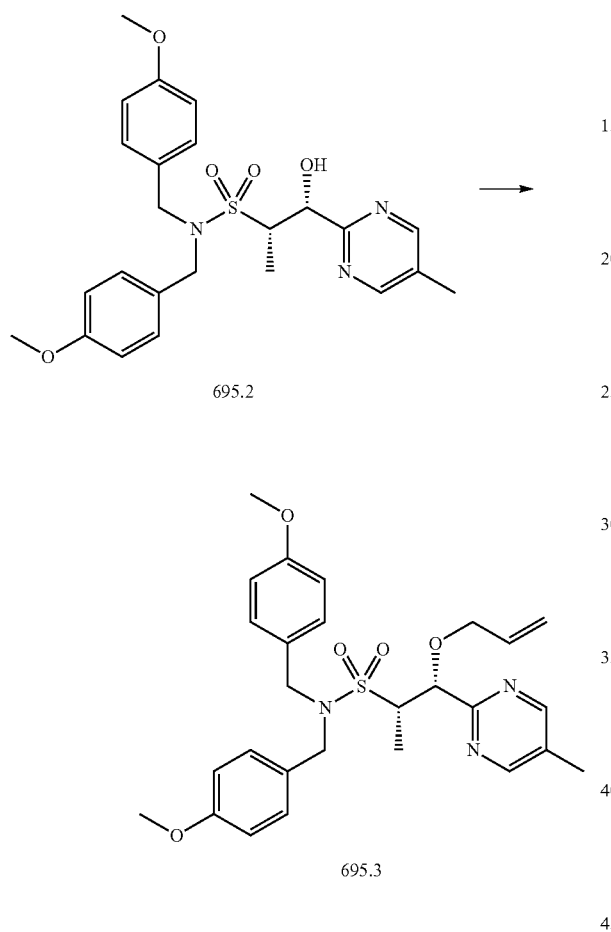

(1R,2S)-1-(allyloxy)-N,N-bis(4-methoxybenzyl)-1-(5-methylpyrimidin-2-yl)propane-2-sulfonamide, Example 695.2

To a −78° C. solution of 695.2 (1.76 g, 3.7 mmol) in THF (40 mL) was added potassium bis(trimethylsilyl)amide, (1.0 M solution in THF, 5.0 mL, 5.0 mmol) slowly via syringe. After 7 min, allyl bromide (1.3 mL, 15.0 mmol) was added slowly via syringe. The resulting bright yellow solution was stirred at −78° C. for 6 min and was then warmed to 0° C. and stirred for an additional 40 min. The reaction mixture was quenched with a 5.5:1 mixture of saturated aqueous ammonium chloride and water (65 mL) and then was extracted with EtOAc (4×). The combined organic layers were dried over anhydrous sodium sulfate and concentrated. The residue was purified by silica gel chromatography (eluent: 5% EtOAc in hexanes grading to 75% EtOAc in hexanes over a 40 min period) to provide 695.3 (1.33 g, 70% yield) as a light yellow oil. LCMS-ESI (POS.) m/z: 512.2 (M+H)+.

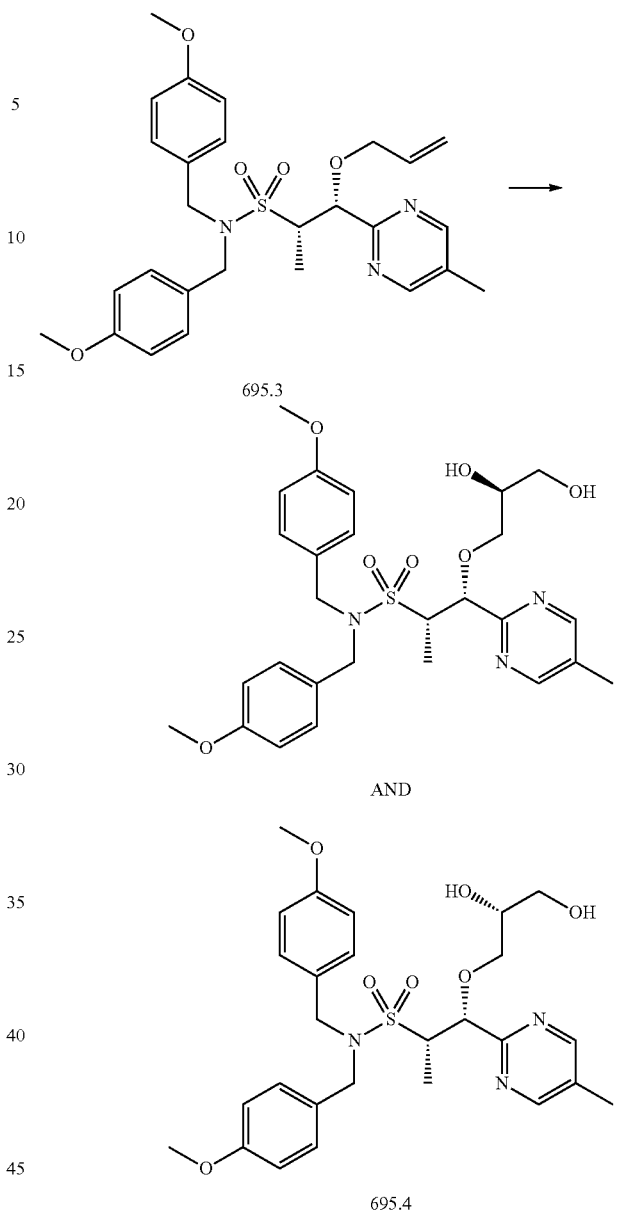

(1R,2S)-1-((S)-2,3-dihydroxypropoxy)-N,N-bis(4-methoxybenzyl)-1-(5-methylpyrimidin-2-yl)propane-2-sulfonamide and (1R,2S)-1-((R)-2,3-dihydroxypropoxy)-N,N-bis(4-methoxybenzyl)-1-(5-methylpyrimidin-2-yl)propane-2-sulfonamide, Example 695.4

To a solution of 695.3 (1.33 g, 2.6 mmol) in a mixture of acetone (45 mL) and water (15 mL) was added a catalytic amount of osmium tetroxide followed by 4-methylmorpholine-N-oxide (1.07 g, 9.1 mmol). The resulting brown solution was stirred at RT for 24 h and then was partially concentrated on a rotary evaporator to remove the acetone. The aqueous residue was diluted with water and extracted with DCM (7×). The combined organic layers were dried over anhydrous sodium sulfate and concentrated. The residue was purified by silica gel chromatography (eluent: pure DCM grading to 10% MeOH in DCM over a 45 min period)

to provide 695.4 (1.32 g, 93% yield) as a tan solid. LCMS-ESI (POS.) m/z: 546.2 (M+H)+.

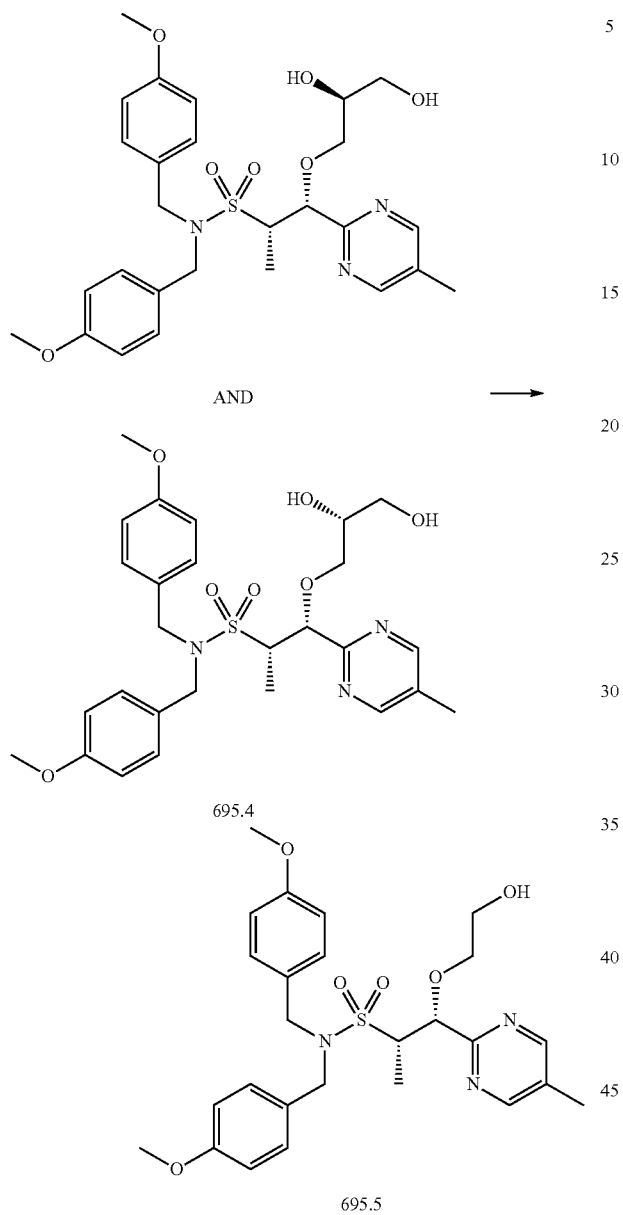

695.4

AND 695.4

695.5

(1R,2S)-1-(2-hydroxyethoxy)-N,N-bis(4-methoxybenzyl)-1-(5-methylpyrimidin-2-yl)propane-2-sulfonamide, Example 695.5

To a solution of 695.4 (1.32 g, 2.4 mmol) in a mixture of THF (30 mL) and water (10 mL) was added sodium periodate (1.44 g, 6.8 mmol). The resulting yellow slurry was stirred at RT for 3.75 h and then was filtered, rinsing the filtrate with DCM. The mixture was partially concentrated on a rotary evaporator to remove the organic solvents, and then it was diluted with water and extracted with DCM (4×). The combined organic layers were dried over anhydrous sodium sulfate and concentrated to afford the aldehyde as a pink solid. To an ice-cooled solution of the aldehyde in MeOH (60 mL) was added sodium borohydride (728 mg, 19.2 mmol). Gas evolution was observed. The resulting yellow solution was stirred at 0° C. for 2 h. The mixture was then quenched with 1 N HCl solution (35 mL). The mixture was then partially concentrated on a rotary evaporator to remove the MeOH and then it was extracted with DCM (4×). The combined organic layers were dried over anhydrous sodium sulfate and concentrated. The residue was purified by silica gel chromatography (eluent: pure DCM grading to 15% MeOH in DCM over a 40 min period) to provide 695.5 (965 mg, 78% yield) as a tan solid. LCMS-ESI (POS.) m/z: 516.0 (M+H)+.

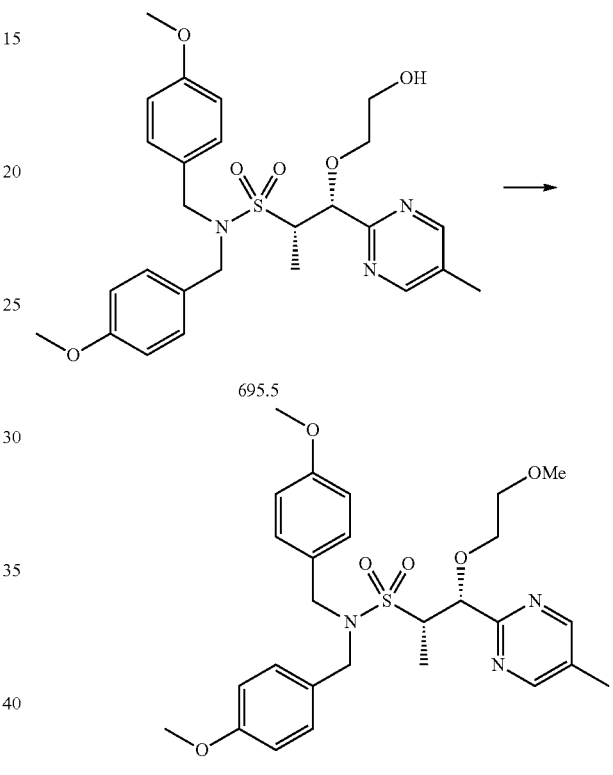

695.5

695.6

(1R,2S)—N,N-bis(4-methoxybenzyl)-1-(2-methoxyethoxy)-1-(5-methylpyrimidin-2-yl)propane-2-sulfonamide, Example 695.6

To a −78° C. solution of 695.5 (964 mg, 1.87 mmol) in THF (50 mL) was added potassium bis(trimethylsilyl)amide, (1.0 M solution in THF, 3.93 mL, 3.93 mmol) slowly via syringe. After stirring for 10 min at −78° C., the reaction was warmed to −40° C. and stirred for an additional 8 min. The reaction was then cooled back to −78° C. and methyl trifluoromethanesulfonate (307 µL, 2.0 mmol) was added slowly via syringe. The resulting red solution was stirred at −78° C. for 25 min and was then quenched with a 2:1 mixture of saturated aqueous ammonium chloride and water (30 mL). The mixture was extracted with DCM (4×), and the combined organic layers were dried over anhydrous sodium sulfate and concentrated. The residue was purified by silica gel chromatography (eluent: pure DCM grading to 12% MeOH in DCM over a 40 min period) to provide 695.6 (376 mg, 38% yield) as an orange oil. LCMS-ESI (POS.) m/z: 530.2 (M+H)+.

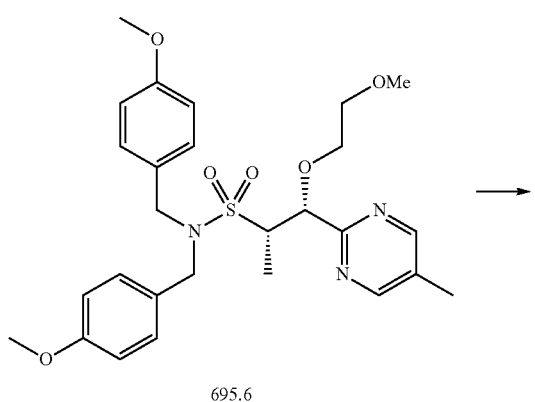

695.6

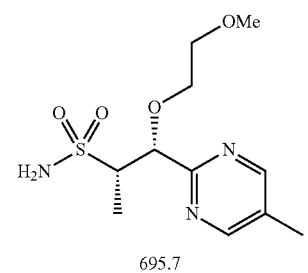

695.7

(1R,2S)-1-(2-methoxyethoxy)-1-(5-methylpyrimidin-2-yl)propane-2-sulfonamide, Example 695.7

Compound 695.6 (1.39 g, 2.7 mmol) was dissolved in TFA (5 mL) and then anisole (170 μL, 1.5 mmol) was added via syringe. The resulting orange solution was stirred at RT for 7 h and was then concentrated. The residue was purified by silica gel chromatography (eluent: pure DCM grading to 7% MeOH in DCM over a 45 min period) to provide 695.7 (143 mg, 70% yield) as a light yellow solid. LCMS-ESI (POS.) m/z: 290.1 (M+H)+.

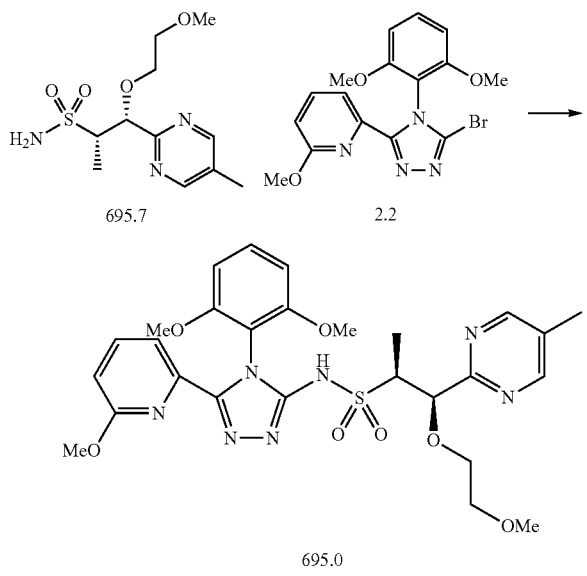

(1R,2S)—N-(4-(2,6-dimethoxyphenyl)-5-(6-methoxypyridin-2-yl)-4H-1,2,4-triazol-3-yl)-1-(2-methoxyethoxy)-1-(5-methylpyrimidin-2-yl)propane-2-sulfonamide, Example 695.0

Following the procedure in Example B, 695.7 (44.7 mg, 0.15 mmol) and Intermediate 2.2 (85 mg, 0.22 mmol) were coupled to provide 695.0 (82.5 mg, 89% yield) as a light yellow solid. ¹H NMR (500 MHz, CDCl₃) δ 8.64 (s, 2H), 7.56-7.64 (m, 2H), 7.26-7.35 (m, 1H), 6.69 (d, J=8.8 Hz, 1H), 6.59 (dd, J=8.4 Hz, 5.5 Hz, 2H), 5.13 (d, J=4.9 Hz, 1H), 3.81-3.89 (m, 1H), 3.71 (s, 3H), 3.71 (s, 3H), 3.69-3.77 (m, 1H), 3.55-3.63 (m, 2H), 3.47-3.54 (m, 1H), 3.35 (s, 3H), 3.17 (s, 3H), 2.34 (s, 3H), 1.41 (d, J=7.0 Hz, 3H). LCMS-ESI (POS.) m/z: 600.0 (M+H)+.

Example 696.0: Preparation of (2S,3R)-3-(5-chloro-2-pyrimidinyl)-N-(4-(2,6-dimethoxyphenyl)-5-(6-methoxy-2-pyridinyl)-4H-1,2,4-triazol-3-yl)-2-butanesulfonamide

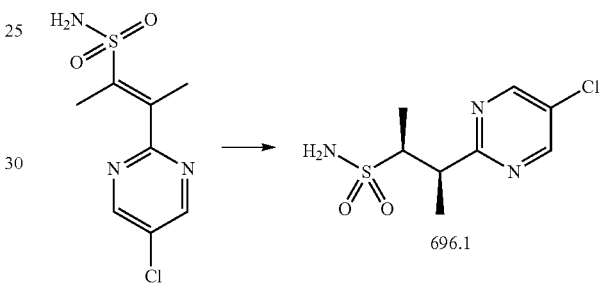

696.1

(2S,3R)-3-(5-chloropyrimidin-2-yl)butane-2-sulfonamide, Example 696.1

A pressure vessel was charged with a solution of (E)-3-(5-chloropyrimidin-2-yl)but-2-ene-2-sulfonamide (prepared in an analogous fashion to 10.05 starting from 2-chloro-5-chloropyrimidine, 70 g, 283 mmol, 1.0 equiv), (S)-1-[(R)-2-(di-1-naphthylphosphino)ferrocenyl]-ethyl-di-tert-butylphosphine (4.54 g, 7.06 mmol, 0.025 equiv, Solvias), bis(1,5-cyclooctadiene)rhodium(i) tetrafluoroborate (2.295 g, 5.65 mmol, 0.02 equiv, Combi Block) and zinc trifluoromethanesulfonate (20.55 g, 56.5 mmol, 0.2 equiv, Sigma Aldrich) in MeOH (1283.3 mL, 18.33 mL/g). The reactor was purged with argon and back filled with hydrogen three times. The reaction mixture was stirred under hydrogen atmosphere (50 psi) at RT for 96 h. The reaction mixture was then filtered through a plug of Celite® brand filter agent, concentrated under reduced pressure and the solid was stirred with IPA (500 mL) and for 15 minutes and filtered to give the title compound (38 g, 90% ee). Recrystallization: Example 696.1 (38 g, 90% ee) was dissolved in isopropanol (400 mL) at 70° C. The homogeneous mixture was cooled to RT and allowed to stand for 12 h. The white solid thus obtained was filtered and dried to provide Example 696.1 (31 g, 95% ee). The same procedure was repeated again with this material to provide Example 696.1 (29.0 g, 100% ee). ¹H NMR (400 MHz, DMSO-d₆) δ 8.93-8.85 (m, 2H), 6.86 (d, J=4.0 Hz, 2H), 3.73-3.59 (m, 2H), 1.31 (dt, J=7.3, 2.4 Hz, 3H), 1.25-1.19 (m, 3H). MS (ESI+ve ion) m/z: 250.2 (M+H)+.

The compounds set forth in the following Table were synthesized following the procedure in Example A using the known starting material as described.

TABLE 30

| Example | Reagents | Structure, Name and Data |
|---|---|---|
| 696.0 | (2S,3R)-3-(5-chloropyrimidin-2-yl)butane-2-sulfonamide (Example 696.1), 6-methoxypicolinohydrazide (commercially available from Sigma-Aldrich Corp, St. Louis, MO, USA), 2-isothiocyanato-1,3-dimethoxybenzene (Example 1.0) | 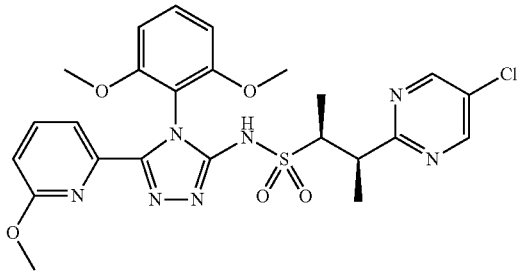 [SMILES: COc1cccc(-c2nnc(NS(=O)(=O)[C@@H](C)[C@H](C)c3ncc(Cl)cn3)n2-c2c(OC)cccc2OC)n1]<br>(2S,3R)-3-(5-chloro-2-pyrimidinyl)-N-(4-(2,6-dimethoxyphenyl)-5-(6-methoxy-2-pyridinyl)-4H-1,2,4-triazol-3-yl)-2-butanesulfonamide.<br>$^1$H NMR (DMSO-d$_6$) δ 13.24 (s, 1H), 8.85 (s, 1H), 7.80 (t, J = 7.9 Hz, 1H), 7.57 (d, J = 7.5 Hz, 1H), 7.40 (t, J = 8.5 Hz, 1H), 6.82 (d, J = 8.3 Hz, 1H), 6.78 (dd, J = 8.4, 3.6 Hz, 2H), 6.66 (br d, J = 8.2 Hz, 1H), 3.68-3.73 (m, 1H), 3.64 (s, 3H), 3.64 (s, 3H), 3.53-3.61 (m, 1H), 3.10 (s, 3H), 1.24 (br d, J = 7.0 Hz, 3H), 1.12 (br d, J = 6.9 Hz, 3H). LCMS-ESI (POS.) m/z: 560.14 (M + H)$^+$. |

Example 697.0: Preparation of (2S,3R)-3-(5-cyano-2-pyrimidinyl)-N-(4-(2,6-dimethoxyphenyl)-5-(5-methyl-3-pyridinyl)-4H-1,2,4-triazol-3-yl)-2-butanesulfonamide

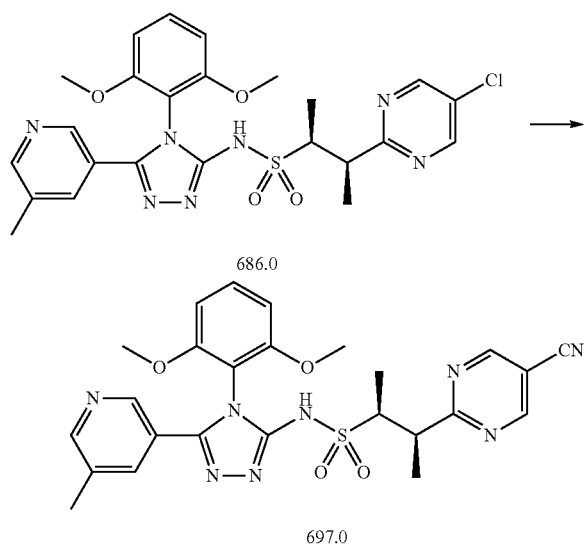

(2S,3R)-3-(5-cyano-2-pyrimidinyl)-N-(4-(2,6-dimethoxyphenyl)-5-(5-methyl-3-pyridinyl)-4H-1,2,4-triazol-3-yl)-2-butanesulfonamide, Example 697.0

(2S,3R)-3-(5-chloropyrimidin-2-yl)-N-(4-(2,6-dimethoxyphenyl)-5-(5-methylpyridin-3-yl)-4H-1,2,4-triazol-3-yl)butane-2-sulfonamide (686.0, 0.020 g, 0.037 mmol), methane sulfonato(2-dicyclohexylphosphino-2',4',6'-tri-i-propyl-1,1'-biphenyl) (2'-amino-1,1'-biphenyl-2-yl)palladium(II) (0.016 g, 0.018 mmol) (commercially available from Strem Chemicals, Inc. Newburyport, Mass., USA), methanesulfonato(2-di-t-butylphosphino-2',4',6'-tri-i-propyl-1,1'-biphenyl)(2'-amino-1,1'-biphenyl-2-yl)palladium (II) (0.015 g, 0.018 mmol) (commercially available from Strem Chemicals, Inc. Newburyport, Mass., USA), methanesulfonato[9,9-dimethyl-4,5-bis(diphenylphosphino)xanthene][2'-amino-1,1'-biphenyl]palladium(II) dichloromethane adduct (0.019 g, 0.018 mmol) (commercially available from Strem Chemicals, Inc. Newburyport, Mass., USA) and zinc cyanide (4.32 mg, 0.037 mmol) (commercially available from Sigma-Aldrich Corp, St. Louis, Mo., USA) were added to a screw-top vial equipped with a magnetic stir bar. After sealing the vessel with a screw-cap septum, the vessel was purged with argon gas. DMA (0.2 mL) was then added to the reaction tube by syringe. The vial was heated to 80° C. and stirred for 2 h. The reaction mixture was allowed to cool to RT and then the resulting mixture was filtered through a syringe filter. The material thus obtained was absorbed onto a plug of silica gel and purified by chromatography through a RediSep-Sep pre-packed silica gel column (12 g), eluting with a gradient of 0% to 100% (3:1 EtOAc:EtOH) in heptanes to provide (2S,3R)-3-(5-cyano-pyrimidin-2-yl)-N-(4-(2,6-dimethoxyphenyl)-5-(5-methyl-pyridin-3-yl)-4H-1,2,4-triazol-3-yl)butane-2-sulfonamide (697.0, 0.010 g, 0.019 mmol, 51% yield). $^1$H NMR (CDCl$_3$) δ 8.93 (s, 2H), 8.56 (br s, 1H), 8.41 (s, 1H), 8.03 (s, 1H), 7.45 (t, J=8.5 Hz, 1H), 6.61-6.72 (m, 2H), 3.90 (quin, J=7.0 Hz, 1H), 3.79-3.82 (m, 1H), 3.79 (s, 3H), 3.76 (s, 3H), 2.44 (s, 3H), 1.39 (d, J=5.5 Hz, 3H), 1.38 (d, J=5.6 Hz, 3H). LCMS-ESI (POS.) m/z: 535.2 (M+H)$^+$.

Example 698.0: Preparation of (1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide and (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide

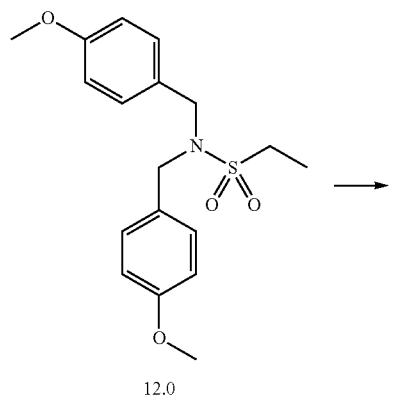

12.0

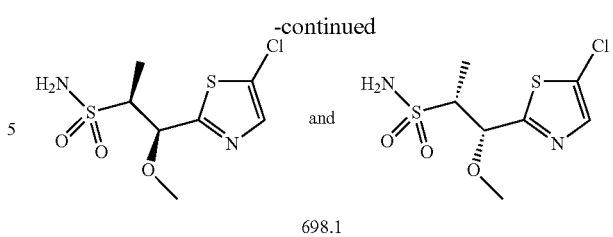

698.1

(1S,2S)-1-(5-chlorothiazol-2-yl)-1-methoxypropane-2-sulfonamide and (1R,2R)-1-(5-chlorothiazol-2-yl)-1-methoxypropane-2-sulfonamide, Example 698.1

The title compound was prepared from N,N-bis(4-methoxybenzyl)ethanesulfonamide 12.0, and 5-chlorothiazole-2-carboxaldehyde (commercially available from Acros Organics) using the procedures described in Example 11.0. LCMS-ESI (POS.) m/z: 271.0 (M+H)$^+$.

The compounds set forth in the following Table were synthesized following the procedure in Example A using the known starting material as described.

TABLE 31

| Example | Reagents | Structure, Name and Data |
|---|---|---|
| 698.0 | (1S,2S)-1-(5-chlorothiazol-2-yl)-1-methoxypropane-2-sulfonamide and (1R,2R)-1-(5-chlorothiazol-2-yl)-1-methoxypropane-2-sulfonamide (Example 698.1), nicotinohydrazide (Aldrich), 2-isothiocyanato-1,3-dimethoxybenzene (Example 1.0). Methane sulfonic acid was used instead of TFA. | AND (1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide and (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide. $^1$H NMR (500 MHz, CD$_3$OD) δ 1.21 (d, J = 7.09 Hz, 3 H) 3.38 (s, 3 H) 3.46-3.57 (m, 1 H) 3.77 (s, 3 H), 3.77 (s, 3 H) 5.13 (d, J = 2.20 Hz, 1 H) 6.76-6.85 (m, 2 H) 7.51 (t, J = 8.56 Hz, 1 H) 7.55-7.61 (m, 1 H) 7.65 (s, 1 H) 8.01 (dt, J = 8.44, 1.65 Hz, 1 H) 8.64-8.71 (m, 2 H). LCMS-ESI (POS.) m/z: 551.0 (M + H)$^+$. |

… continued

| Example | Reagents | Structure, Name and Data |
|---|---|---|
| 699.0 | SFC chiral separation of Example 698.0. was performed. Example 699.0 was the first peak to elute on IA column. SFC condition: run on Thar 80 SFC with 250 × 30 mm IA column with 32 mL/min MeOH (+20 mM $NH_3$) + 48 g/min $CO_2$, 40% co-solvent at 80 g/min. Temp. = 29° C., Outlet pressure = 100 bar, Wavelength = 251 nm. Injected 1.0 mL of 166 mg sample dissolved in 15 mL of 2:1 MeOH:DCM; c = 10.7 mg/mL and 10.7 mg per injection. Cycle time 6.5 min, run time 9 min. | 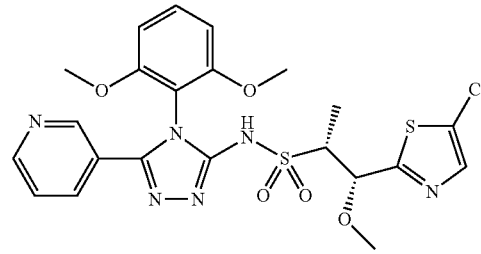<br>OR<br>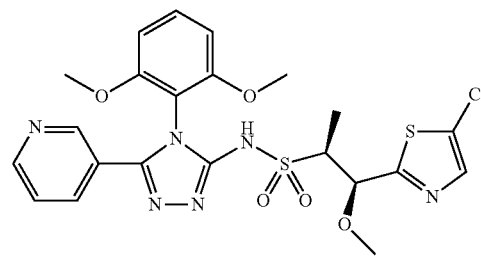<br>(1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide or (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide. 1H NMR (500 MHz, $CD_3OD$) δ 1.21 (d, J = 7.09 Hz, 3 H) 3.38 (s, 3 H) 3.46-3.57 (m, 1 H) 3.77 (s, 3 H), 3.77 (s, 3 H) 5.13 (d, J = 2.20 Hz, 1 H) 6.76-6.85 (m, 2 H) 7.51 (t, J = 8.56 Hz, 1 H) 7.55-7.61 (m, 1 H) 7.65 (s, 1 H) 8.01 (dt, J = 8.44, 1.65 Hz, 1 H) 8.64-8.71 (m, 2 H). LCMS-ESI (POS.) m/z: 551.0 $(M + H)^+$. |
| 700.0 | SFC chiral separation of Example 698.0 was peformed. The title compound Example 700.0 was the second peak to elute on IA column under the conditions described in Example 699.0. | 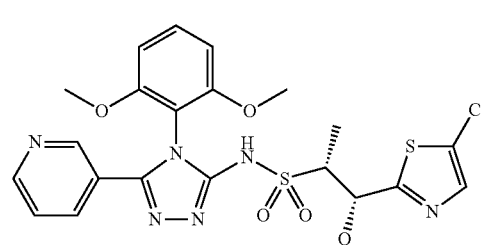<br>OR<br>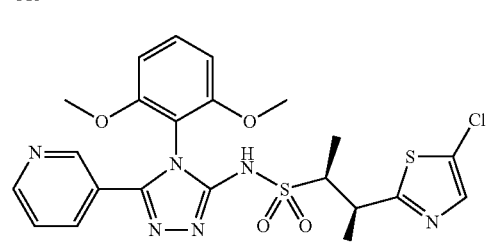<br>(1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide or (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide. 1H NMR (500 MHz, $CD_3OD$) δ 1.21 (d, J = 7.09 Hz, 3 H) 3.38 (s, 3 H) 3.46-3.57 (m, 1 H) |

TABLE 31-continued

| Example | Reagents | Structure, Name and Data |
|---|---|---|
| | | 3.77 (s, 3 H), 3.77 (s, 3 H) 5.13 (d, J = 2.20 Hz, 1 H) 6.76-6.85 (m, 2 H) 7.51 (t, J = 8.56 Hz, 1 H) 7.55-7.61 (m, 1 H) 7.65 (s, 1 H) 8.01 (dt, J = 8.44, 1.65 Hz, 1 H) 8.64-8.71 (m, 2 H). LCMS-ESI (POS.) m/z: 551.0 (M + H)+. |

The compounds set forth in the following Table were synthesized following the procedure in Example B using the known starting material as described.

TABLE 32

| Example | Reagents | Structure, Name and Data |
|---|---|---|
| 701.0 | (2R,3S)-3-(5-methylpyrazin-2-yl)butane-2-sulfonamide and (2S,3R)-3-(5-methylpyrazin-2-yl)butane-2-sulfonamide (racemate of Example 10.2) and 3-(5-bromo-4-(2,6-dimethoxyphenyl)-4H-1,2,4-triazol-3-yl)pyridine Example 2.1 | 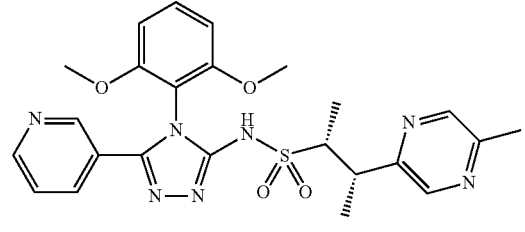 [SMILES: COc1cccc(OC)c1-n1c(NS(=O)(=O)[C@H](C)[C@@H](C)c2cnc(C)cn2)nnc1-c1cccnc1]<br>AND<br>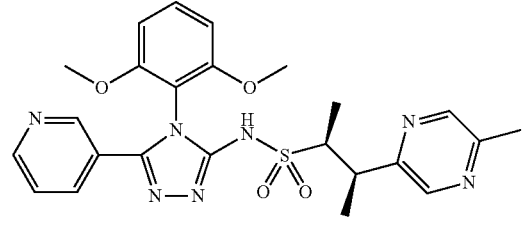 [SMILES: COc1cccc(OC)c1-n1c(NS(=O)(=O)[C@@H](C)[C@H](C)c2cnc(C)cn2)nnc1-c1cccnc1]<br>(2R,3S)-N-(4-(2,6-dimethoxyphenyl)-5-(3-pyridinyl)-4H-1,2,4-triazol-3-yl)-3-(5-methyl-2-pyrazinyl)-2-butanesulfonamide, (2S,3R)-N-(4-(2,6-dimethoxyphenyl)-5-(3-pyridinyl)-4H-1,2,4-triazol-3-yl)-3-(5-methyl-2-pyrazinyl)-2-butanesulfonamide.<br>1H NMR (500 MHz, CDCl3) δ 8.58-8.73 (m, 2H), 8.32-8.43 (m, 2H), 7.76 (dt, J = 8.0, 1.9 Hz, 1H), 7.50 (t, J = 8.6 Hz, 1H), 7.30 (dd, J = 7.8, 4.9 Hz, 1H), 6.66-6.76 (m, 2H), 3.75-3.80 (m, 6H), 3.71 (qd, J = 7.1, 4.5 Hz, 1H), 3.55 (qd, J = 7.0, 4.4 Hz, 1H), 2.53 (s, 3H), 1.37 (d, J = 7.1 Hz, 3H), 1.33 (d, J = 6.8 Hz, 3H). LCMS-ESI (POS.) m/z: 510.2. |
| 702.0 | SFC chiral separation of Example 701.0 was performed. The title compound was the second (later peak vs. its opposite enantiomer) peak on CC4 column. SFC condition: run on Thar 200 SFC with 30 × 250 + 30 × 150 mm CC4 columns in series with 36 mL/min MeOH (20 mM NH3) + 54 g/min CO2, 40% co-solvent at 90 g/min. Temp. = 30° C., Outlet pressure = 100 bar, Wavelength = 277 nm. Injected 0.4 mL of 340 mg sample dissolved in 25 mL MeOH:DCM 19:6; c = 13.6 mg/mL, i.e. 5.4 mg per injection. Cycle tim e6.5 min, run time 20 min. | 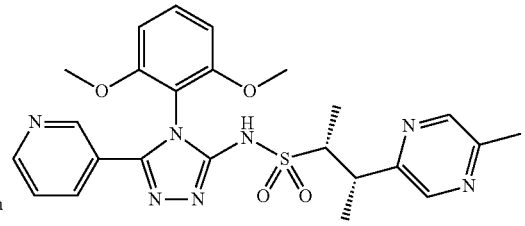<br>OR<br>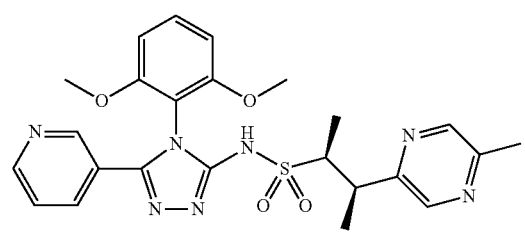 [SMILES: COc1cccc(OC)c1-n1c(NS(=O)(=O)[C@@H](C)[C@H](C)c2cnc(C)cn2)nnc1-c1cccnc1]<br>(2R,3S)-N-(4-(2,6-dimethoxyphenyl)-5-(3-pyridinyl)-4H- |

TABLE 32-continued

| Example Reagents | Structure, Name and Data |
|---|---|
| | 1,2,4-triazol-3-yl)-3-(5-methyl-2-pyrazinyl)-2-butanesulfonamide or (2S,3R)-N-(4-(2,6-dimethoxyphenyl)-5-(3-pyridinyl)-4H-1,2,4-triazol-3-yl)-3-(5-methyl-2-pyrazinyl)-2-butanesulfonamide.<br>$^1$H NMR (500 MHz, CD$_2$Cl$_2$) δ 1.32 (d, J = 7.05 Hz, 3 H) 1.36 (d, J = 7.15 Hz, 3 H) 2.52 (s, 3 H) 3.53 (dd, J = 7.02, 4.33 Hz, 1 H) 3.69 (dd, J = 7.15, 4.41 Hz, 1 H) 3.76 (s, 3 H) 3.76 (s, 3 H) 6.70 (dd, J = 8.55, 2.64 Hz, 2 H) 7.28 (ddd, J = 7.98, 4.85, 0.70 Hz, 1 H) 7.49 (t, J = 8.53 Hz, 1 H) 7.74 (d, J = 7.70 Hz, 1 H) 8.32 (d, J = 1.24 Hz, 1 H) 8.37 (s, 1 H) 8.59-8.68 (m, 2 H) 11.16 (s, 1 H). LCMS-ESI (POS.) m/z: 510.2. |

Example 703.0: Preparation of (1R,2S)—N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide and (1S,2R)—N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide

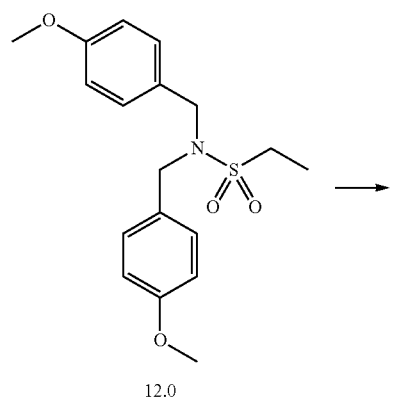

12.0

→

-continued

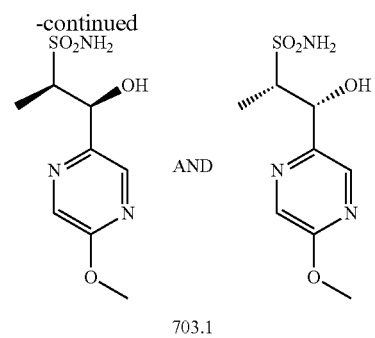

703.1

(1S,2R)-1-hydroxy-1-(5-methoxypyrazin-2-yl)propane-2-sulfonamide and (1R,2S)-1-hydroxy-1-(5-methoxypyrazin-2-yl)propane-2-sulfonamide, Example 703.1

The title compound was prepared from N,N-bis(4-methoxybenzyl)ethanesulfonamide 12.0 and 5-methoxypyrazine-2-carboxaldehyde (commercially available from Frontier Scientific, Inc.) using the procedures described in Example 11.0. LCMS-ESI (POS.) m/z: 269.9 (M+Na)$^+$.

The compounds set forth in the following Table were synthesized following the procedure in Example B using the known starting material as described.

TABLE 33

| Example | Reagents | Structure, Name and Data |
|---|---|---|
| 703.0 | The title compound was prepared from Example 703.1 and 3-(5-bromo-4-(2,6-dimethoxyphenyl)-4H-1,2,4-triazol-3-yl)pyridine Example 2.1. | 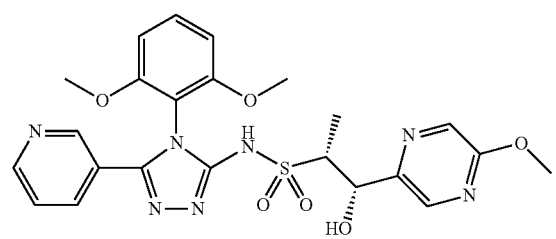 [SMILES: COc1cnc([C@H](O)[C@@H](C)S(=O)(=O)Nc2nnc(-c3cccnc3)n2-c2c(OC)cccc2OC)cn1]<br>AND |

TABLE 33-continued

| Example Reagents | Structure, Name and Data |
|---|---|
| | 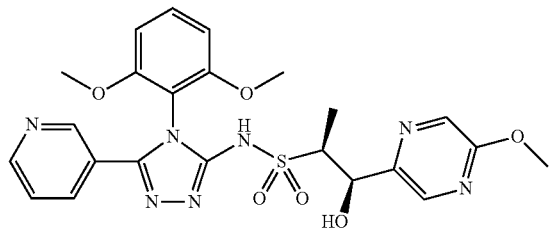 [SMILES: COc1cnc([C@@H](O)[C@H](C)S(=O)(=O)Nc2nnc(-c3cccnc3)n2-c2c(OC)cccc2OC)cn1]<br>(1R,2S)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide and (1S,2R)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide<br>$^1$H NMR (400 MHz, CD$_3$OD) δ 1.16 (d, J = 7.05 Hz, 3 H) 3.58 (qd, J = 7.01, 2.38 Hz, 1 H) 3.76 (s, 3 H) 3.78-3.80 (m, 3 H) 3.95 (s, 3 H) 5.34 (dd, J = 2.49, 0.83 Hz, 1 H) 6.82 (ddd, J = 8.60, 7.77, 0.83 Hz, 2 H) 7.53 (t, J = 8.45 Hz, 1 H) 7.58 (t, J = 6.39 Hz, 1 H) 8.00 (dt, J = 8.09, 1.76 Hz, 1 H) 8.14 (d, J = 1.45 Hz, 1 H) 8.20 (s, 1 H) 8.68 (br. s., 2 H).<br>LCMS-ESI (POS.) m/z: 528.0 (M + H)$^+$. |

Example 704.0: Preparation of (2R,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide 704.1

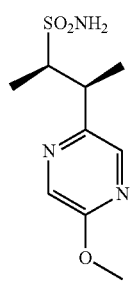 AND 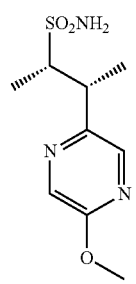 AND

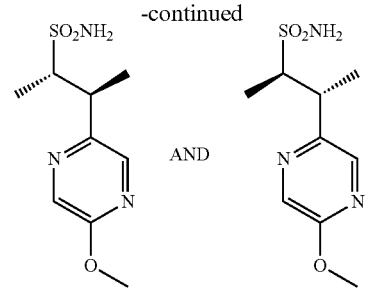

(2R,3R)-3-(5-methoxypyrazin-2-yl)butane-2-sulfonamide and (2R,3S)-3-(5-methoxypyrazin-2-yl)butane-2-sulfonamide and (2S,3R)-3-(5-methoxypyrazin-2-yl)butane-2-sulfonamide and (2S,3S)-3-(5-methoxypyrazin-2-yl)butane-2-sulfonamide, Example 704.1

704.1 was synthesized following the procedure in Example 10.0 using 2-bromo-5-methoxypyrazine (commercially available from Ark Pharm, Inc.). LCMS-ESI (POS.) m/z: 246.2 (M+H)$^+$.

The compounds set forth in the following Table were synthesized following the procedure in Example B using the known starting material as described.

TABLE 34

| Example | Reagents | Structure, Name and Data |
|---|---|---|
| 704.0 | Example 704.1 and 3-(5-bromo-4-(2,6-dimethoxyphenyl)-4H-1,2,4-triazol-3-yl)pyridine Example 2.1. | (structure)<br><br>AND |

| Example | Reagents | Structure, Name and Data |
|---|---|---|
| | | 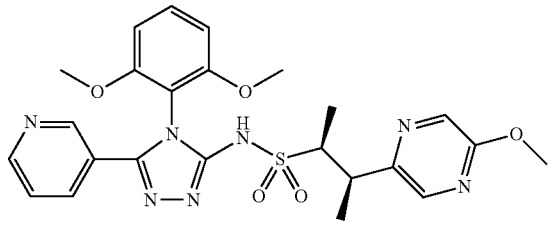 [SMILES: COc1cnc([C@@H](C)[C@H](C)S(=O)(=O)Nc2nnc(-c3cccnc3)n2-c2c(OC)cccc2OC)cn1]<br>AND<br>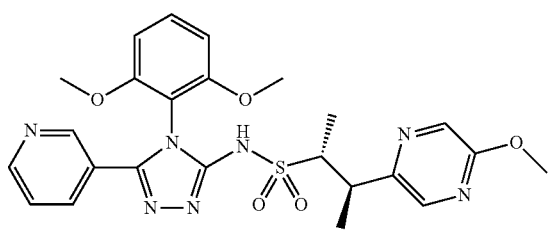 [SMILES: COc1cnc([C@@H](C)[C@@H](C)S(=O)(=O)Nc2nnc(-c3cccnc3)n2-c2c(OC)cccc2OC)cn1]<br>AND<br>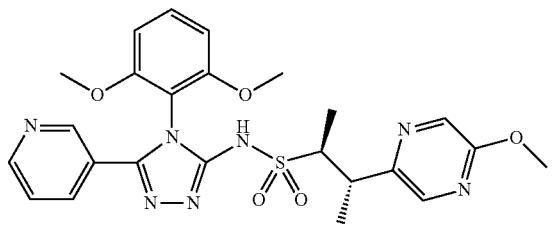<br>(2R,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)-N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)-N-(4-(2,6-dimethoxyphenyl)-5-(3-pyridinyl)-4H-1,2,4-triazol-3-yl)-3-(5-methoxy-2-pyrazinyl)-2-butanesulfonamide. LCMS-ESI (POS.) m/z: 526.1 (M + H)$^+$. |
| 705.0 | (2R,3S)-3-(5-methoxypyrazin-2-yl)butane-2-sulfonamide compound and (2S,3R)-3-(5-methoxypyrazin-2-yl)butane-2-sulfonamide Example 704.1 and 2-(5-bromo-4-(2,6-dimethoxyphenyl)-4H-1,2,4-triazol-3-yl)-6-methoxypyridine Example 2.2. The title compound was obtained (silica gel | 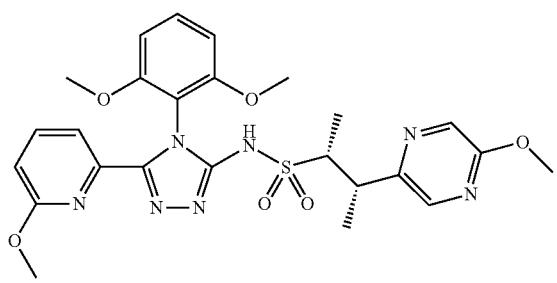 [SMILES: COc1cnc([C@H](C)[C@@H](C)S(=O)(=O)Nc2nnc(-c3cccc(OC)n3)n2-c2c(OC)cccc2OC)cn1]<br>AND |

TABLE 34-continued

| Example | Reagents | Structure, Name and Data |
|---|---|---|
| | chromatography and re-crystallized from i-PrOH) as the major product. | 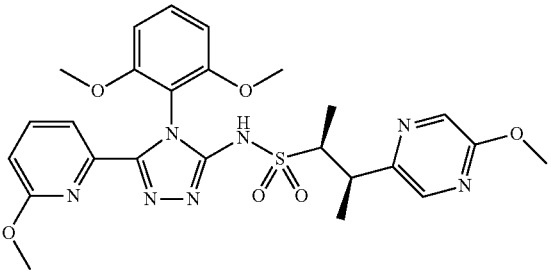 [SMILES: COc1cnc([C@@H](C)[C@H](C)S(=O)(=O)Nc2nnc(-c3cccc(OC)n3)n2-c2c(OC)cccc2OC)cn1] (2R,3S)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide and (2S,3R)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide<br>$^1$H NMR (400 MHz, CD$_3$OD) δ 1.29 (dd, J = 10.39, 7.07 Hz, 6 H) 3.17 (s, 3 H) 3.42 (dd, J = 6.97, 4.85 Hz, 1 H) 3.56 (dd, J = 7.07, 4.85 Hz, 1 H) 3.72 (d, J = 2.07 Hz, 3 H), 3.72 (d, J = 2.07 Hz, 3 H) 3.73-3.75 (m, 1 H) 3.93 (s, 3 H) 6.72-6.81 (m, 3 H) 7.42 (t, J = 8.50 Hz, 1 H) 7.61 (dd, J = 7.41, 0.78 Hz, 1H) 7.68-7.74 (m, 1 H) 7.89 (d, J = 1.09 Hz, 1 H) 8.12 (d, J = 1.35 Hz, 1 H). LCMS-ESI (POS.) m/z: 556.2 (M + H)$^+$. |
| 706.0 | SFC chiral separation of Example 703.0 was performed. This was the first (earlier peak vs. its opposite enantiomer) peak on Whelk-O column. SFC condition: Regis Whelk-O s, s 4.6 × 50 mm, 35% isopropanol with 0.2% DEA. The compound was converted to the HCl salt. | 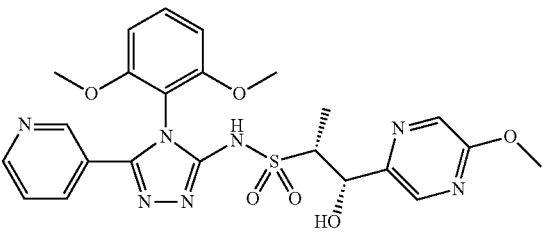 [SMILES: COc1cnc([C@H](O)[C@@H](C)S(=O)(=O)Nc2nnc(-c3cccnc3)n2-c2c(OC)cccc2OC)cn1] OR<br><br>(1S,2R)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide or (1R,2S)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide.<br>$^1$H NMR (400 MHz, CD$_3$OD) δ 1.16 (d, J = 7.05 Hz, 3 H) 3.55-3.71 (m, 1 H) 3.76 (s, 3 H) 3.79 (s, 3 H) 3.96 (s, 3 H) 5.34 (dd, J = 2.41, 0.70 Hz, 1 H) 6.81 (t, J = 7.70 Hz, 2 H) 7.46-7.55 (m, 2 H) 7.90 (ddd, J = 8.29, 1.92, 1.66 Hz, 1 H) 8.14 (d, J = 1.35 Hz, 1 H) 8.20 (s, 1 H) 8.62 (d, J = 4.55 Hz, 1 H) 8.61 (s, 1 H). LCMS-ESI (POS.) m/z: 528.0 (M + H)$^+$. |
| 707.0 | SFC chiral separation of Example 703.0 was performed. This was the second (later peak vs. its opposite enantiomer) peak on Whelk-O column. SFC condition: Regis Whelk-O s, s 4.6 × 50 mm, 35% isopropanol/CO$_2$ with 0.2% DEA. The compound was converted to the HCl salt. | 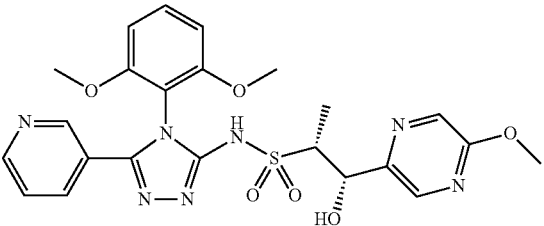 [SMILES: COc1cnc([C@H](O)[C@@H](C)S(=O)(=O)Nc2nnc(-c3cccnc3)n2-c2c(OC)cccc2OC)cn1] OR |

| Example | Reagents | Structure, Name and Data |
|---|---|---|
| | | 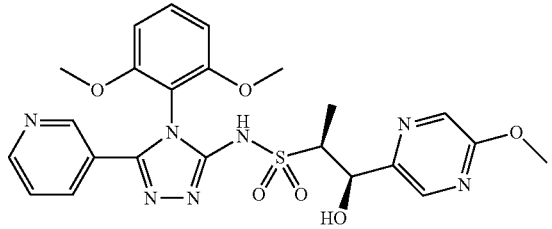 [SMILES: COc1cnc([C@@H](O)[C@H](C)S(=O)(=O)Nc2nnc(-c3cccnc3)n2-c2c(OC)cccc2OC)cn1]
(1S,2R)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide or (1R,2S)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide.
$^1$H NMR (400 MHz, CD$_3$OD) δ 1.16 (d, J = 7.00 Hz, 3 H) 3.55-3.62 (m, 1 H) 3.76 (s, 3 H) 3.79 (s, 3 H) 3.96 (s, 3 H) 5.34 (dd, J = 2.38, 0.67 Hz, 1 H) 6.81 (t, J = 7.77 Hz, 2 H) 7.44 (t, J = 6.41 Hz, 1 H) 8.14 (d, J = 1.35 Hz, 1 H) 8.20 (s, 1 H) 8.59 (d, J = 5.09 Hz, 1 H) 8.58 (s, 1 H). LCMS-ESI (POS.) m/z: 528.0 (M + H)$^+$. |
| 708.0 | SFC chiral separation of Example 705.0 was performed. This was the first (earlier peak vs. its opposite enantiomer) peak on AD-H column SFC condition: Chiralpak AD-H, 25% MeOH/CO$_2$ with 0.2% DEA. | 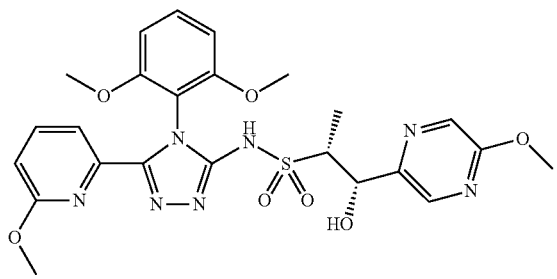 [SMILES: COc1cnc([C@H](O)[C@@H](C)S(=O)(=O)Nc2nnc(-c3cccc(OC)n3)n2-c2c(OC)cccc2OC)cn1]
OR
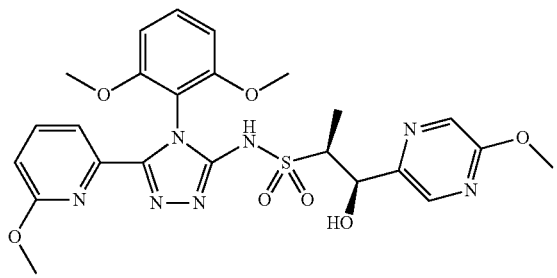 [SMILES: COc1cnc([C@@H](O)[C@H](C)S(=O)(=O)Nc2nnc(-c3cccc(OC)n3)n2-c2c(OC)cccc2OC)cn1]
(2S,3R)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide or (2R,3S)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide
$^1$H NMR (400 MHz, DMSO-d6) δ 1.10 (d, J = 7.05 Hz, 3 H) 1.22 (d, J = 7.15 Hz, 3 H) 3.10 (s, 3 H) 3.24-3.35 (m, 1 H) 3.56 (br dd, J = 7.05, 3.73 Hz, 1 H) 3.64 (s, 3 H) 3.64 (s, 3 H) 3.88 (s, 3 H) 6.77-6.84 (m, 3 H) 7.41 (t, J = 8.47 Hz, 1 H) 7.58 (d, J = 7.41 Hz, 1 H) 7.80 (t, J = 7.89 Hz, 1 H) 7.99 (d, J = 1.14 Hz, 1 H) 8.23 (d, J = 1.35 Hz, 1 H) 13.29 (s, 1 H). LCMS-ESI (POS.) m/z: 556.1 (M + H)$^+$. |

The compounds set forth in the following Table were synthesized following the procedure in Example A using the known starting material as described.

TABLE 35

| Example | Reagents | Structure, Name and Data |
|---|---|---|
| 709.0 | (2S,3R)-3-(5-chloropyrimidin-2-yl)butane-2-sulfonamide (Example 696.1), nicotinohydrazide (Alfa Aesar), 5-isothiocyanato-4,6-dimethoxypyrimidine (Example 1.1) | (2S,3R)-3-(5-chloro-2-pyrimidinyl)-N-(4-(4,6-dimethoxy-5-pyrimidinyl)-5-(3-pyridinyl)-4H-1,2,4-triazol-3-yl)-2-butanesulfonamide. $^1$H NMR (400 MHz, DMSO-$d_6$) δ 1.12 (d, J = 6.88 Hz, 3 H) 1.27 (d, J = 7.07 Hz, 3 H) 3.70 (dd, J = 6.94, 4.02 Hz, 1 H) 3.87 (s, 3 H), 3.88 (s, 3 H) 3.89-3.95 (m, 1 H) 7.45 (dd, J = 7.75, 4.96 Hz, 1 H) 7.72 (d, J = 7.91 Hz, 1 H) 8.57 (s, 1 H) 8.60-8.67 (m, 2 H) 8.82-8.89 (m, 2 H). LCMS-ESI (POS.) m/z: 532.0 (M + H)$^+$. |
| 710.0 | (2S,3R)-3-(5-chloropyrimidin-2-yl)butane-2- (Example 696.1), 6-methoxypicolinohydrazide (Example 3.18), 5-isothiocyanato-4,6-dimethoxypyrimidine (Example 1.1) | (2S,3R)-3-(5-chloro-2-pyrimidinyl)-N-(4-(4,6-dimethoxy-5-pyrimidinyl)-5-(6-methoxy-2-pyridinyl)-4H-1,2,4-triazol-3-yl)-2-butanesulfonamide. $^1$H NMR (400 MHz, CD$_3$OD) δ 1.31 (d, J = 6.95 Hz, 3 H) 1.35 (d, J = 7.10 Hz, 3 H) 3.22-3.26 (m, 3 H) 3.67-3.75 (m, 1 H) 3.75-3.83 (m, 1 H) 3.93 (s, 3 H) 3.94 (s, 3 H) 6.81 (dd, J = 8.21, 0.75 Hz, 1 H) 7.68-7.72 (m, 1 H) 7.72-7.79 (m, 1 H) 8.51 (s, 1 H) 8.73 (s, 2 H). LCMS-ESI (POS.) m/z: 562.0 (M + H)$^+$. |

Example 711.0: Preparation of (1R,2S)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide or (1S,2R)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide

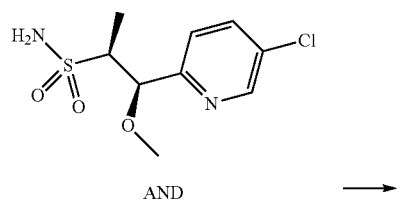

AND

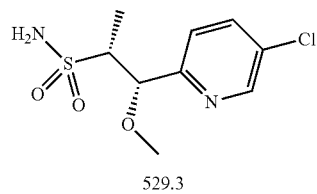

529.3

→

-continued

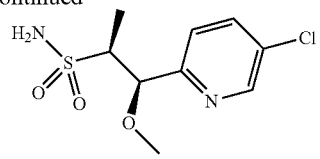

OR

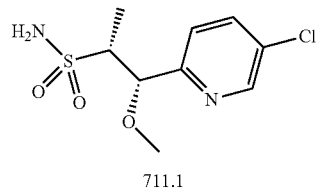

711.1

(1R,2S)-1-(5-chloropyridin-2-yl)-1-methoxypropane-2-sulfonamide or (1S,2R)-1-(5-chloropyridin-2-yl)-1-methoxypropane-2-sulfonamide, Example 711.1

Example 711.1 was prepared by SFC chiral separation of (1R,2S)-1-(5-chloropyridin-2-yl)-1-methoxypropane-2-sulfonamide compound and (1S,2R)-1-(5-chloropyridin-2-yl)-

1-methoxypropane-2-sulfonamide, Example 529.3. The title compound was the second (later peak vs. its opposite enantiomer) peak on AD column. Run on Thar 80 SFC with 250×30 mm AD-H column with 14.4 mL/min EtOH (+20 mM NH$_3$)+65.6 g/min CO$_2$, 18% co-solvent at 80 g/min. Temp.=29° C., Outlet pressure=100 bar, Wavelength=271 nm. Injected 1.0 mL of 360 mg sample dissolved in 36.0 mL of EtOH:MeOH:DCM 22:6:8; c=10 mg/mL and 10 mg per injection. Cycle time 5.8 min, run time 15 min. LCMS-ESI (POS.) m/z: 265.1 (M+H)$^+$.

The compounds set forth in the following Table were synthesized following the procedure in Example A using the known starting material as described.

| Example | Reagents | Structure, Name and Data |
|---|---|---|
| 711.0 | (1R,2S)-1-(5-chloropyridin-2-yl)-1-methoxypropane-2-sulfonamide or (1S,2R)-1-(5-chloropyridin-2-yl)-1-methoxypropane-2-sulfonamide (Example 711.1), nicotinohydrazide (Alfa Aesar), 5-isothiocyanato-4,6-dimethoxypyrimidine (Example 1.1) | 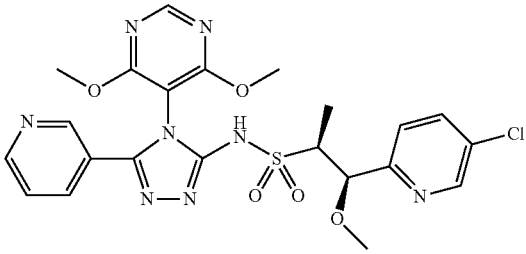 [SMILES: COc1ncnc(OC)c1-n1c(NS(=O)(=O)[C@@H](C)[C@H](OC)c2ccc(Cl)cn2)nnc1-c1cccnc1]<br>OR<br>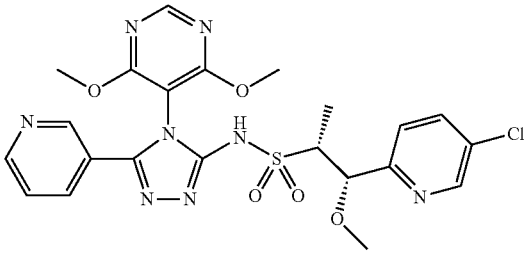 [SMILES: COc1ncnc(OC)c1-n1c(NS(=O)(=O)[C@H](C)[C@@H](OC)c2ccc(Cl)cn2)nnc1-c1cccnc1]<br>(1R,2S)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide or (1S,2R)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide.<br>$^1$H NMR (500 MHz, DMSO-d6) δ 0.98 (d, J = 7.07 Hz, 3 H) 3.22 (s, 3 H) 3.53-3.69 (m, 1 H) 3.85 (s, 3 H) 3.86 (s, 3 H) 3.89-3.94 (m, 1 H) 7.39 (d, J = 8.41 Hz, 1 H) 7.43 (t, J = 7.08 Hz, 1 H) 7.70 (d, J = 7.85 Hz, 1 H) 7.94 (dd, J = 8.43, 2.27 Hz, 1 H) 8.56 (s, 1 H) 8.58-8.66 (m, 3 H). LCMS-ESI (POS.) m/z: 547.0 (M + H)$^+$. |
| 712.0 | (2S,3R)-3-(5-chloropyrimidin-2-yl)butane-2-sulfonamide or (2R,3S)-3-(5-chloropyrimidin-2-yl)butane-2-sulfonamide (Example 711.1), nicotinohydrazide (Alfa Aesar), 3-isothiocyanato-2,4-dimethoxypyridine (Example 771.1) | 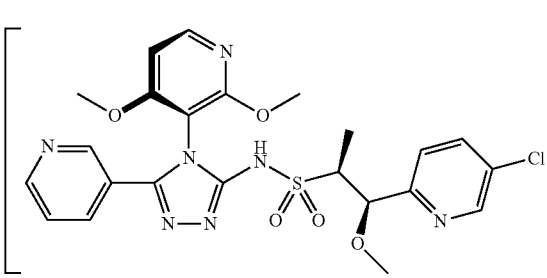<br>AND<br>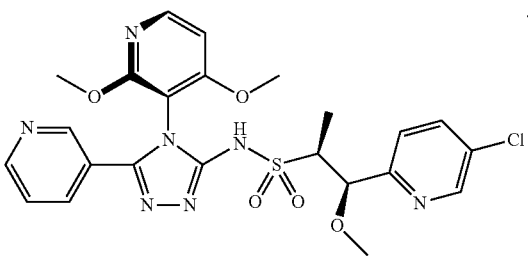 |

-continued

| Example | Reagents | Structure, Name and Data |
|---------|----------|--------------------------|
| | | OR<br>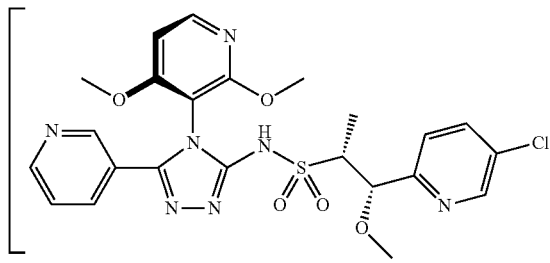<br>AND<br>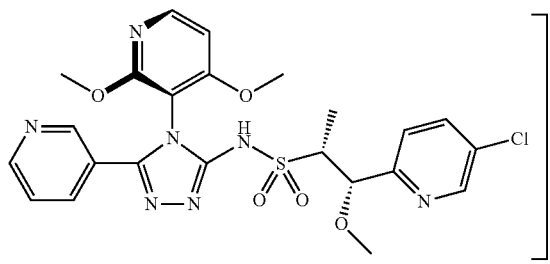<br>(1R,2S,P)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide and (1R,2S,M)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide or (1S,2R,P)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide and (1S,2R,M)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide.<br>$^1$H NMR (400 MHz, CDCl$_3$) δ 1.23 (dd, J = 6.95, 4.46 Hz, 3 H) 3.32 (d, J = 7.05 Hz, 3 H) 3.47-3.57 (m, 1 H) 3.86 (s, 3 H) 3.88 (s, 3 H) 5.04 (dd, J = 6.53, 2.80 Hz, 1 H) 6.69 (dd, J = 5.91, 3.84 Hz, 1 H) 7.43 (d, J = 8.29 Hz, 1 H) 7.58 (dd, J = 8.09, 5.39 Hz, 1 H) 7.76 (dd, J = 8.40, 2.38 Hz, 1 H) 8.05-8.12 (m, 1 H) 8.21 (dd, J = 5.80, 1.45 Hz, 1 H) 8.58 (d, J = 2.07 Hz, 1 H) 8.71-8.76 (m, 2 H). LCMS-ESI (POS.) m/z: 546.1 (M + H)$^+$. |
| 713.0 | (2S,3R)-3-(5-chloropyrimidin-2-yl)butane-2-sulfonamide and (2R,3S)-3-(5-chloropyrimidin-2-yl)butane-2-sulfonamide (racemate of Example 696.1), nicotinohydrazide (Alfa Aesar), 3-isothiocyanato-2,4-dimethoxypyridine (Example 771.1). AcOH was used in the place of ACN and methyl sulfonic acid. | 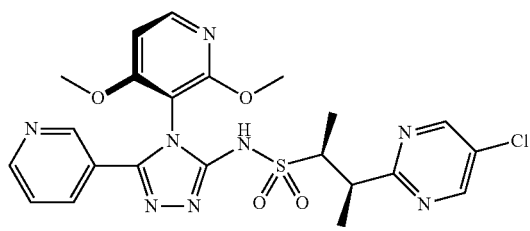<br>AND<br>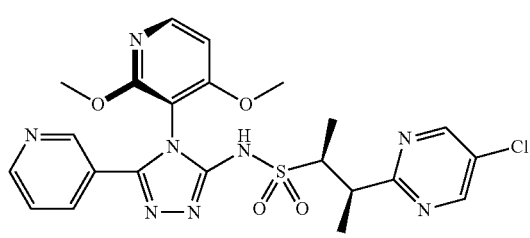<br>AND |

| Example | Reagents | Structure, Name and Data |
|---|---|---|
| | | 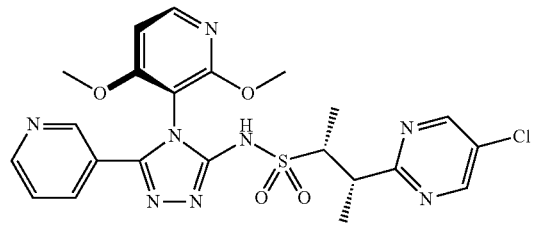<br>AND<br>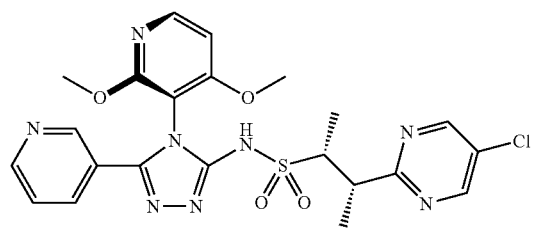<br>(2R,3S,P)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide and (2R,3S,M)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide and (2S,3R,P)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide and (2S,3R,M)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide.<br>$^1$H NMR (400 MHz, CDCl$_3$) δ 1.36-1.44 (m, 6 H) 3.72-3.80 (m, 1 H) 3.84-3.91 (m, 6 H) 3.95-4.05 (m, 1 H) 6.68 (t, J = 6.25 Hz, 1 H) 7.55 (dd, J = 7.98, 5.23 Hz, 1 H) 8.04 (br d, J = 7.93 Hz, 1 H) 8.22 (d, J = 6.01 Hz, 1 H) 8.66 (d, J = 1.40 Hz, 2 H) 8.70-8.74 (m, 2 H). LCMS-ESI (POS.) m/z: 531.2 (M + H)$^+$. |
| 714.0 | SFC chiral separation of Example 712.0 was performed. The title compound was the first (earlier peak vs. its opposite atropisomer) peak on OZ column. SFC condition: Chiralcel OZ-H, 30% MeOH. | 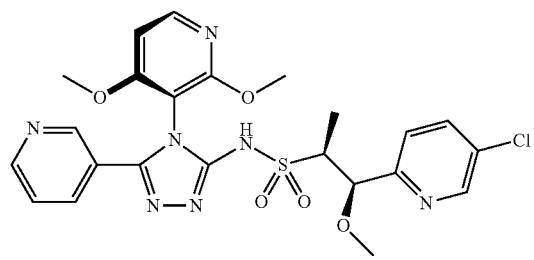<br>OR<br>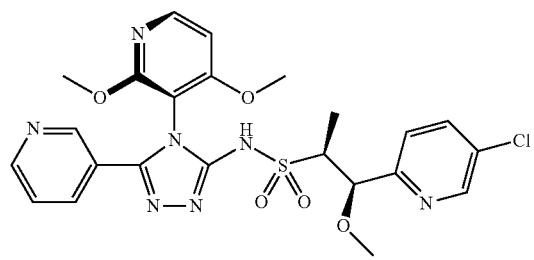<br>(1R,2S,P)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide or (1R,2S,M)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide. |

| Example | Reagents | Structure, Name and Data |
|---|---|---|
| | | $^1$H NMR (400 MHz, CDCl$_3$) δ 1.21 (d, J = 7.10 Hz, 3 H) 3.34 (s, 3 H) 3.54 (qd, J = 7.03, 2.75 Hz, 1 H) 3.81 (s, 3 H) 3.85 (s, 3 H) 5.04 (d, J = 2.70 Hz, 1 H) 6.63 (d, J = 5.96 Hz, 1 H) 7.28-7.33 (m, 1 H) 7.38 (d, J = 8.34 Hz, 1 H) 7.69 (dd, J =8.34, 2.44 Hz, 1 H) 7.76 (dt, J = 8.19, 1.87 Hz, 1 H) 8.17 (d, J = 5.96 Hz, 1 H) 8.53 (dt, J = 2.44 Hz, 1 H) 8.63 (dd, J = 2.20, 0.70 Hz, 1 H) 8.66 (dd, J = 4.90, 1.63 Hz, 1 H) 11.26 (s, 1 H). LCMS-ESI (POS.) m/z: 546.0 (M + H)$^+$. |
| 715.0 | SFC chiral separation of Example 712 was performed. The title compound was the second (later peak vs. its opposite atropisomer) peak on OZ column. SFC condition: Chiralcel OZ-H, 30% MeOH/CO$_2$. | 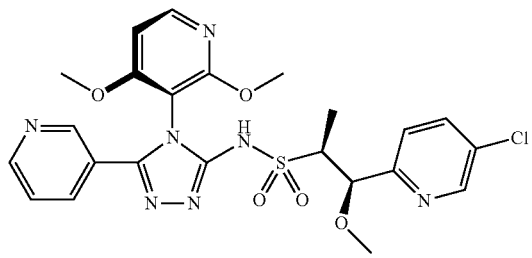<br>OR<br>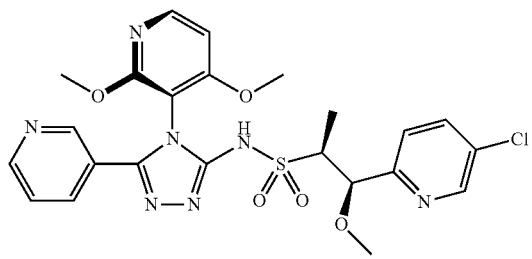<br>(1R,2S,P)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide or (1R,2S,M)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide.<br>$^1$H NMR (400 MHz, CDCl$_3$) δ 1.22 (d, J = 7.10 Hz, 3 H) 3.32 (s, 3 H) 3.55 (qd, J = 7.06, 2.62 Hz, 1 H) 3.81 (s, 3 H) 3.86 (s, 3 H) 5.03 (d, J = 2.59 Hz, 1 H) 6.61 (d, J = 6.01 Hz, 1 H) 7.30 (ddd, J = 7.99, 4.88, 0.80 Hz, 1 H) 7.38 (d, J = 8.40 Hz, 1 H) 7.69 (dd, J = 8.34, 2.44 Hz, 1 H) 7.76 (dt, J = 8.19, 1.87 Hz, 1 H) 8.17 (d, J = 5.96 Hz, 1 H) 8.54 (d, J = 2.44 Hz, 1 H) 8.61-8.64 (m, 1 H) 8.66 (dd, J = 4.87, 1.61 Hz, 1 H) 11.28 (s, 1 H). LCMS-ESI (POS.) m/z: 546.0 (M + H)$^+$. |
| 716.0 | SFC chiral separation of Example 704.0 was performed. The title compound was the first (earlier peak vs. its opposite enantiomer) peak on AD column. SFC condition: Chiralpak AD-H, 25% EtOH/CO$_2$ with 0.2% DEA. | 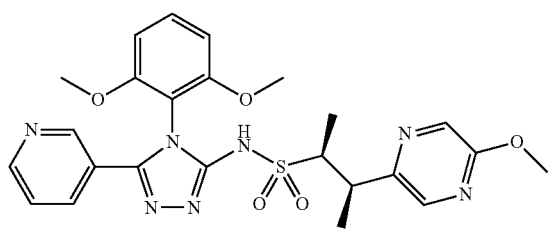 [SMILES: COc1cnc([C@@H](C)[C@H](C)S(=O)(=O)Nc2nnc(-c3cccnc3)n2-c2c(OC)cccc2OC)cn1]<br>OR |

| Example | Reagents | Structure, Name and Data |
|---|---|---|
| | | 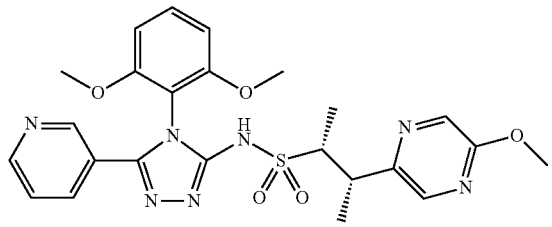 [SMILES: COc1cnc([C@H](C)[C@@H](C)S(=O)(=O)Nc2nnc(-c3cccnc3)n2-c2c(OC)cccc2OC)cn1] |
| | | (2S,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide.<br>$^{1}$H NMR (400 MHz, CD$_{3}$OD) δ 1.28 (d, J = 7.00 Hz, 3 H) 1.31 (d, J = 7.15 Hz, 3 H) 3.39-3.48 (m,1 H) 3.58 (dd, J = 7.10, 4.72 Hz, 1 H) 3.76 (s, 3 H) 3.78 (s, 3 H) 3.93 (s, 3 H) 6.80 (dd, J = 8.58, 3.14 Hz, 2 H) 7.42 (dd, J = 7.88, 4.92 Hz, 1 H) 7.51 (t, J = 8.55 Hz, 1 H) 7.84 (dt, J = 8.03. 1.89 Hz, 1 H) 7.91 (d, J = 1.14 Hz, 1 H) 8.12 (d, J = 1.30 Hz, 1 H) 8.57 (br. s., 2 H). LCMS-ESI (POS.) m/z: 526.2 (M + H)$^{+}$. |
| 717.0 | Chiral separation of Example 713.0 was performed. The title compound was the earlier peak (vs. its opposite atropisomer) peak on AD column. SFC condition: Chiralpak AD-H, 45% isopropanol/CO$_{2}$, with 0.2% DEA. | 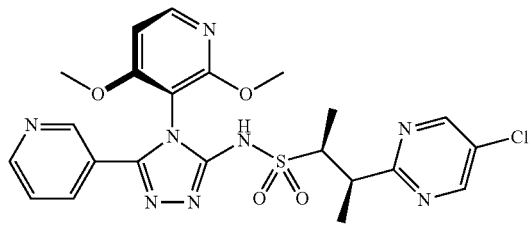<br>OR<br>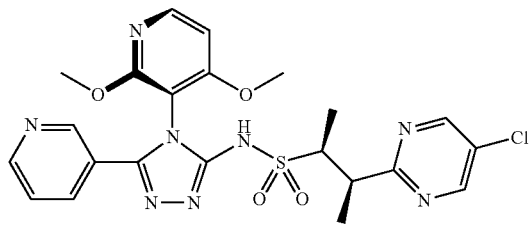<br>(2S,3R,P)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide or (2S,3R,M)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide.<br>$^{1}$H NMR (400 MHz, CD$_{3}$OD) δ 1.31 (d, J = 6.95 Hz, 3 H) 1.35 (d, J = 7.05 Hz, 3 H) 3.66-3.74 (m, 1 H) 3.74-3.83 (m, 1 H) 3.87 (s, 3 H) 3.88 (s, 3 H) 6.92 (d, J = 6.06 Hz, 1 H) 7.63 (ddd, J = 8.10, 5.17, 0.67 Hz, 1 H) 8.02 (dt, J = 8.11. 1.85 Hz, 1 H) 8.23 (d, J = 6.01 Hz, 1 H) 8.69-8.74 (m, 4 H). LCMS-ESI (POS.) m/z: 531.1 (M + H)$^{+}$ |
| 718.0 | Chiral separation of Example 713.0 was performed. The title compound was the later peak (vs. its opposite atropisomer) peak on AD column. SFC condition: Chiralpak AD-H, 45% isopropanol/CO$_{2}$, with 0.2% DEA. | 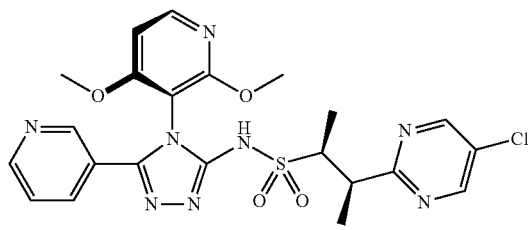<br>OR |

| Example Reagents | Structure, Name and Data |
|---|---|
| | 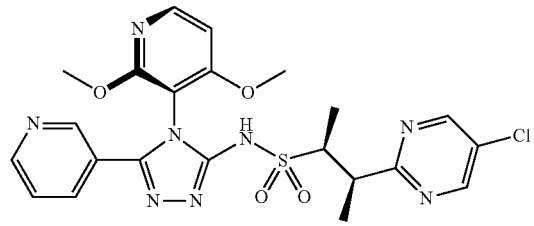<br><br>(2S,3R,P)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide or (2S,3R,M)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide.<br>$^1$H NMR (400 MHz, CD$_3$OD) δ 1.31 (d, J = 6.95 Hz, 3 H) 1.34 (d, J = 7.05 Hz, 3 H) 3.67-3.74 (m, 1 H) 3.74-3.82 (m, 1 H) 3.86 (s, 3 H) 3.88 (s, 3 H) 6.91 (d, J = 6.06 Hz, 1 H) 7.47 (ddd, J = 8.03, 5.00, 0.80 Hz, 1 H) 7.86 (dt, J = 8.07, 1.92 Hz, 1 H) 8.22 (d, J = 6.01 Hz, 1 H) 8.62 (td, J = 5.25, 1.53 Hz, 2 H) 8.72 (s, 2 H). LCMS-ESI (POS.) m/z: 531.0 (M + H)$^+$. |

Example 719.0: Preparation of (1R,2S)-1-cyclobutyl-N-(4-(2,6-(trimethoxyphenyl)-5-(5-methylpyridin-3-yl)-4H-1,2,4-triazol-3-yl)-1-methoxypropane-2-sulfonamide and (1S,2R)-1-cyclobutyl-N-(4-(2,6-(trimethoxyphenyl)-5-(5-methylpyridin-3-yl)-4H-1,2,4-triazol-3-yl)-1-methoxypropane-2-sulfonamide or (1S,2S)-1-cyclobutyl-N-(4-(2,6-dimethoxyphenyl)-5-(5-methylpyridin-3-yl)-4H-1,2,4-triazol-3-yl)-1-methoxypropane-2-sulfonamide and (1R,2R)-1-cyclobutyl-N-(4-(2,6-dimethoxyphenyl)-5-(5-methylpyridin-3-yl)-4H-1,2,4-triazol-3-yl)-1-methoxypropane-2-sulfonamide 719.0

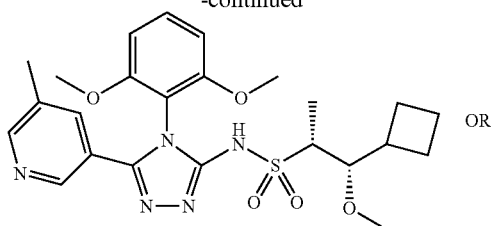 OR

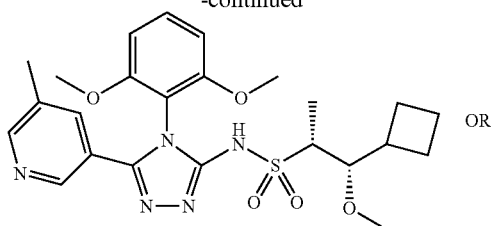 AND

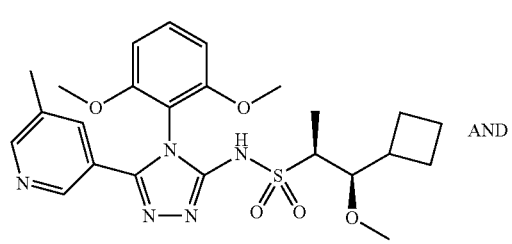 AND

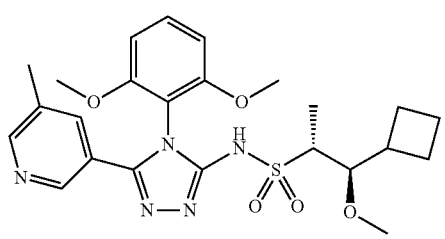

(1R,2S)-1-cyclobutyl-N-(4-(2,6-dimethoxyphenyl)-5-(5-methylpyridin-3-yl)-4H-1,2,4-triazol-3-yl)-1-methoxypropane-2-sulfonamide and (1S,2R)-1-cyclobutyl-N-(4-(2,6-dimethoxyphenyl)-5-(5-methylpyridin-3-yl)-4H-1,2,4-triazol-3-yl)-1-methoxypropane-2-sulfonamide or (1S,2S)-1-cyclobutyl-N-(4-(2,6-dimethoxyphenyl)-5-(5-methylpyridin-3-yl)-4H-1,2,4-triazol-3-yl)-1-methoxypropane-2-sulfonamide and (1R,2R)-1-cyclobutyl-N-(4-(2,6-dimethoxyphenyl)-5-(5-methylpyridin-3-yl)-4H-1,2,4-triazol-3-yl)-1-methoxypropane-2-sulfonamide, Example 719.0

719.0 was prepared following the procedure described in Example A using 1.0, 3.11 and 24.0. This delivered Example 719.0. $^1$H NMR (CDCl$_3$) δ 11.02 (br. s., 1H), 8.44 (d, J=1.46 Hz, 1H), 8.33 (d, J=1.90 Hz, 1H), 7.64 (d, J=0.73 Hz, 1H), 7.38 (t, J=8.55 Hz, 1H), 6.60 (d, J=8.48 Hz, 2H), 3.84 (dd, J=1.53, 8.84 Hz, 1H), 3.75 (s, 3H), 3.75 (s, 3H), 3.33 (s, 3H), 2.83-2.95 (m, 1H), 2.39 (d, J=7.89 Hz, 1H), 2.30 (s, 3H), 2.04-2.16 (m, 1H), 1.70-2.00 (m, 5H), 1.27 (d, J=7.02 Hz, 3H). LCMS-ESI (POS.) m/z: 502.0 (M+H)$^+$.

Example 720.0: Preparation of (1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and or (1R,2S)-1-(3, 3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide

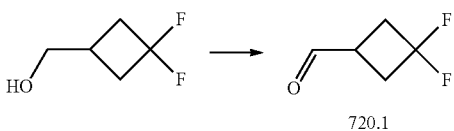 [SMILES: OCC1CC(F)(F)C1 ; O=CC1CC(F)(F)C1]

3,3-Difluorocyclobutanecarbaldehyde, Example 720.1

A 250-mL round-bottomed flask was charged with (3,3-difluorocyclobutyl)methanol (0.513 g, 4.20 mmol, Advanced Chemblocks Inc.) and DCM (20 mL). Dess-Martin periodinate (1.83 g, 4.32 mmol) was added in portions, and the mixture was stirred at RT. After 4 h, the mixture was washed with water (3×20 mL) and passed through a Chem Elute extraction cartridge eluting with DCM (2×10 mL). The organic layer was concentrated carefully to afford a clear liquid as the product (0.54 g). This material was used in the subsequent reaction without purification. $^1$H NMR (300 MHz, CDCl$_3$) δ 9.79 (t, J=1.7 Hz, 1H), 3.13-2.96 (m, 1H), 2.94-2.70 (m, 4H).

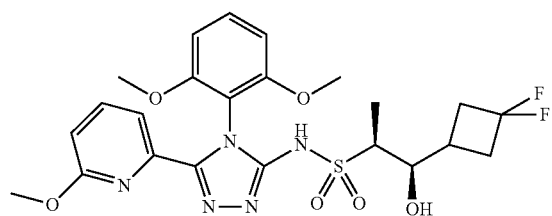 AND 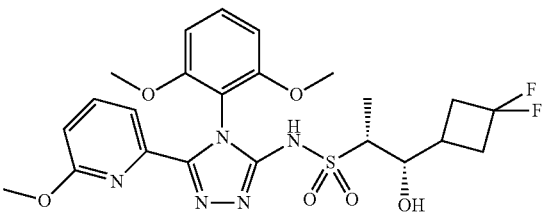

AND AND

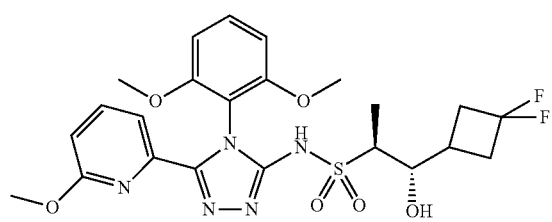 AND 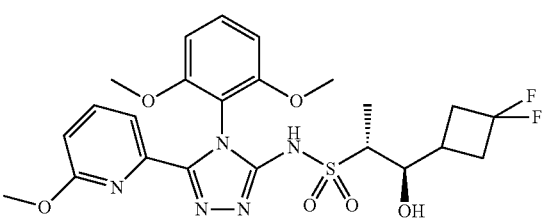

(1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and (1S,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and and (1R,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and (1R,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide, Example 720.2

Example 720.2 was prepared following the procedure described in Example 264.0 using 5.0 and 720.1. This delivered Example 720.2. LCMS-ESI (POS.) m/z: 539.9 (M+H)$^+$.

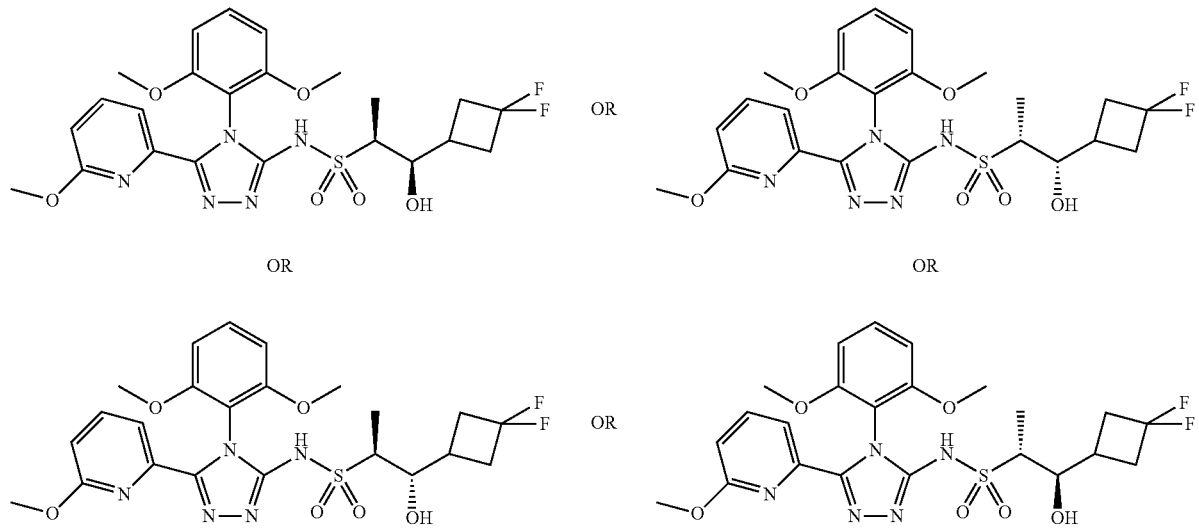

(1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide, Example 720.0

The title compound 720.0 was the first isomer to elute on subjecting 720.2 to the following SFC conditions: AD-H (21×150 mm) column, 20% MeOH with 20 mM NH$_3$/CO$_2$, 100 bar, 70 mL/min, wavelength=220 nm. $^1$H NMR (300 MHz, CD$_3$OD) δ 7.66-7.75 (m, 1H), 7.57-7.63 (m, 1H), 7.41 (t, J=8.48 Hz, 1H), 6.69-6.81 (In, 3H), 4.02-4.10 (m, 1H), 3.74 (s, 3H), 3.72 (s, 3H), 3.17 (s, 3H), 2.90-3.02 (m, 1H), 2.37-2.64 (m, 3H), 2.17-2.35 (m, 2H), 1.27 (d, J=7.02 Hz, 3H). LCMS-ESI (POS.) m/z: 539.9 (M+H)$^+$.

Example 721.0: Preparation of (1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide 721.0

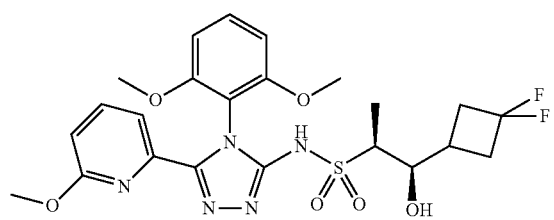 OR 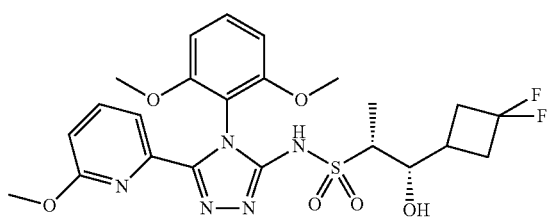

OR OR

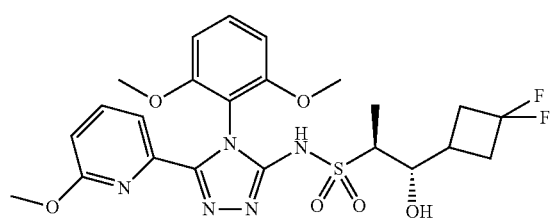 OR 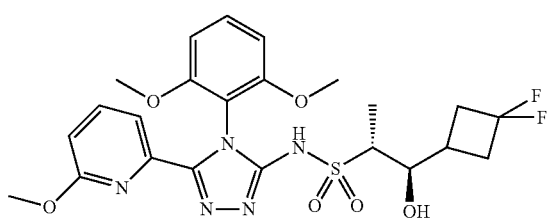

(1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide, Example 721.0

721.0 was prepared from 720.2 by the following two subsequent SFC purifications: A mixture of second and third eluting peaks was obtained by the first purification of 720.2 described in 720.0. The mixture of the peaks was further purified by the second SFC purification: OZ-H (21×150 mm) column, 25% MeOH with 20 mM $NH_3/CO_2$, 100 bar, 70 mL/min, wavelength=220 nm. 721.0 was the second eluting peak of the second purification. $^1$H NMR (300 MHz, $CD_3OD$) δ 7.66-7.75 (m, 1H), 7.54-7.63 (m, 1H), 7.40 (t, J=8.48 Hz, 1H), 6.66-6.81 (m, 3H), 3.85-3.92 (m, 1H), 3.73 (s, 3H), 3.72 (s, 3H), 3.17 (s, 4H), 2.30-2.61 (m, 5H), 1.24 (d, J=7.16 Hz, 3H). LCMS-ESI (POS.) m/z: 539.9 (M+H)$^+$.

Example 722.0: Preparation of (1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide 722.0

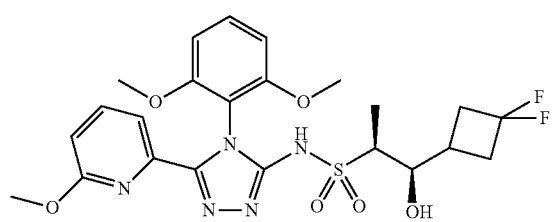 OR 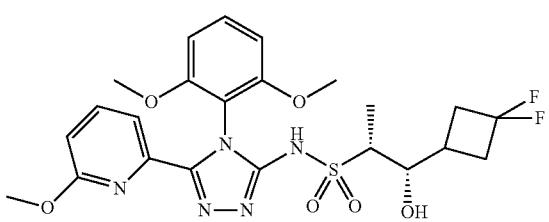

OR                                OR

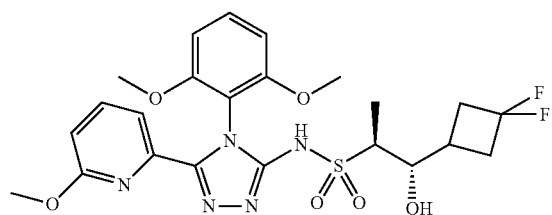 OR 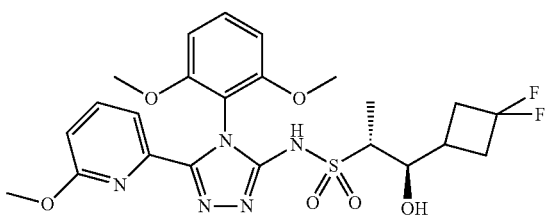

(1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide, Example 722.0

Example 722.0 is the enantiomer of 720.0. 722.0 was the last isomer to elute on subjecting 720.2 to the SFC condition described in 720.0. $^1$H NMR (300 MHz, CD$_3$OD) δ 7.67-7.75 (m, 1H), 7.57-7.63 (m, 1H), 7.41 (t, J=8.48 Hz, 1H), 6.70-6.80 (In, 3H), 4.03-4.09 (m, 1H), 3.74 (s, 3H), 3.72 (s, 3H), 3.17 (s, 3H), 2.90-3.02 (m, 1H), 2.49 (dt, J=6.36, 12.61 Hz, 3H), 2.16-2.33 (m, 2H), 1.27 (d, J=7.02 Hz, 3H). LCMS-ESI (POS.) m/z: 539.9 (M+H)$^+$.

Example 723.0: Preparation of (1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-(trimethoxyphenyl)-5-(6-methoxypyridin-2-yl)-4H-1,2,4-triazol-3-yl)-1-hydroxypropane-2-sulfonamide 723.0

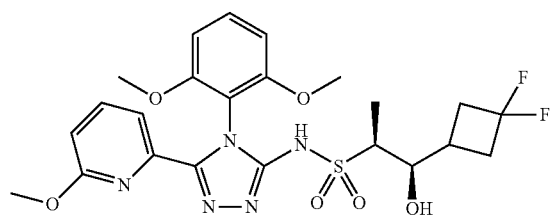 OR 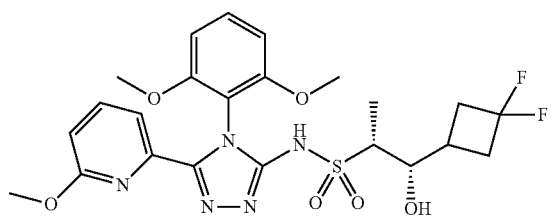

OR OR

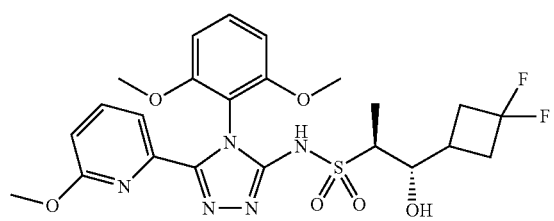 OR 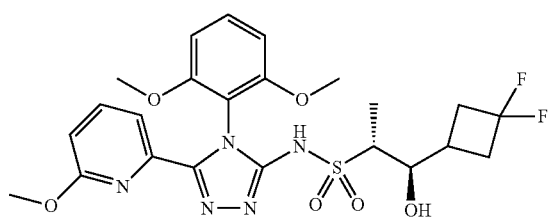

(1S,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1S,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide and or (1R,2S)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide or (1R,2R)-1-(3,3-difluorocyclobutyl)-N-(4-(2,6-dimethoxyphenyl)-5-(6-methoxypyridin-2-yl)-4H-1,2,4-triazol-3-yl)-1-hydroxypropane-2-sulfonamide, Example 723.0

723.0 was prepared from 720.2 by the following two subsequent SFC purifications: A mixture of second and third eluting peaks was obtained by the first purification of 720.2 described in 720.0. The mixture of the peaks was further purified by the second SFC purification: OZ-H (21×150 mm) column, 25% MeOH with 20 mM $NH_3/CO_2$, 100 bar, 70 mL/min, wavelength=220 nm. 723.0 was the first eluting peak of the second purification. $^1$H NMR (300 MHz, $CD_3OD$) δ 7.64-7.73 (m, 1H), 7.56-7.62 (m, 1H), 7.39 (t, J=8.48 Hz, 1H), 6.67-6.80 (m, 3H), 3.85-3.92 (m, 1H), 3.73 (s, 3H), 3.72 (s, 3H), 3.17 (s, 4H), 2.30-2.64 (m, 5H), 1.25 (d, J=7.02 Hz, 3H). LCMS-ESI (POS.) m/z: 540.0 (M+H)$^+$.

Example 724.0: Preparation of (1R,2S)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide or (1S,2S)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide

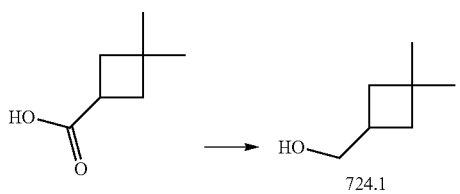

(3,3-Dimethylcyclobutyl)methanol, Example 724.1

To a stirred solution of 3,3-dimethylcyclobutanecarboxylic acid (1.00 g, 7.80 mmol, Parkway Scientific) in THF (30 mL), was added LAH (2.0 M in THF, 4.3 mL, 8.60 mmol) dropwise at 0° C. over 10 min. The mixture was stirred and slowly warmed up to RT as the cold bath expired. After 3 h, the reaction was quenched by adding 0.33 mL water, 0.33 mL of 15% NaOH then 1.0 mL of water sequentially. The mixture was stirred for 15 min and then a part of it was passed through a Chem Elute extraction cartridge eluting with TBME (3×20 mL). The rest was filtered through a paper filter. The organic phase was carefully concentrated to obtain 1.16 g of clear oil. This material was used in the next reaction without purification. $^1$H NMR (300 MHz, CDCl$_3$) δ 3.58 (d, J=6.72 Hz, 2H), 2.34-2.53 (m, 1H), 1.76-1.85 (m, 2H), 1.52 (dd, J=8.77, 11.98 Hz, 2H), 1.16 (s, 3H), 1.06 (s, 1H).

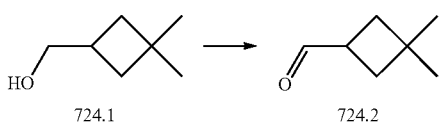

3,3-Dimethylcyclobutanecarbaldehyde, Example 724.2

This compound was prepared as described in the preparation of 720.1 from 724.1. The 724.2 material thus obtained was used in the next reaction without purification.

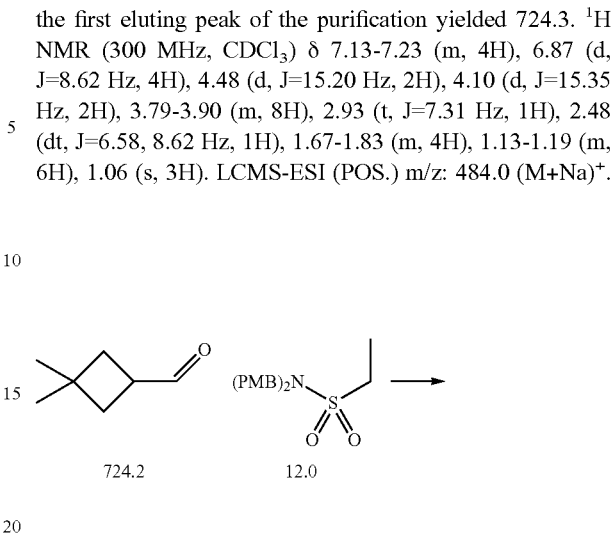

the first eluting peak of the purification yielded 724.3. $^1$H NMR (300 MHz, CDCl$_3$) δ 7.13-7.23 (m, 4H), 6.87 (d, J=8.62 Hz, 4H), 4.48 (d, J=15.20 Hz, 2H), 4.10 (d, J=15.35 Hz, 2H), 3.79-3.90 (m, 8H), 2.93 (t, J=7.31 Hz, 1H), 2.48 (dt, J=6.58, 8.62 Hz, 1H), 1.67-1.83 (m, 4H), 1.13-1.19 (m, 6H), 1.06 (s, 3H). LCMS-ESI (POS.) m/z: 484.0 (M+Na)$^+$.

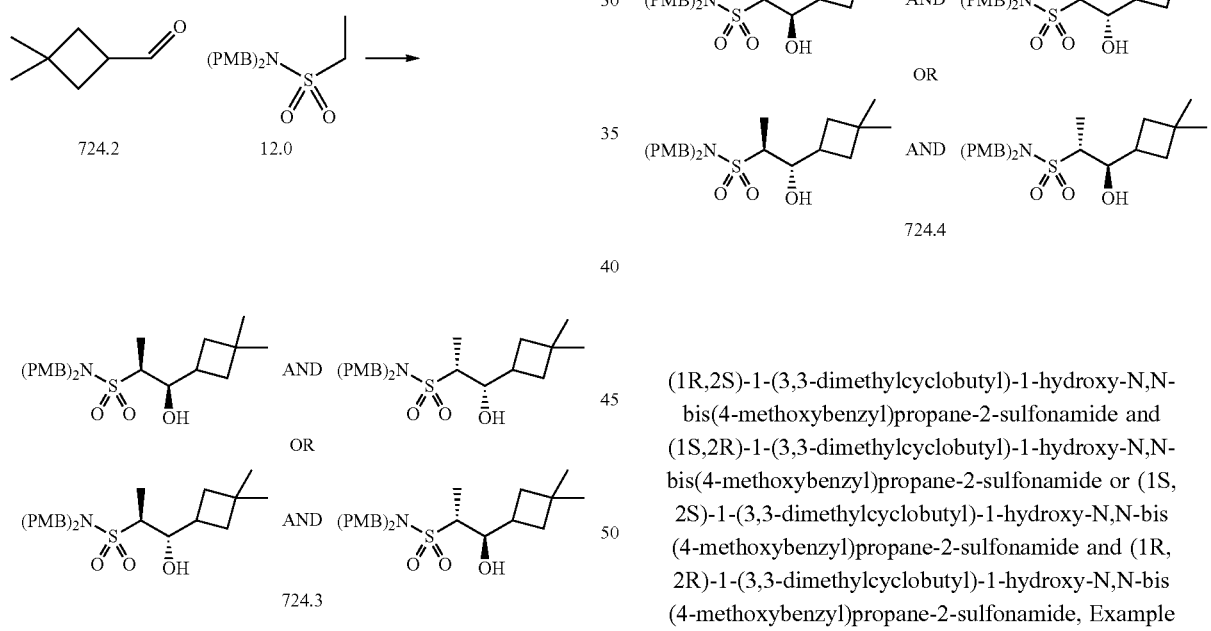

(1R,2S)-1-(3,3-dimethylcyclobutyl)-1-hydroxy-N,N-bis(4-methoxybenzyl)propane-2-sulfonamide and (1S,2R)-1-(3,3-dimethylcyclobutyl)-1-hydroxy-N,N-bis(4-methoxybenzyl)propane-2-sulfonamide or (1S,2S)-1-(3,3-dimethylcyclobutyl)-1-hydroxy-N,N-bis(4-methoxybenzyl)propane-2-sulfonamide and (1R,2R)-1-(3,3-dimethylcyclobutyl)-1-hydroxy-N,N-bis(4-methoxybenzyl)propane-2-sulfonamide, Example 724.4

(1R,2S)-1-(3,3-dimethylcyclobutyl)-1-hydroxy-N,N-bis(4-methoxybenzyl)propane-2-sulfonamide and (1S,2R)-1-(3,3-dimethylcyclobutyl)-1-hydroxy-N,N-bis(4-methoxybenzyl)propane-2-sulfonamide or (1S,2S)-1-(3,3-dimethylcyclobutyl)-1-hydroxy-N,N-bis(4-methoxybenzyl)propane-2-sulfonamide and (1R,2R)-1-(3,3-dimethylcyclobutyl)-1-hydroxy-N,N-bis(4-methoxybenzyl)propane-2-sulfonamide, Example 724.3

Example 724.3 was prepared in an analogous fashion to that described in Example 24.01 using Example 724.2, and The second eluting peak from the purification of 724.3 yielded 724.4. $^1$H NMR (300 MHz, CDCl$_3$) δ 7.23 (d, J=8.62 Hz, 4H), 6.89 (d, J=8.77 Hz, 4H), 4.35-4.44 (m, 2H), 4.20-4.30 (m, 2H), 4.05 (d, J=9.35 Hz, 1H), 3.82 (s, 7H), 2.73-2.85 (m, 2H), 2.24 (q, J=8.62 Hz, 1H), 1.87-1.99 (m, 1H), 1.68 (dd, J=8.48, 11.25 Hz, 1H), 1.21 (d, J=7.16 Hz, 3H), 1.13 (s, 3H), 1.05 (s, 3H). LCMS-ESI (POS.) m/z: 484.0 (M+Na)$^+$.

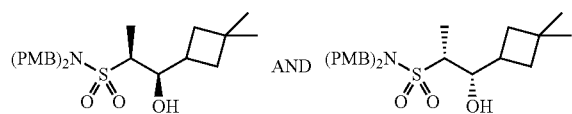

OR

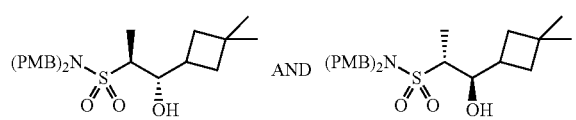

724.3

↓

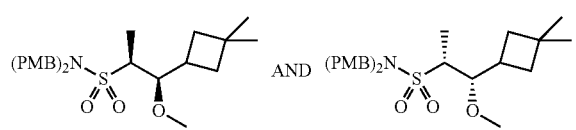

OR

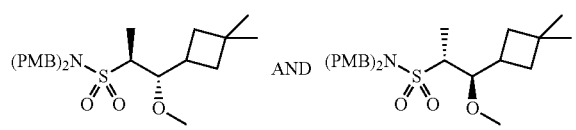

724.5

(1R,2S)-1-(3,3-dimethylcyclobutyl)-1-methoxy-N,
N-bis(4-methoxybenzyl)propane-2-sulfonamide and
(1R,2S)-1-(3,3-dimethylcyclobutyl)-1-methoxy-N,
N-bis(4-methoxybenzyl)propane-2-sulfonamide or
(1R,2S)-1-(3,3-dimethylcyclobutyl)-1-methoxy-N,
N-bis(4-methoxybenzyl)propane-2-sulfonamide and
(1R,2S)-1-(3,3-dimethylcyclobutyl)-1-methoxy-N,
N-bis(4-methoxybenzyl)propane-2-sulfonamide,
Example 724.5

Example 724.5 was prepared in an analogous fashion to that described in Example 24.03 using 724.3. $^1$H NMR (400 MHz, CDCl$_3$) δ 7.19-7.24 (m, 4H), 6.85-6.89 (m, 4H), 4.47 (d, J=15.26 Hz, 2H), 4.12 (d, J=15.26 Hz, 2H), 3.79-3.85 (m, 6H), 3.53-3.57 (m, 1H), 3.31 (s, 3H), 3.14 (dq, J=3.42, 7.07 Hz, 1H), 2.63-2.73 (m, 1H), 1.80-1.87 (m, 1H), 1.77 (d, J=9.00 Hz, 2H), 1.67-1.72 (m, 1H), 1.12-1.18 (m, 6H), 1.03 (s, 3H). LCMS-ESI (POS.) m/z: 498.0 (M+Na)$^+$.

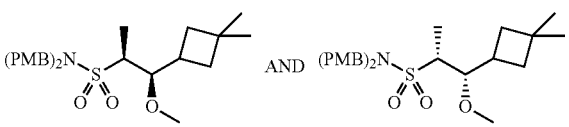

OR

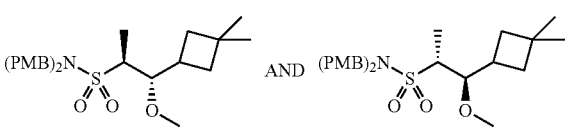

724.5

↓

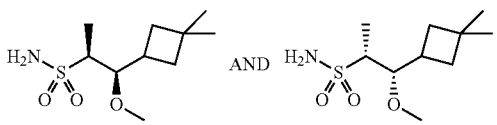

OR

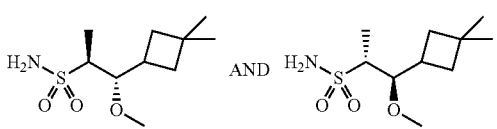

724.6

(1R,2S)-1-(3,3-dimethylcyclobutyl)-1-methoxypropane-2-sulfonamide and (1S,2R)-1-(3,3-dimethylcyclobutyl)-1-methoxypropane-2-sulfonamide or (1S,2S)-1-(3,3-dimethylcyclobutyl)-1-methoxypropane-2-sulfonamide and (1R,2R)-1-(3,3-dimethylcyclobutyl)-1-methoxypropane-2-sulfonamide, Example 724.6

Example 724.6 was prepared in an analogous fashion to that described in Example 24.0 using 724.5. $^1$H NMR (300 MHz, CDCl$_3$) δ 4.52-4.87 (m, 2H), 3.51 (s, 3H), 3.36-3.42 (m, 1H), 3.05-3.15 (m, 1H), 2.58-2.80 (m, 1H), 1.65-1.86 (m, 4H), 1.39 (d, J=7.16 Hz, 3H), 1.17 (s, 3H), 1.06 (s, 3H). LCMS-ESI (POS.) m/z: 258.0 (M+Na)$^+$.

724.7

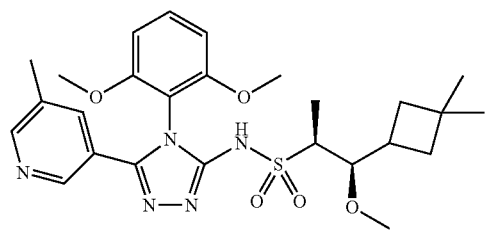 AND 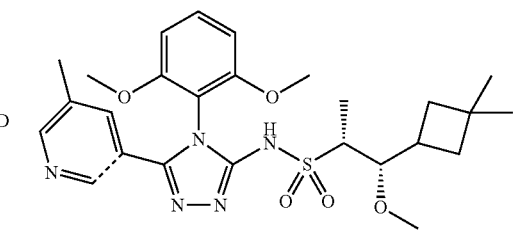

OR

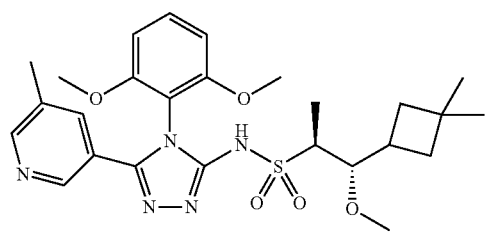 AND 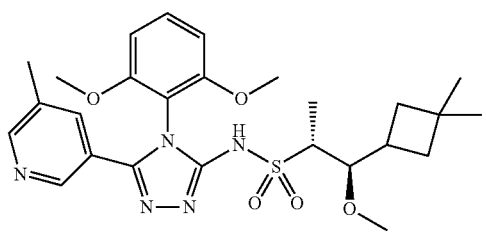

(1R,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide and (1S,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or (1S,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide and (1R,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide, Example 724.7

724.7 was prepared following the procedure described in Example A using 1.0, 3.11 and 724.6. LCMS-ESI (POS.) m/z: 530.0 (M+H)$^+$.

(1R,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or (1S,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or (1S,2S)—N-(4-(2,6-dimethoxyphenyl)-5-(5-methyl-pyridin-3-yl)-4H-1,2,4-triazol-3-yl)-1-(3,3-(trimeth-ylcyclobutyl)-1-methoxypropane-2-sulfonamide or (1R,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide, Example 724.0

The title compound 724.0 was the first isomer to elute on subjecting 724.7 to the following SFC conditions: AD-H (21×250 mm) column, 20-80% iPrOH/CO$_2$, 186 bar, 70 mL/min, wavelength=220 nm. $^1$H NMR (300 MHz, CDCl$_3$)

724.0

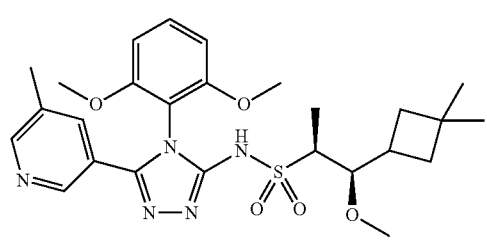 OR 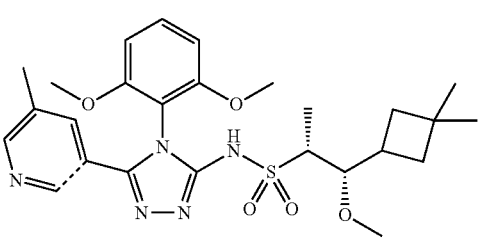

OR OR

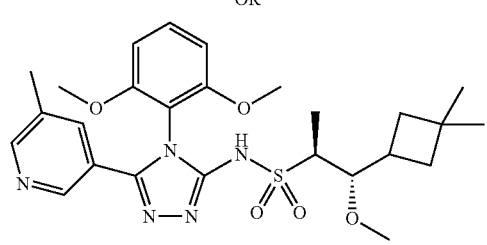 OR 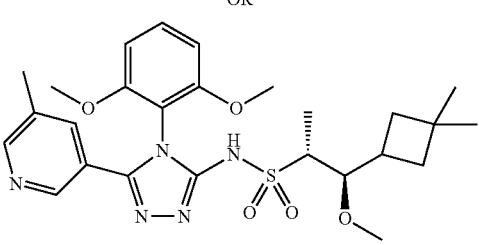

δ 11.01 (br. s., 1H), 8.44 (s, 1H), 8.32 (s, 1H), 7.63 (s, 1H), 7.39 (t, J=8.55 Hz, 1H), 6.61 (t, J=7.75 Hz, 2H), 3.76 (s, 3H), 3.73 (s, 3H), 3.60 (dd, J=3.22, 4.38 Hz, 1H), 3.36 (s, 3H), 3.25-3.35 (m, 1H), 2.62 (dt, J=4.46, 8.81 Hz, 1H), 2.30 (s, 3H), 1.59-1.89 (m, 4H), 1.22 (d, J=7.16 Hz, 3H), 1.07 (s, 3H), 0.99 (s, 3H). LCMS-ESI (POS.) m/z: 530.0 (M+H)⁺.

Example 725.0: Preparation of (1R,2S)—N-(4-(2,6-dimethoxyphenyl)-5-(5-methylpyridin-3-yl)-4H-1,2,4-triazol-3-yl)-1-(3,3-(dimethylcyclobutyl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide or (1S,2S)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide or (1R,2R)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide

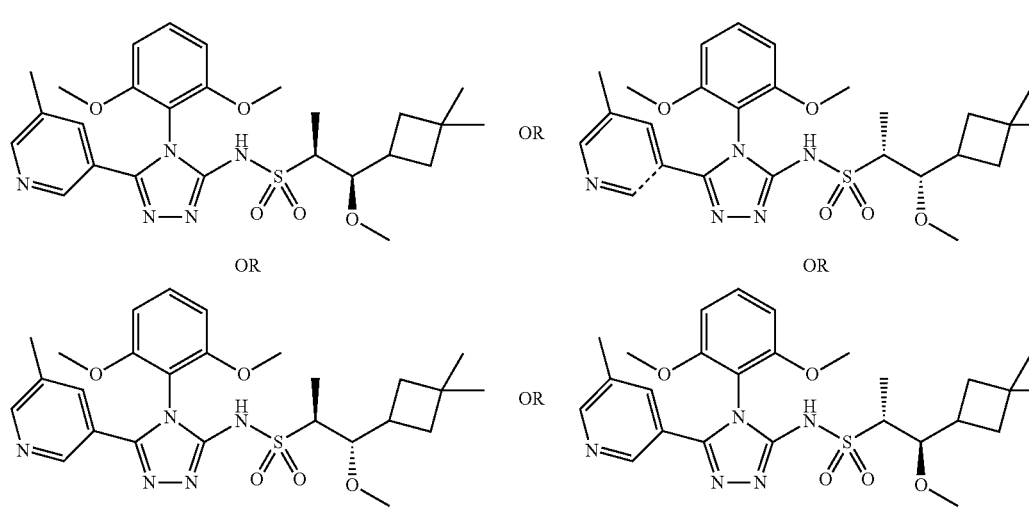

725.0

(1R,2S)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide or (1S,2R)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide or (1S,2S)—N-(4-(2,6-dimethoxyphenyl)-5-(5-methylpyridin-3-yl)-4H-1,2,4-triazol-3-yl)-1-(3,3-(trimethylcyclobutyl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide, Example 725.0

Example 725.0 is the enantiomer of Example 724.0. Example 725.0 was the second isomer to elute on subjecting 724.7 to the SFC conditions described in 724.0. ¹H NMR (300 MHz, CDCl₃) δ 10.99 (br. s., 1H), 8.44 (d, J=1.61 Hz, 1H), 8.32 (d, J=1.75 Hz, 1H), 7.63 (s, 1H), 7.39 (t, J=8.48 Hz, 1H), 6.61 (t, J=7.75 Hz, 2H), 3.76 (s, 3H), 3.73 (s, 3H), 3.56-3.64 (m, 1H), 3.36 (s, 3H), 3.31 (s, 1H), 2.62 (dt, J=4.68, 8.84 Hz, 1H), 2.30 (s, 3H), 1.59-1.90 (m, 4H), 1.22 (d, J=7.16 Hz, 3H), 1.07 (s, 3H), 0.99 (s, 3H). LCMS-ESI (POS.) m/z: 530.0 (M+H)⁺.

Example 726.0: Preparation of (1R,2S)—N-(4-(2,6-dimethoxyphenyl)-5-(5-methylpyridin-3-yl)-4H-1,2,4-triazol-3-yl)-1-(3,3-(dimethylcyclobutyl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide or (1S,2S)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide or (1R,2R)—N-(4-(2,6-dimethoxyphenyl)-5-(5-methylpyridin-3-yl)-4H-1,2,4-triazol-3-yl)-1-(3,3-dimethylcyclobutyl)-1-methoxypropane-2-sulfonamide 726.1

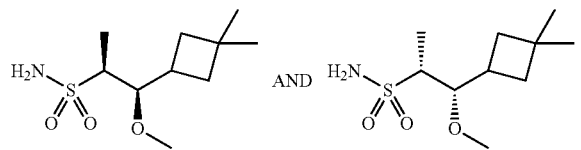

OR

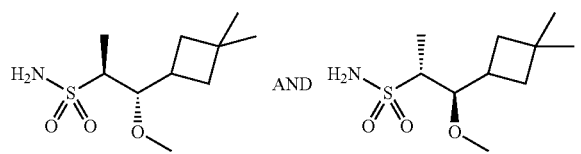

Example 726.1: (1R,2S)-1-(3,3-dimethylcyclobutyl)-1-methoxypropane-2-sulfonamide and (1S,2R)-1-(3,3-dimethylcyclobutyl)-1-methoxypropane-2-sulfonamide or (1S,2S)-1-(3,3-dimethylcyclobutyl)-1-methoxypropane-2-sulfonamide and (1R,2R)-1-(3,3-dimethylcyclobutyl)-1-methoxypropane-2-sulfonamide Example 726.1 was prepared in an analogous fashion to that of 724.6 using 724.4. $^1$H NMR (400 MHz, CDCl$_3$) δ 4.51 (br. s., 2H), 3.93 (d, J=9.39 Hz, 1H), 3.43 (s, 3H), 3.07 (q, J=6.85 Hz, 1H), 2.28-2.43 (m, 1H), 2.05 (t, J=11.54 Hz, 1H), 1.81-1.92 (m, 1H), 1.67-1.78 (m, 1H), 1.45-1.54 (m, 1H), 1.35 (d, J=7.04 Hz, 3H), 1.18 (s, 3H), 1.07 (s, 3H). LCMS-ESI (POS.) m/z: 258.0 (M+Na)$^+$.

726.2

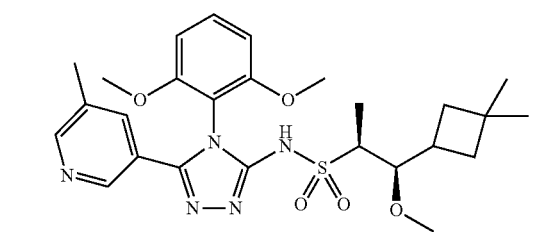 AND 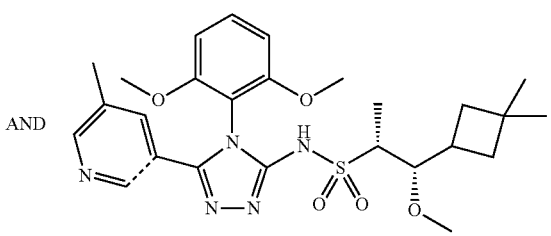

OR

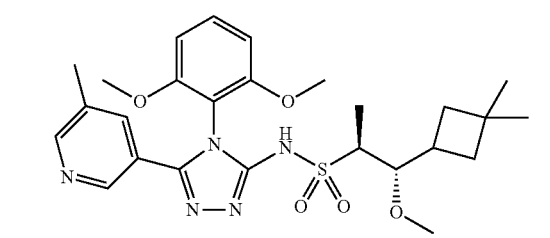 AND 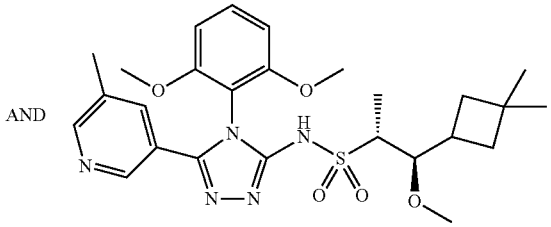

(1R,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide and
(1S,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or
(1S,2S)—N-(4-(2,6-dimethoxyphenyl)-5-(5-methyl-pyridin-3-yl)-4H-1,2,4-triazol-3-yl)-1-(3,3-(trimeth-ylcyclobutyl)-1-methoxypropane-2-sulfonamide and
(1R,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide,
Example 726.2

Example 726.2 was prepared following the procedure described in Example A using 1.0, 3.11 and 726.1. LCMS-ESI (POS.) m/z: 530.0 (M+H)⁺.

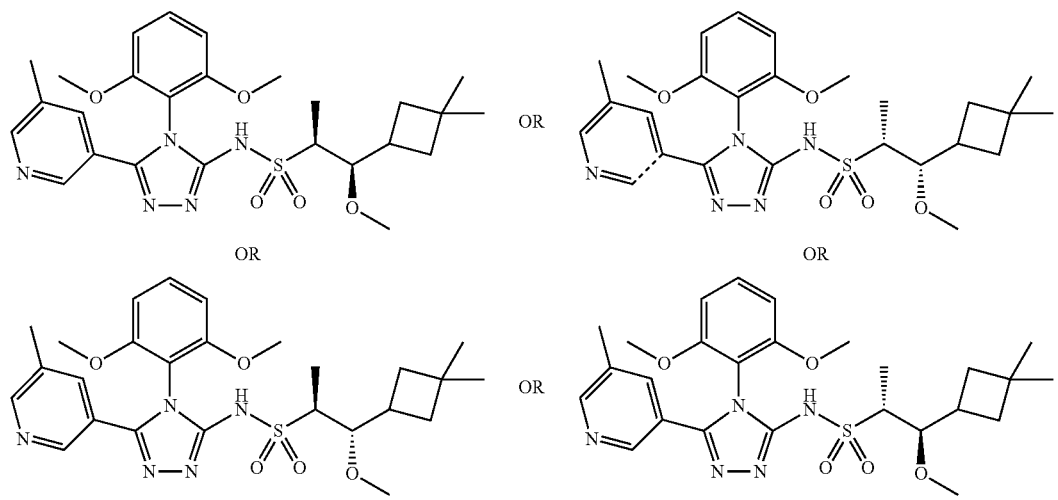

726.0

(1R,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or
(1S,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or
(1S,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or
(1R,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide,
Example 726.0

The title compound 726.0 was the first isomer to elute on subjecting 726.2 to the following SFC conditions: AD-H (21×250 mm) column, 20-80% iPrOH/CO₂, 186 bar, 70 mL/min, wavelength=220 nm. ¹H NMR (300 MHz, CDCl₃) δ 11.03 (br. s., 1H), 8.44 (d, J=1.61 Hz, 1H), 8.33 (d, J=1.75 Hz, 1H), 7.63 (s, 1H), 7.38 (t, J=8.48 Hz, 1H), 6.60 (d, J=8.62 Hz, 2H), 3.83 (dd, J=1.32, 8.92 Hz, 1H), 3.75 (s, 3H), 3.74 (s, 3H), 3.31 (s, 3H), 2.83-2.95 (m, 1H), 2.30 (m, 4H), 1.85-1.97 (m, 1H), 1.59-1.77 (m, 2H), 1.46-1.56 (m, 1H), 1.27 (d, J=7.02 Hz, 3H), 1.12 (s, 3H), 1.04 (s, 3H). LCMS-ESI (POS.) m/z: 530.0 (M+H)⁺.

Example 727.0: Preparation of (1R,2S)—N-(4-(2,6-dimethoxyphenyl)-5-(5-methylpyridin-3-yl)-4H-1,2,4-triazol-3-yl)-1-(3,3-(dimethylcyclobutyl)-1-methoxypropane-2-sulfonamide or (1S,2R)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide or (1S,2S)—N-(4-(2,6-(trimethoxyphenyl)-5-(5-methylpyridin-3-yl)-4H-1,2,4-triazol-3-yl)-1-(3,3-(dimethylcyclobutyl)-1-methoxypropane-2-sulfonamide or (1R,2R)—N-(4-(2,6-(trimethoxyphenyl)-5-(5-methylpyridin-3-yl)-4H-1,2,4-triazol-3-yl)-1-(3,3-dimethylcyclobutyl)-1-methoxypropane-2-sulfonamide

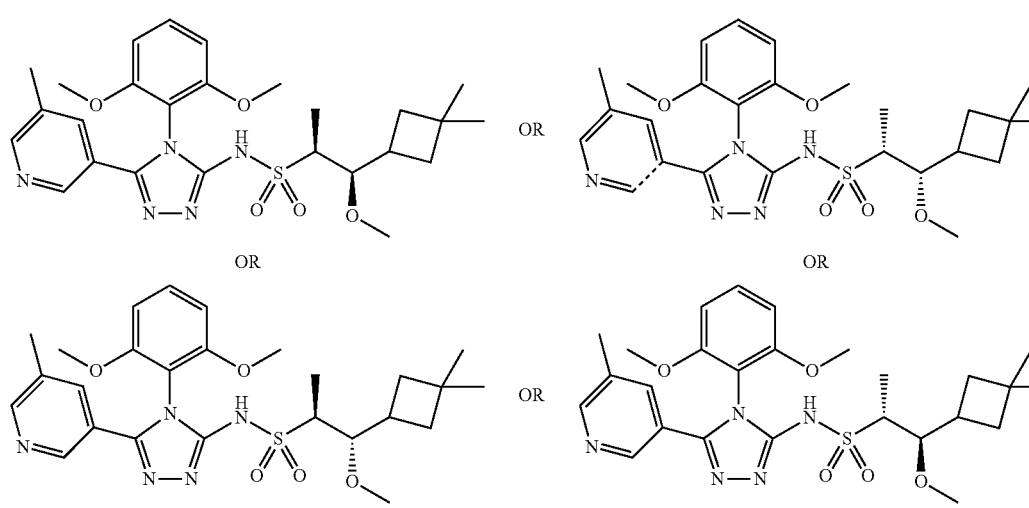

727.0

(1R,2S)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or (1S,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide or (1S,2S)—N-(4-(2,6-dimethoxyphenyl)-5-(5-methyl-pyridin-3-yl)-4H-1,2,4-triazol-3-yl)-1-(3,3-(dimethylcyclobutyl)-1-methoxypropane-2-sulfonamide or (1R,2R)—N-(4-(2,6-dimethoxyphenyl)-5-(5-methyl-pyridin-3-yl)-4H-1,2,4-triazol-3-yl)-1-(3,3-dimethyl-cyclobutyl)-1-methoxypropane-2-sulfonamide, Example 727.0

Example 727.0 is the enantiomer of Example 726.0. Example 727.0 was the second isomer to elute on subjecting 726.2 to the SFC conditions described in 726.0. $^1$H NMR (300 MHz, CDCl$_3$) δ 11.03 (br. s., 1H), 8.44 (d, J=1.46 Hz, 1H), 8.33 (d, J=1.90 Hz, 1H), 7.64 (s, 1H), 7.38 (t, J=8.55 Hz, 1H), 6.60 (d, J=8.62 Hz, 2H), 3.83 (dd, J=1.32, 8.92 Hz, 1H), 3.75 (s, 3H), 3.74 (s, 3H), 3.31 (s, 3H), 2.83-2.93 (m, 1H), 2.30 (m, 4H), 1.91 (ddd, J=3.87, 7.64, 11.14 Hz, 1H), 1.58-1.77 (m, 2H), 1.46-1.56 (m, 1H), 1.27 (d, J=7.16 Hz, 3H), 1.12 (s, 3H), 1.04 (s, 3H). LCMS-ESI (POS.) m/z: 530.0 (M+H)$^+$.

Example 728.0: Preparation of (R)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide or (S)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide

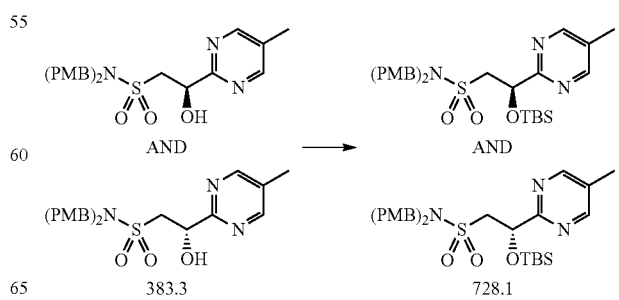

(R)-2-((tert-butyldimethylsilyl)oxy)-N,N-bis(4-methoxybenzyl)-2-(5-methylpyrimidin-2-yl)ethanesulfonamide and (R)-2-((tert-butyldimethylsilyl)oxy)-N,N-bis(4-methoxybenzyl)-2-(5-methylpyrimidin-2-yl)ethanesulfonamide, Example 728.1

A 150-mL round-bottomed flask was charged with 383.2 (0.266 g, 0.58 mmol) and DCM (5 mL). TEA (0.100 mL, 0.72 mmol) was added and the light yellow solution was stirred at 0° C. (1,1-Dimethylethyl)dimethylsilyl trifluoromethanesulfonate (0.150 mL, 0.653 mmol) was added dropwise over 1 min and the mixture was stirred at 0° C. for 10 min. The cold bath was removed and the mixture was stirred at RT. After 3 hrs, TEA (0.20 mL) was added followed by dropwise addition of (1,1-dimethylethyl)dimethylsilyl trifluoromethanesulfonate (0.15 mL). The mixture was stirred at RT for 14 h. The mixture was then diluted with EtOAc (20 mL) and washed with saturated aqueous sodium chloride (2×20 mL). The organic phase was dried by passing through a Chem Elute extraction cartridge (5 mL) eluting with EtOAc (2×10 mL). The organic material was concentrated and the resulting product was purified by silica gel column chromatography (25 g, eluent: EtOAc in hexanes 0-50%) to afford 728.1 (0.33 g, 98% yield) as a clear oil. $^1$H NMR (300 MHz, CDCl$_3$) δ 8.57 (s, 2H), 7.20 (d, J=8.77 Hz, 4H), 6.85 (d, J=8.62 Hz, 4H), 5.41 (dd, J=5.48, 6.94 Hz, 1H), 4.15-4.30 (m, 4H), 3.81 (s, 6H), 3.69-3.78 (m, 1H), 3.38 (dd, J=5.41, 13.59 Hz, 1H), 2.32 (s, 3H), 0.80-0.89 (m, 9H), 0.12 (s, 3H), −0.06 (s, 3H). LCMS-ESI (POS.) m/z: 572.0 (M+H)$^+$.

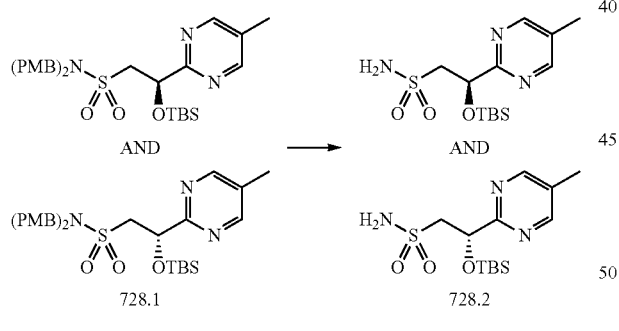

(R)-2-((tert-butyldimethylsilyl)oxy)-2-(5-methylpyrimidin-2-yl)ethanesulfonamide and (S)-2-((tert-butyldimethylsilyl)oxy)-2-(5-methylpyrimidin-2-yl)ethanesulfonamide, Example 728.2

728.2 was prepared in an analogous fashion to that described in Example 15.0 using 728.1. $^1$H NMR (300 MHz, CDCl$_3$) δ 8.59 (s, 2H), 5.41-5.49 (m, 1H), 4.97-5.16 (m, 2H), 3.71-3.82 (m, 1H), 3.58-3.68 (m, 1H), 2.34 (s, 3H), 0.86 (d, J=1.32 Hz, 9H), 0.09 (s, 3H), −0.06 (s, 3H). LCMS-ESI (POS.) m/z: 332.0 (M+H)$^+$.

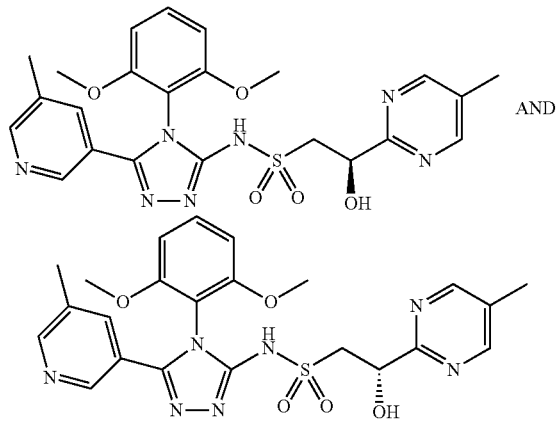

(R)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide and (S)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide, Example 728.3

Example 728.3 was prepared following the procedure described in Example A using 1.0, 3.11 and 728.2. This delivered Example 728.3. LCMS-ESI (POS.) m/z: 512.0 (M+H)$^+$.

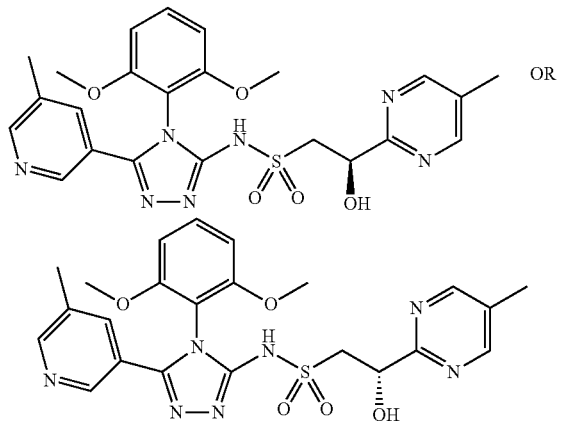

(R)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide or (S)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide, Example 728.0

The title compound 728.0 was the first isomer to elute on subjecting 728.3 to the following SFC conditions: OZ-H (21×250 mm) column, 45% MeOH/CO$_2$, 100 bar, 60 mL/min, wavelength=220 nm. $^1$H NMR (300 MHz, CDCl$_3$)

δ 11.14 (br. s., 1H), 8.58 (s, 2H), 8.45 (d, J=1.61 Hz, 1H), 8.34 (d, J=1.90 Hz, 1H), 7.64 (s, 1H), 7.39 (t, J=8.48 Hz, 1H), 6.61 (dd, J=1.10, 8.55 Hz, 2H), 5.35 (d, J=9.21 Hz, 1H), 4.37 (br. s., 1H), 3.71-3.81 (m, 7H), 3.51 (dd, J=9.28, 14.25 Hz, 1H), 2.32 (d, J=6.58 Hz, 6H). LCMS-ESI (POS.) m/z: 512.0 (M+H)⁺.

Example 729.0: Preparation of (R)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide or (S)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide Example 730.0: Preparation of (1R,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2R)—N-(4-(4,6-(trimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1R,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide 729.0

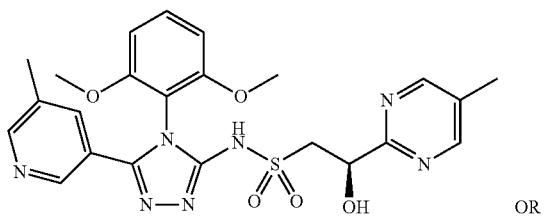

730.1

OR

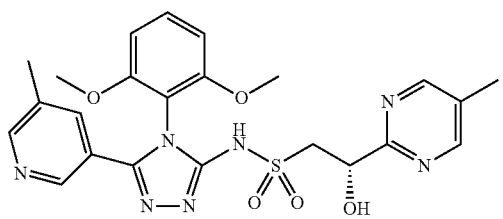

(R)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide or (S)—N-(4-(2,6-dimethoxyphenyl)-5-(5-methylpyridin-3-yl)-4H-1,2,4-triazol-3-yl)-2-hydroxy-2-(5-methylpyrimidin-2-yl)ethanesulfonamide, Example 729.0

Example 729.0 is the enantiomer of 728.0. Example 729.0 was the second isomer to elute on subjecting 728.3 to the SFC conditions described in 728.0. ¹H NMR (300 MHz, CDCl₃) δ 11.14 (br. s., 1H), 8.58 (s, 2H), 8.45 (d, J=1.61 Hz, 1H), 8.34 (d, J=1.90 Hz, 1H), 7.64 (s, 1H), 7.39 (t, J=8.48 Hz, 1H), 6.61 (dd, J=1.10, 8.55 Hz, 2H), 5.35 (d, J=9.21 Hz, 1H), 4.37 (br. s., 1H), 3.71-3.81 (m, 7H), 3.51 (dd, J=9.28, 14.25 Hz, 1H), 2.32 (d, J=6.58 Hz, 6H). LCMS-ESI (POS.) m/z: 512.0 (M+H)⁺.

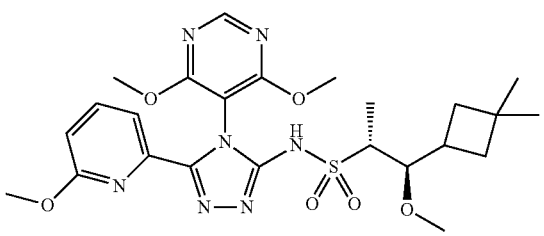

(1R,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide and (1S,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide and (1R,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide, Example 730.1

Example 730.1 was prepared following the procedure described in Example A using 1.1, 3.11 and 726.1. This delivered Example 730.1. LCMS-ESI (POS.) m/z: 548.0 (M+H)+.

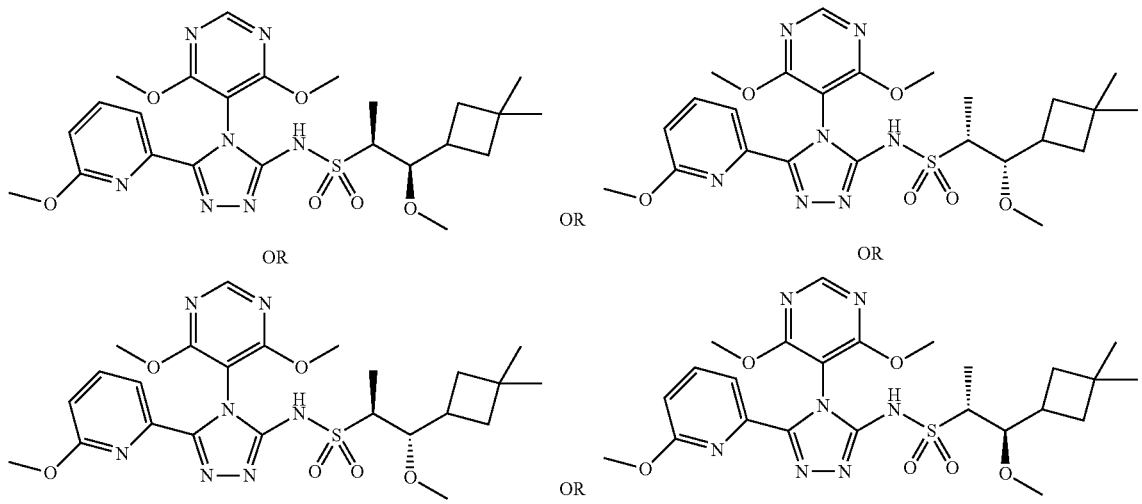

730.0

(1R,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1R,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide, Example 730.0

The title compound 730.0 was the first isomer to elute on subjecting 730.1 to the following SFC conditions: IE (21× 150 mm) column, 30% MeOH with 20 mM $NH_3/CO_2$, 70 mL/min, wavelength=220 nm. $^1$H NMR (300 MHz, CDCl$_3$) δ 10.99 (br. s., 1H), 8.44 (s, 1H), 7.61-7.69 (m, 2H), 6.71-6.80 (m, 1H), 3.93 (s, 6H), 3.85 (dd, J=1.46, 8.92 Hz, 1H), 3.34 (s, 3H), 3.24 (s, 3H), 2.91 (dd, J=1.53, 7.09 Hz, 1H), 2.21-2.39 (m, 1H), 1.87-1.99 (m, 1H), 1.70-1.80 (m, 1H), 1.62-1.69 (m, 1H), 1.46-1.56 (m, 1H), 1.27 (d, J=7.02 Hz, 3H), 1.13 (s, 3H), 1.05 (s, 3H). LCMS-ESI (POS.) m/z: 548.0 (M+H)+.

Example 731.0: Preparation of (1R,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1R,2R)—N-(4-(4,6-dimethoxypyrimidin-5-yl)-5-(6-methoxypyridin-2-yl)-4H-1,2,4-triazol-3-yl)-1-(3,3-(trimethylcyclobutyl)-1-methoxypropane-2-sulfonamide Example 732.0: Preparation of (2S,3R)—N-(4-(3,5-dibromo-2,6-dimethoxyphenyl)-5-(5-methylpyridin-3-yl)-4H-1,2,4-triazol-3-yl)-3-(5-methylpyrimidin-2-yl)butane-2-sulfonamide

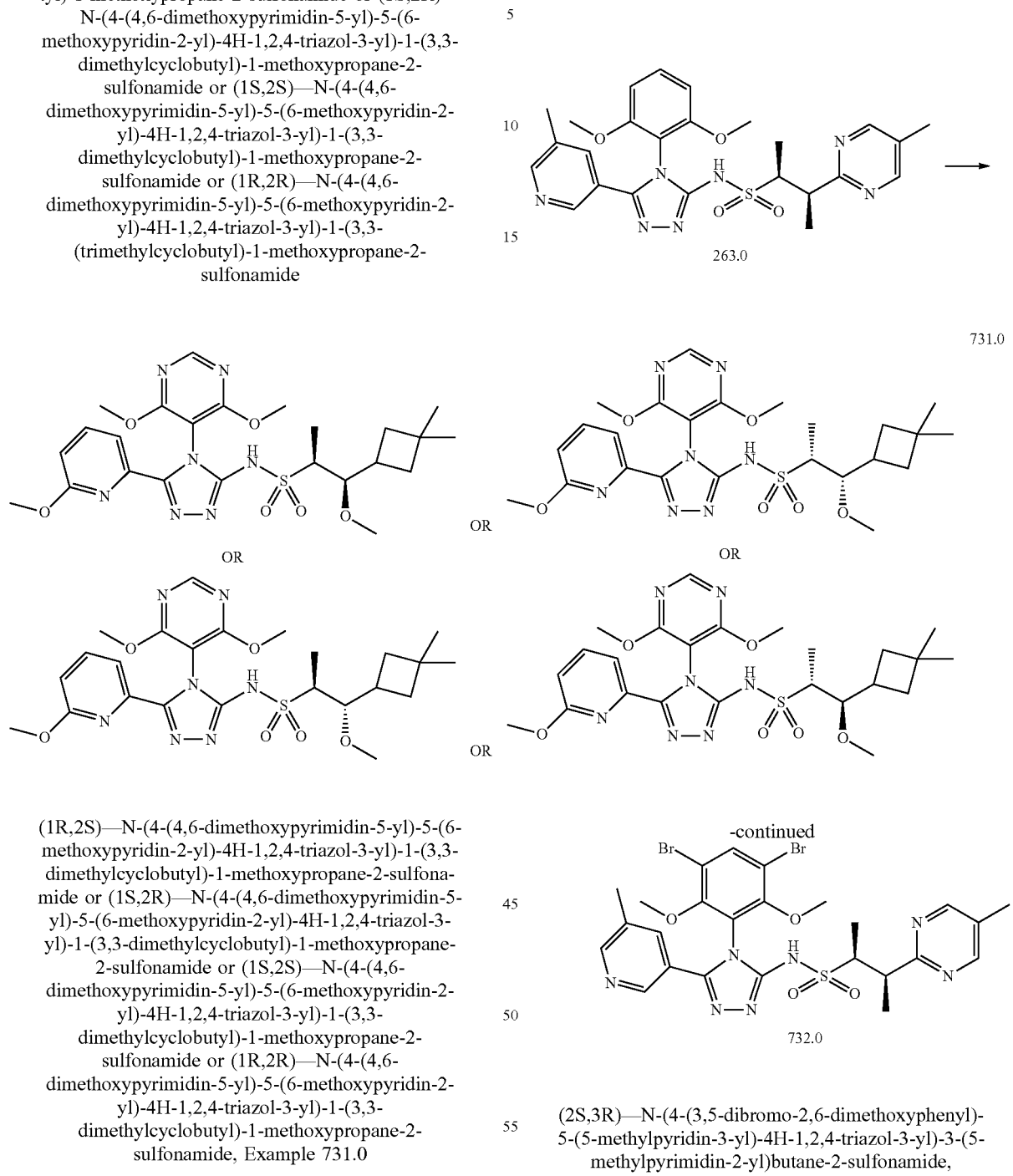

(1R,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1S,2S)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide or (1R,2R)—N-(4-(4,6-dimethoxypyrimidin-5-yl)-5-(6-methoxypyridin-2-yl)-4H-1,2,4-triazol-3-yl)-1-(3,3-dimethylcyclobutyl)-1-methoxypropane-2-sulfonamide, Example 731.0

Example 731.0 was the second isomer to elute on subjecting 730.1 to the SFC conditions described in 730.0. $^1$H NMR (300 MHz, CDCl$_3$) δ 10.99 (br. s., 1H), 8.44 (s, 1H), 7.61-7.71 (m, 2H), 6.72-6.81 (m, 1H), 3.93 (s, 6H), 3.85 (dd, J=1.32, 8.92 Hz, 1H), 3.34 (s, 3H), 3.24 (s, 3H), 2.86-2.97 (m, 1H), 2.22-2.40 (m, 1H), 1.87-1.98 (in. 1H), 1.63-1.79 (m, 2H), 1.54 (d, J=9.79 Hz, 1H), 1.27 (d, J=7.02 Hz, 3H), 1.13 (s, 3H), 1.05 (s, 3H). LCMS-ESI (POS.) m/z: 548.0 (M+H)$^+$.

(2S,3R)—N-(4-(3,5-dibromo-2,6-dimethoxyphenyl)-5-(5-methylpyridin-3-yl)-4H-1,2,4-triazol-3-yl)-3-(5-methylpyrimidin-2-yl)butane-2-sulfonamide, Example 732.0

To a vial containing NBS (436 mg, 2.45 mmol) in DMF (1 mL) at <5° C. was added a heterogeneous solution of (2S,3R)—N-(4-(2,6-dimethoxyphenyl)-5-(5-methylpyridin-3-yl)-4H-1,2,4-triazol-3-yl)-3-(5-methylpyrimidin-2-yl)butane-2-sulfonamide (Example 263.0) (300 mg, 0.57 mmol) in DMF (1 mL). Upon complete addition, the mixture was allowed to warm to 23° C. and monitored with LCMS-ESI. After 19 hours, the mixture was cooled in an ice bath. After 20 minutes, additional NBS (421 mg, 2.37 mmol) was added in portions to try and push the reaction to completion. Upon complete addition of NBS, the mixture was allowed to warm to 23° C. and monitored with LCMS-ESI. After 91 total hours, the mixture was diluted with EtOAc and was then washed three times with aqueous, saturated sodium chloride solution. The aqueous washes were pooled and then extracted twice with EtOAc. The combined organic layers were dried over anhydrous sodium sulfate and then filtered and concentrated under reduced pressure. The residue was loaded onto a silica gel column (0-60% 3:1 EtOAc: EtOH in heptane). Fractions containing product were combined and then concentrated under reduced pressure to afford (2S,3R)—N-(4-(3,5-dibromo-2,6-dimethoxyphenyl)-5-(5-methylpyridin-3-yl)-4H-1,2,4-triazol-3-yl)-3-(5-methylpyrimidin-2-yl)butane-2-sulfonamide (Example 732.0) as a white solid (199 mg, 0.29 mmol, 51% yield). $^1$H NMR (500 MHz, DMSO-$d_6$) δ 13.80 (s, 1H), 8.57 (s, 2H), 8.52 (s, 1H), 8.30 (s, 1H), 8.23 (d, J=1.5 Hz, 1H), 7.71 (s, 1H), 3.72 (s, 3H), 3.72 (s, 3H), 3.70-3.62 (m, 2H), 2.28 (s, 3H), 2.23 (s, 3H), 1.24 (d, J=6.8 Hz, 3H), 1.16 (d, J=6.8 Hz, 3H). LCMS-ESI (POS.) m/z: 682.1 (M+H)$^+$.

Example 733.0: Preparation of (2S,3R)—N-(5-(5-bromopyridin-3-yl)-4-(2,6-dimethoxyphenyl)-4H-1,2,4-triazol-3-yl)-3-(5-methylpyrimidin-2-yl)butane-2-sulfonamide

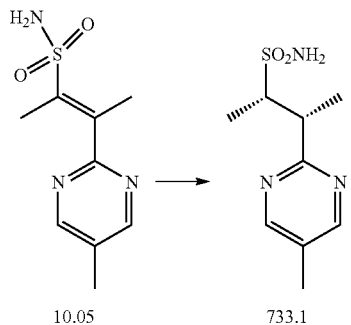

10.05     733.1

(2S,3R)-3-(5-methylpyrimidin-2-yl)butane-2-sulfonamide, Example 733.1

A 900 mL pressure reactor was charged under nitrogen flow with (E)-3-(5-methylpyrimidin-2-yl)but-2-ene-2-sulfonamide, Example 10.05 (40.00 g, 0.1760 mol, 1 equiv), zinc trifluoromethane sulfonate (12.79 g, 0.0352 mol, 0.2 equiv, Aldrich), bis(1,5-cyclooctadiene)rhodium(I) tetrafluoroborate (1.43 g, 0.00352 mol, 0.02 equiv, Stream Chemicals, Inc.), (S)-1-[(R)-2-(di-1-naphthylphosphino)ferrocenyl]-ethyl-di-tert-butylphosphine (2.60 g, 0.00405 mol, 0.023 equiv, Solvias) and MeOH (520 mL). The mixture was purged with nitrogen and then with hydrogen, and the mixture was stirred under 3-4 bars of hydrogen for 20 hours. The reaction was monitored by HPLC and showed a complete conversion. The reactor was purged with nitrogen, and the resulting suspension was concentrated at 35° C. under industrial vacuum to give an orange solid. The material thus obtained was mixed with EtOH (742 mL), and the resulting suspension was stirred at 20-25° C. for 40 minutes. The solid was filtered, washed with EtOH (2×97 mL) and dried at 40° C. under vacuum to give the title compound as a white powder (85.2% yield, 99% ee). $^1$H NMR (400 MHz, DMSO-$d_6$): δ 8.61 (s, 2H), 6.84 (s, 2H), 3.69 (tt, J=12.4, 4.5 Hz, 2H), 2.25 (s, 3H), 1.32 (d, J=6.9 Hz, 3H), 1.20 (d, J=7.0 Hz, 3H). MS (ESI, positive ion) m/z; 230.1 (M+H)$^+$.

The compounds set forth in the following Table were synthesized following the procedure in Example A using the known starting material as described.

TABLE 37

| Example | Reagents | Structure, Name and Data |
|---|---|---|
| 733.0 | (2S,3R)-3-(5-methylpyrimidin-2-yl)butane-2-sulfonamide (Example 733.1), 5-bromonicotinohydrazide (commercially available from Matrix Scientific), 2-isothiocyanato-1,3-dimethoxybenzene (Example 1.0) | (2S,3R)-N-(5-(5-bromopyridin-3-yl)-4-(2,6-dimethoxyphenyl)-4H-1,2,4-triazol-3-yl)-3-(5-methylpyrimidin-2-yl)butane-2-sulfonamide. $^1$H NMR (500 MHz, DMSO-$d_6$) δ 13.51 (br. s., 1H), 8.80 (d, J = 2.0 Hz, 1H), 8.59 (d, J = 0.7 Hz, 2H), 8.43 (d, J = 2.0 Hz, 1H), 7.93 (t, J = 2.0 Hz, 1H), 7.52 (t, J = 8.4 Hz, 1H), 6.84 (dd, J = 3.8, 8.7 Hz, 2H), 3.69 (s, 3H), 3.69 (s, 3H), 3.68-3.65 (m, 1H), 3.63-3.57 (m, 1H), 2.29-2.21 (m, 3H), 1.24 (d, J = 7.1 Hz, 3H), 1.10 (d, J = 6.8 Hz, 3H). Mass Spectrum (pos.) m/z: 588.2 (M + H)$^+$. |

Example 734.0: Preparation of (2S,3R)—N-(5-(5-cyclopropylpyridin-3-yl)-4-(2,6-dimethoxyphenyl)-4H-1,2,4-triazol-3-yl)-3-(5-methylpyrimidin-2-yl)butane-2-sulfonamide

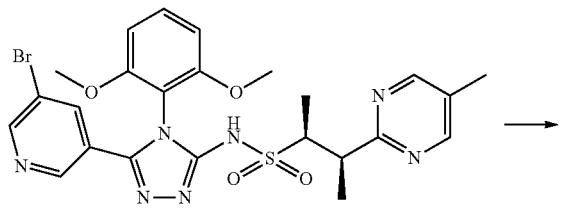

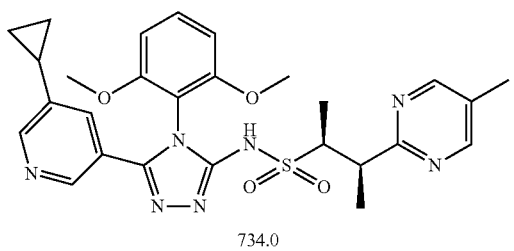

(2S,3R)—N-(5-(5-cyclopropylpyridin-3-yl)-4-(2,6-dimethoxyphenyl)-4H-1,2,4-triazol-3-yl)-3-(5-methylpyrimidin-2-yl)butane-2-sulfonamide, Example 734.0

(2S,3R)—N-(5-(5-Bromopyridin-3-yl)-4-(2,6-dimethoxyphenyl)-4H-1,2,4-triazol-3-yl)-3-(5-methylpyrimidin-2-yl)butane-2-sulfonamide (Example 733.0) (110 mg, 0.19 mmol) was suspended in 1,4-dioxane (0.6 mL) and water (0.06 mL). Potassium cyclopropyltrifluoroborate (84 mg, 0.57 mmol), [1,1'-bis(diphenylphosphino)ferrocene]-dichloropalladium(II), complex with DCM (48 mg, 0.06 mmol), and potassium carbonate (109 mg, 0.79 mmol) were then added to the vial. Nitrogen was bubbled through the mixture for 10 minutes and then the mixture was heated to 90° C. After 20 hours, the reaction was cooled to RT and then loaded onto a silica gel column (20-85% 3:1 EtOAc: EtOH in heptane.) Fractions containing product were combined and then concentrated under reduced pressure to afford (2S,3R)—N-(5-(5-cyclopropylpyridin-3-yl)-4-(2,6-dimethoxyphenyl)-4H-1,2,4-triazol-3-yl)-3-(5-methylpyrimidin-2-yl)butane-2-sulfonamide (Example 734.0) as a brown solid (63 mg, 0.11 mmol, 61% yield). $^1$H NMR (400 MHz, DMSO-$d_6$) δ 13.35 (s, 1H), 8.59 (d, J=0.8 Hz, 2H), 8.50 (d, J=2.1 Hz, 1H), 8.34 (d, J=2.1 Hz, 1H), 7.58-7.47 (m, 2H), 7.09 (t, J=2.2 Hz, 1H), 6.83 (dd, J=2.4, 8.6 Hz, 2H), 3.74-3.65 (m, 7H), 3.59 (dd, J=3.2, 6.9 Hz, 1H), 2.23 (s, 3H), 1.96-1.88 (m, 1H), 1.24 (d, J=7.3 Hz, 3H), 1.10 (d, J=6.8 Hz, 3H), 1.01-0.94 (m, 2H), 0.48-0.42 (m, 2H). Mass Spectrum (pos.) m/z: 550.2 (M+H)$^+$.

Example 735.0: Preparation of (1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide or (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide

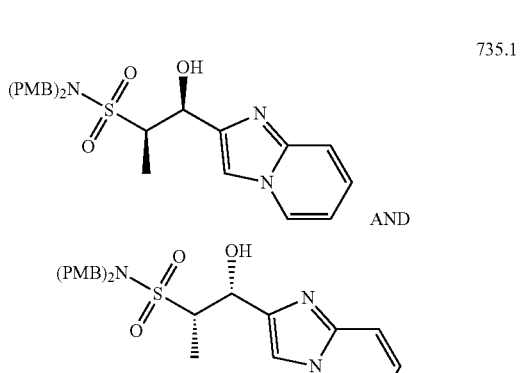

(1S,2R)-1-hydroxy-1-(imidazo[1,2-a]pyridin-2-yl)-N,N-bis(4-methoxybenzyl)propane-2-sulfonamide and (1R,2S)-1-hydroxy-1-(imidazo[1,2-a]pyridin-2-yl)-N,N-bis(4-methoxybenzyl)propane-2-sulfonamide, Example 735.1

To a stirred solution of N,N-bis(4-methoxybenzyl)ethanesulfonamide (Example 12.0) (1.0 g, 2.9 mmol) in THF (9.5 mL) at −78° C. was added n-butyllithium solution, (2.5 M in hexanes, 1.3 mL, 3.15 mmol) dropwise. After 5 minutes, a solution of imidazo[1,2-a]pyridine-2-carbaldehyde (460 mg, 3.15 mmol) in THF was added dropwise over 5 minutes. Upon complete addition, the reaction was maintained at −78° C. and monitored with LCMS-ESI. After 3 hours, the reaction was quenched with saturated aqueous ammonium chloride solution. After extracting three times with EtOAc, the organics were pooled and then dried over anhydrous magnesium sulfate. After filtration and concentration under reduced pressure, the dark brown residue was purified on silica gel eluting with 0-60% of (3:1 EtOAc: EtOH) in heptane to afford the following compounds (in the order off the column): (1S,2R)-1-hydroxy-1-(imidazo[1,2-a]pyridin-2-yl)-N,N-bis(4-methoxybenzyl)propane-2-sulfonamide or (1R,2S)-1-hydroxy-1-(imidazo[1,2-a]pyridin-2-yl)-N,N-bis(4-methoxybenzyl)propane-2-sulfonamide, Example 735.1 (0.5 g, 1.01 mmol, 35% yield).

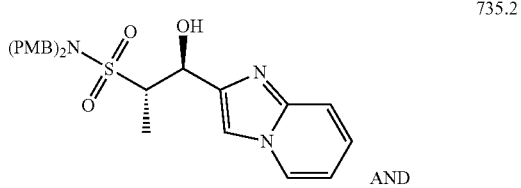

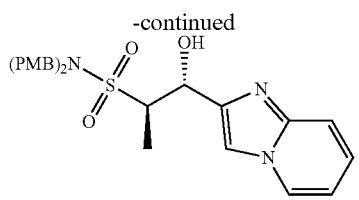

(1S,2S)-1-hydroxy-1-(imidazo[1,2-a]pyridin-2-yl)-N,N-bis(4-methoxybenzyl)propane-2-sulfonamide or (1R,2R)-1-hydroxy-1-(imidazo[1,2-a]pyridin-2-yl)-N,N-bis(4-methoxybenzyl)propane-2-sulfonamide, Example 735.2

Further elution under the conditions described in 735.1 gave Example 735.2 (0.39 g, 0.79 mmol. 78% yield)

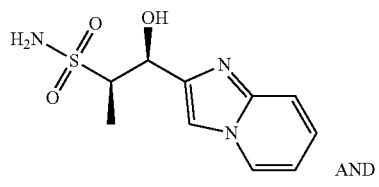

AND

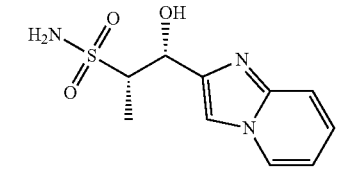

(1S,2R)-1-hydroxy-1-(imidazo[1,2-a]pyridin-2-yl)propane-2-sulfonamide and (1R,2S)-1-hydroxy-1-(imidazo[1,2-a]pyridin-2-yl)propane-2-sulfonamide, Example 735.3

To a flask containing (1S,2R)-1-hydroxy-1-(imidazo[1,2-a]pyridin-2-yl)-N,N-bis(4-methoxybenzyl)propane-2-sulfonamide or (1R,2S)-1-hydroxy-1-(imidazo[1,2-a]pyridin-2-yl)-N,N-bis(4-methoxybenzyl)propane-2-sulfonamide (Example 735.1) (1.01 g, 2.02 mmol) was added DCM (5 mL). Anisole (0.9 mL, 8.15 mmol) was then added. The heterogeneous solution was stirred at 23° C. After 2 minutes, TFA (5.3 mL, 69 mmol) was added dropwise to the reaction solution. The homogeneous reaction was stirred at 23° C. and monitored with LCMS-ESI. After 19 hours, the reaction was concentrated under reduced pressure. The light yellow residue was identified as the TFA salts of (1S,2R)-1-hydroxy-1-(imidazo[1,2-a]pyridin-2-yl)propane-2-sulfonamide and (1R,2S)-1-hydroxy-1-(imidazo[1,2-a]pyridin-2-yl)propane-2-sulfonamide (Example 735.3, 746 mg, 2.02 mmol, 100% yield) that was used without purification. Mass Spectrum (pos.) m/z: 256.2 (M+H)$^+$.

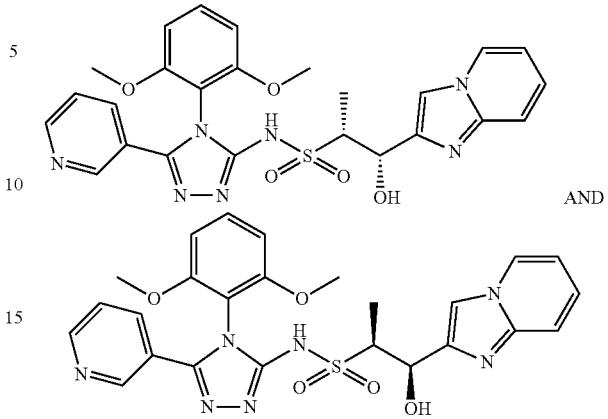

(1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide and (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide, Example 735.4

The title compound 735.4 was prepared from 735.3 (746 mg, 2.02 mmol), using the procedure described in Example A. This provided Example 735.4 (100 mg, 0.19 mmol) as a light yellow film. Mass Spectrum (pos.) m/z: 536.2 (M+H)$^+$.

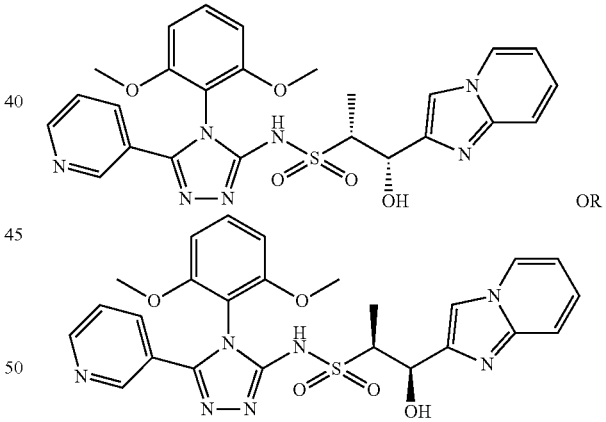

(1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide or (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide, Example 735.0

Purification of Example 735.4 resulted in the title compound 735.0 as the first isomer to elute under the following SFC conditions: AD-H (2×25 cm) 45% isopropanol (0.2% DEA)/CO$_2$, 100 bar 60 mL/min, 220 nm. Inj vol.: 0.5 mL, 10 mg/mL, MeOH solution of Example 735.4. (1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide or (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide. $^1$H NMR (400 MHz, CD$_3$OD) δ 8.68-8.51 (m, 2H), 8.40 (td, J=1.1, 6.8 Hz, 1H), 7.85 (td, J=1.9, 8.0 Hz, 1H), 7.77 (d, J=0.8 Hz, 1H), 7.55-7.41 (m, 3H), 7.30 (ddd, J=1.3, 6.7, 9.2 Hz, 1H), 6.90 (dt, J=1.1, 6.8 Hz, 1H), 6.83-6.76 (m, 2H), 5.63 (dd, J=1.1, 1.8 Hz, 1H), 3.78 (s, 3H), 3.75 (s, 3H), 3.68-3.60 (m, 1H), 1.23-1.19 (m, 3H). Mass Spectrum (pos.) m/z: 536.2 (M+H)$^+$.

Example 736.0: Preparation of (1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide or (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide

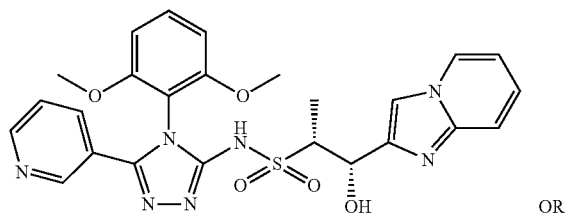

736.0

(1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide or (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide, Example 736.0

Purification of Example 735.4 resulted in the title compound 736.0 as the second isomer to elute under the following SFC conditions: AD-H (2×25 cm) 45% isopropanol (0.2% DEA)/CO$_2$, 100 bar 60 mL/min, 220 nm. Inj vol.: 0.5 mL, 10 mg/mL, MeOH solution of Example 735.4. (1S,2R)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide or (1R,2S)—N-(4-(2,6-dimethoxyphenyl)-5-(pyridin-3-yl)-4H-1,2,4-triazol-3-yl)-1-hydroxy-1-(imidazo[1,2-a]pyridin-2-yl)propane-2-sulfonamide. $^1$H NMR (400 MHz, CD$_3$OD) δ 8.65-8.53 (m, 2H), 8.39 (td, J=1.2, 6.7 Hz, 1H), 7.88-7.81 (m, 1H), 7.76 (s, 1H), 7.55-7.39 (m, 3H), 7.28 (ddd, J=1.2, 6.8, 9.1 Hz, 1H), 6.89 (dt, J=1.1, 6.8 Hz, 1H), 6.83-6.75 (m, 2H), 5.62 (dd, J=1.1, 1.8 Hz, 1H), 3.77 (s, 3H), 3.76-3.72 (m, 3H), 3.63 (dq, J=1.8, 7.0 Hz, 1H), 1.22-1.17 (m, 3H). Mass Spectrum (pos.) m/z: 536.2 (M+H)$^+$.

Example 737.0: Preparation of (1R,2S)—N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide or (1S,2R)—N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide

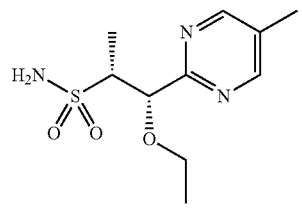

737.1

OR

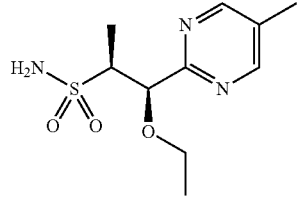

(1S,2R)-1-ethoxy-1-(5-methylpyrimidin-2-yl)propane-2-sulfonamide or (1R,2S)-1-ethoxy-1-(5-methylpyrimidin-2-yl)propane-2-sulfonamide, Example 737.1

Purification of Example 15.0 resulted in the title compound 737.1 as the second isomer to elute under the following SFC conditions: AD-H (250×21 cm) 12% EtOH/CO$_2$, 165-172 bar inlet pressure, 70 mL/min, 220 nm. (1S,2R)-1-ethoxy-1-(5-methylpyrimidin-2-yl)propane-2-sulfonamide or (1R,2S)-1-ethoxy-1-(5-methylpyrimidin-2-yl)propane-2-sulfonamide (Example 737.1) $^1$H NMR (400 MHz, DMSO-d$_6$) δ 8.73-8.60 (m, 2H), 6.74 (s, 2H), 4.97-4.85 (m, 1H), 3.61-3.37 (m, 3H), 2.36-2.23 (m, 3H), 1.36-1.24 (m, 3H), 1.14-1.06 (m, 3H). Mass Spectrum (pos.) m/z: 260.1 (M+H)$^+$.

737.0

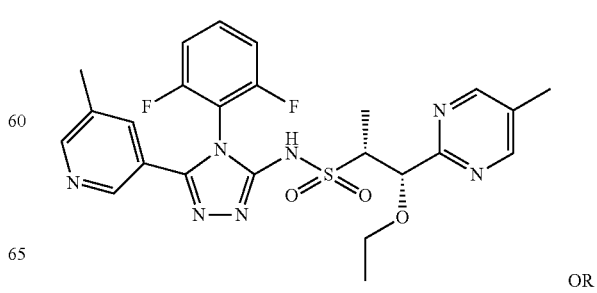

OR

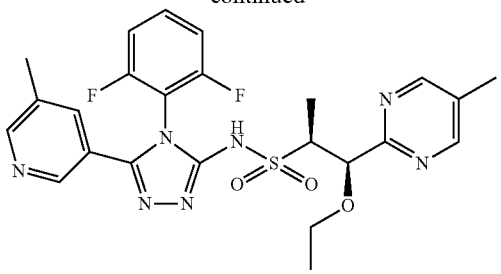

(1S,2R)—N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide or (1R,2S)—N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide, Example 737.0

The title compound 737.0 was prepared from 737.1 (207 mg, 0.8 mmol), using the procedures described in Example A. This provided Example 737.0 (35 mg, 0.07 mmol) as a white solid. $^1$H NMR (400 MHz, DMSO-d$_6$) δ 13.72 (s, 1H), 8.63 (d, J=0.6 Hz, 2H), 8.53 (d, J=1.5 Hz, 1H), 8.25 (d, J=1.9 Hz, 1H), 7.80-7.69 (m, 1H), 7.66 (s, 1H), 7.43 (dt, J=4.3, 8.9 Hz, 2H), 4.96 (d, J=3.7 Hz, 1H), 3.44-3.25 (m, 3H), 2.27 (s, 3H), 2.25 (s, 3H), 1.17 (d, J=7.0 Hz, 3H), 0.93 (t, J=6.9 Hz, 3H). Mass Spectrum (pos.) m/z: 530.2 (M+H)$^+$.

Example 738.0: Preparation of (1S,2S)-1-isopropoxy-1-(5-methylpyrimidin-2-yl)propane-2-sulfonamide

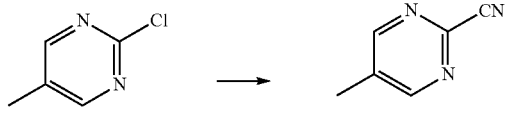

5-methylpyrimidine-2-carbonitrile, Example 738.1

A solution of 2-chloro-5-methylpyrimidine (500 g, 3889 mmol, 1.0 equiv) in DMF (5000 mL) was degassed with N$_2$ for 20 min and then dppf (108 g, 194 mmol, 0.05 equiv) and Pd$_2$(dba)$_3$ (178 g, 194 mmol, 0.05 equiv) were added to the reaction mixture. Zn(CN)$_2$ (685 g, 5834 mmol, 1.5 equiv) was added, and the reaction mixture was heated at 100° C. for 16 h. The reaction was quenched with water (5000 mL) and stirred for 10 min. The reaction mixture was filtered through a pad of Celite® brand filter agent. The filtrate was diluted with water (4000 mL) and extracted with EtOAc (2×4000 mL). The combined organic layer was washed with brine (4000 mL), dried over Na$_2$SO$_4$, filtered and concentrated under reduced pressure to give the initial product which was further purified by column chromatography using silica gel (60-120 mesh) and 0-10% EtOAc in hexane to obtain Example 738.1 (330 g, 71%) as off white solid. $^1$H NMR (400 MHz, DMSO-d$_6$) δ 8.89 (s, 2H), 2.39 (s, 3H).

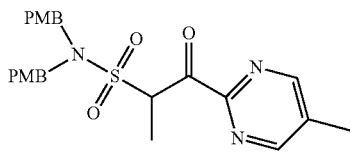

N,N-bis(4-methoxybenzyl)-1-(5-methylpyrimidin-2-yl)-1-oxopropane-2-sulfonamide, Example 738.2

To a solution of Example 12.0 (293 g, 839 mmol, 2.0 equiv) in THF (2000 mL) was added isopropylmagnesium chloride (420 mL, 839 mmol, 2.0 equiv, 2.0 M in diethyl ether) at 0° C. The reaction mixture was stirred at 25° C. for 3 h. To the reaction mixture was added 5-methylpyrimidine-2-carbonitrile (738.1, 50 g, 420 mmol, 1.0 equiv) in THF (100 mL) at 0° C. and stirred at room temperature for 2 h. The reaction was quenched 1.5 N HCl (500 mL), water (2000 mL) and stirred for 10 min. The mixture was extracted with EtOAc (2×1000 mL), and the combined organic layer was washed with brine (500 mL), dried over Na$_2$SO$_4$ and filtered. The organic layer was concentrated under reduced pressure to give the initial compound which was purified by column chromatography using silica gel (100-200 mesh) and 0-50% EtOAc in hexane as eluent to obtain Example 738.2 (60 g, 30% yield) as brown liquid. $^1$H NMR (400 MHz, DMSO-d$_6$) δ 8.90 (s, 2H), 7.15-7.09 (m, 4H), 6.85-6.80 (m, 4H), 4.34-4.18 (m, 5H), 3.71 (s, 6H), 2.39 (s, 3H), 1.50 (d, J=6.9 Hz, 3H). MS (ESI+ve ion) m/z: (M+H)$^+$: 470.0.

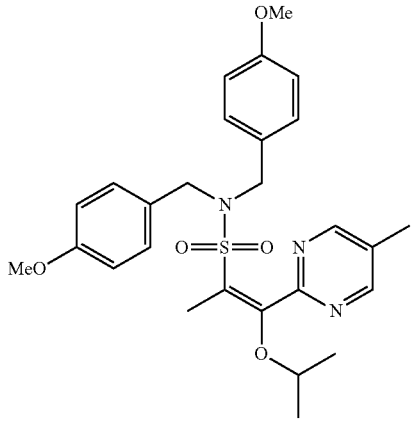

(E)-1-isopropoxy-N,N-bis(4-methoxybenzyl)-1-(5-methylpyrimidin-2-yl)prop-1-ene-2-sulfonamide, Example 738.3

To a solution of Example 738.2 (120 g, 256 mmol, 1.0 equiv) in DMF (1200 mL) was added 2-iodopropane (129 mL, 1278 mmol, 5.0 equiv) and potassium carbonate (70.6 g, 511 mmol, 2.0 equiv). The reaction mixture was stirred at 60° C. for 14 h. The reaction was quenched with water (1000 mL), stirred for 10 min and then extracted with EtOAc (2×1000 mL). The combined organic layer was washed with brine (1000 mL), dried over Na$_2$SO$_4$, filtered and concentrated under reduced pressure to give the initial material. The product thus obtained was purified by column chromatography using silica gel (100-200 mesh) and 0-50% EtOAc in hexane as eluent to obtain Example 738.3 (75 g, 57.4% yield) as off white solid. ¹H NMR (400 MHz, DMSO-d₆) δ 8.72 (s, 2H), 7.09 (d, J=8.3 Hz, 4H), 6.86 (d, J=8.3 Hz, 4H), 4.16 (s, 4H), 3.73 (d, J=1.1 Hz, 6H), 3.71-3.67 (m, 1H), 2.31 (s, 3H), 1.87 (s, 3H), 1.19-1.16 (m, 6H). MS (ESI+ve ion) m/z: (M+H)⁺: 512.1

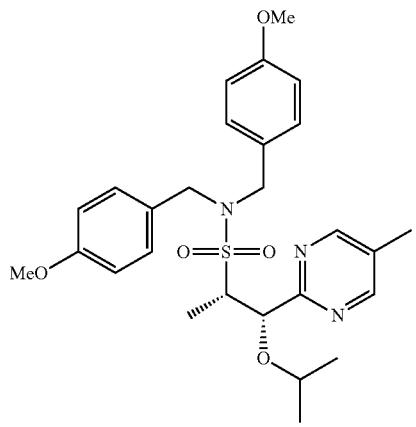

(1S,2R)-1-isopropoxy-N,N-bis(4-methoxybenzyl)-1-(5-methylpyrimidin-2-yl)propane-2-sulfonamide, Example 738.4

To a solution of Example 738.3 (180 g, 352 mmol, 1.0 equiv) in MeOH (1800 mL) was added zinc triflate (256 g, 704 mmol, 2.0 equiv) and (S)—RuCl[(p-cymene(BINAP)]Cl (6.54 g, 7.04 mmol, 0.02 equiv) were added, and the mixture was heated at 60° C. under H₂ pressure (60 psi) for 16 h. The reaction mixture was then concentrated under reduced pressure providing the initial product which was further purified by column chromatography using silica gel (60-120 mesh) and 0-50% EtOAc in DCM as eluent to obtain Example 738.4 (140 g, 77%, 92% ee) as off white solid. ¹H NMR (400 MHz, DMSO-d₆) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (s, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). MS (ESI+ve ion) m/z: (M+H)⁺: 514.2.

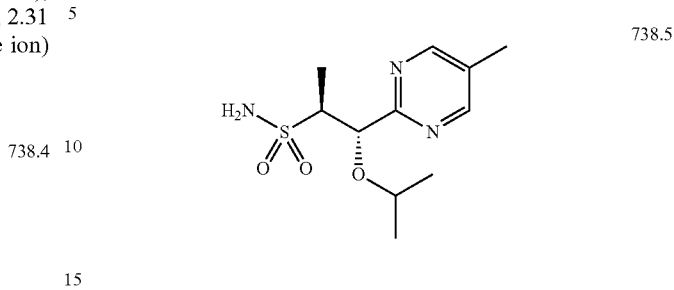

(1S,2S)-1-isopropoxy-1-(5-methylpyrimidin-2-yl)propane-2-sulfonamide, Example 738.5

To a solution of Example 738.4 (140.0 g, 273 mmol, 1.0 equiv) in DCM (500 mL) was added TFA (250 mL) at 0° C. The resulting mixture was then stirred at RT for 16 h. Next, the reaction mixture was concentrated under reduced pressure providing an initial material which was dissolved in DCM (1000 mL) and washed with saturated aqueous NaHCO₃ solution (1000 mL). The organic layer was dried over Na₂SO₄, filtered and concentrated under reduced pressure providing the initial product which was further purified by column chromatography using silica gel (60-120 mesh) and 0-2% MeOH in DCM providing Example 738.5 (72 g, 97% yield, 90% ee) as an off white solid. Example 738.5 (72 g, 90% ee) was suspended in isopropanol (500 mL) and heated to 70° C. until the mixture become homogeneous. Once the solution became homogeneous, the mixture was cooled to RT overnight. The white solid thus obtained was filtered, dried under vacuum to obtain compound-6 (30 g, >99% ee). The mother liquor was concentrated, and the solid obtained was recrystallized again following the same procedure. ¹H NMR (400 MHz, DMSO-d₆) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). MS (ESI+ve ion) m/z: [M+1]: 274.1.

The compounds set forth in the following Table were synthesized following the procedure in Example A using the known starting material as described.

TABLE 38

| Example | Reagents | Structure, Name and Data |
|---------|----------|--------------------------|
| 738.0 | (1S,2S)-1-isopropoxy-1-(5-methylpyrimidin-2-yl)propane-2-sulfonamide, Example 738.5 6-methylpicolinohydrazide (Example 3.4), 2-isothiocyanato-1,3-dimethoxybenzene (Example 1.0) | (1S,2S)-N-(4-(2,6-dimethoxyphenyl)-5-(6-methylpyridin-2-yl)-4H-1,2,4-triazol-3-yl)-1-isopropoxy-1-(5-methylpyrimidin-2-yl)propane-2-sulfonamide. ¹H NMR (400 MHz, DMSO-d₆) δ 13.22 (s, 1H), 8.66 (d, J = 0.6 Hz, 2H), 7.79-7.71 (m, 1H), 7.63 (d, J = 7.7 Hz, 1H), 7.42 (t, J = 8.5 Hz, 1H), 7.24 (d, |

| Example | Reagents | Structure, Name and Data |
|---|---|---|
| | | J = 7.7 Hz, 1H), 6.76 (d, J = 8.3 Hz, 2H), 4.72 (d, J = 7.5 Hz, 1H), 3.67 (s, 3H), 3.65 (s, 3H), 3.45-3.37 (m, 2H), 2.27 (s, 3H), 2.09 (s, 3H), 0.99 (d, J = 6.2 Hz, 3H), 0.94 (d, J = 7.0 Hz, 3H), 0.79 (d, J = 6.0 Hz, 3H). Mass Spectrum (pos.) m/z: 568.0 (M + H)+. |
| 739.0 | (1R,2S)-1-methoxy-1-(5-methylpyrimidin-2-yl)propane-2-sulfonamide (Example 14.0), 6-methoxy-pyridine-2-carboxylic acid hydrazide (commercially available from Milestone Pharmatech), 5-isothiocyanato-4,6-dimethoxypyrimidine (Example 1.8). The atropisomer mixture was purified by the following preparative SFC method: Column: IC (2 × 25 cm) Mobile Phase: 55:45 (A:B) A: Liquid CO$_2$, B: MeOH, Flow Rate: 55 mL/min, 220 nm, 100 bar inlet pressure to deliver the second eluting peak. | (1R,2S,M)-N-(4-(4-hydroxy-6-methoxypyrimidin-5-yl)-5-(6-methoxypyridin-2-yl)-4H-1,2,4-triazol-3-yl)-1-methoxy-1-(5-methylpyrimidin-2-yl)propane-2-sulfonamide or (1R,2S,P)-N-(4-(4-hydroxy-6-methoxypyrimidin-5-yl)-5-(6-methoxypyridin-2-yl)-4H-1,2,4-triazol-3-yl)-1-methoxy-1-(5-methylpyrimidin-2-yl)propane-2-sulfonamide. $^1$H NMR (400 MHz, DMSO-d$_6$) δ 13.32 (br. s., 1H), 13.12 (br. s., 1H), 8.65 (d, J = 0.8 Hz, 2H), 8.36 (s, 1H), 7.84 (dd, J = 7.5, 8.3 Hz, 1H), 7.62 (dd, J = 0.8, 7.5 Hz, 1H), 6.91 (dd, J = 0.6, 8.3 Hz, 1H), 4.82 (d, J = 3.9 Hz, 1H), 3.84 (s, 3H), 3.52-3.46 (m, 1H), 3.43 (s, 3H), 3.18 (s, 3H), 2.27 (s, 3H), 1.18 (d, J = 7.0 Hz, 3H). Mass Spectrum (pos.) m/z: 544.0 (M + H)+. |
| 740.0 | (1R,2S)-1-methoxy-1-(5-methylpyrimidin-2-yl)propane-2-sulfonamide (Example 14.0), 6-methoxy-pyridine-2-carboxylic acid hydrazide (commercially available from Milestone Pharmatech), 5-isothiocyanato-4,6-dimethoxypyrimidine (Example 1.8) The atropisomer mixture was purified by preparative SFC method: Column: IC (2 × 25 cm) Mobile Phase: 55:45 (A:B) A: Liquid CO$_2$, B: MeOH, Flow Rate: 55 mL/min, 220 nm, 100 bar inlet pressure to deliver peak 1. | (1R,2S,M)-N-(4-(4-hydroxy-6-methoxypyrimidin-5-yl)-5-(6-methoxypyridin-2-yl)-4H-1,2,4-triazol-3-yl)-1-methoxy-1-(5-methylpyrimidin-2-yl)propane-2-sulfonamide or (1R,2S,P)-N-(4-(4-hydroxy-6-methoxypyrimidin-5-yl)-5-(6-methoxypyridin-2-yl)-4H-1,2,4-triazol-3-yl)-1-methoxy-1-(5- |

| Example | Reagents | Structure, Name and Data |
|---|---|---|
| | | methylpyrimidin-2-yl)propane-2-sulfonamide. $^1$H NMR (400 MHz, DMSO-$d_6$) δ 13.31 (br. s., 1H), 13.21-13.02 (m, 1H), 8.65 (d, J = 0.6 Hz, 2H), 8.35 (s, 1H), 7.86-7.81 (m, 1H), 7.62 (dd, J = 0.6, 7.5 Hz, 1H), 6.91 (d, J = 8.1 Hz, 1H), 4.87 (d, J = 3.7 Hz, 1H), 3.85 (s, 3H), 3.51-3.44 (m, 1H), 3.43 (s, 3H), 3.18 (s, 3H), 2.27 (s, 3H), 1.16 (d, J = 7.0 Hz, 3H). Mass Spectrum (pos.) m/z: 544.0 (M + H)$^+$. |

Example 741.0: Preparation of (1R,2S)-1-methoxy-N-(4-(2-methoxy-3-pyridinyl)-5-(6-methoxy-2-pyridinyl)-4H-1,2,4-triazol-3-yl)-1-(5-methyl-2-pyrimidinyl)-2-propanesulfonamide

741.1

3-Isothiocyanato-2-methoxypyridine, Example 741.1

To a flask containing 1,1'-thiocarbonyldi-2(1h)-pyridone (2.58 g, 111 mmol) in anhydrous DCM (20 mL) was added a solution of 3-amino-2-methoxypyridine (1.24 g, 10.0 mmol) in anhydrous DCM (20 mL) at 23° C. over 20 min. After 30 min, the reaction was concentrated under reduced pressure to a volume 10 mL. This was then loaded onto a silica gel column (0-30% EtOAc in heptane). Fractions containing pure product were combined and concentrated under reduced pressure to afford a colorless liquid as 3-isothiocyanato-2-methoxypyridine (Example 741.1) (1.34 g, 8.0 mmol, 80% yield) that was used without further purification. $^1$H NMR (400 MHz, DMSO-$d_6$) δ 8.14-8.09 (m, 1H), 7.73-7.68 (m, 1H), 7.03 (tdd, J=1.2, 5.0, 7.6 Hz, 1H), 4.01-3.96 (m, 3H). Mass Spectrum (pos.) m/z: 167.1 (M+H)$^+$.

(Z)—N-(((1R,2S)-1-methoxy-1-(5-methylpyrimidin-2-yl)propan-2-yl)sulfonyl)-2-(6-methoxypicolinoyl)-N'-(2-methoxypyridin-3-yl)hydrazinecarboximidamide, Example 741.2

To a vial containing Intermediate 14.0 (253 mg, 1.03 mmol) was added ACN (4 mL). After 10 minutes, Example 741.1 (188 mg, 1.13 mmol) was added carefully in portions. The mixture was cooled in an ice-bath, and then cesium carbonate (439 mg, 1.35 mmol) was added carefully in portions. Upon complete addition of cesium carbonate, the mixture was allowed to warm to 23° C. After 19 hours, the mixture was cooled in an ice-water bath. After 20 minutes, 6-methoxy-pyridine-2-carboxylic acid hydrazide (174 mg, 1.04 mmol) and then silver nitrate (365 mg, 2.15 mmol) were carefully added in portions. This is an exothermic reaction, and the reaction became bright orange and then dark brown on warming to RT. The mixture was allowed to warm to 23° C. After 25 minutes, the mixture was loaded directly onto a Biotage SNAP Ultra column and purified (25-90% 3:1 EtOAc: EtOH in heptane.) Fractions containing pure product were combined and then concentrated under reduced pressure to afford a white foam as (Z)—N-(((1R,2S)-1-methoxy-1-(5-methylpyrimidin-2-yl)propan-2-yl)sulfonyl)-2-(6-methoxypicolinoyl)-N'-(2-methoxypyridin-3-yl)hydrazinecarboximidamide (Example 741.2) (471.0 mg, 0.865 mmol, 84% yield) which was used without further purification. Mass Spectrum (pos.) m/z: 545.0 (M+H)$^+$.

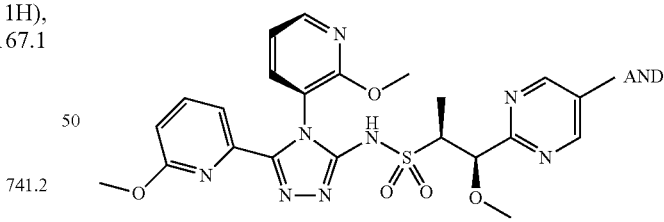

741.0

741.2

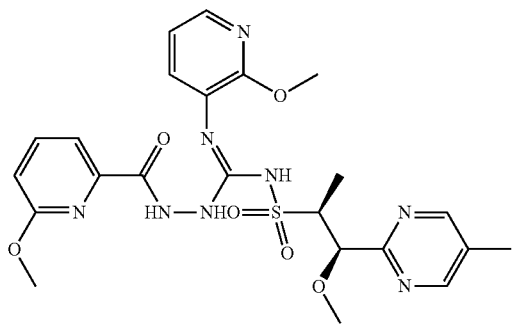

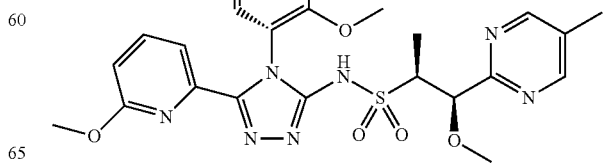

(1R,2S, P)-1-methoxy-N-(4-(2-methoxy-3-pyridinyl)-5-(6-methoxy-2-pyridinyl)-4H-1,2,4-triazol-3-yl)-1-(5-methyl-2-pyrimidinyl)-2-propanesulfonamide and (1R,2S, M)-1-methoxy-N-(4-(2-methoxy-3-pyridinyl)-5-(6-methoxy-2-pyridinyl)-4H-1,2,4-triazol-3-yl)-1-(5-methyl-2-pyrimidinyl)-2-propanesulfonamide, Example 741

To a vial containing Example 741.2 (471 mg, 0.86 mmol) in isopropanol (2 mL) and water (1 mL) was added NaOH 1.0 N solution (1.1 mL, 1.1 mmol) carefully and dropwise to the reaction mixture. Upon complete addition of 1 N NaOH, the mixture was heated on a preheated stir plate at 80° C. After 8 days, the reaction was cooled to RT and then was diluted with water. The pH was carefully adjusted to pH~7 with dropwise addition of 1 N HCl. The reaction mixture was extracted three times with DCM. The organic layers were pooled and then dried over anhydrous magnesium sulfate. After filtration and concentration under reduced pressure, the residue was loaded onto a Biotage Snap Ultra silica gel column (25-75% 3:1 EtOAc: EtOH in heptane). Fractions containing product were combined and then concentrated under reduced pressure to afford a film that was triturated with EtOH to afford a white solid as (1R,2S)-1-methoxy-N-(5-(6-methoxypyridin-2-yl)-4-(2-methoxypyridin-3-yl)-4H-1,2,4-triazol-3-yl)-1-(5-methylpyrimidin-2-yl)propane-2-sulfonamide (Example 741.0) (223 mg, 0.423 mmol, 49.0% yield). $^1$H NMR (400 MHz, DMSO-d$_6$) δ 13.53-13.33 (m, 1H), 8.65 (dd, J=0.7, 3.0 Hz, 2H), 8.27 (ddd, J=1.7, 5.1, 10.5 Hz, 1H), 7.95-7.81 (m, 2H), 7.64 (ddd, J=0.7, 2.0, 7.4 Hz, 1H), 7.19 (ddd, J=5.0, 7.6, 17.7 Hz, 1H), 6.91-6.83 (m, 1H), 4.84 (dd, J=3.3, 15.8 Hz, 1H), 3.72 (d, J=3.9 Hz, 3H), 3.51-3.36 (m, 2H), 3.17-3.07 (m, 3H), 3.04 (d, J=4.8 Hz, 3H), 2.26 (s, 3H), 1.22-1.10 (m, 3H). Mass Spectrum (pos.) m/z: 527.0 (M+H)$^+$.

Example 742.0: Preparation of (1R,2R)—N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide or (1S,2S)—N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide

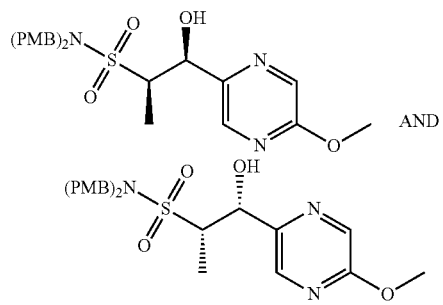

(1R,2S)-1-hydroxy-N,N-bis(4-methoxybenzyl)-1-(5-methoxypyrazin-2-yl)propane-2-sulfonamide and (1S,2R)-1-hydroxy-N,N-bis(4-methoxybenzyl)-1-(5-methoxypyrazin-2-yl)propane-2-sulfonamide, Example 742.1

To a stirred solution of N,N-bis(4-methoxybenzyl)ethanesulfonamide (Example 12.0) (3.0 g, 8.6 mmol) in THF (43 mL) at −78° C. was added n-butyllithium solution, (2.5 M in hexanes, 3.8 mL, 9.5 mmol) dropwise. After 5 minutes, a solution of 5-methoxypyrazine-2-carboxaldehyde (1.19 g, 8.6 mmol) in anhydrous THF (14 mL) was added dropwise over 5 minutes. Upon complete addition, the reaction was maintained at −78° C. and monitored with LCMS-ESI. After 1 hour, the reaction was quenched with saturated aqueous ammonium chloride solution. After extracting three times with EtOAc, the organic layers were pooled and then dried over anhydrous magnesium sulfate. After filtration and concentration under reduced pressure, the dark brown residue was purified on silica gel eluting with 20-100% EtOAc in heptane to afford the following compounds (1R,2S)-1-hydroxy-N,N-bis(4-methoxybenzyl)-1-(5-methoxypyrazin-2-yl)propane-2-sulfonamide and (1S,2R)-1-hydroxy-N,N-bis(4-methoxybenzyl)-1-(5-methoxypyrazin-2-yl)propane-2-sulfonamide (Example 742.1) (1.98 g, 4.06 mmol, 47% yield) as light yellow solid. Mass Spectrum (pos.) m/z: 488.2 (M+H)$^+$.

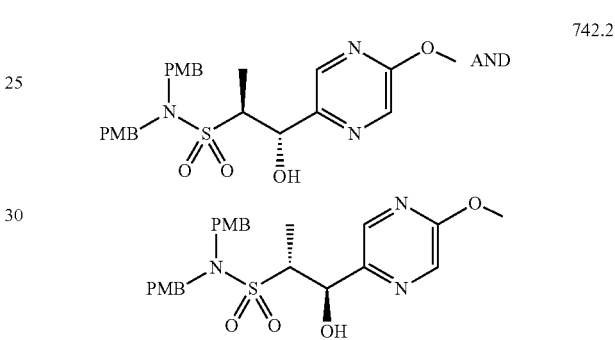

(1R,2R)-1-hydroxy-N,N-bis(4-methoxybenzyl)-1-(5-methoxypyrazin-2-yl)propane-2-sulfonamide and (1S,2S)-1-hydroxy-N,N-bis(4-methoxybenzyl)-1-(5-methoxypyrazin-2-yl)propane-2-sulfonamide, Example 742.2

Further elution using the conditions described in Example 742.1 gave 742.2 (0.83 g, 1.70 mmol, 20% yield) as light-yellow solid. Mass Spectrum (pos.) m/z: 488.2 (M+H)$^+$.

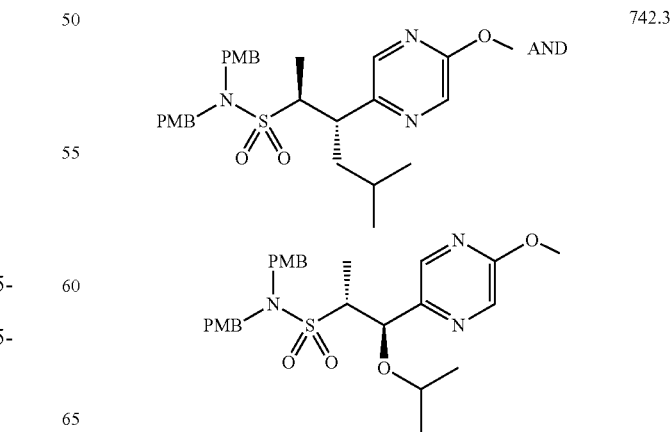

(1S,2S)-1-isopropoxy-N,N-bis(4-methoxybenzyl)-1-
(5-methoxypyrazin-2-yl)propane-2-sulfonamide and
(1R,2R)-1-isopropoxy-N,N-bis(4-methoxybenzyl)-1-
(5-methoxypyrazin-2-yl)propane-2-sulfonamide,
Example 742.3

To a vial containing (1S,2S)-1-hydroxy-N,N-bis(4-methoxybenzyl)-1-(5-methoxypyrazin-2-yl)propane-2-sulfonamide and (1R,2R)-1-hydroxy-N,N-bis(4-methoxybenzyl)-1-(5-methoxypyrazin-2-yl)propane-2-sulfonamide (Example 742.2, 2.00 g, 4.12 mmol) and isopropyl iodide (5.8 mL, 58 mmol) in anhydrous toluene (16 mL) was added silver(I) oxide (1.9 g, 8.3 mmol) carefully in portions. Upon complete addition of silver oxide, the reaction was protected from light and heated to 70° C. After 24 hours, the mixture was cooled to RT and was then filtered through a Chemglass disposable filter that was rinsed with EtOAc. The filtrate was concentrated under reduced pressure. The residue was purified on a silica gel column (0-50% EtOAc in heptanes). Fractions containing product were combined and then concentrated under reduced pressure to afford a dark yellow gum as (1S,2S)-1-isopropoxy-N,N-bis(4-methoxybenzyl)-1-(5-methoxypyrazin-2-yl)propane-2-sulfonamide and (1R,2R)-1-isopropoxy-N,N-bis(4-methoxybenzyl)-1-(5-methoxypyrazin-2-yl)propane-2-sulfonamide, Example 742.3 (776 mg, 1.47 mmol, 36% yield). $^1$H NMR (400 MHz, DMSO-$d_6$) δ 8.33 (d, J=1.5 Hz, 1H), 8.28 (d, J=1.2 Hz, 1H), 7.21-7.15 (m, 4H), 6.89-6.84 (m, 4H), 4.81 (d, J=7.3 Hz, 1H), 4.34 (d, J=15.3 Hz, 2H), 4.15 (d, J=15.3 Hz, 2H), 3.93 (s, 3H), 3.75-3.70 (m, 7H), 3.39 (quin, J=6.1 Hz, 1H), 1.13 (d, J=6.0 Hz, 3H), 1.03 (d, J=7.0 Hz, 3H), 0.99 (d, J=6.2 Hz, 3H). Mass Spectrum (pos.) m/z: 530.0 (M+H)$^+$.

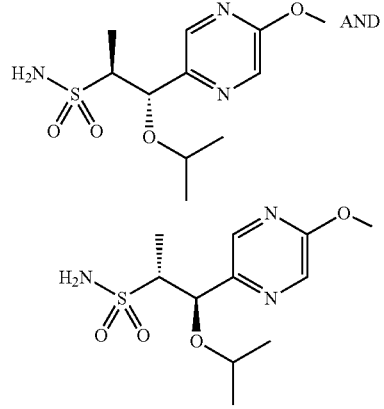

(1S,2S)-1-isopropoxy-1-(5-methoxypyrazin-2-yl)
propane-2-sulfonamide and racemic (1R,2R)-1-
isopropoxy-1-(5-methoxypyrazin-2-yl)propane-2-
sulfonamide, Example 742.4

Anisole (0.64 mL, 5.86 mmol) was added to a vial containing (1S,2S)-1-isopropoxy-N,N-bis(4-methoxybenzyl)-1-(5-methoxypyrazin-2-yl)propane-2-sulfonamide and (1R,2R)-1-isopropoxy-N,N-bis(4-methoxybenzyl)-1-(5-methoxypyrazin-2-yl)propane-2-sulfonamide (Example 742.3, 776 mg, 1.46 mmol) and DCM (3.6 mL). The homogeneous solution was cooled in an ice-water bath. After 15 minutes, TFA (3.6 mL, 47 mmol) was added dropwise to the reaction solution. Upon complete addition of TFA, the reaction was allowed to warm to 23° C. After 20 hours, the brownish reaction solution was concentrated under reduced pressure. The residue was loaded onto a silica gel column (5-75% EtOAc in heptanes). Fractions containing product were concentrated under reduced pressure to afford an off white solid as (1S,2S)-1-isopropoxy-1-(5-methoxypyrazin-2-yl)propane-2-sulfonamide and (1R,2R)-1-isopropoxy-1-(5-methoxypyrazin-2-yl)propane-2-sulfonamide (Example 742.4) that was used without further purification. Mass Spectrum (pos.) m/z: 290.0 (M+H)$^+$.

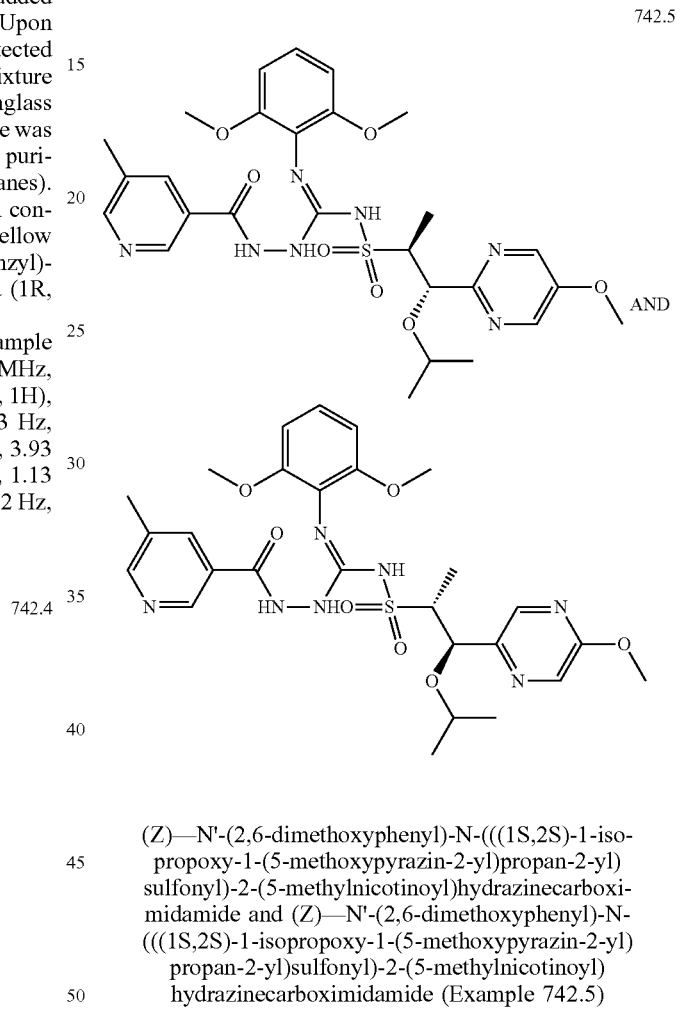

(Z)—N'-(2,6-dimethoxyphenyl)-N-(((1S,2S)-1-iso-
propoxy-1-(5-methoxypyrazin-2-yl)propan-2-yl)
sulfonyl)-2-(5-methylnicotinoyl)hydrazinecarboxi-
midamide and (Z)—N'-(2,6-dimethoxyphenyl)-N-
(((1S,2S)-1-isopropoxy-1-(5-methoxypyrazin-2-yl)
propan-2-yl)sulfonyl)-2-(5-methylnicotinoyl)
hydrazinecarboximidamide (Example 742.5)

To a vial containing (1S,2S)-1-isopropoxy-1-(5-methoxypyrazin-2-yl)propane-2-sulfonamide and (1R,2R)-1-isopropoxy-1-(5-methoxypyrazin-2-yl)propane-2-sulfonamide, Example 742.4 (302 mg, 1.04 mmol) was added ACN (4.1 mL). After 10 minutes, 2-isothiocyanato-1,3-dimethoxybenzene, Intermediate 1.0 (207 mg, 1.06 mmol) was added carefully in portions. The mixture was cooled in an ice-bath and then cesium carbonate (444 mg, 1.36 mmol) was added carefully in portions to the homogeneous solution. Upon complete addition of cesium carbonate, the mixture was allowed to warm to 23° C. After 19 hours, the mixture was cooled in an ice-water bath. After 20 minutes, 5-methylnicotinic acid hydrazide (161 mg, 1.06 mmol) and then silver nitrate (388 mg, 2.28 mmol) were carefully added in portions. This is an exothermic reaction which became bright orange and then turned dark brown on warming to RT.

The mixture was allowed to warm to 23° C. After 25 additional minutes, the mixture was loaded directly onto a Biotage SNAP Ultra column and purified (25-90% 3:1 EtOAc: EtOH in heptane). Fractions containing product were combined and then concentrated under reduced pressure to afford a light pink film as (Z)—N'-(2,6-dimethoxyphenyl)-N-(((1S,2S)-1-isopropoxy-1-(5-methoxypyrazin-2-yl)propan-2-yl)sulfonyl)-2-(5-methylnicotinoyl)hydrazinecarboximidamide and (Z)—N'-(2,6-dimethoxyphenyl)-N-(((1R,2R)-1-isopropoxy-1-(5-methoxypyrazin-2-yl)propan-2-yl)sulfonyl)-2-(5-methylnicotinoyl)hydrazinecarboximidamide, Example 742.5 (361.5 mg, 0.601 mmol, 57.5% yield) which was used without further purification. Mass Spectrum (pos.) m/z: 602.0 (M+H)$^+$.

742.6

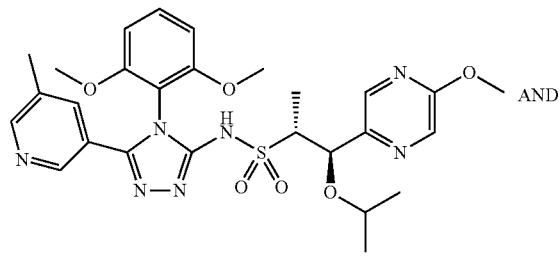

AND

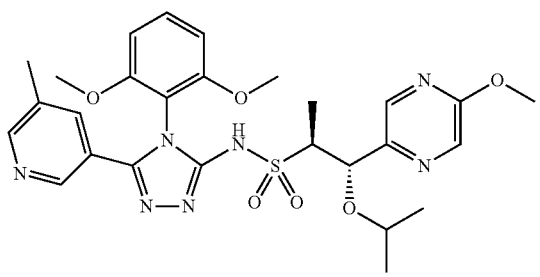

(1R,2R)—N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide, Example 742.6

To a vial containing (Z)—N'-(2,6-dimethoxyphenyl)-N-(((1S,2S)-1-isopropoxy-1-(5-methoxypyrazin-2-yl)propan-2-yl)sulfonyl)-2-(5-methylnicotinoyl)hydrazinecarboximidamide and (Z)—N'-(2,6-dimethoxyphenyl)-N-(((1R,2R)-1-isopropoxy-1-(5-methoxypyrazin-2-yl)propan-2-yl)sulfonyl)-2-(5-methylnicotinoyl)hydrazinecarboximidamide, Example 742.5 (361 mg, 0.60 mmol) in isopropanol (1.6 mL) and water (0.8 mL) was carefully added NaOH 1.0 N solution (0.73 mL, 0.73 mmol) dropwise. Upon complete addition of 1 N NaOH, the mixture was heated on a preheated stir plate at 80° C. and monitored with LCMS-ESI. After 23 hours, the reaction was cooled to RT and then it was diluted with water. The pH was carefully adjusted with dropwise addition of 1 N HCl to pH-7. The reaction mixture was extracted three times with DCM. The organics were pooled and then dried over anhydrous magnesium sulfate. After filtration and concentration under reduced pressure, the residue was loaded onto a Biotage Snap Ultra silica gel column (15-60% 3:1 EtOAc: EtOH in heptane). Fractions containing product were combined and then concentrated under reduced pressure to afford (1R,2R)—N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide and (1S,2S)—N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide, Example 742.6 (137 mg, 0.23 mmol, 39% yield) as a white foam. Mass Spectrum (pos.) m/z: 584.0 (M+H)$^+$.

The compounds set forth in the following Table were purified following the procedure described.

TABLE 39

| Example | Reagents | Structure, Name and Data |
|---|---|---|
| 742.0 | Example 742.6 was purified by preparative SFC using the following method: Column: AD-H (2 × 25 cm) Mobile Phase: 70:30 (A:B) A: Liquid CO$_2$, B: iPrOH, Flow Rate: 60 mL/min, 220 nm, 100 bar inlet pressure to deliver peak 1. | |

OR

TABLE 39-continued

| Example | Reagents | Structure, Name and Data |
|---|---|---|
| | | 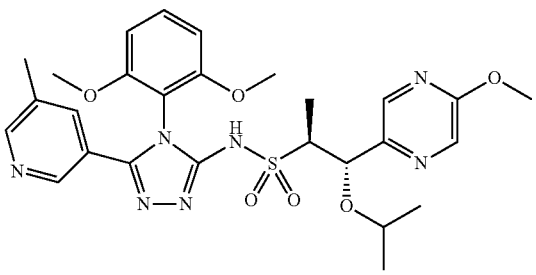 [SMILES: COc1cnc([C@H](OC(C)C)[C@H](C)S(=O)(=O)Nc2nnc(-c3cncc(C)c3)n2-c2c(OC)cccc2OC)cn1]<br>(1R,2R)-N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide or (1S,2S)-N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide. $^1$H NMR (400 MHz, CD$_3$OD) δ 8.43 (d, J = 1.2 Hz, 1H), 8.30 (d, J = 1.7 Hz, 1H), 8.14-8.11 (m, 2H), 7.69 (dt, J = 0.7, 2.0 Hz, 1H), 7.54-7.47 (m, 1H), 6.82 (s, 1H), 6.79 (s, 1H), 4.87 (s, 1H), 3.97 (s, 3H), 3.79 (s, 6H), 3.56-3.46 (m, 2H), 2.30 (s, 3H), 1.14 (d, J = 7.0 Hz, 3H), 1.11 (d, J = 6.0 Hz, 3H), 0.95 (d, J = 6.2 Hz, 3H). Mass Spectrum (pos.) m/z: 584.0 (M + H)$^+$. |
| 743.0 | Example 742.6 was purified by preparative SFC using the following method: Column: AD-H (2 × 25 cm) Mobile Phase: 70:30 (A:B) A: Liquid CO$_2$, B: iPrOH, Flow Rate: 60 mL/min, 220 nm, 100 bar inlet pressure to deliver the second eluting peak. | 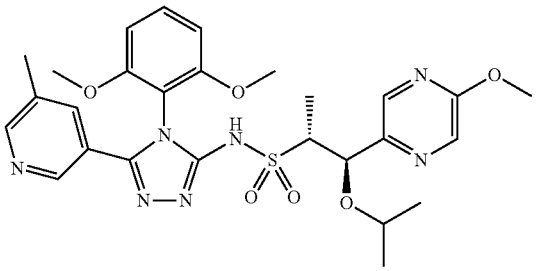 [SMILES: COc1cnc([C@@H](OC(C)C)[C@@H](C)S(=O)(=O)Nc2nnc(-c3cncc(C)c3)n2-c2c(OC)cccc2OC)cn1]<br>OR<br>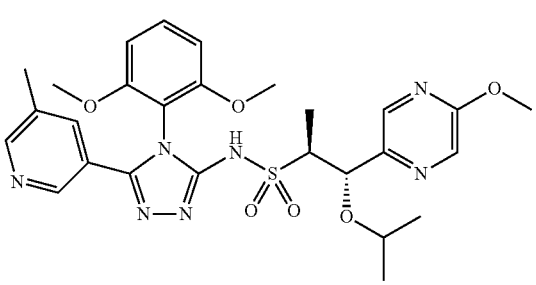 [SMILES: COc1cnc([C@H](OC(C)C)[C@H](C)S(=O)(=O)Nc2nnc(-c3cncc(C)c3)n2-c2c(OC)cccc2OC)cn1]<br>(1R,2R)-N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide or (1S,2S)-N-(4-(2,6-dimethoxyphenyl)-5-(5-methylpyridin-3-yl)-4H-1,2,4-triazol-3-yl)-1-isopropoxy-1-(5-methoxypyrazin-2-yl)propane-2-sulfonamide. $^1$H NMR (400 MHz, CD$_3$OD) δ 8.43 (s, 1H), 8.30 (d, J = 1.5 Hz, 1H), 8.15-8.12 (m, 2H), 7.69 (d, J = 0.6 Hz, 1H), 7.50 (t, J = 8.5 Hz, 1H), 6.82 (s, 1H), 6.79 (s, 1H), 4.87 (br. s., 1H), 3.97 (s, 3H), 3.79 (s, 6H), 3.54-3.46 (m, 2H), 2.30 (s, 3H), 1.16-1.13 (m, 3H), 1.11 (d, J = 6.0 Hz, 3H), 0.95 (d, J = 6.2 Hz, 3H). Mass Spectrum (pos.) m/z: 584.0 (M + H)$^+$. |

Example 744.0: Preparation of (1R,2R)-1-(5-chloro-pyridin-2-yl)-N-(4-(2,6-dimethoxyphenyl)-5-(5-methylpyridin-3-yl)-4H-1,2,4-triazol-3-yl)-1-isopropoxypropane-2-sulfonamide or (1S,2S)-1-(5-chloropyridin-2-yl)-N-(4-(2,6-(trimethoxyphenyl)-5-(5-methylpyridin-3-yl)-4H-1,2,4-triazol-3-yl)-1-isopropoxypropane-2-sulfonamide

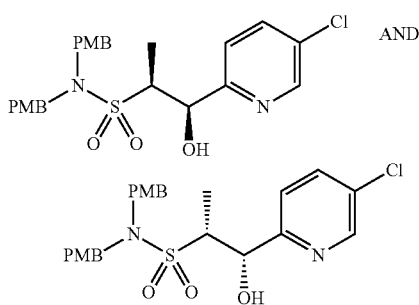

744.1

(1R,2S)-1-(5-chloropyridin-2-yl)-1-hydroxy-N,N-bis(4-methoxybenzyl)propane-2-sulfonamide and (1S,2R)-1-(5-chloropyridin-2-yl)-1-hydroxy-N,N-bis(4-methoxybenzyl)propane-2-sulfonamide, Example 744.1

To a stirred solution of N,N-bis(4-methoxybenzyl)ethanesulfonamide (Example 12.0) (3.46 g, 9.90 mmol) in THF (49 mL) at −78° C. was added n-butyllithium solution (2.5 M in hexanes, 4.4 mL, 10.9 mmol) dropwise. After 5 minutes, a solution of 5-chloro-2-pyridinecarbaldehyde (1.4 g, 9.9 mmol) in anhydrous THF (16.5 mL) was added dropwise over 5 minutes. Upon complete addition, the reaction was maintained at −78° C. and monitored with LCMS-ESI. After 1 hour, the reaction was quenched with saturated aqueous ammonium chloride solution. After extracting three times with EtOAc, the organics were pooled and then dried over anhydrous magnesium sulfate. After filtration and concentration under reduced pressure, the dark brown residue was purified on silica gel eluting with 0-100% 3:1 EtOAc: EtOH in heptane to afford (1R,2S)-1-(5-chloropyridin-2-yl)-1-hydroxy-N,N-bis(4-methoxybenzyl)propane-2-sulfonamide and (1S,2R)-1-(5-chloropyridin-2-yl)-1-hydroxy-N,N-bis(4-methoxybenzyl)propane-2-sulfonamide (Example 744.1) (3.16 g, 6.44 mmol, 65.0% yield) as a light yellow solid. Mass Spectrum (pos.) m/z: 491.1 (M+H)$^+$.

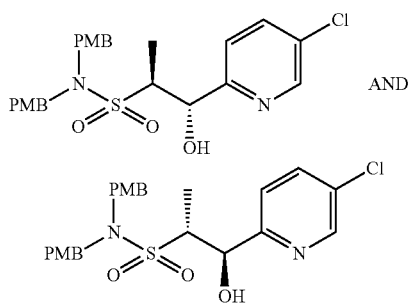

744.2

(1R,2R)-1-(5-chloropyridin-2-yl)-1-hydroxy-N,N-bis(4-methoxybenzyl)propane-2-sulfonamide and (1S,2S)-1-(5-chloropyridin-2-yl)-1-hydroxy-N,N-bis(4-methoxybenzyl)propane-2-sulfonamide, Example 744.2

Further elution using the conditions described in Example 744.1 delivered (1R,2R)-1-(5-chloropyridin-2-yl)-1-hydroxy-N,N-bis(4-methoxybenzyl)propane-2-sulfonamide and (1S,2S)-1-(5-chloropyridin-2-yl)-1-hydroxy-N,N-bis(4-methoxybenzyl)propane-2-sulfonamide (Example 744.2). (1.54 g, 3.14 mmol, 31.7% yield) as a light-yellow solid. Mass Spectrum (pos.) m/z: 491.0 (M+H)$^+$.

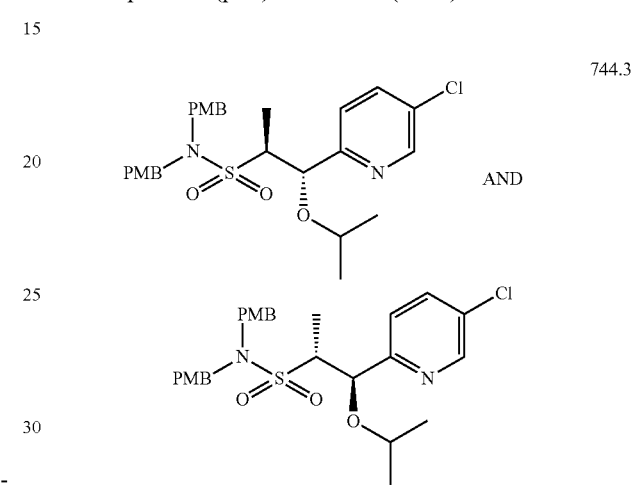

744.3

(1S,2S)-1-(5-chloropyridin-2-yl)-1-isopropoxy-N,N-bis(4-methoxybenzyl)propane-2-sulfonamide and (1R,2R)-1-(5-chloropyridin-2-yl)-1-isopropoxy-N,N-bis(4-methoxybenzyl)propane-2-sulfonamide, Example 744.3

To a vial containing (1R,2R)-1-(5-chloropyridin-2-yl)-1-hydroxy-N,N-bis(4-methoxybenzyl)propane-2-sulfonamide and (1S,2S)-1-(5-chloropyridin-2-yl)-1-hydroxy-N,N-bis(4-methoxybenzyl)propane-2-sulfonamide, (Example 744.2, 1.6 g, 3.3 mmol) and isopropyl iodide (4.6 mL, 46 mmol) in anhydrous toluene (13 mL) was added silver(I) oxide (1.57 g, 6.77 mmol) carefully in portions. Upon complete addition of silver oxide, the reaction was protected from light and heated to 70° C. After 24 hours, the mixture was cooled to RT and then filtered through a Chemglass disposable filter that was rinsed with EtOAc. The filtrate was concentrated under reduced pressure. The residue was loaded onto a silica gel column (0-50% EtOAc in heptanes). Fractions containing product were combined and then concentrated under reduced pressure to afford a dark yellow gum as (1S,2S)-1-(5-chloropyridin-2-yl)-1-isopropoxy-N,N-bis(4-methoxybenzyl)propane-2-sulfonamide and (1R,2R)-1-(5-chloropyridin-2-yl)-1-isopropoxy-N,N-bis(4-methoxybenzyl)propane-2-sulfonamide (Example 744.3) (660.3 mg, 1.239 mmol, 38.0% yield). $^1$H NMR (400 MHz, DMSO-d$_6$) δ 8.62 (dd, J=0.6, 2.5 Hz, 1H), 7.98 (dd, J=2.6, 8.4 Hz, 1H), 7.52 (d, J=8.5 Hz, 1H), 7.20-7.15 (m, 4H), 6.89-6.85 (m, 4H), 4.77 (d, J=7.3 Hz, 1H), 4.33 (d, J=15.3 Hz, 2H), 4.19-4.11 (m, 2H), 3.73 (s, 6H), 3.73-3.68 (m, 1H), 3.37 (td, J=6.1, 12.2 Hz, 1H), 1.12 (d, J=6.0 Hz, 3H), 1.01 (m, 6H). Mass Spectrum (pos.) m/z: 533.0 (M+H)$^+$.

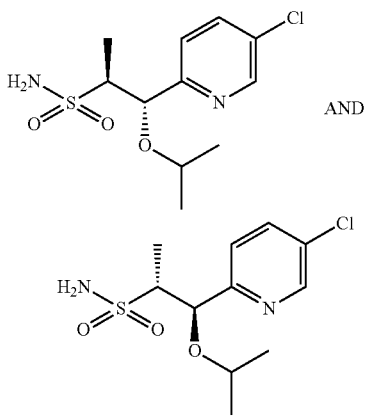

(1S,2S)-1-(5-chloropyridin-2-yl)-1-isopropoxypropane-2-sulfonamide and (1R,2R)-1-(5-chloropyridin-2-yl)-1-isopropoxypropane-2-sulfonamide, Example 744.4

Anisole (0.54 mL, 4.94 mmol) was added to a vial containing (1S,2S)-1-(5-chloropyridin-2-yl)-1-isopropoxy-N,N-bis(4-methoxybenzyl)propane-2-sulfonamide and (1R,2R)-1-(5-chloropyridin-2-yl)-1-isopropoxy-N,N-bis(4-methoxybenzyl)propane-2-sulfonamide (Example 744.3, 660 mg, 1.24 mmol) and DCM (3.1 mL). The homogeneous solution was cooled in an ice-water bath. After 15 minutes, TFA (3.2 mL, 41 mmol) was added dropwise to the reaction solution. Upon complete addition of TFA, the reaction was allowed to warm to 23° C. After 20 hours, the brownish reaction solution was concentrated under reduced pressure. The residue was loaded onto a silica gel column (10-40% 3:1 EtOAc: EtOH in heptanes). Fractions containing product were concentrated under reduced pressure to afford a tan solid as (1S,2S)-1-(5-chloropyridin-2-yl)-1-isopropoxypropane-2-sulfonamide and (1R,2R)-1-(5-chloropyridin-2-yl)-1-isopropoxypropane-2-sulfonamide (Example 744.4, 312.6 mg, 1.07 mmol, 86% yield) that was used without further purification. Mass Spectrum (pos.) m/z: 293.0 (M+H)$^+$.

The compounds set forth in the following Table were synthesized following the procedure in Example 741.0 using the known starting material as described.

TABLE 40

| Example | Reagents | Structure, Name and Data |
| --- | --- | --- |
| 744.0 | 1S,2S)-1-(5-chloropyridin-2-yl)-1-isopropoxypropane-2-sulfonamide and (1R,2R)-1-(5-chloropyridin-2-yl)-1-isopropoxypropane-2-sulfonamide (Example 744.4), 5-methylnicotinic acid hydrazide (commercially available from Bellen Chemistry Co., Ltd.), 2-isothiocyanato-1,3-dimethoxybenzene (Example 1.0). The racemic mixture was purified by preparative SFC using the following method: Column: AD-H (2 × 25 cm) Mobile Phase: 65:35 (A:B) A: Liquid CO$_2$, B: iPrOH, Flow Rate: 60 mL/min, 220 nm, 100 bar inlet pressure to deliver peak 1. | (1R,2R)-1-(5-chloropyridin-2-yl)-N-(4-(2,6-dimethoxyphenyl)-5-(5-methylpyridin-3-yl)-4H-1,2,4-triazol-3-yl)-1-isopropoxypropane-2-sulfonamide or (1S,2S)-1-(5-chloropyridin-2-yl)-N-(4-(2,6-dimethoxyphenyl)-5-(5-methylpyridin-3-yl)-4H-1,2,4-triazol-3-yl)-1-isopropoxypropane-2-sulfonamide. $^1$H NMR (400 MHz, DMSO-d$_6$) δ 13.29 (s, 1H), 8.54 (d, J = 2.5 Hz, 1H), 8.47 (s, 1H), 8.20 (d, J = 1.5 Hz, 1H), 7.90 (dd, J = 2.4, 8.4 Hz, 1H), 7.60 (s, 1H), 7.50 (t, J = 8.5 Hz, 1H), 7.43 (d, J = 8.5 Hz, 1H), 6.83 (d, J = 8.5 Hz, 2H), 4.70 (d, J = 6.8 Hz, 1H), 3.72 (s, 6H), 3.43-3.34 (m, 2H), 2.24 (s, 3H), 1.02 (d, J = 6.0 Hz, 3H), 0.94 (d, J = 7.0 Hz, 3H), 0.85 (d, J = 6.2 Hz, 3H). Mass Spectrum (pos.) m/z: 587.0 (M + H)$^+$. |

TABLE 40-continued

| Example | Reagents | Structure, Name and Data |
|---|---|---|
| 745.0 | 1S,2S)-1-(5-chloropyridin-2-yl)-1-isopropoxypropane-2-sulfonamide and (1R,2R)-1-(5-chloropyridin-2-yl)-1-isopropoxypropane-2-sulfonamide (Example 744.4), 5-methylnicotinic acid hydrazide (commercially available from Bellen Chemistry Co., Ltd.), 2-isothiocyanato-1,3-dimethoxybenzene (Example 1.0). The racemic mixture was purified by preparative SFC method: Column: AD-H (2 × 25 cm) Mobile Phase: 65:35 (A:B) A: Liquid $CO_2$, B: iPrOH, Flow Rate: 60 mL/min, 220 nm, 100 bar inlet pressure to deliver the second eluting peak. | 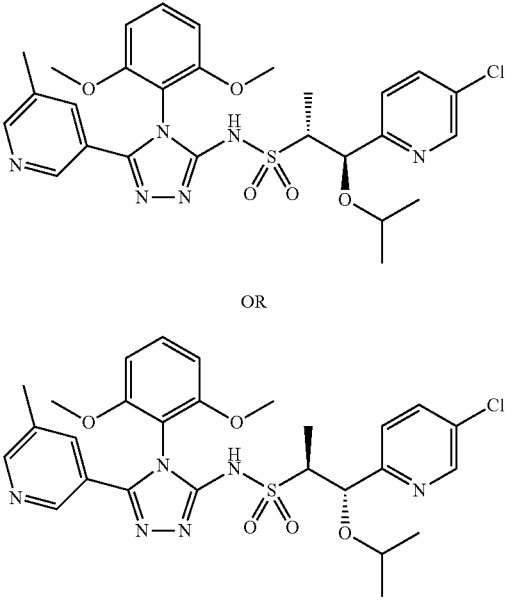<br>(1R,2R)-1-(5-chloropyridin-2-yl)-N-(4-(2,6-dimethoxyphenyl)-5-(5-methylpyridin-3-yl)-4H-1,2,4-triazol-3-yl)-1-isopropoxypropane-2-sulfonamide or (1S,2S)-1-(5-chloropyridin-2-yl)-N-(4-(2,6-dimethoxyphenyl)-5-(5-methylpyridin-3-yl)-4H-1,2,4-triazol-3-yl)-1-isopropoxypropane-2-sulfonamide. $^1$H NMR (400 MHz, DMSO-$d_6$) δ 13.29 (s, 1H), 8.54 (d, J = 2.3 Hz, 1H), 8.47 (d, J = 1.7 Hz, 1H), 8.20 (d, J = 1.9 Hz, 1H), 7.90 (dd, J = 2.5, 8.3 Hz, 1H), 7.60 (s, 1H), 7.49 (t, J = 8.5 Hz, 1H), 7.43 (d, J = 8.3 Hz, 1H), 6.84 (s, 1H), 6.82 (s, 1H), 4.70 (d, J = 6.6 Hz, 1H), 3.72 (s, 6H), 3.44-3.35 (m, 2H), 2.24 (s, 3H), 1.02 (d, J = 6.2 Hz, 3H), 0.94 (d, J = 7.0 Hz, 3H), 0.85 (d, J = 6.2 Hz, 3H). Mass Spectrum (pos.) m/z: 587.0 (M + H)$^+$. |

Example 746.0: Preparation of (1R,2R)—N-(4-(2,6-dimethoxyphenyl)-5-(5-methylpyridin-3-yl)-4H-1,2,4-triazol-3-yl)-1-isopropoxy-1-(5-methylpyrazin-2-yl)propane-2-sulfonamide or (1S,2S)—N-(4-(2,6-dimethoxyphenyl)-5-(5-methylpyridin-3-yl)-4H-1,2,4-triazol-3-yl)-1-isopropoxy-1-(5-methylpyrazin-2-yl)propane-2-sulfonamide 746.1

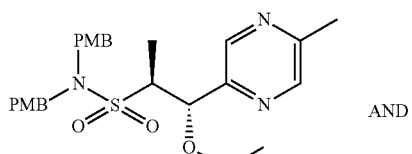 AND 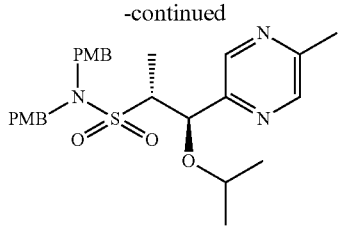

(1S,2S)-1-isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide, Example 746.1

To a flask containing (1S,2S)-1-hydroxy-N,N-bis(4-methoxybenzyl)-1-(5-methylpyrazin-2-yl)propane-2-sulfonamide and (1R,2R)-1-hydroxy-N,N-bis(4-methoxybenzyl)-1-(5-methylpyrazin-2-yl)propane-2-sulfonamide (4.16 g, 8.81 mmol) and isopropyl iodide (12.3 mL, 123 mmol) in anhydrous toluene (35 mL) was added silver(I) oxide (4.17 g, 18.0 mmol) carefully in portions. Upon complete addition of silver oxide, the reaction was protected from light and heated to an internal temperature of 72° C. After 60 hours, the mixture was cooled to RT and then filtered through a Chemglass disposable filter that was rinsed with EtOAc. The filtrate was concentrated under reduced pressure. The dark brown residue was loaded onto a silica gel column (10-55% EtOAc in heptanes). Fractions containing the product were combined and then concentrated under reduced pressure to afford (1S,2S)-1-isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methyl-pyrazin-2-yl)propane-2-sulfonamide (Example 746.1, 1.52 g, 2.97 mmol, 34% yield) as a dark brown oil that was used without further purification. $^1$H NMR (400 MHz, DMSO-$d_6$) δ 8.58 (d, J=1.5 Hz, 1H), 8.54 (d, J=0.8 Hz, 1H), 7.20-7.15 (m, 4H), 6.89-6.85 (m, 4H), 4.81 (d, J=7.0 Hz, 1H), 4.35-4.29 (m, 2H), 4.20-4.13 (m, 2H), 3.76-3.71 (m, 7H), 3.39 (quin, J=6.1 Hz, 1H), 2.51 (s, 3H), 1.13 (d, J=6.0 Hz, 3H), 1.05 (d, J=7.3 Hz, 3H), 0.99 (d, J=6.2 Hz, 3H). Mass Spectrum (pos.) m/z: 514.0 (M+H)$^+$.

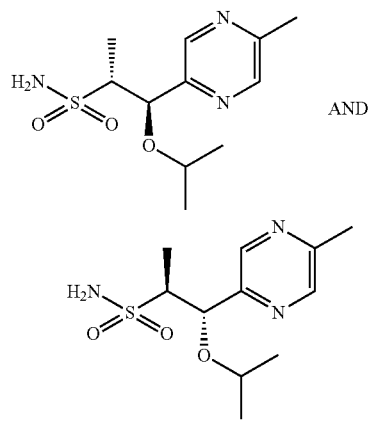

746.2

(1R,2R)-1-isopropoxy-1-(5-methylpyrazin-2-yl)propane-2-sulfonamide and (1S,2S)-1-(5-methylpyrazin-2-yl)propane-2-sulfonamide, Example 746.2

Anisole (1.3 mL, 11.9 mmol) was added to a flask containing (1S,2S)-1-isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide (Example 746.1, 1.5 g, 3 mmol) and DCM (7.5 mL). The homogeneous solution was cooled in an ice-water bath. After 15 minutes, TFA (7.6 mL, 99 mmol) was added dropwise to the reaction solution. Upon complete addition of TFA, the reaction was allowed to warm to 23° C. After 20 hours, the brownish reaction solution was concentrated under reduced pressure. The residue was loaded onto a silica gel column (15-85% EtOAc in heptanes). Fractions containing the product were concentrated under reduced pressure to afford (1R,2R)-1-isopropoxy-1-(5-methylpyrazin-2-yl)propane-2-sulfonamide and (1S,2S)-1-isopropoxy-1-(5-methylpyrazin-2-yl)propane-2-sulfonamide (Example 746.2, 714 mg, 2.6 mmol, 88% yield) as an off white solid. Mass Spectrum (pos.) m/z: 274.0 (M+H)$^+$.

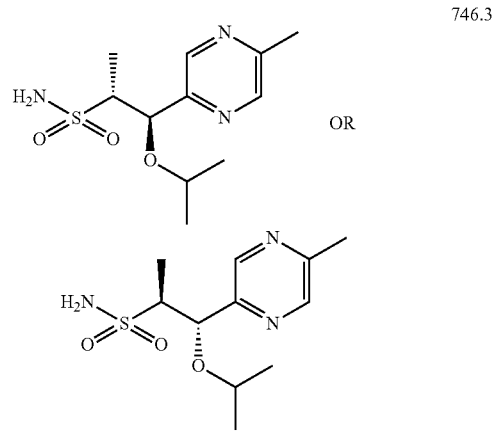

746.3

Preparation of (1R,2R)-1-isopropoxy-1-(5-methyl-pyrazin-2-yl)propane-2-sulfonamide or (1S,2S)-1-isopropoxy-1-(5-methylpyrazin-2-yl)propane-2-sulfonamide, Example 746.3

(1R,2R)-1-isopropoxy-1-(5-methylpyrazin-2-yl)propane-2-sulfonamide and (1S,2S)-1-isopropoxy-1-(5-methyl-pyrazin-2-yl)propane-2-sulfonamide (Example 746.2, 714 mg, 2.6 mmol) was purified by preparative SFC using the following conditions: Column: IC (2×25 cm) Mobile Phase: 70:30 (A:B) A: Liquid CO$_2$, B: iPrOH to afford peak 1 as (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 746.3, 293 mg, 1.07 mmol, 36% yield). $^1$H NMR (400 MHz, DMSO-$d_6$) δ 8.60 (d, J=1.5 Hz, 1H), 8.53 (d, J=0.8 Hz, 1H), 6.52 (s, 2H), 4.77 (d, J=7.0 Hz, 1H), 3.56-3.45 (m, 2H), 1.15 (d, J=6.0 Hz, 3H), 1.05 (d, J=7.0 Hz, 3H), 0.96 (d, J=6.2 Hz, 3H). (Obscured CH$_3$ in DMSO peak). Mass Spectrum (pos.) m/z: 274.2 (M+H)$^+$.

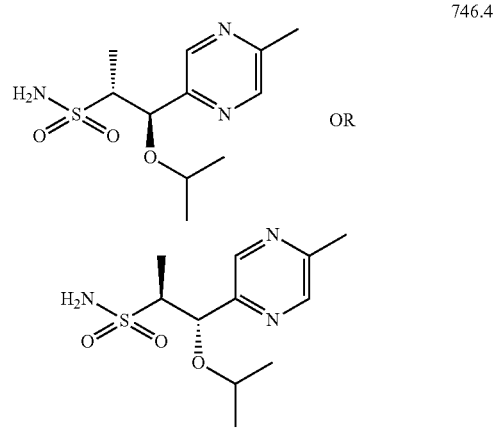

746.4

(1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide, Example 746.4

Further elution under the conditions described in Example 746.3 delivered the second eluting peak as (1R,2R)-1- isopropoxy-1-(5-methylpyrazin-2-yl)propane-2-sulfonamide or (1S,2S)-1-isopropoxy-1-(5-methylpyrazin-2-yl)propane-2-sulfonamide (Example 746.4, 303 mg, 1.11 mmol, 37% yield). $^1$H NMR (400 MHz, DMSO-$d_6$) δ 8.60 (d, J=1.5 Hz, 1H), 8.53 (d, J=1.0 Hz, 1H), 6.52 (s, 2H), 4.77 (d, J=7.0 Hz, 1H), 3.58-3.44 (m, 2H), 1.27-1.14 (m, 3H), 1.05 (d, J=7.0 Hz, 3H), 1.00-0.91 (m, 3H). (Obscured CH$_3$ in DMSO peak). Mass Spectrum (pos.) m/z: 274.2 (M+H)$^+$.

The compounds set forth in the following Table were synthesized following the procedure in Example 741.0 using the known starting material as described.

TABLE 41

| Example | Reagents | Structure, Name and Data |
|---|---|---|
| 746.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 746.3) 5-methylnicotinic acid hydrazide (commercially available from Bellen Chemistry Co., Ltd.), 2-isothiocyanato-1,3-dimethoxybenzene (Example 1.0). | 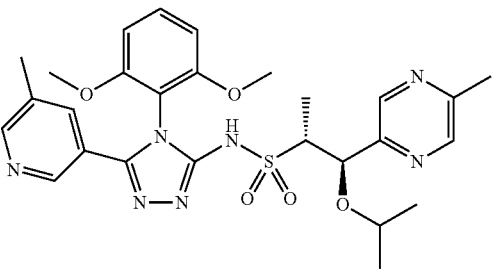 [SMILES: COc1cccc(OC)c1-n1c(NS(=O)(=O)[C@H](C)[C@H](OC(C)C)c2cnc(C)cn2)nnc1-c1cncc(C)c1]<br>OR<br><br>(1R,2R)-N-(4-(2,6-dimethoxyphenyl)-5-(5-methylpyridin-3-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-(5-methylpyridin-3-yl)-4H-1,2,4-triazol-3-yl)-1-isopropoxy-1-(5-methylpyrazin-2-yl)propane-2-sulfonamide. $^1$H NMR (400 MHz, DMSO-$d_6$) δ 13.33 (s, 1H), 8.52-8.40 (m, 3H), 8.20 (d, J = 1.9 Hz, 1H), 7.60 (td, J = 1.0, 2.1 Hz, 1H), 7.50 (t, J = 8.6 Hz, 1H), 6.84 (dd, J = 1.1, 8.6 Hz, 2H), 4.76 (d, J = 6.2 Hz, 1H), 3.72 (s, 3H), 3.72 (s, 3H), 3.50-3.37 (m, 2H), 2.47 (s, 3H), 2.25 (s, 3H), 1.07-0.98 (m, 6H), 0.86 (d, J = 6.0 Hz, 3H). Mass Spectrum (pos.) m/z: 568.0 (M + H)$^+$. |
| 747.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 746.4) 5-methylnicotinic acid hydrazide (commercially available from Bellen Chemistry Co., Ltd.), 2-isothiocyanato-1,3-dimethoxybenzene (Example 1.0). | 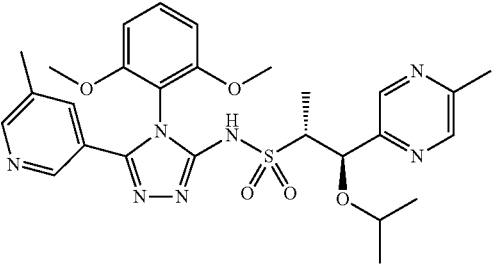 [SMILES: COc1cccc(OC)c1-n1c(NS(=O)(=O)[C@H](C)[C@H](OC(C)C)c2cnc(C)cn2)nnc1-c1cncc(C)c1]<br>OR |

TABLE 41-continued

| Example | Reagents | Structure, Name and Data |
|---------|----------|--------------------------|

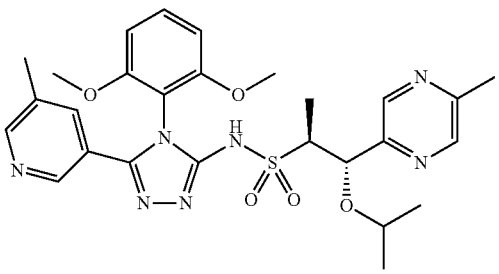 [SMILES: COc1cccc(OC)c1-n1c(NS(=O)(=O)[C@@H](C)[C@@H](OC(C)C)c2cnc(C)cn2)nnc1-c1cncc(C)c1]

(1R,2R)-N-(4-(2,6-dimethoxyphenyl)-5-(5-methylpyridin-3-yl)-4H-1,2,4-triazol-3-yl)-1-isopropoxy-1-(5-methylpyrazin-2-yl)propane-2-sulfonamide or (1S,2S)-N-(4-(2,6-dimethoxyphenyl)-5-(5-methylpyridin-3-yl)-4H-1,2,4-triazol-3-yl)-1-isopropoxy-1-(5-methylpyrazin-2-yl)propane-2-sulfonamide. $^1$H NMR (400 MHz, DMSO-$d_6$) δ 13.33 (s, 1H), 8.53-8.42 (m, 3H), 8.19 (d, J = 1.7 Hz, 1H), 7.60 (dt, J = 0.8, 2.1 Hz, 1H), 7.50 (t, J = 8.6 Hz, 1H), 6.84 (dd, J = 1.1, 8.6 Hz, 2H), 4.76 (d, J = 6.2 Hz, 1H), 3.72 (s, 3H), 3.72 (s, 3H), 3.50-3.37 (m, 2H), 2.47 (s, 3H), 2.25 (s, 3H), 1.02 (dd, J = 6.6, 7.7 Hz, 6H), 0.86 (d, J = 6.2 Hz, 3H). Mass Spectrum (pos.) m/z: 568.0 (M + H)$^+$.

Example 748.0: Preparation of (1S,2S)—N-(4-(2,6-(trimethoxyphenyl)-5-(5-methylpyridin-3-yl)-4H-1,2,4-triazol-3-yl)-1-hydroxy-1-(5-methylpyrimidin-2-yl)propane-2-sulfonamide or (1R,2R)—N-(4-(2,6-(trimethoxyphenyl)-5-(5-methylpyridin-3-yl)-4H-1,2,4-triazol-3-yl)-1-hydroxy-1-(5-methylpyrimidin-2-yl)propane-2-sulfonamide

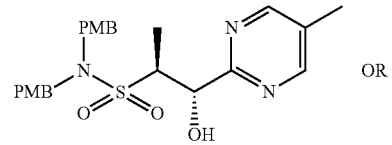

OR

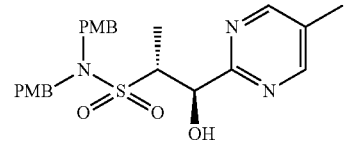

(1S,2S)-1-hydroxy-N,N-bis(4-methoxybenzyl)-1-(5-methylpyrimidin-2-yl)propane-2-sulfonamide or (1R,2R)-1-hydroxy-N,N-bis(4-methoxybenzyl)-1-(5-methylpyrimidin-2-yl)propane-2-sulfonamide, Example 748.1

(1S,2S)-1-hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide (Example 11.05, 41 g, 88 mmol) was purified by preparative SFC method: Column: IC-H (50×250 mm) Mobile Phase: 50:50 (A:B) A: Liquid CO$_2$, B: MeOH to afford peak 1 as (1S,2S)-1-hydroxy-N,N-bis(4-methoxybenzyl)-1-(5-methylpyrimidin-2-yl)propane-2-sulfonamide or (1R,2R)-1-hydroxy-N,N-bis(4-methoxybenzyl)-1-(5-methylpyrimidin-2-yl)propane-2-sulfonamide, Example 748.1 (18.6 g, 39.4 mmol). Mass Spectrum (pos.) m/z: 472.1 (M+H)$^+$.

748.2

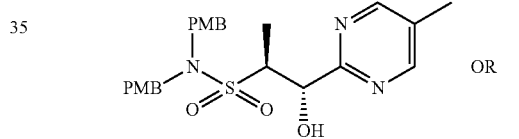

OR

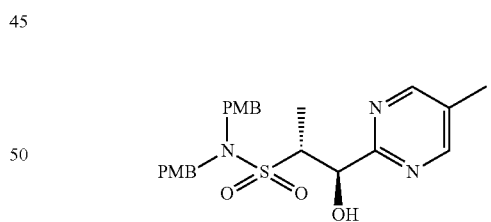

(1S,2S)-1-hydroxy-N,N-bis(4-methoxybenzyl)-1-(5-methylpyrimidin-2-yl)propane-2-sulfonamide or (1R,2R)-1-hydroxy-N,N-bis(4-methoxybenzyl)-1-(5-methylpyrimidin-2-yl)propane-2-sulfonamide, Example 748.2

Further elution under the conditions described in Example 748.1 delivered peak 2 as (1S,2S)-1-hydroxy-N,N-bis(4-methoxybenzyl)-1-(5-methylpyrimidin-2-yl)propane-2-sulfonamide or (1R,2R)-1-hydroxy-N,N-bis(4-methoxybenzyl)-1-(5-methylpyrimidin-2-yl)propane-2-sulfonamide, Example 748.2. (19.1 g, 40.5 mmol). Mass Spectrum (pos.) m/z: 472.1 (M+H)$^+$.

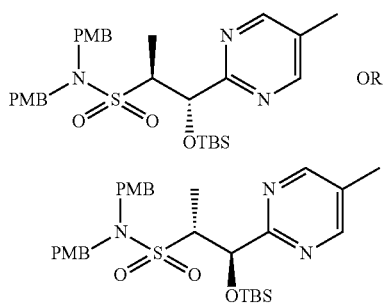

748.3

(1S,2S)-1-((tert-butyldimethylsilyl)oxy)-N,N-bis(4-methoxybenzyl)-1-(5-methylpyrimidin-2-yl)propane-2-sulfonamide or (1R,2R)-1-((tert-butyldimethylsilyl)oxy)-N,N-bis(4-methoxybenzyl)-1-(5-methylpyrimidin-2-yl)propane-2-sulfonamide, Example 748.3

A vial containing (1S,2S)-1-hydroxy-N,N-bis(4-methoxybenzyl)-1-(5-methylpyrimidin-2-yl)propane-2-sulfonamide or (1R,2R)-1-hydroxy-N,N-bis(4-methoxybenzyl)-1-(5-methylpyrimidin-2-yl)propane-2-sulfonamide (748.2, 243 mg, 0.52 mmol) in anhydrous DCM (2.5 mL) was cooled to 0° C. in an ice water bath and then TEA (0.08 mL, 0.57 mmol) and tert-butyldimethylsilyl trifluoromethanesulfonate (0.14 mL, 0.61 mmol) were added carefully dropwise. Upon complete addition of TEA, the reaction was allowed to warm to 23° C. After 1 hour, the reaction was concentrated under reduced pressure to afford a residue that was loaded onto a silica gel column (5-50% EtOAc in heptane.) Fractions containing product were combined and concentrated under reduced pressure to afford (1S,2S)-1-((tert-butyldimethylsilyl)oxy)-N,N-bis(4-methoxybenzyl)-1-(5-methylpyrimidin-2-yl)propane-2-sulfonamide or (1R,2R)-1-((tert-butyldimethylsilyl)oxy)-N,N-bis(4-methoxybenzyl)-1-(5-methylpyrimidin-2-yl)propane-2-sulfonamide (Example 748.3, 236 mg, 0.40 mmol, 78% yield) as a colorless film that was used without further purification. $^1$H NMR (400 MHz, DMSO-$d_6$) δ 8.67 (d, J=0.8 Hz, 2H), 7.18-7.12 (m, 4H), 6.89-6.83 (m, 4H), 5.10 (d, J=6.6 Hz, 1H), 4.35 (d, J=15.3 Hz, 2H), 4.12 (d, J=15.3 Hz, 2H), 3.74-3.69 (m, 7H), 2.27 (s, 3H), 1.05 (d, J=7.3 Hz, 3H), 0.81-0.76 (m, 9H), 0.01-0.02 (m, 3H), −0.19-0.23 (m, 3H). Mass Spectrum (pos.) m/z: 586.0 (M+H)$^+$.

748.4

(1S,2S)-1-((tert-butyldimethylsilyl)oxy)-1-(5-methylpyrimidin-2-yl)propane-2-sulfonamide or (1S,2S)-1-((tert-butyldimethylsilyl)oxy)-1-(5-methylpyrimidin-2-yl)propane-2-sulfonamide, Example 748.4

Anisole (0.18 mL, 1.65 mmol) was added to a vial containing Example 748.3 (236 mg, 0.40 mmol) and DCM (1 mL). The homogeneous solution was cooled in an ice-water bath. After 15 minutes, TFA (1 mL, 13 mmol) was added dropwise to the reaction solution. Upon complete addition of TFA, the reaction was allowed to warm to 23° C. After 41 hours, the brownish reaction solution was concentrated under reduced pressure. The residue was purified on a silica gel column (5-35% (3:1) EtOAc: EtOH in heptane.) Fractions containing the product were combined and then concentrated under reduced pressure to afford Example 748.4 (134 mg, 0.39 mmol, 97% yield) as a colorless film that was used without further purification. Mass Spectrum (pos.) m/z: 346.0 (M+H)$^+$.

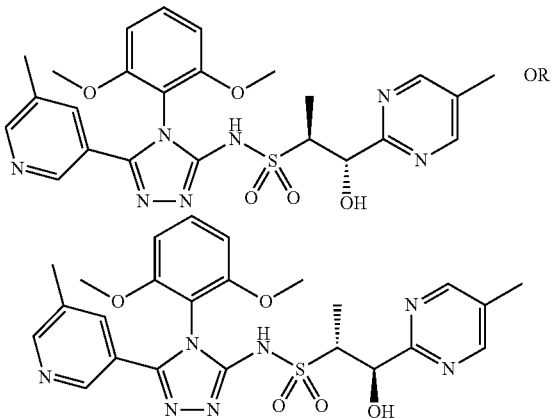

748.0

(1S,2S)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide OR (1R,2R)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide, Example 748.0

A vial containing (1S,2S)-1-((tert-butyldimethylsilyl)oxy)-1-(5-methylpyrimidin-2-yl)propane-2-sulfonamide or (1R,2R)-1-((tert-butyldimethylsilyl)oxy)-1-(5-methylpyrimidin-2-yl)propane-2-sulfonamide (Example 748.4, 134 mg, 0.39 mmol), 3-(5-bromo-4-(2,6-dimethoxyphenyl)-4H-1,2,4-triazol-3-yl)-5-methylpyridine (Intermediate 2.0, 220 mg, 0.59 mmol), copper(I) iodide (48 mg, 0.25 mmol), (1R,2R)-(−)-N,N"-dimethylcyclohexane-1,2-diamine (0.13 mL, 0.82 mmol), and cesium carbonate (326 mg, 1.0 mmol) was degassed and then backfilled with nitrogen. The evacuation and backfilling was repeated three times. Anhydrous 1,4-dioxane (0.8 mL) was then added to the mixture and the dark blue heterogeneous solution was heated on a pre-heated stirplate at 80° C. After 21 hours, the reaction was cooled to RT and then diluted with water. An aqueous solution of 1N HCl was carefully added to adjust the dark blue homogeneous solution to pH 7. After extracting four times with DCM, the organics were pooled and then washed once with aqueous 1 M sodium thiosulfate. After drying the organic layer over anhydrous MgSO$_4$, filtration, and concentration under reduced pressure, the blue green residue was loaded onto a silica gel column (5-40% 3:1 EtOAc: EtOH in heptanes). Fractions containing the product were combined and then concentrated under reduced pressure to afford a colorless film. A vial containing (1S,2S)-1-((tert-butyldimethylsilyl)oxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide or (1R,2R)-1-((tert-butyldimethylsilyl)oxy)-N-(4-(2,6-dimethoxyphenyl)-5-(5-methylpyridin-3-yl)-4H-1,2,4-triazol-3-yl)-1-(5-methylpyrimidin-2-yl)propane-2-sulfonamide (143 mg, 0.22 mmol) in anhydrous THF (0.55 mL) was cooled in an ice bath to 0° C. After 20 minutes, TBAF (1.0 M solution in THF, 0.22 mL, 0.22 mmol) was added carefully dropwise. Upon complete addition of TBAF solution, the mixture was allowed to warm to 23° C. After 20 hours, the mixture was carefully concentrated under reduced pressure. The residue was loaded onto a silica gel column (25-85% (3:1) EtOAc: EtOH in heptane.) Fractions containing product were combined and then concentrated under reduced pressure to afford (1S,2S)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide OR (1R,2R)—N-(4-(2,6-dimethoxyphenyl)-5-(5-methylpyridin-3-yl)-4H-1,2,4-triazol-3-yl)-1-hydroxy-1-(5-methylpyrimidin-2-yl)propane-2-sulfonamide (Example 748.0, 52 mg, 0.10 mmol, 45% yield) as a colorless film. $^1$H NMR (400 MHz, DMSO-d$_6$) δ 13.48 (br. s., 1H), 8.64 (d, J=0.6 Hz, 2H), 8.47 (d, J=1.5 Hz, 1H), 8.20 (d, J=1.9 Hz, 1H), 7.62 (td, J=1.1, 2.0 Hz, 1H), 7.50 (t, J=8.6 Hz, 1H), 6.83 (dd, J=1.3, 8.6 Hz, 2H), 5.13 (br. s., 1H), 4.79 (d, J=7.9 Hz, 1H), 3.74 (s, 3H), 3.71 (s, 3H), 3.46 (quin, J=7.2 Hz, 1H), 2.27 (s, 3H), 2.25 (s, 3H), 0.93 (d, J=7.0 Hz, 3H). Mass Spectrum (pos.) m/z: 526.0 (M+H)$^+$.

Example 749.0: Preparation of (1R,2S)-1-(5-(3,6-dihydro-2H-pyran-4-yl)pyrimidin-2-yl)-N-(4-(2,6-dimethoxyphenyl)-5-(5-methylpyridin-3-yl)-4H-1,2,4-triazol-3-yl)-1-methoxypropane-2-sulfonamide

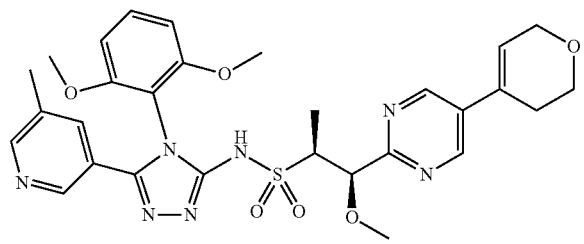

749.0

(1R,2S)-1-(5-(3,6-dihydro-2H-pyran-4-yl)pyrimidin-2-yl)-N-(4-(2,6-dimethoxyphenyl)-5-(5-methylpyridin-3-yl)-4H-1,2,4-triazol-3-yl)-1-methoxypropane-2-sulfonamide, Example 749.0

To a 50 mL round bottomed flask was added (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide Example 428.1 (0.050 g, 0.089 mmol), 2-(3,6-dihydro-2H-pyran-4-yl)-4,4,5,5-tetramethyl-1,3,2-dioxaborolane (0.060 g, 0.286 mmol), potassium phosphate (0.060 g, 0.283 mmol, Aldrich, St. Louis, Mo.), 1,1-bis[(di-t-butyl-p-methylaminophenyl]palladium(II) chloride (8.0 mg, 0.011 mmol, Aldrich, St. Louis, Mo.), 1,4-dioxane (2.0 mL), and water (0.70 mL). To the resulting mixture was attached a condenser and heated at 85° C. under N$_2$ for 2 h. The reaction was then cooled to RT and partitioned between water (10 mL) and 10% iPrOH in CHCl$_3$ (20 mL). The aqueous layer was extracted with 10% iPrOH in CHCl$_3$ (20 mL). The combined organic layers were dried over MgSO$_4$, filtered, and concentrated. The product thus obtained was purified by column chromatography (24 g of silica, 0 to 5% MeOH in DCM) to afford (1R,2S)-1-(5-(3,6-dihydro-2H-pyran-4-yl)pyrimidin-2-yl)-N-(4-(2,6-dimethoxyphenyl)-5-(5-methylpyridin-3-yl)-4H-1,2,4-triazol-3-yl)-1-methoxypropane-2-sulfonamide as a light yellow solid (0.036 g). $^1$H NMR (300 MHz, CDCl$_3$) δ 11.22 (br. s., 1H), 8.64-8.87 (m, 2H), 8.44 (d, J=1.3 Hz, 1H), 8.34 (d, J=1.6 Hz, 1H), 7.58-7.69 (m, 1H), 7.38 (t, J=8.5 Hz, 1H), 6.61 (d, J=8.5 Hz, 2H), 6.30 (d, J=1.5 Hz, 1H), 4.99 (d, J=4.7 Hz, 1H), 4.36 (q, J=2.6 Hz, 2H), 3.96 (t, J=5.5 Hz, 2H), 3.66-3.84 (m, 7H), 3.36 (s, 3H), 2.53 (dd, J=4.3, 2.7 Hz, 2H), 2.30 (s, 3H), 1.33-1.46 (m, 3H), 1.33-1.46 (m, 3H), 1.33-1.46 (m, 3H). LCMS-ESI-ESI (POS.) m/z: 608.0 (M+H)$^+$.

Example 750.0: Preparation of (1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide

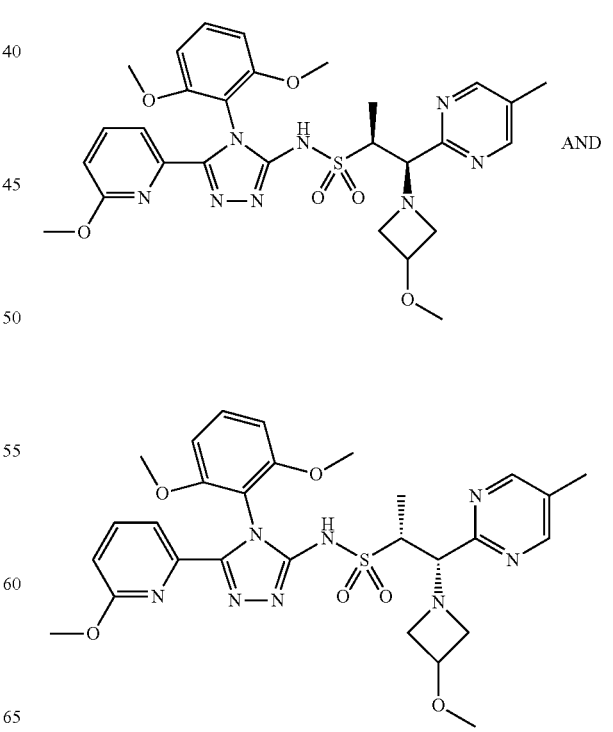

750.0

(1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide, Example 750.0

To a solution of (S)—N-(4-(2,6-dimethoxyphenyl)-5-(6-methoxypyridin-2-yl)-4H-1,2,4-triazol-3-yl)-1-(5-methylpyrimidin-2-yl)-1-oxopropane-2-sulfonamide and (R)—N-(4-(2,6-dimethoxyphenyl)-5-(6-methoxypyridin-2-yl)-4H-1,2,4-triazol-3-yl)-1-(5-methylpyrimidin-2-yl)-1-oxopropane-2-sulfonamide, Example 421.1 (0.100 g, 0.185 mmol) in DCM (3.0 mL) was added 3-methoxyazetidine hydrochloride (0.070 g, 0.57 mmol, J&W Pharmlab, Levittown, Pa.), di-isopropylethylamine (0.100 mL, 0.58 mmol, Aldrich, St. Louis, Mo.), triethyl orthoformate (0.130 mL, 0.782 mmol, Aldrich, St. Louis, Mo.), and 2 drops of AcOH. The resulting mixture was stirred at RT under N₂ for 18 h. To this reaction was added sodium borohydride (0.021 g, 0.56 mmol, Aldrich, St. Louis, Mo.) and MeOH (0.5 mL), and the resulting mixture was stirred at RT for 20 min. The reaction was then quenched with water (3 mL). The resulting mixture was partitioned between water (15 mL) and DCM (30 mL). The aqueous layer was extracted with 10% iPrOH in CHCl₃ (3×30 mL). The combined organic layers were dried over MgSO₄, filtered, and concentrated. The product thus obtained was purified by column chromatography (40 g of silica, 0 to 8% MeOH in DCM) to obtain (1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide and (1S,2R)—N-(4-(2,6-dimethoxyphenyl)-5-(6-methoxypyridin-2-yl)-4H-1,2,4-triazol-3-yl)-1-(3-methoxy azetidin-1-yl)-1-(5-methylpyrimidin-2-yl)propane-2-sulfonamide (Example 750.0). ¹H NMR (300 MHz, CDCl₃) δ 8.62 (s, 2H), 7.54-7.66 (m, 2H), 7.28-7.35 (m, 1H), 6.66-6.73 (m, 1H), 6.56-6.64 (m, 2H), 4.20 (d, J=6.0 Hz, 1H), 3.97-4.09 (m, 1H), 3.76 (s, 3H), 3.65-3.74 (m, 4H), 3.52-3.64 (m, 2H), 3.18 (d, J=4.2 Hz, 6H), 3.01 (t, J=6.6 Hz, 1H), 2.94 (t, J=6.4 Hz, 1H), 2.31-2.37 (m, 3H), 1.28 (s, 3H). One exchangeable proton was not observed. LCMS-ESI-ESI (POS.) m/z: 611.0 (M+H)⁺.

Example 751.0: Preparation of (1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide and (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide

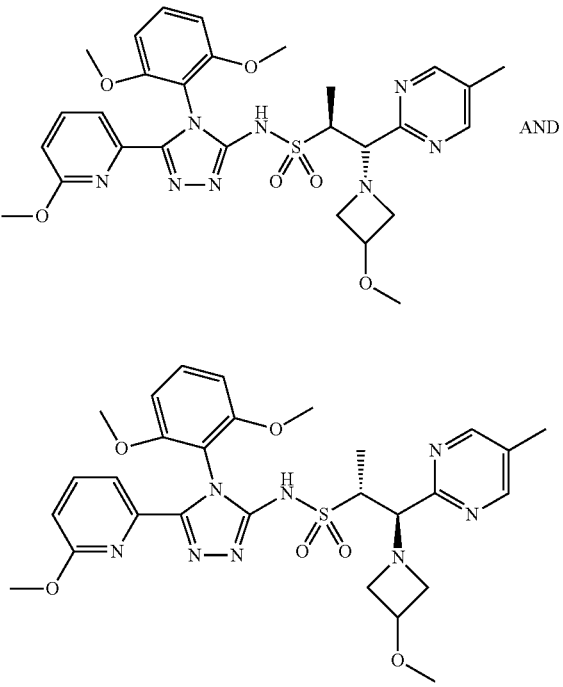

751.0

(1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide and (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide, Example 751.0

Further elution under the conditions described in Example 750.0, provided (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide and (1R,2R)—N-(4-(2,6-dimethoxyphenyl)-5-(6-methoxypyridin-2-yl)-4H-1,2,4-triazol-3-yl)-1-(3-methoxy azetidin-1-yl)-1-(5-methylpyrimidin-2-yl)propane-2-sulfonamide (Example 751.0). ¹H NMR (300 MHz, CDCl₃) δ 8.60 (s, 2H), 7.56-7.66 (m, 2H), 7.28-7.35 (m, 1H), 6.66-6.73 (m, 1H), 6.60 (dd, J=8.5, 2.6 Hz, 2H), 4.22 (d, J=7.0 Hz, 1H), 3.91-4.01 (m, 1H), 3.75-3.84 (m, 2H), 3.74 (s, 3H), 3.69 (s, 3H), 3.39-3.51 (m, 1H), 3.14-3.20 (m, 6H), 3.01-3.12 (m, 2H), 2.32 (s, 3H), 1.50 (d, J=7.2 Hz, 3H). One exchangeable proton was not observed. LCMS-ESI-ESI (POS.) m/z: 611.0 (M+H)⁺.

Example 752.0: Preparation of (1R,2S)—N-(4-(2,6-dimethoxyphenyl)-5-(5-methylpyridin-3-yl)-4H-1,2,4-triazol-3-yl)-1-methoxy-1-(5-(pyridin-3-yl)pyrimidin-2-yl)propane-2-sulfonamide

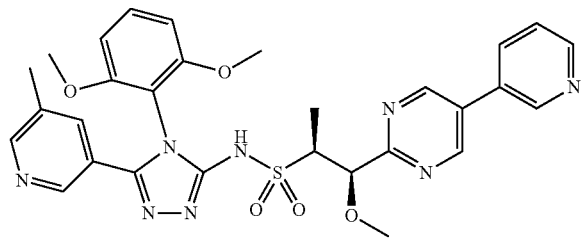

(1R,2S)—N-(4-(2,6-dimethoxyphenyl)-5-(5-methylpyridin-3-yl)-4H-1,2,4-triazol-3-yl)-1-methoxy-1-(5-(pyridin-3-yl)pyrimidin-2-yl)propane-2-sulfonamide, Example 752.0

To a 50 mL round bottomed flask was added (1R,2S)-1-(5-chloropyrimidin-2-yl)-N-(4-(2,6-dimethoxyphenyl)-5-(5-methylpyridin-3-yl)-4H-1,2,4-triazol-3-yl)-1-methoxypropane-2-sulfonamide, Example 428.1 (0.050 g, 0.089 mmol), 3-pyridineboronic acid pinacol ester (0.060 g, 0.293 mmol, Oakwood Products, West Columbia, S.C.), potassium phosphate (0.060 g, 0.283 mmol, Aldrich, St. Louis, Mo.), (AmPhos) 1,1-bis[(di-t-butyl-p-methylaminophenyl]palladium(II) chloride (8.0 mg, 0.011 mmol, Aldrich, St. Louis, Mo.), 1,4-dioxane (2.0 mL), and water (0.70 mL). The resulting mixture was bubbled with Ar for a couple minutes, a condenser was attached, and the reaction mixture was heated at 85° C. under $N_2$ for 20 h. The reaction mixture was then cooled to RT and partitioned between water (20 mL) and 10% iPrOH in $CHCl_3$ (40 mL). The aqueous layer was extracted with 10% iPrOH (2×40 mL). The combined organic layers were dried over $MgSO_4$, filtered, and concentrated. The product thus obtained was purified by column chromatography (12 g of silica, 0 to 10% MeOH in DCM) to afford (1R,2S)—N-(4-(2,6-dimethoxyphenyl)-5-(5-methylpyridin-3-yl)-4H-1,2,4-triazol-3-yl)-1-methoxy-1-(5-(pyridin-3-yl)pyrimidin-2-yl)propane-2-sulfonamide as a light yellow solid (0.015 g). $^1$H NMR (300 MHz, $CDCl_3$) δ 11.18 (br. s., 1H), 8.99 (s, 2H), 8.88 (d, J=1.8 Hz, 1H), 8.73 (dd, J=4.8, 1.5 Hz, 1H), 8.45 (d, J=1.6 Hz, 1H), 8.34 (d, J=1.8 Hz, 1H), 7.91 (dt, J=8.2, 1.8 Hz, 1H), 7.61-7.68 (m, 1H), 7.47 (dd, J=7.4, 4.8 Hz, 1H), 7.39 (t, J=8.5 Hz, 1H), 6.61 (d, J=8.6 Hz, 2H), 5.06 (d, J=4.8 Hz, 1H), 3.79-3.89 (m, 1H), 3.75 (d, J=7.7 Hz, 6H), 3.40 (s, 3H), 2.31 (s, 3H), 1.44 (d, J=7.0 Hz, 3H). LCMS-ESI-ESI (POS.) m/z: 602.9 $(M+H)^+$.

Example 753.0: Preparation of (1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide

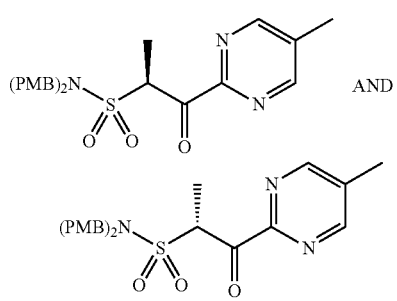

Step 1: (S)—N,N-bis(4-methoxybenzyl)-1-(5-methylpyrimidin-2-yl)-1-oxopropane-2-sulfonamide and (R)—N,N-bis(4-methoxybenzyl)-1-(5-methylpyrimidin-2-yl)-1-oxopropane-2-sulfonamide, Example 753.1

To a solution of (1S,2S)-1-hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide, Example 11.05 (5.0 g, 10.6 mmol) in DCM (80 mL) was added dess-martin periodinane (4.95 g, 11.7 mmol, Aldrich, St. Louis, Mo.). The resulting mixture was stirred at RT under $N_2$ for 7 h. Water (20 mL) and DCM (40 mL) were added. The layers were separated and the aqueous layer was extracted with DCM (40 mL), 10% iPrOH in $CHCl_3$ (4×40 mL). The combined organic layers were dried over $MgSO_4$, filtered, and concentrated. The product thus obtained was purified by column chromatography (220 g of silica, 10 to 40% acetone in hexanes) to obtain Example 753.1 as a light yellow foam (4.9 g). $^1$H NMR ($CDCl_3$) δ 8.74 (s, 2H), 7.13-7.19 (m, 4H), 6.74-6.82 (m, 4H), 5.98 (q, J=7.0 Hz, 1H), 4.26-4.36 (m, 4H), 3.74-3.86 (m, 7H), 2.44 (s, 3H), 1.70 (d, J=7.0 Hz, 3H). MS-ESI (POS.) m/z: 470.0 $(M+H)^+$.

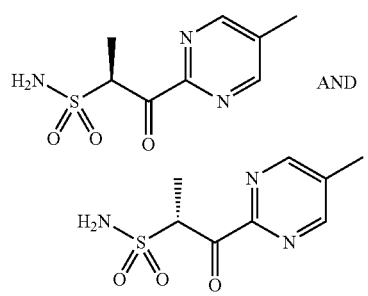

Step 2: (S)-1-(5-methylpyrimidin-2-yl)-1-oxopropane-2-sulfonamide and (R)-1-(5-methylpyrimidin-2-yl)-1-oxopropane-2-sulfonamide, Example 753.2

To a solution of (S)—N,N-bis(4-methoxybenzyl)-1-(5-methylpyrimidin-2-yl)-1-oxopropane-2-sulfonamide and (R)—N,N-bis(4-methoxybenzyl)-1-(5-methylpyrimidin-2-yl)-1-oxopropane-2-sulfonamide (4.9 g, 10.44 mmol) in DCM (30 mL) was added anisole (5.3 mL, 48.8 mmol, Aldrich, St. Louis, Mo.). The reaction mixture was cooled in ice bath and treated with TFA (30.0 mL) dropwise via an addition funnel. After the addition, the resulting mixture was stirred in an ice bath for an hour and then warmed up to RT. The resulting mixture was stirred at RT for 2 days. The reaction mixture was then concentrated. The product thus obtained was purified by column chromatography (330 g of silica, 5 to 50% acetone in hexanes) providing Example 753.2 as a white foam (1.9 g). $^1$H NMR (CDCl$_3$) δ 8.80 (s, 2H), 5.97 (q, J=7.1 Hz, 1H), 4.86 (br. s., 2H), 2.37-2.55 (m, 3H), 1.76 (d, J=7.0 Hz, 3H). MS-ESI (POS.) m/z: 230.0 (M+H)$^+$.

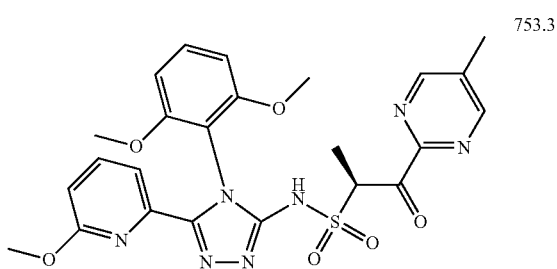

Step 3: (S)—N-(4-(2,6-dimethoxyphenyl)-5-(6-methoxypyridin-2-yl)-4H-1,2,4-triazol-3-yl)-1-(5-methylpyrimidin-2-yl)-1-oxopropane-2-sulfonamide and (R)—N-(4-(2,6-dimethoxyphenyl)-5-(6-methoxypyridin-2-yl)-4H-1,2,4-triazol-3-yl)-1-(5-methylpyrimidin-2-yl)-1-oxopropane-2-sulfonamide, Example 753.3

Following the general procedure described in Example A, the reaction of Example 753.2, 6-methoxypicolinohydrazide Example 3.18, and isothiocyanato-1,3-dimethoxybenzene Example 1.0 provided Example 753.3. $^1$H NMR (CDCl$_3$) δ 8.67-8.76 (m, 2H), 7.47 (dd, J=8.3, 7.5 Hz, 1H), 7.29-7.35 (m, 1H), 6.56-6.68 (m, 3H), 6.43-6.54 (m, 1H), 4.41 (q, J=6.9 Hz, 1H), 3.75-3.80 (m, 3H), 3.67-3.75 (m, 3H), 3.12 (s, 3H), 2.40-2.48 (m, 3H), 1.38 (d, J=7.0 Hz, 3H). One exchangeable proton was not observed. MS-ESI (POS.) m/z: 539.9 (M+H)$^+$.

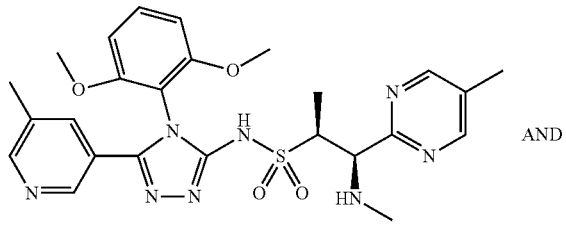

753.0

AND

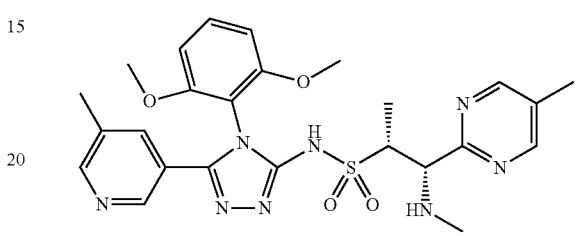

(1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide, Example 753.0

To a solution of (S)—N-(4-(2,6-dimethoxyphenyl)-5-(5-methylpyridin-3-yl)-4H-1,2,4-triazol-3-yl)-1-(5-methylpyrimidin-2-yl)-1-oxopropane-2-sulfonamide and (R)—N-(4-(2,6-dimethoxyphenyl)-5-(5-methylpyridin-3-yl)-4H-1,2,4-triazol-3-yl)-1-(5-methylpyrimidin-2-yl)-1-oxopropane-2-sulfonamide, Example 753.3 (0.200 g, 0.38 mmol) in DCM (3.0 mL) was added methylamine (33% wt. solution in absolute EtOH, 0.401 mL, 3.82 mmol, Aldrich, St. Louis, Mo.), triethyl orthoformate (0.30 mL, 1.80 mmol, Aldrich, St. Louis, Mo.), and 2 drops of AcOH. The resulting mixture was stirred at RT under N$_2$ for 20 h. To this reaction mixture was added sodium borohydride (0.050 g, 1.32 mmol, Aldrich, St. Louis, Mo.) and MeOH (0.5 mL). The reaction mixture was stirred for 20 minutes and was then quenched with water (3 mL). The resulting mixture was partitioned between water (15 mL) and DCM (30 mL). The aqueous layer was extracted with 10% iPrOH in CHCl$_3$ (3×30 mL). The combined organic layers were dried over MgSO$_4$, filtered, and concentrated. The product thus obtained was purified by column chromatography (40 g of silica, 0 to 4% MeOH in DCM) to obtain (1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide and (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide (Example 753.0). $^1$H NMR (CDCl$_3$) δ 8.58 (s, 2H), 8.44 (d, J=1.6 Hz, 1H), 8.34 (d, J=1.8 Hz, 1H), 7.60-7.67 (m, 1H), 7.39 (t, J=8.6 Hz, 1H), 6.53-6.70 (m, 2H), 4.60 (d, J=3.1 Hz, 1H), 3.62-3.82 (m, 8H), 2.36 (s, 3H), 2.31 (d, J=6.9 Hz, 6H), 1.23-1.33 (m, 4H). LCMS-ESI-ESI (POS.) m/z: 539.0 (M+H)$^+$.

Example 754.0: Preparation of (1R,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide and (1S,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide

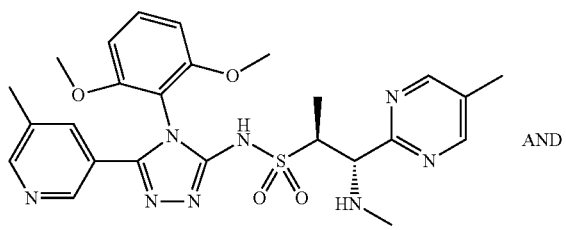

AND

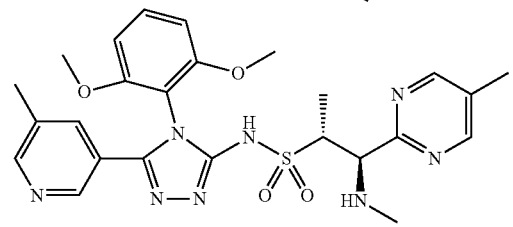

(1R,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide and (1S,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide, Example 754.0

Further elution under the conditions described in Example 753.0 delivered Example 754.0. $^1$H NMR (CDCl$_3$) δ 8.56-8.62 (m, 2H), 8.44 (d, J=1.6 Hz, 1H), 8.35 (d, J=1.8 Hz, 1H), 7.62-7.68 (m, 1H), 7.39 (t, J=8.5 Hz, 1H), 6.62 (dd, J=8.6, 2.0 Hz, 2H), 4.10 (d, J=8.9 Hz, 1H), 3.80 (s, 3H), 3.76 (s, 3H) 3.65-3.71 (m, 2H), 2.28-2.37 (m, 6H), 2.21 (s, 3H), 1.08-1.17 (m, 3H). LCMS-ESI-ESI (POS.) m/z: 539.0 (M+H)$^+$. One exchangeable proton was not observed.

Example 755.0: Preparation of (1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide 755.0

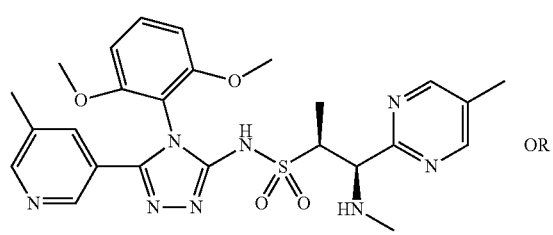

OR

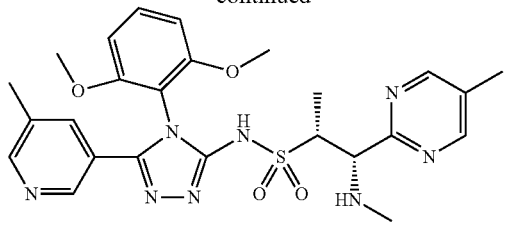

(1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide, Example 755.0

The racemic mixture of Example 753.0 was resolved using preparative SFC (OX column (5 tam, 30 mm×25 cm, 5 tam S/N=2121 regular direction) eluting with 50% liquid CO$_2$ in 50% MeOH with 0.2% isopropylamine at a flow rate of 100 mL/min) to give two products in greater than 99.5% enantiomeric excess. The first eluting peak provided (1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide. $^1$H NMR (CDCl$_3$) δ 8.58 (s, 2H), 8.44 (s, 1H), 8.33 (d, J=1.9 Hz, 1H), 7.64 (s, 1H), 7.38 (t, J=8.5 Hz, 1H), 6.61 (t, J=8.7 Hz, 2H), 4.60 (d, J=2.9 Hz, 1H), 3.69-3.81 (m, 7H), 2.42 (s, 3H), 2.32 (d, J=7.3 Hz, 8H), 1.33 (d, J=7.2 Hz, 3H). LCMS-ESI-ESI (POS.) m/z: 539.0 (M+H)$^+$.

Example 756.0: Preparation of (1R,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide 756.0

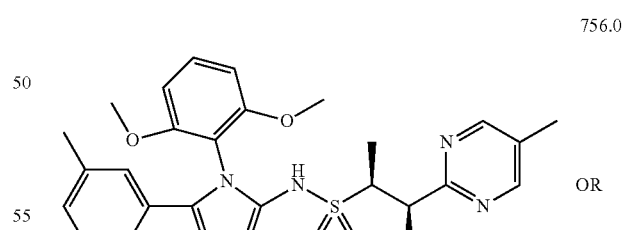

OR

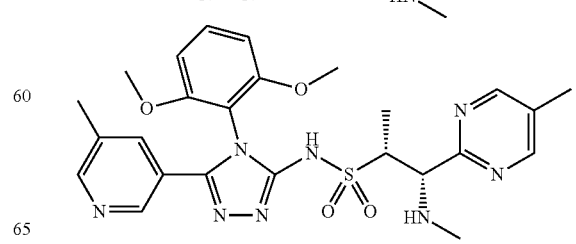

(1R,2S)—N-(4-(2,6-dimethoxyphenyl)-5-(5-methyl-pyridin-3-yl)-4H-1,2,4-triazol-3-yl)-1-(methyl-amino)-1-(5-methylpyrimidin-2-yl)propane-2-sulfo-namide or (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide, Example 756.0

The racemic mixture of Example 753.0 was resolved using preparative SFC (OX column (5 μm, 30 mm×25 cm, 5 μm S/N=2121 regular direction) eluting with 50% liquid $CO_2$ in 50% MeOH with 0.2% isopropylamine at a flow rate of 100 mL/min) to give two products in greater than 99.5% enantiomeric excess. The second eluting peak provided (1R,2S)—N-(4-(2,6-dimethoxyphenyl)-5-(5-methylpyridin-3-yl)-4H-1,2,4-triazol-3-yl)-1-(methylamino)-1-(5-methyl-pyrimidin-2-yl)propane-2-sulfonamide or (1S,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide. $^1$H NMR (CDCl$_3$) δ 8.59 (s, 2H), 8.44 (s, 1H), 8.33 (s, 1H), 7.65 (s, 1H), 7.39 (t, J=8.5 Hz, 1H), 6.62 (dd, J=11.1, 8.3 Hz, 2H), 4.61 (s, 1H), 3.77 (s, 3H), 3.74 (s, 3H), 0.47 (br. s., 3H), 2.32 (d, J=8.5 Hz, 8H), 1.37 (s, 3H). LCMS-ESI-ESI (POS.) m/z: 539.0 (M+H)$^+$. One exchangeable proton was not observed.

Example 757.0: Preparation of (1S,2S)—N-(4-(2,6-dimethoxyphenyl)-5-(5-methylpyridin-3-yl)-4H-1,2,4-triazol-3-yl)-1-(methylamino)-1-(5-methylpyrimi-din-2-yl)propane-2-sulfonamide or (1R,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide

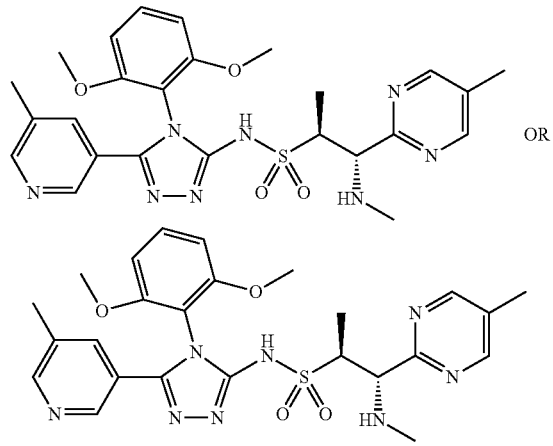

757.0

(1R,2R)—N-(4-(2,6-dimethoxyphenyl)-5-(5-methyl-pyridin-3-yl)-4H-1,2,4-triazol-3-yl)-1-(methyl-amino)-1-(5-methylpyrimidin-2-yl)propane-2-sulfo-namide or (1S,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide, Example 757.0

The racemic mixture Example 754.0 was resolved using preparative SFC (OX column (5 um, 30 mm×25 cm, 5 um S/N=2121 regular direction) eluting with 50% liquid $CO_2$ in 50% MeOH with 0.2% isopropylamine at a flow rate of 100 mL/min) to give two products in greater than 99.5% enantiomeric excess. The first eluting peak provided (1R,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide. $^1$H NMR (CDCl$_3$) δ 8.57 (s, 2H), 8.43 (d, J=1.6 Hz, 1H), 8.34 (d, J=1.9 Hz, 1H), 7.62 (s, 1H), 7.37 (t, J=8.5 Hz, 1H), 6.61 (dd, J=8.6, 1.7 Hz, 2H), 4.08 (d, J=8.8 Hz, 1H), 3.79 (s, 3H), 3.75 (s, 3H), 3.59-3.71 (m, 1H), 2.31 (d, J=9.1 Hz, 6H), 2.16-2.22 (m, 3H), 1.13-1.15 (m, 3H). 2 exchangeable protons were not observed. LCMS-ESI-ESI (POS.) m/z: 539.0 (M+H)$^+$.

Example 758.0: Preparation of (1S,2S)—N-(4-(2,6-dimethoxyphenyl)-5-(5-methylpyridin-3-yl)-4H-1,2,4-triazol-3-yl)-1-(methylamino)-1-(5-methylpyrimi-din-2-yl)propane-2-sulfonamide or (1R,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide

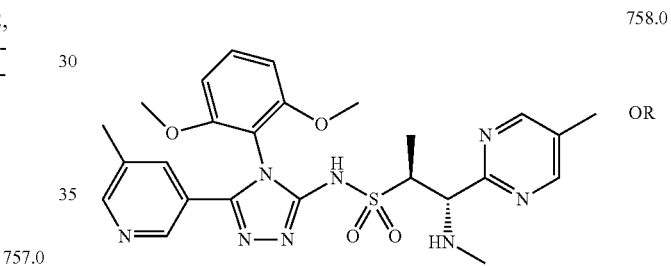

758.0

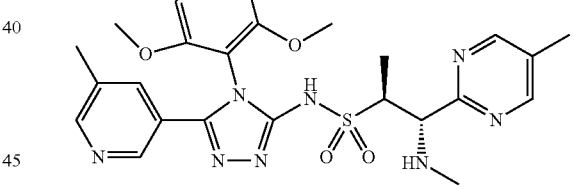

(1R,2R)—N-(4-(2,6-dimethoxyphenyl)-5-(5-methyl-pyridin-3-yl)-4H-1,2,4-triazol-3-yl)-1-(methyl-amino)-1-(5-methylpyrimidin-2-yl)propane-2-sulfo-namide or (1S,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide, Example 758.0

The racemic mixture Example 754.0 was resolved using preparative SFC (OX column (5 μm, 30 mm×25 cm, 5 μm S/N=2121 regular direction) eluting with 50% liquid $CO_2$ in 50% MeOH with 0.2% isopropylamine at a flow rate of 100 mL/min) to give two products in greater than 99.5% enantiomeric excess. The second eluting peak provided (1R,2R)—N-(4-(2,6-dimethoxyphenyl)-5-(5-methylpyridin-3-yl)-4H-1,2,4-triazol-3-yl)-1-(methylamino)-1-(5-methylpyrimidin-2-yl)propane-2-sulfonamide or (1S,2S)—N-(4-(2,6-dimethoxyphenyl)-5-(5-methylpyridin-3-yl)-4H-1,2,4-triazol-3-yl)-1-(methylamino)-1-(5-methylpyrimidin-2-yl)

propane-2-sulfonamide. $^1$H NMR (CDCl$_3$) δ 8.53-8.62 (m, 2H), 8.43 (d, J=1.6 Hz, 1H), 8.34 (d, J=1.8 Hz, 1H), 7.63 (s, 1H), 7.33-7.45 (m, 1H), 6.52-6.68 (m, 2H), 4.07 (d, J=8.9 Hz, 1H), 3.72-3.83 (m, 6H), 3.61-3.71 (m, 1H), 2.31 (d, J=8.8 Hz, 6H), 2.18 (s, 3H), 1.10 (d, J=2.9 Hz, 3H). 2 exchangeable protons were not observed. LCMS-ESI-ESI (POS.) m/z: 539.0 (M+H)$^+$.

Example 759.0: Preparation of (1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide methylpyrimidin-2-yl)propane-2-sulfonamide $^1$H NMR (CDCl$_3$) δ 8.62 (s, 2H), 7.54-7.68 (m, 2H), 7.29-7.36 (m, 1H), 6.66-6.74 (m, 1H), 6.60 (dd, J=8.5, 4.4 Hz, 2H), 4.20 (d, J=6.0 Hz, 1H), 3.96-4.09 (m, 1H), 3.76 (s, 3H), 3.72 (s, 3H), 3.58 (dd, J=13.3, 6.6 Hz, 2H), 3.18 (d, J=4.1 Hz, 6H), 3.01 (t, J=6.7 Hz, 1H), 2.94 (br. s., 1H), 2.34 (s, 3H), 1.27 (d, J=7.0 Hz, 4H). One exchangeable proton was not observed. LCMS-ESI-ESI (POS.) m/z: 611.0 (M+H)$^+$.

Example 760.0: Preparation of (1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide

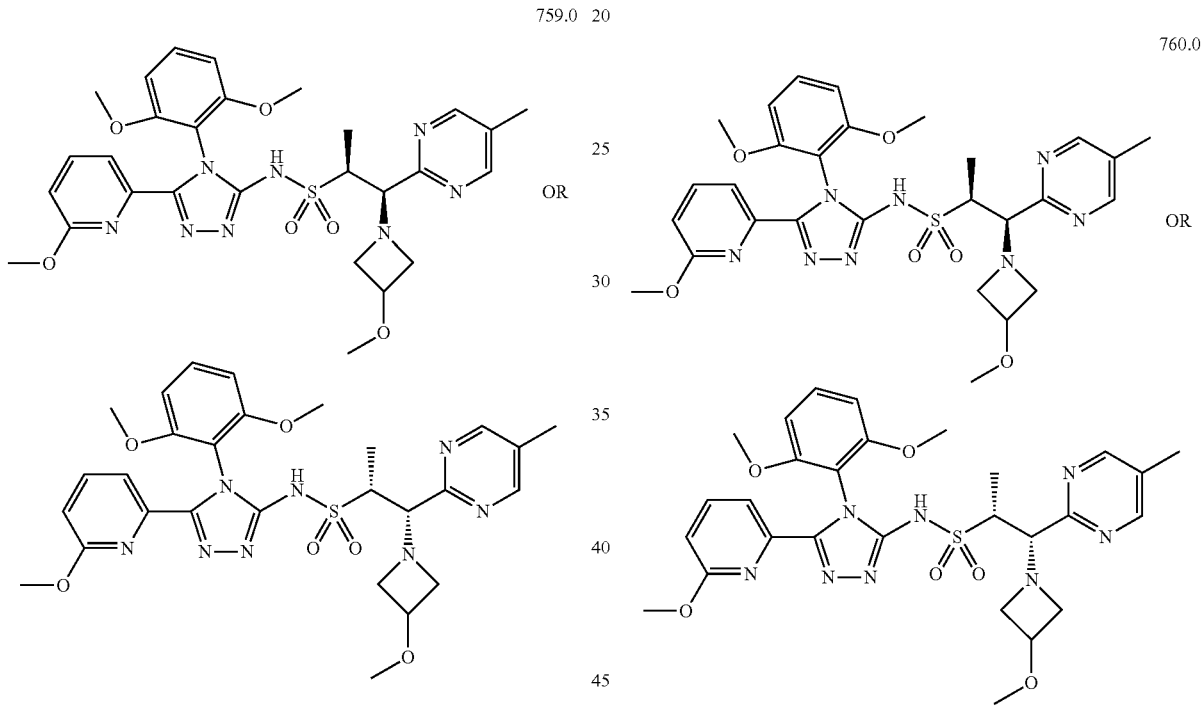

(1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide, Example 759.0

(1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide, Example 760.0

The racemic mixture (Example 750.0) was resolved using preparative SFC (OX column (5 μm, 21 mm×25 cm, 5 μm S/N=402121 regular direction) eluting with 55% liquid CO$_2$ in 45% MeOH with 0.2% isopropylamine at a flow rate of 70 mL/min) to give two products in greater than 99.5% enantiomeric excess. The first eluting peak provided (1R,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(3-methoxy azetidin-1-yl)-1-(5-

The racemic mixture (Example 750.0) was resolved using preparative SFC (OX column (5 μm, 21 mm×25 cm, 5 μm S/N=402121 regular direction) eluting with 55% liquid CO$_2$ in 45% MeOH with 0.2% isopropylamine at a flow rate of 70 mL/min) to give two products in greater than 99.5% enantiomeric excess. The second eluting peak provided (1R,2S)—N-(4-(2,6-dimethoxyphenyl)-5-(6-methoxypyridin-2-yl)-4H-1,2,4-triazol-3-yl)-1-(3-methoxy azetidin-1-yl)-1-(5-methylpyrimidin-2-yl)propane-2-sulfonamide or (1S,2R)—N-(4-(2,6-dimethoxyphenyl)-5-(6-methoxypyridin-2-yl)-4H-1,2,4-triazol-3-yl)-1-(3-methoxy azetidin-1-yl)-1-(5-methylpyrimidin-2-yl)propane-2-sulfonamide $^1$H NMR (CDCl$_3$) δ 8.62 (s, 2H), 7.56-7.67 (m, 2H), 7.29-7.36 (m, 1H), 6.65-6.73 (m, 1H), 6.60 (dd, J=8.5, 4.4 Hz, 2H), 4.21 (d, J=5.8 Hz, 1H), 3.97-4.09 (m, 1H), 3.76 (s, 3H), 3.71 (s, 3H), 3.58 (dd, J=13.4, 6.8 Hz, 2H), 3.18 (d, J=4.1 Hz, 6H), 3.01 (t, J=6.7 Hz, 1H), 2.90-2.98 (m, 1H), 2.34 (s, 3H), 1.27 (d, J=7.0 Hz, 4H). One exchangeable proton was not observed. LCMS-ESI-ESI (POS.) m/z: 611.0 (M+H)$^+$.

Example 761.0: Preparation of (1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide N-(4-(2,6-dimethoxyphenyl)-5-(6-methoxypyridin-2-yl)-4H-1,2,4-triazol-3-yl)-1-(3-methoxy azetidin-1-yl)-1-(5-methylpyrimidin-2-yl)propane-2-sulfonamide. $^1$H NMR (CDCl$_3$) δ 8.60 (s, 2H), 7.56-7.65 (m, 2H), 7.29-7.35 (m, 1H), 6.69 (dd, J=7.0, 2.0 Hz, 1H), 6.59 (dd, J=8.0, 6.0 Hz, 2H), 4.16 (d, J=7.3 Hz, 1H), 3.93 (quin, J=5.9 Hz, 1H), 3.79 (t, J=7.2 Hz, 1H), 3.74 (s, 3H), 3.68 (s, 3H), 3.37 (t, J=5.6 Hz, 1H), 3.18 (s, 3H), 3.15 (s, 3H), 2.98-3.09 (m, 2H), 2.32 (s, 3H), 1.50 (d, J=7.2 Hz, 3H). One exchangeable proton was not observed. LCMS-ESI-ESI (POS.) m/z: 611.0 (M+H)$^+$.

Example 762.0: Preparation of (1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide

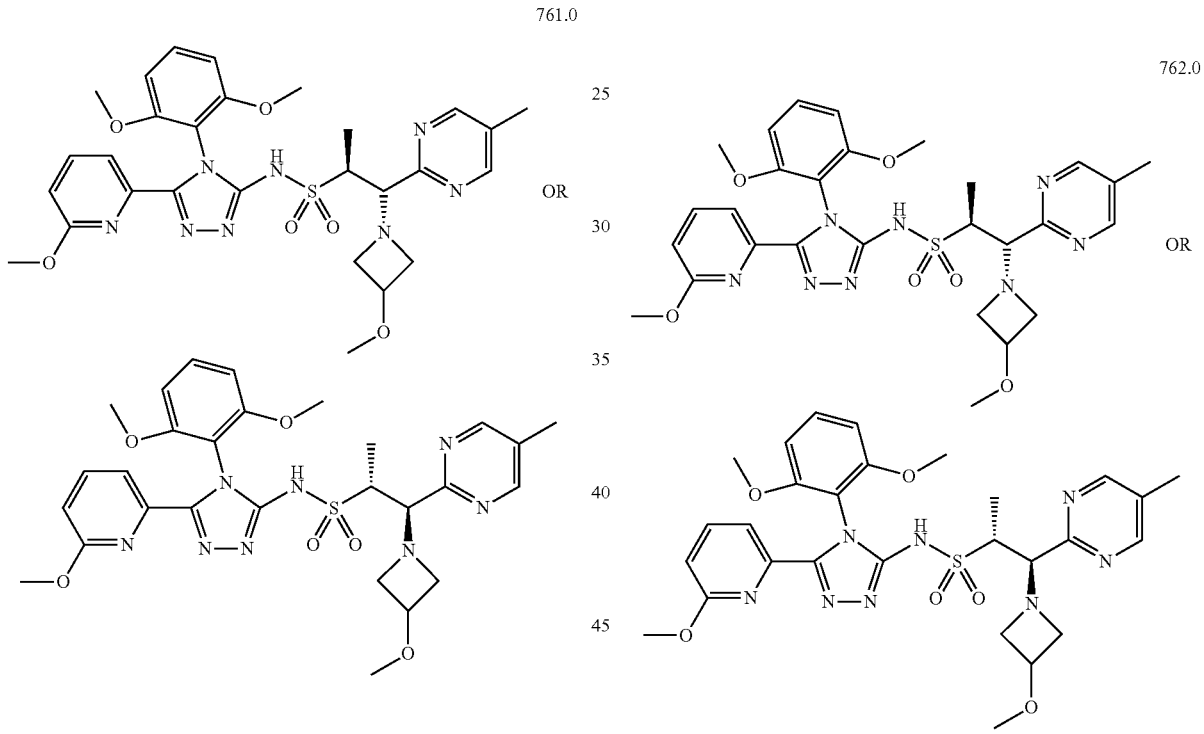

(1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide,
Example 761.0

The racemic mixture (Example 751.0) was resolved using preparative SFC (OX column (5 um, 21 mm×25 cm, 5 um S/N=711051 regular direction) eluting with 85% liquid CO$_2$ in 15% MeOH with 0.2% isopropylamine at a flow rate of 70 mL/min) to give two products in greater than 99.5% enantiomeric excess. The first eluting peak provided (1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2S)—

(1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide,
Example 762.0

The racemic mixture (Example 751.0) was resolved using preparative SFC (OX column (5 um, 21 mm×25 cm, 5 um S/N=711051 regular direction) eluting with 85% liquid CO$_2$ in 15% MeOH with 0.2% isopropylamine at a flow rate of 70 mL/min) to give two products in greater than 99.5% enantiomeric excess. The second eluting peak provided (1R,2R)—N-(4-(2,6-dimethoxyphenyl)-5-(6-methoxypyridin-2-yl)-4H-1,2,4-triazol-3-yl)-1-(3-methoxyazetidin-1-yl)-1-(5-methylpyrimidin-2-yl)propane-2-sulfonamide or (1S,2S)—N-(4-(2,6-dimethoxyphenyl)-5-(6-methoxypyridin-2-yl)-4H-1,2,4-triazol-3-yl)-1-(3-methoxy azetidin-1-yl)-1-(5-methylpyrimidin-2-yl)propane-2-sulfonamide. $^1$H NMR (CDCl$_3$) δ 8.55-8.65 (m, 2H), 7.55-7.67 (m, 2H), 7.29-7.36 (m, 1H), 6.66-6.74 (m, 1H), 6.54-6.64 (m, 2H), 4.16 (d, J=7.2 Hz, 1H), 3.93 (quin, J=6.0 Hz, 1H), 3.76-3.84 (m, 1H), 3.74 (s, 3H), 3.68 (s, 3H), 3.31-3.43 (m, 1H), 3.31-3.43 (m, 1H), 3.16 (d, J=8.5 Hz, 6H), 3.03 (dt, J=9.2, 6.7 Hz, 2H), 2.32 (s, 3H), 1.50 (d, J=7.2 Hz, 3H). One exchangeable proton was not observed. LCMS-ESI-ESI (POS.) m/z: 611.0 (M+H)$^+$.

Example 763.0: Preparation of (2S,3R)—N-(4-(2,6-bis(difluoromethoxy)phenyl)-5-(5-methylpyridin-3-yl)-4H-1,2,4-triazol-3-yl)-3-(5-methylpyrimidin-2-yl)butane-2-sulfonamide

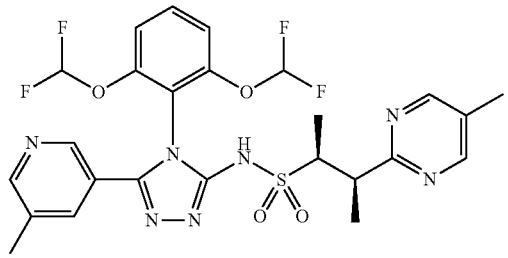

(2S,3R)—N-(4-(2,6-bis(difluoromethoxy)phenyl)-5-(5-methylpyridin-3-yl)-4H-1,2,4-triazol-3-yl)-3-(5-methylpyrimidin-2-yl)butane-2-sulfonamide, Example 763.0

Following the general procedure described in Example A, using bis(difluoromethoxy)-2-isocyanatobenzene (Intermediate 1.5), (2S,3R)-3-(5-methylpyrimidin-2-yl)butane-2-sulfonamide (Example 10.0) delivered (2S,3R)—N-(4-(2,6-bis(difluoromethoxy)phenyl)-5-(5-methylpyridin-3-yl)-4H-1,2,4-triazol-3-yl)-3-(5-methylpyrimidin-2-yl)butane-2-sulfonamide $^1$H NMR (CDCl$_3$) δ 11.91 (br. s., 1H), 8.54 (s, 2H), 8.50 (d, J=1.6 Hz, 1H), 8.32 (d, J=1.9 Hz, 1H), 7.61-7.67 (m, 1H), 7.49-7.60 (m, 1H), 7.19 (d, J=8.3 Hz, 2H), 6.19-6.80 (m, 2H), 3.75-3.90 (m, 1H), 3.64 (quin, J=6.9 Hz, 1H), 2.33 (s, 3H), 2.30 (s, 3H), 1.35-1.40 (m, 6H). LCMS-ESI-ESI (POS.) m/z: 595.8 (M+H)$^+$.

Example 764.0: Preparation of (2R,3S)—N-(4-(2,6-dimethoxyphenyl)-5-(5-methyl-3-pyridinyl)-4H-1,2,4-triazol-3-yl)-3-hydroxy-4-hexyne-2-sulfonamide and (2S,3R)—N-(4-(2,6-dimethoxyphenyl)-5-(5-methyl-3-pyridinyl)-4H-1,2,4-triazol-3-yl)-3-hydroxy-4-hexyne-2-sulfonamide But-2-ynal, Example 764.1

To a 500 mL oven dried round bottomed flask was added manganese(IV) oxide (24.8 g, 285 mmol, Aldrich, St. Louis, Mo.), powdered molecular sieve (0.4 nm, 6 g, Aldrich, St. Louis, Mo.), and DCM (70 mL). To this stirred solution was added 2-butyn-1-ol (2.0 g, 28.5 mmol), The resulting mixture was stirred at RT under N$_2$ for 20 h. The reaction mixture was cooled to RT and filtered through a pad of Celite® brand filter agent. The Celite® brand filter agent was rinsed more with DCM. The filtrate was distilled (50 to 57° C.) to afford but-2-ynal as a brownish liquid (1.3 g). $^1$H NMR (CDCl$_3$) δ 9.06-9.27 (m, 1H), 1.95-2.17 (m, 3H).

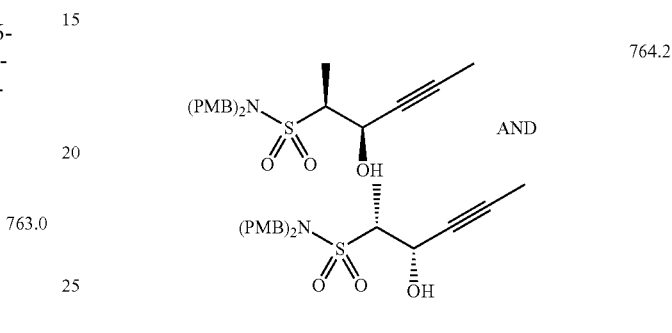

(2S,3R)-3-hydroxy-N,N-bis(4-methoxybenzyl)hex-4-yne-2-sulfonamide and (2R,3S)-3-hydroxy-N,N-bis(4-methoxybenzyl)hex-4-yne-2-sulfonamide, Example 764.2

To an oven-dried 50 mL 3 neck round bottomed flask was added N,N-bis(4-methoxybenzyl)ethanesulfonamide (1.4 g, 4.01 mmol, Example 12.0) and THF (12.0 mL). The resulting mixture was cooled to −70° C. followed by dropwise syringe addition of n-butyllithium solution, (2.5 m in hexanes, 2.0 mL, 5.00 mmol, Aldrich, St. Louis, Mo.). The temperature was maintained below −70° C. After the addition, stirring was continued below −70° C. for 20 min. A solution of but-2-ynal (0.491 g, 7.21 mmol) in THF (1 mL) was added dropwise to the reaction mixture via an addition funnel. After the addition, the reaction was further stirred at −70° C. for 2 h. The reaction was then quenched with saturated NH$_4$Cl (8 mL) and partitioned between EtOAc (70 mL) and water (40 mL). The aqueous layer was extracted with EtOAc (50 mL). The combined organic layers were dried over MgSO$_4$, filtered and concentrated. The product thus obtained was purified by column chromatography (120 g of silica, 10 to 40% EtOAc in heptane) to afford (2S,3R)-3-hydroxy-N,N-bis(4-methoxybenzyl)hex-4-yne-2-sulfonamide and (2R,3S)-3-hydroxy-N,N-bis(4-methoxybenzyl)hex-4-yne-2-sulfonamide. $^1$H NMR (CDCl$_3$) δ 7.13-7.23 (m, 4H), 6.83-6.94 (m, 4H), 4.97 (dt, J=4.0, 2.0 Hz, 1H), 4.33-4.46 (m, 2H), 4.13-4.26 (m, 2H), 3.83 (s, 6H), 3.17 (qd, J=7.1, 1.8 Hz, 1H), 3.09 (d, J=4.1 Hz, 1H), 1.88 (d, J=2.2 Hz, 3H), 1.40-1.49 (m, 3H). LCMS-ESI-ESI (POS.) m/z: 418.2 (M+H)$^+$.

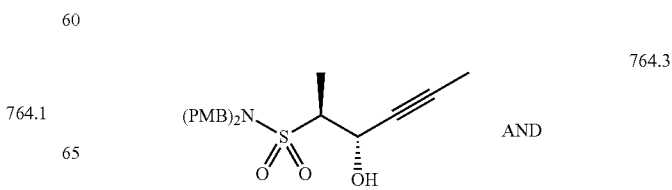

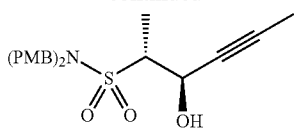

(2S,3S)-3-hydroxy-N,N-bis(4-methoxybenzyl)hex-4-yne-2-sulfonamide and (2R,3R)-3-hydroxy-N,N-bis(4-methoxybenzyl)hex-4-yne-2-sulfonamide, Example 764.3

Further elution under the conditions described in Example 764.2 delivered Example 764.3. $^1$H NMR (CDCl$_3$) δ 7.14-7.22 (m, 4H), 6.84-6.92 (m, 4H), 4.75-4.84 (m, 1H), 4.44 (d, J=15.2 Hz, 2H), 4.11-4.21 (m, 2H), 3.82 (s, 6H), 3.45 (d, J=3.2 Hz, 1H), 3.21 (quin, J=7.2 Hz, 1H), 1.85-1.92 (m, 3H), 1.35-1.45 (m, 3H).

764.4

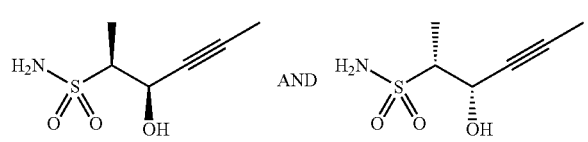

(2R,3S)-3-hydroxyhex-4-yne-2-sulfonamide and (2S,3R)-3-hydroxyhex-4-yne-2-sulfonamide To a solution of (2S,3R)-3-hydroxy-N,N-bis(4-methoxybenzyl)hex-4-yne-2-sulfonamide and (2R,3S)-3-hydroxy-N,N-bis(4-methoxybenzyl)hex-4-yne-2-sulfonamide (0.550 g, 1.317 mmol) in DCM (5.0 mL) was added anisole (0.70 mL, 6.44 mmol, Aldrich, St. Louis, Mo.). The reaction mixture was cooled in an ice bath and treated dropwise with TFA (5.00 mL, Aldrich, St. Louis, Mo.) via an addition funnel. After the addition, the resulting mixture was stirred in an ice bath for 30 min and warmed to RT and stirred for 20 h. Next, the reaction mixture was concentrated. The product thus obtained was purified by column chromatography (40 g of silica, 0 to 5% MeOH in DCM) to afford (2R,3S)-3-hydroxyhex-4-yne-2-sulfonamide and (2S,3R)-3-hydroxyhex-4-yne-2-sulfonamide as a tan solid (0.20 g). $^1$H NMR (CDCl$_3$) δ 4.91-5.11 (m, 1H), 4.65 (br. s., 2H), 3.32 (qd, J=7.1, 2.6 Hz, 1H), 2.52-2.80 (m, 1H), 1.90 (d, J=2.3 Hz, 3H), 1.53-1.58 (m, 3H). LCMS-ESI-ESI (POS.) m/z: 200.0 (M+Na)$^+$.

764.0

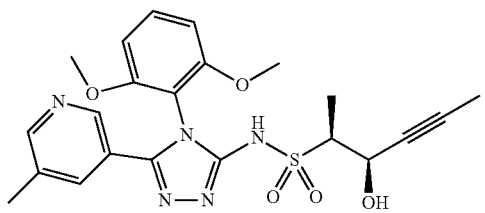

AND

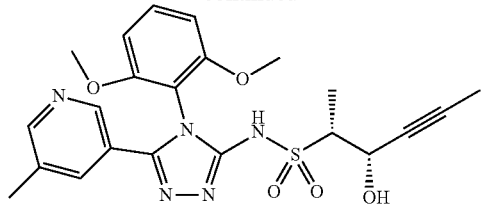

N'-(2,6-dimethoxyphenyl)-N-(((2S,3R)-3-hydroxyhex-4-yn-2-yl)sulfonyl)-2-(5-methylnicotinoyl)hydrazinecarboximidamide and N'-(2,6-dimethoxyphenyl)-N-(((2R,3S)-3-hydroxyhex-4-yn-2-yl)sulfonyl)-2-(5-methylnicotinoyl)hydrazinecarboximidamide, Example 764.0

Following the general procedure of Example A, the reaction used (2R,3S)-3-hydroxyhex-4-yne-2-sulfonamide and (2S,3R)-3-hydroxyhex-4-yne-2-sulfonamide (Example 764.4) and isothiocyanato-1,3-dimethoxybenzene Example 1.0. $^1$H NMR (CDCl$_3$) δ 11.00 (br. s., 1H), 8.46 (d, J=1.5 Hz, 1H), 8.34 (d, J=1.8 Hz, 1H), 7.61-7.69 (m, 1H), 7.41 (t, J=8.6 Hz, 1H), 6.55-6.68 (m, 2H), 5.07 (d, J=1.6 Hz, 1H), 3.81 (s, 3H), 3.72-3.76 (m, 3H), 3.42 (d, J=1.8 Hz, 1H), 3.08-3.23 (m, 1H), 2.32 (s, 3H), 1.83 (d, J=2.2 Hz, 3H), 1.42-1.53 (m, 3H). LCMS-ESI-ESI (POS.) m/z: 472.0 (M+H)$^+$.

Example 765.0: Preparation of (1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide 765.1

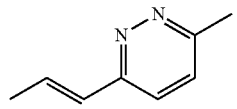

(E)-3-methyl-6-(prop-1-en-1-yl)pyridazine, Example 765.1

Following the general procedure described in Example 11.0, using 3-chloro-6-methylpyridazine afforded (E)-3-methyl-6-(prop-1-en-1-yl)pyridazine. $^1$H NMR (CDCl$_3$) δ 7.38 (d, J=8.8 Hz, 1H), 7.23 (d, J=8.6 Hz, 1H), 6.69-6.76 (m, 2H), 2.69 (s, 3H), 1.94-2.03 (m, 3H). LCMS-ESI-ESI (POS.) m/z: 135.2 (M+H)$^+$.

765.2

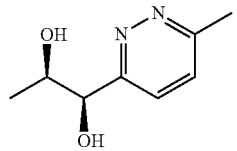

AND

1-(6-methylpyridazin-3-yl)propane-1,2-diol, Example 765.2

Following the general procedure described in Example 11.0, using (E)-3-methyl-6-(prop-1-en-1-yl)pyridazine afforded 1-(6-methylpyridazin-3-yl)propane-1,2-diol. $^1$H NMR (CDCl$_3$) δ 7.46-7.55 (m, 1H), 7.32-7.41 (m, 1H), 4.69 (br. s., 1H), 4.13-4.25 (m, 1H), 4.07 (br. s., 1H), 2.96 (br. s., 1H), 2.73 (s, 3H), 1.29 (d, J=6.4 Hz, 3H). LCMS-ESI-ESI (POS.) m/z: 169.2 (M+H)$^+$.

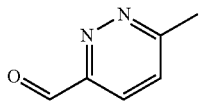

765.3

6-methylpyridazine-3-carbaldehyde, Example 765.3

Following the general procedure described in Example 11.0, using 1-(6-methylpyridazin-3-yl)propane-1,2-diol afforded 6-methylpyridazine-3-carbaldehyde. $^1$H NMR (CDCl$_3$) δ 10.21-10.52 (m, 1H), 7.95 (d, J=8.5 Hz, 1H), 7.40-7.63 (m, 1H), 2.86 (s, 3H). LCMS-ESI-ESI (POS.) m/z: 123.2 (M+H)$^+$.

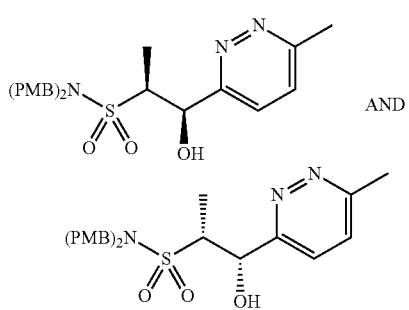

765.4

(1R,2S)-1-hydroxy-N,N-bis(4-methoxybenzyl)-1-(6-methylpyridazin-3-yl)propane-2-sulfonamide and (1S,2R)-1-hydroxy-N,N-bis(4-methoxybenzyl)-1-(6-methylpyridazin-3-yl)propane-2-sulfonamide, Example 765.4

Following the general procedure described in Example 11.0, the reaction of 6-methylpyridazine-3-carbaldehyde provided (1R,2S)-1-hydroxy-N,N-bis(4-methoxybenzyl)-1-(6-methylpyridazin-3-yl)propane-2-sulfonamide and (1S,2R)-1-hydroxy-N,N-bis(4-methoxybenzyl)-1-(6-methylpyridazin-3-yl)propane-2-sulfonamide. $^1$H NMR (CDCl$_3$) δ 7.61-7.69 (m, 1H), 7.39 (d, J=8.6 Hz, 1H), 7.23 (d, J=8.3 Hz, 4H), 6.88 (d, J=8.3 Hz, 4H), 5.67 (s, 1H), 4.28-4.45 (m, 4H), 4.04-4.15 (m, 1H), 3.81-3.85 (m, 7H), 2.75 (s, 3H), 1.18 (d, J=7.2 Hz, 3H). LCMS-ESI-ESI (POS.) m/z: 472.0 (M+H)$^+$.

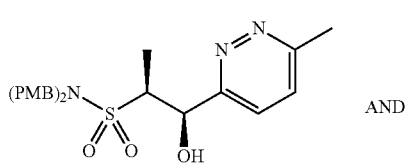

765.5

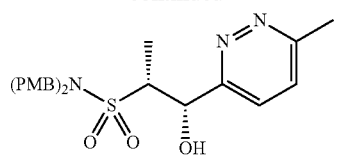

(1R,2S)-1-hydroxy-N,N-bis(4-methoxybenzyl)-1-(6-methylpyridazin-3-yl)propane-2-sulfonamide and (1S,2R)-1-hydroxy-N,N-bis(4-methoxybenzyl)-1-(6-methylpyridazin-3-yl)propane-2-sulfonamide, Example 765.4

Following the procedure described in Example 765.4, further elution delivered (1R,2R)-1-hydroxy-N,N-bis(4-methoxybenzyl)-1-(6-methylpyridazin-3-yl)propane-2-sulfonamide and (1S,2S)-1-hydroxy-N,N-bis(4-methoxybenzyl)-1-(6-methylpyridazin-3-yl)propane-2-sulfonamide. $^1$H NMR (CDCl$_3$) δ 7.66 (d, J=8.6 Hz, 1H), 7.38 (d, J=8.5 Hz, 1H), 7.17 (d, J=8.5 Hz, 4H), 6.86-6.88 (m, 4H), 5.41 (t, J=5.3 Hz, 1H), 4.73 (d, J=5.4 Hz, 1H), 4.47 (d, J=15.2 Hz, 2H), 4.11 (d, J=15.2 Hz, 2H), 3.82 (m, 6H), 3.67-3.76 (m, 1H), 2.74 (s, 3H), 1.17 (d, J=7.0 Hz, 3H). LCMS-ESI-ESI (POS.) m/z: 472.0 (M+H)$^+$.

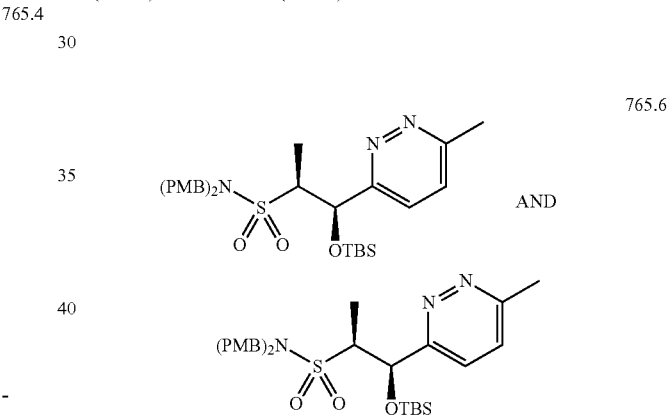

765.6

(1R,2S)-1-((tert-butyldimethylsilyl)oxy)-N,N-bis(4-methoxybenzyl)-1-(6-methylpyridazin-3-yl)propane-2-sulfonamide and (1S,2R)-1-((tert-butyldimethylsilyl)oxy)-N,N-bis(4-methoxybenzyl)-1-(6-methylpyridazin-3-yl)propane-2-sulfonamide, Example 765.5

Following the general procedure described in Example 11.0, using Example 765.4 provided (1R,2S)-1-((tert-butyldimethylsilyl)oxy)-N,N-bis(4-methoxybenzyl)-1-(6-methylpyridazin-3-yl)propane-2-sulfonamide and (1S,2R)-1-((tert-butyldimethylsilyl)oxy)-N,N-bis(4-methoxybenzyl)-1-(6-methylpyridazin-3-yl)propane-2-sulfonamide $^1$H NMR (CDCl$_3$) δ 7.56 (d, J=8.6 Hz, 1H), 7.35 (d, J=8.6 Hz, 1H), 7.15 (d, J=8.5 Hz, 4H), 6.83 (d, J=8.3 Hz, 4H), 5.91 (s, 1H), 4.47 (d, J=15.2 Hz, 2H), 4.13 (d, J=15.2 Hz, 2H), 3.80 (s, 6H), 3.53-3.65 (m, 1H), 2.71-2.79 (m, 3H), 1.16 (d, J=7.0 Hz, 3H), 0.98 (s, 9H), 0.28 (s, 3H), −0.10 (s, 3H). LCMS-ESI-ESI (POS.) m/z: 586.0 (M+H)$^+$.

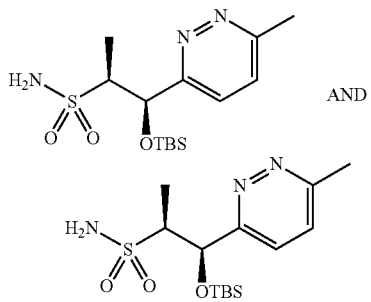

Step 6: (1R,2S)-1-((tert-butyldimethylsilyl)oxy)-1-(6-methylpyridazin-3-yl)propane-2-sulfonamide and (1S,2R)-1-((tert-butyldimethylsilyl)oxy)-1-(6-methylpyridazin-3-yl)propane-2-sulfonamide, Example 765.6

Following the general procedure described in Example 11.0, using Example 765.6 afforded (1R,2S)-1-((tert-butyldimethylsilyl)oxy)-1-(6-methylpyridazin-3-yl)propane-2-sulfonamide and (1S,2R)-1-((tert-butyldimethylsilyl)oxy)-1-(6-methylpyridazin-3-yl)propane-2-sulfonamide. $^1$H NMR (CDCl$_3$) δ 7.56 (d, J=8.8 Hz, 1H), 7.38 (d, J=8.6 Hz, 1H), 5.66 (d, J=4.1 Hz, 1H), 4.75 (s, 2H), 3.49-3.62 (m, 1H), 2.74 (s, 3H), 1.39 (d, J=6.9 Hz, 3H), 0.94 (s, 9H), 0.20 (s, 3H), −0.18 (s, 3H). LCMS-ESI-ESI (POS.) m/z: 346.0 (M+H)$^+$.

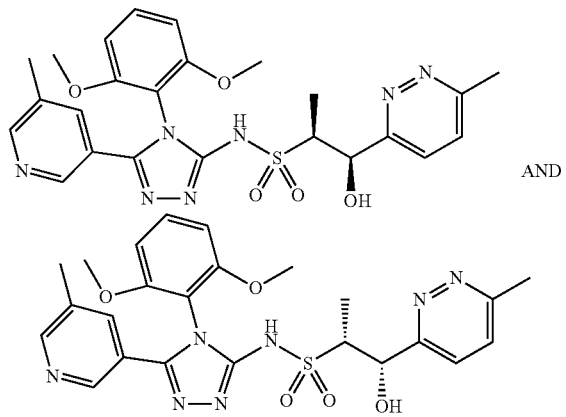

Step 7: (1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide, Example 765.7

Following the general procedure described in Example A, using (1R,2S)-1-((tert-butyldimethylsilyl)oxy)-1-(6-methylpyridazin-3-yl)propane-2-sulfonamide and (1S,2R)-1-((tert-butyldimethylsilyl)oxy)-1-(6-methylpyridazin-3-yl)propane-2-sulfonamide, 5-methylnicotinic acid hydrazide (commercially available from Hellen Chemistry Co., Ltd.), 2-isothiocyanato-1,3-dimethoxybenzene (Example 1.0) afforded (1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide and (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide

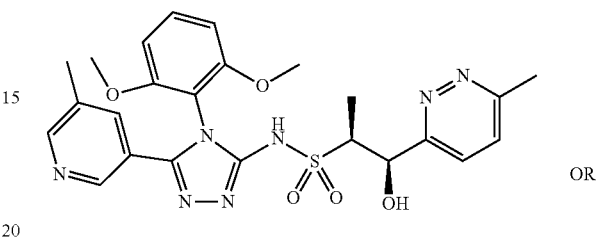

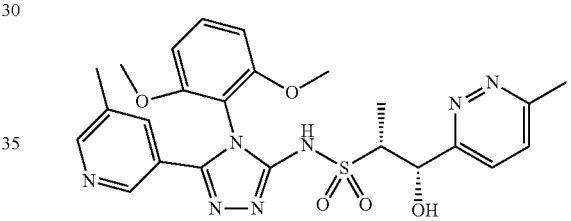

(1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide, Example 765.0

765.8 was purified to separate the two enantiomers using a preparative SFC (OX column (5 μm, 20 mm×25 cm, 5 lam S/N=2121 regular direction) eluting with 70% liquid CO$_2$ in 30% MeOH with 0.1% diethylamine at a flow rate of 60 mL/min) to give two products in greater than 99.5% enantiomeric excess. The first eluting peak was (1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide $^1$H NMR (CDCl$_3$) δ 8.37 (d, J=17.1 Hz, 2H), 7.62 (d, J=9.1 Hz, 2H), 7.38 (t, J=8.6 Hz, 1H), 7.31 (d, J=8.8 Hz, 1H), 6.62 (dd, J=8.5, 2.0 Hz, 2H), 5.70 (s, 1H), 3.89 (q, J=6.7 Hz, 1H), 3.75 (s, 3H), 3.73 (s, 3H), 2.66-2.75 (m, 3H), 2.29 (s, 3H), 1.13 (d, J=7.0 Hz, 3H). Two exchangeable protons were not observed. LCMS-ESI-ESI (POS.) m/z: 526.0 (M+H)$^+$.

Example 766.0: Preparation of (1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide

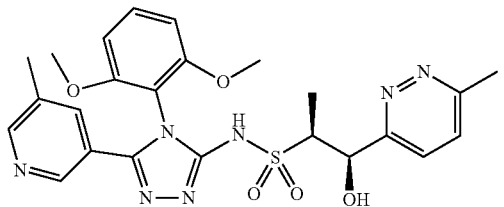

766.0

OR

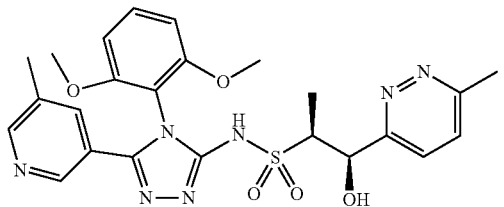

(1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide, Example 765.0

Further elution under the conditions described in 765.0 delivered the second eluting peak (1R,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide. $^1$H NMR (CDCl$_3$) δ 8.30-8.46 (m, 2H), 7.63 (d, J=9.1 Hz, 2H), 7.39 (t, J=8.6 Hz, 1H), 7.31 (d, J=8.5 Hz, 1H), 6.62 (dd, J=8.3, 5.6 Hz, 2H), 5.71 (s, 1H), 3.92 (d, J=6.7 Hz, 1H), 3.75 (s, 3H), 3.73 (s, 3H), 2.70 (s, 3H), 2.29 (s, 3H), 1.15 (d, J=6.9 Hz, 3H). Two exchangeable protons were not observed. LCMS-ESI-ESI (POS.) m/z: 526.0 (M+H)$^+$.

Example 767.0: Preparation of (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide

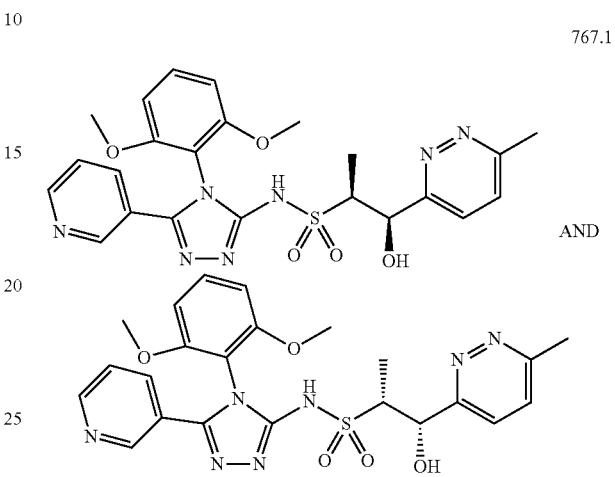

767.1

AND (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide and (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide, Example 767.1

Following the general procedure described in Example A, using Example 765.6, isothiocyanato-1,3-dimethoxybenzene Example 1.0 and nicotinohydrazide (Alfa Aesar) afforded (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide and (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide.

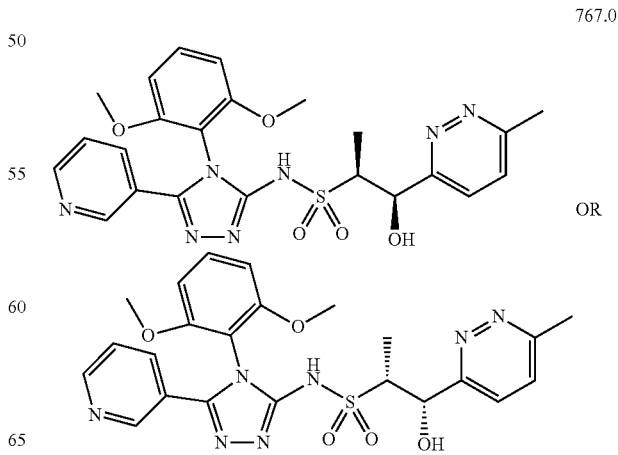

767.0

OR (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide, Example 767.0

Example 767.1 was resolved using preparative SFC (OX column (5 μm, 20 mm×25 cm, 5 lam S/N=2121 regular direction) eluting with 65% liquid $CO_2$ in 35% MeOH with 0.1% diethylamine at a flow rate of 60 mL/min) to give two products in greater than 99.5% enantiomeric excess. The first eluting peak was (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide. $^1$H NMR (CDCl$_3$) δ 8.63 (s, 1H), 8.58 (d, J=4.7 Hz, 1H), 7.74 (d, J=8.0 Hz, 1H), 7.63 (d, J=8.6 Hz, 1H), 7.39 (t, J=8.6 Hz, 1H), 7.31 (d, J=8.6 Hz, 1H), 7.20-7.26 (m, 1H), 6.62 (dd, J=8.5, 3.7 Hz, 2H), 5.70 (s, 1H), 3.85-3.98 (m, 1H), 3.74 (s, 3H), 3.73 (s, 3H), 2.66-2.73 (m, 3H), 1.14 (d, J=7.0 Hz, 3H). 2 exchangeable protons were not observed. LCMS-ESI-ESI (POS.) m/z: 512.0 (M+H)$^+$.

Example 768.0: Preparation of (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide

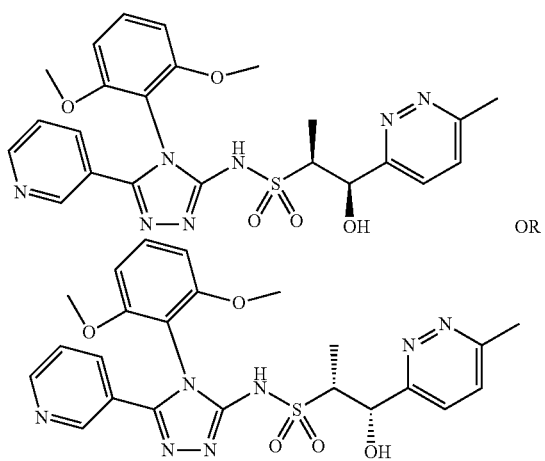

768.0

(1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide, Example 768.0

Further elution under the conditions described in Example 767.0 delivered the second eluting peak (1R,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide. $^1$H NMR (CDCl$_3$) δ 8.63 (s, 1H), 8.59 (d, J=4.7 Hz, 1H), 7.74 (d, J=8.2 Hz, 1H), 7.63 (d, J=8.6 Hz, 1H), 7.40 (t, J=8.5 Hz, 1H), 7.31 (d, J=8.5 Hz, 1H), 7.19-7.26 (m, 1H), 6.62 (dd, J=8.4, 4.6 Hz, 2H), 5.70 (s, 1H), 3.92 (q, J=7.2 Hz, 1H), 3.74 (s, 3H), 3.73 (s, 3H), 2.70 (s, 3H), 1.14 (d, J=7.0 Hz, 3H). 2 exchangeable protons were not observed. LCMS-ESI-ESI (POS.) m/z: 512.0 (M+H)$^+$.

Example 769.0: Preparation of (1S,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide

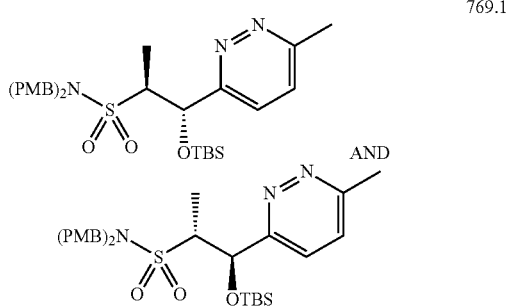

769.1

(1S,2S)-1-((tert-butyldimethylsilyl)oxy)-N,N-bis(4-methoxybenzyl)-1-(6-methylpyridazin-3-yl)propane-2-sulfonamide and (1R,2R)-1-((tert-butyldimethylsilyl)oxy)-N,N-bis(4-methoxybenzyl)-1-(6-methylpyridazin-3-yl)propane-2-sulfonamide, Example 769.1

Following the general procedure described in Example 11.0, using Example 765.5 and (1,1-dimethylethyl)dimethylsilyl trifluoromethanesulfonate (Aldrich, St. Louis, Mo.) provided Example 769.1. $^1$H NMR (CDCl$_3$) δ 7.67 (d, J=8.6 Hz, 1H), 7.34 (d, J=8.6 Hz, 1H), 7.11 (d, J=8.5 Hz, 4H), 6.83 (d, J=8.2 Hz, 4H), 5.39 (d, J=3.5 Hz, 1H), 4.42 (d, J=15.1 Hz, 2H), 3.97 (d, J=15.2 Hz, 2H), 3.80 (s, 6H), 3.73 (dd, J=7.2, 3.8 Hz, 1H), 2.69-2.74 (m, 3H), 1.38 (d, J=7.0 Hz, 3H), 0.96 (s, 9H), 0.15 (s, 3H), −0.16-0.09 (m, 3H). LCMS-ESI-ESI (POS.) m/z: 586.0 (M+H)$^+$.

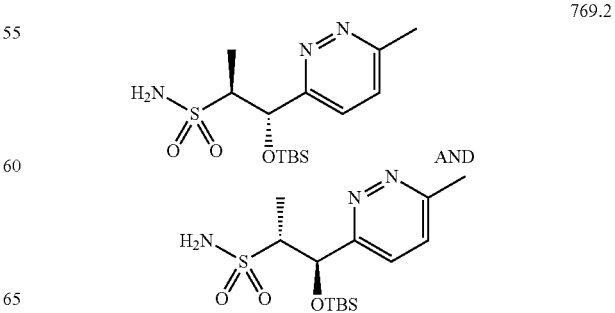

769.2

(1S,2S)-1-((tert-butyldimethylsilyl)oxy)-1-(6-methylpyridazin-3-yl)propane-2-sulfonamide and (1R,2R)-1-((tert-butyldimethylsilyl)oxy)-1-(6-methylpyridazin-3-yl)propane-2-sulfonamide, Example 769.2

Following the general procedure described in Example 11.0, the reaction of Example 769.1 and anisole and TFA afforded (1S,2S)-1-((tert-butyldimethylsilyl)oxy)-1-(6-methylpyridazin-3-yl)propane-2-sulfonamide and (1R,2R)-1-((tert-butyldimethylsilyl)oxy)-1-(6-methylpyridazin-3-yl)propane-2-sulfonamide. $^1$H NMR (CDCl$_3$) δ 7.60 (d, J=8.8 Hz, 1H), 7.40 (d, J=8.6 Hz, 1H), 5.61 (d, J=4.2 Hz, 1H), 5.16 (s, 2H), 3.56-3.70 (m, 1H), 2.74 (s, 3H), 1.28 (d, J=7.0 Hz, 3H), 0.93 (s, 9H), 0.19 (s, 3H), −0.03 (s, 3H). LCMS-ESI-ESI (POS.) m/z: 346.0 (M+H)$^+$.

769.3

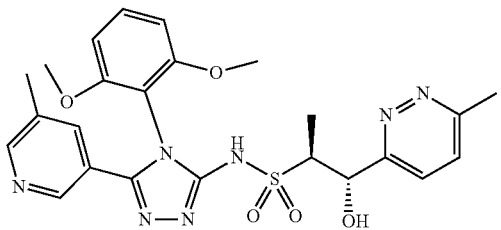

AND

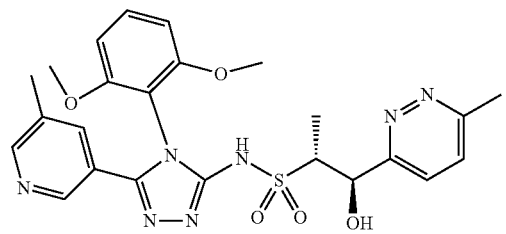

(1S,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide and (1R,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide, Example 769.3

Following the general procedure described in Example A, using 769.2, 2-isothiocyanato-1,3-dimethoxybenzene (Example 1.0) and methylnicotinic acid hydrazide (commercially available from Hellen Chemistry Co., Ltd.), provided (1S,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide and (1R,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide 769.0

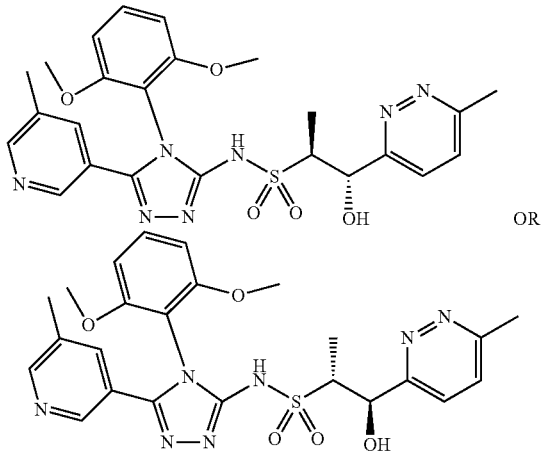

OR (1S,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide, Example 769.0

The racemic mixture from Example 769.3 was resolved using preparative SFC (OX column (5 lam, 20 mm×25 cm, 5 lam S/N=2121 regular direction) eluting with 65% liquid CO$_2$ in 35% EtOH with at a flow rate of 60 mL/min) to give two products in greater than 99.5% enantiomeric excess. The first eluting peak was (1S,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide. $^1$H NMR (CDCl$_3$) δ 8.28-8.49 (m, 2H), 7.50-7.71 (m, 2H), 7.41 (t, J=8.6 Hz, 1H), 7.30 (d, J=8.6 Hz, 1H), 6.56-6.70 (m, 2H), 5.20 (d, J=7.2 Hz, 1H), 3.71-3.88 (m, 6H), 3.56 (br. s., 1H), 2.89-2.99 (m, 2H), 2.71 (s, 3H), 2.30 (br. s., 3H), 1.14-1.24 (m, 3H). LCMS-ESI-ESI (POS.) m/z: 526.4 (M+H)$^+$.

Example 770.0: Preparation of (1R,2R)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide or (1S,2S)—N-(4-(2,6-dimethoxyphenyl)-5-(pyridin-3-yl)-4H-1,2,4-triazol-3-yl)-1-hydroxy-1-(6-methylpyridazin-3-yl)propane-2-sulfonamide 770.0

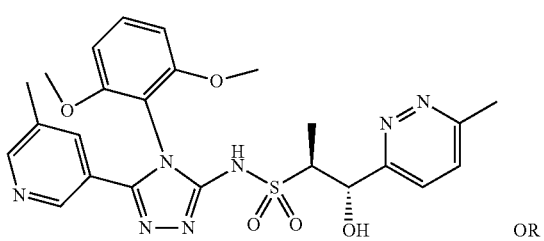

OR

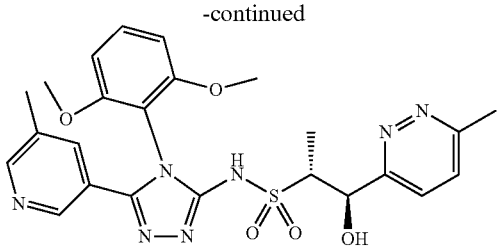

(1S,2S)—N-(4-(2,6-dimethoxyphenyl)-5-(5-methyl-pyridin-3-yl)-4H-1,2,4-triazol-3-yl)-1-hydroxy-1-(6-methylpyridazin-3-yl)propane-2-sulfonamide or (1R,2R)—N-(4-(2,6-dimethoxyphenyl)-5-(5-methyl-pyridin-3-yl)-4H-1,2,4-triazol-3-yl)-1-hydroxy-1-(6-methylpyridazin-3-yl)propane-2-sulfonamide, Example 770.0

Further elution under the conditions described in Example 769.0 delivered the second eluting peak (1S,2S)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide or (1R,2R)—N-(4-(2,6-dimethoxyphenyl)-5-(5-methylpyridin-3-yl)-4H-1,2,4-triazol-3-yl)-1-hydroxy-1-(6-methylpyridazin-3-yl)propane-2-sulfonamide. $^1$H NMR (CDCl$_3$) δ 8.27-8.51 (m, 2H), 7.50-7.71 (m, 2H), 7.41 (t, J=8.3 Hz, 1H), 7.31 (d, J=8.3 Hz, 1H), 6.58-6.71 (m, 2H), 5.22 (br. s., 1H), 3.8 (s, 3H), 3.7 (s, 3H), 3.55 (br. s., 1H), 2.71 (s, 3H), 2.30 (br. s., 3H), 1.18 (d, J=6.1 Hz, 3H). 2 exchangeable protons were not observed. LCMS-ESI-ESI (POS.) m/z: 526.2 (M+H)$^+$.

Example 771.0: Preparation of (1R,2S,P)—N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide 771.1

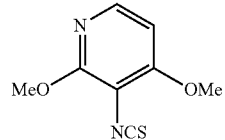

3-isothiocyanato-2,4-dimethoxypyridine, Example 771.1

A 2 L round bottom flask was charged with 1,1"-thiocarbonyldi-2(1H)-pyridone (47.0 g, 202 mmol) and dissolved in dry DCM (405 mL). To that solution was added 2,6-dimethoxyaniline (31 g, 202 mmol) dissolved in DCM (405 mL) via an addition funnel at RT over 40 minutes. After 16 hours, the reaction was concentrated in vacuo and purified on silica gel (0-20% EtOAc in heptanes) to give 2-isothiocyanato-1,3-dimethoxybenzene (32 g, 164 mmol, 81% yield). LCMS-ESI (POS.) m/z: 197.1 (M+H)$^+$.

The compounds set forth in the following Table were synthesized following the procedure in Example 741.0 using the known starting material as described.

TABLE 42

| Example | Reagents | Structure, Name and Data |
|---|---|---|
| 771.0 | (1R,2S)-1-methoxy-1-(5-methylpyrimidin-2-yl)propane-2-sulfonamide (Example 14.0), 6-methoxypicolinohydrazide (Example 3.18), 3-isothiocyanato-2,4-dimethoxypyridine (Example 771.1). The racemic mixture was separated by preparative SFC method: Column: Chiralpak AD-H (2 × 25 cm), Mobile Phase: 65:35 (A:B) A: Liquid CO$_2$; B: iPrOH, Flowrate: 80 mL/min, 215 nm, Inlet Pressure: 83 bar to deliver peak 1 at 1.35 minutes. | (structures) <br><br> or <br><br> (1R,2S,P)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2,4- |

TABLE 42-continued

| Example | Reagents | Structure, Name and Data |
|---|---|---|
| | | dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide<br>¹H NMR (400 MHz, DMSO-d₆) δ ppm 13.38 (1 H, s) 8.66 (2 H, s) 8.20 (1 H, d, J = 5.96 Hz) 7.80-7.86 (1 H, m) 7.64 (1 H, d, J = 6.95 Hz) 7.00 (1 H, d, J = 6.01 Hz) 6.87 (1 H, d, J = 7.93 Hz) 4.82 (1 H, d, J = 3.52 Hz) 3.77 (3 H, s) 3.76 (3 H, s) 3.40-3.47 (1 H, m) 3.15 (3 H, s) 3.13 (3 H, s) 2.27 (3 H, s) 1.14 (3 H, d, J = 7.00 Hz). LCMS-ESI (POS.) m/z: 557.1 (M + H)⁺. |
| 772.0 | (1R,2S)-1-methoxy-1-(5-methylpyrimidin-2-yl)propane-2-sulfonamide (Example 14.0), 6-methoxypicolinohydrazide (Example 3.18), 3-isothiocyanato-2,4-dimethoxypyridine (Example 771.1). The racemic mixture was separated by preparative SFC method: Column: Chiralpak AD-H (2 × 25 cm), Mobile Phase: 65:35 (A:B) A: Liquid CO₂; B: iPrOH, Flowrate: 80 mL/min, 215 nm, Inlet Pressure: 83 bar to deliver the second eluting peak at 1.97 minutes. | 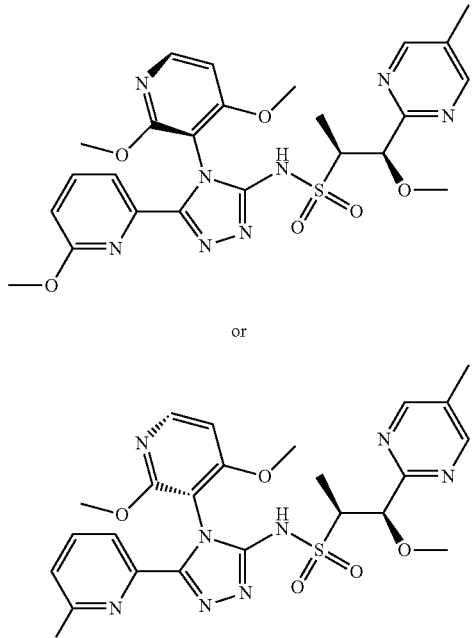<br>or<br>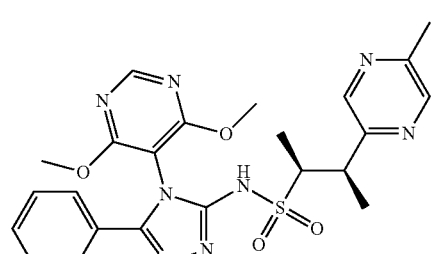<br>(1R,2S,P)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide and (1R,2S,M)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide<br>¹H NMR (400 MHz, DMSO-d₆) δ ppm 13.38 (1 H, s) 8.66 (2 H, s) 8.20 (1 H, d, J = 5.96 Hz) 7.83 (1 H, t, J = 8.09 Hz) 7.64 (1 H, d, J = 7.36 Hz) 6.99 (1 H, d, J = 6.12 Hz) 6.87 (1 H, d, J = 8.24 Hz) 4.83 (1 H, br s) 3.78 (3 H, s) 3.76 (3 H, s) 3.15 (3 H, s) 3.13 (4 H, s) 2.27 (3 H, s) 1.14 (3 H, d, J = 7.00 Hz). LCMS-ESI (POS.) m/z: 557.1 (M + H)⁺. |
| 773.0 | (2S,3R)-3-(5-methylpyrazin-2-yl)butane-2-sulfonamide (Example 10.3), picolinhydrazide (Commercially available from Enamine), 5-isothiocyanato-4,6-dimethoxypyrimidine (Example 1.1). | (2S,3R)-N-(4-(4,6-dimethoxy-5-pyrimidinyl)-5-(2-pyridinyl)-4H-1,2,4-triazol-3-yl)-3-(5-methyl-2-pyrazinyl)-2-butanesulfonamide<br>1H NMR (500 MHz, CD₃OD) δ 8.42 (2 H, d, J = 11.68 Hz) 8.30 (1 H, d, J = 1.04 Hz) 8.22 (1 H, d, J = 4.15 Hz) 7.97 (1 H, d, J = 8.04 Hz) 7.80 (1 H, td, J = 7.79, 1.56 Hz) 7.26 (1 H, dd, J = 7.01, 5.19 Hz) 3.84 (6 H, d, |

TABLE 42-continued

| Example | Reagents | Structure, Name and Data |
|---|---|---|
| | | J = 2.85 Hz) 3.77 (1 H, br dd, J = 6.75, 3.63 Hz) 3.30-3.32 (1 H, m) 2.47 (3 H, s) 1.37 (3 H, d, J = 7.27 Hz) 1.30 (3 H, d, J = 7.01 Hz) 0.79-0.91 (1 H, m). LCMS-ESI (POS.) m/z: 512.1 (M + H)⁺. |
| 774.0 | (2S,3R)-3-(5-methylpyrazin-2-yl)butane-2-sulfonamide (Example 10.3), picolinhydrazide (Commercially available from Enamine), 2-isothiocyanato-1,3-dimethoxybenzene (Example 1.0). | 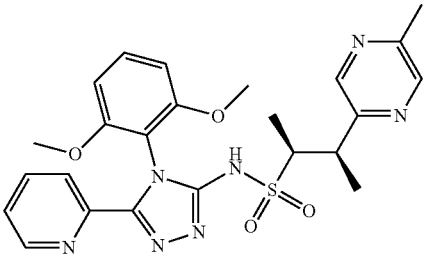 [SMILES: COc1cccc(OC)c1-n1c(NS(=O)(=O)[C@@H](C)[C@H](C)c2cnc(C)cn2)nnc1-c1ccccn1]<br>(2S,3R)-N-(4-(2,6-dimethoxyphenyl)-5-(2-pyridinyl)-4H-1,2,4-triazol-3-yl)-3-(5-methyl-2-pyrazinyl)-2-butanesulfonamide<br>$^1$H NMR (500 MHz, DMSO-d$_6$) δ 13.29 (1 H, s) 8.44 (1 H, s) 8.31(1 H, s) 8.31 (2 H, d, J = 6.70 Hz) 7.89 (1 H, td, J = 7.72, 1.49 Hz) 7.82 (1 H, d, J = 7.91 Hz) 7.38-7.44 (2 H, m) 6.76 (2 H, dd, J = 8.40, 4.90 Hz) 3.62 (6 H, d, J = 1.43 Hz) 3.58 (1 H, br dd, J = 7.10, 3.86 Hz) 3.33 (1 H, br dd, J = 6.97, 3.92 Hz) 1.24 (4 H, d, J = 7.14 Hz) 1.14 (4 H, d, J = 7.01 Hz). LCMS-ESI (POS.) m/z: 510.1 (M + H)⁺. |
| 775.0 | (2S,3R)-3-(5-methylpyrimidin-2-yl)butane-2-sulfonamide (Example 733.1), picolinhydrazide (Commercially available from Enamine), 2-isothiocyanato-1,3-dimethoxybenzene (Example 1.0). | 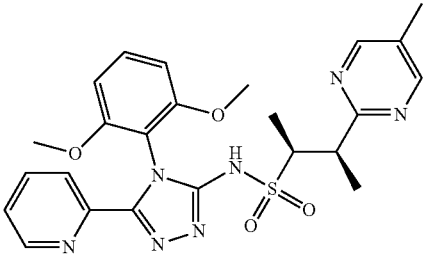 [SMILES: COc1cccc(OC)c1-n1c(NS(=O)(=O)[C@@H](C)[C@H](C)c2ncc(C)cn2)nnc1-c1ccccn1]<br>(2S,3R)-N-(4-(2,6-dimethoxyphenyl)-5-(2-pyridinyl)-4H-1,2,4-triazol-3-yl)-3-(5-methyl-2-pyrimidinyl)-2-butanesulfonamide<br>$^1$H NMR (500 MHz, DMSO-d$_6$) δ 1.08 (br d, J = 6.49 Hz, 3 H) 1.23-1.30 (m, 3 H) 2.23 (s, 3 H) 3.49-3.68 (m, 7 H) 3.72 (br s, 1 H) 6.72 (br t, J = 7.33 Hz, 2 H) 7.36 (br s, 2 H) 7.74-7.93 (m, 2 H) 8.25 (br s, 1 H) 8.58 (s, 2 H) 13.26 (br s, 1 H). LCMS-ESI (POS.) m/z: 510.1 (M + H)⁺. |
| 776.0 | (2S,3R)-3-(5-methylpyrimidin-2-yl)butane-2-sulfonamide (Example 733.1), picolinhydrazide (Commercially available from Enamine), 5-isothiocyanato-4,6-dimethoxypyrimidine (Example 1.1). | 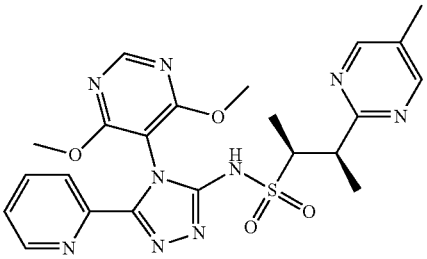 [SMILES: COc1ncnc(OC)c1-n1c(NS(=O)(=O)[C@@H](C)[C@H](C)c2ncc(C)cn2)nnc1-c1ccccn1]<br>(2S,3R)-N-(4-(4,6-dimethoxy-5-pyrimidinyl)-5-(2-pyridinyl)-4H-1,2,4-triazol-3-yl)-3-(5-methyl-2-pyrimidinyl)-2-butanesulfonamide<br>1H NMR (500 MHz, DMSO-d6) δ 1.11 (d, J = 6.88 Hz, 3 H) 1.26 (d, J = 7.01 Hz, 3 H) 2.23 (s, 3 H) 3.69 (br d, J = 4.80 Hz, 2 H) 3.80 (s, 3 H) 3.81 (s, 3 H) 7.42 (br s, 1 H) 7.93 (br t, J = 7.53 Hz, 1 H) 8.02 (d, J = 8.04 Hz, 1 H) 8.29 (br d, J = 3.11 Hz, 1 H) 8.59 (s, 2H) 8.62 (s, 1 H) 13.55 (br s, 1 H). LCMS-ESI (POS.) m/z: 512.1 (M + H)⁺. |

TABLE 42-continued

| Example | Reagents | Structure, Name and Data |
|---|---|---|
| 777.0 | (1S,2S)-1-isopropoxy-1-(5-methylpyrimidin-2-yl)propane-2-sulfonamide (Example 738.5), picolinhydrazide (Enamine), 5-isothiocyanato-4,6-dimethoxypyrimidine (Example 1.1). | 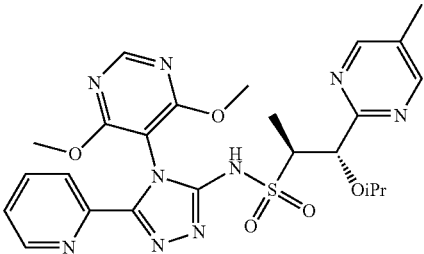 [SMILES: COc1ncnc(OC)c1-n1c(NS(=O)(=O)[C@@H](C)[C@@H](OC(C)C)c2ncc(C)cn2)nnc1-c1ccccn1]<br>(1S,2S)-N-(4-(4,6-dimethoxy-5-pyrimidinyl)-5-(2-pyridinyl)-4H-1,2,4-triazol-3-yl)-1-(1-methylethoxy)-1-(5-methyl-2-pyrimidinyl)-2-propanesulfonamide<br>$^1$H NMR (500 MHz, DMSO-$d_6$) δ 0.79 (d, J = 6.10 Hz, 3 H) 0.95 (d, J = 7.01 Hz, 3 H) 0.98 (d, J = 5.97 Hz, 3 H) 2.27 (s, 3 H) 3.39 (br s, 1 H) 3.44-3.58 (m, 1 H) 3.85 (m, 6 H) 4.73 (br d, J = 6.75 Hz, 1 H) 7.42 (br s, 1 H) 7.93 (br s, 1 H) 8.02 (d, J = 7.91 Hz, 1 H) 8.29 (br s, 1 H) 8.58-8.71 (m, 3 H) 13.48 (br s, 1 H). LCMS-ESI (POS.) m/z: 556.2 (M + H)$^+$. |
| 778.0 | (1S,2S)-1-isopropoxy-1-(5-methylpyrimidin-2-yl)propane-2-sulfonamide (Example 738.5), picolinhydrazide (Enamine), 2-isothiocyanato-1,3-dimethoxybenzene (Example 1.0). | 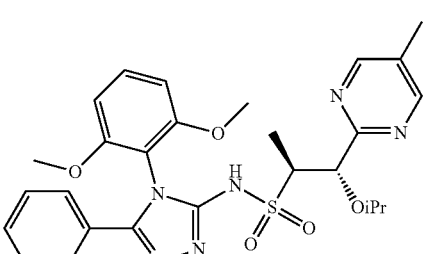<br>(1S,2S)-N-(4-(2,6-dimethoxyphenyl)-5-(2-pyridinyl)-4H-1,2,4-triazol-3-yl)-1-(1-methylethoxy)-1-(5-methyl-2-pyrimidinyl)-2-propanesulfonamide<br>$^1$H NMR (500 MHz, DMSO-$d_6$) δ 0.79 (d, J = 6.10 Hz, 3 H) 0.94 (d, J = 7.14 Hz, 3 H) 0.99 (d, J = 6.10 Hz, 3 H) 2.27 (s, 3 H) 3.35-3.48 (m, 2 H) 3.65 (s, 3 H) 3.66 (s, 3 H) 4.72 (d, J = 7.53 Hz, 1 H) 6.75 (s, 1 H) 6.76 (s, 1 H) 7.36-7.43 (m, 2 H) 7.81 (d, J = 7.91 Hz, 1 H) 7.86-7.92 (m, 1 H) 8.30 (d, J = 4.67 Hz, 1 H) 8.66 (s, 2 H) 13.24 (s, 1 H). LCMS-ESI (POS.) m/z: 554.2 (M + H)$^+$. |
| 779.0 | (1R,2S)-1-methoxy-1-(5-methylpyrazin-2-yl)propane-2-sulfonamide (Example 14.1), picolinhydrazide (Enamine), 5-isothiocyanato-4,6-dimethoxypyrimidine (Example 1.1). | 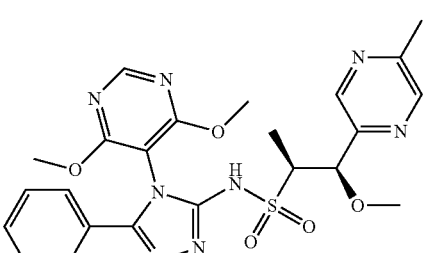<br>(1R,2S)-N-(4-(4,6-dimethoxy-5-pyrimidinyl)-5-(2-pyridinyl)-4H-1,2,4-triazol-3-yl)-1-methoxy-1-(5-methyl-2-pyrazinyl)-2-propanesulfonamide<br>$^1$H NMR (500 MHz, DMSO-$d_6$) δ 1.07 (d, J = 7.01 Hz, 3 H) 2.49 (br s, 3 H) 3.20 (s, 3 H) 3.32-3.42 (m, 1 H) 3.82 (s, 3 H) 3.83 (s, 3 H) 4.87 (d, J = 2.59 Hz, 1 H) 7.35-7.46 (m, 1 H) 7.89-7.97 (m, 1 H) 8.02 (d, J = 7.91 Hz, 1 H) 8.25-8.34 (m, 1 H) 8.45 (s, 1 H) 8.52 (s, 1 H) 8.62 (s, 1 H) 13.57 (s, 1 H). LCMS-ESI (POS.) m/z: 528.1 (M + H)$^+$. |

TABLE 42-continued

| Example | Reagents | Structure, Name and Data |
|---|---|---|
| 780.0 | (1R,2S)-1-methoxy-1-(5-methylpyrazin-2-yl)propane-2-sulfonamide (Example 14.1), picolinhydrazide (Enamine), 2-isothiocyanato-1,3-dimethoxybenzene (Example 1.0). | 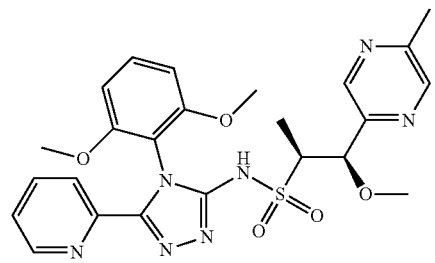<br>(1R,2S)-N-(4-(2,6-dimethoxyphenyl)-5-(2-pyridinyl)-4H-1,2,4-triazol-3-yl)-1-methoxy-1-(5-methyl-2-pyrazinyl)-2-propanesulfonamide<br>$^1$H NMR (500 MHz, DMSO-d$_6$) δ 1.07 (d, J = 7.01 Hz, 3 H) 2.49 (s, 3 H) 3.19 (s, 3 H) 3.25-3.31 (m, 1 H) 3.61 (s, 3 H) 3.63 (s, 3 H) 4.85 (d, J = 2.98 Hz, 1 H) 6.75 (s, 1 H) 6.76 (s, 1 H) 7.38-7.40 (m, 1 H) 7.40-7.43 (m, 1 H) 7.81-7.85 (m, 1 H) 7.86-7.92 (m, 1 H) 8.29-8.32 (m, 1 H) 8.42 (d, J = 1.30 Hz, 1 H) 8.52 (d, J = 0.78 Hz, 1 H) 13.33 (s, 1 H). LCMS-ESI (POS.) m/z: 526.2 (M + H)$^+$. |

Example 781.0: Preparation of (1R,2S)—N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide or (1S,2R)—N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide

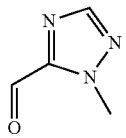

1-methyl-1H-1,2,4-triazole-5-carbaldehyde, Example 781.11

A three necked round-bottomed flask was charged with 1-methyl-1H-1,2,4-triazole (5 g, 60.2 mmol) and diluted with THF (40 mL) and diethyl ether (80 mL). The mixture was cooled to −45° C. under a nitrogen atmosphere and n-butyllithium (25.3 mL, 63.2 mmol) was added dropwise. The reaction mixture was stirred for 90 minutes at −45° C. and then cooled to −78° C. At −78° C., DMF (5.72 g, 78 mmol) in THF (7 mL) was then added dropwise. The reaction was then allowed to warm to RT. After 14 hours, the reaction mixture was quenched with 1.5 N HCl (100 mL). The layers were separated, and the organic layer was washed with 1.5 N HCl (2×40 mL). The combined aqueous layers were then brought to pH 9.0 with aqueous Na$_2$CO$_3$ and extracted with DCM (3×120 mL). The combined organic layers were dried over anhydrous sodium sulphate, filtered and concentrated under reduced pressure to obtain 1-methyl-1H-1,2,4-triazole-5-carbaldehyde (4.5 g, 40.5 mmol, 67% yield) as a brown liquid. LCMS-ESI (pos.) m/z: 112.1 (M+H)$^+$.

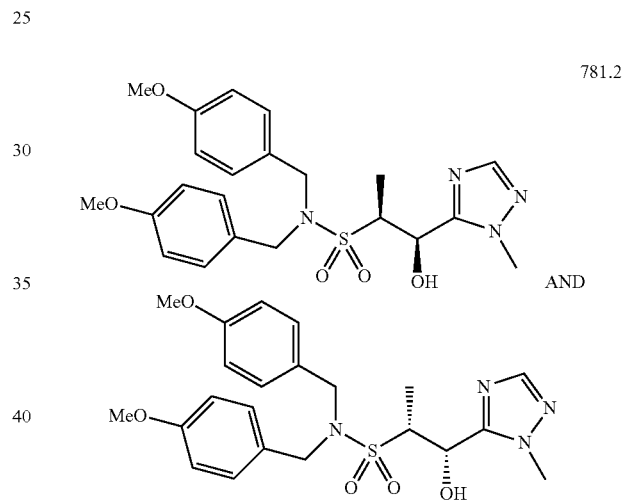

(1R,2S)-1-hydroxy-N,N-bis(4-methoxybenzyl)-1-(1-methyl-1H-1,2,4-triazol-5-yl)propane-2-sulfonamide and (1S,2R)-1-hydroxy-N,N-bis(4-methoxybenzyl)-1-(1-methyl-1H-1,2,4-triazol-5-yl)propane-2-sulfonamide, Example 781.2

A three necked round-bottomed flask was charged with N,N-bis(4-methoxybenzyl)ethanesulfonamide (15.73 g, 45.0 mmol, Example 12.0) and dissolved in THF (150 mL). The mixture was cooled to −78° C. and n-butyllithium (2.5 M solution in hexane, 19.80 mL, 49.5 mmol)) was added dropwise. After five minutes, 1-methyl-1H-1,2,4-triazole-5-carbaldehyde (5.0 g, 45.0 mmol) dissolved in THF (25 mL) was added by dropwise addition. After 10 minutes, the reaction mixture was warmed to RT. After 10 minutes at RT, the reaction mixture was quenched with saturated ammonium chloride (25 mL). Water (75 mL) was then added and the mixture was extracted with EtOAc (3×100 mL). The organic layers were separated, dried over anhydrous sodium sulphate, filtered and concentrated under reduced pressure to obtain a brown liquid. The material thus obtained was absorbed onto a plug of silica gel and purified by column chromatography, eluting with a gradient of 40% to 50% EtOAc in petroleum ether, to provide (1R,2S)-1-hydroxy-N,N-bis(4-methoxybenzyl)-1-(1-methyl-1H-1,2,4-triazol-5-yl)propane-2-sulfonamide and (1S,2R)-1-hydroxy-N,N-bis(4-methoxybenzyl)-1-(1-methyl-1H-1,2,4-triazol-5-yl)propane-2-sulfonamide (2.23 g, 4.84 mmol, 11% yield).

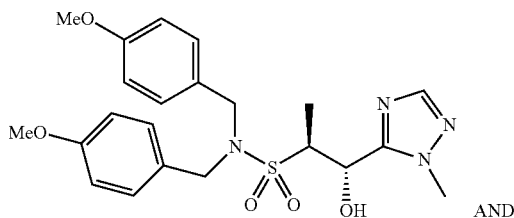

781.3

AND

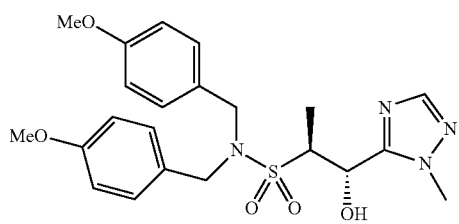

(1R,2R)-1-hydroxy-N,N-bis(4-methoxybenzyl)-1-(1-methyl-1H-1,2,4-triazol-5-yl)propane-2-sulfonamide and (1S,2S)-1-hydroxy-N,N-bis(4-methoxybenzyl)-1-(1-methyl-1H-1,2,4-triazol-5-yl)propane-2-sulfonamide, Example 781.3

Further elution under the conditions described in Example 781.2 delivered (1S,2S)-1-hydroxy-N,N-bis(4-methoxybenzyl)-1-(1-methyl-1H-1,2,4-triazol-5-yl)propane-2-sulfonamide (1.95 g, 4.23 mmol, 9% yield). LCMS-ESI (pos.) m/z: 461.1 (M+H)⁺.

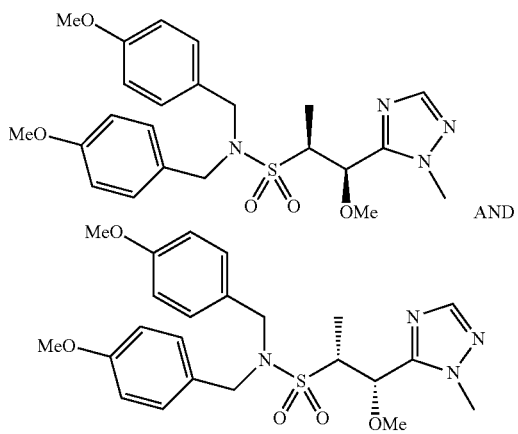

781.4

AND (1R,2S)-1-methoxy-N,N-bis(4-methoxybenzyl)-1-(1-methyl-1H-1,2,4-triazol-5-yl)propane-2-sulfonamide and (1S,2R)-1-methoxy-N,N-bis(4-methoxybenzyl)-1-(1-methyl-1H-1,2,4-triazol-5-yl)propane-2-sulfonamide, Example 781.4

A 24/40-50-mL two neck round-bottomed flask was charged with Example 781.2 (1.0 g, 2.171 mmol) and dissolved in DMF (10 mL, 10.00 mL/g). The mixture was cooled to −10° C. and cesium carbonate (1.42 g, 4.34 mmol) was added. After 30 minutes, MeI (0.163 mL, 2.61 mmol) was added at −10° C. The reaction mixture was allowed to warm to RT. After 16 hours, the reaction mixture was quenched with cold water and extracted with EtOAc (3×50 mL). The combined organic layers were washed with cold water (25 mL) followed by brine solution (25 mL) and dried over Na₂SO₄. The solution was filtered and concentrated in vacuo to give a yellow oil. The material thus obtained was absorbed onto a plug of silica gel and purified by chromatography through a silica gel column using 60-120 mesh silica, eluting with a gradient of 40% to 45% EtOAc in petroleum ether, to provide the title compound (0.52 g, 1.1 mmol, 51% yield) as colorless gum. LCMS-ESI (pos.) m/z: 475.1 (M+H)⁺.

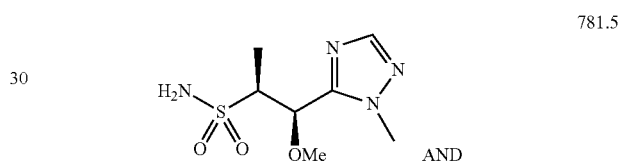

781.5

AND

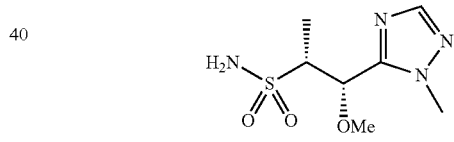

(1R,2S)-1-methoxy-1-(1-methyl-1H-1,2,4-triazol-5-yl)propane-2-sulfonamide and (1S,2R)-1-methoxy-1-(1-methyl-1H-1,2,4-triazol-5-yl)propane-2-sulfonamide, Example 781.5

To a vial containing Example 781.4 (0.465 g, 0.980 mmol) was added DCM (2.58 mL) and then anisole (0.426 mL, 3.92 mmol). The homogeneous solution was stirred at 23° C. After 2 minutes, TFA (2.55 mL, 34.3 mmol) was added dropwise to the reaction solution. Once complete, the reaction was concentrated under reduced pressure. The residue was loaded onto a silica gel column (20-65% 3:1 EtOAc: EtOH in heptanes) and purified to afford (1S,2R)-1-methoxy-1-(1-methyl-1H-1,2,4-triazol-5-yl)propane-2-sulfonamide and (1R,2S)-1-methoxy-1-(1-methyl-1H-1,2,4-triazol-5-yl)propane-2-sulfonamide (0.23 g, 0.98 mmol, 100% yield). LCMS-ESI (pos.) m/z: 235.1 (M+H)⁺.

The compounds set forth in the following Table were synthesized following the procedure in Example 741.0 using the known starting material as described.

TABLE 43

| Example | Reagents | Structure, Name and Data |
|---|---|---|
| 781.0 | (1R,2S)-1-methoxy-1-(1-methyl-1H-1,2,4-triazol-5-yl)propane-2-sulfonamide and (1S,2R)-1-methoxy-1-(1-methyl-1H-1,2,4-triazol-5-yl)propane-2-sulfonamide (Example 781.5), 5-methylnicotinohydrazide (Example 3.11), 2-isothiocyanato-1,3-dimethoxybenzene (Example 1.0). The racemic mixture was separated by preparative SFC using the following method: Column: Chiralpak AS-H, Mobile Phase: 75:25 (A:B) A: Liquid $CO_2$; B: iPrOH to deliver peak 1 at 1.04 minutes. | 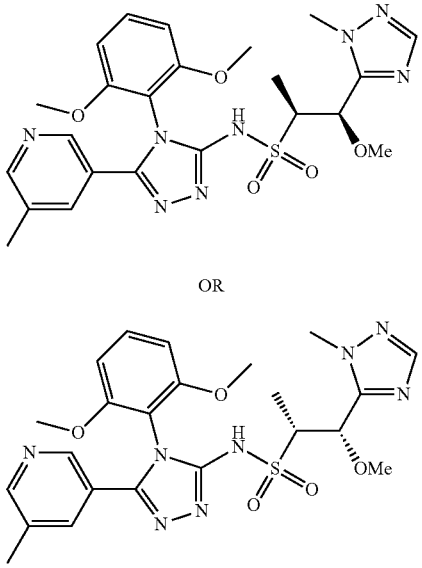<br>OR<br><br>(1R,2S)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide or (1S,2R)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide.<br>$^1$H NMR (500 MHz, DMSO-$d_6$) δ ppm 13.45 (1 H, s) 8.48 (1 H, s) 8.21 (1 H, s) 7.86 (1 H, s) 7.62 (1 H, s) 7.52 (1 H, t, J = 8.50 Hz) 6.86 (1 H, br d, J = 8.56 Hz) 6.84 (1 H, br d, J = 8.69 Hz) 4.83 (1 H, d, J = 5.06 Hz) 3.74 (3 H, s) 3.72 (3 H, s) 3.70 (3 H, s) 3.34-3.40 (1 H, m) 3.10 (3 H, s) 2.25 (3 H, s) 1.29 (3 H, d, J = 6.88 Hz). LCMS-ESI (POS.) m/z: 529.1 (M + H)$^+$. |
| 782.0 | (1R,2S)-1-methoxy-1-(1-methyl-1H-1,2,4-triazol-5-yl)propane-2-sulfonamide and (1S,2R)-1-methoxy-1-(1-methyl-1H-1,2,4-triazol-5-yl)propane-2-sulfonamide (Example 781.5), 5-methylnicotinohydrazide (Example 3.11), 2-isothiocyanato-1,3-dimethoxybenzene (Example 1.0) The racemic mixture was separated by preparative SFC using the following method: Column: Chiralpak AS-H, Mobile Phase: 75:25 (A:B) A: Liquid $CO_2$; B: iPrOH to deliver the second eluting peak at 1.82 minutes. | 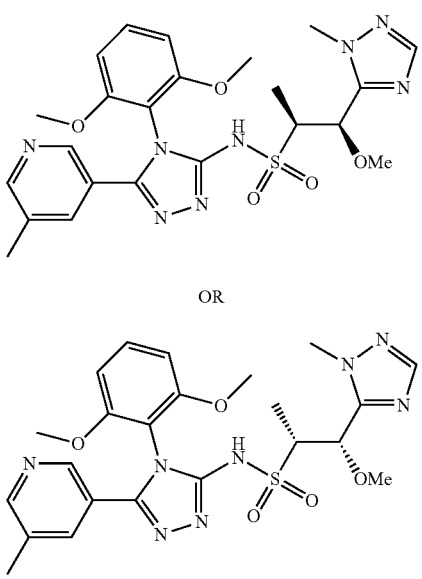<br>OR<br><br>(1R,2S)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide or (1S,2R)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide.<br>$^1$H NMR (500 MHz, DMSO-$d_6$) δ ppm 13.45 (1 H, s) 8.48 (1 H, s) 8.21 (1 H, s) 7.86 (1 H, s) 7.62 (1 H, s) |

TABLE 43-continued

| Example | Reagents | Structure, Name and Data |
|---------|----------|--------------------------|
| | | 7.52 (1 H, t, J = 8.50 Hz) 6.86 (1 H, br d, J = 8.56 Hz) 6.84 (1 H, br d, J = 8.69 Hz) 4.83 (1 H, d, J = 5.06 Hz) 3.74 (3 H, s) 3.72 (3 H, s) 3.70 (3 H, s) 3.34-3.39 (1 H, m) 3.10 (3 H, s) 2.25 (3 H, s) 1.29 (3 H, d, J = 6.88 Hz). LCMS-ESI (POS.) m/z: 529.1 (M + H)⁺. |
| 783.0 | 6-methylpicolinohydrazide (Example 3.4), 1,3-difluoro-2-isothiocyanatobenzene (commercially available from Sigma-Aldrich Corp, St. Louis, MO, USA) and (2S,3R)-3-(5-methylpyrimidin-2-yl)butane-2-sulfonamide (Example 733.1). | 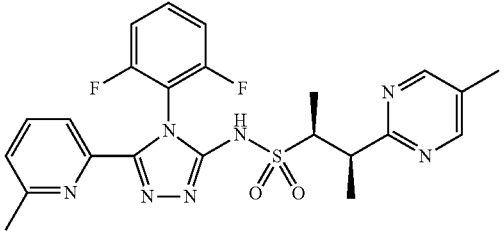<br>(2S,3R)-N-(4-(2,6-difluorophenyl)-5-(6-methyl-2-pyridinyl)-4H-1,2,4-triazol-3-yl)-3-(5-methyl-2-pyrimidinyl)-2-butanesulfonamide. ¹H NMR (400 MHz, CDCl₃) δ 11.47 (br s, 1 H) 8.53 (d, J = 0.62 Hz, 2 H) 7.85 (d, J = 7.88 Hz, 1 H) 7.66 (t, J = 7.88 Hz, 1 H) 7.44 (tt, J = 8.58, 6.14 Hz, 1 H) 7.13 (d, J = 7.88 Hz, 1 H) 6.96-7.07 (m, 2 H) 3.92 (quin, J = 6.84 Hz, 1 H) 3.75 (quin, J = 6.84 Hz, 1 H) 2.29 (s, 3 H) 2.11 (s, 3 H) 1.39 (dd, J = 7.05, 0.83 Hz, 6 H). LCMS-ESI (POS.) m/z: 500.2 (M + H)⁺. |
| 784.0 | (2S,3R)-3-(5-methylpyrimidin-2-yl)butane-2-sulfonamide (Example 733.1), 6-methoxypicolinohydrazide (Example 3.18), 1,3-difluoro-2-isothiocyanatobenzene (commercially available from Sigma-Aldrich Corp, St. Louis, MO, USA) | 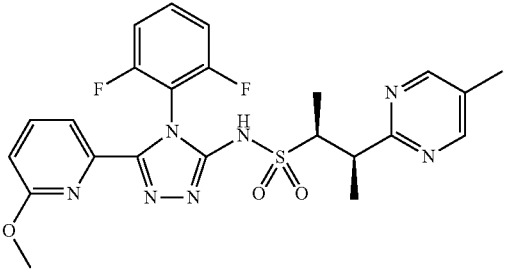 [SMILES: COc1cccc(-c2nnc(NS(=O)(=O)[C@@H](C)[C@H](C)c3ncc(C)cn3)n2-c2c(F)cccc2F)n1]<br>(2S,3R)-N-(4-(2,6-difluorophenyl)-5-(6-methoxy-2-pyridinyl)-4H-1,2,4-triazol-3-yl)-3-(5-methyl-2-pyrimidinyl)-2-butanesulfonamide. ¹H NMR (400 MHz, CDCl₃) δ 8.53 (d, J = 0.62 Hz, 2 H) 7.62-7.73 (m, 2 H) 7.42 (tt, J = 8.56, 6.15 Hz, 1 H) 6.99-7.09 (m, 2 H) 6.76 (dd, J = 7.05, 2.07 Hz, 1 H) 3.90 (quin, J = 6.84 Hz, 1 H) 3.74 (quin, J = 6.87 Hz, 1 H) 3.16 (s, 3 H) 2.29 (s, 3 H) 1.38 (d, J = 6.95 Hz, 6 H). LCMS-ESI (POS.) m/z: 516.2 (M + H)⁺. |
| 785.0 | (2S,3R)-3-(5-methylpyrimidin-2-yl)butane-2-sulfonamide (Example 733.1), picolinohydrazide (commercially available from Enamine LLC, Monmouth Jct., NJ, USA), 1,3-difluoro-2-isothiocyanatobenzene (commercially available from Sigma-Aldrich Corp, St. Louis, MO, USA) | 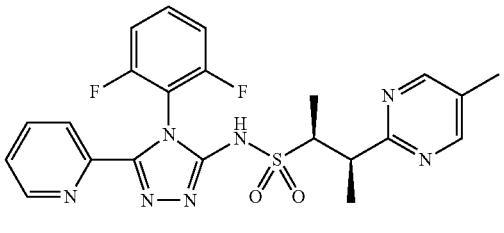 [SMILES: Cc1cnc([C@@H](C)[C@H](C)S(=O)(=O)Nc2nnc(-c3ccccn3)n2-c2c(F)cccc2F)nc1]<br>(2S,3R)-N-(4-(2,6-difluorophenyl)-5-(2-pyridinyl)-4H-1,2,4-triazol-3-yl)-3-(5-methyl-2-pyrimidinyl)-2-butanesulfonamide. ¹H NMR (400 MHz, CDCl₃) δ 11.49 (br s, 1 H) 8.54 (d, J = 0.73 Hz, 2 H) 8.23-8.30 (m, 1 H) 8.05 (dt, J = 7.93, 1.11 Hz, 1 H) 7.79 (td, J = 7.77, 1.76 Hz, 1 H) 7.44 (tt, J = 8.59, 6.13 Hz, 1 H) 7.28-7.31 (m, 1 H) 6.95-7.06 (m, 2 H) 3.92 (quin, J = 6.84 Hz, 1 H) 3.67-3.79 (m, 1 H) 2.30 (s, 3 H) 1.40 (d, J = 1.76 Hz, 3 H) 1.39 (d, J = 1.87 Hz, 3 H). LCMS-ESI (POS.) m/z: 486.2 (M + H)⁺. |

TABLE 43-continued

| Example | Reagents | Structure, Name and Data |
|---|---|---|
| 786.0 | (2S,3R)-3-(5-chloropyrimidin-2-yl)butane-2-sulfonamide (Example 696.1), 6-methoxypicolinohydrazide (Example 3.18), 1,3-difluoro-2-isothiocyanatobenzene (commercially available from Sigma-Aldrich Corp, St. Louis, MO, USA) | (2S,3R)-3-(5-chloro-2-pyrimidinyl)-N-(4-(2,6-difluorophenyl)-5-(6-methoxy-2-pyridinyl)-4H-1,2,4-triazol-3-yl)-2-butanesulfonamide. $^1$H NMR (500 MHz, DMSO-d$_6$) δ 13.72 (br. s., 1 H) 8.85 (s, 2 H) 7.85 (t, J = 7.78 Hz, 1 H) 7.69 (d, J = 7.27 Hz, 1 H) 7.58-7.65 (m, 1 H) 7.37 (t, J = 8.43 Hz, 2 H) 6.88 (d, J = 8.82 Hz, 1 H) 4.10 (d, J = 5.19 Hz, 1 H) 3.17 (d, J = 4.67 Hz, 1 H) 3.09 (s, 3 H) 1.23 (d, J = 7.01 Hz, 3 H) 1.12 (d, J = 7.01 Hz, 3 H). LCMS-ESI (POS.) m/z: 536.11 (M + H)$^+$. |
| 787.0 | (2S,3R)-3-(5-methoxypyrazin-2-yl)butane-2-sulfonamide (Example 803.1), 6-methoxypicolinohydrazide (Example 3.18), 1,3-difluoro-2-isothiocyanatobenzene (commercially available from Sigma-Aldrich Corp, St. Louis, MO, USA) | (2S,3R)-N-(4-(2,6-difluorophenyl)-5-(6-methoxy-2-pyridinyl)-4H-1,2,4-triazol-3-yl)-3-(5-methoxy-2-pyrazinyl)-2-butanesulfonamide. $^1$H NMR (500 MHz, DMSO-d$_6$) δ 13.78 (br. s., 1 H) 8.22 (s, 1 H) 8.01 (s, 1 H) 7.84 (t, J = 7.79 Hz, 1 H) 7.69 (d, J = 7.53 Hz, 1 H) 7.56-7.66 (m, 1 H) 7.36 (t, J = 8.30 Hz, 2 H) 6.85 (d, J = 8.04 Hz, 1 H) 3.87 (s, 3 H) 3.54-3.66 (m, 1 H) 3.17 (d, J = 4.41 Hz, 1 H) 3.09 (s, 3 H) 1.22 (d, J = 7.01 Hz, 3 H) 1.11 (d, J = 7.01 Hz, 3 H). LCMS-ESI (POS.) m/z: 532.16 (M + H)$^+$. |
| 788.0 | (2S,3R)-3-(5-chloropyrimidin-2-yl)butane-2-sulfonamide (Example 696.1), 6-methylpicolinohydrazide (Example 3.4), 1,3-difluoro-2-isothiocyanatobenzene (commercially available from Sigma-Aldrich Corp, St. Louis, MO, USA). | (2S,3R)-3-(5-chloro-2-pyrimidinyl)-N-(4-(2,6-difluorophenyl)-5-(6-methyl-2-pyridinyl)-4H-1,2,4-triazol-3-yl)-2-butanesulfonamide. $^1$H NMR (500 MHz, DMSO-d$_6$) δ 13.70 (br. s., 1 H) 8.85 (s, 2 H) 7.78-7.96 (m, 2 H) 7.60-7.75 (m, 1 H) 7.20-7.46 (m, 3 H) 3.53-3.78 (m, 2 H) 2.04 (s, 3 H) 1.23 (d, J = 6.75 Hz, 3 H) 1.15 (d, J = 6.49 Hz, 3 H). LCMS-ESI (POS.) m/z: 520.11 (M + H)$^+$. |

TABLE 43-continued

| Example | Reagents | Structure, Name and Data |
|---|---|---|
| 789.0 | (2S,3R)-3-(5-methylpyrazin-2-yl)butane-2-sulfonamide (Example 799.1), 6-methoxypicolinohydrazide (Example 3.18), 1,3-difluoro-2-isothiocyanatobenzene (commercially available from Sigma-Aldrich Corp, St. Louis, MO, USA). | 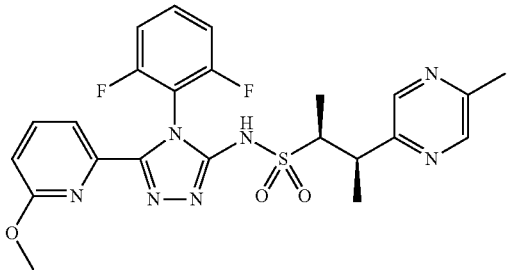 [SMILES: COc1cccc(-c2nnc(NS(=O)(=O)[C@@H](C)[C@H](C)c3cnc(C)cn3)n2-c2c(F)cccc2F)n1]<br>(2S,3R)-N-(4-(2,6-difluorophenyl)-5-(6-methoxy-2-pyridinyl)-4H-1,2,4-triazol-3-yl)-3-(5-methyl-2-pyrazinyl)-2-butanesulfonamide. $^1$H NMR (400 MHz, CDCl$_3$) δ 11.00 (s, 1 H) 8.40 (s, 1 H) 8.34 (d, J = 1.45 Hz, 1 H) 7.55-7.76 (m, 2 H) 7.45 (tt, J = 8.60, 6.12 Hz, 1 H) 7.02-7.13 (m, 2 H) 6.68-6.84 (m, 1 H) 3.75 (qd, J = 7.03, 4.41 Hz, 1 H) 3.59 (qd, J = 7.00, 4.51 Hz, 1 H) 3.17 (s, 3 H) 2.56 (s, 3 H) 1.38 (d, J = 7.05 Hz, 6 H). LCMS-ESI (POS.) m/z: 516.2 (M + H)$^+$. |
| 790.0 | (2S,3R)-3-(5-methylpyrazin-2-yl)butane-2-sulfonamide (Example 799.1), 6-methylpicolinohydrazide (Example 3.4), 1,3-difluoro-2-isothiocyanatobenzene (commercially available from Sigma-Aldrich Corp, St. Louis, MO, USA). | 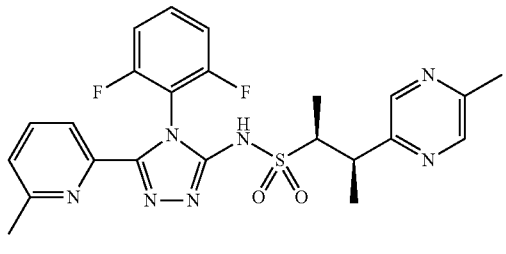 [SMILES: Cc1cnc([C@@H](C)[C@H](C)S(=O)(=O)Nc2nnc(-c3cccc(C)n3)n2-c2c(F)cccc2F)cn1]<br>(2S,3R)-N-(4-(2,6-difluorophenyl)-5-(6-methyl-2-pyridinyl)-4H-1,2,4-triazol-3-yl)-3-(5-methyl-2-pyrazinyl)-2-butanesulfonamide. $^1$H NMR (400 MHz, CDCl$_3$) δ 11.02 (s, 1 H) 8.28-8.42 (m, 2 H) 7.85 (d, J = 7.57 Hz, 1 H) 7.66 (t, J = 7.83 Hz, 1 H) 7.47 (tt, J = 8.59, 6.13 Hz, 1 H) 7.14 (d, J = 7.77 Hz, 1 H) 6.97-7.08 (m, 2 H) 3.77 (qd, J = 7.08, 4.56 Hz, 1 H) 3.60 (qd, J = 7.01, 4.35 Hz, 1 H) 2.55 (s, 3 H) 2.11 (s, 3 H) 1.39 (d, J = 7.05 Hz, 6 H). LCMS-ESI (POS.) m/z: 500.2 (M + H)$^+$. |
| 791.0 | (2S,3R)-3-(5-methylpyrimidin-2-yl)butane-2-sulfonamide (Example 10.0), 6-(methylamino)picolinohydrazide (Example 3.25), 1,3-difluoro-2-isothiocyanatobenzene (commercially available from Sigma-Aldrich Corp, St. Louis, MO, USA). | 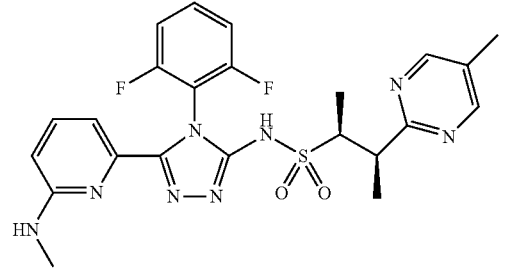 [SMILES: CNc1cccc(-c2nnc(NS(=O)(=O)[C@@H](C)[C@H](C)c3ncc(C)cn3)n2-c2c(F)cccc2F)n1]<br>(2S,3R)-N-(4-(2,6-difluorophenyl)-5-(6-(methylamino)-2-pyridinyl)-4H-1,2,4-triazol-3-yl)-3-(5-methyl-2-pyrimidinyl)-2-butanesulfonamide. $^1$H NMR (500 MHz, CDCl$_3$) δ 11.35 (br. s., 1 H) 8.54 (s, 2 H) 7.43-7.50 (m, 1 H) 7.37-7.43 (m, 1 H) 7.31 (d, J = 7.53 Hz, 1 H) 7.02 (q, J = 8.30 Hz, 2 H) 6.38 (d, J = 8.30 Hz, 1 H) 4.92 (br. s., 1 H) 3.92 (quin, J = 6.81 Hz, 1 H) 3.75 (dt, J = 13.62, 6.68 Hz, 1 H) 2.37 (s, 3 H) 2.30 (s, 3 H) 1.38 (d, J = 7.01 Hz, 6 H). LCMS-ESI (POS.) m/z: 515.2 (M + H)$^+$. |

TABLE 43-continued

| Example | Reagents | Structure, Name and Data |
|---|---|---|
| 792.0 | (1S,2R)-1-methoxy-1-(5-methylpyrimidin-2-yl)propane-2-sulfonamide (using the minor enantiomer from Example 14.02) 6-methoxypicolinohydrazide (Example 3.18), 1,3-difluoro-2-isothiocyanatobenzene (commercially available from Sigma-Aldrich Corp, St. Louis, MO, USA). | 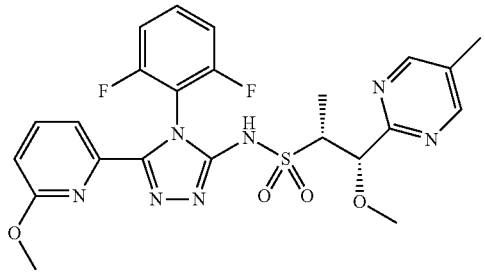 [SMILES: COc1cccc(-c2nnc(NS(=O)(=O)[C@H](C)[C@@H](OC)c3ncc(C)cn3)n2-c2c(F)cccc2F)n1]<br>(1S,2R)-N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide. $^1$H NMR (500 MHz, CDCl$_3$) δ 11.29 (br s, 1 H) 8.62 (s, 2 H) 7.61-7.74 (m, 2 H) 7.35-7.46 (m, 1 H) 7.05 (t, J = 8.11 Hz, 2 H) 6.77 (dd, J = 7.01, 2.08 Hz, 1 H) 4.98 (d, J = 4.54 Hz, 1 H) 3.69-3.84 (m, 1 H) 3.35 (s, 3 H) 3.17 (s, 3 H) 2.34 (s, 3 H) 1.40 (d, J = 7.01 Hz, 3 H). LCMS-ESI (POS.) m/z: 532.2 (M + H)$^+$. |
| 793.0 | (2S,3R)-3-(5-methylpyrimidin-2-yl)butane-2-sulfonamide (Example 733.1), nicotinohydrazide (commercially available from Sigma-Aldrich Corp, St. Louis, MO, USA), 1,3-difluoro-2-isothiocyanatobenzene (commercially available from Sigma-Aldrich Corp, St. Louis, MO, USA). | 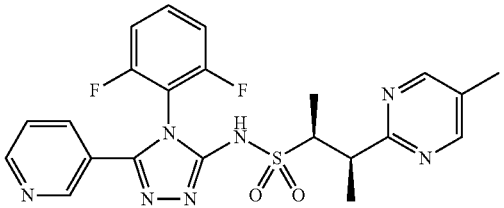 [SMILES: Cc1cnc([C@@H](C)[C@H](C)S(=O)(=O)Nc2nnc(-c3cccnc3)n2-c2c(F)cccc2F)nc1]<br>(2S,3R)-N-(4-(2,6-difluorophenyl)-5-(3-pyridinyl)-4H-1,2,4-triazol-3-yl)-3-(5-methyl-2-pyrimidinyl)-2-butanesulfonamide. $^1$H NMR (400 MHz, CDCl$_3$) δ 8.67 (dd, J = 4.82, 1.40 Hz, 1 H) 8.60 (d, J = 1.56 Hz, 1 H) 8.54 (s, 2 H) 7.77 (dt, J = 7.90, 1.96 Hz, 1 H) 7.45-7.56 (m, 1 H) 7.32 (dd, J = 7.83, 5.13 Hz, 1 H) 7.01-7.14 (m, 2 H) 3.90 (quin, J = 6.84 Hz, 1 H) 3.70-3.82 (m, 1 H) 2.28 (s, 3 H) 1.38 (d, J = 6.95 Hz, 6 H). LCMS-ESI (POS.) m/z: 486.2 (M + H)$^+$. |
| 794.0 | (2S,3R)-3-(5-methoxypyrimidin-2-yl)butane-2-sulfonamide (Example 10.5), 5-methylnicotinohydrazide (commercially available from Bellen Chemistry Co. Sunnyvale, CA, USA), 1,3-difluoro-2-isothiocyanatobenzene (commercially available from Sigma-Aldrich Corp, St. Louis, MO, USA). | 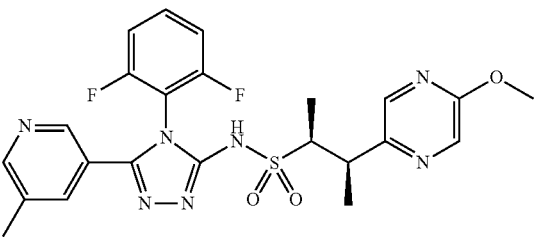 [SMILES: COc1cnc([C@@H](C)[C@H](C)S(=O)(=O)Nc2nnc(-c3cncc(C)c3)n2-c2c(F)cccc2F)cn1]<br>(2S,3R)-N-(4-(2,6-difluorophenyl)-5-(5-methyl-3-pyridinyl)-4H-1,2,4-triazol-3-yl)-3-(5-methoxy-2-pyrazinyl)-2-butanesulfonamide. $^1$H NMR (400 MHz, CDCl$_3$) δ 8.50 (s, 1 H) 8.30 (d, J = 1.66 Hz, 1 H) 8.15 (d, J = 1.14 Hz, 1 H) 7.96 (d, J = 1.14 Hz, 1 H) 7.64-7.69 (m, 1 H) 7.38-7.59 (m, 1 H) 7.01-7.11 (m, 2 H) 3.94 (s, 3 H) 3.75 (qd, J = 7.07, 3.99 Hz, 1 H) 3.43-3.62 (m, 1 H) 2.33 (s, 3 H) 1.35 (t, J = 6.63 Hz, 6 H). LCMS-ESI (POS.) m/z: 516.2 (M + H)$^+$. |

TABLE 43-continued

| Example | Reagents | Structure, Name and Data |
|---|---|---|
| 795.0 | (2S,3R)-3-(5-methylpyrazin-2-yl)butane-2-sulfonamide (Example 799.1), 5-methylnicotinohydrazide (commercially available from Bellen Chemistry Co. Sunnyvale, CA, USA), 1,3-difluoro-2-isothiocyanatobenzene (commercially available from Sigma-Aldrich Corp, St. Louis, MO, USA). | (2S,3R)-N-(4-(2,6-difluorophenyl)-5-(5-methyl-3-pyridinyl)-4H-1,2,4-triazol-3-yl)-3-(5-methyl-2-pyrazinyl)-2-butanesulfonamide. $^1$H NMR (400 MHz, CDCl$_3$) δ 8.39-8.59 (m, 1 H) 8.28-8.39 (m, 3 H) 7.65 (s, 1 H) 7.45-7.57 (m, 1 H) 7.07 (td, J = 8.55, 4.04 Hz, 2 H) 3.70-3.80 (m, 1 H) 3.55-3.66 (m, 1 H) 2.52 (s, 3 H) 2.33 (s, 3 H) 1.36 (br t, J = 6.17 Hz, 6 H). LCMS-ESI (POS.) m/z: 500.2 (M + H)$^+$. |
| 796.0 | (2S,3R)-3-(5-chloropyrimidin-2-yl)butane-2-sulfonamide (Example 696.1), 5-methylnicotinohydrazide (commercially available from Bellen Chemistry Co. Sunnyvale, CA, USA), 1,3-difluoro-2-isothiocyanatobenzene (commercially available from Sigma-Aldrich Corp, St. Louis, MO, USA). | (2S,3R)-3-(5-chloro-2-pyrimidinyl)-N-(4-(2,6-difluorophenyl)-5-(5-methyl-3-pyridinyl)-4H-1,2,4-triazol-3-yl)-2-butanesulfonamide. $^1$H NMR (500 MHz, DMSO-d$_6$) δ 13.79 (br. s., 1 H) 8.85 (s, 2 H) 8.46 (br. s., 1 H) 8.22 (br. s., 1 H) 7.69 (br. s., 1 H) 7.62 (br. s., 1 H) 7.39 (br. s., 2 H) 3.70 (br. s., 1 H) 3.17 (d, J = 4.93 Hz, 1 H) 2.25 (s, 3 H) 1.26 (d, J = 7.01 Hz, 3 H) 1.12 (d, J = 6.23 Hz, 3 H). LCMS-ESI (POS.) m/z: 520.11 (M + H)$^+$. |
| 797.0 | (2S,3R)-3-(5-methylpyrimidin-2-yl)butane-2-sulfonamide (Example 733.1), 5-methylnicotinohydrazide (commercially available from Bellen Chemistry Co. Sunnyvale, CA, USA), 1-isothiocyanato-2-methoxybenzene (commercially available from Acros Organics, Geel, Belgium). | AND |

TABLE 43-continued

| Example | Reagents | Structure, Name and Data |
|---|---|---|
| | | (2S,3R,P)-N-(4-(2-methoxyphenyl)-5-(5-methyl-3-pyridinyl)-4H-1,2,4-triazol-3-yl)-3-(5-methyl-2-pyrimidinyl)-2-butanesulfonamide and (2S,3R,M)-N-(4-(2-methoxyphenyl)-5-(5-methyl-3-pyridinyl)-4H-1,2,4-triazol-3-yl)-3-(5-methyl-2-pyrimidinyl)-2-butanesulfonamide. $^1$H NMR (400 MHz, CDCl$_3$) δ 11.42 (br. s., 1 H) 11.33 (br. s., 1 H) 8.54 (d, J = 0.83 Hz, 4 H) 8.43-8.48 (m, 2 H) 8.33 (dd, J = 5.91, 1.97 Hz, 2 H) 7.62 (d, J = 2.07 Hz, 2 H) 7.47 (td, J = 7.93, 1.55 Hz, 2 H) 7.38 (dd, J = 7.67, 1.66 Hz, 1 H) 7.28-7.31 (m, 1 H) 7.07 (tdd, J = 7.72, 7.72, 6.53, 1.24 Hz, 2 H) 6.97 (ddd, J = 8.45, 5.96, 1.14 Hz, 2 H) 3.90 (ddd, J = 7.15, 5.80, 1.55 Hz, 2 H) 3.74-3.81 (m, 2 H) 3.66 (s, 3 H) 3.63 (s, 3 H) 2.31 (s, 12 H) 1.32-1.46 (m, 12 H). LCMS-ESI (POS.) m/z: 494.2 (M + H)$^+$. |

Example 798.0: Preparation of (2S,3R)—N-(4-(6-bromo-3-methoxy-2-pyridinyl)-5-(6-methoxy-2-pyridinyl)-4H-1,2,4-triazol-3-yl)-3-(5-fluoro-2-pyrimidinyl)-2-butanesulfonamide

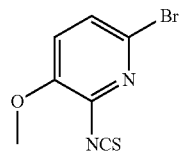

798.1

6-bromo-2-isothiocyanato-3-methoxypyridine, Example 798.1

To a 500-mL round-bottomed flask was added 6-bromo-3-methoxypyridin-2-amine (8.04 g, 39.6 mmol) in DCM (132 mL). 1,1″-thiocarbonyldi-2(1H)-pyridone (9.66 g, 41.6 mmol) was added at RT with stirring. The reaction mixture was stirred at 23° C. for 20 hours. The reaction mixture was then diluted with water and extracted with DCM. The organic extract was washed with water and dried over Na$_2$SO$_4$. The solution was filtered and concentrated in vacuo to give an orange solid. The material thus obtained was absorbed onto a plug of silica gel and purified by chromatography through a RediSep-Sep pre-packed silica gel column (120 g), eluting with a gradient of 0% to 10% EtOAc in DCM, to provide 6-bromo-2-isothiocyanato-3-methoxypyridine (8.6 g, 35.1 mmol, 89% yield) as white solid. $^1$H NMR (400 MHz, DMSO-d$_6$) δ 7.61 (s, 2H) 3.93 (m, 3H). LCMS-ESI (POS.) m/z: 244.7 (M+H)$^+$.

The compounds set forth in the following Table were synthesized following the procedure in Example 741.0 using the known starting material as described.

TABLE 44

| Example | Reagents | Structure, Name and Data |
|---|---|---|
| 798.0 | (2S,3R)-3-(5-fluoropyrimidin-2-yl)butane-2-sulfonamide (Example 733.1), 6-methoxypicolinohydrazide (commercially available from Sigma-Aldrich Corp, St. Louis, MO, USA), 6-bromo-2-isothiocyanato-3-methoxypyridine6-bromo-2-isothiocyanato-3-methoxypyridine (Example 798.1). | (2S,3R)-N-(4-(6-bromo-3-methoxy-2-pyridinyl)-5-(6-methoxy-2-pyridinyl)-4 H-1,2,4-triazol-3-yl)-3-(5-fluoro-2-pyrimidinyl)-2-butanesulfonamide. $^1$H NMR (400 MHz, CDCl$_3$) δ 1.37-1.44 (m, 6 H) 3.16 (s, 3 H) 3.76 (d, J = 2.28 Hz, 3 H) 3.78-3.89 (m, 2 H) 6.74 (d, J = 7.25 Hz, 1 H) 7.25-7.28 (m, 1 H) 7.56 (dd, J = 8.55, 1.61 Hz, 1 H) 7.67 (d, J = 11.12 Hz, 1 H) 7.67 (s, 1 H) 8.57 (s, 2 H). LCMS-ESI (POS.) m/z: 593.0 (M + H)$^+$. |

Example 799.0: Preparation of (2S,3R)—N-(4-(4,6-dimethoxy-5-pyrimidinyl)-5-(6-methoxy-2-pyridinyl)-4H-1,2,4-triazol-3-yl)-3-(5-methyl-2-pyrazinyl)-2-butanesulfonamide

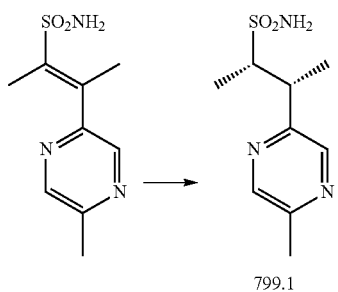

799.1

(2S,3R)-3-(5-methylpyrazin-2-yl) butane-2-sulfonamide, Example 799.1

A pressure vessel was charged with a solution of (E)-3-(5-methylpyrazin-2-yl)but-2-ene-2-sulfonamide (prepared in an analogous fashion to 10.05 starting from 2-bromo-5-methylpyrazine (23 g, 101 mmol, 1.0 equiv), (S)-1-[(R)-2-(di-1-naphthylphosphino)ferrocenyl]-ethyl-di-tert-butyl-phosphine (2.276 g, 3.54 mmol, 0.035 equiv, Solvias), bis(1,5-cyclooctadiene)rhodium(i) tetrafluoroborate (2.66 g, 3.04 mmol, 0.03 equiv, Combi Block) and zinc trifluoromethanesulfonate (11.04 g, 30.4 mmol, 0.3 equiv, Aldrich) in MeOH (230 mL, 10.00 mL/g). The reactor was purged with argon and back filled with hydrogen for three times. The reaction mixture was then stirred under hydrogen atmosphere (150 psi) at 60° C. for 18 h. The reaction mixture was filtered through a Celite® filter aid pad and concentrated under reduced pressure. The resulting material was purified by column chromatography through a Redi-Sep pre-packed silica gel column (80 g), eluting with a gradient of 1% to 3% MeOH in CHCl$_3$, to provide the title compound (22 g, 95% yield, 70% ee) as a yellow solid. $^1$H NMR (400 MHz, DMSO-d$_6$) δ 8.46 (d, J=6.5 Hz, 2H), 6.84 (s, 2H), 3.63 (qd, J=7.0, 4.3 Hz, 1H), 3.44 (qd, J=7.0, 4.3 Hz, 1H), 2.47 (s, 3H), 1.31 (d, J=7.0 Hz, 3H), 1.23 (d, J=7.0 Hz, 3H). MS (ESI, positive ion) m/z; 230.0 (M+H)$^+$. Material was recrystallized to greater than 99% ee for further use.

The compounds set forth in the following Table were synthesized following the procedure in Example A using the known starting material as described.

TABLE 45

| Example | Reagents | Structure, Name and Data |
|---|---|---|
| 799.0 | (2S,3R)-3-(5-methylpyrazin-2-yl)butane-2-sulfonamide (Example 799.1), 6-methoxypicolinohydrazide (commercially available from Sigma-Aldrich Corp, St. Louis, MO, USA), 5-isothiocyanato-4,6-dimethoxypyrimidine, (Example 1.1), AcOH was used instead of methanesulfonic acid and also as solvent. | 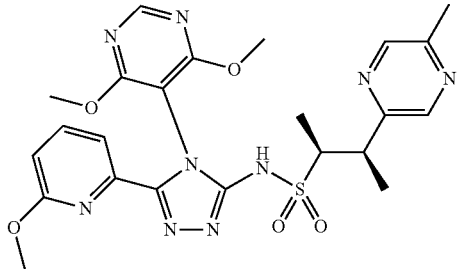 [SMILES: COc1cccc(-c2nnc(NS(=O)(=O)[C@@H](C)[C@H](C)c3cnc(C)cn3)n2-c2c(OC)ncnc2OC)n1]<br>(2S,3R)-N-(4-(4,6-dimethoxy-5-pyrimidinyl)-5-(6-methoxy-2-pyridinyl)-4H-1,2,4-triazol-3-yl)-3-(5-methyl-2-pyrazinyl)-2-butanesulfonamide. $^1$H NMR (400 MHz, CD$_2$Cl$_2$) δ 1.34 (d, J = 7.00 Hz, 3 H) 1.38 (d, J = 7.15 Hz, 3 H) 2.57 (s, 3 H) 3.26 (s, 3 H) 3.53-3.64 (m, 1 H) 3.69 (dd, J = 7.05, 5.03 Hz, 1 H) 3.94 (S, 3 H) 3.94 (S, 3 H) 6.74-6.86 (m, 1 H) 7.64-7.75 (m, 2 H) 8.37 (d, J = 1.35 Hz, 1 H) 8.46 (d, J = 0.62 Hz, 1 H) 8.51 (s, 1 H). LCMS-ESI (POS.) m/z: 542.2 (M + H)$^+$. |

The compounds set forth in the following Table were synthesized following the procedure in Example 741.0 using the known starting material as described.

TABLE 46

| Example | Reagents | Structure, Name and Data |
|---|---|---|
| 800.0 | (3S,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide (Example 462.3), 6-methoxy-picolinohydrazide (commercially available from Sigma-Aldrich Corp, St. Louis, MO, USA), 1,3-difluoro-2-isothiocyanatobenzene, (commercially available from Sigma-Aldrich Corp, St. Louis, MO, USA). The cis isomer was isolated as the major product. Two enantiomers were separated by chiral SFC purification. Example 800.0 was the first (earlier peak vs. its opposite enantiomer) peak on AS-H column. SFC: Chiralpak AS-H, 40% MeOH/CO$_2$. | 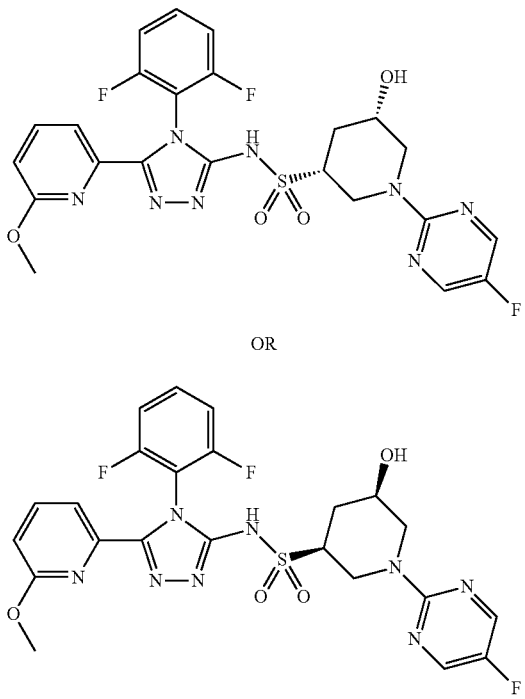   OR   (3R,5S)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide or (3S,5R)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide. $^1$H NMR (400 MHz, CD$_3$OD) δ 1.59-1.74 (m, 1 H) 2.44-2.59 (m, 2H) 2.86 (dd, J = 12.88, 11.38 Hz, 1 H) 3.06-3.16 (m, 1 H) 3.18 (s, 3 H) 3.50-3.63 (m, 1 H) 4.74-4.90 (m, 1 H) 5.03-5.13 (m, 1 H) 6.82 (dd, J = 8.19, 0.78 Hz, 1 H) 7.18-7.31 (m, 2 H) 7.55-7.65 (m, 1 H) 7.69-7.75 (m, 1 H) 7.75-7.82 (m, 1 H) 8.27 (s, 2 H). LCMS-ESI (POS.) m/z: 563.2 (M + H)$^+$. |
| 801.0 | The title compound is the enantiomer of Example 800.0. Further elution under conditions described in Example 800.0 gave the second (later peak vs. its opposite enantiomer) peak on AS-H column. SFC: Chiralpak AS-H, 40% MeOH. | 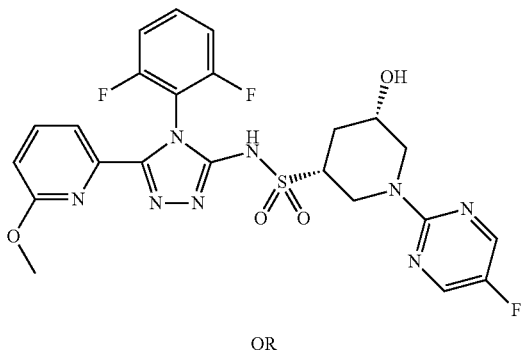 [SMILES: COc1cccc(-c2nnc(NS(=O)(=O)[C@@H]3C[C@H](O)CN(c4ncc(F)cn4)C3)n2-c2c(F)cccc2F)n1]   OR |

TABLE 46-continued

| Example Reagents | Structure, Name and Data |
|---|---|
|  | 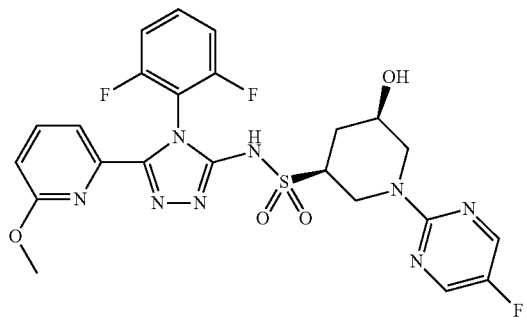 [SMILES: COc1cccc(-c2nnc(NS(=O)(=O)[C@H]3C[C@@H](O)CN(c4ncc(F)cn4)C3)n2-c2c(F)cccc2F)n1](3R,5S)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide or (3S,5R)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide. $^1$H NMR (400 MHz, CD$_3$OD) δ 1.57-1.72 (m, 1 H) 2.45-2.59 (m, 2 H) 2.85 (dd, J = 12.88, 11.38 Hz, 1 H) 3.06-3.16 (m, 1 H) 3.18 (s, 3 H) 3.51-3.62 (m, 1 H) 4.78-4.90 (m, 1 H) 5.02-5.14 (m, 1 H) 6.83 (dd, J = 8.19, 0.83 Hz, 1 H) 7.17-7.33 (m, 2 H) 7.55-7.65 (m, 1 H) 7.68-7.75 (m, 1 H) 7.75-7.83 (m, 1 H) 8.27 (s, 2 H). LCMS-ESI (POS.) m/z: 563.2 (M + H)$^+$. |

Example 802.0: Preparation of (2S,3R)-3-(5-chloro-2-pyridinyl)-N-(4-(4,6-(dimethoxy-5-pyrimidinyl)-5-(3-pyridinyl)-4H-1,2,4-triazol-3-yl)-2-butanesulfonamide

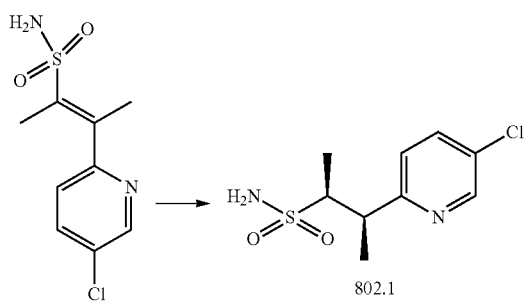

(2S,3R)-3-(5-chloropyridin-2-yl)butane-2-sulfonamide, Example 802.1

To a solution of (E)-2-(5-chloropyridin-2-yl)ethenesulfonamide (10 g, 40.5 mmol) in MeOH (100 mL) was added zinc trifluoromethanesulfonate (2.95 g, 8.11 mmol), bis(1,5-cyclooctadiene)rhodium(I) tetrafluroborate (0.329 g, 0.811 mmol) and (S)-1-[(R)-2-(di-1-naphthylphosphino)ferrocenyl]-ethyl-di-tert-butylphosphine (0.651 g, 1.013 mmol). The reaction mixture was degassed with argon and hydrogen three times. The reaction was then stirred under hydrogen (50 psi) in 200 mL Mini-clave at RT for 16 h followed by heating at 65° C. for 16 h. The reaction was checked with TLC for completion and showed that starting material was completely absent. The reaction mixture was concentrated under reduced pressure to provide the initial product which was purified by column chromatography (silica gel 60-120 mesh) using 40-45% of EtOAc in petroleum ether as an eluent to obtain the desired product (2S,3R)-3-(5-chloropyridin-2-yl)butane-2-sulfonamide (9 g, 36.2 mmol, 89%) as a brownish solid in 82% ee. Recrystalization from i-PrOH yielded >97% ee material. 1H NMR (400 MHz, DMSO-d6) δ 1.19 (d, J=7.05 Hz, 3H) 1.29 (d, J=7.05 Hz, 3H) 3.46 (qd, J=7.08, 3.84 Hz, 1H) 3.63 (qd, J=7.08, 3.84 Hz, 1H) 6.82 (s, 2H) 7.36 (d, J=8.50 Hz, 1H) 7.88 (dd, J=8.50, 2.70 Hz, 1H) 8.56 (d, J=2.28 Hz, 1H). LCMS-ESI (POS.) m/z: 249.0 (M+H)$^+$.

The compounds set forth in the following Table were synthesized following the procedure in Example 741.0 using the known starting material as described.

TABLE 47

| Example | Reagents | Structure, Name and Data |
|---|---|---|
| 802.0 | (2S,3R)-3-(5-chloropyridin-2-yl)butane-2-sulfonamide (Example 802.1), nicotinohydrazide (Alfa Aesar), 5-isothiocyanato-4,6-dimethoxypyrimidine (Example 1.1). | 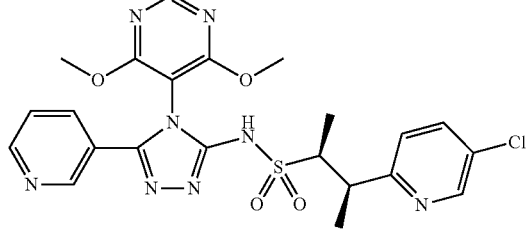<br>(2S,3R)-3-(5-chloro-2-pyridinyl)-N-(4-(4,6-dimethoxy-5-pyrimidinyl)-5-(3-pyridinyl)-4H-1,2,4-triazol-3-yl)-2-butanesulfonamide. $^1$H NMR (400 MHz, CDCl$_3$) δ 1.34 (d, J = 7.00 Hz, 3 H) 1.38 (d, J = 7.05 Hz, 3 H) 3.64-3.78 (m, 2 H) 3.92 (s, 3 H) 3.93 (s, 3 H) 7.19 (d, J = 8.34 Hz, 1 H) 7.31-7.38 (m, 1 H) 7.62 (dd, J = 8.37, 2.51 Hz, 1 H) 7.77 (ddd, J = 8.20, 1.98, 1.79 Hz, 1 H) 8.48 (s, 1 H) 8.51 (s, 1 H) 8.63 (dd, J = 2.20, 0.75 Hz, 1 H) 8.70 (dd, J = 4.87, 1.66 Hz, 1 H) 11.17 (br. s., 1 H). LCMS-ESI (POS.) m/z: 531.2. |

Example 803.0: Preparation of (2S,3R)—N-(4-(4,6-dimethoxy-5-pyrimidinyl)-5-(3-pyridinyl)-4H-1,2,4-triazol-3-yl)-3-(5-methoxy-2-pyrazinyl)-2-butanesulfonamide

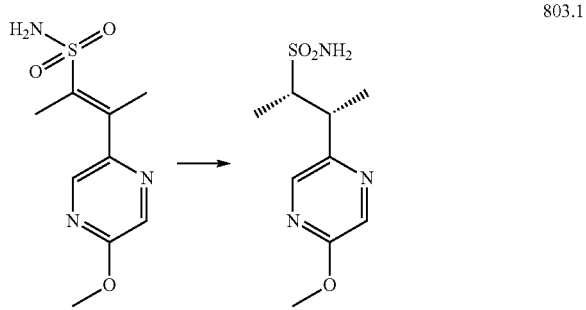 [SMILES: COc1cnc(/C(C)=C(\C)S(N)(=O)=O)cn1 ; COc1cnc([C@@H](C)[C@H](C)S(N)(=O)=O)cn1]

(2S,3R)-3-(5-methoxypyrazin-2-yl) butane-2-sulfonamide, Example 803.1

To a solution of (E)-3-(5-methoxypyrazin-2-yl)but-2-ene-2-sulfonamide (prepared in an analogous fashion to 10.05 starting from 2-bromo-5-methoxypyrazine, 4.5 g, 18.50 mmol) in MeOH (60 mL) was added zinc trifluoromethanesulfonate (2.69 g, 7.40 mmol, 0.4 equiv, Sigma Aldrich), bis(1,5-cyclooctadiene)rhodium(I) tetrafluroborate (0.446 g, 1.110 mmol, 0.06 equiv, Combi Block) and (S)-1-[(R)-2-(di-1-naphthylphosphino)ferrocenyl]-ethyl-di-tert-butylphosphine (1.189 g, 1.85 mmol, 0.1 equiv, Solvias). The reaction mixture was degassed with argon and hydrogen three times and stirred under hydrogen atmosphere (50 psi) at 60° C. for 80 h. The reaction mixture was then concentrated and the material thus obtained was purified by column chromatography silica gel (60-120 mesh) using 35-40% of EtOAc in hexane as eluent to afford the title compound (3.2 g, 13.05 mmol, 70.5%, 93% ee) as an off-white solid. $^1$H NMR (400 MHz, DMSO-d$_6$) δ 8.26 (d, J=1.4 Hz, 1H), 8.12 (d, J=1.4 Hz, 1H), 6.84 (s, 2H), 3.90 (d, J=1.5 Hz, 3H), 3.62 (dd, J=7.1, 4.3 Hz, 1H), 3.42-3.38 (m, 1H), 1.32 (d, J=1.5 Hz, 3H), 1.23-1.21 (m, 3H). MS (ESI+ve ion) m/z: 246.2 (M+H)$^+$.

The compounds set forth in the following Table were synthesized following the procedure in Example A using the known starting material as described.

TABLE 48

| Example | Reagents | Structure, Name and Data |
|---|---|---|
| 803.0 | (2S,3R)-3-(5-methoxypyrazin-2-yl)butane-2-sulfonamide (Example 803.1), nicotinohydrazide (Alfa Aesar), 5-isothiocyanato-4,6-dimethoxypyrimidine (Example 1.1). | 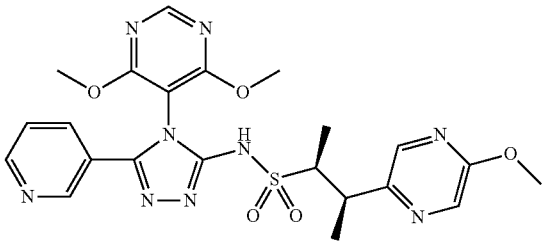 [SMILES: COc1cnc([C@@H](C)[C@H](C)S(=O)(=O)Nc2nnc(-c3cccnc3)n2-c2c(OC)ncnc2OC)cn1]<br>(2S,3R)-N-(4-(4,6-dimethoxy-5-pyrimidinyl)-5-(3-pyridinyl)-4H-1,2,4-triazol-3-yl)-3-(5-methoxy-2-pyrazinyl)-2-butanesulfonamide. $^1$H NMR (400 MHz, |

| Example | Reagents | Structure, Name and Data |
|---|---|---|
| | | CD$_2$Cl$_2$) δ 1.34 (d, J = 7.00 Hz, 3 H) 1.39 (d, J = 7.15 Hz, 3 H) 3.55 (dd, J = 6.97, 5.00 Hz, 1 H) 3.68 (dd, J = 7.10, 5.03 Hz, 1 H) 3.99 (m, 9 H) 7.75 (dd, J = 7.64, 5.31 Hz, 1 H) 8.07 (d, J = 1.19 Hz, 1 H) 8.18 (d, J = 7.72 Hz, 1 H) 8.21 (s, 1 H) 8.57 (s, 1 H) 8.83 (dd, J = 5.34, 1.45 Hz, 1 H) 8.89 (d, J = 1.45 Hz, 1 H) 10.88 (br. s., 3 H). LCMS-ESI (POS.) m/z: 528.2 (M + H)$^+$. |
| 804.0 | (1R,2S)-1-methoxy-1-(5-methoxypyrazin-2-yl)propane-2-sulfonamide and (1S,2R)-1-methoxy-1-(5-methoxypyrazin-2-yl)propane-2-sulfonamide (Example 14.2), nicotinohydrazide (Alfa Aesar), 5-isothiocyanato-4,6-dimethoxypyrimidine (Example 1.1). AcOH was used instead of methanesulfonic acid and also as solvent. | 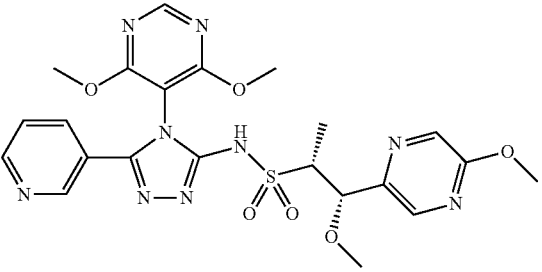

AND

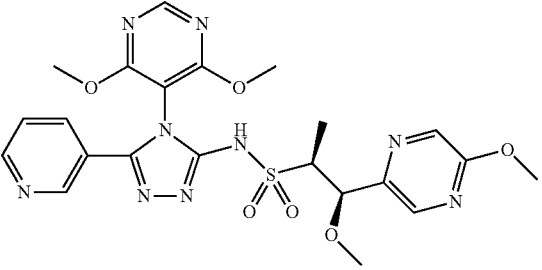 [SMILES: COc1cnc([C@@H](OC)[C@H](C)S(=O)(=O)Nc2nnc(-c3cccnc3)n2-c2c(OC)ncnc2OC)cn1]

(1R,2S)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide and (1S,2R)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide. $^1$H NMR (400 MHz, CDCl$_3$) δ δ 1.24 (d, J = 3.0 Hz, 3 H) 3.27 (s, 3 H) 3.46 (qd, J = 7.03, 3.06 Hz, 1 H) 3.87 (s, 3 H) 3.88 (s, 3 H) 3.92 (s, 3 H) 4.95 (d, J = 3.01 Hz, 1 H) 7.28-7.31 (m, 1 H) 7.71 (dt, J = 8.02, 1.95 Hz, 1 H) 8.08 (s, 1 H) 8.14 (d, J = 1.30 Hz, 1 H) 8.42 (s, 1 H) 8.58 (d, J = 1.76 Hz, 1 H) 8.63 (dd, J = 4.87, 1.61 Hz, 1 H) 11.11 (s, 1 H). LCMS-ESI (POS.) m/z: 544.1 (M + H)$^+$. |

The compounds set forth in the following Table were synthesized following the procedure in Example B using the known starting material as described.

TABLE 49

| Example | Reagents | Structure, Name and Data |
|---|---|---|
| 805.0 | (3R,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide (Example 462.3), the cis isomer was obtained by re-crystallization of the mixture from DCM/EtOAc) and 3-(5-bromo-4-(2,6-dimethoxyphenyl)-4H-1,2,4-triazol-3-yl)pyridine (Example 2.1). | 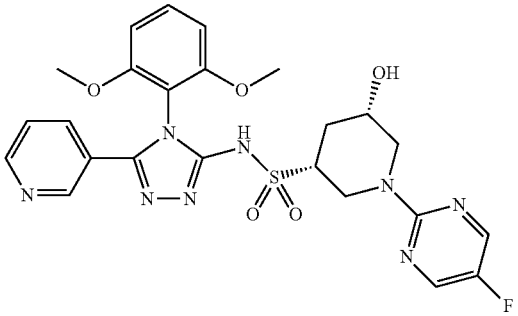<br>AND<br>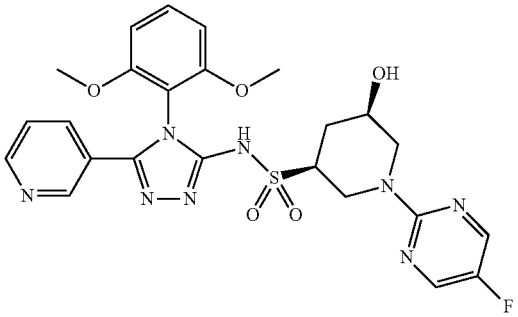 [SMILES: COc1cccc(OC)c1-n1c(NS(=O)(=O)[C@H]2C[C@@H](O)CN(c3ncc(F)cn3)C2)nnc1-c1cccnc1]<br>(3R,5S)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide and (3S,5R)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide. $^1$H NMR (400 MHz, CD$_2$Cl$_2$) δ 0.77-1.87 (m, 1 H) 2.47-2.53 (m, 1 H) 2.87 (dd, J = 12.75, 9.54 Hz, 1 H) 3.07-3.15 (m, 1 H) 3.19-3.26 (m, 1 H) 3.64-3.77 (m, 1 H) 3.70-3.82 (m, 7 H) 4.63 (dd, J = 12.70, 4.46 Hz, 1 H) 4.86 (dd, J = 13.06, 3.89 Hz, 1 H) 6.71 (dd, J = 8.58, 0.86 Hz, 2 H) 7.30 (ddd, J = 8.01, 4.92, 0.75 Hz, 1 H) 7.50 (t, J = 8.53 Hz, 1 H) 7.75 (dt, J = 8.06, 1.96 Hz, 1 H) 8.23 (s, 2 H) 8.62-8.65 (m, 2 H) 11.13 (br. s., 1 H). LCMS-ESI (POS.) m/z: 557.0 (M + H)$^+$. |

The compounds set forth in the following Table were synthesized following the procedure in Example 741.0 using the known starting material as described.

TABLE 50

| Example | Reagents | Structure, Name and Data |
|---|---|---|
| 806.0 | (2S,3R)-3-(5-methylpyrazin-2-yl)butane-2-sulfonamide (Example 799.1), nicotinohydrazide (Alfa Aesar), 5-isothiocyanato-4,6-dimethoxypyrimidine, (Example 1.1). | 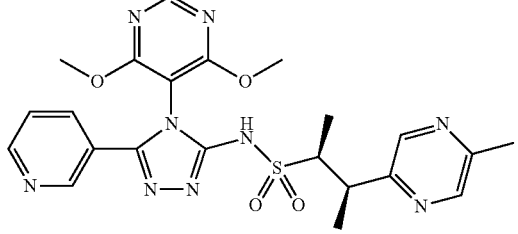<br><br>(2S,3R)-N-(4-(4,6-dimethoxy-5-pyrimidinyl)-5-(3-pyridinyl)-4H-1,2,4-triazol-3-yl)-3-(5-methyl-2-pyrazinyl)-2-butanesulfonamide. $^1$H NMR (400 MHz, CD$_3$OD) δ 1.32 (d, J = 6.95 Hz, 3 H) 1.36 (d, J = 7.05 Hz, 3 H) 2.52 (s, 3 H) 3.52-3.66 (m, 2 H) 3.97 (s 3 H) 3.97 (s 3 H) 7.49 (ddd, J = 8.03, 4.95, 0.80 Hz, 1 H) 7.86 (dt, J = 8.03, 1.94 Hz, 1 H) 8.32 (d, J = 1.35 Hz, 1 H) 8.45 (s, 1 H) 8.56 (s, 1 H) 8.62-8.68 (m, 2 H). LCMS-ESI (POS.) m/z: 512.2 (M + H)$^+$. |
| 807.0 | (2S,3R)-3-(5-chloropyridin-2-yl)butane-2-sulfonamide (Example 802.1), nicotinohydrazide (Alfa Aesar), 5-isothiocyanato-4,6-dimethoxypyrimidine (Example 1.1). The title compound was isolated as a minor product from Example 802.0 | 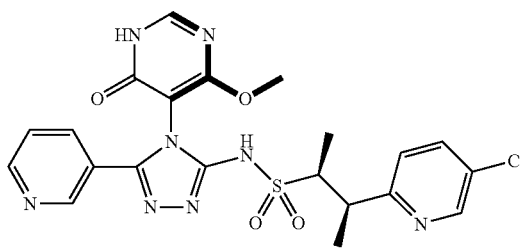<br><br>AND<br><br>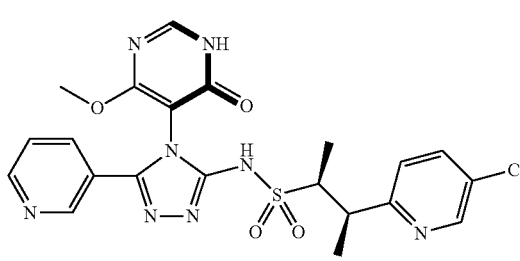<br><br>(2S,3R,M)-3-(5-chloro-2-pyridinyl)-N-(4-(4-methoxy-6-oxo-1,6-dihydro-5-pyrimidinyl)-5-(3-pyridinyl)-4H-1,2,4-triazol-3-yl)-2-butanesulfonamide and (2S,3R,P)-3-(5-chloro-2-pyridinyl)-N-(4-(4-methoxy-6-oxo-1,6-dihydro-5-pyrimidinyl)-5-(3-pyridinyl)-4H-1,2,4-triazol-3-yl)-2-butanesulfonamide. $^1$H NMR (400 MHz, CD$_3$OD) δ 1.28-1.35 (m, 3 H) 1.35-1.42 (m, 3 H) 3.51-3.64 (m, 1 H) 3.64-3.78 (m, 1 H) 3.96 (d, J = 2.23 Hz, 3 H) 7.42 (dd, J = 12.21, 8.47 Hz, 1 H) 7.62 (dd, J = 7.98, 5.08 Hz, 1 H) 7.85 (ddd, J = 8.47, 4.25, 2.57 Hz, 1 H) 8.10 (dt, J = 8.02, 1.69 Hz, 1 H) 8.29 (d, J = 2.13 Hz, 1 H) 8.49-8.56 (m, 1 H) 8.72 (dd, J = 5.08, 1.55 Hz, 1 H) 8.79 (d, J = 2.07 Hz, 1 H). LCMS-ESI (POS.) m/z: 517.0 (M + H)$^+$. |

TABLE 50-continued

| Example | Reagents | Structure, Name and Data |
|---|---|---|
| 808.0 | SFC chiral separation of Example 805.0 on a Chiralpak AS-H, 30% MeOH/CO$_2$, delivered the first (earlier peak vs. its opposite enantiomer) peak on AS column. | 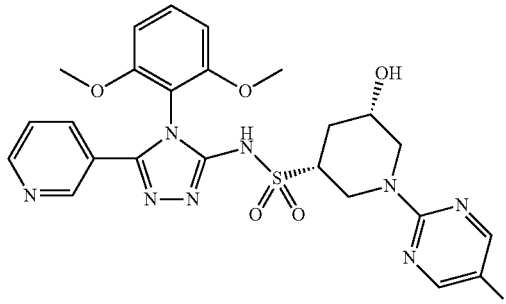<br>OR<br>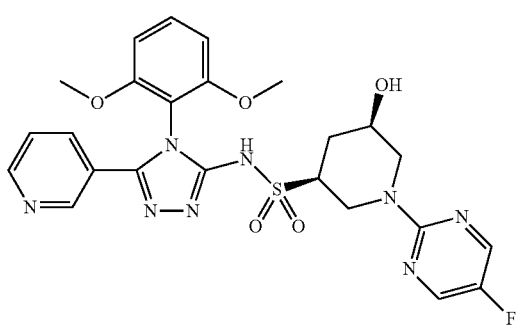 [SMILES: COc1cccc(OC)c1-n1c(NS(=O)(=O)[C@H]2C[C@@H](O)CN(c3ncc(F)cn3)C2)nnc1-c1cccnc1]<br>(3R,5S)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide or (3S,5R)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide. $^1$H NMR (400 MHz, CD$_3$OD) δ: 1.58-1.71 (m, 1 H) 2.51 (dd, J = 12.54, 10.68 Hz, 2 H) 2.84 (dd, J = 12.85, 11.40 Hz, 1 H) 3.04-3.15 (m, 1 H) 3.51-3.64 (m, 1 H) 3.79 (s, 3 H) 3.80 (s, 3 H) 4.78-4.84 (m, 1 H) 5.08 (dt, J = 12.97, 1.94 Hz, 1 H) 6.81 (dd, J = 8.58, 2.51 Hz, 2 H) 7.42 (dd, J = 7.44, 5.00 Hz, 1 H) 7.51 (t, J = 8.53 Hz, 1 H) 7.84 (ddd, J = 8.16, 1.92, 1.79 Hz, 1 H) 8.28 (s, 2 H) 8.55-8.59 (m, 2 H). LCMS-ESI (POS.) m/z: 557.2 (M + H)$^+$. |
| 809.0 | SFC chiral separation of Example 805.0, under the conditions described in Example 808.0 delivered the second (later peak vs. its opposite enantiomer) peak on AS column. | 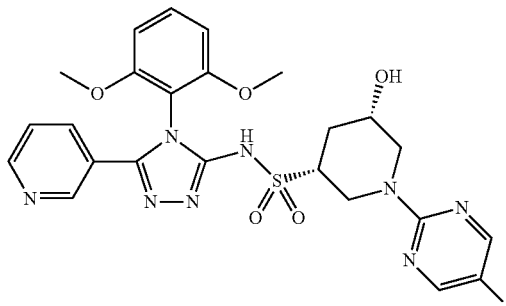<br>OR |

TABLE 50-continued

| Example | Reagents | Structure, Name and Data |
|---|---|---|
| | | 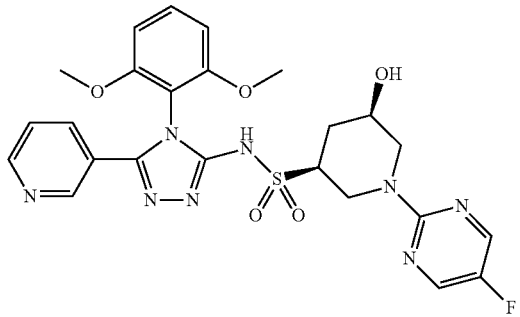 [SMILES: COc1cccc(OC)c1-n1c(NS(=O)(=O)[C@H]2C[C@@H](O)CN(c3ncc(F)cn3)C2)nnc1-c1cccnc1](3R,5S)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide or (3S,5R)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide. $^1$H NMR (400 MHz, CD$_3$OD) δ: 1.56-1.73 (m, 1 H) 2.51 (dd, J = 12.59, 10.68 Hz, 2 H) 2.79-2.90 (m, 1 H) 3.03-3.16 (m, 1 H) 3.51-3.64 (m, 1 H) 3.79 (s, 3 H) 3.80 (s, 3 H) 3.88-3.99 (m, 1 H) 4.83-4.85 (m, 1 H) 5.04-5.12 (m, 1 H) 6.81 (dd, J = 8.58, 2.46 Hz, 2 H) 7.42 (dd, J = 7.46, 4.98 Hz, 1 H) 7.51 (s, 1 H) 7.84 (dt, J = 8.11, 1.88 Hz, 1 H) 8.28 (s, 2 H) 8.56-8.60 (m, 2 H). LCMS-ESI (POS.) m/z: 557.1 (M + H)$^+$. |
| 810.0 | (2S,3R)-3-(5-chloropyridin-2-yl)butane-2-sulfonamide (Example 802.1), nicotinohydrazide (Alfa Aesar), 5-isothiocyanato-4,6-dimethoxypyrimidine (Example 1.1). The title compound was isolated as a minor product from Example 802.0 | 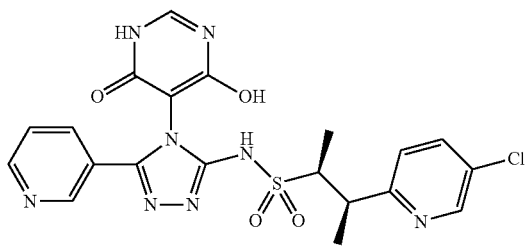 [SMILES: C[C@H](c1ccc(Cl)cn1)[C@H](C)S(=O)(=O)Nc1nnc(-c2cccnc2)n1-c1c(O)nc[nH]c1=O](2S,3R)-3-(5-chloro-2-pyridinyl)-N-(4-(4-hydroxy-6-oxo-1,6-dihydro-5-pyrimidinyl)-5-(3-pyridinyl)-4H-1,2,4-triazol-3-yl)-2-butanesulfonamide. $^1$H NMR (400 MHz, CD$_3$OD) δ 1.34 (d, J = 7.00 Hz, 3 H) 1.40 (d, J = 7.05 Hz, 3 H) 3.56 (dd, J = 6.97, 4.74 Hz, 1 H) 3.74 (dd, J = 7.10, 4.77 Hz, 1 H) 7.45 (d, J = 8.45 Hz, 1 H) 7.67 (dd, J = 7.90, 5.16 Hz, 1 H) 7.86 (dd, J = 8.50, 2.49 Hz, 1 H) 8.23 (d, J = 8.09 Hz, 1 H) 8.53 (d, J = 2.38 Hz, 1 H) 8.64 (s, 1 H) 8.73 (d, J = 4.46 Hz, 1 H) 8.87 (s, 1 H). LCMS-ESI (POS.) m/z: 503.0 (M + H)$^+$. |
| 811.0 | SFC chiral separation of Example 804.0. The title compound was the first peak (earlier peak vs. its opposite enantiomer) on Chiralpak AS-H column, 15% MeOH. | 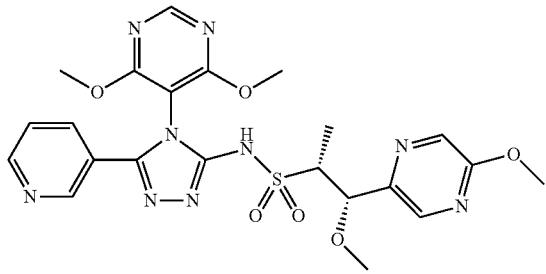AND |

| Example Reagents | Structure, Name and Data |
|---|---|
| | 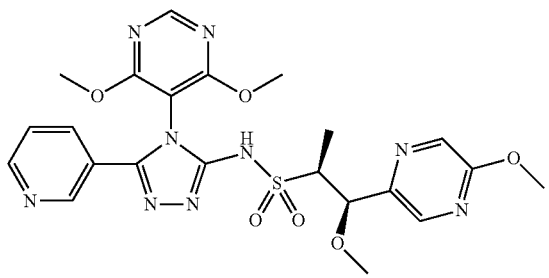 [SMILES: COc1cnc([C@@H](OC)[C@H](C)S(=O)(=O)Nc2nnc(-c3cccnc3)n2-c2c(OC)ncnc2OC)cn1]<br>(1R,2S)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide and (1S,2R)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide. $^1$H NMR (400 MHz, CDCl$_3$) δ 1.29 (d, J = 2.9 Hz, 3 H) 3.34 (s, 3 H) 3.53 (dd, J = 7.07, 3.08 Hz, 1 H) 3.95 (s, 3 H) 3.95 (s, 3 H) 3.99 (s, 3 H) 5.02 (d, J = 2.90 Hz, 1 H) 7.35 (ddd, J = 8.01, 4.90, 0.78 Hz, 1 H) 7.78 (dt, J = 8.01, 1.96 Hz, 1 H) 8.15 (d, J = 0.73 Hz, 1 H) 8.21 (d, J = 1.35 Hz, 1 H) 8.49 (s, 1 H) 8.65 (d, J = 1.55 Hz, 1 H) 8.70 (dd, J = 4.87, 1.66 Hz, 1 H) 11.18 (br. s., 1 H). LCMS-ESI (POS.) m/z: 544.2 (M + H)$^+$. |

Example 812.0: Preparation of (3S,5S)—N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide or (3R,5R)—N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide

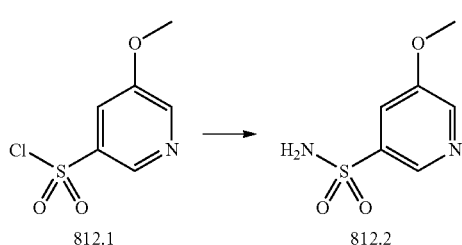

5-methoxypyridine-3-sulfonamide, Example 812.2

A reaction mixture of 5-methoxypyridine-3-sulfonyl chloride (commercially available from Enamine, KIEV, Ukraine) (1.0 g, 4.82 mmol) and ammonia, (0.5 M solution in 1,4-dioxane, 96 mL, 48.2 mmol) was stirred at 0 to 23° C. for 30 min. LCMS indicated the reaction was complete. The reaction was filtered and the filter cake was rinsed with dioxane. The combined solution was concentrated in vacuo to give the title compound (0.91 g, 100% yield) as a light yellow foam, which was used as such for the next step without purification. LCMS-ESI (POS.) m/z: 189.2 (M+H)$^+$.

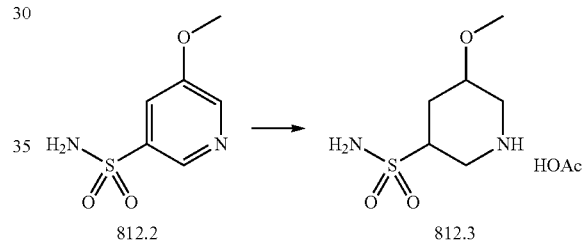

5-methoxypiperidine-3-sulfonamide acetate, Example 812.3

A solution of 5-methoxypyridine-3-sulfonamide (0.9 g, 4.78 mmol) in AcOH (31.9 mL) was bubbled with argon gas for 2 min before platinum (IV) oxide ((1.09 g, 4.78 mmol) was added under an argon stream. The reaction mixture was then stirred at 23° C. under 45 psi of hydrogen gas for 38 hours. The mixture was filtered and the filtrate was concentrated in vacuo to give the title compound (1.22 g, 100% yield) as a light yellow foam, which was used as such for the next step. LCMS-ESI (POS.) m/z: 195.2 (M+H)$^+$.

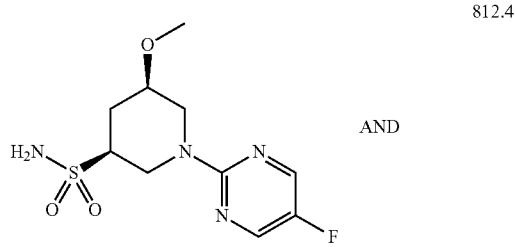

812.4

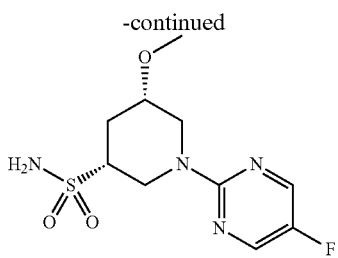

(3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide, Example 812.4

To a 40 mL vial (w/pressure release septa) was added 5-methoxypiperidine-3-sulfonamide acetate, (812.3, 2.45 g, 9.62 mmol), N-ethyl-N-isopropylpropan-2-amine (16.75 mL, 96 mmol) and 2-chloro-5-fluoropyrimidine (6.37 g, 48.1 mmol) in DMSO (48 mL). The reaction mixture was stirred at 100° C. for 23 hours. LCMS indicated formation of the desired product. The reaction mixture was diluted with water and extracted with DCM. The organic extract was washed with saturated aqueous NaCl, brine and then dried over $Na_2SO_4$. The solution was filtered and concentrated in vacuo to give an orange oil. The material thus obtained was absorbed onto a plug of silica gel and purified by chromatography through RediSep-Sep pre-packed silica gel column (40 g), eluting with a gradient of 0% to 100% ⅓ EtOH/EtOAc in heptane to provide the title compound, 812.4 (0.51 g, 18% yield) as a white solid, LCMS-ESI (POS.) m/z: 291.0 $(M+H)^+$.

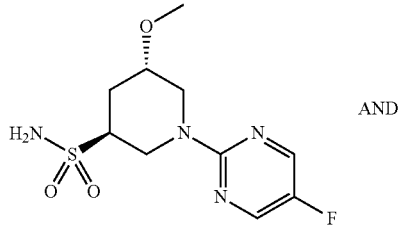

(3S,5S)-1-(5-fluoropyrimidin-2-yl)-5-methoxypiperidine-3-sulfonamide and (3R,5R)-1-(5-fluoropyrimidin-2-yl)-5-methoxypiperidine-3-sulfonamide, Example 812.5

Further elution under the conditions described in Example 812.4 provided 812.5 (0.24 g, 0.832 mmol, 8.65% yield) as a light yellow solid. LCMS-ESI (POS.) m/z: 291.0 $(M+H)^+$.

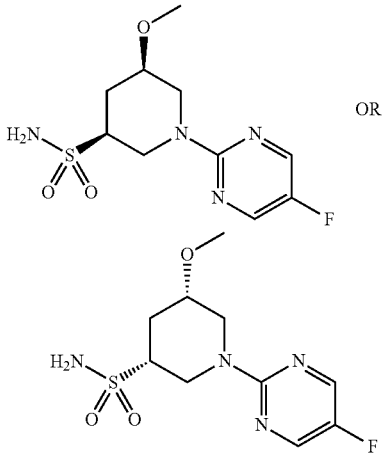

(3S,5R)-1-(5-fluoropyrimidin-2-yl)-5-methoxypiperidine-3-sulfonamide or (3R,5S)-1-(5-fluoropyrimidin-2-yl)-5-methoxypiperidine-3-sulfonamide, Example 812.6

Example 812.6 was obtained by chiral separation of 812.4 on SFC using the following conditions: Chiralpak AD-H, 30% MeOH/CO₂, with 0.2% DEA. Example 812.6 was the earlier peak to elute on Chiralpak AD-H column $^1$H NMR (400 MHz, CD₃OD) δ 1.65 (td, J=12.28, 10.88 Hz, 1H) 2.57-2.72 (m, 2H) 2.98 (dd, J=13.06, 11.40 Hz, 1H) 3.14 (ddt, 1H) 3.27-3.36 (m, 1H) 3.45 (s, 3H) 4.97 (ddt, 1H) 5.17 (ddt, 1H) 8.32 (d, J=0.62 Hz, 2H). LCMS-ESI (POS.) m/z: 291.0 $(M+H)^+$.

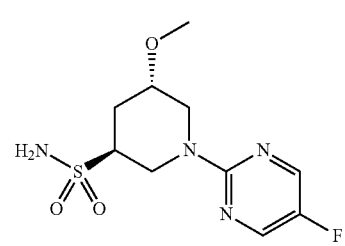

(3S,5R)-1-(5-fluoropyrimidin-2-yl)-5-methoxypiperidine-3-sulfonamide or (3R,5S)-1-(5-fluoropyrimidin-2-yl)-5-methoxypiperidine-3-sulfonamide, Example 812.7

Further elution under the conditions described in Example 812.6 delivered Example 812.7. $^1$H NMR (400 MHz, CD₃OD) δ 1.65 (td, J=12.28, 10.88 Hz, 1H) 2.57-2.71 (m, 2H) 2.94-3.04 (m, 1H) 3.14 (ddt, 1H) 3.31-3.36 (m, 1H) 3.45

(s, 3H) 4.97 (ddt, 1H) 5.17 (ddt, 1H) 8.32 (s, 2H). LCMS-ESI (POS.) m/z: 291.0 (M+H)+.

J=13.06, 11.20 Hz, 1H) 3.29-3.36 (m, 1H) 3.32 (s, 3H) 3.66-3.71 (m, 1H) 4.98 (dq, J=14.38, 2.19 Hz, 1H) 5.18 (ddt, 1H) 8.29 (d, J=0.83 Hz, 2H) LCMS-ESI (POS.) m/z: 291.0 (M+H)+.

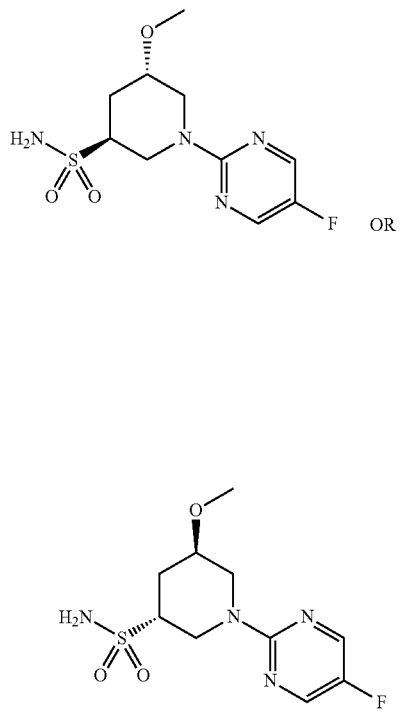

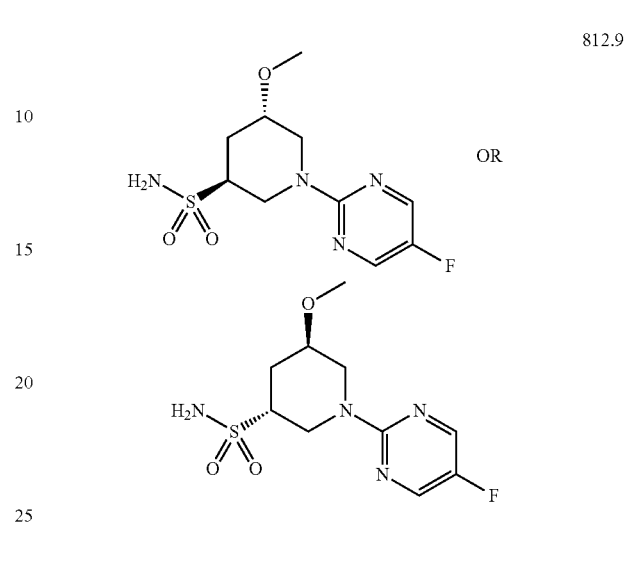

(3R,5R)-1-(5-fluoropyrimidin-2-yl)-5-methoxypiperidine-3-sulfonamide or (3S,5S)-1-(5-fluoropyrimidin-2-yl)-5-methoxypiperidine-3-sulfonamide, Example 812.9

(3S,5S)-1-(5-fluoropyrimidin-2-yl)-5-methoxypiperidine-3-sulfonamide or (3R,5R)-1-(5-fluoropyrimidin-2-yl)-5-methoxypiperidine-3-sulfonamide, Example 812.8

Example 812.8 was obtained by chiral separation of 812.4 on SFC using the following conditions: Chiralpak AD-H, 25% MeOH/CO$_2$, with 0.2% DEA. 812.8 was the earlier peak to elute on Chiralpak AD-H column. $^1$H NMR (400 MHz, CD$_3$OD) δ 1.98 (ddd, J=13.42, 12.39, 3.01 Hz, 1H) 2.41-2.51 (m, 1H) 2.98 (dd, J=14.31, 1.66 Hz, 1H) 3.10 (dd, Further elution under the conditions described in Example 812.7 delivered Example 812.9. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.32 (s, 3H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (POS.) m/z: 291.0 (M+H)+.

The compounds set forth in the following Table were synthesized following the procedure in Example 741.0 using the known starting material as described.

TABLE 51

| Example | Reagents | Structure, Name and Data |
|---|---|---|
| 812.0 | (3S,5S)-1-(5-fluoropyrimidin-2-yl)-5-methoxypiperidine-3-sulfonamide or (3R,5R)-1-(5-fluoropyrimidin-2-yl)-5-methoxypiperdine-3-sulfonamide (Example 812.8), nicotinohydrazide (Alfa Aesar), 5-isothiocyanato-4,6-dimethoxypyrimidine (Example 1.1). | |

OR

| Example | Reagents | Structure, Name and Data |
|---|---|---|
| | | 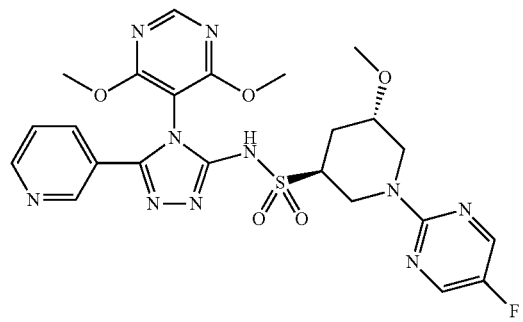 [SMILES: COc1ncnc(OC)c1-n1c(NS(=O)(=O)[C@H]2C[C@H](OC)CN(c3ncc(F)cn3)C2)nnc1-c1cccnc1]<br><br>(3S,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide or (3R,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CD$_3$OD) δ 1.94 (td, J = 12.78, 2.85 Hz, 1 H) 2.36 (d, J = 13.32 Hz, 1 H) 2.94 (d, J = 13.68 Hz, 1 H) 3.02-3.11 (m, 1 H) 3.26-3.29 (m, 3 H) 3.33-3.35 (m, 1 H) 3.65 (br. s., 1 H) 3.98 (s, 3 H) 3.98 (s, 3 H) 4.89-4.98 (m, 1 H) 5.01-5.10 (m, 1 H) 7.55 (dd, J = 8.01, 5.05 Hz, 1 H) 7.93 (dt, J = 8.05, 1.76 Hz, 1 H) 7.90-7.97 (m, 1 H) 8.26 (s, 2 H) 8.57 (s, 1 H) 8.68 (s, 2 H). LCMS-ESI (POS.) m/z: 573.2 (M + H)$^+$. |
| 813.0 | (3S,5R)-1-(5-fluoropyrimidin-2-yl)-5-methoxypiperidine-3-sulfonamide or (3R,5S)-1-(5-fluoropyrimidin-2-yl)-5-methoxypiperidine-3-sulfonamide (Example 812.6), nicotinohydrazide (Alfa Aesar), 5-isothiocyanato-4,6-dimethoxypyrimidine (Example 1.1). | 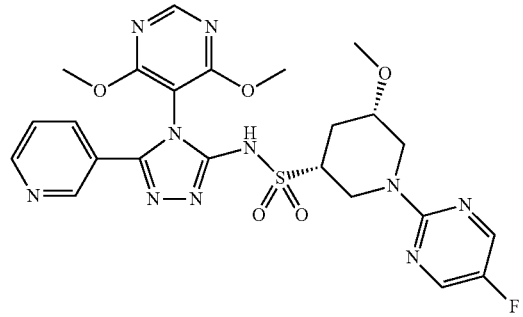<br><br>OR<br><br>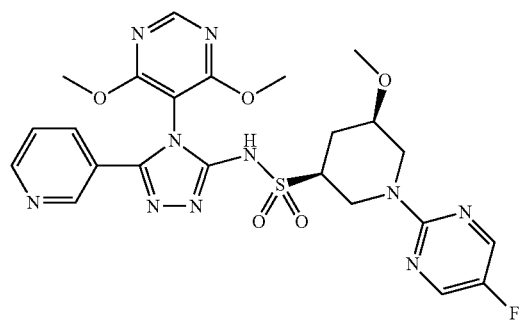<br><br>(3S,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide or (3R,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CD$_3$OD) δ 1.50-1.63 (m, 1 H) 2.49 (dd, J = 12.65, 10.57 Hz, 1 H) 2.54-2.64 (m, 1 H) 2.85 (s, 1 H) 3.12 (tt, J = 11.97, 3.78 Hz, 1 H) 3.22-3.29 (m, 1 H) 3.43 (s, 3 H) 3.99 (s, 3 H) 4.00 (s, 3 H) 4.98 (dd, J = 12.59, 4.41 Hz, 1 H) 5.05-5.13 (m, 1 H) 7.56 (dd, J = 8.03, 5.03 Hz, 1 H) 7.93 (d, J = 7.99 Hz, |

TABLE 51-continued

| Example | Reagents | Structure, Name and Data |
|---|---|---|
| | | 1 H) 8.30 (s, 2 H) 8.58 (s, 1 H) 8.67-8.70 (m, 2 H). LCMS-ESI (POS.) m/z: 573.2 (M + H)+. |
| 814.0 | (3S,5R)-1-(5-fluoropyrimidin-2-yl)-5-methoxypiperidine-3-sulfonamide or (3R,5S)-1-(5-fluoropyrimidin-2-yl)-5-methoxypiperidine-3-sulfonamide (Example 812.7), nicotinohydrazide (Alfa Aesar), 5-isothiocyanato-4,6-dimethoxypyrimidine (Example 1.1). | 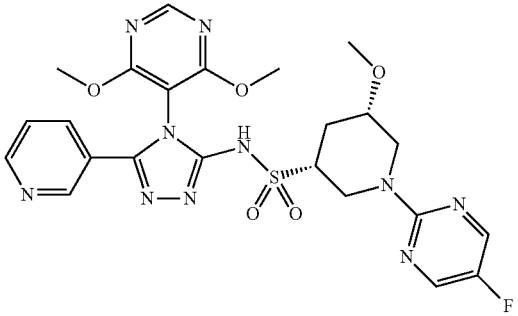<br>OR<br>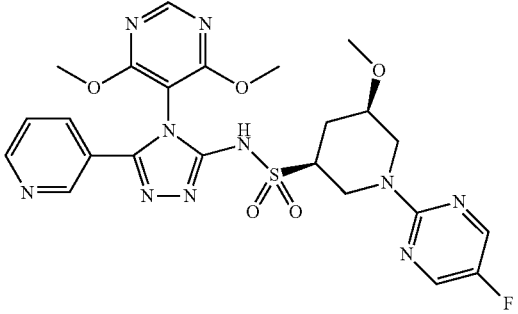 [SMILES: COc1ncnc(OC)c1-n1c(NS(=O)(=O)[C@H]2C[C@@H](OC)CN(c3ncc(F)cn3)C2)nnc1-c1cccnc1]<br>(3S,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide or (3R,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CD$_3$OD) δ 1.56 (q, J = 12.09 Hz, 1 H) 2.49 (dd, J = 12.57, 10.65 Hz, 1 H) 2.59 (d, J = 11.97 Hz, 1 H) 2.86 (d, J = 12.75 Hz, 1 H) 3.12 (tt, J = 11.97, 3.73 Hz, 1 H) 3.22-3.29 (m, 1 H) 3.43 (s, 3 H) 3.99 (s, 3 H) 4.00 (s, 3 H) 4.98 (dd, J = 12.67, 4.54 Hz, 1 H) 5.05-5.14 (m, 1 H) 7.56 (dd, J = 7.98, 5.08 Hz, 1 H) 7.94 (d, J = 7.95 Hz, 1 H) 8.30 (s, 2 H) 8.58 (s, 1 H) 8.69 (s, 2H). LCMS-ESI (POS.) m/z: 573.2 (M + H)+. |
| 815.0 | (3S,5S)-1-(5-fluoropyrimidin-2-yl)-5-methoxypiperidine-3-sulfonamide or (3R,5R)-1-(5-fluoropyrimidin-2-yl)-5-methoxypiperidine-3-sulfonamide (Example 812.9), nicotinohydrazide (Alfa Aesar), 5-isothiocyanato-4,6-dimethoxypyrimidine (Example 1.1). | 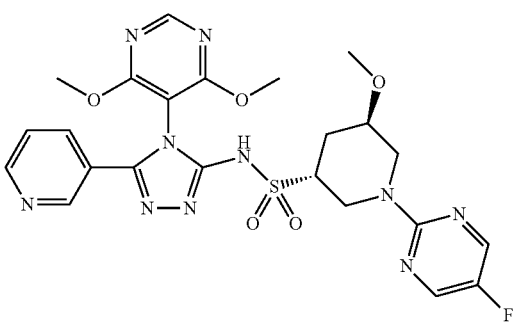<br>OR |

| Example | Reagents | Structure, Name and Data |
|---|---|---|
| | | 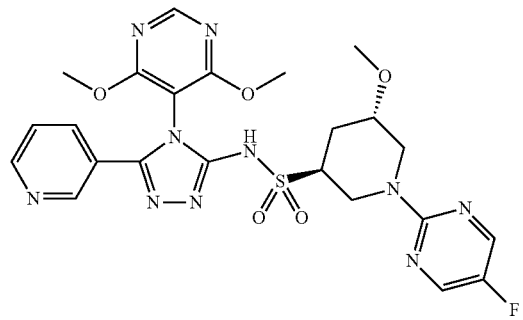 [SMILES: COc1ncnc(OC)c1-n1c(NS(=O)(=O)[C@H]2C[C@H](OC)CN(c3ncc(F)cn3)C2)nnc1-c1cccnc1]

(3S,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide or (3R,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CD$_3$OD) δ 1.94 (td, J = 12.76, 2.93 Hz, 1 H) 2.36 (d, J = 13.48 Hz, 1 H) 2.94 (dd, J = 14.28, 1.43 Hz, 1 H) 3.07 (dd, J = 12.93, 11.01 Hz, 1 H) 3.29 (s, 3 H) 3.30-3.35 (m., 1 H) 3.65 (br. s., 1 H) 3.98 (s, 3 H) 3.98 (s, 3 H) 4.88-4.96 (m, 1 H) 5.05 (dt, J = 12.85, 1.92 Hz, 1 H) 7.55 (dd, J = 7.85, 4.69 Hz, 1 H) 7.93 (dt, J = 8.12, 1.87 Hz, 1 H) 8.26 (s, 2 H) 8.57 (s, 1 H) 8.66-8.70 (m, 2 H). LCMS-ESI (POS.) m/z: 573.2 (M + H)$^+$. |
| 816.0 | (3S,5S)-1-(5-fluoropyrimidin-2-yl)-5-methoxypiperidine-3-sulfonamide or (3R,5R)-1-(5-fluoropyrimidin-2-yl)-5-methoxypiperidine-3-sulfonamide (Example 812.8), nicotinohydrazide (Alfa Aesar), 2-isothiocyanato-1,3-dimethoxybenzene (Example 1.0). | 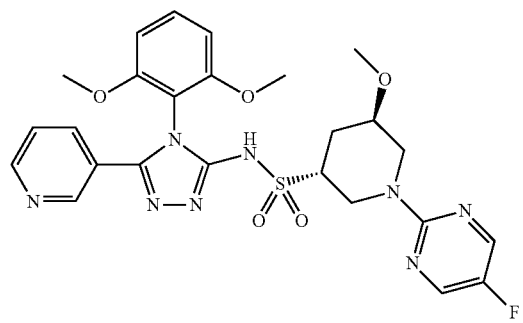

OR

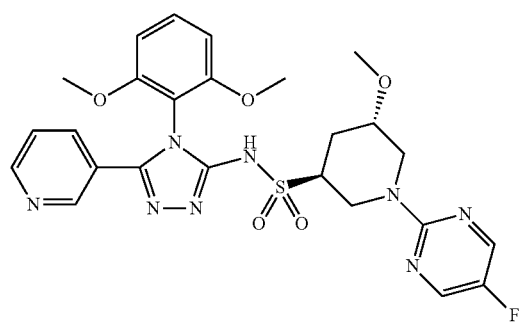 [SMILES: COc1cccc(OC)c1-n1c(NS(=O)(=O)[C@H]2C[C@H](OC)CN(c3ncc(F)cn3)C2)nnc1-c1cccnc1]

(3S,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide or (3R,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CDCl$_3$) δ 1.95 (ddd, J = 13.48, 12.08, 2.95 Hz, 1 H) 2.46 (ddd, J = 13.48, 1.81, 1.71 Hz, 1 H) 2.92 (dd, J = 14.15, 1.71 Hz, 1 H) 3.14 (dd, J = 13.06, 10.99 Hz, 1 H) 3.39-3.47 (m, 1 H) 3.62 (br. s., 1 H) 3.74 (s, 3 H) 3.74 (s, 3 H) 4.89 (d, J = 12.85 Hz, 1 H) 5.09-5.15 (m, 1 H) 6.60 (s, 1 H) 6.62 (s, 1 H) 7.31 (t, J = 6.34 Hz, 1 H) 7.41 (t, J = 8.50 Hz, 1 H) 7.79 (dt, J = 8.06, 1.93 Hz, 1 H) 8.17 |

TABLE 51-continued

| Example Reagents | Structure, Name and Data |
|---|---|

(s, 2 H) 8.61 (s, 1 H) 8.63 (d, J = 4.87 Hz, 1 H) 11.09 (br. s., 1 H). LCMS-ESI (POS.) m/z: 571.2 (M + H)+.

817.0  (3S,5R)-1-(5-fluoropyrimidin-2-yl)-5-methoxypiperidine-3-sulfonamide or (3R,5S)-1-(5-fluoropyrimidin-2-yl)-5-methoxypiperidine-3-sulfonamide (Example 812.4), nicotinohydrazide (Alfa Aesar), 2-isothiocyanato-1,3-dimethoxybenzene (Example 1.0).

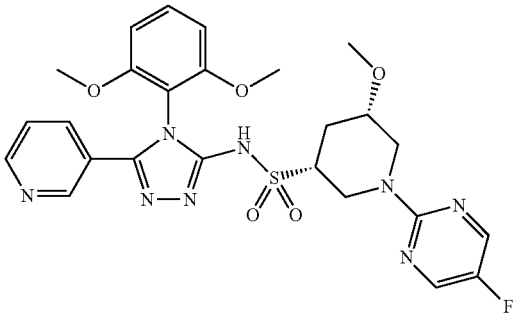

OR

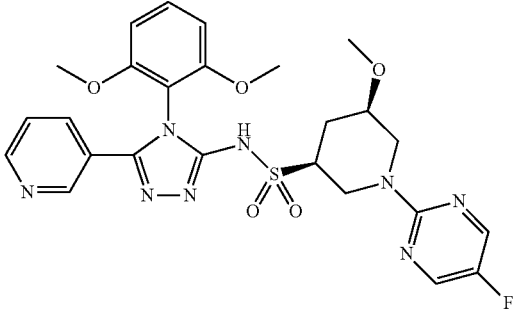 [SMILES: COc1cccc(OC)c1-n1c(NS(=O)(=O)[C@H]2C[C@@H](OC)CN(c3ncc(F)cn3)C2)nnc1-c1cccnc1]

(3R,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide or (3S,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CD$_3$OD) δ 1.48-1.60 (m, 1 H) 2.45 (dd, J = 12.65, 10.57 Hz, 1 H) 2.53-2.63 (m, 1 H) 2.82 (dd, J = 12.85, 11.51 Hz, 1 H) 3.00-3.16 (m, 1 H) 3.20-3.29 (m, 1 H) 3.42 (s, 3 H) 3.79 (s, 3 H) 3.80 (s, 3 H) 4.92-5.00 (m, 1 H) 5.04-5.13 (m, 1 H) 6.81 (dd, J = 8.55, 1.55 Hz, 2 H) 7.43 (dd, J = 7.75, 5.21 Hz, 1 H) 7.51 (t, J = 8.55 Hz, 1 H) 7.81-7.88 (m, 1 H) 8.29 (s, 2 H) 8.54-8.63 (m, 2 H). LCMS-ESI (POS.) m/z: 571.2 (M + H)+.

818.0  (3S,5R)-1-(5-fluoropyrimidin-2-yl)-5-methoxypiperidine-3-sulfonamide or (3R,5S)-1-(5-fluoropyrimidin-2-yl)-5-methoxypiperidine-3-sulfonamide (Example 812.7), nicotinohydrazide (Alfa Aesar), 2-isothiocyanato-1,3-dimethoxybenzene (Example 1.0).

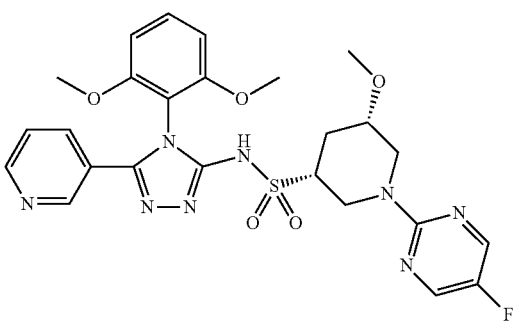

OR

| Example Reagents | Structure, Name and Data |
|---|---|
| | 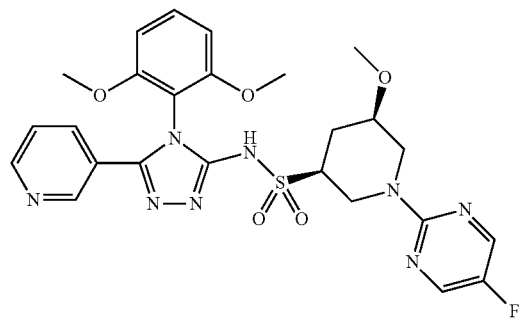 [SMILES: COc1cccc(OC)c1-n1c(NS(=O)(=O)[C@H]2C[C@@H](OC)CN(c3ncc(F)cn3)C2)nnc1-c1cccnc1]<br><br>(3R,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide or (3S,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CDCl$_3$) δ 1.60-1.71 (m, 1 H) 2.49 (dd, J = 12.65, 10.47 Hz, 1 H) 2.63-2.72 (m, 1 H) 2.89 (dd, J = 12.96, 11.51 Hz, 1 H) 3.05-3.14 (m, 1 H) 3.18-3.27 (m, 1 H) 3.42 (s, 3 H) 3.73 (s, 3 H) 3.76 (s, 3 H) 4.96 (ddd, J = 12.65, 2.90, 1.76 Hz, 1 H) 5.12-5.22 (m, 1 H) 6.61 (d, J = 8.29 Hz, 2 H) 7.27-7.31 (m, 1 H) 7.40 (t, J = 8.55 Hz, 1 H) 7.77 (dt, J = 8.03, 2.00 Hz, 1 H) 8.18 (s, 2 H) 8.63 (d, J = 9.21 Hz, 1 H) 8.63 (s, 1 H) 11.33 (br. s., 1 H). LCMS-ESI (POS.) m/z: 571.1 (M + H)$^+$. |
| 819.0 (3S,5S)-1-(5-fluoropyrimidin-2-yl)-5-methoxypiperidine-3-sulfonamide or (3R,5R)-1-(5-fluoropyrimidin-2-yl)-5-methoxypiperidine-3-sulfonamide (Example 812.9), nicotinohydrazide (Alfa Aesar), 2-isothiocyanato-1,3-dimethoxybenzene (Example 1.0). | 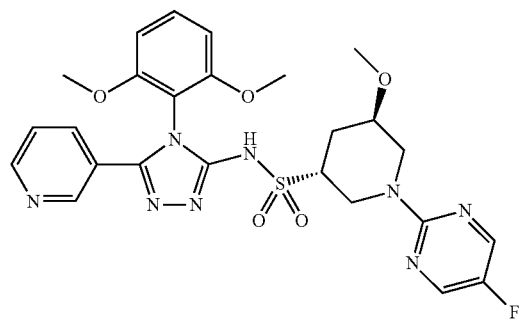<br><br>OR<br><br>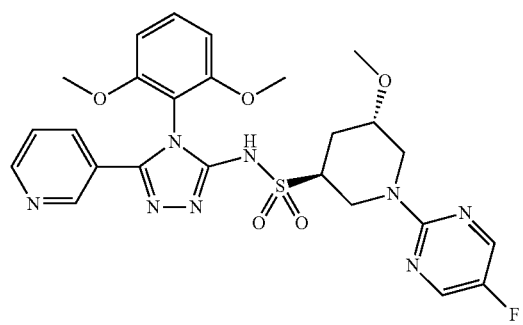 [SMILES: COc1cccc(OC)c1-n1c(NS(=O)(=O)[C@H]2C[C@H](OC)CN(c3ncc(F)cn3)C2)nnc1-c1cccnc1]<br><br>(3S,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide or (3R,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide. $^1$H NMR (400 MHz, CDCl$_3$) δ 1.95 (ddd, J = 13.48, 12.13, 2.90 Hz, 1 H) 2.46 (dt, J = 13.42, 1.79 Hz, 1 H) 2.92 (dd, J = 14.10, 1.76 Hz, 1 H) 3.13 (dd, J = 13.06, 10.99 Hz, 1 H) 3.29 (s, 3 H) 3.43 (t, J = 11.56 Hz, 1 H) 3.58-3.65 (m, 1 H) 3.73 (s, 3 H) 3.74 (s, 3 H) 4.85-4.93 (m, 1 H) 5.08-5.16 (m, 1 H) 6.60 (s, 1 H) 6.62 (s, 1 H) 7.28-7.33 (m, 1 H) |

7.40 (t, J = 8.50 Hz, 1 H) 7.79 (dt, J = 8.01, 1.96 Hz, 1 H) 8.16 (s, 2 H) 8.60-8.66 (m, 2 H) 11.20 (br. s., 1 H). LCMS-ESI (POS.) m/z: 571.2 (M + H)+.

Example 820.0: Preparation of (3R,5S)—N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide or (3S,5R)—N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide

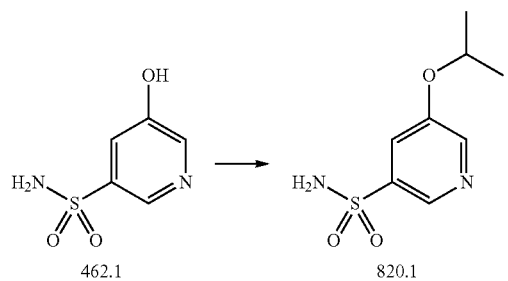

5-isopropoxypyridine-3-sulfonamide, Example 820.1

To a suspension of 5-hydroxypyridine-3-sulfonamide (1.1 g, 6.32 mmol) in THF (16 mL) and isopropanol (16 mL) was added triphenylphosphine (1.99 g, 7.58 mmol). The mixture was bubbled with argon for 3 min before diisopropyl azodicarboxylate (1.49 mL, 7.58 mmol) was added dropwise at 0° C. under $N_2$ stream. The reaction was then stirred at 0° C. to RT for 15 hours. The reaction mixture was concentrated in vacuo. The material thus obtained was absorbed onto a plug of silica gel and purified by chromatography through a RediSep-Sep pre-packed silica gel column (40 g), eluting with a gradient of 0% to 100% EtOAc in heptane, to provide the enriched product fractions, which were combined and extracted with 1N HCl. The desired product was enriched in acidic aqueous solution, which was then modified by saturated aqueous $NaHCO_3$ to pH>8. The basic aqueous solution was then extracted with DCM. The organic extract was washed with brine and dried over $Na_2SO_4$. The solution was filtered and concentrated in vacuo to give 820.1, 5-isopropoxypyridine-3-sulfonamide (0.95 g, 70% yield), as white solid. LCMS-ESI (POS), m/z: 217.2 (M+H)+.

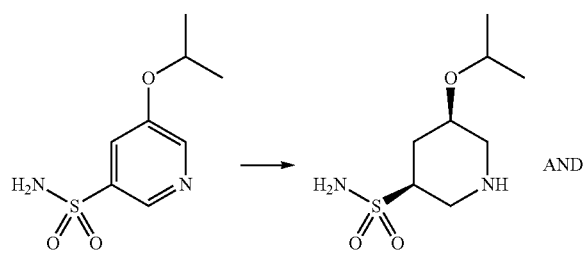

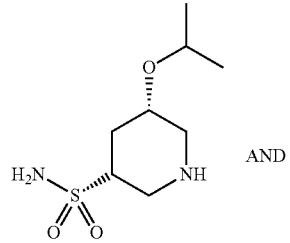

(3S,5R)-5-isopropoxypiperidine-3-sulfonamide and
(3R,5R)-5-isopropoxypiperidine-3-sulfonamide and
(3S,5S)-5-isopropoxypiperidine-3-sulfonamide and
(3R,5S)-5-isopropoxypiperidine-3-sulfonamide,
Example 820.2

A solution of 820.1, 5-isopropoxypyridine-3-sulfonamide (1.8 g, 8.32 mmol), in AcOH (41.6 mL) was bubbled with argon gas for 2 min before platinum (IV) oxide (1.89 g, 8.32 mmol) was added under an argon stream. The reaction mixture was stirred at 23° C. under 45 psi of hydrogen gas for two days. Next, Celite® brand filter agent (5 g) was added to the reaction mixture. The mixture was stirred at 23° C. for 10 min. The mixture was filtered and the solution was concentrated in vacuo to give the product mixture as a light yellow oil, which was used in the next step without further purification. LCMS-ESI (POS), m/z: 223.3 (M+H)+.

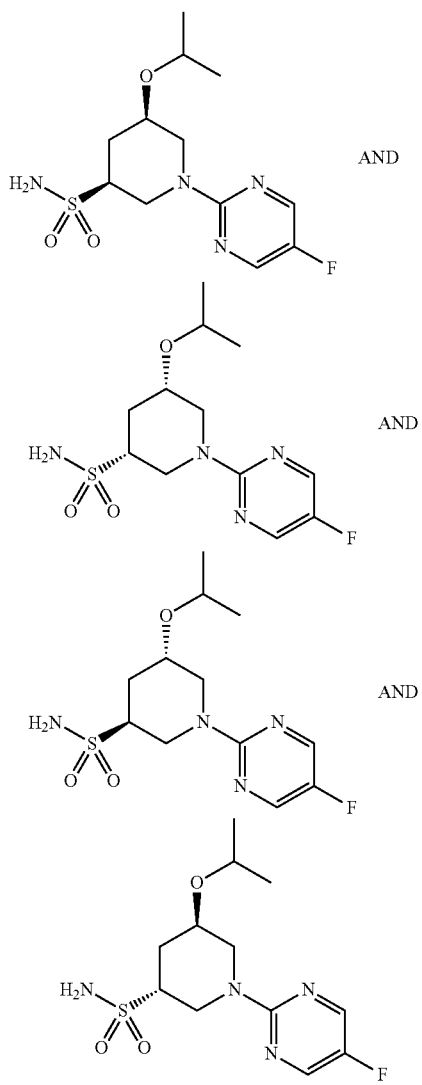

(3R,5R)-1-(5-fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide, Example 820.3

To a 40 mL vial (with pressure release septa) was added (3S,5R)-5-isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide (2.0 g, 4.96 mmol) and 2-chloro-5-fluoropyrimidine (3.29 g, 24.79 mmol). The reaction mixture was stirred at 90° C. for 21 hours. LCMS indicated the reaction was complete. Next, the reaction mixture was concentrated in vacuo. The material thus obtained was absorbed onto a plug of silica gel and purified by chromatography through RediSep-Sep pre-packed silica gel column (40 g), eluting with a gradient of 0% to 100% EOAc in heptane, to provide 820.3 as a mixture of diastereomers (0.5 g, 1.6 mmol, 32% yield) as off-white solid. LCMS-ESI (POS), m/z: 319.2 (M+H)+.

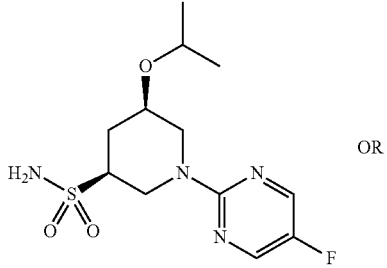

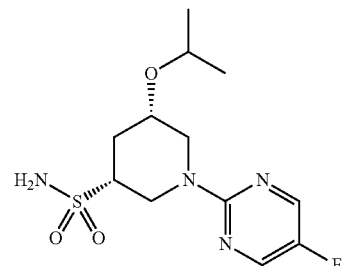

(3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 820.4

820.3 was separated by SFC on Chiralpak AS-H column using 15% MeOH/CO$_2$. 820.4 and 820.5 are a pair of enantiomers, 820.4 was the second peak among 4 isomers (earlier peak vs. its opposite enantiomer) on AS-H column $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (POS.) M/Z: 319.2 (M+H)+.

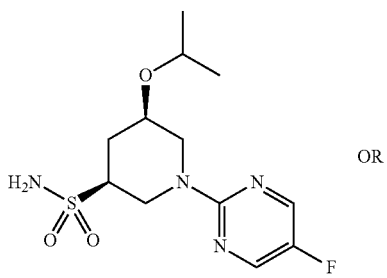

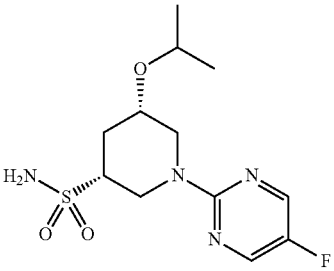

(3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 820.5

Further elution under the conditions described in Example 820.4 gave 820.5 as the third peak. ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (POS.) M/Z: 319.2 (M+H)⁺.

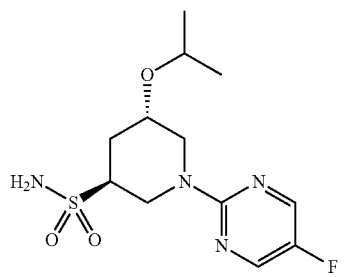

OR

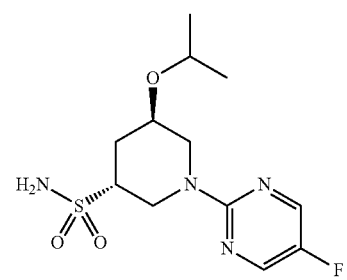

(3R,5R)-1-(5-fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 820.6

820.6 and 820.7 are a pair of enantiomers (3S,5S)-1-(5-fluoropyrimidin-2-yl)-5-isopropoxypiperidine-3-sulfonamide or (3R,5R)-1-(5-fluoropyrimidin-2-yl)-5-isopropoxypiperidine-3-sulfonamide. 820.6 was the first peak among 4 isomers (earlier peak vs. its opposite enantiomer) on an AS-H column under the conditions described in Example 820.4. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (POS.) M/Z: 319.2 (M+H)⁺.

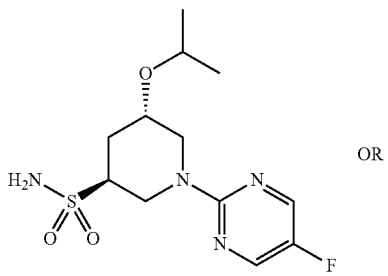

OR

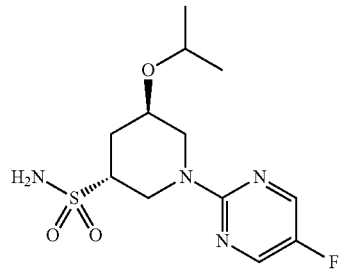

(3R,5R)-1-(5-fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 820.7

Further elution under the conditions described in Example 820.4 gave 820.7 as the fourth peak. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (POS.) M/Z: 319.2 (M+H)⁺.

The compounds set forth in the following Table were synthesized following the procedure in Example 741.0 using the known starting material as described.

TABLE 52

| Example | Reagents | Structure, Name and Data |
|---|---|---|
| 820.0 | (3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide (Example 820.4), nicotinohydrazide (Alfa Aesar), 2-isothiocyanato-1,3-dimethoxybenzene (Example 1.0). | 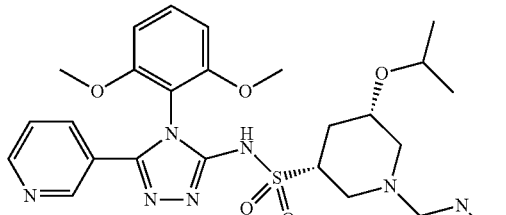<br><br>OR<br><br>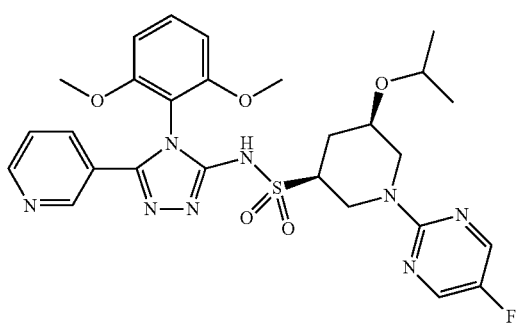 [SMILES: COc1cccc(OC)c1-n1c(NS(=O)(=O)[C@H]2C[C@@H](OC(C)C)CN(c3ncc(F)cn3)C2)nnc1-c1cccnc1]<br><br>(3R,5S)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide or (3S,5R)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide. $^1$H NMR (400 MHz, CDCl$_3$) δ 1.14 (d, J = 6.12 Hz, 3 H) 1.17 (d, J = 6.12 Hz, 3 H) 1.65-1.75 (m, 1 H) 2.45-2.57 (m, 2 H) 2.82-2.91 (m, 1 H) 3.06-3.15 (m, 1 H) 3.32-3.41 (m, 1 H) 3.71-3.83 (m, 1 H) 3.75 (s, 3H) 3.78 (s, 3H) 4.85 (dd, J = 12.85, 4.66 Hz, 1 H) 5.11-5.18 (m, 1 H) 6.64 (d, J = 8.61 Hz, 2 H) 7.43 (t, J = 8.55 Hz, 1 H) 7.49 (dd, J = 7.93, 5.13 Hz, 1 H) 8.00 (dt, J = 8.11, 1.75 Hz, 1 H) 8.17 (s, 2 H) 8.63-8.72 (m, 2 H) 9.35 (br. s., 1 H). LCMS-ESI (POS.) m/z: 599.2 (M + H)$^+$. |
| 821.0 | (3S,5R)-1-(5-fluoropyrimidin-2-yl)-5-isopropoxypiperidine-3-sulfonamide or (3R,5S)-1-(5-fluoropyrimidin-2-yl)-5-isopropoxypiperidine-3-sulfonamide (Example 820.5), nicotinohydrazide (Alfa Aesar), 2-isothiocyanato-1,3-dimethoxybenzene (Example 1.0). | 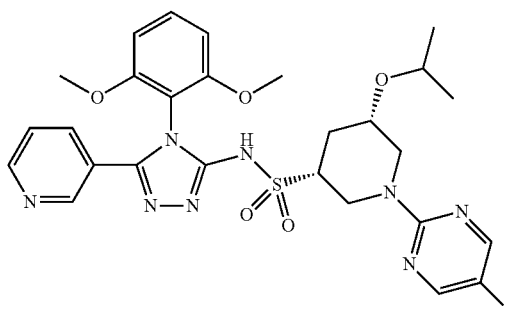<br><br>OR |

TABLE 52-continued

| Example | Reagents | Structure, Name and Data |
|---|---|---|

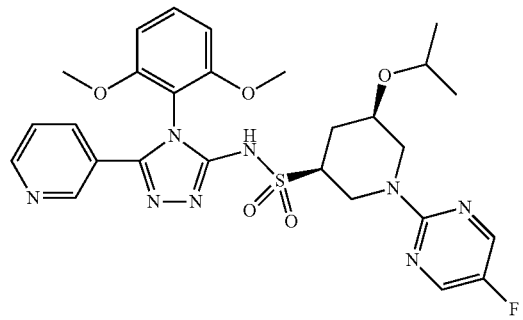 [SMILES: COc1cccc(OC)c1-n1c(NS(=O)(=O)[C@H]2C[C@@H](OC(C)C)CN(c3ncc(F)cn3)C2)nnc1-c1cccnc1]

(3R,5S)-N-(4-(2,6-dimethoxyphenyl)-5-(3-
pyridinyl)-4H-1,2,4-triazol-3-yl)-1-(5-fluoro-2-
pyrimidinyl)-5-(1-methylethoxy)-3-
piperidinesulfonamide or (3S,5R)-N-(4-(2,6-
dimethoxyphenyl)-5-(3-pyridinyl)-4H-1,2,4-triazol-
3-yl)-1-(5-fluoro-2-pyrimidinyl)-5-(1-
methylethoxy)-3-piperidinesulfonamide. H NMR
(400 MHz, CDCl$_3$) δ 1.12 (d, J = 6.12 Hz, 3 H) 1.15
(d, J = 6.12 Hz, 3 H) 1.63-1.73 (m, 1 H) 2.40-2.56
(m, 2 H) 2.84 (dd, J = 12.54, 10.99 Hz, 1 H) 2.99-
3.14 (m, 1 H) 3.28-3.40 (m, 1 H) 3.67-3.82 (m, 1
H) 3.72 (s, 3 H) 3.75 (s, 3 H) 4.83 (dd, J = 12.70, 4.72
Hz, 1 H) 5.06-5.17 (m, 1 H) 6.56-6.65 (m, 2 H)
7.35-7.45 (m, 2 H) 7.89 (dt, J = 8.24, 1.79 Hz, 1 H)
8.15 (s, 2 H) 8.60-8.68 (m, 2 H). LCMS-ESI
(POS.) m/z: 599.2 (M + H)$^+$.

822.0   (3R,5R)-1-(5-fluoropyrimidin-
2-yl)-5-isopropoxypiperidine-
3-sulfonamide or (3S,5S)-1-
(5-fluoropyrimidin-2-yl)-5-
isopropoxypiperidine-3-
sulfonamide (Example 820.6),
nicotinohydrazide (Alfa
Aesar), 2-isothiocyanato-1,3-
dimethoxybenzene (Example
1.0).

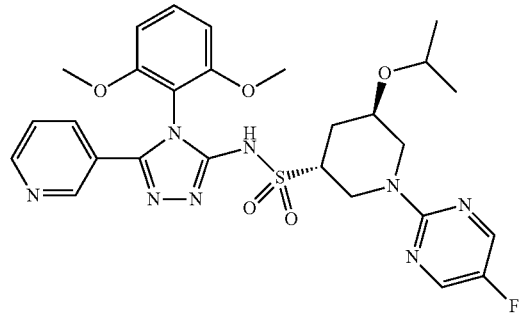

OR

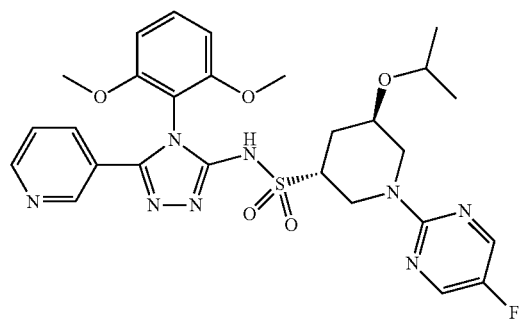 [SMILES: COc1cccc(OC)c1-n1c(NS(=O)(=O)[C@@H]2C[C@@H](OC(C)C)CN(c3ncc(F)cn3)C2)nnc1-c1cccnc1]

(3R,5R)-N-(4-(2,6-dimethoxyphenyl)-5-(3-
pyridinyl)-4H-1,2,4-triazol-3-yl)-1-(5-fluoro-2-
pyrimidinyl)-5-(1-methylethoxy)-3-
piperidinesulfonamide or (3S,5S)-N-(4-(2,6-
dimethoxyphenyl)-5-(3-pyridinyl)-4H-1,2,4-triazol-
3-yl)-1-(5-fluoro-2-pyrimidinyl)-5-(1-
methylethoxy)-3-piperidinesulfonamide. $^1$H NMR
(400 MHz, CDCl$_3$) δ 0.91 (d, J = 6.12 Hz, 3 H) 1.06
(d, J = 6.01 Hz, 3 H) 1.99 (ddd, J = 13.29, 11.53, 3.06
Hz, 1 H) 2.27-2.33 (m, 1 H) 3.01 (dd, J = 13.84, 1.81
Hz, 1 H) 3.24 (dd, J = 13.22, 10.42 Hz, 1 H) 3.47-

| Example | Reagents | Structure, Name and Data |
|---|---|---|
| | | 3.55 (m, 1 H) 3.66-3.73 (m, 1 H) 3.76 (s, 3 H) 3.76 (s, 3 H) 3.82 (br. s., 1 H) 4.63-4.69 (m, 1 H) 4.96-5.02 (m, 1 H) 6.62 (s, 1 H) 6.65 (s, 1 H) 7.43 (t, J = 8.55 Hz, 1 H) 7.49 (t, J = 6.40 Hz, 1 H) 8.00 (d, J = 7.50 Hz, 1 H) 8.17 (s, 2 H) 8.66 (s, 1 H) 8.68 (d, J = 5.08 Hz, 1 H). LCMS-ESI (POS.) m/z: 599.2 (M + H)+. |
| 823.0 | (3S,5S)-1-(5-fluoropyrimidin-2-yl)-5-isopropoxypiperidine-3-sulfonamide or (3R,5R)-1-(5-fluoropyrimidin-2-yl)-5-isopropoxypiperidine-3-sulfonamide (Example 820.7), nicotinohydrazide (Alfa Aesar), 2-isothiocyanato-1,3-dimethoxybenzene (Example 1.0). | 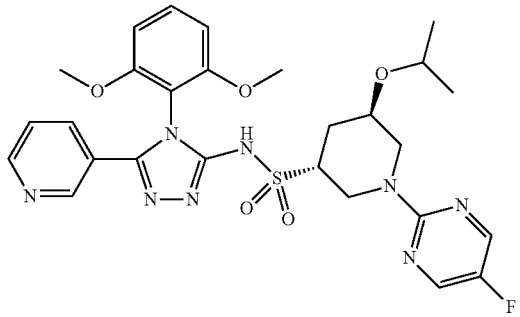 [SMILES: COc1cccc(OC)c1-n1c(NS(=O)(=O)[C@@H]2C[C@@H](OC(C)C)CN(c3ncc(F)cn3)C2)nnc1-c1cccnc1]<br>OR<br>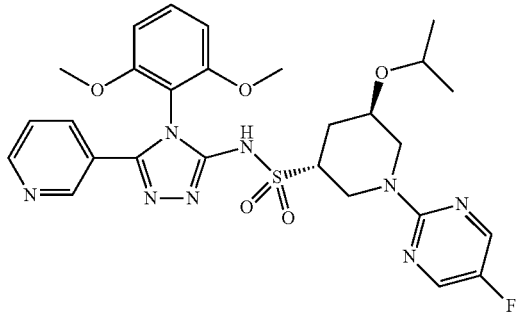<br>(3R,5R)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide or (3S,5S)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide. 1H NMR (400 MHz, CDCl3) δ 0.91 (d, J = 6.12 Hz, 3 H) 1.06 (d, J = 6.01 Hz, 3 H) 1.99 (ddd, J = 13.24, 11.53, 3.11 Hz, 1 H) 2.27-2.34 (m, 1 H) 3.01 (dd, J = 13.89, 1.87 Hz, 1 H) 3.25 (dd, J = 13.16, 10.47 Hz, 1 H) 3.51 (t, J = 10.94 Hz, 1 H) 3.67-3.74 (m, 1 H) 3.76 (s, 3 H) 3.76 (s, 3 H) 3.82 (br. s., 1 H) 4.66 (dt, J = 13.99, 1.55 Hz, 1 H) 4.96-5.02 (m, 1 H) 6.62 (s, 1 H) 6.64 (s, 1 H) 7.40-7.43 (m, 1 H) 7.43-7.46 (m, 1 H) 7.94 (ddd, J = 8.27, 1.89, 1.66 Hz, 1 H) 8.16 (s, 2 H) 8.67 (d, J = 6.11 Hz, 1 H) 8.66 (s, 1 H). LCMS-ESI (POS.) m/z: 599.2 (M + H)+. |
| 824.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 746.4), 6-methylpicolinohydrazide (Example 3.4), 2-isothiocyanato-1,3-dimethoxybenzene (Example 1.0). | 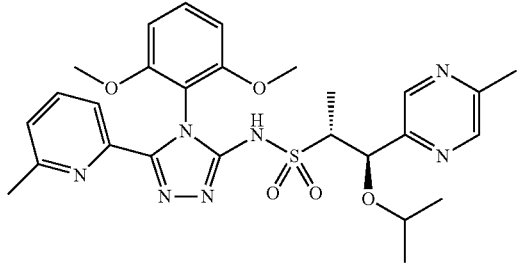<br>OR |

TABLE 52-continued

| Example | Reagents | Structure, Name and Data |
|---|---|---|
| | | 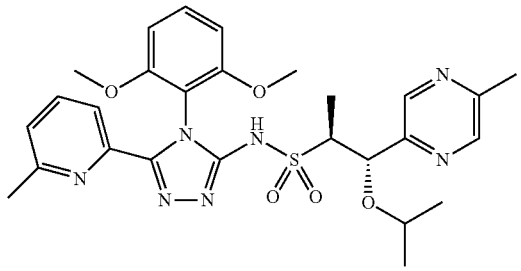
(1S,2S)-N-(4-(2,6-dimethoxyphenyl)-5-(6-methylpyridin-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-(6-methylpyridin-2-yl)-4H-1,2,4-triazol-3-yl)-1-isopropoxy-1-(5-methylpyrazin-2-yl)propane-2-sulfonamide. $^1$H NMR (400 MHz, DMSO-d$_6$) δ 13.23 (s, 1H), 8.48-8.42 (m, 2H), 7.79-7.72 (m, 1H), 7.63 (d, J = 7.9 Hz, 1H), 7.43 (t, J = 8.4 Hz, 1H), 7.24 (d, J = 7.7 Hz, 1H), 6.77 (dd, J = 2.1, 8.7 Hz, 2H), 4.78 (d, J = 6.0 Hz, 1H), 3.65 (s, 3H), 3.65 (s, 3H), 3.48-3.39 (m, 2H), 2.47 (s, 3H), 2.08 (s, 3H), 1.03 (d, J = 1.2 Hz, 3H), 1.02 (d, J = 2.5 Hz, 3H), 0.86 (d, J = 6.0 Hz, 3H). Mass Spectrum (pos.) m/e: 568.2 (M + H)$^+$. |
| 825.0 | (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide (Example 746.4) 6-methoxy-pyridine-2-carboxylic acid hydrazide (commercially available from Milestone Pharmatech), 2-isothiocyanato-1,3-dimethoxybenzene (Example 1.0). | 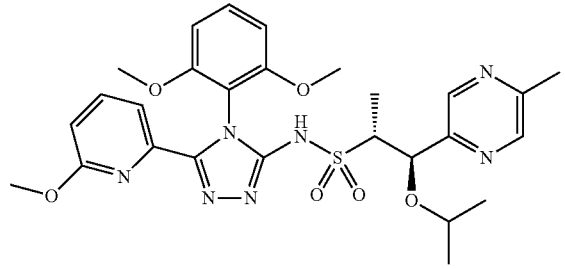
OR
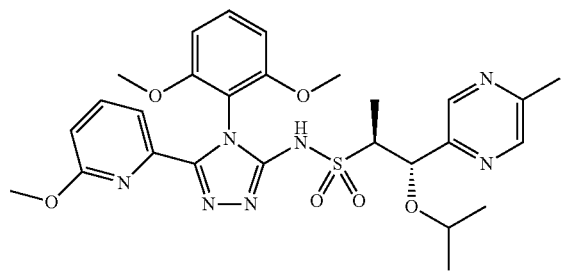
(1S,2S)-N-(4-(2,6-dimethoxyphenyl)-5-(6-methoxypyridin-2-yl)-4H-1,2,4-triazol-3-yl)-1-isopropoxy-1-(5-methylpyrazin-2-yl)propane-2-sulfonamide or (1R,2R)-N-(4-(2,6-dimethoxyphenyl)-5-(6-methoxypyridin-2-yl)-4H-1,2,4-triazol-3-yl)-1-isopropoxy-1-(5-methylpyrazin-2-yl)propane-2-sulfonamide. $^1$H NMR (400 MHz, DMSO-d$_6$) δ 13.27 (s, 1H), 8.44 (dd, J = 1.1, 13.637.08 Hz, 2H), 7.80 (dd, J = 7.5, 8.3 Hz, 1H), 7.57 (dd, J = 0.8, 7.5 Hz, 1H), 7.41 (t, J = 8.5 Hz, 1H), 6.85-6.78 (m, 3H), 4.75 (d, J = 6.2 Hz, 1H), 3.67 (s, 6H), 3.46-3.37 (m, 2H), 3.10 (s, 3H), 2.47 (s, 3H), 1.01 (m, 6H), 0.86 (d, J = 6.2 Hz, 3H). Mass Spectrum (pos.) m/e: 584.2 (M + H)$^+$. |

TABLE 52-continued

| Example | Reagents | Structure, Name and Data |
|---|---|---|
| 826.0 | (2S,3R)-3-(5-methylpyrimidin-2-yl)butane-2-sulfonamide or (2R,3S)-3-(5-methylpyrimidin-2-yl)butane-2-sulfonamide (Example 10), 5-methylnicotinic acid hydrazide (commercially available from Bellen Chemistry Co., Ltd.), 2,6-difluorophenyl isothiocyanate (commercially available from Oakwood Chemical). | OR<br><br>(2S,3R)-N-(4-(2,6-difluorophenyl)-5-(5-methylpyridin-3-yl)-4H-1,2,4-triazol-3-yl)-3-(5-methylpyrimidin-2-yl)butane-2-sulfonamide or (2R,3S)-N-(4-(2,6-difluorophenyl)-5-(5-methylpyridin-3-yl)-4H-1,2,4-triazol-3-yl)-3-(5-methylpyrimidin-2-yl)butane-2-sulfonamide. $^1$H NMR (400 MHz, DMSO-d$_6$) δ 13.78 (br. s., 1H), 8.57 (d, J = 0.6 Hz, 2H), 8.54 (d, J = 1.5 Hz, 1H), 8.27 (d, J = 1.9 Hz, 1H), 7.79-7.71 (m, 1H), 7.69 (s, 1H), 7.42 (t, J = 8.4 Hz, 2H), 3.73-3.61 (m, 2H), 2.27 (s, 3H), 2.23 (s, 3H), 1.22 (d, J = 6.8 Hz, 3H), 1.13 (d, J = 6.8 Hz, 3H). Mass Spectrum (pos.) m/e: 500.0 (M + H)$^+$. |

Example 827.0: Preparation of (1S,2S)—N-(4-(2,6-dimethoxyphenyl)-5-(pyridin-3-yl)-4H-1,2,4-triazol-3-yl)-1-(imidazo[1,2-a]pyridin-2-yl)-1-isopropoxy-propane-2-sulfonamide or (1R,2R)—N-(4-(2,6-dimethoxyphenyl)-5-(pyridin-3-yl)-4H-1,2,4-triazol-3-yl)-1-(imidazo[1,2-a]pyridin-2-yl)-1-isopropoxypropane-2-sulfonamide 827.1

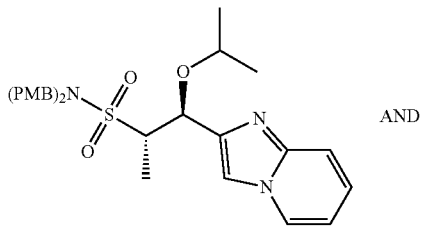

AND

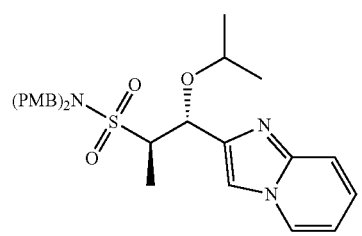

(1S,2S)-1-(imidazo[1,2-a]pyridin-2-yl)-1-isopropoxy-N,N-bis(4-methoxybenzyl)propane-2-sulfonamide and (1R,2R)-1-(imidazo[1,2-a]pyridin-2-yl)-1-isopropoxy-N,N-bis(4-methoxybenzyl)propane-2-sulfonamide (Example 827.1)

To a flask containing Example 735.2 (3.24 g, 6.54 mmol) and isopropyl iodide (9.2 mL, 92 mmol) in anhydrous toluene (26 mL) was added silver(I) oxide (3.12 g, 13.5 mmol) carefully in portions. Upon complete addition of silver oxide, the reaction was protected from light and heated to 75° C. After 70 hours, the mixture was cooled to RT and then filtered. The filtrate was concentrated under reduced pressure. The residue was loaded onto a silica gel column (eluting with 15-75% EtOAc in heptanes). Fractions containing product were combined and then concentrated under reduced pressure to afford Example 827.1 (1.68 g, 3.1 mmol, 4.8% yield) as a light yellow oil that was used without further purification. $^1$H NMR (400 MHz, DMSO-d$_6$) δ=8.54 (td, J=1.2, 6.8 Hz, 1H), 7.98 (s, 1H), 7.55 (dd, J=0.7, 9.0 Hz, 1H), 7.23 (ddd, J=1.3, 6.7, 9.1 Hz, 1H), 7.20-7.15 (m, 4H), 6.92-6.84 (m, 5H), 4.87 (d, J=7.7 Hz, 1H), 4.41 (d, J=15.5 Hz, 2H), 4.12 (d, J=15.5 Hz, 2H), 3.79-3.71 (m, 7H), 3.44 (spt, J=6.1 Hz, 1H), 1.12 (d, J=6.0 Hz, 3H), 1.09 (d, J=7.3 Hz, 3H), 1.00 (d, J=6.2 Hz, 3H). Mass Spectrum (pos.) m/e: 538.2 (M+H)$^+$.

1233

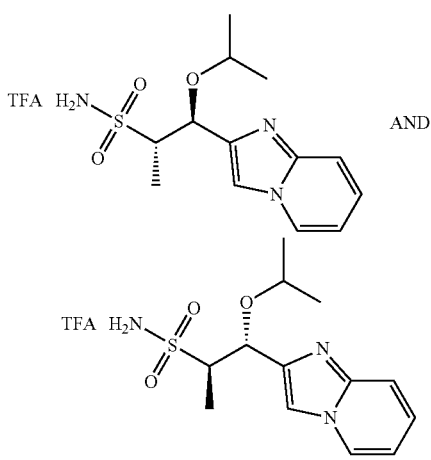

827.2

AND (1S,2S)-1-(imidazo[1,2-a]pyridin-2-yl)-1-isopropoxypropane-2-sulfonamide 2,2,2-trifluoroacetate and (1R,2R)-1-(imidazo[1,2-a]pyridin-2-yl)-1-isopropoxypropane-2-sulfonamide 2,2,2-trifluoroacetate, Example 827.2

Anisole (1.4 mL, 12.8 mmol) was added to a flask containing Example 827.1 (1.68 g, 3.1 mmol) and DCM (8 mL). The homogeneous solution was cooled in an ice-water bath. After 15 minutes, TFA (8 mL, 104 mmol) was added dropwise to the reaction solution. Upon complete addition of TFA, the reaction was allowed to warm to 23° C. After 20 hours, the brownish reaction solution was concentrated under reduced pressure. The residue was diluted with 3:1 EtOAc: EtOH solution and then loaded onto a silica gel column (eluting with 25-100% 3:1 EtOAc: EtOH in heptanes). Fractions containing product were concentrated under reduced pressure to afford Example 827.2 (1.08 g, 2.6 mmol, 84% yield) as an off-white solid that was submitted for chiral purification. $^1$H NMR (400 MHz, DMSO-d$_6$) δ=8.82 (d, J=6.6 Hz, 1H), 8.25 (s, 1H), 7.87-7.81 (m, 1H), 7.80-7.72 (m, 1H), 7.34 (t, J=6.6 Hz, 1H), 6.76 (br. s., 2H), 5.11 (d, J=6.4 Hz, 1H), 3.64 (spt, J=6.1 Hz, 1H), 3.58-3.48 (m, 1H), 1.18 (d, J=6.0 Hz, 3H), 1.16 (d, J=7.0 Hz, 3H), 1.05 (d, J=6.2 Hz, 3H). Mass Spectrum (pos.) m/e: 298.1 (M+H)$^+$.

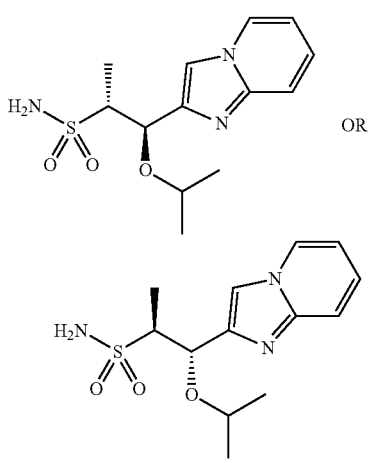

827.3

1234

(1R,2R)-1-(imidazo[1,2-a]pyridin-2-yl)-1-isopropoxypropane-2-sulfonamide or (1S,2S)-(imidazo[1,2-a]pyridin-2-yl)-1-isopropoxypropane-2-sulfonamide, Example 827.3

Example 827.2 (1.08 g, 2.6 mmol) was purified by preparative SFC using the following method: Column: AD-H; Mobile Phase: 75:25 (A:B) A: Liquid CO$_2$, B: iPrOH with 0.2% DEA to afford the first eluting peak as Example 827.3 (336.5 mg, 1.132 mmol, 43.5% yield). $^1$H NMR (400 MHz, DMSO-d$_6$) δ=8.53 (td, J=1.2, 6.8 Hz, 1H), 7.97 (s, 1H), 7.54 (dd, J=0.7, 9.0 Hz, 1H), 7.24 (ddd, J=1.3, 6.8, 9.1 Hz, 1H), 6.90 (dt, J=1.2, 6.7 Hz, 1H), 6.52 (s, 2H), 4.85 (d, J=7.3 Hz, 1H), 3.57 (quin, J=6.1 Hz, 1H), 3.53-3.46 (m, 1H), 1.15 (d, J=6.0 Hz, 3H), 1.03 (d, J=7.0 Hz, 3H), 1.00 (d, J=6.2 Hz, 3H). Mass Spectrum (pos.) m/e: 298.0 (M+H)$^+$.

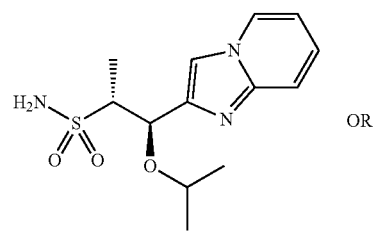

OR

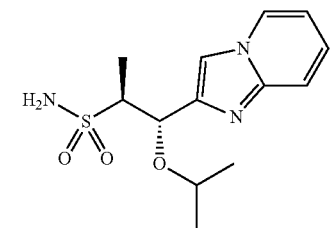

(1R,2R)-1-(imidazo[1,2-a]pyridin-2-yl)-1-isopropoxypropane-2-sulfonamide or (1S,2S)-(imidazo[1,2-a]pyridin-2-yl)-1-isopropoxypropane-2-sulfonamide, Example 827.4

Further elution under the conditions described in Example 827.3 delivered the second eluting peak, Example 827.4 (336.9 mg, 1.133 mmol, 43.6% yield) with arbitrarily assigned stereochemistry. $^1$H NMR (400 MHz, DMSO-d$_6$) δ=8.53 (td, J=1.1, 6.8 Hz, 1H), 7.97 (s, 1H), 7.54 (dd, J=0.8, 9.1 Hz, 1H), 7.24 (ddd, J=1.2, 6.7, 9.1 Hz, 1H), 6.90 (dt, J=1.0, 6.7 Hz, 1H), 6.52 (s, 2H), 4.86 (d, J=7.3 Hz, 1H), 3.62-3.54 (m, 1H), 3.53-3.46 (m, 1H), 1.15 (d, J=6.0 Hz, 3H), 1.04 (d, J=7.0 Hz, 3H), 1.00 (d, J=6.2 Hz, 3H). Mass Spectrum (pos.) m/e: 298.0 (M+H)$^+$.

The compounds set forth in the following Table were synthesized following the procedure in Example 741.0 using the known starting material as described.

TABLE 53

| Example | Reagents | Structure, Name and Data |
|---|---|---|
| 827.0 | (1R,2R)-1-(imidazo[1,2-a]pyridin-2-yl)-1-isopropoxypropane-2-sulfonamide or (1S,2S)-1-(imidazo[1,2-a]pyridin-2-yl)-1-isopropoxypropane-2-sulfonamide (Example 827.3), nicotinic hydrazide, 2-isothiocyanato-1,3-dimethoxybenzene (Example 1.0). | 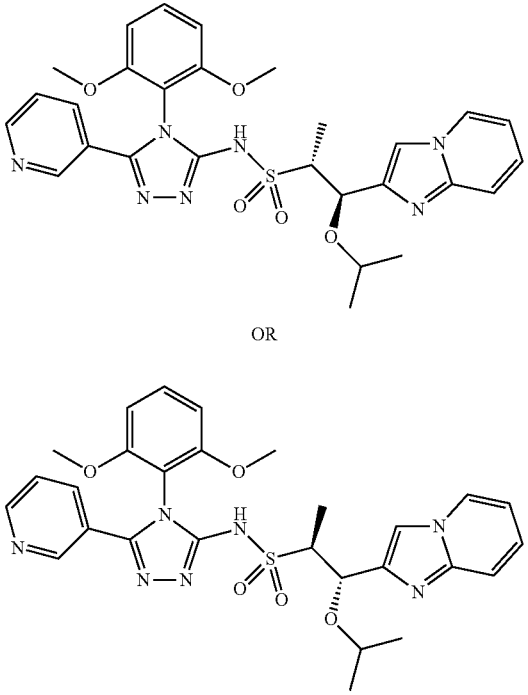<br>OR<br><br>(1R,2R)-N-(4-(2,6-dimethoxyphenyl)-5-(pyridin-3-yl)-4H-1,2,4-triazol-3-yl)-1-(imidazo[1,2-a]pyridin-2-yl)-1-isopropoxypropane-2-sulfonamide or (1S,2S)-N-(4-(2,6-dimethoxyphenyl)-5-(pyridin-3-yl)-4H-1,2,4-triazol-3-yl)-1-(imidazo[1,2-a]pyridin-2-yl)-1-isopropoxypropane-2-sulfonamide. $^1$H NMR (400 MHz, CD$_2$Cl$_2$) δ 8.63 (dd, J = 0.8, 2.3 Hz, 1H), 8.58 (dd, J = 1.7, 4.8 Hz, 1H), 8.16 (td, J = 1.1, 6.7 Hz, 1H), 7.74-7.70 (m, 1H), 7.63 (dd, J = 0.6, 9.1 Hz, 1H), 7.60 (s, 1H), 7.49-7.43 (m, 1H), 7.28-7.21 (m, 2H), 6.84 (dt, J = 1.1, 6.8 Hz, 1H), 6.72-6.67 (m, 2H), 5.06 (d, J = 4.1 Hz, 1H), 3.77 (s, 3H), 3.76 (s, 3H), 3.66-3.61 (m, 1H), 3.60-3.54 (m, 1H), 1.30 (d, J = 7.0 Hz, 3H), 1.14 (d, J = 6.0 Hz, 3H), 1.07 (d, J = 6.2 Hz, 3H). Mass Spectrum (pos.) m/z: 578.2 (M + H)$^+$. |
| 828.0 | (1R,2R)-1-(imidazo[1,2-a]pyridin-2-yl)-1-isopropoxypropane-2-sulfonamide or (1S,2S)-1-(imidazo[1,2-a]pyridin-2-yl)-1-isopropoxypropane-2-sulfonamide (Example 827.4), nicotinic hydrazide, 2-isothiocyanato-1,3-dimethoxybenzene (Example 1.0). | 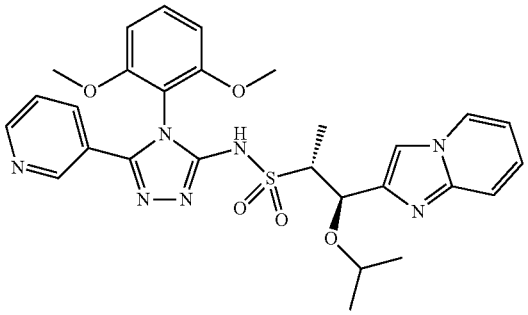<br>OR |

TABLE 53-continued

| Example | Reagents | Structure, Name and Data |
|---|---|---|
| | | 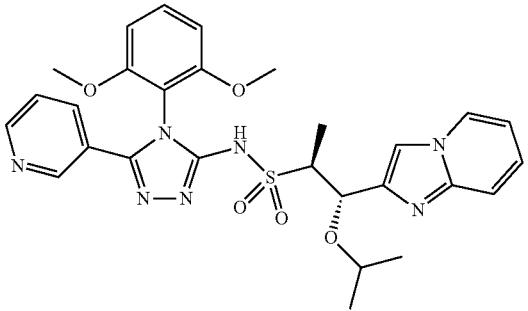 [SMILES: COc1cccc(OC)c1-n1c(NS(=O)(=O)[C@@H](C)[C@@H](OC(C)C)c2cn3ccccc3n2)nnc1-c1cccnc1]<br>(1R,2R)-N-(4-(2,6-dimethoxyphenyl)-5-(pyridin-3-yl)-4H-1,2,4-triazol-3-yl)-1-(imidazo[1,2-a]pyridin-2-yl)-1-isopropoxypropane-2-sulfonamide or (1S,2S)-N-(4-(2,6-dimethoxyphenyl)-5-(pyridin-3-yl)-4H-1,2,4-triazol-3-yl)-1-(imidazo[1,2-a]pyridin-2-yl)-1-isopropoxypropane-2-sulfonamide. $^1$H NMR (400 MHz, CD$_2$Cl$_2$) δ 8.63 (dd, J = 0.8, 2.3 Hz, 1H), 8.58 (dd, J = 1.8, 4.9 Hz, 1H), 8.16 (td, J = 1.1, 6.8 Hz, 1H), 7.74-7.69 (m, 1H), 7.62 (dd, J = 0.8, 9.1 Hz, 1H), 7.60 (s, 1H), 7.48-7.44 (m, 1H), 7.27-7.21 (m, 2H), 6.84 (dt, J = 1.1, 6.8 Hz, 1H), 6.71-6.66 (m, 2H), 5.06 (d, J = 3.9 Hz, 1H), 3.76 (s, 3H), 3.75 (s, 3H), 3.67-3.60 (m, 1H), 3.60-3.54 (m, 1H), 1.29 (d, J = 7.0 Hz, 3H), 1.14 (d, J = 6.0 Hz, 3H), 1.07 (d, J = 6.0 Hz, 3H). Mass Spectrum (pos.) m/z: 578.2 (M + H)$^+$. |
| 829.0 | (1S,2S)-1-isopropoxy-1-(5-methylpyrimidin-2-yl)propane-2-sulfonamide, Example 738.5, 5-methylnicotinic acid hydrazide (commercially available from Bellen Chemistry Co., Ltd.), 5-isothiocyanato-4,6-dimethoxypyrimidine (Intermediate 1.1). | 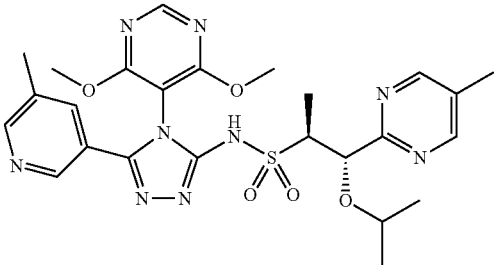 [SMILES: COc1ncnc(OC)c1-n1c(NS(=O)(=O)[C@@H](C)[C@@H](OC(C)C)c2ncc(C)cn2)nnc1-c1cncc(C)c1]<br>(1S,2S)-N-(4-(4,6-dimethoxypyrimidin-5-yl)-5-(5-methylpyridin-3-yl)-4H-1,2,4-triazol-3-yl)-1-isopropoxy-1-(5-methylpyrimidin-2-yl)propane-2-sulfonamide. $^1$H NMR (500 MHz, DMSO-d$_6$) δ = 13.52 (br. s., 1H), 8.70-8.63 (m, 3H), 8.53 (br. s., 1H), 8.28 (s, 1H), 7.65 (s, 1H), 4.70 (d, J = 7.5 Hz, 1H), 3.93 (s, 6H), 3.48 (br. s., 1H), 3.42-3.35 (m, 1H), 2.30 (s, 3H), 2.28 (s, 3H), 0.98 (d, J = 6.2 Hz, 3H), 0.94 (d, J = 7.0 Hz, 3H), 0.79 (d, J = 6.2 Hz, 3H). Mass Spectrum (pos.) m/z: 570.2 (M + H)$^+$. |

Example 830.0: Preparation of (3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide or (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide

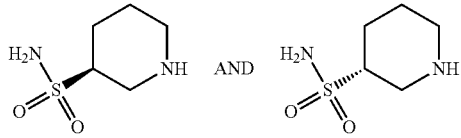

(S)-piperidine-3-sulfonamide hydrochloride and (R)-piperidine-3-sulfonamide hydrochloride, Example 830.1

A solution of 4-chloropyridine-3-sulfonamide (5.0 g, 25.9 mmol) in AcOH (150 mL) was placed in a parr bottle. The resulting mixture was bubbled with nitrogen gas for 5 minutes. To this solution was then added a suspension of platinum (IV) oxide (5.9 g, 25.9 mmol) in AcOH (30 mL). The reaction was then stirred under a hydrogen atmosphere (50 psi) for 72 hours. The reaction mixture was filtered through a pad of Celite® brand filter agent, washing the pad of Celite® brand filter agent with MeOH (2×50 mL). The combined filtrate was concentrated under reduced pressure to provide Example 830.1 (6.0 g) as an oil which was used in the next step without further purification. LCMS-ESI (POS.) m/z: 165.0 (M+H)$^+$.

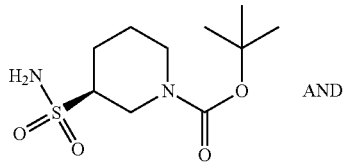

(S)-tert-butyl 3-sulfamoylpiperidine-1-carboxylate and (R)-tert-butyl 3-sulfamoylpiperidine-1-carboxylate, Example 830.2

To a mixture of Example 830.1 (12.0 g, 59.8 mmol) and TEA (41.6 mL, 298.9 mmol) in DCM (215 mL) was added a solution of boc anhydride (15.7 mL, 71.8 mmol) in DCM (70 mL) at RT. The reaction mixture was then stirred for 16 h at RT and then was washed with water (2×200 mL). The combined organic layers were washed with brine (100 mL), dried over sodium sulfate and evaporated under reduced pressure to obtain the initial material which was purified by column chromatography (silica: 100-200 mesh; elution: 0-30% EtOAc in DCM) to provide Example 830.2 (4.6 g, 34% (over two steps) as a white solid. 1H NMR (400 MHz, CD$_3$CN) δ 5.30 (s, 2H), 4.36 (d, J=11.8 Hz, 1H), 3.94 (d, J=13.3 Hz, 1H), 3.01-2.84 (m, 2H), 2.64-2.58 (s, 1H), 2.20 (d, J=13.3 Hz, 1H), 1.78 (d, J=13.5 Hz, 1H), 1.74-1.57 (m, 2H), 1.43 (s, 9H). LCMS-ESI (POS./NEG.) m/z: 263 (M−H)$^−$.

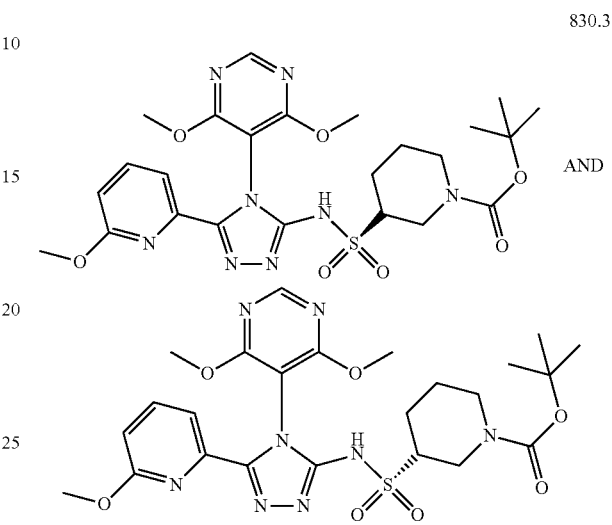

(S)-tert-butyl 3-(N-(4-(4,6-dimethoxypyrimidin-5-yl)-5-(6-methoxypyridin-2-yl)-4H-1,2,4-triazol-3-yl)sulfamoyl)piperidine-1-carboxylate and (R)-tert-butyl 3-(N-(4-(4,6-dimethoxypyrimidin-5-yl)-5-(6-methoxypyridin-2-yl)-4H-1,2,4-triazol-3-yl)sulfamoyl)piperidine-1-carboxylate, Example 830.3

The title compound was synthesized following the procedure in Example 741.0 using known starting materials as described: methoxypicolinohydrazide (Example 3.18), 5-isothiocyanato-4,6-dimethoxypyrimidine (Example 1.1) and (S)-piperidine-3-sulfonamide hydrochloride, and (R)-piperidine-3-sulfonamide hydrochloride (Example 830.2).

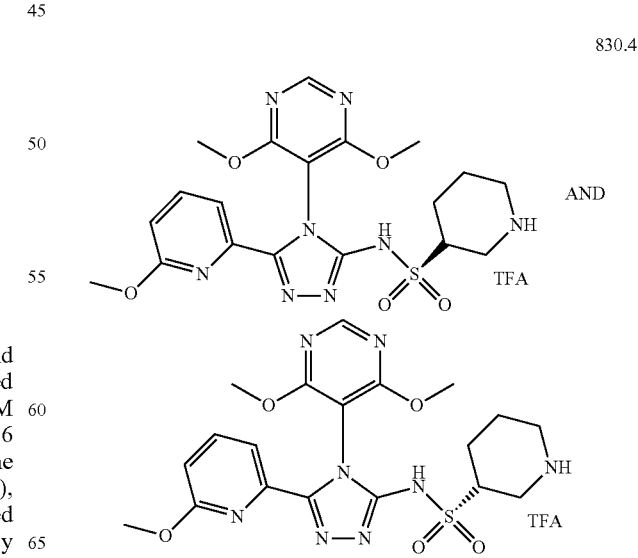

(S)—N-(4-(4,6-dimethoxypyrimidin-5-yl)-5-(6-methoxypyridin-2-yl)-4H-1,2,4-triazol-3-yl)piperidine-3-sulfonamide 2,2,2-trifluoroacetate and (R)—N-(4-(4,6-dimethoxypyrimidin-5-yl)-5-(6-methoxypyridin-2-yl)-4H-1,2,4-triazol-3-yl)piperidine-3-sulfonamide 2,2,2-trifluoroacetate, Example 830.4

A 100 mL round bottom flask was charged with Example 830.3 (643 mg, 1.115 mmol) and dissolved in DCM (10 mL). To that solution was added TFA (1.27 g, 11.15 mmol, 0.828 mL). After 19 hours, LCMS showed complete consumption of the starting material to a polar peak. The reaction mixture was concentrated under reduced pressure to give (S)—N-(4-(4,6-dimethoxypyrimidin-5-yl)-5-(6-methoxypyridin-2-yl)-4H-1,2,4-triazol-3-yl)piperidine-3-sulfonamide 2,2,2-trifluoroacetate and (R)—N-(4-(4,6-dimethoxypyrimidin-5-yl)-5-(6-methoxypyridin-2-yl)-4H-1,2,4-triazol-3-yl)piperidine-3-sulfonamide 2,2,2-trifluoroacetate (657 mg, 100% yield). LCMS-ESI (POS.) m/z: 477.5 (M+H)$^+$.

tography: 50 g Biotage SNAP Ultra –CV=85 mL, eluting with EtOAc:EtOH 3:1 (v/v) in heptane % (2CV), 0-40% (15CV), 40% (2CV) to provide 1-(5-chloropyrimidin-2-yl)-N-(4-(4,6-dimethoxypyrimidin-5-yl)-5-(6-methoxypyridin-2-yl)-4H-1,2,4-triazol-3-yl)piperidine-3-sulfonamide (149 mg, 0.253 mmol, 50% yield) as a white solid.

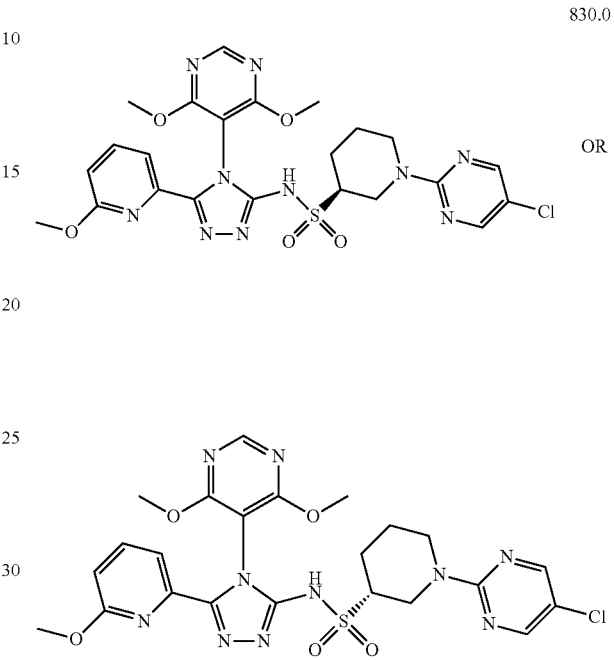

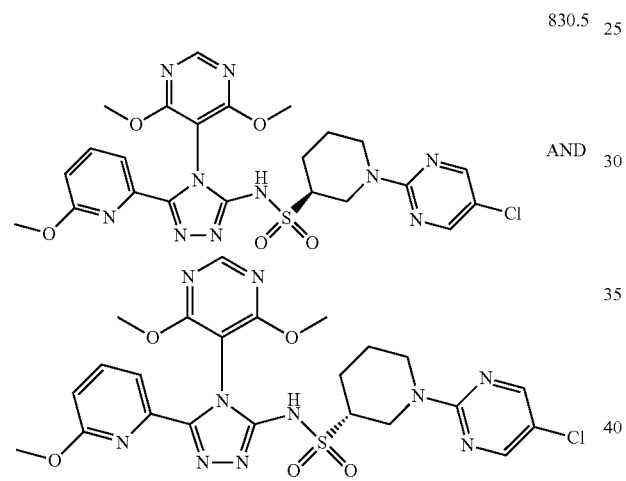

(3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide and (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide, Example 830.5

A 40 mL pressure release vial was charged with Example 830.4 (300 mg, 0.508 mmol) and dissolved in 2-methyltetrahydrofuran (5080 μl). To that solution was added Hunig's base (884 μl, 5.08 mmol) followed by 2,5-dichloropyrimidine (378 mg, 2.54 mmol). The vial was sealed and placed into a reaction block preheated to 80° C. After 21 hours, LCMS showed complete consumption of the starting material. The contents of the vial were transferred into a separatory funnel and the mixture was diluted with DCM and a saturated solution of sodium bicarbonate. The layers were separated and the organic layer was washed with water (×1) and brine (×1). The combined aqueous layers were extracted with DCM, analyzed for product and subsequently discarded. The organic layer was dried with MgSO$_4$, concentrated under reduced pressure and purified by flash chroma- (3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide or (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide, Example 830.0

A chiral supercritical fluid chromatography purification of racemic Example 830.5 was performed. Conditions for the preparative SFC method were as follows: Column: Chiralpak AS-H (20×150 mm), Mobile Phase: 40:60 (A:B), A: Liquid CO$_2$, B: iPrOH, Flow Rate: 60 mL/min, 220 nm, 149 bar inlet pressure and provided two peaks of >99.5% ee: The first eluting peak was assigned as Example 830.0, (3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide or (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide.
$^1$H NMR (500 MHz, DMSO-d6) δ 13.65 (1H, s) 8.65 (1H, s) 8.41 (2H, s) 7.86 (1H, t, J=7.85 Hz) 7.67 (1H, d, J=7.27 Hz) 6.91 (1H, d, J=8.30 Hz) 4.93 (1H, br d, J=10.77 Hz) 4.53 (1H, br d, J=13.23 Hz) 3.90 (3H, s) 3.88 (3H, s) 3.17 (3H, s) 2.96 (1H, br d, J=11.03 Hz) 2.84-2.92 (1H, m) 2.73-2.80 (1H, m) 2.11 (1H, br d, J=12.59 Hz) 1.79 (1H, br d, J=13.10 Hz) 1.60 (1H, br dd, J=12.26, 3.57 Hz) 1.38-1.48 (1H, m). LCMS-ESI (POS.) M/Z: 589.1 (M+H)$^+$. Peak assignment was determined by analytical SFC: Chiralpak AS-H, 40% isopropanol 1.30 minutes.

Example 831.0: Preparation of (3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide or (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide

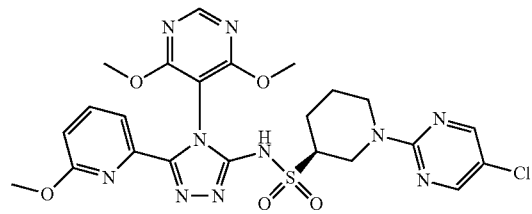

831.0

OR chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide or (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide.
$^1$H NMR (500 MHz, DMSO-d$_6$) δ 13.65 (1H, s) 8.65 (1H, s) 8.41 (2H, s) 7.86 (1H, t, J=7.85 Hz) 7.67 (1H, d, J=7.40 Hz) 6.91 (1H, d, J=8.30 Hz) 4.93 (1H, br d, J=12.46 Hz) 4.53 (1H, br d, J=13.23 Hz) 3.89 (3H, s) 3.88 (3H, s) 3.17 (3H, s) 2.93-3.02 (1H, m) 2.84-2.92 (1H, m) 2.76 (1H, td, J=12.78, 2.47 Hz) 2.10 (1H, br d, J=12.20 Hz) 1.75-1.82 (1H, m) 1.60 (1H, br dd, J=12.26, 3.44 Hz) 1.43 (1H, dt, J=12.49, 3.62 Hz). LCMS-ESI (POS.) M/Z: 589.1 (M+H)$^+$. Peak assignment was determined by analytical SFC: Chiralpak AS-H, 40% isopropanol: 2.61 minutes.

The compound set forth in the following Table was synthesized following the procedure in Example B using the known starting material as described.

TABLE 54

| Example | Reagents | Structure, Name and Data |
|---|---|---|
| 832.0 | Cyclopropylmethanesulfonamide, (commercially available from Enamine LLC, Monmouth Jct., NJ, USA), 2-(5-bromo-4-(2,6-dimethoxyphenyl)-4H-1,2,4-triazol-3-yl)-6-methoxypyridine (Example 2.2). | 1-cyclopropyl-N-(4-(2,6-dimethoxyphenyl)-5-(6-methoxy-2-pyridinyl)-4H-1,2,4-triazol-3-yl)methanesulfonamide. $^1$H NMR (500 MHz, DMSO-d$_6$) δ 7.63 (t, J = 8.05 Hz, 1 H) 7.56 (br d, J = 7.40 Hz, 1 H) 7.26 (br t, J = 8.37 Hz, 1 H) 6.70 (br d, J = 8.43 Hz, 2 H) 6.54 (br d, J = 8.04 Hz, 1 H) 3.60 (m, 6 H) 3.03 (s, 3 H) 2.97-3.02 (m, 2 H) 0.82-1.00 (m, 1 H) 0.38 (br d, J = 6.62 Hz, 2 H) 0.17 (br d, J = 4.54 Hz, 2 H). LCMS-ESI (POS.) m/z: 446.2 (M + H)$^+$. |

-continued

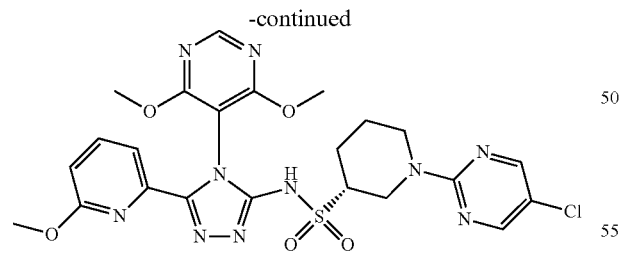

(3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide or (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide, Example 831.0

The second eluting peak from the conditions described in Example 830.0 was assigned Example 831.0, (3R)-1-(5-

Example 833.0: Preparation (2S,3R)—N-(5-(5-cyano-3-pyridinyl)-4-(2,6-dimethoxyphenyl)-4H-1,2,4-triazol-3-yl)-3-(5-methyl-2-pyrimidinyl)-2-butanesulfonamide

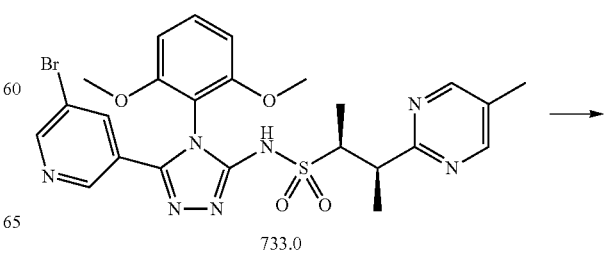

733.0

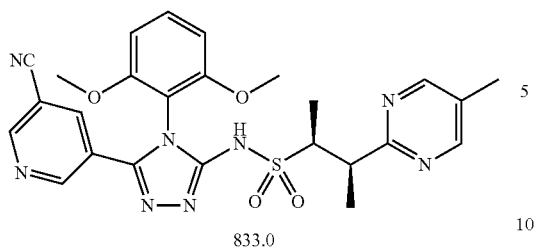

833.0

(2S,3R)—N-(5-(5-cyano-3-pyridinyl)-4-(2,6-dimethoxyphenyl)-4H-1,2,4-triazol-3-yl)-3-(5-methyl-2-pyrimidinyl)-2-butanesulfonamide, Example 833.0

(2S,3R)—N-(5-(5-bromopyridin-3-yl)-4-(2,6-dimethoxyphenyl)-4H-1,2,4-triazol-3-yl)-3-(5-methylpyrimidin-2-yl)butane-2-sulfonamide (Example 733.0) (0.51 g, 0.87 mmol) was suspended in N, N-dimethylacetamide (4 mL) and then methanesulfonato(2-dicyclohexylphosphino-2',4',6'-tri-i-propyl-1,1'-biphenyl)(2'-amino-1,1'-biphenyl-2-yl)palladium(II) (0.37 g, 0.43 mmol, Strem Chemicals, Inc) and zinc cyanide (0.102 g, 0.87 mmol, Pfaltz & Bauer Inc) were added to the vial. The mixture was heated to 80° C. After 20 hours, the reaction was cooled to RT and then loaded onto a silica gel column (0-70% 3:1 EtOAc: EtOH in heptane). Fractions containing product were combined and then concentrated under reduced pressure to afford Example 833.0 (0.316 g, 0.59 mmol, 68% yield) as white solid. $^1$H NMR (500 MHz, CDCl$_3$) δ 11.55 (br s, 1H) 8.87 (d, J=1.95 Hz, 1H) 8.82 (d, J=2.21 Hz, 1H) 8.55 (s, 2H) 8.01 (t, J=2.08 Hz, 1H) 7.44 (t, J=8.50 Hz, 1H) 6.64 (t, J=9.08 Hz, 2H) 3.92 (quin, J=6.75 Hz, 1H) 3.77 (s, 3H) 3.75-3.77 (m, 1H) 3.74 (s, 3H) 2.31 (s, 3H) 1.38 (dd, J=10.57, 7.07 Hz, 6H). LCMS-ESI (POS.) m/z: 535.2 (M+H)$^+$.

Example 834.0: 5-(4-(2,6-dimethoxyphenyl)-5-001S,2R)-1-methyl-2-(5-methyl-2-pyrimidinyl)propyl)sulfonyl)amino)-4H-1,2,4-triazol-3-yl)-3-pyridinecarboxylic acid

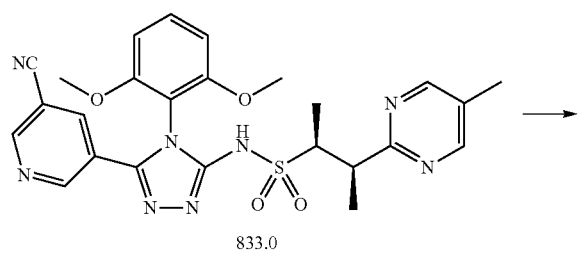

833.0

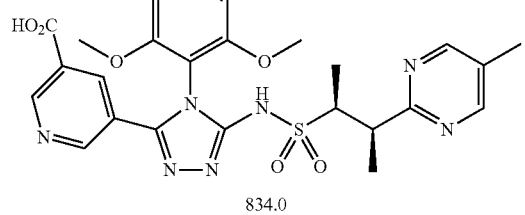

834.0

5-(4-(2,6-dimethoxyphenyl)-5-001S,2R)-1-methyl-2-(5-methyl-2-pyrimidinyl)propyl)sulfonyl)amino)-4H-1,2,4-triazol-3-yl)-3-pyridinecarboxylic acid, Example 834.0

To a vial was added (2S,3R)—N-(5-(5-cyanopyridin-3-yl)-4-(2,6-dimethoxyphenyl)-4H-1,2,4-triazol-3-yl)-3-(5-methylpyrimidin-2-yl)butane-2-sulfonamide, Example 833.0 (0.190 g, 0.36 mmol) and 1.0 M NaOH aqueous solution (1.07 mL, 0.11 mmol, Sigma Aldrich) in EtOH (1.4 mL). The reaction mixture was heated at 80° C. for 20 hours. The reaction mixture was then allowed to cool to RT and then was acidified with a 1M aqueous solution of citric acid until pH-5. A white precipitate formed. The white precipitate was filtered and then dried to give 5-(4-(2,6-dimethoxyphenyl)-5-(((1S,2R)-1-methyl-2-(5-methylpyrimidin-2-yl)propylsulfonamido)-4H-1,2,4-triazol-3-yl)nicotinic acid, Example 834.0 (0.17 g, 0.31 mmol, 86% yield) as a white solid. $^1$H NMR (500 MHz, CD$_3$OD) δ 9.13 (d, J=1.95 Hz, 1H) 8.80 (d, J=2.21 Hz, 1H) 8.56 (s, 2H) 8.34 (t, J=2.01 Hz, 1H) 7.50 (t, J=8.56 Hz, 1H) 6.80 (dd, J=8.43, 5.32 Hz, 2H) 3.79 (s, 3H) 3.77 (s, 3H) 3.66-3.77 (m, 2H) 2.30 (s, 3H) 1.33 (d, J=7.01 Hz, 3H) 1.29 (d, J=6.88 Hz, 3H). LCMS-ESI (POS.) m/z: 554.2 (M+H)$^+$.

The compounds set forth in the following Table were synthesized following the procedure in Example 741.0 using the known starting material as described.

TABLE 55

| Example | Reagents | Structure, Name and Data |
|---|---|---|
| 835.0 | (2S,3R)-3-(5-chloropyrimidin-2-yl)butane-2-sulfonamide (Example 696.1), 6-methoxypicolinohydrazide (commercially available from Sigma-Aldrich Corp, St. Louis, MO, USA), 4-isothiocyanatooxane (commercially available from Oakwood Products, Inc.). | 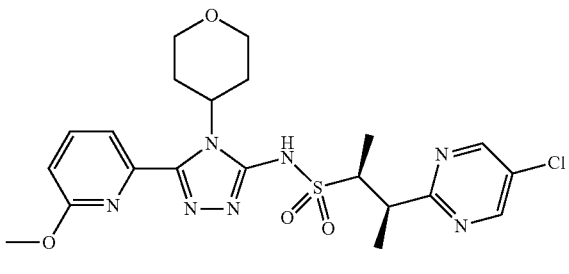(2S,3R)-3-(5-chloro-2-pyrimidinyl)-N-(5-(6-methoxy-2-pyridinyl)-4-(tetrahydro-2H-pyran-4-yl)-4H-1,2,4-triazol-3-yl)-2-butanesulfonamide. $^1$H NMR (400 MHz, CD$_3$OD) δ 1.47 (d, J = 8.71 Hz, 3 H) 1.45 (d, J = 8.71 Hz, 3 H) 1.77 (ddd, J = 6.38, 4.30, 1.97 Hz, 2 H) 2.89 (qd, J = 12.51, 3.73 Hz, 2 H) 3.44 (t, J = 11.82 Hz, 2 H) 3.78-3.86 (m, 1 H) 3.86-3.94 (m, 1 H) 4.00 (s, 3 H) 4.05 (d, J = 11.40 Hz, 2 H) 5.25 (tt, J = 12.18, 4.09 Hz, 1 H) 6.99 (dd, J = 8.40, 0.73 Hz, 1 H) 7.57 (dd, J = 7.36, 0.73 Hz, 1 H) 7.85 (dd, J = 8.29, 7.46 Hz, 1 H) 8.74 (s, 2 H). LCMS-ESI (POS.) m/z: 508.1 (M + H)$^+$. |
| 836.0 | (1R,2S)-1-(5-chloropyrimidin-2-yl)-1-methoxypropane-2-sulfonamide (Example 711.1), 6-methoxypicolinohydrazide (commercially available from Sigma-Aldrich Corp, St. Louis, MO, USA), 4-isothiocyanatooxane (commercially available from Oakwood Products, Inc.). | 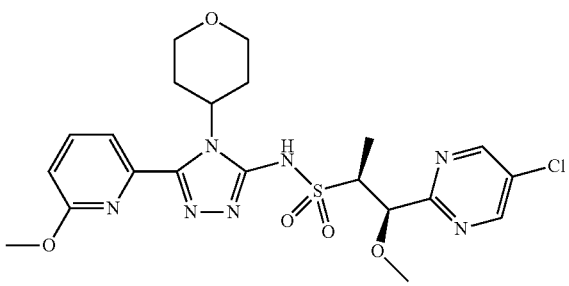 [SMILES: COc1cccc(-c2nnc(NS(=O)(=O)[C@@H](C)[C@H](OC)c3ncc(Cl)cn3)n2C2CCOCC2)n1](1R,2S)-1-(5-chloro-2-pyrimidinyl)-1-methoxy-N-(5-(6-methoxy-2-pyridinyl)-4-(tetrahydro-2H-pyran-4-yl)-4H-1,2,4-triazol-3-yl)-2-propanesulfonamide. $^1$H NMR (400 MHz, CD$_3$OD) δ 1.42 (d, J = 7.05 Hz, 3 H) 1.78-1.87 (m, 2 H) 2.90-3.04 (m, 2 H) 3.31 (s, 3 H) 3.41-3.51 (m, 2 H) 3.68 (qd, J = 7.05, 3.73 Hz, 1 H) 4.01 (s, 3 H) 4.07 (dd, J = 11.71, 4.66 Hz, 2 H) 5.11 (d, J = 3.94 Hz, 1 H) 5.28 (tt, J = 12.18, 4.30 Hz, 1 H) 6.99 (dd, J = 8.50, 0.62 Hz, 1 H) 7.57 (dd, J = 7.36, 0.73 Hz, 1 H) 7.85 (dd, J = 8.40, 7.36 Hz, 1 H) 8.85 (s, 2 H). LCMS-ESI (POS.) m/z: 524.1 (M + H)$^+$. |
| 837.0 | (1S,2S)-1-isopropoxy-1-(5-methylpyrimidin-2-yl)propane-2-sulfonamide (Example 738.5), 6-methoxypicolinohydrazide (commercially available from Sigma-Aldrich Corp, St. Louis, MO, USA), 4-isothiocyanatooxane (commercially available from Oakwood Products, Inc.). | 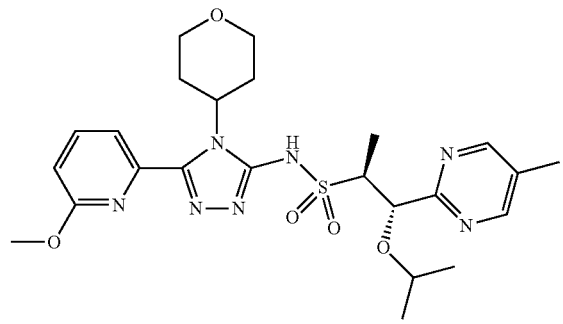(1S,2S)-N-(5-(6-methoxy-2-pyridinyl)-4-(tetrahydro-2H-pyran-4-yl)-4H-1,2,4-triazol-3-yl)-1-(1-methylethoxy)-1-(5-methyl-2-pyrimidinyl)-2-propanesulfonamide. $^1$H NMR (400 MHz, CD$_3$OD) δ: ppm 0.87 (d, J = 6.22 Hz, 3 H) 1.11 (d, J = 6.01 Hz, 3 H) 1.30 (d, J = 7.05 Hz, 3 H) 1.81 (dd, J = 12.34, 2.59 Hz, 2 H) 2.37 (s, 3 H) 2.89-3.06 (m, 2 H) 3.41-3.53 (m, 3 H) 3.75 (quin, J = 6.89 Hz, 1 H) 4.00 (s, 3 H) 4.07 (d, J = 11.61 Hz, 2 H) 4.99 (d, J = 6.63 Hz, 1 H) 5.27 (tt, J = 12.10, 4.17 Hz, 1 H) 6.99 (d, J = 8.29 Hz, 1 H) 7.56 |

TABLE 55-continued

| Example | Reagents | Structure, Name and Data |
|---|---|---|
| | | (d, J = 7.26 Hz, 1 H) 7.86 (t, J = 7.82 Hz, 1 H) 8.69 (s, 2 H). LCMS-ESI (POS.) m/z: 532.3 (M + H)+. |
| 838.0 | (2S,3R)-3-(5-chloropyridin-2-yl)butane-2-sulfonamide (Example 802.1), nicotinohydrazide (Alfa Aesar), 5-isothiocyanato-4,6-dimethoxypyrimidine (Example 1.1). Chiral separation of Example 807.0. The title compound was the first eluting peak (earlier peak vs. its atropisomer) on AD column. SFC condition: Chiralpak AD-H column, 30% MeOH/CO$_2$. | (2S,3R,P)-3-(5-chloropyridin-2-yl)-N-(4-(4-methoxy-6-oxo-1,6-dihydropyrimidin-5-yl)-5-(pyridin-3-yl)-4H-1,2,4-triazol-3-yl)butane-2-sulfonamide or (2S,3R,M)-3-(5-chloropyridin-2-yl)-N-(4-(4-methoxy-6-oxo-1,6-dihydropyrimidin-5-yl)-5-(pyridin-3-yl)-4H-1,2,4-triazol-3-yl)butane-2-sulfonamide. $^1$H NMR (400 MHz, CDCl$_3$) δ: ppm 1.26 (d, J = 6.63 Hz, 3 H) 1.35 (d, J = 6.84 Hz, 3 H) 3.69-3.81 (m, 5 H) 7.16 (d, J = 8.50 Hz, 1 H) 7.22-7.36 (m, 2 H) 7.60 (dd, J = 8.40, 2.38 Hz, 1 H) 7.83 (d, J = 7.88 Hz, 1 H) 8.19 (s, 1 H) 8.48 (d, J = 2.07 Hz, 1 H) 8.63 (d, J = 3.94 Hz, 1 H) 8.82 (s, 1 H). LCMS-ESI (POS.) m/z: 516.0 (M + H)+. |
| 839.0 | (2S,3R)-3-(5-chloropyridin-2-yl)butane-2-sulfonamide (Example 802.1), nicotinohydrazide (Alfa Aesar), 5-isothiocyanato-4,6-dimethoxypyrimidine (Example 1.1). Chiral separation of the Example 807.0. The second eluting peak (later peak vs. its atropisomer) on Chiralpak AD-H, 30% MeOH. | (2S,3R,P)-3-(5-chloropyridin-2-yl)-N-(4-(4-methoxy-6-oxo-1,6-dihydropyrimidin-5-yl)-5-(pyridin-3-yl)-4H-1,2,4-triazol-3-yl)butane-2-sulfonamide or (2S,3R,M)-3-(5-chloropyridin-2-yl)-N-(4-(4-methoxy-6-oxo-1,6-dihydropyrimidin-5-yl)-5-(pyridin-3-yl)-4H-1,2,4-triazol-3-yl)butane-2-sulfonamide. $^1$H NMR (400 MHz, CDCl$_3$) δ 1.29 (d, J = 6.84 Hz, 3 H) 1.38 (d, J = 6.84 Hz, 3 H) 3.65-3.73 (m, 2 H) 3.72 (s, 3 H) 7.13 (d, J = 8.29 Hz, 1 H) 7.20-7.36 (m, 2 H) 7.59 (dd, |

TABLE 55-continued

| Example | Reagents | Structure, Name and Data |
|---|---|---|
| | | J = 8.50, 2.49 Hz, 1 H) 7.82 (d, J = 7.47 Hz, 1 H) 8.17 (s, 1 H) 8.47 (d, J = 2.49 Hz, 1 H) 8.63 (d, J = 4.84 Hz, 1 H) 8.83 (d, J = 1.45 Hz, 1 H). LCMS-ESI (POS.) m/z: 516.1 (M + H)+. |
| 840.0 | (2S,3R)-3-(5-chloropyridin-2-yl)butane-2-sulfonamide (Example 802.1), 6-methoxypicolinohydrazide (commercially available from Sigma-Aldrich Corp, St. Louis, MO, USA), 4-isothiocyanatooxane (commercially available from Oakwood Products, Inc.). | (2S,3R)-3-(5-chloro-2-pyridinyl)-N-(5-(6-methoxy-2-pyridinyl)-4-(tetrahydro-2H-pyran-4-yl)-4H-1,2,4-triazol-3-yl)-2-butanesulfonamide. ¹H NMR (400 MHz, CDCl₃) δ 1.43 (d, J = 6.84 Hz, 3 H) 1.46 (d, J = 7.05 Hz, 3 H) 1.73 (d, J = 10.78 Hz, 2 H) 2.85-2.97 (m, 2 H) 3.38 (t, J = 11.92 Hz, 2 H) 3.71-3.79 (m, 1 H) 3.79-3.87 (m, 1 H) 3.97 (s, 3 H) 4.08 (d, J = 11.20 Hz, 2 H) 5.20 (t, J = 12.13 Hz, 1 H) 6.92 (d, J = 8.29 Hz, 1 H) 7.22-7.29 (m, 1 H) 7.53 (d, J = 7.26 Hz, 1 H) 7.58-7.65 (m, 1 H) 7.74 (t, J = 7.77 Hz, 1 H) 8.48-8.52 (m, 1 H) 11.19 (br. s., 1 H). LCMS-ESI (POS.) m/z: 507.2 (M + H)+. |
| 841.0 | (1R,2S)-1-(5-chloropyrimidin-2-yl)-1-methoxypropane-2-sulfonamide (Example 711.1), 6-methoxypicolinohydrazide (commercially available from Sigma-Aldrich Corp, St. Louis, MO, USA), 4-isothiocyanatooxane (commercially available from Oakwood Products, Inc.). | (1R,2S)-1-(5-chloro-2-pyridinyl)-1-methoxy-N-(5-(6-methoxy-2-pyridinyl)-4-(tetrahydro-2H-pyran-4-yl)-4H-1,2,4-triazol-3-yl)-2-propanesulfonamide. ¹H NMR (400 MHz, CDCl₃) δ 1.32 (d, J = 6.84 Hz, 3 H) 1.77 (d, J = 9.33 Hz, 2 H) 2.91-3.10 (m, 2 H) 3.36-3.44 (m, 5 H) 3.59 (d, J = 6.84 Hz, 1 H) 3.98 (s, 3 H) 4.06-4.13 (m, 2 H) 5.15 (br. s., 1 H) 5.24 (tt, J = 12.13, 4.25 Hz, 1 H) 6.93 (d, J = 8.29 Hz, 1 H) 7.42 (d, J = 8.29 Hz, 1 H) 7.55 (d, J = 7.26 Hz, 1 H) 7.69-7.77 (m, 2 H) 8.56 (br. s., 1 H) 11.21 (br. s., 1 H). LCMS-ESI (POS.) m/z: 523.2 (M + H)+. |
| 842.0 | (2S,3R)-3-(5-methoxypyrimidin-2-yl)butane-2-sulfonamide (Example 672.1), 6-methoxypicolinohydrazide (commercially available from Sigma-Aldrich Corp, St. Louis, MO, USA), 4-isothiocyanatooxane (commercially available from Oakwood Products, Inc.). | (2S,3R)-N-(5-(6-methoxy-2-pyridinyl)-4-(tetrahydro-2H-pyran-4-yl)-4H-1,2,4-triazol-3-yl)-3-(5-methoxy-2-pyrimidinyl)-2-butanesulfonamide. ¹H NMR (400 MHz, CDCl₃) δ 1.45 (d, J = 1.66 Hz, 3 H) 1.46 (d, J = 1.66 Hz, 3 H) 1.69-1.76 (m, 2 H) 2.87-2.99 (m, 2 H) 3.34-3.41 (m, 2 H) 3.83-3.93 (m, 5 H) 3.96 (s, 3 H) 4.06 (d, J = 11.61 Hz, 2 H) 5.19 (tt, J = 12.18, 4.20 Hz, 1 H) 6.91 (d, J = 8.29 Hz, 1 H) 7.53 (d, J = 7.26 Hz, 1 |

TABLE 55-continued

| Example | Reagents | Structure, Name and Data |
|---|---|---|
| | | H) 7.73 (dd, J = 8.29, 7.46 Hz, 1 H) 8.36 (s, 2 H) 11.40 (br. s., 1 H). LCMS-ESI (POS.) m/z: 504.2 (M + H)+. |
| 843.0 | (2S,3R)-3-(5-methylpyrazin-2-yl)butane-2-sulfonamide (Example 799.1), 6-methoxypicolinohydrazide (commercially available from Sigma-Aldrich Corp, St. Louis, MO, USA), 4-isothiocyanatooxane (commercially available from Oakwood Products, Inc.). | 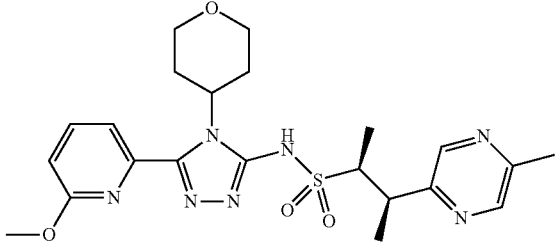<br>(2S,3R)-N-(5-(6-methoxy-2-pyridinyl)-4-(tetrahydro-2H-pyran-4-yl)-4H-1,2,4-triazol-3-yl)-3-(5-methyl-2-pyrazinyl)-2-butanesulfonamide. 1H NMR (400 MHz, CDCl3) δ 1.45 (d, J = 7.05 Hz, 3 H) 1.49 (d, J = 7.05 Hz, 3 H) 1.73 (dd, J = 12.23, 2.70 Hz, 2 H) 2.54 (s, 3 H) 2.87-2.98 (m, 2 H) 3.38 (t, J = 11.71 Hz, 2 H) 3.69 (qd, J = 7.01, 4.66 Hz, 1 H) 3.83-3.89 (m, 1 H) 3.96 (s, 3 H) 4.08 (dd, J = 11.51, 4.25 Hz, 2 H) 5.17-5.25 (m, 1 H) 6.92 (d, J = 7.88 Hz, 1 H) 7.53 (d, J = 7.46 Hz, 1 H) 7.73 (dd, J = 8.29, 7.46 Hz, 1 H) 8.39 (s, 1 H) 8.45 (s, 1 H) 11.22 (br. s., 1 H). LCMS-ESI (POS.) m/z: 488.2 (M + H)+. |
| 844.0 | (2S,3R)-3-(5-methoxypyrazin-2-yl)butane-2-sulfonamide (Example 803.1), 6-methoxypicolinohydrazide (commercially available from Sigma-Aldrich Corp, St. Louis, MO, USA), 4-isothiocyanatooxane (commercially available from Oakwood Products, Inc.). | 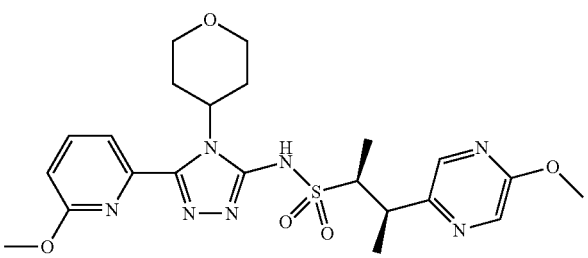<br>(2S,3R)-3-(5-methoxy-2-pyrazinyl)-N-(5-(6-methoxy-2-pyridinyl)-4-(tetrahydro-2H-pyran-4-yl)-4H-1,2,4-triazol-3-yl)-2-butanesulfonamide. 1H NMR (400 MHz, CDCl3) δ 1.44 (d, J = 7.05 Hz, 3 H) 1.49 (d, J = 7.26 Hz, 3 H) 1.66-1.80 (m, 2 H) 2.87-2.98 (m, 2 H) 3.39 (t, J = 11.92 Hz, 2 H) 3.63-3.70 (m, 1 H) 3.80-3.88 (m, 1 H) 3.93-3.97 (m, 3 H) 3.98 (s, 3 H) 4.09 (dd, J = 11.61, 4.15 Hz, 2 H) 5.16-5.25 (m, 1 H) 6.93 (d, J = 8.29 Hz, 1 H) 7.53 (d, J = 7.26 Hz, 1 H) 7.75 (t, J = 7.83 Hz, 1 H) 8.04-8.08 (m, 1 H) 8.18 (d, J = 1.04 Hz, 1 H) 11.03 (br. s., 1 H). LCMS-ESI (POS.) m/z: 504.2 (M + H)+. |

Example 845.0: Preparation of (2S,3R)-3-(5-methoxy-2-pyridinyl)-N-(5-(6-methoxy-2-pyridinyl)-4-(tetrahydro-2H-pyran-4-yl)-4H-1,2,4-triazol-3-yl)-2-butanesulfonamide

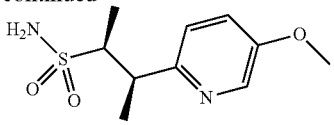

(2S,3R)-3-(5-methoxypyridin-2-yl)butane-2-sulfonamide, Example 845.1

A suspension of (2S,3R)-3-(5-chloropyridin-2-yl)butane-2-sulfonamide (360 mg, 1.45 mmol), 2-(di-tert-butylphosphino)-2',4',6'-triisopropyl-3,6-dimethoxy-1,1'-biphenyl (t-BuBrettPhos, commercially available from Sigma-Aldrich Corp, St. Louis, Mo., USA) (17.54 mg, 0.036 mmol) and [(2-di-tert-butylphosphino-3,6-dimethoxy-2',4',6'-triisopropyl-1,1'-biphenyl)-2-(2'-amino-1,1'-biphenyl)]palladium (II) methanesulfonate (tBuBrettPhos Pd G3, commercially available from Sigma-Aldrich Corp, St. Louis, Mo., USA) (30.9 mg, 0.036 mmol) in toluene (3.6 mL) was bubbled with argon gas for 2 minutes before sodium methoxide (0.5 M solution in MeOH, 685 µl, 4.34 mmol) was added under an argon stream. The reaction mixture was stirred at 40° C. for 14 hours. LCMS analysis indicated no formation of the desired product. The reaction mixture was then stirred at 80° C. for another 8 hours. LCMS showed formation of the desired product. The reaction mixture was allowed to cool to RT. The reaction mixture was then diluted with saturated $NH_4Cl$ and extracted with DCM. The organic extract was concentrated in vacuo to give the product as a light-yellow solid. The material thus obtained was absorbed onto a plug of silica gel and purified by chromatography through a Redi-Sep pre-packed silica gel column (12 g), eluting with a gradient of 0% to 100% EtOAc in heptane, to provide the title compound (2S,3R)-3-(5-methoxypyridin-2-yl)butane-2-sulfonamide (316 mg, 89% yield) as a white solid. LCMS-ESI (POS.) m/z: 245.3 (M+H)+.

The compounds set forth in the following Table were synthesized following the procedure in Example 741.0 using the known starting material as described.

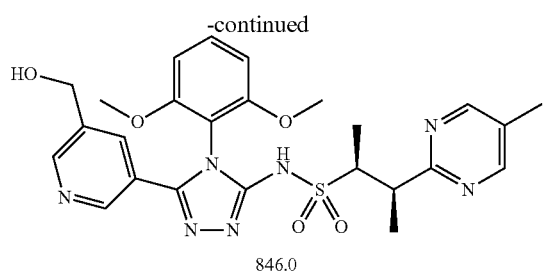

(2S,3R)—N-(4-(2,6-dimethoxyphenyl)-5-(5-(hydroxymethyl)pyridin-3-yl)-4H-1,2,4-triazol-3-yl)-3-(5-methylpyrimidin-2-yl)butane-2-sulfonamide, Example 846.0

A solution of (2S,3R)—N-(5-(5-cyanopyridin-3-yl)-4-(2,6-dimethoxyphenyl)-4H-1,2,4-triazol-3-yl)-3-(5-methylpyrimidin-2-yl)butane-2-sulfonamide Example 833.0 (0.276 g, 0.516 mmol) in anhydrous THF (2.5 mL) was treated dropwise with 1.0 M diisobutylaluminum hydride (1.549 mL, 1.549 mmol, Sigma Aldrich) in toluene at 0° C. under

TABLE 56

| Example | Reagents | Structure, Name and Data |
|---------|----------|--------------------------|
| 845.0 | (2S,3R)-3-(5-methoxypyridin-2-yl)butane-2-sulfonamide (Example 845.1), 6-methoxypicolinohydrazide (commercially available from Sigma-Aldrich Corp, St. Louis, MO, USA), 4-isothiocyanatooxane (commercially available from Oakwood Products, Inc.). | 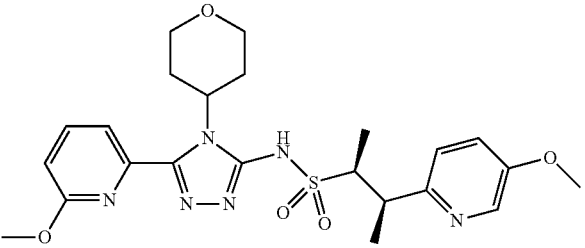 (2S,3R)-3-(5-methoxy-2-pyridinyl)-N-(5-(6-methoxy-2-pyridinyl)-4-(tetrahydro-2H-pyran-4-yl)-4H-1,2,4-triazol-3-yl)-2-butanesulfonamide. $^1$H NMR (400 MHz, CDCl$_3$) δ 1.57 (s, 3 H) 1.58 (s, 3 H) 1.74-1.84 (m, 2 H) 2.77-2.96 (m, 2 H) 3.41 (t, J = 11.40 Hz, 2 H) 3.73-3.83 (m, 2 H) 3.97 (s, 3 H) 4.01 (s, 3 H) 4.07-4.16 (m, 2 H) 5.25 (tt, J = 12.13, 4.15 Hz, 1 H) 6.93 (d, J = 8.38 Hz, 1 H) 7.54 (d, J = 7.05 Hz, 1 H) 7.71-7.77 (m, 2 H) 7.83 (d, J = 9.18 Hz, 1 H) 8.49 (d, J = 2.70 Hz, 1 H). LCMS-ESI (POS.) m/z: 503.2 (M + H)+. |

Example 846.0: Preparation of (2S,3R)—N-(4-(2,6-dimethoxyphenyl)-5-(5-(hydroxymethyl)pyridin-3-yl)-4H-1,2,4-triazol-3-yl)-3-(5-methylpyrimidin-2-yl)butane-2-sulfonamide

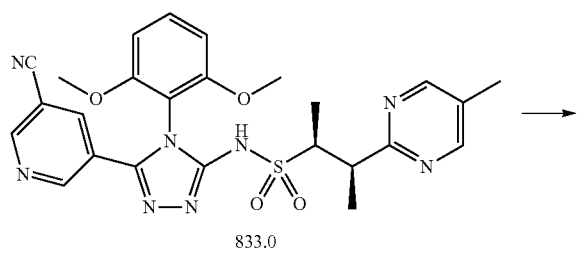

$N_2$ atmosphere. The mixture turned dark orange. After 1 hour at 0° C., the mixture was treated with a few drops of water and a few drops of 1M aqueous solution of citric acid then EtOAc (20 mL). The emulsion was filtered through a pad of Celite® brand filter agent. The filtrate was dried over $Na_2SO_4$, filtered and concentrated in vacuo to give the initial material. The material thus obtained was dissolved in MeOH (2.5 mL) and cooled in ice-water bath. Then sodium borohydride (0.020 g, 0.516 mmol) was added, and the stirring was continued for 1 hour at ambient temperature. The reaction mixture was treated with a few drops of 1M citric acid aqueous solution and concentrated in vacuo to give the initial product. The product thus obtained was absorbed onto a plug of silica gel and purified by chromatography through a Redi-Sep pre-packed silica gel column (12 g), eluting with a gradient of 0% to 100% (3:1 EtOAc:EtOH) in heptane, to provide (2S,3R)—N-(4-(2,6-dimethoxyphenyl)-5-(5-(hydroxymethyl)pyridin-3-yl)-4H-1,2,4-triazol-3-yl)-3-(5- methylpyrimidin-2-yl)butane-2-sulfonamide, Example 846.0 (20 mg, 0.037 mmol, 7.2% yield) as an off-white solid. ¹H NMR (500 MHz, CDCl₃) δ 11.61 (br s, 1H) 8.60 (s, 1H) 8.49 (s, 2H) 8.39 (s, 1H) 8.06 (s, 1H) 7.39 (t, J=8.50 Hz, 1H) 6.60 (t, J=9.02 Hz, 2H) 4.73 (s, 2H) 3.84-3.93 (m, 1H) 3.76-3.80 (m, 1H) 3.74 (s, 3H) 3.71 (s, 3H) 2.83 (br s, 1H) 2.26 (s, 3H) 1.36 (d, J=6.49 Hz, 6H). LCMS-ESI (POS.) m/z: 540.2 (M+H)⁺.

The compounds set forth in the following table were synthesized as described above. As will be known to those skilled in the art, organic compounds may often be correctly named using various formats. For example, the compound of Example 39.0 may be named as (1R,2S)—N-(4-(3,5-bis (trifluoromethyl)phenyl)-5-(6-methoxypyridin-2-yl)-4H-1,2,4-triazol-3-yl)-1-methoxy-1-(5-methylpyrimidin-2-yl) propane-2-sulfonamide or as (1R,2S)—N-(4-(3,5-bis (trifluoromethyl)phenyl)-5-(6-methoxy-2-pyridinyl)-4H-1,2,4-triazol-3-yl)-1-methoxy-1-(5-methyl-2-pyrimidinyl)-2-propanesulfonamide. The M and P designations arising from atropisomerism are not included in the following table. The following table provides alternative names for the Example compounds although some names may be the same as those previously provided in the synthesis sections. Furthermore, where the compound is a salt, the name of the neutral compound is provided.

TABLE 57

| Example | Alternative Names |
|---|---|
| 4.02 | N-(4-(2,6-dimethoxyphenyl)-5-(6-methoxy-2-pyridinyl)-4H-1,2,4-triazol-3-yl)methanesulfonamide |
| 27.0 and 549.0 | (1R,2S)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 28.0 and 543.0 | (1S,2R)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 29.0 | N-(4-(2,6-dimethoxyphenyl)-5-(6-methoxy-2-pyridinyl)-4H-1,2,4-triazol-3-yl)ethanesulfonamide |
| 30.0 | N-(4-(2,6-dimethoxyphenyl)-5-(6-methyl-2-pyridinyl)-4H-1,2,4-triazol-3-yl)ethanesulfonamide |
| 31.0 | (2R)-1-(5-fluoro-2-pyrimidinyl)-N-(4-(2-methoxyphenyl)-5-(6-methoxy-2-pyridinyl)-4H-1,2,4-triazol-3-yl)-2-propanesulfonamide, (2S)-1-(5-fluoro-2-pyrimidinyl)-N-(4-(2-methoxyphenyl)-5-(6-methoxy-2-pyridinyl)-4H-1,2,4-triazol-3-yl)-2-propanesulfonamide |
| 32.0 | (2R)-N-(4-(3,5-dimethyl-4-isoxazolyl)-5-(6-methoxy-2-pyridinyl)-4H-1,2,4-triazol-3-yl)-1-(5-fluoro-2-pyrimidinyl)-2-propanesulfonamide, (2S)-N-(4-(3,5-dimethyl-4-isoxazolyl)-5-(6-methoxy-2-pyridinyl)-4H-1,2,4-triazol-3-yl)-1-(5-fluoro-2-pyrimidinyl)-2-propanesulfonamide |
| 33.0 | (1R,2S)-1-methoxy-N-(5-(6-methoxy-2-pyridinyl)-4-(3-pyridinyl)-4H-1,2,4-triazol-3-yl)-1-(5-methyl-2-pyrimidinyl)-2-propanesulfonamide |
| 34.0 | (1R,2S)-1-methoxy-N-(5-(6-methoxy-2-pyridinyl)-4-phenyl-4H-1,2,4-triazol-3-yl)-1-(5-methyl-2-pyrimidinyl)-2-propanesulfonamide |
| 35.0 | (1R,2S)-N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide |
| 36.0 | (1R,2S)-N-(4-(2,6-bis ([²H₃])methyloxy)phenyl)-5-(6-methoxypyridin-2-yl)-4H-1,2,4-triazol-3-yl)-1-methoxy-1-(5-methylpyrimidin-2-yl)propane-2-sulfonamide |
| 37.0 | (1R,2S)-N-(4-(2,6-bis([²H₃])methyloxy)phenyl)-5-(6-([²H₃]methoxy)-2-pyridinyl)-4H-1,2,4-triazol-3-yl)-1-methoxy-1-(5-methylpyrimidin-2-yl)propane-2-sulfonamide |
| 38.0 | (1R,2S)-N-(4-(2,6-dimethoxyphenyl)-5-(6-([²H₃]methoxy)-2-pyridinyl)-4H-1,2,4-triazol-3-yl)-1-methoxy-1-(5-methylpyrimidin-2-yl)propane-2-sulfonamide |
| 39.0 | (1R,2S)-N-(4-(3,5-bis(trifluoromethyl)phenyl)-5-(6-methoxy-2-pyridinyl)-4H-1,2,4-triazol-3-yl)-1-methoxy-1-(5-methyl-2-pyrimidinyl)-2-propanesulfonamide |
| 40.0 | (1R,2S)-1-methoxy-N-(4-(2-methoxy-5-methylphenyl)-5-(6-methoxy-2-pyridinyl)-4H-1,2,4-triazol-3-yl)-1-(5-methyl-2-pyrimidinyl)-2-propanesulfonamide |
| 41.0 | (1R,2S)-N-(4-(2,6-bis(difluoromethoxy)phenyl)-5-(6-methoxy-2-pyridinyl)-4H-1,2,4-triazol-3-yl)-1-methoxy-1-(5-methyl-2-pyrimidinyl)-2-propanesulfonamide |
| 42.0 | (1R,2S)-1-methoxy-N-(5-(6-methoxy-2-pyridinyl)-4-(4-pyridinyl)-4H-1,2,4-triazol-3-yl)-1-(5-methyl-2-pyrimidinyl)-2-propanesulfonamide |
| 43.0 | (1R,2S)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 44.0 | (1R,2S)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide |
| 45.0 | (1R,2S)-N-(4-(4-chlorophenyl)-5-(6-methoxy-2-pyridinyl)-4H-1,2,4-triazol-3-yl)-1-methoxy-1-(5-methyl-2-pyrimidinyl)-2-propanesulfonamide |
| 46.0 | (1R,2S)-1-methoxy-N-(4-(4-methoxyphenyl)-5-(6-methoxy-2-pyridinyl)-4H-1,2,4-triazol-3-yl)-1-(5-methyl-2-pyrimidinyl)-2-propanesulfonamide |
| 47.0 | (1R,2S)-N-(4-(3-fluorophenyl)-5-(6-methoxy-2-pyridinyl)-4H-1,2,4-triazol-3-yl)-1-methoxy-1-(5-methyl-2-pyrimidinyl)-2-propanesulfonamide |
| 48.0 | (1R,2S)-N-(4-(2,6-dimethoxyphenyl)-5-(6-methoxy-2-pyridinyl)-4H-1,2,4-triazol-3-yl)-1-ethoxy-1-(5-fluoro-2-pyrimidinyl)-2-propanesulfonamide |
| 49.0 | (1R,2S)-N-(4-(2,6-dimethoxyphenyl)-5-(6-methoxy-2-pyridinyl)-4H-1,2,4-triazol-3-yl)-1-methoxy-1-(5-methoxy-2-pyrimidinyl)-2-propanesulfonamide |
| 50.0 | (1R,2S)-1-ethoxy-1-(5-fluoro-2-pyrimidinyl)-N-(5-(6-methoxy-2-pyridinyl)-4-phenyl-4H-1,2,4-triazol-3-yl)-2-propanesulfonamide |
| 51.0 | (1R,2S)-N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide |
| 52.0 | (1R,2S)-1-methoxy-N-(4-(2-methoxyphenyl)-5-(6-methoxy-2-pyridinyl)-4H-1,2,4-triazol-3-yl)-1-(5-methyl-2-pyrimidinyl)-2-propanesulfonamide |
| 53.0 | (1R,2S)-1-methoxy-N-(5-(6-methoxy-2-pyridinyl)-4-(2-naphthalenyl)-4H-1,2,4-triazol-3-yl)-1-(5-methyl-2-pyrimidinyl)-2-propanesulfonamide |

TABLE 57-continued

| Example | Alternative Names |
|---|---|
| 54.0 | methyl 3-(3-(((((1S,2R)-2-methoxy-1-methyl-2-(5-methyl-2-pyrimidinyl)ethyl)sulfonyl)amino)-5-(6-methoxy-2-pyridinyl)-4H-1,2,4-triazol-4-yl)benzoate |
| 55.0 | (1R,2S)-N-(4-(3-chloro-2-methylphenyl)-5-(6-methoxy-2-pyridinyl)-4H-1,2,4-triazol-3-yl)-1-methoxy-1-(5-methyl-2-pyrimidinyl)-2-propanesulfonamide |
| 56.0 | (1R,2S)-N-(4-(3-cyanophenyl)-5-(6-methoxy-2-pyridinyl)-4H-1,2,4-triazol-3-yl)-1-methoxy-1-(5-methyl-2-pyrimidinyl)-2-propanesulfonamide |
| 57.0 | (1R,2S)-N-(4-(2,6-dimethoxyphenyl)-5-(5-methyl-3-pyridinyl)-4H-1,2,4-triazol-3-yl)-1-methoxy-1-(5-methoxy-2-pyrimidinyl)-2-propanesulfonamide |
| 58.0 | (1R,2S)-N-(4-(2,6-dimethoxyphenyl)-5-(3-pyridinyl)-4H-1,2,4-triazol-3-yl)-1-methoxy-1-(5-methoxy-2-pyrimidinyl)-2-propanesulfonamide |
| 59.0 | (1R,2S)-1-methoxy-1-(5-methoxy-2-pyrimidinyl)-N-(5-(5-methyl-3-pyridinyl)-4-phenyl-4H-1,2,4-triazol-3-yl)-2-propanesulfonamide |
| 60.0 | (1R,2S)-N-(4-(3-bromophenyl)-5-(6-methoxy-2-pyridinyl)-4H-1,2,4-triazol-3-yl)-1-methoxy-1-(5-methyl-2-pyrimidinyl)-2-propanesulfonamide |
| 61.0 | (1R,2S)-1-methoxy-N-(5-(6-methoxy-2-pyridinyl)-4-(2-methylphenyl)-4H-1,2,4-triazol-3-yl)-1-(5-methyl-2-pyrimidinyl)-2-propanesulfonamide |
| 62.0 | (1R,2S)-1-methoxy-N-(5-(6-methoxy-2-pyridinyl)-4-(3-methylphenyl)-4H-1,2,4-triazol-3-yl)-1-(5-methyl-2-pyrimidinyl)-2-propanesulfonamide |
| 63.0 | (1R,2S)-N-(4-(4-fluoro-3-(trifluoromethyl)phenyl)-5-(6-methoxy-2-pyridinyl)-4H-1,2,4-triazol-3-yl)-1-methoxy-1-(5-methyl-2-pyrimidinyl)-2-propanesulfonamide |
| 64.0 | (1R,2S)-1-methoxy-N-(4-(3-methoxyphenyl)-5-(6-methoxy-2-pyridinyl)-4H-1,2,4-triazol-3-yl)-1-(5-methyl-2-pyrimidinyl)-2-propanesulfonamide |
| 65.0 | (1R,2S)-N-(4-(4-fluorophenyl)-5-(6-methoxy-2-pyridinyl)-4H-1,2,4-triazol-3-yl)-1-methoxy-1-(5-methyl-2-pyrimidinyl)-2-propanesulfonamide |
| 66.0 | (1R,2S)-N-(4-(3-chlorophenyl)-5-(6-methoxy-2-pyridinyl)-4H-1,2,4-triazol-3-yl)-1-methoxy-1-(5-methyl-2-pyrimidinyl)-2-propanesulfonamide |
| 67.0 | (1R,2S)-N-(4-(2-chloro-4-fluorophenyl)-5-(6-methoxy-2-pyridinyl)-4H-1,2,4-triazol-3-yl)-1-methoxy-1-(5-methyl-2-pyrimidinyl)-2-propanesulfonamide |
| 68.0 | (1R,2S)-N-(4-(3,5-dichlorophenyl)-5-(6-methoxy-2-pyridinyl)-4H-1,2,4-triazol-3-yl)-1-methoxy-1-(5-methyl-2-pyrimidinyl)-2-propanesulfonamide |
| 69.0 | (1R,2S)-N-(4-(2-chlorophenyl)-5-(6-methoxy-2-pyridinyl)-4H-1,2,4-triazol-3-yl)-1-methoxy-1-(5-methyl-2-pyrimidinyl)-2-propanesulfonamide |
| 70.0 | (1R,2S)-N-(4-(2,3-dimethylphenyl)-5-(6-methoxy-2-pyridinyl)-4H-1,2,4-triazol-3-yl)-1-methoxy-1-(5-methyl-2-pyrimidinyl)-2-propanesulfonamide |
| 71.0 | (1R,2S)-N-(4-(3,4-difluorophenyl)-5-(6-methoxy-2-pyridinyl)-4H-1,2,4-triazol-3-yl)-1-methoxy-1-(5-methyl-2-pyrimidinyl)-2-propanesulfonamide |
| 72.0 | (1R,2S)-N-(4-(3-acetylphenyl)-5-(6-methoxy-2-pyridinyl)-4H-1,2,4-triazol-3-yl)-1-methoxy-1-(5-methyl-2-pyrimidinyl)-2-propanesulfonamide |
| 73.0 | (1R,2S)-N-(4-(2,6-dichlorophenyl)-5-(6-methoxy-2-pyridinyl)-4H-1,2,4-triazol-3-yl)-1-methoxy-1-(5-methyl-2-pyrimidinyl)-2-propanesulfonamide |
| 74.0 | (1R,2S)-1-methoxy-N-(5-(6-methoxy-2-pyridinyl)-4-(2-(trifluoromethyl)phenyl)-4H-1,2,4-triazol-3-yl)-1-(5-methyl-2-pyrimidinyl)-2-propanesulfonamide |
| 75.0 | (1R,2S)-1-methoxy-N-(5-(6-methoxy-2-pyridinyl)-4-(3-(trifluoromethyl)phenyl)-4H-1,2,4-triazol-3-yl)-1-(5-methyl-2-pyrimidinyl)-2-propanesulfonamide |
| 76.0 | (1R,2S)-N-(4-(2-fluorophenyl)-5-(6-methoxy-2-pyridinyl)-4H-1,2,4-triazol-3-yl)-1-methoxy-1-(5-methyl-2-pyrimidinyl)-2-propanesulfonamide |
| 77.0 | (1R,2S)-N-(4-(4-(dimethylamino)phenyl)-5-(6-methoxy-2-pyridinyl)-4H-1,2,4-triazol-3-yl)-1-methoxy-1-(5-methyl-2-pyrimidinyl)-2-propanesulfonamide |
| 78.0 | (2S,3R)-3-(5-fluoro-2-pyrimidinyl)-N-(5-(6-methoxy-2-pyridinyl)-4-phenyl-4H-1,2,4-triazol-3-yl)-2-butanesulfonamide |
| 79.0 | (1R,2S)-N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide |
| 80.0 and 242.0 | (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide |
| 81.0 and 244.0 | (1R,2S)-N-(4-(2,6-dimethoxyphenyl)-5-(3-pyridinyl)-4H-1,2,4-triazol-3-yl)-1-(5-fluoro-2-pyrimidinyl)-1-methoxy-2-propanesulfonamide |
| 82.0 | (1R,2S)-N-(4-(2,6-dimethoxyphenyl)-5-(3-pyridinyl)-4H-1,2,4-triazol-3-yl)-1-(5-fluoro-2-pyrimidinyl)-1-hydroxy-2-propanesulfonamide |
| 83.0 | (2R)-N-(4-(2,6-dimethoxyphenyl)-5-(6-methoxy-2-pyridinyl)-4H-1,2,4-triazol-3-yl)-1-oxo-1-(1-pyrrolidinyl)-2-propanesulfonamide, (2S)-N-(4-(2,6-dimethoxyphenyl)-5-(6-methoxy-2-pyridinyl)-4H-1,2,4-triazol-3-yl)-1-oxo-1-(1-pyrrolidinyl)-2-propanesulfonamide |
| 84.0 | (2S,3R)-N-(4-(2,6-dimethoxyphenyl)-5-(2-methoxy-4-pyridinyl)-4H-1,2,4-triazol-3-yl)-3-(5-methyl-2-pyrimidinyl)-2-butanesulfonamide |
| 85.0 | (2S,3R)-N-(4-(2,6-dimethoxyphenyl)-5-(2-methyl-4-pyridinyl)-4H-1,2,4-triazol-3-yl)-3-(5-methyl-2-pyrimidinyl)-2-butanesulfonamide |
| 86.0 | (2S,3R)-N-(4-(2,6-dimethoxyphenyl)-5-(5-methoxy-3-pyridinyl)-4H-1,2,4-triazol-3-yl)-3-(5-methyl-2-pyrimidinyl)-2-butanesulfonamide |
| 87.0 | (2S,3R)-N-(4-(2,6-dimethoxyphenyl)-5-(6-methyl-2-pyridinyl)-4H-1,2,4-triazol-3-yl)-3-(5-methyl-2-pyrimidinyl)-2-butanesulfonamide |
| 88.0 | (1R,2S)-1-(5-chloro-2-pyrimidinyl)-N-(4-(2,6-dimethoxyphenyl)-5-(6-methyl-2-pyridinyl)-4H-1,2,4-triazol-3-yl)-1-methoxy-2-propanesulfonamide |
| 89.0 | (1S,2R)-1-(5-chloro-2-pyrimidinyl)-N-(4-(2,6-dimethoxyphenyl)-5-(6-methyl-2-pyridinyl)-4H-1,2,4-triazol-3-yl)-1-methoxy-2-propanesulfonamide |
| 90.0 | (1R,2S)-N-(4-(4,6-dimethoxy-5-pyrimidinyl)-5-(6-methyl-2-pyridinyl)-4H-1,2,4-triazol-3-yl)-1-methoxy-1-(5-methyl-2-pyrimidinyl)-2-propanesulfonamide |

TABLE 57-continued

| Example | Alternative Names |
|---|---|
| 91.0 | (1S,2S)-N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide |
| 92.0 | (1R,2R)-N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide |
| 93.0 | (1R,2S)-N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide |
| 94.0 | (1S,2R)-N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide |
| 95.0 | (1S,2S)-N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide |
| 96.0 | (1R,2S)-N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide |
| 97.0 | (1S,2R)-N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide |
| 98.0 | (1R,2R)-N-(4-(2,6-dimethoxyphenyl)-5-(6-methoxy-2-pyridinyl)-4H-1,2,4-triazol-3-yl)-1-(1-methylethoxy)-1-(5-methyl-2-pyrimidinyl)-2-propanesulfonamide |
| 99.0 | (1R,2S)-N-(4-(2,6-dimethoxyphenyl)-5-(6-methyl-2-pyridinyl)-4H-1,2,4-triazol-3-yl)-1-hydroxy-1-(5-methyl-2-pyrimidinyl)-2-propanesulfonamide |
| 100.0 | N-(4-(2,6-dimethoxyphenyl)-5-(6-methoxy-2-pyridinyl)-4H-1,2,4-triazol-3-yl)-2-propanesulfonamide |
| 101.0 | (1R,2S)-N-(4-(2,6-dimethoxyphenyl)-5-(2-methoxy-4-pyridinyl)-4H-1,2,4-triazol-3-yl)-1-methoxy-1-(5-methyl-2-pyrimidinyl)-2-propanesulfonamide |
| 102.0 | (1R,2S)-N-(4-(2,6-dimethoxyphenyl)-5-(4-pyridinyl)-4H-1,2,4-triazol-3-yl)-1-methoxy-1-(5-methyl-2-pyrimidinyl)-2-propanesulfonamide |
| 103.0 | (1R,2S)-N-(4-(2,6-dimethoxyphenyl)-5-(6-methyl-2-pyridinyl)-4H-1,2,4-triazol-3-yl)-1-methoxy-1-(5-methyl-2-pyrimidinyl)-2-propanesulfonamide |
| 104.0 | (1R,2S)-N-(4-(2,6-dimethoxyphenyl)-5-(2-methyl-4-pyridinyl)-4H-1,2,4-triazol-3-yl)-1-methoxy-1-(5-methyl-2-pyrimidinyl)-2-propanesulfonamide |
| 105.0 | (1R,2S)-N-(4-(2,6-dimethoxyphenyl)-5-(5-methoxy-3-pyridinyl)-4H-1,2,4-triazol-3-yl)-1-methoxy-1-(5-methyl-2-pyrimidinyl)-2-propanesulfonamide |
| 106.0 | (1S,2R)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide, (1R,2S)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide |
| 107.0 | (1S,2R)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide,, (1R,2S)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide |
| 108.0 | (1S,2R)-N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide |
| 109.0 | (1R,2S)-N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide |
| 110.0 | (1S,2S)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide |
| 111.0 | (1S,2S)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-ethoxy-1-(5-methyl-2-pyrimidinyl)-2-propanesulfonamide |
| 112.0 | (2R)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide, (2S)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide |
| 113.0 | (2S)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide |
| 114.0 | (2S)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methoxy-3-pyridinyl)-4H-1,2,4-triazol-3-yl)-1-(5-fluoro-2-pyrimidinyl)-2-propanesulfonamide |
| 115.0 | (2R)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide, (2S)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide |
| 116.0 | (2S)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide |
| 117.0 | (2S)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methoxy-2-pyridinyl)-4H-1,2,4-triazol-3-yl)-1-(5-fluoro-2-pyrimidinyl)-2-propanesulfonamide |
| 118.0 | (2R)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide, (2S)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide |

TABLE 57-continued

| Example | Alternative Names |
|---|---|
| 119.0 | (2S)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide |
| 120.0 | (2S)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methyl-4-pyridinyl)-4H-1,2,4-triazol-3-yl)-1-(5-fluoro-2-pyrimidinyl)-2-propanesulfonamide |
| 121.0 | (1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide, |
| 122.0 | (1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide, |
| 123.0 | (1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(6-methyl-2-pyridinyl)-4H-1,2,4-triazol-3-yl)-1-(5-fluoro-2-pyrimidinyl)-1-hydroxy-2-propanesulfonamide, |
| 124.0 | (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide |
| 125.0 | (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide |
| 126.0 | (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide |
| 127.0 | (2R,3S)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide |
| 128.0 | (2R,3S)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide |
| 129.0 | (2R,3S)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(6-methoxy-2-pyridinyl)-4H-1,2,4-triazol-3-yl)-3-(5-fluoro-2-pyrimidinyl)-2-butanesulfonamide |
| 130.0 | (1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide |
| 131.0 | (1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide |
| 132.0 | (1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide, (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide |
| 133.0 | (2S)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide |
| 134.0 | (2S)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide |
| 135.0 | (2S)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methoxy-4-pyridinyl)-4H-1,2,4-triazol-3-yl)-1-(5-fluoro-2-pyrimidinyl)-2-propanesulfonamide |
| 136.0 | (2S)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide |
| 137.0 | (2S)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide |
| 138.0 | (2S)-N-(4-(2,6-dimethoxyphenyl)-5-(5-(trifluoromethyl)-3-pyridinyl)-4H-1,2,4-triazol-3-yl)-1-(5-fluoro-2-pyrimidinyl)-2-propanesulfonamide, (2R)-N-(4-(2,6- |

| Example | Alternative Names |
|---|---|
| | dimethoxyphenyl)-5-(5-(trifluoromethyl)-3-pyridinyl)-4H-1,2,4-triazol-3-yl)-1-(5-fluoro-2-pyrimidinyl)-2-propanesulfonamide |
| 139.0 | (2S)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide |
| 140.0 | (2S)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide |
| 141.0 | (2S)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(3-methoxy-2-pyridinyl)-4H-1,2,4-triazol-3-yl)-1-(5-fluoro-2-pyrimidinyl)-2-propanesulfonamide |
| 142.0 | (2S)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide |
| 143.0 | (2S)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-ethoxy-2-pyridinyl)-4H-1,2,4-triazol-3-yl)-1-(5-fluoro-2-pyrimidinyl)-2-propanesulfonamide |
| 144.0 | (2S)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide |
| 145.0 | (2S)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methoxy-2-pyridinyl)-4H-1,2,4-triazol-3-yl)-1-(5-fluoro-2-pyrimidinyl)-2-propanesulfonamide |
| 146.0 | (2R)-N-(5-(5-bromo-3-pyridinyl)-4-(2,6-dimethoxyphenyl)-4H-1,2,4-triazol-3-yl)-1-(5-fluoro-2-pyrimidinyl)-2-propanesulfonamide, (2S)-N-(5-(5-bromo-3-pyridinyl)-4-(2,6-dimethoxyphenyl)-4H-1,2,4-triazol-3-yl)-1-(5-fluoro-2-pyrimidinyl)-2-propanesulfonamide |
| 147.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-methyl-2-pyridinecarboxamide, 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-methyl-2-pyridinecarboxamide |
| 148.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-methyl-2-pyridinecarboxamide, 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-methyl-2-pyridinecarboxamide |
| 149.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-methyl-2-pyridinecarboxamide, 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-methyl-2-pyridinecarboxamide |
| 150.0 | (2S)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide |
| 151.0 | (2S)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide |
| 152.0 | (2S)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-cyano-2-pyridinyl)-4-(2,6-dimethoxyphenyl)-4H-1,2,4-triazol-3-yl)-1-(5-fluoro-2-pyrimidinyl)-2-propanesulfonamide |
| 153.0 | (2S)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide |
| 154.0 | (2S)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide |
| 155.0 | (2S)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methoxy-2-pyridinyl)-4H-1,2,4-triazol-3-yl)-1-(5-fluoro-2-pyrimidinyl)-2-propanesulfonamide |
| 156.0 | (2S)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide |

TABLE 57-continued

| Example | Alternative Names |
|---|---|
| 157.0 | (2S)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide |
| 158.0 | (2S)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-ethyl-2-pyridinyl)-4H-1,2,4-triazol-3-yl)-1-(5-fluoro-2-pyrimidinyl)-2-propanesulfonamide |
| 159.0 | (2S)-N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide |
| 160.0 | (2S)-N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-(1-azetidinylcarbonyl)-2-pyridinyl)-4-(2,6-dimethoxyphenyl)-4H-1,2,4-triazol-3-yl)-1-(5-fluoro-2-pyrimidinyl)-2-propanesulfonamide |
| 161.0 | (2S,3R)-N-(4-(2,6-dimethoxyphenyl)-5-(6-ethoxy-2-pyridinyl)-4H-1,2,4-triazol-3-yl)-3-(5-fluoro-2-pyrimidinyl)-2-butanesulfonamide |
| 162.0 | (2R,3S)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide |
| 163.0 | (2R,3S)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide |
| 164.0 | (2R,3S)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(6-ethyl-2-pyridinyl)-4H-1,2,4-triazol-3-yl)-3-(5-fluoro-2-pyrimidinyl)-2-butanesulfonamide |
| 165.0 | 6-(4-(2,6-dimethoxyphenyl)-5-(((((1R,2S)-2-(5-fluoro-2-pyrimidinyl)-1-methylpropyl)sulfonyl)amino)-4H-1,2,4-triazol-3-yl)-N-methyl-2-pyridinecarboxamide, 6-(4-(2,6-dimethoxyphenyl)-5-(((((1S,2R)-2-(5-fluoro-2-pyrimidinyl)-1-methylpropyl)sulfonyl)amino)-4H-1,2,4-triazol-3-yl)-N-methyl-2-pyridinecarboxamide |
| 166.0 | 6-(4-(2,6-dimethoxyphenyl)-5-(((((1R,2S)-2-(5-fluoro-2-pyrimidinyl)-1-methylpropyl)sulfonyl)amino)-4H-1,2,4-triazol-3-yl)-N-methyl-2-pyridinecarboxamide, 6-(4-(2,6-dimethoxyphenyl)-5-(((((1S,2R)-2-(5-fluoro-2-pyrimidinyl)-1-methylpropyl)sulfonyl)amino)-4H-1,2,4-triazol-3-yl)-N-methyl-2-pyridinecarboxamide |
| 167.0 | 6-(4-(2,6-dimethoxyphenyl)-5-(((((1R,2S)-2-(5-fluoro-2-pyrimidinyl)-1-methylpropyl)sulfonyl)amino)-4H-1,2,4-triazol-3-yl)-N-methyl-2-pyridinecarboxamide, 6-(4-(2,6-dimethoxyphenyl)-5-(((((1S,2R)-2-(5-fluoro-2-pyrimidinyl)-1-methylpropyl)sulfonyl)amino)-4H-1,2,4-triazol-3-yl)-N-methyl-2-pyridinecarboxamide |
| 168.0 | (2S,3R)-N-(4-(2,6-dimethoxyphenyl)-5-(6-oxo-1,6-dihydro-2-pyridinyl)-4H-1,2,4-triazol-3-yl)-3-(5-fluoro-2-pyrimidinyl)-2-butanesulfonamide |
| 169.0 | (2S)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide |
| 170.0 | (2S)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide |
| 171.0 | (2S)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(6-(difluoromethoxy)-2-pyridinyl)-4-(2,6-dimethoxyphenyl)-4H-1,2,4-triazol-3-yl)-1-(5-fluoro-2-pyrimidinyl)-2-propanesulfonamide |
| 172.0 | (1R,2S)-N-(4-(2,6-dimethoxyphenyl)-5-(6-ethoxy-2-pyridinyl)-4H-1,2,4-triazol-3-yl)-1-methoxy-1-(5-methyl-2-pyrimidinyl)-2-propanesulfonamide |
| 173.0 | (1R,2S)-N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide |
| 174.0 | (1R,2S)-N-(4-(2,6-dimethoxyphenyl)-5-(6-ethyl-2-pyridinyl)-4H-1,2,4-triazol-3-yl)-1-methoxy-1-(5-methyl-2-pyrimidinyl)-2-propanesulfonamide |
| 175.0 | (1R,2S)-N-(4-(2,6-dimethoxyphenyl)-5-(6-ethyl-2-pyridinyl)-4H-1,2,4-triazol-3-yl)-1-hydroxy-1-(5-methyl-2-pyrimidinyl)-2-propanesulfonamide |
| 176.0 | (2S,3R)-N-(4-(2,6-dimethoxyphenyl)-5-(6-ethyl-2-pyridinyl)-4H-1,2,4-triazol-3-yl)-3-(5-methyl-2-pyrimidinyl)-2-butanesulfonamide |
| 177.0 | (2S,3R)-N-(4-(2,6-dimethoxyphenyl)-5-(6-methoxy-4-methyl-2-pyridinyl)-4H-1,2,4-triazol-3-yl)-3-(5-fluoro-2-pyrimidinyl)-2-butanesulfonamide |
| 178.0 | (2S,3R)-N-(4-(2,6-dimethoxyphenyl)-5-(6-methoxy-4-methyl-2-pyridinyl)-4H-1,2,4-triazol-3-yl)-3-(5-methyl-2-pyrimidinyl)-2-butanesulfonamide |
| 179.0 | (1R,2S)-N-(4-(2,6-dimethoxyphenyl)-5-(6-methoxy-4-methyl-2-pyridinyl)-4H-1,2,4-triazol-3-yl)-1-methoxy-1-(5-methyl-2-pyrimidinyl)-2-propanesulfonamide |
| 180.0 | (2S,3R)-N-(4-(2,6-dimethoxyphenyl)-5-(6-ethoxy-2-pyridinyl)-4H-1,2,4-triazol-3-yl)-3-(5-methyl-2-pyrimidinyl)-2-butanesulfonamide |

TABLE 57-continued

| Example | Alternative Names |
|---|---|
| 181.0 | N-(5-(5-chloro-3-pyridinyl)-4-(2,6-dimethoxyphenyl)-4H-1,2,4-triazol-3-yl)-2-(2-cyano-4-fluorophenyl)ethanesulfonamide |
| 182.0 | (2R,3S)-N-(4-(2,6-dimethoxyphenyl)-5-(3-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(3-pyridinyl)-4H-1,2,4-triazol-3-yl)-3-(5-fluoro-2-pyrimidinyl)-2-butanesulfonamide |
| 183.0 | (2R,3S)-N-(4-(2,6-dimethoxyphenyl)-5-(3-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(3-pyridinyl)-4H-1,2,4-triazol-3-yl)-3-(5-fluoro-2-pyrimidinyl)-2-butanesulfonamide |
| 184.0 | (2R,3S)-N-(4-(2,6-dimethoxyphenyl)-5-(3-pyridinyl)-4H-1,2,4-triazol-3-yl)-3-(5-fluoro-2-pyrimidinyl)-2-butanesulfonamide, (2S,3R)-N-(4-(2,6-dimethoxyphenyl)-5-(3-pyridinyl)-4H-1,2,4-triazol-3-yl)-3-(5-fluoro-2-pyrimidinyl)-2-butanesulfonamide |
| 185.0 | (2S,3R)-N-(4-(2,6-dimethoxyphenyl)-5-(6-(2,2,2-trifluoroethoxy)-2-pyridinyl)-4H-1,2,4-triazol-3-yl)-3-(5-fluoro-2-pyrimidinyl)-2-butanesulfonamide |
| 186.0 | (2S,3R)-N-(4-(2,6-dimethoxyphenyl)-5-(6-(2-hydroxyethoxy)-2-pyridinyl)-4H-1,2,4-triazol-3-yl)-3-(5-fluoro-2-pyrimidinyl)-2-butanesulfonamide |
| 187.0 | (1R,2S)-N-(4-(2,6-dimethoxyphenyl)-5-(6-(2,2,2-trifluoroethoxy)-2-pyridinyl)-4H-1,2,4-triazol-3-yl)-1-methoxy-1-(5-methyl-2-pyrimidinyl)-2-propanesulfonamide |
| 188.0 | (1R,2S)-N-(4-(2,6-dimethoxyphenyl)-5-(6-(2-hydroxyethoxy)-2-pyridinyl)-4H-1,2,4-triazol-3-yl)-1-methoxy-1-(5-methyl-2-pyrimidinyl)-2-propanesulfonamide |
| 189.0 | (1R,2S)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide, (1S,2R)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide |
| 190.0 | (1R,2S)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide, (1S,2R)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide |
| 191.0 | (1R,2S)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide, (1S,2R)-1-(6-chloro-2-pyridinyl)-N-(4-(2,6-dimethoxyphenyl)-5-(3-pyridinyl)-4H-1,2,4-triazol-3-yl)-1-hydroxy-2-propanesulfonamide |
| 192.0 | (2S,3R)-N-(4-(2,6-dimethoxyphenyl)-5-(6-(2-hydroxy-2-methylpropoxy)-2-pyridinyl)-4H-1,2,4-triazol-3-yl)-3-(5-fluoro-2-pyrimidinyl)-2-butanesulfonamide |
| 193.0 | (1R,2S)-N-(4-(2,6-dimethoxyphenyl)-5-(6-(2-hydroxy-2-methylpropoxy)-2-pyridinyl)-4H-1,2,4-triazol-3-yl)-1-methoxy-1-(5-methyl-2-pyrimidinyl)-2-propanesulfonamide |
| 194.0 | (2S,3R)-N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(5-fluoro-2-pyrimidinyl)-2-butanesulfonamide |
| 195.0 | (1R,2S)-N-(4-(2,6-dimethoxyphenyl)-5-(6-(methylamino)-2-pyridinyl)-4H-1,2,4-triazol-3-yl)-1-methoxy-1-(5-methyl-2-pyrimidinyl)-2-propanesulfonamide |
| 196.0 | (1R,2S)-N-(4-(2,6-dimethoxyphenyl)-5-(6-(2-methoxyethoxy)-2-pyridinyl)-4H-1,2,4-triazol-3-yl)-1-methoxy-1-(5-methyl-2-pyrimidinyl)-2-propanesulfonamide |
| 197.0 | (1R,2S)-N-(4-(2,6-dimethoxyphenyl)-5-(6-(dimethylamino)-2-pyridinyl)-4H-1,2,4-triazol-3-yl)-1-methoxy-1-(5-methyl-2-pyrimidinyl)-2-propanesulfonamide |
| 198.0 | (2S,3R)-N-(4-(2,6-dimethoxyphenyl)-5-(3-pyridinyl)-4H-1,2,4-triazol-3-yl)-3-(5-methyl-2-pyrazinyl)-2-butanesulfonamide |
| 199.0 | (2R,3S)-N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide |
| 200.0 | 2-(2-cyano-4-fluorophenyl)-N-(4-(2,6-dimethoxyphenyl)-5-(6-methoxy-2-pyridinyl)-4H-1,2,4-triazol-3-yl)ethanesulfonamide |
| 201.0 | N-(4-(2,6-dimethoxyphenyl)-5-(5-methyl-3-pyridinyl)-4H-1,2,4-triazol-3-yl)-2-((6S)-3,6-dimethyl-2-oxotetrahydro-1(2H)-pyrimidinyl)ethanesulfonamide |
| 202.0 | (2R)-N-(4-(2,6-dimethoxyphenyl)-5-(2-pyridinyl)-4H-1,2,4-triazol-3-yl)-1-(5-fluoro-2-pyrimidinyl)-2-propanesulfonamide, (2S)-N-(4-(2,6-dimethoxyphenyl)-5-(2-pyridinyl)-4H-1,2,4-triazol-3-yl)-1-(5-fluoro-2-pyrimidinyl)-2-propanesulfonamide |
| 203.0 and 544.0 | (1R,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 204.0 | 2-(2-cyano-4-fluorophenyl)-N-(4-(4,6-dimethoxy-5-pyrimidinyl)-5-(6-methoxy-2-pyridinyl)-4H-1,2,4-triazol-3-yl)ethanesulfonamide |
| 205.0 | (2S)-N-(4-(2,6-dimethoxyphenyl)-5-(3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(3-pyridinyl)-4H-1,2,4-triazol-3-yl)-1-(5-fluoro-2-pyrimidinyl)-2-propanesulfonamide |
| 205.1 | (2S)-N-(4-(2,6-dimethoxyphenyl)-5-(3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(3-pyridinyl)-4H-1,2,4-triazol-3-yl)-1-(5-fluoro-2-pyrimidinyl)-2-propanesulfonamide |
| 206.0 | (2S)-N-(4-(2,6-dimethoxyphenyl)-5-(3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(3-pyridinyl)-4H-1,2,4-triazol-3-yl)-1-(5-fluoro-2-pyrimidinyl)-2-propanesulfonamide |
| 207.0 | (2S)-N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide |
| 208.0 | (2S)-N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide |

TABLE 57-continued

| Example | Alternative Names |
|---|---|
| 209.0 | (2S)-N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-methyl-3-pyridinyl)-4H-1,2,4-triazol-3-yl)-1-(5-fluoro-2-pyrimidinyl)-2-propanesulfonamide |
| 210.0 | (2S)-N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide |
| 211.0 | (2S)-N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide |
| 212.0 | (2S)-N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(2-methyl-3-pyridinyl)-4H-1,2,4-triazol-3-yl)-1-(5-fluoro-2-pyrimidinyl)-2-propanesulfonamide |
| 213.0 | (2S)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide |
| 214.0 | (2S)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide |
| 215.0 | (2S)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methyl-3-pyridinyl)-4H-1,2,4-triazol-3-yl)-1-(5-fluoro-2-pyrimidinyl)-2-propanesulfonamide |
| 216.0 | (2S)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide |
| 217.0 | (2S)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide |
| 218.0 | (2S)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methyl-3-pyridinyl)-4H-1,2,4-triazol-3-yl)-1-(5-fluoro-2-pyrimidinyl)-2-propanesulfonamide |
| 219.0 | (2S)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide |
| 220.0 | (2S)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide |
| 221.0 | (2S)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide, (2R)-N-(5-(5-chloro-3-pyridinyl)-4-(2,6-dimethoxyphenyl)-4H-1,2,4-triazol-3-yl)-1-(5-fluoro-2-pyrimidinyl)-2-propanesulfonamide |
| 222.0 | (2S)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide |
| 223.0 | (2S)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide |
| 224.0 | (2S)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(4-methyl-2-pyridinyl)-4H-1,2,4-triazol-3-yl)-1-(5-fluoro-2-pyrimidinyl)-2-propanesulfonamide |
| 225.0 | (2S)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide |
| 226.0 | (2S)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide |
| 227.0 | (2S)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-fluoro-3-pyridinyl)-4H-1,2,4-triazol-3-yl)-1-(5-fluoro-2-pyrimidinyl)-2-propanesulfonamide |
| 228.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-ethyl-2-pyridinecarboxamide, |

TABLE 57-continued

| Example | Alternative Names |
|---|---|
| 229.0 | 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-ethyl-2-pyridinecarboxamide 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-ethyl-2-pyridinecarboxamide, 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-ethyl-2-pyridinecarboxamide |
| 230.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N-ethyl-2-pyridinecarboxamide, 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N-ethyl-2-pyridinecarboxamide |
| 231.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N,N-dimethyl-2-pyridinecarboxamide. 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N,N-dimethyl-2-pyridinecarboxamide |
| 232.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N,N-dimethyl-2-pyridinecarboxamide. 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N,N-dimethyl-2-pyridinecarboxamide |
| 233.0 | 6-(4-(2,6-dimethoxyphenyl)-5-((((1S)-2-(5-fluoro-2-pyrimidinyl)-1-methylethyl)sulfonyl)amino)-4H-1,2,4-triazol-3-yl)-N,N-dimethyl-2-pyridinecarboxamide. 6-(4-(2,6-dimethoxyphenyl)-5-((((1R)-2-(5-fluoro-2-pyrimidinyl)-1-methylethyl)sulfonyl)amino)-4H-1,2,4-triazol-3-yl)-N,N-dimethyl-2-pyridinecarboxamide |
| 234.0 | (2S,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2S,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide |
| 235.0 | (2S,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2S,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide |
| 236.0 | (2S,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2S,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide |
| 237.0 | (2S,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2R,3R)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide, (2S,3S)-N-(4-(2,6-dimethoxyphenyl)-5-(5-methyl-3-pyridinyl)-4H-1,2,4-triazol-3-yl)-3-(5-fluoro-2-pyrimidinyl)-2-butanesulfonamide |
| 238.0 | (2R,3S)-N-(4-(2,6-dimethoxyphenyl)-5-(5-methylpyridin-3-yl)-4H-1,2,4-triazol-3-yl)-3-(5-methylpyrimidin-2-yl)butane-2-sulfonamide |
| 239.0 | (1S,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide |
| 240.0 | (1R,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide |
| 241.0 | (1S,2R)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide |
| 242.0 and 80.0 | (1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide |
| 243.0 | (1S,2R)-N-(4-(2,6-dimethoxyphenyl)-5-(3-pyridinyl)-4H-1,2,4-triazol-3-yl)-1-(5-fluoro-2-pyrimidinyl)-1-methoxy-2-propanesulfonamide |
| 244.0 and 81.0 | (1R,2S)-N-(4-(2,6-dimethoxyphenyl)-5-(3-pyridinyl)-4H-1,2,4-triazol-3-yl)-1-(5-fluoro-2-pyrimidinyl)-1-methoxy-2-propanesulfonamide |
| 245.0 | (1S,2R)-N-(4-(2,6-dimethoxyphenyl)-5-(6-methyl-2-pyridinyl)-4H-1,2,4-triazol-3-yl)-1-(5-fluoro-2-pyrimidinyl)-1-methoxy-2-propanesulfonamide |
| 246.0 | (1R,2S)-N-(4-(2,6-dimethoxyphenyl)-5-(6-methyl-2-pyridinyl)-4H-1,2,4-triazol-3-yl)-1-(5-fluoro-2-pyrimidinyl)-1-methoxy-2-propanesulfonamide |
| 247.0 | (1R,2S)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide |

TABLE 57-continued

| Example | Alternative Names |
|---|---|
| 248.0 | (1R,2S)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide |
| 249.0 | (1R,2S)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(5-methyl-3-pyridinyl)-4H-1,2,4-triazol-3-yl)-1-hydroxy-2-propanesulfonamide |
| 250.0 | (1R,2S)-N-(4-(2,6-dimethoxyphenyl)-5-(5-methyl-3-pyridinyl)-4H-1,2,4-triazol-3-yl)-1-methoxy-1-(2-pyrimidinyl)-2-propanesulfonamide |
| 251.0 | (1S,2R)-N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide |
| 252.0 | (1R,2S)-N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide |
| 253.0 | (1S,2S)-N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide |
| 254.0 | (1R,2R)-N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide |
| 256.0 | (1S,2R)-N-(4-(2,6-dimethoxyphenyl)-5-(6-methoxy-2-pyridinyl)-4H-1,2,4-triazol-3-yl)-1-hydroxy-1-imidazo[1,2-a]pyridin-2-yl-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-imidazo[1,2-a]pyridin-2-yl-2-propanesulfonamide |
| 257.0 | (2S)-N-(4-(2,6-dimethoxyphenyl)-5-(6-methoxy-2-pyridinyl)-4H-1,2,4-triazol-3-yl)-2-hydroxy-2-imidazo[1,2-a]pyridin-2-ylethanesulfonamide, (2R)-N-(4-(2,6-dimethoxyphenyl)-5-(6-methoxy-2-pyridinyl)-4H-1,2,4-triazol-3-yl)-2-hydroxy-2-imidazo[1,2-a]pyridin-2-ylethanesulfonamide |
| 258.0 | (1S,2R)-N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide |
| 259.0 | (1R,2R)-N-(4-(2,6-dimethoxyphenyl)-5-(6-methoxy-2-pyridinyl)-4H-1,2,4-triazol-3-yl)-1-hydroxy-1-(1-methyl-1H-imidazol-4-yl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1(1-methyl-1H-imidazol-4-yl)-2-propanesulfonamide |
| 260.0 | (1S,2R)-N-(4-(2,6-dimethoxyphenyl)-5-(6-methoxy-2-pyridinyl)-4H-1,2,4-triazol-3-yl)-1-(1,5-dimethyl-1H-pyrazol-3-yl)-1-hydroxy-2-propanesulfonamide, (1R,2S)-N-(4-(2,6-dimethoxyphenyl)-5-(6-methoxy-2-pyridinyl)-4H-1,2,4-triazol-3-yl)-1-(l,5-dimethyl-1H-pyrazol-3-yl)-1-hydroxy-2-propanesulfonamide |
| 263.0 | (2S,3R)-N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide |
| 264.0 | (2R)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide, (2S)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide |
| 265.0 | (2R)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide, (2S)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide |
| 266.0 | (2R)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide, (2S)-2-(4-chlorophenyl)-N-(4-(2,6-dimethoxyphenyl)-5-(6-methoxy-2-pyridinyl)-4H-1,2,4-triazol-3-yl)-2-hydroxyethanesulfonamide |
| 267.0 | (2R)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide, (2S)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide |
| 268.0 | (2R)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide, (2S)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide |
| 269.0 | (2R)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide, (2S)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-hydroxyethanesulfonamide |
| 270.0 | (2R)-N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide, (2S)-N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide |
| 271.0 | (2R)-N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide, (2S)-N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide |
| 272.0 | (2R)-N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide, (2S)-N-(4-(2,6-dimethoxyphenyl)-5-(6-methoxy-2-pyridinyl)-4H-1,2,4-triazol-3-yl)-2-(4-fluorophenyl)-2-hydroxyethanesulfonamide |
| 273.0 | (2R)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide, (2S)-N-(4-(2,6- |

TABLE 57-continued

| Example | Alternative Names |
|---|---|
| | dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide |
| 274.0 | (2R)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide, (2S)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide |
| 275.0 | (2R)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide, (2S)-N-(4-(2,6-dimethoxyphenyl)-5-(6-methoxy-2-pyridinyl)-4H-1,2,4-triazol-3-yl)-2-(4-fluoro-2-(methylsulfonyl)phenyl)-2-methoxyethanesulfonamide |
| 276.0 | (2R)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide, (2S)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide |
| 277.0 | (2R)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide, (2S)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide |
| 278.0 | (2R)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide, (2S)-2-(2-cyano-4-fluorophenyl)-N-(4-(2,6-dimethoxyphenyl)-5-(6-methoxy-2-pyridinyl)-4H-1,2,4-triazol-3-yl)-2-methoxyethanesulfonamide |
| 279.0 | (1R,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide |
| 280.0 | (1R,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide |
| 281.0 | (1R,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide |
| 282.0 | (1R,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(2,4-difluorophenyl)-N-(4-(2,6-dimethoxyphenyl)-5-(6-methoxy-2-pyridinyl)-4H-1,2,4-triazol-3-yl)-1-hydroxy-2-propanesulfonamide |
| 283.0 | (1R,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1R,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide |
| 284.0 | (1R,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1R,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide |
| 285.0 | (1R,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1R,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide |
| 286.0 | (1R,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1R,2R)-N-(4-(2,6- |

TABLE 57-continued

| Example | Alternative Names |
|---|---|
| | dimethoxyphenyl)-5-(6-methoxy-2-pyridinyl)-4H-1,2,4-triazol-3-yl)-1-(4-fluorophenyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide |
| 287.0 | (1R,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1R,2R)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(4-fluorophenyl)-1-hydroxy-2-propanesulfonamide |
| 288.0 | (1R,2S)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide, (1R,2R)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide |
| 289.0 | (1R,2S)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide |
| 290.0 | (1R,2S)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide, (1S,2R)-N-(4-(2,6-dimethoxyphenyl)-5-(6-methoxy-2-pyridinyl)-4H-1,2,4-triazol-3-yl)-1-(4-fluoro-2-(methylsulfonyl)phenyl)-1-hydroxy-2-propanesulfonamide |
| 291.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide |
| 292.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide |
| 293.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide |
| 294.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide |
| 295.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide |
| 296.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-hydroxy-2-propanesulfonamide |
| 297.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2R)-N- |

TABLE 57-continued

| Example | Alternative Names |
|---|---|
| | (4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide |
| 298.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide |
| 299.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide |
| 300.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide |
| 301.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide |
| 303.0 | (1S,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide, (1R,2S)-N-(4-(2,6-dimethoxyphenyl)-5-(5-methyl-3-pyridinyl)-4H-1,2,4-triazol-3-yl)-1-(4,5-dimethyl-1,3-thiazol-2-yl)-1-methoxy-2-propanesulfonamide |
| 304.0 | (1R,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide |
| 305.0 | (1R,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide |
| 306.0 | (1R,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide |
| 307.0 | (1R,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide |

TABLE 57-continued

| Example | Alternative Names |
|---|---|
| 308.0 | (1R,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide |
| 309.0 | (1R,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methoxy-2-pyrazinyl)-2-propanesulfonamide |
| 310.0 | (1R,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide |
| 311.0 | (1R,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide |
| 312.0 | (1R,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide |
| 313.0 | (2S,3R)-N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide |
| 314.0 | (2R,3S)-N-(4-(2,6-dimethoxyphenyl)-5-(6-methoxy-2-pyridinyl)-4H-1,2,4-triazol-3-yl)-3-(5-methyl-2-pyrimidinyl)-2-butanesulfonamide |
| 315.0 | (2R)-N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide, (2S)-N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide |
| 316.0 | (2R)-N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide, (2S)-N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide |
| 317.0 | (2R)-N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide, (2S)-N-(4-(2,6-dimethoxyphenyl)-5-(6-methoxy-2-pyridinyl)-4H-1,2,4-triazol-3-yl)-2-(5-fluoro-2-pyridinyl)-2-hydroxyethanesulfonamide |
| 319.0 | (1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide |
| 320.0 | (1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide |
| 321.0 | (1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide |

TABLE 57-continued

| Example | Alternative Names |
| --- | --- |
| 322.0 | (1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide |
| 323.0 | (1R,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(4-cyanophenyl)-N-(4-(2,6-dimethoxyphenyl)-5-(6-methoxy-2-pyridinyl)-4H-1,2,4-triazol-3-yl)-1-hydroxy-2-propanesulfonamide |
| 324.0 | (1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide |
| 325.0 | (1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide |
| 326.0 | (1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide |
| 327.0 | (1R,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methoxyphenyl)-2-propanesulfonamide |
| 328.0 | (2R)-N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide, (2S)-N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide |
| 329.0 | (2R)-N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide, (2S)-N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide |
| 330.0 | (2R)-N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide, (2S)-N-(4-(2,6-dimethoxyphenyl)-5-(6-methoxy-2-pyridinyl)-4H-1,2,4-triazol-3-yl)-2-(5-fluoro-2-pyridinyl)-2-methoxyethanesulfonamide |
| 331.0 | (2R)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide, (2S)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide |
| 332.0 | (2R)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide, (2S)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide |
| 333.0 | (2R)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide, (2S)-2-(5-cyano-2-pyridinyl)-N-(4-(2,6-dimethoxyphenyl)-5-(6-methoxy-2-pyridinyl)-4H-1,2,4-triazol-3-yl)-2-hydroxyethanesulfonamide |
| 334.0 | (2R)-N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide |
| 335.0 | (2R)-N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-3-isoxazolyl)ethanesulfonamide |

TABLE 57-continued

| Example | Alternative Names |
|---|---|
| 336.0 | (2R)-N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide |
| 337.0 | (2R)-N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide |
| 338.0 | (2R)-N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(3-methyl-5-isoxazolyl)ethanesulfonamide |
| 339.0 | (2R)-N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide |
| 340.0 | (2R)-N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide |
| 341.0 | (2R)-N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-2-pyrimidinyl)ethanesulfonamide |
| 342.0 | (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide |
| 343.0 | (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide |
| 344.0 | (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide, (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-hydroxy-2-propanesulfonamide |
| 345.0 | (1R,2S)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide |
| 346.0 | (1R,2S)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide |
| 347.0 | (1R,2S)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1S,2R)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide, (1R,2R)-N-(4-(2,6-dimethoxyphenyl)-5-(5-methyl-3-pyridinyl)-4H-1,2,4-triazol-3-yl)-1-(5-fluoro-2-pyridinyl)-1-hydroxy-2-propanesulfonamide |
| 348.0 | (2R)-N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide, (2S)-N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide |
| 349.0 | (2R)-N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide, (2S)-N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide |

TABLE 57-continued

| Example | Alternative Names |
|---|---|
| 350.0 | (2R)-N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide, (2S)-N-(4-(2,6-dimethoxyphenyl)-5-(5-methyl-3-pyridinyl)-4H-1,2,4-triazol-3-yl)-2-(5-fluoro-2-pyridinyl)-2-hydroxyethanesulfonamide |
| 351.0 | (1R,2S)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide |
| 352.0 | (1R,2S)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide |
| 353.0 | (1R,2S)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(5-fluoro-2-pyridinyl)-1-methoxy-2-propanesulfonamide |
| 354.0 | (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide |
| 355.0 | (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide |
| 356.0 | (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide |
| 357.0 | (1R,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(4-cyano-2-fluorophenyl)-N-(4-(2,6-dimethoxyphenyl)-5-(5-methyl-3-pyridinyl)-4H-1,2,4-triazol-3-yl)-1-methoxy-2-propanesulfonamide |
| 358.0 | (1R,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide |
| 359.0 | (1R,2R)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyrimidinyl)-1-hydroxy-2-propanesulfonamide |
| 360.0 | (1R,2R)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide |
| 361.0 | (1R,2R)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide |
| 362.0 | (1R,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide, (1S,2S)-N-(4-(2,6- |

TABLE 57-continued

| Example | Alternative Names |
|---|---|
| | dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide |
| 363.0 | (1R,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide, (1S,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-hydroxy-2-propanesulfonamide |
| 364.0 | (1R,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide, (1S,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide |
| 365.0 | (1R,2R)-N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide, (1S,2S)-N-(4-(2,6-dimethoxyphenyl)-5-(6-methoxy-2-pyridinyl)-4H-1,2,4-triazol-3-yl)-1-(5-fluoro-2-pyrimidinyl)-1-methoxy-2-propanesulfonamide |
| 366.0 | (2S)-2-(2,4-difluorophenyl)-N-(4-(2,6-dimethoxyphenyl)-5-(5-methyl-3-pyridinyl)-4H-1,2,4-triazol-3-yl)-2-hydroxyethanesulfonamide, (2R)-2-(2,4-difluorophenyl)-N-(4-(2,6-dimethoxyphenyl)-5-(5-methyl-3-pyridinyl)-4H-1,2,4-triazol-3-yl)-2-hydroxyethanesulfonamide |
| 367.0 | (2S)-2-(2,4-difluorophenyl)-N-(4-(2,6-dimethoxyphenyl)-5-(5-methyl-3-pyridinyl)-4H-1,2,4-triazol-3-yl)-2-hydroxyethanesulfonamide, (2R)-2-(2,4-difluorophenyl)-N-(4-(2,6-dimethoxyphenyl)-5-(5-methyl-3-pyridinyl)-4H-1,2,4-triazol-3-yl)-2-hydroxyethanesulfonamide |
| 368.0 | 2-(4-chlorophenyl)-N-(4-(2,6-dimethoxyphenyl)-5-(2-pyridinyl)-4H-1,2,4-triazol-3-yl)ethanesulfonamide |
| 369.0 | 2-(4-chlorophenyl)-N-(4-(2,6-dimethoxyphenyl)-5-(3-pyridinyl)-4H-1,2,4-triazol-3-yl)ethanesulfonamide |
| 370.0 | 2-(4-chlorophenyl)-N-(4-(2,6-dimethoxyphenyl)-5-(6-methyl-3-pyridinyl)-4H-1,2,4-triazol-3-yl)ethanesulfonamide |
| 371.0 and 541.0 | (1R,2S)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide |
| 372.0 | (1R)-N-(4-(2,6-dimethoxyphenyl)-5-(5-methyl-3-pyridinyl)-4H-1,2,4-triazol-3-yl)-1-(5-methyl-2-pyrimidinyl)ethanesulfonamide, (1S)-N-(4-(2,6-dimethoxyphenyl)-5-(5-methyl-3-pyridinyl)-4H-1,2,4-triazol-3-yl)-1-(5-methyl-2-pyrimidinyl)ethanesulfonamide |
| 373.0 | 4-(3-chloro-2,6-dimethoxyphenyl)-N-(2-(4-chlorophenyl)ethyl)-5-(5-methyl-3-pyridinyl)-4H-1,2,4-triazole-3-sulfonamide |
| 374.0 | (2R)-N-(4-(2,6-dimethoxyphenyl)-5-(5-methyl-3-pyridinyl)-4H-1,2,4-triazol-3-yl)-2-methyl-3-phenylpropanamide, (2S)-N-(4-(2,6-dimethoxyphenyl)-5-(5-methyl-3-pyridinyl)-4H-1,2,4-triazol-3-yl)-2-methyl-3-phenylpropanamide |
| 375.0 | (1R,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1R,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide |
| 376.0 | (1R,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1R,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide |
| 377.0 | (1R,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1R,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide |
| 378.0 | (1R,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1R,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide |
| 379.0 | (1R,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1R,2R)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2S)-1-amino-N-(4-(2,6-dimethoxyphenyl)-5-(6-methoxy-2-pyridinyl)-4H-1,2,4-triazol-3-yl)-1-(5-methyl-2-pyrimidinyl)-2-propanesulfonamide, (1S,2R)-1-amino-N-(4-(2,6-dimethoxyphenyl)- |

TABLE 57-continued

| Example | Alternative Names |
|---|---|
| | 5-(6-methoxy-2-pyridinyl)-4H-1,2,4-triazol-3-yl)-1-(5-methyl-2-pyrimidinyl)-2-propanesulfonamide |
| 381.0 | (2R)-N-(4-(2,6-dimethoxyphenyl)-5-(5-methyl-3-pyridinyl)-4H-1,2,4-triazol-3-yl)-2-hydroxy-2-(3-methyl-3-oxetanyl)ethanesulfonamide, (2S)-N-(4-(2,6-dimethoxyphenyl)-5-(5-methyl-3-pyridinyl)-4H-1,2,4-triazol-3-yl)-2-hydroxy-2-(3-methyl-3-oxetanyl)ethanesulfonamide |
| 382.0 | (2R)-2-cyclobutyl-N-(4-(2,6-dimethoxyphenyl)-5-(5-methyl-3-pyridinyl)-4H-1,2,4-triazol-3-yl)-2-hydroxyethanesulfonamide, (2S)-2-cyclobutyl-N-(4-(2,6-dimethoxyphenyl)-5-(5-methyl-3-pyridinyl)-4H-1,2,4-triazol-3-yl)-2-hydroxyethanesulfonamide |
| 383.0 | (2R)-N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide, (2S)-N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide |
| 384.0 | (2R)-N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide, (2S)-N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide |
| 385.0 | (2R)-N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide, (2S)-N-(4-(2,6-dimethoxyphenyl)-5-(6-methoxy-2-pyridinyl)-4H-1,2,4-triazol-3-yl)-2-methoxy-2-(5-methyl-2-pyrimidinyl)ethanesulfonamide |
| 386.0 | (1R,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide |
| 387.0 | (1R,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide |
| 388.0 | (1R,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide |
| 389.0 | (1R,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide |
| 390.0 | (1R,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide |
| 391.0 | (1R,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-cyclobutyl-N-(4-(2,6-dimethoxyphenyl)-5-(6-methoxy-2-pyridinyl)-4H-1,2,4-triazol-3-yl)-1-methoxy-2-propanesulfonamide |
| 392.0 | N-(4-(2,6-dimethoxyphenyl)-5-(5-methyl-3-pyridinyl)-4H-1,2,4-triazol-3-yl)-N'-((1S)-1-(5-fluoro-2-pyrimidinyl)ethyl)sulfamide |
| 393.0 | (1S,2R)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide |
| 394.0 | (1S,2R)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide |
| 395.0 | (1S,2R)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide |

TABLE 57-continued

| Example | Alternative Names |
|---|---|
| 396.0 | (1S,2R)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide |
| 397.0 | (1S,2R)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide |
| 398.0 | (1S,2R)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide |
| 399.0 | (1S,2R)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide |
| 400.0 | (1S,2R)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide |
| 401.0 | (1S,2R)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide |
| 402.0 | (1S,2R)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide |
| 403.0 | (1S,2R)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2R)-2-hydroxypropyl)oxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(((2S)-2-hydroxypropyl)oxy)-1-(5-methyl-2-pyrimidinyl)-2-propanesulfonamide |
| 404.0 | (1S,2R)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide |
| 405.0 | (1S,2R)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide |
| 406.0 | (1S,2R)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide |
| 407.0 | (1S,2S)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide |
| 408.0 | (1S,2S)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide, |

TABLE 57-continued

| Example | Alternative Names |
|---|---|
| | (1R,2R)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide |
| 409.0 | (1S,2S)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(2-hydroxyethoxy)-1-(5-methyl-2-pyrimidinyl)-2-propanesulfonamide |
| 410.0 | (1S,2S)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide |
| 411.0 | (1S,2S)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide |
| 412.0 | (1S,2S)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(2-hydroxy-2-methylpropoxy)-1-(5-methyl-2-pyrimidinyl)-2-propanesulfonamide |
| 413.0 | (1S,2S)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(2-methoxyethoxy)-1-(5-methyl-2-pyrimidinyl)-2-propanesulfonamide |
| 414.0 | (1S,2R)-N-(4-(2,6-dimethoxyphenyl)-5-(6-methoxy-2-pyridinyl)-4H-1,2,4-triazol-3-yl)-1-(2-hydroxyethoxy)-1-(5-methyl-2-pyrimidinyl)-2-propanesulfonamide, (1R,2S)-N-(4-(2,6-dimethoxyphenyl)-5-(6-methoxy-2-pyridinyl)-4H-1,2,4-triazol-3-yl)-1-(2-hydroxyethoxy)-1-(5-methyl-2-pyrimidinyl)-2-propanesulfonamide |
| 415.0 | (1S,2R)-N-(4-(2,6-dimethoxyphenyl)-5-(6-methoxy-2-pyridinyl)-4H-1,2,4-triazol-3-yl)-1-(2-hydroxyethoxy)-1-(5-methyl-2-pyrimidinyl)-2-propanesulfonamide, (1R,2S)-N-(4-(2,6-dimethoxyphenyl)-5-(6-methoxy-2-pyridinyl)-4H-1,2,4-triazol-3-yl)-1-(2-hydroxyethoxy)-1-(5-methyl-2-pyrimidinyl)-2-propanesulfonamide |
| 416.0 | (1S,2R)-N-(4-(2,6-dimethoxyphenyl)-5-(6-methoxy-2-pyridinyl)-4H-1,2,4-triazol-3-yl)-1-(2-hydroxyethoxy)-1-(5-methyl-2-pyrimidinyl)-2-propanesulfonamide, (1R,2S)-N-(4-(2,6-dimethoxyphenyl)-5-(6-methoxy-2-pyridinyl)-4H-1,2,4-triazol-3-yl)-1-(2-hydroxyethoxy)-1-(5-methyl-2-pyrimidinyl)-2-propanesulfonamide |
| 417.0 | (2S)-N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-ethenyl-3-pyridinyl)-4H-1,2,4-triazol-3-yl)-1-(5-fluoro-2-pyrimidinyl)-2-propanesulfonamide |
| 418.0 | (2S)-N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide |
| 419.0 | (2S)-N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide |
| 420.0 | (2S)-N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(5-ethyl-3-pyridinyl)-4H-1,2,4-triazol-3-yl)-1-(5-fluoro-2-pyrimidinyl)-2-propanesulfonamide |
| 421.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |
| 422.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |
| 423.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |

TABLE 57-continued

| Example | Alternative Names |
|---|---|
| 424.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |
| 425.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |
| 426.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |
| 427.0 | (1R,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-(methylamino)-1-(5-methyl-2-pyrimidinyl)-2-propanesulfonam |
| 428.0 | (1R,2S)-N-(4-(2,6-dimethoxyphenyl)-5-(5-methyl-3-pyridinyl)-4H-1,2,4-triazol-3-yl)-1-methoxy-1-(5-phenyl-2-pyrimidinyl)-2-propanesulfonamide |
| 429.0 | (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide |
| 430.0 and 605.0 | (1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide |
| 433.0 | (2R,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2R,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide |
| 434.0 | (2R,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2R,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide |
| 435.0 | (2R,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2R,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide |
| 436.0 | (2R,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2R,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide |
| 437.0 | (2R,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2R,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3S)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide, (2S,3R)-N-(4-(2,6-dimethoxyphenyl)-5-(6-methoxy-2-pyridinyl)-4H-1,2,4-triazol-3-yl)-3-hydroxy-4,4-dimethyl-2-pentanesulfonamide |
| 438.0 | (1R,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, |

TABLE 57-continued

| Example | Alternative Names |
|---|---|
| | (1S,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide |
| 439.0 | (1R,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide |
| 440.0 | (1R,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-cyclopropyl-N-(4-(2,6-dimethoxyphenyl)-5-(6-methoxy-2-pyridinyl)-4H-1,2,4-triazol-3-yl)-1-hydroxy-2-propanesulfonamide |
| 441.0 | (1R,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, (1S,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide |
| 442.0 | (1R,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide |
| 443.0 | (1R,2S)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-cyclohexyl-N-(4-(2,6-dimethoxyphenyl)-5-(6-methoxy-2-pyridinyl)-4H-1,2,4-triazol-3-yl)-1-hydroxy-2-propanesulfonamide |
| 444.0 | (1R,2R)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide |
| 445.0 | (1S,2R)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide |
| 446.0 | (1S,2S)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide |
| 447.0 | (1S,2R)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide |
| 448.0 | (1S,2S)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(tetrahydro-2H-pyran-4-yl)-2-propanesulfonamide |
| 449.0 | (2S,3R)-N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide, (2R,3S)-N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide |
| 450.0 | (2S,3R)-N-(4-(4,6-dimethoxy-5-pyrimidinyl)-5-(5-methyl-3-pyridinyl)-4H-1,2,4-triazol-3-yl)-3-(5-fluoro-2-pyrimidinyl)-2-butanesulfonamide |
| 451.0 | (2S,3R)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butanesulfonamide, (2R,3S)-3-(5-fluoro-2-pyrimidinyl)-N-(5-(6-methoxy-2-pyridinyl)-4-(1-methyl-1H-indol-3-yl)-4H-1,2,4-triazol-3-yl)-2-butanesulfonamide |
| 452.0 | (2S,3R)-N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide, (2R,3S)-N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide |
| 453.0 | (2S,3R)-N-(4-(2,6-dimethoxyphenyl)-5-(6-methyl-2-pyridinyl)-4H-1,2,4-triazol-3-yl)-3-(5-fluoro-2-pyrimidinyl)-2-butanesulfonamide |
| 454.0 | (2S,3R)-N-(5-(6-chloro-2-pyridinyl)-4-(2,6-dimethoxyphenyl)-4H-1,2,4-triazol-3-yl)-3-(5-fluoro-2-pyrimidinyl)-2-butanesulfonamide |
| 455.0 | (2S,3R)-N-(4-(2,6-dimethoxyphenyl)-5-(6-phenyl-2-pyridinyl)-4H-1,2,4-triazol-3-yl)-3-(5-fluoro-2-pyrimidinyl)-2-butanesulfonamide |
| 456.0 | (2S,3R)-N-(4-(2,6-dimethoxyphenyl)-5-(1-oxido-6-phenyl-2-pyridinyl)-4H-1,2,4-triazol-3-yl)-3-(5-fluoro-2-pyrimidinyl)-2-butanesulfonamide |

TABLE 57-continued

| Example | Alternative Names |
|---|---|
| 457.0 | (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide |
| 458.0 | (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide |
| 459.0 | (2R)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, (2S)-2-(4-chloro-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide |
| 460.0 | N-(4-(2,6-dimethoxyphenyl)-5-(5-methyl-3-pyridinyl)-4H-1,2,4-triazol-3-yl)-2-((6R)-3,6-dimethyl-2-oxotetrahydro-1(2H)-pyrimidinyl)ethanesulfonamide |
| 461.0 | 2-(2-cyano-4-fluorophenyl)-N-(4-(2,6-dimethoxyphenyl)-5-(6-oxo-1,6-dihydro-2-pyridinyl)-4H-1,2,4-triazol-3-yl)ethanesulfonamide |
| 462.0 | (3R,5S)-N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide |
| 463.0 | (3R,5S)-N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide |
| 464.0 | (3R,5S)-N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(6-methyl-2-pyridinyl)-4H-1,2,4-triazol-3-yl)-1-(5-fluoro-2-pyrimidinyl)-5-hydroxy-3-piperidinesulfonamide |
| 465.0 | (3R,5S)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, (3S,5S)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide |
| 466.0 | (3R,5R)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide |
| 467.0 | (3R,5S)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide |
| 468.0 | (3R,5S)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(5-methyl-3-pyridinyl)-4H-1,2,4-triazol-3-yl)-1-(5-fluoro-2-pyrimidinyl)-5-hydroxy-3-piperidinesulfonamide |
| 469.0 | (3R,5S)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide |
| 470.0 | (3R,5R)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, (3S,5S)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide |
| 471.0 | (3S,5R)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, (3R,5S)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide |
| 472.0 | (3R,5S)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(6-methoxy-2-pyridinyl)-4H-1,2,4-triazol-3-yl)-1-(5-fluoro-2-pyrimidinyl)-5-hydroxy-3-piperidinesulfonamide |
| 473.0 | (1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide |
| 474.0 | (1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide |
| 475.0 | (1R,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide |
| 476.0 | (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-(2,4- |

TABLE 57-continued

| Example | Alternative Names |
|---|---|
| | dicyanophenyl)-N-(4-(2,6-dimethoxyphenyl)-5-(6-methoxy-2-pyridinyl)-4H-1,2,4-triazol-3-yl)-1-methoxy-2-propanesulfonamide |
| 477.0 | (1R,2R)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide, (1S,2S)-1-(2,4-dicyanophenyl)-N-(4-(2,6-dimethoxyphenyl)-5-(6-methoxy-2-pyridinyl)-4H-1,2,4-triazol-3-yl)-1-methoxy-2-propanesulfonamide |
| 478.0 | (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide |
| 479.0 | (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide |
| 480.0 | (1R,2S)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(2,4-dicyanophenyl)-N-(4-(2,6-dimethoxyphenyl)-5-(5-methyl-3-pyridinyl)-4H-1,2,4-triazol-3-yl)-1-methoxy-2-propanesulfonamide |
| 481.0 | (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide, (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide |
| 482.0 | (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide, (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide |
| 483.0 | (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide, (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-hydroxyethanesulfonamide |
| 484.0 | (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide, (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide |
| 485.0 | (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide, (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide |
| 486.0 | (2R)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide, (2S)-2-(4-cyano-2-(methylsulfonyl)phenyl)-N-(4-(2,6-dimethoxyphenyl)-5-(6-methoxy-2-pyridinyl)-4H-1,2,4-triazol-3-yl)-2-methoxyethanesulfonamide |
| 487.0 | (2R)-N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide |
| 488.0 | (2R)-N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide |
| 489.0 | (2R)-N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(5-methyl-2-pyrazinyl)ethanesulfonamide |
| 490.0 | (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide |
| 491.0 | (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide |
| 492.0 | (2R)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide, (2S)-2-(4-cyano-2-(methylsulfonyl)phenyl)-N-(4-(2,6-dimethoxyphenyl)-5-(5-methyl-3-pyridinyl)-4H-1,2,4-triazol-3-yl)-2-hydroxyethanesulfonamide |
| 493.0 | (2R)-N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide |
| 494.0 | (2R)-N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide |
| 495.0 | (2R)-N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide, (2S)-N-(4-(2,6-dimethoxyphenyl)-5-(6-methoxy-2-pyridinyl)-4H-1,2,4-triazol-3-yl)-2-hydroxy-2-(2-methyl-5-pyrimidinyl)ethanesulfonamide |

TABLE 57-continued

| Example | Alternative Names |
|---|---|
| 496.0 | (1R,2S)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide |
| 497.0 | (1R,2S)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide |
| 498.0 | (1R,2S)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(2-methyl-5-pyrimidinyl)-2-propanesulfonamide |
| 499.0 | (1R,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide |
| 500.0 | (1R,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide |
| 501.0 | (1R,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide |
| 502.0 | (1R,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide |
| 503.0 | (1R,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-methoxy-1-(2-methyl-5-pyrimidinyl)-2-propanesulfonamide |
| 504.0 | (2E)-N-(4-(2,6-dimethoxyphenyl)-5-(5-methyl-3-pyridinyl)-4H-1,2,4-triazol-3-yl)-3-(5-fluoro-2-pyrimidinyl)-2-butene-2-sulfonamide |
| 505.0 | (2E)-N-(4-(2,6-dimethoxyphenyl)-5-(6-methoxy-2-pyridinyl)-4H-1,2,4-triazol-3-yl)-3-(5-fluoro-2-pyrimidinyl)-2-butene-2-sulfonamide |
| 506.0 | (2S,3R)-N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide |
| 507.0 | (2S,3R)-N-(4-(2,6-dimethoxyphenyl)-5-(6-methoxy-2-pyridinyl)-4H-1,2,4-triazol-3-yl)-3-(5-methyl-2-pyrazinyl)-2-butanesulfonamide |
| 508.0 | (1S,2R)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1S,2S)-N-(4-(2,6- |

TABLE 57-continued

| Example | Alternative Names |
|---|---|
| | dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide |
| 509.0 | (1S,2R)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide |
| 510.0 | (1S,2R)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide |
| 511.0 | (1R,2R)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide |
| 512.0 | (1R,2R)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(3-methoxy-5-methyl-2-pyrazinyl)-2-propanesulfonamide |
| 513.0 | (1R,2S)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide |
| 514.0 | (1R,2R)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide |
| 515.0 | (1R,2S)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide |
| 516.0 | (1R,2S)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide |
| 517.0 | (1R,2R)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide |
| 518.0 | (1R,2R)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(3-methoxy-5-methyl-2-pyrazinyl)-2-propanesulfonamide |
| 519.0 | (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide, (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide |
| 520.0 | (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide, (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide |
| 521.0 | (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide, (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-hydroxyethanesulfonamide |
| 522.0 | (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide, (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide |
| 523.0 | (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide, (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide |
| 524.0 | (2R)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide, (2S)-2-(5-chloro-1,3-thiazol-2-yl)-N-(4-(2,6-dimethoxyphenyl)-5-(6-methoxy-2-pyridinyl)-4H-1,2,4-triazol-3-yl)-2-methoxyethanesulfonamide |
| 525.0 | (2S,3R)-N-(4-(2,4-dimethoxy-3-pyridinyl)-5-(6-methoxy-2-pyridinyl)-4H-1,2,4-triazol-3-yl)-3-(5-fluoro-2-pyrimidinyl)-2-butanesulfonamide |
| 526.0 | (2S,3R)-3-(5-fluoro-2-pyrimidinyl)-N-(4-(4-methoxy-2-oxo-1,2-dihydro-3-pyridinyl)-5-(6-methoxy-2-pyridinyl)-4H-1,2,4-triazol-3-yl)-2-butanesulfonamide |
| 527.0 | (2S,3R)-3-(5-fluoro-2-pyrimidinyl)-N-(4-(4-methoxy-2-oxo-1,2-dihydro-3-pyridinyl)-5-(6-methoxy-2-pyridinyl)-4H-1,2,4-triazol-3-yl)-2-butanesulfonamide |
| 528.0 | (2S,3R)-3-(5-fluoro-2-pyrimidinyl)-N-(4-(4-methoxy-2-oxo-1,2-dihydro-3-pyridinyl)-5-(6-methoxy-2-pyridinyl)-4H-1,2,4-triazol-3-yl)-2-butanesulfonamide |
| 529.0 | (1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide, (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide |

TABLE 57-continued

| Example | Alternative Names |
|---|---|
| 530.0 | (1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide, (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide |
| 531.0 | (1S,2R)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide, (1R,2S)-1-(5-chloro-2-pyridinyl)-N-(4-(2,6-dimethoxyphenyl)-5-(3-pyridinyl)-4H-1,2,4-triazol-3-yl)-1-methoxy-2-propanesulfonamide |
| 532.0 | (1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 533.0 | (1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 534.0 | (1S,2R)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 535.0 | (1R,2S)-N-(4-(2,6-dimethoxyphenyl)-5-(5-methyl-3-pyridinyl)-4H-1,2,4-triazol-3-yl)-1-methoxy-1-(5-(1-propyn-1-yl)-2-pyrimidinyl)-2-propanesulfonamide |
| 536.0 | (2S,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2R,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2R,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2S,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide |
| 537.0 | (2S,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2R,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2R,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2S,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide |
| 538.0 | (2S,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2R,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2R,3S)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide, (2S,3R)-3-(5-cyano-2-pyrimidinyl)-N-(4-(2,6-dimethoxyphenyl)-5-(5-methyl-3-pyridinyl)-4H-1,2,4-triazol-3-yl)-3-fluoro-2-butanesulfonamide |
| 539.0 | (1R,2S)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide |
| 540.0 | (1S,2R)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide |
| 541.0 | (1R,2S)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide |
| 542.0 | (1S,2R)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide, (1R,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 543.0 and 28.0 | (1S,2R)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 544.0 and 203.0 | (1R,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 545.0 | (1R,2R)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 546.0 | (1R,2R)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide |
| 547.0 | (1R,2S)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-methoxy- |

TABLE 57-continued

| Example | Alternative Names |
|---|---|
| | 1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 548.0 | (1S,2R)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 549.0 and 27.0 | (1R,2S)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 550.0 | 2-(5-cyano-2-pyridinyl)-N-(4-(2,6-dimethoxyphenyl)-5-(6-methoxy-2-pyridinyl)-4H-1,2,4-triazol-3-yl)ethanesulfonamide |
| 551.0 | (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 552.0 | (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 553.0 | (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 554.0 | (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 555.0 | (1S,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-cyano-2-pyridinyl)-N-(4-(2,6-dimethoxyphenyl)-5-(5-methyl-3-pyridinyl)-4H-1,2,4-triazol-3-yl)-1-methoxy-2-propanesulfonamide |
| 556.0 | (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide |
| 557.0 | (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide |
| 558.0 | (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide |
| 559.0 | (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-chloro-2-pyrimidinyl)-N-(4-(2,6-dimethoxyphenyl)-5-(5-methyl-3-pyridinyl)-4H- |

TABLE 57-continued

| Example | Alternative Names |
|---|---|
| | 1,2,4-triazol-3-yl)-1-methoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide |
| 560.0 | (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide |
| 561.0 | (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide |
| 562.0 | (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide |
| 563.0 | (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-hydroxy-2-propanesulfonamide |
| 564.0 | (1S,2R)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide |
| 565.0 | (1S,2R)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide |
| 566.0 | (1S,2R)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-ethoxy-1-(5-methyl-2-pyrazinyl)-2-propanesulfonamide |
| 567.0 | (1R,2S)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide |
| 568.0 | (1S,2R)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide |
| 569.0 | (1S,2R)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide |
| 570.0 | (1R,2S)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide, (1R,2R)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide, (1S,2R)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide |
| 571.0 | (1S,2R)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide |
| 572.0 | (1S,2R)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide, (1R,2S)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide |
| 573.0 | (1R,2S)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide, (1R,2R)-N-(4-(2,6-dimethoxyphenyl)-5- |

| Example | Alternative Names |
|---|---|
| | (6-methoxy-2-pyridinyl)-4H-1,2,4-triazol-3-yl)-1-methoxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide |
| 574.0 | (1R,2S)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide |
| 575.0 | (1R,2S)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-methoxy-1-(5-methyl-2-pyrazinyl)-2-propanesulfonamide |
| 576.0 | (1R,2S)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide |
| 577.0 | (1R,2S)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide |
| 578.0 | (1R,2S)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(5-methyl-2-pyrazinyl)-2-propanesulfonamide |
| 579.0 | (1S,2R)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide, (1R,2S)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide, (1R,2R)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide, (1S,2S)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide |
| 580.0 | (1S,2R)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide, (1R,2S)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide |
| 581.0 | (1S,2R)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide, (1R,2S)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide |
| 582.0 | (1S,2S)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide |
| 583.0 | (1S,2S)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide, (1R,2S)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide, (1R,2R)-N-(4-(2,6-dimethoxyphenyl)-5-(6-methoxy-2-pyridinyl)-4H-1,2,4-triazol-3-yl)-1-hydroxy-1-(5-methyl-2-pyrimidinyl)-2-propanesulfonamide |
| 584.0 | (2S,3R)-N-(4-(2,6-dimethoxyphenyl)-5-(3-pyridinyl)-4H-1,2,4-triazol-3-yl)-3-(5-methyl-2-pyrimidinyl)-2-butanesulfonamide, (2R,3S)-N-(4-(2,6-dimethoxyphenyl)-5-(3-pyridinyl)-4H-1,2,4-triazol-3-yl)-3-(5-methyl-2-pyrimidinyl)-2-butanesulfonamide |
| 585.0 | (2R,3S)-N-(4-(2,6-dimethoxyphenyl)-5-(3-pyridinyl)-4H-1,2,4-triazol-3-yl)-3-(5-methyl-2-pyrimidinyl)-2-butanesulfonamide |
| 586.0 | (2S,3R)-N-(4-(2,6-dimethoxyphenyl)-5-(3-pyridinyl)-4H-1,2,4-triazol-3-yl)-3-(5-methyl-2-pyrimidinyl)-2-butanesulfonamide |
| 587.0 | (1R,2S)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide, (1S,2S)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide, (1R,2R)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide, (1S,2R)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide |
| 588.0 | (1S,2R)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide, (1R,2S)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide |

TABLE 57-continued

| Example | Alternative Names |
|---|---|
| 589.0 | (1S,2R)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide, (1R,2S)-N-(4-(2,6-dimethoxyphenyl)-5-(6-methoxy-2-pyridinyl)-4H-1,2,4-triazol-3-yl)-1-ethoxy-1-(5-methyl-2-pyrazinyl)-2-propanesulfonamide |
| 590.0 | (1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide |
| 591.0 | (1R,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide |
| 592.0 | (1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide |
| 593.0 | (1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide |
| 594.0 | (1S,2S)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide |
| 595.0 | (1S,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide |
| 596.0 | (1S,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide |
| 597.0 | (1S,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide |
| 598.0 | (1S,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide |
| 599.0 | (1S,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1S,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2S)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide, (1R,2R)-1-(5-chloro-2-pyrimidinyl)-N-(4-(2,6-dimethoxyphenyl)-5-(6-methoxy-2-pyridinyl)-4H-1,2,4-triazol-3-yl)-1-methoxy-2-propanesulfonamide |
| 600.0 | (1R,2S)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide, (1S,2S)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide, (1R,2R)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide, (1S,2R)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide |
| 601.0 | (1S,2R)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide, (1R,2S)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide |
| 602.0 | (1S,2R)-N-(4-(2,6-dimethoxyphenyl)-5-(3-pyridinyl)-4H-1,2,4-triazol-3-yl)-1-ethoxy-1-(5-methyl-2-pyrazinyl)-2-propanesulfonamide, (1R,2S)-N-(4-(2,6- |

TABLE 57-continued

| Example | Alternative Names |
|---|---|
| | dimethoxyphenyl)-5-(3-pyridinyl)-4H-1,2,4-triazol-3-yl)-1-ethoxy-1-(5-methyl-2-pyrazinyl)-2-propanesulfonamide |
| 603.0 | (1S,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide |
| 604.0 | (1S,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide |
| 605.0 and 430.0 | (1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide |
| 606.0 | (1S,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide |
| 607.0 | (1S,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide |
| 608.0 | (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide |
| 609.0 | (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide |
| 610.0 | (1R,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide |
| 611.0 | (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide |
| 612.0 | (1S,2S)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide, (1R,2R)-1-(5-chloro-2-pyrimidinyl)-N-(4-(2,6-dimethoxyphenyl)-5-(5-methyl-3-pyridinyl)-4H-1,2,4-triazol-3-yl)-1-ethoxy-2-propanesulfonamide |
| 613.0 | (1S,2R)-N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide, (1R,2S)-N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide |
| 614.0 | (1S,2R)-N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide |
| 615.0 | (1R,2S)-N-(4-(2,6-dimethoxyphenyl)-5-(3-pyridinyl)-4H-1,2,4-triazol-3-yl)-1-hydroxy-1-(5-methyl-2-pyrazinyl)-2-propanesulfonamide |
| 616.0 | (1R,2S)-N-(4-(2,6-dimethoxyphenyl)-5-(3-pyridinyl)-4H-1,2,4-triazol-3-yl)-1-hydroxy-1-(5-methyl-2-pyrimidinyl)-2-propanesulfonamide |
| 618.0 | (2S)-N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide |
| 619.0 | (2S)-N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide |
| 620.0 | (2S)-N-(4-(2,6-dimethoxyphenyl)-5-(6-methyl-2-pyridinyl)-4H-1,2,4-triazol-3-yl)-1-(5-fluoro-2-pyrimidinyl)-2-propanesulfonamide, (2R)-N-(4-(2,6-dimethoxyphenyl)-5- |

TABLE 57-continued

| Example | Alternative Names |
|---|---|
| | (6-methyl-2-pyridinyl)-4H-1,2,4-triazol-3-yl)-1-(5-fluoro-2-pyrimidinyl)-2-propanesulfonamide |
| 621.0 | 2-(2-cyano-4-fluorophenyl)-N-(4-(2,6-dimethoxyphenyl)-5-(5-methyl-3-pyridinyl)-4H-1,2,4-triazol-3-yl)ethanesulfonamide |
| 622.0 | (2R,3S)-N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide |
| 623.0 | (1R,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1S,2S)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide, (1R,2R)-1-(2-cyano-4-fluorophenyl)-N-(4-(2,6-dimethoxyphenyl)-5-(5-methyl-3-pyridinyl)-4H-1,2,4-triazol-3-yl)-1-methoxy-2-propanesulfonamide |
| 624.0 | (1S,2R)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide, (1R,2S)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide |
| 625.0 | (1R,2R)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide, 1S,2S)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide |
| 626.0 | (1S,2R)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide, (1R,2S)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide |
| 627.0 | (1R,2R)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide, (1S,2S)-N-(4-(2,6-dimethoxyphenyl)-5-(3-pyridinyl)-4H-1,2,4-triazol-3-yl)-1-(1-methylethoxy)-1-(5-methyl-2-pyrimidinyl)-2-propanesulfonamide |
| 628.0 | (1R,2S)-N-(4-(4,6-dimethoxy-5-pyrimidinyl)-5-(2-pyridinyl)-4H-1,2,4-triazol-3-yl)-1-methoxy-1-(5-methyl-2-pyrimidinyl)-2-propanesulfonamide |
| 629.0 | (1R,2S)-N-(4-(2,6-dimethoxyphenyl)-5-(2-pyridinyl)-4H-1,2,4-triazol-3-yl)-1-methoxy-1-(5-methyl-2-pyrimidinyl)-2-propanesulfonamide |
| 630.0 | (1R,2R)-N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide |
| 631.0 | (2S,3R)-N-(4-(2,6-dimethoxyphenyl)-5-(5-methylpyridin-3-yl)-4H-1,2,4-triazol-3-yl)-N-methyl-3-(5-methylpyrimidin-2-yl)butane-2-sulfonamide, (2S,3R,Z)-N-(4-(2,6-dimethoxyphenyl)-1-methyl-3-(5-methylpyridin-3-yl)-1H-1,2,4-triazol-5(4H)-ylidene)-3-(5-methylpyrimidin-2-yl)butane-2-sulfonamide |
| 632.0 | (1S,2R)-N-(4-(2,6-dimethoxyphenyl)-5-(5-methyl-3-pyridinyl)-4H-1,2,4-triazol-3-yl)-1-methoxy-1-(5-methyl-1,3-oxazol-2-yl)-2-propanesulfonamide, (1R,2S)-N-(4-(2,6-dimethoxyphenyl)-5-(5-methyl-3-pyridinyl)-4H-1,2,4-triazol-3-yl)-1-methoxy-1-(5-methyl-1,3-oxazol-2-yl)-2-propanesulfonamide |
| 633.0 | (1S,2R)-N-(4-(2,6-dimethoxyphenyl)-5-(5-methyl-3-pyridinyl)-4H-1,2,4-triazol-3-yl)-1-methoxy-1-(5-methyl-1,3-oxazol-2-yl)-2-propanesulfonamide, (1R,2S)-N-(4-(2,6-dimethoxyphenyl)-5-(5-methyl-3-pyridinyl)-4H-1,2,4-triazol-3-yl)-1-methoxy-1-(5-methyl-1,3-oxazol-2-yl)-2-propanesulfonamide |
| 634.0 | (1R,2R)-N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide |
| 635.0 | (1R,2R)-N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide, (1S,2S)-N-(4-(2,6-dimethoxyphenyl)-5-(5-methyl-3-pyridinyl)-4H-1,2,4-triazol-3-yl)-1-methoxy-1-(4-methyl-1,3-thiazol-2-yl)-2-propanesulfonamide |
| 636.0 | (1R,2S)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide |
| 637.0 | (1S,2R)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide, (1R,2S)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide |
| 638.0 | (2S,3R)-N-(4-(2,6-dimethoxyphenyl)-5-(6-(2-methoxyethoxy)-2-pyridinyl)-4H-1,2,4-triazol-3-yl)-3-(5-fluoro-2-pyrimidinyl)-2-butanesulfonamide |
| 639.0 | (2S,3R)-N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(4-((2R)-1,4-dioxan-2-yl)-5-fluoro-2-pyrimidinyl)-2-butanesulfonamide, (2S,3R)-N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(4-((2S)-1,4-dioxan-2-yl)-5-fluoro-2-pyrimidinyl)-2-butanesulfonamide |
| 640.0 | (2S,3R)-N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(4-((2R)-1,4-dioxan-2-yl)-5-fluoro-2-pyrimidinyl)-2-butanesulfonamide, (2S,3R)-N-(4-(2,6-dimethoxyphenyl)-5-(6-(3,3,3-trifluoro-2-hydroxy-2-(trifluoromethyl)propoxy)-2-pyridinyl)-4H-1,2,4-triazol-3-yl)-3-(4-((2S)-1,4-dioxan-2-yl)-5-fluoro-2-pyrimidinyl)-2-butanesulfonamide |

TABLE 57-continued

| Example | Alternative Names |
|---|---|
| 641.0 | (2S,3R)-N-(4-(2,6-dimethoxyphenyl)-5-(6-(methylamino)-2-pyridinyl)-4H-1,2,4-triazol-3-yl)-3-(5-fluoro-2-pyrimidinyl)-2-butanesulfonamide |
| 642.0 | (1R,2S)-1-(5-bromo-6-methyl-2-pyridinyl)-N-(4-(2,6-dimethoxyphenyl)-5-(3-pyridinyl)-4H-1,2,4-triazol-3-yl)-1-hydroxy-2-propanesulfonamide, (1S,2R)-1-(5-bromo-6-methyl-2-pyridinyl)-N-(4-(2,6-dimethoxyphenyl)-5-(3-pyridinyl)-4H-1,2,4-triazol-3-yl)-1-hydroxy-2-propanesulfonamide |
| 643.0 | (2R,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide |
| 644.0 | (2R,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide |
| 645.0 | (2R,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide |
| 646.0 | (2R,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(5-methyl-3-pyridinyl)-4H-1,2,4-triazol-3-yl)-2-(5-methyl-2-pyrimidinyl)tetrahydro-2H-pyran-3-sulfonamide |
| 647.0 | (2S,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2S,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide |
| 648.0 | (2S,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2R,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide |
| 649.0 | (2S,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2S,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide |
| 650.0 | (2S,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide |
| 651.0 | (2S,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide |
| 652.0 | (2S,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(5- |

TABLE 57-continued

| Example | Alternative Names |
|---|---|
| | methyl-3-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide |
| 653.0 | (2S,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(5-methyl-3-pyridinyl)-4H-1,2,4-triazol-3-yl)-3-(4-methyl-1H-pyrazol-1-yl)-2-butanesulfonamide |
| 654.0 | (2R,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide |
| 655.0 | (2R,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide |
| 656.0 | (2R,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide |
| 657.0 | (2R,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2S,3R)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide, (2R,3S)-N-(4-(2,6-dimethoxyphenyl)-5-(6-methoxy-2-pyridinyl)-4H-1,2,4-triazol-3-yl)-2-(5-methyl-2-pyrimidinyl)tetrahydro-2H-pyran-3-sulfonamide |
| 658.0 | (2S,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide |
| 659.0 | (2S,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide |
| 660.0 | (2S,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide |
| 661.0 | (2S,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2S,3S)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide, (2R,3R)-N-(4-(2,6-dimethoxyphenyl)-5-(6-methoxy-2-pyridinyl)-4H-1,2,4-triazol-3-yl)-3-(4-methyl-1H-pyrazol-1-yl)-2-butanesulfonamide |
| 662.0 | (2R)-N-(4-(2,6-dimethoxyphenyl)-5-(6-(methylamino)-2-pyridinyl)-4H-1,2,4-triazol-3-yl)-1-(5-fluoro-2-pyrimidinyl)-2-propanesulfonamide, (2S)-N-(4-(2,6-dimethoxyphenyl)-5-(6-(methylamino)-2-pyridinyl)-4H-1,2,4-triazol-3-yl)-1-(5-fluoro-2-pyrimidinyl)-2-propanesulfonamide |
| 663.0 | (2R)-N-(4-(2,6-dimethoxyphenyl)-5-(6-(methylamino)-2-pyridinyl)-4H-1,2,4-triazol-3-yl)-1-(5-fluoro-2-pyrimidinyl)-2-propanesulfonamide, (2S)-N-(4-(2,6-dimethoxyphenyl)-5-(6-(methylamino)-2-pyridinyl)-4H-1,2,4-triazol-3-yl)-1-(5-fluoro-2-pyrimidinyl)-2-propanesulfonamide |

TABLE 57-continued

| Example | Alternative Names |
| --- | --- |
| 664.0 | (1R,2S)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 665.0 | (1R,2S)-N-(4-(2-ethoxy-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 666.0 | (1R,2S)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 667.0 | (1R,2S)-N-(4-(2-(difluoromethoxy)-6-methoxyphenyl)-5-(3-pyridinyl)-4H-1,2,4-triazol-3-yl)-1-methoxy-1-(5-methyl-2-pyrimidinyl)-2-propanesulfonamide |
| 668.0 | (1R,2S)-N-(4-(2-(difluoromethoxy)-6-methoxyphenyl)-5-(5-methyl-3-pyridinyl)-4H-1,2,4-triazol-3-yl)-1-methoxy-1-(5-methyl-2-pyrimidinyl)-2-propanesulfonamide |
| 669.0 | (1R,2S)-N-(4-(2,6-bis(difluoromethoxy)phenyl)-5-(3-pyridinyl)-4H-1,2,4-triazol-3-yl)-1-methoxy-1-(5-methyl-2-pyrimidinyl)-2-propanesulfonamide |
| 670.0 | (1R,2S)-N-(4-(2,6-bis(difluoromethoxy)phenyl)-5-(5-methyl-3-pyridinyl)-4H-1,2,4-triazol-3-yl)-1-methoxy-1-(5-methyl-2-pyrimidinyl)-2-propanesulfonamide |
| 671.0 | (2R,3R)-N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide, (2S,3S)-N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide |
| 672.0 | (2S,3R)-N-(4-(2,6-dimethoxyphenyl)-5-(3-pyridinyl)-4H-1,2,4-triazol-3-yl)-3-(5-methoxy-2-pyrimidinyl)-2-butanesulfonamide |
| 673.0 | (1R,2S)-N-(4-(2,6-dimethylphenyl)-5-(5-methyl-3-pyridinyl)-4H-1,2,4-triazol-3-yl)-1-methoxy-1-(5-methyl-2-pyrimidinyl)-2-propanesulfonamide |
| 674.0 | (1R,2S)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 675.0 | (1R,2S)-N-(4-(2,6-dichlorophenyl)-5-(5-methyl-3-pyridinyl)-4H-1,2,4-triazol-3-yl)-1-methoxy-1-(5-methyl-2-pyrimidinyl)-2-propanesulfonamide |
| 676.0 | N-(4-(2,6-dimethoxyphenyl)-5-(6-methoxy-2-pyridinyl)-4H-1,2,4-triazol-3-yl)-2-(5-fluoro-2-pyrimidinyl)ethanesulfonamide |
| 677.0 | (1R,2S)-N-(4-(2,6-difluorophenyl)-5-(5-methyl-3-pyridinyl)-4H-1,2,4-triazol-3-yl)-1-methoxy-1-(5-methyl-2-pyrimidinyl)-2-propanesulfonamide |
| 678.0 | (1R,2S)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 679.0 | (1R,2S)-N-(4-(2-fluoro-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 680.0 | (2R,3S)-3-(5-chloro-2-pyrimidinyl)-N-(4-(2,6-dimethoxyphenyl)-5-(5-methyl-3-pyridinyl)-4H-1,2,4-triazol-3-yl)-2-butanesulfonamide, (2S,3R)-3-(5-chloro-2-pyrimidinyl)-N-(4-(2,6-dimethoxyphenyl)-5-(5-methyl-3-pyridinyl)-4H-1,2,4-triazol-3-yl)-2-butanesulfonamide |
| 681.0 | (2R,3S)-3-(5-chloro-2-pyrimidinyl)-N-(4-(2,6-dimethoxyphenyl)-5-(3-pyridinyl)-4H-1,2,4-triazol-3-yl)-2-butanesulfonamide, (2S,3R)-3-(5-chloro-2-pyrimidinyl)-N-(4-(2,6-dimethoxyphenyl)-5-(3-pyridinyl)-4H-1,2,4-triazol-3-yl)-2-butanesulfonamide |
| 682.0 | (2S,3R)-N-(4-(2,6-dimethoxyphenyl)-5-(5-methyl-3-pyridinyl)-4H-1,2,4-triazol-3-yl)-3-(5-methoxy-2-pyrimidinyl)-2-butanesulfonamide |
| 683.0 | (2R,3S)-3-(5-chloro-2-pyrimidinyl)-N-(4-(2,6-dimethoxyphenyl)-5-(3-pyridinyl)-4H-1,2,4-triazol-3-yl)-2-butanesulfonamide, (2S,3R)-3-(5-chloro-2-pyrimidinyl)-N-(4-(2,6-dimethoxyphenyl)-5-(3-pyridinyl)-4H-1,2,4-triazol-3-yl)-2-butanesulfonamide |
| 684.0 | (1R,2S)-N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide |
| 685.0 | (2R,3S)-3-(5-chloro-2-pyrimidinyl)-N-(4-(2,6-dimethoxyphenyl)-5-(5-methyl-3-pyridinyl)-4H-1,2,4-triazol-3-yl)-2-butanesulfonamide, (2S,3R)-3-(5-chloro-2-pyrimidinyl)-N-(4-(2,6-dimethoxyphenyl)-5-(5-methyl-3-pyridinyl)-4H-1,2,4-triazol-3-yl)-2-butanesulfonamide |
| 686.0 | (2R,3S)-3-(5-chloro-2-pyrimidinyl)-N-(4-(2,6-dimethoxyphenyl)-5-(5-methyl-3-pyridinyl)-4H-1,2,4-triazol-3-yl)-2-butanesulfonamide, (2S,3R)-3-(5-chloro-2-pyrimidinyl)-N-(4-(2,6-dimethoxyphenyl)-5-(5-methyl-3-pyridinyl)-4H-1,2,4-triazol-3-yl)-2-butanesulfonamide |
| 687.0 | (1R,2R)-N-(4-(2,6-dimethoxyphenyl)-5-(5-methyl-3-pyridinyl)-4H-1,2,4-triazol-3-yl)-1-methoxy-1-(5-methoxy-2-pyrimidinyl)-2-propanesulfonamide |
| 688.0 | (2S,3R)-N-(4-(2-fluoro-6-methoxyphenyl)-5-(5-methyl-3-pyridinyl)-4H-1,2,4-triazol-3-yl)-3-(5-methyl-2-pyrimidinyl)-2-butanesulfonamide |
| 689.0 | (1R,2S)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide |
| 690.0 | (1R,2S)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 691.0 | (1R,2S)-N-(4-(2-(difluoromethoxy)-6-methoxyphenyl)-5-(6-methoxy-2-pyridinyl)-4H-1,2,4-triazol-3-yl)-1-methoxy-1-(5-methyl-2-pyrimidinyl)-2-propanesulfonamide |
| 692.0 | (1R,2S)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide |
| 693.0 | (1R,2S)-N-(4-(2-fluoro-6-methoxyphenyl)-5-(5-methyl-3-pyridinyl)-4H-1,2,4-triazol-3-yl)-1-methoxy-1-(5-methyl-2-pyrimidinyl)-2-propanesulfonamide |
| 694.0 | (2S,3R)-3-(5-chloro-2-pyrimidinyl)-N-(4-(2,6-dimethoxyphenyl)-5-(3-pyridinyl)-4H-1,2,4-triazol-3-yl)-2-butanesulfonamide, (2R,3S)-3-(5-chloro-2-pyrimidinyl)-N-(4-(2,6-dimethoxyphenyl)-5-(3-pyridinyl)-4H-1,2,4-triazol-3-yl)-2-butanesulfonamide |
| 695.0 | (1R,2S)-N-(4-(2,6-dimethoxyphenyl)-5-(6-methoxy-2-pyridinyl)-4H-1,2,4-triazol-3-yl)-1-(2-methoxyethoxy)-1-(5-methyl-2-pyrimidinyl)-2-propanesulfonamide |
| 696.0 | (2S,3R)-3-(5-chloro-2-pyrimidinyl)-N-(4-(2,6-dimethoxyphenyl)-5-(6-methoxy-2-pyridinyl)-4H-1,2,4-triazol-3-yl)-2-butanesulfonamide |

TABLE 57-continued

| Example | Alternative Names |
|---|---|
| 697.0 | (2S,3R)-3-(5-cyano-2-pyrimidinyl)-N-(4-(2,6-dimethoxyphenyl)-5-(5-methyl-3-pyridinyl)-4H-1,2,4-triazol-3-yl)-2-butanesulfonamide |
| 698.0 | (1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide, (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide |
| 699.0 | (1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide, (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide |
| 700.0 | (1R,2R)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide, (1S,2S)-1-(5-chloro-1,3-thiazol-2-yl)-N-(4-(2,6-dimethoxyphenyl)-5-(3-pyridinyl)-4H-1,2,4-triazol-3-yl)-1-methoxy-2-propanesulfonamide |
| 701.0 | (2R,3S)-N-(4-(2,6-dimethoxyphenyl)-5-(3-pyridinyl)-4H-1,2,4-triazol-3-yl)-3-(5-methyl-2-pyrazinyl)-2-butanesulfonamide, (2S,3R)-N-(4-(2,6-dimethoxyphenyl)-5-(3-pyridinyl)-4H-1,2,4-triazol-3-yl)-3-(5-methyl-2-pyrazinyl)-2-butanesulfonamide |
| 702.0 | (2R,3S)-N-(4-(2,6-dimethoxyphenyl)-5-(3-pyridinyl)-4H-1,2,4-triazol-3-yl)-3-(5-methyl-2-pyrazinyl)-2-butanesulfonamide, (2S,3R)-N-(4-(2,6-dimethoxyphenyl)-5-(3-pyridinyl)-4H-1,2,4-triazol-3-yl)-3-(5-methyl-2-pyrazinyl)-2-butanesulfonamide |
| 703.0 | (1R,2S)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide, (1S,2R)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide |
| 704.0 | (2R,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide, (2R,3S)-N-(4-(2,6-dimethoxyphenyl)-5-(3-pyridinyl)-4H-1,2,4-triazol-3-yl)-3-(5-methoxy-2-pyrazinyl)-2-butanesulfonamide (2S,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide, (2S,3S)-N-(4-(2,6-dimethoxyphenyl)-5-(3-pyridinyl)-4H-1,2,4-triazol-3-yl)-3-(5-methoxy-2-pyrazinyl)-2-butanesulfonamide |
| 705.0 | (2R,3S)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide, (2S,3R)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide |
| 706.0 | (1S,2R)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide, (1R,2S)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide |
| 707.0 | (1S,2R)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide, (1R,2S)-N-(4-(2,6-dimethoxyphenyl)-5-(3-pyridinyl)-4H-1,2,4-triazol-3-yl)-1-hydroxy-1-(5-methoxy-2-pyrazinyl)-2-propanesulfonamide |
| 708.0 | (2S,3R)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide, (2R,3S)-N-(4-(2,6-dimethoxyphenyl)-5-(6-methoxy-2-pyridinyl)-4H-1,2,4-triazol-3-yl)-3-(5-methoxy-2-pyrazinyl)-2-butanesulfonamide |
| 709.0 | (2S,3R)-3-(5-chloro-2-pyrimidinyl)-N-(4-(4,6-dimethoxy-5-pyrimidinyl)-5-(3-pyridinyl)-4H-1,2,4-triazol-3-yl)-2-butanesulfonamide |
| 710.0 | (2S,3R)-3-(5-chloro-2-pyrimidinyl)-N-(4-(4,6-dimethoxy-5-pyrimidinyl)-5-(6-methoxy-2-pyridinyl)-4H-1,2,4-triazol-3-yl)-2-butanesulfonamide |
| 711.0 | (1R,2S)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide, (1S,2R)-1-(5-chloro-2-pyridinyl)-N-(4-(4,6-dimethoxy-5-pyrimidinyl)-5-(3-pyridinyl)-4H-1,2,4-triazol-3-yl)-1-methoxy-2-propanesulfonamide |
| 712.0 | (1R,2S)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide, (1S,2R)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide |
| 713.0 | (2R,3S)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide, (2S,3R)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide |
| 714.0 | (1R,2S)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide |
| 715.0 | (1R,2S)-1-(5-chloro-2-pyridinyl)-N-(4-(2,4-dimethoxy-3-pyridinyl)-5-(3-pyridinyl)-4H-1,2,4-triazol-3-yl)-1-methoxy-2-propanesulfonamide |
| 716.0 | (2S,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide |
| 717.0 | (2S,3R)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide |
| 718.0 | (2S,3R)-3-(5-chloro-2-pyrimidinyl)-N-(4-(2,4-dimethoxy-3-pyridinyl)-5-(3-pyridinyl)-4H-1,2,4-triazol-3-yl)-2-butanesulfonamide |
| 719.0 | (1R,2S)-1-cyclobutyl-N-(4-(2,6-dimethoxyphenyl)-5-(5-methyl-3-pyridinyl)-4H-1,2,4-triazol-3-yl)-1-methoxy-2-propanesulfonamide, (1S,2R)-1-cyclobutyl-N-(4-(2,6-dimethoxyphenyl)-5-(5-methyl-3-pyridinyl)-4H-1,2,4-triazol-3-yl)-1-methoxy-2-propanesulfonamide, (1S,2S)-1-cyclobutyl-N-(4-(2,6-dimethoxyphenyl)-5-(5-methyl-3-pyridinyl)-4H-1,2,4-triazol-3-yl)-1-methoxy-2-propanesulfonamide, (1R,2R)-1- |

TABLE 57-continued

| Example | Alternative Names |
|---|---|
| | cyclobutyl-N-(4-(2,6-dimethoxyphenyl)-5-(5-methyl-3-pyridinyl)-4H-1,2,4-triazol-3-yl)-1-methoxy-2-propanesulfonamide |
| 720.0 | (1S,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide |
| 721.0 | (1S,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide |
| 722.0 | (1S,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide |
| 723.0 | (1S,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1S,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2S)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide, (1R,2R)-1-(3,3-difluorocyclobutyl)-N-(4-(2,6-dimethoxyphenyl)-5-(6-methoxy-2-pyridinyl)-4H-1,2,4-triazol-3-yl)-1-hydroxy-2-propanesulfonamide |
| 724.0 | (1R,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide |
| 725.0 | (1R,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide |
| 726.0 | (1R,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide |
| 727.0 | (1R,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1S,2S)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide, (1R,2R)-N-(4-(2,6-dimethoxyphenyl)-5-(5-methyl-3-pyridinyl)-4H-1,2,4-triazol-3-yl)-1-(3,3-dimethylcyclobutyl)-1-methoxy-2-propanesulfonamide |
| 728.0 | (2R)-N-(4-(2,6-dimethoxyphenyl)-5-(5-methyl-3-pyridinyl)-4H-1,2,4-triazol-3-yl)-2-hydroxy-2-(5-methyl-2-pyrimidinyl)ethanesulfonamide, (2S)-N-(4-(2,6-dimethoxyphenyl)-5-(5-methyl-3-pyridinyl)-4H-1,2,4-triazol-3-yl)-2-hydroxy-2-(5-methyl-2-pyrimidinyl)ethanesulfonamide |
| 729.0 | (2R)-N-(4-(2,6-dimethoxyphenyl)-5-(5-methyl-3-pyridinyl)-4H-1,2,4-triazol-3-yl)-2-hydroxy-2-(5-methyl-2-pyrimidinyl)ethanesulfonamide, (2S)-N-(4-(2,6-dimethoxyphenyl)-5-(5-methyl-3-pyridinyl)-4H-1,2,4-triazol-3-yl)-2-hydroxy-2-(5-methyl-2-pyrimidinyl)ethanesulfonamide |
| 730.0 | (1R,2S)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide, (1S,2R)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide, (1S,2S)-N-(4-(4,6- |

TABLE 57-continued

| Example | Alternative Names |
|---|---|
| | dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide, (1R,2R)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide |
| 731.0 | (1R,2S)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide, (1S,2R)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide, (1S,2S)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide, (1R,2R)-N-(4-(4,6-dimethoxy-5-pyrimidinyl)-5-(6-methoxy-2-pyridinyl)-4H-1,2,4-triazol-3-yl)-1-(3,3-dimethylcyclobutyl)-1-methoxy-2-propanesulfonamide |
| 732.0 | (2S,3R)-N-(4-(3,5-dibromo-2,6-dimethoxyphenyl)-5-(5-methyl-3-pyridinyl)-4H-1,2,4-triazol-3-yl)-3-(5-methyl-2-pyrimidinyl)-2-butanesulfonamide |
| 733.0 | (2S,3R)-N-(5-(5-bromo-3-pyridinyl)-4-(2,6-dimethoxyphenyl)-4H-1,2,4-triazol-3-yl)-3-(5-methyl-2-pyrimidinyl)-2-butanesulfonamide |
| 734.0 | (2S,3R)-N-(5-(5-cyclopropyl-3-pyridinyl)-4-(2,6-dimethoxyphenyl)-4H-1,2,4-triazol-3-yl)-3-(5-methyl-2-pyrimidinyl)-2-butanesulfonamide |
| 735.0 | (1S,2R)-N-(4-(2,6-dimethoxyphenyl)-5-(3-pyridinyl)-4H-1,2,4-triazol-3-yl)-1-hydroxy-1-imidazo[1,2-a]pyridin-2-yl-2-propanesulfonamide, (1R,2S)-N-(4-(2,6-dimethoxyphenyl)-5-(3-pyridinyl)-4H-1,2,4-triazol-3-yl)-1-hydroxy-1-imidazo[1,2-a]pyridin-2-yl-2-propanesulfonamide |
| 736.0 | (1S,2R)-N-(4-(2,6-dimethoxyphenyl)-5-(3-pyridinyl)-4H-1,2,4-triazol-3-yl)-1-hydroxy-1-imidazo[1,2-a]pyridin-2-yl-2-propanesulfonamide, (1R,2S)-N-(4-(2,6-dimethoxyphenyl)-5-(3-pyridinyl)-4H-1,2,4-triazol-3-yl)-1-hydroxy-1-imidazo[1,2-a]pyridin-2-yl-2-propanesulfonamide |
| 737.0 | (1R,2S)-N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide, (1S,2R)-N-(4-(2,6-difluorophenyl)-5-(5-methyl-3-pyridinyl)-4H-1,2,4-triazol-3-yl)-1-ethoxy-1-(5-methyl-2-pyrimidinyl)-2-propanesulfonamide |
| 738.0 | (1S,2S)-N-(4-(2,6-dimethoxyphenyl)-5-(6-methyl-2-pyridinyl)-4H-1,2,4-triazol-3-yl)-1-(1-methylethoxy)-1-(5-methyl-2-pyrimidinyl)-2-propanesulfonamide |
| 739.0 | (1R,2S)-1-methoxy-N-(4-(4-methoxy-6-oxo-1,6-dihydropyrimidin-5-yl)-5-(6-methoxypyridin-2-yl)-4H-1,2,4-triazol-3-yl)-1-(5-methylpyrimidin-2-yl)propane-2-sulfonamide (name of tautomer) |
| 740.0 | (1R,2S)-1-methoxy-N-(4-(4-methoxy-6-oxo-1,6-dihydro-5-pyrimidinyl)-5-(6-methoxy-2-pyridinyl)-4H-1,2,4-triazol-3-yl)-1-(5-methyl-2-pyrimidinyl)-2-propanesulfonamide (name of tautomer). |
| 741.0 | (1R,2S)-1-methoxy-N-(4-(2-methoxy-3-pyridinyl)-5-(6-methoxy-2-pyridinyl)-4H-1,2,4-triazol-3-yl)-1-(5-methyl-2-pyrimidinyl)-2-propanesulfonamide |
| 742.0 | (1R,2R)-N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide, (1S,2S)-N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide |
| 743.0 | (1R,2R)-N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide, (1S,2S)-N-(4-(2,6-dimethoxyphenyl)-5-(5-methyl-3-pyridinyl)-4H-1,2,4-triazol-3-yl)-1-(5-methoxy-2-pyrazinyl)-1-(1-methylethoxy)-2-propanesulfonamide |
| 744.0 | (1R,2R)-1-(5-chloro-2-pyridinyl)-N-(4-(2,6-dimethoxyphenyl)-5-(5-methyl-3-pyridinyl)-4H-1,2,4-triazol-3-yl)-1-(1-methylethoxy)-2-propanesulfonamide, (1S,2S)-1-(5-chloro-2-pyridinyl)-N-(4-(2,6-dimethoxyphenyl)-5-(5-methyl-3-pyridinyl)-4H-1,2,4-triazol-3-yl)-1-(1-methylethoxy)-2-propanesulfonamide |
| 745.0 | (1R,2R)-1-(5-chloro-2-pyridinyl)-N-(4-(2,6-dimethoxyphenyl)-5-(5-methyl-3-pyridinyl)-4H-1,2,4-triazol-3-yl)-1-(1-methylethoxy)-2-propanesulfonamide, (1S,2S)-1-(5-chloro-2-pyridinyl)-N-(4-(2,6-dimethoxyphenyl)-5-(5-methyl-3-pyridinyl)-4H-1,2,4-triazol-3-yl)-1-(1-methylethoxy)-2-propanesulfonamide |
| 746.0 | (1R,2R)-N-(4-(2,6-dimethoxyphenyl)-5-(5-methyl-3-pyridinyl)-4H-1,2,4-triazol-3-yl)-1-(1-methylethoxy)-1-(5-methyl-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-(1-methylethoxy)-1-(5-methyl-2-pyrazinyl)-2-propanesulfonamide |
| 747.0 | (1R,2R)-N-(4-(2,6-dimethoxyphenyl)-5-(5-methyl-3-pyridinyl)-4H-1,2,4-triazol-3-yl)-1-(1-methylethoxy)-1-(5-methyl-2-pyrazinyl)-2-propanesulfonamide, (1S,2S)-N-(4-(2,6-dimethoxyphenyl)-5-(5-methyl-3-pyridinyl)-4H-1,2,4-triazol-3-yl)-1-(1-methylethoxy)-1-(5-methyl-2-pyrazinyl)-2-propanesulfonamide |
| 748.0 | (1S,2S)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide |
| 749.0 | (1R,2S)-1-(5-(3,6-dihydro-2H-pyran-4-yl)-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide |
| 750.0 | (1R,2S)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide |
| 751.0 | (1R,2R)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide, |

TABLE 57-continued

| Example | Alternative Names |
|---|---|
| | (1S,2S)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide |
| 752.0 | (1R,2S)-N-(4-(2,6-dimethoxyphenyl)-5-(5-methyl-3-pyridinyl)-4H-1,2,4-triazol-3-yl)-1-methoxy-1-(5-(3-pyridinyl)-2-pyrimidinyl)-2-propanesulfonamide |
| 753.0 | (1R,2S)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide |
| 754.0 | (1R,2R)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide |
| 755.0 | (1R,2S)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide |
| 756.0 | (1R,2S)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide, (1S,2R)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide |
| 757.0 | (1S,2S)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide, (1R,2R)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide |
| 758.0 | (1R,2R)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide, (1S,2S)-N-(4-(2,6-dimethoxyphenyl)-5-(5-methyl-3-pyridinyl)-4H-1,2,4-triazol-3-yl)-1-(methylamino)-1-(5-methyl-2-pyrimidinyl)-2-propanesulfonamide |
| 759.0 | (1R,2S)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide |
| 760.0 | (1R,2S)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide, (1S,2R)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide |
| 761.0 | (1R,2R)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide |
| 762.0 | (1R,2R)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide, (1S,2S)-N-(4-(2,6-dimethoxyphenyl)-5-(6-methoxy-2-pyridinyl)-4H-1,2,4-triazol-3-yl)-1-(3-methoxy-1-azetidinyl)-1-(5-methyl-2-pyrimidinyl)-2-propanesulfonamide |
| 763.0 | (2S,3R)-N-(4-(2,6-bis(difluoromethoxy)phenyl)-5-(5-methyl-3-pyridinyl)-4H-1,2,4-triazol-3-yl)-3-(5-methyl-2-pyrimidinyl)-2-butanesulfonamide |
| 764.0 | (2R,3S)-N-(4-(2,6-dimethoxyphenyl)-5-(5-methyl-3-pyridinyl)-4H-1,2,4-triazol-3-yl)-3-hydroxy-4-hexyne-2-sulfonamide, (2S,3R)-N-(4-(2,6-dimethoxyphenyl)-5-(5-methyl-3-pyridinyl)-4H-1,2,4-triazol-3-yl)-3-hydroxy-4-hexyne-2-sulfonamide |
| 765.0 | (1R,2S)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide |
| 766.0 | (1R,2S)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide, (1S,2R)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide |
| 767.0 | (1R,2S)-N-(4-(2,6-dimethoxyphenyl)-5-(3-pyridinyl)-4H-1,2,4-triazol-3-yl)-1-hydroxy-1-(6-methyl-3-pyridazinyl)-2-propanesulfonamide, (1S,2R)-N-(4-(2,6-dimethoxyphenyl)-5-(3-pyridinyl)-4H-1,2,4-triazol-3-yl)-1-hydroxy-1-(6-methyl-3-pyridazinyl)-2-propanesulfonamide |
| 768.0 | (1R,2S)-N-(4-(2,6-dimethoxyphenyl)-5-(3-pyridinyl)-4H-1,2,4-triazol-3-yl)-1-hydroxy-1-(6-methyl-3-pyridazinyl)-2-propanesulfonamide, (1S,2R)-N-(4-(2,6-dimethoxyphenyl)-5-(3-pyridinyl)-4H-1,2,4-triazol-3-yl)-1-hydroxy-1-(6-methyl-3-pyridazinyl)-2-propanesulfonamide |
| 769.0 | (1S,2S)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide |
| 770.0 | (1S,2S)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide, (1R,2R)-N-(4-(2,6-dimethoxyphenyl)-5-(5-methyl-3-pyridinyl)-4H-1,2,4-triazol-3-yl)-1-hydroxy-1-(6-methyl-3-pyridazinyl)-2-propanesulfonamide |
| 771.0 | (1R,2S)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide |
| 772.0 | (1R,2S)-N-(4-(2,4-dimethoxy-3-pyridinyl)-5-(6-methoxy-2-pyridinyl)-4H-1,2,4-triazol-3-yl)-1-methoxy-1-(5-methyl-2-pyrimidinyl)-2-propanesulfonamide |

TABLE 57-continued

| Example | Alternative Names |
| --- | --- |
| 773.0 | (2S,3R)-N-(4-(4,6-dimethoxy-5-pyrimidinyl)-5-(2-pyridinyl)-4H-1,2,4-triazol-3-yl)-3-(5-methyl-2-pyrazinyl)-2-butanesulfonamide |
| 774.0 | (2S,3R)-N-(4-(2,6-dimethoxyphenyl)-5-(2-pyridinyl)-4H-1,2,4-triazol-3-yl)-3-(5-methyl-2-pyrazinyl)-2-butanesulfonamide |
| 775.0 | (2S,3R)-N-(4-(2,6-dimethoxyphenyl)-5-(2-pyridinyl)-4H-1,2,4-triazol-3-yl)-3-(5-methyl-2-pyrimidinyl)-2-butanesulfonamide |
| 776.0 | (2S,3R)-N-(4-(4,6-dimethoxy-5-pyrimidinyl)-5-(2-pyridinyl)-4H-1,2,4-triazol-3-yl)-3-(5-methyl-2-pyrimidinyl)-2-butanesulfonamide |
| 777.0 | (1S,2S)-N-(4-(4,6-dimethoxy-5-pyrimidinyl)-5-(2-pyridinyl)-4H-1,2,4-triazol-3-yl)-1-(1-methylethoxy)-1-(5-methyl-2-pyrimidinyl)-2-propanesulfonamide |
| 778.0 | (1S,2S)-N-(4-(2,6-dimethoxyphenyl)-5-(2-pyridinyl)-4H-1,2,4-triazol-3-yl)-1-(1-methylethoxy)-1-(5-methyl-2-pyrimidinyl)-2-propanesulfonamide |
| 779.0 | (1R,2S)-N-(4-(4,6-dimethoxy-5-pyrimidinyl)-5-(2-pyridinyl)-4H-1,2,4-triazol-3-yl)-1-methoxy-1-(5-methyl-2-pyrazinyl)-2-propanesulfonamide |
| 780.0 | (1R,2S)-N-(4-(2,6-dimethoxyphenyl)-5-(2-pyridinyl)-4H-1,2,4-triazol-3-yl)-1-methoxy-1-(5-methyl-2-pyrazinyl)-2-propanesulfonamide |
| 781.0 | (1R,2S)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide, (1S,2R)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide |
| 782.0 | (1R,2S)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide, (1S,2R)-N-(4-(2,6-dimethoxyphenyl)-5-(5-methyl-3-pyridinyl)-4H-1,2,4-triazol-3-yl)-1-methoxy-1-(1-methyl-1H-1,2,4-triazol-5-yl)-2-propanesulfonamide |
| 783.0 | (2S,3R)-N-(4-(2,6-difluorophenyl)-5-(6-methyl-2-pyridinyl)-4H-1,2,4-triazol-3-yl)-3-(5-methyl-2-pyrimidinyl)-2-butanesulfonamide |
| 784.0 | (2S,3R)-N-(4-(2,6-difluorophenyl)-5-(6-methoxy-2-pyridinyl)-4H-1,2,4-triazol-3-yl)-3-(5-methyl-2-pyrimidinyl)-2-butanesulfonamide |
| 785.0 | (2S,3R)-N-(4-(2,6-difluorophenyl)-5-(2-pyridinyl)-4H-1,2,4-triazol-3-yl)-3-(5-methyl-2-pyrimidinyl)-2-butanesulfonamide |
| 786.0 | (2S,3R)-3-(5-chloro-2-pyrimidinyl)-N-(4-(2,6-difluorophenyl)-5-(6-methoxy-2-pyridinyl)-4H-1,2,4-triazol-3-yl)-2-butanesulfonamide |
| 787.0 | (2S,3R)-N-(4-(2,6-difluorophenyl)-5-(6-methoxy-2-pyridinyl)-4H-1,2,4-triazol-3-yl)-3-(5-methoxy-2-pyrazinyl)-2-butanesulfonamide |
| 788.0 | (2S,3R)-3-(5-chloro-2-pyrimidinyl)-N-(4-(2,6-difluorophenyl)-5-(6-methyl-2-pyridinyl)-4H-1,2,4-triazol-3-yl)-2-butanesulfonamide |
| 789.0 | (2S,3R)-N-(4-(2,6-difluorophenyl)-5-(6-methoxy-2-pyridinyl)-4H-1,2,4-triazol-3-yl)-3-(5-methyl-2-pyrazinyl)-2-butanesulfonamide |
| 790.0 | (2S,3R)-N-(4-(2,6-difluorophenyl)-5-(6-methyl-2-pyridinyl)-4H-1,2,4-triazol-3-yl)-3-(5-methyl-2-pyrazinyl)-2-butanesulfonamide |
| 791.0 | (2S,3R)-N-(4-(2,6-difluorophenyl)-5-(6-(methylamino)-2-pyridinyl)-4H-1,2,4-triazol-3-yl)-3-(5-methyl-2-pyrimidinyl)-2-butanesulfonamide |
| 792.0 | (1S,2R)-N-(4-(2,6-difluorophenyl)-5-(6-methoxy-2-pyridinyl)-4H-1,2,4-triazol-3-yl)-1-methoxy-1-(5-methyl-2-pyrimidinyl)-2-propanesulfonamide |
| 793.0 | (2S,3R)-N-(4-(2,6-difluorophenyl)-5-(3-pyridinyl)-4H-1,2,4-triazol-3-yl)-3-(5-methyl-2-pyrimidinyl)-2-butanesulfonamide |
| 794.0 | (2S,3R)-N-(4-(2,6-difluorophenyl)-5-(5-methyl-3-pyridinyl)-4H-1,2,4-triazol-3-yl)-3-(5-methoxy-2-pyrazinyl)-2-butanesulfonamide |
| 795.0 | (2S,3R)-N-(4-(2,6-difluorophenyl)-5-(5-methyl-3-pyridinyl)-4H-1,2,4-triazol-3-yl)-3-(5-methyl-2-pyrazinyl)-2-butanesulfonamide |
| 796.0 | (2S,3R)-3-(5-chloro-2-pyrimidinyl)-N-(4-(2,6-difluorophenyl)-5-(5-methyl-3-pyridinyl)-4H-1,2,4-triazol-3-yl)-2-butanesulfonamide |
| 797.0 | (2S,3R)-N-(4-(2-methoxyphenyl)-5-(5-methyl-3-pyridinyl)-4H-1,2,4-triazol-3-yl)-3-(5-methyl-2-pyrimidinyl)-2-butanesulfonamide |
| 798.0 | (2S,3R)-N-(4-(6-bromo-3-methoxy-2-pyridinyl)-5-(6-methoxy-2-pyridinyl)-4H-1,2,4-triazol-3-yl)-3-(5-fluoro-2-pyrimidinyl)-2-butanesulfonamide |
| 799.0 | (2S,3R)-N-(4-(4,6-dimethoxy-5-pyrimidinyl)-5-(6-methoxy-2-pyridinyl)-4H-1,2,4-triazol-3-yl)-3-(5-methyl-2-pyrazinyl)-2-butanesulfonamide |
| 800.0 | (3R,5S)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide |
| 801.0 | (3R,5S)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide, (3S,5R)-N-(4-(2,6-difluorophenyl)-5-(6-methoxy-2-pyridinyl)-4H-1,2,4-triazol-3-yl)-1-(5-fluoro-2-pyrimidinyl)-5-hydroxy-3-piperidinesulfonamide |
| 802.0 | (2S,3R)-3-(5-chloro-2-pyridinyl)-N-(4-(4,6-dimethoxy-5-pyrimidinyl)-5-(3-pyridinyl)-4H-1,2,4-triazol-3-yl)-2-butanesulfonamide |
| 803.0 | (2S,3R)-N-(4-(4,6-dimethoxy-5-pyrimidinyl)-5-(3-pyridinyl)-4H-1,2,4-triazol-3-yl)-3-(5-methoxy-2-pyrazinyl)-2-butanesulfonamide |
| 804.0 | (1R,2S)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide, (1S,2R)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide |
| 805.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide |

TABLE 57-continued

| Example | Alternative Names |
|---|---|
| 806.0 | (2S,3R)-N-(4-(4,6-dimethoxy-5-pyrimidinyl)-5-(3-pyridinyl)-4H-1,2,4-triazol-3-yl)-3-(5-methyl-2-pyrazinyl)-2-butanesulfonamide |
| 807.0 | (2S,3R)-3-(5-chloro-2-pyridinyl)-N-(4-(4-methoxy-6-oxo-1,6-dihydro-5-pyrimidinyl)-5-(3-pyridinyl)-4H-1,2,4-triazol-3-yl)-2-butanesulfonamide |
| 808.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide |
| 809.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-hydroxy-3-piperidinesulfonamide |
| 810.0 | (2S,3R)-3-(5-chloro-2-pyridinyl)-N-(4-(4-hydroxy-6-oxo-1,6-dihydro-5-pyrimidinyl)-5-(3-pyridinyl)-4H-1,2,4-triazol-3-yl)-2-butanesulfonamide |
| 811.0 | (1R,2S)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide, (1S,2R)-N-(4-(4,6-dimethoxy-5-pyrimidinyl)-5-(3-pyridinyl)-4H-1,2,4-triazol-3-yl)-1-methoxy-1-(5-methoxy-2-pyrazinyl)-2-propanesulfonamide |
| 812.0 | (3S,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide, (3R,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide |
| 813.0 | (3S,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide, (3R,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide |
| 814.0 | (3R,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide, (3R,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide |
| 815.0 | (3S,5S)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide, (3R,5R)-N-(4-(4,6-dimethoxy-5-pyrimidinyl)-5-(3-pyridinyl)-4H-1,2,4-triazol-3-yl)-1-(5-fluoro-2-pyrimidinyl)-5-methoxy-3-piperidinesulfonamide |
| 816.0 | (3S,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide, (3R,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide |
| 817.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide |
| 818.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide |
| 819.0 | (3S,5S)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide, (3R,5R)-N-(4-(2,6-dimethoxyphenyl)-5-(3-pyridinyl)-4H-1,2,4-triazol-3-yl)-1-(5-fluoro-2-pyrimidinyl)-5-methoxy-3-piperidinesulfonamide |
| 820.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide |
| 821.0 | (3R,5S)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide, (3S,5R)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide |
| 822.0 | (3R,5R)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide, (3S,5S)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide |
| 823.0 | (3R,5R)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide, (3S,5S)-N-(4-(2,6-dimethoxyphenyl)-5-(3-pyridinyl)-4H-1,2,4-triazol-3-yl)-1-(5-fluoro-2-pyrimidinyl)-5-(1-methylethoxy)-3-piperidinesulfonamide |
| 824.0 | (1S,2S)-N-(4-(2,6-dimethoxyphenyl)-5-(6-methyl-2-pyridinyl)-4H-1,2,4-triazol-3-yl)-1-(1-methylethoxy)-1-(5-methyl-2-pyrazinyl)-2-propanesulfonamide, (1R,2R)-N-(4-(2,6-dimethoxyphenyl)-5-(6-methyl-2-pyridinyl)-4H-1,2,4-triazol-3-yl)-1-(1-methylethoxy)-1-(5-methyl-2-pyrazinyl)-2-propanesulfonamide |
| 825.0 | (1S,2S)-N-(4-(2,6-dimethoxyphenyl)-5-(6-methoxy-2-pyridinyl)-4H-1,2,4-triazol-3-yl)-1-(1-methylethoxy)-1-(5-methyl-2-pyrazinyl)-2-propanesulfonamide, (1R,2R)-N-(4-(2,6-dimethoxyphenyl)-5-(6-methoxy-2-pyridinyl)-4H-1,2,4-triazol-3-yl)-1-(1-methylethoxy)-1-(5-methyl-2-pyrazinyl)-2-propanesulfonamide |
| 826.0 | (2S,3R)-N-(4-(2,6-difluorophenyl)-5-(5-methyl-3-pyridinyl)-4H-1,2,4-triazol-3-yl)-3-(5-methyl-2-pyrimidinyl)-2-butanesulfonamide, (2R,3S)-N-(4-(2,6-difluorophenyl)-5-(5-methyl-3-pyridinyl)-4H-1,2,4-triazol-3-yl)-3-(5-methyl-2-pyrimidinyl)-2-butanesulfonamide |

TABLE 57-continued

| Example | Alternative Names |
|---|---|
| 827.0 | (1R,2R)-N-(4-(2,6-dimethoxyphenyl)-5-(3-pyridinyl)-4H-1,2,4-triazol-3-yl)-1-imidazo[1,2-a]pyridin-2-yl-1-(1-methylethoxy)-2-propanesulfonamide, (1S,2S)-N-(4-(2,6-dimethoxyphenyl)-5-(3-pyridinyl)-4H-1,2,4-triazol-3-yl)-1-imidazo[1,2-a]pyridin-2-yl-1-(1-methylethoxy)-2-propanesulfonamide |
| 828.0 | (1R,2R)-N-(4-(2,6-dimethoxyphenyl)-5-(3-pyridinyl)-4H-1,2,4-triazol-3-yl)-1-imidazo[1,2-a]pyridin-2-yl-1-(1-methylethoxy)-2-propanesulfonamide, (1S,2S)-N-(4-(2,6-dimethoxyphenyl)-5-(3-pyridinyl)-4H-1,2,4-triazol-3-yl)-1-imidazo[1,2-a]pyridin-2-yl-1-(1-methylethoxy)-2-propanesulfonamide |
| 829.0 | (1S,2S)-N-(4-(4,6-dimethoxy-5-pyrimidinyl)-5-(5-methyl-3-pyridinyl)-4H-1,2,4-triazol-3-yl)-1-(1-methylethoxy)-1-(5-methyl-2-pyrimidinyl)-2-propanesulfonamide |
| 830.0 | (3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide, (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide |
| 831.0 | (3R)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide, (3S)-1-(5-chloro-2-pyrimidinyl)-N-(4-(4,6-dimethoxy-5-pyrimidinyl)-5-(6-methoxy-2-pyridinyl)-4H-1,2,4-triazol-3-yl)-3-piperidinesulfonamide |
| 832.0 | 1-cyclopropyl-N-(4-(2,6-dimethoxyphenyl)-5-(6-methoxy-2-pyridinyl)-4H-1,2,4-triazol-3-yl)methanesulfonamide |
| 833.0 | (2S,3R)-N-(5-(5-cyano-3-pyridinyl)-4-(2,6-dimethoxyphenyl)-4H-1,2,4-triazol-3-yl)-3-(5-methyl-2-pyrimidinyl)-2-butanesulfonamide |
| 834.0 | 5-(4-(2,6-dimethoxyphenyl)-5-(((((1S,2R)-1-methyl-2-(5-methyl-2-pyrimidinyl)propyl)sulfonyl)amino)-4H-1,2,4-triazol-3-yl)-3-pyridinecarboxylic acid |
| 835.0 | (2S,3R)-3-(5-chloro-2-pyrimidinyl)-N-(5-(6-methoxy-2-pyridinyl)-4-(tetrahydro-2H-pyran-4-yl)-4H-1,2,4-triazol-3-yl)-2-butanesulfonamide |
| 836.0 | (1R,2S)-1-(5-chloro-2-pyrimidinyl)-1-methoxy-N-(5-(6-methoxy-2-pyridinyl)-4-(tetrahydro-2H-pyran-4-yl)-4H-1,2,4-triazol-3-yl)-2-propanesulfonamide |
| 837.0 | (1S,2S)-N-(5-(6-methoxy-2-pyridinyl)-4-(tetrahydro-2H-pyran-4-yl)-4H-1,2,4-triazol-3-yl)-1-(1-methylethoxy)-1-(5-methyl-2-pyrimidinyl)-2-propanesulfonamide |
| 838.0 | (2S,3R)-3-(5-chloro-2-pyrimidinyl)-N-(4-(4-methoxy-2-oxo-1,2-dihydro-3-pyridinyl)-5-(3-pyridinyl)-4H-1,2,4-triazol-3-yl)-2-butanesulfonamide |
| 839.0 | (2S,3R)-3-(5-chloro-2-pyrimidinyl)-N-(4-(4-methoxy-2-oxo-1,2-dihydro-3-pyridinyl)-5-(3-pyridinyl)-4H-1,2,4-triazol-3-yl)-2-butanesulfonamide |
| 840.0 | (2S,3R)-3-(5-chloro-2-pyrimidinyl)-N-(5-(6-methoxy-2-pyridinyl)-4-(tetrahydro-2H-pyran-4-yl)-4H-1,2,4-triazol-3-yl)-2-butanesulfonamide |
| 841.0 | (1R,2S)-1-(5-chloro-2-pyridinyl)-1-methoxy-N-(5-(6-methoxy-2-pyridinyl)-4-(tetrahydro-2H-pyran-4-yl)-4H-1,2,4-triazol-3-yl)-2-propanesulfonamide |
| 842.0 | (2S,3R)-N-(5-(6-methoxy-2-pyridinyl)-4-(tetrahydro-2H-pyran-4-yl)-4H-1,2,4-triazol-3-yl)-3-(5-methoxy-2-pyrimidinyl)-2-butanesulfonamide |
| 843.0 | (2S,3R)-N-(5-(6-methoxy-2-pyridinyl)-4-(tetrahydro-2H-pyran-4-yl)-4H-1,2,4-triazol-3-yl)-3-(5-methyl-2-pyrazinyl)-2-butanesulfonamide |
| 844.0 | (2S,3R)-3-(5-methoxy-2-pyrazinyl)-N-(5-(6-methoxy-2-pyridinyl)-4-(tetrahydro-2H-pyran-4-yl)-4H-1,2,4-triazol-3-yl)-2-butanesulfonamide |
| 845.0 | (2S,3R)-3-(5-methoxy-2-pyridinyl)-N-(5-(6-methoxy-2-pyridinyl)-4-(tetrahydro-2H-pyran-4-yl)-4H-1,2,4-triazol-3-yl)-2-butanesulfonamide |
| 846.0 | (2S,3R)-N-(4-(2,6-dimethoxyphenyl)-5-(5-(hydroxymethyl)-3-pyridinyl)-4H-1,2,4-triazol-3-yl)-3-(5-methyl-2-pyrimidinyl)-2-butanesulfonamide |

Biological Activity
[$^{35}$S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, MgCl$_2$, and NaCl in the assay buffer were initially determined. The assay was performed in assay buffer [20 mM HEPES, pH 7.5, 5 mM MgCl$_2$, and 0.1% (w/v) BSA with 200 mM NaCl, 3 µM GDP] and membranes expressing human APJ receptor/well along with WGA PS beads. The reaction was initiated by addition of 0.2 nM [$^{35}$S]GTPγS (Perkin Elmer Life and Analytical Sciences, Waltham USA) in the absence or presence of various ligands and incubated at RT for 90 min. Nonspecific binding was determined in the presence of 100 1.11\4 GTPγS and was always less than 0.2% of total binding. All the results presented are means of several independent experiments and analyzed by non-linear regression methods using commercially available program Prism (GraphPad, San Diego, Calif.) to obtain EC$_{50}$ detailed in Table 58.

Evidence for Load Independent Inotropic Effects with APJ Agonists Using Ex Vivo Assay (Isolated Perfused Rat Hearts)

Naive Sprague Dawley® SD rats (Harlan laboratories (Livermore, Calif. USA)) were anaesthetized and hearts were excised followed by cannulation in the Langendorff apparatus (Harvard apparatus, Holliston, Mass. USA) via aorta. The heart was perfused retrograde with modified oxygenated Krebs-Henseleit buffer (Skrzypiec-Spring M et al., (2007) J. Pharmacol Toxicol Methods 55: 113-126). The pressure of the solution causes the aortic valve to shut and the perfusate is then forced into the ostium and the coronary vessels. This allows the heart to beat for several h. A balloon was inserted into the left ventricle (LV) to measure dP/dt$_{max}$ (derivative of left ventricular pressure) as an index of cardiac contractility. The APJ agonist was perfused constantly in a dose dependent manner into the heart to examine cardiac contractility. Administration of APJ agonist showed a dose-dependent increase in inotropic and lusitropic effects (FIGS. 1A, 1B, 2A, 2B, 3A, 3B, 4A, 4B, 5A, 5B, 6A, and 6B and Table 59).

Figure 1B:
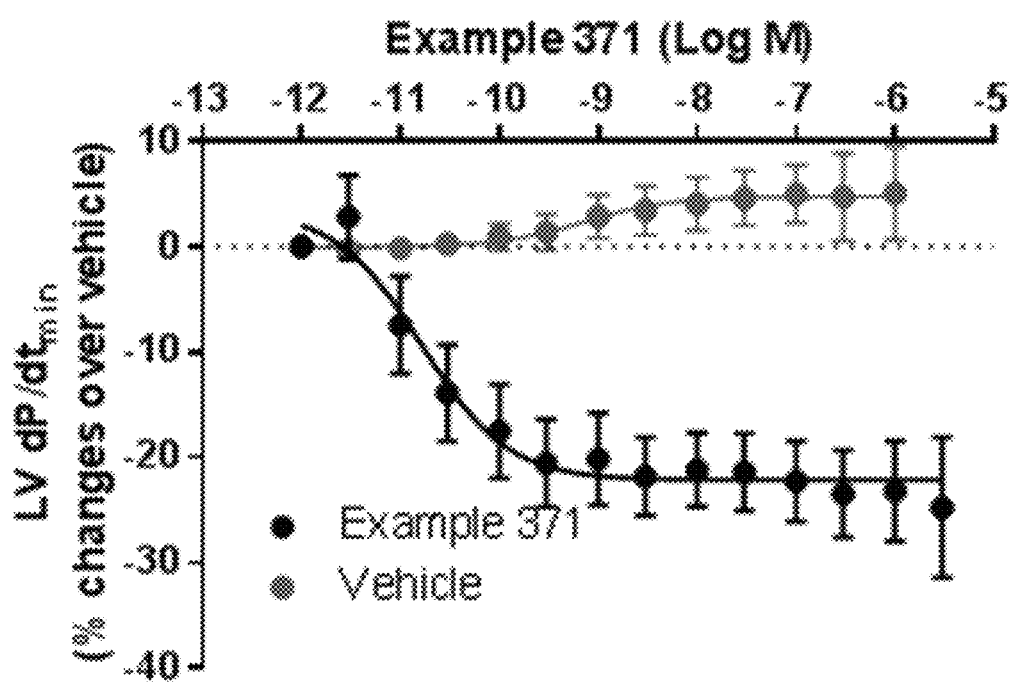
FIG. 1B is a graph of left ventricular dP/dt$_{min}$ as a function of concentration of Example 371 compared with vehicle in ex vivo naive Sprague Dawley rat hearts obtained using the Langendorff apparatus. This shows Example 371 increases load independent cardiac relaxation in isolated perfused rat hearts.
Figure 2A:
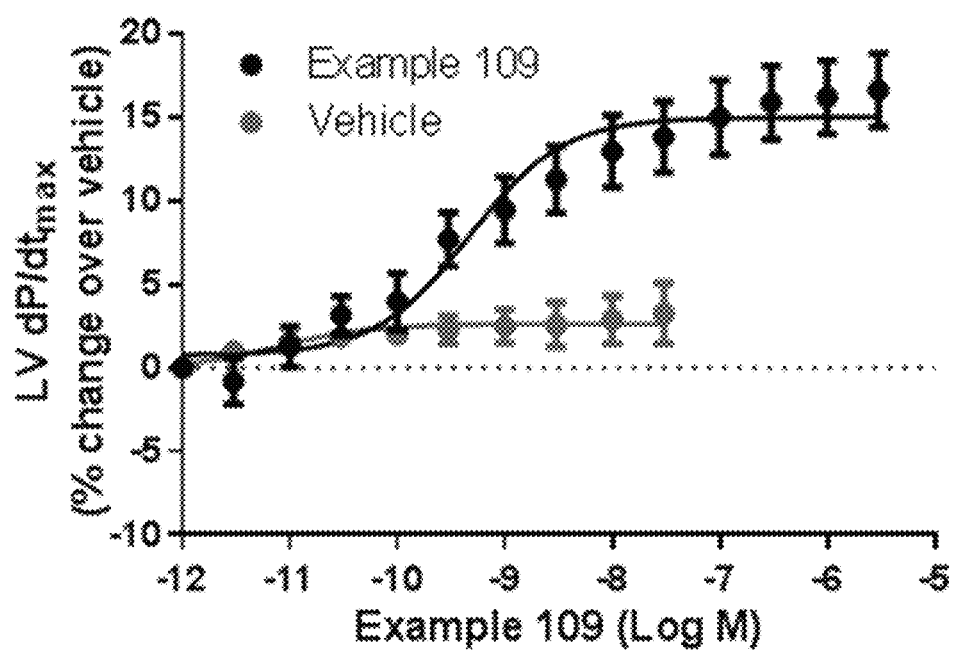
FIG. 2A is a graph of left ventricular dP/dt$_{max}$ as a function of concentration of Example 109 compared with vehicle in ex vivo naive Sprague Dawley rat hearts obtained using the Langendorff apparatus. This shows Example 109 increases load independent cardiac contractility in isolated perfused rat hearts.
Figure 2B:
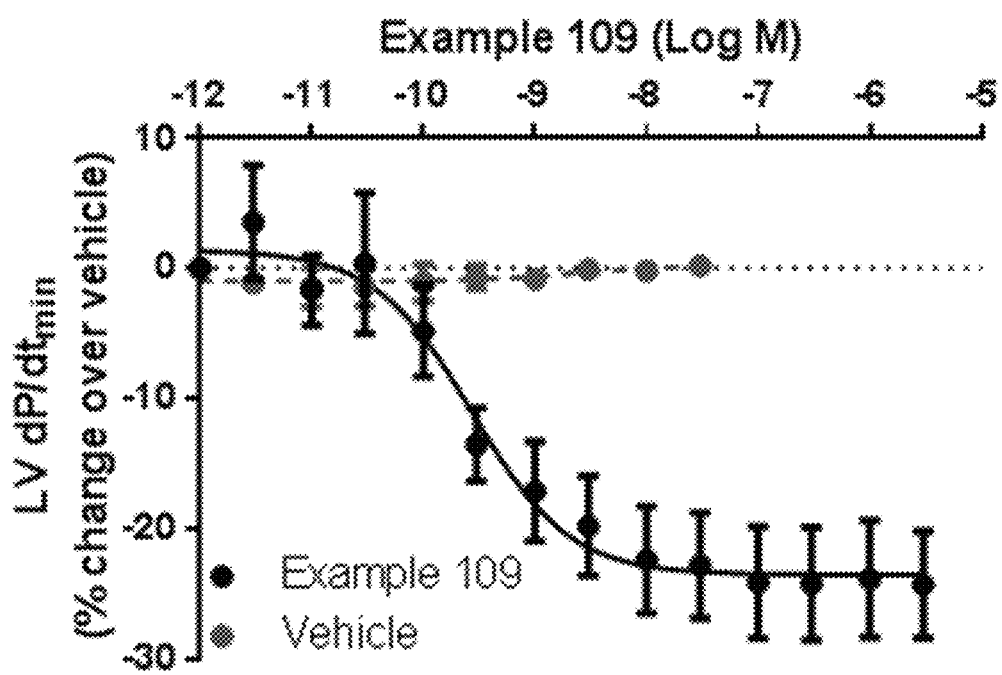
FIG. 2B is a graph of left ventricular dP/dt$_{min}$ as a function of concentration of Example 109 compared with vehicle in ex vivo naive Sprague Dawley rat hearts obtained using the Langendorff apparatus. This shows Example 109 increases load independent cardiac relaxation in isolated perfused rat hearts.
Figure 3A:
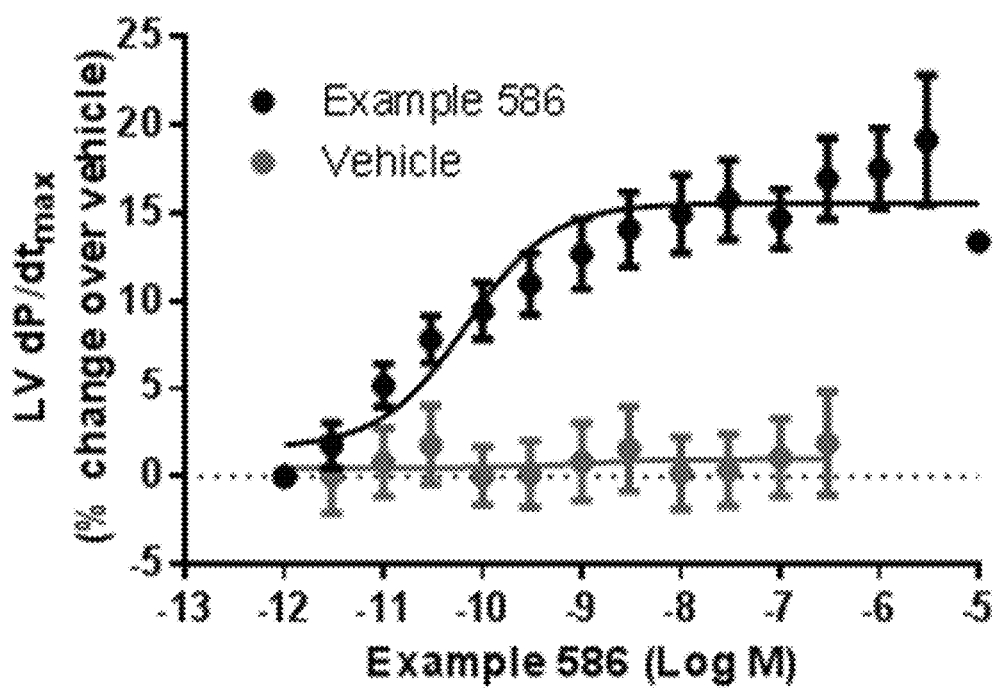
FIG. 3A is a graph of left ventricular dP/dt$_{max}$ as a function of concentration of Example 586 compared with vehicle in ex vivo naive Sprague Dawley rat hearts obtained using the Langendorff apparatus. This shows Example 586 increases load independent cardiac contractility in isolated perfused rat hearts.
Figure 3B:
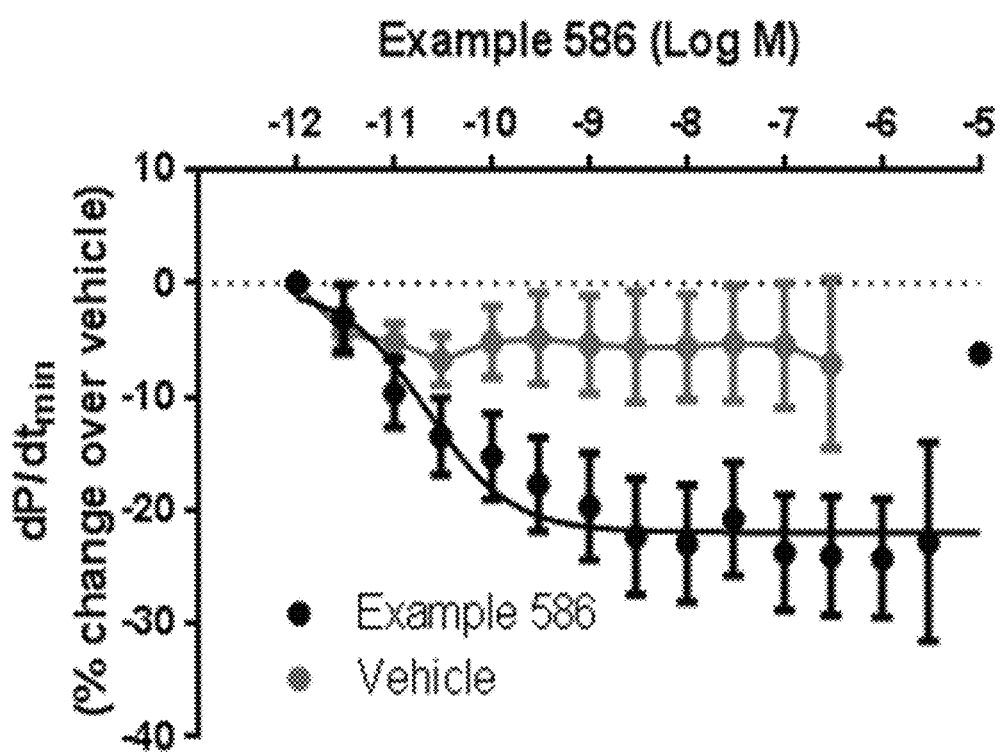
FIG. 3B is a graph of left ventricular dP/dt$_{min}$ as a function of concentration of Example 586 compared with vehicle in ex vivo naive Sprague Dawley rat hearts obtained using the Langendorff apparatus. This shows Example 586 increases load independent cardiac relaxation in isolated perfused rat hearts.
Figure 4A:
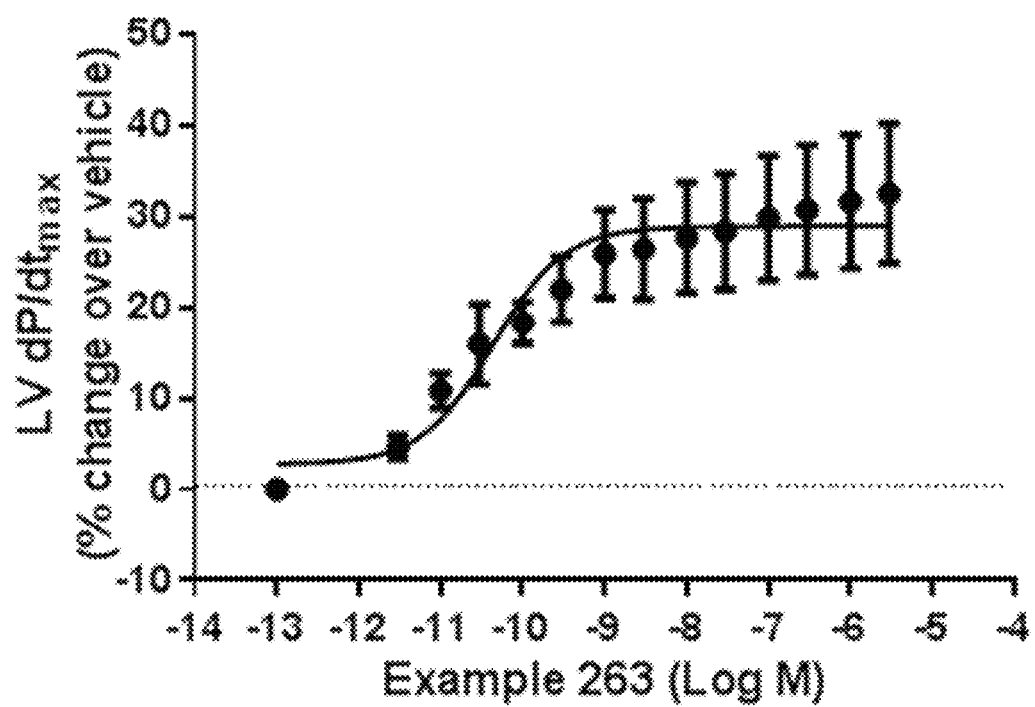
FIG. 4A is a graph of left ventricular dP/dt$_{max}$ as a function of concentration of Example 263 in ex vivo naive Sprague Dawley rat hearts obtained using the Langendorff apparatus. This shows Example 263 increases load independent cardiac contractility in isolated perfused rat hearts.
Figure 4B:
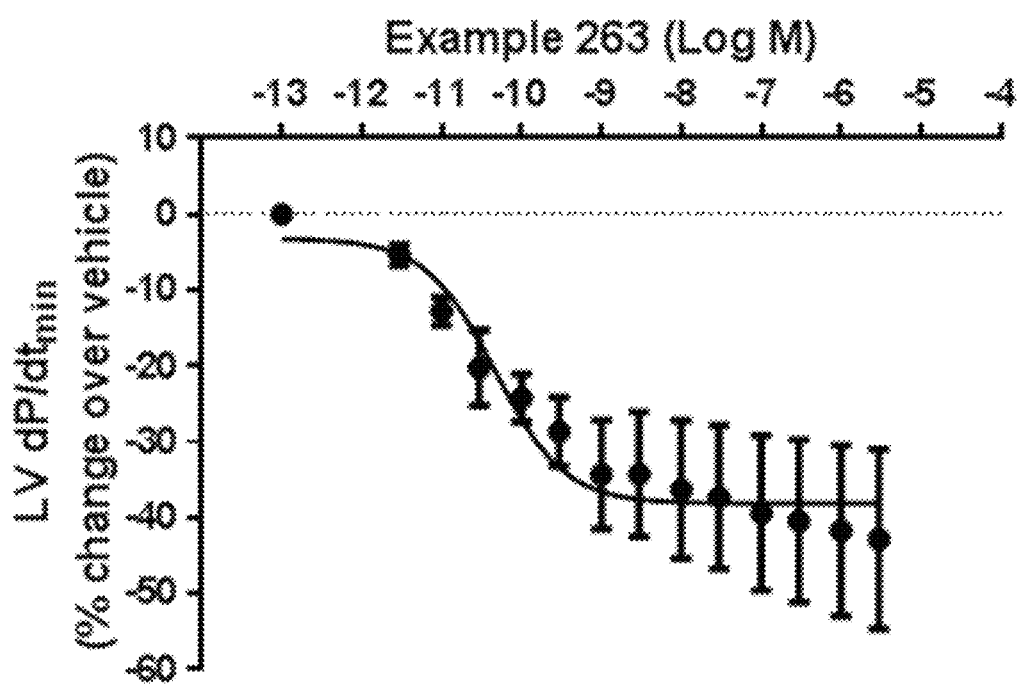
FIG. 4B is a graph of left ventricular dP/dt$_{min}$ as a function of concentration of Example 263 in ex vivo naive Sprague Dawley rat hearts obtained using the Langendorff apparatus. This shows Example 263 increases load independent cardiac relaxation in isolated perfused rat hearts.
Figure 5A:
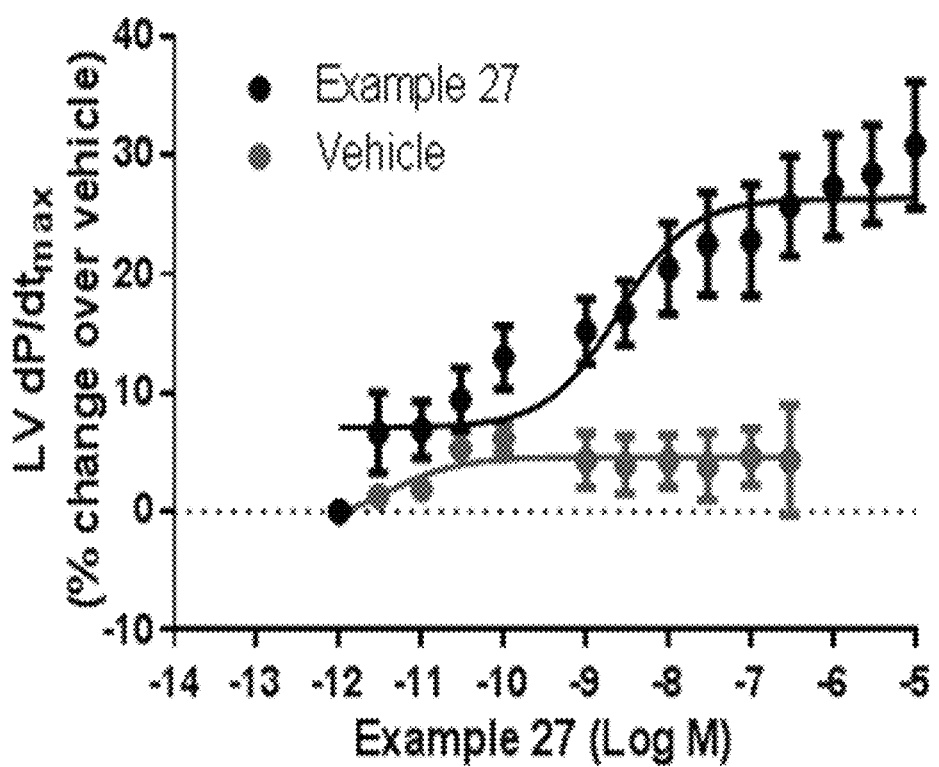
FIG. 5A is a graph of left ventricular dP/dt$_{max}$ as a function of concentration of Example 27 compared with vehicle in ex vivo naive Sprague Dawley rat hearts obtained using the Langendorff apparatus. This shows Example 27 increases load independent cardiac contractility in isolated perfused rat hearts.
Figure 5B:
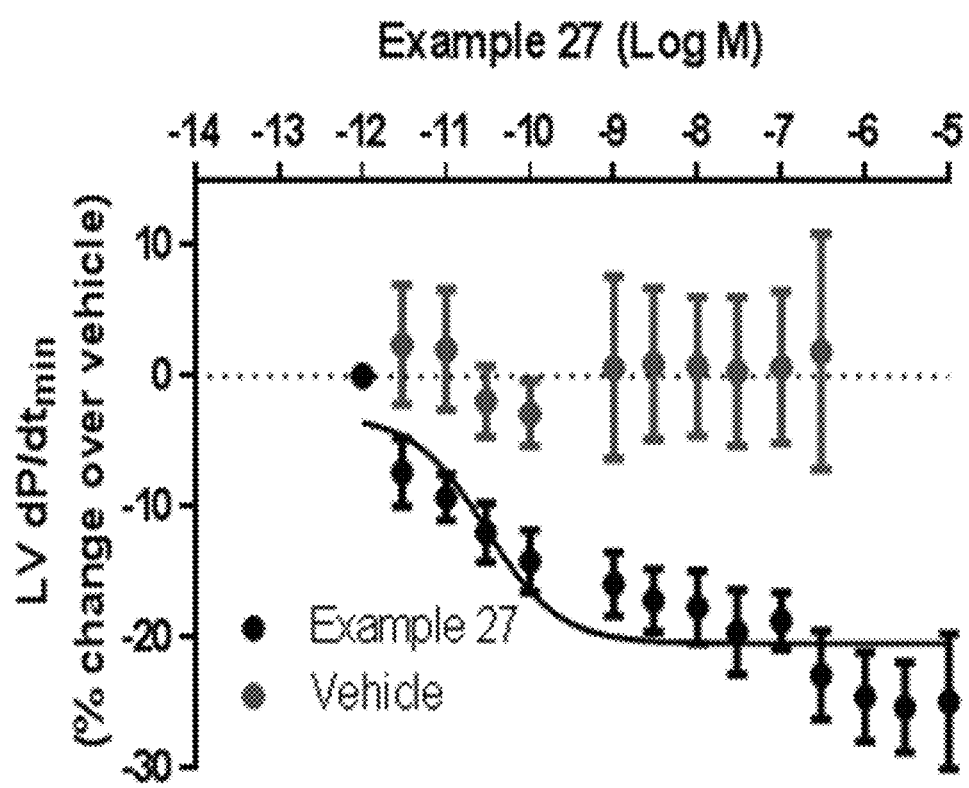
FIG. 5B is a graph of left ventricular dP/dt$_{min}$ as a function of concentration of Example 27 compared with vehicle in ex vivo naive Sprague Dawley rat hearts obtained using the Langendorff apparatus. This shows Example 27 increases load independent cardiac relaxation in isolated perfused rat hearts.
Figure 6A:
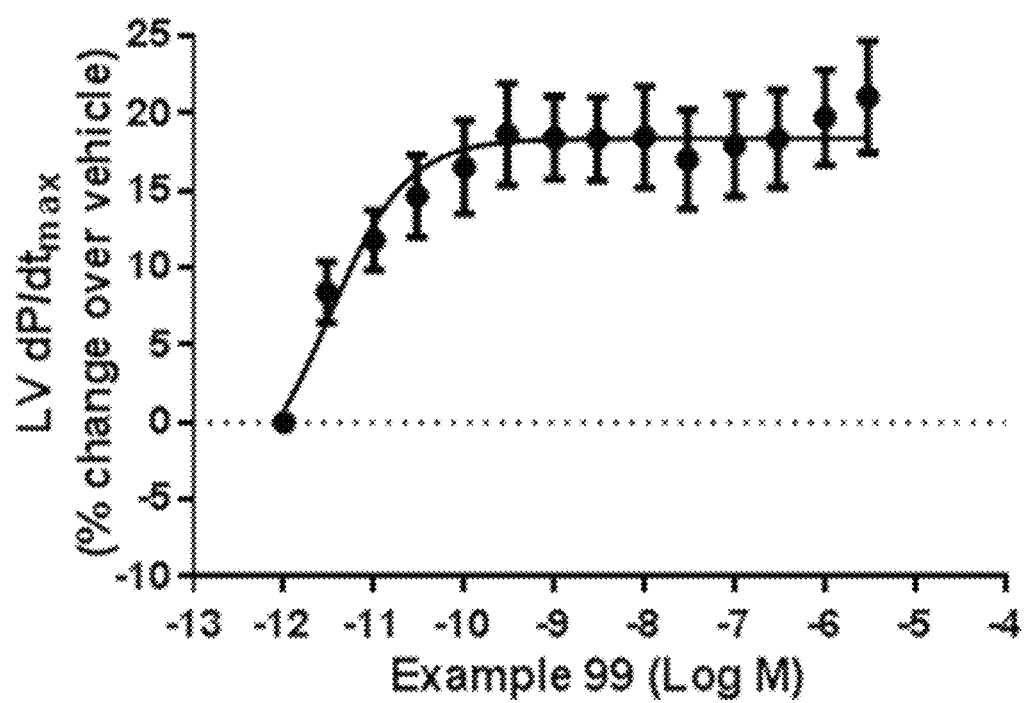
FIG. 6A is a graph of left ventricular dP/dt$_{max}$ as a function of concentration of Example 99 in ex vivo naive Sprague Dawley rat hearts obtained using the Langendorff apparatus. This shows Example 99 increases load independent cardiac contractility in isolated perfused rat hearts.
Figure 6B:
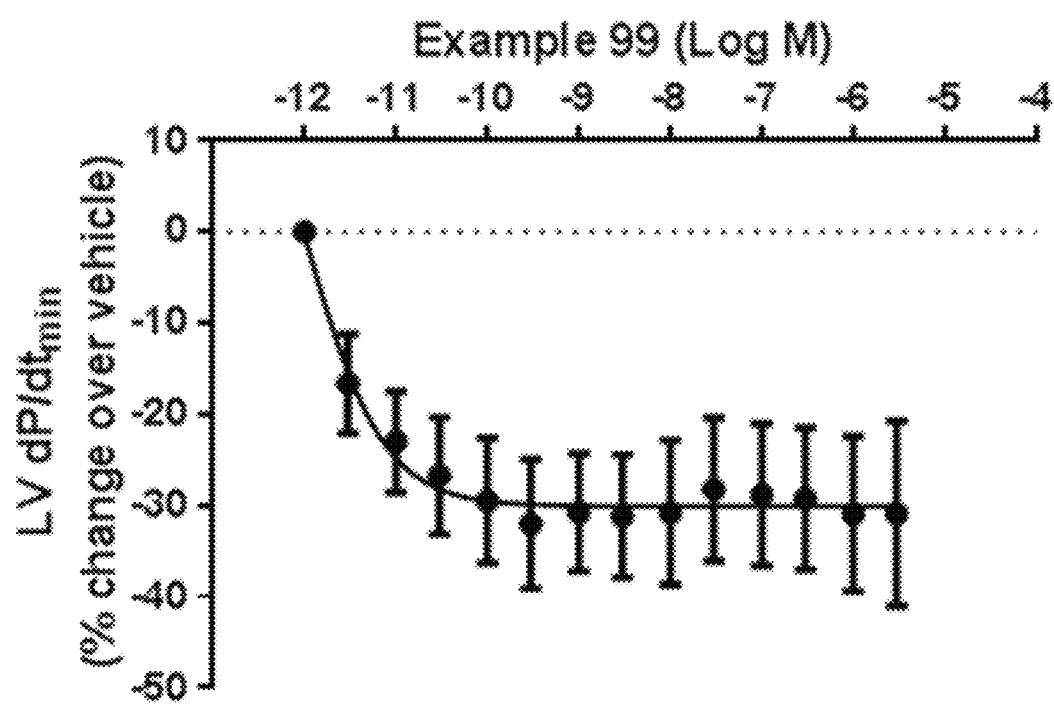
FIG. 6B is a graph of left ventricular dP/dt$_{min}$ as a function of concentration of Example 99 in ex vivo naive Sprague Dawley rat hearts obtained using the Langendorff apparatus. This shows Example 99 increases load independent cardiac relaxation in isolated perfused rat hearts.

FIG. 1A shows the effect of Example 371 on load independent contractility in isolated perfused rat hearts. Example 371 was infused at different concentrations and load independent contractility was measured by index of LV dP/dt$_{max}$ and the results are expressed as a percent change over vehicle. FIG. 1B shows the effect of Example 371 on left ventricular relaxation in isolated perfused rat hearts. Example 371 was infused at different concentrations and load independent lusitropic effect (relaxation) was measured by index of LV dP/dt$_{min}$ where results are expressed as percent change over vehicle. For Example 371, data are mean+/−SEM (n=8) and (n=4-6) for vehicle. FIG. 2A shows the effect of Example 109 on load independent contractility in isolated perfused rat hearts. Example 109 was infused at different concentrations and load independent contractility was measured by index of LV dP/dt$_{max}$ and the results are expressed as a percent change over vehicle. FIG. 2B shows the effect of Example 109 on left ventricular relaxation in isolated perfused rat hearts. Example 109 was infused at different concentrations and load independent lusitropic effect (relaxation) was measured by index of LV dP/dt$_{min}$ where results are expressed as percent change over vehicle. For Example 109, data are mean+/−SEM (n=8) and (n=2) for vehicle. FIG. 3A shows the effect of Example 586 on load independent contractility in isolated perfused rat hearts. Example 586 was infused at different concentrations and load independent contractility was measured by index of LV dP/dt and the results are expressed as a percent change over vehicle. FIG. 3B shows the effect of Example 586 on left ventricular relaxation in isolated perfused rat hearts. Example 586 was infused at different concentrations and load independent lusitropic effect (relaxation) was measured by index of LV dP/dt$_{min}$ where results are expressed as percent change over vehicle. For Example 586, data are mean+/−SEM (n=8) and (n=5) for vehicle. FIG. 4A shows the effect of Example 263 on load independent contractility in isolated perfused rat hearts. Example 263 was infused at different concentrations and load independent contractility was measured by index of LV dP/dt and the results are expressed as a percent change. FIG. 4B shows the effect of Example 263 on left ventricular relaxation in isolated perfused rat hearts. Example 263 was infused at different concentrations and load independent lusitropic effect (relaxation) was measured by index of LV dP/dt$_{min}$, where results are expressed as percent change. For Example 263, data are mean+/−SEM (n=8). FIG. 5A shows the effect of Example 27 on load independent contractility in isolated perfused rat hearts. Example 27 was infused at different concentrations and load independent contractility was measured by index of LV dP/dt$_{max}$ and the results are expressed as a percent change over vehicle. FIG. 5B shows the effect of Example 27 on left ventricular relaxation in isolated perfused rat hearts. Example 27 was infused at different concentrations and load independent lusitropic effect (relaxation) was measured by index of LV dP/dt$_{min}$, where results are expressed as percent change over vehicle. For Example 27, data are mean+/−SEM (n=8) and (n=5) for vehicle. FIG. 6A shows the effect of Example 99 on load independent contractility in isolated perfused rat hearts. Example 99 was infused at different concentrations and load independent contractility was measured by index of LV dP/dt and the results are expressed as a percent change. FIG. 6B shows the effect of Example 99 on left ventricular relaxation in isolated perfused rat hearts. Example 99 was infused at different concentrations and load independent lusitropic effect (relaxation) was measured by index of LV dP/dt$_{min}$, where results are expressed as percent change. For Example 99, data are mean+/−SEM (n=8).

Evidence for Improvement in Cardiac Contractility In Vivo in Heart Failure Rat Model Based on the ex vivo findings in isolated heart assay, APJ agonists were dosed in vivo to investigate the translation of cardiac contractility in in vivo settings. Male Lewis rats (Charles River, USA) at 2-3 months of age were used for the study. Heart failure was induced by permanent ligation of the left descending coronary artery which results in injury to the heart with an ejection fraction of <35%. APJ agonists were administered dose dependently acutely for a period of 30 min. Administration of Examples 371, 109, 586, 263, 27, and 99 lead to an increase in cardiac contractility as measured by dP/dt$_{max}$ (derivative of left ventricular pressure) (Table 59).

The following table includes biological activity data obtained using the procedures and assays set forth above for the Example compounds described herein.

TABLE 58

Biological Activity Information for Example Compounds.

| Example(s) | Activity hAPJ SPA EC$_{50}$ IP (µM) |
|---|---|
| 4.02 | 0.22 |
| 27.0 and 549.0 | 0.00019 |
| 28.0 and 543.0 | 0.062 |
| 29.0 | 0.15 |
| 30.0 | 0.83 |
| 31.0 | 0.0024 |
| 32.0 | 0.14 |
| 33.0 | 0.056 |
| 34.0 | 0.0042 |
| 35.0 | 0.00054 |
| 36.0 | 0.00028 |
| 37.0 | 0.00018 |
| 38.0 | 0.00014 |
| 39.0 | 0.54 |
| 40.0 | 0.0047 |
| 41.0 | 0.00022 |
| 42.0 | 0.051 |
| 43.0 | 0.00047 |
| 44.0 and 580.0 | 0.00126 |
| 45.0 | 0.096 |
| 46.0 | 0.075 |
| 47.0 | 0.0088 |
| 48.0 | 0.00018 |
| 49.0 | 0.00017 |
| 50.0 | 0.0093 |
| 51.0 | 0.00071 |
| 52.0 | 0.0042 |
| 53.0 | 0.053 |
| 54.0 | 0.012 |
| 55.0 | 0.017 |
| 56.0 | 0.031 |
| 57.0 | 0.00055 |
| 58.0 | 0.00050 |
| 59.0 | 0.026 |
| 60.0 | 0.012 |
| 61.0 | 0.0065 |
| 62.0 | 0.0060 |
| 63.0 | 0.35 |
| 64.0 | 0.010 |
| 65.0 | 0.18 |
| 66.0 | 0.024 |
| 67.0 | 0.015 |
| 68.0 | 0.060 |
| 69.0 | 0.0021 |
| 70.0 | 0.0026 |
| 71.0 | 0.21 |

TABLE 58-continued

Biological Activity Information for Example Compounds.

| Example(s) | Activity hAPJ SPA EC$_{50}$ IP (µM) |
|---|---|
| 72.0 | 0.0091 |
| 73.0 | 0.00076 |
| 74.0 | 0.0025 |
| 75.0 | 0.012 |
| 76.0 | 0.0030 |
| 77.0 | .0070 |
| 78.0 | .0094 |
| 79.0 | .00041 |
| 80.0 and 242.0 | .00078 |
| 81.0 and 244.0 | .0011 |
| 82.0 | .0028 |
| 83.0 | .048 |
| 84.0 | .0052 |
| 85.0 | .0052 |
| 86.0 | .0013 |
| 87.0 | .00040 |
| 88.0 | .00037 |
| 89.0 | .011 |
| 90.0 | .0024 |
| 91.0 | .0014 |
| 92.0 | .14 |
| 93.0 | .00057 |
| 94.0 | .15 |
| 95.0 | .00011 |
| 96.0 | .00026 |
| 97.0 | .0020 |
| 98.0 | .0099 |
| 99.0 | .0023 |
| 100.0 | .11 |
| 101.0 | .0070 |
| 102.0 | .018 |
| 103.0 | 0.00051 |
| 104.0 | 0.0024 |
| 105.0 | 0.0018 |
| 106.0 | 0.015 |
| 107.0 | 0.000090 |
| 108.0 | 0.15 |
| 109.0 | 0.00085 |
| 110.0 | 0.000078 |
| 111.0 | 0.0053 |
| 112.0 | 0.012 |
| 113.0 | 0.0047 |
| 114.0 | 0.033 |
| 115.0 | 0.00018 |
| 116.0 | 0.00025 |
| 117.0 | 0.00127 |
| 118.0 | 0.0058 |
| 119.0 | 0.011 |
| 120.0 | 0.0033 |
| 121.0 | 0.0034 |
| 122.0 | 0.020 |
| 123.0 | 0.00075 |
| 124.0 | 0.0011 |
| 125.0 | 0.0257 |
| 126.0 | 0.0011 |
| 127.0 | 0.00011 |
| 128.0 | 0.0011 |
| 129.0 | 0.000095 |
| 130.0 | 0.00046 |
| 131.0 | 0.0033 |
| 132.0 | 0.00025 |
| 133.0 | 0.011 |
| 134.0 | 0.030 |
| 135.0 | 0.0056 |
| 136.0 | 0.036 |
| 137.0 | 0.066 |
| 138.0 | 0.27 |
| 139.0 | 0.15 |
| 140.0 | 0.11 |
| 141.0 | 0.20 |
| 142.0 | 0.00012 |
| 143.0 | 0.00023 |
| 144.0 | 0.012 |
| 145.0 | 0.014 |
| 146.0 | 0.0021 |
| 147.0 | 0.0034 |
| 148.0 | 0.0043 |
| 149.0 | 0.0097 |
| 150.0 | 0.074 |
| 151.0 | 0.039 |
| 152.0 | 0.12 |
| 153.0 | 0.16 |
| 154.0 | 0.15 |
| 155.0 | 0.093 |
| 156.0 | 0.00054 |
| 157.0 | 0.00021 |
| 158.0 | 0.00095 |
| 159.0 | 0.076 |
| 160.0 | 0.028 |
| 161.0 | 0.000062 |
| 162.0 | 0.00026 |
| 163.0 | 0.0019 |
| 164.0 | 0.00017 |
| 165.0 | 0.0025 |
| 166.0 | 0.0068 |
| 167.0 | 0.0011 |
| 168.0 | 0.11 |
| 169.0 | 0.0018 |
| 170.0 | 0.0012 |
| 171.0 | 0.0048 |
| 172.0 | 0.000065 |
| 173.0 | 0.0012 |
| 174.0 | 0.00020 |
| 175.0 | 0.00039 |
| 176.0 | 0.00015 |
| 177.0 | 0.00012 |
| 178.0 | 0.00012 |
| 179.0 | 0.0048 |
| 180.0 | 0.000068 |
| 181.0 | 0.012 |
| 182.0 | 0.0011 |
| 183.0 | 0.060 |
| 184.0 | 0.00054 |
| 185.0 | 0.00012 |
| 186.0 | 0.00012 |
| 187.0 | 0.00014 |
| 188.0 | 0.00096 |
| 190.0 | 0.0016 |
| 191.0 | 0.041 |
| 192.0 | 0.26 |
| 193.0 | 0.061 |
| 194.0 | 0.036 |
| 195.0 | 0.00035 |
| 196.0 | 0.0034 |
| 197.0 | 0.00021 |
| 198.0 | 0.0011 |
| 199.0 | 0.019 |
| 200.0 | 0.00057 |
| 201.0 | 0.0025 |
| 202.0 | 0.0154 |
| 203.0 and 544.0 | 0.00068 |
| 204.0 | 0.0015 |
| 205.0 | 0.025 |
| 205.1 | 0.0064 |
| 206.0 | 0.0013 |
| 207.0 | 0.0033 |
| 208.0 | 0.0010 |
| 209.0 | 0.0049 |
| 211.0 | 0.38 |
| 212.0 | 0.31 |
| 214.0 | 0.11 |
| 215.0 | 0.090 |
| 216.0 | 0.57 |
| 217.0 | 0.18 |
| 218.0 | 0.30 |
| 219.0 | 0.0085 |
| 220.0 | 0.0071 |
| 221.0 | 0.035 |

TABLE 58-continued

Biological Activity Information for Example Compounds.

| Example(s) | Activity hAPJ SPA EC$_{50}$ IP (μM) |
|---|---|
| 222.0 | 0.011 |
| 223.0 | 0.0082 |
| 224.0 | 0.011 |
| 225.0 | 0.022 |
| 226.0 | 0.0097 |
| 227.0 | 0.088 |
| 228.0 | 0.0053 |
| 229.0 | 0.0063 |
| 230.0 | 0.0042 |
| 231.0 | 0.027 |
| 232.0 | 0.011 |
| 233.0 | 0.045 |
| 234.0 | 0.016 |
| 235.0 | 0.00028 |
| 236.0 | 0.10 |
| 237.0 | 0.014 |
| 238.0 | 0.012 |
| 239.0 | 0.012 |
| 240.0 | 0.000092 |
| 241.0 | 0.057 |
| 80.0 and 242.0 | 0.00078 |
| 243.0 | 0.15 |
| 81.0 and 244.0 | 0.0011 |
| 245.0 | 0.12 |
| 246.0 | 0.00033 |
| 247.0 | 0.0038 |
| 248.0 | 0.060 |
| 249.0 | 0.0011 |
| 250.0 | 0.0028 |
| 251.0 | 0.073 |
| 252.0 | 0.00080 |
| 253.0 | 0.00086 |
| 254.0 | 0.024 |
| 256.0 | 0.00040 |
| 257.0 | 0.00073 |
| 258.0 | 0.0020 |
| 259.0 | 0.011 |
| 260.0 | 0.0024 |
| 263.0 | 0.00032 |
| 264.0 | 0.00034 |
| 265.0 | 0.00077 |
| 266.0 | 0.00033 |
| 267.0 | 0.00015 |
| 268.0 | 0.00017 |
| 269.0 | 0.00035 |
| 271.0 | 0.00075 |
| 272.0 | 0.0021 |
| 273.0 | 0.00014 |
| 274.0 | 0.00012 |
| 275.0 | 0.00030 |
| 276.0 | 0.00021 |
| 277.0 | 0.00033 |
| 278.0 | 0.00037 |
| 279.0 | 0.028 |
| 280.0 | 0.00027 |
| 281.0 | 0.043 |
| 282.0 | 0.00071 |
| 283.0 | 0.00096 |
| 284.0 | 0.013 |
| 285.0 | 0.00057 |
| 286.0 | 0.00068 |
| 287.0 | 0.014 |
| 288.0 | 0.0011 |
| 289.0 | 0.011 |
| 290.0 | 0.00057 |
| 291.0 | 0.0018 |
| 292.0 | 0.00090 |
| 293.0 | 0.013 |
| 294.0 | 0.011 |
| 295.0 | 0.098 |
| 296.0 | 0.0047 |
| 297.0 | 0.0021 |
| 298.0 | 0.043 |
| 299.0 | 0.00068 |
| 300.0 | 0.0052 |
| 301.0 | 0.078 |
| 303.0 | 0.0073 |
| 304.0 | 0.0017 |
| 305.0 | 0.00039 |
| 306.0 | 0.020 |
| 307.0 | 0.041 |
| 308.0 | 0.076 |
| 309.0 | 0.0095 |
| 310.0 | 0.00066 |
| 311.0 | 0.00026 |
| 312.0 | 0.027 |
| 313.0 | 0.00030 |
| 314.0 | 0.0034 |
| 315.0 | 0.00032 |
| 316.0 | 0.00050 |
| 317.0 | 0.00053 |
| 319.0 | 0.0015 |
| 320.0 | 0.025 |
| 321.0 | 0.049 |
| 322.0 | 0.00091 |
| 323.0 | 0.00075 |
| 324.0 | 0.014 |
| 325.0 | 0.17 |
| 326.0 | 0.022 |
| 327.0 | 0.0020 |
| 328.0 | 0.00033 |
| 329.0 | 0.00023 |
| 330.0 | 0.00030 |
| 331.0 | 0.00024 |
| 332.0 | 0.00056 |
| 333.0 | 0.00058 |
| 334.0 | 0.00099 |
| 335.0 | 0.00099 |
| 336.0 | 0.0016 |
| 337.0 | 0.0040 |
| 338.0 | 0.0045 |
| 339.0 | 0.00091 |
| 340.0 | 0.00070 |
| 341.0 | 0.00075 |
| 342.0 | 0.00047 |
| 343.0 | 0.064 |
| 344.0 | 0.00060 |
| 345.0 | 0.00049 |
| 346.0 | 0.00040 |
| 347.0 | 0.018 |
| 348.0 | 0.0010 |
| 349.0 | 0.0012 |
| 350.0 | 0.0037 |
| 351.0 | 0.00087 |
| 352.0 | 0.00032 |
| 353.0 | 0.10 |
| 354.0 | 0.0013 |
| 355.0 | 0.00046 |
| 356.0 | 0.043 |
| 357.0 | 0.0035 |
| 358.0 | 0.069 |
| 359.0 | 0.0048 |
| 360.0 | 0.010 |
| 361.0 | 0.083 |
| 362.0 | 0.0096 |
| 363.0 | 0.00028 |
| 364.0 | 0.00015 |
| 365.0 | 0.031 |
| 366.0 | 0.0011 |
| 367.0 | 0.0023 |
| 368.0 | 0.059 |
| 369.0 | 0.016 |
| 370.0 | — |
| 371.0 and 541.0 | 0.00091 |
| 372.0 | 0.12 |
| 373.0 | 0.31 |
| 374.0 | 0.41 |
| 376.0 | 0.023 |

TABLE 58-continued

Biological Activity Information for Example Compounds.

| Example(s) | Activity hAPJ SPA $EC_{50}$ IP (μM) |
|---|---|
| 377.0 | 0.0012 |
| 378.0 | 0.046 |
| 379.0 | 0.00057 |
| 381.0 | 0.16 |
| 382.0 | 0.073 |
| 383.0 | 0.00039 |
| 384.0 | 0.00035 |
| 385.0 | 0.00060 |
| 386.0 | 0.024 |
| 387.0 | 0.0057 |
| 388.0 | 0.040 |
| 389.0 | 0.021 |
| 390.0 | 0.0038 |
| 391.0 | 0.059 |
| 392.0 | 0.048 |
| 394.0 | 0.012 |
| 395.0 | 0.00011 |
| 396.0 | 0.030 |
| 397.0 | 0.00090 |
| 398.0 | 0.013 |
| 400.0 | 0.017 |
| 401.0 | 0.021 |
| 402.0 | 0.00086 |
| 403.0 | 0.00021 |
| 405.0 | 0.00069 |
| 406.0 | 0.039 |
| 408.0 | 0.00088 |
| 409.0 | 0.029 |
| 411.0 | 0.0033 |
| 412.0 | 0.025 |
| 413.0 | 0.00046 |
| 415.0 | 0.0089 |
| 416.0 | 0.00026 |
| 417.0 | 0.011 |
| 418.0 | 0.0079 |
| 419.0 | 0.0067 |
| 420.0 | 0.0063 |
| 422.0 | 0.0013 |
| 423.0 | 0.00044 |
| 424.0 | 0.0071 |
| 425.0 | 0.0035 |
| 426.0 | 0.0126 |
| 427.0 | 0.00034 |
| 428.0 | 0.0025 |
| 429.0 | 0.00027 |
| 430.0 and 605.0 | 0.00053 |
| 433.0 | 0.042 |
| 434.0 | 0.12 |
| 435.0 | 0.024 |
| 436.0 | 0.10 |
| 437.0 | 0.031 |
| 438.0 | 0.052 |
| 439.0 | 0.11 |
| 440.0 | 0.049 |
| 441.0 | 0.0012 |
| 442.0 | 0.013 |
| 443.0 | 0.0025 |
| 444.0 | 0.080 |
| 445.0 | 0.10 |
| 446.0 | 0.085 |
| 447.0 | 0.029 |
| 448.0 | 0.014 |
| 449.0 | 0.0049 |
| 450.0 | 0.0032 |
| 451.0 | 0.045 |
| 452.0 | 0.0010 |
| 453.0 | 0.00060 |
| 454.0 | 0.00084 |
| 455.0 | 0.0049 |
| 456.0 | 0.0093 |
| 457.0 | 0.00030 |
| 458.0 | 0.00016 |
| 459.0 | 0.00031 |
| 460.0 | 0.0097 |
| 461.0 | 0.67 |
| 462.0 | 0.0090 |
| 463.0 | 0.047 |
| 464.0 | 0.0078 |
| 465.0 | 0.0014 |
| 466.0 | 0.012 |
| 467.0 | 0.035 |
| 468.0 | 0.0010 |
| 469.0 | 0.00073 |
| 470.0 | 0.0020 |
| 471.0 | 0.019 |
| 472.0 | 0.00073 |
| 473.0 | 0.00023 |
| 474.0 | 0.00035 |
| 475.0 | 0.027 |
| 476.0 | 0.00055 |
| 477.0 | 0.016 |
| 478.0 | 0.00026 |
| 479.0 | 0.00016 |
| 480.0 | 0.0074 |
| 481.0 | 0.00024 |
| 482.0 | 0.00020 |
| 483.0 | 0.00035 |
| 484.0 | 0.00026 |
| 485.0 | 0.000098 |
| 486.0 | 0.000073 |
| 488.0 | 0.0012 |
| 489.0 | 0.00088 |
| 491.0 | 0.00033 |
| 492.0 | 0.00061 |
| 494.0 | 0.0028 |
| 495.0 | 0.0032 |
| 496.0 | 0.015 |
| 497.0 | 0.087 |
| 498.0 | 0.0072 |
| 499.0 | 0.0061 |
| 500.0 | 0.093 |
| 501.0 | 0.0077 |
| 502.0 | 0.0068 |
| 503.0 | 0.062 |
| 504.0 | 0.018 |
| 505.0 | 0.0019 |
| 506.0 | 0.0012 |
| 507.0 | 0.00039 |
| 509.0 | 0.0059 |
| 510.0 | 0.0014 |
| 511.0 | 0.0069 |
| 512.0 | 0.00093 |
| 513.0 | 0.0017 |
| 514.0 | 0.00040 |
| 515.0 | 0.0022 |
| 516.0 | 0.076 |
| 517.0 | 0.051 |
| 518.0 | 0.00019 |
| 519.0 | 0.0054 |
| 520.0 | 0.00049 |
| 521.0 | 0.00024 |
| 522.0 | 0.00032 |
| 523.0 | 0.00033 |
| 524.0 | 0.00026 |
| 525.0 | 0.12 |
| 526.0 | 0.0010 |
| 527.0 | 0.002 |
| 528.0 | 0.027 |
| 529.0 | 0.00048 |
| 530.0 | 0.0485 |
| 531.0 | 0.0002 |
| 532.0 | 0.00049 |
| 533.0 | 0.019 |
| 534.0 | 0.001 |
| 535.0 | 0.0013 |
| 537.0 | 0.057 |
| 538.0 | 0.0045 |
| 540.0 | 0.032 |

TABLE 58-continued

Biological Activity Information for Example Compounds.

| Example(s) | Activity hAPJ SPA $EC_{50}$ IP (μM) |
|---|---|
| 371.0 and 541.0 | 0.00091 |
| 28.0 and 543.0 | 0.062 |
| 203.0 and 544.0 | 0.00068 |
| 545.0 | 0.0049 |
| 546.0 | 0.037 |
| 548.0 | 0.014 |
| 27.0 and 549.0 | 0.00019 |
| 550.0 | 0.00080 |
| 552.0 | 0.00028 |
| 553.0 | 0.041 |
| 554.0 | 0.0027 |
| 555.0 | 0.041 |
| 557.0 | 0.00031 |
| 558.0 | 0.030 |
| 559.0 | 0.12 |
| 560.0 | 0.00088 |
| 562.0 | 0.0063 |
| 563.0 | 0.00019 |
| 565.0 | 0.10 |
| 566.0 | 0.062 |
| 568.0 | 0.0071 |
| 569.0 | 0.00026 |
| 571.0 | 0.00034 |
| 572.0 | 0.036 |
| 574.0 | 0.00023 |
| 575.0 | 0.0043 |
| 577.0 | 0.00024 |
| 578.0 | 0.0027 |
| 44.0 and 580.0 | 0.0013 |
| 581.0 | 0.0051 |
| 583.0 | 0.00019 |
| 585.0 | 0.025 |
| 586.0 | 0.00030 |
| 588.0 | 0.00052 |
| 589.0 | 0.020 |
| 591.0 | 0.00021 |
| 592.0 | 0.010 |
| 593.0 | 0.00037 |
| 594.0 | 0.020 |
| 596.0 | 0.00011 |
| 597.0 | 0.0013 |
| 598.0 | 0.000093 |
| 599.0 | 0.0020 |
| 601.0 | 0.0012 |
| 602.0 | 0.19 |
| 604.0 | 0.030 |
| 430.0 and 605.0 | 0.00053 |
| 606.0 | 0.000082 |
| 607.0 | 0.021 |
| 609.0 | 0.0094 |
| 610.0 | 0.00030 |
| 611.0 | 0.00019 |
| 612.0 | 0.013 |
| 614.0 | 0.0017 |
| 615.0 | 0.065 |
| 616.0 | 0.00046 |
| 618.0 | 0.0054 |
| 619.0 | 0.0015 |
| 620.0 | 0.011 |
| 621.0 | 0.00084 |
| 622.0 | 0.012 |
| 623.0 | 0.13 |
| 624.0 | 0.16 |
| 625.0 | 0.11 |
| 626.0 | 0.0018 |
| 627.0 | 0.0011 |
| 628.0 | 0.0065 |
| 629.0 | 0.0016 |
| 630.0 | 0.0053 |
| 631.0 | 0.14 |
| 632.0 | 0.21 |
| 633.0 | 0.0069 |
| 634.0 | 0.071 |
| 635.0 | 0.0026 |
| 636.0 | 0.00040 |
| 637.0 | 0.15 |
| 638.0 | 0.00065 |
| 639.0 | 0.16 |
| 640.0 | 0.33 |
| 641.0 | 0.00014 |
| 642.0 | 0.00048 |
| 643.0 | 0.15 |
| 644.0 | 0.18 |
| 645.0 | 0.060 |
| 646.0 | 0.053 |
| 647.0 | 0.0017 |
| 648.0 | 0.033 |
| 649.0 | 0.00028 |
| 650.0 | 0.039 |
| 651.0 | 0.085) |
| 652.0 | 0.00043 |
| 653.0 | 0.079 |
| 654.0 | 0.15 |
| 655.0 | 0.13 |
| 656.0 | 0.013 |
| 657.0 | 0.014 |
| 658.0 | 0.0068 |
| 659.0 | 0.052 |
| 660.0 | 0.016 |
| 661.0 | 0.00022 |
| 662.0 | 0.00018 |
| 663.0 | 0.00082 |
| 664.0 | 0.00031 |
| 665.0 | 0.0039 |
| 666.0 | 0.00020 |
| 667.0 | 0.0026 |
| 668.0 | 0.00076 |
| 669.0 | 0.0027 |
| 670.0 | 0.00055 |
| 671.0 | 0.0092 |
| 672.0 | 0.00032 |
| 673.0 | 0.022 |
| 674.0 | 0.00072 |
| 675.0 | 0.0026 |
| 676.0 | 0.0060 |
| 677.0 | 0.0072 |
| 678.0 | 0.00057) |
| 679.0 | 0.00042 |
| 680.0 | 0.00017 |
| 681.0 | 0.00025 |
| 682.0 | 0.00020 |
| 683.0 | 0.0069 |
| 684.0 | 0.00081 |
| 685.0 | 0.0034 |
| 686.0 | 0.000091 |
| 687.0 | 0.0047 |
| 688.0 | 0.00066 |
| 689.0 | 0.0020 |
| 690.0 | 0.00020 |
| 691.0 | 0.00026 |
| 692.0 | — |
| 693.0 | 0.0060 |
| 694.0 | 0.00013 |
| 695.0 | 0.00012 |
| 696.0 | 0.00010 |
| 697.0 | 0.00070 |
| 698.0 | 0.00057 |
| 699.0 | 0.0014 |
| 700.0 | 0.0068 |
| 701.0 | 0.0020 |
| 702.0 | 0.029 |
| 703.0 | 0.0020 |
| 704.0 | 0.00093 |
| 705.0 | 0.00017 |
| 706.0 | 0.00034 |
| 707.0 | 0.0044 |
| 708.0 | 0.00018 |
| 709.0 | 0.00071 |

TABLE 58-continued

Biological Activity Information for Example Compounds.

| Example(s) | Activity hAPJ SPA $EC_{50}$ IP (μM) |
|---|---|
| 710.0 | 0.00021 |
| 711.0 | 0.0021 |
| 712.0 | 0.00090 |
| 713.0 | 0.0010 |
| 714.0 | 0.0016 |
| 715.0 | 0.00031 |
| 716.0 | 0.00032 |
| 717.0 | 0.00095 |
| 718.0 | 0.00034 |
| 719.0 | 0.044 |
| 720.0 | 0.035 |
| 721.0 | — |
| 722.0 | 0.0017 |
| 723.0 | 0.0025 |
| 724.0 | 0.22 |
| 725.0 | 0.036 |
| 726.0 | 0.0075 |
| 727.0 | 0.20 |
| 728.0 | 0.00088 |
| 729.0 | 0.0015 |
| 730.0 | 0.0041 |
| 731.0 | 0.038 |
| 732.0 | 0.037 |
| 733.0 | 0.00042 |
| 734.0 | 0.0020 |
| 735.0 | 0.00048 |
| 736.0 | 0.019 |
| 737.0 | 0.0058 |
| 738.0 | 0.00010 |
| 739.0 | 0.0015 |
| 740.0 | 0.056 |
| 741.0 | 0.0031 |
| 742.0 | 0.035 |
| 743.0 | 0.010 |
| 744.0 | 0.026 |
| 745.0 | 0.00040 |
| 746.0 | 0.080 |
| 747.0 | 0.0076 |
| 748.0 | 0.0055 |
| 749.0 | 0.015 |
| 750.0 | 0.00036 |
| 751.0 | 0.0014 |
| 752.0 | 0.0036 |
| 753.0 | 0.0059 |
| 754.0 | 0.0096 |
| 755.0 | 0.0025 |
| 756.0 | 0.019 |
| 757.0 | 0.061 |
| 758.0 | 0.0058 |
| 759.0 | 0.0068 |
| 760.0 | 0.000095 |
| 761.0 | 0.015 |
| 762.0 | 0.00016 |
| 763.0 | 0.00071 |
| 764.0 | 0.027 |
| 765.0 | 0.0020 |
| 766.0 | 0.071 |
| 767.0 | 0.0038 |
| 768.0 | 0.12 |
| 769.0 | 0.31 |
| 770.0 | 0.047 |
| 771.0 | 0.0020 |
| 772.0 | 0.000032 |
| 773.0 | 0.014 |
| 774.0 | 0.0082 |
| 775.0 | 0.0021 |
| 776.0 | 0.0039 |
| 777.0 | 0.0022 |
| 778.0 | 0.00077 |
| 779.0 | 0.017 |
| 780.0 | 0.0088 |
| 781.0 | 0.59 |
| 782.0 | 0.028 |
| 783.0 | 0.0042 |
| 784.0 | 0.00040 |
| 785.0 | 0.0049 |
| 786.0 | 0.00016 |
| 787.0 | 0.00053 |
| 788.0 | 0.00084 |
| 789.0 | 0.0019 |
| 790.0 | 0.020 |
| 791.0 | 0.00063 |
| 792.0 | 0.051 |
| 793.0 | 0.015 |
| 794.0 | 0.0066 |
| 795.0 | 0.030 |
| 796.0 | 0.0011 |
| 797.0 | 0.0024 |
| 798.0 | 0.00043 |
| 799.0 | 0.00061 |
| 800.0 | 0.0086 |
| 801.0 | 0.0012 |
| 802.0 | 0.00018 |
| 803.0 | 0.0017 |
| 804.0 | 0.0046 |
| 805.0 | 0.0023 |
| 806.0 | 0.019 |
| 807.0 | 0.0035 |
| 808.0 | 0.033 |
| 809.0 | 0.00097 |
| 810.0 | 0.77 |
| 811.0 | 0.016 |
| 812.0 | 0.23 |
| 813.0 | 0.14 |
| 814.0 | 0.56 |
| 815.0 | 0.17 |
| 816.0 | 0.018 |
| 817.0 | 0.016 |
| 818.0 | 0.11 |
| 819.0 | 0.033 |
| 820.0 | 0.0013 |
| 821.0 | 0.030 |
| 822.0 | 0.027 |
| 823.0 | 0.014 |
| 824.0 | 0.00047 |
| 825.0 | 0.00015 |
| 826.0 | 0.0017 |
| 827.0 | 0.010 |
| 828.0 | 0.48 |
| 829.0 | 0.0095 |
| 830.0 | 0.014 |
| 831.0 | 0.00089 |
| 832.0 | 0.11 |
| 833.0 | 0.070 |
| 834.0 | 1.07 |
| 835.0 | 0.013 |
| 836.0 | 0.0029 |
| 837.0 | 0.0051 |
| 838.0 | 0.034 |
| 839.0 | 0.00058 |
| 840.0 | 0.013 |
| 841.0 | 0.0086 |
| 842.0 | 0.14 |
| 843.0 | 0.97 |
| 844.0 | 0.086 |
| 845.0 | 0.14 |
| 846.0 | 0.0066 |

The following table includes data obtained using the procedures and assays set forth above for the Example compounds described herein.

TABLE 59

Contractile Effects of Examples Observed in ex vivo (Isolated Heart Assay) and in vivo (MI Rat Model).

| Example(s) | Isolated Heart Assay | | MI Rat Model |
|---|---|---|---|
| | dP/dt$_{max}$ (%) | dP/dt$_{min}$ (%) | dP/dt$_{max}$ (%) |
| 371.0 | 19 | 25 | 15 |
| 109.0 | 15 | 25 | 20 |
| 586.0 | 15 | 21 | nd$^a$ |
| 263.0 | 29 | 32 | 25 |
| 27.0 | 26 | 20 | 20 |
| 99.0 | 18 | 30 | 30 |
| 621.0 | 7.4 | 6.0 | nd |
| 203.0 and 544.0 | No effect | No effect | 12 |
| 184.0 | 14.5 | 14.0 | nd |
| 557.0 | 17.0 | 20.0 | No effect |
| 571.0 | 13.3 | 18.8 | nd |
| 569.0 | 12.4 | 12.7 | nd |
| 99.0 | 19.7 | 31 | 31 |
| 44.0 and 580.0 | 10.8 | 9.05 | nd |
| 173.0 | 39 | 41.7 | 14 |
| 252.0 | 15.7 | 16.3 | nd |
| 591.0 | 8.0 | 0.0 | nd |
| 430.0 and 605.0 | 10.0 | 9.7 | nd |
| 610.0 | 6.0 | No effect | nd |
| 614.0 | 6.6 | 6.2 | nd |
| 80.0 and 242.0 | 5.0 | -2.7 | nd |
| 81.0 and 244.0 | 14.0 | 15.0 | nd |
| 91.0 | 20.0 | 43.0 | 25 |
| 506.0 | 9.0 | 3.0 | nd |
| 93.0 | 19.0 | 27.0 | 20 |
| 198.0 | 15.0 | 19.0 | 15 |
| 79.0 | 10.0 | 5.0 | nd |
| 51.0 | 2.0 | 2.0 | nd |
| 82.0 | 13.5 | 16.2 | nd |
| 57.0 | 4.0 | 2.0 | nd |
| 531.0 | 4.1 | 1.9 | nd |
| 627.0 | No effect | No effect | nd |
| 694.0 | 18.0 | 32.0 | 8 |
| 684.0 | 19.0 | 18.3 | 20 |
| 706.0 | 9.1 | 4.0 | nd |
| 709.0 | 6.0 | 3.0 | nd |
| 710.0 | 12.7 | 10.3 | nd |
| 711.0 | 9.4 | 1.1 | nd |
| 741.0 | 1.4 | 6.6 | nd |
| 628.0 | 18.3 | 18.0 | 15 |
| 826.0 | 6.02 | 5.16 | nd |
| 803.0 | 11.4 | 10.0 | nd |
| 799.0 | 7.8 | 14.1 | nd |
| 784.0 | 4.3 | 1.93 | nd |

$^a$nd means not determined

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun, 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sun, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117 (2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of the APJ pathway resulted in positive cooperativity of AngII by shifting its potency to the left and also increasing the efficacy of the IP response (see methods and results section below). Conversely, blocking the AT receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signalling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor as such as captopril which may play an important role in providing greater efficacy in treating heart failure patients, for example in improving contractility and ejection fraction without changing the heart rate.

Evidence for Allosteric Interaction Between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F$_{12}$ and 10% FBS at a density of 15 k/well in a 96 well plate overnight. The next day, the culture medium was replaced with medium containing no serum for 4 hours. The compound AngII at a range of concentrations (1 pM-10 μM) with or without different concentrations of APJ agonists were diluted in stimulation buffer and added to the cell plate. The plate was sealed and incubated for 1 hour. This was followed by addition of IP-d2 conjugate followed by europium cryptate antibody conjugate into the wells. The plate was sealed, followed with incubation for 2 hours at room temperature. Time-resolved fluorescence resonance energy (TR-FRET) at 620 nm and 665 nm was measured after 2 hours with an Envision reader. The signal ratios and delta F were calculated and the amount of IP1 produced was inversely proportional to the TR-FRET ratio, 665/620 nm.

Results

Figure 7:
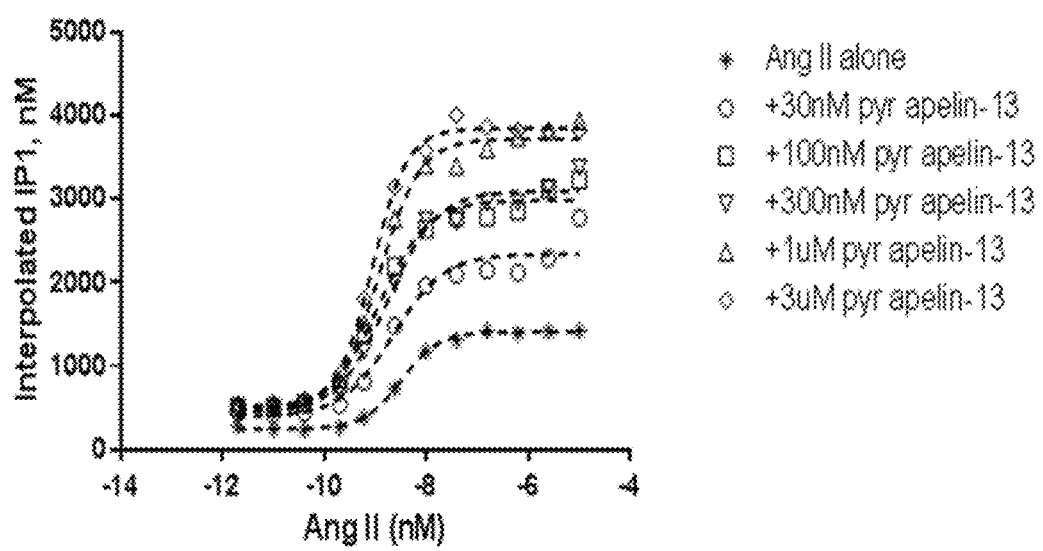
FIG. 7 is a graph plotting different concentrations of angiotensin (AngII) with fixed concentration of pyr apelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyr apelin-13 induces the positive cooperativity on the AT1R upon activation by APJ receptor.
Figure 8:
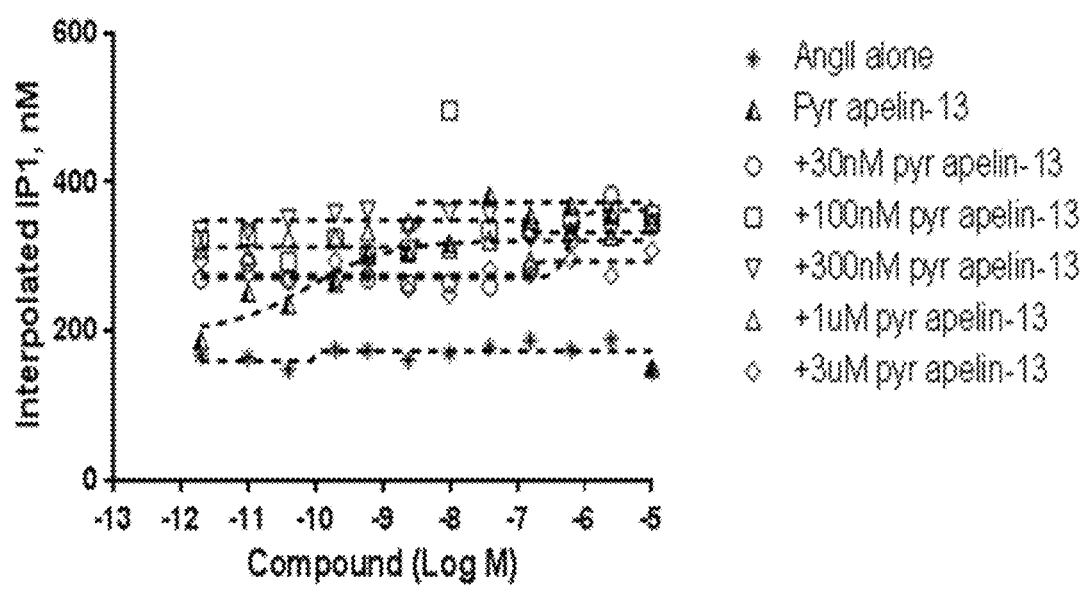
FIG. 8 is a graph plotting different concentrations of angiotensin (AngII) with fixed concentration of pyr apelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyr apelin-13 when the human APJ receptor is expressed alone.
Figure 9:
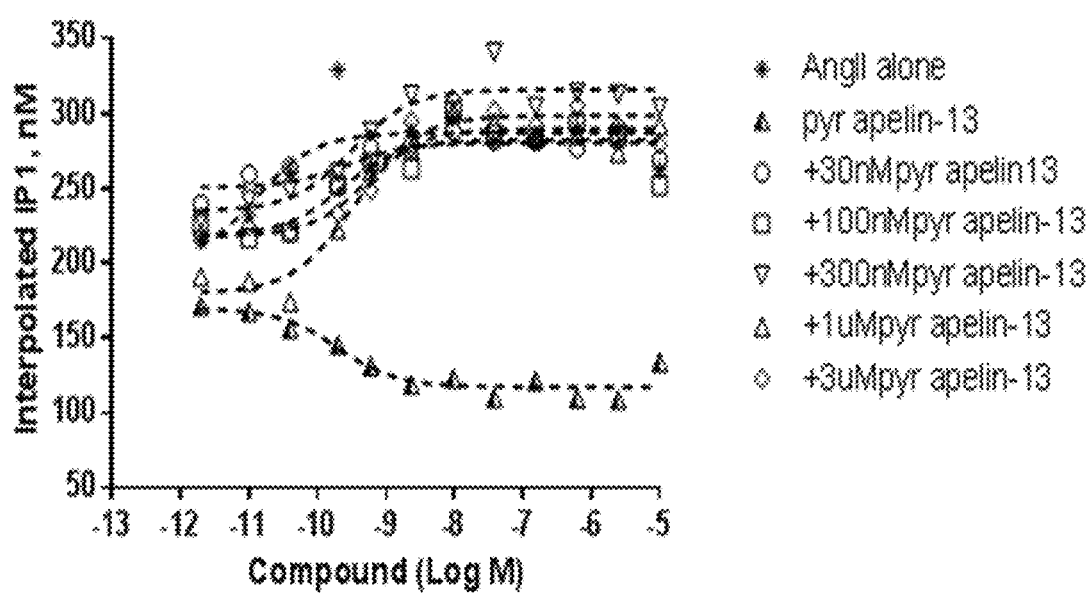
FIG. 9 is a graph plotting different concentrations of angiotensin (AngII) with fixed concentration of pyr apelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyr apelin-13 in the absence of APJ expression.

In cells expressing both APJ and the AT1R receptor, addition of APJ agonists at different concentrations increased the maximal response of AngII and also shifted the potency to the left. The increase in IP1 response reached a maximal effect both in potency and Emax indicating a ceiling effect which is a hallmark for allosteric cooperativity between the AT1R and APJ receptor (FIG. 7). However, this effect of cooperativity was not observed in either APJ or AT1R recombinant stable cell lines indicating that there is functional cross-talk between the two receptors through physical interaction or with downstream effectors (FIG. 8 and FIG. 9). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound or a pharmaceutically acceptable salt thereof, wherein the compound is
   (1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propane sulfonamide;
   (2S,3R)—N-(4-(2,6-dimethoxyphenyl)-5-(5-methyl-3-pyridinyl)-4H-1,2,4-triazol-3-yl)-3-(5-methyl-2-pyrimidinyl)-2-butane sulfonamide;
   (1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propane sulfonamide;
   (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propane sulfonamide;
   (1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propane sulfonamide;
   (1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propane sulfonamide;
   (1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propane sulfonamide;
   (1R,2S)—N-(4-(2,6-dimethoxyphenyl)-5-(3-pyridinyl)-4H-1,2,4-triazol-3-yl)-1-methoxy-1-(5-methyl-2-pyrimidinyl)-2-propane sulfonamide;
   (2S,3R)—N-(4-(2,6-dimethoxyphenyl)-5-(3-pyridinyl)-4H-1,2,4-triazol-3-yl)-3-(5-methyl-2-pyrimidinyl)-2-butane sulfonamide;
   (1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propane sulfonamide;
   (1R,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propane sulfonamide;
   (1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propane sulfonamide;
   (1R,2S)—N-(4-(2,6-dimethoxyphenyl)-5-(6-methyl-2-pyridinyl)-4H-1,2,4-triazol-3-yl)-1-hydroxy-1-(5-methyl-2-pyrimidinyl)-2-propane sulfonamide;
   (1R,2S)—N-(4-(2,6-dimethoxyphenyl)-5-(3-pyridinyl)-4H-1,2,4-triazol-3-yl)-1-ethoxy-1-(5-methyl-2-pyrimidinyl)-2-propane sulfonamide;
   (1R,2S)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide;
   (2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide;
   (1R,2S)—N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide;
   (1S,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;
   (1R,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;
   (1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propane sulfonamide;
   (1R,2S)—N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide;
   (2S,3R)—N-(4-(2,6-dimethoxyphenyl)-5-(3-pyridinyl)-4H-1,2,4-triazol-3-yl)-3-(5-methyl-2-pyrazinyl)-2-butanesulfonamide;
   (1R,2S)—N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide;
   (1R,2S)—N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide;
   (1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide; or
   (1S,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide, or
the pharmaceutically acceptable salt of any of the above compounds.

2. The compound of claim 1 or the pharmaceutically acceptable salt thereof, wherein the compound is
(1R,2S)—N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide or the pharmaceutically acceptable salt thereof.

3. The compound of claim 1 or the pharmaceutically acceptable salt thereof, wherein the compound is
(2S,3R)—N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide or the pharmaceutically acceptable salt thereof.

4. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide or the pharmaceutically acceptable salt thereof.

5. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide or the pharmaceutically acceptable salt thereof.

6. The compound of claim 1 or the pharmaceutically acceptable salt thereof, wherein the compound is
(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide or the pharmaceutically acceptable salt thereof.

7. The compound of claim 1 or the pharmaceutically acceptable salt thereof, wherein the compound is
(1S,2R)—N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide or the pharmaceutically acceptable salt thereof.

8. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide or the pharmaceutically acceptable salt thereof.

9. The compound of claim 1 or the pharmaceutically acceptable salt thereof, wherein the compound is
(1R,2S)—N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide or the pharmaceutically acceptable salt thereof.

10. The compound of claim 1 or the pharmaceutically acceptable salt thereof, wherein the compound is
(2S,3R)—N-(4-(2,6-dimethoxyphenyl)-5-(3-pyridinyl)-4H-1,2,4-triazol-3-yl)-3-(5-methyl-2-pyrimidinyl)-2-butanesulfonamide or the pharmaceutically acceptable salt thereof.

11. The compound of claim 1 or the pharmaceutically acceptable salt thereof, wherein the compound is
(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propane sulfonamide or the pharmaceutically acceptable salt thereof.

12. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide or the pharmaceutically acceptable salt thereof.

13. The compound of claim 1 or the pharmaceutically acceptable salt thereof, wherein the compound is
(1S,2R)—N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide or the pharmaceutically acceptable salt thereof.

14. The compound of claim 1 or the pharmaceutically acceptable salt thereof, wherein the compound is
(1R,2S)—N-(4-(2,6-dimethoxyphenyl)-5-(6-methyl-2-pyridinyl)-4H-1,2,4-triazol-3-yl)-1-hydroxy-1-(5-methyl-2-pyrimidinyl)-2-propanesulfonamide or the pharmaceutically acceptable salt thereof.

15. The compound of claim 1 or the pharmaceutically acceptable salt thereof, wherein the compound is
(1R,2S)—N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide or the pharmaceutically acceptable salt thereof.

16. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide or the pharmaceutically acceptable salt thereof.

17. The compound of claim 1 or the pharmaceutically acceptable salt thereof, wherein the compound is
(2S,3R)—N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide or the pharmaceutically acceptable salt thereof.

18. The compound of claim 1 or the pharmaceutically acceptable salt thereof, wherein the compound is
(1R,2S)—N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide or the pharmaceutically acceptable salt thereof.

19. The compound of claim 1 or the pharmaceutically acceptable salt thereof, wherein the compound is
(1S,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide or the pharmaceutically acceptable salt thereof.

20. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide or the pharmaceutically acceptable salt thereof.

21. The compound of claim 1 or the pharmaceutically acceptable salt thereof, wherein the compound is
(1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide or the pharmaceutically acceptable salt thereof.

22. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide or the pharmaceutically acceptable salt thereof.

23. The compound of claim 1 or the pharmaceutically acceptable salt thereof, wherein the compound is
(2S,3R)—N-(4-(2,6-dimethoxyphenyl)-5-(3-pyridinyl)-4H-1,2,4-triazol-3-yl)-3-(5-methyl-2-pyrazinyl)-2-butanesulfonamide or the pharmaceutically acceptable salt thereof.

24. The compound of claim 1 or the pharmaceutically acceptable salt thereof, wherein the compound is
(1R,2S)—N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide or the pharmaceutically acceptable salt thereof.

25. The compound of claim 1 or the pharmaceutically acceptable salt thereof, wherein the compound is
(1R,2S)—N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide or the pharmaceutically acceptable salt thereof.

26. The compound of claim 1 or the pharmaceutically acceptable salt thereof, wherein the compound is
(1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide or the pharmaceutically acceptable salt thereof.

27. The compound of claim 1 or the pharmaceutically acceptable salt thereof, wherein the compound is
(1S,2S)—N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide or the pharmaceutically acceptable salt thereof.

28. A pharmaceutical composition, comprising the compound of claim 1 or the pharmaceutically acceptable salt thereof, and at least one pharmaceutically acceptable excipient, carrier, or diluent.

29. The pharmaceutical composition of claim 28, further comprising at least one additional therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

30. The pharmaceutical composition of claim 28, further comprising at least one additional therapeutic agent selected from an angiotensin converting enzyme (ACE) inhibitor or an angiotensin-receptor blocker (ARB).

31. A pharmaceutical composition, comprising the compound of claim 2 or the pharmaceutically acceptable salt thereof, and at least one pharmaceutically acceptable excipient, carrier, or diluent.

32. A pharmaceutical composition, comprising the compound of claim 3 or the pharmaceutically acceptable salt thereof, and at least one pharmaceutically acceptable excipient, carrier, or diluent.

33. A pharmaceutical composition, comprising the compound of claim 4 or the pharmaceutically acceptable salt thereof, and at least one pharmaceutically acceptable excipient, carrier, or diluent.

34. A pharmaceutical composition, comprising the compound of claim 5 or the pharmaceutically acceptable salt thereof, and at least one pharmaceutically acceptable excipient, carrier, or diluent.

35. A pharmaceutical composition, comprising the compound of claim 6 or the pharmaceutically acceptable salt thereof, and at least one pharmaceutically acceptable excipient, carrier, or diluent.

36. A pharmaceutical composition, comprising the compound of claim 7 or the pharmaceutically acceptable salt thereof, and at least one pharmaceutically acceptable excipient, carrier, or diluent.

37. A pharmaceutical composition, comprising the compound of claim 8 or the pharmaceutically acceptable salt thereof, and at least one pharmaceutically acceptable excipient, carrier, or diluent.

38. A pharmaceutical composition, comprising the compound of claim 9 or the pharmaceutically acceptable salt thereof, and at least one pharmaceutically acceptable excipient, carrier, or diluent.

39. A pharmaceutical composition, comprising the compound of claim 10 or the pharmaceutically acceptable salt thereof, and at least one pharmaceutically acceptable excipient, carrier, or diluent.

40. A pharmaceutical composition, comprising the compound of claim 11 or the pharmaceutically acceptable salt thereof, and at least one pharmaceutically acceptable excipient, carrier, or diluent.

41. A pharmaceutical composition, comprising the compound of claim 12 or the pharmaceutically acceptable salt thereof, and at least one pharmaceutically acceptable excipient, carrier, or diluent.

42. A pharmaceutical composition, comprising the compound of claim 13 or the pharmaceutically acceptable salt thereof, and at least one pharmaceutically acceptable excipient, carrier, or diluent.

43. A pharmaceutical composition, comprising the compound of claim 14 or the pharmaceutically acceptable salt thereof, and at least one pharmaceutically acceptable excipient, carrier, or diluent.

44. A pharmaceutical composition, comprising the compound of claim 15 or the pharmaceutically acceptable salt thereof, and at least one pharmaceutically acceptable excipient, carrier, or diluent.

45. A pharmaceutical composition, comprising the compound of claim 16 or the pharmaceutically acceptable salt thereof, and at least one pharmaceutically acceptable excipient, carrier, or diluent.

46. A pharmaceutical composition, comprising the compound of claim 17 or the pharmaceutically acceptable salt thereof, and at least one pharmaceutically acceptable excipient, carrier, or diluent.

47. A pharmaceutical composition, comprising the compound of claim 18 or the pharmaceutically acceptable salt thereof, and at least one pharmaceutically acceptable excipient, carrier, or diluent.

48. A pharmaceutical composition, comprising the compound of claim 19 or the pharmaceutically acceptable salt thereof, and at least one pharmaceutically acceptable excipient, carrier, or diluent.

49. A pharmaceutical composition, comprising the compound of claim 20 or the pharmaceutically acceptable salt thereof, and at least one pharmaceutically acceptable excipient, carrier, or diluent.

50. A pharmaceutical composition, comprising the compound of claim 21 or the pharmaceutically acceptable salt thereof, and at least one pharmaceutically acceptable excipient, carrier, or diluent.

51. A pharmaceutical composition, comprising the compound of claim 22 or the pharmaceutically acceptable salt thereof, and at least one pharmaceutically acceptable excipient, carrier, or diluent.

52. A pharmaceutical composition, comprising the compound of claim 23 or the pharmaceutically acceptable salt thereof, and at least one pharmaceutically acceptable excipient, carrier, or diluent.

53. A pharmaceutical composition, comprising the compound of claim 24 or the pharmaceutically acceptable salt thereof, and at least one pharmaceutically acceptable excipient, carrier, or diluent.

54. A pharmaceutical composition, comprising the compound of claim 25 or the pharmaceutically acceptable salt thereof, and at least one pharmaceutically acceptable excipient, carrier, or diluent.

55. A pharmaceutical composition, comprising the compound of claim 26 or the pharmaceutically acceptable salt thereof, and at least one pharmaceutically acceptable excipient, carrier, or diluent.

56. A pharmaceutical composition, comprising the compound of claim 27 or the pharmaceutically acceptable salt thereof, and at least one pharmaceutically acceptable excipient, carrier, or diluent.

57. A kit, the kit comprising: the compound of claim 1 or the pharmaceutically acceptable salt thereof and at least one additional therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

58. A kit, the kit comprising: the compound of claim 1 or the pharmaceutically acceptable salt thereof and at least one additional therapeutic agent selected from an angiotensin converting enzyme (ACE) inhibitor or an angiotensin-receptor blocker (ARB).

59. A pharmaceutical composition comprising a compound of Formula I or Formula II or a pharmaceutically acceptable salt thereof, and at least one pharmaceutically acceptable excipient, carrier, or diluent, wherein the compound of Formula I or Formula II has the following structure:

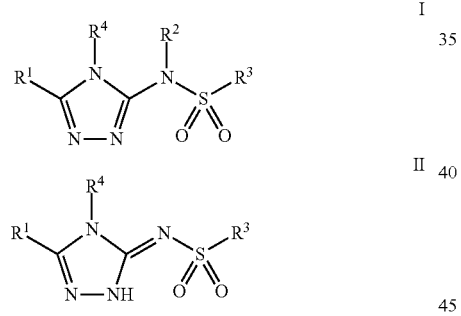

wherein:
  $R^1$ is an unsubstituted pyridyl, pyridonyl, or pyridine N-oxide, or is a pyridyl, pyridonyl, or pyridine N-oxide substituted with 1, 2, 3, or 4 $R^{1a}$ substituents;
  $R^{1a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —C(=O)-(heterocyclyl), or a heterocyclyl group, wherein the heterocyclyl group of the —C(=O)-(heterocyclyl) or heterocyclyl group is a 3 to 7 membered ring containing 1, 2, or 3 heteroatoms selected from N, O, or S;
  $R^2$ is selected from —H, or $C_1$-$C_4$ alkyl or is absent in the compounds of Formula II;
  $R^3$ is a group of formula —($CR^{3d}R^{3e}$)—($CR^{3f}R^{3g}$)-Q;
  $R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
  $R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
  Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;
  $R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo substituent;
  $R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, or a monocyclic or bicyclic heterocyclyl group with 5 to 10 ring members containing 1, 2, 3, or 4 heteroatoms independently selected from N, O, or S, wherein the $C_6$-$C_{10}$ aryl group, the heteroaryl group, or the heterocyclyl group are unsubstituted or are substituted with 1, 2, or 3 $R^{4a}$ substituents; and
  $R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$, and the heterocyclyl $R^4$ group may be further substituted with 1 oxo substituent.

60. The pharmaceutical composition of claim 59, further comprising at least one additional therapeutic agent selected from an angiotensin converting enzyme (ACE) inhibitor or an angiotensin-receptor blocker (ARB).

* * * * *

UNITED STATES PATENT AND TRADEMARK OFFICE
CERTIFICATE OF CORRECTION

PATENT NO. : 9,868,721 B2
APPLICATION NO. : 15/297272
DATED : January 16, 2018
INVENTOR(S) : Chen et al.

It is certified that error appears in the above-identified patent and that said Letters Patent is hereby corrected as shown below:

In the Claims

In Claim 1, Column 1359, Line 51 through Column 1360, Line 67, please replace Claim 1 in its entirety with the following:
--1. A compound or a pharmaceutically acceptable salt thereof, wherein the compound is
(1R,2S)-N-(4-(2,6-dimethoxyphenyl)-5-(6-methoxy-2-pyridinyl)-4H-1,2,4-triazol-3-yl)-1-methoxy-1-(5-methyl-2-pyrimidinyl)-2-propanesulfonamide;
(2S,3R)-N-(4-(2,6-dimethoxyphenyl)-5-(5-methyl-3-pyridinyl)-4H-1,2,4-triazol-3-yl)-3-(5-methyl-2-pyrimidinyl)-2-butanesulfonamide;
(1R,2S)-N-(4-(2,6-dimethoxyphenyl)-5-(5-methyl-3-pyridinyl)-4H-1,2,4-triazol-3-yl)-1-methoxy-1-(5-methyl-2-pyrimidinyl)-2-propanesulfonamide;
(1R,2S)-N-(4-(2,6-dimethoxyphenyl)-5-(5-methyl-3-pyridinyl)-4H-1,2,4-triazol-3-yl)-1-hydroxy-1-(5-methyl-2-pyrimidinyl)-2-propanesulfonamide;
(1S,2R)-1-(5-chloro-2-pyrimidinyl)-N-(4-(2,6-dimethoxyphenyl)-5-(5-methyl-3-pyridinyl)-4H-1,2,4-triazol-3-yl)-1-methoxy-2-propanesulfonamide;
(1S,2R)-N-(4-(2,6-dimethoxyphenyl)-5-(5-methyl-3-pyridinyl)-4H-1,2,4-triazol-3-yl)-1-methoxy-1-(5-methyl-2-pyrazinyl)-2-propanesulfonamide;
(1R,2S)-N-(4-(2,6-dimethoxyphenyl)-5-(5-methyl-3-pyridinyl)-4H-1,2,4-triazol-3-yl)-1-hydroxy-1-(5-methyl-2-pyrazinyl)-2-propanesulfonamide;
(1R,2S)-N-(4-(2,6-dimethoxyphenyl)-5-(3-pyridinyl)-4H-1,2,4-triazol-3-yl)-1-methoxy-1-(5-methyl-2-pyrimidinyl)-2-propanesulfonamide;
(2S,3R)-N-(4-(2,6-dimethoxyphenyl)-5-(3-pyridinyl)-4H-1,2,4-triazol-3-yl)-3-(5-methyl-2-pyrimidinyl)-2-butanesulfonamide;
(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide;
(1R,2S)-N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide;
(1S,2R)-N-(4-(2,6-dimethoxyphenyl)-5-(3-pyridinyl)-4H-1,2,4-triazol-3-yl)-1-methoxy-1-(5-methyl-2-pyrazinyl)-2-propanesulfonamide;

Signed and Sealed this
Tenth Day of July, 2018

Andrei Iancu
*Director of the United States Patent and Trademark Office*

CERTIFICATE OF CORRECTION (continued)
U.S. Pat. No. 9,868,721 B2

(1R,2S)-N-(4-(2,6-dimethoxyphenyl)-5-(6-methyl-2-pyridinyl)-4H-1,2,4-triazol-3-yl)-1-hydroxy-1-(5-methyl-2-pyrimidinyl)-2-propanesulfonamide;

(1R,2S)-N-(4-(2,6-dimethoxyphenyl)-5-(3-pyridinyl)-4H-1,2,4-triazol-3-yl)-1-ethoxy-1-(5-methyl-2-pyrimidinyl)-2-propanesulfonamide;

(1R,2S)-N-(4-(2,6-dimethoxyphenyl)-5-(5-methyl-3-pyridinyl)-4H-1,2,4-triazol-3-yl)-1-(5-fluoro-2-pyrimidinyl)-1-methoxy-2-propanesulfonamide;

(2S,3R)-N-(4-(2,6-dimethoxyphenyl)-5-(5-methyl-3-pyridinyl)-4H-1,2,4-triazol-3-yl)-3-(5-methyl-2-pyrazinyl)-2-butanesulfonamide;

(1R,2S)-N-(4-(2,6-dimethoxyphenyl)-5-(3-pyridinyl)-4H-1,2,4-triazol-3-yl)-1-ethoxy-1-(5-fluoro-2-pyrimidinyl)-2-propanesulfonamide;

(1S,2S)-N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1R,2S)-N-(4-(2,6-dimethoxyphenyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1S,2R)-1-(5-chloro-2-pyrimidinyl)-N-(4-(2,6-dimethoxyphenyl)-5-(3-pyridinyl)-4H-1,2,4-triazol-3-yl)-1-methoxy-2-propanesulfonamide;

(1R,2S)-N-(4-(2,6-dimethoxyphenyl)-5-(5-methyl-3-pyridinyl)-4H-1,2,4-triazol-3-yl)-1-methoxy-1-(5-methoxy-2-pyrazinyl)-2-propanesulfonamide;

(2S,3R)-N-(4-(2,6-dimethoxyphenyl)-5-(3-pyridinyl)-4H-1,2,4-triazol-3-yl)-3-(5-methyl-2-pyrazinyl)-2-butanesulfonamide;

(1R,2S)-N-(4-(2,6-dimethoxyphenyl)-5-(5-methyl-3-pyridinyl)-4H-1,2,4-triazol-3-yl)-1-ethoxy-1-(5-fluoro-2-pyrimidinyl)-2-propanesulfonamide;

(1R,2S)-N-(4-(4,6-dimethoxy-5-pyrimidinyl)-5-(6-methoxy-2-pyridinyl)-4H-1,2,4-triazol-3-yl)-1-methoxy-1-(5-methyl-2-pyrimidinyl)-2-propanesulfonamide;

(1R,2R)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide; or (1S,2S)-N-(4-(2,6-dimethoxyphenyl)-5-(5-methyl-3-pyridinyl)-4H-1,2,4-triazol-3-yl)-1-ethoxy-1-(5-methyl-2-pyrimidinyl)-2-propanesulfonamide, or the pharmaceutically acceptable salt of any of the above compounds.--

In Claim 11, Column 1361, Lines 58-60, replace the phrase:
"(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propane sulfonamide"
With the phrase:
--(1R,2S)-1-(5-chloro-2-pyrimidinyl)-N-(4-(2,6-dimethoxyphenyl)-5-(3-pyridinyl)-4H-1,2,4-triazol-3-yl)-1-ethoxy-2-propanesulfonamide--